(12) United States Patent
Priestley et al.

(10) Patent No.: US 12,037,324 B2
(45) Date of Patent: Jul. 16, 2024

(54) BIARYLMETHYL HETEROCYCLES

(71) Applicants: Université de Montréal, Montréal (CA); Bristol-Myers Squibb Company, Princeton, NJ (US)

(72) Inventors: Eldon Scott Priestley, Hopewell, NJ (US); Samuel Kaye Reznik, Brookline, MA (US); Edward H. Ruediger, Montreal (CA); James R. Gillard, Montreal (CA); Oz Scott Halpern, Hopewell, NJ (US); Wen Jiang, Hopewell, NJ (US); Jeremy Richter, Hopewell, NJ (US); Rejean Ruel, Montreal (CA); Sasmita Tripathy, Montreal (CA); Wu Yang, Hopewell, NJ (US); Xiaojun Zhang, Hopewell, NJ (US)

(73) Assignees: Bristol-Myers Squibb Company, Princeton, NJ (US); Université de Montréal (CA)

( * ) Notice: Subject to any disclaimer, the term of this patent is extended or adjusted under 35 U.S.C. 154(b) by 0 days.

(21) Appl. No.: 17/861,809

(22) Filed: Jul. 11, 2022

(65) Prior Publication Data
US 2023/0045357 A1 Feb. 9, 2023

Related U.S. Application Data

(62) Division of application No. 16/311,835, filed as application No. PCT/US2017/039646 on Jun. 28, 2017, now Pat. No. 11,407,733.

(Continued)

(51) Int. Cl.
| | | |
|---|---|---|
| C07D 401/14 | (2006.01) |
| A61K 31/41 | (2006.01) |
| A61K 31/4245 | (2006.01) |
| A61K 31/427 | (2006.01) |
| A61K 31/437 | (2006.01) |
| A61K 31/4439 | (2006.01) |
| A61K 31/4709 | (2006.01) |
| A61K 31/497 | (2006.01) |
| A61K 31/501 | (2006.01) |
| A61P 9/04 | (2006.01) |
| C07D 233/90 | (2006.01) |
| C07D 235/26 | (2006.01) |
| C07D 239/20 | (2006.01) |
| C07D 257/04 | (2006.01) |
| C07D 271/07 | (2006.01) |
| C07D 401/10 | (2006.01) |
| C07D 403/10 | (2006.01) |
| C07D 403/14 | (2006.01) |
| C07D 405/14 | (2006.01) |
| C07D 413/10 | (2006.01) |
| C07D 413/14 | (2006.01) |

(Continued)

(52) U.S. Cl.
CPC ............ *C07D 401/14* (2013.01); *A61K 31/41* (2013.01); *A61K 31/4245* (2013.01); *A61K 31/427* (2013.01); *A61K 31/437* (2013.01); *A61K 31/4439* (2013.01); *A61K 31/4709* (2013.01); *A61K 31/497* (2013.01); *A61K 31/501* (2013.01); *A61P 9/04* (2018.01); *C07D 233/90* (2013.01); *C07D 235/26* (2013.01); *C07D 239/20* (2013.01); *C07D 257/04* (2013.01); *C07D 271/07* (2013.01); *C07D 401/10* (2013.01); *C07D 403/10* (2013.01); *C07D 403/14* (2013.01); *C07D 405/14* (2013.01); *C07D 413/10* (2013.01); *C07D 413/14* (2013.01); *C07D 417/14* (2013.01); *C07D 471/04* (2013.01); *C07D 498/10* (2013.01)

(58) Field of Classification Search
CPC .......................... C07D 401/14; A61K 31/513
See application file for complete search history.

(56) References Cited

U.S. PATENT DOCUMENTS

| | | |
|---|---|---|
| 4,444,770 A | 4/1984 | Meyer et al. |
| 5,140,037 A | 8/1992 | Chiu et al. |

(Continued)

FOREIGN PATENT DOCUMENTS

| | | |
|---|---|---|
| AU | 655458 B2 | 12/1994 |
| CA | 2024137 A1 | 3/1991 |

(Continued)

OTHER PUBLICATIONS

Abraham, et al., "β-Arrestin mediates the Frank-Starling mechanism of cardiac contractility," PNAS, Dec. 13, 2016, vol. 113, No. 50, 14426-14431.

(Continued)

*Primary Examiner* — Paul V Ward
(74) *Attorney, Agent, or Firm* — Hoffmann & Baron, LLP

(57) ABSTRACT

The present invention provides compounds of Formula (I):

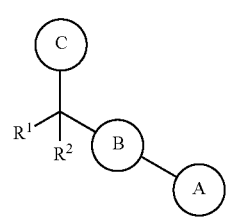

(I)

wherein all variables are as defined in the specification, and compositions comprising any of such novel compounds. These compounds are biased agonists, or β-Arrestin agonists of the angiotensin II receptor, which may be used as medicaments.

17 Claims, No Drawings

Related U.S. Application Data

(60) Provisional application No. 62/356,215, filed on Jun. 29, 2016.

(51) Int. Cl.
*C07D 417/14* (2006.01)
*C07D 471/04* (2006.01)
*C07D 498/10* (2006.01)

(56) References Cited

U.S. PATENT DOCUMENTS

| | | |
|---|---|---|
| 5,171,748 A | 12/1992 | Roberts et al. |
| 5,177,074 A | 1/1993 | Allen et al. |
| 5,198,438 A | 3/1993 | Allen et al. |
| 5,223,499 A | 6/1993 | Greenlee et al. |
| 5,256,667 A | 10/1993 | Allen et al. |
| 5,268,377 A | 12/1993 | Honma et al. |
| 5,281,614 A | 1/1994 | Ashton et al. |
| 5,308,846 A | 5/1994 | Allen et al. |
| 5,332,744 A | 7/1994 | Chakravarty et al. |
| 5,409,936 A | 4/1995 | Honma et al. |
| 5,411,980 A | 5/1995 | Ashton et al. |
| 5,412,097 A | 5/1995 | Chakravarty et al. |
| 5,424,316 A | 6/1995 | Honma et al. |
| 5,424,432 A | 6/1995 | Fredenburgh et al. |
| 5,424,450 A | 6/1995 | Boswell et al. |
| 5,444,067 A | 8/1995 | Kivlighn et al. |
| 5,510,354 A | 4/1996 | Honma et al. |
| 5,512,681 A | 4/1996 | Boswell et al. |
| 5,554,625 A | 9/1996 | Rivero et al. |
| 5,594,010 A | 1/1997 | Fey et al. |
| 5,627,191 A | 5/1997 | Birch et al. |
| 5,798,364 A | 8/1998 | Mederski et al. |
| 6,235,766 B1 | 5/2001 | Heitsch et al. |
| 6,264,914 B1 | 7/2001 | Klaveness et al. |
| 6,300,356 B1 | 10/2001 | Segal et al. |
| 6,429,222 B2 | 8/2002 | Heitsch et al. |
| 6,524,552 B2 | 2/2003 | Klaveness et al. |
| 6,538,144 B2 | 3/2003 | Heitsch |
| 6,653,306 B1 | 11/2003 | Alexander et al. |
| 6,921,525 B2 | 7/2005 | Klaveness et al. |
| 6,984,660 B2 | 1/2006 | Heitsch |
| 7,129,264 B2 | 10/2006 | Smallheer et al. |
| 7,182,934 B2 | 2/2007 | Klaveness et al. |
| 7,652,054 B2 | 1/2010 | Alterman et al. |
| 8,124,638 B2 | 2/2012 | Alterman et al. |
| 8,486,885 B2 | 7/2013 | Yamashita et al. |
| 8,796,204 B2 | 8/2014 | Yamashita et al. |
| 8,809,260 B2 | 8/2014 | Yamashita et al. |
| 8,993,511 B2 | 3/2015 | Yamashita et al. |
| 9,534,017 B2 | 1/2017 | Yamashita et al. |
| 9,624,181 B2 | 4/2017 | Seki |
| 9,732,074 B2 | 8/2017 | Petasis et al. |
| 10,016,397 B2 | 7/2018 | Springer et al. |
| 10,301,298 B2 | 5/2019 | Petasis et al. |
| 2003/0186978 A1 | 10/2003 | Bargiotti et al. |
| 2004/0067915 A1 | 4/2004 | McMahon et al. |
| 2004/0102423 A1 | 5/2004 | MacLaughlan et al. |
| 2004/0167176 A1 | 8/2004 | Alterman et al. |
| 2006/0211866 A1 | 9/2006 | Joshi et al. |
| 2010/0029609 A1 | 2/2010 | Berst et al. |
| 2011/0046090 A1 | 2/2011 | Barlow et al. |
| 2011/0269717 A1 | 11/2011 | Barlow et al. |
| 2012/0035232 A1 | 2/2012 | Steckelings et al. |

FOREIGN PATENT DOCUMENTS

| | | |
|---|---|---|
| CA | 2063866 A1 | 9/1992 |
| CA | 2066094 C | 10/1992 |
| CN | 102816126 A | 12/2012 |
| DE | 4320432 A1 | 12/1994 |
| DE | 19920815 A1 | 11/2000 |
| DE | 102012004589 A1 | 9/2013 |
| EP | 0324377 A2 | 7/1989 |
| EP | 0399731 A1 | 11/1990 |
| EP | 0399732 A1 | 11/1990 |
| EP | 0400835 A1 | 12/1990 |
| EP | 0400974 A2 | 12/1990 |
| EP | 0415886 A2 | 3/1991 |
| EP | 0505893 A1 | 9/1992 |
| EP | 0512675 A1 | 11/1992 |
| EP | 0513979 A1 | 11/1992 |
| EP | 0531874 A1 | 3/1993 |
| EP | 0531876 A2 | 3/1993 |
| EP | 0534706 A1 | 3/1993 |
| GB | 2263637 A | 8/1993 |
| GB | 2272899 A | 6/1994 |
| GB | 2281298 A | 3/1995 |
| GB | 2337701 A | 12/1999 |
| JP | H 5-140153 A | 6/1993 |
| JP | H 5-140154 A | 6/1993 |
| JP | 06312926 A | 11/1994 |
| JP | H 7-509464 A | 10/1995 |
| JP | 2003-034684 A | 2/2003 |
| WO | 91/14367 A1 | 10/1991 |
| WO | 92/00067 A2 | 1/1992 |
| WO | 92/20662 A1 | 11/1992 |
| WO | 93/01177 A1 | 1/1993 |
| WO | 93/03033 A1 | 2/1993 |
| WO | 93/04045 A1 | 3/1993 |
| WO | 93/04046 A1 | 3/1993 |
| WO | 93/19067 A1 | 9/1993 |
| WO | 94/01436 A1 | 1/1994 |
| WO | 94/02142 A1 | 2/1994 |
| WO | 96/40256 A1 | 12/1996 |
| WO | 96/40257 A1 | 12/1996 |
| WO | 96/40258 A2 | 12/1996 |
| WO | 98/18496 A2 | 5/1998 |
| WO | 98/30216 A1 | 7/1998 |
| WO | 99/43210 A1 | 9/1999 |
| WO | 00/68226 A1 | 11/2000 |
| WO | 01/96339 A1 | 12/2001 |
| WO | 02/072569 A1 | 9/2002 |
| WO | 02/096883 A1 | 12/2002 |
| WO | 03/064414 A1 | 8/2003 |
| WO | 2004/046137 A1 | 6/2004 |
| WO | 2004/094372 A2 | 11/2004 |
| WO | 2008/028937 A1 | 3/2008 |
| WO | 2010/077339 A2 | 7/2010 |
| WO | 2014/034868 A1 | 3/2014 |
| WO | 2014/145331 A1 | 9/2014 |
| WO | 2015/014634 A1 | 2/2015 |
| WO | 2016/011420 A1 | 1/2016 |
| ZA | 20018801 B | 8/2002 |

OTHER PUBLICATIONS

Bundgaard, H., "5. Design and Application of Prodrugs," A Textbook of Drug Design and Development, Krogsgaard-Larsen and Bundgaard, eds., Harwood Academic Publishers, 1991, 113-191.

Bundgaard, H., "(C) Means to Enhance Penetration (1) Prodrugs as a means to improve the delivery of peptide drugs," Advanced Drug Delivery Reviews, 8 (1992) 1-38.

Casimiro-Garcia, et al., "Discovery of a Series of Imidazo[4,5-b]pyridines with Dual Activity at Angiotensin II Type 1 Receptor and Peroxisome Proliferator-Activated Receptor-γ," J. Med. Chem. 2011, 54, 4219-4233. dx.doi.org/10.1021/jm200409s.

Chang, et al., "2,6,8-Trisubstituted 1-Deazapurines as Adenosine Receptor Antagonists," J. Med. Chem. 2007, 50, 828-834.

Du, et al., "Palladium-Catalyzed Highly Selective ortho-Halogenation (I, Br, Cl) of Arylnitriles via $sp^2$ C—H Bond Activation Using Cyano as Directing Group," J. Org. Chem. 2013, 78, 2786-2791. dx.doi.org/10.1021/jo302765g.

Gooβen and Ghosh, "Palladium-Catalyzed Synthesis of Aryl Ketones from Boronic Acids and Carboxylic Acids or Anhydrides," Angew. Chem. Int. Ed. 2001, 40, No. 18, 3458-3460.

Kakeya, et al., "Studies on Proilrugs of Cephalosporins. I. Synthesis and Biological Properties of Glycyloxybenzoyloxymethyl and Glycylaminobenzoyloxymethyl Esters of 7P-[2-(2-Aminothiazol-4-yl)-(Z)-2-methoxyiminoacetamido]-3-methyl-3-cephem-4-carboxylic Acid," Chem. Pharm. Bull. 32{ 2) 692-698 (1984).

(56) References Cited

OTHER PUBLICATIONS

Katritzky, et al., eds., "Comprehensive Organic Functional Group Transformations," First edition, Elsevier Science Ltd., Kidlington, Oxford (1995), Contents pages.
King, F.D., ed., "Medicinal Chemistry: Principles and Practice," The Royal Society of Chemistry, Jan. 1994, Contents pages.
Lyse'n, et al., "Synthesis of Substituted 2-Cyanoarylboronic Esters," J. Org. Chem. 2006, 71, 2518-2520.
Larock, R.C., "Comprehensive Organic Transformations, A Guide to Functional Group Preparations," VCH Publishers, Inc., New York, New York 1989, Contents pp. xiii-xxviii.
Nielsen and Bundgaard, "Glycolamide Esters as Biolabile Prodrugs of Carboxylic Acid Agents: Synthesis, Stability, Bioconversion, and Physicochemical Properties," Journal of Pharmaceutical Sciences, vol. 77, No. 4, Apr. 1988, 285-298.
Notari, R.E., "[24] Theory and Practice of Prodrug Kinetics", Methods in Enzymology, vol. 112, Drug and Enzyme Targeting Part A, Widder and Green, eds., Academic Press, Inc., Orlando (1985) 309-351.
Rautio, Jarkko, ed., "Prodrugs and Targeted Delivery," WILEY-VCH Verlag GmbH & Co. KGaA, Weinheim, Germany (2011), Contents pp. v-xv.
Satyanarayana, et al., (2005) "Improved Synthesis of Irbesartan, an Antihypertensive Active Pharmaceutical Ingredient," Synthetic Communications, 35, 1979-1982. DOI: 10.1081/SCC-200065008.
Smith and March, "March's Advanced Organic Chemistry: Reactions, Mechanisms, and Structure," Sixth Edition, John Wiley & Sons, Inc., Hoboken, New Jersey (2007), Contents pp. xiii-xiv.
Testa and Mayer, "Hydrolysis in Drug and Prodrug Metabolism. Chemistry, Biochemistry and Enzymology," VHCA, Zürich, Switzerland and WILEY-VCH GmbH & Co. KGaA, Weinheim (Federal Republic of Germany) (2003), Contents pages.
Trost and Fleming, eds., "Comprehensive Organic Synthesis: Selectivity, Strategy & Efficiency in Modern Organic Chemistry," vol. 9, Cumulative Indexes, Pergamon Press, Inc., Tarrytown, New York (1991), Contents pp. v-xv.
Wermuth, et al., "31. Designing Prodrugs and Bioprecursors I: Carrier Prodrugs", The Practice of Medicinal Chemistry, Wermuth, C.G., ed., Academic Press, London (1996), 671-696.
Wittenberger and Donner, "Dialkyltin Oxide Mediated Addition of Trimethylsilyl Azide to Nitriles. A Novel Preparation of 5-Substituted Tetrazolest," J. Org. Chem. 1993, 58, 4139-4141.
Wuts and Greene, "Greene's Protective Groups in Organic Synthesis," Fourth Edition, John Wiley & Sons, Inc., Hoboken, New Jersey, 2007, pp. v-vii and ix-xxviii.
Chang, L.L. et al., "Potent Triazolinone-Based Angiotensin II Receptor Antagonists With Equivalent Affinity For Both the AT1 and AT2 Subtypes," Bioorganic & Medicinal Chemistry Letters, 1994, 4(23):2787-2792.
De Witt, Bracken J. et al., "L-163,491 is a partial angiotensin AT1 receptor agonist in the hindquarters vascular bed of the cat," European Journal of Pharmacology, 2000, 404:213-219.
Green, Barbara Gordan et al., "Inhibition of Bacterial Peptide Deformylase by Biaryl Acid Analogs," Archives of Biochemistry and Biophysics, 2000, 375(2):355-358.
Kaye, Alan D. et al., "Responses to L-163,491, a nonpeptide angiotensin II mimic, in the pulmonary vascular bed of the cat," European Journal of Pharmacology, 1995, 287:163-168.

Kaye, Alan D. et al., "Responses To A Nonpeptide Angiotensin Receptor Agonist, L 163491, In The Feline Pulmonary Vascular Bed," Life Sciences, 1995, 57(20):301-305.
Liu, Jie et al., "Design, synthesis, and biological evaluation of 1,2,4-triazol bearing 5-substituted biphenyl-2-sulfonamide derivatives as potential antihypertensive candidates," Bioorganic & Medicinal Chemistry, 2013, 21:7742-7751.
Miura, Shin-Ichiro et al., "Small Molecules with Similar Structures Exhibit Agonist, Neutral Antagonist or Inverse Agonist Activity toward Angiotensin II Type 1 Receptor," PLOS One 7(6):e37974, Jun. 14, 2012, available at https://doi.org/10.1371/journal.pone.0037974.
Nirula, Vaneet et al., "Interaction of biphenylimidazole and imidazoleacrylic acid nonpeptide antagonists with valine 108 in TM III of the AT1 angiotensin receptor," British Journal of Pharmacology (1996) 119:1505-1507.
Nirula, Vaneet et al., "Identification of nonconserved amino acids in the AT1 receptor which comprise a general binding site for biphenylimidazole antagonists," FEBS Letters (1996) 394:361-364.
Pandya, Trupti et al., "Structure-Activity Relationship Study of Some Triazolinone Based Compounds with Antagonistic Balanced Activity on Angiotensin II Receptor Subtypes AT1 and AT2," Arzneim.-Forsch./Drug Res., 2005, 55(5):265-270.
Perlman, Signe et al., "Dual Agonistic and Antagonistic Property of Nonpeptide Angiotensin AT1 Ligands: Susceptibility to Receptor Mutations," Molecular Pharmacology (1997) 51:301-311.
Rivero, R.A. et al., "L-162,389: A Potent Orally Active Angiotensin II Receptor Antagonist With Balanced Affinity To Both AT1 and AT2 Receptor Subtypes," Bioorganic & Medicinal Chemistry Letters (1996) 6(3):307-310.
Sallander, Jessica et al., "Structural determinants of subtype selectivity and functional activity of angiotensin II receptors," Bioorganic & Medicinal Chemistry Letters (2016) 26:1355-1359.
Skold, Christian et al., "Development of CoMFA models of affinity and selectivity to angiotensin II type-1 and type-2 receptors," Journal of Molecular Graphics and Modelling (2007) 26:145-153.
Wallinder, Charlotta et al., "Interconversion of Functional Activity by Minor Structural Alterations in Nonpeptide AT2 Receptor Ligands," ACS Med. Chem. Lett. (2015) 6:178-182.
Wan, Yiqian et al., "First Reported Nonpeptide AT1 Receptor Agonist (L-162,313) Acts as an AT2 Receptor Agonist in Vivo," J. Med. Chem. (2004) 47:1536-1546.
Wu, Xiongyu et al., "Selective Angiotensin II AT2 Receptor Agonists: Arylbenzylimidazole Structure-Activity Relationships," J. Med. Chem. (2006) 49:7160-7168.
International Preliminary Report On Patentability and Written Opinion issued in International Application No. PCT/US2017/039646, mailed Jan. 10, 2019 (8 pages).
Ikeda, Yuichi, et al.,"Biased Agonism of the Angiotensin II Type I Receptor," International Heart Journal, 56(5):485-488, Jul. 14, 2015.
Kevin, N.J., "Substituted Phenylthiophene Benzoylsulfonamides with Potent Binding Affinity to Angiotensin II AT1 and AT2 Receptors," BioOrganic and Medicinal Chemistry Letters, 4(1):189-194, Jan. 1, 1994.
Zhang, Haitao, et al., "Structural Basis for Ligand Recognition and Functional Selectivity as Angiotensin Receptor," Journal of Biological Chemistry, 290(49):29127-29139, Sep. 29, 2015.
International Search Report issued in International Application No. PCT/US2017/039646, mailed Oct. 25, 2017 (5 pages).
Written Opinion issued in International Application No. PCT/US2017/039646, mailed Oct. 25, 2017 (8 pages).

BIARYLMETHYL HETEROCYCLES

CROSS-REFERENCE TO RELATED APPLICATIONS

This application is a divisional of U.S. application Ser. No. 16/311,835, filed Dec. 20, 2018, which is a National Stage Entry of PCT/US2017/039646, filed Jun. 28, 2017, which claims the benefit of U.S. Provisional Application No. 62/356,215, filed on Jun. 29, 2016. The contents of each of these aforementioned applications are incorporated herein by reference in their entirety.

FIELD OF THE INVENTION

The present invention provides substituted biaryl compounds and their analogues thereof, acting as biased agonists at the Angiotensin II receptor, compositions containing them, and methods of using them, for example, for the treatment or prophylaxis of cardiovascular diseases, such as chronic heart failure or chronic hypertensive conditions.

BACKGROUND OF THE INVENTION

Cardiovascular disease and mortality continue to represent the leading cause of death in developed countries despite significant advances in understanding of disease progression and the availability of new treatments. Within this context, heart failure continues to be a growing healthcare problem with millions of new cases occurring worldwide annually. Morbidity and mortality of those patients presenting in hospital for decompensation is high with approximately 35% of these patients dying or requiring re-hospitalization within 3 months of discharge (Bhatia, Tu et al. 2006, Fonarow, Stough et al. 2007, Gheorghiade, Vaduganathan et al. 2013); 50% of heart failure patients die within 5 years of diagnosis (Go, Mozaffarian et al. 2013, Mozaffarian, Benjamin et al. 2015). As a result, heart failure represents a significant burden to human health and the efficient administration of healthcare services (Desai and Stevenson 2012, Go, Mozaffarian et al. 2013, Mozaffarian, Benjamin et al. 2015).

There are currently two forms of heart failure recognized and classified based upon their etiology and pathogenesis (Satomura, Wada et al.). Heart failure with reduced ejection fraction (HFrEF, systolic heart failure) typically follows ischemic insult such as myocardial infarction, coronary artery disease or underlying cardiomyopathies and is characterized by significant cardiac scarring, fibrosis, thinning of the left ventricular wall, left ventricular dilation and a concomitant reduction in left ventricular ejection fraction.

Heart failure with preserved ejection fraction (HFpEF, diastolic heart failure) is generally a result of chronic increased cardiac load associated with chronic hypertension resulting in cardiac remodeling, thickening of the left ventricular wall, fibrosis and reduced left ventricular volume. In the early stages of HFpEF, tissue remodeling and thickening of the ventricular wall can compensate for the increased load and maintain ejection fraction.

However, as the disease progresses continued maladaptive remodeling leads to failure of ventricular function. The impact of heart failure on the health of the-patient can be assessed by the myriad of symptoms associated with the disease including dyspnea, exercise intolerance, pulmonary and peripheral edema and chronic fatigue. Current effective therapies exist for HFrEF but not HFpEF.

Among the clinically accepted standard of care for HFrEF are diuretics that reduce volume overload and dyspnea associated with reduced perfusion, as well as angiotensin-converting enzyme (ACE) inhibitors (ACEi) and angiotensin receptor blockers (ARBs) (Yancy, Jessup et al. 2013). Drugs such as ACEi and ARBs target the renin-angiotensin aldosterone system (RAAS). The RAAS system is a physiologically important endocrine/paracrine pathway through its actions to maintain homeostatic blood pressure and cardiac output. The RAAS pathway is generally activated during conditions such as renal dysfunction and heart failure due to reduced kidney function that induces release of renin by the kidneys. Renin is a circulating enzyme that converts angiotensinogen to angiotensin I. In turn, angiotensin I is converted to the vasoactive hormone angiotensin II (AII) by angiotensin-converting enzyme (ACE) in the lung and other tissues. AII exerts its effects on target tissues through binding to specific receptors on these cells, the AT1R and AT2R receptors.

AT1R is thought to be the predominant AII receptor based upon expression level. The ATIR works primarily through activation of the Gq signaling pathway within cells. However, AT1R has also been shown to activate other signaling pathways including non-G-protein-mediated pathways such as $\beta$-arrestin (Wei, Ahn et al. 2003, Aplin, Christensen et al. 2007).

Therapeutically, ACEi block AII production through inhibition of the conversion of angiotensin I to ALL (Brown and Vaughan 1998), while ARBs specifically block AII action via competitive antagonism of the AII receptor, AT1R (Gring and Francis 2004). The resultant blockade of AII activity results in lowering of blood pressure and cardiac load. ARBs have the added benefit of improving kidney function through maintenance of glomerular filtration and therefore improved diuresis and natriuresis. Recently, combination therapy containing an ARB+ neprilysin inhibitor has shown improved benefit in tolerant HFrEF patients over ARB alone (McMurray, Packer et al. 2014). Furthermore, ATIR biased agonist peptides have also shown the ability to improve renal function in preclinical models of heart failure (Boerrigter, Soergel et al. 2012) and in humans (Soergel, Subach et al. 2013, Felker, Butler et al. 2015).

Despite their differences in mechanism, ACEi and ARBs continue to be mainstays of therapeutic intervention in heart failure patients (Yancy, Jessup et al. 2013). However, it is now appreciated that, in addition to the detrimental effects of AII action on the cardio-renal system, AII can also have some beneficial effects through activation of non-Gq signaling pathways, most notably $\beta$-arrestin. Indeed, peptidergic analogs of AII (e.g. SII) have been found to be biased agonists of AT1R. For example, the SII peptide has been found to bind AT1R and activate $\beta$-arrestin signaling but not Gq signaling (Rajagopal, Whalen et al. 2006, Kendall, Strungs et al. 2011). This peptide has been shown to stimulate cardiomyocyte contractility and prevent apoptosis (Rajagopal, Whalen et al. 2006). Biased agonist peptides to AT1 R, have also been shown to lower blood pressure and improve cardiac function in animal models of heart failure (Violin, DeWire et al. 2010, Kim, Abraham et al. 2012) and in human clinical trials (Soergel, Subach et al. 2013, Felker, Butler et al. 2015).

In addition to being recognized as key treatments for HFrEF, blockade of ATIR signaling has been used extensively in the clinic to treat hypertension. Hypertension is a recognized risk factor for microvascular and macrovascular diseases and there is significant literature supporting the beneficial effects of reducing blood pressure in improving these risks (Staessen, Li et al. 2005, Farsang 2011). AII blockade is a first line therapy for the treatment of clinical hypertension (James, Oparil et al. 2014) and has been shown to decrease the relative risk for both heart failure (Ong, Ong et al. 2013) and stroke (Ravenni, Jabre et al. 2011) in susceptible patients. Furthermore, chronic hypertension is a key determinant for HFpEF (Kitzman, Little et al. 2002, Owan and Redfield 2005). In addition to increasing blood pressure via activation of Gq signaling pathways in smooth muscle cells, AII also is a pro-inflammatory stimulus for the vascular endothelium through its regulation of key anti-inflammatory genes (Luft 2002, Dandona, Dhindsa et al. 2006). ARBs have been shown to inhibit the pro-inflammatory effects of AII in endothelial cells at least partially through blocking Gq-dependent negative regulation of endothelial nitric oxide synthase (eNOS) (Main 2005, Mason, Jacob et al. 2012). Interestingly, the impact of AT1R activation to affect endothelial function does not require AII but can also be impacted by mechanical forces imposed on the cell (Mederos y Schnitzler, Storch et al. 2011, Tang, Strachan et al. 2014). In one instance, the impact of mechanical force on AT1R has been shown to allosterically promote β-arrestin signaling by an AT1 R biased agonist (Tang, Strachan et al. 2014). Activation of AT1 R by mechanical stretch has also been noted in cardiomyocytes (Mederos y Schnitzler, Storch et al. 2011).

These data suggest that biased agonism (preferential activation of some signaling pathways (including β-arrestin) over the Gq signaling pathway) of the AT1R could have long term benefit in heart failure patients by altering AII signaling via AT1R in several cell types. Biasing of AT1R signaling could prove a significant improvement on ARBs that block all the signaling outputs of the AT1R. Unfortunately, peptide-based therapies have limitations in dosing that restrict their ability to be used as a chronic therapy and in less advanced heart failure. Therefore, development of safe and efficacious synthetic biased agonists or modulators of AT1R could significantly improve treatment of HFrEF and HFpEF patients through not only unloading the heart but also through activation of beneficial signaling pathways directly in cardiomyocytes. Similarly, anti-fibrotic activities combined with antihypertensive effects associated with AT1R biased agonism further suggests potential for this mechanism in treatment of HFpEF.

Recently, a series of peptidic compounds have been disclosed in WO10077339 demonstrating the possible therapeutic effects of preferentially agonizing β-Arrestin recruitment while minimizing Gq signaling at the AT1 receptor. These peptides have exhibited the potential for cardiovascular benefits in an acute clinical setting following intravenous administration (Soergel, Subach et al. 2013, Felker, Butler et al. 2015, Pang, Butler et al. 2017). However, study of an AT1R biased agonist peptide in acute decompensated heart failure patients using a 48-96 h infusion did not meet its composite primary end point (Pang, Butler et al. 2017). Interestingly, acute treatment of stable, chronic heart failure patients with an infusion of this biased agonist peptide did show significant improvement in left ventricular filling pressure and arterial pressure, especially those with elevated RAAS (Soergel, R. A. Subach et al. 2013). Furthermore, preclinical data in mouse models of heart failure using this peptide or close analogs have found that they have direct cardiac effects to improve cardiac function not seen with ARBs (Abraham, Davis et al. 2016). Taken together, these data suggest it is possible that this mechanism does not lend itself to acute/sub-acute treatment but perhaps is better suited as a chronic therapy alone or in combination with other heart failure medicines, such as ACEi. In light of this potential, the discovery of an orally bioavailable biased modulator of the AT1 receptor remains an important research goal.

In this application we describe the invention of a series of non-peptide, β-arrestin biased modulators of the AT1 receptor intended for the chronic treatment of cardiovascular disease. Though non-peptide agonists of the AT1 receptor have been previously described in U.S. Pat. No. 5,444,067 and in several academic publications (Perlman, Schambye et al. 1995, Perlman, Costa-Neto et al. 1997, Miura, Kiya et al. 2012), the agonist activity observed in these documents was correlated to an increased stimulus in phosphoinositide hydrolysis, which is a known biomarker for increased Gq signaling. Thus, when a representative agonist from these works was examined in vivo it was found to cause increased vascular resistance in a manner analogous to the native AII ligand (De Witt, Garrison et al. 2000). The desire for, or identification of, a non-peptide biased agonist preferentially agonizing the β-arrestin signaling pathway via AT1R is not contemplated in any of these documents. The present invention describes the identification of non-peptide small molecule AT1 R biased agonists that selectively agonize β-arresting signaling in preference to Gq signaling.

SUMMARY OF THE INVENTION

The present invention provides substituted biaryl compounds, and analogues thereof, which are useful as Angiotensin II biased agonists, or β-Arrestin agonists of the Angiotensin II Receptor, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of diseases or disorder associated with biased agonism of the Angiotensin II Receptor (defined as preferential activation of some AT1R-dependent signaling pathways (including β-arrestin) over AT1 R-dependent Gq signaling), such as heart failure with preserved ejection fraction (HFpEF), heart failure with reduced ejection fraction (HFrEF), and renal disease.

In addition to the effects as biased agonists of AT1R, as selective ligands to the AT1R, the compounds of the invention may be used in the treatment and/or prophylaxis of multiple diseases or disorders associated with the AT1R, such as heart failure, coronary artery disease, cardiomyopathy, fibrosis, atrial fibrillation, diabetes and related conditions including but not limited to acute coronary syndrome, myocardial ischemia, hypertension, atherosclerosis, pulmonary hypertension, peripheral arterial disease, coronary vasospasm, cerebral vasospasm, ischemia/reperfusion injury, angina, renal disease, obesity, metabolic syndrome and insulin resistance.

The compounds of the invention may be used in the treatment and/or prophylaxis of multiple diseases or disorders associated with AT1R-mediated recruitment of β-arrestin and/or other non-Gq mediated signaling, such as HFpEF, HFrEF, and renal disease.

The compounds of the invention may be used in therapy.

The compounds of the invention may be used for the manufacture of a medicament for the treatment and/or prophylaxis of multiple diseases or disorders associated with AT1R-mediated recruitment of β-arrestin and/or other non-Gq mediated signaling.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

In a first aspect, the present disclosure provides, inter alia, a compound of Formula (X):

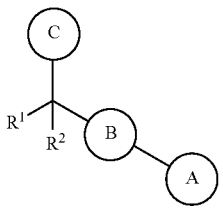

(X)

or a stereoisomer, an enantiomer, a diastereoisomer, a tautomer, a pharmaceutically acceptable salt, or a solvate thereof, wherein:
ring A is

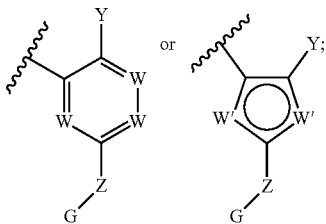

W is N, or $CR^{16}$;
W', at each occurrence, is independently selected from N, O, S and $CR^{16}$, wherein at least one W' is not $CR^{16}$, and at most only one W' is selected as O or S;
$R^1$ and $R^2$ are independently selected from H, $C_1$-$C_6$ alkyl, $C_1$-$C_6$ haloalkyl, $C_1$-$C_6$ hydroxyalkyl, $C_1$-$C_6$ alkoxyalkyl, and $C_3$-$C_6$ cycloalkyl;
alternatively, $R^1$ and $R^2$, together with the atom to which they are attached, join together to form a $C_3$-$C_6$ cycloalkyl, or a 4 to 6 membered heterocycle having 1-2 heteroatoms, the cycloalkyl or heterocycle is substituted with 0-4 F and 0-1 OH;
$R^{16}$, at each occurrence, is independently selected from H, F, Cl, Br, I, CN, OH, $N(R^a)_2$, $C_1$-$C_3$-alkyl, $C_1$-$C_3$-haloalkyl, $C_1$-$C_3$-alkoxy, $C_1$-$C_4$-hydroxyalkyl, $C_1$-$C_3$-haloalkoxy, $C_3$-$C_6$-cycloalkyl, and $C_3$-$C_6$-halocycloalkyl
$R^a$ is, at each occurrence, independently selected from H, $C_1$-$C_4$-alkyl, $C_1$-$C_4$-haloalkyl, $C_1$-$C_4$-hydroxyalkyl, and $C_3$-$C_6$-cycloalkyl;
or two $R^a$, along with the nitrogen atom to which they are attached, join to form a 5 to 6 membered heterocycle containing 0-2 additional heteroatoms selected from N, O and S;
Y is 5-tetrazolyl, $SO_3H$, $PO_2H$, $PO_3H_2$, COOR,

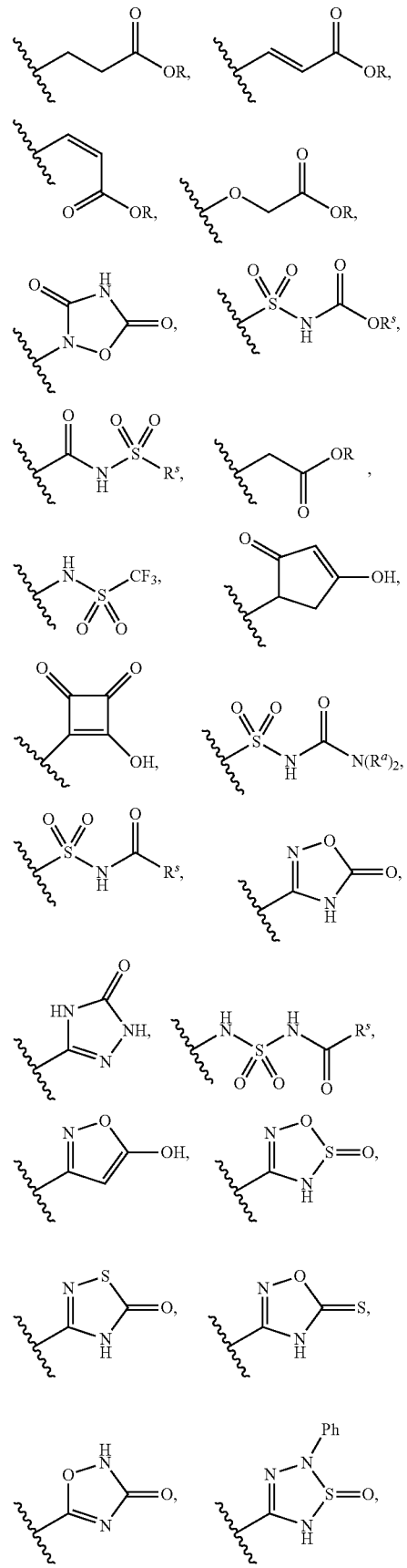

-continued

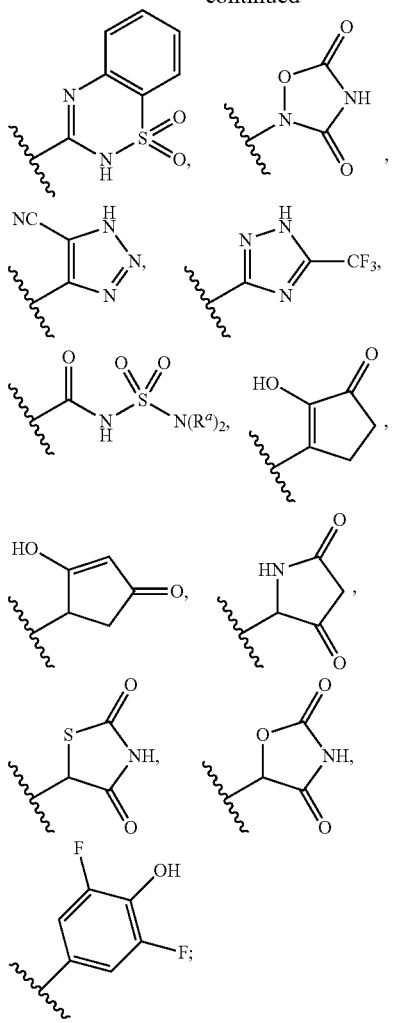

R, at each occurrence, is independently selected from H, $C_1$-$C_6$ alkyl, $C_1$-$C_6$-haloalkyl, $C_1$-$C_6$-hydroxyalkyl, $C_3$-$C_7$ cycloalkyl, $C_{6-10}$-aryl-$C_1$-$C_6$ alkyl, heterocycle-$C_1$-$C_6$ alkyl, wherein said heterocycle is a 4-10 membered group having 1-3 heteroatoms selected from N, O, or S, said aryl and heterocycle are each substituted with 0-3 groups chosen from $C_1$-$C_3$ alkyl, halo, OH, or $C_1$-$C_3$ fluoroalkyl;

$R^s$ at each occurrence, is independently selected from H, $C_1$-$C_6$ alkyl, $C_1$-$C_6$-haloalkyl, $C_1$-$C_6$-hydroxyalkyl, $C_3$-$C_7$ cycloalkyl, $C_3$-$C_7$ cycloalkyl $C_1$-$C_3$ alkyl, $C_{6-10}$ aryl, $C_{6-10}$-aryl-$C_1$-$C_6$-alkyl, heteroaryl, heteroaryl-$C_1$-$C_6$-alkyl, heterocyclyl, heterocycle-$C_1$-$C_6$-alkyl, wherein the heteroaryl is a 5-10 membered group and the heterocycle is a 4-10 membered each having 1-3 heteroatoms selected from N, O, or S Z, at each occurrence, is independently selected from a bond, O, S, $N(R^z)$, $C(R^z)_2$, C=O, C(=O)$N(R^z)$, $N(R^z)$C(=O), $C(R^z)_2C(R^z)_2$, $OC(R^z)_2$, $SC(R^z)_2$, $N(R^z)C(R^z)_2$, $C(RX)_2O$, $C(R^z)_2S$, $C(R^z)_2N(R)$;

$R^z$ is at each occurrence independently selected from H, $C_1$-$C_4$-alkyl, $C_1$-$C_6$-hydroxyalkyl, $C_1$-$C_6$-alkoxyalkyl, $C_1$-$C_4$-haloalkyl, $C_3$-$C_{10}$-cycloalkyl, 5-10-membered heterocycle-$C_1$-$C_6$-alkyl, 5-10-membered heterocycle, $C_3$-$C_{10}$-cycloalkyl-$C_1$-$C_6$-alkyl, 4 to 7 membered heterocyclyl having 1-2 heteroatoms selected from N, O, or S, or, alternatively, two $R^z$ groups either on the same atom or on adjacent atoms can join to form a $C_3$-$C_6$-cycloalkyl or a 4 to 7 membered heterocycle containing 1-2 heteroatoms selected from N, O and S;

G is selected from a 4 to 11 membered heterocycle having 1-4 atoms selected from N, O, and S, a $C_3$-$C_8$-cycloalkyl, $C_6$-$C_{10}$-aryl or a 5 to 10 membered heteroaryl having 1-4 atoms selected from N, O, and S; wherein the heterocycle, cycloalkyl, aryl and heteroaryl are substituted with 0-3 substituents independently selected from the group consisting of =O, F, Cl, Br, I, $C_1$-$C_6$-alkyl, $C_1$-$C_6$-alkoxy, $C_1$-$C_6$-haloalkyl, $C_1$-$C_6$-hydroxyalkyl, $C_3$-$C_8$ cycloalkyl, $C_3$-$C_8$ cycloalkenyl, $CH_2$-phenyl, OH, $OR^x$, $SR^x$, $N(R^x)_2$, $CO(R^x)$, $CON(R^x)_2$, $CO_2R^x$, $N(R^x)CO_2(R^x)$, $N(R^x)CO(R^x)$, $N(R^x)CON(R^x)_2$, $S(O)_2(R^x)$, $S(O)_2N(R^x)_2$, or $N(R^x)S(O)_2(R^x)$;

$R^x$ is H, $C_{1-6}$ alkyl, $C_{1-4}$ haloalkyl, $C_{1-4}$ hydroxyalkyl, phenyl, $CH_2$-phenyl; ring B is

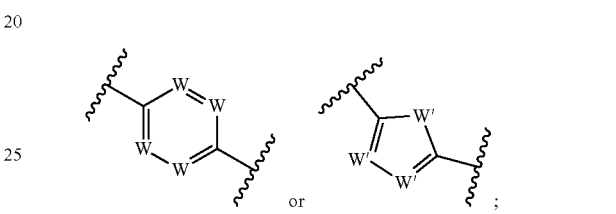

Group C is

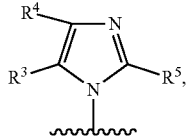
IA

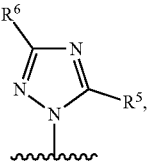
IB

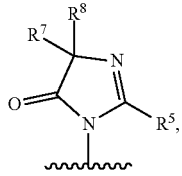
IC

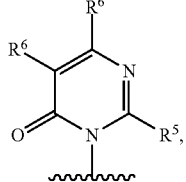
ID

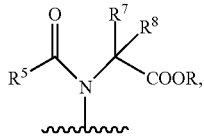
IG

-continued

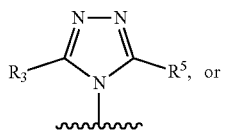
IH

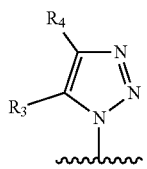
IJ

R³ is C₁₋₄ hydroxyalkyl, C₁₋₄ haloalkyl, C₁₋₆-hydroxycycloalkyl, C₁₋₆-halocycloalkyl, COOR, CON(R^z)₂, 5-6 membered heteroaryl or

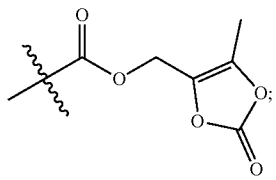 [SMILES: *C(=O)OCc1oc(=O)oc1C]

R⁴ is H, F, Cl, Br, CF₃, CN, N(R^z)₂, CON(R^z)₂, C₁₋₄ alkyl, C₁₋₄ haloalkyl C₁₋₄ alkoxyalkyl, C₁₋₄ hydroxyalkyl, C₃₋₆-cycloalkyl, C₃₋₆-halocycloalkyl, C₃₋₆-alkoxycycloalkyl, C₃-C₆-cycloalkyl-C₁-C₆-alkyl, or C₃₋₆-hydroxycycloalkyl;

R⁵ is C₁-C₆ alkyl, C₁₋₆ haloalkyl; C₁₋₆ alkoxyalkyl, C₃₋₆-cycloalkyl-C₀₋₄-alkyl which may be substituted with 1-3 halogens or a C₁₋₃-alkoxy group;

R⁶ is H, F, Cl, Br, CF₃, CN, N(R^z)₂, CON(R^z)₂, C₁₋₄-alkyl, C₁₋₄-haloalkyl, C₁₋₄-alkoxyalkyl, C₁₋₄ hydroxyalkyl, C₃₋₆-cycloalkyl, C₃₋₆-halocycloalkyl, C₁₋₆-alkoxy-C₃-C₆-cycloalkyl, or C₃₋₆-hydroxycycloalkyl; and R⁷ and R⁸, are independently selected from H, C₁-C₄-alkyl, C₁-C₄-hydroxyalkyl, C₁-C₄-haloalkyl, C₃-C₆-cycloalkyl or, alternatively, R⁷ and R⁸, along with the atom to which they are attached, can join to form a C₃-C₉ cycloalkyl, a C₃-C₉-halocycloalkyl, a C₃-C₉-hydroxycycloalkyl or a 4 to 7 membered heterocycle having 1-2 heteroatoms selected from N, O, or S each of said cycloalkyl and heterocycle being optionally substituted with 1-4 F, OH, C₁₋₄ alkyl, C₁₋₄ haloalkyl C₁₋₄ alkoxyalkyl, or C₁₋₄ hydroxyalkyl, and may be fused with a 6-membered aryl or 5-6 membered heteroaryl ring, provided the compounds of Formula (X) are not

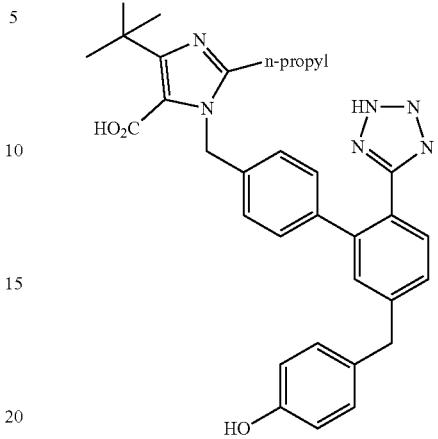

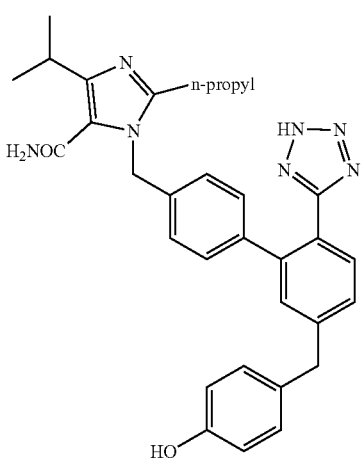

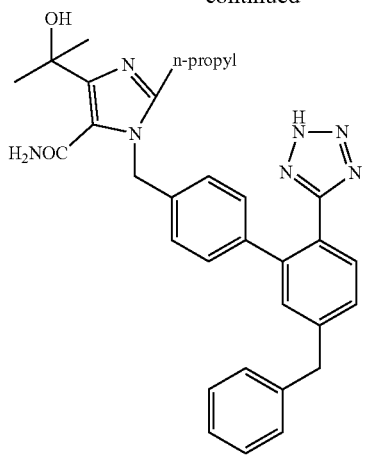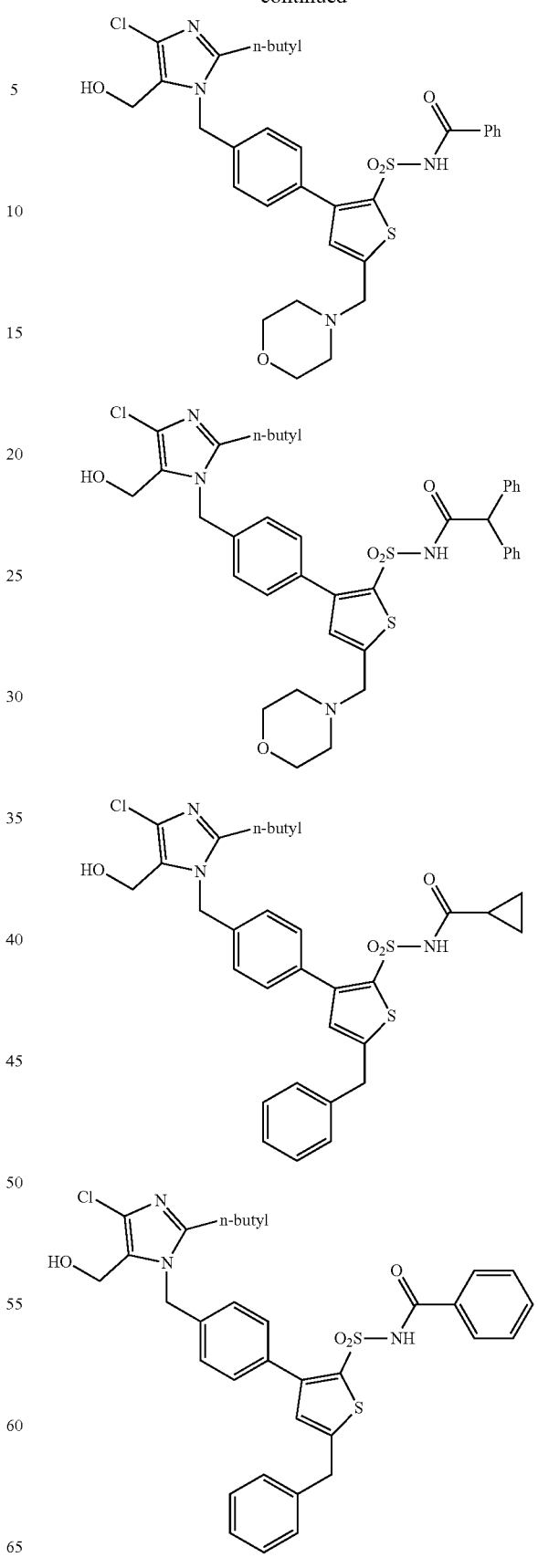

In another aspect, the present disclosure provides, inter alia, a compound of Formula (I):

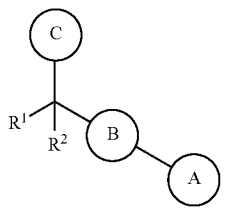
(I)

or a stereoisomer, an enantiomer, a diastereoisomer, a tautomer, a pharmaceutically acceptable salt, or a solvate thereof, wherein:
ring A is

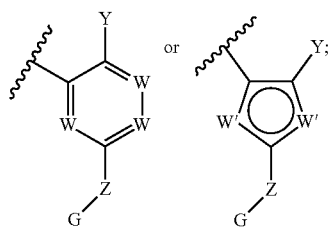

W is N, or $CR^{16}$
W', at each occurrence, is independently selected from N, O, S and $CR^{16}$, wherein at least one W' is not $CR'^6$, and at most only one W' is selected as O or S;
$R^1$ and $R^2$ are independently selected from H, $C_1$-$C_6$ alkyl, $C_1$-$C_6$ haloalkyl, $C_1$-$C_6$ hydroxyalkyl, $C_1$-$C_6$ alkoxyalkyl, and $C_3$-$C_6$ cycloalkyl;
alternatively, $R^1$ and $R^2$, together with the atom to which they are attached, join together to form a $C_3$-$C_6$ cycloalkyl, or a 4 to 6 membered heterocycle having 1-2 heteroatoms, the cycloalkyl or heterocycle is substituted with 0-4 F and 0-1 OH;
$R^{16}$, at each occurrence, is independently selected from H, F, Cl, Br, I, CN, OH, $N(R^a)_2$, $C_1$-$C_3$-alkyl, $C_1$-$C_3$-haloalkyl, $C_1$-$C_3$-alkoxy, $C_1$-$C_4$-hydroxyalkyl, $C_1$-$C_3$-haloalkoxy, $C_3$-$C_6$-cycloalkyl, and $C_3$-$C_6$-halocycloalkyl
$R^a$ is, at each occurrence, independently selected from H, $C_1$-$C_4$-alkyl, $C_1$-$C_4$-haloalkyl, $C_1$-$C_4$-hydroxyalkyl, and $C_3$-$C_6$-cycloalkyl;
or two $R^a$, along with the nitrogen atom to which they are attached, join to form a 5 to 6 membered heterocycle containing 0-2 additional heteroatoms selected from N, O and S;
Y is 5-tetrazolyl, $SO_3H$, $PO_2H$, $PO_3H_2$, COOR,

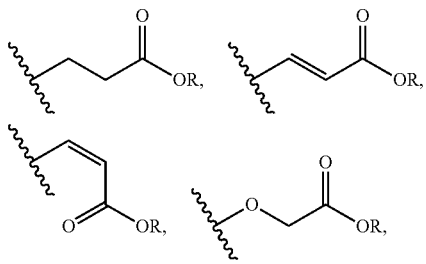

-continued

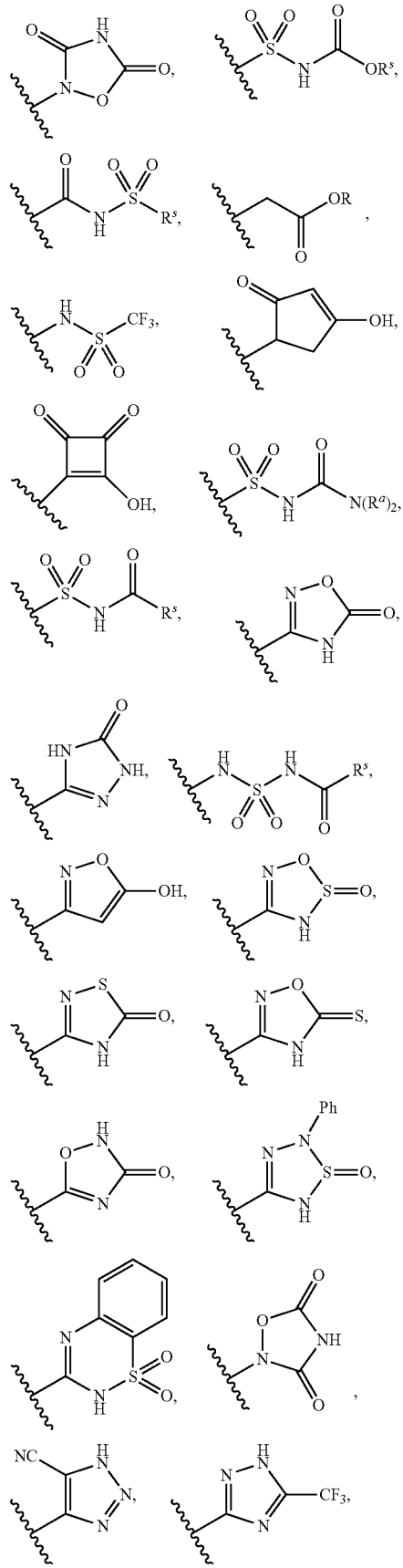

-continued

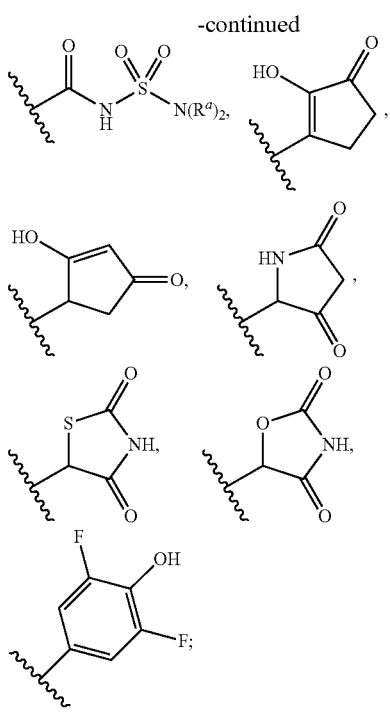

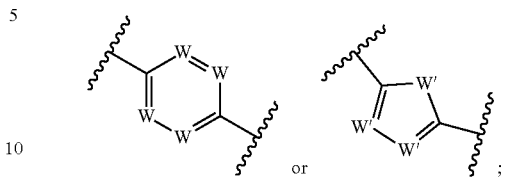

Group C is

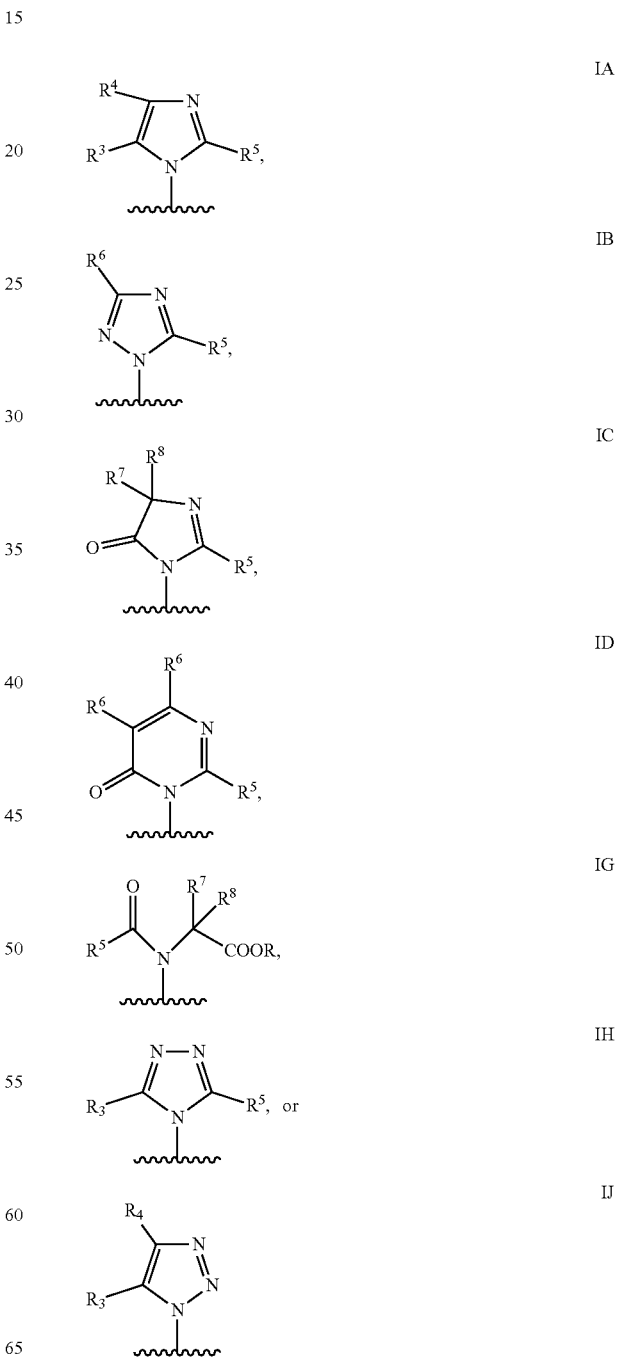

R, at each occurrence, is independently selected from H, $C_1$-$C_6$ alkyl, $C_1$-$C_6$-haloalkyl, $C_1$-$C_6$-hydroxyalkyl, $C_3$-$C_7$ cycloalkyl, $C_{6-10}$-aryl-$C_1$-$C_6$ alkyl, heterocycle-$C_1$-$C_6$ alkyl, wherein said heterocycle is a 4-10 membered group having 1-3 heteroatoms selected from N, O, or S, said aryl and heterocycle are each substituted with 0-3 groups chosen from $C_1$-$C_3$ alkyl, halo, OH, or $C_1$-$C_3$ fluoroalkyl;

$R^s$ at each occurrence, is independently selected from H, $C_1$-$C_6$ alkyl, $C_1$-$C_6$-haloalkyl, $C_1$-$C_6$-hydroxyalkyl, $C_3$-$C_7$ cycloalkyl, $C_3$-$C_7$ cycloalkyl $C_1$-$C_3$ alkyl, $C_6$-$C_{10}$ aryl, $C_{6-10}$-aryl-$C_1$-$C_6$-alkyl, heteroaryl, heteroaryl-$C_1$-$C_6$-alkyl, heterocyclyl, heterocycle-$C_1$-$C_6$-alkyl, wherein the heteroaryl is a 5-10 membered group and the heterocycle is a 4-10 membered each having 1-3 heteroatoms selected from N, O, or S;

Z, at each occurrence, is independently selected from a bond, O, S, $N(R^z)$, $C(R^z)_2$, C=O, C(=O)N($R^z$), N(R)C(=O), $C(R^z)_2C(R^x)_2$, $OC(R^z)_2$, $SC(R^z)_2$, $N(R^z)C(R^z)_2$, $C(R^z)_2O$, $C(R^z)_2S$, $C(R^z)_2N(R^z)$;

$R^z$ is at each occurrence independently selected from H, $C_1$-$C_4$-alkyl, $C_1$-$C_4$-hydroxyalkyl, $C_1$-$C_4$-haloalkyl, $C_3$-$C_6$-cycloalkyl or, alternatively, two $R^z$ groups either on the same atom or on adjacent atoms can join to form a $C_3$-$C_6$-cycloalkyl or a 4 to 7 membered heterocycle containing 1-2 heteroatoms selected from N, O and S;

G is selected from a 4 to 11 membered heterocycle having 1-4 atoms selected from N, O, and S, a $C_3$-$C_5$-cycloalkyl, $C_6$-$C_{10}$-aryl or a 5 to 10 membered heteroaryl having 1-4 atoms selected from N, O, and S; wherein the heterocycle, cycloalkyl, aryl and heteroaryl are substituted with 0-3 substituents independently selected from the group consisting of =O, F, Cl, Br, I, $C_1$-$C_6$-alkyl, $C_1$-$C_6$-alkoxy, $C_1$-$C_6$-haloalkyl, $C_1$-$C_6$-hydroxyalkyl, OH, $OR^x$, $SR^x$, $N(R^x)_2$, $CO(R^x)$, $CON(R)_2$, $CO_2R^x$, $N(R^x)CO_2(R^x)$, $N(R^x)CO(R^x)$, $N(R^x)CON(R)_2$, $S(O)_2(R^x)$, $S(O)_2N(R^x)_2$, or $N(R^x)S(O)_2(R^x)$;

$R^x$ is H, $C_{1-6}$ alkyl, $C_{1-4}$ haloalkyl, $C_{1-4}$ hydroxyalkyl, phenyl, $CH_2$-phenyl; ring B is R³ is C₁₋₄ hydroxyalkyl, C₁₋₄ haloalkyl, C₁₋₆-hydroxycycloalkyl, C₁₋₆-halocycloalkyl, COOR, CON(Rᶻ)₂, or

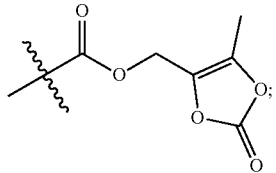 [SMILES: *C(=O)OCc1oc(=O)oc1C]

R⁴ is H, F, Cl, Br, CF₃, CN, N(Rᶻ)₂, CON(Rᶻ)₂,C₁₋₄ alkyl, C₁₋₄ haloalkyl C₁₋₄ alkoxyalkyl, C₁₋₄ hydroxyalkyl, C₁₋₆-cycloalkyl, C₁₋₆-halocycloalkyl, C₁₋₆-alkoxycycloalkyl, or C₁₋₆-hydroxycycloalkyl;
R⁵ is C₁₋₆ alkyl, C₁₋₆ haloalkyl; C₁₋₆ alkoxyalkyl, C₁₋₆-cycloalkyl-C₀₋₄-alkyl which may be substituted with 1-3 halogens or a C₁-C₃-alkoxy group; R⁶ is H, F, Cl, Br, CF₃, CN, N(Rᶻ)₂, CON(Rᶻ)₂, C₁₋₄-alkyl, C₁₋₄-haloalkyl, C₁₋₄-alkoxyalkyl, C₁₋₄ hydroxyalkyl, C₁₋₆-cycloalkyl, C₁-halocycloalkyl, C₁₋₆-alkoxycycloalkyl, or C₁-C₆-hydroxycycloalkyl; and
R⁷ and R⁸, are independently selected from H, C₁-C₄-alkyl, C₁-C₄-hydroxyalkyl, C₁-C₄-haloalkyl, C₃-C₆-cycloalkyl or, alternatively, R⁷ and R⁸, along with the atom to which they are attached, can join to form a C₃-C₆-cycloalkyl, a C₃-C₆-halocycloalkyl, a C₃-C₆-hydroxycycloalkyl or a 4 to 7 membered heterocycle having 1-2 heteroatoms selected from N, O, or S and the potential for further substitution with 1-4 F, OH, C₁₋₄-alkyl, C₁₋₄-haloalkyl C₁₋₄-alkoxyalkyl, C₁₋₄-hydroxyalkyl,
provided the compounds of Formula (I) are not

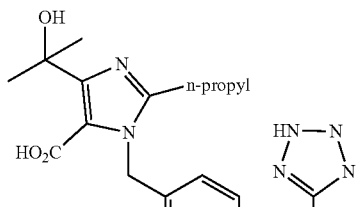

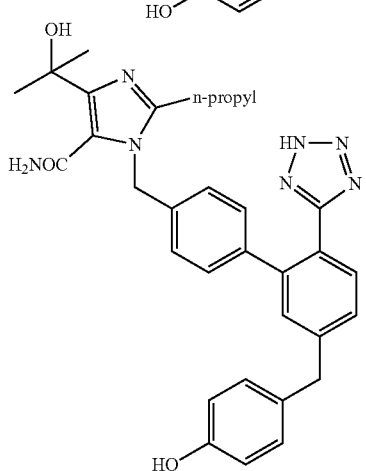

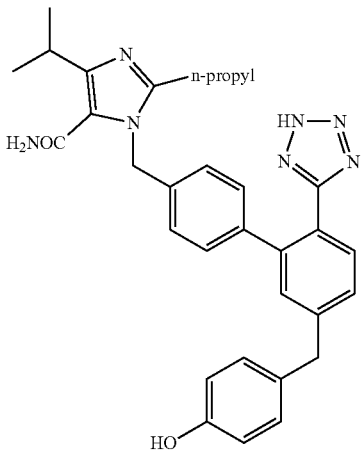

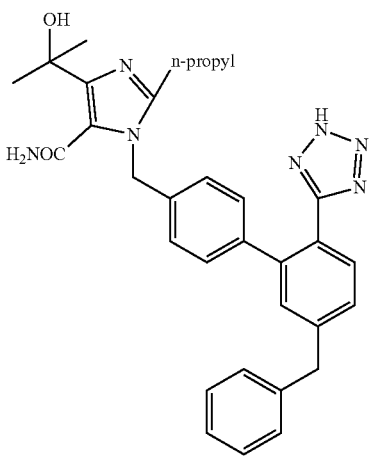

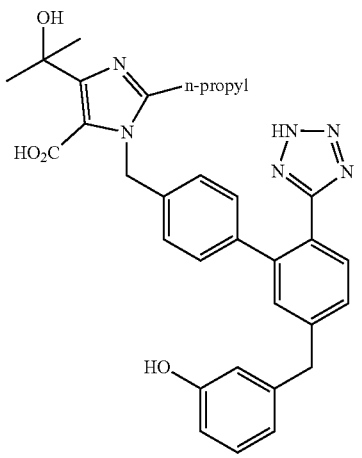

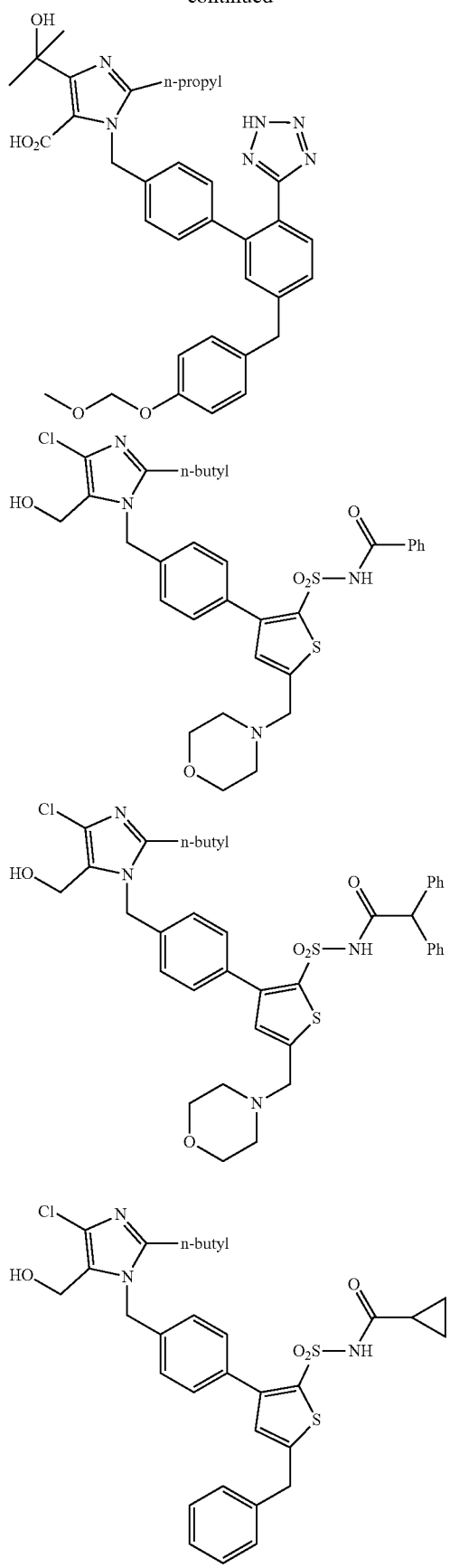

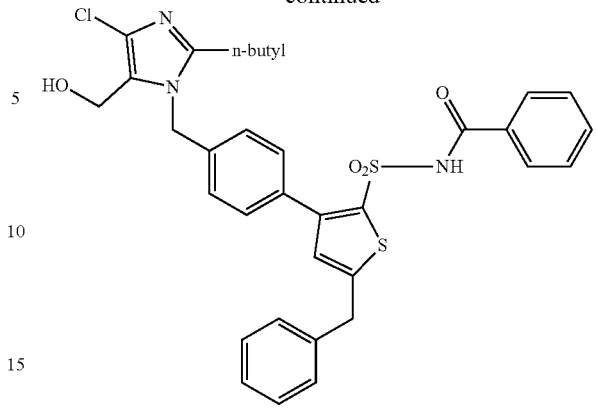

In the various aspects described hereinafter below, the various embodiments are equally applicable to Formula (1) or Formula (X), even if they state only one of Formula (1) and Formula (X).

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: Group C is

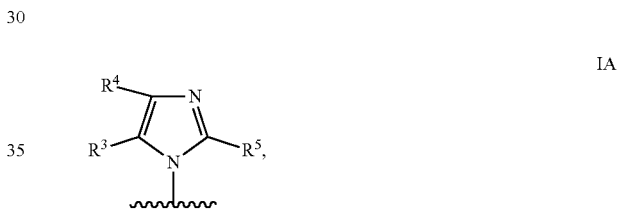

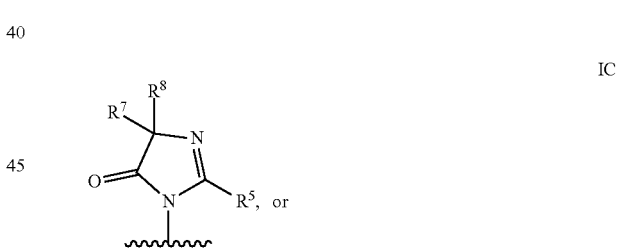

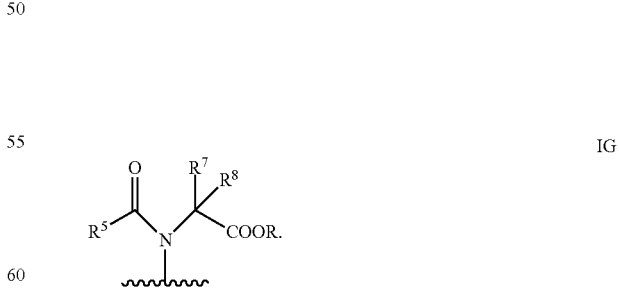

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^1$ and $R^2$ are H;
$R^3$ is H, $C_{1-2}$ hydroxyalkyl, $CO_2H$, $CO_2$—$C_{1-6}$-alkyl, $CONH_2$, $CONH(C_{1-6}$-alkyl), $CON(C_{1-6}$-alkyl$)_2$, or

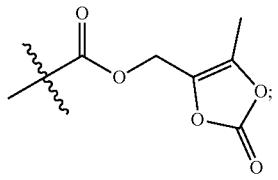 [SMILES: *C(=O)OCc1oc(=O)oc1C]

$R^4$ is H, F, Cl, Br, $CF_3$, CN, $C_{1-3}$ alkyl, $C_{1-3}$ haloalkyl, or $C_{1-2}$ hydroxyalkyl;
$R^5$ is $C_{1-6}$ alkyl, $C_{3-6}$ cycloalkyl or $O(C_{1-6}$ alkyl);
$R^6$ is hydrogen, or $C_{1-4}$ alkyl;
$R^7$ and $R^8$ are H, $C_{1-4}$ alkyl, $C_{1-4}$ haloalkyl, or $C_{1-3}$ hydroxyalkyl alternatively, $R^7$ and $R^8$, along with the atom to which they are attached, join to form a $C_3$-$C_6$-cycloalkyl or a $C_4$-$C_7$-heterocycle; and

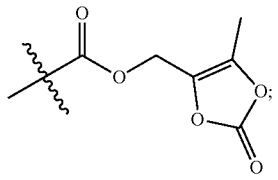 [SMILES: *C(=O)OCc1oc(=O)oc1C]

R is H, $C_{1-6}$ alkyl, $C_{1-6}$ hydroxyalkyl, or 0;

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: Group C is

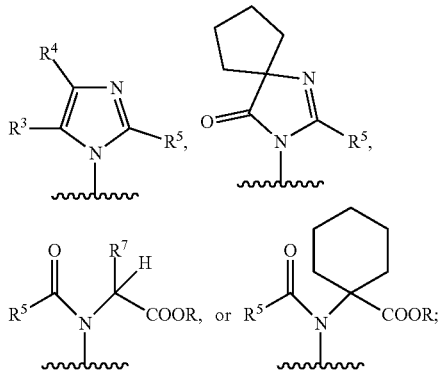

$R^1$ and $R^2$ are H;
$R^3$ is hydroxyalkyl, $CO_2H$, or

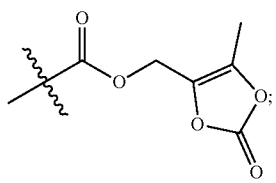 [SMILES: *C(=O)OCc1oc(=O)oc1C]

$R^4$ is $C_{1-3}$ alkyl, $C_{1-3}$ haloalkyl, or $C_{1-3}$ hydroxyalkyl; and
$R^5$ is ethyl, n-propyl, or n-butyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:
G is selected from a 5 to 10 membered heterocycle having 1-3 atoms selected from N, O, and S, phenyl or a $C_6$-$C_{10}$-heteroaryl having 1-3 atoms selected from N, O, and S; wherein the heterocycle, phenyl and heteroaryl are substituted with 0-3 substituents independently selected from the group consisting of =O, Cl, Br, I, F, $C_1$-$C_6$-alkyl, $C_1$-$C_6$-alkoxy, $C_1$-$C_6$-haloalkyl, $C_1$-$C_6$-alkylthio, $C_1$-$C_6$-hydroxyalkyl, OH, $OR^x$, $N(R^x)_2$, $CO(R^x)$, $CON(R^x)_2$, $CO_2R^x$, $N(R^x)CO_2(R^x)$, $N(R^x)CO(R^x)$, $N(R^x)CON(R^x)_2$, $S(O)_2(R^x)$, $S(O)_2 R^x$, $S(O)_2N(R)_2$, $N(R^x)S(O)_2(R^x)$, or $N(R^x)S(O)_2R^x$;
$R^x$ is H, $C_{1-6}$ alkyl, $CF_3$, phenyl, $CH_2$-phenyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: Ring B is

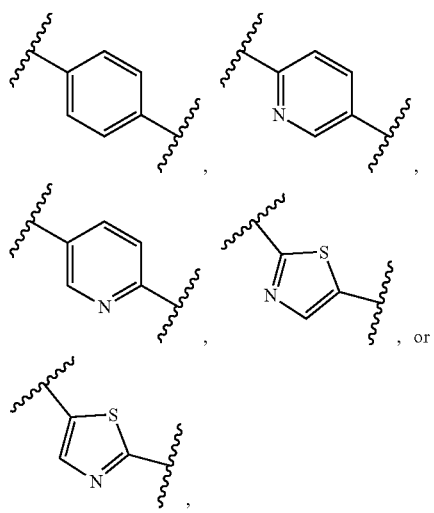

any of which are optionally substituted with 0-2 F, Y is COOH, COOMe, COOEt,

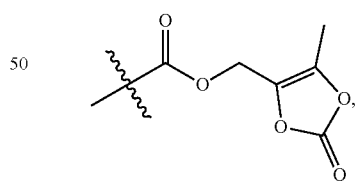

5-tetrazolyl, $SO_3H$,

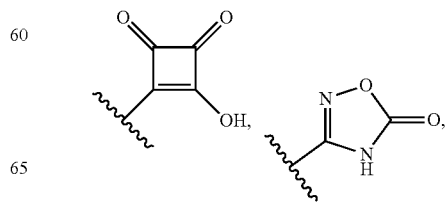

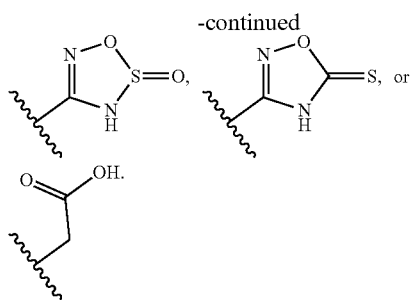

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: wherein Y is COOH, 5-tetrazolyl, SO₃H,

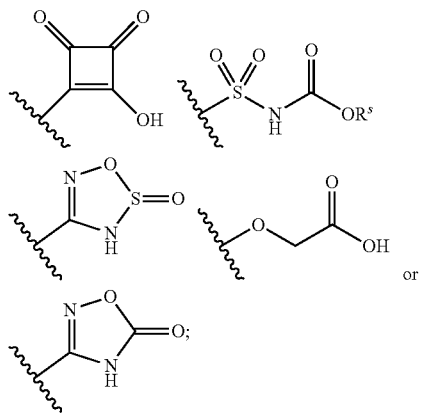

$R^s$ is $C_{1-6}$ alkyl, $C_{6-10}$-aryl-$C_1$-$C_6$-alkyl, or (CH₂Ph).

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: Ring A is

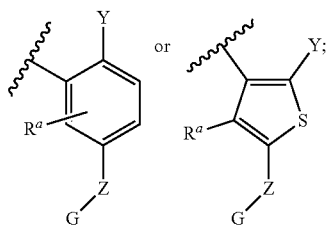

and
$R^a$ is H or F.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:
G is selected from a phenyl, thiophenyl, quinolinyl, isoquinolinyl, indolyl, pyrazolyl, pyrrolyl, pyridinyl, isoindolinyl, pyrrolidinyl; any of which are substituted with 0-3 substituents independently selected from the group consisting of =O, Cl, Br, I, F, $C_1$-$C_6$-alkyl, $C_1$-$C_6$-haloalkyl, $C_1$-$C_6$-hydroxyalkyl, OH, $OR^x$, $N(R^x)_2$, $CO(R^x)$, CON$(R^x)_2$, $CO_2R^x$, $N(R^x)CO_2(R^x)$, $N(R^x)CO(R^x)$, $N(R^x)CON(R)_2$, $S(O)_2(R^x)$, $S(O)_2N(R^x)_2$, or $N(R^x)S(O)_2R^x$; and
$R^x$ is H, $C_{1-3}$ alkyl, $CF_3$, phenyl, $CH_2$-phenyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: Y is COOH, 5-tetrazolyl,

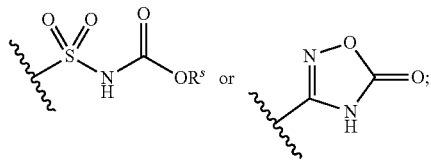

$R^s$ is $C_{1-6}$ alkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: Ring B is

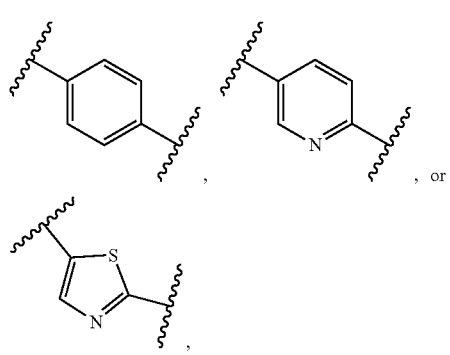

any of which are substituted with 0-2 F.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: Ring B is

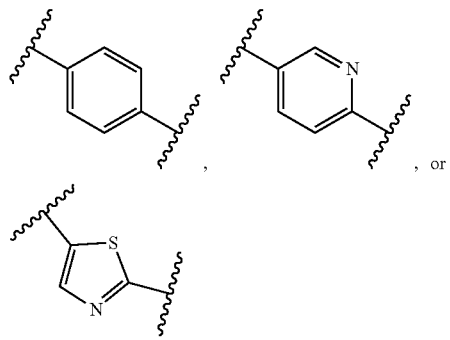

any of which are substituted with 0-2 F;

Ring A is

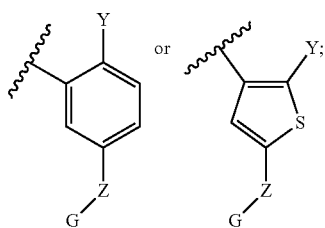

Z is a bond or NR$^a$;
G is isoindolinyl-1,3-dione, pyrrolidine-2,5-dione, phenyl, thiazolyl, pyridinyl, pyrrolyl, pyrazolyl, quinolinyl, isoquinolinyl, any of which may be substituted with 0-3 substituents selected from =O, $C_{1-4}$ alkyl, -O-R$^x$, $C_{1-4}$ haloalkyl, —C(O)NR$^x$, -N(R$^x$)$_2$, and F;
R$^5$ is $C_{3-4}$ alkyl;
R$^6$ is $C_{3-4}$ alkyl;
R$^a$ is hydrogen, $C_{1-4}$-alkyl, and $C_{1-2}$-haloalkyl; and
Y is tetrazolyl, COOH, 1,2,4-oxadiazol-5(4H)-one, or —SO$_2$NHCOO-nbutyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: ring A is

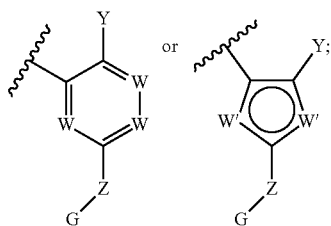

W is N, or CR$^{16}$;
W', at each occurrence, is independently selected from N, O, S and CR$^{16}$ where at least one W' is not CR$^{16}$, and at most only one W' is selected as O or S;
R$^1$ and R$^2$ are independently selected from H, $C_1$-$C_6$ alkyl, $C_1$-$C_6$ haloalkyl, $C_1$-$C_6$ hydroxyalkyl, $C_1$-$C_6$ alkoxyalkyl, and $C_3$-$C_6$ cycloalkyl;
alternatively, R$^1$ and R$^2$, together with the atom to which they are attached, join together to form a $C_3$-$C_6$ cycloalkyl, or a 4- to 6-membered heterocycle having 1-2 heteroatoms, the cycloalkyl or heterocycle is substituted with 0-4 F and 0-1 OH;
R$^{16}$, at each occurrence, is independently selected from H, F, Cl, Br, I, CN, OH, N(R$^a$)$_2$, $C_1$-$C_3$-alkyl, $C_1$-$C_3$-haloalkyl, $C_1$-$C_3$-alkoxy, $C_1$-$C_4$-hydroxyalkyl, $C_1$-$C_3$-haloalkoxy, $C_3$-$C_6$-cycloalkyl, and $C_3$-$C_6$-halocycloalkyl;
R$^a$ is, at each occurrence, independently selected from H, $C_1$-$C_4$-alkyl, $C_1$-$C_4$-haloalkyl, $C_1$-$C_4$-hydroxyalkyl, and $C_3$-$C_6$-cycloalkyl;
or two R$^a$, along with the nitrogen atom to which they are attached, join to form a 5 to 6 membered heterocycle containing 0-2 additional heteroatoms selected from N, O and S;
Y is 5-tetrazolyl, SO$_3$H, PO$_2$H, PO$_3$H$_2$, COOR,

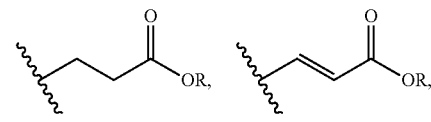

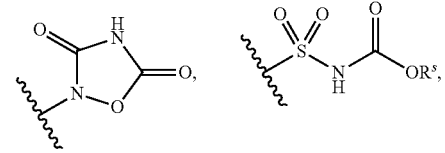

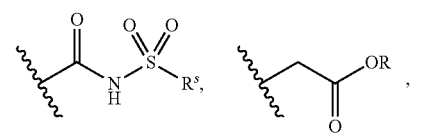

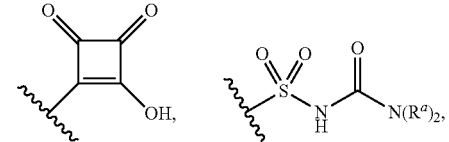

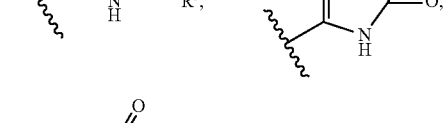

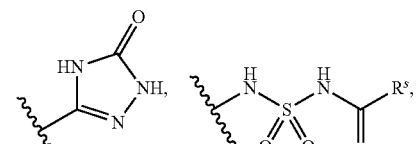

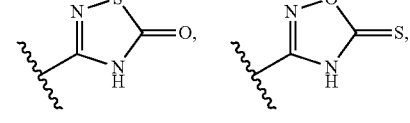

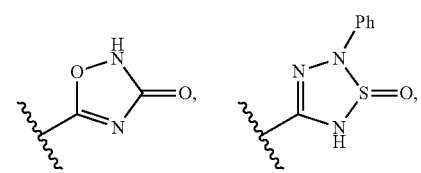

-continued

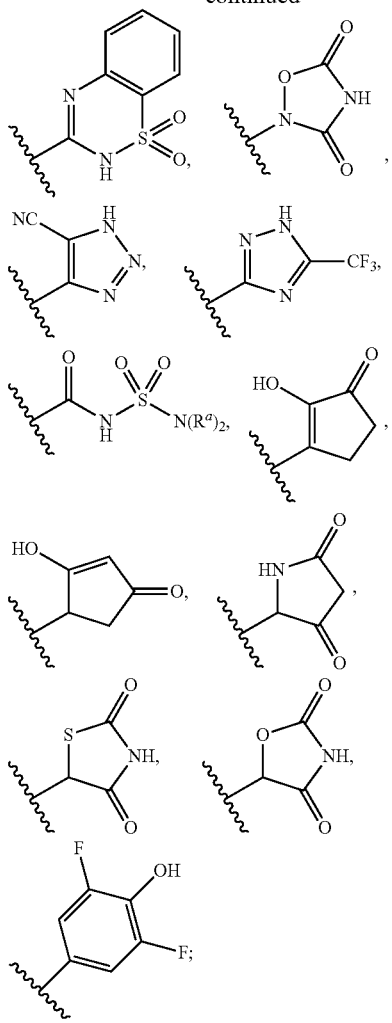

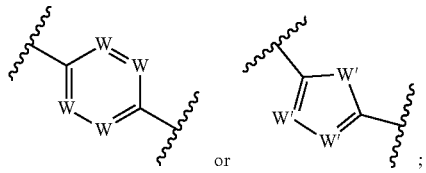

Group C is

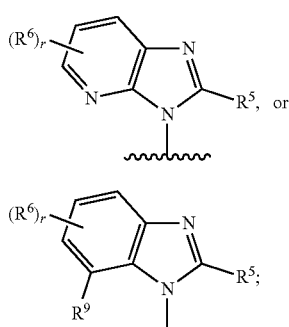

R, at each occurrence, is independently selected from H, $C_1$-$C_6$ alkyl, $C_1$-$C_6$-haloalkyl, $C_1$-$C_6$-hydroxyalkyl, $C_3$-$C_7$ cycloalkyl, $C_{6-10}$-aryl-$C_1$-$C_6$ alkyl, heterocycle-$C_1$-$C_6$ alkyl, wherein said heterocycle is a 4-10 membered group having 1-3 heteroatoms selected from N, O, or S, said aryl and heterocycle are each substituted with 0-3 groups chosen from $C_1$-$C_3$ alkyl, halo, OH, or $C_1$-$C_3$ fluoroalkyl;

$R^s$ at each occurrence, is independently selected from H, $C_1$-$C_6$ alkyl, $C_1$-$C_6$-haloalkyl, $C_1$-$C_6$-hydroxyalkyl, $C_3$-$C_7$ cycloalkyl, $C_3$-$C_7$ cycloalkyl-$C_1$-$C_3$ alkyl, $C_{6-10}$ aryl, $C_{6-10}$-aryl-$C_1$-$C_6$-alkyl, heteroaryl, heteroaryl-$C_1$-$C_6$-alkyl, heterocyclyl, heterocycle-$C_1$-$C_6$-alkyl, wherein the heteroaryl and heterocycle are each a 4-10 membered group having 1-3 heteroatoms selected from N, O, or S;

Z, at each occurrence, is independently selected from a bond, O, S, N($R^z$), C($R^z$)$_2$, C=O, C(=O)N($R^z$), N($R^z$)C(=O), C($R^x$)$_2$C($R^z$)$_2$, OC($R^x$)$_2$, SC(R$_2$), N($R^x$)C($R^z$)$_2$, C($R^x$)$_2$O, C($R^x$)$_2$S, C($R^z$)$_2$N($R^x$);

$R^z$ is at each occurrence independently selected from H, $C_1$-$C_4$-alkyl, $C_1$-$C_4$-hydroxyalkyl, $C_1$-$C_4$-haloalkyl, $C_3$-$C_6$-cycloalkyl or, alternatively, two $R^z$ groups either on the same atom or on adjacent atoms can join to form a $C_3$-$C_6$-cycloalkyl or a 4 to 7 membered heterocycle containing 1-2 heteroatoms selected from N, O and S;

G is selected from a 4 to 11 membered heterocycle having 1-4 atoms selected from N, O, and S, a $C_3$-$C_8$-cycloalkyl, $C_6$-$C_{10}$-aryl or a 5 to 10 membered heteroaryl having 1-4 atoms selected from N, O, and S; wherein the heterocycle, cycloalkyl, aryl and heteroaryl are substituted with 0-3 substituents independently selected from the group consisting of =O, F, Cl, Br, I, $C_1$-$C_6$-alkyl, $C_1$-$C_6$-alkoxy, $C_1$-$C_6$-haloalkyl, $C_1$-$C_6$-hydroxyalkyl, OH, $OR^x$, $SR^x$, $N(R^x)_2$, $CO(R^x)$, $CON(R^x)_2$, $CO_2R^x$, $N(R^x)CO_2(R^x)$, $N(R^x)CO(R^x)$, $N(R^x)CON(R^x)_2$, $S(O)_2(R^x)$, $S(O)_2N(R^x)_2$, or $N(R^x)S(O)_2(R^x)$;

$R^x$ is H, $C_{1-6}$ alkyl, $C_{1-4}$ haloalkyl, $C_{1-4}$hydroxyalkyl, phenyl, $CH_2$-phenyl; ring B is

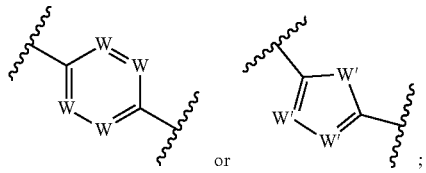

Group C is

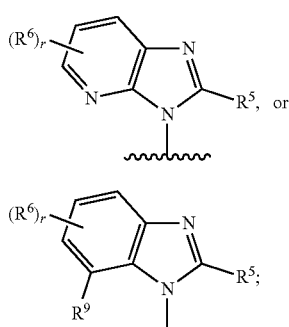

$R^5$ is $C_{1-6}$ alkyl, $C_{1-6}$ haloalkyl $C_{1-6}$ alkoxyalkyl, $C_{3-6}$-cycloalkyl$C_{0-4}$-alkyl which may be substituted with 1-3 halogens or a $C_{1-3}$-alkoxy group;

$R^6$ is H, F, Cl, Br, $CF_3$, CN, $N(R^z)_2$, $CON(R^z)_2$, $C_{1-4}$ alkyl, $C_{1-4}$ haloalkyl $C_{1-4}$ alkoxyalkyl, $C_{1-4}$ hydroxyalkyl, $C_{3-6}$-cycloalkyl, $C_{3-6}$-halocycloalkyl, $C_{1-6}$-alkoxy-$C_3$-$C_6$-cycloalkyl, or $C_1$-$C_6$-hydroxycycloalkyl;

$R^9$ is COOR, $CON(R^z)_2$; and r is 0 to 3;

provided that the compounds of Formula (I) are not

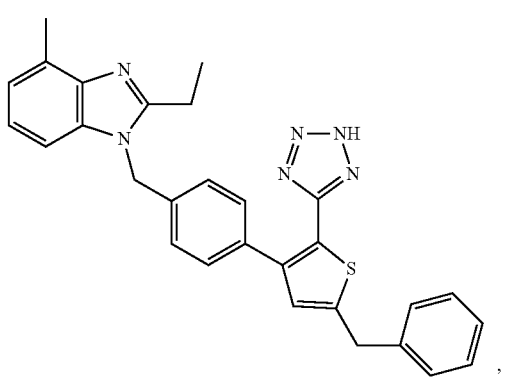

29
-continued
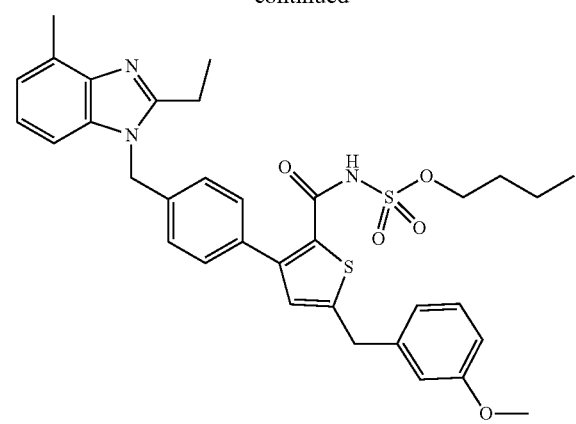
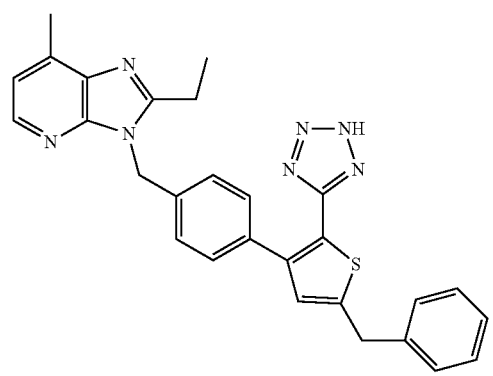
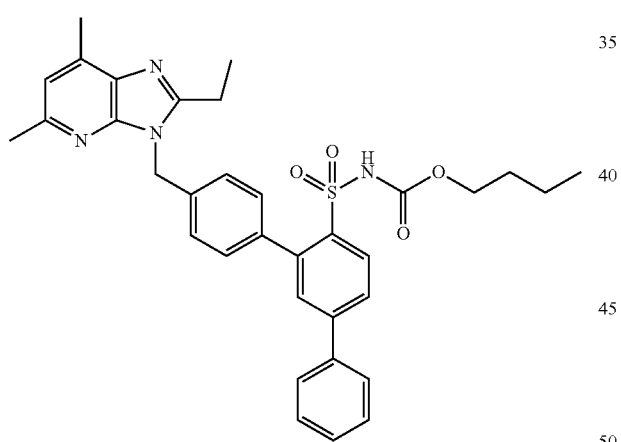
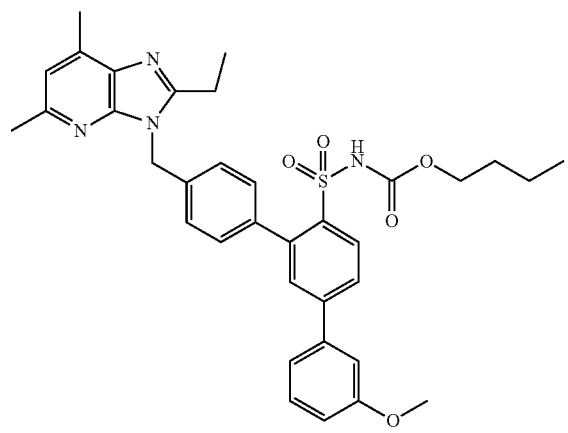
30
-continued
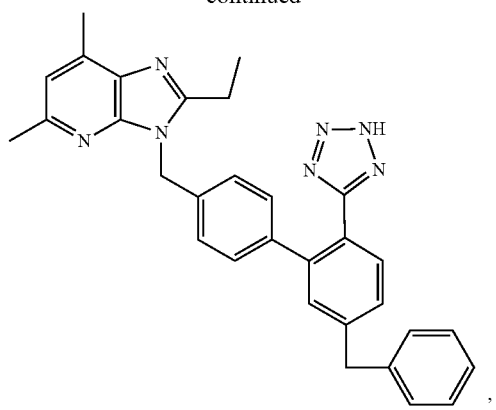
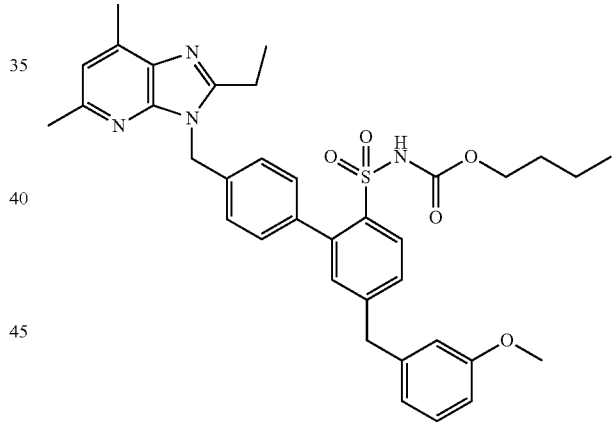
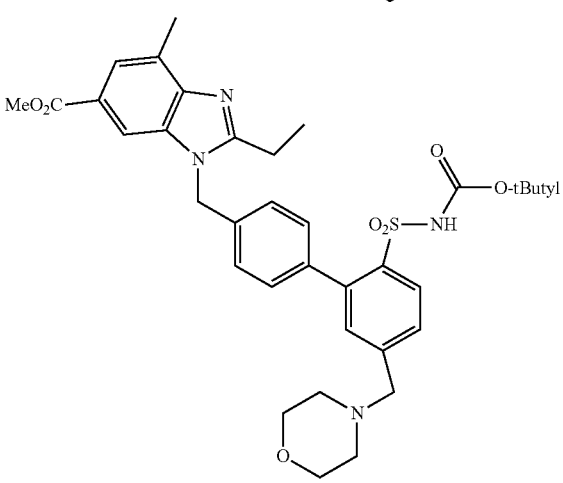

31
-continued
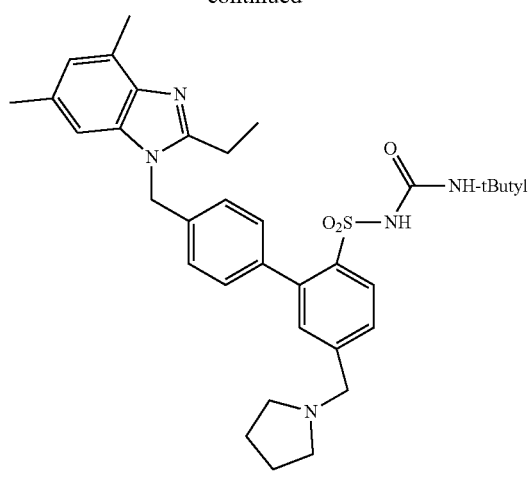
32
-continued
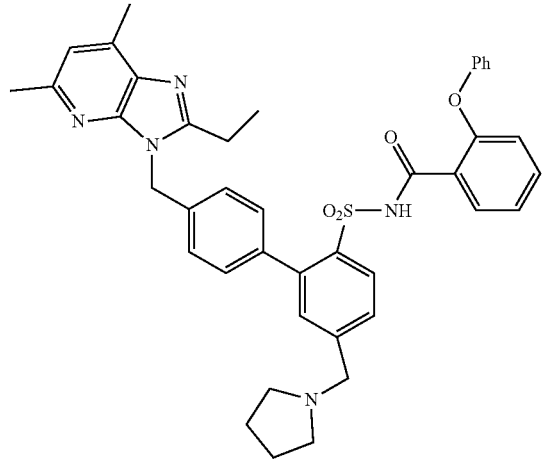
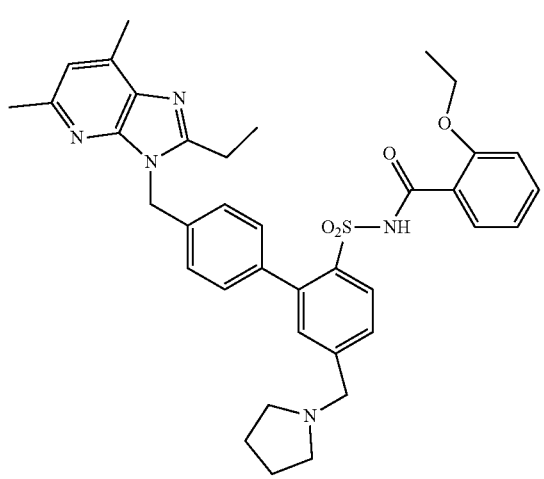
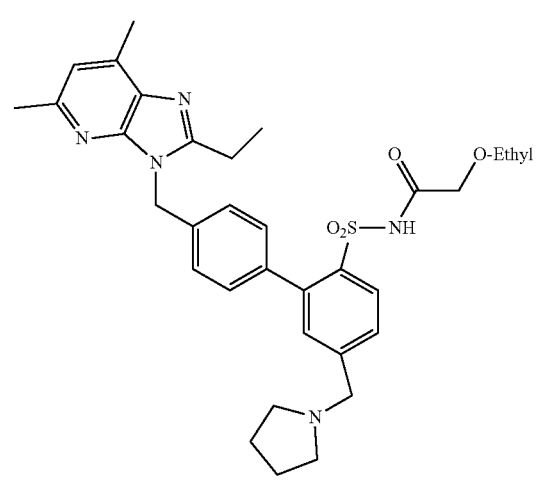
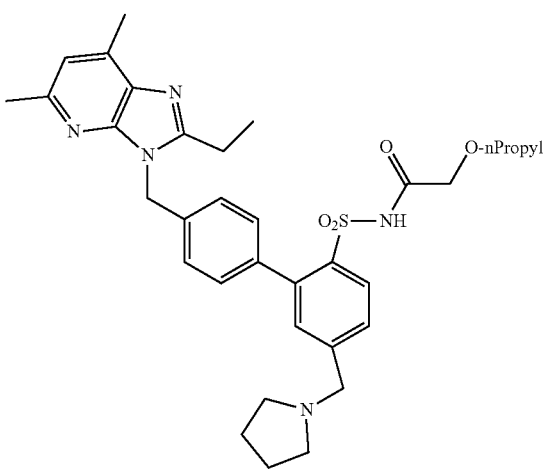
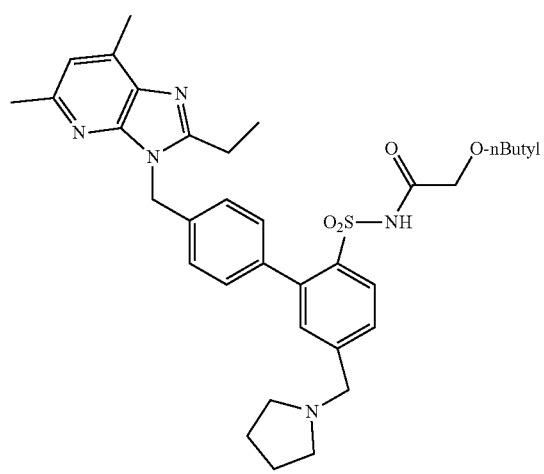

33
-continued
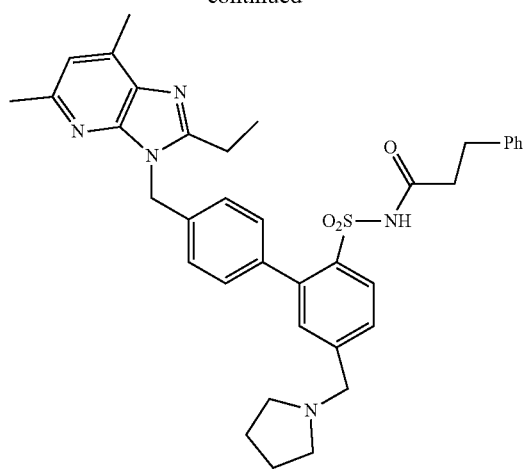
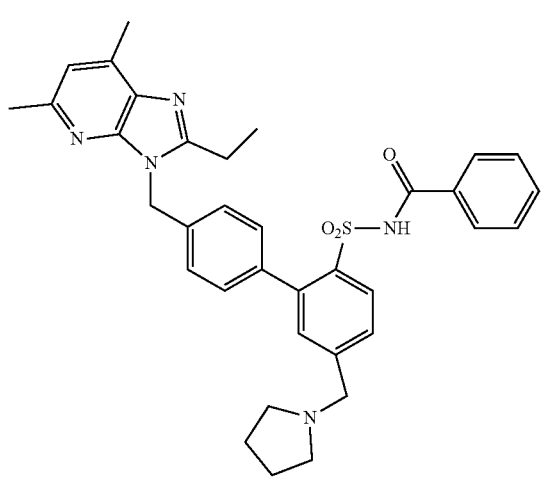
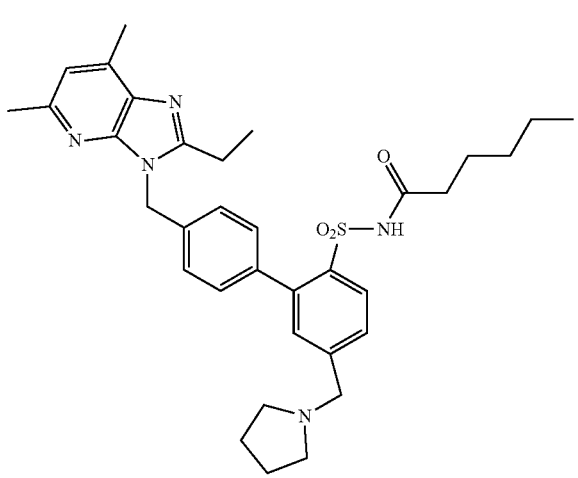
34
-continued
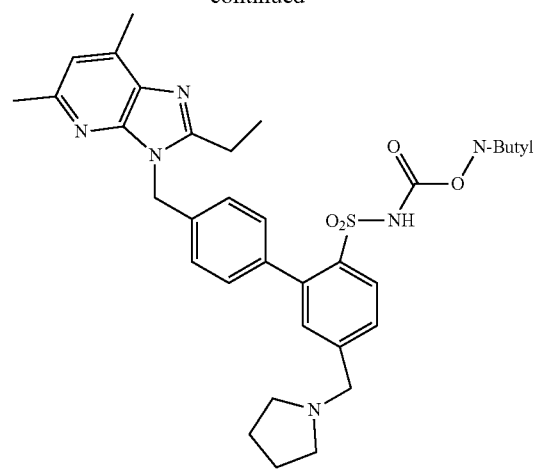
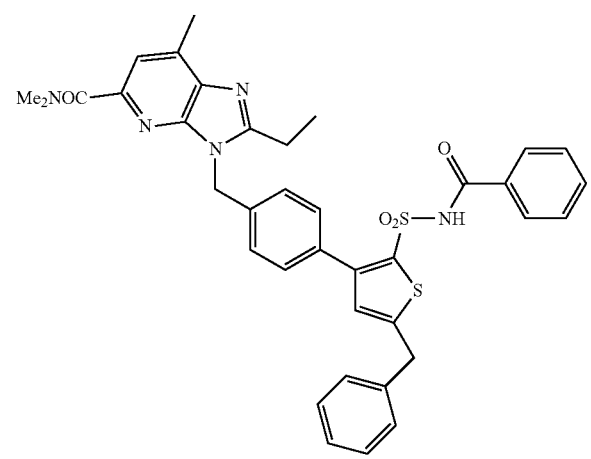
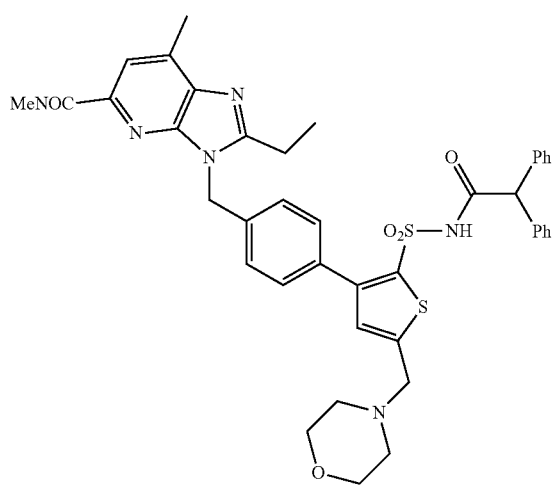

35
-continued
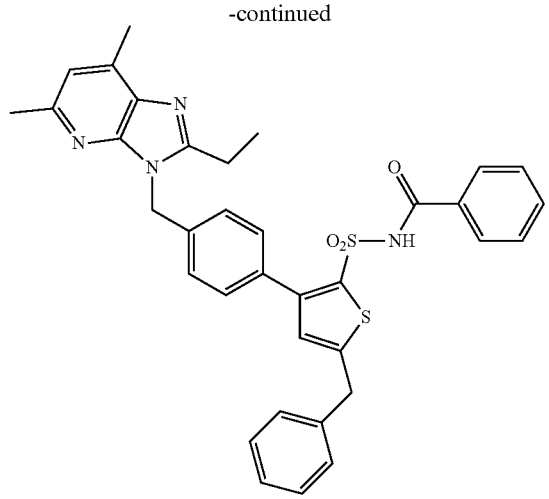
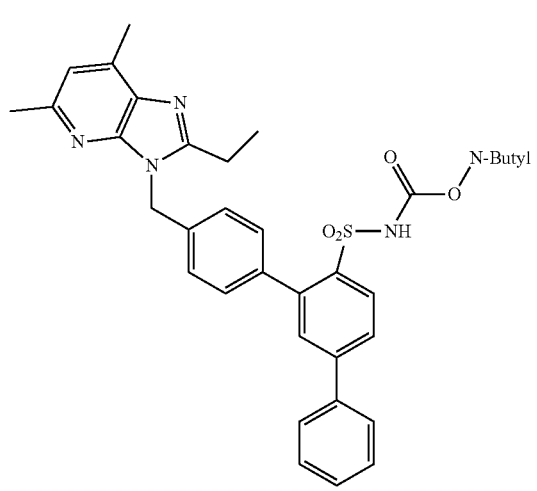
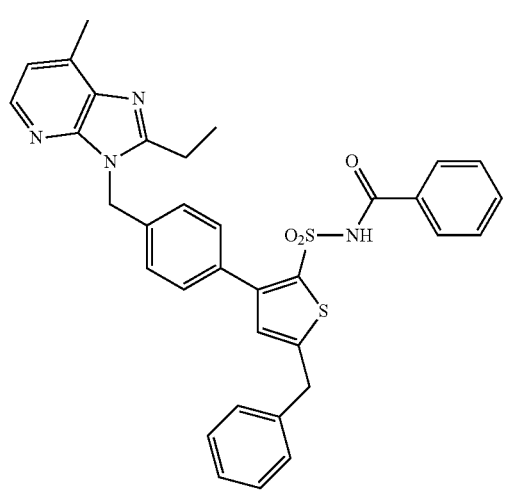
36
-continued
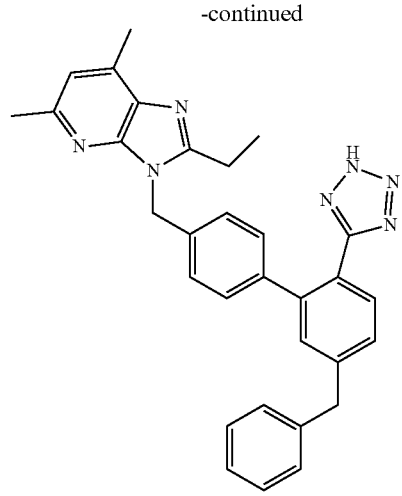
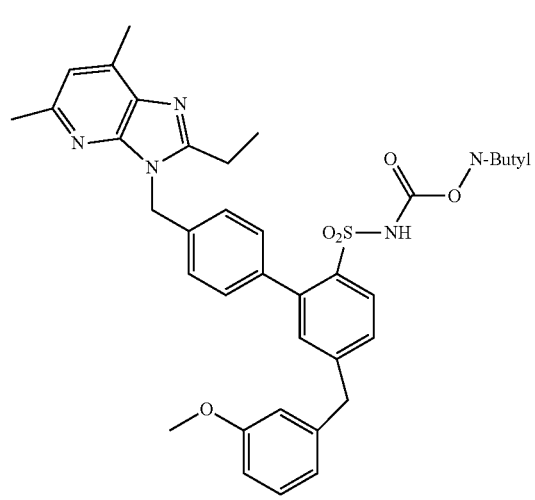
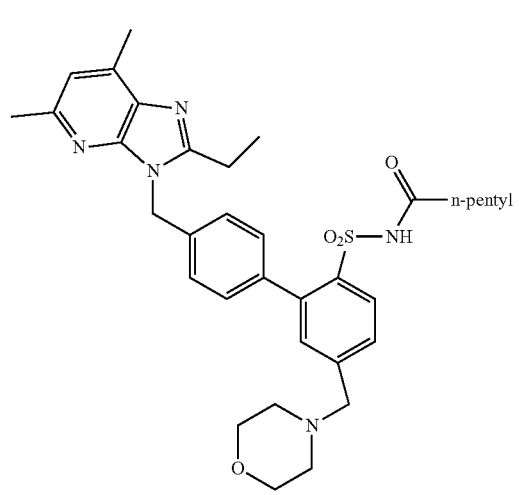

37
-continued
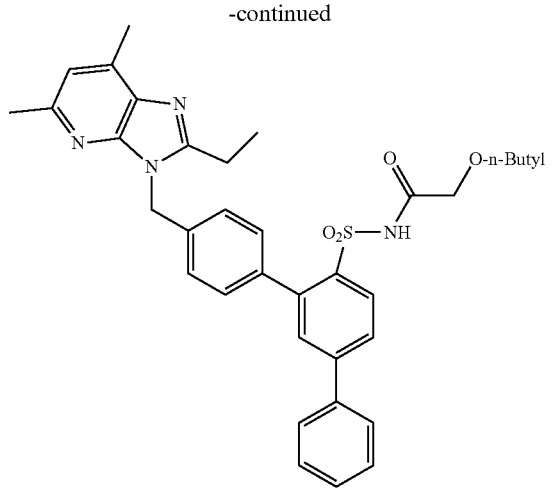
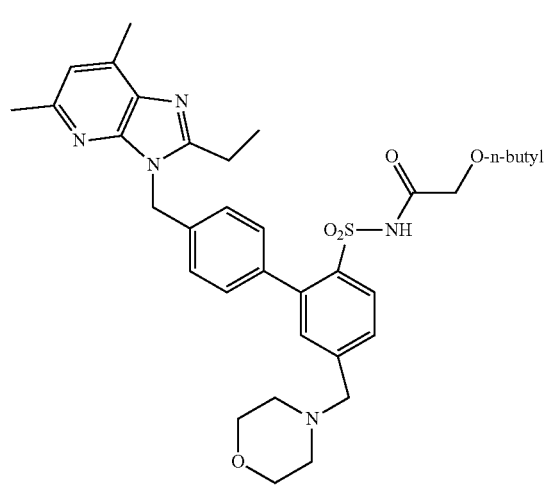
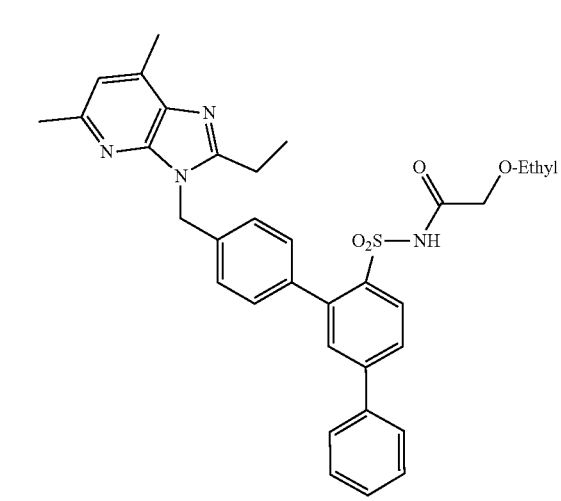
38
-continued
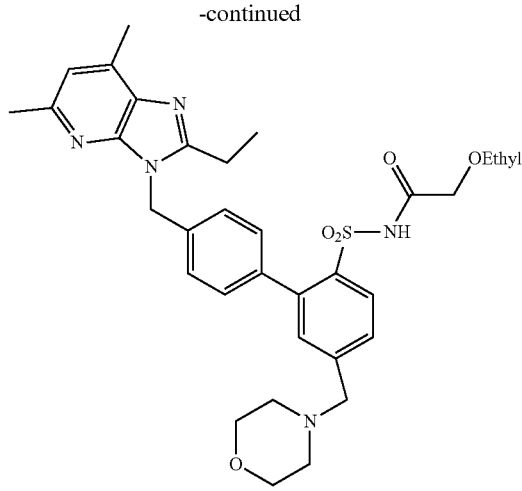
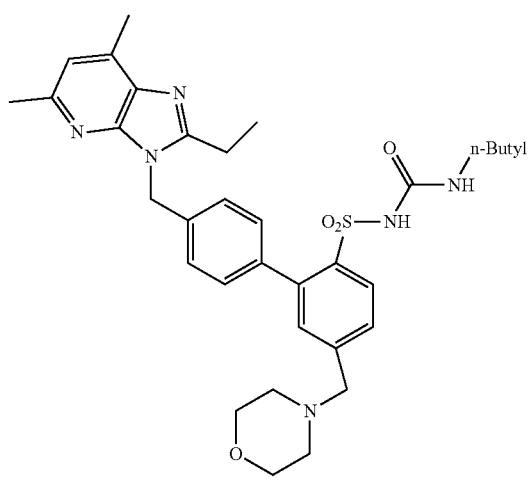

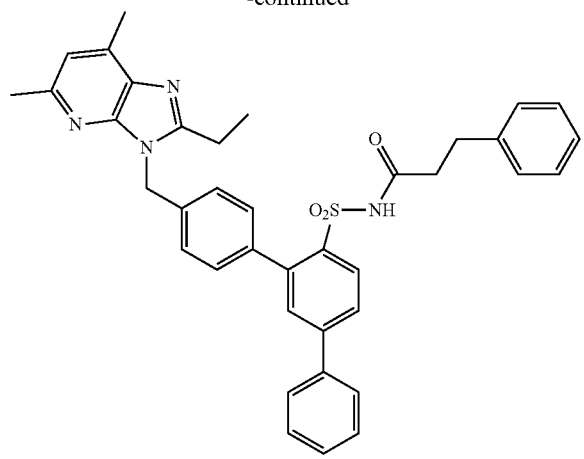
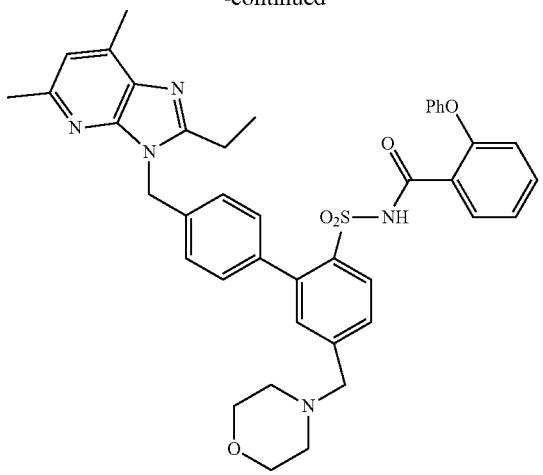
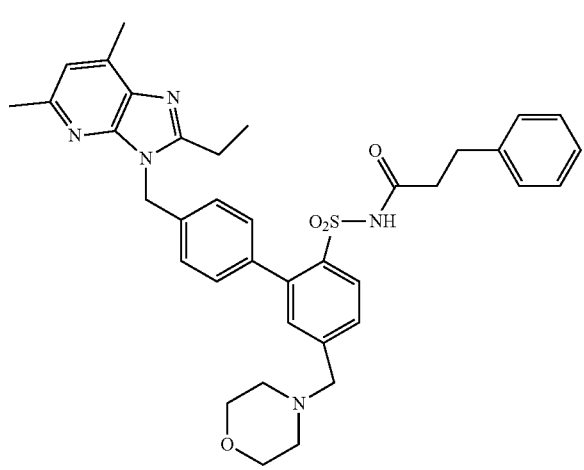
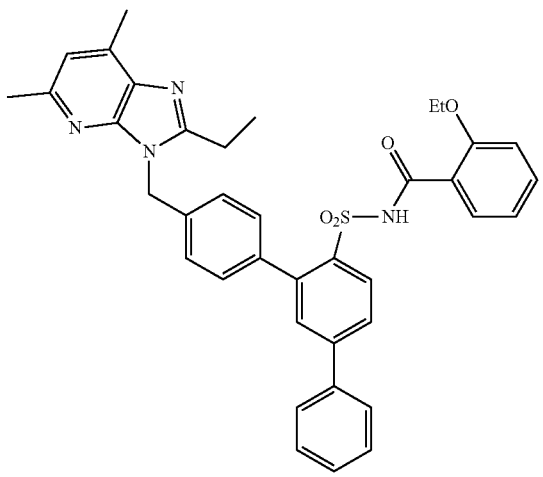
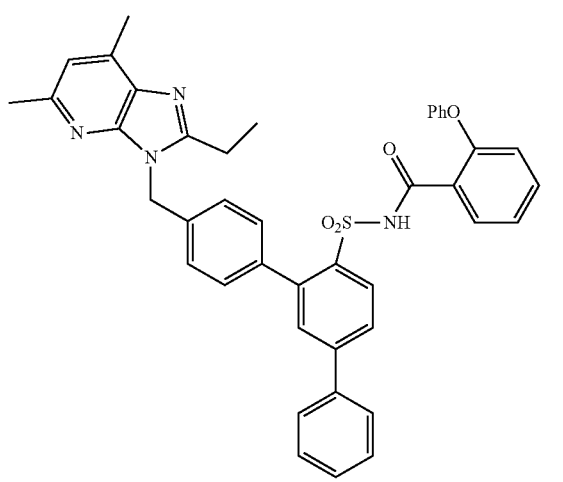
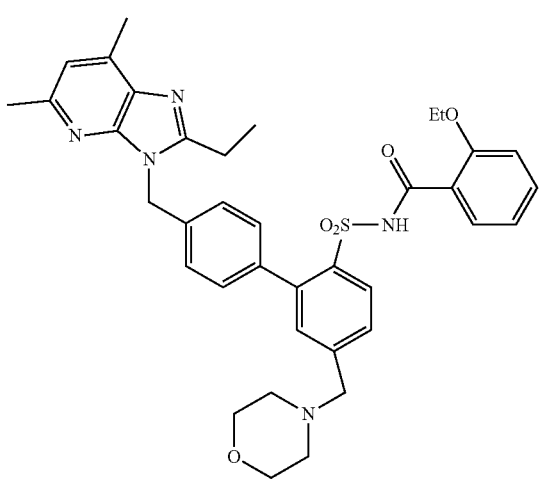

41
-continued
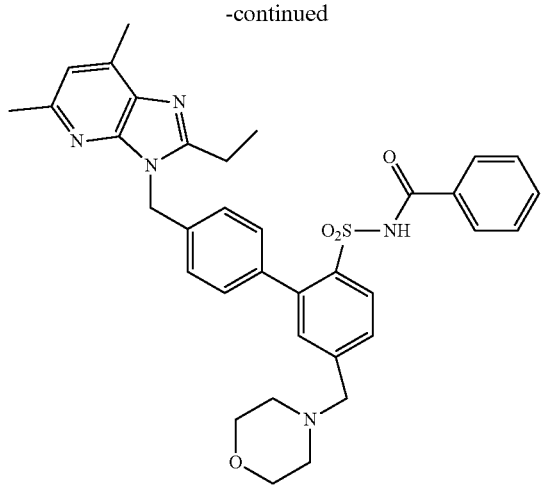
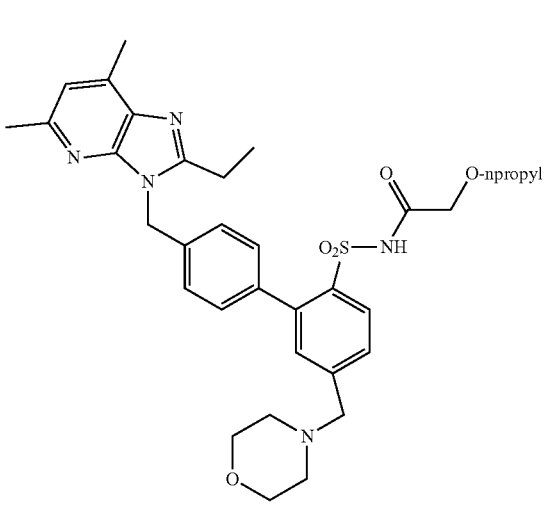
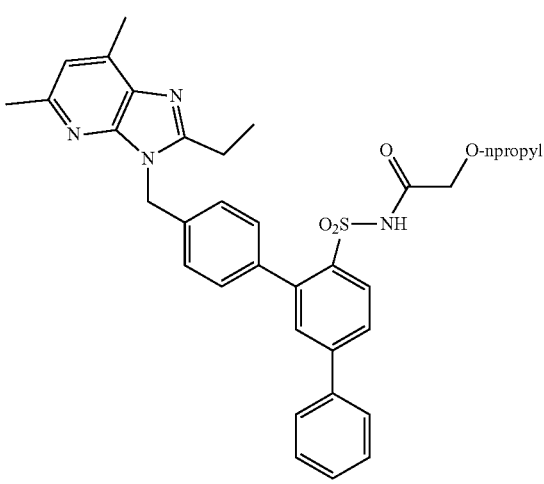
42
-continued
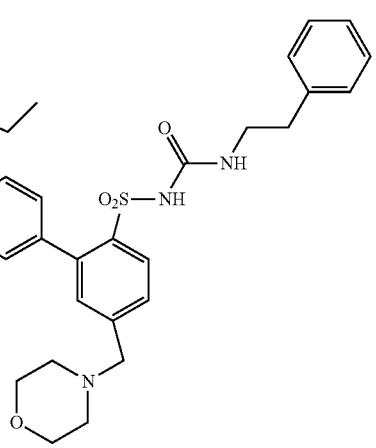
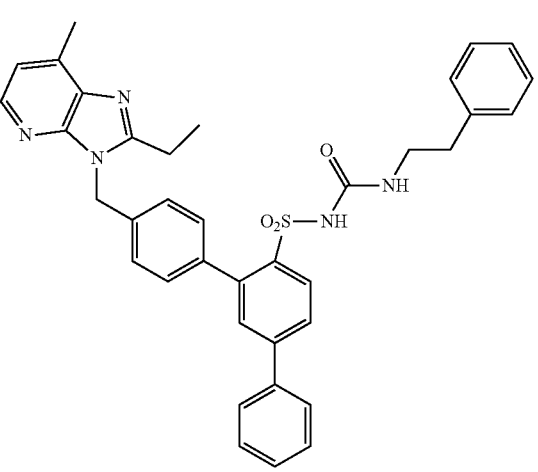
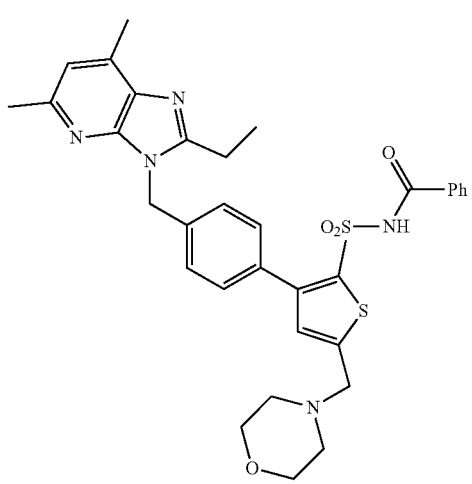

-continued
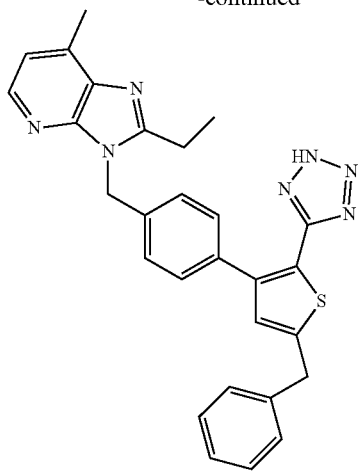
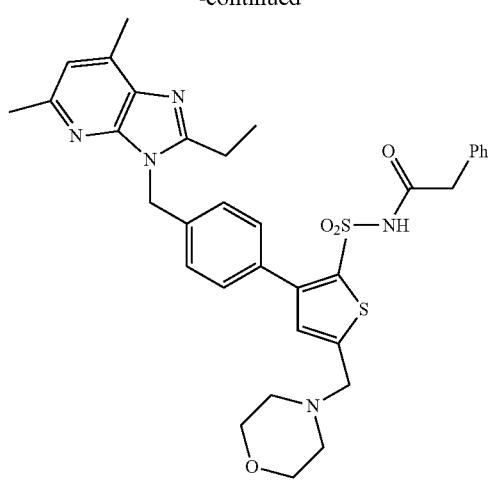
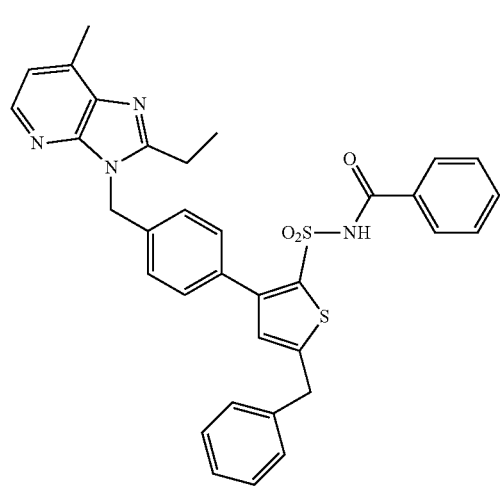
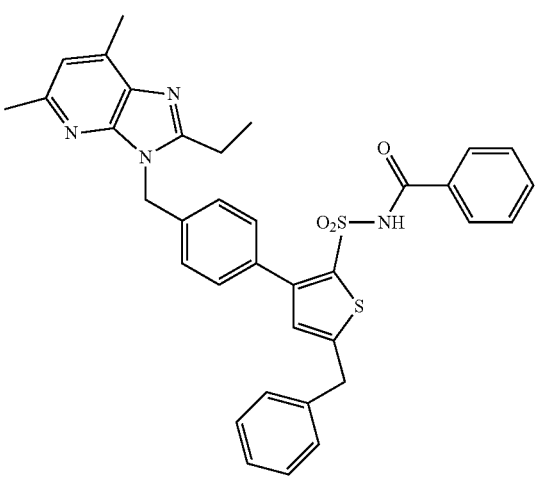
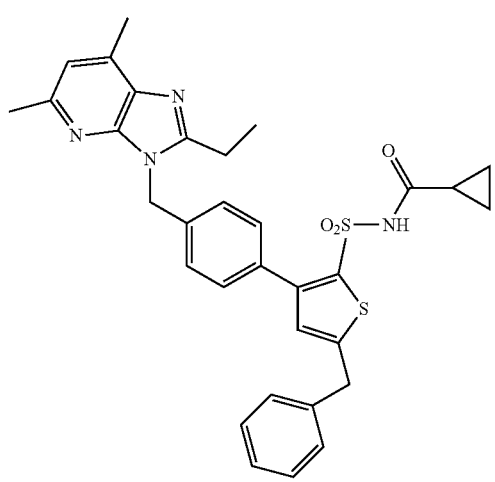

45
-continued
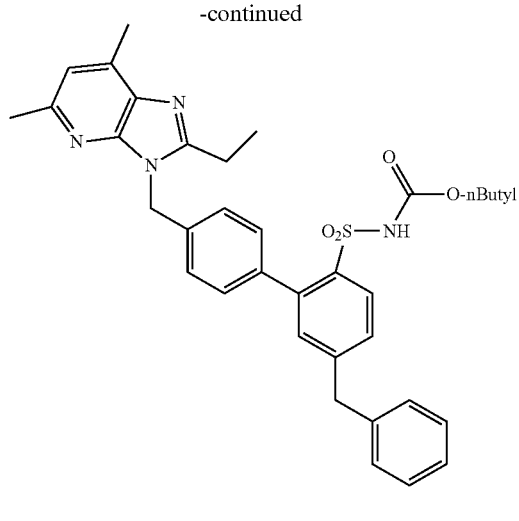
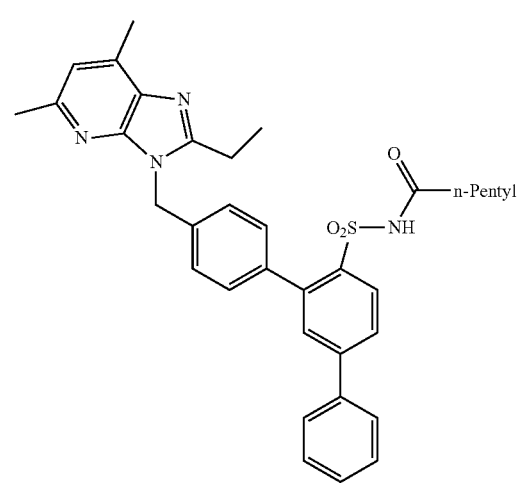
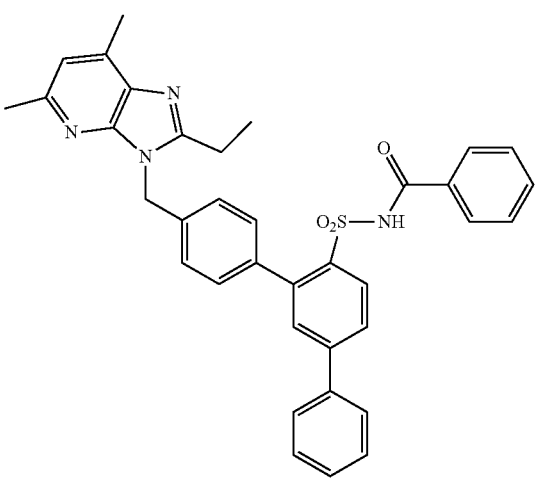
46
-continued
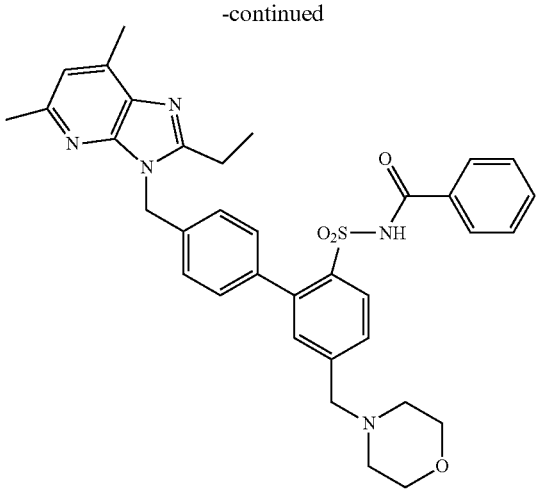
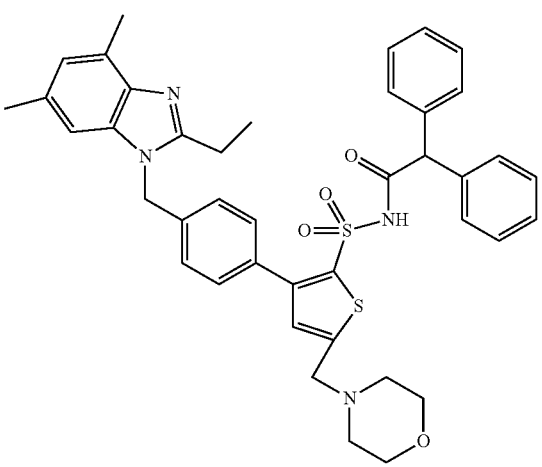
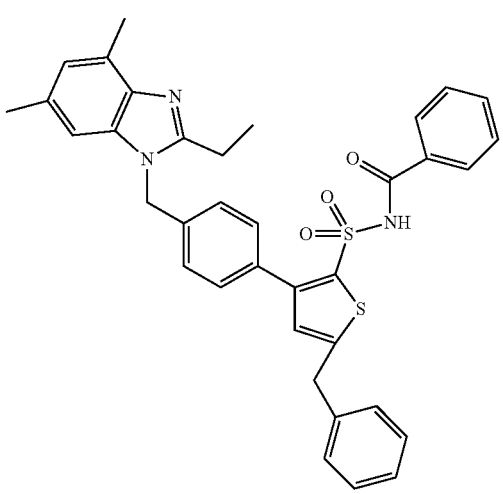

-continued

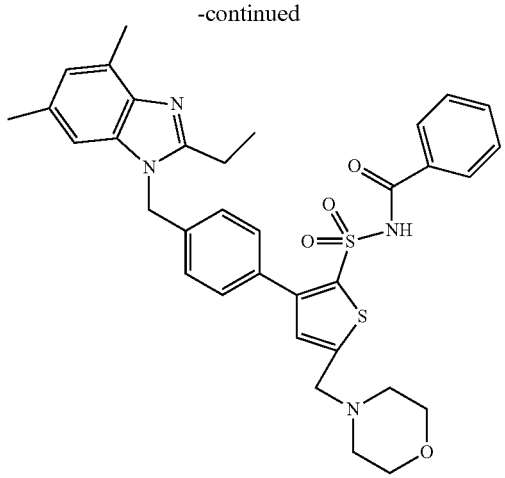

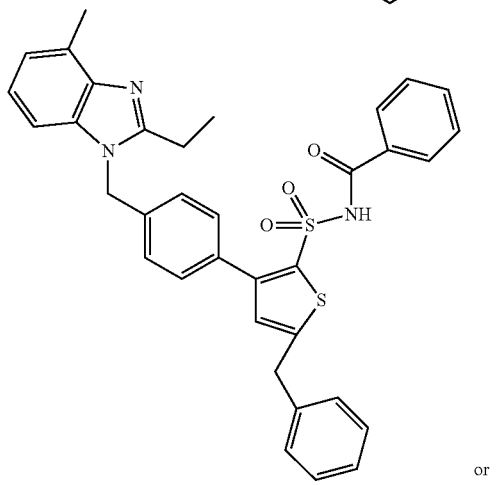

or

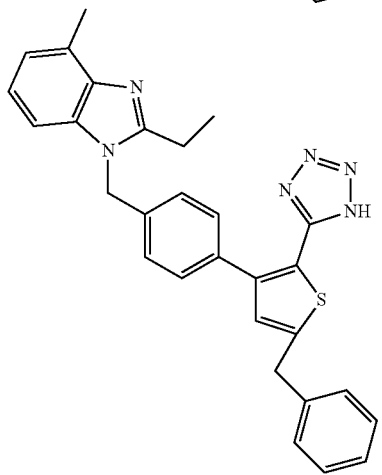

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:
$R^5$ is $C_{1-6}$ alkyl, $C_{3-6}$ cycloalkyl or $O(C_{1-6}$ alkyl); and
$R^6$ is hydrogen, or $C_{1-4}$ alkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

G is selected from a 5 to 10 membered heterocycle having 1-3 atoms selected from N, O, and S, phenyl or a $C_6$-$C_{10}$-heteroaryl having 1-3 atoms selected from N, O, and S; wherein the heterocycle, phenyl and heteroaryl are substituted with 0-3 substituents independently selected from the group consisting of =O, Cl, Br, I, F, $C_1$-$C_6$-alkyl, C-$C_6$-alkoxy, $C_1$-$C_6$-haloalkyl, $C_1$-$C_6$-alkylthio, $C_1$-$C_6$-hydroxyalkyl, OH, $OR^x$, $N(R^x)_2$, $CO(R^x)$, CON$(R^x)_2$, $CO_2R^x$, $N(R^x)CO_2(R^x)$, $N(R^x)CO(R^x)$, $N(R^x)CON(R^x)_2$, $S(O)_2(R^x)$, $S(O)_2N(R^x)_2$, or $N(R^x)S(O)_2R^x$;

$R^x$ is H, $C_{1-6}$ alkyl, $CF_3$, phenyl, $CH_2$-phenyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: Ring B is

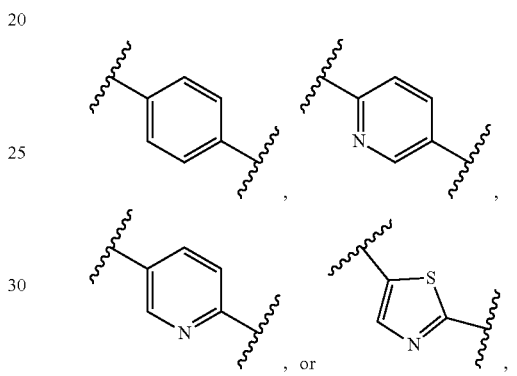

any of which are optionally substituted with 0-2 F,

In another aspect, there are disclosed compounds of Formula (IF) as described by any of the other embodiments or aspects, including salts, enantiomers, diastereomers, tautomers, pharmaceutically-acceptable salts, hydrates, or solvates thereof, wherein $R^9$ is $CO_2H$, $CO_2$-$C_{1-6}$-alkyl, $CO_2NH_2$, $CO_2NH(C_{1-6}$-alkyl), $CO_2N(C_{1-6}$-alkyl)$_2$.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: Ring B is

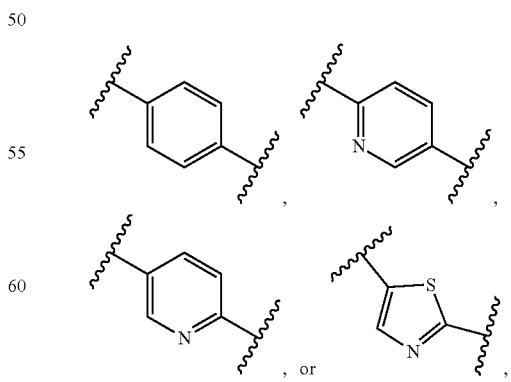

any of which are optionally substituted with 0-2 F Y is COOH, COOMe, COOEt,

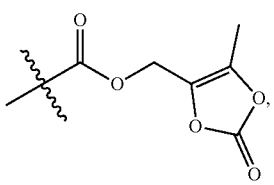 [SMILES: *C(=O)OCc1oc(=O)oc1C]

5-tetrazolyl, SO₃H,

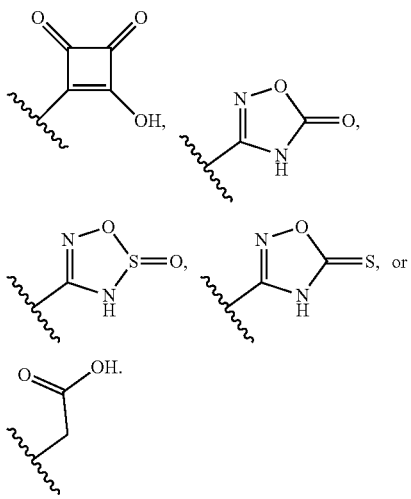

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

wherein Y is COOH, 5-tetrazolyl, SO₃H,

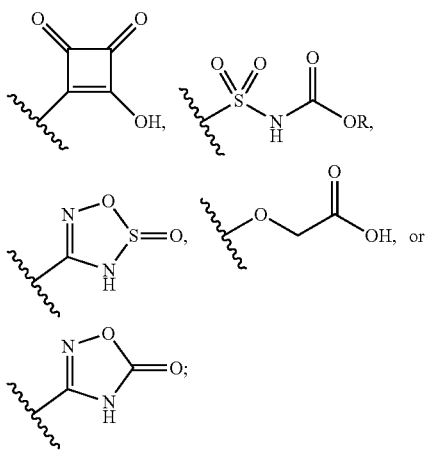

R is $C_{1-6}$ alkyl, $C_{6-10}$-aryl-$C_1$-$C_6$-alkyl, or (CH₂Ph).

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring A is

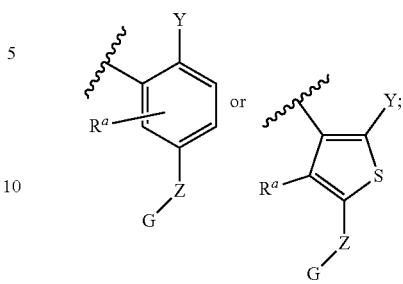

$R^a$ is H or F.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

G is selected from a phenyl, thiophenyl, quinolinyl, isoquinolinyl, indolyl, pyrazolyl, pyrrolyl, pyridinyl, isoindolinyl, pyrrolidinyl; any of which are substituted with 0-3 substituents independently selected from the group consisting of =O, Cl, Br, I, F, $C_1$-$C_6$-alkyl, $C_1$-$C_6$-haloalkyl, $C_1$-$C_6$-hydroxyalkyl, OH, $OR^x$, $N(R^x)_2$, $CO(R^x)$, $CON(R)_2$, $CO_2R^x$, $N(R^x)CO_2(R^x)$, $N(R^x)CO(R^x)$, $N(R^x)CON(R^x)_2$, $S(O)_2(R^x)$, $S(O)_2N(R)_2$, or $N(R^x)S(O)_2R'$;

$R^x$ is H, $C_{1-3}$ alkyl, CF₃, phenyl, CH₂phenyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Y is carboxyl, 5-tetrazolyl,

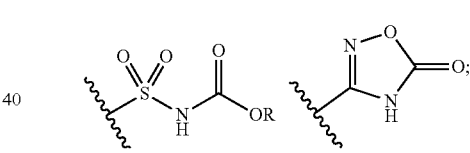

and

R is $C_{1-6}$ alkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring B is

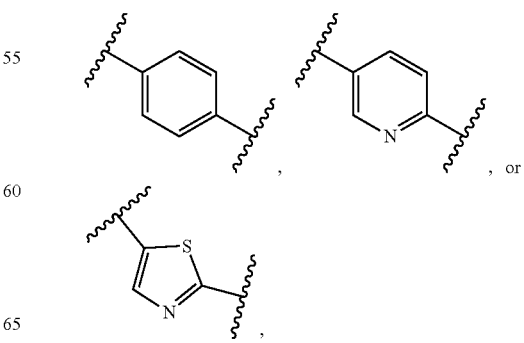

any of which are substituted with 0-2 F.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:
Ring B is

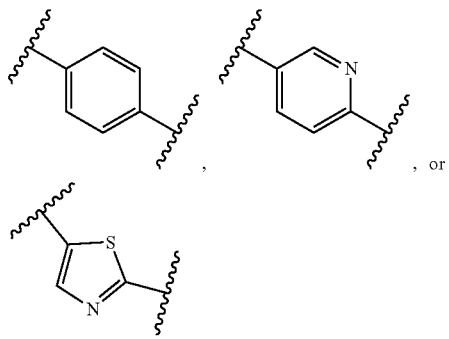

Ring A is

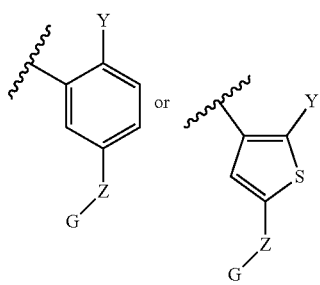

Z is a bond or NR$^a$;
G is isoindolinyl-1,3-dione, pyrrolidine-2,5-dione, phenyl, thiazolyl, pyridinyl, pyrrolyl, pyrazolyl, quinolinyl, isoquinolinyl, any of which may be substituted with 0-3 substituents selected from =O, C$_{1-4}$ alkyl, -O-R$^x$, C$_{1-4}$ haloalkyl, —C(O)NR$^x$, -N(R$^x$)$_2$, and F;
R$^5$ is C$_{3-4}$ alkyl;
R$^6$ is C$_{3-4}$ alkyl;
R$^a$ is hydrogen, C$_{1-4}$alkyl, and C$_{1-2}$ haloalkyl; and
Y is tetrazolyl, COOH, 1,2,4-oxadiazol-5(4H)-one, or —SO$_2$NHCOO-nbutyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:
Ring A is G G

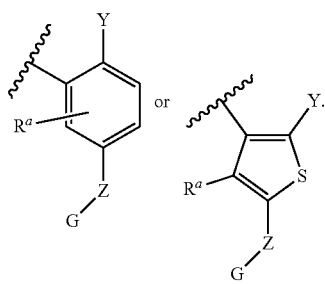

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:
Ring A is

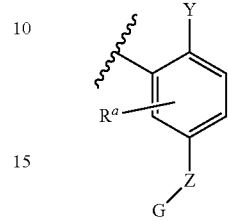

R$^a$ is H or F,
or R$^a$ is H.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:
Y is COOH, COOMe, COOEt,

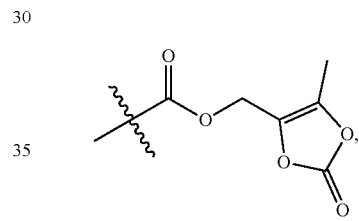

5-tetrazolyl, SO$_3$H,

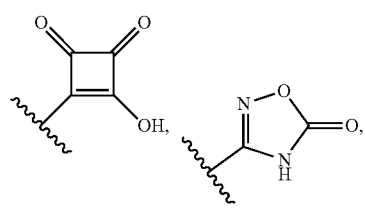

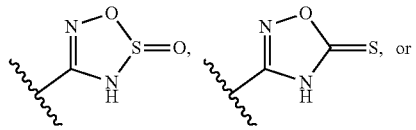

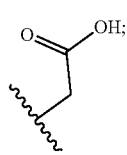

or Y is tetrazolyl, COOH, 1,2,4-oxadiazol-5(4H)-one, or —SO$_2$NHCOO-nbutyl; or Y is carboxyl, 5-tetrazolyl,

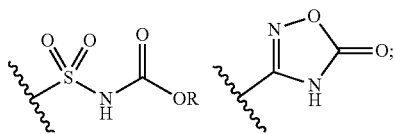

or Y is tetrazolyl, COOH, 1,2,4-oxadiazol-5(4H)-one, or —SO$_2$NHCOO-nbutyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: Z is a bond or NR$^a$, where R$^a$ is hydrogen, C$_{1-4}$alkyl, or C$_{1-2}$ haloalkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: Z is a bond.

In another aspect, there are disclosed compounds of Formula (1), or compounds of Formula (I) as described by any of the other embodiments or aspects, including salts, enantiomers, diastereomers, tautomers, pharmaceutically-acceptable salts, hydrates, or solvates thereof, wherein:

G is selected from a phenyl, thiophenyl, quinolinyl, isoquinolinyl, indolyl, pyrazolyl, pyrrolyl, pyridinyl, isoindolinyl, pyrrolidinyl; any of which are substituted with 0-3 substituents independently selected from the group consisting of =O, Cl, Br, I, F, C$_1$-C$_6$-alkyl, C$_1$-C$_6$-haloalkyl, C$_1$-C$_6$-hydroxyalkyl, OH, OR$^x$, N(R$^x$)$_2$, CO(R$^x$), CON(R$^x$)$_2$, CO$_2$R$^x$, N(R$^x$)CO$_2$(R$^x$), N(R$^x$)CO(R$^x$), N(R$^x$)CON(R)$_2$, S(O)$_2$(R$^x$), S(O)$_2$ R$^x$, S(O)$_2$N(R)$_2$, N(R$^x$)S(O)$_2$(R$^x$), or N(R$^x$)S(O)$_2$R$^x$;

or G is isoindolinyl-1,3-dione, pyrrolidine-2,5-dione, phenyl, thiazolyl, pyridinyl, pyrrolyl, pyrazolyl, quinolinyl, isoquinolinyl, any of which may be substituted with 0-3 substituents selected from =O, C$_{1-4}$ alkyl, -O-R$^x$, C$_{1-4}$ haloalkyl, —C(O)NR$^x$, -N(R$^x$)$_2$, and F.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: wherein Y is COOH, 5-tetrazolyl, SO$_3$H,

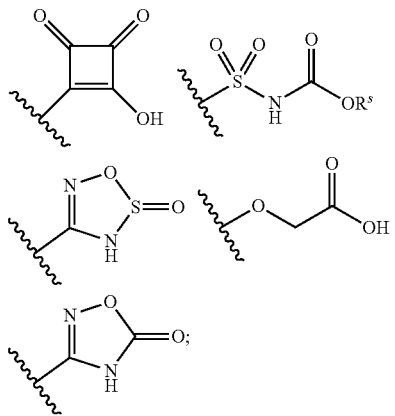

R$^s$ is C$_{1-6}$ alkyl, or (CH$_2$Ph).

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

Ring B is

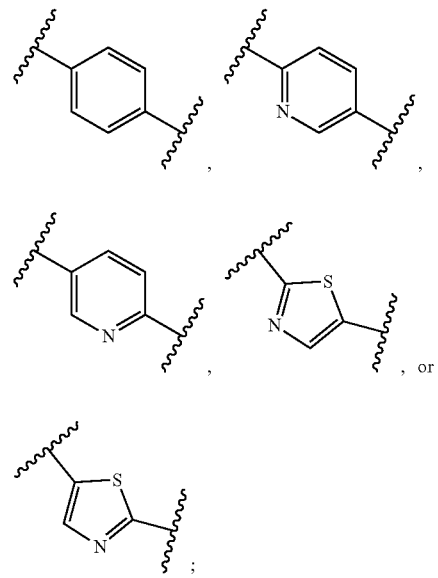

or Ring B is

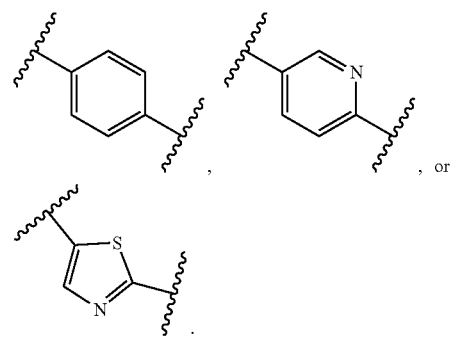

In another aspect, there are disclosed compounds of Formula (1), or compounds of Formula (I) as described by any of the other embodiments or aspects, including salts, enantiomers, diastereomers, tautomers, pharmaceutically-acceptable salts, hydrates, or solvates thereof, wherein:

Group C is

IA

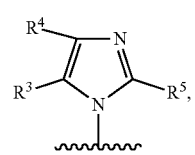

or Group C is

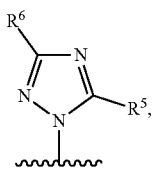

or Group C is

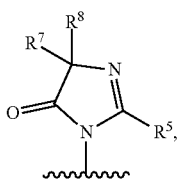

or Group C is

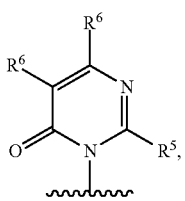

or Group C is

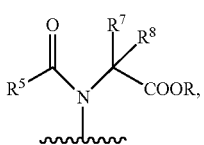

or Group C is

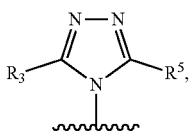

or Group C is

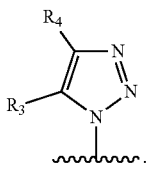

or Group C is

IB or Group C is

IC or Group C is

ID

IG

IH

IJ or Group C is

IE or Group C is

IF

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: $R^1$ and $R^2$ are H.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein:

$R^x$ is H, $C_{1-6}$ alkyl, $CH_2$-phenyl; and $R^s$ is $C_{1-6}$ alkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the moiety:

C is selected from the following:

where $R^5$ is $C_{1-4}$ alkyl, methoxymethyl, ethoxymethyl or cyclopropyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the moiety:

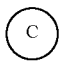

is selected from the following:

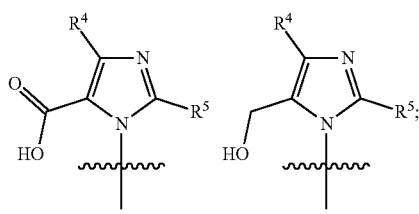

where $R^4$ is H, F, Cl, methyl or ethyl and $R^5$ is $C_{1-4}$ alkyl, methoxymethyl, ethoxymethyl or cyclopropyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the moiety:

is:

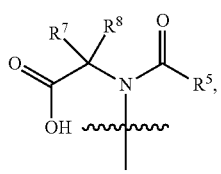

wherein
$R^5$ is $C_{1-4}$ alkyl, $C_{1-4}$ haloalkyl, or cyclopropyl
$R^7$ and $R^8$ are independently H, $C_{1-3}$ alkyl, or taken together join to form cyclopentyl, cyclohexyl, cycloheptyl, or tetrahydropyranyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the moiety:

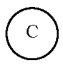

is selected from:

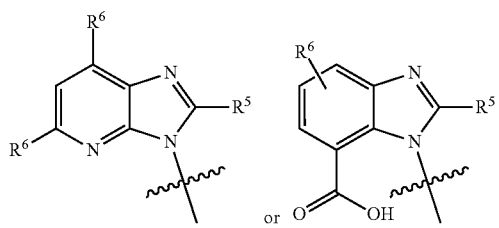

wherein $R^6$ is independently H or Me; and
$R^5$ is $C_{12}$ alkyl, $C_{12}$ haloalkyl, methoxymethyl, or cyclopropyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the moiety:

is selected from:

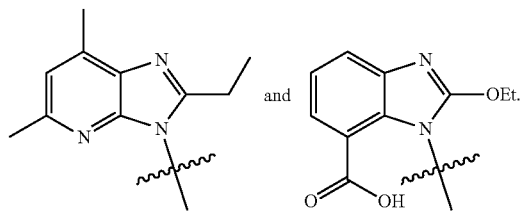 [SMILES: *n1c(CC)nc2c(C)cc(C)nc21 ; *n1c(OCC)nc2cccc(C(=O)O)c21]

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the moiety:

is

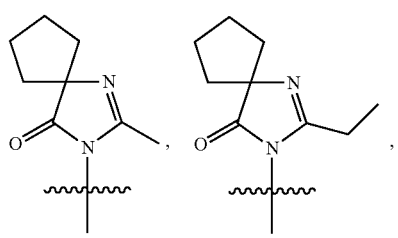

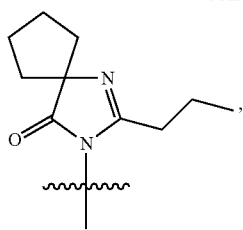

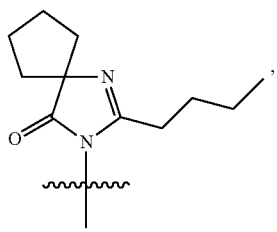

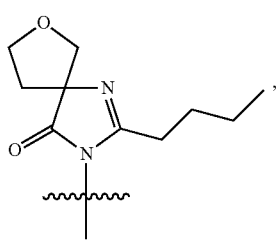

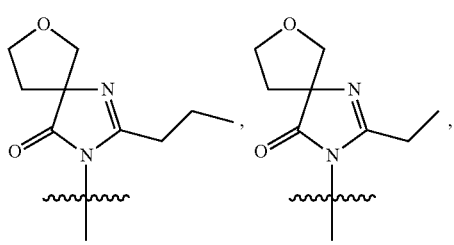

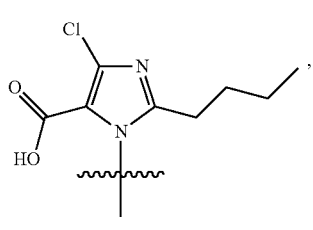

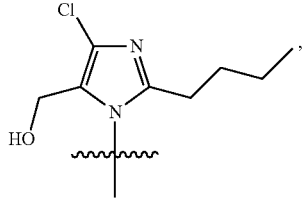

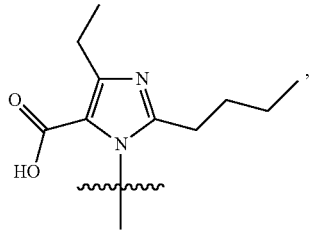

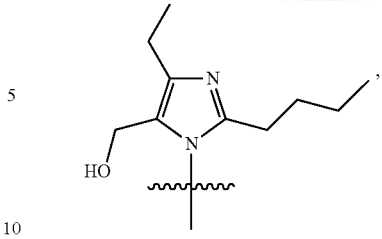

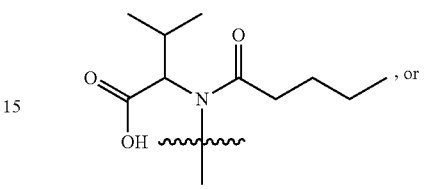

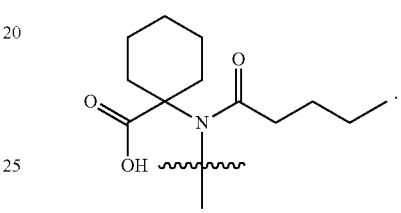

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the moiety (B)

is selected from phenyl, pyridyl, pyrimidinyl or pyrazinyl, and ring (A)

is phenyl or thiophenyl and $R^{16}$ is as defined earlier.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the moiety (B)—(A)

is selected from the following:

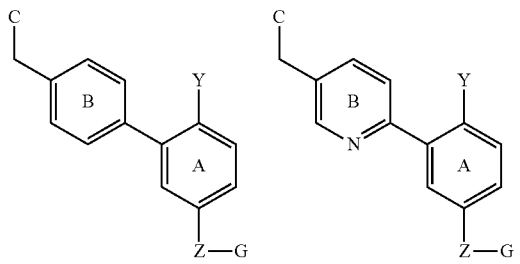

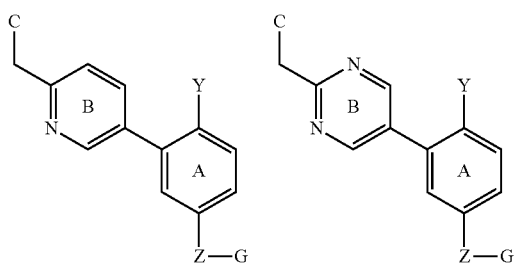

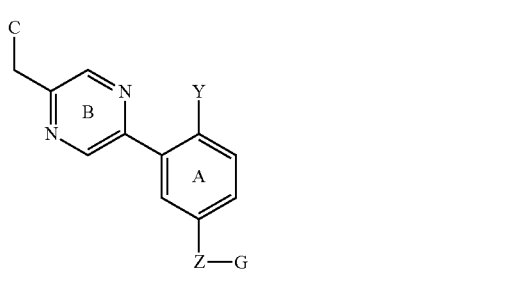

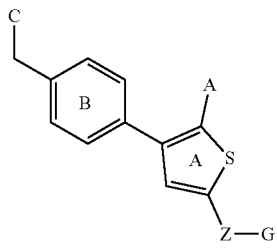

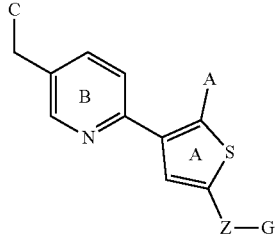

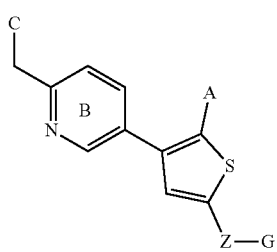

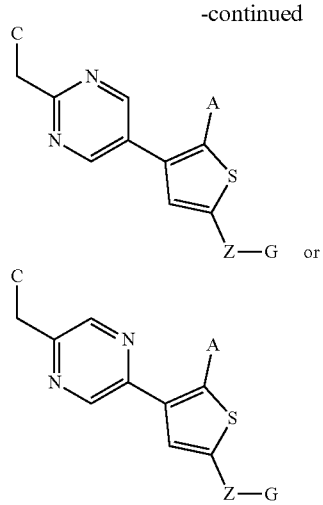

where rings B and A can be substituted with 0-4 substituents chosen independently from F, Cl, CN, methyl, ethyl, methoxy, or $OCHF_2$; and "C" indicates:

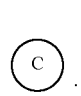

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the moiety

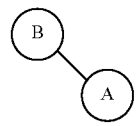

is selected from the following:

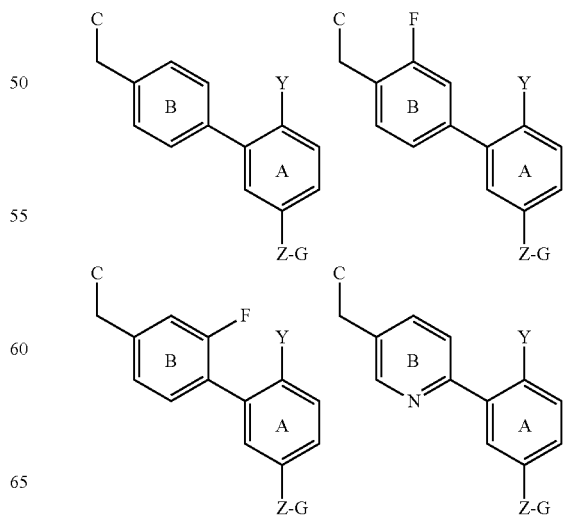

-continued

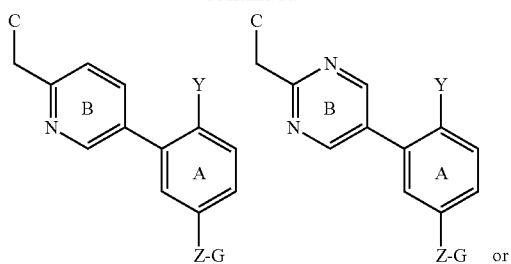

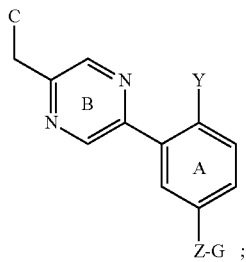

where rings B and A are substituted with 0-4 substituents selected independently from F, Cl, CN, methyl, ethyl, methoxy, or OCHF$_2$;

and "C" indicates:

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the moiety Y is selected from the following:

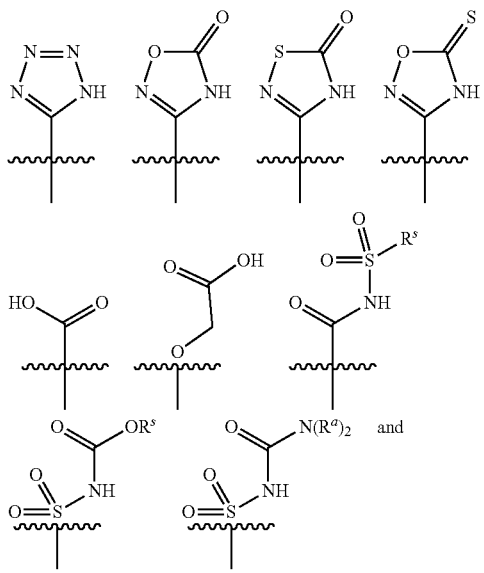

-continued

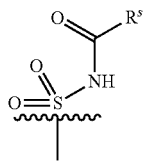

wherein $R^a$ is, at each occurrence, independently selected from H, $C_1$-$C_4$-alkyl, $C_1$-$C_4$-haloalkyl, $C_1$-$C_4$-hydroxyalkyl, and $C_3$-$C_6$-cycloalkyl; and $R^s$ at each occurrence, is independently selected from H, $C_1$-$C_6$ alkyl, $C_1$-$C_6$-haloalkyl, $C_1$-$C_6$-hydroxyalkyl, $C_3$-$C_7$ cycloalkyl, $C_3$-$C_7$ cycloalkyl $C_1$-$C_3$ alkyl, $C_6$-10 aryl, $C_6$-10-aryl-$C_1$-$C_6$-alkyl, heteroaryl, heteroaryl-$C_1$-$C_6$-alkyl, heterocyclyl, heterocycle-$C_1$-$C_6$-alkyl, wherein the heteroaryl is a 5-10 membered group and the heterocycle is a 4-10 membered each having 1-3 heteroatoms selected from N, O, or S.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the moiety Y is selected from the following

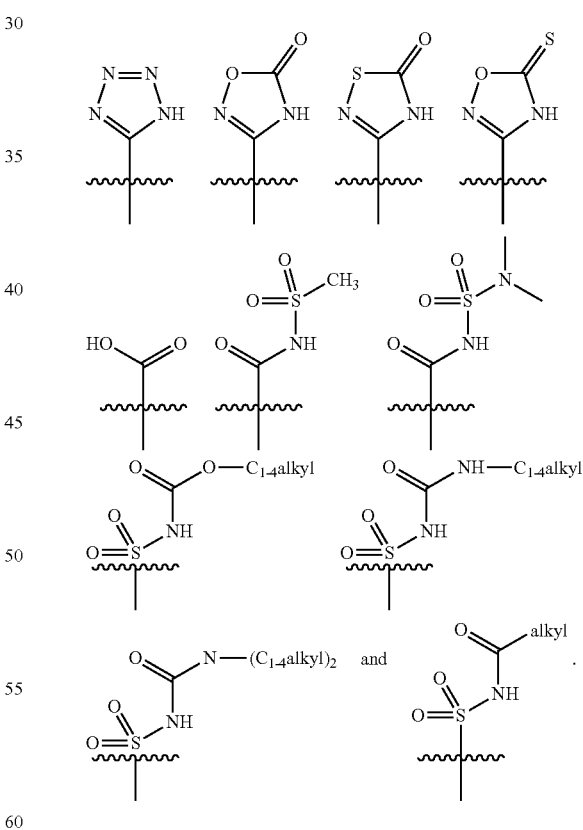

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein the moiety Y is selected from the following:

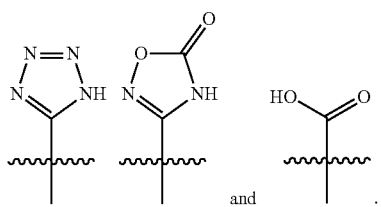

and.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein Z is a bond and the moiety Z-G is selected from the following: phenyl, pyridyl, pyrazolyl, triazolyl, tetrahydropyranyl, tetrahydrofuranyl, morpholinyl, thiazolyl, isothiazolyl and imidazolyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein Z is a bond and the moiety Z-G is selected from the following: phenyl, pyrid-2-yl, pyrid-3-yl, pyrazol-1-yl, 1,2,3-triazol-4-yl, 1,2,3-triazol-1-yl, indazol-1-yl, indazol-2-yl, benzotriazol-1-yl, tetrahydropyran-2-yl, tetrahydrofuran-2-yl, morpholin-2-yl, thiazol-2-yl, and isothiazol-3-yl, each said moiety being substituted with 0-3 substituents selected from F, Cl, OH, CN, $C_{1-3}$ alkyl, $C_{1-3}$ alkoxy, $C_{1-3}$ fluoroalkyl, methoxy$C_{1-2}$alkyl, hydroxy$C_{1-2}$alkyl, and N($C_{1-2}$alkyl)$_2$.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein Z is a bond and the moiety Z-G is selected from the following:

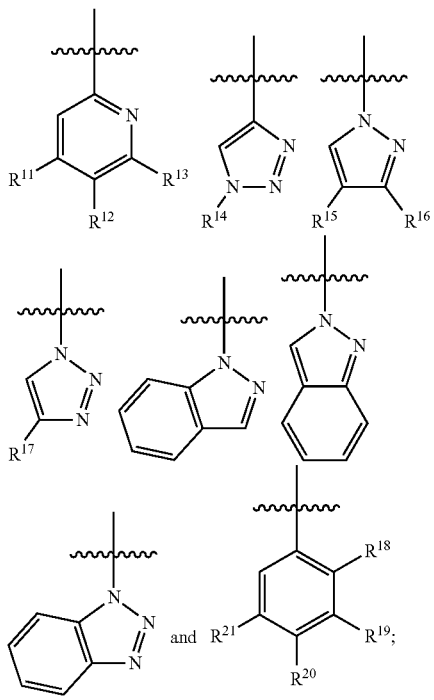

wherein $R^{11}$ is H, $C_1$, F, methyl, ethyl, cyclopropyl, methoxy, $CHF_2$, $CF_3$, $CF_2CH_3$, $OCHF_2$, $N(CH_3)_2$, or methoxymethyl;

$R^{12}$ is H, $C_1$, F, methyl, methoxy, hydroxymethyl, $CHF_2$, or $CF_3$;

$R^3$ is H, F, Cl, $CH_3$, $CHF_2$, $CF_3$, or methoxy;

$R^{14}$ is methyl, ethyl, i-propyl, cyclopropylmethyl, cyclobutylmethyl, n-butyl, i-butyl, $CH_2CH_2F$, $CH_2CHF_2$, or hydroxyethyl;

$R^{15}$ is H, methyl, $CF_3$, $CHF_2$, hydroxymethyl, or hydroxyethyl;

$R^{16}$ is H, methyl, $CF_3$, or CHF; $R^{17}$ is methyl, ethyl, propyl, cyclopropyl, i-propyl or t-butyl;

$R^{18}$ is H, F, or OH;

$R^{19}$ is H, F, Cl, methyl, or methoxy;

$R^{20}$ is H, or F; and $R^{21}$ is H, F, Cl, methyl, or methoxy.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein Z is a bond and the moiety Z-G is selected from the following:

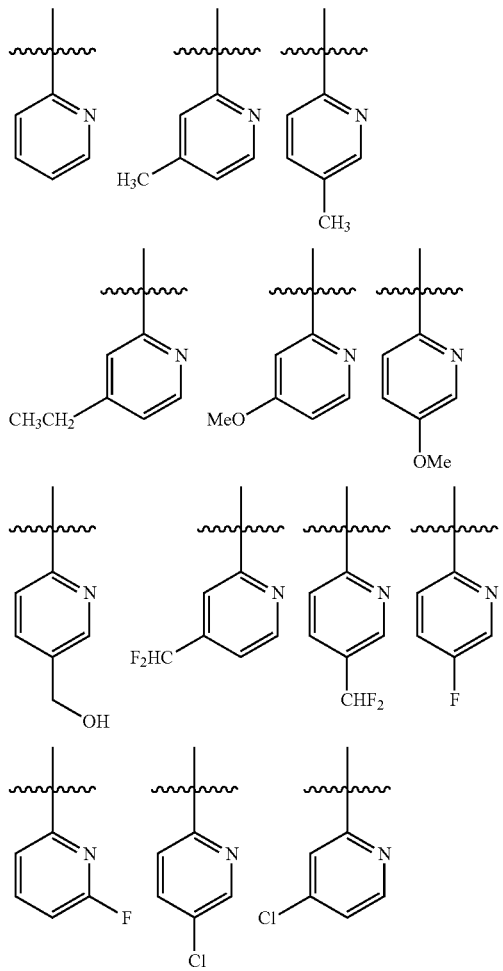

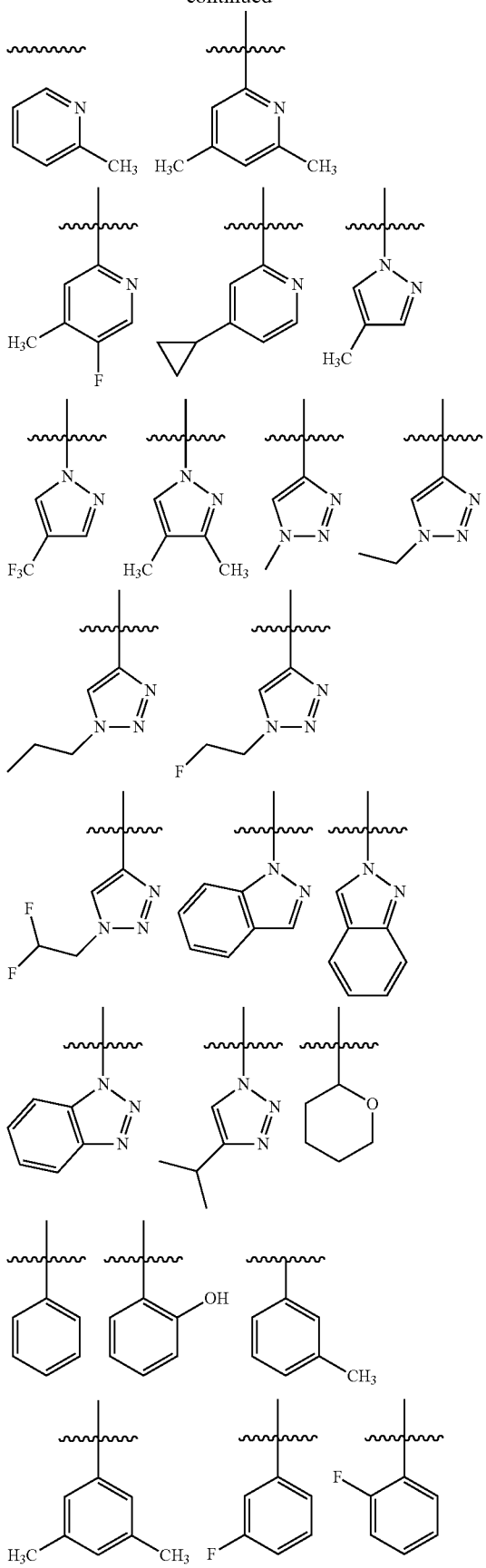

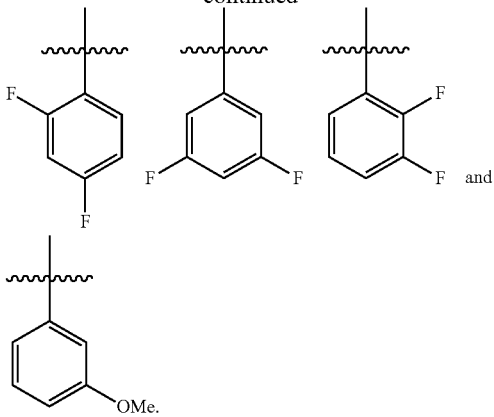

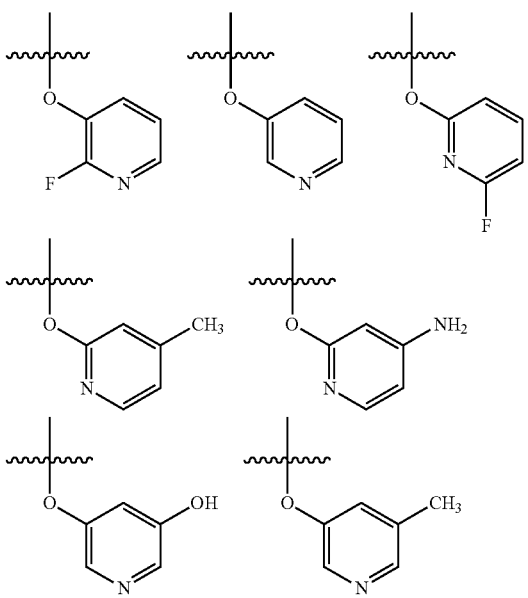

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein Z is O, N, or C=O;

G is phenyl, pyridyl, or $C_{3-7}$ cycloalkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein Z is 0, N, or C=O;

G is phenyl, pyrid-2-yl, pyrid-3-yl, cyclohexyl, cyclopentyl, each being substituted with 0-2 substituents selected from F, Cl, OH, $NH_2$, $C_{1-3}$alkyl, $C_{1-3}$alkoxy, and $C_{1-2}$fluoroalkyl.

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein Z-G is selected from the following:

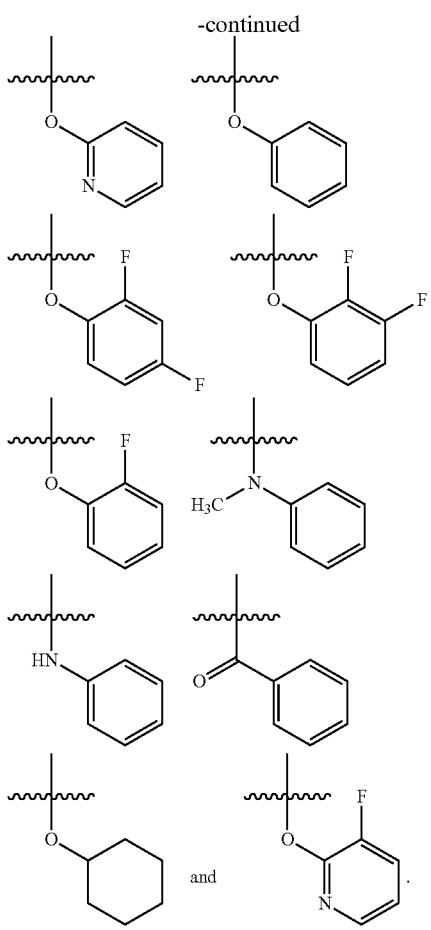

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: the compound is selected from Examples 1-462.

In another aspect, there is disclosed a pharmaceutical composition, comprising a pharmaceutically acceptable carrier and any one or more compounds of Formula (I), or compounds of Formula (I) as described by any of the other embodiments or aspects, or a pharmaceutically acceptable salt thereof.

In another aspect, there is disclosed a method for the treatment or prophylaxis of one or more disease or disorder which can be modulated by biased agonism of the angiotensin II receptor, comprising administering to a patient in need of such treatment or prophylaxis a therapeutically effective amount of at least one of the compounds of Formula (I), or compounds of Formula (I) as described by any of the other embodiments or aspects, wherein the disease or disorder is heart failure with preserved ejection fraction, reduced ejection heart failure, and/or renal disease.

In another aspect, there is disclosed a method for the treatment or prophylaxis of one or more disease or disorder which can be modulated by biased agonism of the angiotensin II receptor, wherein the compound of any of the embodiments is administered in combination with at least one other type of therapeutic agent.

In another aspect, there is disclosed a method for the treatment or prophylaxis of multiple diseases or disorders, comprising administering to a patient in need of such treatment or prophylaxis a therapeutically effective amount of at least one of the compounds of Formula (I), or compounds of Formula (I) as described by any of the other embodiments or aspects, wherein the disease or disorder is heart failure with preserved ejection fraction, reduced ejection heart failure, and/or renal disease.

In another aspect, there is disclosed a method for the treatment or prophylaxis of diseases or disorders, wherein the compound of any of the embodiments is administered in combination with at least one other type of therapeutic agent. In another aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the tenth aspect.

In another embodiment, the compounds of the present invention have $EC_{50}$ values≤10 µM, in stimulating β-arrestin recruitment using the assays disclosed herein, preferably, $EC_{50}$ values≤5 µM, more preferably, $EC_{50}$ values≤1 µM, even more preferably, $EC_{50}$ values≤0.5 µM. Additionally, compounds of the present invention show efficacy in stimulating β-arrestin recruitment relative to AII of≥30% Ymax, more preferably >50% Ymax, and even more preferably >70% Ymax. Moreover, compounds of the present invention show activity in at least one of the three β-arrestin assays disclosed herein. Preferred compounds of the invention show activity in the BRET β-arrestin assay, and more preferred compounds of the invention show activity in the BRET β-arrestin low AT1R expression assay. Additionally, the compounds may stimulate Gq activity with efficacy (Ymax or Emax) less than 50% that of angiotensin II using the assays disclosed herein, preferably, Ymax≤30%, more preferably Ymax≤20%, even more preferably Ymax≤10%. In addition, preferred compounds of the invention may show reduced potency (higher $EC_{50}$) in Gq signaling assays relative to β-arrestin assays. These compounds may also have ability to activate other AT1R-dependent G-protein signaling including: Gs isoforms, Gi isoforms, Go isoforms, G11 isoforms, G12 isoforms, G13 isoforms, and Gz isoforms.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

The present invention provides a pharmaceutical composition further comprising additional therapeutic agent(s). In a preferred embodiment, the present invention provides pharmaceutical composition, wherein the additional therapeutic agent is, for example, angiotensin converting enzyme (ACE) inhibitor, β-adrenergic receptor blocker, neprilysin inhibitor, diuretic, aldosterone antagonist, Ca2+ channel blocker, nitrates and/or *digitalis* compound.

In another embodiment, the present invention provides a method for the treatment and/or prophylaxis of multiple diseases or disorders associated with angiotensin II biased agonism activity, or β-Arrestin agonism of the angiotensin II receptor, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of the AT1R and AII, or β-Arrestin agonists of the Angiotensin II Receptor, that can be prevented, modulated, or treated according to the present invention include, but are not limited to heart failure such as acute decompensated heart failure (ADHF), chronic heart failure, fibrosis, atrial fibrillation, coronary artery disease, peripheral vascular disease, atherosclerosis, renal disease, diabetes, obesity, metabolic syndrome, hypertension, pulmonary hypertension, cerebrovascular disorders and the sequelae thereof, cardiovascular disorders, angina, ischemia, stroke, myocardial infarction, acute coronary syndrome, reperfusion injury, angioplastic restenosis, vascular complications of diabetes and obesity.

In another embodiment, the present invention provides a method for the treatment and/or prophylaxis of heart failure, coronary artery disease, cardiomyopathy, atrial fibrillation, and related conditions including but not limited to acute coronary syndrome, myocardial ischemia, hypertension, atherosclerosis, pulmonary hypertension, peripheral arterial disease, ischemia/reperfusion injury, angina, renal disease, Examples of diseases or disorders associated with the activity of the biased agonism, or β-Arrestin agonism of the angiotensin II receptor, that can be prevented, modulated, or treated and/or prophylaxis according to the present invention include, but are not limited to HFpEF, HFrEF, and renal disease.

In another embodiment, the present invention provides a method for the treatment and/or prophylaxis of heart failure with preserved ejection fraction, heart failure with reduced ejection fraction, and renal disease, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of renal disease, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of heart failure with preserved ejection fraction, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of reduced ejection fracton heart failure, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of multiple diseases or disorders associated with biased agonism, or β-Arrestin agonism of the angiotensin 1I receptor.

In another embodiment, the present invention also provides the use of a compound of the present invention for the manufacture of a medicament for the treatment and/or prophylaxis of multiple diseases or disorders associated with biased agonism, or β-Arrestin agonism of the Angiotensin II Receptor.

In another embodiment, the present invention provides a method for the treatment and/or prophylaxis of multiple diseases or disorders associated with biased agonism, or β-Arrestin agonism of the angiotensin II receptor, comprising administering to a patient in need thereof a therapeutically effective amount of a first and second therapeutic agent, wherein the first therapeutic agent is a compound of the present invention. Preferably, the second therapeutic agent, for example ACEi (e.g. enalapril) or a selected inotropic agent such as β-adrenergic agonist (for example dobutamine) or other therapeutically relevant agent that elevates natriuretic peptide levels such as a neprilysin inhibitor (for example, sacubitril).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with ATIR and angiotensin II.

In another embodiment compounds within the present invention may be utilized alone or in combination with additional therapeutic agents described herein for the treatment of various conditions associated with heart failure: heart failure with reduced ejection fraction, heart failure with preserved ejection fraction, acute decompensated heart failure, fibrotic disease. Additionally the compounds presented within the present invention may be used alone or in combination with additional therapeutic agents described herein as either acute, sub-acute or chronic therapy.

Where desired, the compound of the present invention may be used in combination with one or more other types of cardiovascular agents and/or one or more other types of therapeutic agents which may be administered orally in the same dosage form, in a separate oral dosage form or by injection. The other type of cardiovascular agents that may be optionally employed in combination with the biased agonist of the angiotensin II receptor of the present invention may be one, two, three or more cardiovascular agents administered orally in the same dosage form, in a separate oral dosage form, or by injection to produce an additional pharmacological benefit.

The compounds of the present invention may be employed in combination with additional therapeutic agent(s) selected from one or more, preferably one to three, of the following therapeutic agents: anti-hypertensive agents, ACE inhibitors, mineralocorticoid receptor antagonists, calcium channel blockers, β-adrenergic receptor blockers, diuretics, vasorelaxation agents such as nitrates, inotropic agents, *digitalis* compounds, anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-obesity agents, anti-hyperlipidemic agents, anti-hypertri-glyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating heart failure: ACE inhibitors, β-blockers, diuretics, mineralocorticoid receptor antagonists, renin inhibitors, calcium channel blockers, nitrates, *digitalis* compounds, inotropic agents, APJ receptor agonists, relaxin receptor agonists, formyl peptide receptor 2 agonists/biased agonists, nitroxyl donors and neprilysin inhibitors.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans-(or Z- and E-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For examples, "$C_1$ to $C_{12}$ alkyl" or "$C_{1-12}$ alkyl" (or alkylene), is intended to include $C_1$, $C_2$, $C_3$, $C_4$, $C_5$, $C_6$, $C_7$, $C_8$, $C_9$, $C_{10}$, $C_{11}$ and $C_{12}$ alkyl groups; "$C_4$ to $C_{18}$ alkyl" or "$C_{4-18}$ alkyl" (or alkylene), is intended to include $C_4$, $C_5$, $C_6$, $C_7$, $C_8$, $C_9$, $C_{10}$, $C_{11}$, $C_{12}$, $C_{1-3}$, $C_{1-4}$, $C_{15}$, $C_{1-6}$, $C_{17}$, and $C_{18}$ alkyl groups. Additionally, for example, "$C_1$ to $C_6$ alkyl" or "$C_{1-6}$ alkyl" denotes alkyl having 1 to 6 carbon atoms.

Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

When the term "hydrocarbon chain" is used, it is intended to include "alkyl", "alkenyl" and "alkynyl", unless otherwise specified.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S- and ethyl-S-.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S-, and pentafluoroethyl-S-.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R.J., ed., Hawley's Condensed Chemical Dictionary, 15th Edition, John Wiley & Sons, Inc., New York (2007). "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)p, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 1,3-dioxol-2-one, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted.

The nitrogen atom is substituted or unsubstituted (i.e., N or NR wherein R is H or another substituent, if defined). The nitrogen and sulfur heteroatoms may optionally be oxidized (i.e., N→O and S(O)p, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., Protecting Groups in Organic Synthesis, 4th Edition, Wiley (2007) and The Peptides: Analysis, Synthesis, Biology, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and β-toluenesulfonyl; (2) aromatic carbamate types such as benzyloxycarbonyl (Cbz) and substituted benzyloxycarbonyls, 1-(β-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

Compounds of the Formula (I) and/or the Examples herein may in some cases form salts which are also within the scope of this invention. Reference to a compound of the Formula (I) and/or Examples herein is understood to include reference to salts thereof, unless otherwise indicated. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the Formula (I) may be formed, for example, by reacting a compound I with an amount of acid or base, such as an equivalent amount, in a medium such as one in which the salt precipitates or in an aqueous medium followed by lyophilization. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., Remington: *The Science and Practice of Pharmacy*, 22nd Edition, Pharmaceutical Press, London, UK (2012), the disclosure of which is hereby incorporated by reference.

"Base addition salt" refers to those salts which retain the biological effectiveness and properties of the free acids, which are not biologically or otherwise undesirable.

These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. In one aspect, inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. In another aspect, organic bases are isopropylamine, diethylamine, ethanolamine, trimethylamine, dicyclohexylamine, choline and caffeine.

"Acid addition salts" and "base addition salts" which are not pharmaceutically acceptable may be useful in the preparation and/or purification of the compounds.

The present invention is intended to cover the compounds in their neutral state, salts of those compounds, or mixtures of the compounds in their neutral state with one or more salt forms, or mixtures of salt forms.

In addition, compounds of Formula (I) may have prodrug forms. Any compound that will be converted in vivo to provide the bioactive agent (i.e., a compound of Formula (I)) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J., ed., Prodrugs and Targeted Delivery (Methods and Principles in Medicinal Chemistry), Vol. 47, Wiley-VCH (2011).

Compounds containing a carboxy group can form physiologically hydrolyzable esters that serve as prodrugs by being hydrolyzed in the body to yield Formula (I) compounds per se. Such prodrugs are preferably administered orally since hydrolysis in many instances occurs principally under the influence of the digestive enzymes.

Parenteral administration may be used where the esterper se is active, or in those instances where hydrolysis occurs in the blood. Examples of physiologically hydrolyzable esters of compounds of Formula (I) include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., Medicinal Chemistry: Principles and Practice, The Royal Society of Chemistry, Cambridge, UK (2nd Edition, reproduced (2006)); Testa, B. et al., Hydrolysis in Drug and Prodrug Metabolism. Chemistry, *Biochemistry and Enzymology*, VCHA and Wiley-VCH, Zurich, Switzerland (2003); Wermuth, C.G., ed., *The Practice of Medicinal Chemistry*, 3rd Edition, *Academic Press, San Diego, CA* (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^3$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates.

Other Definitions

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat" d for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "I H" for proton, "δ" for delta, "s" for singlet, "d" for doublet, "t" for triplet, "q" for quartet, "in" for multiplet, "br" for broad, "Hz" for hertz, and "α", "β", "R", "S", "E", "Z" and "ee" are stereochemical designations familiar to one skilled in the art.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and deprotection in the processes below may be carried out by procedures generally known in the art (see, for example, Wuts, P. G. M. et al., *Protecting Groups in Organic Synthesis*, 4th Edition, *Wiley* (2007)). General methods of organic synthesis and functional group transformations are found in: Trost, B. M. et al., eds., Comprehensive Organic Synthesis: Selectivity, Strategy & Efficiency in Modern Organic Chemistry, *Pergamon Press*, New York, NY (1991); Smith, M. B. et al., *March's Advanced Organic Chemistry: Reactions, Mechanisms, and Structure*. 6 th Edition, *Wiley & Sons*, New York, NY (2007); Katritzky, A. R. et al, eds., *Comprehensive Organic Functional Groups Transformations II*, 2nd Edition, *Elsevier Science Inc., Tarrytown, N Y* (2004); Larock, R. C., Comprehensive Organic Transformations, VCH Publishers, Inc., New York, NY (1999), and references therein.

Imidazolone biphenyl compounds with general structure IX may be prepared according to the synthetic scheme shown below. Thus, a functionalized imidazolone is alkylated with benzyl bromide VI using a base such as $K_2CO_3$ to form a boronate with general structure VII. Boronate VII is then reacted with a phenylbromide with general structure VIII in a Suzuki reaction using conditions such as 2M $K_3PO_4$, dioxane, $PdCl_2(dppf)_2$ at 100° C. to form imidazolone biphenyl compounds with general structure IX.

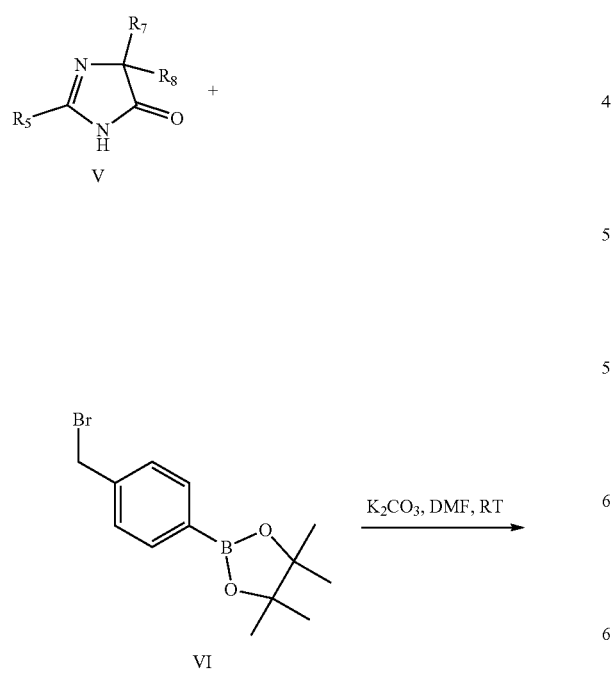

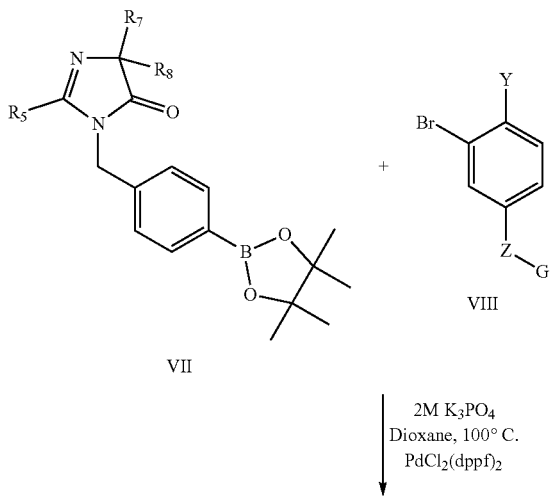

Imidazole biphenyl compounds with general structure XII, XIII and XIV may be prepared with the following scheme. Thus, a functionalized imidazole is alkylated with benzyl bromide VI using a base such as $K_2CO_3$ to form a boronate with general structure XI. Boronate XI is then reacted with phenyl bromide with general structure VIII in a Suzuki reaction using conditions such as 2M $K_3PO_4$, dioxane, $PdCl_2(dppf)_2$ at 100° C. to form biphenyl compounds with general structure XII. When $R_3$ is an ester, the ester may be hydrolyzed using NaOH in MeOH at 60° C. to form the free acid XIII. Free acid XIII may then be converted to an amide using T3P, Hunig's base, $NHR_2$ in DMF to form secondary and tertiary amides or CDI and $NH_4OH$ to form the primary amide.

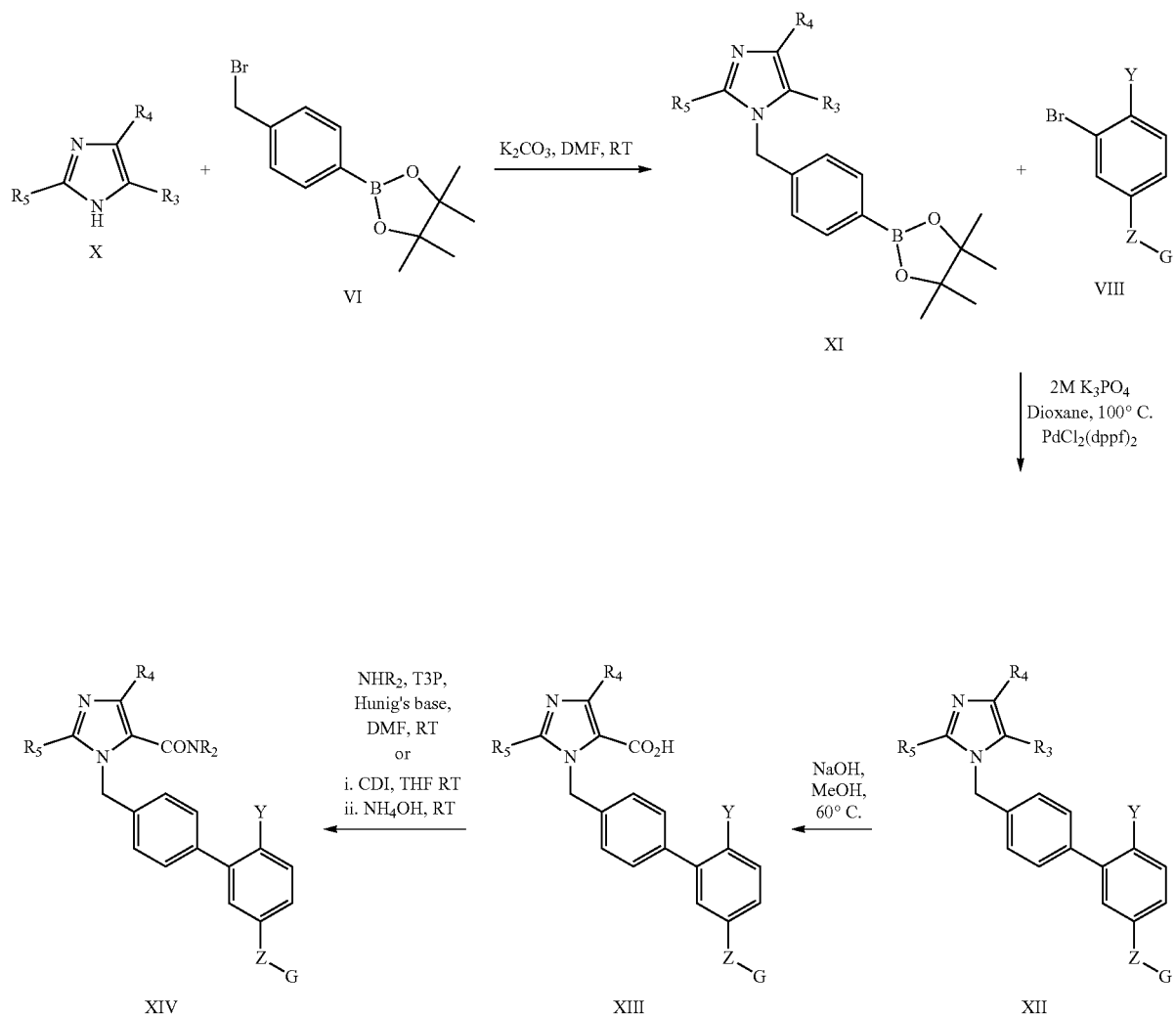

Biphenyl alpha-amido carboxylic acid with general structure XVIII may be prepared with the following scheme. Thus, a functionalized alpha-amido ester with general structure XV may be alkylated with benzyl bromide VI using a base such as $K_2CO_3$ to form a boronate with general structure XVI. Alkylated alpha-amido ester XVI may then be reacted with a phenylbromide with general structure VIII in a Suzuki reaction using conditions such as 2M $K_3PO_4$, dioxane, $PdCl_2(dppf)_2$ at 100° C. to form compounds with general structure XVII. The ester may be hydrolyzed using NaOH in MeOH at 60° C. to form the free acid with general structure XVIII.

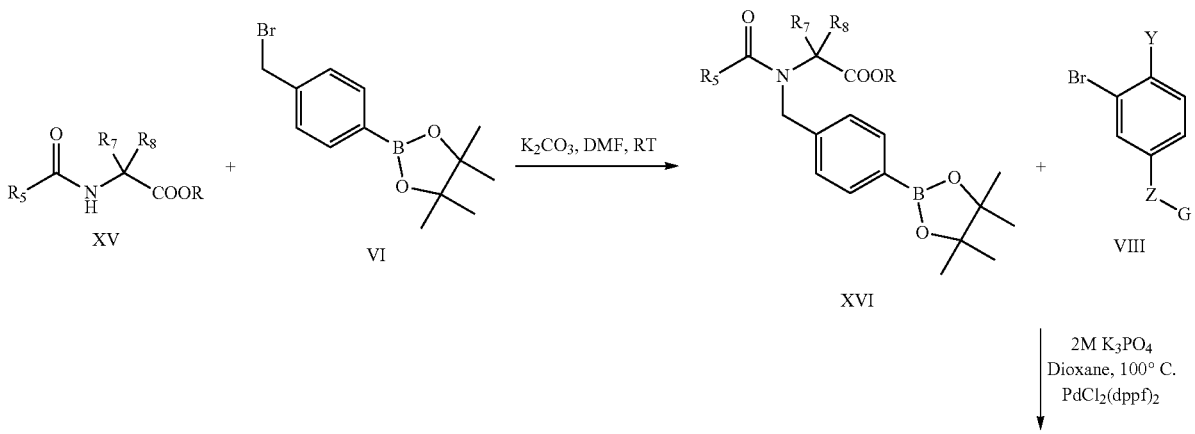


XVIII


XVII

Biphenyl tetrazoles with general structure XXII and biphenyl oxadiazolones with general structure XXIII may be prepared with the following scheme. Thus, boronates with general structure XIX may be reacted with a bromophenyl nitrile with general structure XX in a Suzuki reaction using conditions such as 2M $K_3PO_4$, dioxane, $PdCl_2(dppf)_2$ at 100° C. to form biphenyl nitrile with general structure XXI. The biphenyl nitrile may then be reacted with TMS-azide, dibutyltin oxide in toluene at 100° C. to form biphenyl tetrazole with general structure XXII. The biphenyl nitrile may also be reacted with KOt-Bu, hydroxylamine hydrochloride in THF, followed by CDI to form biphenyl oxadiazolone with general structure XXIII.

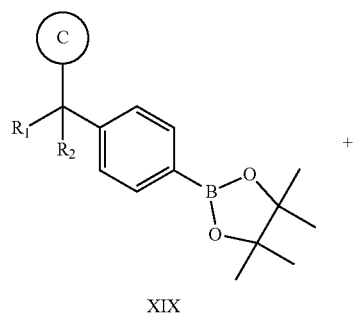

XIX

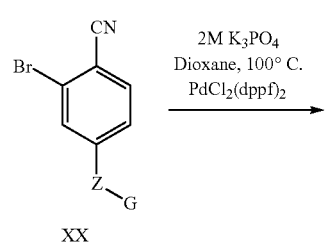

XX

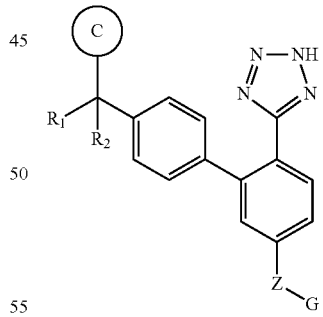

XXI

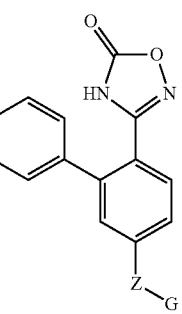

XXII  XXIII

Biphenyl acids with general structure XXVII may be prepared according to the following scheme. Thus, boronates with general structure XIX may be reacted with a bromophenyl ester with general structure XXIV in a Suzuki reaction using conditions such as 2M $K_3PO_4$, dioxane, $PdCl_2(dppf)_2$ at 100° C. to form biphenyl ester with general structure XXV. The biphenyl ester may then be hydrolyzed with NaOH in MeOH at 100° C. to form biphenyl acid with general structure XXVI.

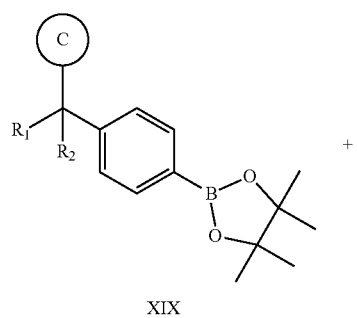

XIX

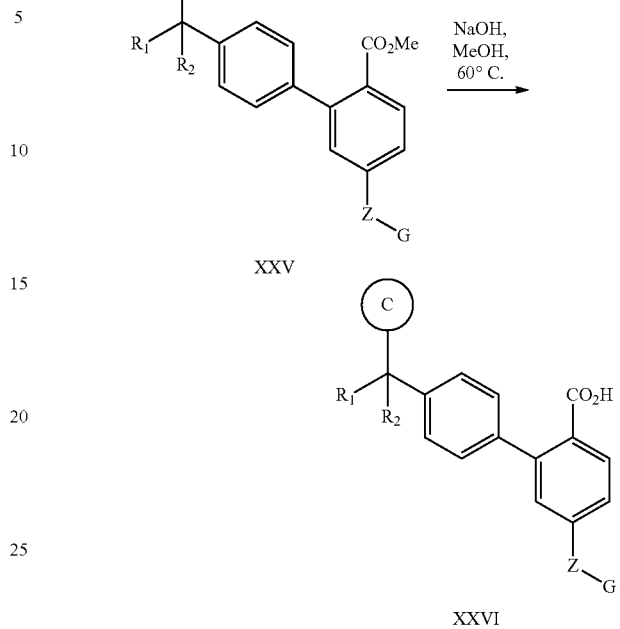

XXV

XXVI

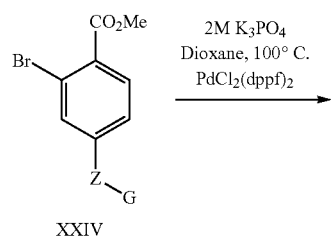

XXIV

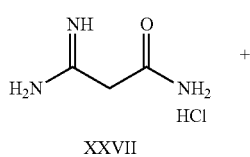

XXVII

Imidazopyridines may be prepared according the synthetic scheme shown below. Thus, a functionalized amidine XXVII is condensed with diketone XXVIII to afford the desired pyridine XXIX. This core then undergoes an oxidative cyclization followed by condensation with an acid derivative to furnish the imidazopyridine XXXI. This imidazopyridine is then alkylated with a boronic ester intermediate VI to give boronic ester XXXII. Subsequent Suzuki cross coupling with substituted arene VIII affords biaryl XXXIII.

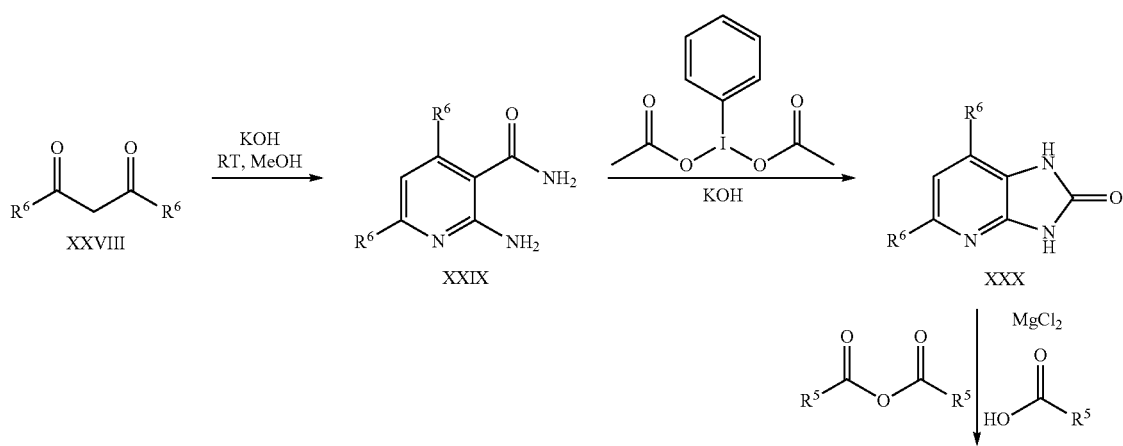

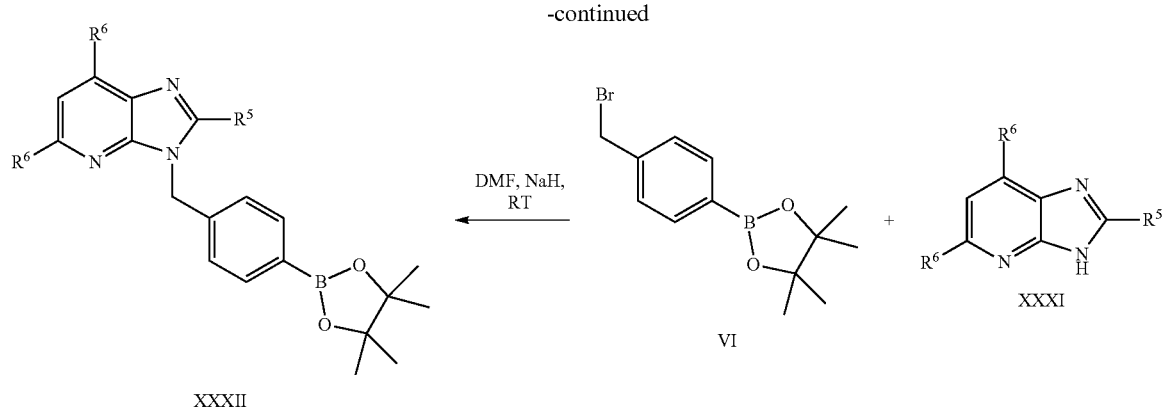

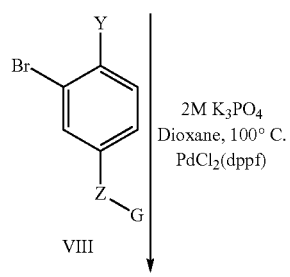

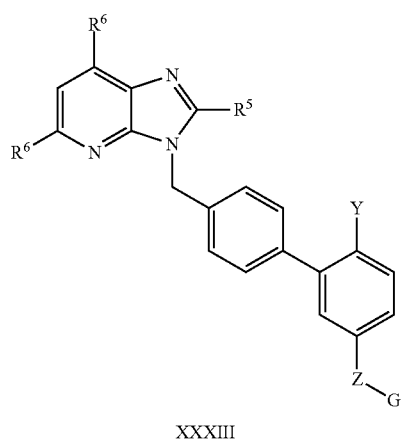

General synthetic pathway to access to the biarylacid imidazopyridine analogs: The imidazopyridine headpiece previously synthesized can also be alkylated with an aryl bromide which allows for Suzuki cross-coupling with a variety of substituted boronic acids containing a protected t-butyl-sulfonamide moiety. The t-butyl group can be subsequently removed to allow for further functionalization of the sulfonamide, thus providing the examples shown below.

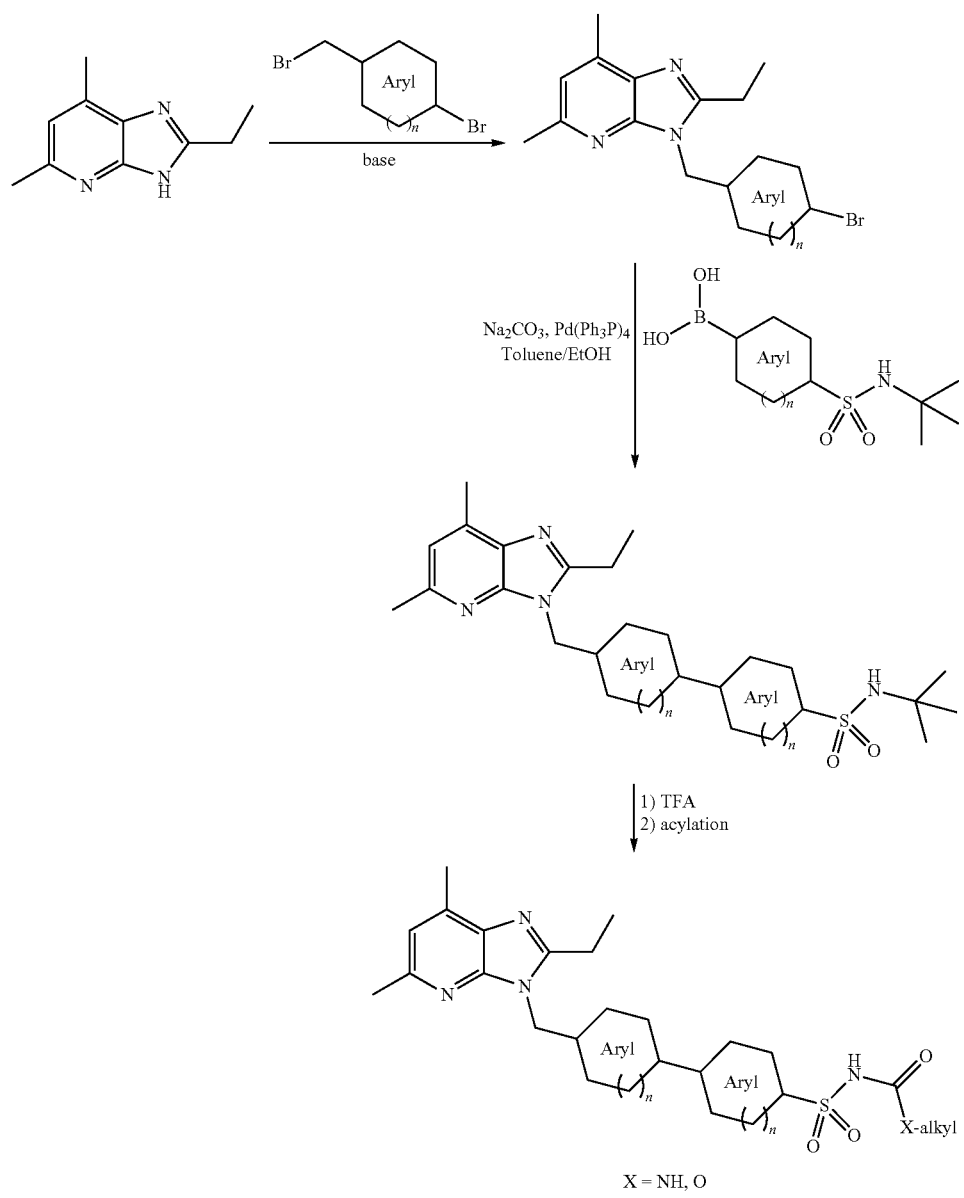
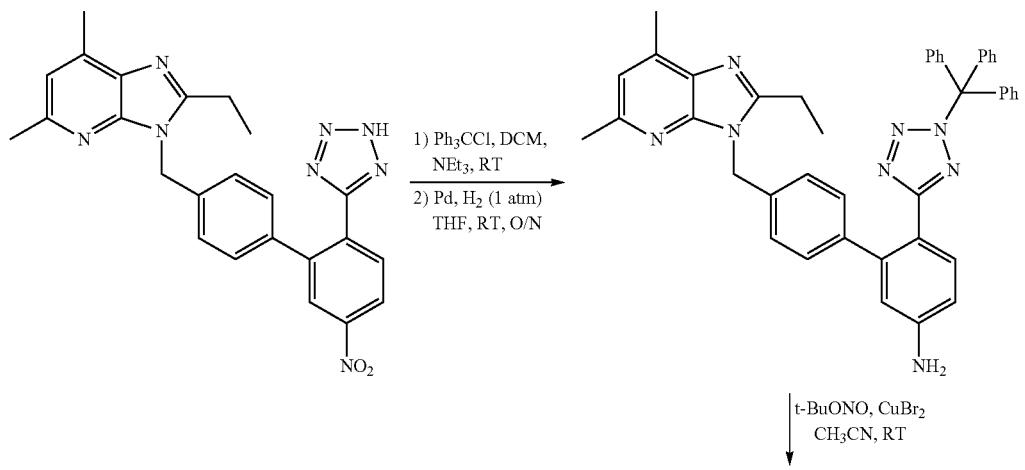

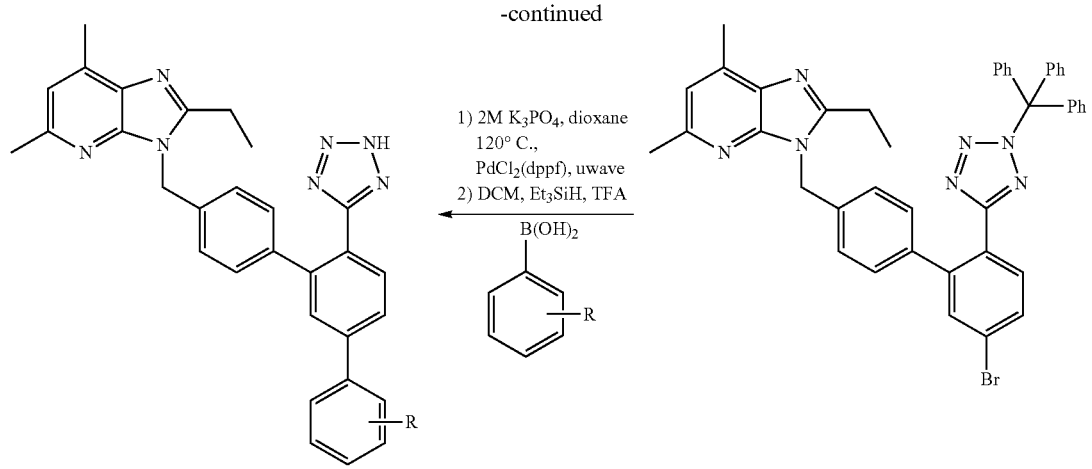
Compounds in which the Z-G group is an N-linked 1,2,3-triazole can be synthesized using the route shown in the scheme below:
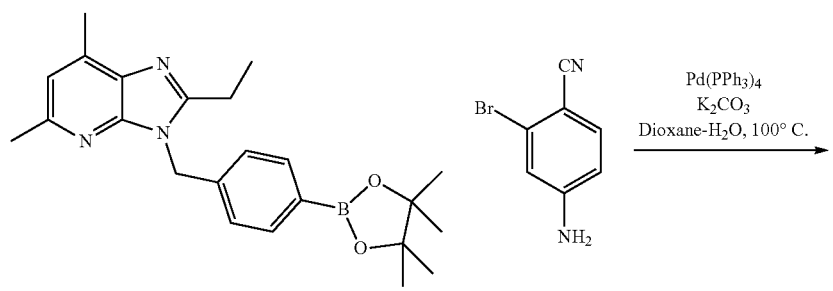
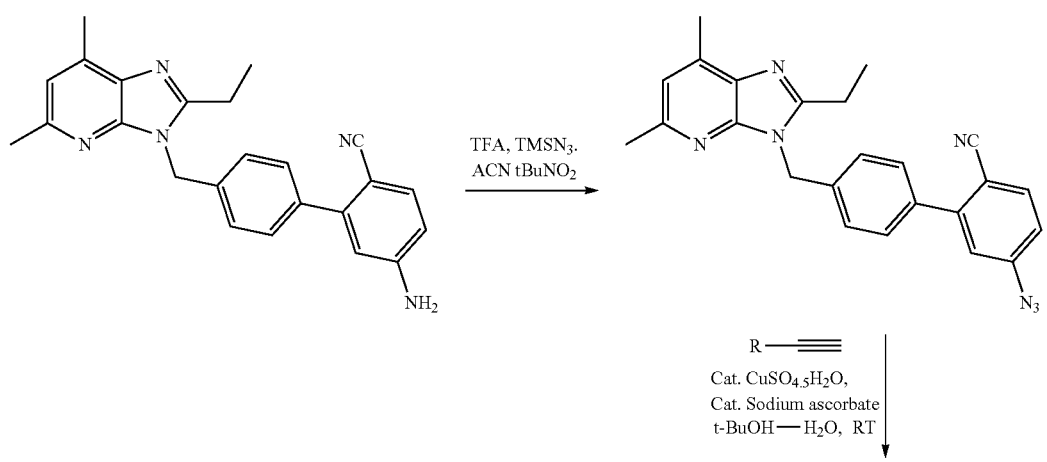

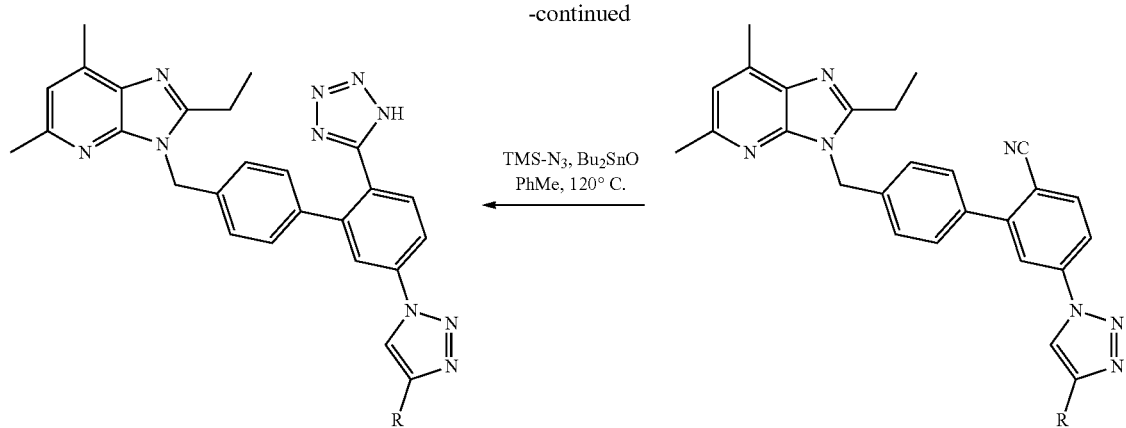
Compounds in which the Z-G group is a C-linked 1,2,3-triazole can be synthesized using the route shown in the scheme below:

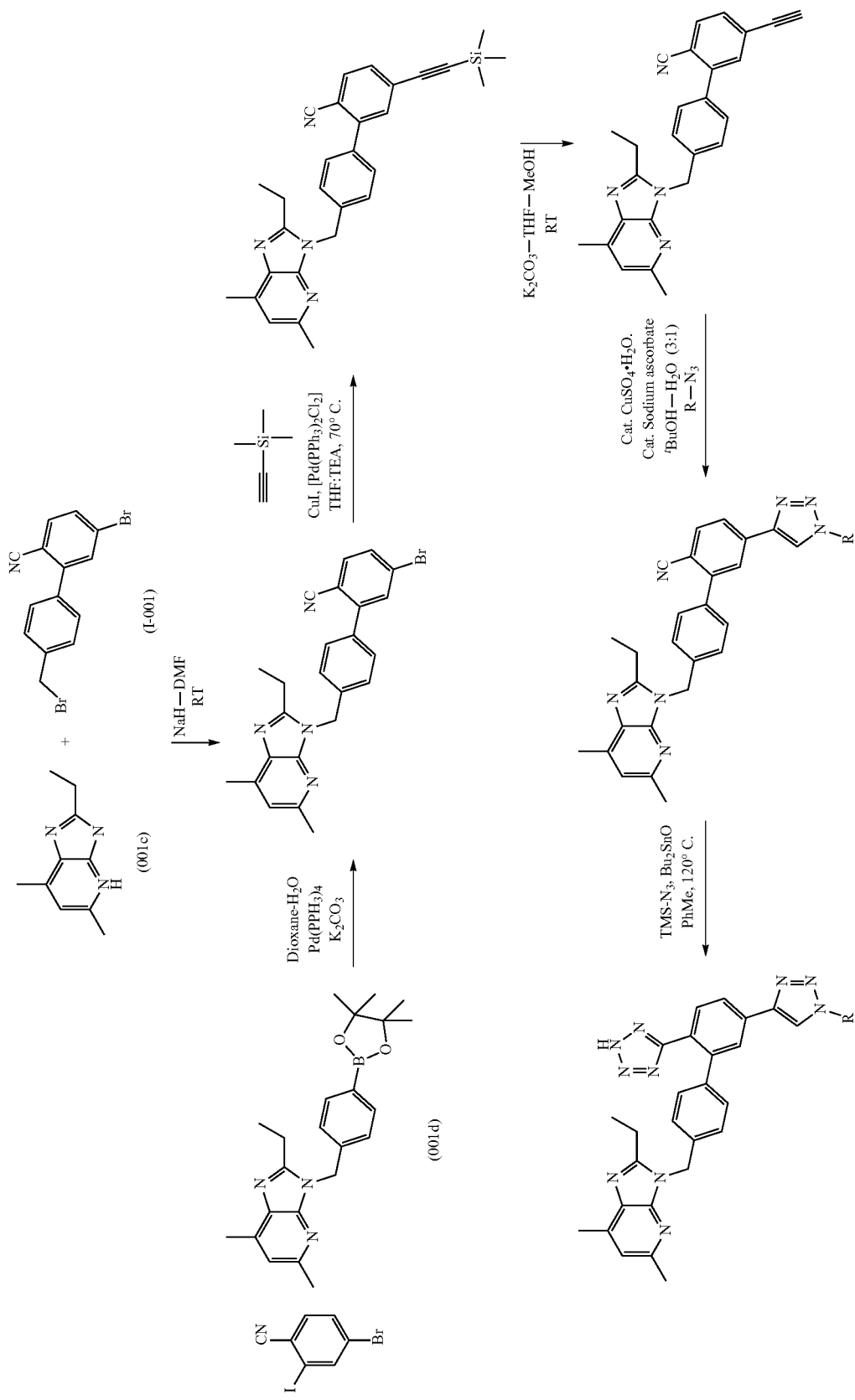

Benzimidazole compounds with general structure XL and XLI may be prepared with the following scheme. Thus, benzimidazole XXXIV is alkylated with benzyl bromide XXXV using a base such as $K_2CO_3$ to form a boronate XXXVI. Boronate XXXVI is then reacted with iodobenzonitrile XXXVII in a Suzuki reaction using conditions such as 2M $K_3PO_4$, dioxane, $PdCl_2(dppf)_2$ at 100° C. to form biphenyl compound XXXVIII.

For analogs in which Z-G is a substituted 2-pyridyl group, XXXVIII is reacted with BisPIN $Pd_2(dba)_3$ and Xphos in dioxane at 100° C. to form a boronate which is then reacted with a substituted 2-pyridyl bromide Z-G-Br using conditions such as $PdCl_2(dppf)_2$ and 2M $K_3PO_4$ in dioxane, at 100° C. to form nitrile XXXIX.

For analogs in which Z-G is not a substituted 2-pyridyl group, XXXVIII is reacted with a boronate or boronic acid Z-G-B(OR)$_2$ using conditions such as $PdCl_2(dppf)_2$ and 2M $K_3PO_4$ in dioxane, at 100° C. to form nitrile XXXIX.

Nitrile XXXIX can then be reacted with $Bu_3SnCl$, $NaN_3$ in xylenes at 140° C. followed by NaOH in MeOH/THF at 65° C. to form compounds with general structure XL. Alternatively, XXXIX can be reacted with BMIM[OAc], hydroxylamine HCl at 50° C. followed by NaOH in MeOH/THF at 65° C. to form compounds with general structure XLI.

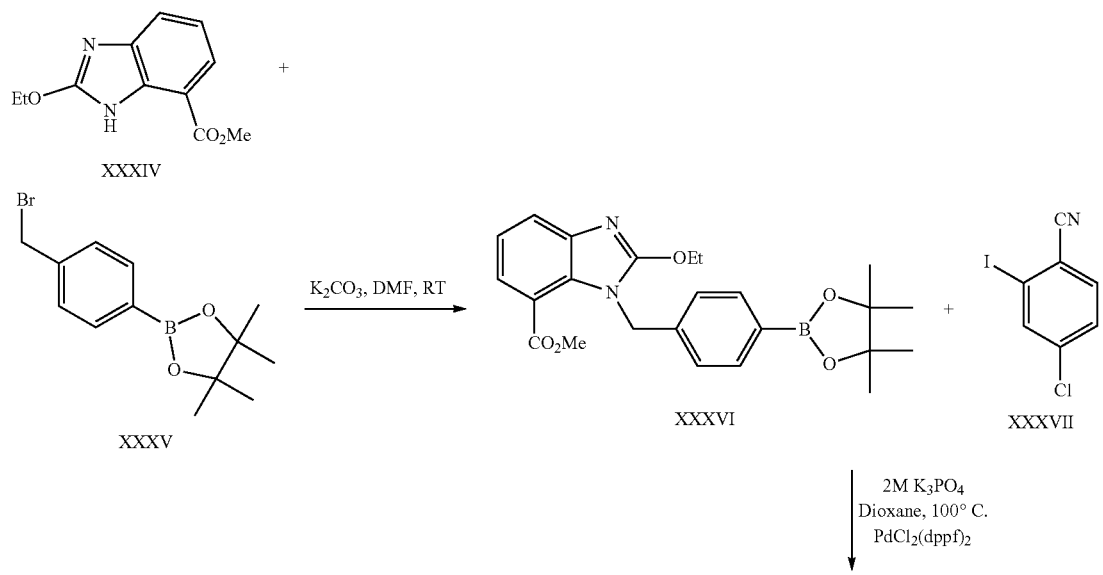

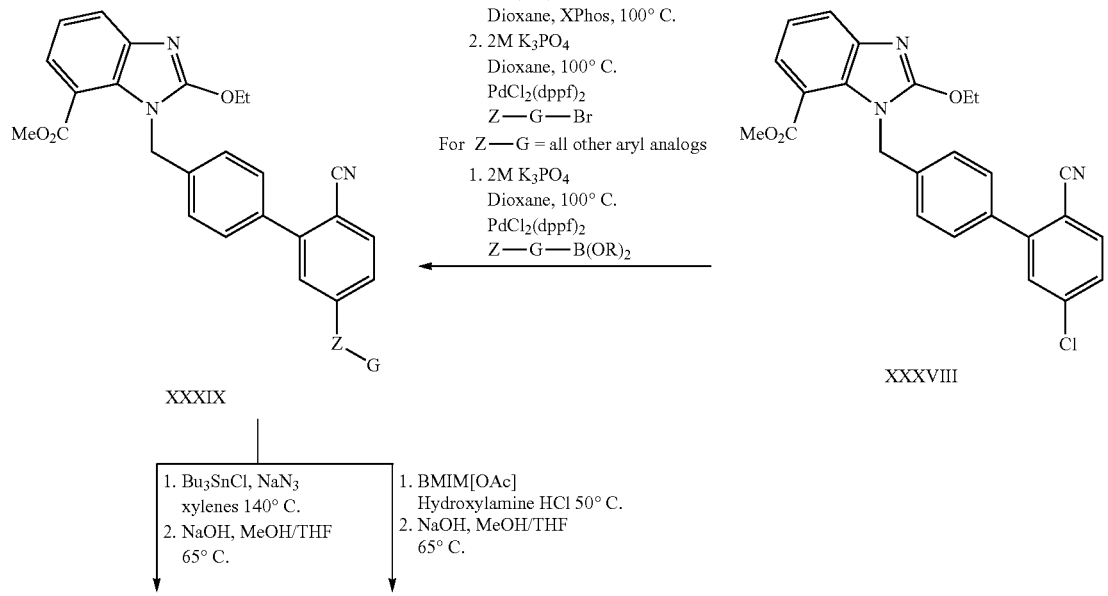

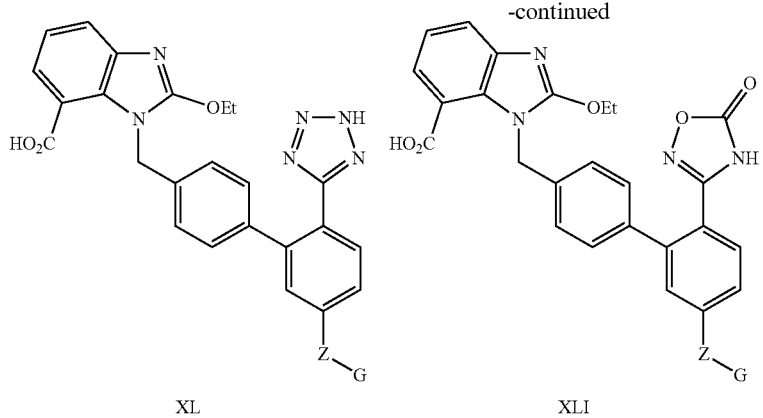

XL    XLI

Examples

The following compounds of the invention have been prepared, isolated and characterized using the methods disclosed herein. They demonstrate a partial scope of the invention and are not meant to be limiting of the scope of the invention. In the experimental procedures, solution ratios express a volume relationship, unless stated otherwise. NMR chemical shifts (δ) are reported in parts per million (ppm). Products were purified by reverse phase preparative HPLC and analyzed by reverse phase analytical LC-MS and HPLC using the following methods:

Method A1: Column: Waters Acquity UPLC BEH C18, 2.1×50 mm, 1.7-m particles; Mobile Phase A: 5:95 ACN:$H_2O$ with 10 mM $NH_4OAc$; Mobile Phase B: 95:5 ACN:$H_2O$ with 10 mM $NH_4OAc$; Temperature: 50° C.; Gradient: 0-100% B over 3 minutes, then a 0.75-minute hold at 100% B; Flow: 1.0 mL/min; Detection: MS and UV at 220 nm.

Method A2: Waters Acquity UPLC BEH C18, 2.1×50 mm, 1.7 μm particles; Mobile Phase A: $H_2O$ with 0.05% TFA; Mobile Phase B: ACN with 0.05% TFA; Gradient: 2-98% B over 1 minute, then a 0.5 minute hold at 98% B; Flow: 0.8 mL/min; Detection: MS and UV at 220 nm.

Method A3: Column: Waters XBridge C18, 2.1 mm×50 mm, 1.7 μm particles; Mobile Phase A: 5:95 ACN:$H_2O$ with 10 mM $NH_4OAc$; Mobile Phase B: 95:5 ACN:$H_2O$ with 10 mM $NH_4OAc$; Temperature: 50° C.; Gradient: 0% B to 100% B over 3 min, then a 0.75 min hold at 100% B; Flow: 1 mL/min; Detection: MS and UV (220 nm).

Method A4: Column: Waters XBridge C18, 2.1 mm×50 mm, 1.7 μm particles; Mobile Phase A: 5:95 ACN:$H_2O$ with 0.1% trifluoroacetic acid; Mobile Phase B: 95:5 ACN:$H_2O$ with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Method A5: Column: Phenomenex Luna C18 4.6×50 mm: Mobile Phase A: 10:90 MeOH:$H_2O$ with 0.1% trifluoroacetic acid; Mobile Phase B: 90:10 MeOH:$H_2O$ with 0.1% trifluoroacetic acid; Gradient: 0% B to 100% B over 2 min, then a 1 min hold at 100% B; Flow: 4 mL/min; Detection: MS and UV (220 nm).

Method B: Column Zorbax XDB-C18, 4.6×30 mm, 3.5 micron; Mobile Phase A: 5/95/0.05 MeOH/$H_2O$/TFA; Mobile Phase B: 95/5/0.05 MeOH/$H_2O$/TFA, gradient: 100% A to 100% B in 2 min then hold 100% B for 2 min, flow rate 3 mL/min, monitoring absorbance at 220 nm and 254 nm.

Method C: Column: Kinetex C18, 21.2×100 mm, 5 micron; Mobile Phase A: 5/95/0.05 MeOH/$H_2O$/TFA; Mobile Phase B: 95/5/0.05 MeOH/$H_2O$/TFA. Gradient: 3-minute at 30% B, then 30-100% B over 7 minutes and a 5-minute hold at 100% B; Flow: 20 mL/min; stop time at 15 minutes, monitoring absorbance at 220 nm and 254 nm.

Method D: Kinetex C18, 21×100 mm, 5 micron; Mobile Phase A: 5/95/0.1 MeOH/$H_2O$/$HCO_2H$; Mobile Phase B: 95/5/0.1 MeOH/$H_2O$/$HCO_2H$. Gradient: 3 minute at 30% B, then 30-100% B over 7 minutes and 5 minutes hold at 100% B; Flow: 20 mL/min; stop time 15 minutes, monitoring absorbance at 220 nm and 254 nm.

Method E: C18 Phenomenex Luna AXIA column 30×100 mm, 5 micron; Mobile Phase A: 10% MeOH-90% $H_2O$-0.1% TFA; Mobile Phase B: 90% MeOH-10% $H_2O$-0.1% TFA. Gradient: 20-100% B in 10 min; then 100% B in 2 min with a flow rate of 40 mL/min; stop time 12 minutes, monitoring absorbance at 220 nm and 254 nm.

Method F: Column: Kinetex C18, 21.2×100 mm, 5 micron; Mobile Phase A: 5/95/0.05 MeOH/$H_2O$/TFA or 5/95/0.1 MeOH/$H_2O$/$HCO_2H$; Mobile Phase B: 95/5/0.05 MeOH/$H_2O$/TFA or 95/5/0.1 MeOH/$H_2O$/$HCO_2H$. Gradient: 0.5 minute at 50% B, then 50-100% B over 8 minutes and a 2.5 minutes hold at 100% B; Flow: 20 mL/min; stop time at 11 minutes, monitoring absorbance at 220 nm and 254 nm.

Method G: Column: XBridge C18, 19×200 mm, 5 micron; Mobile Phase A: 5:95 ACN: $H_2O$ with 0.1% trifluoroacetic acid; Mobile Phase B: 95:5 ACN: $H_2O$ with 0.1% trifluoroacetic acid; Gradient: 10-50% B over 19 minutes, then a 5-minute hold at 100% B; Flow: 20 mL/min., monitoring absorbance at 220 nm and 254 nm.

Method H: Column Kinetex C18, 3.0×30 mm, 2.6 micron; Mobile Phase A: 5/95/0.1 MeOH/$H_2O$/AcOH; Mobile Phase B: 95/5/0.1 MeOH/$H_2O$/AcOH. Gradient: 100% A to 100% B over 0.5 min, then hold at 100% B for 1.5 min; Flow: 1.5 mL/min; stop time at 2 minutes, monitoring absorbance at 220 nm and 254 nm.

Method I: Column: XBridge C18, 19×200 mm, 5-μm particles; Mobile Phase A: 5:95 ACN: $H_2O$ with 10 mM $NH_4OAc$; Mobile Phase B: 95:5 ACN: $H_2O$ with 10 mM $NH_4OAc$; Gradient: 11-51% B over 25 minutes, then a 5-minute hold at 100% B; Flow: 20 mL/min.

Method J: Column: Kinetex-C18, 3.0×30 mm, 2.6 m particles; Mobile Phase A: 5:95 MeOH:$H_2O$ with 0.1% AcOH; Mobile Phase B: 95:5 MeOH:$H_2O$ with 0.1% AcOH; Gradient: 0-100% B over 2 minutes, flow 1.5 mL/min; Detector wavelength=220 nm and 254 nm Common Intermediate I-001:5-bromo-4'-(hydroxymethyl)-[1,1'-biphenyl]-2-carbonitrile

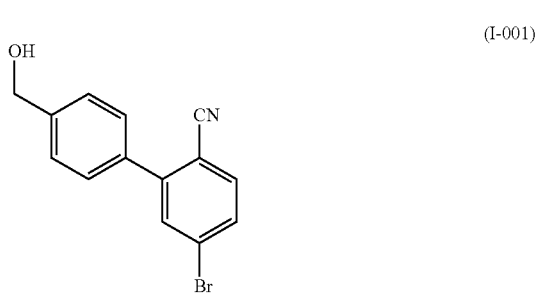 [SMILES: N#Cc1ccc(Br)cc1-c1ccc(CBr)cc1]
(I-001)

To a solution of (4-(hydroxymethyl)phenyl)boronic acid (400 mg, 2.6 mmol), 4-bromo-2-iodobenzonitrile (800 mg, 2.6 mmol) and Pd(PPh$_3$)$_4$ (66 mg, 0.057 mmol) in THF/MeOH (3:1, 12 ml) was added 1.5 N Na$_2$CO$_3$ (2.6 ml, 3.9 mmol). The reaction mixture was sealed, placed in a microwave reactor and heated at 120° C. for 60 min. LC-MS indicated completion of reaction. The reaction mixture was diluted with EtOAc/H$_2$O. The organic layer was collected, washed with brine, dried over Na$_2$SO$_4$ and concentrated. The crude product was purified by flash chromatography (2% to 60% EtOAc in hexane over 18 min using a 40 g silica gel cartridge). The desired fractions were combined and concentrated to yield I-001 (446 mg, 1.5 mmol, 60% yield) as a white solid. $^1$H NMR (500 MHz, CDCl$_3$) δ 7.72 (d, J=1.4 Hz, 1H), 7.67-7.60 (m, 2H), 7.60-7.51 (m, 4H), 4.81 (d, J=5.5 Hz, 2H), 1.80 (br t, J=5.8 Hz, 1H). $^{13}$C NMR (126 MHz, MeOH-d$_4$) δ 148.4, 144.1, 137.1, 136.2, 134.5, 132.3, 130.0, 129.3, 128.5, 119.3, 65.1. LC-MS: Waters Aquity BEH C18 2.1×50 mm, 1.7m; A: 90% H$_2$O+0.05% TFA; B: 90% ACN+0.05% TFA; wavelength 220 nm; flow rate 0.8 mL/min; gradient time 1.0 min; 2 to 98% B. RT=0.86 min, MS (ESI) m/z: 270.0 and 272.0 (M-18)$^+$.

Common Intermediate I-002:5-bromo-4'-(bromomethyl)-[1,1'-biphenyl]-2-carbonitrile

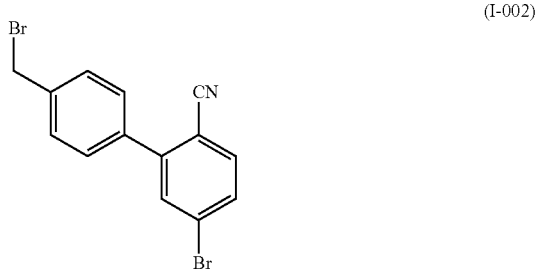
(I-002)

To a suspension of I-001 (522 mg, 1.8 mmol) in CH$_2$Cl$_2$ (10 ml) at 0° C. was added PBr$_3$ (0.19 ml, 2.0 mmol) in CH$_2$Cl$_2$ (1.0 mL). The reaction mixture was stirred at 0° C. for 15 min, and rt overnight. The mixture was diluted with CH$_2$Cl$_2$ and poured into a stirred ice-cold sat. NaHCO$_3$ solution. The organic layer was collected, washed with brine, dried over Na$_2$SO$_4$ and concentrated to yield I-002 (574 mg, 1.6 mmol, 90% yield) as a white solid. $^1$H NMR (400 MHz, CDCl$_3$) δ 7.69 (dd, J=1.5, 0.7 Hz, 1H), 7.64-7.58 (m, 2H), 7.53 (s, 4H), 4.54 (s, 2H).

Common Intermediate I-003: (6'-(2-trityl-2H-tetrazol-5-yl)-[1,1':3',1''-terphenyl]-4-yl)methanol

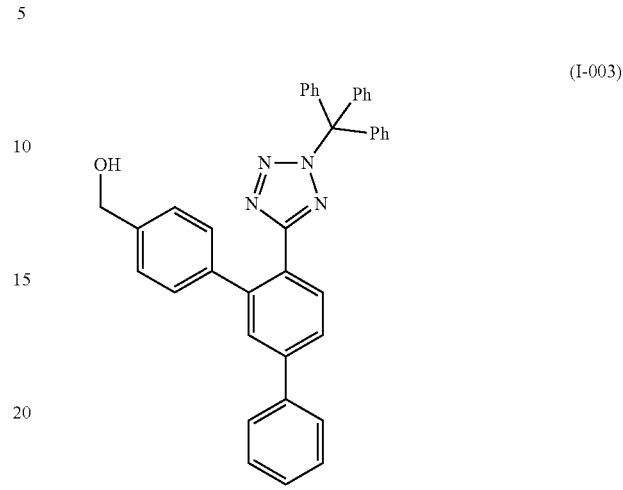
(I-003)

Intermediate I-003A: 3-bromo-[1,1'-biphenyl]-4-carbonitrile

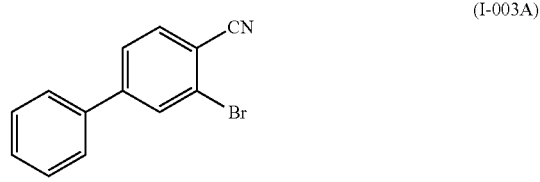 [SMILES: N#Cc1ccc(-c2ccccc2)cc1Br]
(I-003A)

To a solution of 3-amino-[1,1'-biphenyl]-4-carbonitrile (22 g, 113 mmol) in ACN (250 mL) was added copper(II) bromide (0.253 g, 1.133 mmol), CSA (31.6 g, 136 mmol), tetrabutylammonium bromide (73.0 g, 227 mmol) and tert-butyl nitrite (17.96 mL, 136 mmol) dropwise and the reaction mixture was stirred at 60° C. overnight. On the next day, the reaction mixture was filtered over celite, washed with EtOAc (100 ml) and the filtrate was concentrated. H$_2$O (500 ml) was added to the crude residue, followed by extraction with EtOAc (3×300 ml). The combined organic layers were washed with water (400 ml), brine (300 ml), dried over sodium sulfate and concentrated. The crude product was purified by silica gel chromatography and eluted with 30% EtOAc in petroleum ether.

The desired fractions were concentrated to give the desired product I-003A (20.5 g, 74.7 mmol, 65.9% yield) as a white solid. $^1$H NMR (400 MHz, DMSO-d$_6$) 8.20 (d, J=1.6 Hz, 1H), 8.027 (d, J=8 Hz, 1H), 7.92-7.89 (m, 1H), 7.81-7.79 (m, 2H), 7.55-7.48 (m, 3H).

Intermediate I-003B: methyl 6'-cyano-[1,1':3',1''-terphenyl]-4-carboxylate

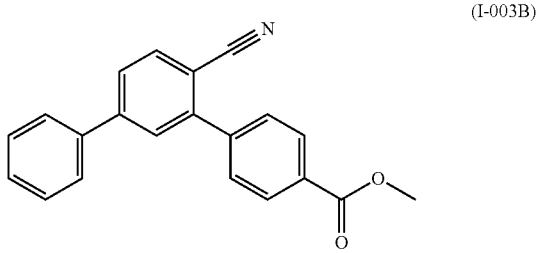 [SMILES: COC(=O)c1ccc(-c2cc(-c3ccccc3)ccc2C#N)cc1]

(I-003B)

In a flask charged with a stirring bar, a solution of I-003A (19 g, 73.6 mmol), (4-(methoxycarbonyl)phenyl)boronic acid (15.90 g, 88 mmol) and potassium phosphate, tribasic (73.6 mL, 147 mmol) in 1,4-dioxane (250 mL) was purged with $N_2$ for 10 min. Then bis(triphenylphosphine)palladium (II) chloride (5.17 g, 7.36 mmol) was added, and the mixture was again purged with $N_2$ for 5 min. The mixture was heated at 100° C. for 5 h. The reaction mixture was cooled to RT, filtered over celite bed, washed with EtOAc (100 ml) and concentrated to give the crude residue, to which $H_2O$ (500 ml) was added, stirred for 15 min, filtered and dried to give the crude product. The crude product was triturated with MTBE (100 ml) and the solid obtained was stirred for 15 min, filtered and dried to get the product which was slightly black in color. The product was dissolved in THF and was treated with charcoal at 60° C., filtered and concentrated to give the desired I-003B (18 g, 57.4 mmol, 78% yield) as a yellow solid. $^1$H NMR (500 MHz, CDCl$_3$) 8.27-8.15 (m, 2H), 7.93-7.84 (m, 1H), 7.78-7.70 (m, 4H), 7.68-7.63 (m, 2H), 7.58-7.43 (m, 3H), 3.99 (s, 3H).

Intermediate I-003C: methyl 6'-(2H-tetrazol-5-yl)-[1,1':3',1''-terphenyl]-4-carboxylate

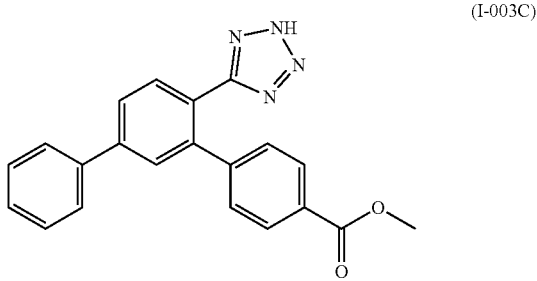 [SMILES: COC(=O)c1ccc(-c2cc(-c3ccccc3)ccc2-c2nn[nH]n2)cc1]

(I-003C)

A solution of I-003B (7.5 g, 23.93 mmol), TMS-$N_3$ (15.88 mL, 120 mmol) and dibutyltin oxide (5.96 g, 23.93 mmol) in toluene (175 mL) was heated in a sealed tube at 100° C. overnight. Methanol (20 ml) was first added to the reaction and the resulting solution was diluted with EtOAc. To this organic phase was added ceric ammonium nitrate (75 g dissolved in 1 L of $H_2O$) dropwise and with swirling until bubbling ceased ($N_2$ gas evolution). To the mixture was added sat. NH$_4$Cl solution (250 ml) and then it was extracted with EtOAc (150 ml×3). The combined organic layers were washed with $H_2O$ (500 ml), brine (400 ml), dried over sodium sulphate, and concentrated to give the crude product. The crude product was triturated with MTBE (150 ml) and the solid obtained was stirred for 30 min, filtered, washed with MTBE (50 ml) and dried to give the I-003C (7.25 g, 18.43 mmol, 77% yield) as the product. $^1$H NMR (500 MHz, MeOH-d$_4$) δ 8.01 (d, J=8.3 Hz, 2H), 7.92-7.87 (m, 1H), 7.86-7.81 (m, 2H), 7.77 (d, J=7.7 Hz, 2H), 7.58-7.49 (m, 2H), 7.45 (d, J=7.4 Hz, 1H), 7.35 (d, J=8.5 Hz, 2H), 3.93 (s, 3H);); LC-MS: method A2, Rt=0.89 min, MS (ESI) m/z: 357.10 (M+H)$^+$.

Intermediate I-003D: methyl 6'-(2-trityl-2H-tetrazol-5-yl)-[1,1':3',1''-terphenyl]-4-carboxylate

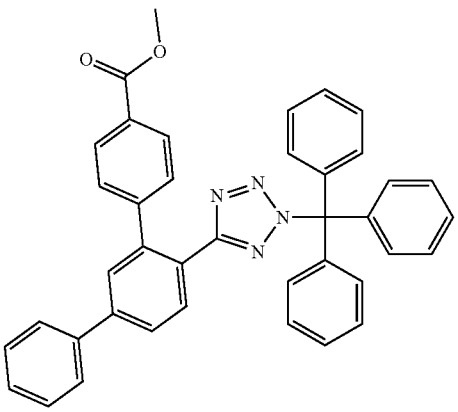

(I-003D)

To a solution of I-003C (14.5 g, 40.7 mmol) and TEA (11.34 mL, 81 mmol) in DCM (200 mL) was added trityl-C$_1$ (17.01 g, 61.0 mmol) and the reaction mixture was stirred at RT overnight. To the reaction mixture $H_2O$ (300 ml) was added and extracted with DCM (2×200 ml). The combined organic layers was washed with $H_2O$ (300 ml), brine (200 ml), dried over sodium sulphate and concentrated to get the crude product. The crude product was triturated with MeOH (300 ml) and the solid obtained was stirred for 30 min, filtered, washed with MeOH (100 ml) and dried to give I-003D (22 g, 34.5 mmol, 85% yield) as the product. $^1$H NMR (500 MHz, CDCl$_3$) δ 8.14 (d, J=8.0 Hz, 1H), 7.84 (d, J=8.3 Hz, 2H), 7.76 (dd, 1=8.1, 1.8 Hz, 1H), 7.68 (d, J=7.4 Hz, 2H), 7.63 (d, J=1.7 Hz, 1H), 7.52-7.46 (m, 2H), 7.44-7.40 (m, 1H), 7.38-7.16 (m, 11H), 6.93 (d, J=7.7 Hz, 7H), 3.96 (s, 3H).

Common Intermediate I-003

I-003D (1 g, 1.670 mmol) was dissolved in THF (20 mL). Methanol (0.135 mL, 3.34 mmol) was added at 0° C. followed by 2M lithium borohydride in THF (1.670 mL, 3.34 mmol). The reaction was allowed to stir at 40° C. overnight. The reaction was quenched with ~10 mL of $H_2O$ at 0° C. and allowed to stir at RT for 3 hours. The reaction mixture was then extracted with EtOAc (3x) and the combined organic layer was washed with brine, dried with sodium sulfate, filtered and concentrated. The residue was purified on 80 g silica gel cartridge on ISCO, which was eluted with a 30 min gradient of 0-100% EtOAc in hexane. The desired fraction was evaporated to give Common Intermediate I-003 (0.736 g, 1.290 mmol, 77% yield) as a white solid. $^1$H NMR (400 MHz, CDCl$_3$) δ 8.05 (s, 1H), 7.73-7.68

(m, 1H), 7.64 (d, J=6.2 Hz, 3H), 7.46 (s, 2H), 7.40-7.24 (m, 10H), 7.21-7.16 (m, 2H), 7.14 (s, 2H), 6.94-6.81 (m, 6H), 4.59 (d, J=5.9 Hz, 2H).

Common Intermediate I-004:5-(4"-(bromomethyl)-[1,1':3',1"-terphenyl]-4'-yl)-2-trityl-2H-tetrazole

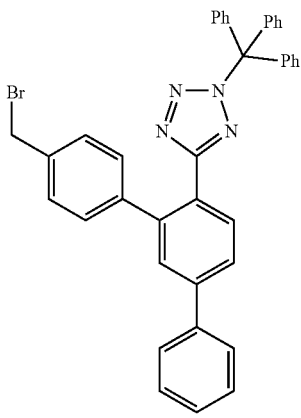
(I-004)

To an ice-cold mixture of (6'-(2-trityl-2H-tetrazol-5-yl)-[1,1':3',1"-terphenyl]-4-yl)methanol
(Intermediate I-003, 0.750 g, 1.31 mmol) in DCM (15 mL) was added triphenylphosphine (0.479 g, 1.45 mmol) and 2,6-dimethylpyridine (0.169 g, 1.58 mmol). To this mixture was added carbon tetrabromide (0.470 g, 1.45 mmol) in one portion and the reaction mixture was stirred for 15 min. The volatiles were then evaporated while maintaining a pot temperature of 0° C. The oily residue was dissolved in DCM (5 ml), a minimum volume of hexane was added and the resulting slightly turbid mixture was applied to a 40 gram ISCO-type silica gel column. Flash chromatography (0 to 30% EtOAc/hexane gradient) then afforded the title compound (0.760 g, 1.20 mmol, 91% yield) as a white solid. $^1$H NMR (CDCl$_3$) δ ppm 8.08 (d, J=7.8 Hz, 1H), 7.71 (dd, J=8.0, 1.8 Hz, 1H), 7.59-7.68 (m, 3H), 7.42-7.49 (m, 2H), 7.31-7.41 (m, 4H), 7.23-7.31 (m, 6H), 7.11-7.18 (m, 4H), 6.88-6.95 (m, 6H), 4.40 (s, 2H).

Common Intermediate I-005: methyl 2-ethoxy-1-(4-(4,4,5,5-tetramethyl-1,3,2-dioxaborolan-2-yl)benzyl)-1H-benzo[d]imidazole-7-carboxylate

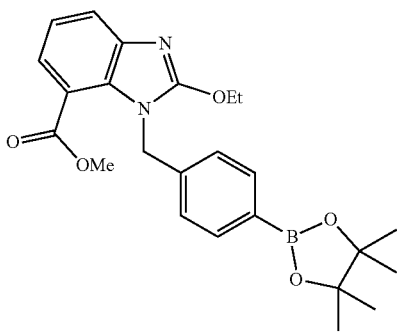
(I-005)

To a solution of methyl 2-ethoxy-1H-benzo[d]imidazole-7-carboxylate (1.00 g, 4.54 mmol) in 2-propanol (15 ml) was added potassium carbonate (1.26 g, 9.08 mmol) and this was stirred at 30° C. for 5 minutes. To this mixture were added 2-(4-(bromomethyl)phenyl)-4,4,5,5-tetramethyl-1,3,2-dioxaborolane (1.44 g, 4.77 mmol) and tetrabutylammonium iodide (0.084 g, 0.227 mmol) and the temperature was increased to ° C. After stirring for 2.5 hours, another portion of 2-(4-(bromomethyl)phenyl)-4,4,5,5-tetramethyl-1,3,2-dioxaborolane (0.250 g, 0.842 mmol) was added and the reaction was stirred for an additional 18 hours. The reaction was cooled to RT and diluted with EtOAc (200 ml), and H$_2$O (50 ml) was added. The layers were separated and the organic layer was washed with brine (50 ml), then dried over anhydrous sodium sulfate, filtered, and evaporated under reduced pressure. The residue was dissolved in DCM (10 ml) and injected on a 40-gram ISCO-type silica gel column pre-equilibrated with hexane and the title compound was purified by elution using a 0 to 60% EtOAc/hexane gradient to provide the title compound as a yellow solid. (1.44 g, 3.31 mmol, 72% yield). LC-MS (Method H): 1.42 min, [M+H]$^+$= 437.2; $^1$H NMR (400 MHz, CDCl$_3$) δ ppm 7.73 (dd, J=8.0, 1.0 Hz, 1H) 7.67 (m, J=8.2 Hz, 2H) 7.53 (dd, J=7.8, 1.2 Hz, 1H) 7.16 (t, J=7.8 Hz, 1H) 6.96 (m, J=8.2 Hz, 2H) 5.63 (s, 2H) 4.65 (q, J=7.0 Hz, 2H) 3.72 (s, 3H) 1.46 (t, J=7.0 Hz, 3H) 1.31 (s, 12H).

Example 001: 3-((6'-(2H-tetrazol-5-yl)-2"-(trifluoromethoxy)-[1,1':3',1"-terphenyl]-4-yl)methyl)-2-ethyl-5,7-dimethyl-3H-imidazo[4,5-b]pyridine

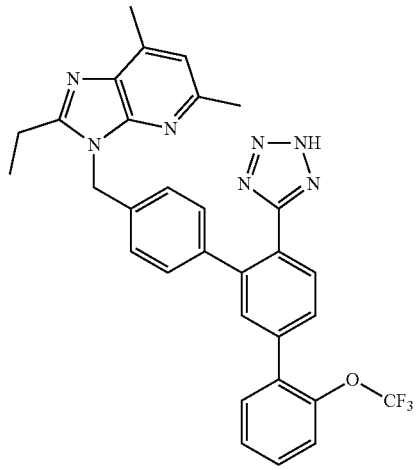
(Ex. 001)

Intermediate 001a:
2-amino-4,6-dimethylnicotinamide

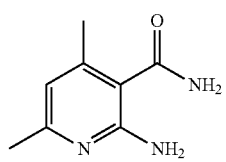
(001a)

The title compound was prepared from 3-amino-3-iminopropanamide hydrochloride (1.376 g, 10 mmol) and pentane-2,4-dione (1.073 mL, 10.50 mmol) according to the procedure described in J. Med. Chem. 2007, 50, 828. The crude was purified by ISCO (DCM/MeOH, 0-20%) to afford 001a (1.54 g, 9.32 mmol, 93% yield) as a white solid. LC-MS (Method A2): 0.32 min, [M+H]$^+$=166.0; $^1$H NMR (400 MHz, MeOD) δ ppm 6.43 (s, 1H), 2.28 (s, 3H), 2.28 (s, 3H).

Intermediate 001b: 5,7-dimethyl-1H-imidazo[4,5-b]pyridin-2(3H)-one (001b)

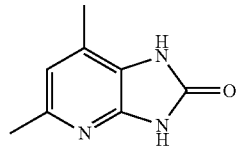

A solution of 2-amino-4,6-dimethylnicotinamide (001a, 0.470 g, 2.85 mmol) in MeOH (14.2 mL) was treated with potassium hydroxide (0.559 g, 9.96 mmol) and iodobenzene diacetate (1.375 g, 4.27 mmol) as described in J. Med. Chem. 2011, 54, 4219. The crude was purified by ISCO (DCM/MeOH, 0-20%) to afford the title compound as an off-white solid (0.235 g, 1.440 mmol, 50.6% yield). LC-MS (Method A2): 0.42 min, [M+H]$^+$=164.1; $^1$H NMR (400 MHz, DMSO-d$_6$) δ ppm 11.03 (br s, 1H), 10.76 (s, 1H), 6.64 (s, 1H), 2.33 (s, 3H), 2.23 (s, 3H).

Intermediate 001c: 2-ethyl-5,7-dimethyl-3H-imidazo[4,5-b]pyridine (001c)

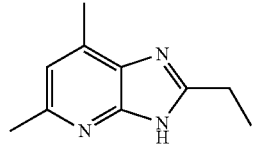

Intermediate 001b (0.224 g, 1.373 mmol) was treated with propionic acid (1.95 mL, 26.1 mmol), propionic anhydride (1.94 mL, 15.10 mmol) and magnesium chloride (0.196 g, 2.059 mmol) as described in J. Med. Chem. 2007, 50, 828. The crude was purified by ISCO (DCM/MeOH, 0-20%) to yield the title compound as a brown oil (0.220 g, 1.130 mmol, 82% yield). LC-MS (Method A2): 0.42 min, [M+H]J=176.7; $^1$H NMR (400 MHz, MeOD) δ ppm 7.05 (s, 1H), 2.98 (q, J=7.6 Hz, 2H), 2.59 (s, 6H), 1.43 (t, J=7.7 Hz, 3H).

Intermediate 001d: 2-ethyl-5,7-dimethyl-3-(4-(4,4,5,5-tetramethyl-1,3,2-dioxaborolan-2-yl)benzyl)-3H-imidazo[4,5-b]pyridine (001d)

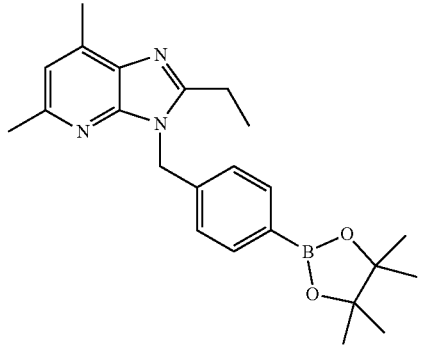

To a solution of Intermediate 001c (1.2 g, 6.85 mmol) in DMF (41.5 mL) was added sodium hydride (0.498 g, 12.45 mmol) at RT and the reaction was stirred vigorously for 30 min. Then a solution of 2-(4-(bromomethyl)phenyl)-4,4,5,5-tetramethyl-1,3,2-dioxaborolane (1.849 g, 6.23 mmol) in DMF (20.75 mL) was added and the resulting reaction mixture was allowed to stir for 2 h before being quenched with a saturated aqueous solution of NH$_4$Cl. The mixture was diluted with EtOAc and extracted. The organic phase was dried over MgSO$_4$, filtered and concentrated before being purified by ISCO (hexane/EtOAc, 0-100%) to afford the title compound (1.35 g, 3.45 mmol, 55.4% yield) as a light yellow solid. LC-MS (Method A2): 0.81 min, [M+H]$^+$=392.4; $^1$H NMR (500 MHz, CDCl$_3$) δ ppm 7.71 (d, J=8.0 Hz, 2H), 7.08 (d, J=8.0 Hz, 2H), 6.88 (s, 1H), 5.46 (s, 2H), 2.74 (q, J=7.5 Hz, 2H), 2.63 (s, 3H), 2.57 (s, 3H), 1.31 (s, 12H), 1.27 (t, J=7.6 Hz, 3H).

Intermediate 001e: 2-bromo-4-nitrobenzonitrile (001e)

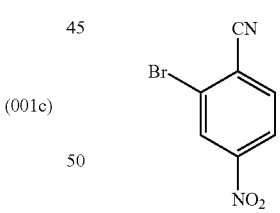

A solution of 4-nitrobenzonitrile (1.0 g, 6.75 mmol) in DCE (27.0 mL) was treated with NBS (1.322 g, 7.43 mmol), CSA (0.784 g, 3.38 mmol) and diacetoxypalladium (0.152 g, 0.675 mmol) according to the procedure described in JOC, 2013, 78, 2786. After 16 h at 70° C., LC-MS analysis only showed about 60% conversion. Another portion of diacetoxypalladium (0.152 g, 0.675 mmol) was added along with NBS (0.5 eq., 0.600 g) and the reaction mixture was reheated at 70° C. for 7.5 h. The cooled reaction mixture was diluted with DCM, washed with 1.5 M aqueous K$_2$HPO$_4$, followed by saturated aqueous NH$_4$Cl. The organic phase was dried over MgSO$_4$, filtered, concentrated and purified by ISCO (Hexanes/EtOAc, 0-100%) to afford the title compound Intermediate 001e(1.01 g, 4.45 mmol, 65.9% yield) as a white solid. LC-MS (Method A2): 0.82 min, [M+H] No ion observed; $^1$H NMR (400 MHz, CDCl$_3$) δ ppm 8.56 (d, J=2.2 Hz, 1H), 8.29 (dd, J=8.6, 2.2 Hz, 1H), 7.88 (d, J=8.6 Hz, 1H).

Intermediate 001f: 4'-((2-ethyl-5,7-dimethyl-3H-imidazo[4,5-b]pyridin-3-yl)methyl)--nitro-[1,1'-biphenyl]-2-carbonitrile

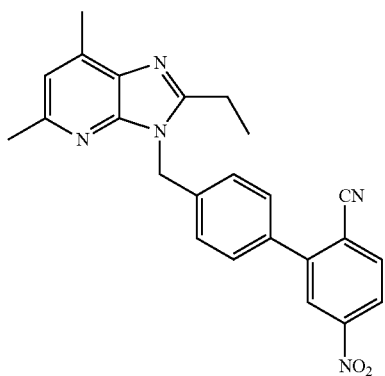

(001f)

A mixture of Intermediate 001d (0.670 g, 1.712 mmol) and Intermediate 001e (0.466 g, 2.055 mmol) in dioxane (11.4 mL) was treated with K$_3$PO$_4$ (2M aq., 2.14 ml, 4.28 mmol) followed by PdCl$_2$(dppf) (0.125 g, 0.171 mmol). The resulting mixture was degassed with N$_2$ for 2 min before the reaction vessel was sealed and heated at 100° C. overnight. The cooled reaction mixture was concentrated to dryness and the residue purified by ISCO (Hexanes/AcOEt, 0-100%) to afford the title compound (Intermediate 001f, 0.540 g, 1.312 mmol, 77% yield) as an amber oil. LC-MS (Method A2): 0.79 min, [M+H]$^+$=412.2; $^1$H NMR (500 MHz, CDCl$_3$) δ ppm 8.33 (d, J=2.2 Hz, 1H), 8.27 (dd, J=8.4, 2.3 Hz, 1H), 7.95 (d, J=8.5 Hz, 1H), 7.53 (d, J=8.3 Hz, 2H), 7.30 (d, J=8.3 Hz, 2H), 6.92 (s, 1H), 5.55 (s, 2H), 2.83 (q, J=7.4 Hz, 2H), 2.64 (s, 3H), 2.60 (s, 3H), 1.35 (t, J=7.6 Hz, 3H).

Intermediate 001 g: 2-ethyl-5,7-dimethyl-3-((5'-nitro-2'-(2H-tetrazol-5-yl)-[1,1'-biphenyl]-4-yl)methyl)-3H-imidazo[4,5-b]pyridine (001g)

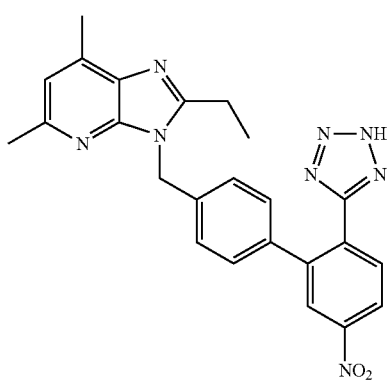

To a solution of Intermediate 001f (0.250 g, 0.608 mmol) in toluene (6.1 mL) was added dibutyltin oxide (0.151 g, 0.608 mmol) and TMS-N$_3$ (0.403 mL, 3.04 mmol). Then the reaction vessel was sealed and the mixture was heated at 110° C. overnight behind a blast shield (according to the procedure described in J. Org. Chen, 1993, 58, 4139). After cooling, the reaction mixture was diluted with MeOH and EtOAc and quenched by the portionwise addition of a 10% aqueous solution of CAN (16.700 g, 3.05 mmol) until bubbling ceased. The resulting mixture was stirred at RT for 30 min, then partitioned with saturated aqueous NH$_4$Cl and EtOAc. The organic phase was dried over MgSO$_4$, filtered and concentrated to give a yellow foam which was purified by ISCO (DCM/MeOH, 0-20%) to afford the title compound as a light yellow foam (0.250 g, 0.550 mmol, 91% yield). LC-MS (Method A2): 0.71 min, [M+H]$^{*,2}$ 455.3; $^1$H NMR (400 MHz, CDCl$_3$) δ ppm 8.37-8.19 (m, 2H), 8.08 (br. s., 1H), 7.18-7.10 (m, 2H), 7.08-7.02 (m, 2H), 6.97 (s, 1H), 5.50 (s, 2H), 2.77 (q, J=7.2 Hz, 2H), 2.60 (s, 3H), 2.48 (s, 3H), 1.05 (t, J=7.4 Hz, 3H).

Intermediate 001h: 2-ethyl-5,7-dimethyl-3-((5'-nitro-2'-(2-trityl-2H-tetrazol-5-yl)-[1,1'-biphenyll-4-yl)methyl)-3H-imidazo[4,5-b]pyridine (001h)

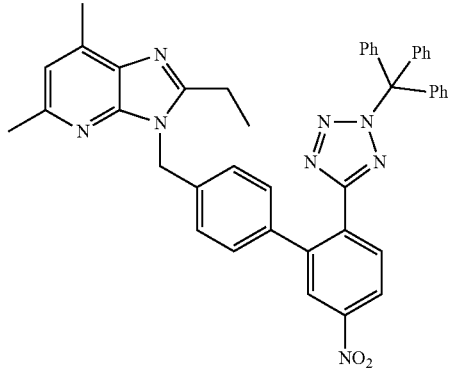

To a solution of Intermediate 001 g (1.6 g, 3.52 mmol) in DCM (17.6 mL) at RT was added triethylamine (0.638 mL, 4.58 mmol) followed by trityl chloride (1.030 g, 3.70 mmol). After 20 min, the reaction mixture was quenched with few drops of MeOH, diluted with DCM and washed with 1 M aqueous K$_2$HPO$_4$. The organic phase was dried over MgSO$_4$, filtered and concentrated. A quantitative yield was assumed and the product was taken to the subsequent reduction step without further purification. LC-MS (Method A2): 1.06 min, [M+H]$^+$=697.1.

Intermediate 001i: 4'-((2-ethyl-5,7-dimethyl-3H-imidazo[4,5-b]pyridin-3-yl)methyl)-6-(2-trityl-2H-tetrazol-5-yl)-[1,1'-biphenyl]-3-amine

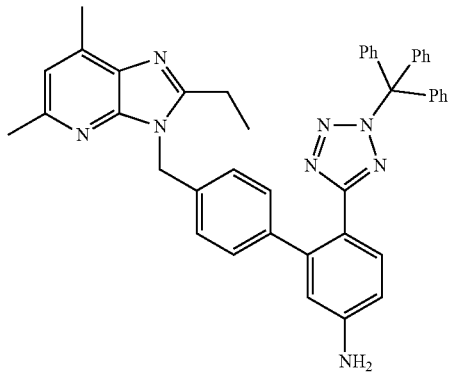

(001i)

Intermediate 001h (2.15 g, 3.09 mmol) was diluted in THF (61.7 mL) and treated with Pd-C(Degussa) (0.328 g, 0.309 mmol). The resulting suspension was purged with $H_2$ (3×flask volume, approximatively 1.5 L) and allowed to stir under a balloon atmosphere of $H_2$ overnight. The reaction mixture was then diluted with EtOAc, filtered over Celite and concentrated. The crude residue was used as such in the next step. LC-MS (Method A2): 0.98 min, [M+H]$^+$=667.1; $^1$H NMR (400 MHz, CDCl$_3$) δ ppm 7.75 (d, J=8.4 Hz, 1H), 7.47-7.41 (m, 2H), 7.34-7.27 (m, 4H), 7.25-7.17 (m, 6H), 7.03 (d, J=8.1 Hz, 2H), 6.90 (dd, J=7.4, 1.7 Hz, 5H), 6.83 (d, J=8.1 Hz, 2H), 6.72 (dd, J=8.6, 2.4 Hz, 1H), 6.58 (d, J=2.2 Hz, 1H), 5.33 (s, 2H), 3.86 (s, 2H), 2.70-2.63 (m, 5H), 2.58 (s, 3H), 1.26 20-1.21 (m, 3H).

Intermediate 001j: 3-((5'-bromo-2'-(2-trityl-2H-tetrazol-5-yl)-[1,1'-biphenyl]-4-yl)methyl)-2-ethyl-5,7-dimethyl-3H-imidazo[4,5-b]pyridine

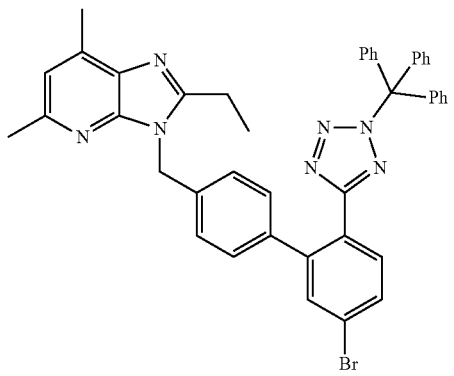

(001j)

To a suspension of Intermediate 001i (1.15 g, 1.725 mmol) in ACN (17.3 mL) was added copper (II) bromide (0.501 g, 2.242 mmol) followed by t-butyl nitrite (0.456 mL, 3.45 mmol). The reaction was stirred at RT for 45 min then diluted with EtOAc (100 mL). The organic phase was then washed with 1 M aqueous HCl rapidly followed by 1 M aqueous K$_2$HPO$_4$ to re-basify the organic phase. The organic phase was then dried over MgSO$_4$, filtered, concentrated and purified by ISCO (Hexanes/EtOAc, 0-100%). The title compound was isolated as a viscous, pale yellow oil (Intermediate 001j, 0.560 g, 0.766 mmol, 44.4% yield over the three-step sequence). LC-MS (Method A2): 1.10 min, [M+H]$^+$=732.3; $^1$H NMR (400 MHz, CDCl$_3$) δ ppm 7.81 (d, J=8.1 Hz, 1H), 7.60-7.55 (m, 1H), 7.49 (d, J=2.0 Hz, 1H), 7.37-7.27 (m, 4H), 7.26-7.19 (m, 5H), 7.02 (d, J=8.1 Hz, 2H), 6.96-6.82 (m, 9H), 5.35 (s, 2H), 2.71-2.61 (m, 5H), 2.57 (s, 3H), 1.25 (t, J=7.6 Hz, 3H).

Example 001: 3-((6'-(2H-tetrazol-5-yl)-2''-(trifluoromethoxy)-[1,1':3',1''-terphenyl]-4-yl)methyl)-2-ethyl-5,7-dimethyl-3H-imidazo[4,5-b]pyridine To a solution of Intermediate 001j (0.020 g, 0.027 mmol) and (2-(trifluoromethoxy) phenyl)boronic acid (0.028 g, 0.137 mmol) in dioxane (2 mL) was added 2M aqueous K$_3$PO$_4$ (0.068 mL, 0.137 mmol) followed by PdCl$_2$(dppf) (0.002 g, 2.74 µmol). The resulting mixture was sparged with N$_2$ for 2 min before the reaction vessel was sealed and heated at 120° C. for 30 min under microwave irradiation. The reaction mixture was cooled to RT, diluted with EtOAc and filtered over a pad of Celite/MgSO$_4$. The filtrate was concentrated to a brown residue which was dissolved in DCM (2 mL) and treated with triethylsilane (0.022 mL, 0.137 mmol) followed by TFA (0.105 mL, 1.369 mmol) for 10 min. The reaction mixture was then concentrated, resolvated in DMF, filtered then purified via preparative HPLC (Column: XBridge C18, 19×200 mm, 5-µm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 20-60% B over 20 minutes, then a 5-minute hold at 100% B; Flow: 20 mL/min) to afford 0.0065 g (0.011 mmol, 40% yield) of the title compound Example 001. LC-MS (Method A2): 0.86 min, [M+H]$^+$=570.1; $^1$H NMR (500 MHz, DMSO-d$_6$) δ ppm 7.76-7.52 (m, 5H), 7.51 (br s, 2H), 7.13-6.99 (m, 4H), 6.95 (s, 1H), 5.44 (s, 2H), 2.75 (q, J=7.4 Hz, 2H), 2.50-2.47 (m, 6H), 1.19 (t, J=7.4 Hz, 3H).

The following examples have been similarly prepared from Intermediate 001j as described above for the synthesis of Example 001. Two analytical LC-MS injections were used to determine the final purity. The retention time of one of them is reported for each compound and is referred as Method A1 or Method A2.

| Ex | Structure | MW | LC-MS m/z [M + H]+; RT (Method) | 1H NMR (500 MHz, DMSO-d6) δ ppm |
|---|---|---|---|---|
| 002 | 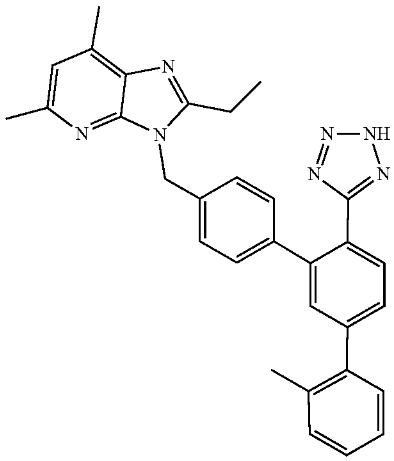 [SMILES: CCc1nc2c(C)cc(C)nc2n1Cc1ccc(-c2cc(-c3ccccc3C)ccc2-c2nn[nH]n2)cc1] | 499.61 | 500.10; 0.83 min (Method A2) | 7.70 (d, J = 7.9 Hz, 1H), 7.52 (d, J = 7.8 Hz, 1H), 7.41 (s, 1H), 7.36-7.25 (m, 4H), 7.13-7.07 (m, 2H), 7.04 (d, J = 8.1 Hz, 2H), 6.95 (s, 1H), 5.45 (s, 2H), 2.79-2.71 (m, 3H), 2.55 (s, 6H), 2.30 (s, 3H), 1.21 (t, J = 7.4 Hz, 3H) |
| 003 | 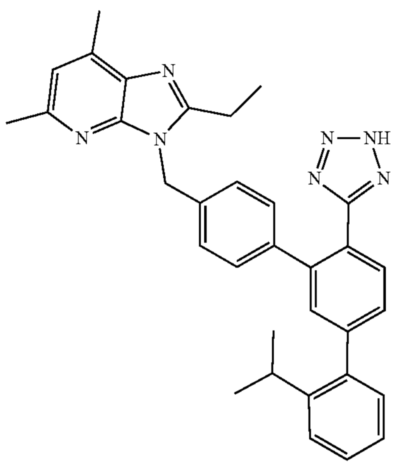 [SMILES: CCc1nc2c(C)cc(C)nc2n1Cc1ccc(-c2cc(-c3ccccc3C(C)C)ccc2-c2nn[nH]n2)cc1] | 527.66 | 528.30; 0.90 min (Method A2) | 7.72 (d, J = 7.8 Hz, 1H), 7.53-7.44 (m, 2H), 7.43-7.34 (m, 2H), 7.30-7.21 (m, 3H), 7.17 (s, 1H), 7.14-7.08 (m, 2H), 7.07 (s, 1H), 5.53 (s, 2H), 3.02 (dt, J = 13.4, 6.8 Hz, 1H), 2.93-2.84 (m, 2H), 2.54 (d, J = 2.7 Hz, 6H), 1.20 (t, J = 7.5 Hz, 3H), 1.14 (d, J = 6.7 Hz, 6H) |
| 004 | 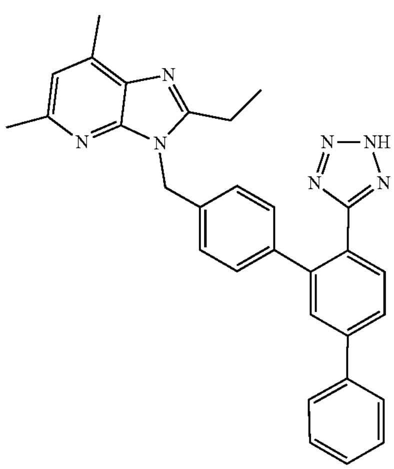 [SMILES: CCc1nc2c(C)cc(C)nc2n1Cc1ccc(-c2cc(-c3ccccc3)ccc2-c2nn[nH]n2)cc1] | 485.58 | 486.10; 0.81 min (Method A2) | 7.83-7.74 (m, 3H), 7.73-7.64 (m, 2H), 7.53-7.45 (m, 2H), 7.44-7.36 (m, 1H), 7.13 (d, J = 7.9 Hz, 2H), 7.04 (d, J = 7.9 Hz, 2H), 6.95 (s, 1H), 5.45 (s, 2H), 2.77 (d, J = 7.3 Hz, 2H), 2.55 (s, 6H), 1.22 (t, J = 7.5 Hz, 3H) |

| Ex | Structure | MW | LC-MS m/z [M + H]+; RT (Method) | 1H NMR (500 MHz, DMSO-d6) δ ppm |
|---|---|---|---|---|
| 005 | 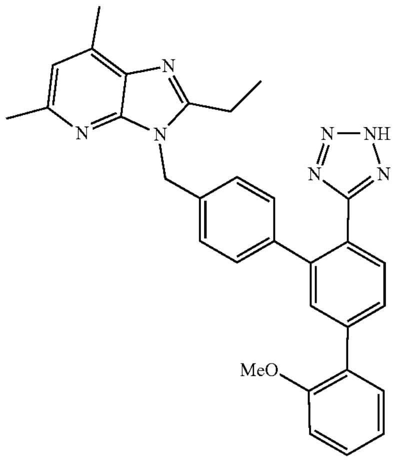 [SMILES: CCc1nc2c(C)cc(C)nc2n1Cc1ccc(-c2cc(-c3ccccc3OC)ccc2-c2nn[nH]n2)cc1] | 515.61 | 516.10; 0.81 min (Method A2) | |
| 006 | 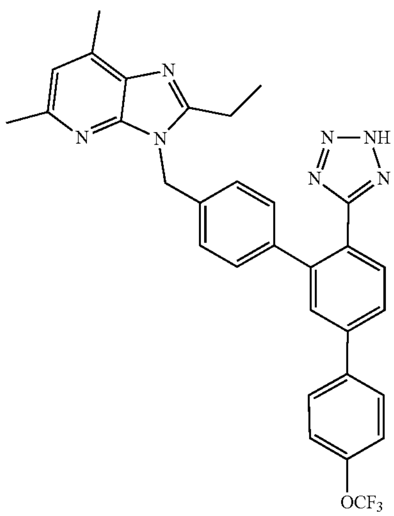 | 569.58 | 570.20; 0.88 min (Method A2) | 7.90 (d, J = 8.3 Hz, 2H), 7.82 (d, J = 7.5 Hz, 1H), 7.77-7.66 (m, 2H), 7.46 (d, J = 8.1 Hz, 2H), 7.10 (br s, 2H), 7.04 (d, J = 7.5 Hz, 2H), 6.95 (s, 1H), 5.44 (s, 2H), 2.80-2.74 (m, 2H), 2.50 (d, J = 2.9 Hz, 6H), 1.20 (t, J = 7.4 Hz, 3H) |
| 007 | 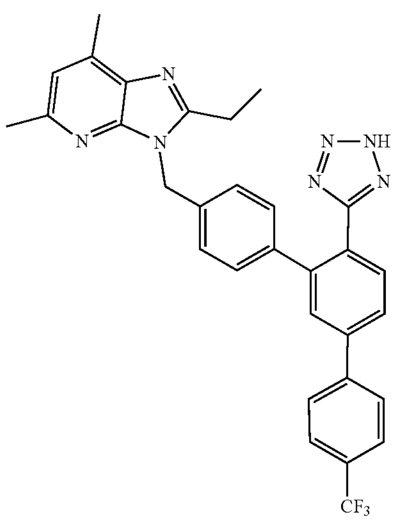 [SMILES: CCc1nc2c(C)cc(C)nc2n1Cc1ccc(-c2cc(-c3ccc(C(F)(F)F)cc3)ccc2-c2nn[nH]n2)cc1] | 553.58 | 554.20; 0.88 min (Method A2) | 8.02 (d, J = 7.9 Hz, 2H), 7.91-7.72 (m, 5H), 7.21-7.01 (m, 4H), 6.95 (s, 1H), 5.46 (s, 2H), 2.78 (q, J = 7.3 Hz, 2H), 2.51 (br. s., 6H), 1.23 (d, J = 3.1 Hz, 3H) |

| Ex | Structure | MW | LC-MS m/z [M + H]+; RT (Method) | 1H NMR (500 MHz, DMSO-d6) δ ppm |
|---|---|---|---|---|
| 008 | 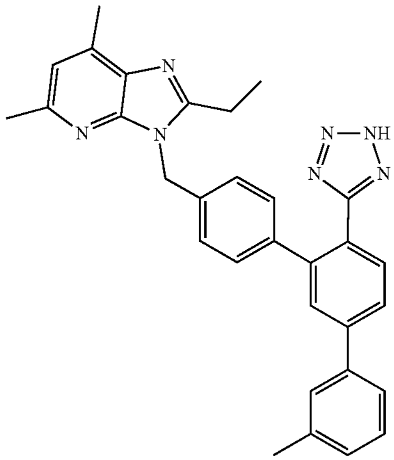 [SMILES: CCc1nc2c(C)cc(C)nc2n1Cc1ccc(-c2cc(-c3cccc(C)c3)ccc2-c2nn[nH]n2)cc1] | 499.61 | 500.10; 1.800 min (Method A1) | 7.79 (d, J = 7.9 Hz, 1H), 7.71 (d, J = 7.9 Hz, 1H), 7.68 (s, 1H), 7.60 (s, 1H), 7.56 (d, J = 7.6 Hz, 1H), 7.37 (t, J = 7.6 Hz, 1H), 7.22 (d, J = 7.3 Hz, 1H), 7.14 (d, J = 7.9 Hz, 2H), 7.05 (d, J = 7.9 Hz, 2H), 6.95 (s, 1H), 5.45 (s, 2H), 2.78 (q, J = 7.5 Hz, 2H), 2.55 (s, 6H), 2.38 (s, 3H), 1.27-1.19 (m, 3H) |
| 009 | 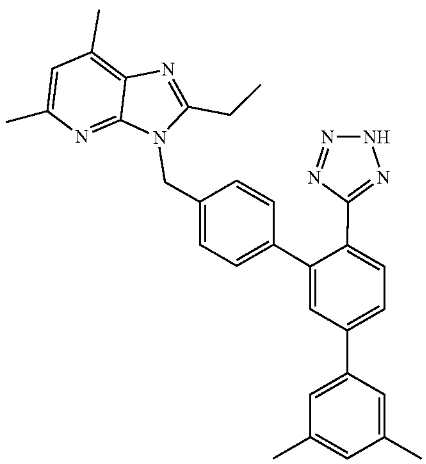 | 513.64 | 514.30; 1.970 min (Method A1) | 7.79 (d, J = 7.9 Hz, 1H), 7.70 (d, J = 7.9 Hz, 1H), 7.68 (s, 1H), 7.39 (s, 2H), 7.15-7.10 (m, 2H), 7.08-7.01 (m, 3H), 6.95 (s, 1H), 5.46 (s, 2H), 2.77 (q, J = 7.5 Hz, 2H), 2.55 (s, 6H), 2.33 (s, 6H), 1.25-1.21 (m, 5H) |
| 010 | 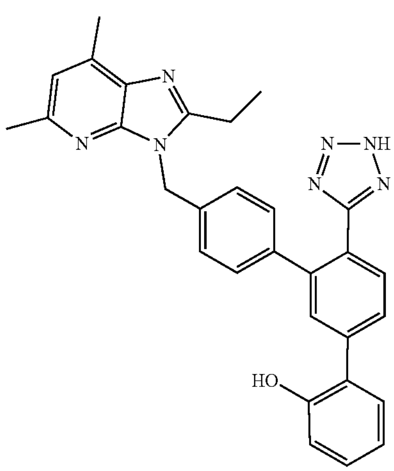 [SMILES: CCc1nc2c(C)cc(C)nc2n1Cc1ccc(-c2cc(-c3ccccc3O)ccc2-c2nn[nH]n2)cc1] | 501.58 | 502.30; 1.500 min (Method A1) | 7.77-7.72 (m, 1H), 7.67 (d, J = 7.9 Hz, 1H), 7.64 (s, 1H), 7.38 (d, J = 7.3 Hz, 1H), 7.26 (s, 1H), 7.24-7.18 (m, 1H), 7.15 (s, 1H), 7.13-7.08 (m, 4H), 7.05 (s, 1H), 6.98 (d, J = 7.9 Hz, 1H), 6.91 (t, J = 7.6 Hz, 1H), 5.53 (s, 2H), 2.88 (q, J = 7.6 Hz, 2H), 2.54-2.52 (m, 6H), 1.23-1.20 (m, 3H) |

-continued

| Ex | Structure | MW | LC-MS m/z [M + H]+; RT (Method) | 1H NMR (500 MHz, DMSO-d6) δ ppm |
|---|---|---|---|---|
| 011 | 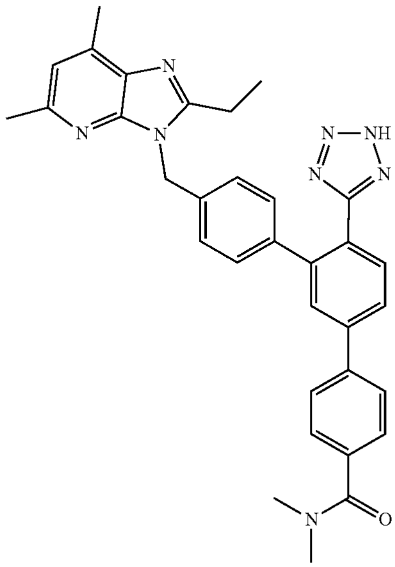 [SMILES: CCc1nc2c(C)cc(C)nc2n1Cc1ccc(-c2cc(-c3ccc(C(=O)N(C)C)cc3)ccc2-c2nn[nH]n2)cc1] | 556.66 | 557.00; 1.380 min (Method A1) | 7.90-7.82 (m, 3H), 7.78-7.73 (m, 2H), 7.51 (d, J = 8.2 Hz, 2H), 7.15 (d, J = 7.9 Hz, 2H), 7.06 (d, J = 7.9 Hz, 2H), 6.96 (s, 1H), 5.46 (s, 2H), 3.00 (br s, 3H), 2.95 (br s, 3H), 2.77 (q, J = 7.4 Hz, 2H), 2.55 (s, 6H), 1.26-1.19 (m, 3H) |
| 012 | 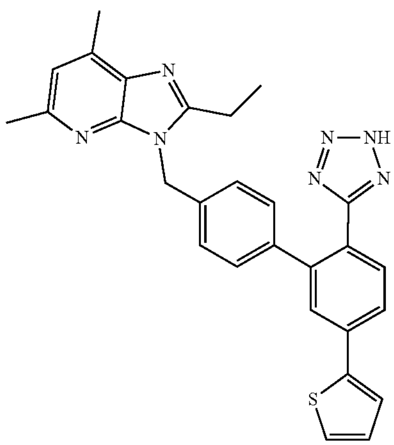 [SMILES: CCc1nc2c(C)cc(C)nc2n1Cc1ccc(-c2cc(-c3cccs3)ccc2-c2nn[nH]n2)cc1] | 491.61 | 492.40; 1.600 min (Method A1) | 7.79 (d, J = 7.6 Hz, 1H), 7.68 (br s, 3H), 7.62 (d, J = 4.9 Hz, 1H), 7.20-7.15 (m, 1H), 7.13-7.08 (m, 2H), 7.08-7.03 (m, 2H), 6.96 (s, 1H), 5.46 (s, 2H), 2.81-2.74 (m, 2H), 2.55 (s, 6H), 1.26-1.19 (m, 3H) |
| 013 | 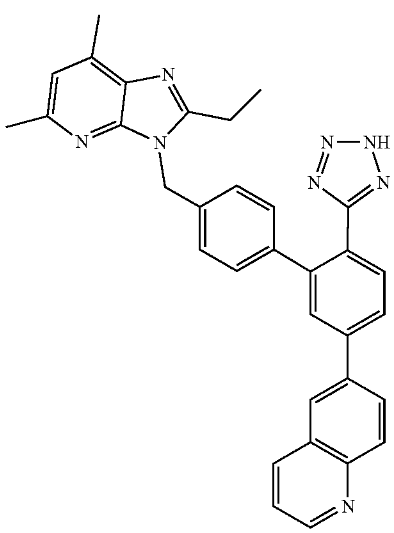 [SMILES: CCc1nc2c(C)cc(C)nc2n1Cc1ccc(-c2cc(-c3ccc4ncccc4c3)ccc2-c2nn[nH]n2)cc1] | 536.63 | 537.20; 1.140 min (Method A1) | 8.97 (d, J = 2.8 Hz, 1H), 8.55-8.48 (m, 2H), 8.28 (d, J = 8.8 Hz, 1H), 8.15 (d, J = 8.8 Hz, 1H), 8.06 (d, J = 7.9 Hz, 1H), 7.96 (s, 1H), 7.84 (d, J = 8.0 Hz, 1H), 7.64 (dd, J = 8.2, 4.2 Hz, 1H), 7.27-7.02 (m, 5H), 5.56 (s, 2H), 2.90 (q, J = 7.2 Hz, 2H), 2.51 (br. s., 6H), 1.25 (t, J = 7.4 Hz, 3H) |

| Ex | Structure | MW | LC-MS m/z [M + H]+; RT (Method) | 1H NMR (500 MHz, DMSO-d6) δ ppm |
|---|---|---|---|---|
| 014 | 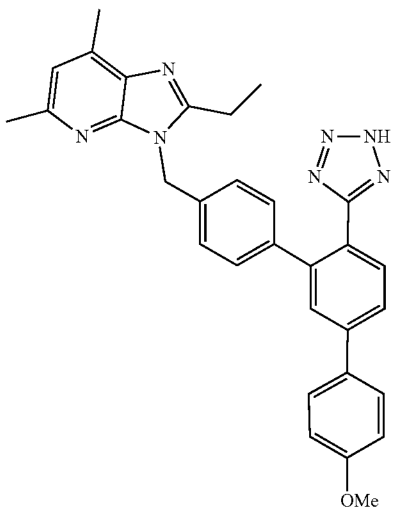 [SMILES: CCc1nc2c(C)cc(C)nc2n1Cc1ccc(-c2cc(-c3ccc(OC)cc3)ccc2-c2nn[nH]n2)cc1] | 515.61 | 516.30; 1.640 min (Method A1) | 7.82 (d, J = 7.3 Hz, 2H), 7.76 (d, J = 8.5 Hz, 2H), 7.71 (br s, 2H), 7.18-7.07 (m, 3H), 7.07-6.97 (m, 3H), 5.49 (s, 2H), 3.81 (s, 3H), 2.81 (q, J = 6.8 Hz, 2H), 2.55 (s, 3H), 2.53 (br. s., 3H), 1.24 (t, J = 7.3 Hz, 3H) |
| 015 | 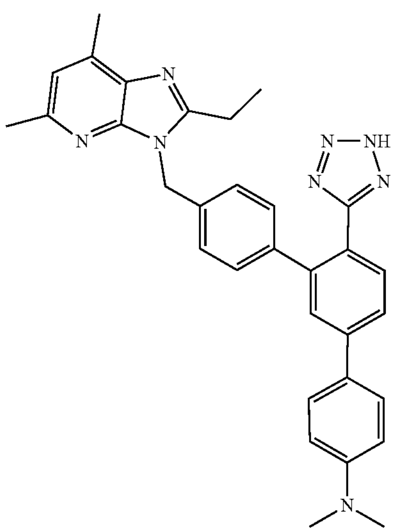 [SMILES: CCc1nc2c(C)cc(C)nc2n1Cc1ccc(-c2cc(-c3ccc(N(C)C)cc3)ccc2-c2nn[nH]n2)cc1] | 528.65 | 529.20; 1.700 min (Method A1) | 7.65-7.54 (m, 4H), 7.50 (s, 1H), 7.12 (d, J = 8.2 Hz, 2H), 6.99 (d, J = 7.9 Hz, 2H), 6.95 (s, 1H), 6.79 (d, J = 8.8 Hz, 2H), 5.43 (s, 2H), 2.93 (s, 6H), 2.78 (q, J = 7.5 Hz, 2H), 2.55 (s, 6H), 1.24 (t, J = 7.5 Hz, 3H) |
| 016 | 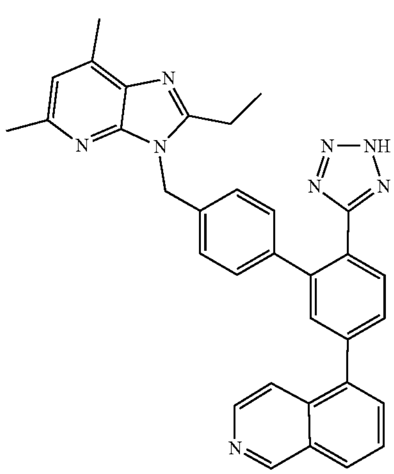 [SMILES: CCc1nc2c(C)cc(C)nc2n1Cc1ccc(-c2cc(-c3cccc4cnccc34)ccc2-c2nn[nH]n2)cc1] | 536.63 | 536.90; 1.470 min (Method A1) | 9.40 (br s, 1H), 8.51 (br s, 1H), 8.19 (d, J = 8.1 Hz, 1H), 7.85 (d, J = 6.8 Hz, 1H), 7.79 (d, J = 7.7 Hz, 3H), 7.59 (d, J = 7.3 Hz, 1H), 7.47 (br s, 1H), 7.15 (br s, 2H), 6.99 (d, J = 7.4 Hz, 2H), 6.93 (s, 1H), 5.43 (s, 2H), 2.77 (q, J = 7.3 Hz, 2H), 2.55 (s, 6H), 1.22 (t, J = 7.4 Hz, 3H) |

| Ex | Structure | MW | LC-MS m/z [M + H]+; RT (Method) | 1H NMR (500 MHz, DMSO-d6) δ ppm |
|---|---|---|---|---|
| 017 | 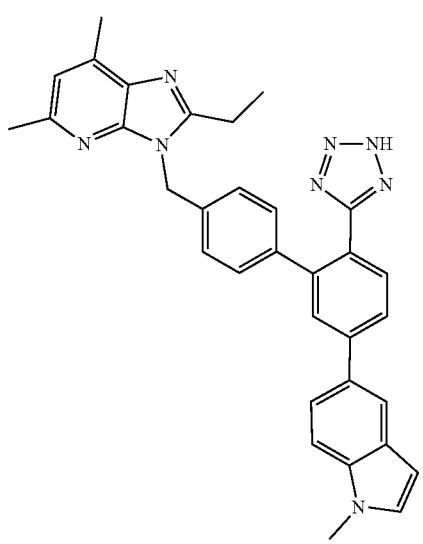 [SMILES: CCc1nc2c(C)cc(C)nc2n1Cc1ccc(-c2cc(-c3ccc4c(ccn4C)c3)ccc2-c2nn[nH]n2)cc1] | 538.64 | 539.00; 1.650 min (Method A1) | |
| 018 | 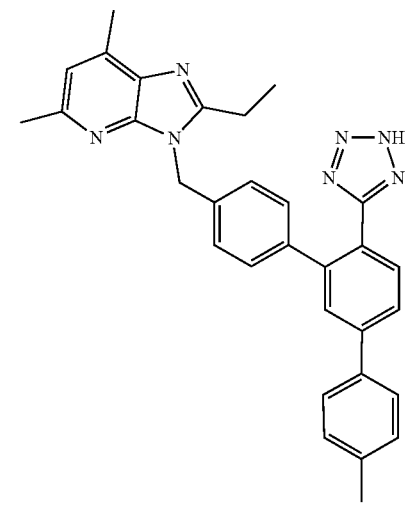 [SMILES: CCc1nc2c(C)cc(C)nc2n1Cc1ccc(-c2cc(-c3ccc(C)cc3)ccc2-c2nn[nH]n2)cc1] | 499.61 | 500.30; 1.750 min (Method A1) | |
| 019 | 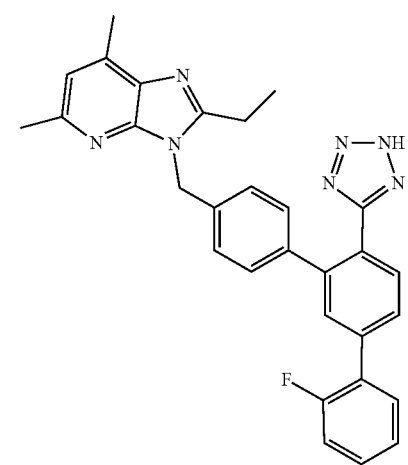 | 503.57 | 504.10; 0.81 min (Method A2) | 7.79-7.69 (m, 2H), 7.66 (t, J = 7.6 Hz, 1H), 7.60 (s, 1H), 7.51-7.43 (m, 1H), 7.40-7.29 (m, 2H), 7.15-7.08 (m, 2H), 7.04 (d, J = 8.0 Hz, 2H), 6.95 (s, 1H), 5.45 (s, 2H), 2.81-2.70 (m, 2H), 2.55 (s, 6H), 1.22 (t, J = 7.4 Hz, 3H) |

-continued

| Ex | Structure | MW | LC-MS m/z [M + H]+; RT (Method) | ¹H NMR (500 MHz, DMSO-d$_6$) δ ppm |
|---|---|---|---|---|
| 020 | 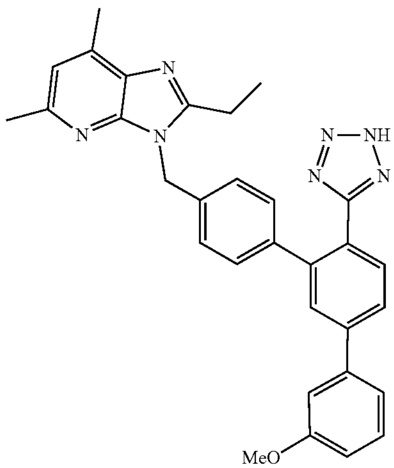 [SMILES: CCc1nc2c(C)cc(C)nc2n1Cc1ccc(-c2cc(-c3cccc(OC)c3)ccc2-c2nn[nH]n2)cc1] | 515.61 | 516.10; 0.81 min (Method A2) | 7.79 (d, J = 7.7 Hz, 1H), 7.73-7.64 (m, 2H), 7.43-7.36 (m, 1H), 7.33 (d, J = 7.6 Hz, 1H), 7.28 (br s, 1H), 7.14 (d, J = 7.9 Hz, 2H), 7.04 (d, J = 7.9 Hz, 2H), 7.00-6.92 (m, 2H), 5.45 (s, 2H), 3.82 (s, 3H), 2.78 (q, J = 7.3 Hz, 2H), 2.55 (s, 6H), 1.23 (t, J = 7.4 Hz, 3H) |
| 021 | 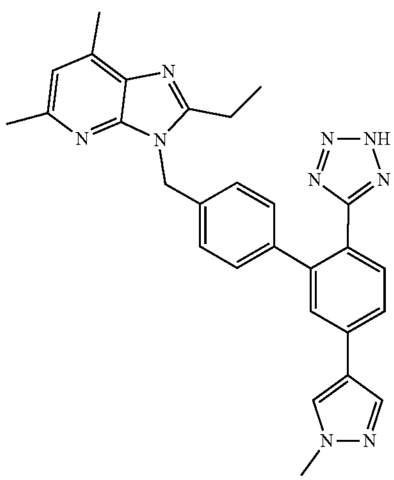 [SMILES: CCc1nc2c(C)cc(C)nc2n1Cc1ccc(-c2cc(-c3cnn(C)c3)ccc2-c2nn[nH]n2)cc1] | 489.57 | 490.10; 0.66 min (Method A2) | 8.26 (s, 1H), 7.96 (s, 1H), 7.68-7.62 (m, 1H), 7.60-7.55 (m, 2H), 7.12-7.06 (m, 2H), 7.02 (d, J = 8.0 Hz, 2H), 6.95 (s, 1H), 5.45 (s, 2H), 3.85 (s, 3H), 2.78 (q, J = 7.3 Hz, 2H), 2.55 (s, 6H), 1.25 (t, J = 7.4 Hz, 3H) |
| 022 | 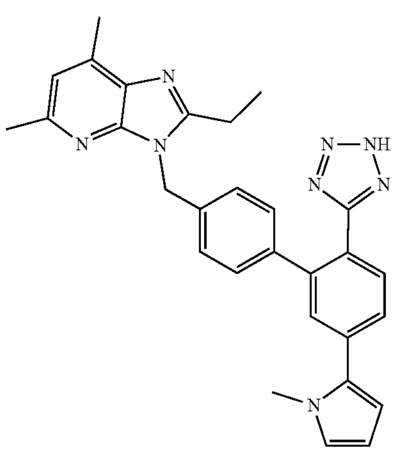 [SMILES: CCc1nc2c(C)cc(C)nc2n1Cc1ccc(-c2cc(-c3cccn3C)ccc2-c2nn[nH]n2)cc1] | 488.59 | 489.10; 0.77 min (Method A2) | 7.95 (s, 1H), 7.72-7.67 (m, 1H), 7.66-7.62 (m, 1H), 7.52 (s, 1H), 7.25 (s, 1H), 7.15 (s, 1H), 7.05 (s, 2H), 6.92 (s, 1H), 6.37 (br s, 1H), 6.11 (d, J = 2.7 Hz, 1H), 5.51 (s, 2H), 3.74 (s, 3H), 2.85 (q, J = 7.4 Hz, 2H), 2.53 (s, 6H), 1.23 (t, J = 7.5 Hz, 3H) |

| Ex | Structure | MW | LC-MS m/z [M + H]+; RT (Method) | 1H NMR (500 MHz, DMSO-d6) δ ppm |
|---|---|---|---|---|
| 023 | 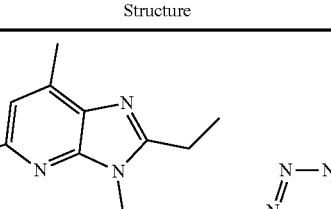 | 556.66 | 557.1; 0.72 min (Method A2) | 7.82 (d, J = 7.9 Hz, 1H), 7.76-7.71 (m, 2H), 7.70-7.66 (m, 1H), 7.60 (d, J = 1.6 Hz, 1H), 7.53 (t, J = 7.7 Hz, 1H), 7.38 (d, J = 7.5 Hz, 1H), 7.15 (d, J = 7.9 Hz, 2H), 6.99 (d, J = 8.3 Hz, 2H), 6.95 (s, 1H), 5.44 (s, 2H), 3.00 (br. s., 3H), 2.93 (br. s., 3H), 2.79 (q, J = 7.5 Hz, 2H), 2.55 (s, 3H), 2.51 (s, 3H), 1.25 (t, J = 7.4 Hz, 3H) |

Example 024: 2-ethyl-3-((5'-(2-methoxypyridin-3-yl)-2'-(2H-tetrazol-5-yl)-[1,1'-biphenyl]-4-yl)methyl)-5,7-dimethyl-3H-imidazo[4,5-b]pyridine (Ex. 024)

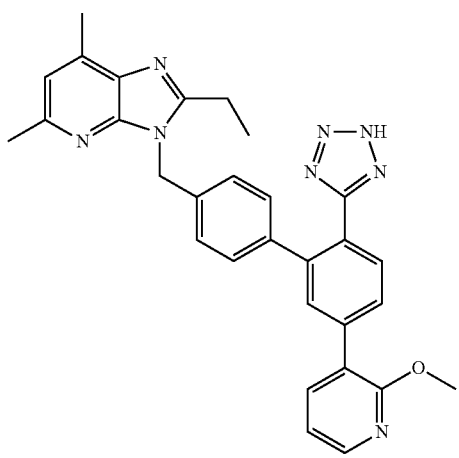

A solution of Intermediate 001j (0.030 g, 0.041 mmol) and 2-methoxy-3-(4,4,5,5-tetramethyl-1,3,2-dioxaborolan-2-yl)pyridine (0.029 g, 0.123 mmol) in dioxane (3 mL) was treated with 2M aqueous K₃PO₄ (0.103 mL, 0.205 mmol) and PdCl₂(dppf) (0.003 g, 4.11 µmol) and reacted as described in Ex. 001. The crude residue was purified via preparative HPLC (Column: XBridge C18, 19×200 mm, 5-µm particles; Mobile Phase A: 5:95 ACN: H₂O with 10 mM NH₄OAc; Mobile Phase B: 95:5 ACN: H₂O with 10 mM NH₄OAc; Gradient: 15-55% B over 19 minutes, then a 5-minute hold at 100% B; Flow: 20 mL/min) to afford (0.0099 g, 0.019 mmol, 47%) of the title compound Example 024. LC-MS (Method A2): 0.77 min, [M+H]+= 517.1; 1H NMR (500 MHz, DMSO-d₆) δ ppm 8.20 (d, J=4.8 Hz, 1H), 7.87 (d, J=7.2 Hz, 1H), 7.67 (s, 2H), 7.56 (s, 1H), 7.16-7.06 (m, 3H), 7.02 (d, J=8.0 Hz, 2H), 6.95 (s, 1H), 5.44 (s, 2H), 3.89 (s, 3H), 2.77 (q, J=7.4 Hz, 2H), 2.55 (s, 6H), 1.23 (t, J=7.4 Hz, 3H).

Example 025: 3-((5'-(1H-pyrazol-1-yl)-2'-(2H-tetrazol-5-yl)-[1,1'-biphenyl-4-yl)methyl)-2-ethyl-5,7-dimethyl-3H-imidazo[4,5-b]pyridine (Ex. 025)

To a vial charged with Intermediate 001j (0.030 g, 0.041 mmol), 1H-pyrazole (0.0084 g, 0.123 mmol), copper(I) iodide (0.0039 g, 0.021 mmol), potassium carbonate (0.028 g, 0.205 mmol) and L-proline (0.0047 g, 0.041 mmol) was added DMSO (0.821 mL). The mixture was heated at 100° C. for 24 h and at 150° C. for an additional 24 h. The reaction mixture was allowed to cool to RT and filtered through a microfilter. The residue was rinsed with DMSO and the filtrate purified via preparative HPLC (Column: XBridge C18, 19×200 mm, 5-µm particles; Mobile Phase A: 5:95 ACN: H₂O with 10 mM NH₄OAc; Mobile Phase B: 95:5

ACN: H₂O with 10 mM NH₄OAc; Gradient: 10-50% B over 20 minutes, then a 3-minute hold at 100% B; Flow: 20 mL/min) to afford the title compound (Example 025, 0.0051 g, 0.011 mmol, 27%). LC-MS (Method A2): 0.69 min, [M+H]⁺=476.1; $^1$H NMR (500 MHz, DMSO-d₆) δ ppm 8.58 (d, J=2.1 Hz, 1H), 7.88 (dd, J=8.4, 2.0 Hz, 1H), 7.82-7.73 (m, 2H), 7.69 (d, J=8.2 Hz, 1H), 7.13 (d, J=7.9 Hz, 2H), 7.01 (d, J=7.9 Hz, 2H), 6.95 (s, 1H), 6.55 (s, 1H), 5.45 (s, 2H), 2.79 (q, J=7.3 Hz, 2H), 1.91 (s, 6H), 1.25 (t, J=7.5 Hz, 3H).

Example 026: 4'-((2-ethyl-5,7-dimethyl-3H-imidazo[4,5-b]pyridin-3-yl)methyl)-N-(4-fluorophenyl)-6-(2H-tetrazol-5-yl)-[1,1'-biphenyl]-3-amine

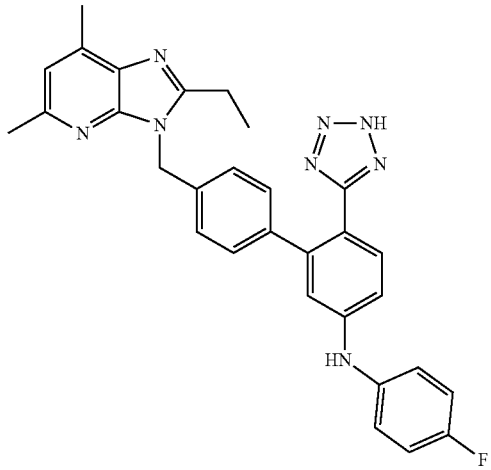

(Ex. 026)

Intermediate 026a: 4'-((2-ethyl-5,7-dimethyl-3H-imidazo[4,5-b]pyridin-3-yl)methyl)-N-(4-fluorophenyl)-6-(2-trityl-2H-tetrazol-5-yl)-[1,1'-biphenyl]-3-amine

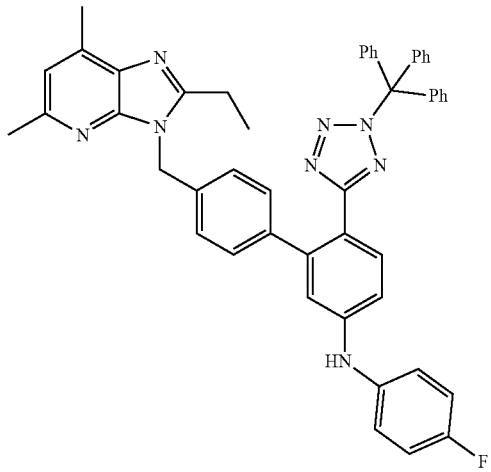

(026a)

To a solution of Intermediate 001i (0.040 g, 0.060 mmol) in DCE (2 mL) containing 4A molecular sieves (previously heated at 110° C. under vacuum for 1 h prior to use) was added triethylamine (0.017 mL, 0.120 mmol), pyridine (0.0097 mL, 0.120 mmol) and (4-fluorophenyl)boronic acid (0.025 g, 0.180 mmol). The reaction mixture was stirred for 15 min, then copper (II) acetate (0.011 mg, 0.060 mmol) was added. The reaction vial was sealed under an air atmosphere and allowed to stir at RT overnight. After 16 h, the reaction mixture was filtered over Celite, washed with DCM and concentrated to afford a green residue (Intermediate 026a) which was used as such in the next step. LC-MS (Method A2): 1.07 min, [M+H]⁺=761.5.

Example 026: 4'-((2-ethyl-5,7-dimethyl-3H-imidazo[4,5-b]pyridin-3-yl)methyl)-N-(4-fluorophenyl)-6-(2H-tetrazol-5-yl)-[1,1'-biphenyl]-3-amine A solution of Intermediate 026a (0.040 g, 0.053 mmol) in DCM (2 mL) was treated with triethylsilane (0.084 mL, 0.526 mmol) followed by TFA (0.203 mL, 2.63 mmol). The reaction was stirred at RT for 10 min, then concentrated to dryness. The residue was taken up in DMF, the mixture was neutralized with a few drops of triethylamine, filtered and purified via preparative HPLC (Column: XBridge C18, 19×200 mm, 5-μm particles; Mobile Phase A: 5:95 ACN:H₂O with 10 mM NH₄OAc; Mobile Phase B: 95:5 ACN:H₂O with 10 mM NH₄OAc; Gradient: 20-60% B over 20 minutes, then a 5-minute hold at 100% B; Flow: 20 mL/min). A further purification by preparative LC-MS was performed on the resulting sample (Column: XBridge C18, 19×200 mm, 5-μm particles; Mobile Phase A: 5:95 ACN:H₂O with 0.1% TFA; Mobile Phase B: 95:5 ACN:H₂O with 0.1% TFA; Gradient: 20-60% B over 20 minutes, then a 3-minute hold at 100% B; Flow: 20 mL/min) to afford the title compound (Example 026, 0.0021 g, 0.004 mmol, 8%). LC-MS (Method A2): 0.78 min, [M+H]⁺=519.1; $^1$H NMR (500 MHz, DMSO-d₆) δ ppm 7.94 (s, 1H), 7.47 (d, J=8.5 Hz, 1H), 7.23-7.00 (m, 9H), 6.95 (d, J=1.8 Hz, 1H), 5.55 (s, 2H), 2.96-2.90 (m, 2H), 2.51 (br s, 6H), 1.21 (t, J=7.5 Hz, 3H).

Example 027: 2-(4'-((2-ethyl-5,7-dimethyl-3H-imidazo[4,5-b]pyridin-3-yl)methyl)-6-(2H-tetrazol-5-yl)-[1,1'-biphenyl]-3-yl)isoindoline-1,3-dione

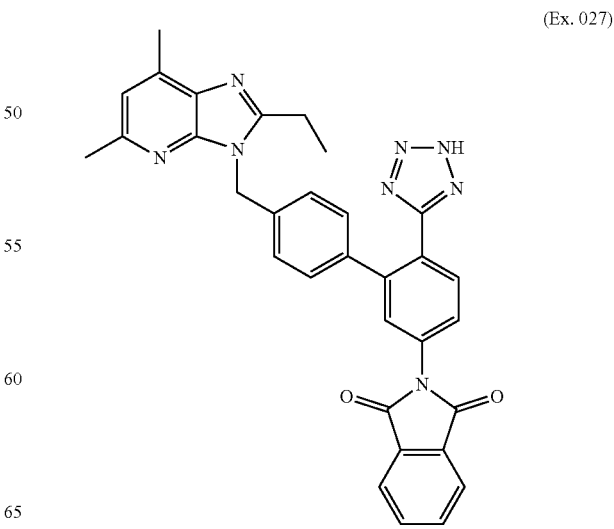

(Ex. 027)

Intermediate 027a 4'-((2-ethyl-5,7-dimethyl-3H-imidazo[4,5-b]pyridin-3-yl)methyl)-6-(2H-tetrazol-5-yl)-[1,1'-biphenyl]-3-amine

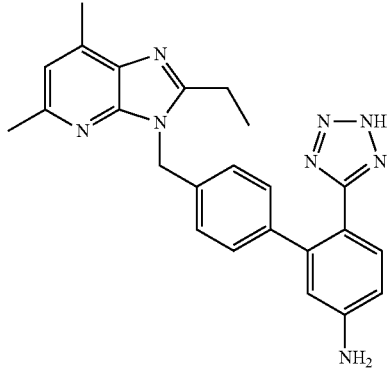
(027a)

To a solution of Intermediate 001 g (0.270 g, 0.594 mmol) in MeOH (30 mL) was added zinc powder (0.777 g, 11.88 mmol) followed by ammonium chloride (0.953 g, 17.82 mmol) and the mixture was heated at reflux at 70° C. overnight. Then the reaction mixture was partially concentrated under reduced pressure and the residue was partitioned between EtOAc (30 mL) and saturated aqueous NH$_4$Cl (30 mL). The corresponding mixture was stirred vigorously for 2 h and filtered. The filtrate was further diluted with EtOAc and the aqueous phase was separated and again extracted with EtOAc (2×). The combined organic phase was dried over MgSO$_4$, filtered and concentrated to afford the title compound (Intermediate 027a, 0.148 g, 0.349 mmol, 59%). LC-MS (Method A2): 0.59 min, [M+H]$^+$=425.3; $^1$H NMR (500 MHz, DMSO-d$_6$) δ ppm 7.26 (d, J=8.3 Hz, 1H), 7.03-6.92 (m, 5H), 6.66 (d, J=8.3 Hz, 1H), 6.59 (s, 1H), 5.43 (s, 2H), 2.74 (q, J=7.3 Hz, 2H), 2.55 (s, 6H), 1.18 (t, J=7.5 Hz, 3H).

Example 027: 2-(4'-((2-ethyl-5,7-dimethyl-3H-imidazo[4,5-b]pyridin-3-yl)methyl)-6-(2H-tetrazol-5-yl)-[1,1'-biphenyl]-3-yl)isoindoline-1,3-dione A solution of Intermediate 027a (0.010 g, 0.024 mmol) in AcOH (0.5 mL) was treated with phthalic anhydride (0.035 g, 0.236 mmol). The reaction vial was sealed and heated at/at 100° C. for 16 h. The mixture was concentrated, dissolved in DMF, filtered and purified via preparative HPLC (Column: XBridge C18, 19×200 mm, 5-µm particles; Mobile Phase A: 5:95 ACN: H$_2$O with 0.1% TFA; Mobile Phase B: 95:5 ACN: H$_2$O with 0.1% TFA; Gradient: 15-55% B over 20 minutes, then a 5-minute hold at 100% B; Flow: 20 mL/min) to afford the title compound (Example 027, 0.0081 g, 0.015 mmol, 62%). LC-MS (Method A2): 0.74 min, [M+H]$^+$=555.4; $^1$H NMR (500 MHz, DMSO-d$_6$) δ ppm 7.98 (br. s., 2H), 7.94 (br s, 2H), 7.82 (d, J=8.1 Hz, 1H), 7.71-7.62 (m, 2H), 7.18-7.05 (m, 5H), 5.55 (s, 2H), 2.90 (q, J=7.4 Hz, 2H), 2.54 (br s, 6H), 1.21 (t, J=7.4 Hz, 3H).

Example 028: 1-(4'-((2-ethyl-5,7-dimethyl-3H-imidazo[4,5-b]pyridin-3-yl)methyl)-6-(2H-tetrazol-5-yl)-[1,1'-biphenyl]-3-yl)pyrrolidin-2-one

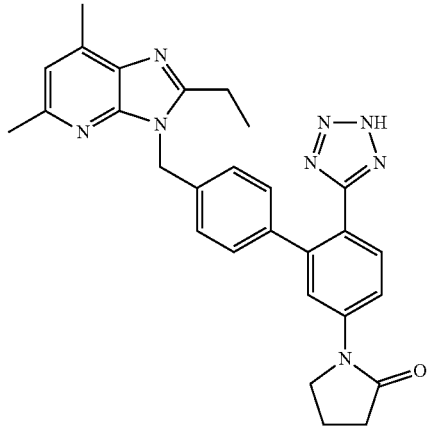
(Ex. 028)

A suspension of Intermediate 027a (0.009 g, 0.021 mmol) in DMF (1 mL) was treated with 4-chlorobutanoyl chloride (7.13 µL, 0.064 mmol) and NaH (0.0025 g, 0.064 mmol). The corresponding reaction mixture was allowed to stir at RT overnight. The reaction was quenched with a few drops of H$_2$O, filtered and purified via preparative HPLC (Column: XBridge C18, 19×200 mm, 5-µm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 10-50% B over 19 minutes, then a 5-minute hold at 100% B; Flow: 20 mL/min). The material was further purified via a second preparative LC-MS (Column: XBridge C18, 19×200 mm, 5-µm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 10-50% B over 19 minutes, then a 5-minute hold at 100% B; Flow: 20 mL/min) to afford the title compound (Example 028, 0.008 g, 0.020 mmol, 95%). LC-MS (Method A2): 0.66 min, [M+H]$^+$=493.3; $^1$H NMR (500 MHz, DMSO-d$_6$) δ ppm 7.65-7.60 (m, 1H), 7.59-7.51 (m, 2H), 7.07 (d, J=8.1 Hz, 2H), 6.95 (d, J=9.2 Hz, 3H), 5.42 (s, 2H), 3.88 (t, J=6.9 Hz, 2H), 2.79 (q, J=7.5 Hz, 2H), 2.52-2.48 (m, 8H), 2.12-2.00 (m, 2H), 1.26 (t, J=7.4 Hz, 3H).

Example 029: 2-Ethyl-3-((5'-(6-methoxypyridin-2-yl)-2'-(2H-tetrazol-5-yl)-[1,1'-biphenyl]-4-yl)methyl)-5,7-dimethyl-3H-imidazo[4,5-b]pyridine Example 030: 2-Ethyl-5,7-dimethyl-3-((5'-(pyridin-2-yl)-2'-(2H-tetrazol-5-yl)-[1,1'-biphenyl]-4-yl)methyl)-3H-imidazo[4,5-b]pyridine

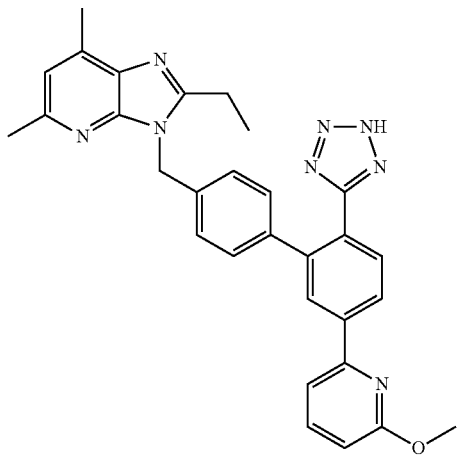

(Ex. 029)

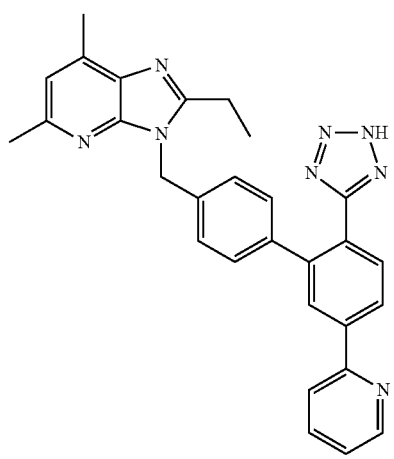

(Ex. 030)

To a vial containing (Intermediate 001j (0.030 g, 0.041 mmol), Pd(Ph₃P)₄ (4.74 mg, 4.11 μmol) and 2-methoxy-6-(tributylstannyl)pyridine (0.033 g, 0.082 mmol) was added toluene (1 mL). The mixture was sparged with N₂ for 2 min before the reaction vessel was sealed and heated at 110° C. for 3 h. The reaction mixture was cooled to RT and concentrated. The crude residue was taken up in DCM (1 mL) and treated with triethylsilane (0.033 mL, 0.205 mmol) followed by TFA (0.127 mL, 1.642 mmol). The resulting reaction mixture was stirred for 10 min before being concentrated, taken up in DMF and purified via preparative HPLC with the following conditions: Column: XBridge C18, 19×200 mm, 5-μm particles; Mobile Phase A: 5:95 ACN: H₂O with 10 mM NH₄OAc; Mobile Phase B: 95:5 ACN: H₂O with 10 mM NH₄OAc; Gradient: 15-57% B over 20 minutes, then a 3-minute hold at 100% B; Flow: 20 mL/min. Fractions containing the desired product were combined and dried via centrifugal evaporation to afford the title compound (Example 029, 0.008 g, 0.015 mmol, 36%). LC-MS (Method A2): 0.83 min, [M+H]$^+$=517.0; $^1$H NMR (600 MHz, DMSO-d₆) δ ppm 8.13 (dd, J=8.1, 1.8 Hz, 1H), 8.02 (d, J=1.4 Hz, 1H), 7.78 (t, J=7.9 Hz, 1H), 7.71 (d, J=8.1 Hz, 1H), 7.65 (d, J=7.5 Hz, 1H), 7.13 (d, J=7.9 Hz, 2H), 7.01 (d, J=8.1 Hz, 2H), 6.95 (s, 1H), 6.80 (d, J=8.1 Hz, 1H), 5.45 (s, 2H), 3.93 (s, 3H), 2.79 (q, J=7.5 Hz, 2H), 2.55 (s, 9H), 1.25 (t, J=7.5 Hz, 3H).

A mixture of Intermediate 001j(0.030 g, 0.041 mmol), Pd(Ph₃P)₄ (0.005 mg, 4.11 μmol), 2-(tributylstannyl)pyridine (0.030 g, 0.082 mmol) and toluene (1 mL) was treated as described in Example 29. After cooling at RT, the reaction mixture was concentrated, retaken in DCM (1 mL) and treated with triethylsilane (0.033 mL, 0.205 mmol) followed by TFA (0.127 mL, 1.642 mmol) for 20 min. Then the reaction mixture was concentrated, the crude was taken up in DMF and purified via preparative LC-MS with the following conditions: Column: XBridge C18, 19×200 mm, 5-μm particles; Mobile Phase A: 5:95 ACN: H₂O with 10 mM NH₄OAc; Mobile Phase B: 95:5 ACN: H₂O with 10 mM NH₄OAc; Gradient: 10-52% B over 20 minutes, then a 3-minute hold at 100% B; Flow: 20 mL/min. Fractions containing the desired product were combined and dried via centrifugal evaporation to afford the title compound Example 030 (0.014 g, 0.027 mmol, 67%). LC-MS (Method A2): 0.64 min, [M+H]$^+$=487.0; $^1$H NMR (600 MHz, DMSO-d₆) δ ppm 8.68 (d, J=4.0 Hz, 1H), 8.17 (d, J=5.2 Hz, 1H), 8.13-8.03 (m, 2H), 7.90 (t, J=7.6 Hz, 1H), 7.75 (br. s., 1H), 7.40 (dd, J=7.2, 4.9 Hz, 1H), 7.12 (br. s., 2H), 7.03 (d, J=6.3 Hz, 2H), 6.95 (s, 1H), 5.45 (s, 2H), 2.77 (q, J=7.3 Hz, 2H), 2.55 (s, 6H), 1.23 (t, J=7.4 Hz, 3H).

Example 031: 4"-((2-ethyl-5,7-dimethyl-3H-imidazo[4,5-b]pyridin-3-yl)methyl)-[1,1':3',1"-terphenyl]-4'-carboxylic acid

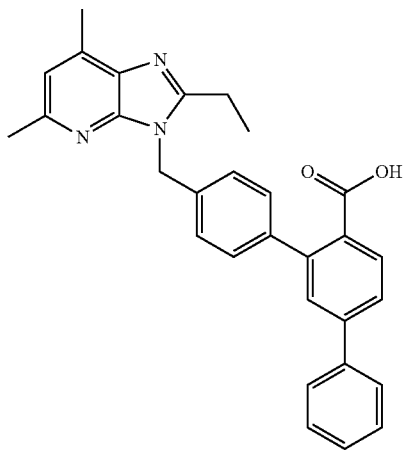

(Ex. 031)

Example 032: 3-(4"-((2-ethyl-5,7-dimethyl-3H-imidazo[4,5-b]pyridin-3-yl)methyl)-[1,1':3',1"-terphenyl]-4'-yl)-1,2,4-oxadiazol-5(4H)-one

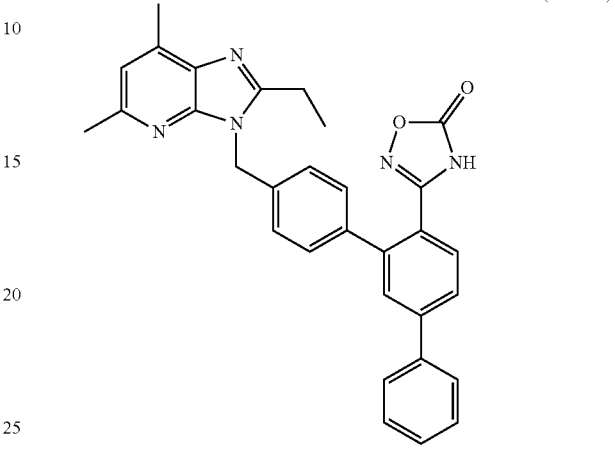

(Ex. 032)

Intermediate 032a: 3-bromo-[1,1'-biphenyl]-4-carbonitrile

(032a)

A solution of Intermediate 001d (0.035 g, 0.089 mmol) and 3-chloro-[1,1'-biphenyl]-4-carboxylic acid (0.031 g, 0.134 mmol) in dioxane (2.5 mL) was was treated with 2M aqueous $K_3PO_4$ (0.224 mL, 0.447 mmol) followed by $PdCl_2$(dppf) (0.0065 g, 8.94 μmol) as described in Example 001. LC-MS showed only traces of the desired compound. More $PdCl_2$(dppf) was added (0.0065 g, 8.94 μmol) and the reaction mixture was heated at 100° C. overnight. The reaction mixture was cooled to RT, filtered over a pad of Celite/$MgSO_4$ and concentrated. The resulting residue was dissolved in DMF, filtered and purified via preparative LC-MS with the following conditions: Column: XBridge C18, 19×200 mm, 5-μm particles; Mobile Phase A: 5:95 ACN: $H_2O$ with 10 mM $NH_4OAc$; Mobile Phase B: 95:5 ACN: $H_2O$ with 10 mM $NH_4OAc$; Gradient: 15-55% B over 20 minutes, then a 4-minute hold at 100% B; Flow: 20 mL/min. Fractions containing the desired product were combined and dried via centrifugal evaporation. to afford the title compound Example 031 (0.005 g, 0.011 mmol, 12%). LC-MS (Method A2): 0.87 min, $[M+H]^+$=462.0. $^1$H NMR (400 MHz, DMSO-$d_6$) δ 7.81-7.66 (m, 4H), 7.56 (s, 1H), 7.51-7.44 (m, 2H), 7.43-7.36 (m, 3H), 7.16 (d, J=8.1 Hz, 2H), 6.96 (s, 1H), 5.51 (s, 2H), 2.83 (q, J=7.5 Hz, 2H), 2.53 (s, 6H), 1.27 (t, J=7.5 Hz, 3H).

To a vial charged with [1,1'-biphenyl]-4-carbonitrile (500 mg, 2.79 mmol), NBS (447 mg, 2.51 mmol) (recrystallized), CSA (324 mg, 1.395 mmol) and diacetoxypalladium (62.6 mg, 0.279 mmol) was added DCE (11.2 mL). The reaction mixture was sealed and heated at 80° C. for 15 h (*J. Org. Chem*, 2013, 78, 2786). The reaction mixture was diluted with EtOAc and concentrated directly onto Celite® for ISCO purification (0-50% EtOAc/Hex) to afford the title compound Intermediate 032a (400 mg, 1.550 mmol, 55.5% yield) as a white solid. LC-MS (Method A2): 1.07 min, [M+H] No ion observed; $^1$H NMR (400 MHz, DMSO-$d_6$) 8.20 (d, J=1.6 Hz, 1H), 8.027 (d, J=8 Hz, 1H), 7.92-7.89 (m, 1H), 7.81-7.79 (m, 2H), 7.55-7.48 (m, 3H).

Intermediate 032b: 4''-((2-ethyl-5,7-dimethyl-3H-imidazo[4,5-b]pyridin-3-yl)methyl)-[1,1':3',1''-terphenyl]-4'-carbonitrile

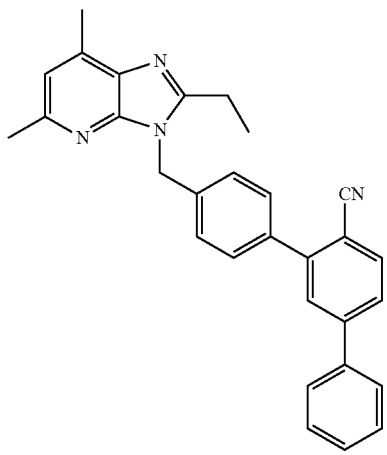

(032b)

To a solution of Intermediate 001d(150 mg, 0.383 mmol) and I-003A (189 mg, 0.498 mmol) in dioxane (3 mL) was added K$_3$PO$_4$ (2 M, aq) (0.575 mL, 1.150 mmol) followed by PdCl2(dppf) (28.0 mg, 0.038 mmol). The resulting mixture was sparged with N$_2$ for 2 min before the vessel was sealed and heated at 120° C. for 45 min in the microwave. The crude reaction was diluted with EtOAc and filtered through celite. The filtrate was concentrated and the residue was dissolved in a small amount of methylene chloride and charged to a 40 g silica gel cartridge which was eluted with a 30 min gradient ofof 0-100% EtOAc in hexane to afford the title compound (Intermediate 032b, 133 mg, 0.301 mmol, 78% yield), as a white solid. LC-MS (Method A2): 0.92 min, [M+H]$^+$=443.1; $^1$H NMR (500 MHz, CDCl$_3$) δ 7.83 (d, J=8.0 Hz, 1H), 7.70-7.65 (m, 2H), 7.64-7.61 (m, 2H), 7.56 (d, J=8.3 Hz, 2H), 7.53-7.47 (m, 2H), 7.47-7.42 (m, 1H), 7.31-7.26 (m, 3H), 6.94 (s, 1H), 5.56 (s, 2H), 2.90-2.83 (m, 2H), 2.67 (s, 3H), 2.63 (s, 3H), 1.37 (t, J=7.6 Hz, 3H).

Example 032: 3-(4''-((2-ethyl-5,7-dimethyl-3H-imidazo[4,5-b]pyridin-3-yl)methyl)-[1,1':3',1''-terphenyl]-4'-yl)-1,2,4-oxadiazol-5(4H)-one Hydroxylamine hydrochloride (70.7 mg, 1.017 mmol) was dissolved in DMSO (1 mL). TEA (0.142 mL, 1.017 mmol) was added and the reaction was allowed to stir at RT for 5 minutes. The mixture was then diluted with THF (1 mL) and filtered. The THF was then concentrated from the filtrate under reduced pressure and the resulting DMSO solution was added to a solution of Intermediate 032b (15 mg, 0.034 mmol) in 0.5 mL of DMSO. The mixture was heated at 80° C. for 15 hours. The reaction was diluted with 4 mL of H$_2$O and the precipitate was filtered off. This precipitate was redissolved in DMF (2 mL) and DBU (0.026 mL, 0.169 mmol) was added. CDI (55.0 mg, 0.339 mmol) was then added and the reaction mixture was allowed to stir at RT for 10 minutes before being filtered and purified by preparative LC-MS with the following conditions: Column: XBridge C18, 19×200 mm, 5-μm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 20-60% B over 20 minutes, then a 4-minute hold at 100% B; Flow: 20 mL/min. Fractions containing the desired product were combined and dried via centrifugal evaporation to afford the title compound (Example 032, 1.9 mg, 0.004 mmol, 11% yield). LC-MS (Method A2): 0.84 min, [M+H]$^+$=502.1; $^1$H NMR (500 MHz, CDCl$_3$) δ 7.80-7.71 (m, 1H), 7.69-7.58 (m, 1H), 7.51-7.44 (m, 1H), 7.42-7.37 (m, 1H), 7.34 (d, J=7.6 Hz, 2H), 7.13 (d, J=7.9 Hz, 2H), 6.96 (s, 1H), 5.49 (s, 2H), 2.80 (q, J=7.4 Hz, 2H), 2.55 (s, 6H), 1.23 (t, J=7.5 Hz, 3H).

Example 033: 3-((6'-(2H-tetrazol-5-yl)-[1,1':3',1''-terphenyll-4-yl)methyl)-2-butyl-1,3-diazaspiro[4.4]non-1-en-4-one

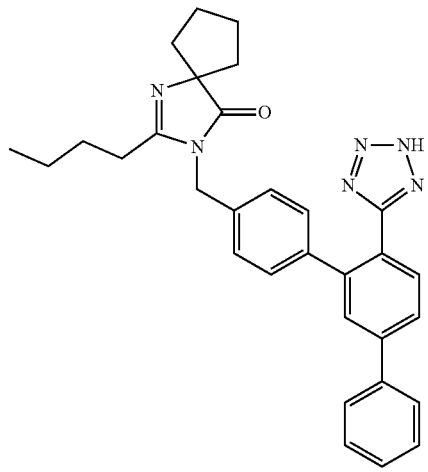

(Ex. 033)

Intermediate 033a: 2-butyl-3-(4-(4,4,5,5-tetramethyl-1,3,2-dioxaborolan-2-yl)benzyl)-1,3-diazaspiro[4.41 non-1-en-4-one

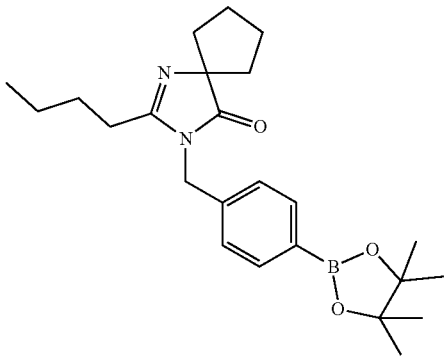

(033a)

A suspension of 2-butyl-1,3-diazaspiro[4.4]non-1-en-4-one, HCl (0.150 g, 0.650 mmol) and 2-(4-(bromomethyl)phenyl)-4,4,5,5-tetramethyl-1,3,2-dioxaborolane (0.232 g, 0.780 mmol) in DMF (3.25 mL) was treated with potassium carbonate (0.270 g, 1.950 mmol) according to the procedure described in Synth. Commun., 2005, 35, 1979. After 20 h of stirring, the reaction mixture was diluted with EtOAc and filtered over Celite®. The organic phase was washed with brine, dried over MgSO₄, re-filtered over Celite®, concentrated and purified by ISCO (EtOAc/Hexanes, 0-100%) to afford the title compound (Intermediate 033a, 0.200 g, 0.487 mmol, 75.0% yield) as a viscous oil. LC-MS (Method A2): 0.89 min, [M+H]⁺=411.2; ¹H NMR (400 MHz, CDCl₃) δ ppm 7.77 (d, J=8.1 Hz, 2H), 7.15 (d, J=8.1 Hz, 2H), 4.68 (s, 2H), 2.29-2.21 (m, 2H), 2.03-1.87 (m, 6H), 1.86-1.74 (m, 2H), 1.59-1.49 (m, 2H), 1.38-1.21 (m, 14H), 0.85 (t, J=7.4 Hz, 3H).

Intermediate 033b: 4"-((2-butyl-4-oxo-1,3-diazaspiro[4.4]non-1-en-3-yl)methyl)-[1,1':3',1"-terphenyl]-4'-carbonitrile

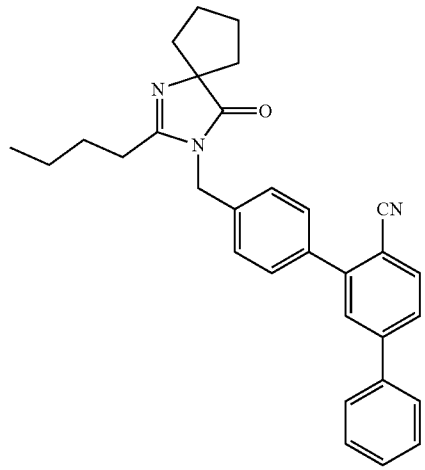

(033b)

To a solution of Intermediate 033a (0.050 g, 0.122 mmol) and Intermediate 032a (0.047 g, 0.183 mmol) in dioxane (3 mL) was added K₃PO₄ (2 M, aq., 0.183 mL, 0.366 mmol) followed by PdCl₂(dppf) (0.009 g, 0.012 mmol). The resulting mixture was sparged with N₂ for 2 min before the vessel was sealed and heated at 120° C. for 45 min under microwave irradiation. The reaction mixture was cooled to RT, diluted with EtOAc and filtered over a pad of Celite®/MgSO₄. The filtrate was concentrated to a brown residue which was purified by ISCO (EtOAc/Hexanes, 0-100%) to afford the title compound (Intermediate 033b, 0.053 g, 0.115 mmol, 94% yield) as a viscous oil. LC-MS (Method A2): 0.96 min, [M+H]⁺=462.2; ¹H NMR (400 MHz, CDCl₃) δ ppm 7.83 (d, J=7.9 Hz, 1H), 7.71-7.64 (m, 2H), 7.64-7.57 (m, 4H), 7.53-7.40 (m, 3H), 7.30 (d, J=8.1 Hz, 2H), 4.76 (s, 2H), 2.39-2.33 (m, 2H), 2.04-1.90 (m, 6H), 1.90-1.80 (m, 2H), 1.61 (dt, J=15.5, 7.6 Hz, 2H), 1.42-1.30 (m, 2H), 0.88 (t, J=7.4 Hz, 3H).

Example 033: 3-((6'-(2H-Tetrazol-5-yl)-[1,1':3',1"-terphenyl]-4-yl)methyl)-2-butyl-1,3-diazaspiro[4.4]non-1-en-4-one A vial containing Intermediate 033b (0.053 g, 0.115 mmol) and dibutyltin oxide (0.057 g, 0.230 mmol) in toluene (1.15 mL) was treated with TMS-N₃ (0.152 mL, 1.148 mmol) according to the procedure described for Intermediate 001 g. After cooling, the reaction mixture was diluted with MeOH and EtOAc and quenched by the portionwise addition of a 10% aqueous solution of CAN (6.30 g, 1.148 mmol) until bubbling ceased. Then the organic phase was washed with saturated aqueous NH₄Cl and brine, dried over MgSO₄, filtered over Celite® and concentrated. The crude residue was taken up in DMF, filtered and purified via preparative LC-MS (Column: XBridge C18, 19×200 mm, 5-μm particles; Mobile Phase A: 5:95 ACN: H₂O with 10 mM NH₄OAc; Mobile Phase B: 95:5 ACN: H₂O with 10 mM NH₄OAc; Gradient: 10-100% B over 25 minutes, then a 10-minute hold at 100% B; Flow: 20 mL/min) to afford 0.0055 g (0.011 mmol, 10%) of the title compound Example 033. LC-MS (Method A2): 0.85 min, [M+H]⁺=505.1; ¹H NMR (500 MHz, DMSO-d₆) δ ppm 7.88-7.78 (m, 3H), 7.77-7.70 (m, 2H), 7.55-7.47 (m, 2H), 7.46-7.39 (m, 1H), 7.19 (d, J=7.7 Hz, 2H), 7.09 (d, J=7.8 Hz, 2H), 4.69 (s, 2H), 2.31 (t, J=7.5 Hz, 2H), 1.92-1.76 (m, 6H), 1.67 (d, J=6.6 Hz, 2H), 1.48 (quint, J=7.4 Hz, 2H), 1.27 (sext, J=7.4 Hz, 2H), 0.81 (t, J=7.3 Hz, 3H).

Example 034: (S)-2-(N-((6'-(2H-Tetrazol-5-yl)-[1,1':3',1"-terphenyl-4-yl)methyl) pentanamido)-3-methylbutanoic acid

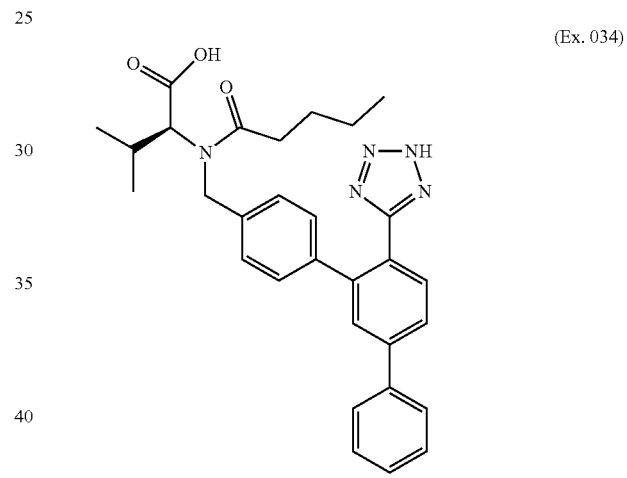

(Ex. 034)

Intermediate 034a: (S)-Methyl 3-methyl-2-((4-(4,4,5,5-tetramethyl-1,3,2-dioxaborolan-2-yl)benzyl)amino)butanoate

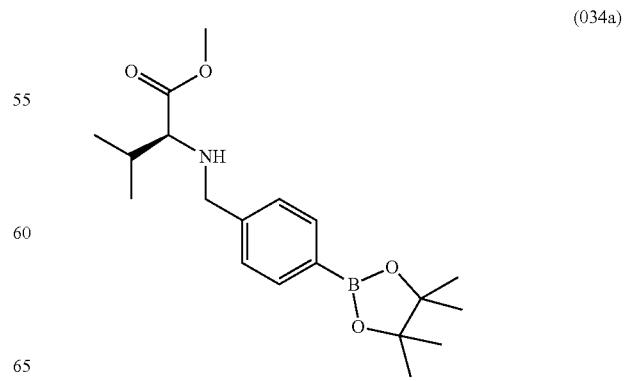

(034a)

To a suspension containing (S)-methyl 2-amino-3-methylbutanoate, HCl (0.169 g, 1.010 mmol) and 2-(4-(bromomethyl)phenyl)-4,4,5,5-tetramethyl-1,3,2-dioxaborolane (0.250 g, 0.842 mmol) in ACN (2.81 mL) was added potassium carbonate (0.465 g, 3.37 mmol). The reaction vessel was sealed and the mixture was heated at 70° C. for 5 h. The cooled reaction mixture was diluted with EtOAc and filtered over Celite®. The resulting mixture was concentrated to afford the crude product, which was used as such in the next step. LC-MS (Method A2): 0.75 min, [M+H]$^+$=348.1.

Intermediate 034b: (S)-Methyl 3-methyl-2-(N-(4-(4,4,5,5-tetramethyl-1,3,2-dioxaborolan-2-yl)benzyl) pentanamido)butanoate

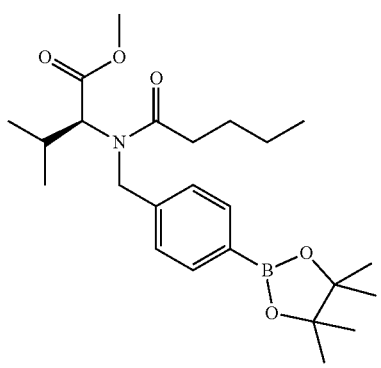

(034b)

To a solution of crude Intermediate 034a (0.250 g, 0.720 mmol) in DCM (7.2 mL) was added Hunig's base (0.63 mL, 3.60 mmol) followed by valeryl chloride (0.17 mL, 1.440 mmol). After 15 min of stirring, the reaction mixture was concentrated and purified by ISCO (EtOAc/Hexanes, 0-50%) to afford the title compound (Intermediate 034b, 0.250 g, 0.406 mmol, 56.4% yield) as a yellow oil. LC-MS (Method A2): 1.18 min, [M+H]$^+$=432.2; $^1$H NMR (400 MHz, CDCl$_3$) δ ppm 7.75 (d, J=7.9 Hz, 2H), 7.14 (d, J=7.9 Hz, 2H), 4.98 (d, J=10.6 Hz, 1H), 4.63 (s, 2H), 3.44 (s, 3H), 2.32-2.23 (m, 2H), 2.21-2.12 (m, 1H), 1.67-1.52 (m, 2H), 1.35-1.31 (m, 12H), 1.29-1.15 (m, 2H), 1.00-0.93 (m, 3H), 0.88 (d, J=6.8 Hz, 3H), 0.86-0.77 (m, 3H).

Intermediate 034c: (S)-Methyl 2-(N-((6'-cyano-[1,1':3',1''-terphenyl]-4-yl)methyl)pentanamido)-3-methylbutanoate

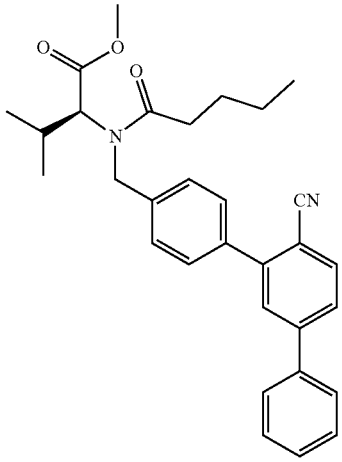

(034c)

To a solution of Intermediate 034b (0.060 g, 0.139 mmol) and Intermediate 032a (0.054 g, 0.209 mmol) in dioxane (3 mL) was added K$_3$PO$_4$ (2M aq, 0.209 mL, 0.417 mmol) followed by PdCl$_2$(dppf) (0.011 g, 0.014 mmol) and the resulting mixture was reacted as described in Example 033b. The cooled reaction mixture was diluted with EtOAc and filtered over a pad of Celite®/MgSO$_4$. The filtrate was concentrated to a brown residue which was purified by ISCO (EtOAc/Hexanes, 0-100%) to afford the title compound (Intermediate 034c, 0.064 g, 0.080 mmol, 57.2%) as a yellow oil. LC-MS (Method A2): 1.21 min, [M+H]$^+$=483.1; $^1$H NMR (400 MHz, CDCl$_3$) δ ppm 7.85-7.78 (m, 1H), 7.72-7.66 (m, 1H), 7.65-7.56 (m, 4H), 7.54-7.39 (m, 4H), 7.36-7.28 (m, 2H), 4.97 (d, J=10.3 Hz, 1H), 4.70 (s, 2H), 3.47 (s, 3H), 2.53-2.34 (m, 3H), 1.70-1.56 (m, 2H), 1.36-1.28 (m, 2H), 1.00 (d, J=6.6 Hz, 6H), 0.93-0.89 (m, 3H).

Intermediate 034d: (S)-Methyl 2-(N-((6'-(1H-tetrazol-5-yl)-[1,1':3',1''-terphenyl1-4-yl)methyl) pentanamido)-3-methylbutanoate

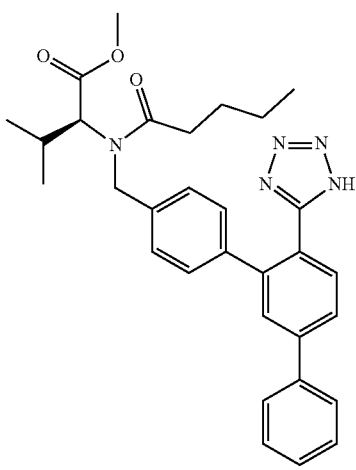

(034d)

To a vial containing Intermediate 034c (0.060 g, 0.124 mmol) was added dibutyltin oxide (0.031 g, 0.124 mmol) and toluene (2 mL) followed by TMS-N$_3$ (0.083 mL, 0.622 mmol). The reaction vial was sealed and the mixture heated at 100° C. overnight. After 14 h of heating, LC-MS showed 70% conversion to the desired tetrazole. Another aliquot of TMS-N$_3$ (0.083 mL, 0.622 mmol) was added and heating was continued for another 6 h.

The cooled reaction mixture was then diluted with EtOAc and a small amount of MeOH was added to fully solubilize the tetrazole product. To this organic phase was added CAN (10% aqueous) (6.82 g, 1.244 mmol) and the residue was vigorously stirred until bubbling ceased. The organic phase was separated, concentrated and used as such in the next step (quantitative yield of Intermediate 034d was assumed). LC-MS (Method A2): 1.07 min, [M+H]$^+$=526.1.

Example 034: (S)-2-(N-((6'-(2H-Tetrazol-5-yl)-[1,1':3',1"-terphenyl]-4-yl)methyl) pentanamido)-3-methylbutanoic acid To a solution of crude Intermediate 034d (0.050 g, 0.095 mmol) in THF (1 mL) was added H$_2$O (1 mL) followed by LiOH monohydrate (0.040 g, 0.951 mmol). The resulting emulsion was sonicated and vigorously stirred for min before being heated at 65° C. overnight. After cooling to RT, the mixture was diluted with EtOAc and washed with 1 M HCl. The cloudy organic phase was concentrated to a crude yellow oil, which was taken up in DMF, filtered and purified via preparative LC-MS (Column: XBridge C18, 19×200 mm, 5-µm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 15-55% B over 19 minutes, then a 5-minute hold at 100% B; Flow: 20 mL/min) to afford 0.012 g (0.024 mmol, 25%) of the title compound Example 034. LC-MS (Method A2): 1.01 min, [M+H]$^+$=512.1; $^1$H NMR (500 MHz, DMSO-d$_6$ at 100° C.) δ ppm 7.79-7.67 (m, 4H), 7.62-7.58 (m, 1H), 7.49 (t, J=7.6 Hz, 2H), 7.43-7.36 (m, J=7.7 Hz, 1H), 7.26-7.11 (m, 4H), 4.70-4.47 (m, 2H), 3.58-3.50 (m, 1H), 2.40-2.15 (m, 3H), 1.61-1.43 (m, 2H), 1.36-1.21 (m, 2H), 0.98 (d, J=6.3 Hz, 3H), 0.81 (d, J=6.9 Hz, 6H). [Note: VT NMR used to coalesce rotomer peaks].

Example 035: (1-((6'-(1H-Tetrazol-5-yl)-[1,1':3',1"-terphenyl]-4-yl)methyl)-2-butyl-4-chloro-1H-imidazol-5-yl)methanol

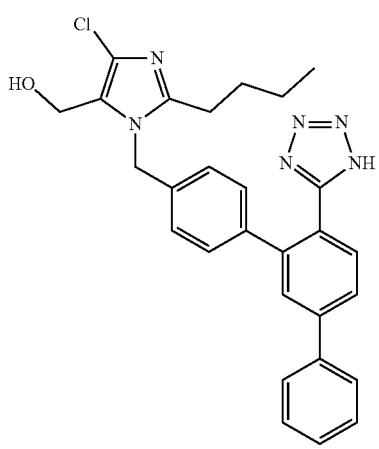

(Ex. 035)

Intermediate 035a: 2-Butyl-4-chloro-1-(4-(4,4,5,5-tetramethyl-1,3,2-dioxaborolan-2-yl)benzyl)-1H-imidazole-5-carbaldehyde

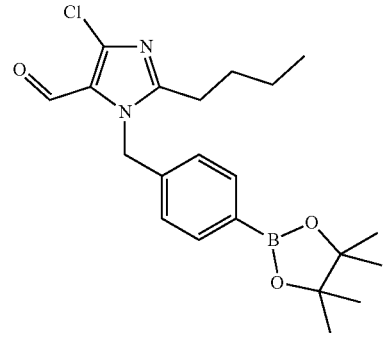

(035a)

A solution of 2-butyl-4-chloro-1H-imidazole-5-carbaldehyde (300 mg, 1.607 mmol) and 4-(bromomethyl)benzenboronic acid pinacol ester (501 mg, 1.688 mmol) in N,N-dimethylacetamide (5358 µl) was cooled to −10° C. To this cooled solution was added potassium carbonate (244 mg, 1.768 mmol) (9:15 am) and the mixture was stirred vigorously for 1 h before being allowed to warm to RT and stir for an additional 3 h. The crude reaction mixture was filtered over Celite® and rinsed with a 3 mL of DMA. This solution containing the title compound (Intermediate 035a) was taken directly into the subsequent sodium borohydride reduction without further purification. LC-MS (Method A2): 1.19 min, [M+H]$^+$=403.1, 405.1.

Intermediate 035b: (2-Butyl-4-chloro-1-(4-(4,4,5,5-tetramethyl-1,3,2-dioxaborolan-2-yl)benzyl)-1H-imidazol-5-yl)methanol

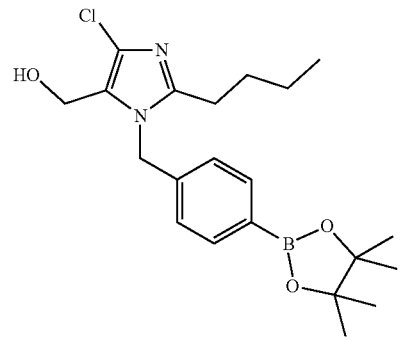

(035b)

To the crude solution of Intermediate 035a (483 mg, 1.200 mmol) in DMA (9 mL) was added MeOH (9 mL) followed by sodium borohydride (113 mg, 3.00 mmol). After 2 h of stirring, 2 mL of AcOH was added to quench the reaction, and the resulting reaction mixture was concentrated to a crude residue. This residue was purified by ISCO (0-100% EtOAc/Hex) to afford the title compound (Intermediate 035b, 380 mg, 0.939 mmol, 78% yield over the two-step process) as an amorphous white solid. LC-MS (Method A2): 0.91 min, [M+H]$^+$=405.1, 407.1. $^1$H NMR (400 MHz, CDCl$_3$) δ 7.76 (d, J=8.1 Hz, 2H), 6.98 (d, J=8.1 Hz, 2H), 5.23 (s, 2H), 4.46 (s, 2H), 2.57-2.50 (m, 2H), 1.70-1.57 (m, 2H), 1.38-1.29 (m, 14H), 0.86 (t, J=7.4 Hz, 3H).

Intermediate 035c: 4"-((2-Butyl-4-chloro-5-(hydroxymethyl)-1H-imidazol-1-yl)methyl)-[1,1':3',1"-terphenyl]-4'-carbonitrile

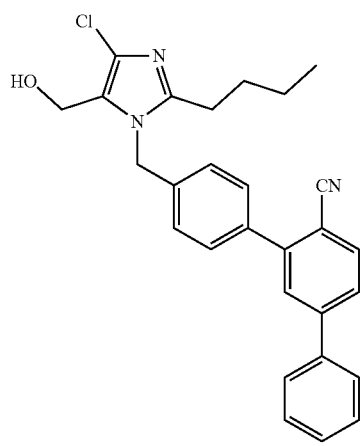

(035c)

To a solution of Intermediate 035b (90 mg, 0.222 mmol) and Intermediate 032a (86 mg, 0.334 mmol) in dioxane (3 mL) was added K$_3$PO$_4$ (2 M, aq) (0.222 mL, 0.445 mmol) followed by PdCl$_2$(dppf) (16.27 mg, 0.022 mmol). The resulting mixture was sparged with N$_2$ for 2 min before being sealed and heated at 120° C. for 45 min in the microwave. The reaction mixture was cooled to RT, diluted with EtOAc and filtered over a pad of Celite®/MgSO$_4$. The filtrate was concentrated to a brown residue which was purified by ISCO (0-100% EtOAc/Hex) to afford the title compound (Intermediate 035c, 65 mg, 0.143 mmol, 64.1% yield) as a light brown oil. LC-MS (Method A2): 0.97 min, [M+H]$^+$=456.0, 458.0. $^1$H NMR (400 MHz, CDCl$_3$) δ 7.85-7.80 (m, 1H), 7.70-7.65 (m, 2H), 7.64-7.56 (m, 4H), 7.53-7.42 (m, 3H), 7.14 (d, J=8.4 Hz, 2H), 5.30 (s, 2H), 4.54 (d, J=5.3 Hz, 2H), 2.65-2.57 (m, 2H), 1.75-1.64 (m, 2H), 1.43-1.31 (m, 2H), 0.89 (t, J=7.3 Hz, 3H).

Example 035: (1-((6'-(1H-Tetrazol-5-yl)-[1,1':3',1"-terphenyl]-4-yl)methyl)-2-butyl-4-chloro-1H-imidazol-5-yl)methanol To a vial containing Intermediate 035c (65 mg, 0.143 mmol) was added dibutyltin oxide (35.5 mg, 0.143 mmol) and toluene (1.5 mL) followed by TMS-N$_3$ (0.095 mL, 0.713 mmol). The reaction mixture was sealed and heated at 100° C. behind a blast shield. After 16 h of heating, the reaction mixture was diluted with EtOAc and a small amount of MeOH was added to fully solubilize the tetrazole product. To this organic phase was added CAN (10% aqueous) and the residue was vigorously stirred until bubbling ceased. The organic phase was separated, concentrated, retaken in DMF, filtered and purified via preparative LC-MS with the following conditions: Column: XBridge Phenyl, 19×200 mm, 5-µm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 20-60% B over 19 minutes, then a 5-minute hold at 100% B; Flow: 20 mL/min. Fractions containing the desired product were combined and dried via centrifugal evaporation to afford the title compound (Example 035, 0.001 g, 0.001 mmol, 1%). LC-MS (Method A2): 0.87 min, [M+H]$^+$=499.0; $^1$H NMR (500 MHz, DMSO-d$_6$) δ 7.74 (d, J=7.6 Hz, 1H), 7.68 (br. s., 1H), 7.54 (s, 1H), 7.47 (t, J=7.5 Hz, 2H), 7.41-7.34 (m, 1H), 7.19 (br. s., 2H), 6.94 (d, J=7.3 Hz, 2H), 5.23 (s, 2H), 4.32 (s., 2H), 2.51-2.45 (m, 2H), 1.49 (quin, J=7.4 Hz, 2H), 1.32-1.21 (m, 2H), 0.82 (t, J=7.3 Hz, 3H).

Example 039: Butyl (3-(5-((2-ethyl-5,7-dimethyl-3H-imidazo[4,5-b]pyridin-3-yl) methyl) pyridin-2-yl)-5-(o-tolyl)thiophen-2-yl)sulfonylcarbamate

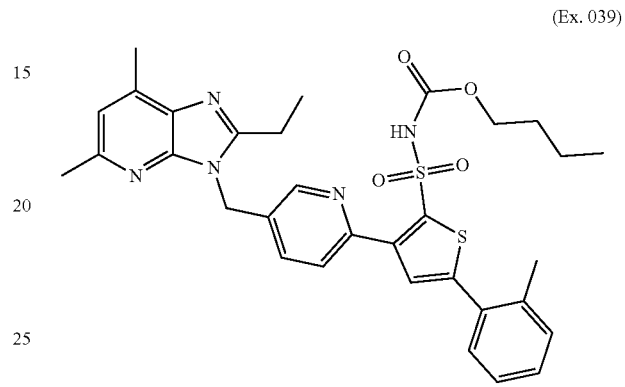

(Ex. 039)

Intermediate 039a: 3-((6-Bromopyridin-3-yl)methyl)-2-ethyl-5,7-dimethyl-3H-imidazo[4,5-b]pyridine

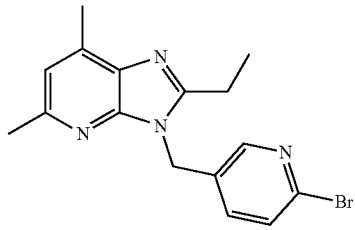

(039a)

To a solution of Intermediate 001c (0.491 g, 2.800 mmol) in NMP (15 mL) was added freshly pulverized NaOH (0.230 g, 5.74 mmol). The resulting mixture was stirred at RT under N$_2$ for 1 h and then it was cooled at 0° C. and a solution of 2-bromo-5-(bromomethyl)pyridine (0.738 g, 2.94 mmol) in NMP (3 mL) was added over 5 min. The cooling bath was subsequently removed and the reaction mixture was stirred at RT for 48 h. The resulting mixture was cooled at 0° C. and H$_2$O (40 mL) was added dropwise over ca. 15 min. The cooling bath was then removed and the resulting solution was stirred at RT for several hours. The resulting homogenous mixture was extracted with EtOAc (×2) and the combined organic phase was washed with brine, dried (Na$_2$SO$_4$) and evaporated to give an amber solid which was purified by ISCO (0-100%, EtOAc-DCM) to afford the pure product as a white solid (Intermediate 039a, 0.757 g, 78%). LC (Method B): 1.586 min; HRMS (ESI): Calcd. for C$_{16}$H$_{18}$BrN$_4$ [M+H]$^+$ n/z 345.0719; found 345.0715; 1H NMR (400 MHz, DMSO-d$_6$) δ ppm 8.33 (d, J=2.35 Hz, 1H), 7.57 (d, J=8.22 Hz, 1H), 7.44 (dd, J=8.22, 2.35 Hz, 1H), 6.94 (s, 1H), 5.45 (s, 2H), 2.81 (q, J=7.43 Hz, 2H), 2.50 (s, 6H under DMSO), 1.22 (t, J=7.43 Hz, 3H).

Intermediate 039b: N-(tert-Butyl-5-(o-tolyl)thiophene-2-sulfonamide

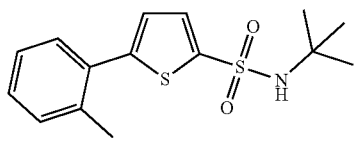

(039b)

A mixture of 5-bromo-N-(tert-butyl)thiophene-2-sulfonamide (0.596 g, 2.000 mmol) and o-tolylboronic acid (0.408 g, 3.00 mmol) in toluene-ethanol (9:1, 10 mL) was purged with a stream of $N_2$ for 20 min in a sealable vial. To this mixture was added $Pd(Ph_3P)_4$ (0.231 g, 0.200 mmol) and 2 M aqueous $Na_2CO_3$ (3.00 mL, 6.00 mmol), the vial was sealed and the mixture was stirred at 95° C. overnight. The cooled mixture was filtered and the residue was washed with EtOAc. The filtrate was washed (sat. aq. $NaHCO_3$), dried ($Na_2SO_4$) and evaporated to give a dark brown gum. This material was purified by ISCO (0-50%, EtOAc-hexane) to give the title compound (Intermediate 039b, 0.490 g, 79% yield) as a white solid. LC (Method B): 2.124 min; HRMS (ESI): Calcd. for $C_{15}H_{20}NO_2S_2$ $[M+H]^+$ m/z 310.0935; found: 310.0923; $^1$H NMR (400 MHz, DMSO-$d_6$) δ ppm 7.76 (s, 1H), 7.56 (d, J=3.91 Hz, 1H), 7.40 (d, J=7.83 Hz, 1H), 7.32-7.36 (m, 2H), 7.28 (d, J=7.43 Hz, 1H), 7.18 (d, J=3.91 Hz, 1H), 2.37 (s, 3H), 1.18 (s, 9H).

Intermediate 039c: (2-(N-(tert-Butyl)sulfamoyl)-5-(o-tolyl)thiophen-3-yl)boronic acid

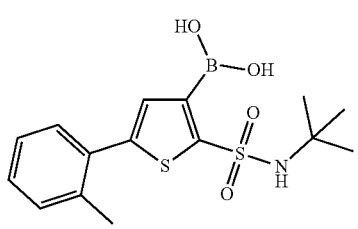

(039c)

A solution of Intermediate 039b (0.409 g, 1.322 mmol) in dry THF (15 mL) was cooled at −78° C. under $N_2$ and a solution of 1.6 M n-BuLi in hexanes (2.065 mL, 3.30 mmol) was added dropwise over 5 min. The mixture was stirred for 30 min and then the temperature was raised to about −20° C. (−10° C. to −18° C. using ice-MeOH) and stirring was continued at that temperature for 3 h. The resulting light yellow solution was recooled at −78° C. and triisopropyl borate (0.460 mL, 1.983 mmol) was added dropwise. Stirring was continued as the cooling bath discharged overnight. The resulting turbid mixture was quenched with 2M HCl (9.91 mL, 19.83 mmol) and the mixture was stirred for 30 min. This mixture was then partitioned with EtOAc-$H_2O$ and the organic phase was separated, washed ($H_2O$, brine), dried ($Na_2SO_4$) and evaporated to give a gum. This gum was purified by flash chromatography (ISCO 0-100%, EtOAc-hex) to afford the title compound (Intermediate 039c, 0.192 g, 41%). LC-MS (APCI): Calcd. for $C_{15}H_{19}BNO_4S_2[M-H]^-$ m/z 352.0849; found: 352.2; $^1$H NMR (400 MHz, DMSO-$d_6$) δ ppm 8.60 (s, 1H), 7.39 (d, J=7.83 Hz, 1H), 7.23-7.33 (m, 4H), 2.38 (s, 3H), 1.18 (s, 9H).

Intermediate 039d: N-(tert-Butyl)-3-(5-((2-ethyl-5,7-dimethyl-3H-imidazo[4,5-[pyridin-3-yl)methyl)pyridin-2-yl)-5-(o-tolyl)thiophene-2-sulfonamide

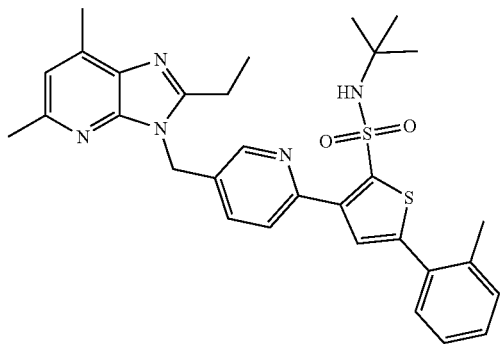

(039d)

A mixture of Intermediate 039a (0.086 g, 0.250 mmol), Intermediate 039c (0.132 g, 0.375 mmol), 2 M aqueous $Na_2CO_3$ (0.50 mL, 1.00 mmol) and $Pd(Ph_3P)_4$ (0.029 g, 0.025 mmol) in toluene-ethanol (9:1, 10 mL) was treated as described in Example 039b. The cooled mixture was diluted with EtOAc and the organic phase was separated, dried ($Na_2SO_4$) and evaporated to give an amber gum. This material was taken up in DMF and purified by preparative LC (Method C) to give the title compound (Intermediate 039d, 0.163 g, 81% yield) as a colourless gum which was used as such in the next step. LC (Method B): 2.169 min; HRMS (ESI): Calcd. for $C_{31}H_{36}N_5O_2S_2[M+H]^+$ m/z 574.2310; found: 574.2332; $^1$H NMR (400 MHz, DMSO-$d_6$) δ ppm 8.71 (s, 1H), 7.84-7.93 (m, 2H), 7.68 (d, J=7.83 Hz, 1H), 7.59 (s, 1H), 7.47 (d, J=7.43 Hz, 1H), 7.34 (dd, J=3.72, 2.15 Hz, 2H), 7.24-7.32 (m, 1H), 7.08 (br s, 1H), 5.62 (br s, 2H), 2.97 (d, J=7.04 Hz, 2H), 2.53 (d, J=2.74 Hz, 6H), 2.40 (s, 3H), 1.28 (t, J=7.43 Hz, 3H), 1.13 (s, 9H).

Intermediate 039e: 3-(5-((2-Ethyl-5,7-dimethyl-3H-imidazo[4,5-b]pyridin-3-yl)methyl)pyridin-2-yl)-5-(o-tolyl)thiophene-2-sulfonamide

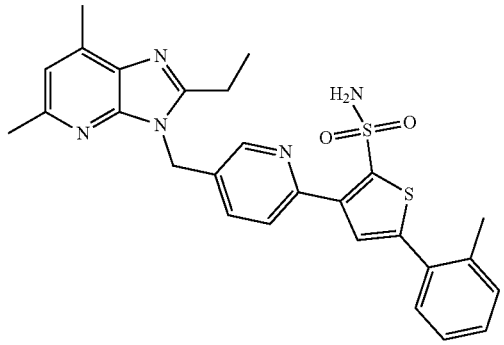

(039e)

To a mixture of Intermediate 039d (0.144 g, 0.180 mmol) in DCM (3 mL) and anisole (0.196 mL, 1.796 mmol) was added TFA (5 mL) and the mixture was stirred at RT in a sealed flask overnight. The volatiles were removed under reduced pressure and the residue was evaporated from ACN solution (×2) to give a colourless gum. Quantitative yield of Intermediate 039e was assumed and this material was used as such in the next step without further purification. LC-MS (APCI): Calcd. for $C_{27}H_{28}N_5O_2S_2[M+H]^+$ m/z 518.1684; found: 518.1.

Example 039: Butyl (3-(5-((2-ethyl-5,7-dimethyl-3H-imidazo[4,5-b]pyridin-3-yl) methyl)pyridin-2-yl)-5-(o-tolyl)thiophen-2-yl)sulfonylcarbamate A solution of Intermediate 039e (0.045 g, 0.060 mmol) in pyridine (1 mL) was treated with triethylamine (0.063 mL, 0.450 mmol), 4-(pyrrolidin-1-yl)pyridine (0.027 g, 0.180 mmol) and butyl carbonochloridate (0.024 mL, 0.180 mmol) and the reaction mixture was stirred at RT overnight. The reaction mixture was subsequently evaporated to dryness to give a solid residue. The residue was taken up in DMF, the mixture was acidified with AcOH and the solution was submitted to preparative LC purification (Method D) to give the title compound (Example 039, 0.023 g, 0.037 mmol, 62% yield) as a white solid. LC (Method B): 2.125 min; HRMS (ESI): Calcd. for $C_{32}H_{36}N_5O_4S_2[M+H]^+$ m/z 618.2209; found 618.2224; $^1$H NMR (400 MHz, DMSO-$d_6$) δ ppm 8.52-8.56 (m, 1H), 7.83 (d, J=7.83 Hz, 1H), 7.65 (dd, J=8.41, 2.15 Hz, 1H), 7.56 (s, 1H), 7.47 (d, J=7.43 Hz, 1H), 7.34-7.38 (m, 2H), 7.27-7.33 (m, 1H), 6.98 (s, 1H), 5.56 (s, 2H), 3.96 (t, J=6.46 Hz, 2H), 2.85 (q, J=7.43 Hz, 2H), 2.51-2.52 (m, 6H), 2.39-2.44, (m, 3H), 1.36-1.45 (m, 2H), 1.26 (t, J=7.43 Hz, 3H), 1.15-1.20 (m, 3H), 0.76 (t, J=7.43 Hz, 3H).

Example 040: Butyl (3-(4-((2-ethyl-5,7-dimethyl-3H-imidazo[4,5-b]pyridin-3-yl)methyl) phenyl)-5-(o-tolyl) thiophen-2-yl)sulfonylcarbamate

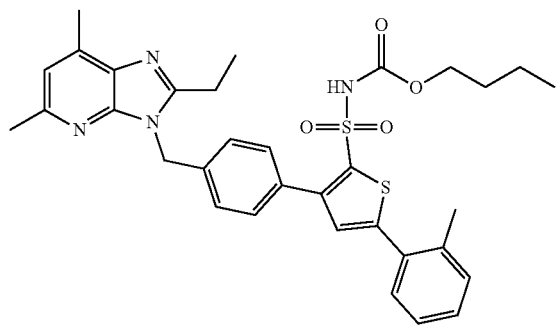
(Ex. 040)

Intermediate 040a: 3-(4-Bromobenzyl)-2-ethyl-5,7-dimethyl-3H-imidazo[4,5-b]pyridine

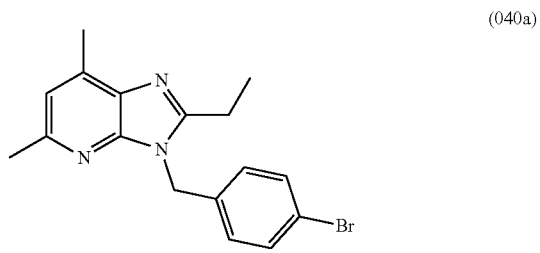 [SMILES: CCc1nc2c(C)cc(C)nc2n1Cc1ccc(Br)cc1]
(040a)

A solution of Intermediate 001c (0.491 g, 2.800 mmol) in NMP (10 mL) was treated with a solution of NaOH (0.230 g, 5.74 mmol) in NMP (2 mL) followed with a solution of 1-bromo-4-(bromomethyl)benzene (0.735 g, 2.94 mmol) in NMP (2 mL) as described in Example 039a. The cooling bath was then removed and the reaction mixture was stirred at RT for 1.5 h. The mixture was cooled at 0° C. and H$_2$O (40 mL) was added dropwise over ca. 15 min. The cooling bath was then removed and the resulting slurry was stirred at RT for 1 h. The mixture was then filtered and the filter cake was washed with NMP-H$_2$O (1:3, 10 mL) and then H$_2$O (2×20 mL). The resulting solid was dried in vacuo in a dessicator to give the title compound (Intermediate 040a, 0.637 g, 66.1% yield) as a beige solid. This material was used as such in the next step. LC (Method B): 1.815 min; HRMS (ESI): Calcd. for $C_{17}H_{19}BrN_3$ $[M+H]^+$ m/z 344.0762; found 344.0756; $^1$H NMR (400 MHz, DMSO-$d_6$) δ ppm 7.47-7.53 (m, 2H), 7.02-7.08 (m, 2H), 6.93 (s, 1H), 5.41 (s, 2H), 2.74 (q, J=7.4 Hz, 2H), 2.50 (s, 6H, under DMSO), 1.20 (t, J=7.6 Hz, 3H).

Intermediate 040b: N-(tert-Butyl)-3-(4-((2-ethyl-5,7-dimethyl-3H-imidazo[4,5-b]pyridin-3-yl)methyl) phenyl)-5-(o-tolyl)thiophene-2-sulfonamide

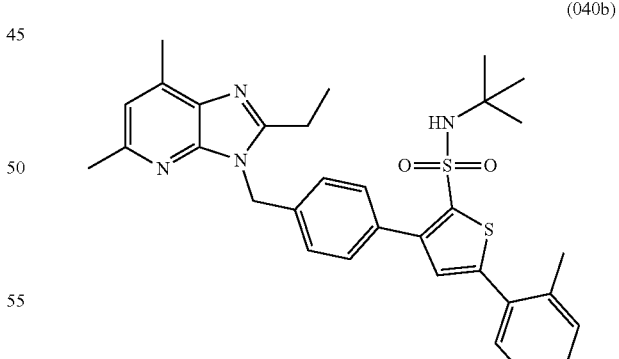
(040b)

A mixture of Intermediate 040a (0.070 g, 0.203 mmol) and Intermediate 039c (0.090 g, 0.254 mmol), 2 M aqueous Na$_2$CO$_3$ (0.434 mL, 0.869 mmol) and Pd(Ph$_3$P)$_4$ (0.023 g, 0.020 mmol) in toluene-ethanol (9:1, 5 mL) was treated as described in Example 039b. The cooled mixture was diluted with EtOAc, filtered through Na$_2$SO$_4$ and evaporated to give an amber gum. This material was purified by ISCO (0-100% EtOAc-DCM) to give the product (117 mg) as a gum. This material was taken up in DMF and was repurified by preparative LC (Method C) to give the title compound (Intermediate 040b, 0.082 g, 58.7% yield) as a colourless gum which was used as such in the next step. LC (Method B): 2.211 min; HRMS (ESI): Calcd. for $C_{32}H_{37}N_4O_2S_2[M+H]^+$ m/z 573.2358; found: 573.2377; $^1H$ NMR (400 MHz, DMSO-$d_6$) δ ppm 7.60 (d, J=8.2 Hz, 2H), 7.46 (d, J=7.4 Hz, 1H), 7.42 (s, 1H), 7.19-7.36 (m, 6H), 7.08 (br. s., 1H), 5.57 (br. s., 2H), 2.88 (d, J=7.0 Hz, 2H), 2.53 (s, 6H), 2.41 (s, 3H), 1.25 (t, J=7.4 Hz, 3H), 0.96 (s, 9H).

Intermediate 040c: 3-(4-((2-Ethyl-5,7-dimethyl-3H-imidazo[4,5-b]pyridin-3-yl)methyl)phenyl)-5-(o-tolyl) thiophene-2-sulfonamide

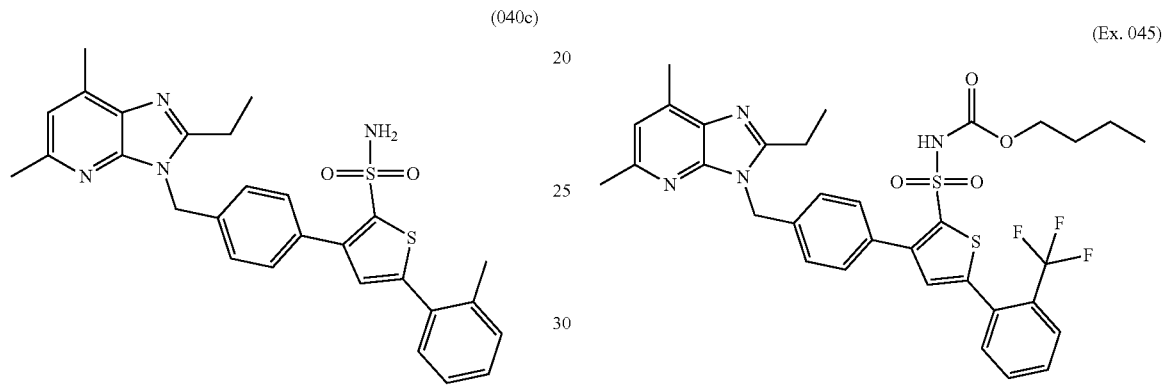

To a solution of Intermediate 040b (0.074 g, 0.108 mmol) in DCM (3 mL) was added anisole (0.118 mL, 1.077 mmol) and then TFA (5 mL). The mixture was stirred at RT in a sealed flask for two days and then the volatiles were removed under reduced pressure and the residue was evaporated from ACN solution (×2) to give a nearly colourless gum.

Quantitative yield was assumed and this material Intermediate 040c was used as such in the next step without further purification. LC-MS (APCI): Calcd. for $C_{28}H_{29}N_4O_2S_2[M+H]^+$ m/z 517.1732; found: 517.2.

Example 040: Butyl (3-(4-((2-ethyl-5,7-dimethyl-3H-imidazo[4,5-b]pyridin-3-yl)methyl) phenyl)-5-(o-tolyl) thiophen-2-yl)sulfonylcarbamate A solution of Intermediate 040c (0.034 g, 0.054 mmol) in pyridine (1 mL) was treated with triethylamine (0.056 mL, 0.405 mmol), 4-(pyrrolidin-1-yl)pyridine (0.024 g, 0.162 mmol) and butyl carbonochloridate (0.021 mL, 0.162 mmol) and the reaction mixture was stirred at RT overnight. The reaction mixture was subsequently evaporated to dryness to give a solid residue. The residue was taken up in DMF, the mixture was acidified with AcOH and the solution was submitted to preparative LC purification (Method C) to give the title compound (Example 040, 0.034 g, 86% yield) as a white solid. LC (Method B): 2.202 min; HRMS (ESI): Calcd. for $C_{33}H_{37}N_4O_4S_2[M+H]^+$ m/z 617.2256; found 617.2274; $^1H$ NMR (400 MHz, DMSO-$d_6$) δ ppm 7.75-7.62 (m, 1H), 7.53 (d, J=7.8 Hz, 20 2H), 7.47 (d, J=7.4 Hz, 1H), 7.27-7.36 (m, 4H), 7.21-7.25 (m, 2H), 7.07 (br s, 1H), 5.57 (br s, 2H), 3.95 (t, J=6.5 Hz, 2H), 2.89 (m, 2H), 2.53 (s, 6H), 2.42 (s, 3H), 1.36-1.42 (m, 2H), 1.26 (t, J=7.4 Hz, 3H), 1.15 (m, 2H), 0.77 (t, J=7.2 Hz, 3H).

Example 045: Butyl (3-(4-((2-ethyl-5,7-dimethyl-3H-imidazo[4,5-b]pyridin-3-yl)methyl) phenyl)-5-(2-(trifluoromethyl)phenyl)thiophen-2-yl)sulfonylcarbamate

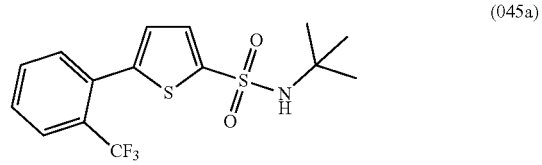 [SMILES: CC(C)(C)NS(=O)(=O)c1ccc(-c2ccccc2C(F)(F)F)s1]

Intermediate 045a: N-(tert-Butyl)-5-(2-(trifluoromethyl)phenyl)thiophene-2-sulfonamide A vial charged with 5-bromo-N-(tert-butyl)thiophene-2-sulfonamide (1.00 g, 3.35 mmol), (2-(trifluoromethyl)phenyl)boronic acid (0.955 g, 5.03 mmol), 2M aqueous $Na_2CO_3$ (4.50 mL, 10.06 mmol) and $Pd(Ph_3P)_4$ (0.194 g, 0.168 mmol) in a mixture of toluene-ethanol (9:1, 20 mL) was reacted as described in Example 039b. The crude material was pre-adsorbed on 10 g of silica gel and purified by flash chromatography (ISCO 10-40%, EtOAc-hexane) to give the title compound (Intermediate 045a, 1.141 g, 3.14 mmol, 94%) as a white solid. LC-MS (Method H): 1.300 min, Calcd. for $C_{15}H_{15}F_3NO_2S_2[M-H]^-$ m/z 362.1; found 362.0; $^1H$ NMR (400 MHz, DMSO-$d_6$) δ ppm 7.88 (d, J=7.4 Hz, 1H), 7.82 (s, 1H), 7.75 (d, J=7.4 Hz, 1H), 7.70 (d, J=7.4 Hz, 1H), 7.61 (d, J=7.4 Hz, 1H), 7.55 (d, J=3.9 Hz, 1H), 7.13 (d, J=3.9 Hz, 1H), 1.16 (s, 9H).

Intermediate 045b: (2-(N-(tert-Butyl)sulfamoyl)-5-(2-(trifluoromethyl)phenyl)thiophen-3-yl)boronic acid

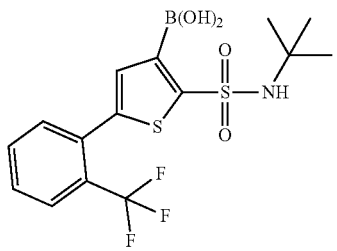

(045b)

A solution of Intermediate 045a (1.12 g, 3.08 mmol) in dry THF (25 mL) was treated with a solution of 1.2 M n-BuLi in hexanes (6.42 mL, 7.70 mmol) and triisopropyl borate (2.13 mL, 9.25 mmol) as described in Example 039c. The resulting turbid mixture was quenched with 2M aqueous HCl (9.91 mL, 19.83 mmol), then partitioned with EtOAc-H$_2$O and the organic phase was separated, washed with H$_2$O and brine, dried over Na$_2$SO$_4$ and evaporated. The resulting residue was purified by ISCO (10-40%, EtOAc/Hexane) to afford the desired compound as a pale yellow foam (Intermediate 045b, 0.717 g, 1.761 mmol, 57%). LC-MS (Method H): 1.296 min, Calcd. for C$_{15}$H$_{17}$BF$_3$NO$_4$S$_2$[M–H]$^-$ m/z 406.1; found 406.0; $^1$H NMR (400 MHz, DMSO-d$_6$) δ ppm 8.65 (s, 2H), 7.89 (d, J=7.0 Hz, 1H), 7.75 (d, J=7.4 Hz, 1H), 7.70 (d, J=7.8 Hz, 1H), 7.60 (d, J=7.4 Hz, 1H), 7.29-7.34 (m, 1H), 7.25 (s, 1H), 1.19 (s, 9H).

Intermediate 045c: N-(tert-Butyl)-3-(4-((2-ethyl-5,7-dimethyl-3H-imidazo[4,5-b]pyridin-3-yl)methyl)phenyl)-5-(2-(trifluoromethyl)phenyl)thiophene-2-sulfonamide

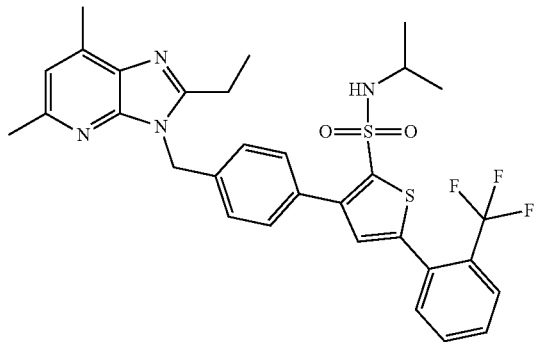

(045c)

A mixture of Intermediate 045b (0.059 g, 0.145 mmol) and Intermediate 040a (0.050 g, 0.145 mmol) in toluene-ethanol (9:1, 5 mL) was treated as described in Example 039b. The volatiles were then evaporated and the residue was dissolved in DMSO (4.5 mL), then H$_2$O (0.5 mL) was added and the mixture was acidified with formic acid (0.10 mL). This solution was filtered through a 0.45 micron filter disk and purified by preparative LC (Method F, with 0.1% HCO$_2$H as modifier) to give the title compound (Intermediate 045c, 0.052 g, 0.083 mmol, 57%) as a pale yellow solid. HRMS (ESI): Calcd. for C$_{32}$H$_{34}$F$_3$N$_4$O$_2$S$_2$ [M+H]$^+$ m/z 627.2070; found: 627.2090.

Intermediate 045d: 3-(4-((2-Ethyl-5,7-dimethyl-3H-imidazo[4,5-b]pyridin-3-yl)methyl)phenyl)-5-(2-(trifluoromethyl)phenyl)thiophene-2-sulfonamide

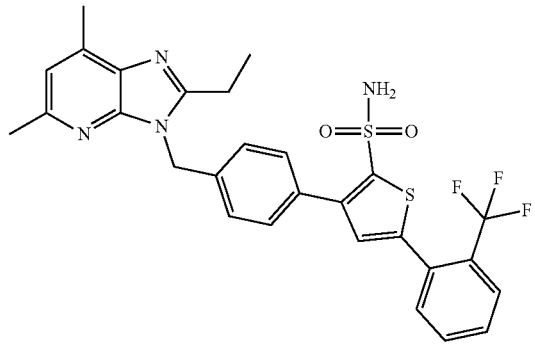

(045d)

A solution of Intermediate 045c (0.052 g, 0.083 mmol) in DCM (3 mL) was treated with anisole (0.091 mL, 0.830 mmol) and TFA (5 mL) as described in Example 040c to afford the title compound Intermediate 045d quantitatively as a TFA salt. LC-MS (Method H): 1.340 min, Calcd. for C$_{28}$H$_{26}$F$_3$N$_4$O$_2$S$_2$ [M+H]$^+$ m/z 571.1; found 571.1.

Example 045: Butyl (3-(4-((2-ethyl-5,7-dimethyl-3H-imidazo[4,5-b]pyridin-3-yl)methyl) phenyl)-5-(2-(trifluoromethyl)phenyl)thiophen-2-yl)sulfonylcarbamate

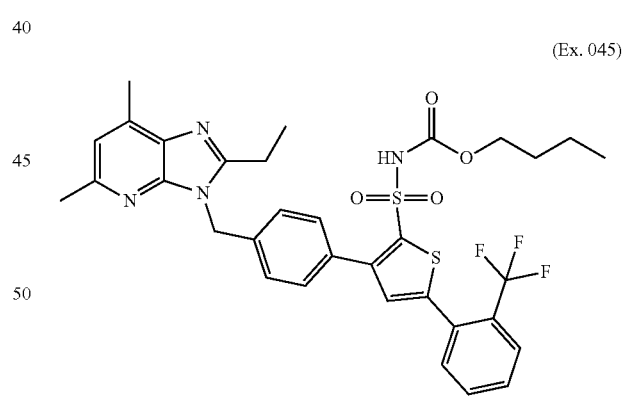

(Ex. 045)

A solution of Intermediate 045d (0.030 g, 0.044 mmol) in pyridine (1 mL) was treated with triethylamine (0.046 mL, 0.329 mmol), 4-(pyrrolidin-1-yl)pyridine (0.0195 g, 0.13110 mmol) and butyl carbonochloridate (0.017 mL, 0.131 mmol) as described in Example 040. The reaction mixture was then evaporated to dryness to give a solid residue which was taken up in DMSO (1.6 mL), acidified with formic acid (0.10 mL) and purified by preparative LC (Method F, with 0.1% of HCO$_2$H as modifier) to give the title compound (Example 045, 0.021 g, 0.031 mmol, 72%) as a white solid. LC (Method B): 1.989 min; HRMS (ESI): Calcd for C$_{33}$H$_{34}$F$_3$N$_4$O4S$_2$ [M+H]$^+$ m/z 671.1968; found 671.1907;

$^1$H NMR (400 MHz, DMSO-d$_6$) δ ppm 7.90 (d, J=7.4 Hz, 1H), 7.64-7.80 (m, 4H), 7.50 (d, J=8.2 Hz, 2H), 7.23 (s, 1H), 7.18 (d, J=8.2 Hz, 2H), 6.96 (s, 1H), 5.51 (s, 2H), 3.93 (t, J=6.5 Hz, 2H), 2.79 (q, J=7.7 Hz, 2H), 2.51 (s, 6H), 1.34-1.43 (m, 2H), 1.24 (t, J=7.4 Hz, 3H), 1.16 (m, 2H), 0.78 (t, J=7.4 Hz, 3H).

Example 046: Butyl (3-(5-((2-ethyl-5,7-dimethyl-3H-imidazo[4,5-b]pyridin-3-yl)methyl) pyridin-2-yl)-5-(2-(trifluoromethyl)phenyl)thiophen-2-yl)sulfonylcarbamate

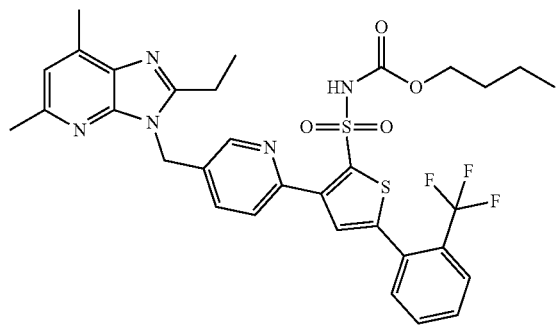
(Ex. 046)

Intermediate 046a: N-(tert-Butyl)-3-(5-((2-ethyl-5,7-dimethyl-3H-imidazo[4,5-b]pyridin-3-yl)methyl)pyridin-2-yl)-5-(2-(trifluoromethyl)phenyl)thiophene-2-sulfonamide

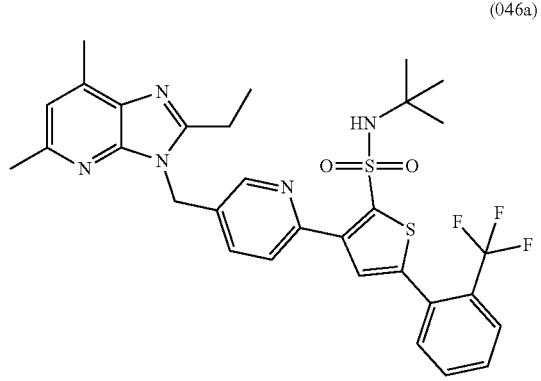 [SMILES: CCc1nc2c(C)cc(C)nc2n1Cc1ccc(-c2cc(-c3ccccc3C(F)(F)F)sc2S(=O)(=O)NC(C)(C)C)nc1]
(046a)

A mixture of Intermediate 045b (0.059 g, 0.145 mmol), Intermediate 039a (0.050 g, 0.145 mmol), 2M aq. Na$_2$CO$_3$ (0.22 mL, 0.434 mmol) and Pd(Ph$_3$P)$_4$ (0.017 g, 0.014 mmol) in toluene-ethanol (9:1, 5 mL) was treated as described in Example 039b. The volatiles were subsequently evaporated and the residue was dissolved in DMSO (4.5 mL), then H$_2$O (0.5 mL) was added and the mixture was acidified with formic acid (0.10 mL). This solution was filtered through a 0.45 micron filter disk and purified by preparative LC (Method F with 0.1% HCO$_2$H as modifier) to give the title compound (Intermediate 046a, 0.076 g, 0.121 mmol, 84%) as a pale yellow solid. HRMS (ESI): Calcd. for C$_{31}$H$_{33}$F$_3$N$_5$O$_2$S$_2$ [M+H]$^+$ m/z 628.2022; found: 628.2066.

Intermediate 046b: 3-(5-((2-Ethyl-5,7-dimethyl-3H-imidazo[4,5-b]pyridin-3-yl)methyl)pyridin-2-yl)-5-(2-(trifluoromethyl)phenyl)thiophene-2-sulfonamide

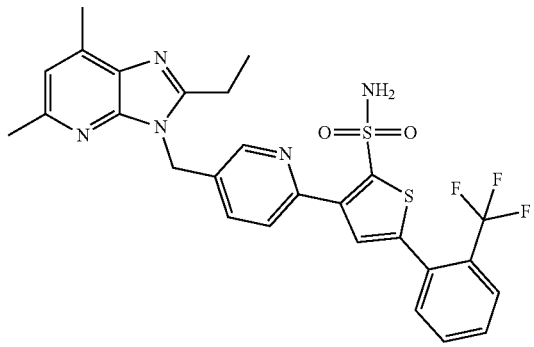
(046b)

A solution of Intermediate 046a (0.076 g, 0.121 mmol) in DCM (3 mL) was treated with anisole (0.132 mL, 1.211 mmol) and TFA (5 mL) as described in Example 40c to afford the title compound Intermediate 046b quantitatively as a TFA salt. LC-MS (Method H): 1.300 min, Calcd. for C$_{27}$H$_{25}$F$_3$N$_5$O$_2$S$_2$ [M+H]$^+$ m/z 572.14; found 572.1.

Example 046: Butyl (3-(5-((2-ethyl-5,7-dimethyl-3H-imidazo[4,5-b]pyridin-3-yl)methyl) pyridin-2-yl)-5-(2-(trifluoromethyl)phenyl)thiophen-2-yl)sulfonylcarbamate A solution of Intermediate 046b (0.030 g, 0.044 mmol) in pyridine (1 mL) was treated with triethylamine (0.046 mL, 0.329 mmol), 4-(pyrrolidin-1-yl)pyridine (0.0195 g, 0.131 mmol) and butyl carbonochloridate (0.017 mL, 0.131 mmol) as described in Example 040. The reaction mixture was then evaporated to dryness to give a solid residue which was taken up in DMSO (1.6 mL), acidified with formic acid (0.10 mL) and purified by preparative LC (Method F with 0.1% of HCO$_2$H as modifier) to give the title compound (Example 046, 0.021 g, 0.031 mmol, 71%) as a white solid. LC (Method B): 1.949 min; HRMS (ESI): Calcd for C$_{32}$H$_{33}$F$_3$N$_5$O$_4$S$_2$ [M+H]$^+$ m/z 672.1921; found 672.1870; $^1$H NMR (400 MHz, DMSO-d$_6$) δ ppm 8.54 (d, J=2.0 Hz, 1H), 7.91 (d, J=8.2 Hz, 1H), 7.85 (d, J=7.8 Hz, 1H), 7.77 (d, J=7.0 Hz, 1H), 7.61-7.75 (m, 4H), 7.52 (s, 1H), 6.98 (s, 1H), 5.56 (s, 2H), 3.94 (t, J=6.7 Hz, 2H), 2.84 (q, J=7.4 Hz, 2H), 2.50-2.54 (m, 6H), 1.36-1.45 (m, 2H), 1.25 (t, J=7.4 Hz, 3H), 1.13-1.22 (m, 2H), 0.76 (t, J=7.4 Hz, 20 3H).

Example 047: Butyl (3-(4-((2-ethyl-5,7-dimethyl-3H-imidazo[4,5-b]pyridin-3-yl)methyl) phenyl)-5-(2-methoxypyridin-3-yl)thiophen-2-yl)sulfonylcarbamate

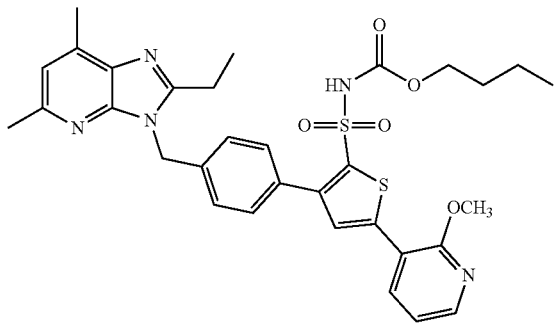
(Ex. 047)

Intermediate 047a: N-(tert-butyl)-5-(2-Methoxypyridin-3-yl)thiophene-2-sulfonamide

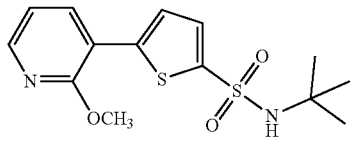
(047a)

A vial charged with 5-bromo-N-(tert-butyl)thiophene-2-sulfonamide (1.00 g, 3.35 mmol), (2-methoxypyridin-3-yl)boronic acid (0.769 g, 5.03 mmol), 2M aqueous $Na_2CO_3$ (5.03 mL, 10.06 mmol) and $Pd(Ph_3P)_4$ (0.194 g, 0.168 mmol) in a mixture of toluene-ethanol (9:1, 20 mL) was treated as described in Example 039b. After cooling, the reaction mixture was diluted with EtOAc (100 mL) and $H_2O$ (50 mL). The organic phase was separated, washed with sat. aq. $NaHCO_3$ and brine, then dried over $Na_2SO_4$, filtered and evaporated to give a dark brown gum. This material was pre-adsorbed on 10 g of silica gel and purified by flash chromatography (ISCO 10-50%, EtOAc-hexane) to give the title compound (Intermediate 047a, 1.050 g, 3.22 mmol, 10 96%) as a white solid. LC-MS (Method H): 1.250 min, Calcd. for $C_{14}H_7N_2O_3S_2$ [M–H]-m/z 325.07; found 325.1; $^1$H NMR (400 MHz, DMSO-$d_6$) δ ppm 8.29 (dd, J=7.6, 1.8 Hz, 1H), 8.21 (dd, J=4.9, 1.8 Hz, 1H), 7.71-7.77 (m, 2H), 7.57 (d, J=3.9 Hz, 1H), 7.11-7.17 (m, 1H), 4.05 (s, 3H), 1.17 (s, 9H).

Intermediate 047b: (2-(N-(tert-Butyl)sulfamoyl)-5-(2-methoxypyridin-3-yl)thiophen-3-yl)boronic acid

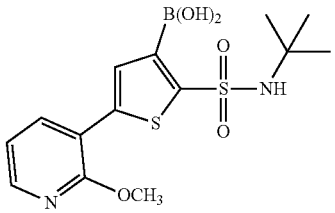
(047b)

A solution of Intermediate 047a (1.03 g, 3.16 mmol) in dry THF (25 mL) was treated with a solution of 1.2 M n-BuLi in hexanes (6.57 mL, 7.89 mmol) and triisopropyl borate (2.18 mL, 9.47 mmol) as described in Example 039c. The resulting turbid mixture was quenched with 2M aqueous HCl (9.91 mL, 19.83 mmol), then partitioned with EtOAc-$H_2O$ and the organic phase was separated, washed with $H_2O$ and brine, dried over $Na_2SO_4$ and evaporated. The resulting residue was purified by ISCO (20-70%, EtOAc/Hexane) to afford the desired compound as a dark red solid (Intermediate 047b, 0.275 g, 0.743 mmol, 24%). LC-MS (Method H): 1.248 min, Calcd. for $C_{14}H_{18}BN_2O_5S_2$ [M–H]$^-$ m/z 369.1; found 369.0; $^1$H NMR (400 MHz, DMSO-$d_6$) δ ppm 8.62 (s, 2H), 8.25 (dd, J=7.6, 1.8 Hz, 1H), 8.20 (dd, J=4.9, 1.8 Hz, 1H), 7.86 (s, 1H), 7.23 (s, 1H), 7.14 (dd, J=7.6, 4.9 Hz, 1H), 4.04 (s, 3H), 1.18 (s, 9H).

Intermediate 047c: N-(tert-Butyl)-3-(4-((2-ethyl-5,7-dimethyl-3H-imidazo[4,5-b]pyridin-3-yl)methyl) phenyl)-5-(2-methoxypyridin-3-yl)thiophene-2-sulfonamide

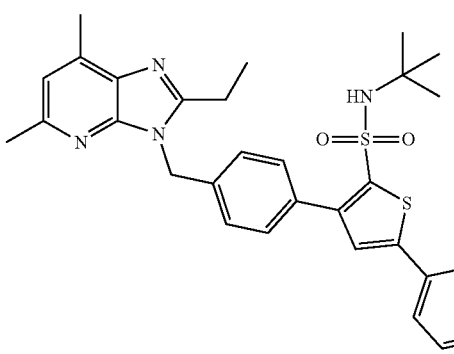
(047c)

A mixture of Intermediate 047b (0.054 g, 0.145 mmol), Intermediate 040a (0.050 g, 0.145 mmol), 2M aq. $Na_2CO_3$ (0.22 mL, 0.436 mmol) and $Pd(Ph_3P)_4$ (0.017 g, 0.015 mmol) in toluene-ethanol (9:1, 5 mL) was treated as described in Example 039b. The volatiles were subsequently evaporated and the residue was dissolved in DMSO (4.5 mL), then $H_2O$ (0.5 mL) was added and the mixture was acidified with formic acid (0.10 mL). This solution was filtered through a 0.45 micron filter disk and purified by preparative LC (Method F with 0.1% $HCO_2H$ as modifier) to give the title compound (0.054 g, 0.092 mmol, 63%) as a pale yellow solid. HRMS (ESI): Calcd. for $C_{31}H_{36}N_5O_3S_2$ [M+H]$^+$ m/z 590.2254; found: 590.2281.

Intermediate 047d: 3-(4-((2-Ethyl-5,7-dimethyl-3H-imidazo[4,5-b]pyridin-3-yl)methyl)phenyl)-5-(2-methoxypyridin-3-yl)thiophene-2-sulfonamide

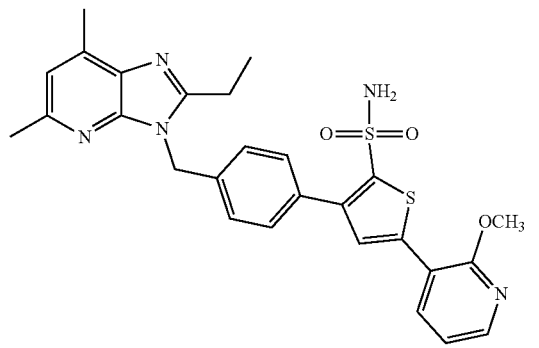

(047d)

A solution of Intermediate 047c (0.054 g, 0.092 mmol) in DCM (3 mL) was treated with anisole (0.100 mL, 0.916 mmol) and TFA (5 mL) as described in Example 040c to afford the title compound Intermediate 047d quantitatively as a TFA salt. LC-MS (Method H): 1.290 min, Calcd. for $C_{27}H_{28}N_5O_3S_2[M+H]^+$ m/z 534.2; found 534.1.

Example 047: Butyl (3-(4-((2-ethyl-5,7-dimethyl-3H-imidazo[4,5-b]pyridin-3-yl)methyl) phenyl)-5-(2-methoxypyridin-3-yl)thiophen-2-yl)sulfonylcarbamate A solution of Intermediate 047d (0.030 g, 0.046 mmol) in pyridine (1 mL) was treated with triethylamine (0.048 mL, 0.347 mmol), 4-(pyrrolidin-1-yl)pyridine (0.021 g, 0.139 mmol) and butyl carbonochloridate (0.018 mL, 0.139 mmol) as described in Example 040. The reaction mixture was then evaporated to dryness to give a solid residue which was taken up in DMSO (1.6 mL), acidified with formic acid (0.10 mL) and purified by preparative LC (Method F with 0.1% of HCO$_2$H as modifier) to give the title compound (Example 047, 0.018 g, 0.028 mmol, 61%) as a white solid. LC (Method B): 1.927 min; HRMS (ESI): Calcd for $C_{32}H_{36}N_5O_5S_2[M+H]^+$ m/z 634.2152; found 634.2088; $^1$H NMR (400 MHz, DMSO-d$_6$) δ ppm 8.37 (dd, J=7.4, 1.6 Hz, 1H), 8.22 (dd, J=5.1, 1.6 Hz, 1H), 7.82 (s, 1H), 7.47-7.54 (m, J=8.2 Hz, 2H), 7.15-7.21 (m, J=8.2 Hz, 2H), 7.13 (dd, J=7.6, 4.9 Hz, 1H), 6.96 (s, 1H), 5.51 (s, 2H), 4.05 (s, 3H), 3.90 (t, J=6.5 Hz, 2H), 2.79 (q, J=7.4 Hz, 2H), 2.51 (s, 6H), 1.32-1.40 (m, 2H), 1.25 (t, J=7.6 Hz, 3H), 1.08-1.17 (m, 2H), 0.74 (t, J=7.4 Hz, 3H).

Example 048: Butyl (3-(5-((2-ethyl-5,7-dimethyl-3H-imidazo[4,5-b]pyridin-3-yl)methyl) pyridin-2-yl)-5-(2-methoxypyridin-3-yl)thiophen-2-yl)sulfonylcarbamate

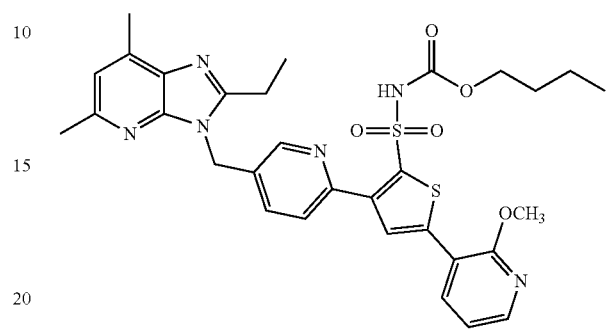

(Ex. 048)

Intermediate 048a: N-(tert-Butyl)-3-(5-((2-ethyl-5,7-dimethyl-3H-imidazo[4,5-b]pyridin-3-yl)methyl) pyridin-2-yl)-5-(2-methoxypyridin-3-yl)thiophene-2-sulfonamide

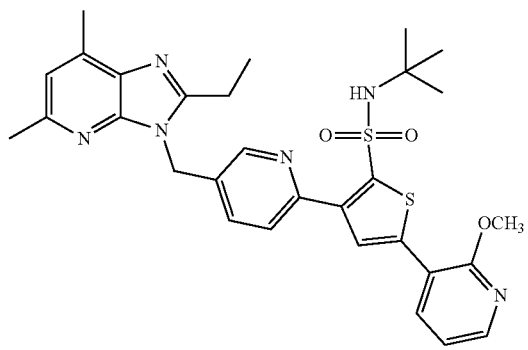

(048a)

A mixture of Intermediate 047b (0.054 g, 0.145 mmol), Intermediate 039a (0.050 g, 0.145 mmol), 2M aq. Na$_2$CO$_3$ (0.22 mL, 0.434 mmol) and Pd(Ph$_3$P)$_4$ (0.017 g, 0.015 mmol) in toluene-ethanol (9:1, 5 mL) was treated as described in Example 039c. The volatiles were then evaporated and the residue was dissolved in DMSO (4.5 mL), then H$_2$O (0.5 mL) was added and the mixture was acidified with formic acid (0.10 mL). This solution was filtered through a 0.45 micron filter disk and purified by preparative LC (Method F with 0.1% HCO$_2$H as modifier) to give the title compound (Intermediate 048a, 0.060 g, 0.102 mmol, 70%) as a pale yellow solid. HRMS (ESI): Calcd. for $C_{30}H_{35}N_6O_3S_2[M+H]^+$ m/z 591.2207; found: 591.2230.

Intermediate 048b: 3-(5-((2-Ethyl-5,7-dimethyl-3H-imidazo[4,5-b]pyridin-3-yl)methyl)pyridin-2-yl)-5-(2-methoxypyridin-3-yl)thiophene-2-sulfonamide

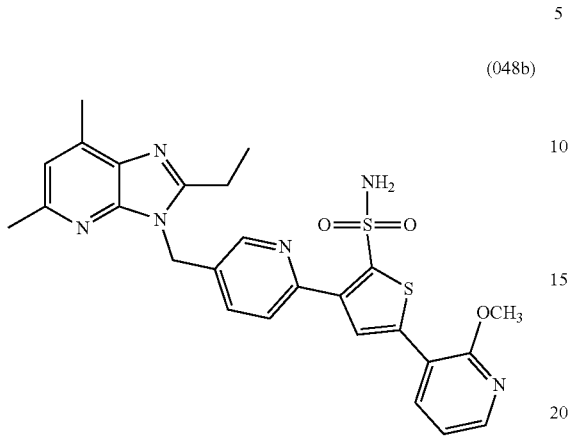

(048b)

A solution of Intermediate 048a (0.060 g, 0.102 mmol) in DCM (3 mL) was treated with anisole (0.111 mL, 1.016 mmol) and TFA (5 mL) as described in Example 040c to afford the title compound Intermediate 048b quantitatively as a TFA salt. LC-MS (Method H): 1.258 min, Calcd. for $C_{26}H_{27}N_6O_3S_2$ [M+H]$^+$ m/z 535.16; found 535.1.

Example 048: Butyl (3-(5-((2-ethyl-5,7-dimethyl-3H-imidazo[4,5-b]pyridin-3-yl)methyl) pyridin-2-yl)-5-(2-methoxypyridin-3-yl)thiophen-2-yl)sulfonylcarbamate A solution of Intermediate 048b (0.030 g, 0.046 mmol) in pyridine (1 mL) was treated with triethylamine (0.048 mL, 0.347 mmol), 4-(pyrrolidin-1-yl)pyridine (0.021 g, 0.139 mmol) and butyl carbonochloridate (0.018 mL, 0.139 mmol) as described in Example 040. The reaction mixture was then evaporated to dryness to give a solid residue which was taken up in DMSO (1.6 mL), acidified with formic acid (0.10 mL) and purified by preparative LC (Method F with 0.1% of HCO$_2$H as modifier) to give the title compound (Example 048, 0.017 g, 0.027 mmol, 58%) as a white solid. LC (Method B): 1.907 min; HRMS (ESI): Calcd for $C_{31}H_{35}N_6O_5S_2$[M+H]$^+$ m/z 635.2105; found 635.2051; $^1$H NMR (400 MHz, DMSO-d$_6$) δ ppm 8.54 (d, J=2.0 Hz, 1H), 8.39 (dd, J=7.6, 1.8 Hz, 1H), 8.23 (dd, J=4.7, 1.6 Hz, 1H), 8.08 (s, 1H), 7.85 (d, J=7.8 Hz, 1H), 7.66 (dd, J=8.2, 2.3 Hz, 1H), 7.14 (dd, J=7.6, 4.9 Hz, 1H), 6.97 (s, 1H), 5.56 (s, 2H), 4.06 (s, 3H), 3.92 (t, J=6.5 Hz, 2H), 2.84 (q, J=7.4 Hz, 2H), 2.51 (d, J=2.0 Hz, 6H), 1.34-1.42 (m, 2H), 1.26 (t, J=7.4 Hz, 3H), 1.09-1.20 (m, 2H), 0.73 (t, J=7.4 Hz, 3H).

Example 049: Butyl (3-(4-((2-ethyl-5,7-dimethyl-3H-imidazo[4,5-b]pyridin-3-yl)methyl) phenyl)-5-phenylthiophen-2-yl)sulfonylcarbamate

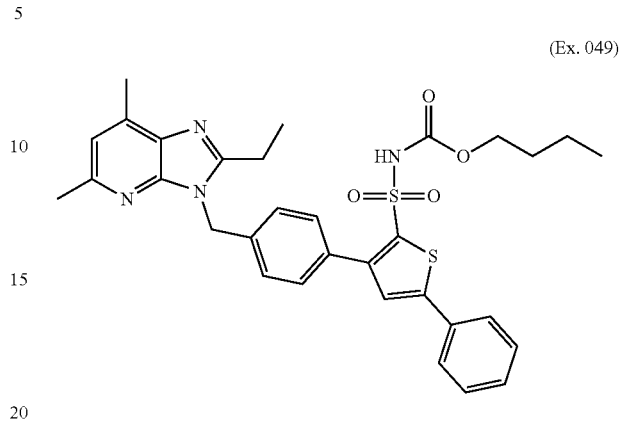

(Ex. 049)

Intermediate 049a
N-(tert-Butyl)-5-phenylthiophene-2-sulfonamide

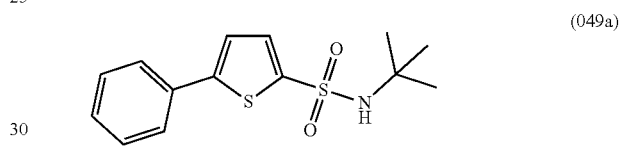

(049a)

A vial charged with 5-bromo-N-(tert-butyl)thiophene-2-sulfonamide (1.00 g, 3.35 mmol), phenylboronic acid (0.825 g, 5.03 mmol), 2M aqueous Na$_2$CO$_3$ (5.03 mL, 10.06 mmol) and Pd(Ph$_3$P)$_4$ (0.194 g, 0.168 mmol) in a mixture of toluene-ethanol (9:1, 20 mL) was treated as described in Example 39b. After cooling, the reaction mixture was diluted with EtOAc (100 mL) and H$_2$O (50 mL). The organic phase was separated, washed with sat. aq. NaHCO$_3$ and brine, then dried over Na$_2$SO$_4$, filtered and evaporated to give a dark brown gum. This material was pre-adsorbed on 10 g of silica gel and purified by flash chromatography (ISCO 10-40%, EtOAc-hexane) to give the title compound (Intermediate 049a, 0.977 g, 3.31 mmol, 99%) as a white solid. LC-MS (Method H): 1.280 min, Calcd. for $C_{14}H_{16}NO_2S_2$[M−H]$^-$ m/z 294.06; found 294.0; $^1$H NMR (400 MHz, DMSO-d$_6$) δ ppm 7.80 (s, 1H), 7.69-7.75 (m, 2H), 7.54-7.57 (m, 1H), 7.51-7.54 (m, 1H), 7.43-7.50 (m, 2H), 7.37-7.43 (m, 1H), 1.19 (s, 9H).

Intermediate 049b: (2-(N-(tert-Butyl)sulfamoyl)-5-phenylthiophen-3-yl)boronic acid

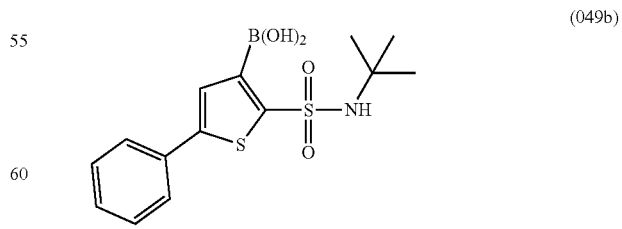

(049b)

A solution of Intermediate 049a (0.950 g, 3.22 mmol) in dry THF (25 mL) was treated with a solution of 1.2 M n-BuLi in hexanes (6.70 mL, 8.04 mmol) and triisopropyl borate (2.23 mL, 9.65 mmol) as described in Example 039c. The resulting turbid mixture was quenched with 2M aqueous HCl (9.91 mL, 19.83 mmol) then partitioned with EtOAc-H₂O and the organic phase was separated, washed with H₂O and brine, dried over Na₂SO₄ and evaporated. The residue was purified by ISCO (20-60%, EtOAc/Hexane) to afford the title compound as a pale yellow solid (Intermediate 049b, 0.681 g, 2.007 mmol, 62%). LC-MS (Method H): 1.281 min, Calcd. for C₁₄H₁₇BNO₄S₂[M−H]⁻ m/z 338.07; found 338.0; ¹H NMR (400 MHz, DMSO-d₆) δ ppm 8.62 (s, 2H), 7.67-7.72 (m, 2H), 7.63 (s, 1H), 7.42-7.49 (m, 2H), 7.33-7.42 (m, 1H), 7.25 (s, 1H), 1.20 (s, 9H).

Intermediate 049c: N-(tert-Butyl)-3-(4-((2-ethyl-5,7-dimethyl-3H-imidazo[4,5-b]pyridin-3-yl) methyl) phenyl)-5-phenylthiophene-2-sulfonamide

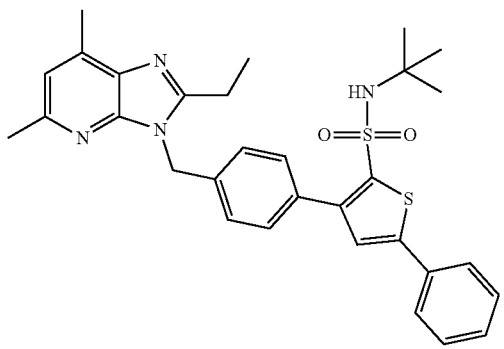

(049c)

A mixture of Intermediate 049b (0.049 g, 0.145 mmol), Intermediate 040a (0.050 g, 0.145 mmol), 2M aq. Na₂CO₃ (0.22 mL, 0.436 mmol) and Pd(Ph₃P)₄ (0.017 g, 0.015 mmol) in toluene-ethanol (9:1, 5 mL) was treated as described in Example 039b. The volatiles were then evaporated and the residue was dissolved in DMSO (4.5 mL), then H₂O (0.5 mL) was added and the mixture was acidified with formic acid (0.10 mL). This solution was filtered through a 0.45 micron filter disk and purified by preparative LC (Method F with 0.1% HCO₂H as modifier) to give the title compound (Intermediate 049c, 0.059 g, 0.106 mmol, 73%) as a pale yellow solid. HRMS (ESI): Calcd. for C₃₁H₃₅N₄O₂S₂[M+H]⁺ m/z 559.2196; found: 559.2227.

Intermediate 049d: 3-(4-((2-Ethyl-5,7-dimethyl-3H-imidazo[4,5-b]pyridin-3-yl)methyl)phenyl)-5-phenylthiophene-2-sulfonamide

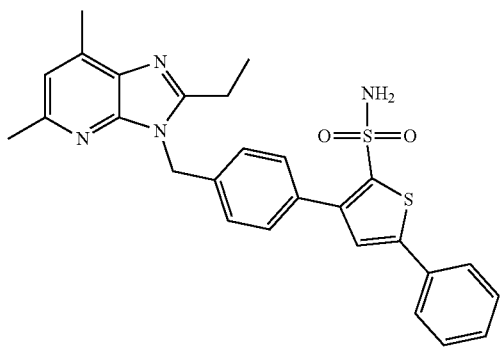

(049d)

A solution of Intermediate 049c (0.059 g, 0.106 mmol) in DCM (3 mL) was treated with anisole (0.115 mL, 1.056 mmol) and TFA (5 mL) as described in Example 040c to afford the title compound Intermediate 049d quantitatively as a TFA salt. LC-MS (Method H): 1.323 min, Calcd. for C₂₇H₂₇N₄O₂S₂ [M+H]⁺ m/z 503.16; found 503.1.

Example 049: Butyl (3-(4-((2-ethyl-5,7-dimethyl-3H-imidazo[4,5-b]pyridin-3-yl)methyl) phenyl)-5-phenylthiophen-2-yl)sulfonylcarbamate A solution of Intermediate 049d (0.030 g, 0.049 mmol) in pyridine (1 mL) was treated with triethylamine (0.051 mL, 0.365 mmol), 4-(pyrrolidin-1-yl)pyridine (0.022 g, 0.146 mmol) and butyl carbonochloridate (0.019 mL, 0.146 mmol) as described in Example 040. The reaction mixture was subsequently evaporated to dryness to give a solid residue which was taken up in DMSO (1.6 mL), acidified with formic acid (0.10 mL) and purified by preparative LC (Method F, with 0.1% of HCO₂H as modifier) to give the title compound (Example 049, 0.023 g, 0.038 mmol, 78%) as a white solid. LC (Method B): 1.967 min; HRMS (ESI): Calcd for C₃₂H₃₅N₄O₄S₂[M+H]⁺ m/z 603.2094; found 603.2052; ¹H NMR (400 MHz, DMSO-d₆) δ ppm 7.72-7.78 (m, 2H), 7.62 (s, 1H), 7.50-7.56 (m, 2H), 7.38-7.49 (m, 4H), 7.15-7.21 (m, 2H), 6.96 (s, 1H), 5.51 (s, 2H), 3.91 (t, J=6.5 Hz, 2H), 2.79 (d, J=7.4 Hz, 2H), 2.51 (s, 6H), 1.32-1.41 (m, 2H), 1.25 (t, J=7.4 Hz, 3H), 1.09-1.16 (m, 2H), 0.75 (t, J=7.2 Hz, 3H).

Example 050: Butyl (3-(5-((2-ethyl-5,7-dimethyl-3H-imidazo[4,5-b]pyridin-3-yl)methyl) pyridin-2-yl)-5-phenylthiophen-2-yl)sulfonylcarbamate

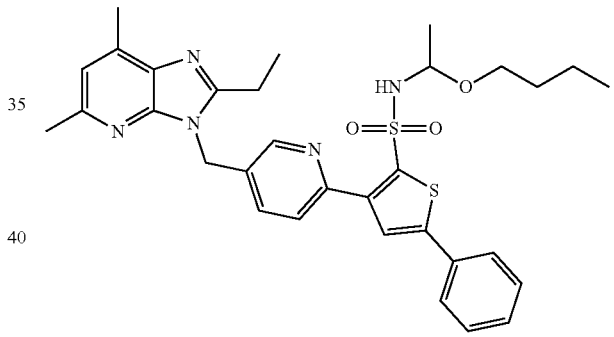

(Ex. 050)

Intermediate 050a: N-(tert-Butyl)-3-(5-((2-ethyl-5,7-dimethyl-3H-imidazo[4,5-b]pyridin-3-yl)methyl) pyridin-2-yl)-5-phenylthiophene-2-sulfonamide

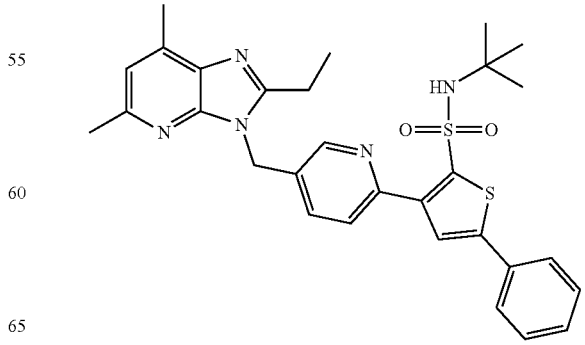

(050a)

A mixture of Intermediate 049b (0.049 g, 0.145 mmol), Intermediate 039a (0.050 g, 0.145 mmol), 2M aq. Na₂CO₃ (0.22 mL, 0.434 mmol) and Pd(Ph₃P)₄ (0.017 g, 0.014 mmol) in toluene-ethanol (9:1, 5 mL) was treated as described in Example 039b. The volatiles were then evaporated and the residue was dissolved in DMSO (4.5 mL), then H₂O (0.5 mL) was added and the mixture was acidified with formic acid (0.10 mL). This solution was filtered through a 0.45 micron filter disk and purified by preparative LC (Method F with 0.1% HCO₂H as modifier) to give the title compound (Example 050a, 0.072 g, 0.129 mmol, 89%) as a pale yellow solid. HRMS (ESI): Calcd. for $C_{30}H_{34}N_5O_2S_2$ [M+H]⁺ m/z 560.2148; found: 560.2168.

Intermediate 050b: 3-(5-((2-Ethyl-5,7-dimethyl-3H-imidazo[4,5-b]pyridin-3-yl)methyl)pyridin-2-yl)-5-phenylthiophene-2-sulfonamide

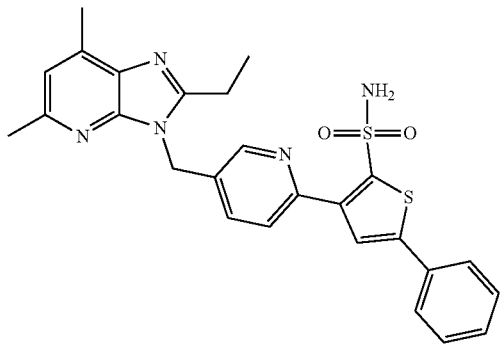

(050b)

A solution of Intermediate 050a (0.072 g, 0.129 mmol) in DCM (3 mL) was treated with anisole (0.141 mL, 1.286 mmol) and TFA (5 mL), as described in Example 040c to afford the title compound Example 050b quantitatively as a 2.TFA salt. LC-MS (Method H): 1.288 min, Calcd. for $C_{26}H_{26}N_5O_2S_2$[M+H]⁺ m/z 504.15; found 504.0.

Example 050: butyl (3-(5-((2-ethyl-5,7-dimethyl-3H-imidazo[4,5-b]pyridin-3-yl)methyl) pyridin-2-yl)-5-phenylthiophen-2-yl)sulfonylcarbamate A solution of Intermediate 050b (0.030 g, 0.049 mmol) in pyridine (1 mL) was treated with triethylamine (0.051 mL, 0.364 mmol), 4-(pyrrolidin-1-yl)pyridine (0.022 g, 0.146 mmol) and butyl carbonochloridate (0.019 mL, 0.146 mmol) as described in Example 040. The reaction mixture was subsequently evaporated to dryness to give a solid residue which was taken up in DMSO (1.6 mL), acidified with formic acid (0.10 mL) and purified by preparative LC (Method F with 0.1% of HCO₂H as modifier) to give the title compound (Example 050, 0.022 g, 0.036 mmol, 75%) as a white solid. LC (Method B): 1.930 min; HRMS (ESI): Calcd for $C_{31}H_{34}N_5O_4S_2$[M+H]⁺ m/z 604.2047; found 604.2082; ¹H NMR (400 MHz, DMSO-d₆) δ ppm 8.54 (d, J=1.6 Hz, 1H), 7.82-7.90 (m, 2H), 7.73-7.80 (m, 2H), 7.67 (dd, J=8.2, 2.3 Hz, 1H), 7.37-7.51 (m, 4H), 6.98 (s, 1H), 5.56 (s, 2H), 3.93 (t, J=6.5 Hz, 2H), 2.85 (q, J=7.4 Hz, 2H), 2.51 (2s, 6H), 1.34-1.42 (m, 2H), 1.26 (t, J=7.4 Hz, 3H), 1.14 (d, J=7.4 Hz, 2H), 0.74 (t, J=7.4 Hz, 3H).

Example 051: 3-((5'-(3,3-Difluoropyrrolidin-1-yl)-2'-(2H-tetrazol-5-yl)-[1,1'-biphenyl-4-yl)methyl)-2-ethyl-5,7-dimethyl-3H-imidazo[4,5-b]pyridine

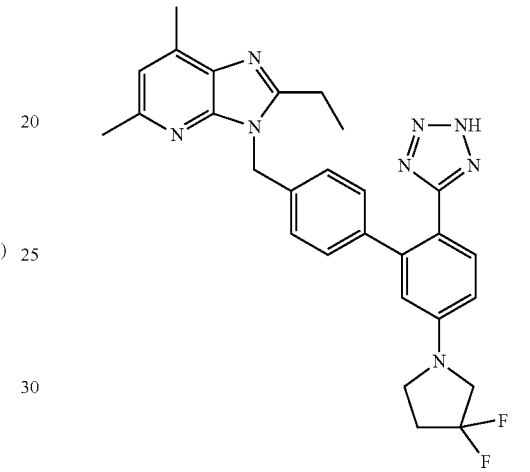

(Ex. 051)

To a vial charged with 2nd generation RuPhos precatalyst (4.78 mg, 6.16 µmol) was added Intermediate 001j (30 mg, 0.041 mmol) and sodium tert-butoxide (15.78 mg, 0.164 mmol). THF (1 mL) was then added followed by 3,3-difluoropyrrolidine, HCl (17.68 mg, 0.123 mmol). The reaction vial was sealed and heated at 65° C. for 1.5 h. The crude reaction mixture was then diluted with EtOAc, filtered over Celite® and concentrated to a brown residue. This crude intermediate was retaken DCM (2 mL) and subjected to triethylsilane (0.032 mL, 0.198 mmol) followed by TFA (0.092 mL, 1.189 mmol). After 10 min of stirring at RT, the reaction mixture was concentrated, retaken in DMF, filtered and purified by preparative HPLC (Column: XBridge C18, 19×200 mm, -µm particles; Mobile Phase A: 5:95 ACN:H₂O with 10 mM NH₄OAc; Mobile Phase B: 95:5 ACN:H₂O with 10 mM NH₄OAc; Gradient: 15-55% B over 20 minutes, then a 3-minute hold at 100% B; Flow: 20 mL/min.) to afford 7.2 mg (0.013 mmol, 34% yield) of the title compound Example 051. LC-MS (Method A2): 0.76 min, [M+H]⁺=515.0; ¹H NMR (500 MHz, DMSO-d₆) δ ppm 7.43 (d, J=8.2 Hz, 1H), 7.08 (d, J=7.9 Hz, 2H), 6.98 (d, J=7.9 Hz, 2H), 6.94 (s, 1H), 6.68 (d, J=8.2 Hz, 1H), 6.52 (s, 1H), 5.43 (s, 2H), 3.75 (t, J=13.3 Hz, 2H), 3.53 (t, J=7.2 Hz, 2H), 2.79 (q, J=7.4 Hz, 2H), 2.51 (s, 6H), 1.26 (t, J=7.3 Hz, 3H).

The compounds listed in the table below were synthesized using the same methods that were used to prepare Example 001.

| Ex # | Structure | MW | LC-MS m/z [M + H]+; RT (Method) | 1H NMR |
|---|---|---|---|---|
| 052 | 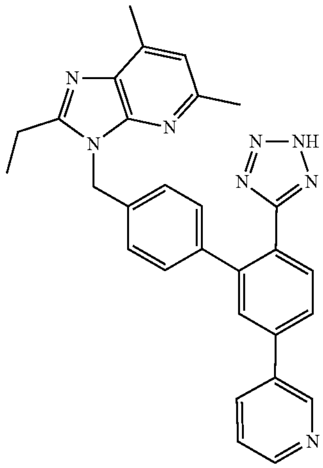 [SMILES: CCc1nc2c(C)cc(C)nc2n1Cc1ccc(-c2cc(-c3cccnc3)ccc2-c2nn[nH]n2)cc1] | 486.570 | 487.0; 1.31 min (Method A1) | 1H NMR (500 MHz, DMSO-d$_6$) δ 9.00 (br s, 1H), 8.60 (br s, 1H), 8.20 (br d, J = 7.3 Hz, 1H), 7.85 (br d, J = 7.3 Hz, 1H), 7.74 (br s, 2H), 7.51 (br s, 1H), 7.15 (br d, J = 7.3 Hz, 2H), 7.04 (br d, J = 7.6 Hz, 2H), 6.95 (s, 1H), 5.45 (s, 2H), 2.78 (q, J = 7.5 Hz, 2H), 2.53 (d, J = 19.5 Hz, 6H), 1.29-1.19 (m, 3H) (1 exchangeable proton not observed) |
| 053 | 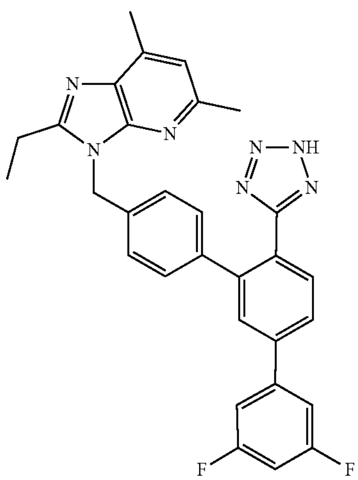 [SMILES: CCc1nc2c(C)cc(C)nc2n1Cc1ccc(-c2cc(-c3cc(F)cc(F)c3)ccc2-c2nn[nH]n2)cc1] | 521.563 | 522.3; 0.85 (Method A2) | 1H NMR (500 MHz, DMSO-d$_6$) δ 7.87 (d, J = 7.9 Hz, 1H), 7.77 (s, 1H), 7.73 (d, J = 8.0 Hz, 1H), 7.60 (d, J = 7.2 Hz, 2H), 7.27 (t, J = 9.1 Hz, 1H), 7.15 (d, J = 7.8 Hz, 2H), 7.04 (d, J = 7.9 Hz, 2H), 6.95 (s, 1H), 5.46 (s, 2H), 2.78 (q, J = 7.4 Hz, 2H), 2.55 (s, 6H), 1.24 (t, J = 7.4 Hz, 3H) (1 exchangeable proton not observed) |
| 054 | 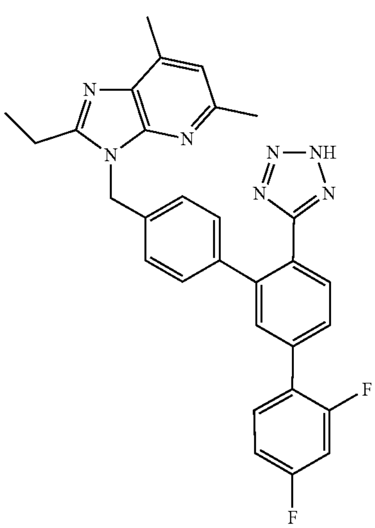 [SMILES: CCc1nc2c(C)cc(C)nc2n1Cc1ccc(-c2cc(-c3ccc(F)cc3F)ccc2-c2nn[nH]n2)cc1] | 521.563 | 522.0; 0.86 min (Method A2) | 1H NMR (500 MHz, DMSO-d$_6$) δ 7.77-7.68 (m, 2H), 7.63 (d, J = 7.7 Hz, 1H), 7.53 (s, 1H), 7.40 (t, J = 10.1 Hz, 1H), 7.21 (t, J = 7.6 Hz, 1H), 7.12 (d, J = 7.8 Hz, 2H), 7.02 (d, J = 7.9 Hz, 2H), 6.94 (s, 1H), 5.45 (s, 2H), 2.77 (q, J = 7.3 Hz, 2H), 2.55 (s, 6H), 1.24 (t, J = 7.4 Hz, 3H) (1 exchangeable proton not observed) |

Example 055: 2-butyl-3-((4"-methyl-6'-(2H-tetrazol-5-yl)-[1,1':3',1"-terphenyl]-4-yl)methyl)-1,3-diazaspiro[4.4]non-1-en-4-one

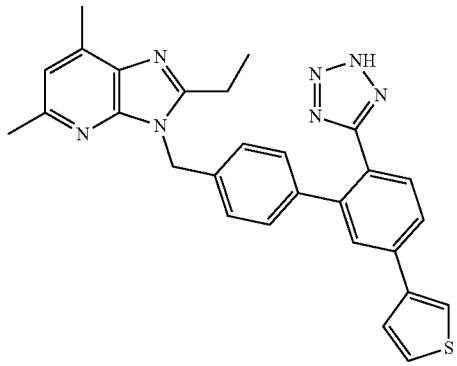 [SMILES: CCc1nc2c(C)cc(C)nc2n1Cc1ccc(-c2cc(-c3ccsc3)ccc2-c2nn[nH]n2)cc1]

Intermediate 055a: 4'-((2-Butyl-4-oxo-1,3-diazaspiro[4.4]non-1-en-3-yl)methyl)-5-chloro-[1,1'-biphenyl]-2-carbonitrile

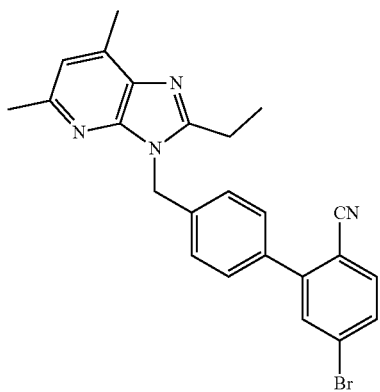 [SMILES: CCc1nc2c(C)cc(C)nc2n1Cc1ccc(-c2cc(Br)ccc2C#N)cc1]

Intermediate 001d (1 g, 2.56 mmol), 4-bromo-2-iodobenzonitrile (0.944 g, 3.07 mmol), and PdCl$_2$(dppf)-CH$_2$Cl$_2$ Adduct (0.209 g, 0.256 mmol) were dissolved in toluene (20.4 mL), ethanol (5.11 mL), and tripotassium phosphate (2 M aq, 2.56 mL, 5.11 mmol) and the reaction was degassed for 15 minutes by bubbling with N$_2$. The reaction was sealed and heated at 100° C. for 18 hours. The reaction was cooled to ambient temperature, filtered through celite, diluted with EtOAc, washed with saturated NaHCO$_3$, then brine, dried (Na$_2$SO$_4$), filtered, and concentrated in vacuo. The crude material was purified by column chromatography (ISCO, 80 g silica gel column, 29 minute gradient of 0 to 100% EtOAc in hexanes) to yield Intermediate 055a (0.649 g, 1.49 mmol, 57%) as a tan solid. LC-MS (Method A2) RT=0.85 min, MS (ESI) m/z: 445 (M+H)$^+$. $^1$H NMR (500 MHz, CDCl$_3$) δ 7.66 (d, J=1.4 Hz, 1H), 7.64-7.58 (m, 2H), 7.51-7.47 (m, 2H), 7.27 (d, J=8.3 Hz, 2H), 6.94 (s, 1H), 5.55 (s, 2H), 2.84 (q, J=7.4 Hz, 2H), 2.67 (s, 3H), 2.62 (s, 3H), 1.36 (t, J=7.6 Hz, 3H)

Intermediate 055b: 4'-((2-butyl-4-oxo-1,3-diazaspiro[4.4]non-1-en-3-yl)methyl)-5-chloro-[1,1'-biphenyl]-2-carbonitrile

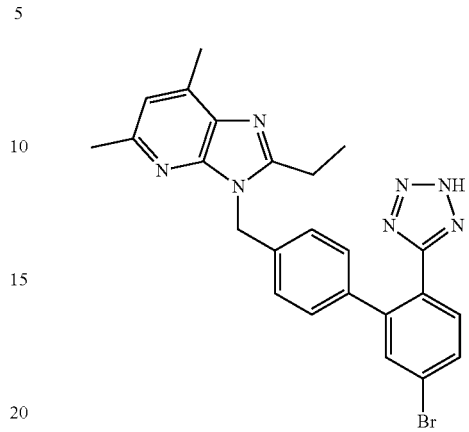

Intermediate 055a (0.649 g, 1.46 mmol) was dissolved in toluene (14.6 mL). Dibutyltin oxide (0.363 g, 1.46 mmol) and TMS-N$_3$ (1.94 mL, 14.6 mmol) were added and the reaction sealed in a pressure vial and heated at 100° C. for 18 hours. The reaction was cooled to ambient temperature and diluted with EtOAc into an erlenmeyer. A 10% aqueous solution of CAN (9.60 g, 17.5 mmol) was added slowly to mild bubbling. An aliquot of the reaction was added to an aqueous 0.02 M FeCl$_3$ solution to confirm complete consumption of azide (no red color). The layers were separated and the organic layer was further washed twice with saturated NH$_4$C$_1$, then brine, dried (Na$_2$SO$_4$), filtered, and concentrated in vacuo. The crude material was purified by column chromatography (ISCO, 40 g silica gel column, 19 minute gradient of 0 to 20% MeOH in DCM) to give Intermediate 055b (0.580 g, 1.19 mmol, 81%) as a tan solid. LC-MS (Method A2) RT=0.76 min, MS (ESI) m/z: 486 (M+H)$^+$. $^1$H NMR (400 MHz, CDCl$_3$) δ 7.83 (d, J=8.4 Hz, 1H), 7.64 (dd, J=8.4, 2.0 Hz, 1H), 7.55 (d, J=1.8 Hz, 1H), 7.11-7.04 (m, 2H), 7.03-6.97 (m, 2H), 6.93 (s, 1H), 5.44 (s, 2H), 3.48 (s, 1H), 2.71 (q, J=7.6 Hz, 2H), 2.57 (s, 3H), 2.49 (s, 3H), 1.17 (t, J=7.5 Hz, 3H)

Intermediate 055c: 4'-((2-butyl-4-oxo-1,3-diazaspiro[4.4]non-1-en-3-yl)methyl)-5-chloro-[1,1'-biphenyl]-2-carbonitrile

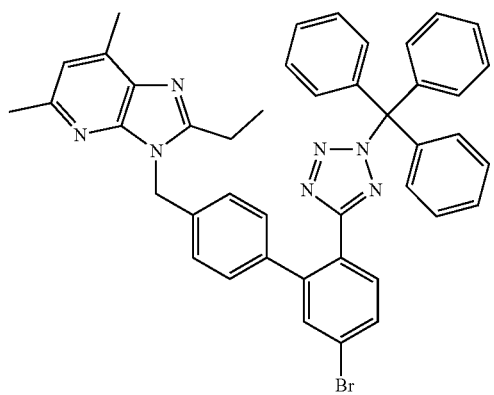 [SMILES: CCc1nc2c(C)cc(C)nc2n1Cc1ccc(-c2cc(Br)ccc2-c2nnn(C(c3ccccc3)(c3ccccc3)c3ccccc3)n2)cc1]

Intermediate 055b (580 mg, 1.19 mmol), TEA (215 μL, 1.54 mmol) and trityl chloride (381 mg, 1.37 mmol) were dissolved in DCM (5.94 mL). After 1 hour, the reaction was diluted with DCM and washed with 1M $K_2HPO_4$, then brine, then dried ($Na_2SO_4$), filtered, and concentrated in vacuo. The crude material was purified by column chromatography (ISCO, 80 g silica gel column, 29 minute gradient of 0 to 100% EtOAc in hexanes) to give Intermediate 055c (707 mg, 0.97 mmol, 81%) as a clear oil. LC-MS (Method A2) RT=1.07 min, MS (ESI) m/z: 731 (M+H)$^+$. $^1$H NMR (500 MHz, CDCl$_3$) δ 7.84 (d, J=8.3 Hz, 1H), 7.60 (dd, J=8.3, 1.9 Hz, 1H), 7.52 (d, J=1.9 Hz, 1H), 7.37-7.32 (m, 4H), 7.28-7.25 (m, 5H), 7.05 (d, J=8.3 Hz, 2H), 6.96-6.87 (m, 9H), 5.38 (s, 2H), 2.74-2.66 (m, 5H), 2.60 (s, 3H), 1.31-1.25 (m, 3H)

Intermediate 055d: 4'-((2-butyl-4-oxo-1,3-diazaspiro[4.4]non-1-en-3-yl)methyl)-5-chloro-[1,1'-biphenyl]-2-carbonitrile

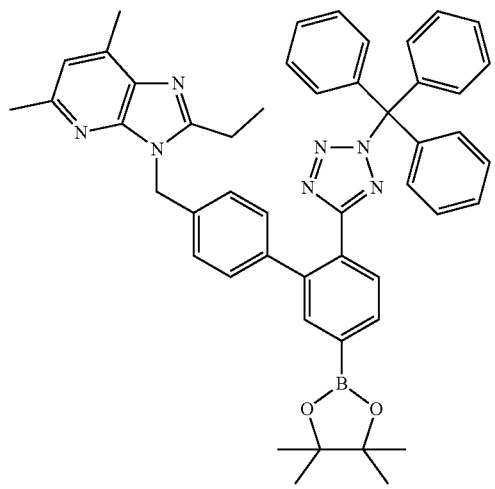 [SMILES: CCc1nc2c(C)cc(C)nc2n1Cc1ccc(-c2cc(B3OC(C)(C)C(C)(C)O3)ccc2-c2nnn(C(c3ccccc3)(c3ccccc3)c3ccccc3)n2)cc1]

Intermediate 055c (1.46 g, 2.00 mmol), bispinacolatodiboron (760 mg, 2.99 mmol), and KOAc (492 mg, 4.99 mmol) were dissolved in 1,4-dioxane (20 mL) and degassed for 5 minutes by bubbling with Ar. PdCl$_2$(dppf)-CH$_2$Cl$_2$ adduct (130 mg, 0.159 mmol) was added and the reaction degassed for an additional 10 minutes. The reaction was heated at 130° C. in the microwave for 60 minutes. The reaction was diluted with EtOAc and washed with H$_2$O then brine, dried (Na$_2$SO$_4$), filtered, and concentrated in vacuo. The crude material was purified by column chromatography (ISCO, 80 g silica gel column, 29 minute gradient of 0 to 100% EtOAc in hexanes) to give Intermediate 055d (1.03 g, 1.32 mmol, 66%) as a white solid. LC-MS (Method A2) RT=1.11 min, MS (ESI) m/z: 778.7 (M+H)$^+$. $^1$H NMR (500 MHz, CDCl$_3$) δ 7.97 (d, J=7.4 Hz, 1H), 7.88 (dd, J=7.7, 1.1 Hz, 1H), 7.77 (s, 1H), 7.38-7.31 (m, 4H), 7.30-7.22 (m, 4H), 7.07 (d, J=8.3 Hz, 2H), 6.93 (br d, J=7.4 Hz, 8H), 6.87 (d, J=8.3 Hz, 2H), 5.37 (s, 2H), 2.74-2.65 (m, 5H), 2.60 (s, 3H), 1.33-1.24 (m, 15H)

Example 055

Intermediate 055d was reacted with 3-bromothiophene in a method analogous to Example 122 to give Example 055. LC-MS (Method A1) RT=1.41 min, MS (ESI) m/z: 492.2 (M+H)$^+$. $^1$H NMR (500 MHz, DMSO-d$_6$) δ 7.99 (s, 1H), 7.78 (br d, J=6.7 Hz, 1H), 7.68 (s, 1H), 7.65-7.59 (m, 3H), 7.12 (br d, J=7.9 Hz, 2H), 7.02 (br d, J=8.2 Hz, 2H), 6.95 (s, 1H), 5.44 (s, 2H), 2.79 (q, J=7.6 Hz, 2H), 2.53 (d, J=18.6 Hz, 6H), 1.25 (t, J=7.5 Hz, 3H) (1 exchangeable proton not observed).

The compounds listed in the table below were synthesized using the same methods that were used to prepare Example 055.

| Ex # | Structure | MW | LC-MS m/z [M + H]$^+$; RT (Method) | $^1$H NMR |
|---|---|---|---|---|
| 056 | 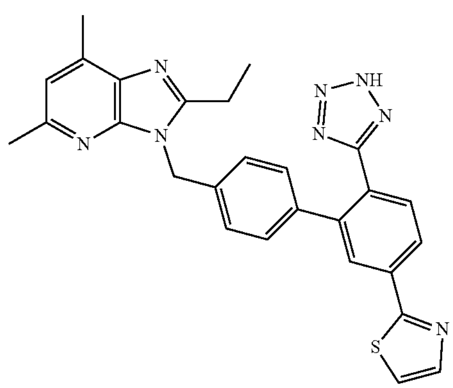 [SMILES: CCc1nc2c(C)cc(C)nc2n1Cc1ccc(-c2cc(-c3nccs3)ccc2-c2nn[nH]n2)cc1] | 492.598 | 493.1; 1.43 min (Method A1) | $^1$H NMR (500 MHz, DMSO-d$_6$) δ 8.13 (br d, J = 8.2 Hz, 1H), 8.01 (d, J = 3.4 Hz, 2H), 7.89 (d, J = 3.1 Hz, 1H), 7.82 (d, J = 7.9 Hz, 1H), 7.16 (s, 1H), 7.16-7.12 (m, 2H), 7.12-7.08 (m, 2H), 5.49 (s, 2H), 2.79 (q, J = 7.3 Hz, 2H), 2.57-2.48 (m, 6H), 1.22 (t, J = 7.5 Hz, 3H) (1 exchangeable proton not observed) |

-continued

| Ex # | Structure | MW | LC-MS m/z [M + H]+; RT (Method) | 1H NMR |
|---|---|---|---|---|
| 057 | 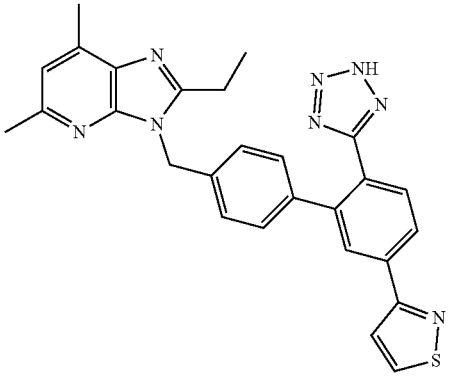 [SMILES: CCc1nc2c(C)cc(C)nc2n1Cc1ccc(-c2cc(-c3ccsn3)ccc2-c2nn[nH]n2)cc1] | 492.598 | 493.1; 1.46 min (Method A1) | 1H NMR (500 MHz, DMSO-d6) δ 9.19 (br d, J = 4.6 Hz, 1H), 8.20 (br s, 1H), 8.09 (br s, 2H), 7.95 (s, 1H), 7.23-7.00 (m, 4H), 6.95 (s, 1H), 5.45 (br s, 2H), 2.77 (br s, 2H), 2.53 (br d, J = 18.9 Hz, 6H), 1.23 (br s, 3H) (1 exchangeable proton not observed) |
| 058 | 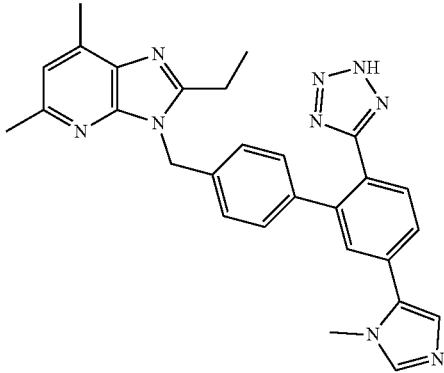 [SMILES: CCc1nc2c(C)cc(C)nc2n1Cc1ccc(-c2cc(-c3cncn3C)ccc2-c2nn[nH]n2)cc1] | 489.574 | 490.2; 1.17 min (Method A1) | 1H NMR (500 MHz, DMSO-d6) δ 9.18 (s, 1H), 8.02 (s, 1H), 7.90-7.82 (m, 2H), 7.76 (s, 1H), 7.20-7.13 (m, 2H), 7.12-7.06 (m, 3H), 5.55 (s, 2H), 3.94 (s, 3H), 2.95-2.87 (m, 2H), 2.59-2.47 (m, 6H), 1.24 (t, J = 7.3 Hz, 3H) (1 exchangeable proton not observed) |
| 059 | 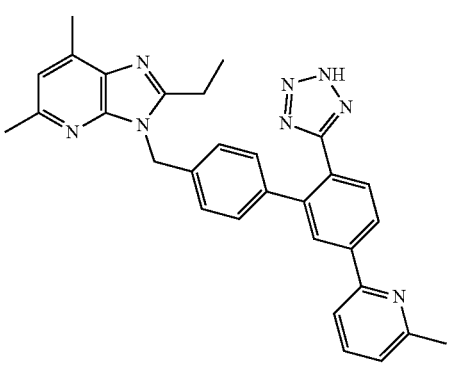 | 500.610 | 501.4; 1.39 min (Method A1) | 1H NMR (500 MHz, DMSO-d6) δ 8.16 (br d, J = 8.2 Hz, 1H), 8.09 (s, 1H), 7.87 (d, J = 7.6 Hz, 1H), 7.78 (t, J = 7.6 Hz, 1H), 7.74 (d, J = 7.9 Hz, 1H), 7.26 (d, J = 7.3 Hz, 1H), 7.13 (d, J = 7.9 Hz, 2H), 7.05 (br d, J = 8.2 Hz, 2H), 6.95 (s, 1H), 5.46 (s, 2H), 2.78 (q, J = 7.3 Hz, 2H), 2.59-2.48 (m, 9H), 1.28-1.19 (m, 3H) (1 exchangeable proton not observed) |

-continued

| Ex # | Structure | MW | LC-MS m/z [M + H]+; RT (Method) | 1H NMR |
|---|---|---|---|---|
| 060 | 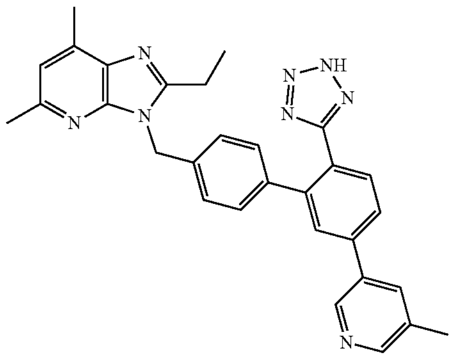 | 500.610 | 501.2; 1.38 min (Method A1) | 1H NMR (500 MHz, DMSO-d6) δ 8.11 (br s, 1H), 7.93 (br d, J = 8.2 Hz, 1H), 7.83 (s, 1H), 7.78 (br d, J = 7.9 Hz, 1H), 7.19 (s, 1H), 7.17-7.13 (m, 2H), 7.12-7.05 (m, 4H), 5.48 (s, 2H), 2.80 (q, J = 7.6 Hz, 2H), 2.60-2.46 (m, 6H), 2.39 (s, 3H), 1.26-1.20 (m, 3H) (1 exchangeable proton not observed) |
| 061 | 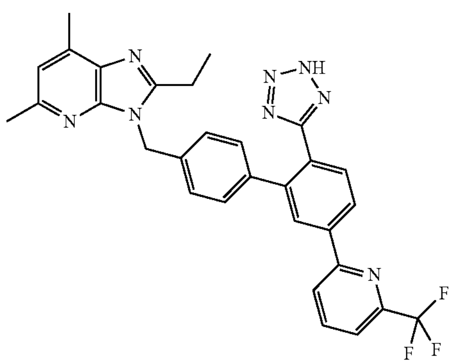 [SMILES: CCc1nc2c(C)cc(C)nc2n1Cc1ccc(-c2cc(-c3cccc(C(F)(F)F)n3)ccc2-c2nn[nH]n2)cc1] | 554.568 | 555.3; 1.59 min (Method A1) | 1H NMR (500 MHz, DMSO-d6) δ 8.46 (d, J = 7.9 Hz, 1H), 8.33-8.28 (m, 1H), 8.23 (br t, J = 7.9 Hz, 1H), 8.20 (s, 1H), 7.93 (d, J = 7.9 Hz, 1H), 7.85 (d, J = 8.2 Hz, 1H), 7.20-7.10 (m, 5H), 5.51 (s, 2H), 2.83 (q, J = 7.6 Hz, 2H), 2.60-2.46 (m, 6H), 1.23 (br t, J = 7.5 Hz, 3H) (1 exchangeable proton not observed) |

Example 062: 2-Ethyl-3-((5'-(4-methoxypyridin-2-yl)-2'-(2H-tetrazol-5-yl)-[1,1'-biphenyl]-4-yl)methyl)-5,7-dimethyl-3H-imidazo[4,5-b]pyridine

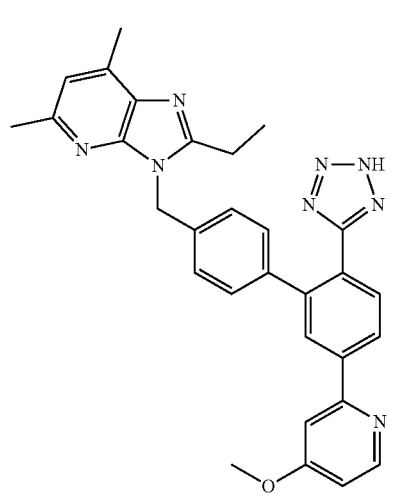 [SMILES: CCc1nc2c(C)cc(C)nc2n1Cc1ccc(-c2cc(-c3cc(OC)ccn3)ccc2-c2nn[nH]n2)cc1]

Intermediate 062a: 4'-((2-Ethyl-5,7-dimethyl-3H-imidazo[4,5-b]pyridin-3-yl)methyl)-5-(4,4,5,5-tetramethyl-1,3,2-dioxaborolan-2-yl)-[1,1'-biphenyl]-2-carbonitrile

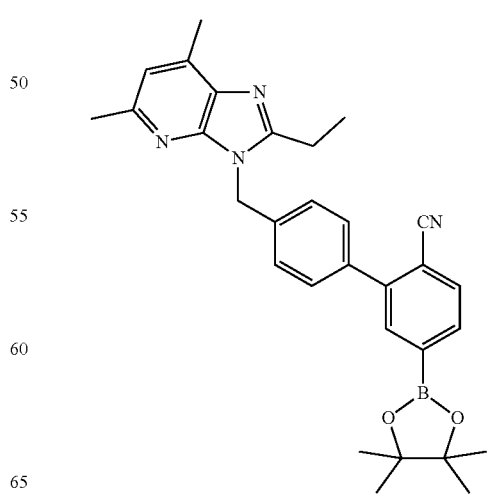

Intermediate 055a (2.18 g, 4.90 mmol), bispinacolatodiboron (2.49 g, 9.80 mmol), X-PHOS (0.234 g, 0.490 mmol), Pd$_2$(dba)$_3$ (0.449 g, 0.490 mmol), and KOAc (2.40 g, 24.5 mmol) were dissolved in 1,4-dioxane (49.0 mL). The reaction was heated at 105° C. After hour, the reaction was cooled to ambient temperature and diluted with EtOAc, filtered through celite, and concentrated in vacuo. The crude material was purified by column chromatography (ISCO, 80 g silica gel column, 19 minute gradient of 0 to 100% EtOAc in hexanes) to give Intermediate 062a (1.49 g, 2.41 mmol, 62%) as a yellow solid. LC-MS (Method A2) RT=0.96 min, MS (ESI) m/z: 493.2 (M+H)$^+$. $^1$H NMR (500 MHz, CDCl$_3$) δ 7.90 (s, 1H), 7.85 (d, J=7.7 Hz, 1H), 7.75 (d, J=7.7 Hz, 1H), 7.52 (d, J=8.3 Hz, 2H), 7.25 (d, J=8.3 Hz, 2H), 6.93 (s, 1H), 5.55 (s, 2H), 2.85 (q, J=7.4 Hz, 2H), 2.67 (s, 3H), 2.63 (s, 3H), 1.39-1.33 (m, 15H).

Intermediate 062b: 4'-((2-Ethyl-5,7-dimethyl-3H-imidazo[4,5-b]pyridin-3-yl)methyl)-5-(4-methoxypyridin-2-yl)-[1,1'-biphenyl]-2-carbonitrile (062b)

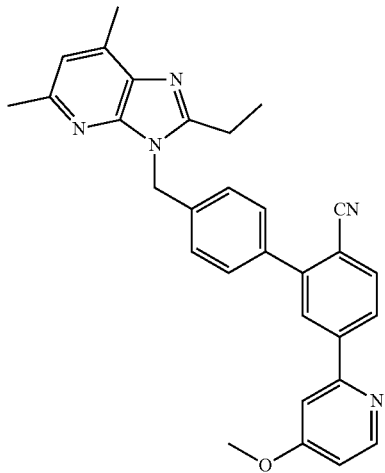

Intermediate 062a (50 mg, 0.102 mmol), 2-bromo-4-methoxypyridine (57.3 mg, 0.305 mmol), and 2nd generation XPHOS precatalyst (7.99 mg, 10.2 μmol) were dissolved in toluene (1.62 mL), ethanol (406 μL), and tripotassium phosphate (2 M aq, 102 μL, 0.203 mmol). The reaction was heated at 100° C. After 2 hours, the reaction was cooled to ambient temperature and diluted with EtOAc, filtered through celite and concentrated in vacuo. The crude material was purified by column chromtography (ISCO, 24 g silica gel column, 19 minute gradient of 0 to 100% EtOAc in hexanes) to give Intermediate 062b (17.7 mg, 0.037 mmol, 37%) as a yellow oil. LC-MS (Method A2) RT=0.68 min, MS (ESI) m/z: 474.1 (M+H)$^+$.

Example 062

Intermediate 062b (17.7 mg, 0.038 mmol), dibutyltin oxide (18.9 mg, 0.076 mmol), and TMS-N$_3$ (25.2 μL, 0.190 mmol) were dissolved in toluene (760 μL) and heated at 100° C. for 18 hours. The reaction was cooled to ambient temperature then diluted with MeOH and concentrated in vacuo. The crude material was purified via preparative LC-MS with the following conditions: Column: XBridge C18, 19×200 mm, 5-μm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 10-50% B over 19 minutes, then a 5-minute hold at 100% B; Flow: 20 mL/min to give Example 062 (6.4 mg, 32%). LC-MS (Method A2) RT=0.62 min, MS (ESI) m/z: 517.1 (M+H)$^+$. $^1$H NMR (500 MHz, DMSO-d$_6$) δ 8.49 (d, J=5.6 Hz, 1H), 8.18 (br d, J=8.1 Hz, 1H), 8.12 (s, 1H), 7.75 (d, J=8.1 Hz, 1H), 7.59 (d, J=1.5 Hz, 1H), 7.16 (d, J=8.1 Hz, 2H), 7.07 (d, J=8.1 Hz, 2H), 6.97 (dd, J=5.6, 2.3 Hz, 1H), 6.94 (s, 1H), 5.46 (s, 2H), 3.93 (s, 3H), 2.79 (q, J=7.5 Hz, 2H), 2.59-2.48 (m, 6H), 1.26 (t, J=7.4 Hz, 3H) (1 exchangeable proton not observed)

The compounds listed in the table below were synthesized using the same methods that were used to prepare Example 62.

| Ex # | Structure | MW | LC-MS m/z [M + H]$^+$; RT (Method) | $^1$H NMR |
|---|---|---|---|---|
| 063 | 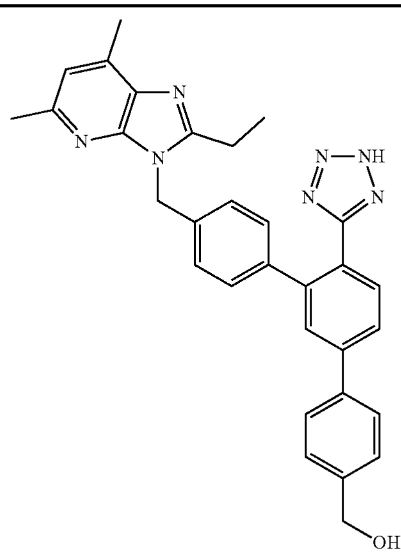 | 515.621 | 516.3; 0.72 min (Method A2) | $^1$H NMR (500 MHz, DMSO-d$_6$) δ 7.96 (s, 1H), 7.83-7.66 (m, 5H), 7.43 (br d, J = 7.9 Hz, 2H), 7.15 (br d, J = 7.9 Hz, 2H), 7.06 (br d, J = 7.9 Hz, 2H), 6.96 (s, 1H), 5.46 (s, 2H), 4.56 (s, 2H), 2.90 (s, 3H), 2.79 (q, J = 7.5 Hz, 2H), 2.74 (s, 3H), 1.25 (t, J = 7.5 Hz, 3H) (1 exchangeable proton not observed) |

| Ex # | Structure | MW | LC-MS m/z [M + H]+; RT (Method) | 1H NMR |
|---|---|---|---|---|
| 064 | 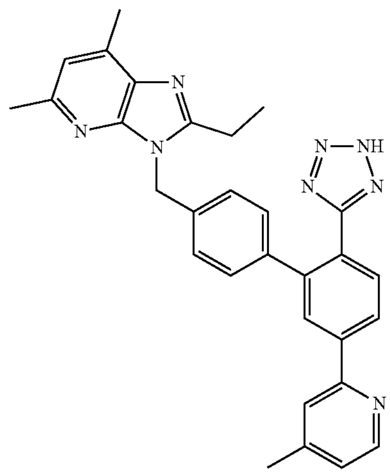 [SMILES: CCc1nc2c(C)cc(C)nc2n1Cc1ccc(-c2cc(-c3cc(C)ccn3)ccc2-c2nn[nH]n2)cc1] | 500.610 | 501.1; 0.63 min (Method A2) | 1H NMR (500 MHz, DMSO-d6) δ 8.53 (d, J = 4.9 Hz, 1H), 8.14 (dd, J = 8.0, 1.4 Hz, 1H), 8.07 (s, 1H), 7.91 (s, 1H), 7.75 (d, J = 8.0 Hz, 1H), 7.20 (br d, J = 4.7 Hz, 1H), 7.16 (d, J = 8.1 Hz, 2H), 7.06 (d, J = 8.0 Hz, 2H), 6.94 (s, 1H), 5.46 (s, 2H), 2.80 (q, J = 7.4 Hz, 2H), 2.58-2.49 (m, 6H), 2.40 (s, 3H), 1.27 (t, J = 7.4 Hz, 3H) (1 exchangeable proton not observed) |
| 065 | 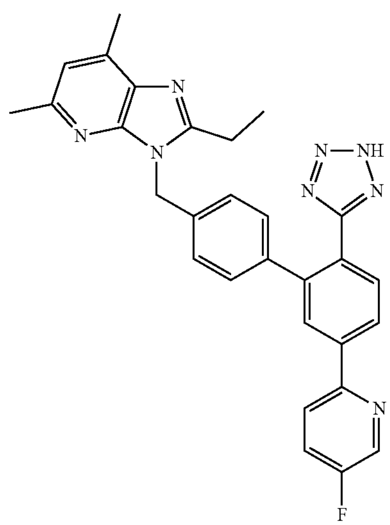 [SMILES: CCc1nc2c(C)cc(C)nc2n1Cc1ccc(-c2cc(-c3ccc(F)cn3)ccc2-c2nn[nH]n2)cc1] | 504.573 | 505.1; 0.78 min (Method A2) | 1H NMR (500 MHz, DMSO-d6) δ 8.67 (d, J = 2.8 Hz, 1H), 8.24-8.15 (m, 2H), 8.12 (s, 1H), 7.83 (td, J = 8.8, 2.9 Hz, 1H), 7.77 (d, J = 8.0 Hz, 1H), 7.20-7.13 (m, 2H), 7.11-7.04 (m, 2H), 6.95 (s, 1H), 5.47 (s, 2H), 2.78 (q, J = 7.5 Hz, 2H), 2.61-2.47 (m, 6H), 1.25 (br t, J = 1A Hz, 3H) (1 exchangeable proton not observed) |
| 066 | 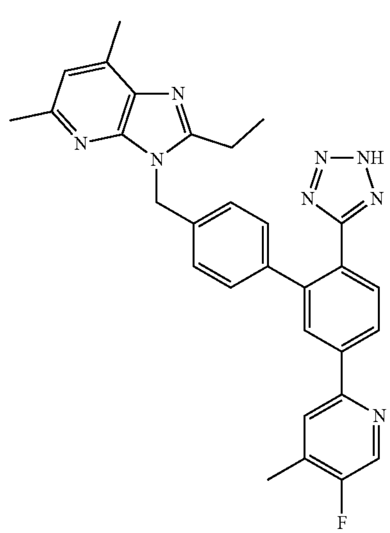 [SMILES: CCc1nc2c(C)cc(C)nc2n1Cc1ccc(-c2cc(-c3cc(C)c(F)cn3)ccc2-c2nn[nH]n2)cc1] | 518.600 | 519.1; 1.57 min (Method A1) | 1H NMR (500 MHz, DMSO-d6) δ 8.51 (s, 1H), 8.14-8.05 (m, 2H), 8.01 (s, 1H), 7.75 (br d, J = 8.3 Hz, 1H), 7.16 (br d, J = 8.0 Hz, 2H), 7.05 (br d, J = 8.1 Hz, 2H), 6.94 (s, 1H), 5.46 (s, 2H), 2.80 (q, J = 7.2 Hz, 2H), 2.61-2.47 (m, 6H), 2.37 (s, 3H), 1.30-1.24 (m, 3H) (1 exchangeable proton not observed) |

-continued

| Ex # | Structure | MW | LC-MS m/z [M + H]+; RT (Method) | 1H NMR |
|---|---|---|---|---|
| 067 | 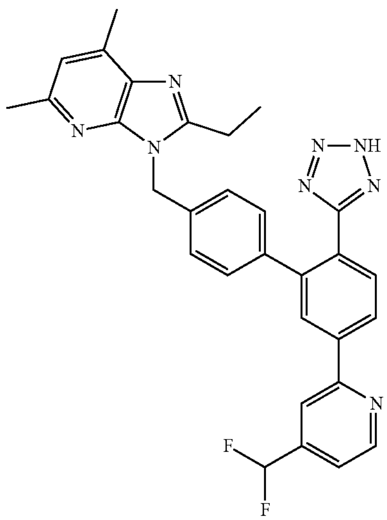 [SMILES: CCc1nc2c(C)cc(C)nc2n1Cc1ccc(-c2cc(-c3cc(C(F)F)ccn3)ccc2-c2nn[nH]n2)cc1] | 536.591 | 537.1; 0.80 min (Method A2) | 1H NMR (500 MHz, DMSO-d$_6$) δ 8.87 (d, J = 4.9 Hz, 1H), 8.33-8.25 (m, 2H), 8.20 (d, J = 1.3 Hz, 1H), 7.81 (br d, J = 8.0 Hz, 1H), 7.59 (br d, J = 4.8 Hz, 1H), 7.28-7.00 (m, 5H), 6.95 (s, 1H), 5.47 (s, 2H), 2.79 (q, J = 7.5 Hz, 2H), 2.60-2.47 (m, 6H), 1.25 (br t, J = 7.5 Hz, 3H) (1 exchangeable proton not observed) |
| 068 | 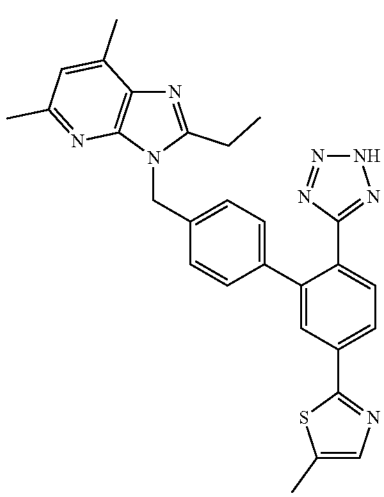 [SMILES: CCc1nc2c(C)cc(C)nc2n1Cc1ccc(-c2cc(-c3ncc(C)s3)ccc2-c2nn[nH]n2)cc1] | 506.632 | 507.2; 0.78 min (Method A2) | 1H NMR (500 MHz, DMSO-d$_6$) δ 7.90 (br d, J = 7.0 Hz, 1H), 7.79 (s, 1H), 7.71 (br d, J = 7.9 Hz, 1H), 7.61 (s, 1H), 7.10 (br d, J = 7.9 Hz, 2H), 7.01 (br d, J = 7.9 Hz, 2H), 6.96 (s, 1H), 5.44 (s, 2H), 2.77 (q, J = 7.3 Hz, 2H), 2.59-2.45 (m, 9H), 1.22 (t, J = 7.5 Hz, 3H) (1 exchangeable proton not observed) |

Example 069: 2-((4"-((2-ethyl-5,7-dimethyl-3H-imidazo[4,5-b]pyridin-3-yl)methyl)-[1,1':3',1"-terphenyl]-4'-yl)oxy)acetic acid

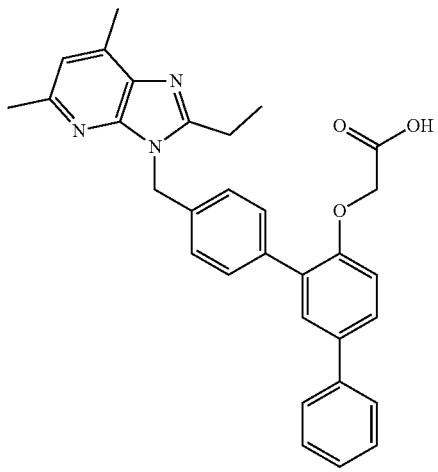 [SMILES: CCc1nc2c(C)cc(C)nc2n1Cc1ccc(-c2cc(-c3ccccc3)ccc2OCC(=O)O)cc1]

Intermediate 069a: Methyl 2-((3-bromo-[1,1'-biphenyl]-4-yl)oxy)acetate

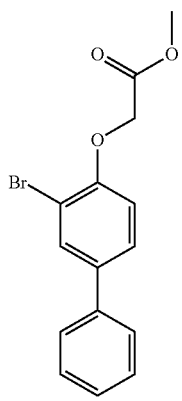

To a solution of 3-bromo[1,1'-biphenyl]-4-ol (100 mg, 0.401 mmol) in DMF (2.01 mL) was added potassium carbonate (166 mg, 1.20 mmol) followed by methyl bromoacetate (41.8 µL, 0.442 mmol). The reaction was stirred vigorously at RT. After 30 min, the reaction mixture was diluted with EtOAc, filtered over celite and washed with 10% LiCl (aq). The organic phase was dried over $MgSO_4$, filtered and concentrated in vacuo to give Intermediate 069a (117 mg, 0.364 mmol, 91% yield) as a white amorphous solid. $^1$H NMR (400 MHz, $CDCl_3$) δ 7.81 (d, J=2.2 Hz, 1H), 7.54-7.49 (m, 2H), 7.46 (dd, J=8.5, 2.3 Hz, 1H), 7.44-7.39 (m, 2H), 7.36-7.30 (m, 1H), 6.88 (d, J=8.6 Hz, 1H), 4.75 (s, 2H), 3.82 (s, 3H).

Example 069

To a solution of Intermediate 001d (40 mg, 0.102 mmol) and Intermediate 069a (36.1 mg, 0.112 mmol) in dioxane (2 mL) was added tripotassium phosphate (2 M aq, 102 µL, 0.204 mmol) followed by $PdCl_2$(dppf) (7.48 mg, 10.2 µmol). The resulting mixture was sparged with $N_2$ for 2 min before being sealed and heated at 120° C. for 45 min in the microwave. The organic phase was diluted with EtOAc and filtered over a mixture of $MgSO_4$/Celite. The filtrate was concentrated, dissolved in a 2:1 mixture of THF (2 mL) and LiOH (1 M aq, 1.02 mL, 1.02 mmol) and heated at 65° C. After 30 min the reaction mixture was quenched with Sat. $NH_4Cl$ and diluted with EtOAc. The organic phase was concentrated in vacuo and purified via preparative LC-MS with the following conditions: Column: XBridge C18, 19×200 mm, 5-µm particles; Mobile Phase A: 5:95 ACN: $H_2O$ with 0.1% TFA; Mobile Phase B: 95:5 ACN: $H_2O$ with 10.1% TFA; Gradient: 30-70% B over 27 minutes, then a 3-minute hold at 100% B; Flow: 20 mL/min. The material was repurified via preparative LC-MS with the following conditions: Column: XBridge C18, 19×200 mm, 5-µm particles; Mobile Phase A: 5:95 ACN: $H_2O$ with 10 mM $NH_4OAc$; Mobile Phase B: 95:5 ACN: $H_2O$ with 10 mM $NH_4OAc$; Gradient: 25-50% B over 25 minutes, then a 2-minute hold at 100% B; Flow: 20 mL/min to give Example 69 (11 mg, 0.021 mmol, 21%). LC-MS (Method A2) RT=0.86 min, MS (ESI) m/z: 492.1 (M+H)$^+$. $^1$H NMR (500 MHz, DMSO-$d_6$) δ 7.64 (t, J=9.0 Hz, 4H), 7.57 (d, J=8.5 Hz, 1H), 7.53 (s, 1H), 7.42 (t, J=7.3 Hz, 2H), 7.35-7.27 (m, 1H), 7.17 (d, J=7.9 Hz, 2H), 7.04 (d, J=8.5 Hz, 1H), 6.96 (s, 1H), 5.51 (s, 2H), 4.68 (br. s., 2H), 2.85 (q, J=7.3 Hz, 2H), 2.52 (br. s., 3H), 2.51 (br. s., 3H), 1.29 (t, J=7.3 Hz, 3H) (1 exchangeable proton not observed).

Example 070: 3-((6'-(2H-Tetrazol-5-yl)-2",3",4",5"-tetrahydro-[1,1':3',1"-terphenyl]-4-yl)methyl)-2-ethyl-5,7-dimethyl-3H-imidazo[4,5-b]pyridine

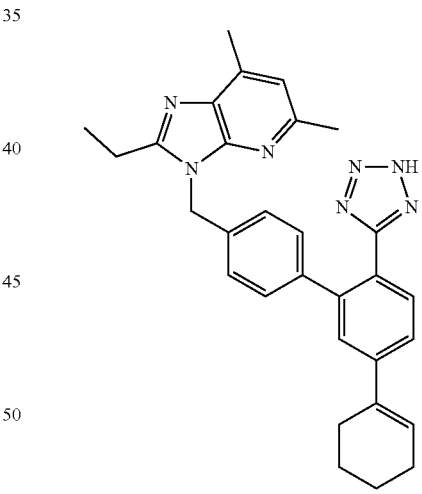

To a microwave vial containing $PdCl_2$(dppf) (2.00 mg, 2.74 µmol) and cyclohex-1-en-1-ylboronic acid (6.90 mg, 0.055 mmol) was added a solution of Intermediate 055c (20 mg, 0.027 mmol) in toluene (1 mL) followed by ethanol (250 µL) and tripotassium phosphate (2 M aq, 34.2 µL, 0.068 mmol). $N_2$ was sparged through the reaction mixture for 5 min before the vial was sealed and heated at 120° C. in the microwave for 30 min. The solution was then filtered over a pad of Celite/$MgSO_4$ then concentrated in vacuo. The crude residue was dissolved in DCM (2 mL), and triethylsilane (21.9 µL, 0.137 mmol) was added followed by TFA (63.3 µL, 0.821 mmol). After 5 minutes, the reaction mixture was concentrated in vacuo and purified via preparative LC-MS with the following conditions: Column: XBridge C18, 19×200 mm, 5-μm particles; Mobile Phase A: 5:95 ACN: H₂O with 10 mM NH₄OAc; Mobile Phase B: 95:5 ACN: H₂O with 10 mM NH₄OAc; Gradient: 20-60% B over 20 minutes, then a 4-minute hold at 100% B; Flow: 20 mL/min to give Example 070 (4.9 mg, 0.010 mmol, 37%). LC-MS (Method A2) RT=0.93 min, MS (ESI) m/z: 490.4 (M+H)⁺. ¹H NMR (500 MHz, DMSO-d₆) δ 7.61-7.49 (m, 2H), 7.42 (br. s., 1H), 7.10-6.99 (m, 4H), 6.95 (s, 1H), 6.33 (br. s., 1H), 5.45 (br. s., 2H), 2.77 (q, J=7.0 Hz, 2H), 2.55 (s, 6H), 2.41 (br. s., 2H), 2.19 (br. s., 2H), 1.73 (br. s., 2H), 1.61 (br. s., 2H), 1.23 (t, J=7.0 Hz, 3H.

Example 071: 3-((5'-Cyclohexyl-2'-(2H-tetrazol-5-yl)-[1,1'-biphenyl]-4-yl)methyl)-2-ethyl-5,7-dimethyl-3H-imidazo[4,5-b]pyridine

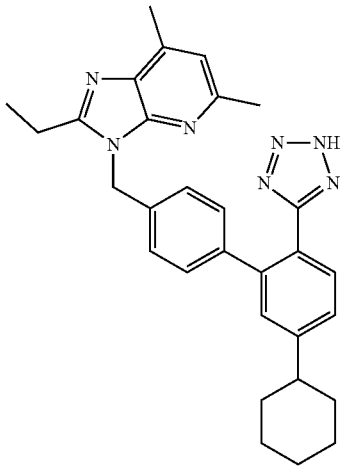 [SMILES: CCc1nc2c(C)cc(C)nc2n1Cc1ccc(-c2cc(C3CCCCC3)ccc2-c2nn[nH]n2)cc1]

Intermediate 71a: 2-ethyl-5,7-dimethyl-3-((6'-(2-trityl-2H-tetrazol-5-yl)-2'',3'',4'',5''-tetrahydro-[1,1':3',1''-terphenyl]-4-yl)methyl)-3H-imidazo[4,5-b]pyridine

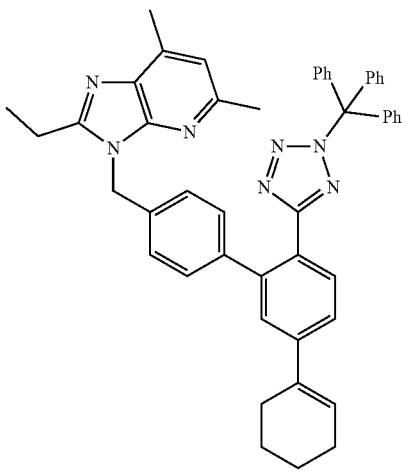 [SMILES: CCc1nc2c(C)cc(C)nc2n1Cc1ccc(-c2cc(C3=CCCCC3)ccc2-c2nnn(C(c3ccccc3)(c3ccccc3)c3ccccc3)n2)cc1]

To a microwave vial containing PdCl₂(dppf) (3.00 mg, 4.11 μmol) and cyclohex-1-en-1-ylboronic acid (10.34 mg, 0.082 mmol) was added a solution of Intermediate 55c (30 mg, 0.041 mmol) in toluene (1 mL) followed by ethanol (250 μL) and tripotassium phosphate (2 M aq, 51.3 μL, 0.103 mmol). N₂ was sparged through the reaction mixture for 5 min before the vial was sealed and heated at 120° C. in the microwave for 30 min.

The solution was then filtered over a pad of Celite/MgSO₄ before being concentrated in vacuo. This crude residue was purified by column chromatography (ISCO, 12 g silica gel column, gradient of 0 to 100% EtOAc in hexanes) to give Intermediate 71a (25 mg, 0.034 mmol, 83% yield) as an off-white solid. LC-MS (Method A2) RT=1.22 min, MS (ESI) m/z: 732.3 (M+H)⁺.

Example 71

To a flask containing Intermediate 71a (25 mg, 0.034 mmol) was added THF (2 mL). Palladium on carbon (Degussa, 3.63 mg, 3.42 μmol) was added and the resulting suspension was sparged with hydrogen. The reaction mixture was stirred vigorously under a balloon atmosphere of hydrogen. After 6 h, ethanol (1 mL) was added. After 18 hours, the reaction mixture was diluted with EtOAc and filtered over Celite. The resulting solution was concentrated in vacuo then dissolved in DCM (2 mL). Triethylsilane (0.027 mL, 0.171 mmol) was added, followed TFA (0.079 mL, 1.02 mmol). After 5 min, the reaction mixture was concentrated in vacuo and purified via preparative LC-MS with the following conditions: Column: XBridge C18, 19×200 mm, 5-μm particles; Mobile Phase A: 5:95 ACN: H₂O with 10 mM NH₄OAc; Mobile Phase B: 95:5 ACN: H₂O with 10 mM NH₄OAc; Gradient: 10-80% B over 20 minutes, then a 5-minute hold at 100% B; Flow: 20 mL/min to give Example 71 (5.7 mg, 0.012 mmol, 34%). LC-MS (Method A2) RT=0.96 min, MS (ESI) m/z: 492.4 (M+H)⁺. ¹H NMR (500 MHz, DMSO-d₆) δ 7.53 (d, J=7.8 Hz, 1H), 7.38 (d, J=7.7 Hz, 1H), 7.30 (s, 1H), 7.03 (s, 4H), 6.95 (s, 1H), 5.44 (s, 2H), 2.76 (q, J=7.3 Hz, 2H), 2.61 (t, J=11.4 Hz, 1H), 2.55 (s, 6H), 1.81 (t, J=14.9 Hz, 4H), 1.70 (d, J=11.9 Hz, 1H), 1.55-1.42 (m, 2H), 1.37 (q, J=12.4 Hz, 2H), 1.24 (m, 4H) (1 exchangeable proton not observed).

Example 72: 3-(4''-((2-ethyl-5,7-dimethyl-3H-imidazo[4,5-b]pyridin-3-yl)methyl)-[1,1':3',1''-terphenyl]-4'-yl)-1,2,4-oxadiazole-5(4H)-thione

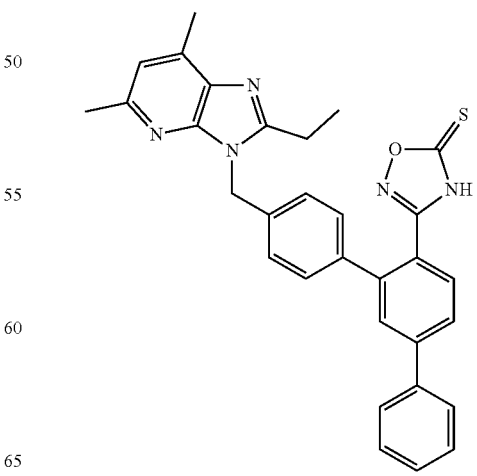

Intermediate 72a: 4"-((2-ethyl-5,7-dimethyl-3H-imidazo[4,5-b]pyridin-3-yl)methyl)-[1,1':3',1"-terphenyl]-4'-carbonitrile

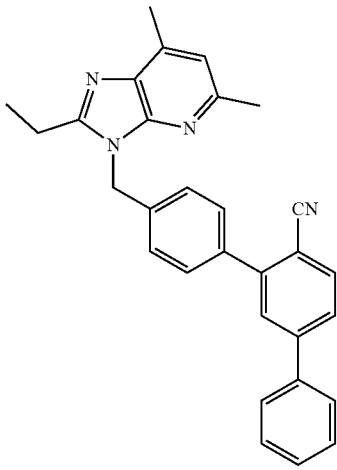 [SMILES: CCc1nc2c(C)cc(C)nc2n1Cc1ccc(-c2cc(-c3ccccc3)ccc2C#N)cc1]

To a solution of Intermediate 001d (120 mg, 0.307 mmol) and 3-bromo-[1,1'-biphenyl]-4-carbonitrile (103 mg, 0.399 mmol) in 1,4-dioxane (3 mL) was added tripotassium phosphate (2 M aq, 0.460 mL, 0.920 mmol) followed by $PdCl_2$ (dppf) (22.4 mg, 0.031 mmol). The resulting mixture was sparged with $N_2$ for 2 min before being sealed and heated at 120° C. for 45 min in the microwave. The reaction mixture was diluted with EtOAc and filtered through celite. The filtrate was concentrated in vacuo. The crude material was purified by column chromatography (ISCO, 24 g silica gel column, 30 minute gradient of 0 to 100% EtOAc in hexanes) to give Intermediate 72a (130 mg, 0.294 mmol, 96%). LC-MS (Method A2) RT=0.93 min, MS (ESI) m/z: 443.1 (M+H)+. 1H NMR (400 MHz, CDCl3) δ 7.81 (d, J=7.9 Hz, 1H), 7.69-7.58 (m, 4H), 7.54 (d, J=8.4 Hz, 2H), 7.50-7.39 (m, 3H), 7.28-7.22 (m, 2H), 6.91 (s, 1H), 5.54 (s, 2H), 2.84 (q, J=7.5 Hz, 2H), 2.64 (s, 3H), 2.60 (s, 3H), 1.37-1.31 (m, 3H).

Intermediate 72b: (Z)-4"-((2-ethyl-5,7-dimethyl-3H-imidazo[4,5-b]pyridin-3-yl)methyl)-N'-hydroxy-[1,1':3',1'''-terphenyl]-4'-carboximidamide

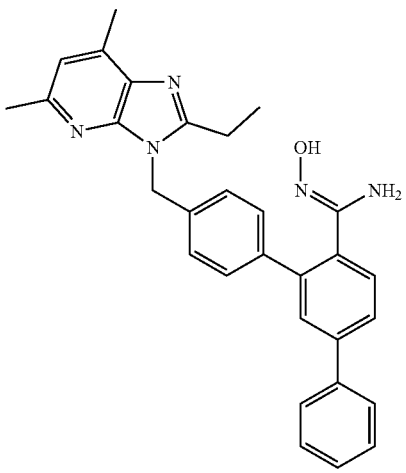 [SMILES: CCc1nc2c(C)cc(C)nc2n1Cc1ccc(-c2cc(-c3ccccc3)ccc2/C(N)=N/O)cc1]

To a vial containing hydroxylamine hydrochloride (56.5 mg, 0.813 mmol) and potassium hydroxide (38.0 mg, 0.678 mmol) was added ethanol (678 μL). The mixture was stirred vigorously for 15 min, then the suspension was added directly to a vial containing Intermediate 72a (30 mg, 0.068 mmol) in its own solution of ethanol (678 μL). The vial was sealed and heated at 85° C. After 16 h of heating, another 5 equiv of hydroxylamine (24 mg) was added and heating was resumed for an additional 4 h. The reaction mixture was diluted with EtOAc and washed with sat. NH4Cl. The organic phase was dried over MgSO4 and filtered over celite with an EtOAc rinse. The organic phase was concentrated in vacuo and was used directly in the subsequent reaction as Intermediate 72b (15 mg, 0.032 mmol). LC-MS (Method A2) RT=0.72 min, MS (ESI) m/z: 476.1 (M+H)+.

Example 72

To a solution of Intermediate 72b (15 mg, 0.032 mmol) in DMF (2 mL) was added DBU (0.024 mL, 0.158 mmol) followed by 1,1'-thiocarbonyldiimidazole (28.1 mg, 0.158 mmol). After 5 min, the reaction mixture was quenched with a few drops of H2O, filtered and purified via preparative LC-MS with the following conditions: Column: XBridge C18, 19×200 mm, 5-μm particles; Mobile Phase A: 5:95 ACN:H2O with 10 mM NH4OAc; Mobile Phase B: 95:5 ACN:H2O with 10 mM NH4OAc; Gradient: 20-60% B over 20 minutes, then a 3-minute hold at 100% B; Flow: 20 mL/min to give Example 72 (7.8 mg, 0.015 mmol, 46%). LC-MS (Method A2) RT=0.95 min, MS (ESI) m/z: 518.3 (M+H)+. 1H NMR (500 MHz, DMSO-d6) δ 7.80-7.58 (m, 4H), 7.55-7.35 (m, 3H), 7.33-6.92 (m, 6H), 5.50 (br. s., 2H), 2.82 (q, J=7.0 Hz, 2H), 2.55 (s, 6H), 1.26 (t, J=7.2 Hz, 3H) (1 exchangeable proton not observed).

Example 73: 2-ethyl-5,7-dimethyl-3-((5'-(tetrahydrofuran-2-yl)-2'-(2H-tetrazol-5-yl)-[1,1'-biphenyl]-4-yl)methyl)-3H-imidazo[4,5-b]pyridine

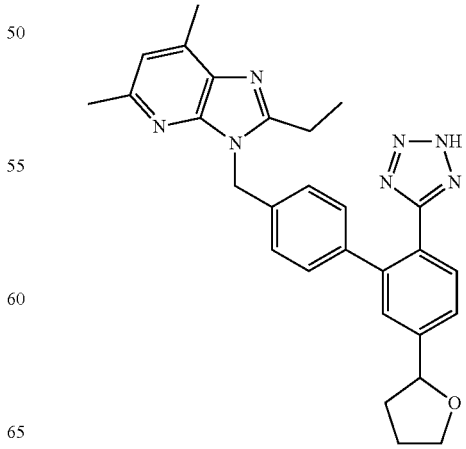

193

Intermediate 73a: 4'-((2-ethyl-5,7-dimethyl-3H-imidazo[4,5-b]pyridin-3-yl)methyl)--(tetrahydrofuran-2-yl)-[1,1'-biphenyl]-2-carbonitrile

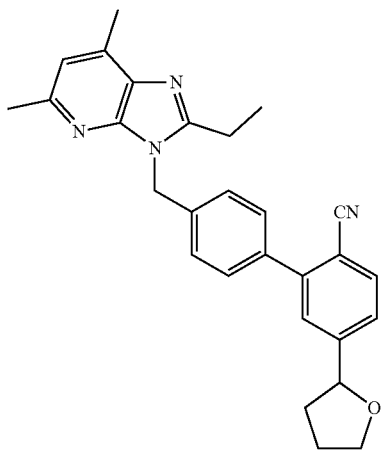 [SMILES: CCc1nc2c(C)cc(C)nc2n1Cc1ccc(-c2cc(C3CCCO3)ccc2C#N)cc1]

Intermediate 55a (100 mg, 0.225 mmol), tetrahydrofuran-2-carboxylic acid (78 mg, 0.674 mmol), [IR(DFCF$_3$PPY)$_2$(BPY)]PF$_6$ (2.27 mg, 2.24 μmol), nickel(II) chloride ethylene glycol dimethyl ether complex (9.87 mg, 0.045 mmol), 4,4'-di-tert-butyl-2,2'-dipyridyl (18.1 mg, 0.067 mmol), and cesium carbonate (219 mg, 0.674 mmol) were dissolved in DMF (4.49 mL). The reaction was degassed by bubbling with N$_2$ for 20 minutes, then irradiated with a 34 W Blue LED lamp. After 18 hours, the reaction was diluted with EtOAc and washed with saturated NaHCO$_3$, H$_2$O, then brine, dried (Na$_2$SO$_4$), filtered, and concentrated in vacuo. The crude material was purified by column chromatography (ISCO, 40 g silica gel column, 19 minute gradient of 0 to 100% EtOAc in DCM) to give Intermediate 73a (42.3 mg, 0.097 mmol, 43%). LC-MS (Method A2) RT=0.82 min, MS (ESI) m/z: 437.7 (M+H)$^+$. $^1$H NMR (500 MHz, CDC$_3$) δ7.73 (d, J=8.0 Hz, 1H), 7.51 (d, J=8.3 Hz, 2H), 7.45 (s, 1H), 7.41 (dd, J=8.0, 1.1 Hz, 1H), 7.26 (br d, J=8.3 Hz, 2H), 6.93 (s, 1H), 5.55 (s, 2H), 4.97 (t, J=7.3 Hz, 1H), 4.23-4.05 (m, J=19.5, 7.7 Hz, 1H), 4.05-3.95 (m, 1H), 2.90-2.79 (m, 2H), 2.67 (s, 3H), 2.65-2.61 (m, 3H), 2.45-2.38 (m, 1H), 2.12-1.99 (m, 2H), 1.79 (br dd, J=12.2, 7.8 Hz, 1H), 1.42-1.34 (m, 3H).

194

Intermediate 73b & Intermediate 73c: 4'-((2-ethyl-5,7-dimethyl-3H-imidazo[4,5-b]pyridin-3-yl)methyl)-5-(tetrahydrofuran-2-yl)-[1,1'-biphenyl]-2-carbonitrile

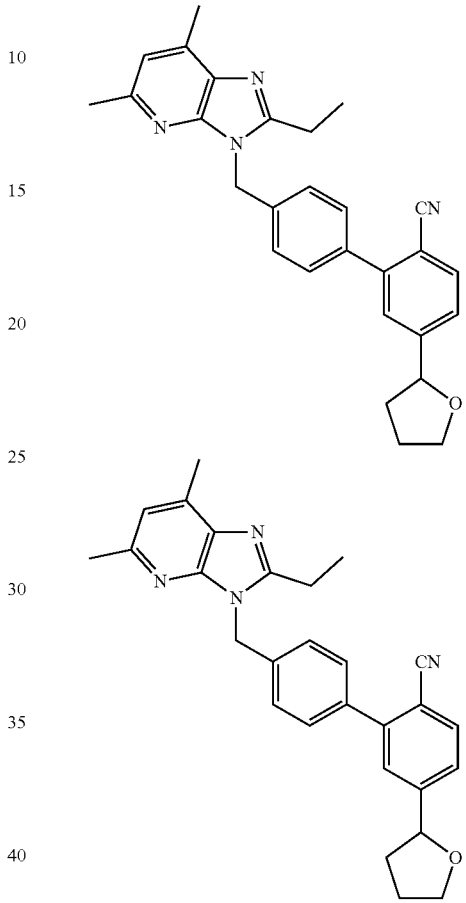

Intermediate 73a (42.3 mg, 0.097 mmol) was separated by chiral SFC (Regis Whelk-01, 21×250 mm, 5 micron column; 20% MeOH/80% CO$_2$ mobile phase; 45 mL/min, 150 bar, 40° C.) to give two peaks, the first eluting of which was Intermediate 73b (9.2 mg, 0.021 mmol, 22%) as a clear glassy solid. The second eluting isomer was Intermediate 73c (11.6 mg, 0.027 mmol, 27%) as a clear glassy solid.

Example 73

Intermediate 73b (9 mg, 0.021 mmol) was reacted with dibutyltin oxide (5.1 mg, 0.021 mmol) and TMS-N$_3$ (27.4 μL, 0.206 mmol) in a manner analogous to Example 62 to give Example 73 (1.7 mg, 0.0034 mmol, 17%). LC-MS (Method A2) RT=0.73 min, MS (ESI) m/z: 480.4 (M+H)$^+$. $^1$H NMR (500 MHz, DMSO-d$_6$) δ 7.56 (br d, J=7.9 Hz, 1H), 7.44 (br d, J=7.3 Hz, 1H), 7.35 (s, 1H), 7.02 (s, 4H), 6.96 (s, 1H), 5.43 (s, 2H), 4.90 (br t, J=7.2 Hz, 1H), 3.98 (q, J=7.1 Hz, 1H), 2.75 (q, J=7.4 Hz, 2H), 2.55 (s, 6H), 2.35 (br dd, J=12.2, 6.4 Hz, 1H), 2.00-1.84 (m, 2H), 1.79-1.62 (m, 1H), 1.28-1.13 (m, 3H), 1.00 (d, J=6.4 Hz, 1H) (1 exchangeable proton not observed).

Example 74: 2-ethyl-5,7-dimethyl-3-((5'-(tetrahydrofuran-2-yl)-2'-(2H-tetrazol-5-yl)-[1,1'-biphenyl]-4-yl)methyl)-3H-imidazo[4,5-b]pyridine

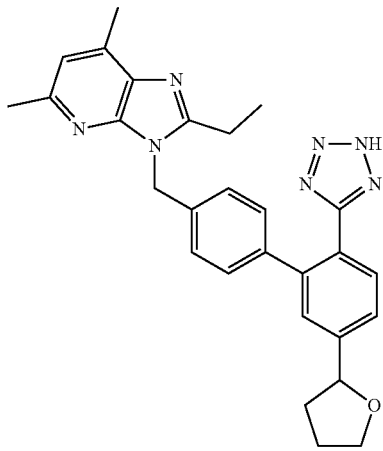 [SMILES: CCc1nc2c(C)cc(C)nc2n1Cc1ccc(-c2cc(C3CCCO3)ccc2-c2nn[nH]n2)cc1]

Intermediate 73c (9 mg, 0.021 mmol) was reacted with dibutyltin oxide (6.3 mg, 0.025 mmol) and TMS-N$_3$ (33.4 µL, 0.252 mmol) in a manner analogous to Example 62 to give Example 74 (5.9 mg, 0.012 mmol, 47%). LC-MS (Method A2) RT=0.73 min, MS (ESI) m/z: 480.4 (M+H)$^+$. $^1$H NMR (500 MHz, DMSO-d$_6$) δ 7.56 (br d, J=7.9 Hz, 1H), 7.44 (br d, J=7.3 Hz, 1H), 7.35 (s, 1H), 7.02 (s, 4H), 6.96 (s, 1H), 5.43 (s, 2H), 4.90 (br t, J=7.2 Hz, 1H), 3.98 (q, J=7.1 Hz, 1H), 2.75 (q, J=7.4 Hz, 2H), 2.55 (s, 6H), 2.35 (br dd, J=12.2, 6.4 Hz, 1H), 2.00-1.84 (m, 2H), 1.79-1.62 (m, 1H), 1.28-1.13 (m, 3H), 1.00 (d, J=6.4 Hz, 11H) (1 exchangeable proton not observed).

Example 75: 2-ethyl-5,7-dimethyl-3-((5'-(piperidin-2-yl)-2'-(2H-tetrazol-5-yl)-[1,1'-biphenyl]-4-yl)methyl)-3H-imidazo[4,5-b]pyridine

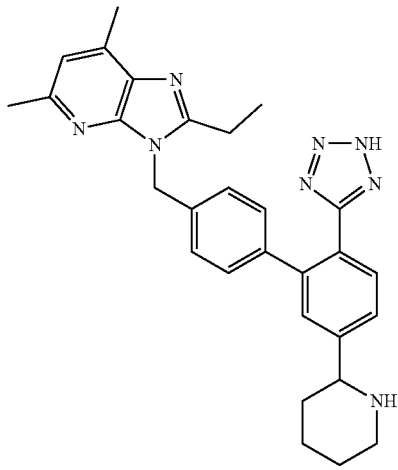 [SMILES: CCc1nc2c(C)cc(C)nc2n1Cc1ccc(-c2cc(C3CCCCN3)ccc2-c2nn[nH]n2)cc1]

Intermediate 75a: tert-butyl 2-(6-cyano-4'-((2-ethyl-5,7-dimethyl-3H-imidazo[4,5-b]pyridin-3-yl)methyl)-[1,1'-biphenyl]-3-yl)piperidine-1-carboxylate

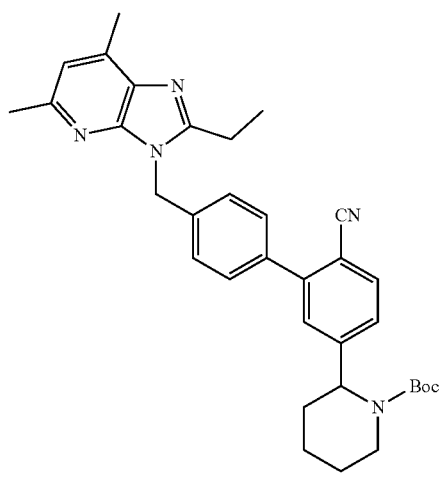 [SMILES: CCc1nc2c(C)cc(C)nc2n1Cc1ccc(-c2cc(C3CCCCN3C(=O)OC(C)(C)C)ccc2C#N)cc1]

Intermediate 55a (150 mg, 0.337 mmol) was reacted with Boc-L-pipecolic acid (232 mg, 1.01 mmol) in a manner analogous to Intermediate 73a to give Intermediate 75a (195.2 mg, 0.355 mmol). LC-MS (Method A2) RT=0.94 min, MS (ESI) m/z: 550.8 (M+H)$^+$.

Intermediate 75b & Intermediate 75c: tert-butyl 2-(6-cyano-4'-((2-ethyl-5,7-dimethyl-3H-imidazo[4,5-b]pyridin-3-yl)methyl)-[1,1'-biphenyl]-3-yl)piperidine-1-carboxylate

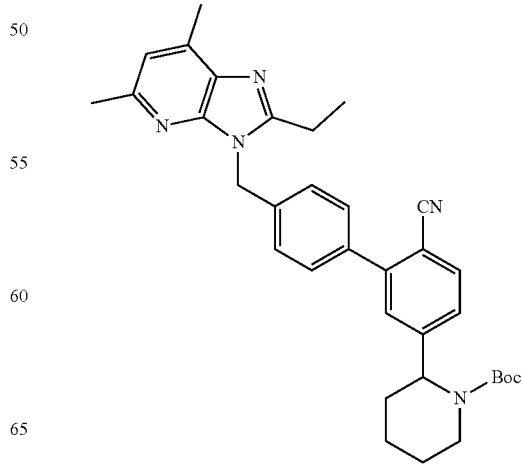

-continued

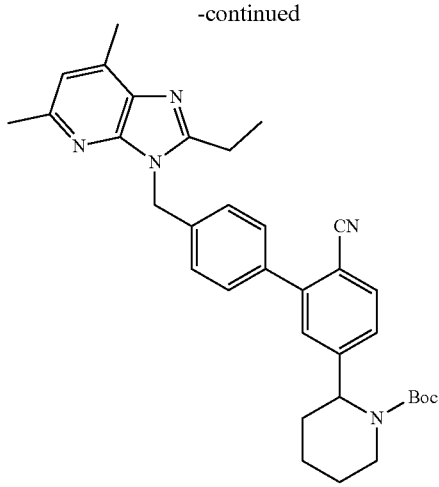

Intermediate 75a (317.4 mg, 0.577 mmol) was separated by chiral SFC (Regis Whelk-01, 30×250 mm, 5 micron column; 30% MeOH/70% Co$_2$ mobile phase; 85 mL/min, 150 bar, 40° C.) to give two peaks, the first eluting of which was Intermediate 75b (72.4 mg, 0.132 mmol, 23%) as a clear glassy solid. The second eluting isomer was Intermediate 75c (80.2 mg, 0.146 mmol, 25%) as a clear glassy solid. Analytical data for both enantiomers: LC-MS (Method A2) RT=0.94 min, MS (ESI) m/z: 550.8 (M+H)[1]. $^1$H NMR (500 MHz, CDCl$_3$) δ 7.74 (d, J=8.5 Hz, 1H), 7.49 (d, J=8.3 Hz, 2H), 7.33-7.30 (m, 2H), 7.26 (d, J=8.3 Hz, 2H), 6.93 (s, 1H), 5.55 (s, 2H), 5.45 (br d, J=2.2 Hz, 1H), 4.08 (br d, J=14.6 Hz, 1H), 2.86 (q, J=7.4 Hz, 2H), 2.77 (td, J=12.9, 3.6 Hz, 1H), 2.67 (s, 3H), 2.62 (s, 3H), 2.28 (br d, J=12.9 Hz, 1H), 2.02-1.91 (m, 1H), 1.70-1.60 (m, 4H), 1.46 (s, 9H), 1.37 (t, J=7.4 Hz, 3H).

Intermediate 75d: 4'-((2-ethyl-5,7-dimethyl-3H-imidazo[4,5-b]pyridin-3-yl)methyl)--(piperidin-2-yl)-[1,1'-biphenyl]-2-carbonitrile, 2 TFA

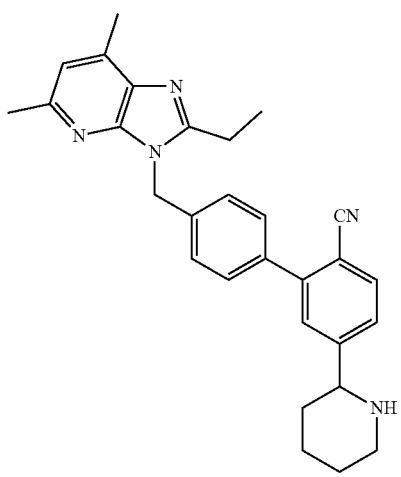 [SMILES: CCc1nc2c(C)cc(C)nc2n1Cc1ccc(-c2cc(C3CCCCN3)ccc2C#N)cc1]

Intermediate 75b (70 mg, 0.127 mmol) was dissolved in DCM (1.27 mL) and TFA (98 µL, 1.27 mmol). After 18 hours, the reaction was concentrated in vacuo to give Intermediate 75d. LC-MS (Method A2) RT=0.61 min, MS (ESI) m/z: 450.4 (M+H)$^+$.

Example 75: Intermediate 75d (10 mg, 0.022 mmol) was reacted with dibutyltin oxide (5.5 mg, 0.022 mmol) and TMS-N$_3$ (29.5 µL, 0.222 mmol) in a manner analogous to Example 62 to give Example 75 (3.6 mg, 0.007 mmol, 32%). LC-MS (Method A2) RT=0.57 min, MS (ESI) m/z: 493.3 (M+H)$^+$. $^1$H NMR (500 MHz, DMSO-d$_6$) δ 7.95 (s, 1H), 7.56 (br d, J=8.2 Hz, 1H), 7.40 (br s, 2H), 7.06 (br d, J=8.2 Hz, 2H), 7.00-6.91 (m, 3H), 5.43 (s, 2H), 4.18 (br d, J=11.9 Hz, 1H), 3.05-2.95 (m, 1H), 2.78 (q, J=7.6 Hz, 2H), 2.55 (s, 6H), 1.97 (br d, J=12.2 Hz, 1H), 1.89-1.74 (m, 3H), 1.70-1.55 (m, 2H), 1.25 (t, J=7.5 Hz, 3H) (2 exchangeable protons not observed).

Example 76: 2-ethyl-5,7-dimethyl-3-((5'-(piperidin-2-yl)-2'-(2H-tetrazol-5-yl)-[1,1'-biphenyl]-4-yl)methyl)-3H-imidazo[4,5-b]pyridine

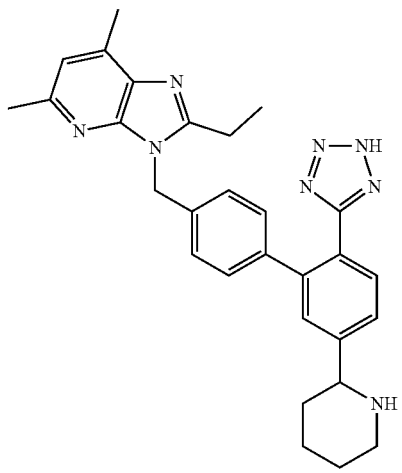 [SMILES: CCc1nc2c(C)cc(C)nc2n1Cc1ccc(-c2cc(C3CCCCN3)ccc2-c2nn[nH]n2)cc1]

Intermediate 76a: 4'-((2-ethyl-5,7-dimethyl-3H-imidazo[4,5-b]pyridin-3-yl)methyl)--(piperidin-2-yl)-[1,1'-biphenyl]-2-carbonitrile, 2 TFA

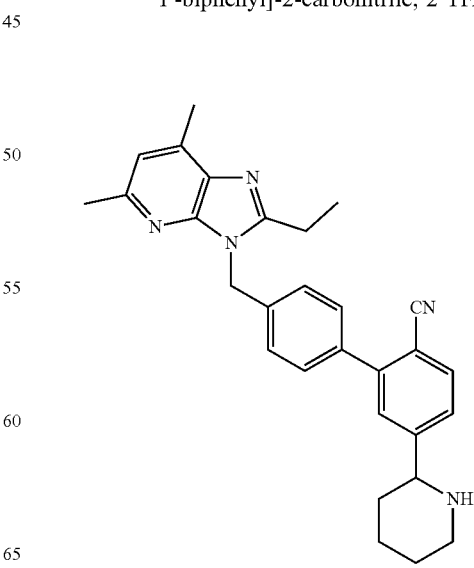

Intermediate 75c (80 mg, 0.146 mmol) was reacted in a manner analogous to Intermediate 75d to give Intermediate 76a. LC-MS (Method A2) RT=0.61 min, MS (ESI) m/z: 450.4 (M+H)+

Example 76

Intermediate 76a (10 mg, 0.022 mmol) was reacted with dibutyltin oxide (5.5 mg, 0.022 mmol) and TMS-N$_3$ (29.5 µL, 0.222 mmol) in a manner analogous to Example 62 to give Example 76 (3.6 mg, 0.007 mmol, 32%). LC-MS (Method A2) RT=0.57 min, MS (ESI) m/z: 493.3 (M+H)+. $^1$H NMR (500 MHz, DMSO-d$_6$) δ 7.59 (d, J=7.8 Hz, 1H), 7.49-7.36 (m, 2H), 7.07 (br d, J=8.1 Hz, 2H), 6.99 (br d, J=8.2 Hz, 2H), 6.94 (s, 1H), 5.42 (s, 2H), 3.58-3.27 (m, 3H), 2.77 (q, J=7.5 Hz, 3H), 2.55 (s, 6H), 2.09-1.60 (m, 6H), 1.24 (t, J=7.5 Hz, 3H) (1 exchangeable proton not observed).

Example 77: 3-((5'-(3,4-dihydro-2H-pyrrol-5-yl)-2'-(2H-tetrazol-5-yl)-[1,1'-biphenyl]-4-yl)methyl)-2-ethyl-5,7-dimethyl-3H-imidazo[4,5-b]pyridine

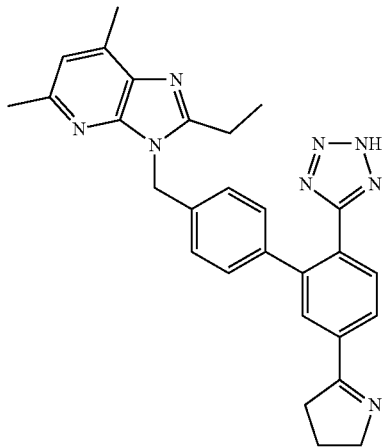 [SMILES: CCc1nc2c(C)cc(C)nc2n1Cc1ccc(-c2cc(C3=NCCC3)ccc2-c2nn[nH]n2)cc1]

Intermediate 77a: tert-butyl 2-(6-cyano-4'-((2-ethyl-5,7-dimethyl-3H-imidazo[4,5-b]pyridin-3-yl)methyl)-[1,1'-biphenyl]-3-yl)pyrrolidine-1-carboxylate

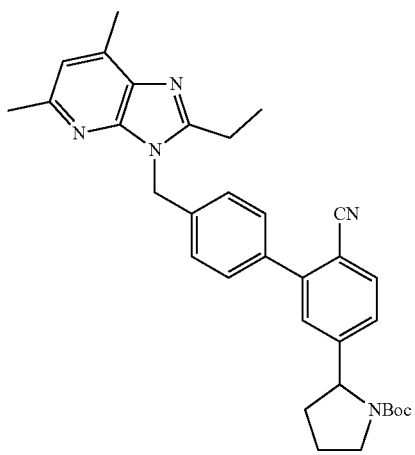 [SMILES: CCc1nc2c(C)cc(C)nc2n1Cc1ccc(-c2cc(C3CCCN3C(=O)OC(C)(C)C)ccc2C#N)cc1]

Intermediate 55a (150 mg, 0.337 mmol) was reacted with 1-(tert-butoxycarbonyl)pyrrolidine-2-carboxylic acid (217 mg, 1.01 mmol) in a manner analogous to Intermediate 73a to give Intermediate 77a (66.3 mg, 0.124 mmol). LC-MS (Method A2) RT=0.88 min, MS (ESI) m/z: 536.8 (M+H)+.

Intermediate 77b: tert-butyl 2-(6-cyano-4'-((2-ethyl-5,7-dimethyl-3H-imidazo[4,5-b]pyridin-3-yl)methyl)-[1,1'-biphenyl]-3-yl)pyrrolidine-1-carboxylate

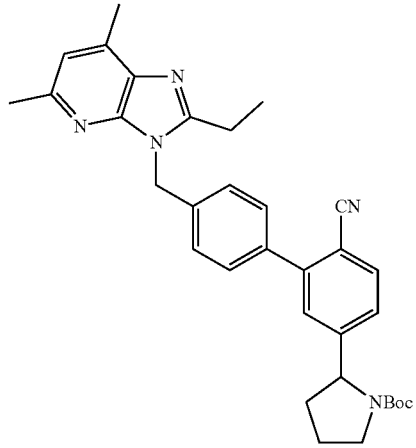 [SMILES: CCc1nc2c(C)cc(C)nc2n1Cc1ccc(-c2cc(C3CCCN3C(=O)OC(C)(C)C)ccc2C#N)cc1]

Intermediate 77a (289.3 mg, 0.541 mmol) was separated by chiral SFC (Regis Whelk-01, 30×250 mm, 5 micron column; 30% MeOH/70% CO$_2$ mobile phase; 85 mL/min, 150 bar, 40° C.) to give two peaks, the first eluting of which was Intermediate 77b (122.1 mg, 0.228 mmol, 42%) as a clear glassy solid. LC-MS (Method A2) RT=0.89 min, MS (ESI) m/z: 536.5 (M+H)+. $^1$H NMR (500 MHz, CDCl$_3$) δ 7.71 (d, J=8.3 Hz, 1H), 7.51-7.44 (m, 2H), 7.28-7.23 (m, 4H), 6.93 (s, 1H), 5.55 (s, 2H), 5.03-4.77 (m, 1H), 3.72-3.54 (m, 2H), 2.85 (q, J=7.6 Hz, 2H), 2.67 (s, 3H), 2.63 (s, 3H), 2.44-2.34 (m, 1H), 1.97-1.78 (m, 3H), 1.58 (s, 9H), 1.37 (t, J=7.6 Hz, 3H).

Intermediate 77c: 4'-((2-ethyl-5,7-dimethyl-3H-imidazo[4,5-b]pyridin-3-yl)methyl)--(pyrrolidin-2-yl)-[1,1'-biphenyl]-2-carbonitrile, 2 TFA

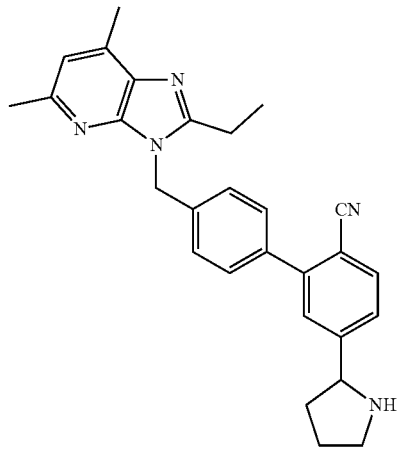 [SMILES: CCc1nc2c(C)cc(C)nc2n1Cc1ccc(-c2cc(C3CCCN3)ccc2C#N)cc1]

Intermediate 77b (110 mg, 0.205 mmol) was reacted in a manner analogous to

Intermediate 75d to give Intermediate 77c. LC-MS (Method A2) RT=0.59 min, MS (ESI) m/z: 436.3 (M+H)+.

Example 77

Intermediate 77b (13 mg, 0.030 mmol) was reacted with dibutyltin oxide (7.4 mg, 0.030 mmol) and TMS-N$_3$ (39.6 µL, 0.298 mmol) in a manner analogous to Example 62 with concomitant partial oxidation to give Example 77 (3.7 mg, 0.008 mmol, 26%). LC-MS (Method A1) RT=1.20 min, MS (ESI) m/z: 477.0 (M+H)$^+$. $^1$H NMR (500 MHz, DMSO-d$_6$) δ 7.93 (br d, J=7.6 Hz, 1H), 7.83 (s, 1H), 7.72 (br d, J=7.6 Hz, 1H), 7.13-6.99 (m, 4H), 6.95 (s, 1H), 5.45 (s, 2H), 4.04-3.93 (m, 2H), 2.98 (br t, J=7.8 Hz, 2H), 2.77 (q, J=7.0 Hz, 2H), 2.55 (s, 6H), 2.03-1.93 (m, 2H), 1.23 (br t, J=7.3 Hz, 3H) (1 exchangeable proton not observed).

Example 78: 2-ethyl-5,7-dimethyl-3-((5'-(tetrahydro-2H-pyran-2-yl)-2'-(2H-tetrazol-5-yl)-[1,1'-biphenyl]-4-yl)methyl)-3H-imidazo[4,5-b]pyridine

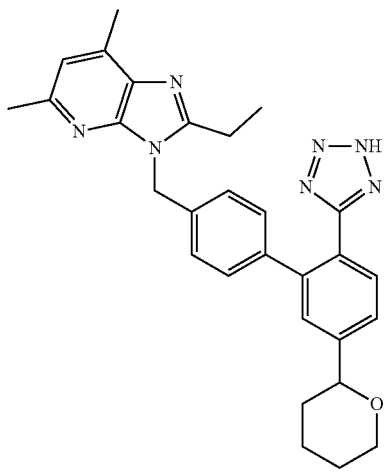 [SMILES: CCc1nc2c(C)cc(C)nc2n1Cc1ccc(-c2cc(C3CCCCO3)ccc2-c2nn[nH]n2)cc1]

Intermediate 78a: 5-(3,4-dihydro-2H-pyran-6-yl)-4'-((2-ethyl-5,7-dimethyl-3H-imidazo[4,5-b]pyridin-3-yl)methyl)-[1,1'-biphenyl]-2-carbonitrile

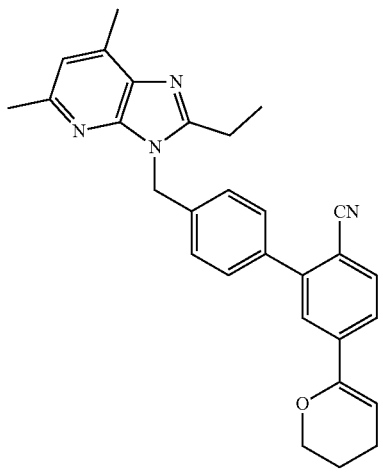 [SMILES: CCc1nc2c(C)cc(C)nc2n1Cc1ccc(-c2cc(C3=CCCCO3)ccc2C#N)cc1]

Intermediate 055a (215 mg, 0.536 mmol), 2-(3,4-dihydro-2H-pyran-6-yl)-4,4,5,5-tetramethyl-1,3,2-dioxaborolane (338 mg, 1.61 mmol), and 2nd Generation XPHOS Precatalyst (42.2 mg, 0.054 mmol) were dissolved in toluene (4.29 mL), ethanol (1.07 mL), and tripotassium phosphate (536 µL, 1.07 mmol). The reaction was degassed with N$_2$ for 10 minutes and heated at 100° C. After 3 hours, the reaction was diluted with EtOAc, filtered through celite/Na$_2$SO$_4$ and concentrated in vacuo. The crude material was purified by column chromatography (ISCO, 40 g silica gel column, 19 minute gradient of 0 to 100% EtOAc in hexanes) to give Intermediate 78a (182.8 mg, 0.408 mmol, 76%). LC-MS (Method A2) RT=0.91 min, MS (ESI) m/z: 449.2 (M+H)$^+$. $^1$H NMR (500 MHz, CDCl$_3$) δ 7.75-7.57 (m, 3H), 7.51 (d, J=8.3 Hz, 2H), 7.25 (d, J=8.3 Hz, 2H), 6.94 (s, 1H), 5.62-5.50 (m, 3H), 4.25-4.15 (m, 2H), 2.86 (q, J=7.5 Hz, 2H), 2.67 (s, 3H), 2.63 (s, 3H), 2.32-2.23 (m, 2H), 2.00-1.90 (m, 2H), 1.37 (t, J=7.6 Hz, 3H).

Intermediate 78b: 4'-((2-ethyl-5,7-dimethyl-3H-imidazo[4,5-b]pyridin-3-yl)methyl)-5-(tetrahydro-2H-pyran-2-yl)-[1,1'-biphenyl]-2-carbonitrile

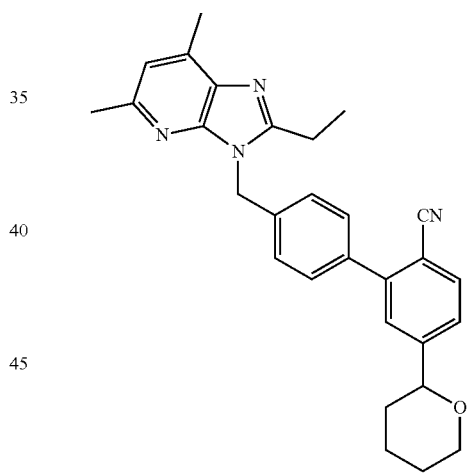

Intermediate 78a (180 mg, 0.401 mmol) and palladium on carbon (42.7 mg, 0.040 mmol) were dissolved in MeOH (8.03 µL). The reaction was purged with hydrogen (0.809 mg, 0.401 mmol). After 1 hour, the reaction was filtered through celite and concentrated in vacuo to give Intermediate 78b (180.3 mg, 0.400 mmol, 100%). LC-MS (Method A2) RT=0.89 min, MS (ESI) m/z: 451.3 (M+H)$^+$. $^1$H NMR (500 MHz, CDCl$_3$) δ 7.73 (d, J=7.7 Hz, 1H), 7.55-7.46 (m, 3H), 7.42 (d, J=8.0 Hz, 1H), 7.26 (br d, J=8.0 Hz, 2H), 6.95 (s, 1H), 5.56 (s, 2H), 4.46-4.37 (m, 1H), 4.22-4.13 (m, 1H), 3.68-3.58 (m, 1H), 2.94-2.84 (m, 2H), 2.68 (s, 3H), 2.63 (s, 3H), 1.98 (br dd, J=4.1, 2.2 Hz, 1H), 1.89 (br d, J=13.2 Hz, 1H), 1.75-1.64 (m, 4H), 1.37 (t, J=7.6 Hz, 3H).

Intermediate 78c: 4'-((2-ethyl-5,7-dimethyl-3H-imidazo[4,5-b]pyridin-3-yl)methyl)-5-(tetrahydro-2H-pyran-2-yl)-[1,1'-biphenyl]-2-carbonitrile

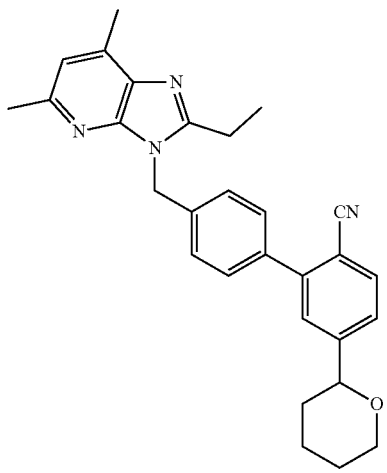 [SMILES: CCc1nc2c(C)cc(C)nc2n1Cc1ccc(-c2cc(C3CCCCO3)ccc2C#N)cc1]

Intermediate 78b (180 mg, 0.399 mmol) was separated by chiral SFC (Chiralcel OJ-H, 21×250 mm, 5 micron column; 20% MeOH/80% CO$_2$ mobile phase; 45 mL/min, 120 bar, 40° C.) to give two peaks, the first eluting of which was Intermediate 78c (65.9 mg, 0.146 mmol, 37%)

Example 78

Intermediate 78c (65.9 mg, 0.146 mmol) was reacted with dibutyltin oxide (72.8 mg, 0.293 mmol) and TMS-N$_3$ (97 μL, 0.731 mmol) in a manner analogous to Example 62 to give Example 78 (63.7 mg, 0.129 mmol, 85%). LC-MS (Method A2) RT=0.81 min, MS (ESI) m/z: 494.3 (M+H)$^+$. $^1$H NMR (500 MHz, DMSO-d$_6$) δ 7.59 (br d, J=7.9 Hz, 1H), 7.49 (br d, J=7.9 Hz, 1H), 7.42 (s, 1H), 7.04 (s, 4H), 6.96 (s, 1H), 5.45 (s, 2H), 4.45 (br d, J=11.1 Hz, 1H), 4.04 (br d, J=112 Hz, 1H), 3.17 (br d, J=3.3 Hz, 1H), 2.78-2.73 (m, 2H), 2.51 (s, 6H), 1.93-1.84 (m, 2H), 1.56 (br s, 2H), 1.50-1.42 (m, 1H), 1.21 (br t, J=7.4 Hz, 3H) (1 exchangeable proton not observed).

Example 79: 2-ethyl-5,7-dimethyl-3-((5'-(tetrahydro-2H-pyran-3-yl)-2'-(2H-tetrazol-5-yl)-[1,1'-biphenyl-4-yl)methyl)-3H-imidazo[4,5-b]pyridine

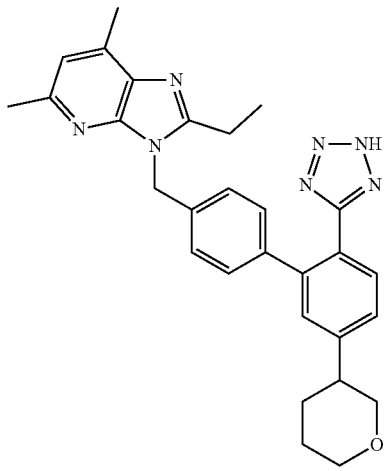 [SMILES: CCc1nc2c(C)cc(C)nc2n1Cc1ccc(-c2cc(C3CCCOC3)ccc2-c2nn[nH]n2)cc1]

Example 79 was prepared in a manner analogous to Example 78. LC-MS (Method A2) RT=0.75 min, MS (ESI) m/z: 494.2 (M+H)$^+$. $^1$H NMR (500 MHz, DMSO-d$_6$) δ 7.52 (br d, J=7.7 Hz, 1H), 7.34 (br d, J=7.6 Hz, 1H), 7.26 (s, 1H), 7.09-7.04 (m, 2H), 7.03-6.98 (m, 2H), 6.94 (s, 1H), 5.43 (s, 2H), 3.92-3.83 (m, 2H), 3.42 (br t, J=10.7 Hz, 1H), 2.87 (br t, J=10.9 Hz, 1H), 2.78 (q, J=7.4 Hz, 2H), 2.58-2.49 (m, 6H), 1.99 (br d, J=12.5 Hz, 1H), 1.85-1.74 (m, 1H), 1.67 (br d, J=3.4 Hz, 2H), 1.26 (t, J=7.4 Hz, 4H) (1 exchangeable proton not observed).

Example 80: 3-((5'-cyclopentyl-2'-(2H-tetrazol-5-yl)-[1,1'-biphenyl]-4-yl)methyl)-2-ethyl-5,7-dimethyl-3H-imidazo[4,5-b]pyridine

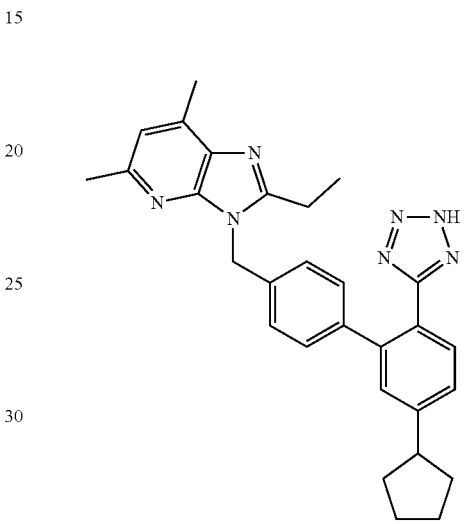

Intermediate 80a: 5-cyclopentyl-4'-((2-ethyl-5,7-dimethyl-3H-imidazo[4,5-b]pyridin-3-yl)methyl)-[1,1'-biphenyl]-2-carbonitrile

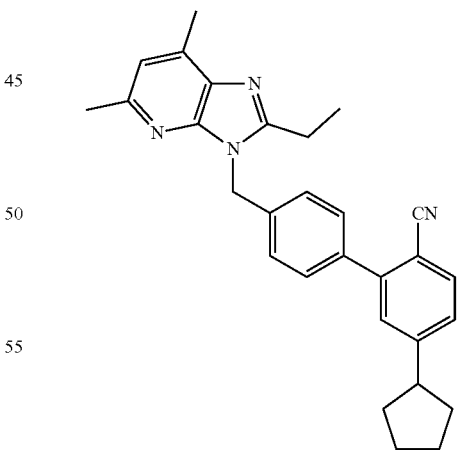

Intermediate 55a (50 mg, 0.112 mmol), bromocyclopentane (18.8 μL, 0.168 mmol), [IR(DFCF$_3$PPY)$_2$(BPY)]PF$_6$ (1.13 mg, 1.12 μmol), Tris(trimethylsilyl)silane (34.6 μL, 0.112 mmol), Na$_2$CO$_3$ (23.8 mg, 0.225 mmol), nickel chloride dimethoxyethane adduct (2.47 mg, 0.011 mmol), and 4,4'-di-tert-butyl-2,2'-dipyridyl (3.01 mg, 0.011 mmol) were dissolved in DME (2.24 mL). The solution was degassed with N₂ for 10 min. The mixture was then sealed and irradiated with a 34W Blue LED lamp. After 18 hours, the reaction was diluted with EtOAc, filtered, and concentrated in vacuo. The crude material was purified by column chromatography (ISCO, 12 g silica gel column, 17 minute gradient of 0 to 100% EtOAc in DCM) to give Intermediate 80a (58.6 mg, 0.135 mmol), which was contaminated with des-bromo product and was used directly in the subsequent reaction. LC-MS (Method A2) RT=0.99 min, MS (ESI) m/z: 435.2 (M+H)⁺.

Example 80

Intermediate 80a (58.6 mg, 0.135 mmol) was reacted with dibutyltin oxide (67.1 mg, 0.270 mmol) and TMS-N₃ (89 μL, 0.674 mmol) in a manner analogous to Example 62 to give Example 80 (8.8 mg, 0.018 mmol, 13%). LC-MS (Method A2) RT=0.88 min, MS (ESI) m/z: 478.2 (M+H)⁺. ¹H NMR (500 MHz, DMSO-d₆) δ 7.62-7.51 (m, 1H), 7.45 (br s, 1H), 7.35 (br s, 1H), 7.05 (br s, 4H), 6.97 (s, 1H), 5.45 (s, 2H), 3.09 (br t, J=8.2 Hz, 1H), 2.76 (br d, J=5.2 Hz, 2H), 2.62-2.48 (m, 6H), 2.06 (br s, 2H), 1.78 (br s, 2H), 1.71-1.55 (m, 4H), 1.22 (br s, 3H) (1 exchangeable proton not observed).

Example 81: 3-((5'-cycloheptyl-2'-(2H-tetrazol-5-yl)-[1,1'-biphenyll-4-yl)methyl)-2-ethyl-5,7-dimethyl-3H-imidazo[4,5-b]pyridine

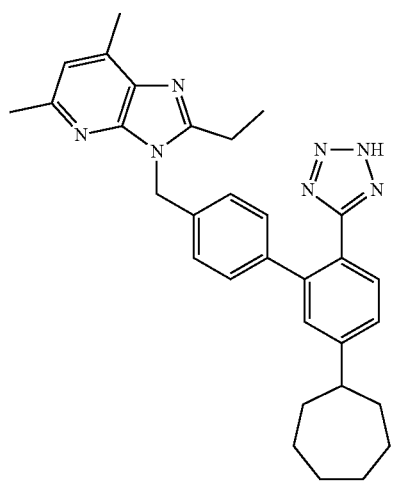 [SMILES: CCc1nc2c(C)cc(C)nc2n1Cc1ccc(-c2cc(C3CCCCCC3)ccc2-c2nn[nH]n2)cc1]

Example 81 was prepared in a manner analogous to Example 80. LC-MS (Method A2) RT=0.96 min, MS (ESI) m/z: 506.2 (M+H)⁺. ¹H NMR (500 MHz, DMSO-d₆) δ 7.53 (br d, J=7.9 Hz, 1H), 7.38 (br d, J=7.6 Hz, 1H), 7.30 (s, 1H), 7.04 (s, 4H), 6.96 (s, 1H), 5.45 (s, 2H), 2.77 (q, J=7.4 Hz, 3H), 2.56 (s, 6H), 1.86 (br s, 2H), 1.81-1.63 (m, 6H), 1.62-1.49 (m, 4H), 1.23 (br t, J=7.5 Hz, 3H) (1 exchangeable proton not observed).

Example 82: 3-((5'-(4,4-difluoropiperidin-1-yl)-2'-(2H-tetrazol-5-yl)-[1,1'-biphenyl]-4-yl)methyl)-2-ethyl-5,7-dimethyl-3H-imidazo[4,5-b]pyridine

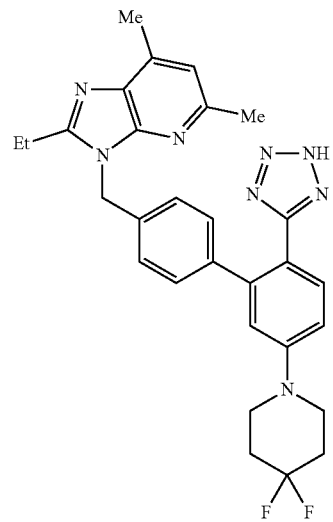 [SMILES: CCc1nc2c(C)cc(C)nc2n1Cc1ccc(-c2cc(N3CCC(F)(F)CC3)ccc2-c2nn[nH]n2)cc1]

Intermediate 82a: 5-chloro-4'-((2-ethyl-5,7-dimethyl-3H-imidazo[4,5-b]pyridin-3-yl)methyl)-[1,1'-biphenyl]-2-carbonitrile

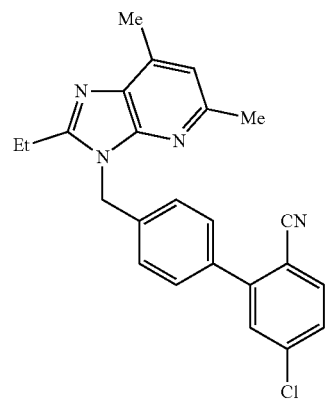 [SMILES: CCc1nc2c(C)cc(C)nc2n1Cc1ccc(-c2cc(Cl)ccc2C#N)cc1]

To a microwave vial containing PdCl₂(dppf) (0.224 g, 0.307 mmol), Intermediate 001d (1.200 g, 3.07 mmol) and 4-chloro-2-iodobenzonitrile (1.050 g, 3.99 mmol) was added toluene (12.27 ml) followed by ethanol (3.07 ml) and K₃PO₄ (2 M, aq.) (3.07 ml, 6.13 mmol). N₂ was sparged through the reaction mixture for 5 min before the vial was sealed and heated at 110° C. overnight. The reaction mixture was diluted with EtOAc and washed with saturated aqueous NaHCO₃. The organic phase was concentrated and purified by ISCO (0-100% EtOAc/Hex) to afford Intermediate 82a (0.852 g, 2.125 mmol, 69.3% yield) as a yellow oil. LC-MS (Method A2) RT=0.83 min, MS (ESI) m/z: 401.4 (M+H)⁺. ¹H NMR (400 MHz, CDCl₃) δ 7.70 (d, J=8.4 Hz, 1H), 7.52-7.42 (m, 4H), 7.26 (s, 2H), 6.93 (s, 1H), 5.55 (s, 2H), 2.84 (q, J=7.5 Hz, 2H), 2.67 (s, 3H), 2.62 (s, 3H), 1.36 (t, J=7.5 Hz, 3H).

Intermediate 82b: 5-(4,4-difluoropiperidin-1-yl)-4'-((2-ethyl-5,7-dimethyl-3H-imidazo[4,5-b]pyridin-3-yl)methyl)-[1,1'-biphenyl]-2-carbonitrile

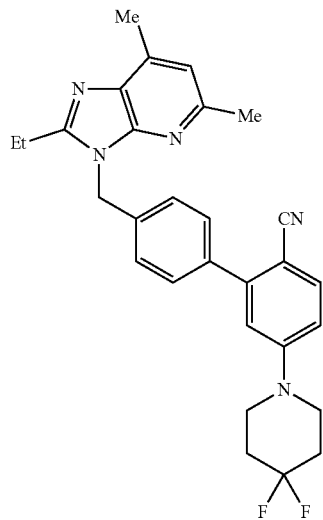 [SMILES: CCc1nc2c(C)cc(C)nc2n1Cc1ccc(-c2cc(N3CCC(F)(F)CC3)ccc2C#N)cc1]

To a vial containing Intermediate 82a (0.050 g, 0.125 mmol) was added 2nd generation RuPhos precatalyst (9.69 mg, 0.012 mmol) followed sodium t-butoxide (0.072 g, 0.748 mmol). THF (3 mL) was then added followed by 4,4-difluoropiperidine (0.015 g, 0.125 mmol). The reaction vial was sealed and heated at 65° C. overnight. Reaction was concentrated and purified on ISCO using a 24 g column eluting with 0-100% EtOAc in hexanes to yield Intermediate 82b (0.061 g, 0.126 mmol, 100% yield). LC-MS (Method A2) RT=0.85 min, MS (ESI) m/z: 486.7 (M+H)+. 1H NMR (400 MHz, CDCl3) δ 7.61 (d, J=8.8 Hz, 1H), 7.48 (d, J=8.4 Hz, 2H), 7.24 (d, J=8.4 Hz, 2H), 6.93 (s, 1H), 6.91-6.87 (m, 1H), 6.85 (d, J=2.4 Hz, 1H), 5.54 (s, 2H), 3.62-3.47 (m, 4H), 2.85 (q, J=7.6 Hz, 2H), 2.67 (s, 3H), 2.62 (s, 3H), 2.15-2.07 (m, 4H), 1.37 (t, J=7.5 Hz, 3H).

Example 82: 3-((5'-(4,4-difluoropiperidin-1-yl)-2'-(2H-tetrazol-5-yl)-[1,1'-biphenyl]-4-yl)methyl)-2-ethyl-5,7-dimethyl-3H-imidazo[4,5-b]pyridine To a vial containing Intermediate 82b (0.061 g, 0.126 mmol) was added dibutyltin oxide (0.063 g, 0.251 mmol) and toluene (3 mL) followed by TMS-N3 (0.083 mL, 0.628 mmol). The reaction mixture was sealed and heated at 100° C. behind a blast shield for 18 hours. Reaction was diluted with EtOAc and CAN (10% Aqueous) (0.689 g, 1.256 mmol) solution was added to quench remaining TMSN3 until bubbling ceased. Layers were separated and the organic layer was washed with brine, dried with sodium sulfate, and concentrated. Purified on Preparative HPLC using Solvent A: 10% MeOH/90% H2O/0.1% TFA and Solvent B 90% MeOH/10% H2O/0.1% TFA on Phenomenex AXIA C18 30×100 mm with a 10 min gradient and 5 min hold time with a flow rate of 40 mL/min to yield Example 82 (13.37 mg, 0.024 mmol, 19.29% yield). LC-MS (Method A2) RT=0.86 min, MS (EST) m/z: 529.4 (M+H)+. 1H NMR (500 MHz, DMSO-d6) δ 7.49 (br d, J=8.9 Hz, 1H), 7.15 (br d, J=8.5 Hz, 1H), 7.06 (s, 4H), 6.99 (br s, 1H), 6.96 (s, 1H), 5.45 (s, 2H), 2.77 (q, J=7.0 Hz, 2H), 2.55 (s, 4H), 2.51-2.49 (m, 6H), 2.09-1.98 (m, 4H), 1.23 (br t, J=7.3 Hz, 3H) (1 exchangeable proton not observed).

The compounds listed in the table below were synthesized using the same methods that were used to prepare Example 82.

| Ex # | Structure | MW | LC-MS m/z [M + H]+; RT (Method) | 1H NMR |
|---|---|---|---|---|
| 83 | 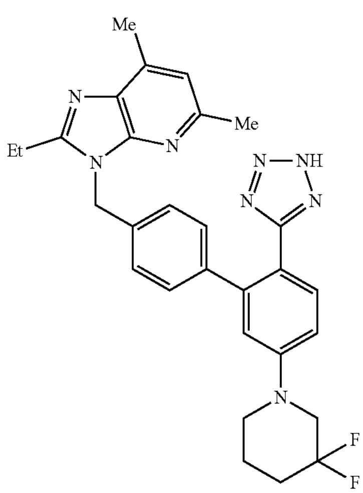 [SMILES: CCc1nc2c(C)cc(C)nc2n1Cc1ccc(-c2cc(N3CCCC(F)(F)C3)ccc2-c2nn[nH]n2)cc1] | 528.612 | 529.2; 0.78 min (Method A2) | 1H NMR (400 MHz, CDCl3) δ 8.13 (d, J = 8.8 Hz, 1H), 7.19 (s, 4H), 7.02 (dd, J = 8.8, 2.6 Hz, 1H), 6.91 (s, 1H), 6.76 (d, J = 2.6 Hz, 1H), 5.50 (s, 2H), 3.55 (t, J = 11.3 Hz, 2H), 3.41-3.34 (m, 2H), 2.87-2.77 (m, 2H), 2.60 (d, J = 7.5 Hz, 6H), 2.14-1.96 (m, 4H), 1.36 (t, J = 7.6 Hz, 3H) (1 exchangeable proton not observed) |

| Ex # | Structure | MW | LC-MS m/z [M + H]+; RT (Method) | 1H NMR |
|---|---|---|---|---|
| 84 | 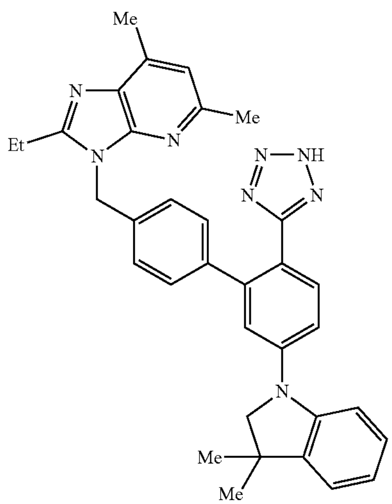 [SMILES: CCc1nc2c(C)cc(C)nc2n1Cc1ccc(-c2cc(N3CC(C)(C)c4ccccc43)ccc2-c2nn[nH]n2)cc1] | 554.291 | 555.6; 0.90 min (Method A2) | 1H NMR (500 MHz, DMSO-d6) δ 7.95 (s, 1H), 7.57 (br d, J = 7.3 Hz, 1H), 7.34 (br d, J = 8.5 Hz, 1H), 7.21 (br dd, J = 15.7, 7.5 Hz, 2H), 7.15-7.07 (m, 3H), 7.02 (br d, J = 7.6 Hz, 2H), 6.95 (s, 1H), 6.81 (br t, J = 7.5 Hz, 1H), 5.45 (s, 2H), 3.76 (s, 2H), 2.89 (s, 3H), 2.82-2.75 (m, 2H), 2.74 (s, 3H), 1.31 (s, 6H), 1.24 (br t, J = 7.5 Hz, 3H) (1 exchangeable proton not observed) |
| 85 | 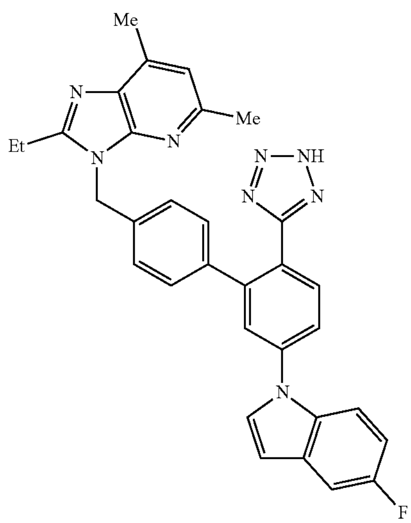 [SMILES: CCc1nc2c(C)cc(C)nc2n1Cc1ccc(-c2cc(-n3ccc4cc(F)ccc43)ccc2-c2nn[nH]n2)cc1] | 542.609 | 543.9; 0.87 min (Method A2) | 1H NMR (500 MHz, DMSO-d6) δ 7.85 (br d, J = 2.5 Hz, 1H), 7.78 (br d, J = 8.0 Hz, 1H), 7.72-7.61 (m, 2H), 7.54 (s, 1H), 7.44 (dd, J = 9.6, 2.4 Hz, 1H), 7.16 (br d, J = 7.7 Hz, 2H), 7.11-6.98 (m, 3H), 6.95 (s, 1H), 6.72 (d, J = 3.1 Hz, 1H), 5.44 (s, 2H), 3.67 (br s, 6H), 2.76 (br d, J = 7.4 Hz, 2H), 1.21 (br t, Hz, 3H) (1 exchangeable proton not observed) |
| 86 | 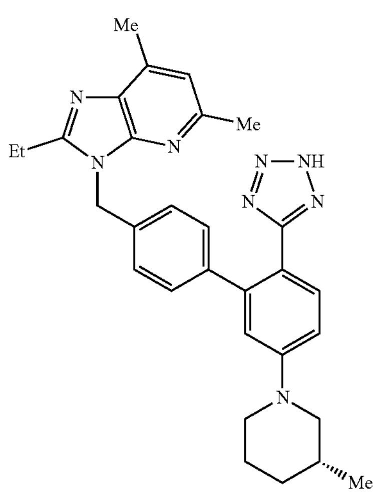 [SMILES: CCc1nc2c(C)cc(C)nc2n1Cc1ccc(-c2cc(N3CCC[C@@H](C)C3)ccc2-c2nn[nH]n2)cc1] | 506.645 | 507.3; 0.78 min (Method A2) | 1H NMR (500 MHz, DMSO-d6) δ 7.46-7.39 (m, 1H), 7.03 (br s, 5H), 6.95 (s, 1H), 6.85 (br s, 1H), 5.44 (s, 2H), 3.53 (br s, 2H), 3.33-3.25 (m, 2H), 2.80-2.74 (m, 2H), 2.55 (s, 6H), 2.18 (br t, J = 8.1 Hz, 2H), 1.95-1.86 (m, 2H), 1.52 (br d, J = 12.8 Hz, 1H), 1.23 (s, 3H), 1.00 (d, J = 6.1 Hz, 3H) (1 exchangeable proton not observed) |

| Ex # | Structure | MW | LC-MS m/z [M + H]+; RT (Method) | 1H NMR |
|---|---|---|---|---|
| 87 | 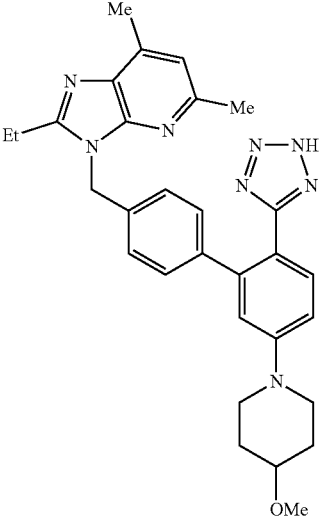 [SMILES: CCc1nc2c(C)cc(C)nc2n1Cc1ccc(-c2cc(N3CCC(OC)CC3)ccc2-c2nn[nH]n2)cc1] | 522.644 | 523.6; 0.72 min (Method A2) | 1H NMR (500 MHz, DMSO-d6) δ 7.44 (d, J = 8.9 Hz, 1H), 7.09-7.02 (m, 5H), 6.95 (s, 1H), 6.88 (d, J = 2.4 Hz, 1H), 5.44 (s, 2H), 3.45-3.34 (m, 1H), 3.25 (s, 3H), 3.04 (br s, 2H), 2.92 (q, J = 7.2 Hz, 4H), 2.81-2.72 (m, 2H), 2.52-2.51 (m, 6H), 1.90 (br d, J = 6.7 Hz, 2H), 1.21 (t, J = 7.5 Hz, 3H) (1 exchangeable proton not observed) |
| 88 | 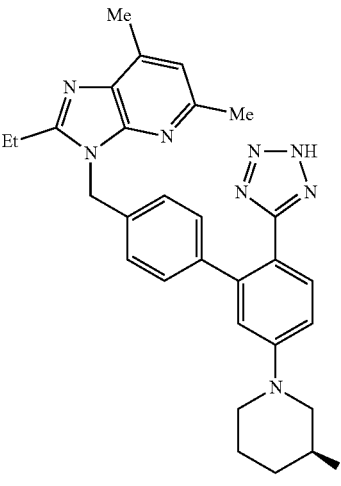 | 506.645 | 507.3; 0.78 min (Method A2) | 1H NMR (500 MHz, DMSO-d6) δ 7.37 (m, 1H), 7.03 (br s, 5H), 6.95 (s, 1H), 6.85 (br s, 1H), 5.44 (s, 2H), 3.53 (br s, 2H), 3.33-3.25 (m, 2H), 2.80-2.74 (m, 2H), 2.53 (s, 6H), 2.18 (br t, J = 8.1 Hz, 2H), 1.95-1.86 (m, 2H), 1.52 (br d, J = 12.8 Hz, 1H), 1.22 (s, 3H), 1.00 (d, J = 6.1 Hz, 3H) (1 exchangeable proton not observed) |
| 89 | 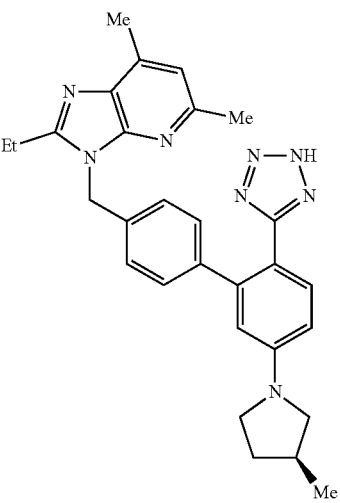 [SMILES: CCc1nc2c(C)cc(C)nc2n1Cc1ccc(-c2cc(N3CC[C@H](C)C3)ccc2-c2nn[nH]n2)cc1] | 492.618 | 493.7; 0.82 min (Method A2) | 1H NMR (500 MHz, DMSO-d6) δ 7.38 (d, J = 8.5 Hz, 1H), 7.06 (d, J = 8.1 Hz, 2H), 6.97 (br d, J = 8.1 Hz, 2H), 6.95 (s, 1H), 6.56 (dd, J = 8.5, 2.1 Hz, 1H), 6.39 (d, J = 2.1 Hz, 1H), 5.43 (s, 2H), 3.91 (s, 1H), 3.28 (br d, J = 8.5 Hz, 1H), 2.93-2.69 (m, 4H), 2.55 (s, 6H), 2.40-2.05 (m, 2H), 1.59 (br dd, J = 11.9, 8.5 Hz, 1H), 1.26 (t, J = 7.4 Hz, 3H), 1.08 (d, J = 6.6 Hz, 3H) (1 exchangeable proton not observed) |

| Ex # | Structure | MW | LC-MS m/z [M + H]+; RT (Method) | 1H NMR |
|---|---|---|---|---|
| 90 | 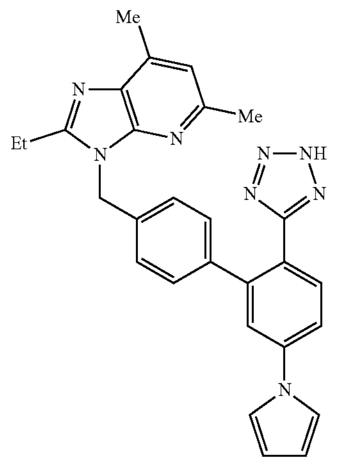 [SMILES: CCc1nc2c(C)cc(C)nc2n1Cc1ccc(-c2cc(-n3cccc3)ccc2-c2nn[nH]n2)cc1] | 474.572 | 475.3; 0.77 min (Method A2) | 1H NMR (500 MHz, DMSO-d6) δ 7.78-7.68 (m, 2H), 7.64 (d, J = 1.5 Hz, 1H), 7.54 (br s, 2H), 7.14 (br d, J = 7.9 Hz, 2H), 7.07 (br d, J = 7.9 Hz, 2H), 6.96 (s, 1H), 6.30 (s, 2H), 5.46 (s, 2H), 2.78 (q, J = 7.3 Hz, 2H), 2.55-2.54 (m, 3H), 2.51-2.50 (m, 3H), 1.24 (br d, J = 3.4 Hz, 3H) (1 exchangeable proton not observed) |
| 91 | 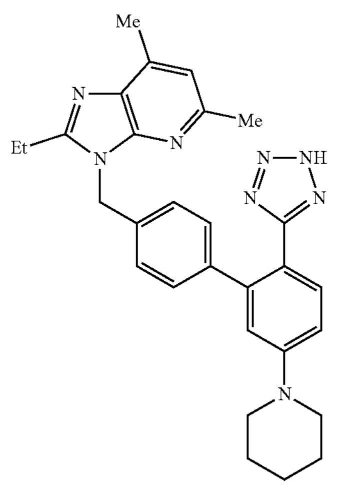 [SMILES: CCc1nc2c(C)cc(C)nc2n1Cc1ccc(-c2cc(N3CCCCC3)ccc2-c2nn[nH]n2)cc1] | 492.631 | 493.2; 0.73 min (Method A2) | 1H NMR (500 MHz, DMSO-d6) δ 7.42 (br d, J = 5.3 Hz, 1H), 7.03 (br d, J = 12.1 Hz, 5H), 6.95 (s, 1H), 6.84 (br s, 1H), 5.43 (s, 2H), 3.27 (br s, 2H), 2.77 (q, J = 7.4 Hz, 2H), 2.55 (s, 3H), 2.53-2.52 (m, 3H), 1.91 (s, 2H), 1.57 (br s, 6H), 1.23 (br t, J = 7.4 Hz, 3H) (1 exchangeable proton not observed) |
| 92 | 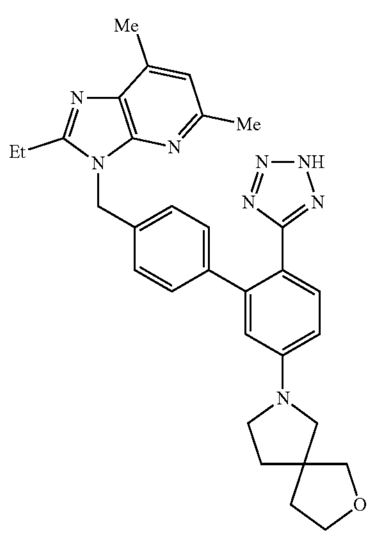 [SMILES: CCc1nc2c(C)cc(C)nc2n1Cc1ccc(-c2cc(N3CCC4(CCOC4)C3)ccc2-c2nn[nH]n2)cc1] | 534.668 | 535.2; 0.75 min (Method A2) | 1H NMR (500 MHz, DMSO-d6) δ 7.44 (d, J = 8.5 Hz, 1H), 7.06 (s, 4H), 6.96 (s, 1H), 6.66 (br d, J = 8.5 Hz, 1H), 6.50 (s, 1H), 5.46 (s, 2H), 3.82 (t, J = 7.2 Hz, 2H), 3.59 (s, 2H), 2.78 (q, J = 7.3 Hz, 2H), 2.55 (s, 6H), 2.50-2.47 (m, 2H), 2.05-1.97 (m, 2H), 1.94-1.87 (m, 2H), 1.25 (t, J = 7.5 Hz, 5H) (1 exchangeable proton not observed) |

Example 93: 4'-((2-ethyl-5,7-dimethyl-3H-imidazo[4,5-b]pyridin-3-yl)methyl)-N-phenyl-6-(2H-tetrazol-5-yl)-[1,1'-biphenyl]-3-amine

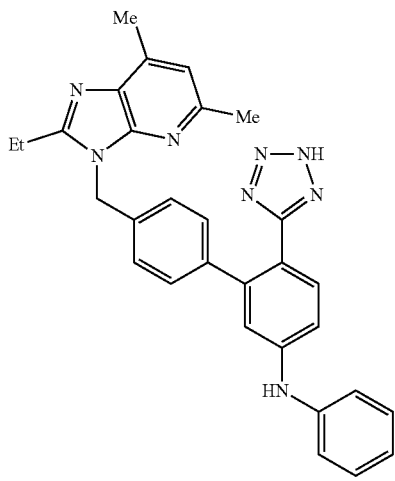 [SMILES: CCc1nc2c(C)cc(C)nc2n1Cc1ccc(-c2cc(Nc3ccccc3)ccc2-c2nn[nH]n2)cc1]

Aniline (0.012 g, 0.123 mmol), BrettPhos 3rd generation precatalyst (7.44 mg, 8.21 µmol), and sodium t-butoxide (15.78 mg, 0.164 mmol) were charged to a reaction flask. Intermediate 001j (0.030 g, 0.041 mmol) was dissolved in THF (0.8 mL) and added to the reaction. The flask was evacuated and backfilled with N$_2$ and stirred at 65° C. for 1 h. The crude reaction was passed through 0.45 µm syringe filters and concentrated. The crude residue was dissolved in CH$_2$Cl$_2$ (1.0 mL). Triethylsilane (0.030 mL, 0.185 mmol) and TFA (0.089 mL, 1.150 mmol) were added, and the resulting mixture stirred for 1 h. The solution was concentrated and dissolved in 1.8 mL DMF. The crude material was purified via preparative LC-MS with the following conditions: Column: XBridge C18, 19×200 mm, 5-µm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 20-100% B over 20 minutes, then a 2-minute hold at 100% B; Flow: 20 mL/min to yield Example 93 (0.007 g, 0.014 mmol, 34%): LC-MS (Method A1) RT=1.54 min, MS (ESI) m/z: 501.0 (M+H)$^+$. $^1$H NMR (500 MHz, DMSO-d$_6$) δ 8.58 (s, 1H), 7.47 (br d, J=8.2 Hz, 1H), 7.33-7.27 (m, 2H), 7.20-7.13 (m, 3H), 7.09-7.00 (m, 5H), 6.96-6.90 (m, 2H), 5.44 (s, 2H), 3.47 (br s, 1H), 2.76 (q, J=7.3 Hz, 2H), 2.51 (br s, 6H), 1.21 (br t, J=7.3 Hz, 3H).

Example 94: 4'-((2-ethyl-5,7-dimethyl-3H-imidazo[4,5-b]pyridin-3-yl)methyl)-N-methyl-N-phenyl-6-(2H-tetrazol-5-yl)-[1,1'-biphenyl]-3-amine Synthesized in an analogous manner to Example 93 using Intermediate 001j (0.030 g, 0.041 mmol) and N-methylaniline (0.013 g, 0.123 mmol) to yield Example 94 (0.0023 g, 0.0045 mmol, 11%): LC-MS (Method A1) RT=1.77 min, MS (ESI) m/z: 515.0 (M+H)$^+$. $^1$H NMR (500 MHz, DMSO-d$_6$) δ 7.46-7.36 (m, 3H), 7.23 (br d, J=7.6 Hz, 2H), 7.15 (br t, J=7.2 Hz, 1H), 6.97 (br d, J=17.4 Hz, 5H), 6.90 (br d, J=7.9 Hz, 1H), 6.77 (br s, 1H), 5.41 (br s, 2H), 3.31 (s, 3H), 2.73 (br d, J=7.0 Hz, 2H), 2.49 (br d, J=4.9 Hz, 6H), 1.18 (br t, J=7.2 Hz, 3H) (1 exchangeable proton not observed).

Example 95: 3-((5'-(azepan-1-yl)-2'-(2H-tetrazol-5-yl)-[1,1'-biphenyl]-4-yl)methyl)-2-ethyl-5,7-dimethyl-3H-imidazo[4,5-b]pyridine Synthesized in an analogous manner to Example 93 using Intermediate 001j (0.030 g, 0.041 mmol) and azepane (0.012 g, 0.123 mmol) to yield Example 95 (0.0015 g, 0.0030 mmol, 5.9%): LC-MS (Method A1) RT=1.74 min, MS (ESI) m/z: 507.0 (M+H)$^+$. $^1$H NMR (500 MHz, DMSO-d$_6$) δ 7.40 (d, J=8.5 Hz, 1H), 7.29-7.13 (m, 1H), 7.07-7.04 (m, 3H), 6.97 (s, 1H), 6.81 (br d, J=9.2 Hz, 1H), 6.61 (s, 1H), 5.45 (s, 2H), 3.53-3.46 (m, 4H), 2.78 (q, J=7.3 Hz, 2H), 2.50-2.49

(m, 6H), 1.72 (br s, 4H), 1.47 (br s, 4H), 1.23 (br t, J=7.5 Hz, 3H) (1 exchangeable proton not observed).

Example 96: 2-ethyl-3-((5'-(indolin-1-yl)-2'-(2H-tetrazol-5-yl)-[1,1'-biphenyl]-4-yl)methyl)-5,7-dimethyl-3H-imidazo[4,5-b]pyridine

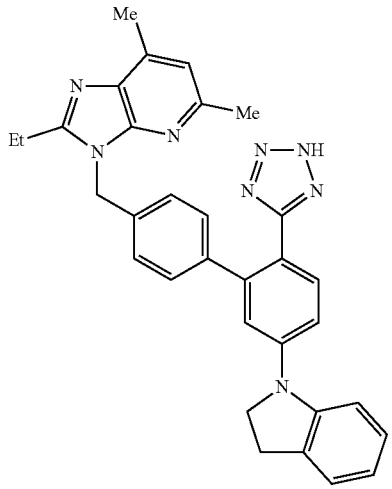 [SMILES: CCc1nc2c(C)cc(C)nc2n1Cc1ccc(-c2cc(N3CCc4ccccc43)ccc2-c2nn[nH]n2)cc1]

Synthesized in an analogous manner to Example 93 using Intermediate 001j (0.025 g, 0.034 mmol), indoline (0.012 g, 0.103 mmol), and 2nd generation XPhos precatalyst (0.0027 g, 0.0003 mmol) to yield Example 96 (0.009 g, 0.017 mmol, 50%): LC-MS (Method A2) RT=0.90 min, MS (ESI) m/z: 527.1 (M+H)⁺. ¹H NMR (500 MHz, DMSO-d₆) δ 7.62 (d, J=8.5 Hz, 1H), 7.41 (d, J=8.5 Hz, 1H), 7.30-7.18 (m, 4H), 7.18-7.08 (m, 4H), 7.06 (s, 1H), 6.81 (t, J=7.2 Hz, 1H), 5.54 (s, 2H), 4.04 (t, J=8.2 Hz, 2H), 3.13 (t, J=8.2 Hz, 2H), 2.90 (q, J=7.1 Hz, 2H), 2.55 (s, 6H), 1.24 (t, J=7.5 Hz, 3H) (1 exchangeable proton not observed).

Example 97: 2-ethyl-5,7-dimethyl-3-((5'-(4-methylpiperidin-1-yl)-2'-(2H-tetrazol-5-yl)-[1,1'-biphenyl]-4-yl)methyl)-3H-imidazo[4,5-b]pyridine

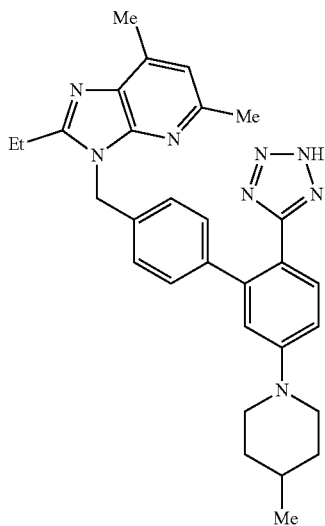 [SMILES: CCc1nc2c(C)cc(C)nc2n1Cc1ccc(-c2cc(N3CCC(C)CC3)ccc2-c2nn[nH]n2)cc1]

Synthesized in an analogous manner to Example 93 using Intermediate 001j (0.030 g, 0.041 mmol), 4-methylpiperidine (0.012 g, 0.123 mmol), and 3nd generation tBuXPhos precatalyst (0.0036 g, 0.0004 mmol) to yield Example 97 (0.013 g, 0.026 mmol, 64%): LC-MS (Method A2) RT=0.88 min, MS (ESI) m/z: 507.4 (M+H)⁺. ¹H NMR (500 MHz, DMSO-d₆) δ 7.44 (d, J=8.8 Hz, 1H), 7.09-6.99 (m, 5H), 6.95 (s, 1H), 6.87 (br. s., 1H), 5.44 (s, 2H), 3.85 (d, J=12.6 Hz, 2H), 2.82-2.71 (m, 4H), 2.55-2.54 (m, 6H), 1.67 (d, J=12.5 Hz, 2H), 1.55 (br. s., 1H), 1.27-1.11 (m, 5H), 0.92 (d, J=6.3 Hz, 3H) (1 exchangeable proton not observed).

Example 98: 3-((5'-(3,3-dimethylpiperidin-1-yl)-2'-(2H-tetrazol-5-yl)-[1,1'-biphenyl]-4-yl)methyl)-2-ethyl-5,7-dimethyl-3H-imidazo[4,5-b]pyridine

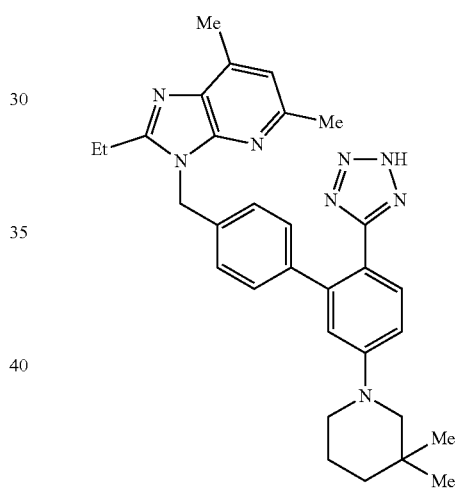

3-((5'-(3,3-dimethylpiperidin-1-yl)-2'-(2H-tetrazol-5-yl)-[1,1'-biphenyl]-4-yi)methyl)-2-ethyl-5,7-dimethyl-3H-imidazo[4,5-b]pyridine Synthesized in an analogous manner to Example 93 using Intermediate 001j (0.030 g, 0.041 mmol), 3,3-dimethylpiperidine (0.009 g, 0.082 mmol), and 3nd generation tBuXPhos precatalyst (0.0036 g, 0.0004 mmol) to yield Example 98 (0.006 g, 0.001 mmol, 25%): LC-MS (Method A2) RT=0.94 min, MS (ESI) m/z: 521.4 (M+H)⁺. ¹H NMR (500 MHz, DMSO-d₆) δ 7.43 (br d, J=8.5 Hz, 1H), 7.26 (s, 1H), 7.17-7.11 (m, 2H), 7.09-7.03 (m, 3H), 6.85 (br s, 1H), 5.55 (br s, 2H), 3.24 (br s, 2H), 3.02 (br s, 2H), 2.94 (br d, J=7.3 Hz, 2H), 2.57-2.55 (m, 6H), 1.63 (br s, 2H), 1.37 (br s, 2H), 1 0.25 (br t, J=7.2 Hz, 3H), 0.94 (s, 6H) (1 exchangeable proton not observed).

Example 99: 2-butyl-3-((5'-(phenylamino)-2'-(2H-tetrazol-5-yl)-[1,1'-biphenyl]-4-yl)methyl)-1,3-diazaspiro[4.4]non-1-en-4-one

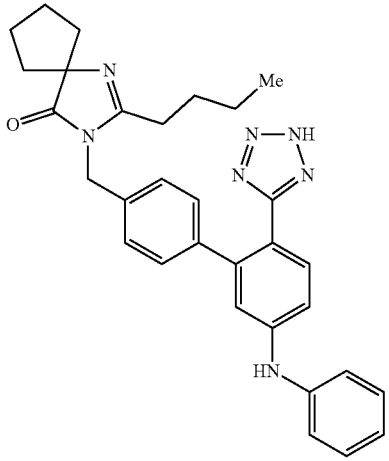 [SMILES: CCCCC1=NC2(CCCC2)C(=O)N1Cc1ccc(-c2cc(Nc3ccccc3)ccc2-c2nn[nH]n2)cc1]

Intermediate 99a: 4'-((2-butyl-4-oxo-1,3-diazaspiro[4.4]non-1-en-3-yl)methyl)-5-chloro-[1,1'-biphenyl]-2-carbonitrile

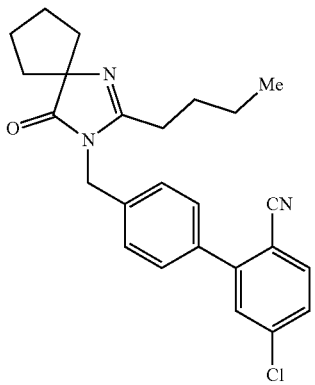 [SMILES: CCCCC1=NC2(CCCC2)C(=O)N1Cc1ccc(-c2cc(Cl)ccc2C#N)cc1]

To a microwave vial containing PdCl$_2$(dppf) (0.196 g, 0.268 mmol), Intermediate 033a (1.1 g, 2.68 mmol) and 4-chloro-2-iodobenzonitrile (0.918 g, 3.48 mmol) was added toluene (10.72 ml) followed by ethanol (2.68 ml) and K$_3$PO$_4$ (2 M, aq.) (2.68 ml, 5.36 mmol). N$_2$ was sparged through the reaction mixture for 5 min before the vial was sealed and heated at 120° C. in the microwave for 30 min. The reaction mixture was diluted with EtOAc and washed with saturated aqueous NaHCO$_3$. The organic phase was concentrated and purified by ISCO (0-100% EtOAc in hexanes) to afford Intermediate 99a (0.789 g, 1.879 mmol, 70.1% yield) as a white solid. LC-MS (Method A2) RT=0.95 min, MS (ESI) m/z: 420.3 (M+H)$^+$. $^1$H NMR (400 MHz, CDCl$_3$) δ 7.72 (d, J=8.1 Hz, 1H), 7.59-7.51 (m, 3H), 7.46 (dd, J=8.4, 2.0 Hz, 1H), 7.32 (d, J=8.1 Hz, 2H), 4.77 (s, 2H), 2.40-2.32 (m, 2H), 2.09-1.95 (m, 6H), 1.86 (dd, J=7.0, 4.6 Hz, 2H), 1.61 (d, J=7.7 Hz, 2H), 1.43-1.31 (m, 2H), 0.90 (t, J=7.4 Hz, 3H).

Intermediate 99b: 4'-((2-butyl-4-oxo-1,3-diazaspiro[4.4]non-1-en-3-yl)methyl)-5-(phenylamino)-[1,1'-biphenyl]-2-carbonitrile

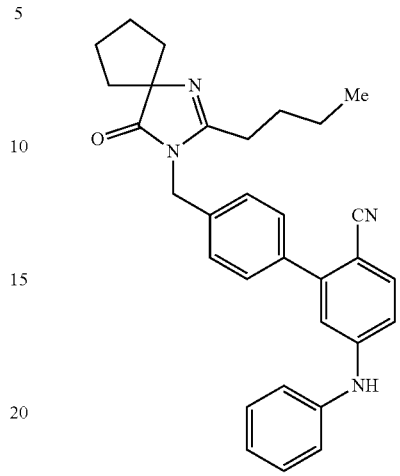

To a vial containing Intermediate 99a (100 mg, 0.238 mmol) was added 2nd generation RuPhos precatalyst (18.50 mg, 0.024 mmol) followed sodium t-butoxide (137 mg, 1.429 mmol). THF (3 mL) was then added followed by aniline (66.5 mg, 0.714 mmol). The reaction vial degassed with N$_2$ for 5 minutes, sealed, and heated at 65° C. for 16 hours. The reaction mixture was diluted with EtOAc, filtered over Celite, concentrated on to Celite for dry loading and purified by ISCO (0-100% EtOAc in hexanes) to afford Intermediate 99b (95 mg, 0.199 mmol, 84% yield) as a colorless oil. LC-MS (Method A2) RT=1.07 min, MS (ESI) m/z: 477.4. $^1$H NMR (400 MHz, CDCl$_3$) δ 7.62-7.57 (m, 1H), 7.56-7.50 (m, 2H), 7.43-7.35 (m, 2H), 7.26 (s, 2H), 7.21 (dd, J=8.5, 0.8 Hz, 2H), 7.15 (t, J=7.4 Hz, 1H), 7.00-6.95 (m, 2H), 6.12 (s, 1H), 4.75 (s, 2H), 2.40-2.32 (m, 2H), 2.06-1.94 (m, 6H), 1.89-1.81 (m, 2H), 1.62 (t, J=7.7 Hz, 2H), 1.37 (dd, J=15.0, 7.5 Hz, 2H), 0.90 (t, J=7.4 Hz, 3H).

Example 99: 2-butyl-3-((5'-(phenylamino)-2'-(2H-tetrazol-5-yl)-[1,1'-biphenyl]-4-yl)methyl)-1,3-diazaspiro[4.4]non-1-en-4-one To a vial containing Intermediate 99b (95 mg, 0.199 mmol) was added dibutyltin oxide (99 mg, 0.399 mmol) and toluene (5 mL) followed by TMS-N$_3$ (0.265 mL, 1.993 mmol). The reaction mixture was sealed and heated at 110° C. behind a blast shield. After 16 h of heating, the reaction was cooled to RT, and MeOH was added to solubilize the solution. The reaction was diluted with EtOAc and CAN (10% Aqueous) solution (1093 mg, 1.993 mmol) was added to quench remaining TMSN$_3$ until bubbling ceased. Layers were separated and the organic layer was washed with saturated aqueous ammonium chloride, washed with brine, dried with sodium sulfate, and concentrated. The residue was dissolved in DMF, and the crude material was purified via preparative LC-MS with the following conditions: Column: XBridge C18, 19×200 mm, 5-μm particles; Mobile Phase A: 5:95 ACN: H$_2$O with 0.1% trifluoroacetic acid; Mobile Phase B: 95:5 ACN: H$_2$O with 0.1% trifluoroacetic acid; Gradient: 20-60% B over 19 minutes, then a 5-minute hold at 100% B; Flow: 20 mL/min to yield Example 99 (5.4 mg, 10.29 μmol, 5.16% yield): LC-MS (Method A2) RT=0.98 min, MS (ESI) m/z: 520.4. $^1$H NMR (500 MHz, DMSO-d$_6$) δ 8.68 (br. s., 1H), 7.48 (d, J=8.3 Hz, 1H), 7.35-7.27 (m, 2H), 7.22-7.14 (m, 3H), 7.10-7.03 (m, 5H), 6.95 (t, J=7.3 Hz, 1H), 4.67 (s, 2H), 2.28 (t, J=7.5 Hz, 2H), 1.91-1.76 (m, 6H), 1.66 (d, J=6.9 Hz, 2H), 1.43 (d, J=6.9 Hz, 2H), 1.26-1.18 (m, 2H), 0.77 (t, J=7.3 Hz, 3H) One exchangeable proton not observed.

The compounds listed in the table below were synthesized using the same methods that were used to prepare Example 99.

| Ex # | Structure | MW | LC-MS m/z [M + H]+; RT (Method) | 1H NMR |
|---|---|---|---|---|
| 100 | 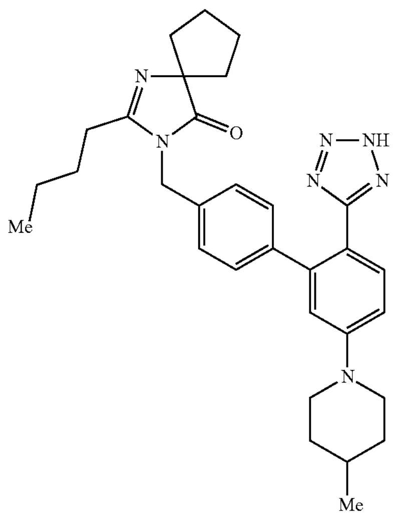 [SMILES: CCCCC1=NC2(CCCC2)C(=O)N1Cc1ccc(-c2cc(N3CCC(C)CC3)ccc2-c2nn[nH]n2)cc1] | 525.32 | 526.5; 1.08 min (Method A2) | 1H NMR (500 MHz, DMSO-$d_6$) δ 7.42 (d, J = 8.5 Hz, 1H), 7.12-7.08 (m, 2H), 7.02 (d, J = 7.9 Hz, 3H), 6.84 (s, 1H), 4.66 (s, 2H), 3.81 (d, J = 12.2 Hz, 2H), 2.75 (d, J = 12.8 Hz, 2H), 2.30 (t, J = 7.5 Hz, 2H), 1.88-1.78 (m, 6H), 1.72-1.63 (m, 4H), 1.55 (br. s., 1H), 1.51-1.43 (m, 2H), 1.31-1.16 (m, 4H), 0.93 (d, J = 6.7 Hz, 3H), 0.80 (t, J = 7.2 Hz, 3H) (1 exchangeable proton not observed) |
| 101 | 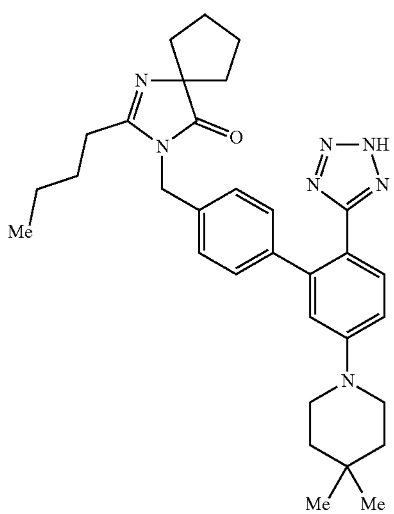 [SMILES: CCCCC1=NC2(CCCC2)C(=O)N1Cc1ccc(-c2cc(N3CCC(C)(C)CC3)ccc2-c2nn[nH]n2)cc1] | 539.714 | 540.5; 1.07 min (Method A2) | 1H NMR (500 MHz, DMSO-$d_6$) δ 7.93 (s, 1H), 7.41 (d, J = 8.5 Hz, 1H), 7.08 (d, J = 7.6 Hz, 2H), 7.01 (d, J = 7.9 Hz, 3H), 6.84 (s, 1H), 4.65 (s, 2H), 3.26 (br. s., 4H), 2.29 (t, J = 7.5 Hz, 2H), 1.88-1.77 (m, 6H), 1.66 (d, J = 7.0 Hz, 2H), 1.50-1.44 (m, 2H), 1.42 (br. s., 4H), 1.31-1.21 (m, 2H), 0.95 (s, 6H), 0.78 (t, J = 7.2 Hz, 3H) (1 exchangeable proton not observed) |
| 102 | 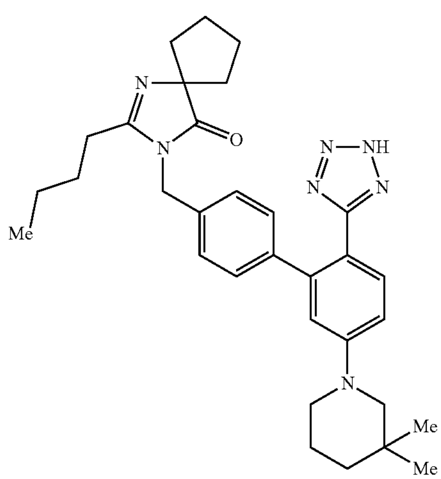 [SMILES: CCCCC1=NC2(CCCC2)C(=O)N1Cc1ccc(-c2cc(N3CCCC(C)(C)C3)ccc2-c2nn[nH]n2)cc1] | 539.714 | 540.5; 1.17 min (Method A2) | 1H NMR (500 MHz, DMSO-$d_6$) δ 7.40 (br s, 1H), 7.05 (br d, J = 15.7 Hz, 5H), 6.85 (br s, 1H), 4.66 (br s, 2H), 3.56 (br s, 4H), 3.23 (br s, 2H), 2.29 (br t, J = 7.5 Hz, 2H), 1.89-1.77 (m, 8H), 1.64 (br s, 4H), 1.48-1.42 (m, 2H), 0.95 (s, 6H), 0.79 (br t, J = 7.3 Hz, 3H) (1 exchangeable protons not observed) |

-continued

| Ex # | Structure | MW | LC-MS m/z [M + H]+; RT (Method) | 1H NMR |
|---|---|---|---|---|
| 103 | 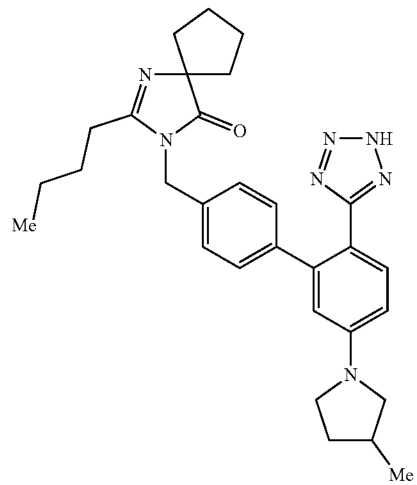 [SMILES: CCCCC1=NC2(CCCC2)C(=O)N1Cc1ccc(-c2cc(N3CCC(C)C3)ccc2-c2nn[nH]n2)cc1] | 511.661 | 512.5; 0.86 min (Method A2) | 1H NMR (500 MHz, DMSO-d6) δ 7.45 (d, J = 8.7 Hz, 1H), 7.24 (s, 2H), 7.03 (s, 2H), 6.66 (dd, J = 8.63 Hz, 2.23 Hz, 1H), 6.48 (s, 1H), 4.78 (s, 2H), 3.37-2.63 (m, 3H), 2.42-2.05 (m, 3H), 1.87 (d, J = 7.0 Hz, 9H), 1.56-1.46 (m, 3H), 1.35-1.23 (m, 3H), 1.09 (d, J = 6.6 Hz, 3H), 0.82 (t, J = 7.4 Hz, 3H) (1 exchangeable proton not observed) |
| 104 | 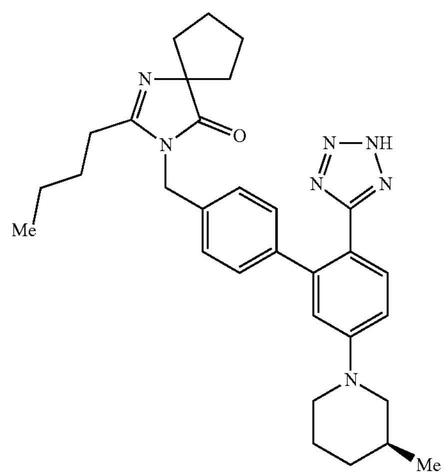 [SMILES: CCCCC1=NC2(CCCC2)C(=O)N1Cc1ccc(-c2cc(N3CCC[C@H](C)C3)ccc2-c2nn[nH]n2)cc1] | 525.688 | 526.5; 0.85 min (Method A2) | 1H NMR (500 MHz, DMSO-d6) δ 7.42 (d, J = 8.7 Hz, 1H), 7.09-7.06 (m, 2H), 7.02 (d, J = 8.1 Hz, 3H), 6.84 (s, 1H), 4.65 (s, 2H), 3.90-3.72 (m, 4H), 2.77-2.67 (m, 1H), 2.42 (t, J = 11.5 Hz, 1H), 2.29 (t, J = 7.5 Hz, 2H), 1.88-1.77 (m, 6H), 1.66 (d, J = 7.4 Hz, 4H), 1.47-1.40 (m, 2H), 1.27-1.20 (m, 2H), 1.07 (d, J = 11.9 Hz, 1H), 0.90 (d, J = 6.5 Hz, 3H), 0.78 (t, J = 7.3 Hz, 3H) (1 exchangeable proton not observed) |
| 105 | 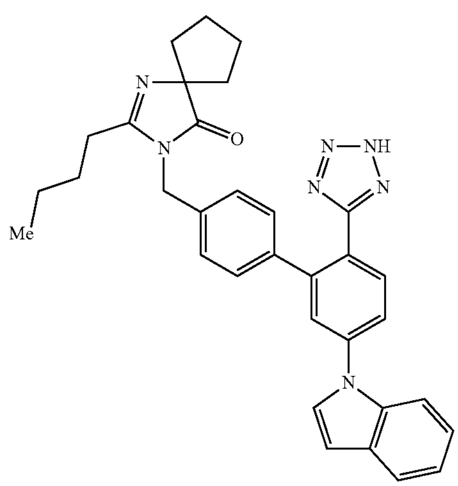 [SMILES: CCCCC1=NC2(CCCC2)C(=O)N1Cc1ccc(-c2cc(-n3ccc4ccccc43)ccc2-c2nn[nH]n2)cc1] | 543.677 | 544.3; 1.86 min (Method A1) | 1H NMR (500 MHz, DMSO-d6) δ 7.79-7.73 (m, 2H), 7.70-7.63 (m, 2H), 7.49 (s, 1H), 7.21 (d, J = 7.9 Hz, 2H), 7.15 (d, J = 4.9 Hz, 1H), 7.03 (d, J = 7.9 Hz, 2H), 6.73 (d, J = 2.7 Hz, 1H), 4.66 (s, 2H), 3.82-3.61 (m, 4H), 2.30 (t, J = 6.4 Hz, 2H), 1.90-1.74 (m, 6H), 1.65 (br. s., 2H), 1.45 (br. s., 2H), 1.30-1.19 (m, 2H), 0.77 (t, J = 7.2 Hz, 3H) (1 exchangeable proton not observed) |

| Ex # | Structure | MW | LC-MS m/z [M + H]+; RT (Method) | 1H NMR |
|---|---|---|---|---|
| 106 | 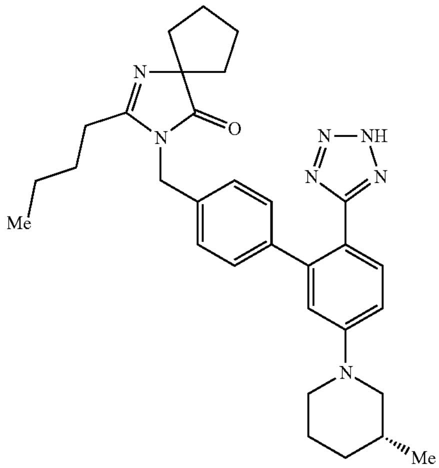 [SMILES: CCCCC1=NC2(CCCC2)C(=O)N1Cc1ccc(-c2cc(N3CCC[C@@H](C)C3)ccc2-c2nn[nH]n2)cc1] | 525.688 | 526.6; 0.85 min (Method A2) | 1H NMR (500 MHz, DMSO-d6) δ 7.44 (d, J = 8.7 Hz, 1H), 7.06 (q, J = 8.0 Hz, 5H), 6.88 (s, 1H), 4.66 (s, 2H), 2.29 (t, J = 7.5 Hz, 2H), 1.88-1.78 (m, 6H), 1.66 (d, J = 7.6 Hz, 4H), 1.47-1.41 (m, 2H), 1.25 (td, J = 14.6, 7.0 Hz, 8H), 1.15 (t, J = 7.3 Hz, 1H), 0.85 (br. s., 3H), 0.78 (t, J = 7.3 Hz, 3H) (1 exchangeable proton not observed) |
| 107 | 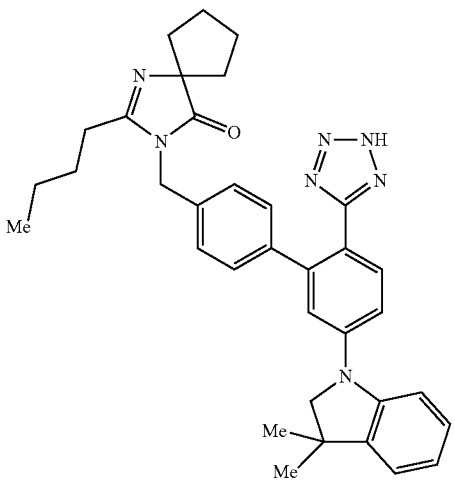 [SMILES: CCCCC1=NC2(CCCC2)C(=O)N1Cc1ccc(-c2cc(N3CC(C)(C)c4ccccc43)ccc2-c2nn[nH]n2)cc1] | 573.730 | 574.7; 0.94 min (Method A2) | 1H NMR (500 MHz, DMSO-d6) δ 7.62 (d, J = 8.5 Hz, 1H), 7.42 (d, J = 8.5 Hz, 1H), 7.29 (d, J = 7.9 Hz, 1H), 7.23 (d, J = 7.3 Hz, 1H), 7.18 (d, J = 11.9 Hz, 2H), 7.16-7.11 (m, 2H), 7.09 (d, J = 8.0 Hz, 2H), 6.86 (t, J = 7.4 Hz, 1H), 4.69 (s, 2H), 2.30 (t, J = 7.5 Hz, 2H), 1.92-1.77 (m, 6H), 1.66 (br. s., 2H), 1.45 (d, J = 7.3 Hz, 2H), 1.36-1.18 (m, 10H), 0.86 (t, J = 7.2 Hz, 3H) (1 exchangeable proton not observed) |
| 108 | 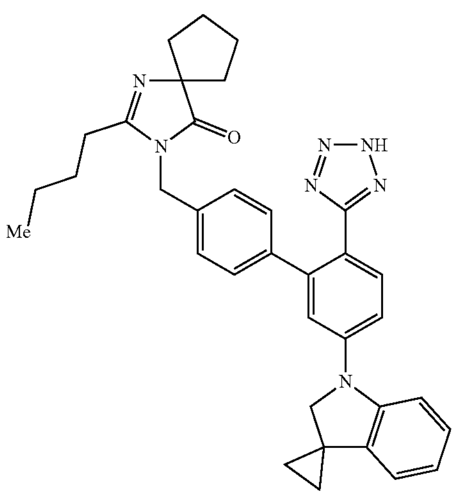 [SMILES: CCCCC1=NC2(CCCC2)C(=O)N1Cc1ccc(-c2cc(N3CC4(CC4)c4ccccc43)ccc2-c2nn[nH]n2)cc1] | 571.306 | 572.3; 0.96 min (Method A2) | 1H NMR (500 MHz, DMSO-d6) δ 7.55 (br d, J = 8.2 Hz, 1H), 7.33-7.28 (m, 1H), 7.20-7.13 (m, 3H), 7.10-7.02 (m, 2H), 6.99 (br d, J = 7.9 Hz, 2H), 6.82-6.66 (m, 2H), 4.66 (s, 2H), 4.05 (s, 2H), 2.33 (br t, J = 7.5 Hz, 2H), 1.84 (br d, J = 8.5 Hz, 6H), 1.68 (br d, J = 6.7 Hz, 2H), 1.54-1.44 (m, 2H), 1.28 (br d, J = 7.6 Hz, 2H), 1.09 (br s, 1H), 1.04 (br s, 1H), 1.01 (d, J = 6.1 Hz, 2H), 0.81 (br t, J = 7.3 Hz, 3H) (1 exchangeable proton not observed) |

Example 109: 2-butyl-3-((5'-(6-fluoro-1H-indol-1-Yl)-2'-(2H-tetrazol-5-yl)-[1,1-biphenyll-4-yl)methyl)-1,3-diazaspiro[4.4]non-1-en-4-one

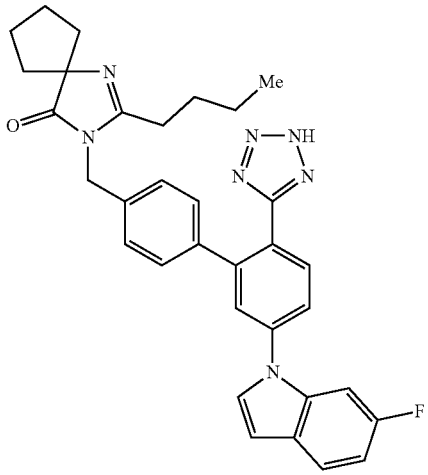 [SMILES: CCCCC1=NC2(CCCC2)C(=O)N1Cc1ccc(-c2cc(-n3ccc4ccc(F)cc43)ccc2-c2nn[nH]n2)cc1]

Intermediate 109a: 5-bromo-4'-((2-butyl-4-oxo-1,3-diazaspiro[4.4]non-1-en-3-yl)methyl)-[1,1'-biphenyl]-2-carbonitrile

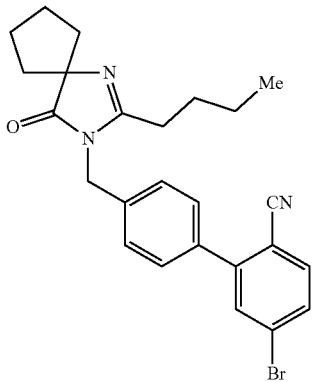

To a microwave vial containing PdCl$_2$(dppf) (0.196 g, 0.268 mmol), Intermediate 033a (1.00 g, 2.44 mmol) and 4-bromo-2-iodobenzonitrile (0.975 g, 3.17 mmol) was added toluene (9.75 ml) followed by ethanol (2.44 ml) and K$_3$PO$_4$ (2 M, aq.) (2.44 ml, 4.87 mmol). N$_2$ was sparged through the reaction mixture for 5 min before the vial was sealed and heated at 120° C. in the microwave for 30 min. The reaction mixture was diluted with EtOAc and washed with saturated aqueous NaHCO$_3$. The organic phase was concentrated and purified by ISCO (0-100% EtOAc in hexanes) to afford Intermediate 109a (0.906 g, 1.95 mmol, 80% yield) as a white solid. LC-MS (Method A2) RT=0.87 min, MS (ESI) m/z: 464.6 (M+H)$^+$. $^1$H NMR (400 MHz, CDCl$_3$) δ 7.70-7.68 (m, 1H), 7.65-7.61 (m, 2H), 7.55 (d, J=8.4 Hz, 2H), 7.31 (d, J=8.4 Hz, 2H), 4.77 (s, 2H), 2.40-2.32 (m, 2H), 2.02 (br d, J=4.6 Hz, 6H), 1.86 (br s, 2H), 1.67-1.58 (m, 2H), 1.44-1.31 (m, 2H), 0.90 (t, J=7.4 Hz, 3H).

Intermediate 109b: 4'-((2-butyl-4-oxo-1,3-diazaspiro[4.4]non-1-en-3-yl)methyl)-5-(6-fluoro-1H-indol-1-yl)-[1,1'-biphenyl]-2-carbonitrile

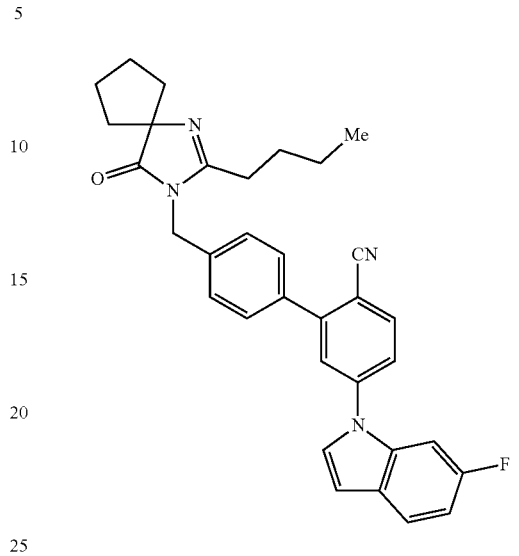

To a vial charged with Intermediate 109a (0.050 g, 0.108 mmol), 6-fluoro-1H-indole (0.044 g, 0.323 mmol), copper(I) iodide (10.25 mg, 0.054 mmol), potassium carbonate (0.074 g, 0.538 mmol) and L-proline (0.012 g, 0.108 mmol) was added DMSO (2.153 ml). The mixture was and heated at 120° C. for 16 hours. The reaction was diluted with EtOAc and filtered through Celite. The filtrate was washed with H$_2$O×3, washed with brine, and dried over sodium sulfate. The reaction was purified on ISCO using 24 g column eluting with 0-100% EtOAc in hexanes to yield Intermediate 109b (0.031 g, 0.060 mmol, 55.5% yield). LC-MS (Method A2) RT=0.96 min, MS (ESI) m/z: 519.8 (M+H). $^1$H NMR (400 MHz, CDCl$_3$) δ 7.94 (s, 1H), 7.68-7.50 (m, 5H), 7.40-7.29 (m, 4H), 7.06-6.96 (m, 1H), 6.76 (dd, J=3.4, 0.8 Hz, 1H), 4.79 (s, 2H), 2.45-2.29 (m, 2H), 2.07-1.95 (m, 6H), 1.87 (td, J=4.3, 1.3 Hz, 2H), 1.71-1.59 (m, 2H), 1.44-1.34 (m, 2H), 0.94-0.88 (m, 3H).

Example 109: 2-butyl-3-((5'-(phenylamino)-2'-(2H-tetrazol-5-yl)-[1,1'-biphenyll-4-yl)methyl)-1,3-diazaspiro[4.4]non-1-en-4-one Synthesized in an analogous manner to Example 99 using Intermediate 109b (0.031 g, 0.060 mmol). Purified using preparative LC-MS with the following conditions: Column: XBridge C18, 19×200 mm, 5-μm particles; Mobile Phase A: 5:95 ACN: H$_2$O with 0.1% trifluoroacetic acid; Mobile Phase B: 95:5 ACN: H$_2$O with 0.1% trifluoroacetic acid; Gradient: 30-70% B over 19 minutes, then a 5-minute hold at 100% B; Flow: 20 mL/min to yield Example 109 (13.1 mg, 0.023 mmol, 39.0% yield): LC-MS (Method A2) RT=0.87 min, MS (ESI) m/z: 562.8 (M+H)$^+$. $^1$H NMR (500 MHz, DMSO-d$_6$) δ 7.82 (br d, J=9.7 Hz, 3H), 7.73-7.61 (m, 2H), 7.47 (br d, J=9.5 Hz, 1H), 7.20 (br d, J=7.8 Hz, 2H), 7.09 (br d, J=7.8 Hz, 2H), 7.04 (br t, J=9.0 Hz, 1H), 6.78 (br d, J=3.0 Hz, 1H), 4.68 (s, 2H), 2.29 (br t, J=7.4 Hz, 2H), 1.82 (br d, J=10.0 Hz, 6H), 1.67 (br d, J=7.6 Hz, 2H), 1.52 (br d, J=6.9 Hz, 2H), 1.24-1.18 (m, 2H), 0.75 (br t, J=7.2 Hz, 3H) (1 exchangeable proton not observed).

Example 110: 3-((6'-(2H-tetrazol-5-yl)-[1,1':3',1''-terphenyl]-4-yl)methyl)-2-methyl-1,3-diazaspiro[4.4]non-1-en-4-one

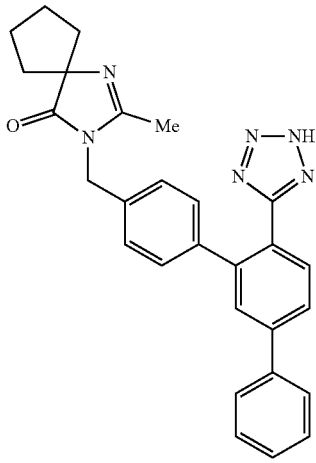 [SMILES: CC1=NC2(CCCC2)C(=O)N1Cc1ccc(-c2cc(-c3ccccc3)ccc2-c2nn[nH]n2)cc1]

Intermediate 10a: 1-acetamidocyclopentane-1-carboxamide

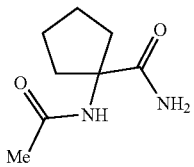

To a solution of 1-aminocyclopentane-1-carboxamide (1.15 g, 8.97 mmol) and DCM (32 mL) was added acetic anhydride (1.191 g, 11.66 mmol). The reaction mixture was stirred at RT for 18 hours. Reaction was concentrated and used without further purification in the next step. Intermediate 110a (1.53 g, 8.99 mmol, 100% yield). LC-MS (Method A2) RT=0.43 min, MS (ESI) m/z: 171.1 (M+H)+. 1H NMR (400 MHz, CDCl3) δ 7.09-6.89 (m, 1H), 5.72 (br s, 1H), 5.38-5.19 (m, 1H), 2.40-2.30 (m, 2H), 2.07-1.98 (m, 5H), 1.86-1.75 (m, 4H)

Intermediate 110b: 2-methyl-1,3-diazaspiro[4.4]non-1-en-4-one

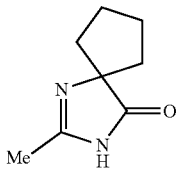

To a solution of Intermediate 110a (1.53 g, 8.99 mmol) in MeOH (20 mL) was added 3.0 N NaOH (23.97 mL, 71.9 mmol). The reaction mixture was heated at 50° C. for 5 hours. The reaction was cooled to RT, and the mixture was acidified with 1.0 N HCl to pH 6-7 and extracted with DCM. The organic layer was dried over sodium sulfate and concentrated to give crude Intermediate 110b (0.162 g, 1.064 mmol, 11.84% yield).

This was used for the next step without purification. LC-MS (Method A2) RT=0.44 min, MS (ESI) m/z: 153.0 (M+H)+. 1H NMR (400 MHz, CDCl3) δ 2.25 (s, 3H), 2.08 (s, 1H), 2.02-1.92 (m, 6H), 1.86-1.80 (m, 2H).

Intermediate 110c: 5-bromo-4'-((2-methyl-4-oxo-1,3-diazaspiro[4.4]non-1-en-3-yl)methyl)-[1,1'-biphenyl]-2-carbonitrile

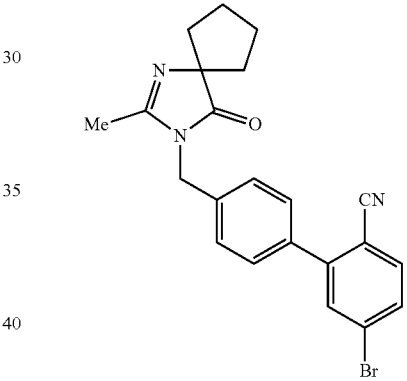

Intermediate 110b (0.162 g, 1.064 mmol) was dissolved in DMF (2.129 ml). NaH (0.106 g, 2.66 mmol) was added and allowed to stir for 15 min. Intermediate 1-002 (0.448 g, 1.277 mmol) was added. The reaction was stirred for 30 min and was diluted with EtOAc.

The organic layer was washed with saturated NH4Cl, washed with brine, dried (Na2SO4), filtered, and concentrated in vacuo. The material was purified by column chromatography (ISCO, 80 g silica gel column, 36 minute gradient of 0 to 100% EtOAc in hexanes) to yield Intermediate 110c (0.310 g, 0.734 mmol, 69.0% yield). LC-MS (Method A2) RT=0.84 min, MS (ESI) m/z: 422.0 (M+H)+. 1H NMR (400 MHz, CDCl3) δ 7.61-7.59 (m, 1H), 7.54 (dd, J=2.8, 1.2 Hz, 2H), 7.48-7.44 (m, 2H), 7.24 (d, J=8.4 Hz, 2H), 4.68 (s, 2H), 2.05 (s, 3H), 1.99-1.87 (m, 6H), 1.76 (br dd, J=7.3, 5.3 Hz, 2H).

Intermediate 110d: 4'-((2-methyl-4-oxo-1,3-diazaspiro[4.4]non-1-en-3-yl)methyl)-5-(4,4,5,5-tetramethyl-1,3,2-dioxaborolan-2-yl)-[1,1'-biphenyl]-2-carbonitrile

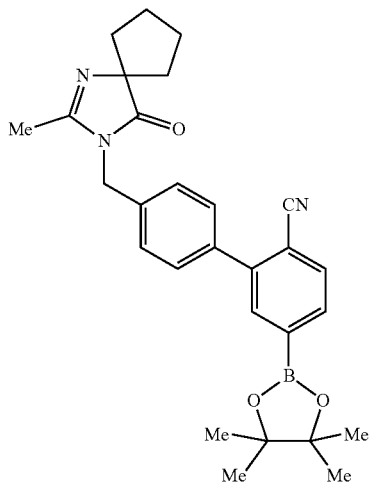 [SMILES: CC1=NC2(CCCC2)C(=O)N1Cc1ccc(-c2cc(B3OC(C)(C)C(C)(C)O3)ccc2C#N)cc1]

Intermediate 110c (0.315 g, 0.834 mmol), bis(pinacolato)diboron (0.423 g, 1.667 mmol), XPhos (0.040 g, 0.083 mmol), Pd₂(dba)₃ (0.076 g, 0.083 mmol), and KOAc (0.409 g, 4.17 mmol) were dissolved in dioxane (8.34 ml). The reaction was heated at 100° C. for 2 hours. The reaction was cooled to ambient temperature, diluted with EtOAc, filtered through Celite, and concentrated in vacuo. The crude material was purified by column chromatography (ISCO, 24 g silica gel column, 19 minute gradient of 0 to 100% EtOAc in DCM) to yield Intermediate 110d (0.300 g, 0.639 mmol, 77%). LC-MS (Method A2) RT=0.68 min, MS (ESI) m/z: 388.1 (M+H)⁺ for boronic acid. ¹H NMR (400 MHz, CDCl₃) δ 7.93 (s, 1H), 7.89-7.85 (m, 1H), 7.77 (d, J=7.7 Hz, 1H), 7.59 (d, J=8.4 Hz, 2H), 7.31 (d, J=8.4 Hz, 2H), 5.32 (s, 2H), 2.14 (s, 3H), 2.04-1.97 (m, 6H), 1.84 (br d, J=4.0 Hz, 2H), 1.29 (s, 12H).

Intermediate 110e: 4"-((2-methyl-4-oxo-1,3-diazaspiro[4.4]non-1-en-3-yl)methyl)-[1,1':3',1"-terphenyl]-4'-carbonitrile Intermediate 110d (40 mg, 0.085 mmol), bromobenzene (40.1 mg, 0.256 mmol), and 2nd generation XPhos precatalyst (6.70 mg, 8.52 µmol) were dissolved in toluene (1363 µl), EtOH (341 µl), and 2M tripotassium phosphate (85 µl, 0.170 mmol) was added. The reaction was heated at 100° C. for one hour. The reaction was diluted with EtOAc, filtered through Celite and concentrated in vacuo. The crude material will be used as-is without further purification for the subsequent reaction. Intermediate 110e (36 mg, 0.086 mmol, 101% yield): LC-MS (Method A2) RT=0.92 min, MS (ESI) m/z: 420.1 (M+H)⁺.

Example 110: 3-((6'-(2H-tetrazol-5-yl)-[1,1':3',1"-terphenyl]-4-yl)methyl)-2-methyl-1,3-diazaspiro[4.4]non-1-en-4-one Synthesized in an analogous manner to Example 99 using Intermediate 110e (0.040 g, 0.095 mmol). Purified using preparative LC-MS with the following conditions: Column: XBridge C18, 19×200 mm, 5-µm particles; Mobile Phase A: 5:95 ACN: H₂O with 10 mM NH₄OAc; Mobile Phase B: 95:5 ACN: H₂O with 10 mM NH₄OAc; Gradient: 12-56% B over 23 minutes, then a 6-minute hold at 100% B; Flow: 20 mL/min. Example 110 (1.2 mg, 2.491 µmol, 2.61% yield): LC-MS (Method A2) RT=0.83 min, MS (ESI) m/z: 463.2 (M+H)⁺. ¹H NMR (500 MHz, DMSO-d₆) δ 7.78 (br d, J=7.3 Hz, 2H), 7.75-7.69 (m, 2H), 7.63 (s, 1H), 7.49 (t, J=7.6 Hz, 2H), 7.42-7.38 (m, 1H), 7.21 (d, J=7.9 Hz, 2H), 7.06 (br d, J=8.2 Hz, 2H), 4.68 (s, 2H), 2.05 (s, 3H), 1.88-1.79 (m, 6H), 1.69 (br d, J=7.3 Hz, 2H) (1 exchangeable proton not observed).

Example 111: 2-methyl-3-((5'-(4-methylpyridin-2-yl)-2'-(2H-tetrazol-5-yl)-[1,1'-biphenyl]-4-yl)methyl)-1,3-diazaspiro[4.4]non-1-en-4-one

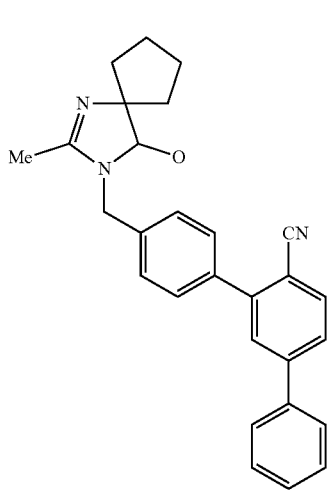

(110d)

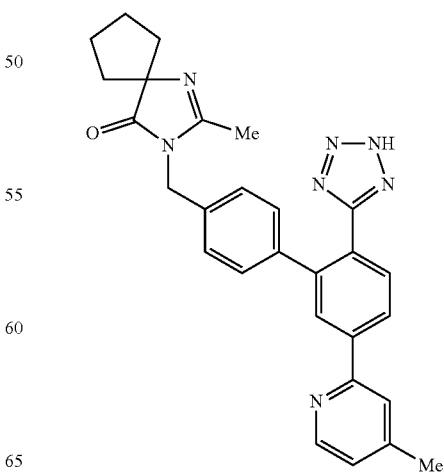

(Ex. 111)

Intermediate 111a: 4'-((2-methyl-4-oxo-1,3-diazaspiro[4.4]non-1-en-3-yl)methyl)-5-(4-methylpyridin-2-yl)-[1,1'-biphenyl]-2-carbonitrile Example 112: 3-((6'-(2H-tetrazol-5-yl)-[1,1':3',1''-terphenyl]-4-yl)methyl)-2-ethyl-1,3-diazaspiro[4.4]non-1-en-4-one

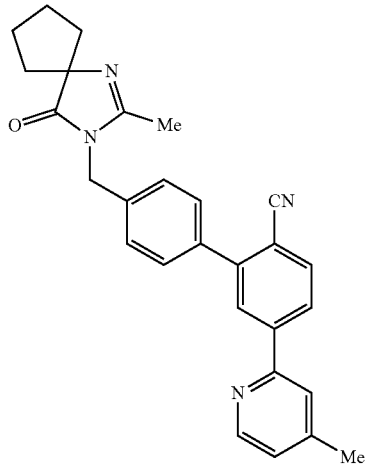

(111a)

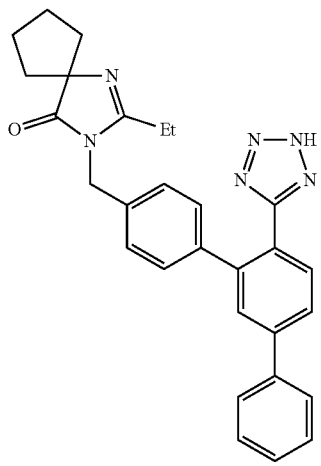

(ex. 112)

Intermediate 112a: 1-propionamidocyclopentane-1-carboxamide

Synthesized in an analogous manner to Example 110e using Intermediate 110d (0.040 g, 0.085 mmol) and 2-bromo-4-methylpyridine (0.044 g, 0.256 mmol) to yield Intermediate 111a (0.037 g, 0.085 mmol, 100%). LC-MS (Method A2) RT=0.72 min, MS (ESI) m/z: 435.2 (M+H)y.

Example 111: 2-methyl-3-((5'-(4-methylpyridin-2-yl)-2'-(2H-tetrazol-5-yl)-[1,1'-biphenyl]-4-yl)methyl)-1,3-diazaspiro[4.4]non-1-en-4-one

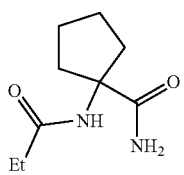

(112a)

Synthesized in an analogous manner to Example 99 using Intermediate 111a (0.040 g, 0.092 mmol). Purified using preparative LC-MS with the following conditions: Column: XBridge C18, 19×200 mm, 5-μm particles; Mobile Phase A: 5:95 ACN: H$_2$O with 0.1% trifluoroacetic acid; Mobile Phase B: 95:5 ACN: H$_2$O with 0.1% trifluoroacetic acid; Gradient: 2-42% B over 23 minutes, then a 6-minute hold at 100% B; Flow: 20 mL/min. Example 111: LC-MS (Method A2) RT=0.61 min, MS (ESI) m/z: 478.3 (M+H)$^+$. $^1$H NMR (500 MHz, DMSO-d$_6$) δ 8.55 (d, J=4.9 Hz, 1H), 8.19 (br d, J=8.2 Hz, 1H), 8.13 (s, 1H), 7.98 (s, 1H), 7.77 (d, J=8.2 Hz, 1H), 7.24 (br d, J=4.9 Hz, 1H), 7.20 (d, J=7.9 Hz, 2H), 7.10 (br d, J=7.9 Hz, 2H), 4.70 (s, 2H), 2.42 (s, 3H), 2.05 (s, 3H), 1.90-1.81 (m, 6H), 1.68 (br s, 2H) (1 exchangeable proton not observed).

To a solution of 1-aminocyclopentane-1-carboxamide (1.00 g, 7.80 mmol) in DCM (16 mL) was added TEA (2.72 mL, 19.50 mmol). The mixture was cooled to 0° C. with an ice bath. Propionyl chloride (1.011 g, 10.92 mmol) in DCM (4 mL) was added dropwise to the stirred solution, and the reaction mixture was at RT for 18 hours. The reaction was diluted with H$_2$O and DCM. The organic phase was collected. The aqueous phase was extracted (2X) with DCM. The combined organic phase was washed with brine, dried over sodium sulfate and concentrated to give Intermediate 112a (0.586 g, 3.18 mmol, 40.8% yield) as a solid. LC-MS (Method A2) RT=0.46 min, MS (ESI) m/z: 185.1 (M+H)$^+$. $^1$H NMR (400 MHz, CDCl$_3$) δ 9.37-9.15 (m, 2H), 8.71 (br d, J=0.9 Hz, 1H), 2.42 (q, J=7.4 Hz, 2H), 2.39-2.29 (m, 2H), 1.85-1.68 (m, 4H), 1.67-1.58 (m, 2H), 1.14-1.10 (m, 3H).

Intermediate 112b: 2-ethyl-1,3-diazaspiro[4.4]non-1-en-4-one

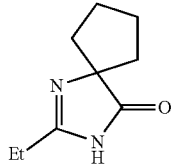
(112b)

Synthesized in an analogous manner to Example 110b using Intermediate 112a (0.586 g, 3.18 mmol) to yield Intermediate 112b (0.445 g, 2.68 mmol, 84%). LC-MS (Method A2) RT=0.46 min, MS (ESI) m/z: 167.1 (M+H)⁺. $^1$H NMR (400 MHz, CDCl$_3$) δ 5.53 (br s, 1H), 2.42 (q, J=7.7 Hz, 2H), 1.82 (br d, J=3.7 Hz, 2H), 1.77-1.70 (m, 6H), 1.18 (t, J=7.6 Hz, 3H).

Intermediate 112c: 5-bromo-4'-((2-ethyl-4-oxo-1,3-diazaspiro[4.4]non-1-en-3-yl)methyl)-[1,1'-biphenyl]-2-carbonitrile

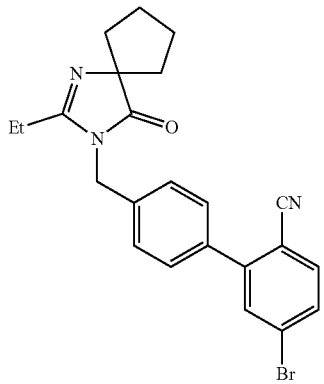
(112c)

Synthesized in an analogous manner to Example 110c using Intermediate 112b (0.176 g, 1.059 mmol) and Intermediate 1-002 (0.446 g, 1.271 mmol) to yield Intermediate 112c (0.232 g, 0.532 mmol, 50%). LC-MS (Method A2) RT=0.87 min, MS (ESI) m/z: 436.0 [M+H]⁺ $^1$H NMR (400 MHz, CDCl$_3$) δ 7.70-7.68 (m, 1H), 7.65-7.62 (m, 2H), 7.55 (d, J=8.4 Hz, 2H), 7.32 (d, J=8.6 Hz, 2H), 5.32 (s, 2H), 2.43-2.36 (m, 2H), 2.06-1.95 (m, 6H), 1.90-1.85 (m, 2H), 1.22 (t, J=7.5 Hz, 3H).

Intermediate 112d: 4'-((2-ethyl-4-oxo-1,3-diazaspiro[4.4]non-1-en-3-yl)methyl)-5-(4,4,5,5-tetramethyl-1,3,2-dioxaborolan-2-yl)-[1,1'-biphenyl]-2-carbonitrile

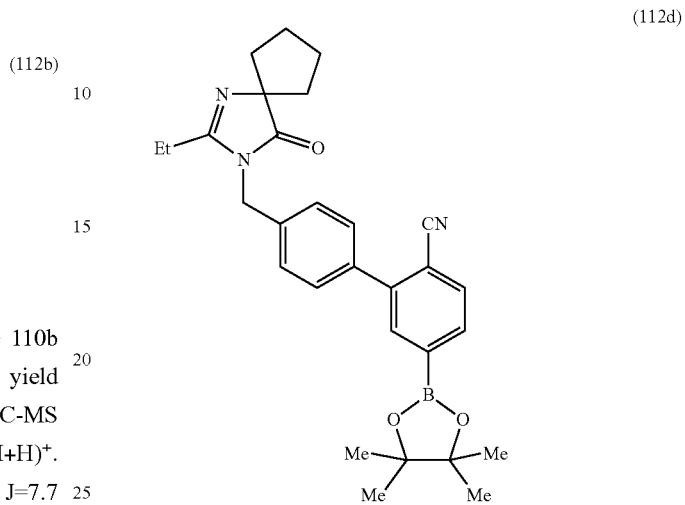
(112d)

Synthesized in an analogous manner to Example 110d using Intermediate 112c (0.232 g, 0.532 mmol) to yield Intermediate 112d (0.257 g, 0.455 mmol, 86%). LC-MS (Method A2) RT=0.67 min, MS (ESI) m/z: 402.1 (M+H)⁺ for boronic acid. $^1$H NMR (400 MHz, CDCl$_3$) δ 7.90 (s, 1H), 7.85 (dd, J=7.7, 1.1 Hz, 1H), 7.74 (d, J=7.7 Hz, 1H), 7.56 (d, J=8.1 Hz, 2H), 7.30-7.26 (m, 2H), 4.74 (s, 2H), 2.42-2.30 (m, 2H), 2.07-1.94 (m, 6H), 1.90-1.79 (m, 2H), 1.37-1.26 (m, 12H), 1.19 (t, J=7.4 Hz, 3H).

Intermediate 112e: 4''-((2-ethyl-4-oxo-1,3-diazaspiro[4.4]non-1-en-3-yl)methyl)-[1,1':3',1''-terphenyl]-4'-carbonitrile

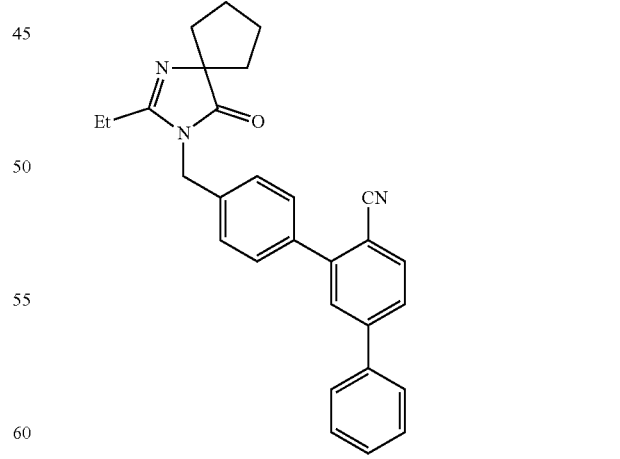
(112e)

Synthesized in an analogous manner to Example 110e using Intermediate 112d (0.030 g, 0.069 mmol) and bromobenzene (0.029 g, 0.186 mmol) to yield Intermediate 112e (0.030 g, 0.062 mmol, 100%). LC-MS (Method A2) RT=0.90 min, MS (ESI) m/z: 434.1 (M+H)⁺.

Example 112: 3-((6'-(2H-tetrazol-5-yl)-[1,1':3',1"-terphenyl]-4-yl)methyl)-2-ethyl-1,3-diazaspiro[4.4]non-1-en-4-one Synthesized in an analogous manner to Example 99 using Intermediate 112e (0.030 g, 0.062 mmol). Purified using preparative LC-MS with the following conditions: Column: XBridge C18, 19×200 mm, 5-μm particles; Mobile Phase A: 5:95 ACN: H₂O with 10 mM NH₄OAc; Mobile Phase B: 95:5 ACN: H₂O with 10 mM NH₄OAc; Gradient: 15-60% B over 19 minutes, then a 5-minute hold at 100% B; Flow: 20 mL/min. Example 112 (0.0015 g, 0.00308 mmol, 3.11%): LC-MS (Method A2) RT=0.81 min, MS (ESI) m/z: 477.2 (M+H)⁺. ¹H NMR (500 MHz, DMSO-d₆) δ 7.90-7.87 (m, 1H), 7.83 (br d, J=7.3 Hz, 2H), 7.80-7.76 (m, 2H), 7.52 (br t, J=7.6 Hz, 2H), 7.46 (br d, J=7.3 Hz, 1H), 7.20 (br d, J=7.6 Hz, 2H), 7.12 (br d, J=7.6 Hz, 2H), 4.70 (s, 2H), 2.34 (br d, J=7.3 Hz, 2H), 2.06-1.74 (m, 6H), 1.70 (br d, J=5.8 Hz, 2H), 1.05 (t, J=7.3 Hz, 3H) (1 exchangeable proton not observed).

Example 113: 2-ethyl-3-((5'-(4-methylpyridin-2-yl)-2'-(2H-tetrazol-5-yl)-[1,1'-biphenyl]-4-yl)methyl)-1,3-diazaspiro[4.4]non-1-en-4-one

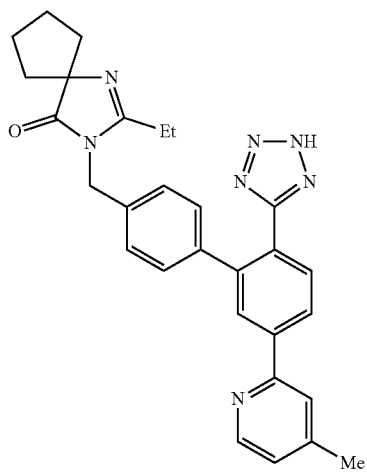

(ex. 113)

Intermediate 113a: 5-(4-methylpyridin-2-yl)-4'-((4-oxo-2-ethyl-1,3-diazaspiro[4.4]non-1-en-3-yl)methyl)-[1,1'-biphenyl]-2-carbonitrile

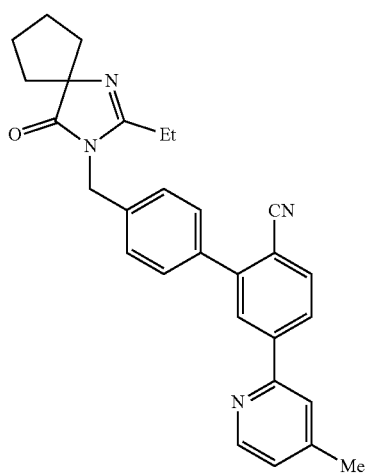

(113a)

Synthesized in an analogous manner to Example 110e using Intermediate 112d (0.030 g, 0.069 mmol) and 2-bromo-4-methylpyridine (0.032 g, 0.186 mmol) to yield Intermediate 113a (0.030 g, 0.067 mmol, 100%). LC-MS (Method A2) RT=0.75 min, MS (ESI) m/z: 449.0 (M+H)⁺.

Example 113: 2-ethyl-3-((5'-(4-methylpyridin-2-yl)-2'-(2H-tetrazol-5-yl)-[1,1'-biphenyl]-4-yl)methyl)-1,3-diazaspiro[4.4]non-1-en-4-one Synthesized in an analogous manner to Example 99 using Intermediate 113a (0.030 g, 0.067 mmol). Purified using preparative LC-MS with the following conditions: Column: XBridge C18, 19×200 mm, 5-μm particles; Mobile Phase A: 5:95 ACN: H₂O with 10 mM NH₄OAc; Mobile Phase B: 95:5 ACN: H₂O with 10 mM NH₄OAc; Gradient: 13-53% B over 20 minutes, then a 4-minute hold at 100% B; Flow: 20 mL/min. Example 113 (0.0041 g, 0.00782 mmol, 8.3%): LC-MS (Method A2) RT=0.65 min, MS (ESI) m/z: 492.2 (M+H)⁺. ¹H NMR (500 MHz, DMSO-d₆) δ 8.57 (d, J=5.0 Hz, 1H), 8.27 (br d, J=7.9 Hz, 1H), 8.22 (s, 1H), 8.00 (s, 1H), 7.80 (d, J=8.0 Hz, 11H), 7.27 (br d, J=4.8 Hz, 1H), 7.22-7.19 (m, 2H), 7.19-7.14 (m, 2H), 4.74 (s, 2H), 2.47-2.40 (m, 5H), 1.89 (br d, J=7.3 Hz, 6H), 1.81-1.69 (m, 2H), 1.09 (t, J=7.4 Hz, 3H) (1 exchangeable proton not observed).

Example 114: (R)-3-((5'-(3-methylpiperidin-1-yl)-2'-(2H-tetrazol-5-yl)-[1,1'-biphenyl]-4-yl)methyl)-2-propyl-1,3-diazaspiro[4.4]non-1-en-4-one

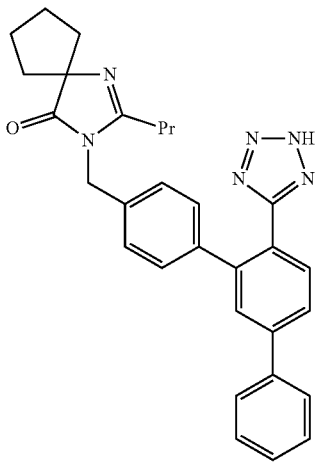

(Ex. 114)

Intermediate 114a: 1-butyramidocyclopentane-1-carboxamide

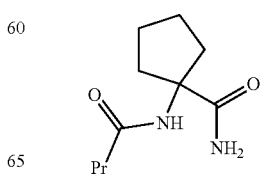

(114a)

To a solution of 1-aminocyclopentane-1-carboxamide (0.500 g, 3.90 mmol) in DCM (16 mL) was added TEA (1.359 mL, 9.75 mmol). The mixture was cooled with an ice bath.

Butyryl chloride (0.572 mL, 5.46 mmol) in DCM (4 mL) was added dropwise to the stirred solution, and the reaction mixture was at RT for 18 hours. The reaction was diluted with H₂O and DCM. The organic phase was collected. The aqueous phase was extracted (2X) with DCM. The combined organic phase was washed with brine, dried over sodium sulfate, and concentrated to give Intermediate 114a (0.300 g, 1.513 mmol, 38.8% yield) as a solid. LC-MS (Method A2) RT=0.54 min, MS (ESI) m/z: 199.1 (M+H)⁺. ¹H NMR (400 MHz, CDCl₃) δ 7.15-6.86 (m, 2H), 5.38-5.27 (m, 11H), 2.28-2.18 (m, 2H), 2.14-2.07 (m, 2H), 1.98-1.89 (m, 2H), 1.75-1.65 (m, 4H), 1.62-1.56 (m, 2H), 0.90-0.87 (m, 3H).

Intermediate 114b: 2-propyl-1,3-diazaspiro[4.4]non-1-en-4-one

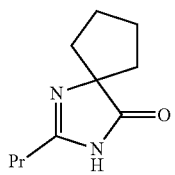
(114b)

Synthesized in an analogous manner to Example 110b using Intermediate 114a (0.307 g, 1.548 mmol) to yield Intermediate 114b (0.110 g, 0.610 mmol, 39%). LC-MS (Method A2) RT=0.48 min, MS (ESI) m/z: 181.0 (M+H)⁺. ¹H NMR (400 MHz, CDCl₃) δ 5.64-5.45 (m, 1H), 2.36 (t, J=7.4 Hz, 2H), 2.20 (t, J=7.5 Hz, 2H), 2.13-1.96 (m, 2H), 1.92-1.78 (m, 2H), 1.76-1.65 (m, 4H), 1.02-0.98 (m, 3H)

Intermediate 114c: 5-bromo-4'-((4-oxo-2-propyl-1,3-diazaspiro[4.4]non-1-en-3-yl)methyl)-[1,1'-biphenyl]-2-carbonitrile

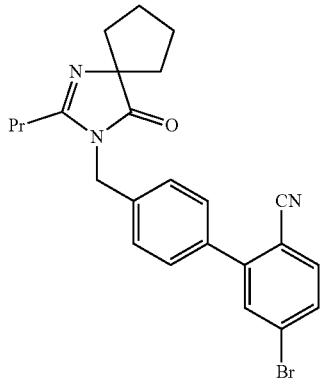
(114c)

Synthesized in an analogous manner to Example 110c using Intermediate 114b (0.555 g, 3.08 mmol) and Intermediate 1-002 (1.297 g, 3.69 mmol) to yield Intermediate 114c (0.668 g, 1.483 mmol, 48%). LC-MS (Method A2) RT=0.87 min, MS (ESI) m/z: 436.0 [M+H]⁺

Intermediate 114d: 4'-((4-oxo-2-propyl-1,3-diazaspiro[4.4]non-1-en-3-yl)methyl)-5-(4,4,5,5-tetramethyl-1,3,2-dioxaborolan-2-yl)-[1,1'-biphenyl]-2-carbonitrile

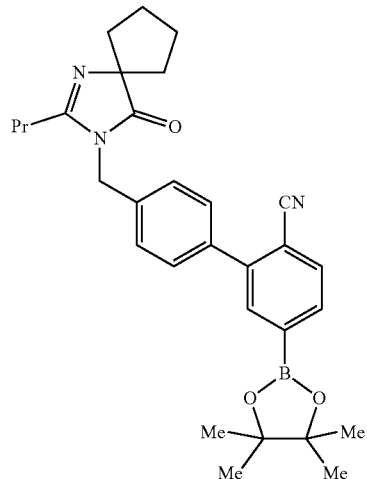
(114d)

Synthesized in an analogous manner to Example 110d using Intermediate 114c (0.450 g, 0.999 mmol) to yield Intermediate 114d (0.442 g, 0.889 mmol, 89%). LC-MS (Method A2) RT=0.96 min, MS (ESI) m/z: 498.3 (M+H)⁺. ¹H NMR (400 MHz, CDCl₃) δ 7.91 (s, 1H), 7.84 (d, J=1.1 Hz, 1H), 7.77-7.73 (m, 11H), 7.56 (d, J=8.4 Hz, 2H), 7.28 (s, 2H), 4.74 (s, 2H), 2.38-2.26 (m, 2H), 2.04-1.94 (m, 6H), 1.84 (td, J=4.8, 2.8 Hz, 2H), 1.70-1.62 (m, 2H), 1.35 (s, 12H), 0.95 (t, J=7.4 Hz, 3H).

Intermediate 114e: 4"-((4-oxo-2-propyl-1,3-diazaspiro[4.4]non-1-en-3-yl)methyl)-[1,1':3',1"-terphenyl]-4'-carbonitrile

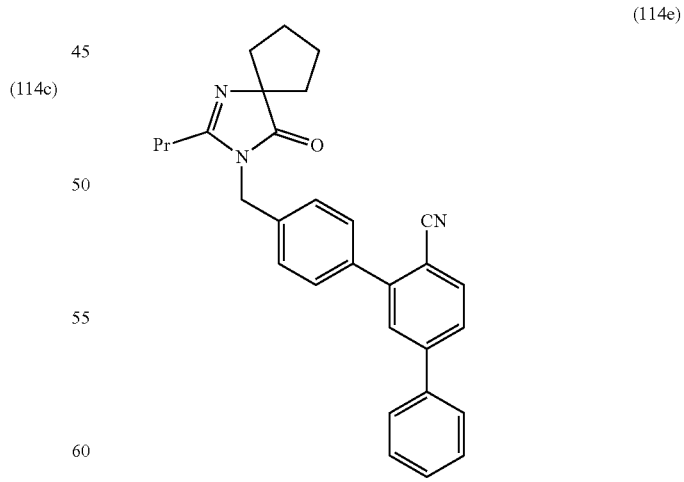
(114e)

Synthesized in an analogous manner to Example 110e using Intermediate 114d (0.030 g, 0.060 mmol) and bromobenzene (0.028 g, 0.181 mmol) to yield Intermediate 114e (0.030 g, 0.067 mmol, 100%). LC-MS (Method A2) RT=0.93 min, MS (ESI) m/z: 448.2 (M+H)⁺.

Example 114: 3-((6'-(2H-tetrazol-5-yl)-[1,1':3',1''-terphenyl]-4-yl)methyl)-2-propyl-1,3-diazaspiro[4.4]non-1-en-4-one Synthesized in an analogous manner to Example 99 using Intermediate 114e (0.030 g, 0.060 mmol). Purified using preparative LC-MS with the following conditions: Column: XBridge C18, 19×200 mm, 5-μm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 17-57% B over 25 minutes, then a 6-minute hold at 100% B; Flow: 20 mL/min. Example 114 (0.0112 g, 0.022 mmol, 23%): LC-MS (Method A2) RT=0.83 min, MS (ESI) m/z: 491.2 (M+H)$^+$. $^1$H NMR (500 MHz, DMSO-d$_6$) δ 7.81-7.76 (m, 3H), 7.74-7.70 (m, 1H), 7.67 (s, 1H), 7.50 (t, J=7.6 Hz, 2H), 7.44-7.39 (m, 1H), 7.19 (br d, J=7.9 Hz, 2H), 7.06 (br d, J=7.9 Hz, 2H), 4.68 (s, 2H), 2.30 (t, J=7.3 Hz, 2H), 1.90-1.79 (m, 6H), 1.68 (br d, J=7.6 Hz, 2H), 1.58-1.50 (m, 2H), 0.86 (t, J=7.3 Hz, 3H). (1 exchangeable proton not observed).

Example 115: 3-((5'-(4-methoxypyridin-2-yl)-2'-(2H-tetrazol-5-yl)-[1,1'-biphenyl]-4-yl)methyl)-2-propyl-1,3-diazaspiro[4.4]non-1-en-4-one

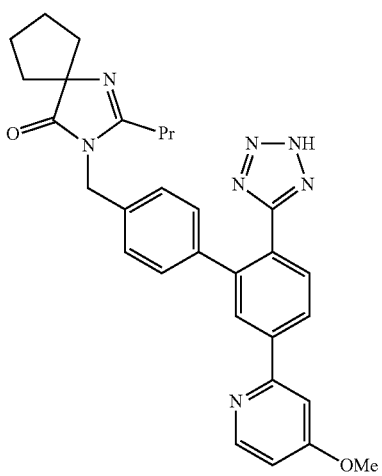

(Ex. 115)

Intermediate 115a: 5-(4-methoxypyridin-2-yl)-4'-((4-oxo-2-propyl-1,3-diazaspiro[4.4]non-1-en-3-yl)methyl)-[1,1'-biphenyl]-2-carbonitrile (115a)

Synthesized in an analogous manner to Example 110e using Intermediate 114d (0.030 g, 0.060 mmol) and 2-bromo-4-methoxypyridine (0.034 g, 0.181 mmol) to yield Intermediate 115a (0.030 g, 0.060 mmol, 100%). LC-MS (Method A2) RT=0.67 min, MS (ESI) m/z: 479.2 (M+H)$^+$.

Example 115: 3-((5'-(4-methoxypyridin-2-yl)-2'-(2H-tetrazol-5-yl)-[1,1'-biphenyl]-4-yl)methyl)-2-propyl-1,3-diazaspiro[4.4]non-1-en-4-one Synthesized in an analogous manner to Example 99 using Intermediate 115a (0.030 g, 0.060 mmol). Purified using preparative LC-MS with the following conditions: Column: XBridge C18, 19×200 mm, 5-m particles; Mobile Phase A: 5:95 ACN: H$_2$O with 10 mM NH$_4$OAc; Mobile Phase B: 95:5 ACN: H$_2$O with 10 mM NH$_4$OAc; Gradient: 8-48% B over 25 minutes, then a 6-minute hold at 100% B; Flow: 20 mL/min. Example 115 (0.0083 g, 0.016 mmol, 17.4%): LC-MS (Method A2) RT=0.59 min, MS (ESI) m/z: 522.2 (M+H)$^+$. $^1$H NMR (500 MHz, DMSO-d$_6$) δ 8.49 (d, J=5.6 Hz, 1H), 8.13 (dd, J=8.0, 1.6 Hz, 1H), 8.09 (d, J=1.4 Hz, 1H), 7.75 (d, J=8.0 Hz, 1H), 7.58 (d, J=2.1 Hz, 1H), 7.21 (d, J=8.1 Hz, 2H), 7.07 (d, J=8.1 Hz, 2H), 6.96 (dd, J=5.6, 2.3 Hz, 1H), 4.68 (s, 2H), 3.94 (s, 3H), 2.32 (t, J=7.3 Hz, 2H), 1.90-1.81 (m, 6H), 1.70 (br d, J=7.2 Hz, 2H), 1.63-1.53 (m, 2H), 0.89 (t, J=7.4 Hz, 3H) (1 exchangeable proton not observed).

Example 116: 3-((5'-(4-methylpyridin-2-yl)-2'-(2H-tetrazol-5-yl)-[1,1'-biphenyl]-4-yl)methyl)-2-propyl-1,3-diazaspiro[4.4]non-1-en-4-one

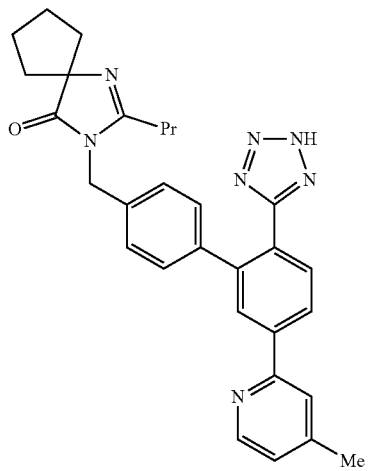

(ex. 116)

Intermediate 116a: 5-(4-methylpyridin-2-yl)-4'-((4-oxo-2-propyl-1,3-diazaspiro[4.4]non-1-en-3-yl)methyl)-[1,1'-biphenyl]-2-carbonitrile

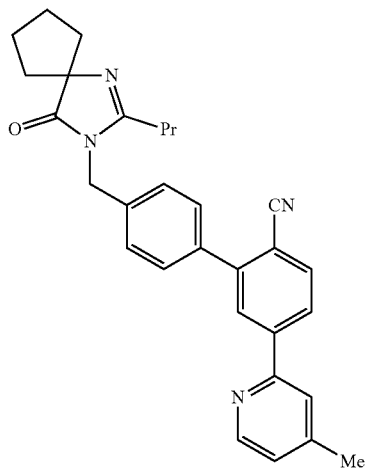

(116a)

Synthesized in an analogous manner to Example 110e using Intermediate 114d (0.030 g, 0.060 mmol) and 2-bromo-4-methylpyridine (0.031 g, 0.181 mmol) to yield Intermediate 116a (0.030 g, 0.060 mmol, 100%). LC-MS (Method A2) RT=0.75 min, MS (ESI) m/z: 463.2 (M+H)+.

Example 116: 3-((5'-(4-methylpyridin-2-yl)-2'-(2H-tetrazol-5-yl)-[1,1'-biphenyl]-4-yl)methyl)-2-propyl-1,3-diazaspiro[4.4]non-1-en-4-one Synthesized in an analogous manner to Example 99 using Intermediate 116a (0.030 g, 0.060 mmol). Purified using preparative LC-MS with the following conditions: Column: XBridge C18, 19×200 mm, 5-μm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 12-52% B over 20 minutes, then a 5-minute hold at 100% B; Flow: 20 mL/min. Example 116 (0.018 g, 0.035 mmol, 38%): LC-MS (Method A2) RT=1.21 min, MS (ESI) m/z: 506.3 (M+H)+. $^1$H NMR (500 MHz, DMSO-d$_6$) δ 8.53 (d, J=4.9 Hz, 1H), 8.13-8.08 (m, 1H), 8.04 (s, 1H), 7.90 (s, 1H), 7.75 (d, J=8.1 Hz, H), 7.25-7.17 (m, 3H), 7.05 (d, J=7.9 Hz, 2H), 4.68 (s, 2H), 2.41 (s, 3H), 2.33 (t, J=7.3 Hz, 2H), 1.92-1.83 (m, 6H), 1.70 (br d, J=6.9 Hz, 2H), 1.59 (sxt, J=7.3 Hz, 2H), 0.90 (t, J=7.4 Hz, 3H) (1 exchangeable proton not observed).

Example 117: (R)-3-((5'-(3-methylpiperidin-1-yl)-2'-(2H-tetrazol-5-yl)-[1,1'-biphenyl]-4-yl)methyl)-2-propyl-1,3-diazaspiro[4.4]non-1-en-4-one

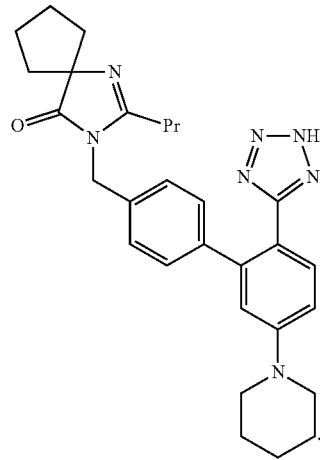

(Ex. 117)

Intermediate 117a: 2-propyl-3-(4-(4,4,5,5-tetramethyl-1,3,2-dioxaborolan-2-yl)benzyl)-1,3-diazaspiro[4.4]non-1-en-4-one

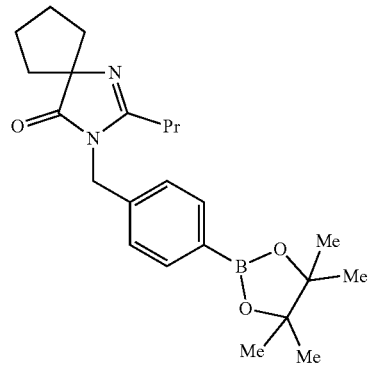

(117a)

Synthesized in an analogous manner to Example 110c using Intermediate 114b (0.555 g, 3.08 mmol) and 2-(4-(bromomethyl)phenyl)-4,4,5,5-tetramethyl-1,3,2-dioxaborolane (0.463 g, 1.558 mmol) to yield Intermediate 117a (0.214 g, 0.540 mmol, 42%). LC-MS (Method A2) RT=0.85 min, MS (ESI) m/z: 397.2 (M+H)+. $^1$H NMR (400 MHz, CDCl$_3$) δ 7.79 (d, J=8.1 Hz, 2H), 7.17 (d, J=8.1 Hz, 2H), 4.71 (s, 2H), 2.30-2.22 (m, 2H), 2.08-1.93 (m, 6H), 1.87-1.79 (m, 2H), 1.65-1.59 (m, 2H), 1.36 (s, 12H), 0.93 (t, J=7.4 Hz, 3H).

Intermediate 117b: 5-chloro-4'-((4-oxo-2-propyl-1,3-diazaspiro[4.4]non-1-en-3-yl)methyl)-[1,1'-biphenyl]-2-carbonitrile

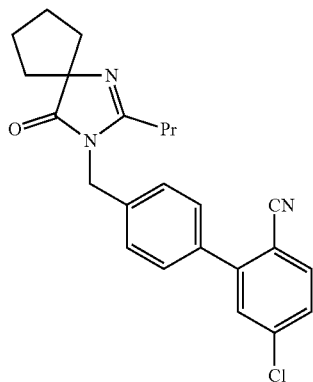

(117b)

To a microwave vial containing PdCl₂(dppf) (0.036 g, 0.049 mmol), Intermediate 117a (0.194 g, 0.489 mmol) and 4-chloro-2-iodobenzonitrile (0.168 g, 0.636 mmol) was added toluene (1.958 ml) followed by ethanol (0.489 ml) and K₃PO₄ (2 M, aq.) (0.489 ml, 0.979 mmol). N₂ was sparged through the reaction mixture for 5 min before the vial was sealed and heated at 110° C. for 18 hours. The reaction mixture was diluted with EtOAc and washed with sat. NaHCO₃. The organic phase was concentrated and purified by ISCO (0-100% EtOAc in hexanes) to afford Intermediate 117b (0.181 g, 0.446 mmol, 91% yield) as a yellow oil. LC-MS (Method A2) RT=0.80 min, MS (ESI) m/z: 406.1 (M+H)⁺. ¹H NMR (400 MHz, CDCl₃) δ 7.72 (d, J=8.1 Hz, 1H), 7.55 (d, J=8.4 Hz, 2H), 7.52 (d, J=1.8 Hz, 1H), 7.46 (dd, J=8.4, 2.2 Hz, 1H), 7.32 (d, J=8.6 Hz, 2H), 4.77 (s, 2H), 2.37-2.32 (m, 2H), 2.10-1.97 (m, 6H), 1.90-1.83 (m, 2H), 1.72-1.63 (m, 2H), 0.97 (t, J=7.5 Hz, 3H).

Intermediate 117c: (R)-5-(3-methylpiperidin-1-yl)-4'-((4-oxo-2-propyl-1,3-diazaspiro[4.4]non-1-en-3-yl)methyl)-[1,1'-biphenyl]-2-carbonitrile

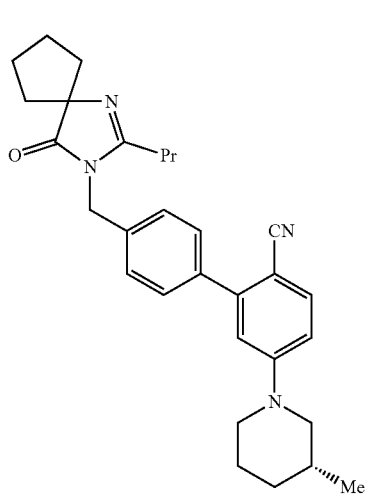

(117c)

Synthesized in an analogous manner to Intermediate 99b using Intermediate 117b (0.040 g, 0.099 mmol) and (R)-3-methylpiperidine (0.0097 g, 0.099 mmol) to yield Intermediate 117c (0.032 g, 0.069 mmol, 70%). LC-MS (Method A2) RT=1.01 min, MS (ESI) m/z: 469.3 (M+H)⁺. ¹H NMR (400 MHz, CDCl₃) δ 7.57 (d, J=8.8 Hz, 1H), 7.54 (d, J=8.4 Hz, 2H), 7.26 (s, 2H), 6.88-6.82 (m, 2H), 4.75 (s, 2H), 3.90-3.70 (m, 2H), 2.87 (td, J=12.3, 3.1 Hz, 1H), 2.56 (dd, J=12.7, 10.7 Hz, 1H), 2.36 (dd, J=8.3, 7.2 Hz, 2H), 2.11-1.93 (m, 7H), 1.89-1.81 (m, 3H), 1.81-1.62 (m, 4H), 1.23-1.11 (m, 1H), 1.03-0.91 (m, 6H).

Example 117: (R)-3-((5'-(3-methylpiperidin-1-yl)-2'-(2H-tetrazol-5-yl)-[1,1'-biphenyl]-4-yl)methyl)-2-propyl-1,3-diazaspiro[4.4]non-1-en-4-one Synthesized in an analogous manner to Example 99 using Intermediate 117c (0.032 g, 0.069 mmol). Purified using preparative LC-MS with the following conditions: Column: XBridge C18, 19×200 mm, 5-μm particles; Mobile Phase A: 5:95 ACN: H₂O with 10 mM NH₄OAc; Mobile Phase B: 95:5 ACN: H₂O with 10 mM NH₄OAc; Gradient: 33-58% B over 25 minutes, then a 2-minute hold at 100% B; Flow: 20 mL/min. Example 117 (0.0049 g, 0.0093 mmol, 13%): LC-MS (Method A2) RT=0.81 min, MS (ESI) m/z: 512.3 (M+H)⁺. ¹H NMR (500 MHz, DMSO-d₆) δ 7.43 (br s, 1H), 7.10 (br s, 2H), 7.02 (br d, J=6.9 Hz, 3H), 6.85 (br s, 1H), 4.65 (s, 2H), 3.72 (br t, J=12.0 Hz, 2H), 2.29 (br t, J=7.2 Hz, 2H), 1.94-1.77 (m, 10H), 1.74-1.64 (m, 4H), 1.56 (dt, J=14.6, 7.3 Hz, 2H), 1.09 (br dd, J=11.5, 2.9 Hz, 1H), 0.93 (d, J=6.5 Hz, 3H), 0.88 (t, J=7.3 Hz, 3H) (1 exchangeable proton not observed).

Example 118: 2-isopropyl-3-((5'-(4-methylpyridin-2-yl)-2'-(2H-tetrazol-5-yl)-[1,1'-biphenyl]-4-yl)methyl)-1,3-diazaspiro[4.4]non-1-en-4-one

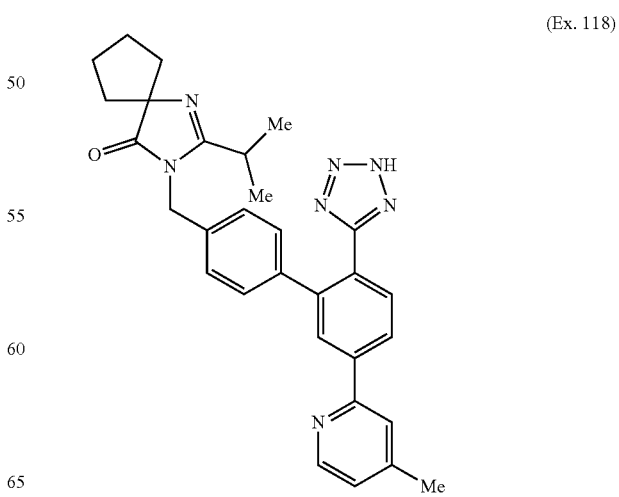

(Ex. 118)

Intermediate 118a:

1-isobutyramidocyclopentane-1-carboxamide

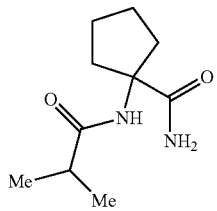

(118a)

To a solution of 1-aminocyclopentane-1-carboxamide (1.00 g, 7.80 mmol) in DCM (16 mL) was added TEA (2.72 mL, 19.50 mmol). The mixture was cooled with an ice bath. Isobutyryl chloride (1.164 g, 10.92 mmol) in DCM (4 mL) was added dropwise to the stirred solution, and the reaction mixture was at RT for 18 hours. The reaction was diluted with H$_2$O and DCM. The organic phase was collected. The aqueous phase was extracted (2X) with DCM. The combined organic phase was washed with brine, dried over sodium sulfate, and concentrated to give Intermediate 118a (998 mg, 5.03 mmol, 64.5% yield) as a solid. RT=0.52 min, MS (ESI) m/z: 199.1 (M+H)$^+$. $^1$H NMR (400 MHz, CDCl$_3$) δ 5.64 (br s, 1H), 5.55 (br s, 2H), 2.47-2.29 (m, 4H), 2.08-2.00 (m, 2H), 1.92-1.83 (m, 2H), 1.78-1.75 (m, 1H), 1.17 (d, J=6.8 Hz, 6H).

Intermediate 118b:

2-isopropyl-1,3-diazaspiro[4.4]non-1-en-4-one

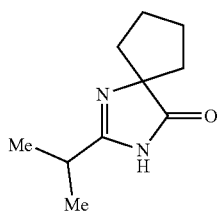

(118b)

Synthesized in an analogous manner to Example 110b using Intermediate 118a (0.548 g, 2.76 mmol) to yield Intermediate 118b (0.448 g, 2.485 mmol, 90%). LC-MS (Method A2) RT=0.44 min, MS (ESI) m/z: 181.0 (M+H)$^+$. $^1$H NMR (400 MHz, CDCl$_3$) δ 2.76 (dt, J=14.0, 7.0 Hz, 1H), 2.01-1.88 (m, 6H), 1.83 (br d, J=2.4 Hz, 2H), 1.25 (d, J=7 Hz, 6H).

Intermediate 118c: 5-bromo-4'-((2-isopropyl-4-oxo-1,3-diazaspiro[4.4]non-1-en-3-yl)methyl)-[1,1'-biphenyl]-2-carbonitrile

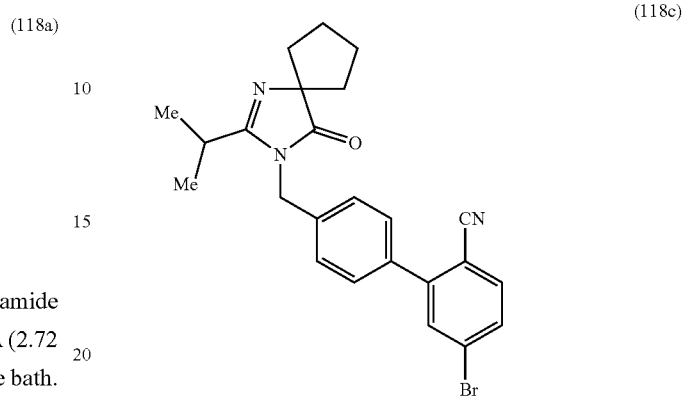

(118c)

Synthesized in an analogous manner to Example 110c using Intermediate 118b (0.536 g, 2.97 mmol) and Intermediate I-002 (1.253 g, 3.57 mmol) to yield Intermediate 118c (0.899 g, 1.996 mmol, 67%). LC-MS (Method A2) RT=0.85 min, MS (ESI) m/z: 450.1 (M+H). $^1$H NMR (400 MHz, CDCl$_3$) δ 7.67 (d, J=1.1 Hz, 1H), 7.62-7.59 (m, 2H), 7.52 (d, J=8.1 Hz, 2H), 7.28 (s, 2H), 4.77 (s, 2H), 2.59 (dt, J=13.6, 6.7 Hz, 1H), 2.04-1.92 (m, 6H), 1.89-1.81 (m, 2H), 1.17 (d, J=6.8 Hz, 6H).

Intermediate 118d 4'-((2-isopropyl-4-oxo-1,3-diazaspiro[4.4]non-1-en-3-yl)methyl)-5-(4,4,5,5-tetramethyl-1,3,2-dioxaborolan-2-yl)-[1,1'-biphenyl]-2-carbonitrile

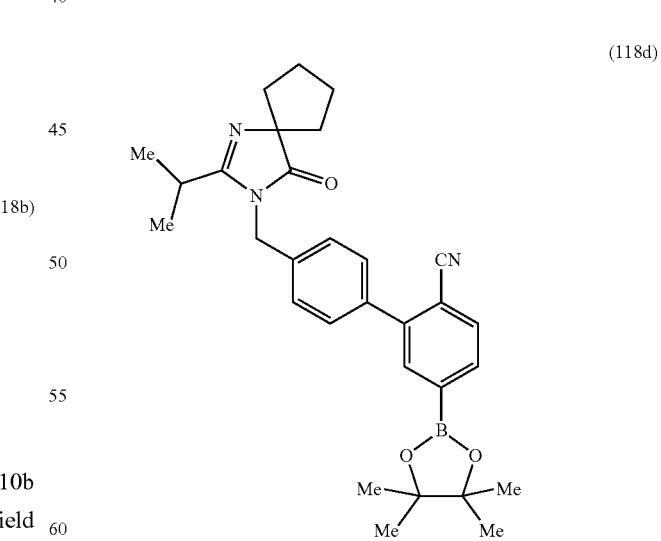

(118d)

Synthesized in an analogous manner to Example 110d using Intermediate 118c (0.400 g, 1.776 mmol) to yield Intermediate 118d (0.398 g, 0.800 mmol, 90%). $^1$H NMR (400 MHz, CDCl$_3$) δ 7.90 (s, 1H), 7.84 (dd, J=7.7, 1.1 Hz, 1H), 7.74 (d, J=7.7 Hz, 1H), 7.55 (d, J=8.4 Hz, 2H), 7.24 (s, 2H), 4.77 (s, 2H), 2.65-2.55 (m, 1H), 2.05-1.93 (m, 6H), 1.88-1.80 (m, 2H), 1.26-1.24 (m, 12H), 1.17 (d, J=6.8 Hz, 6H).

Intermediate 118e: 4'-((2-isopropyl-4-oxo-1,3-diazaspiro[4.41non-1-en-3-yl)methyl)-5-(4-methylpyridin-2-yl)-[1,1'-biphenyl]-2-carbonitrile

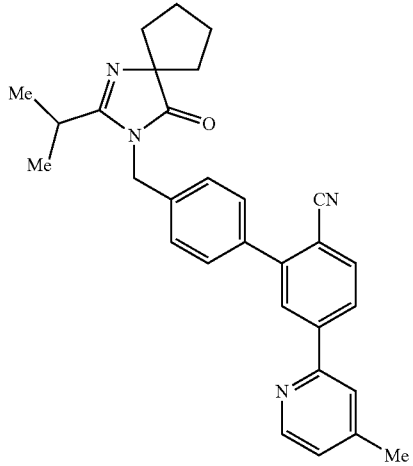

(118e)

Synthesized in an analogous manner to Example 110e using Intermediate 118d (0.050 g, 0.101 mmol) and 2-bromo-4-methylpyridine (0.052 g, 0.302 mmol) to yield Intermediate 118e (0.040 g, 0.086 mmol, 86%). LC-MS (Method A2) RT=0.75 min, MS (ESI) m/z: 463.1 (M+H)+.

Example 118: 2-isopropyl-3-((5'-(4-methylpyridin-2-yl)-2'-(2H-tetrazol-5-yl)-[1,1'-biphenyl]-4-yl)methyl)-1,3-diazaspiro[4.41non-1-en-4-one Synthesized in an analogous manner to Example 99 using Intermediate 118e (0.040 g, 0.086 mmol). Purified using preparative LC-MS with the following conditions: Column: XBridge C18, 19×200 mm, 5-µm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 12-52% B over 22 minutes, then a 4-minute hold at 100% B; Flow: 20 mL/min. Example 118 (0.0078 g, 0.015 mmol, 16%): LC-MS (Method A2) RT=0.68 min, MS (ESI) m/z: 506.2 (M+H)+. $^1$H NMR (500 MHz, DMSO-d$_6$) δ 8.54 (d, J=4.9 Hz, 1H), 8.17 (br d, J=8.1 Hz, 1H), 8.11 (s, 1H), 7.94 (s, 1H), 7.76 (d, J=8.1 Hz, 1H), 7.31-7.16 (m, 3H), 7.08 (d, J=8.1 Hz, 2H), 4.72 (s, 2H), 2.67 (dt, J=13.6, 6.6 Hz, 1H), 2.42 (s, 3H), 1.93-1.78 (m, 6H), 1.69 (br d, J=7.6 Hz, 2H), 1.06 (d, J=6.7 Hz, 6H) (1 exchangeable proton not observed).

Example 119: 2-cyclopropyl-3-((5'-(4-methoxypyridin-2-yl)-2'-(2H-tetrazol-5-yl)-[1,1'-biphenyl]-4-yl)methyl)-1,3-diazaspiro[4.4]non-1-en-4-one

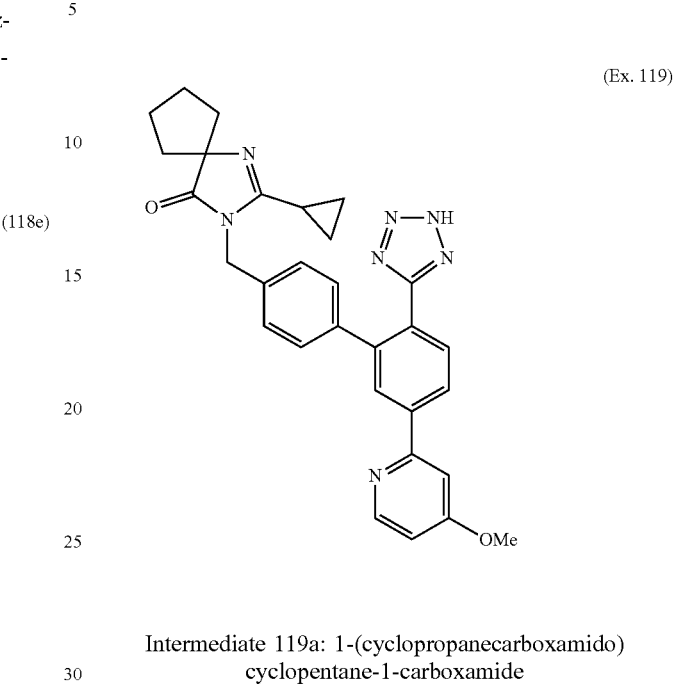

(Ex. 119)

Intermediate 119a: 1-(cyclopropanecarboxamido)cyclopentane-1-carboxamide

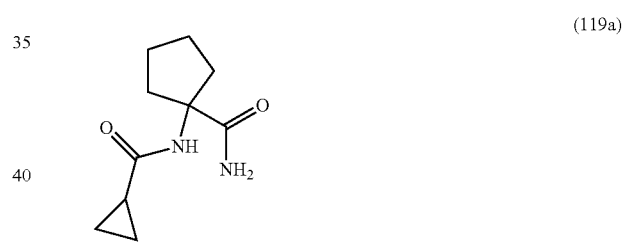

(119a)

To a solution of 1-aminocyclopentane-1-carboxamide (1.00 g, 7.80 mmol) in DCM (16 mL) was added TEA (2.72 mL, 19.50 mmol). The mixture was cooled with an ice bath.

Cyclopropanecarbonyl chloride (1.142 g, 10.92 mmol) in DCM (4 mL) was added dropwise to the stirred solution, and the reaction mixture was at RT for 18 hours. The reaction was diluted with H$_2$O and DCM. The organic phase was collected. The aqueous phase was extracted (2X) with DCM. The combined organic phase was washed with brine, dried over sodium sulfate, and concentrated to give Intermediate 119a (0.889 g, 4.53 mmol, 58.1% yield) as a solid. RT=0.49 min, MS (ESI) m/z: 197.1 (M+H)+. $^1$H NMR (400 MHz, CDCl$_3$) δ 5.91 (br s, 2H), 5.76-5.57 (m, 1H), 2.49-2.25 (m, 1H), 2.07 (br d, J=16.7 Hz, 1H), 1.93-1.74 (m, 2H), 1.67-1.28 (m, 2H), 1.28-1.19 (m, 2H), 1.03-0.97 (m, 2H), 0.90-0.82 (m, 2H), 0.81-0.74 (m, 1H).

Intermediate 119b: 2-cyclopropyl-1,3-diazaspiro[4.4]non-1-en-4-one

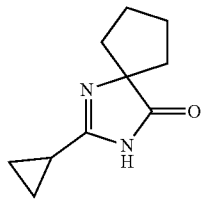

(119b)

Synthesized in an analogous manner to Example 110b using Intermediate 119a (0.599 g, 3.06 mmol) to yield Intermediate 119b (0.258 g, 0.1.448 mmol, 47%). LC-MS (Method A2) RT=0.43 min, MS (ESI) m/z: 178.0 (M+H)$^+$. $^1$H NMR (400 MHz, CDCl$_3$) δ 2.00-1.86 (m, 3H), 1.85-1.72 (m, 2H), 1.30-1.22 (m, 1H), 1.08-1.01 (m, 3H), 0.97-0.89 (m, 1H).

Intermediate 119c: 5-bromo-4'-((2-cyclopropyl-4-oxo-1,3-diazaspiro[4.4]non-1-en-3-yl)methyl)-[1,1'-biphenyl]-2-carbonitrile

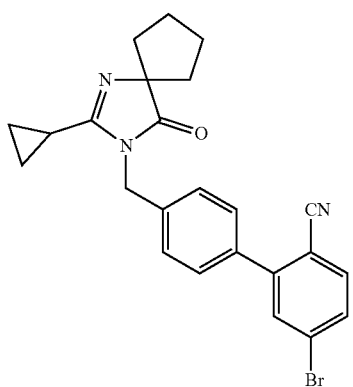

(119c)

Synthesized in an analogous manner to Example 110c using Intermediate 119b (0.473 g, 2.65 mmol) and Intermediate I-002 (1.12 g, 3.19 mmol) to yield Intermediate 119c (0.510 g, 1.14 mmol, 43%). LC-MS (Method A2) RT=0.84 min, MS (ESI) m/z: 449.1 (M+H)$^+$. $^1$H NMR (400 MHz, CDCl$_3$) δ 7.67 (dd, J=1.8, 0.7 Hz, 1H), 7.62-7.60 (m, 2H), 7.52 (d, J=8.4 Hz, 2H), 7.34 (d, J=8.4 Hz, 2H), 4.87 (s, 2H), 2.01-1.89 (m, 6H), 1.80-1.72 (m, 2H), 1.49 (tt, J=8.2, 5.0 Hz, 1H), 1.00-0.94 (m, 2H), 0.89-0.82 (m, 2H).

Intermediate 119d: 4'-((2-cyclopropyl-4-oxo-1,3-diazaspiro[4.4]non-1-en-3-yl)methyl)-5-(4,4,5,5-tetramethyl-1,3,2-dioxaborolan-2-yl)-[1,1'-biphenyl]-2-carbonitrile

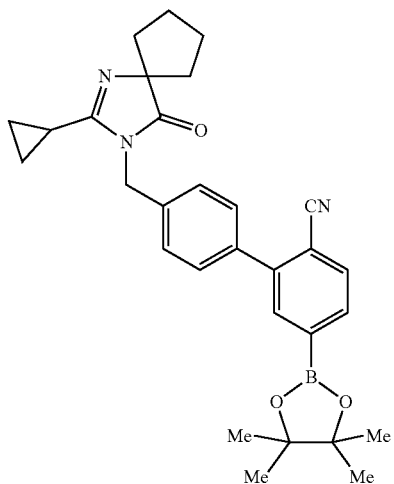

(119d)

Synthesized in an analogous manner to Example 110d using Intermediate 119c (0.510 g, 1.137 mmol) to yield Intermediate 119d (0.448 g, 0.904 mmol, 79%). $^1$H NMR (400 MHz, CDCl$_3$) δ 7.91 (s, 1H), 7.85 (dd, J=7.7, 1.1 Hz, 1H), 7.77-7.71 (m, 1H), 7.58-7.53 (m, 2H), 7.31 (d, J=8.4 Hz, 2H), 4.86 (s, 2H), 2.02-1.91 (m, 6H), 1.80-1.74 (m, 2H), 1.53-1.47 (m, 1H), 1.26 (d, J=3.3 Hz, 12H), 1.00-0.94 (m, 2H), 0.89-0.82 (m, 2H).

Intermediate 119e: 4'-((2-cyclopropyl-4-oxo-1,3-diazaspiro[4.4]non-1-en-3-yl)methyl)-5-(4-methoxypyridin-2-yl)-[1,1'-biphenyl]-2-carbonitrile

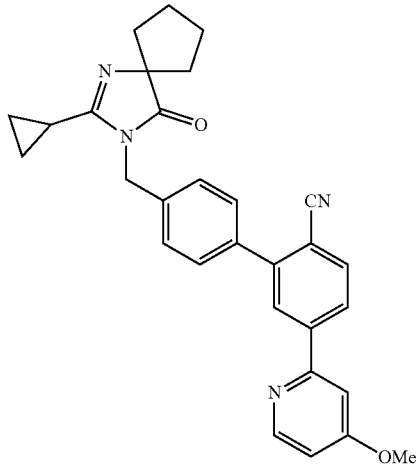

(119e)

Synthesized in an analogous manner to Example 110e using Intermediate 119d (0.051 g, 0.272 mmol) and 2-bromo-4-methoxy-pyridine (0.052 g, 0.272 mmol) to yield Intermediate 119e (0.040 g, 0.084 mmol, 92%). LC-MS (Method A2) RT=0.66 min, MS (ESI) m/z: 477.1 (M+H)$^+$.

Example 119: 2-cyclopropyl-3-((5'-(4-methoxypyridin-2-yl)-2'-(2H-tetrazol-5-yl)-[1,1'-biphenyl]-4-yl)methyl)-1,3-diazaspiro[4.4]non-1-en-4-one Synthesized in an analogous manner to Example 99 using Intermediate 119e (0.040 g, 0.084 mmol). Purified using preparative LC-MS with the following conditions: Column: XBridge C18, 19×200 mm, 5-μm particles; Mobile Phase A: 5:95 ACN: $H_2O$ with 0.1% trifluoroacetic acid; Mobile Phase B: 95:5 ACN: $H_2O$ with 0.1% trifluoroacetic acid; Gradient: 0-40% B over 22 minutes, then a 4-minute hold at 100% B; Flow: 20 mL/min.

Example 119 (0.0025 g, 0.0048 mmol, 5%): LC-MS (Method A2) RT=0.58 min, MS (ESI) m/z: 520.1 (M+H)$^+$. $^1$H NMR (500 MHz, DMSO-d$_6$) δ 8.51 (d, J=5.5 Hz, 1H), 8.20 (br d, J=7.9 Hz, 1H), 8.16 (s, 1H), 7.75 (d, J=8.2 Hz, 1H), 7.64 (d, J=1.8 Hz, 1H), 7.22-7.17 (m, 2H), 7.16-7.11 (m, 2H), 6.99 (dd, J=5.5, 2.1 Hz, 1H), 4.81 (s, 2H), 3.94 (s, 3H), 1.86-1.78 (m, 6H), 1.72 (br t, J=5.3 Hz, 1H), 1.62 (br d, J=7.0 Hz, 2H), 0.86-0.76 (m, 4H) (1 exchangeable proton not observed).

Example 120: $^2$-cyclopropyl-3-((5'-(4-methylpyridin-2-yl)-2'-(2H-tetrazol-5-yl)-[1,1'-biphenyl]-4-yl)methyl)-1,3-diazaspiro[4.4]non-1-en-4-one

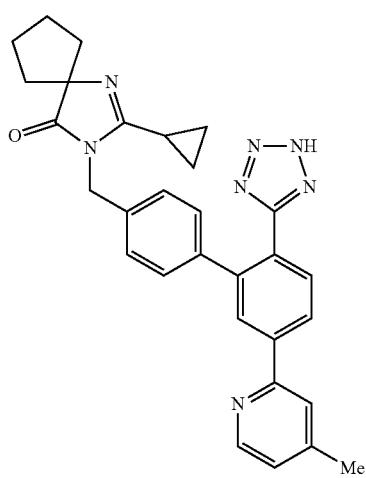

(ex. 120)

Intermediate 120a: 4'-((2-cyclopropyl-4-oxo-1,3-diazaspiro[4.4]non-1-en-3-yl)methyl)-5-(4-methylpyridin-2-yl)-[1,1'-biphenyl]-2-carbonitrile

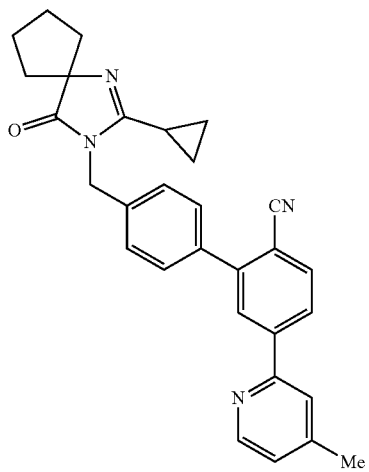

(120a)

Synthesized in an analogous manner to Example 110e using Intermediate 119d (0.045 g, 0.091 mmol) and 2-bromo-4-methylpyridine (0.047 g, 0.272 mmol) to yield Intermediate 120a (0.040 g, 0.087 mmol, 96%). LC-MS (Method A2) RT=0.74 min, MS (ESI) m/z: 461.1 (M+H)$^+$.

Example 120: $^2$-cyclopropyl-3-((5'-(4-methylpyridin-2-yl)-2'-(2H-tetrazol-5-yl)-[1,1'-biphenyl]-4-yl)methyl)-1,3-diazaspiro[4.4]non-1-en-4-one Synthesized in an analogous manner to Example 99 using Intermediate 120a (0.040 g, 0.087 mmol). Purified using preparative LC-MS with the following conditions: Column: XBridge C18, 19×200 mm, 5-μm particles; Mobile Phase A: 5:95 ACN: $H_2O$ with 10 mM NH$_4$OAc; Mobile Phase B: 95:5 ACN: $H_2O$ with 10 mM NH$_4$OAc; Gradient: 10-50% B over 19 minutes, then a 5-minute hold at 100% B; Flow: 20 mL/min. Example 120 (0.0022 g, 0.00384 mmol, 3.9%): LC-MS (Method A2) RT=0.62 min, MS (ESI) m/z: 504.1 (M+H)$^+$. $^1$H NMR (500 MHz, DMSO-d$_6$) δ 8.54 (br d, J=4.6 Hz, 1H), 8.19 (br s, 1H), 8.13 (br s, 1H), 7.97 (br s, 1H), 7.76 (br s, 1H), 7.23 (br d, J=4.6 Hz, 1H), 7.17 (br s, 2H), 7.13 (br s, 2H), 4.80 (s, 2H), 2.41 (s, 3H), 1.86-1.78 (m, 6H), 1.75-1.66 (m, 2H), 1.61 (br s, 2H), 0.84-0.79 (m, 3H). (1 exchangeable proton not observed).

Example 121: 3-(4'-((2-butyl-4-oxo-1,3-diazaspiro[4.4]non-1-en-3-yl)methyl)-5-(3,3-difluoropiperidin-1-yl)-[1,1'-biphenyl]-2-yl)-1,2,4-oxadiazol-5(4H)-one

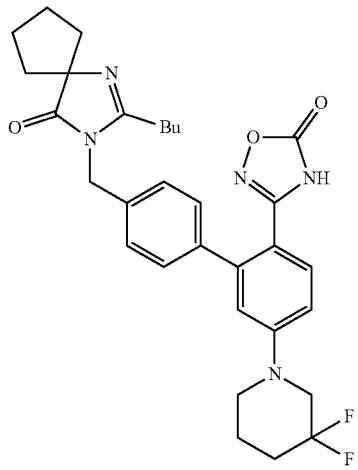
(Ex. 121)

Intermediate 121a: 4'-((2-butyl-4-oxo-1,3-diazaspiro[4.4]non-1-en-3-yl)methyl)-5-(3,3-difluoropiperidin-1-yl)-[1,1'-biphenyl]-2-carbonitrile

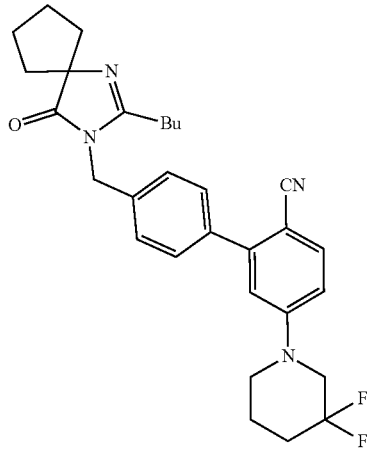
(121a)

Synthesized in an analogous manner to Intermediate 99b using Intermediate 99a (0.135 g, 0.321 mmol) and 3,3-difluoropiperidine hydrochloride (0.025 g, 0.032 mmol) to yield Intermediate 121a (0.100 g, 0.198 mmol, 62%). LC-MS (Method A2) RT=0.94 min, MS (ESI) m/z: 505.1 (M+H)$^+$. $^1$H NMR (400 MHz, CDC$_3$) δ7.59 (d, J=8.6 Hz, 1H), 7.52 (d, J=8.1 Hz, 2H), 7.26 (d, J=7.9 Hz, 2H), 6.91-6.83 (m, 2H), 4.74 (s, 2H), 3.59 (t, J=11.4 Hz, 2H), 3.45-3.38 (m, 2H), 2.39-2.31 (m, 2H), 2.16-1.80 (m, 12H), 1.61 (dt, J=15.5, 7.6 Hz, 2H), 1.35 (dq, J=15.0, 7.4 Hz, 2H), 0.88 (t, J=7.3 Hz, 3H).

Intermediate 121b: (Z)-4'-((2-butyl-4-oxo-1,3-diazaspiro[4.4]non-1-en-3-yl)methyl)-5-(3,3-difluoropiperidin-1-yl)-N'-hydroxy-[1,1'-biphenyl]-2-carboximidamide

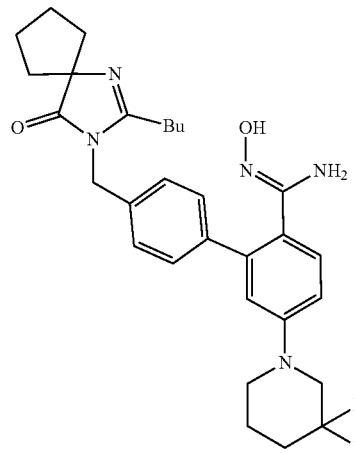
(121b)

To a vial containing hydroxylamine hydrochloride (174 mg, 2.497 mmol) and potassium t-butoxide (233 mg, 2.081 mmol) was added ethanol (2081 μl). The mixture was stirred vigorously at RT for 1 min before being pipetted into a vial containing Intermediate 121a (105 mg, 0.208 mmol). The reaction was heated at 85° C. for 48 hours. The reaction mixture was diluted with DCM and washed with H$_2$O. The organic phase was concentrated and azeotroped with toluene to yield Intermediate 121b (0.015 g, 0.028 mmol, 13%) which was used without further purification in the next step. LC-MS (Method A2) RT=0.79 min, MS (ESI) m/z: 538.1 (M+H)$^+$.

Example 121: 3-(4'-((2-butyl-4-oxo-1,3-diazaspiro[4.4]non-1-en-3-yl)methyl)-5-(3,3-difluoropiperidin-1-yl)-[1,1'-biphenyl]-2-yl)-1,2,4-oxadiazol-5(4H)-one To a vial charged with Intermediate 121b (15 mg, 0.028 mmol) was added DMF (2 mL) followed by DBU (0.021 mL, 0.139 mmol) and CDI (22.62 mg, 0.139 mmol). The reaction was allowed to stir at RT for 18 hours. The reaction was filtered and concentrated. The crude reaction mixture was dissolved in 2 mL of DMF. The crude material was purified via preparative LC-MS with the following conditions: Column: XBridge C18, 19×200 mm, 5-μm particles; Mobile Phase A: 5:95 ACN: H$_2$O with 0.1% trifluoroacetic acid; Mobile Phase B: 95:5 ACN: H$_2$O with 0.1% trifluoroacetic acid; Gradient: 20-65% B over 30 minutes, then a 3-minute hold at 100% B; Flow: 20 mL/min to yield Example 121 (0.005 g, 0.0085 mmol, 31%): LC-MS (Method A2) RT=0.92 min, MS (ESI) m/z: 564.1 (M+H)$^+$. $^1$H NMR (500 MHz, DMSO-d$_6$) δ 7.44 (d, J=8.5 Hz, 1H), 7.30 (d, J=7.6 Hz, 2H), 7.16 (d, J=7.9 Hz, 2H), 7.10 (d, J=8.5 Hz, 1H), 6.92 (br. s., 1H), 4.72 (s, 2H), 3.69 (t, J=11.6 Hz, 2H), 3.51 (d, J=7.9 Hz, 1H), 3.42 (br. s., 1H), 2.33 (t, J=7.3 Hz, 2H), 2.07 (br. s., 2H), 1.90-1.81 (m, 6H), 1.77 (br. s., 2H), 1.68 (br. s., 2H), 1.56-1.41 (m, 2H), 1.34-1.24 (m, 2H), 0.80 (t, J=7.3 Hz, 3H) (one exchangeable proton not observed).

Example 122: 2-butyl-3-((4"-methyl-6'-(2H-tetrazol-5-yl)-[1,1':3',1"-terphenyl]4-yl)methyl)-1,3-diazaspiro[4.4]non-1-en-4-one

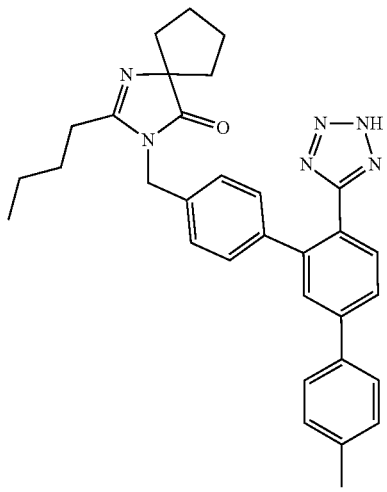

(ex. 122)

Intermediate 122a: 4'-((2-butyl-4-oxo-1,3-diazaspiro[4.4]non-1-en-3-yl)methyl)-5-chloro-[1,1'-biphenyl]-2-carbonitrile

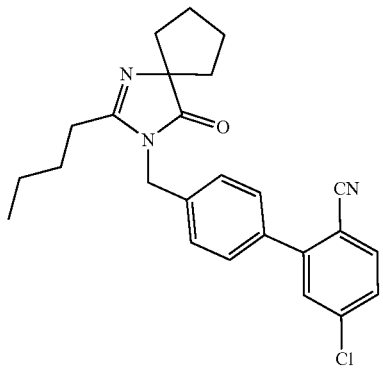

(122a)

Intermediate 033a (1.21 g, 2.95 mmol), 4-chloro-2-iodobenzonitrile (0.932 g, 3.54 mmol), and PdCl₂(dppf)-CH₂Cl₂Adduct (0.241 g, 0.295 mmol) were dissolved in toluene (23.6 mL), ethanol (5.90 mL), and tripotassium phosphate (2 M aq, 2.95 mL, 5.90 mmol) and the reaction was degassed for 15 minutes by bubbling with Ar. The reaction was sealed and heated at 100° C. for 18 hours. The reaction was cooled to ambient temperature, filtered through celite, diluted with EtOAc, washed with saturated NaHCO₃, then brine, dried (Na₂SO₄), filtered, and concentrated in vacuo. The crude material was purified by column chromatography (ISCO, 80 g silica gel column, 29 minute gradient of 0 to 100% EtOAc in hexanes) to give Intermediate 122a (1.03 g, 2.45 mmol, 83%). LC-MS (Method A2) RT=1.00 min, MS (ESI) m/z: 420.3 (M+H)⁺. ¹H NMR (500 MHz, CDCl₃) δ 7.72 (d, J=8.3 Hz, 1H), 7.58-7.54 (m, 2H), 7.52 (d, J=2.2 Hz, 1H), 7.46 (dd, J=8.4, 2.1 Hz, 1H), 7.32 (d, J=8.3 Hz, 2H), 4.77 (s, 2H), 2.40-2.33 (m, 2H), 2.06-1.94 (m, 6H), 1.90-1.83 (m, 2H), 1.67-1.60 (m, 2H), 1.42-1.33 (m, 2H), 0.90 (t, J=7.4 Hz, 3H).

Intermediate 122b: 2-butyl-3-((5'-chloro-2'-(2H-tetrazol-5-yl)-[1,1'-biphenyll-4-yl)methyl)-1,3-diazaspiro[4.4]non-1-en-4-one

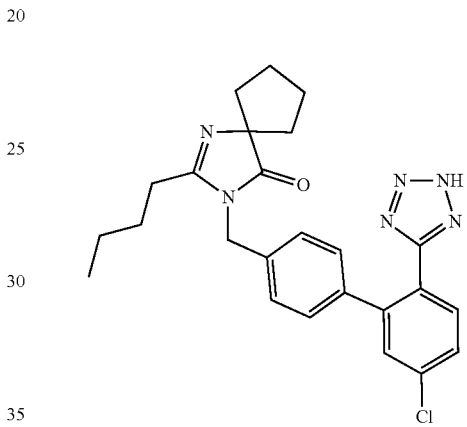

(122b)

Intermediate 122a (1.03 g, 2.45 mmol) was dissolved in toluene (24.5 mL). Dibutyltin oxide (0.611 g, 2.45 mmol) and TMS-N₃ (1.63 mL, 12.3 mmol) were added. The reaction was sealed in a pressure vial and heated at 100° C. for 18 hours. The reaction was cooled to ambient temperature and diluted with EtOAc into a large erlenmeyer. A 10% aqueous solution of ceric ammonium nitrate (6.72 g, 12.3 mmol) was added slowly to mild bubbling. An aliquot of the reaction was added to an aqueous 0.02 M iron trichloride solution to confirm complete consumption of azide (no red color). The layers were separated and the organic layer was further washed twice with saturated NH₄C₁, then brine, dried (Na₂SO₄), filtered, and concentrated in vacuo. The crude material was purified by column chromatography (ISCO, 40 g silica gel olumn, 19 minute gradient of 0 to 20% MeOH in DCM) to give Intermediate 122b (0.946 g, 2.04 mmol, 83%) as a tan solid. LC-MS (Method A2) RT=0.93 min, MS (ESI) m/z: 463.3 (M+H)⁺. ¹H NMR (500 MHz, CDCl₃) δ 8.03 (d, J=8.5 Hz, 1H), 7.56 (dd, J=8.3, 2.2 Hz, 1H), 7.47 (d, J=2.2 Hz, 1H), 7.25-7.17 (m, 4H), 4.73 (s, 2H), 2.33-2.27 (m, 2H), 2.06 (d, J=6.6 Hz, 1H), 1.99-1.93 (m, 2H), 1.93-1.86 (m, 4H), 1.80 (dd, J=11.6, 5.0 Hz, 3H), 1.58 (dt, J=15.3, 7.6 Hz, 2H), 1.39-1.30 (m, 2H), 0.88 (t, J=7.3 Hz, 3H)

Intermediate 122c: 2-butyl-3-((5'-chloro-2'-(2-trityl-2H-tetrazol-5-yl)-[1,1'-biphenyl]-4-yl)methyl)-1,3-diazaspiro[4.4]non-1-en-4-one

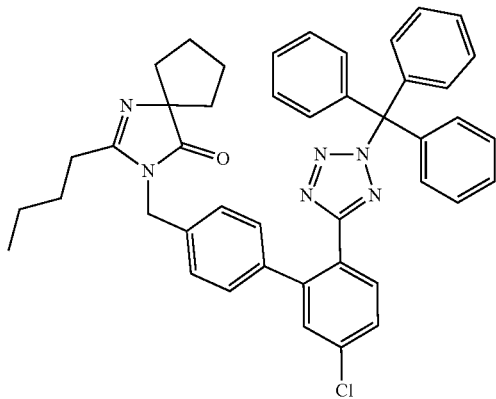

(122c)

Intermediate 122b (0.900 g, 1.94 mmol), TEA (0.352 mL, 2.53 mmol) and tritylchloride (0.623 g, 2.24 mmol) were dissolved in DCM (9.72 mL). After stirring for 3 hours, the reaction was diluted with DCM and washed with 1M $K_2HPO_4$, then brine, then dried ($Na_2SO_4$), filtered, and concentrated in vacuo. The crude material was purified by column chromatography (ISCO, 80 g silica gel column, 29 minute gradient of 0 to 100% EtOAc in hexanes) to give Intermediate 122c (0.879 g, 1.25 mmol, 63%) as a white solid. LC-MS (Method A2) RT=1.26 min, MS (ESI) m/z: 705.5 (M+H)+. $^1$H NMR (500 MHz, $CDCl_3$) δ 7.92 (d, J=8.5 Hz, 1H), 7.46 (dd, J=8.3, 2.2 Hz, 1H), 7.41-7.35 (m, 4H), 7.32-7.27 (m, 6H), 7.11 (d, J=8.0 Hz, 2H), 6.97-6.90 (m, 8H), 2.25 (t, J=7.8 Hz, 2H), 2.06-1.95 (m, 6H), 1.84 (br. s., 2H), 1.61-1.52 (m, 2H), 1.34-1.26 (m, 2H), 0.87 (t, J=7.3 Hz, 3H).

Example 122: 2-butyl-3-((4''-methyl-6'-(2H-tetrazol-5-yl)-[1,1':3',1''-terphenyl]-4-yl)methyl)-1,3-diazaspiro[4.4]non-1-en-4-one Intermediate 122c (20 mg, 0.028 mmol), β-tolylboronic acid (11.6 mg, 0.085 mmol), and 2nd Generation XPHOS Precatalyst (2.23 mg, 2.84 μmol) were dissolved in toluene (1.13 mL), EtOH (284 μL), and tripotassium phosphate (2 M aq, 28.4 μL, 0.057 mmol).

The reaction was heated at 100° C. for 18 hours. The reaction was cooled to ambient temperature then diluted with EtOAc, filtered through celite/$Na_2SO_4$ and concentrated in vacuo. The residue was dissolved in DCM (1.42 mL). Triethylsilane (22.6 μL, 0.142 mmol) and TFA (109 μL, 1.42 mmol) were added. After 30 minutes, the reaction was concentrated in vacuo. The crude material was purified via preparative LC-MS with the following conditions: Column: XBridge C18, 19×200 mm, 5-m particles; Mobile Phase A: 5:95 ACN: $H_2O$ with 0.1% trifluoroacetic acid; Mobile Phase B: 95:5 ACN: $H_2O$ with 0.1% trifluoroacetic acid; Gradient: 40-80% B over 19 minutes, then a 5-minute hold at 100% B; Flow: 20 mL/min to give Example 122 (3.9 mg, 7.14 μmol, 25%). LC-MS (Method A2) RT=1.14 min, MS (ESI) m/z: 519.5 (M+H)+. $^1$H NMR (500 MHz, DMSO-$d_6$) δ7.81 (d, J=7.3 Hz, 1H), 7.74-7.64 (m, 4H), 7.31 (d, J=7.9 Hz, 2H), 7.16 (d, J=7.3 Hz, 2H), 7.07 (d, J=7.6 Hz, 2H), 4.67 (s, 2H), 2.35 (s, 3H), 2.29 (t, J=7.5 Hz, 2H), 1.89-1.77 (m, 6H), 1.67 (d, J=6.4 Hz, 2H), 1.45 (quin, J=7.4 Hz, 2H), 1.24 (dq, J=14.6, 7.1 Hz, 2H), 0.78 (t, J=7.3 Hz, 3H) (1 exchangeable proton not observed).

Example 123: 2-butyl-3-((5'-(isothiazol-3-yl)-2'-(2H-tetrazol-5-yl)-[1,1'-biphenyl]-4-yl)methyl)-1,3-diazaspiro[4.4]non-1-en-4-one

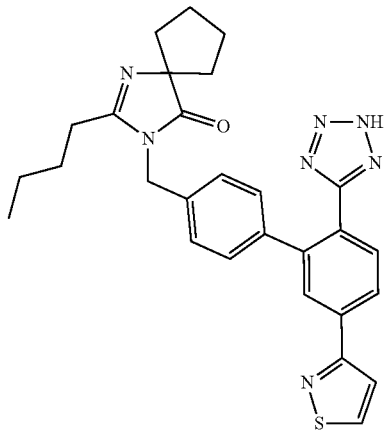

(ex. 123)

Intermediate 123a: 5-bromo-4'-((2-butyl-4-oxo-1,3-diazaspiro[4.4]non-1-en-3-yl)methyl)-[1,1'-biphenyl]-2-carbonitrile

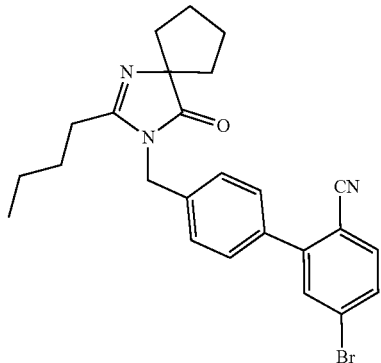

(123a)

Intermediate 033a was reacted with 4-bromo-2-iodobenzonitrile in a method analogous to Intermediate 122a to give Intermediate 123a. LC-MS (Method A2) RT=0.89 min, MS (ESI) m/z: 464 (M+H)+. $^1$H NMR (500 MHz, $CDCl_3$) δ 7.69 (d, J=1.4 Hz, 1H), 7.66-7.59 (m, 2H), 7.55 (d, J=8.3 Hz, 2H), 7.32 (d, J=8.3 Hz, 2H), 4.77 (s, 2H), 2.40-2.33 (m, 2H), 2.06-1.94 (m, 5H), 1.91-1.82 (m, 2H), 1.63 (dt, J=15.4, 7.7 Hz, 3H), 1.42-1.32 (m, 2H), 0.90 (t, J=7.4 Hz, 3H).

Intermediate 123b: 3-((5'-bromo-2'-(2H-tetrazol-5-yl)-[1,1'-biphenyl]-4-yl)methyl)-2-butyl-1,3-diazaspiro[4.4]non-1-en-4-one

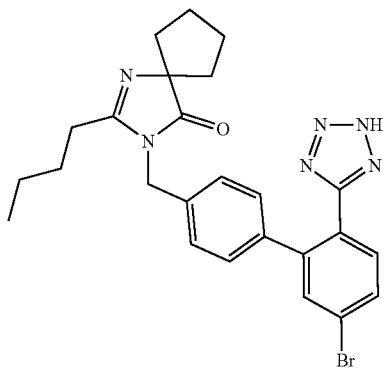

(123b)

Intermediate 123a was reacted in a method analogous to Intermediate 122b to give Intermediate 123b. LC-MS (Method A2) RT=0.79 min, MS (ESI) m/z: 507 (M+H)$^+$. $^1$H NMR (500 MHz, CDCl$_3$) δ 7.93 (d, J=8.3 Hz, 1H), 7.71 (dd, J=8.3, 1.9 Hz, 1H), 7.63 (d, J=1.9 Hz, 1H), 7.25-7.20 (m, 2H), 7.18-7.13 (m, 2H), 4.72 (s, 2H), 2.34-2.26 (m, 2H), 1.99-1.87 (m, 6H), 1.85-1.74 (m, 3H), 1.58 (dt, J=15.3, 7.6 Hz, 2H), 1.37-1.32 (m, 2H), 0.88 (t, J=7.4 Hz, 3H).

Intermediate 123c: 3-((5'-bromo-2'-(2-trityl-2H-tetrazol-5-yl)-[1,1'-biphenyl]-4-yl)methyl)-2-butyl-1,3-diazaspiro[4.4]non-1-en-4-one

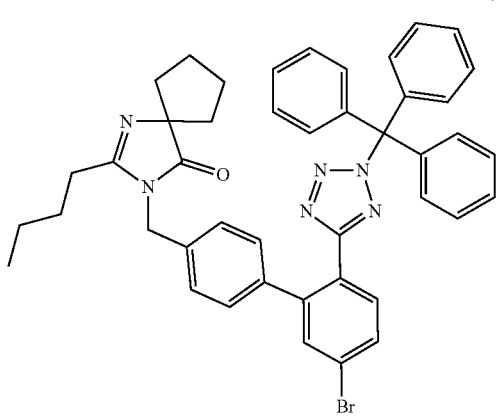

(123c)

Intermediate 123b was reacted in a method analogous to Intermediate 122c to give Intermediate 123c. LC-MS (Method A2) RT=1.09 min, MS (ESI) m/z: 750 (M+H)$^+$. $^1$H NMR (500 MHz, CDCl$_3$) δ 7.85 (d, J=8.3 Hz, 1H), 7.62 (dd, J=8.3, 1.9 Hz, 1H), 7.55 (d, J=2.2 Hz, 1H), 7.40-7.35 (m, 3H), 7.32-7.26 (m, 7H), 7.11 (d, J=8.0 Hz, 2H), 6.96-6.91 (m, 7H), 4.59 (s, 2H), 2.28-2.23 (m, 2H), 2.05-1.97 (m, 6H), 1.84 (d, J=5.8 Hz, 2H), 1.33-1.27 (m, 4H), 0.87 (t, J=7.3 Hz, 3H).

Intermediate 123d: 2-butyl-3-((5'-(4,4,5,5-tetramethyl-1,3,2-dioxaborolan-2-yl)-2'-(2-trityl-2H-tetrazol-5-yl)-[1,1'-biphenyl]-4-yl)methyl)-1,3-diazaspiro[4.4]non-1-en-4-one

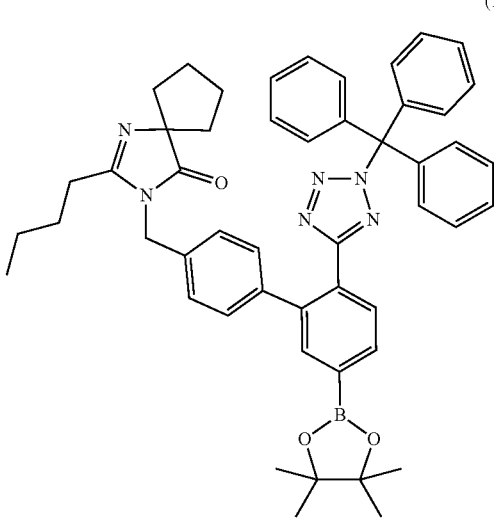

(123d)

Intermediate 123c (540 mg, 0.720 mmol), bispinacolatodiboron (274 mg, 1.08 mmol), and KOAc (177 mg, 1.80 mmol) were dissolved in 1,4-dioxane (7.20 mL) and degassed for 5 minutes by bubbling with Ar. PdCl$_2$(dppf)-CH$_2$Cl$_2$ Adduct (47.1 mg, 0.058 mmol) was added and the reaction degassed for an additional 10 minutes. The reaction was heated at 130° C. in the microwave for 60 minutes. The reaction was diluted with EtOAc and washed with H$_2$O then brine, dried (Na$_2$SO$_4$), filtered, and concentrated in vacuo. The crude material was purified by column chromatography (ISCO, 40 g silica gel column, 19 minute gradient of 0 to 100% EtOAc in hexanes) to give Intermediate 123d (350 mg, 0.439 mmol, 61%) as a white solid. LC-MS (Method A2) RT=1.12 min, MS (ESI) m/z: 798 (M+H)$^+$. $^1$H NMR (500 MHz, CDCl$_3$) δ 7.99 (d, J=7.7 Hz, 1H), 7.90 (d, J=6.9 Hz, 1H), 7.80 (s, 1H), 7.41-7.34 (m, 5H), 7.31-7.26 (m, 2H), 7.13 (d, J=8.0 Hz, 2H), 6.97-6.90 (m, 10H), 4.59 (s, 2H), 2.28-2.21 (m, 2H), 2.09-1.97 (m, 6H), 1.88-1.81 (m, 2H), 1.37 (s, 12H), 1.35-1.30 (m, 4H), 0.89 (t, J=7.3 Hz, 3H).

Example 123: 2-butyl-3-((5'-(isothiazol-3-yl)-2'-(2H-tetrazol-5-yl)-[1,1'-biphenyll-4-yl)methyl)-1,3-diazaspiro[4.41non-1-en-4-one Intermediate 123d was reacted with 3-bromoisothiazole in a method analogous to Example 122 to give Example 123 (5.9 mg, 11.5 μmol, 46%). LC-MS (Method A1) RT=1.39 min, MS (ESI) m/z: 512.4 (M+H)$^+$. $^1$H NMR (500 MHz, DMSO-d$_6$) δ 9.18 (d, J=4.6 Hz, 1H), 8.12 (br d, J=7.9 Hz, 1H), 8.09-8.01 (m, 2H), 7.75 (br d, J=7.9 Hz, 1H), 7.17 (br d, J=7.9 Hz, 2H), 7.07 (br d, J=7.9 Hz, 2H), 4.68 (s, 2H), 2.32 (t, J=7.6 Hz, 2H), 1.90-1.77 (m, 6H), 1.67 (br d, J=6.7 Hz, 2H), 1.49 (quin, J=7.5 Hz, 2H), 1.27 (dq, J=14.9, 7.4 Hz, 2H), 0.81 (t, J=7.3 Hz, 3H) (1 exchangeable proton not observed).

The compounds listed in the table below were synthesized using the same methods that were used to prepare Example 122 and Example 123.

| Ex # | Structure | MW | LC-MS m/z [M + H]+; RT (Method) | 1H NMR |
|---|---|---|---|---|
| 124 | 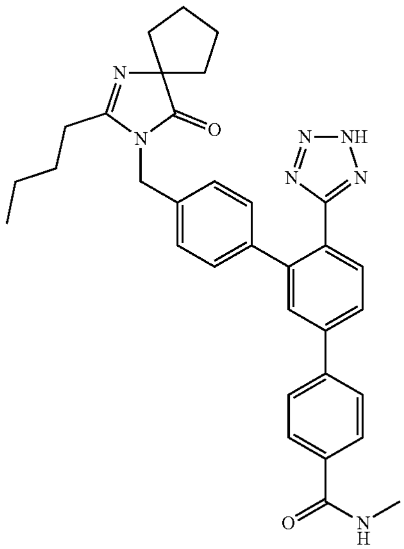 [SMILES: CCCCC1=NC2(CCCC2)C(=O)N1Cc1ccc(-c2cc(-c3ccc(C(=O)NC)cc3)ccc2-c2nn[nH]n2)cc1] | 561.677 | 562.0; 1.44 min (Method A1) | 1H NMR (500 MHz, DMSO-d6) δ 8.57 (br s, 1H), 7.98-7.87 (m, 5H), 7.82-7.73 (m, 2H), 7.18 (br d, J = 7.7 Hz, 2H), 7.08 (br d, J = 8.0 Hz, 2H), 4.68 (s, 2H), 2.81 (d, J = 4.4 Hz, 3H), 2.29 (br t, J = 7.4 Hz, 2H), 1.90-1.76 (m, 6H), 1.66 (br d, J = 7.7 Hz, 2H), 1.50-1.41 (m, 2H), 1.29-1.18 (m, 2H), 0.78 (br t, J = 7.2 Hz, 3H) (1 exchangeable proton not observed) |
| 125 | 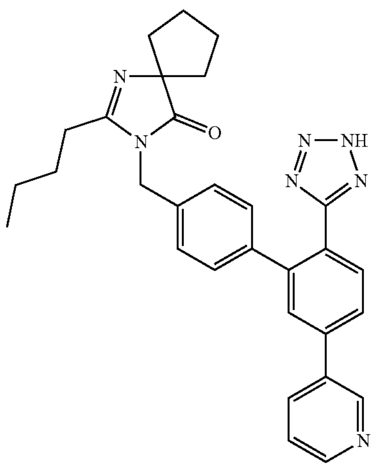 [SMILES: CCCCC1=NC2(CCCC2)C(=O)N1Cc1ccc(-c2cc(-c3cccnc3)ccc2-c2nn[nH]n2)cc1] | 505.613 | 505.9; 1.48 min (Method A1) | 1H NMR (500 MHz, DMSO-d6) δ 9.03 (d, J = 1.6 Hz, 1H), 8.62 (d, J = 3.8 Hz, 1H), 8.24 (br d, J = 8.0 Hz, 1H), 7.90 (dd, J = 8.0, 1.6 Hz, 1H), 7.84-7.74 (m, 2H), 7.53 (dd, J = 7.9, 4.8 Hz, 1H), 7.20 (d, J = 8.0 Hz, 2H), 7.09 (d, J = 8.1 Hz, 2H), 4.69 (s, 2H), 2.31 (t, J = 7.5 Hz, 2H), 1.90-1.76 (m, 6H), 1.67 (br d, J = 6.6 Hz, 2H), 1.49 (quin, J = 7.5 Hz, 2H), 1.27 (dq, J = 14.9, 7.4 Hz, 2H), 0.81 (t, J = 7.3 Hz, 3H) (1 exchangeable proton not observed) |
| 126 | 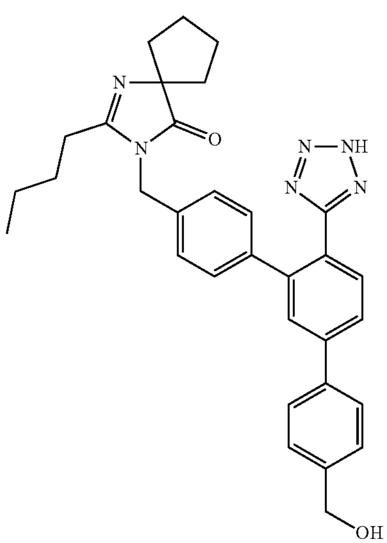 [SMILES: CCCCC1=NC2(CCCC2)C(=O)N1Cc1ccc(-c2cc(-c3ccc(CO)cc3)ccc2-c2nn[nH]n2)cc1] | 534.651 | 535.2; 1.48 min (Method A1) | 1H NMR (500 MHz, DMSO-d6) δ 7.87 (br d, J = 8.2 Hz, 1H), 7.81-7.71 (m, 3H), 7.45 (br d, J = 7.9 Hz, 2H), 7.29-7.04 (m, 5H), 4.73 (s, 2H), 4.56 (s, 2H), 2.38 (br t, J = 7.4 Hz, 2H), 1.92-1.66 (m, 7H), 1.54-1.41 (m, 2H), 1.30-1.18 (m, 4H), 0.80 (br t, J = 7.2 Hz, 3H) (1 exchangeable proton not observed) |

| Ex # | Structure | MW | LC-MS m/z [M + H]+; RT (Method) | 1H NMR |
|---|---|---|---|---|
| 127 | 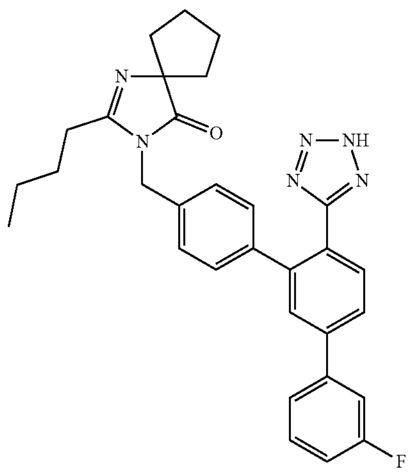 [SMILES: CCCCC1=NC2(CCCC2)C(=O)N1Cc1ccc(-c2cc(-c3cccc(F)c3)ccc2-c2nn[nH]n2)cc1] | 522.616 | 523.0; 1.86 min (Method A1) | 1H NMR (500 MHz, DMSO-d6) δ 7.79-7.72 (m, 1H), 7.67 (d, J = 8.0 Hz, 1H), 7.64-7.57 (m, 3H), 7.55-7.49 (m, 1H), 7.24-7.14 (m, 3H), 7.02 (br d, J = 8.0 Hz, 2H), 4.65 (s, 2H), 2.30 (br t, J = 7.5 Hz, 2H), 1.92-1.75 (m, 8H), 1.66 (br d, J = 7.9 Hz, 2H), 1.44 (quin, J = 7.3 Hz, 2H), 1.27-1.17 (m, 3H) (1 exchangeable proton not observed) |
| 128 | 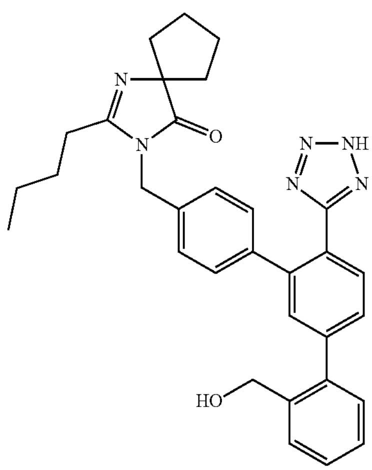 [SMILES: CCCCC1=NC2(CCCC2)C(=O)N1Cc1ccc(-c2cc(-c3ccccc3CO)ccc2-c2nn[nH]n2)cc1] | 534.651 | 535.0; 1.40 min (Method A1) | 1H NMR (500 MHz, DMSO-d6) δ 7.60 (dd, J = 18.5, 7.8 Hz, 2H), 7.45-7.31 (m, 5H), 7.14 (br d, J = 7.9 Hz, 2H), 6.99 (br d, J = 7.9 Hz, 2H), 4.64 (s, 2H), 4.49 (s, 2H), 2.73 (s, 1H), 2.30 (br t, J = 7.5 Hz, 2H), 1.88-1.75 (m, 6H), 1.66 (br d, J = 6.7 Hz, 2H), 1.46 (quin, J = 7.5 Hz, 2H), 1.24 (sxt, J = 7.4 Hz, 2H), 0.77 (t, J = 7.3 Hz, 3H) (1 exchangeable proton not observed) |
| 129 | 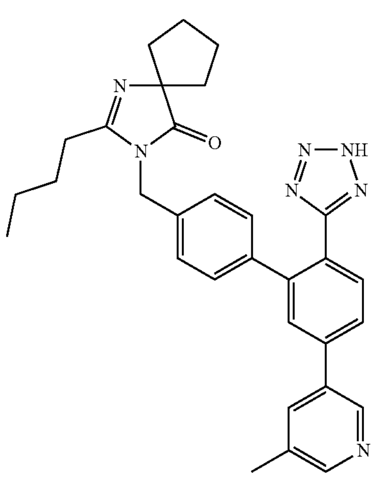 [SMILES: CCCCC1=NC2(CCCC2)C(=O)N1Cc1ccc(-c2cc(-c3cncc(C)c3)ccc2-c2nn[nH]n2)cc1] | 519.640 | 520.1; 1.37 min (Method A1) | 1H NMR (500 MHz, DMSO-d6) δ 8.83 (s, 1H), 8.47 (s, 1H), 8.08 (s, 1H), 7.91 (br d, J = 7.9 Hz, 1H), 7.82 (s, 1H), 7.78 (d, J = 7.9 Hz, 1H), 7.20 (br d, J = 7.9 Hz, 2H), 7.10 (br d, J = 7.9 Hz, 2H), 4.69 (s, 2H), 2.39 (s, 3H), 2.31 (br t, J = 7.5 Hz, 2H), 1.89-1.79 (m, 6H), 1.67 (br d, J = 5.8 Hz, 2H), 1.49 (quin, J = 7.5 Hz, 2H), 1.33-1.23 (m, 2H), 0.82 (t, J = 7.3 Hz, 3H) (1 exchangeble proton not observed) |

| Ex # | Structure | MW | LC-MS m/z [M + H]+; RT (Method) | 1H NMR |
|---|---|---|---|---|
| 130 | 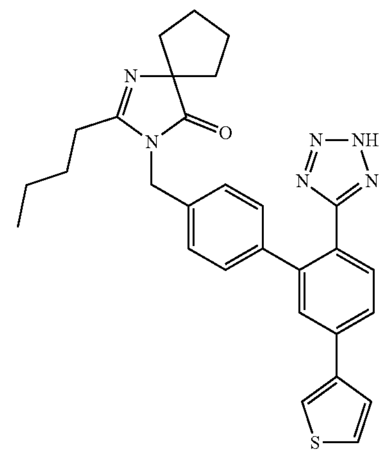 [SMILES: CCCCC1=NC2(CCCC2)C(=O)N1Cc1ccc(-c2cc(-c3ccsc3)ccc2-c2nn[nH]n2)cc1] | 510.653 | 511.4; 1.61 min (Method A1) | 1H NMR (500 MHz, DMSO-d$_6$) δ 8.11 (br s, 1H), 7.91 (br d, J = 8.2 Hz, 1H), 7.84 (s, 1H), 7.75-7.67 (m, 3H), 7.21-7.14 (m, 2H), 7.10 (br d, J = 7.9 Hz, 2H), 4.69 (s, 2H), 2.31 (br t, J = 7.5 Hz, 2H), 1.90-1.78 (m, 6H), 1.68 (br d, J = 5.2 Hz, 2H), 1.50 (quin, J = 7.6 Hz, 2H), 1.28 (sxt, J = 7.4 Hz, 2H), 0.82 (t, J = 7.3 Hz, 3H) (1 exchangeable proton not observed) |
| 131 | 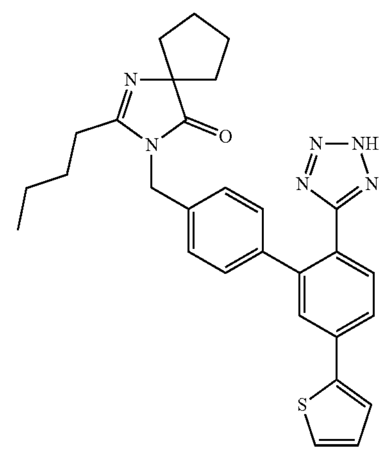 [SMILES: CCCCC1=NC2(CCCC2)C(=O)N1Cc1ccc(-c2cc(-c3cccs3)ccc2-c2nn[nH]n2)cc1] | 510.653 | 511.2; 1.71 min (Method A2) | 1H NMR (500 MHz, DMSO-d$_6$) δ 7.96 (s, 1H), 7.83 (br s, 1H), 7.72 (br s, 3H), 7.65 (br d, J = 4.9 Hz, 1H), 7.24-7.05 (m, 4H), 4.69 (s, 2H), 2.31 (br t, J = 7.2 Hz, 2H), 1.93-1.79 (m, 6H), 1.67 (br s, 2H), 1.49 (quin, J = 7.4 Hz, 2H), 1.34-1.22 (m, 2H), 0.82 (t, J = 7.2 Hz, 3H) (1 exchangeable proton not observed) |
| 132 | 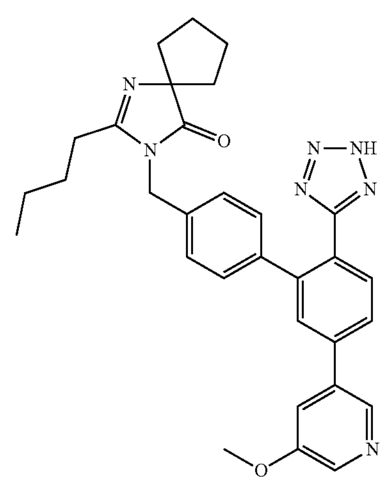 [SMILES: CCCCC1=NC2(CCCC2)C(=O)N1Cc1ccc(-c2cc(-c3cncc(OC)c3)ccc2-c2nn[nH]n2)cc1] | 535.639 | 536.5; 1.36 min (Method A1) | 1H NMR (500 MHz, DMSO-d$_6$) δ 8.60 (s, 1H), 8.33 (d, J = 2.1 Hz, 1H), 7.90 (br d, J = 8.1 Hz, 1H), 7.82 (s, 1H), 7.79-7.73 (m, 2H), 7.20 (br d, J = 7.9 Hz, 2H), 7.08 (br d, J = 8.0 Hz, 2H), 4.68 (s, 2H), 3.92 (s, 3H), 2.31 (br t, J = 7.4 Hz, 2H), 1.89-1.77 (m, 6H), 1.67 (br d, J = 6.6 Hz, 2H), 1.54-1.42 (m, 2H), 1.30-1.24 (m, 2H), 0.80 (br t, J = 7.3 Hz, 3H) (1 exchangeable proton not observed) |

| Ex # | Structure | MW | LC-MS m/z [M + H]+; RT (Method) | 1H NMR |
|---|---|---|---|---|
| 133 | 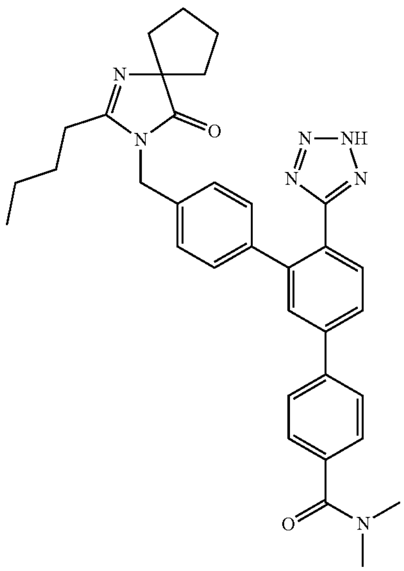 [SMILES: CCCCC1=NC2(CCCC2)C(=O)N1Cc1ccc(-c2cc(-c3ccc(C(=O)N(C)C)cc3)ccc2-c2nn[nH]n2)cc1] | 575.703 | 576.2; 1.43 min (Method A1) | 1H NMR (500 MHz, DMSO-$d_6$) δ 7.85 (br d, J = 7.9 Hz, 2H), 7.82 (br d, J = 7.9 Hz, 1H), 7.74 (br d, J = 7.9 Hz, 1H), 7.72 (s, 1H), 7.52 (br d, J = 8.2 Hz, 2H), 7.20 (br d, J = 7.9 Hz, 2H), 7.06 (br d, J = 7.9 Hz, 2H), 4.68 (s, 2H), 2.99 (br d, J = 17.4 Hz, 6H), 2.32 (br t, J = 7.5 Hz, 2H), 1.90-1.79 (m, 6H), 1.67 (br d, J = 5.8 Hz, 2H), 1.49 (quin, J = 7.5 Hz, 2H), 1.31-1.24 (m, 2H), 0.81 (t, J = 7.3 Hz, 3H) (1 exchangeable proton not observed) |
| 134 | 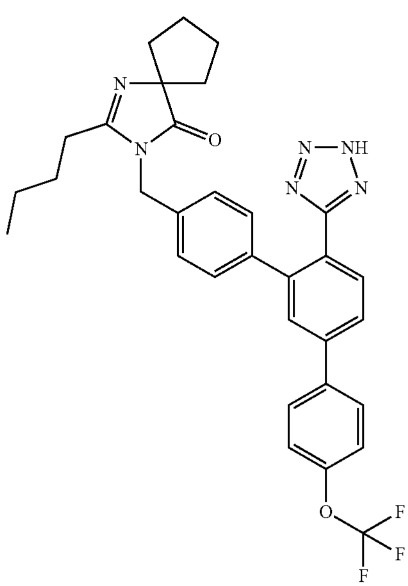 [SMILES: CCCCC1=NC2(CCCC2)C(=O)N1Cc1ccc(-c2cc(-c3ccc(OC(F)(F)F)cc3)ccc2-c2nn[nH]n2)cc1] | 588.623 | 589.2; 1.99 min (Method A1) | 1H NMR (500 MHz, DMSO-$d_6$) δ 7.93 (br d, J = 8.9 Hz, 2H), 7.84-7.77 (m, 1H), 7.74 (br d, J = 8.2 Hz, 1H), 7.71 (s, 1H), 7.48 (br d, J = 7.9 Hz, 2H), 7.20 (br d, J = 7.9 Hz, 2H), 7.06 (br d, J = 7.9 Hz, 2H), 4.68 (s, 2H), 2.32 (br t, J = 7.5 Hz, 2H), 1.89-1.78 (m, 6H), 1.67 (br d, J = 4.9 Hz, 2H), 1.49 (quin, J = 7.5 Hz, 2H), 1.32-1.22 (m, 2H), 0.81 (t, J = 7.3 Hz, 3H) (1 exchangeable proton not observed) |

| Ex # | Structure | MW | LC-MS m/z [M + H]+; RT (Method) | 1H NMR |
|---|---|---|---|---|
| 135 | 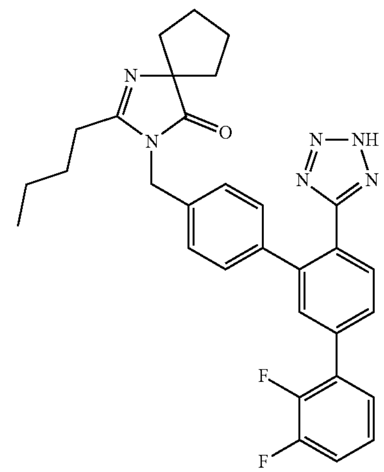 [SMILES: CCCCC1=NC2(CCCC2)C(=O)N1Cc1ccc(-c2cc(-c3cccc(F)c3F)ccc2-c2nn[nH]n2)cc1] | 540.606 | 541.1; 2.27 min (Method A1) | 1H NMR (500 MHz, DMSO-d$_6$) δ 7.78 (q, J = 7.9 Hz, 2H), 7.67 (s, 1H), 7.56-7.47 (m, 2H), 7.39-7.31 (m, 1H), 7.17 (br d, J = 7.9 Hz, 2H), 7.09 (br d, J = 7.9 Hz, 2H), 4.68 (s, 2H), 2.29 (br t, J = 7.5 Hz, 2H), 1.90-1.76 (m, 6H), 1.67 (br d, J = 6.1 Hz, 2H), 1.46 (quin, J = 7.3 Hz, 2H), 1.25 (sxt, J = 7.3 Hz, 2H), 0.79 (t, J = 7.3 Hz, 3H) (1 exchangeable proton not observed) |
| 136 | 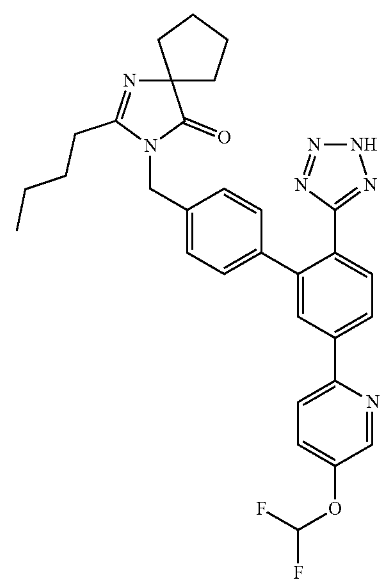 [SMILES: CCCCC1=NC2(CCCC2)C(=O)N1Cc1ccc(-c2cc(-c3ccc(OC(F)F)cn3)ccc2-c2nn[nH]n2)cc1] | 571.620 | 572.4; 1.60 min (Method A1) | 1H NMR (500 MHz, DMSO-d$_6$) δ 8.48 (br s, 1H), 7.98-7.90 (m, 1H), 7.84 (s, 1H), 7.82-7.76 (m, 1H), 7.70 (s, 1H), 7.52-7.44 (m, 1H), 7.15-7.07 (m, 2H), 6.98 (br s, 2H), 4.65 (s, 2H), 2.33 (d, J = 5.3 Hz, 2H), 2.23-2.15 (m, 1H), 1.89-1.73 (m, 6H), 1.59 (d, J = 5.9 Hz, 2H), 1.41 (br s, 2H), 1.12 (br s, 2H), 0.76-0.65 (m, 3H) (1 exchangeable proton not observed) |
| 137 | 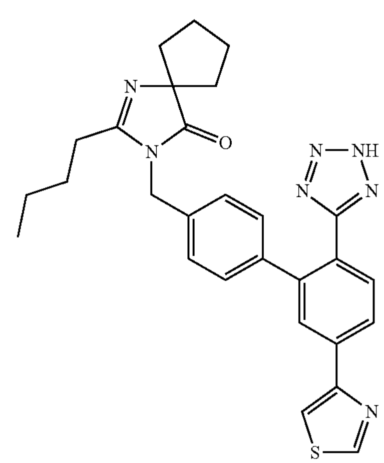 [SMILES: CCCCC1=NC2(CCCC2)C(=O)N1Cc1ccc(-c2cc(-c3cscn3)ccc2-c2nn[nH]n2)cc1] | 511.641 | 512.5; 1.33 min (Method A1) | 1H NMR (500 MHz, DMSO-d$_6$) δ 9.24 (s, 1H), 8.42 (br s, 1H), 8.15 (br d, J = 8.0 Hz, 1H), 8.11 (s, 1H), 7.75 (d, J = 8.1 Hz, 1H), 7.16 (br d, J = 7.8 Hz, 2H), 7.10 (br d, J = 8.0 Hz, 2H), 4.69 (s, 2H), 2.30 (br t, J = 7.4 Hz, 2H), 1.92-1.77 (m, 6H), 1.67 (br d, J = 6.8 Hz, 2H), 1.55-1.42 (m, 2H), 1.32-1.20 (m, 2H), 0.80 (br t, J = 7.2 Hz, 3H) (1 exchangeable proton not observed) |

| Ex # | Structure | MW | LC-MS m/z [M + H]+; RT (Method) | 1H NMR |
|---|---|---|---|---|
| 138 | 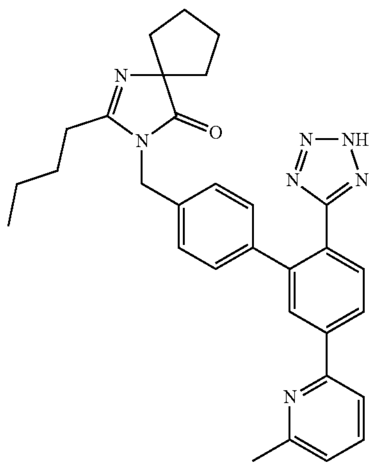 [SMILES: CCCCC1=NC2(CCCC2)C(=O)N1Cc1ccc(-c2cc(-c3cccc(C)n3)ccc2-c2nn[nH]n2)cc1] | 519.640 | 520.1; 1.55 min (Method A1) | 1H NMR (500 MHz, DMSO-d$_6$) δ 8.20 (br d, J = 7.6 Hz, 1H), 8.15 (s, 1H), 7.90 (d, J = 7.9 Hz, 1H), 7.81 (t, J = 7.6 Hz, 1H), 7.77 (br d, J = 6.4 Hz, 1H), 7.28 (d, J = 7.6 Hz, 1H), 7.17 (br d, J = 7.0 Hz, 2H), 7.09 (br d, J = 7.9 Hz, 2H), 4.69 (s, 2H), 2.55 (s, 3H), 2.31 (t, J = 7.5 Hz, 2H), 1.93-1.76 (m, 6H), 1.68 (br d, J = 7.6 Hz, 2H), 1.47 (quin, J = 7.5 Hz, 2H), 1.26 (dq, J = 14.8, 7.4 Hz, 2H), 0.81 (t, J = 7.3 Hz, 3H) (1 exchangeable proton not observed) |
| 139 | 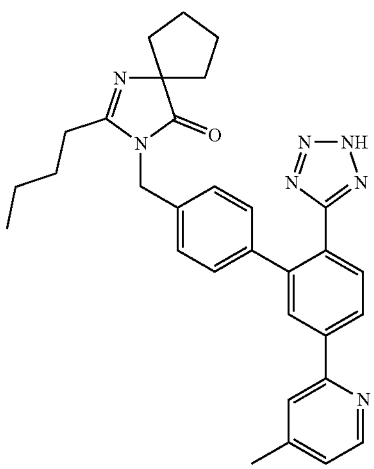 [SMILES: CCCCC1=NC2(CCCC2)C(=O)N1Cc1ccc(-c2cc(-c3cc(C)ccn3)ccc2-c2nn[nH]n2)cc1] | 519.640 | 519.9; 1.52 min (Method A1) | 1H NMR (500 MHz, DMSO-d$_6$) δ 8.51 (d, J = 4.9 Hz, 1H), 8.06 (br d, J = 7.9 Hz, 1H), 8.01 (s, 1H), 7.89 (s, 1H), 7.70 (br s, 1H), 7.18 (br dd, J = 10.7, 5.5 Hz, 3H), 7.02 (br d, J = 7.9 Hz, 2H), 4.67 (s, 2H), 2.39 (s, 3H), 2.33 (br t, J = 7.5 Hz, 2H), 1.94-1.77 (m, 6H), 1.68 (br d, J = 7.0 Hz, 2H), 1.50 (quin, J = 7.6 Hz, 2H), 1.33-1.22 (m, 2H), 0.81 (t, J = 7.3 Hz, 3H) (1 exchangeable proton not observed) |
| 140 | 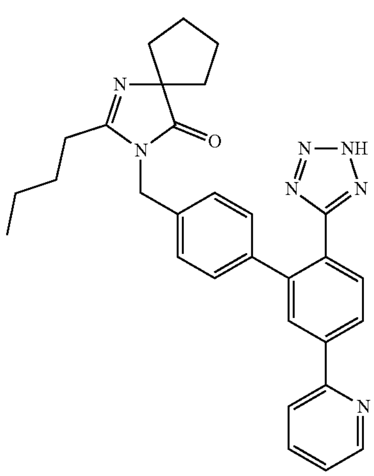 [SMILES: CCCCC1=NC2(CCCC2)C(=O)N1Cc1ccc(-c2cc(-c3ccccn3)ccc2-c2nn[nH]n2)cc1] | 505.613 | 506.2; 0.71 min (Method A2) | 1H NMR (500 MHz, DMSO-d$_6$) δ 8.67 (br d, J = 4.3 Hz, 1H), 8.12-8.00 (m, 3H), 7.89 (br t, J = 7.2 Hz, 1H), 7.73 (br d, J = 7.6 Hz, 1H), 7.41-7.32 (m, 1H), 7.19 (br d, J = 7.6 Hz, 2H), 7.03 (br d, J = 7.9 Hz, 2H), 4.67 (s, 2H), 2.34 (br t, J = 7.5 Hz, 2H), 1.90-1.78 (m, 6H), 1.68 (br d, J = 7.3 Hz, 2H), 1.51 (quin, J = 7.5 Hz, 2H), 1.29 (dq, J = 15.0, 7.5 Hz, 2H), 0.83 (t, J = 7.3 Hz, 3H) (1 exchangeable proton not observed) |

| Ex # | Structure | MW | LC-MS m/z [M + H]+; RT (Method) | 1H NMR |
|---|---|---|---|---|
| 141 | 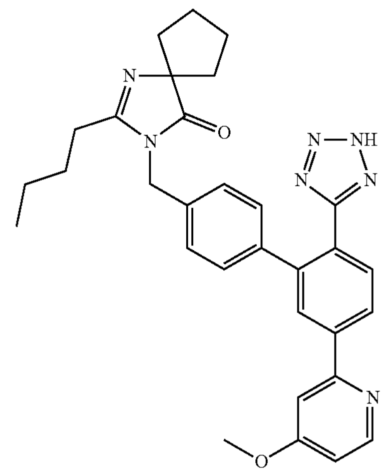 | 535.652 | 536.1; 0.68 min (Method A2) | 1H NMR (500 MHz, CDCl3) δ 8.14 (br d, J = 5.8 Hz, 1H), 7.69-7.57 (m, 3H), 7.14 (d, J = 2.2 Hz, 1H), 6.95 (dd, J = 5.9, 2.3 Hz, 1H), 6.90-6.80 (m, 4H), 4.64 (s, 2H), 4.02 (s, 3H), 2.32-2.23 (m, 2H), 2.10-1.95 (m, 7H), 1.89-1.81 (m, 1H), 1.62 (dt, J = 15.4, 7.7 Hz, 2H), 1.36 (dq, J = 15.0, 7.4 Hz, 2H), 0.91 (t, J = 7.4 Hz, 3H) (1 exchangeable proton not observed) |
| 142 | 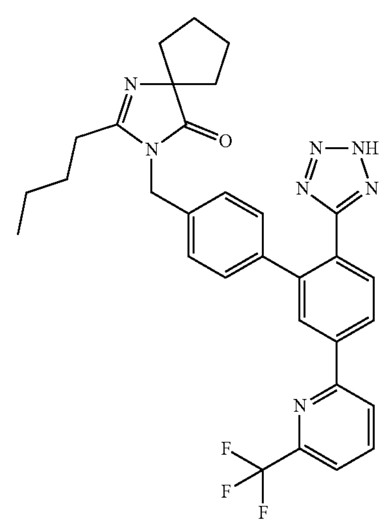 [SMILES: CCCCC1=NC2(CCCC2)C(=O)N1Cc1ccc(-c2cc(-c3cccc(C(F)(F)F)n3)ccc2-c2nn[nH]n2)cc1] | 573.611 | 574.5; 1.66 min (Method A1) | 1H NMR (500 MHz, DMSO-d6) δ 8.40 (d, J = 8.2 Hz, 1H), 8.25-8.17 (m, 2H), 8.13 (s, 1H), 7.90 (d, J = 7.6 Hz, 1H), 7.81 (d, J = 8.2 Hz, 1H), 7.17 (d, J = 7.9 Hz, 2H), 7.08 (d, J = 7.9 Hz, 2H), 4.68 (s, 2H), 2.30 (t, J = 7.6 Hz, 2H), 1.92-1.78 (m, 6H), 1.67 (br d, J = 8.2 Hz, 2H), 1.44 (quin, J = 7.5 Hz, 2H), 1.24 (dq, J = 14.8, 7.3 Hz, 2H), 0.78 (t, J = 7.3 Hz, 3H) (1 exchangeable proton not observed) |

Example 143: 3-(4"-((2-butyl-4-oxo-1,3-diazaspiro[4.4]non-1-en-3-yl)methyl)-[1,1':3',1"-terphenyl]-4'-yl)-1,2,4-oxadiazol-5(4H)-one

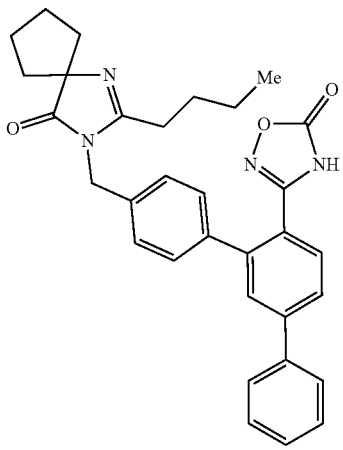

(Ex. 143)

Intermediate 143a: 4"-((2-butyl-4-oxo-1,3-diazaspiro[4.4]non-1-en-3-yl)methyl)-[1,1':3',1"-terphenyl]-4'-carbonitrile

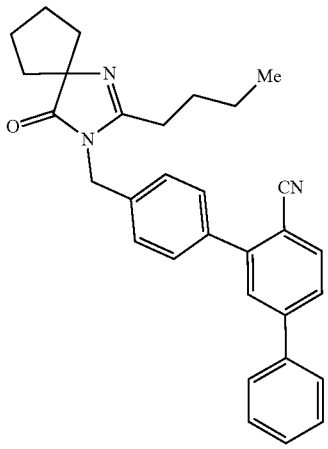

(143a)

To a solution of Intermediate 033a (160 mg, 0.390 mmol) and Intermediate 032a (131 mg, 0.507 mmol) in dioxane (3 mL) was added $K_3PO_4$ (2 M, aq) (0.585 mL, 1 0.170 mmol) followed by $PdCl_2(dppf)_2$ (28.5 mg, 0.039 mmol). The resulting mixture was sparged with $N_2$ for 2 minutes before being sealed and heated at 120° C. for 45 min in the microwave.

The reaction mixture was cooled to RT, diluted with EtOAc, washed with 1 M $K_2HPO_4$, dried over $MgSO_4$, filtered over Celite, and concentrated. The residue was purified by ISCO (⁴0 g, 0-100% EtOAc/Hex) to afford Intermediate 143a (149 mg, 0.323 mmol, 83% yield) as a yellow oil. LC-MS (Method A2) RT=0.95 min, MS (ESI) m/z: 462.0 (M+H)⁺. ¹H NMR (400 MHz, CDCl₃) δ 7.83 (d, J=7.9 Hz, 1H), 7.71-7.64 (m, 2H), 7.64-7.57 (m, 4H), 7.53-7.40 (m, 3H), 7.30 (d, J=8.1 Hz, 2H), 4.76 (s, 2H), 2.39-2.33 (m, 2H), 2.04-1.90 (m, 6H), 1.90-1.80 (m, 2H), 1.61 (dt, J=15.5, 7.6 Hz, 2H), 1.42-1.30 (m, 2H), 0.88 (t, J=7.4 Hz, 3H).

Intermediate 143b: (Z)-4"-((2-butyl-4-oxo-1,3-diazaspiro[4.4]non-1-en-3-yl)methyl)-N'-hydroxy-[1,1':3',1"-terphenyl]-4'-carboximidamide

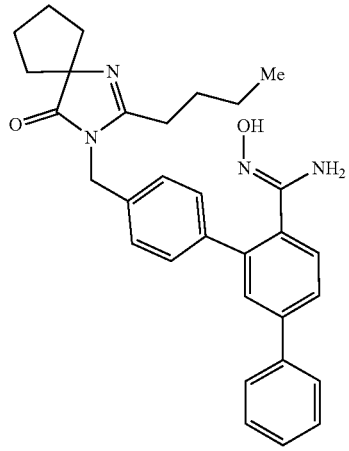

(143b)

To a suspension of Intermediate 143a (145 mg, 0.314 mmol) and hydroxylamine hydrochloride (109 mg, 1.571 mmol) in DMSO (2 mL) was added $NaHCO_3$ (132 mg, 1.571 mmol). The reaction mixture was sealed and heated at 120° C. overnight. The reaction was cooled to RT and $H_2O$ was added. The formed solid was filtered and washed with $H_2O$. The solid residue was solvated in DCM and washed with 10% LiCl (aq). The organic phase was dried over $MgSO_4$ and concentrated. The residue was dissolved in DMF and purified via preparative HPLC with the following conditions: Column: XBridge C18, 19×200 mm, 5-.m particles; Mobile Phase A: 5:95 ACN: $H_2O$ with 0.1% trifluoroacetic acid; Mobile Phase B: 95:5 ACN: $H_2O$ with 0.1% trifluoroacetic acid; Gradient: 10-100% B over 20 minutes, then a 2-minute hold at 100% B; Flow: 20 mL/min to yield Intermediate 143b (9.7 mg, 0.020 mmol. 31%). LC-MS (Method A2) RT=0.69 min, MS (ESI) m/z: 495.1 (M+H)⁺. ¹H NMR (500 MHz, DMSO-d₆) δ 8.03-7.83 (m, 2H), 7.81-7.72 (m, 3H), 7.68 (d, J=7.9 Hz, 1H), 7.56-7.40 (m, 6H), 7.26 (d, J=7.9 Hz, 2H), 4.77 (s, 2H), 2.39 (t, J=7.6 Hz, 2H), 1.87 (d, J=5.8 Hz, 6H), 1.72 (br. s., 2H), 1.52 (quin, J=7.4 Hz, 2H), 1.37-1.21 (m, 2H), 0.82 (t, J=7.3 Hz, 3H).

Example 143: 3-(4"-((2-butyl-4-oxo-1,3-diazaspiro[4.41non-1-en-3-yl)methyl)-[1,1':3',1"-terphenyl]-4'-yl)-1,2,4-oxadiazol-5(4H)-one To a solution of Intermediate 143b (35 mg, 0.071 mmol) in DMF (2 mL) was added DBU (0.053 mL, 0.354 mmol) followed by CDI (57.4 mg, 0.354 mmol). The reaction was allowed to stir at RT for 5 minutes. The reaction mixture was quenched with a few drops of methanol, filtered, and purified via preparative HPLC with the following conditions: Column: XBridge C18, 19×200 mm, 5-μm particles; Mobile Phase A: 5:95 ACN: $H_2O$ with 10 mM $NH_4OAc$; Mobile Phase B: 95:5 ACN: $H_2O$ with 10 mM $NH_4OAc$; Gradient: 30-85% B over 30 minutes, then a 3-minute hold at 100% B; Flow: 20 mL/min to yield Example 143 (26.2 mg. 0.047 mmol, 67%). LC-MS (Method A2) RT=0.87 min, MS (ESI) m/z: 521.1 (M+H)+. $^1$H NMR (500 MHz, DMSO-$d_6$) δ 7.87 (d, J=8.1 Hz, 1H), 7.81 (d, J=7.5 Hz, 2H), 7.76 (d, J=5.6 Hz, 2H), 7.54-7.48 (m, 2H), 7.47-7.37 (m, 3H), 7.22 (d, J=7.8 Hz, 2H), 4.75 (s, 2H), 2.33 (t, J=7.4 Hz, 2H), 1.92-1.79 (m, 6H), 1.73-1.63 (m, 2H), 1.49 (quin, J=7.4 Hz, 2H), 1.27 (sxt, J=7.4 Hz, 2H), 0.81 (t, J=7.3 Hz, 3H) One exchangeable proton not observed.

Example 144: 3-(4''-((2-butyl-4-oxo-1,3-diazaspiro[4.4]non-1-en-3-yl)methyl)-2,3-difluoro-[1,1':3',1'''-terphenyl]-4'-yl)-1,2,4-oxadiazol-5(4H)-one (Ex. 144)

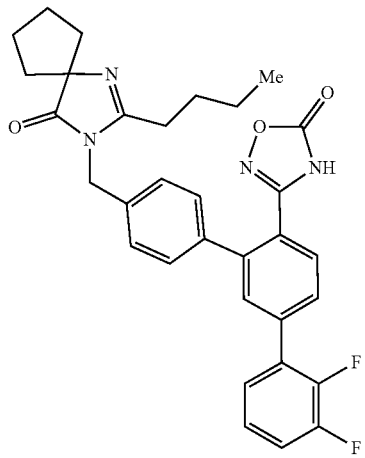

Intermediate 144a: 4''-((2-butyl-4-oxo-1,3-diazaspiro[4.4]non-1-en-3-yl)methyl)-2,3-difluoro-[1,1':3',1'''-terphenyl]-4'-carbonitrile (144a)

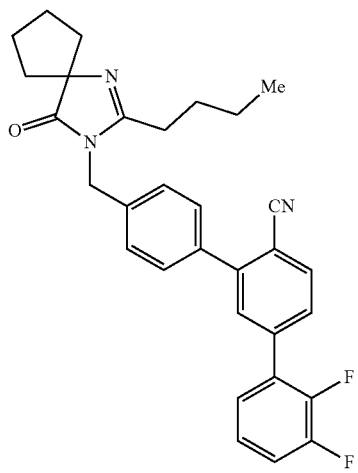

Synthesized in an analogous manner to Intermediate 143a using Intermediate 99a (0.135 g, 0.231 mmol) and (2,3-difluorophenyl)boronic acid (0.102 g, 0.643 mmol) to yield Intermediate 144a (0.115 g, 0.231 mmol, 71.9% yield): LC-MS (Method A2) RT=1.03 min, MS (ESI) m/z: 498.0 (M+H)+. $^1$H NMR (400 MHz, CDCl$_3$) δ 7.85 (d, J=8.1 Hz, 1H), 7.79-7.39 (m, 5H), 7.34-7.26 (m, 2H), 7.25-7.15 (m, 2H), 4.75 (d, J=3.3 Hz, 2H), 2.40-2.31 (m, 2H), 2.08-1.90 (m, 6H), 1.89-1.79 (m, 2H), 1.66-1.54 (m, 2H), 1.42-1.29 (m, 2H), 0.88 (t, J=7.4 Hz, 3H).

Intermediate 144b: (Z)-4''-((2-butyl-4-oxo-1,3-diazaspiro[4.4]non-1-en-3-yl)methyl)-2,3-difluoro-N'-hydroxy-[1,1':3',1'''-terphenyl]-4'-carboximidamide (144b)

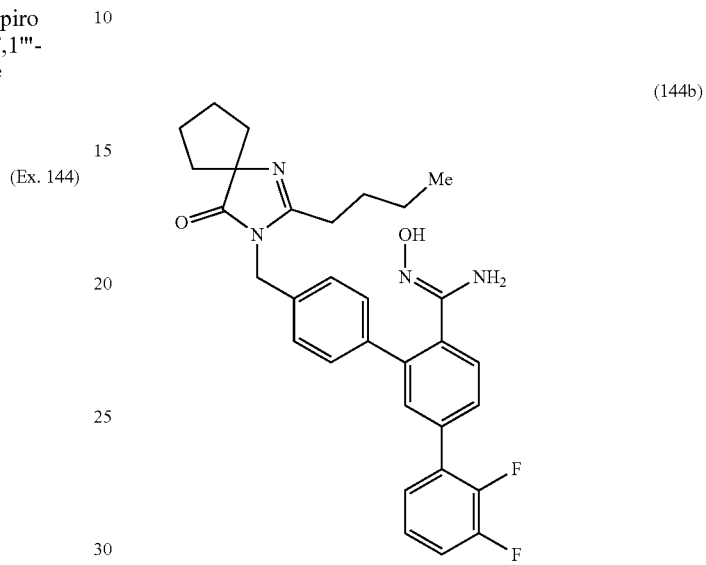

Synthesized in an analogous manner to Intermediate 143b using Intermediate 144a (0.110 g, 0.221 mmol) and potassium tert-butoxide (0.184 g 2.65 mmol) to yield Intermediate 144b (0.035 g, 0.066 mmol, 30% yield): LC-MS (Method A2) RT=0.82 min, MS (ESI) m/z: 531.1 (M+H)+. Used without further purification in the next step.

Example 144: 3-(4''-((2-butyl-4-oxo-1,3-diazaspiro[4.4]non-1-en-3-yl)methyl)-2,3-difluoro-[1,1':3',1'''-terphenyl]-4'-yl)-1,2,4-oxadiazol-5(4H)-one Synthesized in an analogous manner to Intermediate 143 using Intermediate 144b (0.030 g, 0.057 mmol). Purified via preparative HPLC with the following conditions: Column: XBridge C18, 19×200 mm, 5-μm particles; Mobile Phase A: 5:95 ACN: H$_2$O with 0.1% trifluoroacetic acid; Mobile Phase B: 95:5 ACN: H$_2$O with 0.1% trifluoroacetic acid; Gradient: 25-65% B over 27 minutes, then a 3-minute hold at 100% B; Flow: 20 mL/min to yield Example 144 (0.005 g, 0.009 mmol, 16% yield): LC-MS (Method A2) RT=0.98 min, MS (ESI) m/z: 557.0 (M+H)+. $^1$H NMR (500 MHz, DMSO-$d_6$) δ 7.81-7.69 (m, 2H), 7.62 (s, 1H), 7.53-7.43 (m, 2H), 7.41-7.27 (m, 3H), 7.19 (d, J=7.9 Hz, 2H), 4.72 (s, 2H), 2.32 (t, J=7.5 Hz, 2H), 1.89-1.77 (m, 6H), 1.67 (d, J=7.6 Hz, 2H), 1.52-1.41 (m, 2H), 1.30-1.19 (m, 2H), 0.78 (t, J=7.3 Hz, 3H). One exchangeable proton not observed.

Example 145: 4''-((2-butyl-4-oxo-1,3-diazaspiro[4.4]non-1-en-3-yl)methyl)-[1,1':3',1''-terphenyl]-4'-carboxylic acid

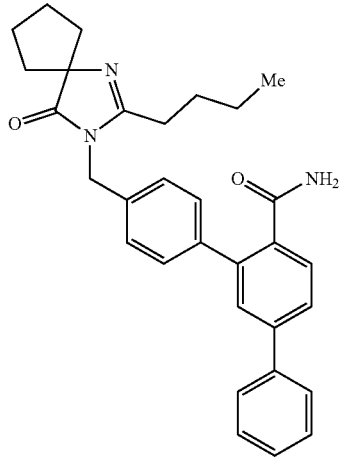

(ex. 145)

Intermediate 145a: methyl 4'-((2-butyl-4-oxo-1,3-diazaspiro[4.4]non-1-en-3-yl)methyl)-5-chloro-[1,1'-biphenyl]-2-carboxylate

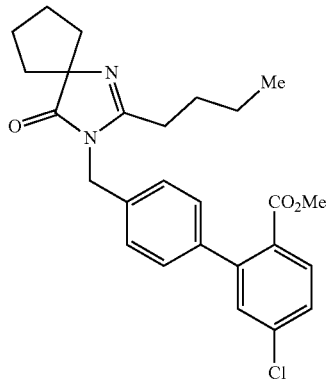

(145a)

Synthesized in an analogous manner to Intermediate 143a using Intermediate 033a (0.080 g, 0.195 mmol) and methyl 4-chloro-2-iodobenzoate (0.0694 g, 0.234 mmol) to yield Intermediate 145a (0.050 g, 0.110 mmol, 57% yield): LC-MS (Method A2) RT=0.93 min, MS (ESI) m/z: 453.1 (M+H)'. $^1$H NMR (400 MHz, CDCl$_3$) δ 7.80 (d, J=8.4 Hz, 1H), 7.39 (dd, J=8.4, 2.2 Hz, 1H), 7.33 (d, J=2.0 Hz, 1H), 7.29-7.24 (m, 2H), 7.21-7.16 (m, 2H), 4.73 (s, 2H), 3.63 (s, 3H), 2.37-2.29 (m, 2H), 2.06-1.91 (m, 6H), 1.88-1.77 (m, 2H), 1.65-1.54 (m, 2H), 1.34 (dq, J=14.9, 7.4 Hz, 2H), 0.88 (t, J=7.4 Hz, 3H).

Intermediate 145b: methyl 4''-((2-butyl-4-oxo-1,3-diazaspiro[4.4]non-1-en-3-yl)methyl)-[1,1':3',1''-terphenyl]-4'-carboxylate

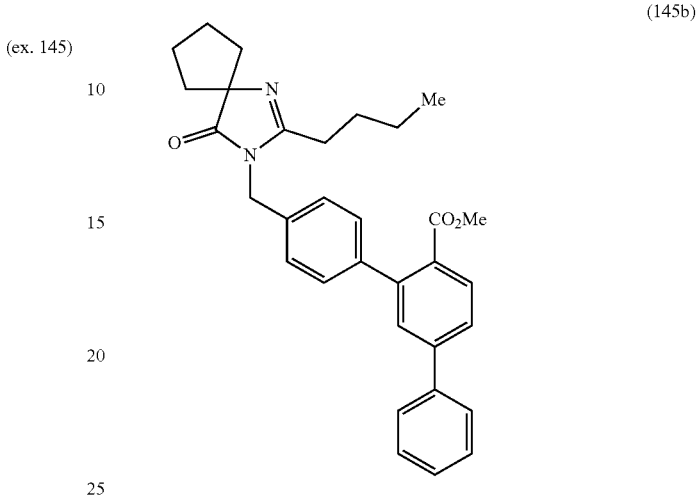

(145b)

Synthesized in an analogous manner to Intermediate 143a using Intermediate 145a (0.050 g, 0.110 mmol) and phenyl boronic acid (0.020 g, 0.166 mmol) to yield Intermediate 145b (0.050 g, 0.076 mmol, 69% yield): LC-MS (Method A2) RT=0.99 min, MS (ESI) m/z: 495.1 (M+H)$^+$. $^1$H NMR (500 MHz, CDCl$_3$) δ 7.97 (d, J=8.3 Hz, 1H), 7.69-7.62 (m, 3H), 7.58 (d, J=1.7 Hz, 1H), 7.52-7.45 (m, 2H), 7.44-7.39 (m, 1H), 7.38-7.35 (m, 1H), 7.31-7.27 (m, 1H), 7.23 (d, J=8.0 Hz, 2H), 4.77 (s, 2H), 3.68 (s, 3H), 2.41-2.35 (m, 2H), 2.09-1.94 (m, 6H), 1.90-1.80 (m, 2H), 1.67-1.58 (m, 2H), 1.43-1.32 (m, 2H), 0.93-0.88 (m, 3H).

Example 145: 4''-((2-butyl-4-oxo-1,3-diazaspiro[4.41non-1-en-3-yl)methyl)-11,1':3',1''-terphenyl]-4'-carboxylic acid To a vial containing Intermediate 145b (0.040 g, 0.081 mmol) was added dioxane (647 µl) followed by MeOH (162 µl). NaOH (1 M aq) (323 µl, 0.323 mmol) was added, and the vial was sealed and heated at 80° C. overnight. The reaction mixture was cooled to RT and concentrated. The residue was dissolved in 2 mL of DMF and purified via preparative LC-MS with the following conditions: Column: XBridge C18, 19×200 mm, 5-µm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 20-60% B over 20 minutes, then a 4-minute hold at 100% B; Flow: 20 mL/min to yield Example 145 (0.015 g, 0.030 mmol, 38%): LC-MS (Method A2) RT=0.91 min, MS (ESI) m/z: 481.1 (M+H)$^+$. $^1$H NMR (500 MHz, DMSO-d$_6$) δ 7.81-7.76 (m, 1H), 7.76-7.69 (m, 3H), 7.56 (s, 1H), 7.51-7.45 (m, 2H), 7.41 (d, J=7.6 Hz, 3H), 7.18 (d, J=7.9 Hz, 2H), 4.73 (s, 2H), 2.34 (t, J=7.5 Hz, 2H), 1.91-1.77 (m, 6H), 1.68 (d, J=7.9 Hz, 2H), 1.48 (quin, J=7.4 Hz, 2H), 1.32-1.23 (m, 2H), 0.79 (t, J=7.3 Hz, 3H). One exchangeable proton not observed.

Example 146: 3-((6'-(1H-tetrazol-5-yl)-[1,1':3',1''-terphenyl]-4-yl)methyl)-2-butyl-7-oxa-1,3-diazaspiro[4.4]non-1-en-4-one

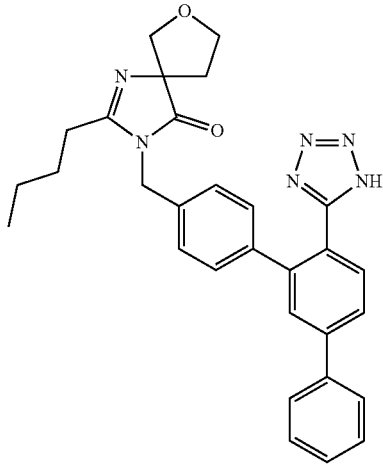

(Ex. 146)

Intermediate 146a: methyl 3-pentanamidotetrahydrofuran-3-carboxylate

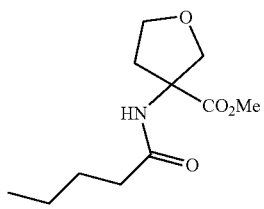

(146a)

To a solution of methyl 3-aminotetrahydrofuran-3-carboxylate hydrochloride (1.0 g, 5.5 mmol) in CH₂Cl₂ (18 mL) was added 25% K₂CO₃ (18 mL, 36 mmol). The mixture was cooled with an ice bath. Pentanoyl chloride (0.91 mL, 7.7 mmol) in CH₂Cl₂ (4 mL) was added dropwise to the stirred solution. The reaction mixture was stirred at 0° C. for 2 h, and at rt for 3 h. The organic phase was collected. The aqueous phase was extracted (2X) with CH₂Cl₂. The combined organic phase was washed with brine, dried over Na₂SO₄ and concentrated. The crude product was purified by flash chromatography (0% to 100% EtOAc in hexane over 15 min using a 40 g silica gel cartridge) to give Intermediate 146a (1.1 g, 4.8 mmol, 87% yield) as an oil. ¹H NMR (500 MHz, CDCl₃) δ 6.05 (br s, 1H), 4.17 (d, J=9.6 Hz, 1H), 4.06-3.98 (m, 2H), 3.95 (d, J=9.4 Hz, 1H), 3.78 (s, 3H), 2.59 (dt, J=13.2, 7.8 Hz, 1H), 2.28-2.19 (m, 3H), 1.68-1.60 (m, 3H), 1.42-1.32 (m, 2H), 0.94 (t, J=7.3 Hz, 3H). LC-MS (Method A2): RT=0.62 min, MS (ESI) m/z: 230.1 (M+H)⁺.

Intermediate 146b: 3-pentanamidotetrahydrofuran-3-carboxamide

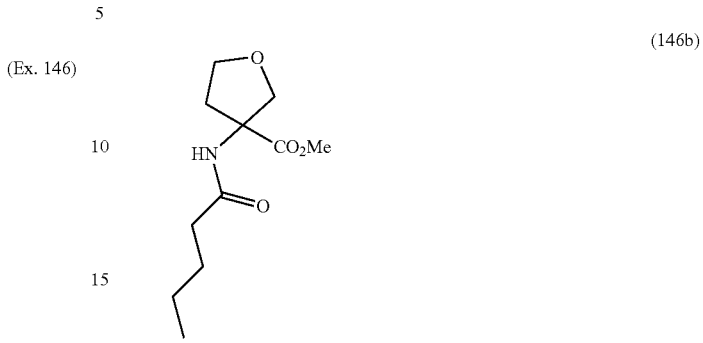

(146b)

A mixture of Intermediate 146a (1.0 g, 4.4 mmol), NaCN (0.032 g, 0.65 mmol) in 7.0 N ammonia in MeOH (16 ml, 110 mmol) was sealed in a pressure flask and heated at 60° C. over the weekend. LC-MS indicated completion of reaction. Without removing the solvent, the crude product Intermediate 146b was taken to the next step. LC-MS (Method A2): RT=0.50 min, MS (ESI) m/z: 215.1 (M+H)⁺.

Intermediate 146c: 2-butyl-7-oxa-1,3-diazaspiro[4.4]non-1-en-4-one

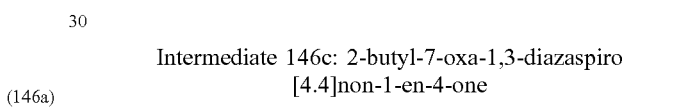

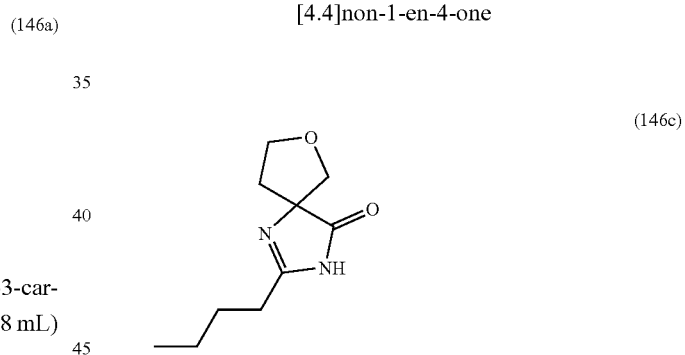

(146c)

To a solution of Intermediate 146b (0.9 g, 4.20 mmol) in MeOH (15 mL) was added 2.0 N NaOH (11 mL, 21 mmol). The reaction mixture was heated at 50° C. overnight. LC-MS indicated completion of reaction. After cooling to rt, the reaction mixture was acidified with 3.0 N HCl to pH 6-7, extracted with THF/EtOAc (2:1, 3×80 mL). The organic layer was washed with brine, dried over Na₂SO₄ and concentrated to give Intermediate 146c (0.57 g, 2.9 mmol, 69% yield) as oil. It was used for the next step without purification. ¹H NMR (500 MHz, CDCl₃) δ 4.20-4.09 (m, 2H), 3.98-3.88 (m, 2H), 2.51 (t, J=7.7 Hz, 2H), 2.35 (dtd, J=12.4, 7.9, 1.4 Hz, 1H), 2.16 (dt, J=12.2, 6.0 Hz, 1H), 1.69 (quin, J=7.6 Hz, 2H), 1.48-1.39 (m, 2H), 0.98 (td, J=7.3, 0.8 Hz, 3H). LC-MS (Method A2): RT=0.45 min, MS (ESI) m/z: 197.1 (M+H)⁺.

Intermediate 146d-racemate: 5-bromo-4'-((2-butyl-4-oxo-7-oxa-1,3-diazaspiro[4.4]non-1-en-3-yl)methyl)-[1,1'-biphenyl]-2-carbonitrile

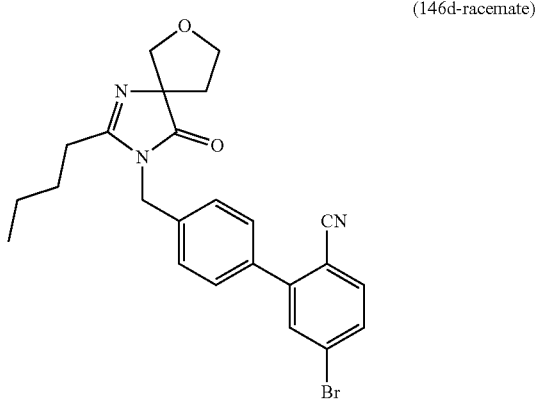 [SMILES: CCCCC1=NC2(CCOC2)C(=O)N1Cc1ccc(-c2cc(Br)ccc2C#N)cc1]

(146d-racemate)

Intermediate 146c (570 mg, 2.9 mmol) was dissolved in DMF (12 ml). NaH (128 mg, 3.2 mmol) was added. The mixture was stirred at rt for 15 min, 1-002 (1.1 g, 3.1 mmol) was added at 0° C. The reaction mixture was stirred at rt for 1 h. LC-MS indicated completion of reaction. The reaction mixture was diluted with EtOAc, washed with saturated NH$_4$Cl, brine, dried over Na$_2$SO$_4$, filtered, and concentrated in vacuo. The crude product was purified by flash chromatography (5% to 100% EtOAc in hexane over 18 min using a 40 g silica gel cartridge) to yield Intermediate 146d-racemate (920 mg, 2.0 mmol, 68% yield) as a white solid. $^1$H NMR (500 MHz, CDCl$_3$) δ 7.68 (d, J=1.1 Hz, 1H), 7.66-7.60 (m, 2H), 7.56 (d, J=8.3 Hz, 2H), 7.32 (d, J=8.0 Hz, 2H), 4.84-4.71 (m, 2H), 4.25-4.14 (m, 2H), 4.03-3.97 (m, 1H), 3.95-3.90 (m, 1H), 2.44-2.35 (m, 3H), 2.17 (ddd, J=12.2, 6.7, 5.2 Hz, 1H), 1.66 (quin, J=7.6 Hz, 2H), 1.37 (sxt, J=7.4 Hz, 2H), 0.90 (t, J=7.3 Hz, 3H). $^{13}$C NMR (126 MHz, CDCl$_3$) δ 183.7, 163.3, 146.2, 137.4, 136.6, 134.9, 133.2, 131.2, 129.4, 128.0, 127.4, 117.9, 110.1, 76.2, 75.8, 69.1, 43.5, 38.0, 28.8, 27.4, 22.3, 13.7. LC-MS (Method A2): RT=0.91 min, MS (ESI) m/z: 466.4 and 468.4 (M+H)$^+$.

Intermediate 146e-enantiomer 1: 5-bromo-4'-((2-butyl-4-oxo-7-oxa-1,3-diazaspiro[4.4]non-1-en-3-yl)methyl)-[1,1'-biphenyl]-2-carbonitrile (146e-enantiomer 1)

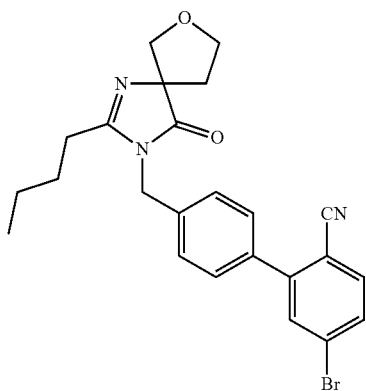

Intermediate 146d-racemate (920 mg, 2.0 mmol) was resolved into two peaks by chiral HPLC using a Berger MG II instrument with the following preparative chromatographic conditions: Column: Chiralpak AD-H, 30×250 mm, 5 micron; Mobile Phase: 15% IPA/85% CO$_2$; Flow Conditions: 70 mL/min, 120 Bar, 40° C.; Detector Wavelength: 220 nm; injection details: 0.5 mL of ~26 mg/mL in IPA: MeOH (1:1). Purity of each fraction was determined using the analytical chromatographic condition below: Instrument: Aurora Analytical SFC; Column: Chiralpak IC, 4.6×100 mm, 3 micron; Mobile Phase: 15% IPA/85% CO$_2$; Flow Conditions: 1.0 mL/min, 150 Bar, 40° C.; Detector Wavelength: 220 nm; Injection Details: 5 µL of ~1 mg/mL in IPA. Peak 1 was collected and concentrated to give Intermediate 146e-enantiomer 1 (400 mg, 0.86 mmol, 44% yield): enantiomeric excess>99%. Chiral analytical RT=9.4 min. $^1$H NMR (400 MHz, CDC$_3$) δ7.68-7.66 (m, 1H), 7.65-7.59 (m, 2H), 7.57-7.51 (m, 2H), 7.30 (d, J=8.4 Hz, 2H), 4.81-4.71 (m, 2H), 4.23-4.13 (m, 2H), 3.98 (d, J=8.6 Hz, 1H), 3.93-3.88 (m, 1H), 2.42-2.33 (m, 3H), 2.15 (ddd, J=12.3, 7.0, 5.2 Hz, 1H), 1.69-1.60 (m, 2H), 1.43-1.32 (m, 2H), 0.89 (t, J=7.4 Hz, 3H). LC-MS (Method A2): RT=0.92 min, MS (ESI) m/z: 466.1 and 468.1 (M+H)$^+$.

Intermediate 146f-enantiomer 2: 5-bromo-4'-((2-butyl-4-oxo-7-oxa-1,3-diazaspiro[4.4]non-1-en-3-yl)methyl-[1,1'-biphenyl]-2-carbonitrile (146f-enantiomer 2)

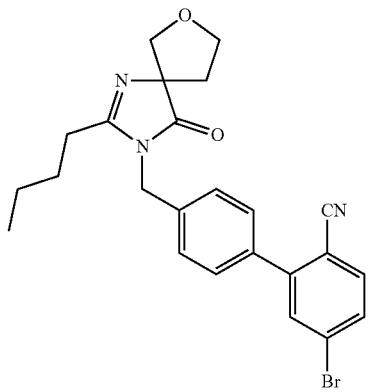

Peak 2 was collected from the chiral separation of Intermediate 146d-racemate, and concentrated to give Intermediate 146f-enantiomer 2 (206 mg, 0.44 mmol, 22% yield): enantiomeric excess 91%. Chiral analytical RT=11.8 min. $^1$H NMR (500 MHz, CDC$_3$) δ 7.70 (d, J=1.1 Hz, 1H), 7.67-7.61 (m, 2H), 7.56 (d, J=8.3 Hz, 2H), 7.32 (d, J=8.0 Hz, 2H), 4.84-4.74 (m, 2H), 4.26-4.15 (m, 2H), 4.03-3.98 (m, 1H), 3.96-3.91 (m, 1H), 2.44-2.36 (m, 3H), 2.18 (ddd, J=12.3, 6.9, 5.2 Hz, 1H), 1.67 (dt, J=15.4, 7.7 Hz, 2H), 1.43-1.34 (m, 2H), 0.91 (t, J=7.3 Hz, 3H). LC-MS (Method A2): RT=0.93 min, MS (ESI) m/z: 466.1 and 468.1 (M+H)$^+$.

Intermediate 146 g: 4'''-((2-butyl-4-oxo-7-oxa-1,3-diazaspiro[4.4]non-1-en-3-yl)methyl)-[1,1':3',1''-terphenyl]-4'-carbonitrile

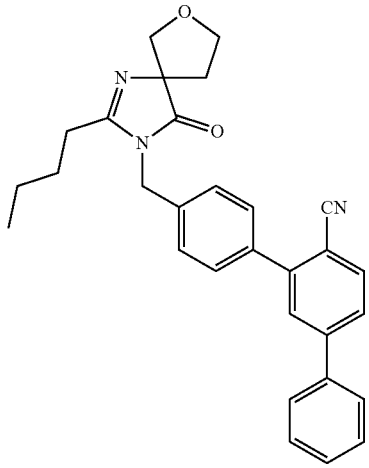
(146g)

A solution of Intermediate 146e-enantiomer 1 (30 mg, 0.064 mmol), phenylboronic acid (17 mg, 0.14 mmol) and Pd-XPhos G3 (2.2 mg, 2.6 μmol) in THF (1.5 mL) and $K_3PO_4$ (1.0 M, 0.13 mL, 0.13 mmol) was degassed with Ar for 1 min. The reaction mixture was sealed in a pressure vial and heated at 120° C. in a microwave reactor for 45 min. LC-MS indicated completion of reaction. The reaction mixture was concentrated and purified by flash chromatography (10% to 100% EtOAc in hexane over 10 min using a 4 g silica gel cartridge) to yield Intermediate 146 g (30 mg, 0.065 mmol, 100% yield) as a white solid. $^1$H NMR (500 MHz, CDCl$_3$) δ 7.85 (d, J=8.0 Hz, 1H), 7.74-7.67 (m, 2H), 7.64 (br dd, J=7.4, 4.4 Hz, 4H), 7.54-7.48 (m, 2H), 7.48-7.43 (m, 1H), 7.33 (d, J=8.0 Hz, 2H), 4.85-4.73 (m, 2H), 4.26-4.16 (m, 2H), 4.04-3.98 (m, 1H), 3.96-3.91 (m, 1H), 2.45-2.37 (m, 3H), 2.22-2.14 (m, 1H), 1.67 (quin, J=7.6 Hz, 2H), 1.39 (dq, J=15.0, 7.4 Hz, 2H), 0.91 (t, J=7.4 Hz, 3H). LC-MS (Method A2): RT=0.96 min, MS (ESI) m/z: 464.2 (M+H)$^+$.

Example 146

Intermediate 146 g (30 mg, 0.065 mmol) was dissolved in toluene (1294 μl). Bu$_2$SnO (35 mg, 0.14 mmol) and TMS-N$_3$ (103 μl, 0.78 mmol) were added and the reaction sealed in a pressure vial and heated at 100° C. overnight. LC-MS indicated completion of reaction. Toluene was removed by blowing a slow stream of N$_2$. The mixture was purified using a preparative HPLC (method E) to yield Example 146 (22 mg, 0.042 mmol, 65% yield) $^1$H NMR (500 MHz, CDCl$_3$) δ 8.10 (d, J=8.0 Hz, 1H), 7.75 (dd, J=8.1, 1.8 Hz, 1H), 7.68-7.63 (m, 3H), 7.53-7.47 (m, 2H), 7.47-7.42 (m, 1H), 7.28-7.24 (m, 2H), 7.23-7.19 (m, 2H), 4.86 (s, 2H), 4.25-4.15 (m, 2H), 4.08-4.01 (m, 2H), 2.68-2.62 (m, 2H), 2.52-2.44 (m, 1H), 2.41-2.34 (m, 1H), 1.72 (quin, J=7.7 Hz, 2H), 1.43 (sxt, J=7.4 Hz, 2H), 0.94 (t, J=7.4 Hz, 3H). LC-MS (Method A2): RT=0.84 min, MS (ESI) m/z: 507.0 (M+H)$^+$. Analytical HPLC purity (Method A2): 98%

Example 147: 3-((6'-(1H-tetrazol-5-yl)-[1,1':3',1''-terphenyl]-4-yl)methyl)-2-butyl-7-oxa-1,3-diazaspiro[4.4]non-1-en-4-one

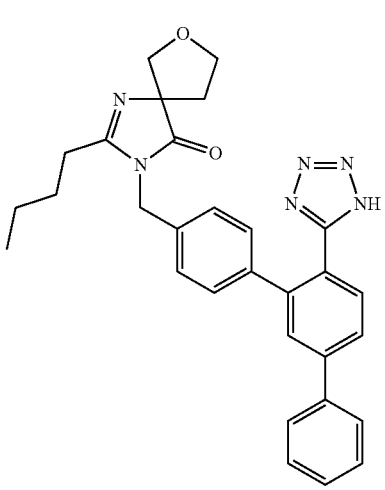
(Ex. 147)

Intermediate 147a: 4''-((2-butyl-4-oxo-7-oxa-1,3-diazaspiro[4.4]non-1-en-3-yl)methyl)-[1,1':3',1''-terphenyl]-4'-carbonitrile

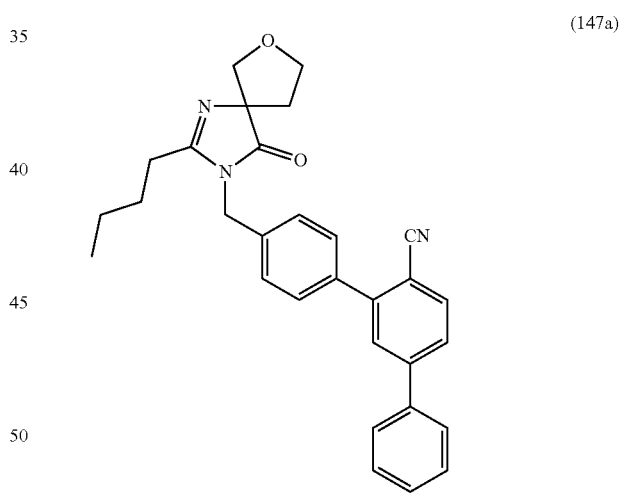
(147a)

In a procedure similar to that of 146 g, using Intermediate 146f-enantiomer 2 (30 mg, 0.064 mmol), phenylboronic acid (17 mg, 0.14 mmol), Pd-XPhos G3 (2.2 mg, 2.6 μmol) and K$_3$PO$_4$ salt (1.0 M, 0.13 mL, 0.123 mmol), Intermediate 147a (30 mg, 0.065 mmol, 100% yield) was obtained as a white solid. $^1$H NMR (500 MHz, CDCl$_3$) δ 7.85 (d, J=8.0 Hz, 1H), 7.74-7.67 (m, 2H), 7.64 (br dd, J=7.4, 4.4 Hz, 4H), 7.54-7.48 (m, 2H), 7.48-7.43 (m, 1H), 7.33 (d, J=8.0 Hz, 2H), 4.85-4.73 (m, 2H), 4.26-4.16 (m, 2H), 4.04-3.98 (m, 1H), 3.96-3.91 (m, 1H), 2.45-2.37 (m, 3H), 2.22-2.14 (m, 1H), 1.67 (quin, J=7.6 Hz, 2H), 1.39 (dq, J=15.0, 7.4 Hz, 2H), 0.91 (t, J=7.4 Hz, 3H). LC-MS (Method A2): RT=0.96 min, MS (ESI) m/z: 464.2 (M+H)$^+$.

Example 147

In a procedure similar to that of Example 146, using Intermediate 147a (30 mg, 0.065 mmol), Bu$_2$SnO (35 mg, 0.14 mmol) and TMS-N$_3$ (103 pd, 0.78 mmol), Example 147 (19 mg, 0.037 mmol, 56.8% yield) was obtained as a white solid. $^1$H NMR (500 MHz, CDCl$_3$) δ 8.10 (d, J=8.0 Hz, 1H), 7.75 (dd, J=8.1, 1.8 Hz, 1H), 7.68-7.63 (m, 3H), 7.53-7.47 (m, 2H), 7.47-7.42 (m, 1H), 7.28-7.24 (m, 2H), 7.23-7.19 (m, 2H), 4.86 (s, 2H), 4.25-4.15 (m, 2H), 4.08-4.01 (m, 2H), 2.68-2.62 (m, 2H), 2.52-2.44 (m, 1H), 2.41-2.34 (m, 1H), 1.72 (quin, J=7.7 Hz, 2H), 1.43 (sxt, J=7.4 Hz, 2H), 0.94 (t, J=7.4 Hz, 3H). LC-MS (Method A2): RT=0.84 min, MS (ESI) m/z: 507.0 (M+H)$^+$. Analytical HPLC purity (Method A2): 100%.

The following examples have been similarly prepared from Intermediate 146e-enantiomer 1 and Intermediate 146f-enantiomer 2 with selected boronic acids as described above for Example 146. Two analytical LC-MS injections were used to determine the final purity. The retention time of one of them is reported for each compound and is referred as Method A1 or Method A2.

| Ex | Structure | MW | LC-MS m/z [M + H]$^+$; RT; Purity (Method) | $^1$H NMR (500 MHz, DMSO-d$_6$) δ ppm |
|---|---|---|---|---|
| 148 | 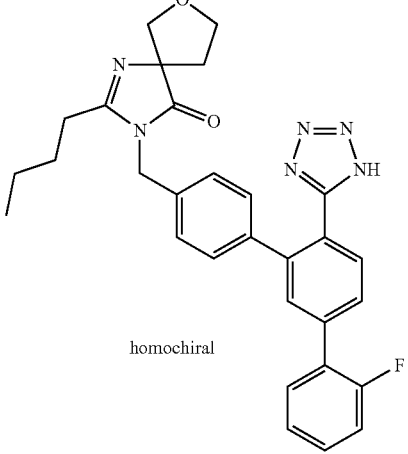 homochiral | 524.6 | 525.1; 1.70 min; 97% (Method A2) | 7.80-7.72 (m, 2H), 7.72-7.61 (m, 2H), 7.53-7.44 (m, 1H), 7.40-7.31 (m, 2H), 7.16 (s, 2H), 7.14-7.06 (m, 2H), 4.70 (s, 2H), 3.98 (br t, J = 7.0 Hz, 2H), 3.78-3.68 (m, 1H), 2.33 (br t, J = 7.3 Hz, 2H), 2.17 (dt, J = 12.4, 7.7 Hz, 1H), 2.00 (dt, J = 12.0, 5.8 Hz, 1H), 1.48 (quin, J = 7.4 Hz, 2H), 1.32-1.18 (m, 2H), 0.79 (t, J = 7.3 Hz, 3H). |
| 149 | 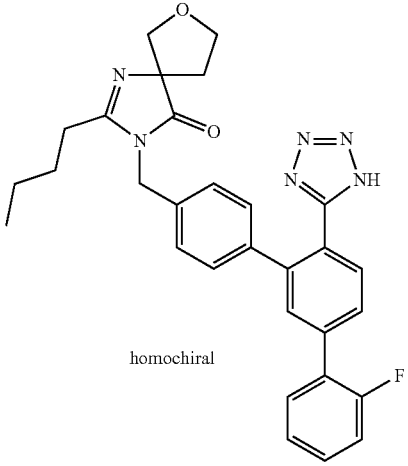 [SMILES: CCCCC1=NC2(CCOC2)C(=O)N1Cc1ccc(-c2cc(-c3ccccc3F)ccc2-c2nnn[nH]2)cc1] homochiral | 524.6 | 525.1; 1.67 min; 95% (Method A2) | 7.80-7.72 (m, 2H), 7.72-7.61 (m, 2H), 7.54-7.44 (m, 1H), 7.41-7.30 (m, 2H), 7.20-7.14 (m, 2H), 7.14-7.06 (m, 2H), 4.70 (s, 2H), 3.98 (br t, J = 6.9 Hz, 2H), 3.77-3.68 (m, 1H), 2.33 (br t, J = 7.5 Hz, 2H), 2.17 (dt, J = 12.5, 7.9 Hz, 1H), 2.00 (dt, J = 12.1, 5.9 Hz, 1H), 1.48 (quin, J = 7.5 Hz, 2H), 1.30-1.20 (m, 2H), 0.79 (t, J = 7.3 Hz, 3H). |

| Ex | Structure | MW | LC-MS m/z [M + H]+; RT; Purity (Method) | 1H NMR (500 MHz, DMSO-d6) δ ppm |
|---|---|---|---|---|
| 150 | 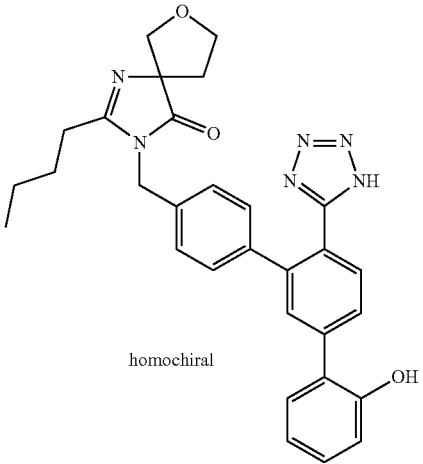 [SMILES: CCCCC1=NC2(CCOC2)C(=O)N1Cc1ccc(-c2cc(-c3ccccc3O)ccc2-c2nnn[nH]2)cc1] homochiral | 522.6 | 523.4; 1.49 min; 96% (Method A2) | 7.65-7.57 (m, 2H), 7.53 (s, 1H), 7.37 (br d, J = 7.6 Hz, 1H), 7.22-7.12 (m, 3H), 7.05 (br d, J = 7.9 Hz, 2H), 6.97 (d, J = 8.2 Hz, 1H), 6.91 (br t, J = 7.3 Hz, 1H), 4.69 (s, 2H), 3.99 (br t, J = 6.9 Hz, 2H), 3.79-3.74 (m, 1H), 3.74-3.69 (m, 1H), 2.37 (br t, J = 7.3 Hz, 2H), 2.22-2.14 (m, 1H), 2.01 (dt, J = 12.0, 5.8 Hz, 1H), 1.52 (quin, J = 7.5 Hz, 2H), 1.29 (dq, J = 14.7, 7.3 Hz, 2H), 0.82 (t, J = 7.3 Hz, 3H). |
| 151 | 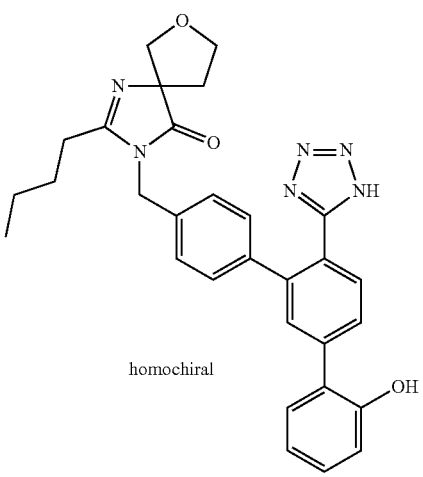 [SMILES: CCCCC1=NC2(CCOC2)C(=O)N1Cc1ccc(-c2cc(-c3ccccc3O)ccc2-c2nnn[nH]2)cc1] homochiral | 522.6 | 523.2; 1.45 min; 97% (Method A2) | 7.62 (s, 2H), 7.53 (s, 1H), 7.37 (br d, J = 7.3 Hz, 1H), 7.23-7.13 (m, 3H), 7.05 (br d, J = 7.9 Hz, 2H), 6.98 (d, J = 7.9 Hz, 1H), 6.91 (t, J = 7.3 Hz, 1H), 4.69 (s, 2H), 3.99 (br t, J = 6.9 Hz, 2H), 3.80-3.75 (m, 1H), 3.74-3.69 (m, 1H), 2.37 (t, J = 7.3 Hz, 2H), 2.18 (dt, J = 12.4, 7.9 Hz, 1H), 2.04-1.98 (m, 1H), 1.56-1.48 (m, 2H), 1.29 (dq, J = 14.9, 7.3 Hz, 2H), 0.82 (t, J = 7.3 Hz, 3H). |

| Ex | Structure | MW | LC-MS m/z [M + H]+; RT; Purity (Method) | 1H NMR (500 MHz, DMSO-d6) δ ppm |
|---|---|---|---|---|
| 152 | 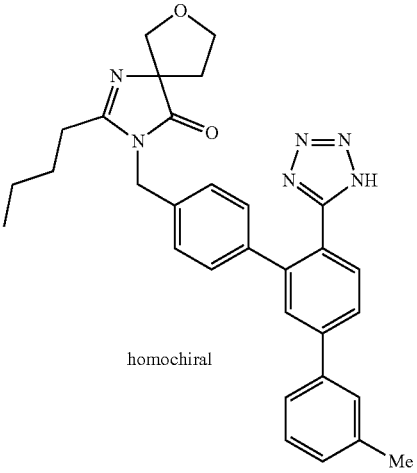 [SMILES: CCCCC1=NC2(CCOC2)C(=O)N1Cc1ccc(-c2cc(-c3cccc(C)c3)ccc2-c2nnn[nH]2)cc1] homochiral | 520.6 | 521.2; 1.84 min; 99% (Method A2) | 7.82 (br d, J = 7.0 Hz, 1H), 7.76-7.69 (m, 2H), 7.63 (s, 1H), 7.59 (br d, J = 7.9 Hz, 1H), 7.40 (t, J = 7.6 Hz, 1H), 7.25 (br d, J = 7.3 Hz, 1H), 7.21 (br d, J = 8.2 Hz, 2H), 7.12 (br d, J = 7.9 Hz, 2H), 4.72 (s, 2H), 4.00 (br t, J = 6.7 Hz, 2H), 3.80-3.75 (m, 1H), 3.75-3.69 (m, 1H), 2.41 (s, 3H), 2.36 (br t, J = 7.3 Hz, 2H), 2.19 (dt, J = 12.4, 7.9 Hz, 1H), 2.01 (dt, J = 12.1, 6.0 Hz, 1H), 1.52 (quin, J = 7.5 Hz, 2H), 1.30 (sxt, J = 7.4 Hz, 2H), 0.83 (t, J = 7.3 Hz, 3H) |
| 153 | 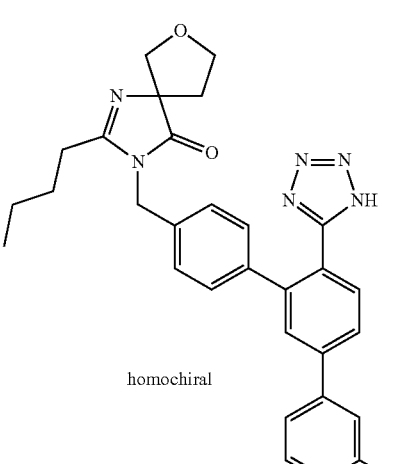 homochiral | 520.6 | 521.3; 1.80 min; 100% (Method A2) | 7.84 (br d, J = 7.6 Hz, 1H), 7.78-7.70 (m, 2H), 7.65 (s, 1H), 7.61 (br d, J = 7.6 Hz, 1H), 7.41 (t, J = 7.5 Hz, 1H), 7.26 (br d, J = 7.3 Hz, 1H), 7.22 (br d, J = 7.6 Hz, 2H), 7.13 (br d, J = 7.9 Hz, 2H), 4.73 (s, 2H), 4.01 (br t, J = 6.7 Hz, 2H), 3.82-3.76 (m, 1H), 3.75-3.70 (m, 1H), 2.42 (s, 3H), 2.37 (br t, J = 7.5 Hz, 2H), 2.19 (dt, J = 12.4, 7.9 Hz, 1H), 2.02 (dt, J = 12.0, 5.8 Hz, 1H), 1.53 (quin, J = 7.5 Hz, 2H), 1.35-1.26 (m, 2H), 0.84 (t, J = 7.3 Hz, 3H) |

Example 154: 2-butyl-3-((5'-(4-methylpyridin-2-yl)-2'-(1H-tetrazol-5-yl)-[1,1'-biphenyl]-4-yl)methyl)-7-oxa-1,3-diazaspiro[4.4]non-1-en-4-one

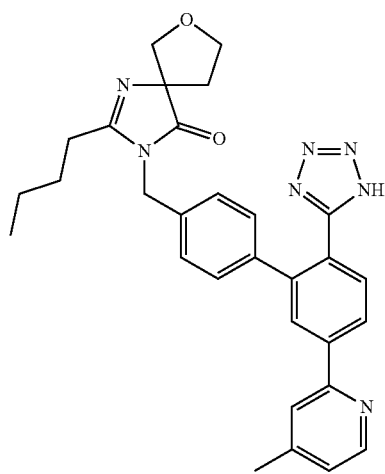

(Ex. 154)

Intermediate 154a: 4'-((2-butyl-4-oxo-7-oxa-1,3-diazaspiro[4.4]non-1-en-3-yl)methyl)-5-(4,4,5,5-tetramethyl-1,3,2-dioxaborolan-2-yl)-[1,1'-biphenyl]-2-carbonitrile

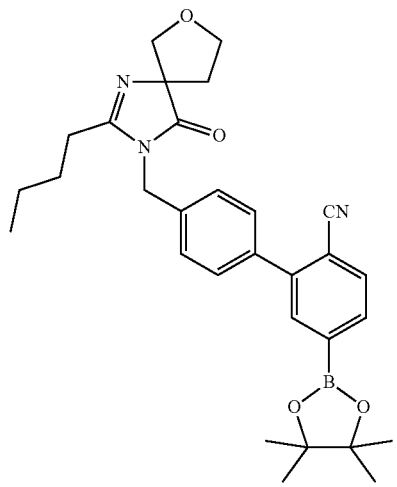

(154a)

Intermediate 146e-enantiomer 1 (140 mg, 0.30 mmol), 4,4,4',4',5,5,5',5'-octamethyl-2,2'-bi(1,3,2-dioxaborolane) (99 mg, 0.39 mmol), KOAc (74 mg, 0.75 mmol) in dioxane (2 mL) was degassed by bubbling Ar for 1 min, then Pd(dppf)Cl₂ complex with CH₂Cl₂ (1:1) (12 mg, 0.015 mmol) was added. The mixture was sealed in a pressure vial and heated in an oil bath at 125° C. for 1 h. The reaction mixture was directly loaded onto a silica gel cartridge, purified by flash chromatography (0% to 15% MeOH in CH₂Cl₂ over 12 min using a 12 g silica gel cartridge). The desired fractions were combined, concentrated and lyophilized to yield Intermediate 154a (123 mg, 0.24 mmol, 80% yield) as solid. 1H NMR (500 MHz, CDCl₃) δ 7.93 (s, 1H), 7.88 (d, J=7.7 Hz, 1H), 7.82-7.75 (m, 1H), 7.60 (d, J=8.0 Hz, 2H), 7.30 (d, J=8.3 Hz, 2H), 4.83-4.74 (m, 2H), 4.27-4.16 (m, 2H), 4.03-3.99 (m, 1H), 3.96-3.92 (m, 1H), 2.45-2.38 (m, 3H), 2.23-2.16 (m, 1H), 1.67 (br t, J=7.6 Hz, 2H), 1.38 (s, 12H), 0.92 (t, J=7.3 Hz, 3H). LC-MS (Method A2): RT=0.70 min, MS (ESI) m/z: 432.1 (M+H)⁺.

Intermediate 154b: 4'-((2-butyl-4-oxo-7-oxa-1,3-diazaspiro[4.4]non-1-en-3-yl)methyl)-5-(4-methylpyridin-2-yl)-[1,1'-biphenyl]-2-carbonitrile

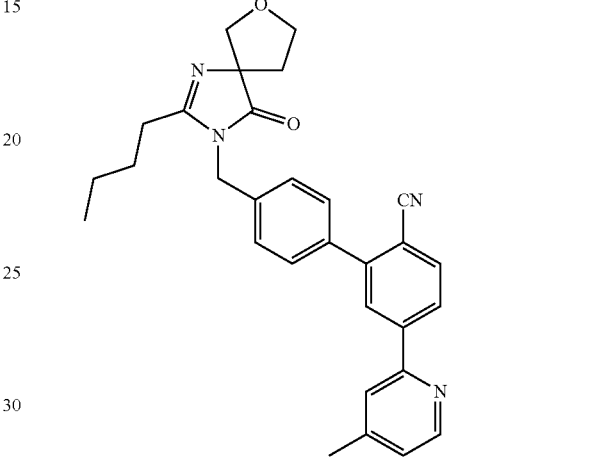

(154b)

A solution of Intermediate 154a (37 mg, 0.073 mmol), 2-bromo-4-methylpyridine (25 mg, 0.15 mmol) and Pd-XPhos G3 (2.5 mg, 2.9 μmol) in THF (1.5 mL) and K₃PO₄ (1.0 M, 0.15 mL, 0.15 mmol) was degassed with Ar for 1 min. The reaction mixture was sealed in a pressure vial and heated at 120° C. in a microwave reactor for 45 min. LC-MS indicated completion of reaction. The reaction mixture was concentrated and purified by column chromatography (0% to 15% MeOH in CH₂Cl₂ over 10 min using a 4 g silica gel cartridge). The desired fractions were combined and further purified by preparative HPLC (method E) to yield Intermediate 154b (20 mg, 0.042 mmol, 58% yield) as a white lyophilate. LC-MS (Method A2): RT=0.75 min, MS (ESI) m/z: 479.0 (M+H)⁺.

Example 154

Intermediate 154b (20 mg, 0.042 mmol) was dissolved in toluene (836 μl). Bu₂SnO (26 mg, 0.10 mmol) and TMS-N₃ (83 μl, 0.63 mmol) were added, and the reaction sealed in a pressure vial and heated at 105° C. overnight. LC-MS indicated completion of reaction. Toluene was removed by blowing a slow stream of N₂. The mixture was purified by preparative HPLC (method G) to yield Example 154 (7.3 mg, 0.011 mmol, 26.7% yield). ¹H NMR (500 MHz, DMSO-d₆) δ 8.59 (d, J=5.2 Hz, 1H), 8.28 (br d, J=7.9 Hz, 1H), 8.22 (s, 1H), 8.07 (s, 1H), 7.82 (d, J=8.2 Hz, 1H), 7.33 (br d, J=4.9 Hz, 1H), 7.25 (s, 1H), 7.23-7.16 (m, 4H), 7.15 (s, 1H), 7.05 (s, 1H), 4.76 (s, 2H), 4.01 (t, J=6.7 Hz, 2H), 3.81-3.75 (m, 1H), 2.45 (s, 3H), 2.41 (br t, J=7.6 Hz, 2H), 2.21 (dt, J=12.6, 7.7 Hz, 1H), 2.10-2.02 (m, 1H), 1.53 (quin, J=7.5 Hz, 2H), 1.30 (dq, J=14.9, 7.3 Hz, 2H), 0.84 (t, J=7.3 Hz, 3H). LC-MS (Method A2): RT=1.0 min, MS (ESI) m/z: 522.0 (M+H)⁺. Analytical HPLC purity (Method A2): 97%.

Example 155: 2-butyl-3-((3"-methyl-6'-(2H-tetrazol-5-yl)-[1,1':3',1"-terphenyl]-4-yl)methyl)-8-oxa-1,3-diazaspiro[4.5]dec-1-en-4-one

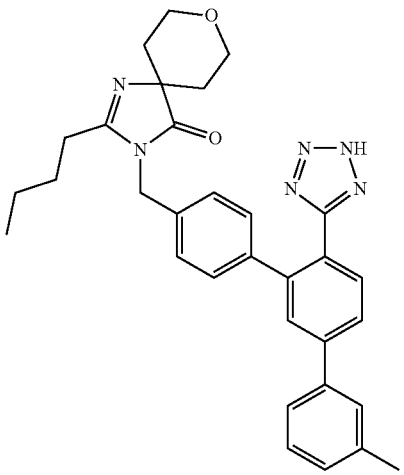
(Ex. 155)

Intermediate 155a:
4-aminotetrahydro-2H-pyran-4-carbonitrile hydrochloride

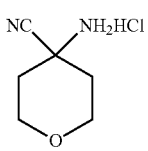
(155a)

To a solution of tetrahydro-4H-pyran-4-one (1.3 g, 13 mmol) in MeOH (4 mL) was added 7N ammonia/MeOH (3.71 mL, 26.0 mmol) at rt. The mixture was cooled with an ice bath and AcOH (0.82 mL, 14.28 mmol) was added dropwise. The mixture was stirred at rt for min then NaCN (0.636 g, 12.98 mmol) was added in one portion. The mixture was heated up to 50° C. in oil bath for 2h and rt overnight. The mixture was concentrated, EtOAc was added to the concentrated mixture and stir for 15 min. The slurry was removed by filtration and the wet cake was washed with EtOAc twice. The combined filtrates were concentrated and the crude sample was resolved in DCM (20 mL) and treated with 4N HCl in dioxane (4.87 mL, 19.48 mmol) at rt for 15 min. Precipitation was formed and the mixture was concentrated. The residual was triturated in ether. The title compound (Intermediate 155a, 2.1 g, 12.91 mmol, 99% yield) was obtained by filtration as an off-white solid. $^1$H NMR (500 MHz, MeOH-d$_4$) δ 4.13 (dd, J=12.7, 4.7 Hz, 2H), 3.71-3.63 (m, 2H), 2.24 (dd, J=12.9, 1.4 Hz, 2H), 2.08-1.91 (m, 2H).

Intermediate 155b:
N-(4-cyanotetrahydro-2H-pyran-4-yl)pentanamide

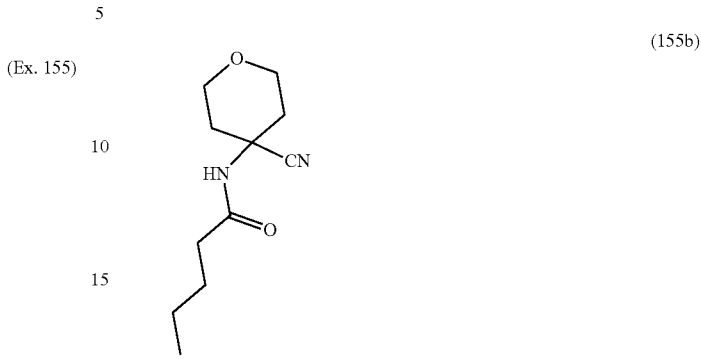
(155b)

To a solution of 4-aminotetrahydro-2H-pyran-4-carbonitrile hydrochloride (155a, 230 mg, 1.414 mmol) in DCM (4 mL) was added potassium carbonate (1016 mg, 7.35 mmol) in H$_2$O (4 mL). The mixture was cooled with an ice bath. Pentanoyl chloride (0.235 mL, 1.980 mmol) in DCM (4 mL) was added dropwise to the stirred solution. The reaction mixture was stirred at 0° C. for 2 h, and at rt for 3 h. The organic phase was collected. The aqueous phase was extracted (2X) with DCM. The combined organic phase was washed with brine, dried over Na$_2$SO$_4$ and concentrated. The residue was purified by ISCO (Hexanes/AcOEt, 0-100%) to give the title compound (Intermediate 155b, 240 mg, 1.141 mmol, 81% yield) as oil. LC-MS (Method A5): 1.63 min, [M+H]$^+$=221.1; $^1$H NMR (500 MHz, MeOH-d$_4$) δ 8.43 (br s, 1H), 3.91 (dt, J=12.6, 4.0 Hz, 2H), 3.72 (ddd, J=12.4, 10.1, 2.5 Hz, 2H), 2.33 (dt, J=13.5, 1.9 Hz, 2H), 2.26 (t, J=7.4 Hz, 2H), 1.93 (ddd, J=13.8, 10.0, 4.0 Hz, 2H), 1.74-1.56 (m, 2H), 1.46-1.29 (m, 2H), 0.96 (t, J=7.4 Hz, 3H).

Intermediate 155c: 2-butyl-8-oxa-1,3-diazaspiro[4.5]dec-1-en-4-one hydrochloride

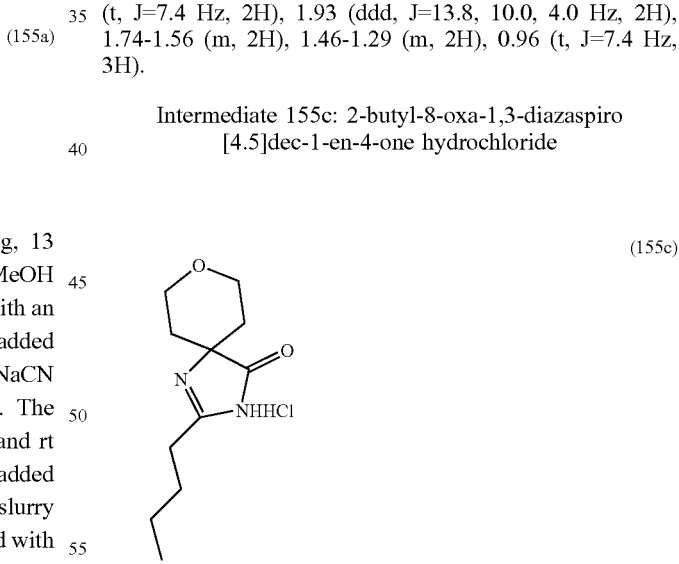
(155c)

To a solution of N-($^4$-cyanotetrahydro-2H-pyran-4-yl)pentanamide (Intermediate 155b, 160 mg, 0.761 mmol) in n-propanol (2 mL) was added 4N HCl in dioxane (1.902 mL, 7.61 mmol) dropwise. The mixture was heated up to 50° C. in oil bath for overnight. The mixture was concentrated and dried under vacuum to give the title compound (Intermediate 155c, 188 mg, 0.761 mmol, 100% yield) as a whit solid. LC-MS (Method A5): 0.91 min, [M+H]$^+$=221.1; $^1$H NMR (500 MHz, MeOH-d$_4$) δ 4.16-3.93 (m, 2H), 3.86-3.73 (m, 2H), 2.99-2.70 (m, 2H), 2.18-2.03 (m, 2H), 1.90 (br dd, J=7.6, 4.0 Hz, 2H), 1.86-1.75 (m, 2H), 1.55-1.45 (m, 2H), 1.04 (t, J=7.4 Hz, 3H).

Intermediate 155d: 5-bromo-4'-((2-butyl-4-oxo-8-oxa-1,3-diazaspiro[4.5dec-1-en-3-yl)methyl)biphenyl-2-carbonitrile

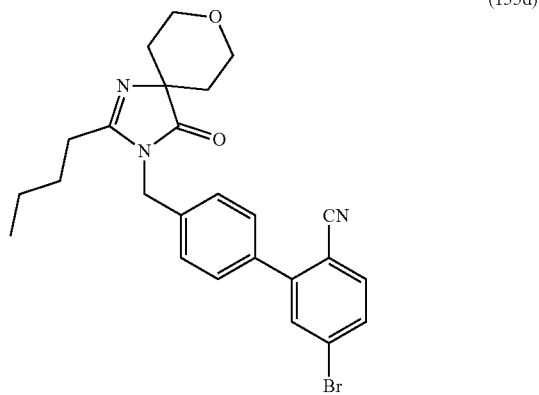

(155d)

2-butyl-8-oxa-1, 3-diazaspiro[4.5]dec-1-en-4-one, HCl (Intermediate 155c, 260 mg, 1.054 mmol) was dissolved in DMF (5 mL). NaH (105 mg, 2.63 mmol) was added. The mixture was stirred at rt for 15 min, 5-bromo-4'-(bromomethyl)-[1,1'-biphenyl]-2-carbonitrile (I-002, 388 mg, 1.106 mmol) was added at 0° C. The reaction mixture was stirred at rt for 1 h. The reaction mixture was diluted with EtOAc, washed with saturated NH$_4$Cl, brine, dried over Na$_2$SO$_4$, filtered, and concentrated in vacuo. The residue was purified by ISCO (Hexanes/AcOEt, 0-100%) to give the title compound (Intermediate 155d, 383 mg, 0.797 mmol, 76% yield) as off white solid. LC-MS (Method A5): 2.44 min, [M+H]$^+$=480.1 and 482.1; $^1$H NMR (500 MHz, CDCl$_3$) δ 7.68 (d, J=1.1 Hz, 1H), 7.66-7.58 (m, 2H), 7.55 (d, J=8.3 Hz, 2H), 7.31 (d, J=8.0 Hz, 2H), 4.77 (s, 2H), 4.09-4.02 (m, 2H), 4.01-3.94 (m, 2H), 2.45-2.35 (m, 2H), 2.11-1.99 (m, 2H), 1.64 (dt, J=15.1, 7.6 Hz, 2H), 1.50 (br d, J=13.5 Hz, 2H), 1.42-1.35 (m, 2H), 0.91 (t, J=7.3 Hz, 3H).

Intermediate 155e: 4"-((2-butyl-4-oxo-8-oxa-1,3-diazaspiro[4.5dec-1-en-3-yl)methyl)-3-methyl-[1,1':3',1"-terphenyl]-4'-carbonitrile

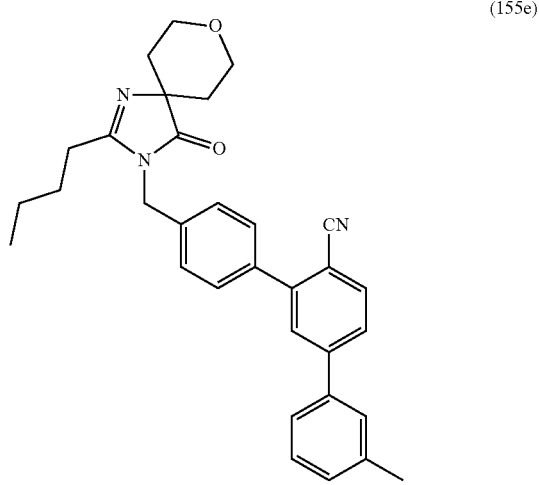 [SMILES: CCCCC1=NC2(CCOCC2)C(=O)N1Cc1ccc(-c2cc(-c3cccc(C)c3)ccc2C#N)cc1]

(155e)

A mixture of 5-bromo-4'-((2-butyl-4-oxo-8-oxa-1,3-diazaspiro[4.5]dec-1-en-3-yl)methyl)-[1,1'-biphenyl]-2-carbonitrile (Intermediate 155d, 25 mg, 0.052 mmol) and m-tolylboronic acid (21.23 mg, 0.156 mmol) in THF (1 mL) was treated with 1.5 M Na$_2$CO$_3$ (0.104 mL, 0.156 mmol) followed by PdCl$_2$(dppf) (4.25 mg, 5.20 µmol). The resulting mixture was degassed with N$_2$ for 2 min before the reaction vessel was sealed and irradiated in a microwave reactor at 120° C. for 30 min. The cooled reaction mixture was concentrated to dryness and the residue purified by ISCO (Hexanes/AcOEt, 0-100%) to afford the title compound (Intermediate 155e, 25 mg, 0.051 mmol, 98% yield) as an amber oil. LC-MS (Method A5): 2.57 min, [M+H]$^+$=492.2; $^1$H NMR (500 MHz, CDCl$_3$) δ 7.84 (d, J=8.0 Hz, 1H), 7.70 (d, J=1.4 Hz, 1H), 7.70-7.65 (m, 1H), 7.62 (d, J=8.0 Hz, 2H), 7.44 (d, J=7.2 Hz, 2H), 7.42-7.37 (m, 1H), 7.33 (d, J=8.0 Hz, 2H), 7.29-7.26 (m, 1H), 4.78 (s, 2H), 4.09-4.03 (m, 2H), 4.02-3.95 (m, 2H), 2.46 (s, 3H), 2.44-2.39 (m, 2H), 2.11-2.02 (m, 2H), 1.71-1.59 (m, 2H), 1.52 (br d, J=13.2 Hz, 2H), 1.40 (sxt, J=7.4 Hz, 2H), 0.92 (t, J=7.3 Hz, 3H).

Example 155: 2-butyl-3-((3"-methyl-6'-(2H-tetrazol-5-yl)-[1,1':3',1"-terphenyl]-4-yl)methyl)-8-oxa-1,3-diazaspiro[4.5]dec-1-en-4-one To a solution of 4"-((4-oxo-2-propyl-7-oxa-1,3-diazaspiro[4.4]non-1-en-3-yl)methyl)-[1,1':3',1"-terphenyl]-4'-carbonitrile (Intermediate 155e, 24 mg, 0.051 mmol) in toluene (1.5 mL) was added dibutyltin oxide (25.3 mg, 0.102 mmol) and TMS-N$_3$ (0.067 mL, 0.509 mmol). Then the reaction vessel was sealed and the mixture was heated at 100° C. overnight behind a blast shield (according to the procedure described in J. Org. Chem, 1993, 58, 4139). After cooling, the reaction mixture was concentrated, re-solvated in DMF, filtered then purified via preparative HPLC (Column: XBridge C18, 19×200 mm, 5-µm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 24-64% B over 20 minutes, then a 4-minute hold at 100% B; Flow: 20 mL/min) to afford 14.1 mg (0.026 mmol, 51.9% yield) of the title compound Example 155. LC-MS (Method A3): 1.41 min, [M+H]$^+$=535.25; $^1$H NMR (500 MHz, DMSO-d$_6$) δ 7.84-7.76 (m, 1H), 7.75-7.70 (m, 1H), 7.66 (d, J=1.4 Hz, 1H), 7.59 (s, 1H), 7.56 (br d, J=7.7 Hz, 1H), 7.38 (t, J=7.6 Hz, 1H), 7.23 (br d, J=7.6 Hz, 1H), 7.20 (br d, J=8.0 Hz, 2H), 7.08 (br d, J=8.1 Hz, 2H), 4.69 (s, 2H), 3.99-3.84 (m, 2H), 3.82-3.73 (m, 2H), 2.40 (s, 3H), 2.35 (t, J=7.5 Hz, 2H), 1.89-1.76 (m, 2H), 1.52 (quin, J=7.3 Hz, 2H), 1.39-1.24 (m, 4H), 0.82 (t, J=7.3 Hz, 3H).

The following examples have been similarly prepared from Intermediate 155d as described above for Example 155. Two analytical LC-MS injections were used to determine the final purity. The retention time of one of them is reported for each compound and is referred as Method A3, Method A4 or Method A5.

| Ex | Structure | MW | LC-MS m/z [M + H]+; RT; (Method) | 1H NMR (500 MHz, DMSO-d6) δ ppm |
|---|---|---|---|---|
| 156 | 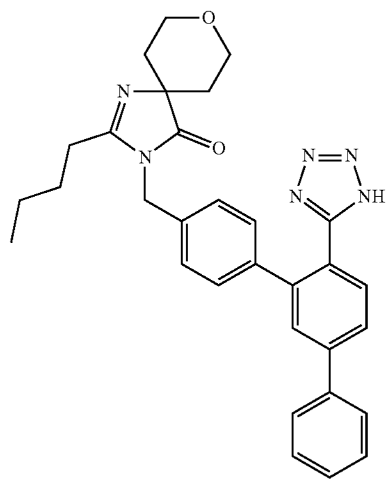 [SMILES: CCCCC1=NC2(CCOCC2)C(=O)N1Cc1ccc(-c2cc(-c3ccccc3)ccc2-c2nnn[nH]2)cc1] | 520.64 | 521.06; 1.53 min (Method A3) | 7.85-7.76 (m, 3H), 7.74 (d, J = 7.9 Hz, 1H), 7.70 (s, 1H), 7.55-7.48 (m, 2H), 7.46-7.40 (m, 1H), 7.20 (d, J = 7.9 Hz, 2H), 7.09 (br d, J = 7.9 Hz, 2H), 4.71 (s, 2H), 3.88 (br d, J = 11.3 Hz, 2H), 3.83-3.68 (m, 2H), 2.52 (br s, 6H), 2.36 (t, J = 7.5 Hz, 2H), 1.87-1.77 (m, 2H), 1.57-1.43 (m, 2H), 1.40-1.20 (m, 4H), 0.82 (t, J = 7.3 Hz, 3H). |
| 157 | 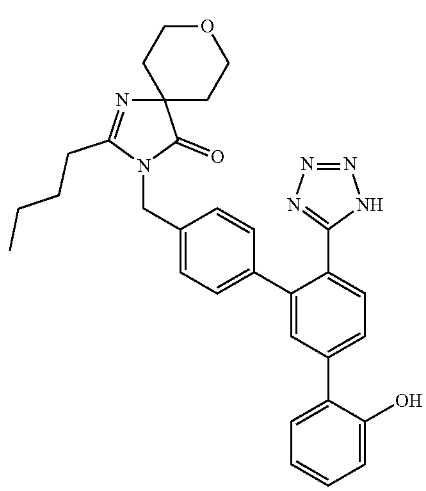 [SMILES: CCCCC1=NC2(CCOCC2)C(=O)N1Cc1ccc(-c2cc(-c3ccccc3O)ccc2-c2nnn[nH]2)cc1] | 536.64 | 537.13; 1.34 (Method A3) | 7.64 (s, 2H), 7.57 (s, 1H), 7.37 (br d, J = 7.6 Hz, 1H), 7.23-7.18 (m, 1H), 7.16 (br d, J = 8.0 Hz, 2H), 7.05 (br d, J = 8.0 Hz, 2H), 6.97 (d, J = 8.1 Hz, 1H), 6.91 (t, J = 7.5 Hz, 1H), 4.68 (s, 2H), 3.92-3.84 (m, 2H), 3.82-3.72 (m, 2H), 2.35 (br t, J = 7.5 Hz, 2H), 1.87-1.72 (m, 2H), 1.51 (dt, J = 14.7, 7.4 Hz, 2H), 1.38-1.21 (m, 4H), 0.81 (t, J = 7.3 Hz, 3H) |

Example 158-enantiomer 1:3-((6'-(2H-tetrazol-5-yl)-[1,1':3',1''-terphenyl]-4-yl)methyl)-2-propyl-7-oxa-1,3-diazaspiro[4.4]non-1-en-4-one

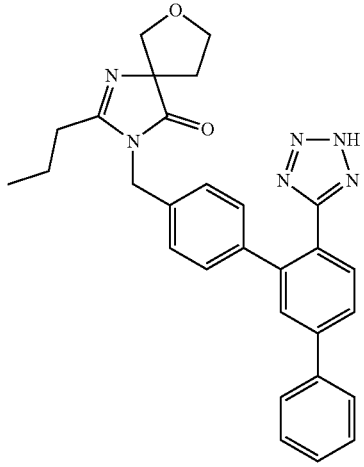

(Ex. 158)

Intermediate 158a:
3-aminotetrahydrofuran-3-carbonitrile hydrochloride

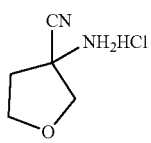

(158a)

To a solution of dihydrofuran-3(2H)-one (0.8 g, 9.29 mmol) in MeOH (4 mL) was added 7N ammonia/MeOH (2.66 mL, 18.59 mmol) at rt. The mixture was cooled with an ice bath and AcOH (0.585 mL, 10.22 mmol) was added dropwise. The mixture was stirred at rt for 10 min then NaCN (0.455 g, 9.29 mmol) was added in one portion. The mixture was heated up to 50° C. in oil bath for 2h and rt for overnight. The mixture was concentrated, EtOAc was added to the concentrated mixture and stir for 15 min. The slurry was removed by filtration and the wet cake was washed with EtOAc for 2 times. The combined filtrates were concentrated and the crude sample was resolved in DCM (20 mL) and treated with 4N HCl in dioxane (3.48 mL, 13.94 mmol) at rt for 15 min. Precipitation was formed and the mixture was concentrated. The residual was triturated in ether. The title compound (Intermediate 158a, 1.30 g, 8.92 mmol, 96% yield) was obtained by filtration as an off-white solid. $^1$H NMR (500 MHz, MeOH-d$_4$) δ 4.22-4.14 (m, 2H), 4.13-4.09 (m, 1H), 4.02 (td, J=8.9, 6.6 Hz, 1H), 2.80 (ddd, J=14.2, 8.7, 5.5 Hz, 1H), 2.46 (dt, J=14.4, 7.3 Hz, 1H).

Intermediate 158b:
N-(3-cyanotetrahydrofuran-3-yl)butyramide

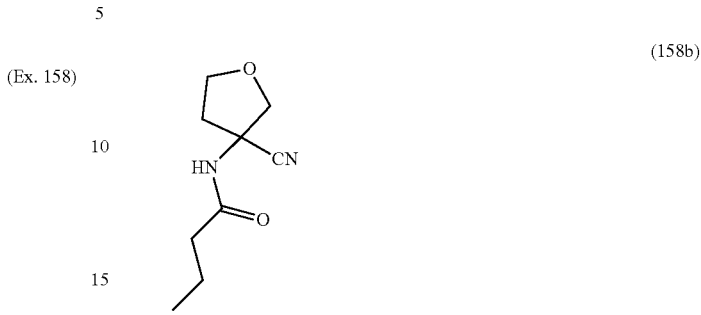

(158b)

To a solution of 3-aminotetrahydrofuran-3-carbonitrile, HCl (Intermediate 158a, 400 mg, 2.69 mmol) in DCM (8 mL) was added potassium carbonate (1935 mg, 14.00 mmol) in H$_2$O (8 mL). The mixture was cooled with an ice bath, butyryl chloride (0.394 mL, 3.77 mmol) in DCM (4 mL) was added dropwise to the stirred solution. The reaction mixture was stirred at 0° C. for 2 h, and at rt for 3 h. The organic phase was collected. The aqueous phase was extracted (2X) with DCM. The combined organic phase was washed with brine, dried over Na$_2$SO$_4$ and concentrated. The residue was purified by ISCO (Hexanes/AcOEt, 0-100%) to give the title compound (Intermediate 158b, 410 mg, 2.250 mmol, 84% yield) as oil. LC-MS (Method A5): 0.92 min, [M+H]$^+$= 183.1; $^1$H NMR (500 MHz, MeOH-d$_4$) δ 4.24 (d, J=9.4 Hz, 1H), 4.05-3.98 (m, 1H), 3.98-3.92 (m, 2H), 2.69-2.55 (m, 1H), 2.50-2.36 (m, 1H), 2.28-2.12 (m, 2H), 1.76-1.58 (m, 2H), 1.04-0.85 (m, 3H).

Intermediate 158c: 2-propyl-7-oxa-1,3-diazaspiro[4.4]non-1-en-4-one hydrochloride

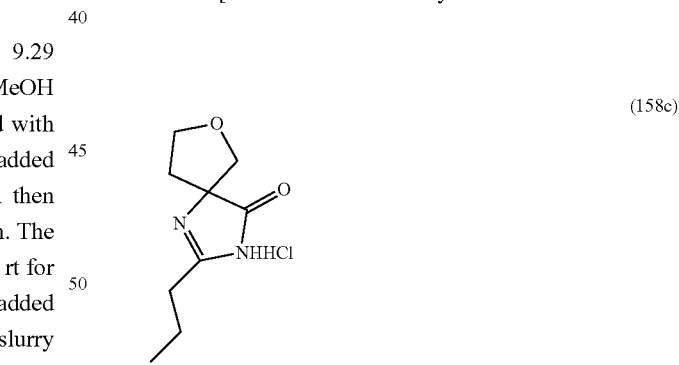

(158c)

To a solution of N-(3-cyanotetrahydrofuran-3-yl)butyramide (Intermediate 158b, 410 mg, 2.250 mmol) in n-propanol (6 mL) was added 4N HCl in dioxane (5.62 mL, 22.50 mmol) dropwise. The mixture was heated up to 50° C. in oil bath for overnight. The mixture was concentrated and dried under vacuum to give the title compound (Intermediate 158c, 492 mg, 2.250 mmol, 100% yield) as a white solid. LC-MS (Method A5): 0.40 min, [M+H]$^+$=221.1; $^1$H NMR (500 MHz, MeOH-d$_4$) δ 4.23-4.12 (m, 2H), 4.11-4.00 (m, 1H), 3.93 (d, J=10.2 Hz, 1H), 2.85 (t, J=7.7 Hz, 2H), 2.62-2.49 (m, 1H), 2.41 (dt, J=13.7, 6.8 Hz, 1H), 1.98-1.74 (m, 2H), 1.11 (t, J=7.4 Hz, 3H).

Intermediate 158d: 5-bromo-4'-((4-oxo-2-propyl-7-oxa-1,3-diazaspiro[4.4]non-1-en-3-yl)methyl)biphenyl-2-carbonitrile

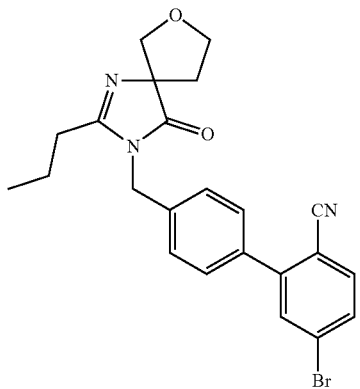

(158d)

2-Propyl-7-oxa-1,3-diazaspiro[4.4]non-1-en-4-one, HCl (Intermediate 158c, 492 mg, 2.25 mmol) was dissolved in DMF (10 mL). NaH (225 mg, 5.63 mmol) was added. The mixture was stirred at rt for 15 min, 5-bromo-4'-(bromomethyl)-[1,1'-biphenyl]-2-carbonitrile (I-002, 829 mg, 2.363 mmol) was added at 0° C. The reaction mixture was stirred at rt for 1 h. The reaction mixture was diluted with EtOAc, washed with saturated $NH_4Cl$, brine, dried over $Na_2SO_4$, filtered, and concentrated in vacuo. The residue was purified by ISCO (Hexanes/AcOEt, 0-100%) to give the title compound (Intermediate 158d, 620 mg, 1.371 mmol, 60.9% yield) as as a white solid. LC-MS (Method A5): 2.30 min, $[M+H]^+$=452.1 and 454.1; $^1$H NMR (500 MHz, $CDC_3$) δ7.70 (d, J=1.1 Hz, 1H), 7.67-7.62 (m, 2H), 7.56 (d, J=8.3 Hz, 2H), 7.33 (d, J=8.3 Hz, 2H), 4.78 (d, J=6.6 Hz, 2H), 4.27-4.17 (m, 2H), 4.05-3.97 (m, 1H), 3.96-3.89 (m, 1H), 2.50-2.32 (m, 3H), 2.18 (ddd, J=12.3, 6.8, 5.4 Hz, 1H), 1.79-1.63 (m, 2H), 0.99 (t, J=7.4 Hz, 3H).

Intermediate 158e-enantiomer 1:5-bromo-4'-((4-oxo-2-propyl-7-oxa-1,3-diazaspiro[4.4]non-1-en-3-yl)methyl)biphenyl-2-carbonitrile

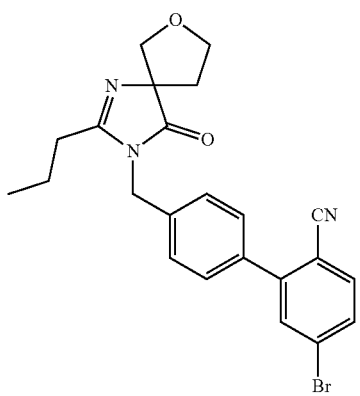

(158e, enantiomer 1)

Intermediate 158d-racemate (620 mg, 1.371 mmol) were resolved into two peaks on Instrument PIC Solution SFC Prep-200 with the following preparative chromatographic conditions: Column: Chiralpak AD-H, 30×250 mm, 5 micron; Mobile Phase: 20% IPA/80% $CO_2$; Flow Conditions: 85 mL/min, 120 Bar, 40° C.; Detector Wavelength: 220 nm; injection details: 0.5 mL of-155 mg/mL in IPA/ACN. Purity of each fraction was determined using the analytical chromatographic condition below: Instrument: Aurora Analytical SFC; Column: Chiralpak AD-H, 4.6×250 mm, 5 micron; Mobile Phase: 20% IPA/80% C02; Flow Conditions: 2.0 mL/min, 150 Bar, 40° C.; Detector Wavelength: 220 nm; Injection Details: 10 μL of-0.2 mg/mL in MeOH.

Peak 1 was collected and concentrated to give Intermediate 158e-enantiomer 1 (200 mg, 0.44 mmol, 32% yield): enantiomeric excess>99%. Chiral analytical RT=7.75 min. LC-MS (Method A5): 2.30 min, $[M+H]^+$=452.1 and 454.1; $^1$H NMR (500 MHz, $CDCl_3$) δ 7.70 (d, J=1.4 Hz, 1H), 7.68-7.60 (m, 2H), 7.56 (d, J=8.3 Hz, 2H), 7.32 (d, J=8.3 Hz, 2H), 4.78 (d, J=6.6 Hz, 2H), 4.28-4.09 (m, 2H), 4.03-3.98 (m, 1H), 3.96-3.91 (m, 1H), 2.52-2.28 (m, 3H), 2.18 (ddd, J=12.3, 6.9, 5.2 Hz, 1H), 1.76-1.65 (m, 2H), 0.99 (t, J=7.3 Hz, 3H).

Intermediate 158f-enantiomer 2:5-bromo-4'-((4-oxo-2-propyl-7-oxa-1,3-diazaspiro[4.4]non-1-en-3-yl)methyl)biphenyl-2-carbonitrile

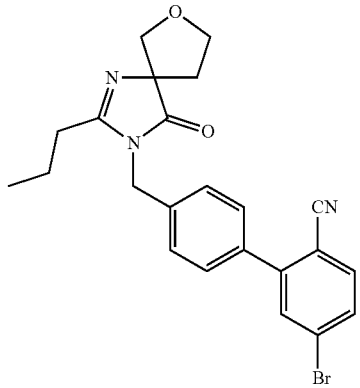

(158f, enantiomer 2)

Peak 2 was collected and concentrated to give Intermediate 158f-enantiomer 2 (200 mg, 0.44 mmol, 32% yield): enantiomeric excess: 94%. Chiral analytical RT=10.01 min. LC-MS (Method A5): 2.30 min, $[M+H]^+$=452.1 and 454.1; $^1$H NMR (500 MHz, $CDCl_3$) δ 7.68 (d, J=1.4 Hz, 1H), 7.64-7.60 (m, 2H), 7.54 (d, J=8.0 Hz, 2H), 7.31 (d, J=8.0 Hz, 2H), 4.77 (d, J=6.3 Hz, 2H), 4.26-4.11 (m, 2H), 3.99 (d, J=8.8 Hz, 1H), 3.94-3.86 (m, 1H), 2.49-2.31 (m, 3H), 2.16 (ddd, J=12.3, 6.7, 5.5 Hz, 1H), 1.83-1.64 (m, 2H), 0.97 (t, J=7.4 Hz, 3H).

Intermediate 158 g: 4"-((4-oxo-2-propyl-7-oxa-1,3-diazaspiro[4.4]non-1-en-3-yl)methyl)-[1,1':3',1"-terphenyl]-4'-carbonitrile

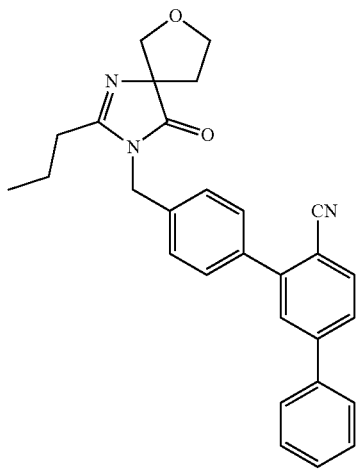

(158g)

A mixture of 5-bromo-4'-((4-oxo-2-propyl-7-oxa-1,3-diazaspiro[4.4]non-1-en-3-yl)methyl)biphenyl-2-carbonitrile (Intermediate 158e, 25 mg, 0.055 mmol) and phenylboronic acid (10.11 mg, 0.083 mmol) in THF (1 mL) was treated with 1.5 M Na₂CO₃ (0.111 mL, 0.166 mmol) followed by PdCl₂(dppf) (4.51 mg, 5.53 μmol). The resulting mixture was degassed with N₂ for 2 min before the reaction vessel was sealed and irradiated in a microwave reactor at 120° C. for 30 min. The cooled reaction mixture was concentrated to dryness and the residue purified by ISCO (Hexanes/AcOEt, 0-100%) to afford the title compound (Intermediate 158 g, 24 mg, 0.055 mmol, 100% yield) as an amber oil. LC-MS (Method A5): 2.46 min, [M+H]⁺=450.2; ¹H NMR (500 MHz, CDCl₃) δ 7.84 (d, J=8.0 Hz, 1H), 7.70 (d, J=1.4 Hz, 1H), 7.70-7.65 (m, 1H), 7.62 (d, J=8.0 Hz, 2H), 7.44 (d, J=7.2 Hz, 2H), 7.42-7.37 (m, 1H), 7.33 (d, J=8.0 Hz, 2H), 7.29-7.26 (m, 1H), 4.78 (s, 2H), 4.09-4.03 (m, 2H), 4.02-3.95 (m, 2H), 2.46 (s, 3H), 2.44-2.39 (m, 2H), 2.11-2.02 (m, 2H), 1.71-1.59 (m, 2H), 1.52 (br d, J=13.2 Hz, 2H), 1.40 (sxt, J=7.4 Hz, 2H), 0.92 (t, J=7.3 Hz, 3H).

Example 158-enantiomer 1:3-((6'-(2H-tetrazol-5-yl)-[1,1':3',1"-terphenyl]-4-yl)methyl)-2-propyl-7-oxa-1,3-diazaspiro[4.4]non-1-en-4-one To a solution of 4"-((4-oxo-2-propyl-7-oxa-1,3-diazaspiro[4.4]non-1-en-3-yl)methyl)-[1,1':3',1"-terphenyl]-4'-carbonitrile (Intermediate 158 g, 24 mg, 0.055 mmol) in toluene (1.5 mL) was added dibutyltin oxide (27.7 mg, 0.111 mmol) and TMS-N₃ (0.074 mL, 0.556 mmol). Then the reaction vessel was sealed and the mixture was heated at 100° C. overnight behind a blast shield (according to the procedure described in J. Org. Chem, 1993, 58, 4139). After cooling, the reaction mixture was concentrated, re-solvated in DMF, filtered then purified via preparative HPLC for two times (First: Column: XBridge C18, 19×200 mm, 5-μm particles; Mobile Phase A: 5:95 ACN: H₂O with 10 mM NH₄OAc; Mobile Phase B: 95:5 ACN: H₂O with 10 mM NH₄OAc; Gradient: 6-52% B over 20 minutes, then a 4-minute hold at 100% B; Flow: 20 mL/min; Second: Column: XBridge C18, 19×200 mm, 5-μm particles; Mobile Phase A: 5:95 ACN: H₂O with 10 mM NH₄OAc; Mobile Phase B: 95:5 ACN: H₂O with 10 mM NH₄OAc; Gradient: 11-51% B over 20 minutes, then a 4-minute hold at 100% B; Flow: 20 mL/min.) to afford 8.0 mg (0.016 mmol, 29.2% yield) of the title compound Example 158-enantiomer 1. LC-MS (Method A3): 1.38 min, [M+H]⁺=493.18; ¹H NMR (500 MHz, DMSO-d₆) δ 7.78 (br d, J=7.4 Hz, 2H), 7.74 (s, 2H), 7.64 (s, 1H), 7.50 (br t, J=7.7 Hz, 2H), 7.45-7.34 (m, 1H), 7.23 (br d, J=8.0 Hz, 2H), 7.08 (br d, J=7.9 Hz, 2H), 4.70 (s, 2H), 4.01 (t, J=6.8 Hz, 2H), 3.82-3.70 (m, 2H), 2.36 (t, J=7.2 Hz, 2H), 2.19 (dt, J=12.3, 7.7 Hz, 1H), 2.09-1.98 (m, 1H), 1.67-1.55 (m, 2H), 0.91 (t, J=7.4 Hz, 3H).

The following examples have been similarly prepared from Intermediate 158e-enantiomer 1 as described above for Example 158-enantiomer 1. Two analytical LC-MS injections were used to determine the final purity. The retention time of one of them is reported for each compound and is referred as Method A3, Method A4 or Method A5.

| Ex | Structure | MW | LC-MS m/z [M + H]⁺; RT; (Method) | ¹H NMR (500 MHz, DMSO-d₆) δ ppm |
|---|---|---|---|---|
| 159 | 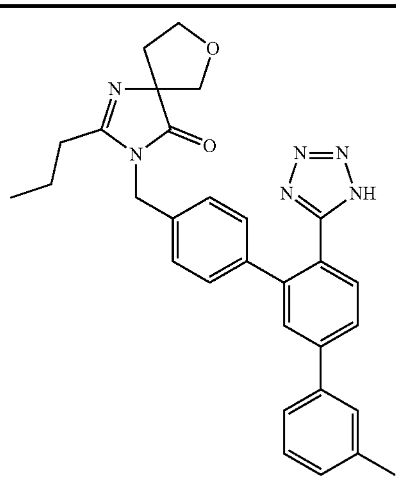 | 506.61 | 507.03; 1.5 min (Method A3) | 7.79-7.69 (m, 2H), 7.64 (d, J = 1.4 Hz, 1H), 7.59 (s, 1H), 7.55 (br d, J = 7.7 Hz, 1H), 7.38 (t, J = 7.6 Hz, 1H), 7.26-7.17 (m, 3H), 7.08 (br d, J = 8.0 Hz, 2H), 4.69 (s, 2H), 4.00 (dd, J = 7.6, 6.0 Hz, 2H), 3.82-3.66 (m, 2H), 2.39 (s, 3H), 2.38-2.29 (m, 2H), 2.18 (dt, J = 12.4, 7.8 Hz, 1H), 2.02 (td, J = 11.8, 5.4 Hz, 1H), 1.73-1.50 (m, 2H), 0.88 (t, J = 7.4 Hz, 3H) |

| Ex | Structure | MW | LC-MS m/z [M + H]+; RT; (Method) | 1H NMR (500 MHz, DMSO-d6) δ ppm |
|---|---|---|---|---|
| 160 | 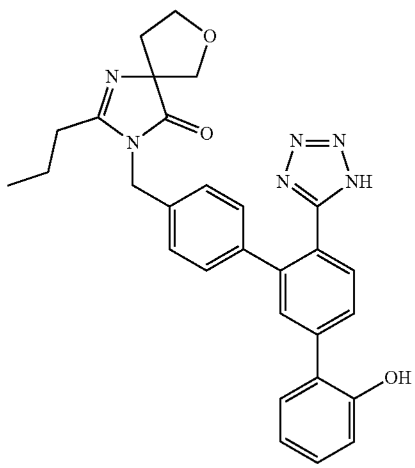 [SMILES: CCCC1=NC2(CCOC2)C(=O)N1Cc1ccc(-c2cc(-c3ccccc3O)ccc2-c2nnn[nH]2)cc1] | 508.58 | 509.01; 1.19 min (Method A3) | 7.65 (s, 2H), 7.58 (s, 1H), 7.38 (br d, J = 6.9 Hz, 1H), 7.26-7.13 (m, 3H), 7.07 (br d, J = 7.7 Hz, 2H), 6.98 (d, J = 8.0 Hz, 1H), 6.91 (br t, J = 7.4 Hz, 1H), 4.69 (s, 2H), 4.05-3.96 (m, 2H), 3.80-3.68 (m, 2H), 2.34 (br t, J = 7.2 Hz, 2H), 2.23-2.15 (m, 1H), 2.07-1.97 (m, 1H), 1.58 (br dd, J = 14.6, 7.4 Hz, 2H), 0.88 (q, J = 7.2 Hz, 3H) |
| 161 | 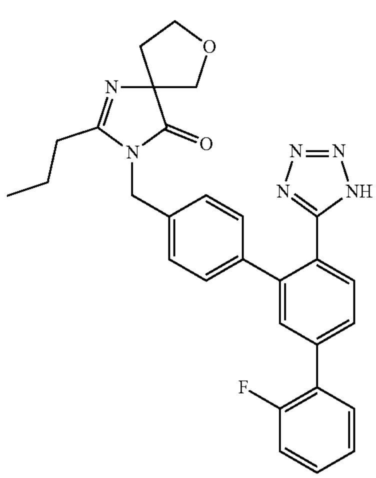 [SMILES: CCCC1=NC2(CCOC2)C(=O)N1Cc1ccc(-c2cc(-c3ccccc3F)ccc2-c2nnn[nH]2)cc1] | 510.57 | 511.01; 1.38 min (Method A3) | 7.72 (d, J = 7.9 Hz, 1H), 7.69-7.61 (m, 2H), 7.55 (s, 1H), 7.52-7.41 (m, 1H), 7.40-7.30 (m, 2H), 7.17 (br d, J = 7.9 Hz, 2H), 7.07 (br d, J = 7.9 Hz, 2H), 4.69 (s, 2H), 3.99 (br t, J = 6.7 Hz, 2H), 3.86-3.66 (m, 2H), 2.33 (br t, J = 7.2 Hz, 2H), 2.17 (dt, J = 12.4, 7.8 Hz, 1H), 2.01 (dt, J = 12.1, 5.9 Hz, 1H), 1.64-1.46 (m, 2H), 0.87 (t, J = 7.3 Hz, 3H) |

The following examples have been similarly prepared from Intermediate 158f-enantiomer 2 as described above for Example 158. Two analytical LC-MS injections were used to determine the final purity. The retention time of one of them is reported for each compound and is referred as Method A3, Method A4 or Method A.

| Ex | Structure | MW | LC-MS m/z [M + H]+; RT; (Method) | ¹H NMR (500 MHz, DMSO-d$_6$) δ ppm |
|---|---|---|---|---|
| 162 | 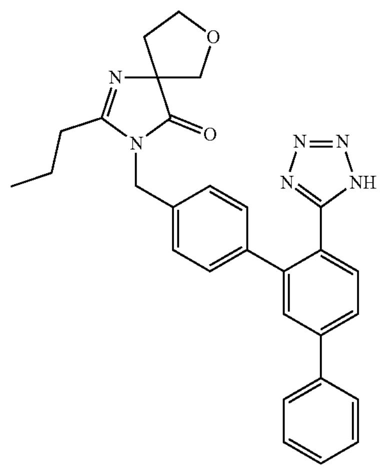 [SMILES: CCCC1=NC2(CCOC2)C(=O)N1Cc1ccc(-c2cc(-c3ccccc3)ccc2-c2nnn[nH]2)cc1] | 492.58 | 493.32; 1.34 min (Method A3) | 7.77 (br d, J = 7.6 Hz, 2H), 7.72 (s, 2H), 7.62 (s, 1H), 7.49 (br t, J = 7.4 Hz, 2H), 7.44-7.34 (m, 1H), 7.22 (br d, J = 7.9 Hz, 2H), 7.07 (br d, J = 7.7 Hz, 2H), 4.69 (s, 2H), 4.00 (br t, J = 6.7 Hz, 2H), 3.84-3.63 (m, 2H), 2.36 (br t, J = 7.2 Hz, 2H), 2.19 (dt, J = 12.2, 7.8 Hz, 1H), 2.07-1.95 (m, 1H), 1.67-1.46 (m, 2H), 0.90 (br t, J = 7.3 Hz, 3H) |
| 163 | 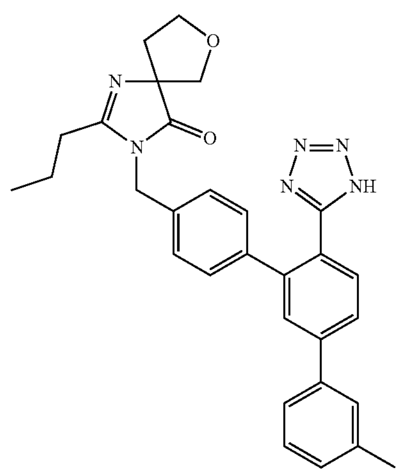 [SMILES: CCCC1=NC2(CCOC2)C(=O)N1Cc1ccc(-c2cc(-c3cccc(C)c3)ccc2-c2nnn[nH]2)cc1] | 506.61 | 507.4; 1.73 min (Method A3) | 7.79-7.66 (m, 2H), 7.62 (br d, J = 10.1 Hz, 2H), 7.57 (br d, J = 7.3 Hz, 1H), 7.41-7.35 (m, 1H), 7.38 (t, J = 7.8 Hz, 1H), 7.25-7.18 (m, 3H), 7.07 (br d, J = 8.2 Hz, 2H), 4.70 (s, 2H), 4.00 (br t, J = 6.7 Hz, 2H), 3.79-3.70 (m, 2H), 2.40 (s, 3H), 2.36 (br t, J = 7.3 Hz, 2H), 2.25-2.14 (m, 1H), 2.06-1.96 (m, 1H), 1.65-1.54 (m, 2H), 0.90 (t, J = 7.3 Hz, 3H) |
| 164 | 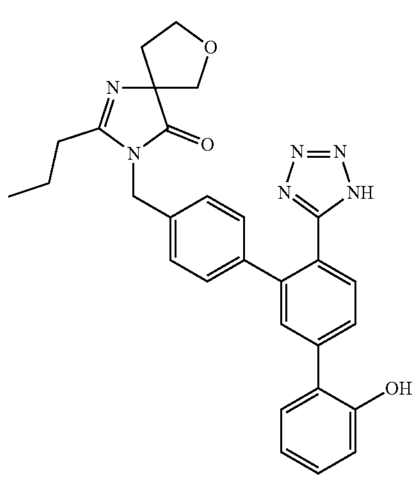 [SMILES: CCCC1=NC2(CCOC2)C(=O)N1Cc1ccc(-c2cc(-c3ccccc3O)ccc2-c2nnn[nH]2)cc1] | 508.58 | 509.01; 1.18 min (Method A3) | 7.76 (br s, 1H), 7.68 (br s, 2H), 7.41 (br d, J = 7.6 Hz, 1H), 7.23 (br t, J = 7.6 Hz, 1H), 7.13 (br s, 4H), 6.99 (d, J = 8.2 Hz, 1H), 6.93 (br t, J = 7.5 Hz, 1H), 4.70 (s, 2H), 3.99 (br t, J = 6.6 Hz, 2H), 3.81-3.68 (m, 2H), 2.32 (br t, J = 7.2 Hz, 2H), 2.18 (dt, J = 12.2, 7.6 Hz, 1H), 2.01 (dt, J = 11.8, 5.8 Hz, 1H), 1.61-1.49 (m, 2H), 0.88-0.84 (m, 3H) |

Example 165: 4"-((2-ethyl-4-oxo-7-oxa-1,3-diazaspiro[4.4]non-1-en-3-yl)methyl)-[1,1':3',1"-terphenyl]-4'-carbonitrile

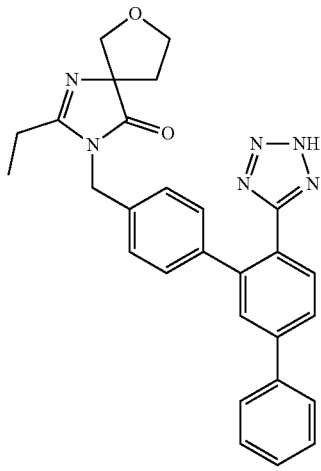

(Ex. 165, enantiomer 1)

Intermediate 165a:
N-(3-cyanotetrahydrofuran-3-yl)propionamide

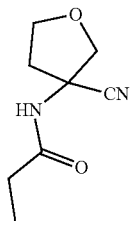

(165a)

To a solution of Intermediate 158a (600 mg, 4.04 mmol) in DCM (10 mL) was added potassium carbonate (2902 mg, 21.00 mmol) in H₂O (10 mL). The mixture was cooled with an ice bath, ropionyl chloride (523 mg, 5.65 mmol) in DCM (4 mL) was added dropwise to the stirred solution. The reaction mixture was stirred at 0° C. for 2 h, and at rt for 3 h. The organic phase was collected. The aqueous phase was extracted (2X) with DCM. The combined organic phase was washed with brine, dried over Na₂SO₄ and concentrated. The residue was purified by ISCO (Hexanes/AcOEt, 0-100%) to give the title compound (Intermediate 165a, 500 mg, 2.97 mmol, 73.6% yield) as oil. LC-MS (Method A5): 0.39 min, [M+H]$^+$=169.1; $^1$H NMR (500 MHz, MeOH-d$_4$) δ 9.37 (br s, 1H), 4.80 (d, J=9.4 Hz, 1H), 4.61-4.43 (m, 3H), 3.18 (ddd, J=13.3, 7.6, 6.9 Hz, 1H), 3.05 (ddd, J=13.3, 7.5, 5.9 Hz, 1H), 2.82 (q, J=7.7 Hz, 2H), 1.63 (t, J=7.6 Hz, 3H)

Intermediate 165b: 2-ethyl-7-oxa-1,3-diazaspiro[4.4]non-1-en-4-one hydrochloride

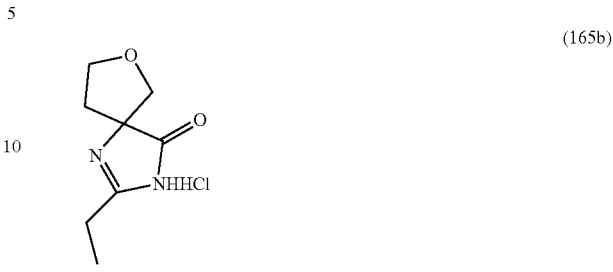

(165b)

To a solution of Intermediate 165a (500 mg, 2.97 mmol) in n-propanol (7.5 mL) was added 4N HCl in dioxane (7.43 mL, 29.7 mmol) dropwise. The mixture was heated up to 50° C. in oil bath for overnight. The mixture was concentrated and dried under vacuum to give the title compound (Intermediate 165b, 600 mg, 2.93 mmol, 99% yield) as a whit solid. LC-MS (Method A5): 0.28 min, [M+H]$^+$=169.1; $^1$H NMR (500 MHz, MeOH-d$_4$) δ 4.77-4.72 (m, 2H), 4.65-4.61 (m, 1H), 4.53 (d, J=9.9 Hz, 1H), 3.57 (q, J=7.4 Hz, 2H), 3.11-2.99 (m, 1H), 2.94 (dt, J=13.4, 8.0 Hz, 1H), 1.98 (t, J=7.6 Hz, 3H).

Intermediate 165c: 5-bromo-4'-((2-ethyl-4-oxo-7-oxa-1,3-diazaspiro[4.4]non-1-en-3-yl)methyl)biphenyl-2-carbonitrile

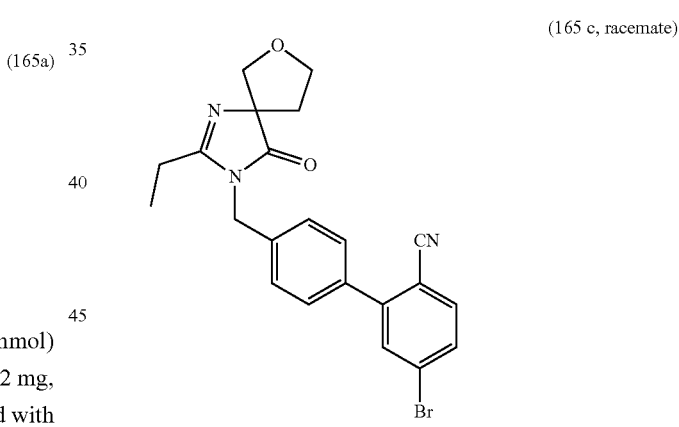

(165 c, racemate)

Intermediate 165b (400 mg, 1.954 mmol) was dissolved in DMF (10 mL). NaH (176 mg, 4.40 mmol) was added. The mixture was stirred at rt for 15 min, 5-bromo-4'-(bromomethyl)-[1,1'-biphenyl]-2-carbonitrile (I-002, 720 mg, 2.052 mmol) was added at 0° C. The reaction mixture was stirred at rt for 1 h. The reaction mixture was diluted with EtOAc, washed with saturated NH₄C₁, brine, dried over Na₂SO₄, filtered, and concentrated in vacuo. The residue was purified by ISCO (DCM/AcOEt, 0-100%) to give the title compound (Intermediate 165c, 450 mg, 1.027 mmol, 52.5% yield) as a white solid. LC-MS (Method A5): 2.29 min, [M+H]$^+$=438.1 and 440.1; $^1$H NMR (500 MHz, MeOH-d$_4$) δ 7.76 (d, J=1.4 Hz, 1H), 7.73-7.69 (m, 2H), 7.58 (d, J=8.3 Hz, 2H), 7.38 (d, J=8.3 Hz, 2H), 4.85 (d, J=5.0 Hz, 2H), 4.23-4.12 (m, 2H), 4.00-3.93 (m, 1H), 3.92-3.80 (m, 1H), 2.51 (q, J=7.2 Hz, 2H), 2.37 (dt, J=12.7, 7.7 Hz, 1H), 2.17 (ddd, J=12.4, 6.9, 5.4 Hz, 1H), 1.20 (t, J=7.4 Hz, 3H).

Intermediate 165d-enantiomer 1: 5-bromo-4'-((2-ethyl-4-oxo-7-oxa-1,3-diazaspiro[4.4]non-1-en-3-yl)methyl)biphenyl-2-carbonitrile

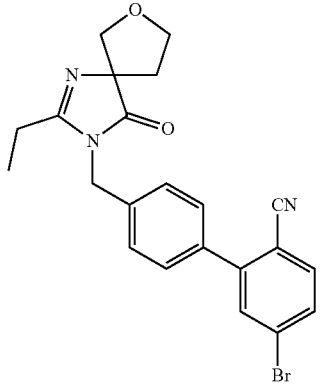

(165d)

Intermediate 165c-racemate (450 mg, 1.027 mmol) were resolved into two peaks on Instrument PIC Solution SFC Prep-200 with the following preparative chromatographic conditions: Column: Chiralpak AD-H, 30×250 mm, 5 micron; Mobile Phase: 20% IPA/80% $CO_2$; Flow Conditions: 85 mL/min, 120 Bar, 40° C.; Detector Wavelength: 220 nm; injection details: 0.5 mL of ~155 mg/mL in IPA/MeOH. Purity of each fraction was determined using the analytical chromatographic condition below: Instrument: Aurora Analytical SFC; Column: Chiralpak AD-H, 4.6×250 mm, 5 micron; Mobile Phase: 20% IPA/80% CO2; Flow Conditions: 2.0 mL/min, 150 Bar, 40° C.; Detector Wavelength: 220 nm; Injection Details: 10 µL of ~0.2 mg/mL in MeOH.

Peak 1 was collected and concentrated to give Intermediate 165d-enantiomer 1 (100 mg, 0.23 mmol, 22% yield): enantiomeric excess>99%. Chiral analytical RT=8.72 min. LC-MS (Method A5): 2.29 min, $[M+H]^+$=438.1 and 440.1; $^1H$ NMR (500 MHz, $CDCl_3$) δ 7.69 (d, J=1.1 Hz, 1H), 7.67-7.60 (m, 2H), 7.56 (d, J=8.3 Hz, 2H), 7.33 (d, J=8.3 Hz, 2H), 4.78 (d, J=6.6 Hz, 2H), 4.30-4.12 (m, 2H), 4.02-3.97 (m, 1H), 3.96-3.85 (m, 1H), 2.55-2.28 (m, 3H), 2.19 (ddd, J=12.4, 6.9, 5.5 Hz, 1H), 1.27-1.23 (m, 3H).

Intermediate 165e-enantiomer 2: 5-bromo-4'-((2-ethyl-4-oxo-7-oxa-1,3-diazaspiro[4.4]non-1-en-3-yl)methyl)biphenyl-2-carbonitrile

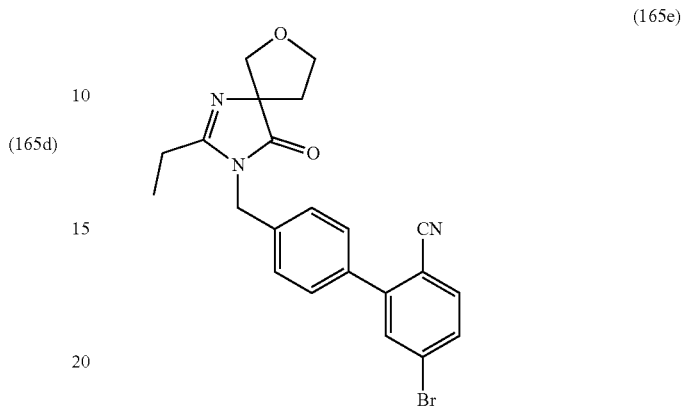

(165e)

Peak 2 was collected and concentrated to give Intermediate 165e-enantiomer 2 (100 mg, 0.23 mmol, 22% yield): enantiomeric excess 95.4%. Chiral analytical RT=11.52 min. LC-MS (Method A5): 2.29 min, $[M+H]^+$=438.1 and 440.1; $^1H$ NMR (500 MHz, $CDCl_3$) δ 7.69 (s, 1H), 7.64 (d, J=2.8 Hz, 2H), 7.56 (d, J=8.0 Hz, 2H), 7.33 (d, J=8.0 Hz, 2H), 4.78 (d, J=6.6 Hz, 2H), 4.28-4.11 (m, 2H), 4.02-3.98 (m, 1H), 3.97-3.87 (m, 1H), 2.49-2.31 (m, 3H), 2.25-2.10 (m, 1H), 1.25-1.22 (m, 3H).

Intermediate 165f: 4"-((2-ethyl-4-oxo-7-oxa-1,3-diazaspiro[4.4]non-1-en-3-yl)methyl)-[1,1':3',1"-terphenyl]-4'-carbonitrile

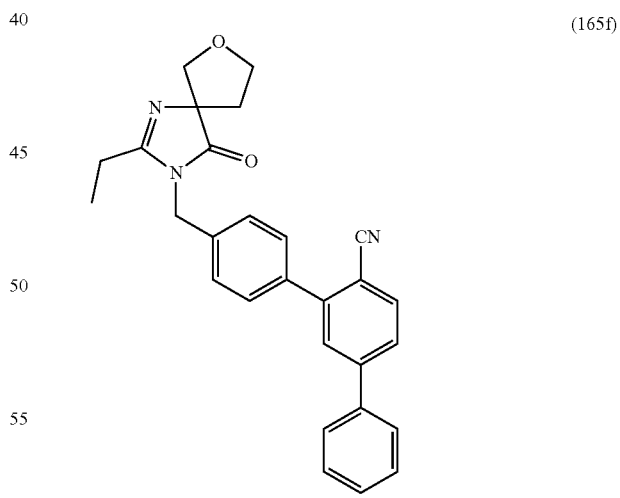

(165f)

A mixture of Intermediate 165d-enantiomer 1, 25 mg, 0.057 mmol) and phenylboronic acid (10.43 mg, 0.086 mmol) in THF (1 mL) was treated with 1.5 M $Na_2CO_3$ (0.114 mL, 0.171 mmol) followed by $PdCl_2$(dppf) (4.66 mg, 5.70 µmol). The resulting mixture was degassed with $N_2$ for 2 min before the reaction vessel was sealed and irradiated in a microwave reactor at 120° C. for 30 min. The cooled reaction mixture was concentrated to dryness and the residue purified by ISCO (Hexanes/AcOEt, 0-100%) to afford the title compound (Intermediate 165f, 24 mg, 0.057 mmol, 100% yield) as an amber oil. LC-MS (Method A5): 2.48 min, [M+H]$^+$=436.2; $^1$H NMR (500 MHz, CDCl$_3$) δ 7.86 (d, J=8.0 Hz, 1H), 7.72 (s, 1H), 7.70 (br d, J=8.0 Hz, 1H), 7.64 (t, J=7.6 Hz, 4H), 7.55-7.49 (m, 2H), 7.49-7.43 (m, 1H), 7.34 (d, J=8.0 Hz, 2H), 4.79 (d, J=6.3 Hz, 2H), 4.29-4.16 (m, 2H), 4.11-3.98 (m, 1H), 3.97-3.86 (m, 1H), 2.68-2.35 (m, 3H), 2.20 (dt, J=12.4, 6.2 Hz, 1H), 1.27-1.23 (m, 3H).

Example 165-enantiomer 1:4"-((2-ethyl-4-oxo-7-oxa-1,3-diazaspiro[4.4]non-1-en-3-yl)methyl)-[1,1':3',1"-terphenyl]-4'-carbonitrile To a solution of Intermediate 165f, 25 mg, 0.057 mmol) in toluene (1.5 mL) was added dibutyltin oxide (28.4 mg, 0.114 mmol) and TMS-N$_3$ (0.076 mL, 0.570 mmol). Then the reaction vessel was sealed and the mixture was heated at 100° C. overnight behind a blast shield (according to the procedure described in J. Org. Chem, 1993, 58, 4139). After cooling, the reaction mixture was concentrated, re-solvated in DMF, filtered then purified via preparative HPLC (Column: XBridge C18, 19×200 mm, 5-μm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 11-51% B over 25 minutes, then a 5-minute hold at 100% B; Flow: 20 mL/min.) to afford 22.7 mg (0.047 mmol, 83% yield) of the title compound Example 165-enantiomer 1. LC-MS (Method A3): 1.29 min, [M+H]$^+$=479.04; $^1$H NMR (500 MHz, DMSO-d$_6$) δ 7.87-7.79 (m, 3H), 7.75 (br d, J=10.1 Hz, 2H), 7.57-7.49 (m, 2H), 7.47-7.40 (m, 1H), 7.39-7.38 (m, 1H), 7.20 (br d, J=7.9 Hz, 2H), 7.12 (br d, J=7.9 Hz, 2H), 4.71 (s, 2H), 4.00 (br t, J=6.7 Hz, 2H), 3.81-3.69 (m, 2H), 2.39 (q, J=7.3 Hz, 2H), 2.18 (dt, J=12.4, 7.7 Hz, 1H), 2.02 (dt, J=12.2, 5.8 Hz, 1H), 1.08 (t, J=7.3 Hz, 3H).

The following examples have been similarly prepared from Intermediate 165d-enantiomer 1 as described above for Example 165-enantiomer 1. Two analytical LC-MS injections were used to determine the final purity. The retention time of one of them is reported for each compound and is referred as Method A3, Method A4 or Method A5.

| Ex | Structure | MW | LC-MS m/z [M + H]$^+$; RT; (Method) | $^1$H NMR (500 MHz, DMSO-d$_6$) δ ppm |
|---|---|---|---|---|
| 166 | 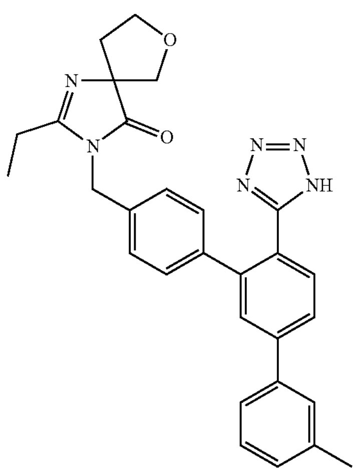 [SMILES: CCC1=NC2(CCOC2)C(=O)N1Cc1ccc(-c2cc(-c3cccc(C)c3)ccc2-c2nnn[nH]2)cc1] | 492.58 | 493.3; 1.46 min (Method A3) | 7.81-7.76 (m, 1H), 7.75-7.71 (m, 1H), 7.69 (s, 1H), 7.61 (s, 1H), 7.57 (br d, J = 7.7 Hz, 1H), 7.38 (t, J = 7.6 Hz, 1H), 7.25-7.18 (m, 3H), 7.11 (d, J = 8.0 Hz, 2H), 4.70 (s, 2H), 4.01 (dd, J = 7.4, 6.1 Hz, 2H), 3.80-3.64 (m, 2H), 2.45-2.33 (m, 5H), 2.19 (dt, J = 12.4, 7.7 Hz, 1H), 2.03 (dt, J = 12.2, 5.9 Hz, 1H), 1.09 (t, J = 7.3 Hz, 3H) |
| 167 | 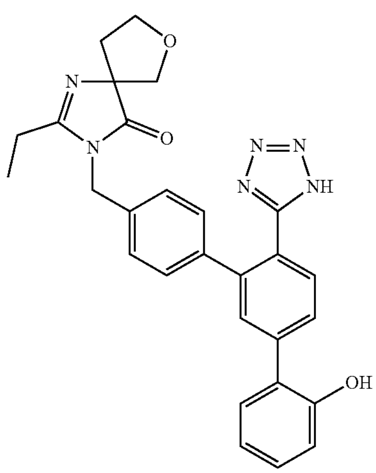 [SMILES: CCC1=NC2(CCOC2)C(=O)N1Cc1ccc(-c2cc(-c3ccccc3O)ccc2-c2nnn[nH]2)cc1] | 494.56 | 495.38; 1.15 min (Method A3) | 7.72-7.64 (m, 2H), 7.62 (s, 1H), 7.40 (br d, J = 7.6 Hz, 1H), 7.21 (br t, J = 7.3 Hz, 1H), 7.18-7.13 (m, 2H), 7.12-7.06 (m, 2H), 6.98 (br d, J = 7.6 Hz, 1H), 6.92 (br t, J = 7.2 Hz, 1H), 4.69 (br s, 2H), 4.00 (br t, J = 6.6 Hz, 2H), 3.81-3.69 (m, 2H), 2.43-2.31 (m, 2H), 2.24-2.11 (m, 1H), 2.06-1.99 (m, 1H), 1.07 (br t, J = 7.3 Hz, 3H) |

The following examples have been similarly prepared from 5-bromo-4'-((2-ethyl-4-oxo-7-oxa-1,3-diazaspiro[4.4]non-1-en-3-yl)methyl)biphenyl-2-carbonitrile (165-enantiomer 2 as described above for Example 165-enantiomer 1. Two analytical LC-MS injections were used to determine the final purity. The retention time of one of them is reported for each compound and is referred as Method A3, Method A4 or Method A5.

| Ex | Structure | MW | LC-MS m/z [M + H]+; RT; (Method) | 1H NMR (500 MHz, DMSO-d6) δ ppm |
|---|---|---|---|---|
| 168 | 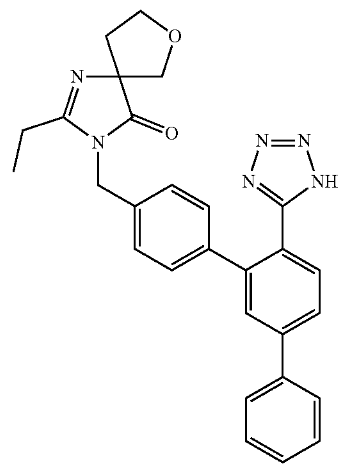 [SMILES: CCC1=NC2(CCOC2)C(=O)N1Cc1ccc(-c2cc(-c3ccccc3)ccc2-c2nnn[nH]2)cc1] | 478.56 | 479.23; 1.33 min (Method A3) | 7.84-7.76 (m, 3H), 7.75-7.72 (m, 1H), 7.68 (s, 1H), 7.50 (t, J = 7.6 Hz, 2H), 7.45-7.36 (m, 1H), 7.21 (d, J = 8.1 Hz, 2H), 7.10 (d, J = 8.0 Hz, 2H), 4.70 (s, 2H), 4.01 (dd, J = 7.5, 6.1 Hz, 2H), 3.80-3.68 (m, 2H), 2.39 (q, J = 7.3 Hz, 2H), 2.18 (dt, J = 12.3, 7.8 Hz, 1H), 2.09-1.96 (m, 1H), 1.09 (t, J = 7.3 Hz, 3H) |
| 169 | 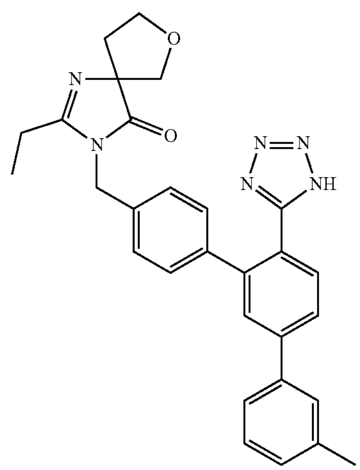 [SMILES: CCC1=NC2(CCOC2)C(=O)N1Cc1ccc(-c2cc(-c3cccc(C)c3)ccc2-c2nnn[nH]2)cc1] | 492.58 | 493.02; 1.4 min (Method A3) | 7.84-7.77 (m, 1H), 7.75-7.69 (m, 2H), 7.63 (s, 1H), 7.59 (br d, J = 7.9 Hz, 1H), 7.39 (t, J = 7.6 Hz, 1H), 7.24 (br d, J = 7.3 Hz, 1H), 7.19 (d, J = 7.9 Hz, 2H), 7.11 (br d, J = 7.9 Hz, 2H), 4.70 (s, 2H), 4.00 (t, J = 6.7 Hz, 2H), 3.82-3.66 (m, 2H), 2.46-2.32 (m, 5H), 2.18 (dt, J = 12.5, 7.8 Hz, 1H), 2.02 (dt, J = 12.1, 5.9 Hz, 1H), 1.08 (t, J = 7.3 Hz, 3H) |
| 170 | 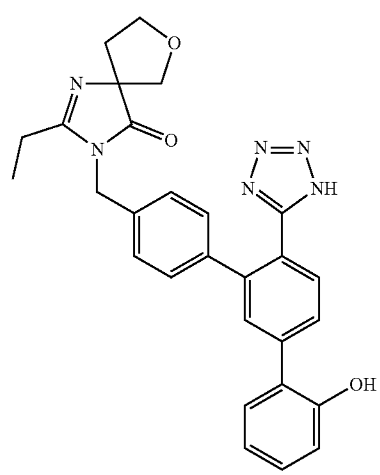 [SMILES: CCC1=NC2(CCOC2)C(=O)N1Cc1ccc(-c2cc(-c3ccccc3O)ccc2-c2nnn[nH]2)cc1] | 494.56 | 495.25; 1.09 min (Method A3) | 7.70-7.58 (m, 2H), 7.56 (s, 1H), 7.42-7.31 (m, 1H), 7.23-7.12 (m, 3H), 7.07 (br d, J = 8.1 Hz, 2H), 6.97 (d, J = 7.9 Hz, 1H), 6.91 (t, J = 7.3 Hz, 1H), 4.68 (s, 2H), 4.00 (dd, J = 7.6, 6.0 Hz, 2H), 3.87-3.61 (m, 2H), 2.39 (q, J = 7.3 Hz, 2H), 2.18 (dt, J = 12.4, 7.8 Hz, 1H), 2.08-1.97 (m, 1H), 1.08 (t, J = 7.3 Hz, 3H) |

Example 171: 2-butyl-3-((5'-(4-methylpyridin-2-yl)-2'-(2H-tetrazol-5-yl)-1,1'-biphenyll-4-yl)methyl)-8-oxa-1, 3-diazaspiro[4.5]dec-1-en-4-one

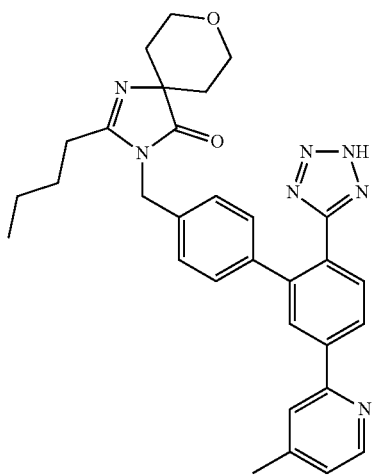
(Ex. 171)

Intermediate 171a: 4'-((2-butyl-4-oxo-8-oxa-1,3-diazaspiro[4.5]dec-1-en-3-yl)methyl)-5-(4,4,5,5-tetramethyl-1,3,2-dioxaborolan-2-yl)-[1,1'-biphenyl]-2-carbonitrile

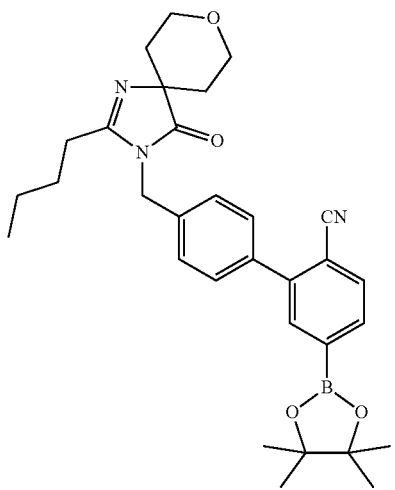
(171a)

Intermediate 155d (240 mg, 0.500 mmol), 4,4,4',4',5,5,5',5'-octamethyl-2,2'-bi(1,3,2-dioxaborolane) (190 mg, 0.749 mmol), KOAc (123 mg, 1.249 mmol) in dioxane (4 mL) was degassed by bubbling Ar for 1 min, then Pd(dppf)Cl$_2$ (20.40 mg, 0.025 mmol) was added. The mixture was sealed in a pressure vial and heated in an oil bath at 125° C. for 1 h. The reaction mixture was directly loaded onto a silica gel cartridge, purified by ISCO (DCM/MeOH, 0-20%) to afford the title compound (Intermediate 171a, 240 mg, 0.455 mmol, 91% yield). LC-MS (Method A5): 2.22 min, [M+H]$^+$=446.1; $^1$H NMR (500 MHz, CDC$_3$) δ7.92 (s, 1H), 7.87 (dd, J=7.7, 0.8 Hz, 1H), 7.77 (d, J=7.7 Hz, 1H), 7.58 (d, J=8.0 Hz, 2H), 7.32-7.26 (m, 2H), 4.77 (s, 2H), 4.09-4.03 (m, 2H), 4.02-3.94 (m, 2H), 2.46-2.32 (m, 2H), 2.06 (ddd, J=13.5, 9.6, 4.4 Hz, 2H), 1.65 (br t, J=7.7 Hz, 2H), 1.52 (br d, J=13.5 Hz, 2H), 1.42-1.38 (m, 2H), 1.27 (s, 12H), 0.92 (t, J=7.3 Hz, 3H).

Intermediate 171b: 4'-((2-butyl-4-oxo-8-oxa-1,3-diazaspiro[4.5]dec-1-en-3-yl)methyl)-5-(4-methylpyridin-2-yl)-[1,1'-biphenyll-2-carbonitrile

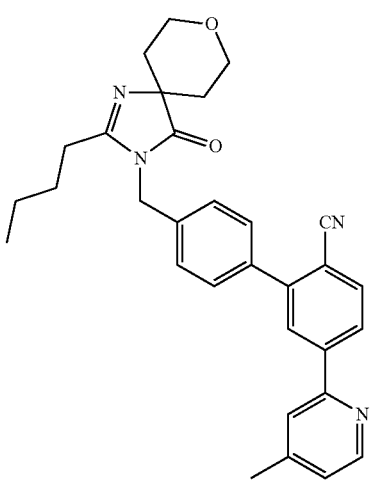
(171b)

A solution of Intermediate 171a (30 mg, 0.057 mmol), 2-bromo-4-methylpyridine (24.46 mg, 0.142 mmol) and Pd-XPhos G3 (1.926 mg, 2.275 µmol) in THF (1.5 mL) was added K$_3$PO$_4$ (1.0 M, 0.114 mL, 0.114 mmol). The mixture was degassed with Ar for 1 min. then sealed in a pressure vial and heated at 120° C. in a microwave reactor for 45 min. The reaction mixture was concentrated and purified by ISCO (DCM/MeOH, 0-20%) to afford the title compound (Intermediate 171b, 28 mg, 0.057 mmol, 100% yield). LC-MS (Method A5): 2.18 min, [M+H]$^+$=393.3; $^1$H NMR (500 MHz, CDCl$_3$) δ 8.62-8.51 (m, 1H), 8.26-8.13 (m, 1H), 8.09-7.80 (m, 1H), 7.67-7.60 (m, 2H), 7.52 (d, J=8.3 Hz, 1H), 7.32 (d, J=8.0 Hz, 1H), 7.26 (d, J=8.0 Hz, 1H), 7.17 (dd, J=8.3, 5.2 Hz, 1H), 6.95-6.84 (m, 1H), 4.77 (d, J=12.7 Hz, 2H), 4.11-4.03 (m, 2H), 4.02-3.93 (m, 2H), 2.47 (d, J=8.0 Hz, 3H), 2.44-2.38 (m, 2H), 2.10-2.01 (m, 2H), 1.72-1.57 (m, 2H), 1.53 (br d, J=13.2 Hz, 2H), 1.38 (br dd, J=14.6, 7.4 Hz, 2H), 0.93-0.83 (m, 3H).

Example 171: 2-butyl-3-((5'-(4-methylpyridin-2-yl)-2'-(2H-tetrazol-5-yl)-[1,1'-biphenyl]-4-yl)methyl)-8-oxa-1,3-diazaspiro[4.5]dec-1-en-4-one To a solution of 4'-((2-butyl-4-oxo-8-oxa-1,3-diazaspiro[4.5]dec-1-en-3-yl)methyl)-5-(4-methylpyridin-2-yl)-[1,1'-biphenyl]-2-carbonitrile (Intermediate 171b, 28.1 mg, 0.057 mmol) in toluene (1.5 mL) was added dibutyltin oxide (28.4 mg, 0.114 mmol) and TMS-N$_3$ (0.076 mL, 0.570 mmol). Then the reaction vessel was sealed and the mixture was heated at 100° C. overnight behind a blast shield (according to the procedure described in J. Org. Chem, 1993, 58, 4139). After cooling, the reaction mixture was concentrated, resolvated in DMF, filtered then purified via preparative HPLC (Column: XBridge C18, 19 200 mm, 5-m particles; Mobile Phase A: 5:95 ACN: H$_2$O with 10 mM NH$_4$OAc; Mobile Phase B: 95:5 ACN: H₂O with 10 mM NH₄OAc; Gradient: 12-52% B over 20 minutes, then a 4-minute hold at 100% B; Flow: 20 mL/min) to afford 5.4 mg (9.68 μmol, 16.98% yield) of the title compound Example 171. LC-MS (Method A3): 1.36 min, [M+H]⁺=536.09; ¹H NMR (500 MHz, DMSO-d₆) δ 8.55 (br s, 2H), 8.35-7.71 (m, 4H), 7.33-6.91 (m, 4H), 4.68 (br s, 2H), 3.99-3.81 (m, 2H), 3.80-3.61 (m, 2H), 2.40 (br s, 3H), 2.34 (br d, J=7.9 Hz, 2H), 1.94-1.64 (m, 2H), 1.60-1.40 (m, 2H), 1.37-1.23 (m, 4H), 0.91-0.77 (m, 3H).

Example 172: 3-((6'-(2H-tetrazol-5-yl)-[1,1':3',1''-terphenyl]-4-yl)methyl)-2-methyl-8-oxa-1,3-diazaspiro[4.5]dec-1-en-4-one

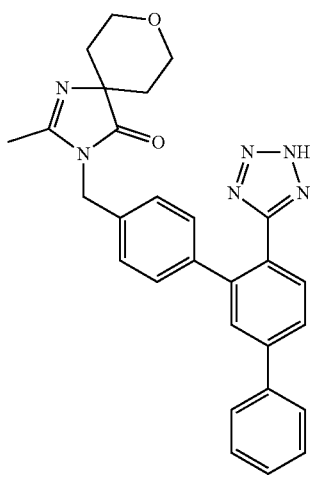

(Ex. 172)

Intermediate 172a:
N-(4-cyanotetrahydro-2H-pyran-4-yl)acetamide

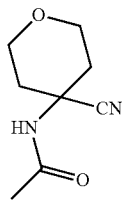

(172a)

To a solution of Intermediate 155a (500 mg, 3.07 mmol) in DCM (6 mL) was added potassium carbonate (2.2 g, 16 mmol) in H₂O (8 mL). The mixture was cooled with an ice bath. Acetyl chloride (0.306 mL, 4.30 mmol) in DCM (4 mL) was added dropwise to the stirred solution. The reaction mixture was stirred at 0° C. for 2 h, and at rt for 3 h. The organic phase was collected. The aqueous phase was extracted (2X) with DCM. The combined organic phase was washed with brine, dried over Na₂SO₄ and concentrated. The residue was purified by ISCO (DCM/AcOEt, 0-100%) to give the title compound (Intermediate 172a, 100 mg, 0.595 mmol, 19.34% yield) as oil. ¹H NMR (500 MHz, MeOH-d₄) δ 3.92 (dt, J=12.4, 4.1 Hz, 2H), 3.78-3.62 (m, 2H), 2.33 (br d, J=13.5 Hz, 2H), 2.01 (s, 3H), 1.93 (ddd, J=13.8, 10.0, 4.0 Hz, 2H).

Intermediate 172b: 2-methyl-8-oxa-1,3-diazaspiro[4.5]dec-1-en-4-one hydrochloride

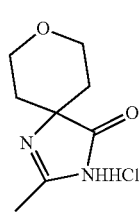

(172b)

To a solution of Intermediate 172a (100 mg, 0.595 mmol) in n-propanol (1.5 mL) was added 4N HCl in dioxane (1.486 mL, 5.95 mmol) dropwise. The mixture was heated up to 50° C. in oil bath for overnight. The mixture was concentrated and dried under vacuum to give the title compound (Intermediate 172b, 120 mg, 0.586 mmol, 99% yield) as a whit solid. ¹H NMR (500 MHz, MeOH-d₄) δ 4.11-4.01 (m, 2H), 3.76 (ddd, J=12.3, 9.4, 3.0 Hz, 2H), 2.61 (s, 3H), 2.11 (ddd, J=14.0, 9.6, 4.4 Hz, 2H), 1.93-1.80 (m, 2H).

Intermediate 172c: (6'-(2-trityl-2H-tetrazol-5-yl)-[1,1':3',1''-terphenyl]-4-yl)methyl methanesulfonate

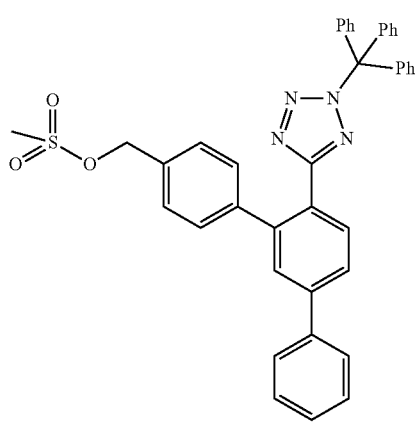

(172c)

A solution of 1-003 (3 g, 5.26 mmol) and TEA (1.832 ml, 13.14 mmol) in THF (10 mL) was cooled to 0° C. and treated with methanesulfonyl chloride (0.498 ml, 6.31 mmol) dropwise. The mixture was slowly warmed to rt and stirred at rt for 1 h. The reaction was diluted with DCM, quenched with sat. NH₄Cl and extracted with DCM. The combined organic phase was washed with brine, dried over Na₂SO₄ and concentrated to the title compound (Intermediate 172c, 3.4 g, 5.24 mmol, 100% yield) as a white solid. ¹H NMR (500 MHz, CDCl₃) δ 8.11 (d, J=8.0 Hz, 1H), 7.75 (dd, J=8.1, 1.8 Hz, 1H), 7.68 (d, J=7.4 Hz, 2H), 7.64 (d, J=1.7 Hz, 1H), 7.53-7.47 (m, 2H), 7.44-7.35 (m, 4H), 7.33-7.30 (m, 4H), 7.29 (s, 3H), 7.28-7.24 (m, 2H), 7.23-7.20 (m, 2H), 6.95 (d, J=7.7 Hz, 5H), 5.17 (s, 2H), 2.87 (s, 3H).

Example 172: 3-((6'-(2H-tetrazol-5-yl)-[1,1':3',1''-terphenyl]-4-yl)methyl)-2-methyl-8-oxa-1,3-diazaspiro[4.5]dec-1-en-4-one Intermediate 172b (23 mg, 0.112 mmol) was dissolved in DMF (1 mL). NaH (10.11 mg, 0.253 mmol) was added. The mixture was stirred at rt for 15 min, Intermediate 172c (72.9 mg, 0.112 mmol) was added at 0° C. The reaction mixture was stirred at rt for 1 h. The reaction mixture was diluted with EtOAc, washed with saturated NH₄C₁, brine, dried over Na₂SO₄, filtered, and concentrated in vacuo. The residue was purified by ISCO (Hexanes/AcOEt, 0-100%) and concentrated. The sample was re-dissolved in DCM (1 mL) and treated with 0.1 ml of 4N HCl in dioxane for 1 h. The reaction mixture was concentrated, re-solvated in DMF, filtered then purified via preparative HPLC (Column: XBridge C18, 19×200 mm, 5-μm particles; Mobile Phase A: 5:95 ACN: H₂O with 10 mM NH₄OAc; Mobile Phase B: 95:5 ACN: H₂O with 10 mM NH₄OAc; Gradient: 8-48% B over 23 minutes, then a 5-minute hold at 100% B; Flow: 20 mL/min) to afford 22.4 mg (0.047 mmol, 41.6% yield) of the title compound Example 172. LC-MS (Method A3): Retention Time: 1.26 min, [M+H]⁺=479.1; ¹H NMR (500 MHz, DMSO-d₆) δ 7.79 (br d, J=7.8 Hz, 3H), 7.76-7.71 (m, 1H), 7.69 (s, 1H), 7.50 (t, J=7.6 Hz, 2H), 7.45-7.36 (m, 1H), 7.21 (d, J=7.9 Hz, 2H), 7.10 (d, J=8.0 Hz, 2H), 4.70 (s, 2H), 3.87 (dt, J=11.3, 3.8 Hz, 2H), 3.80-3.67 (m, 2H), 2.09 (s, 3H), 1.86-1.74 (m, 2H), 1.34 (br d, J=13.5 Hz, 2H).

Example 173: 2-methyl-3-((5'-(4-methylpyridin-2-yl)-2'-(2H-tetrazol-5-yl)-[1,1'-biphenyl]-4-yl)methyl)-8-oxa-1,3-diazaspiro[4.5]dec-1-en-4-one

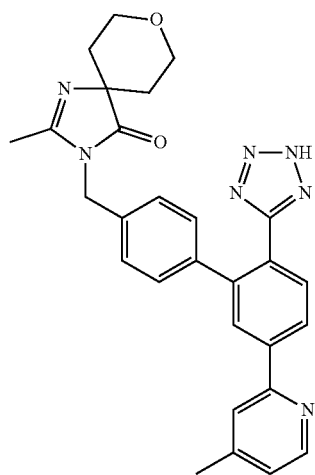

(Ex. 173)

Intermediate 173a: 5-bromo-4'-((2-methyl-4-oxo-8-oxa-1,3-diazaspiro[4.5]dec-1-en-3-yl)methyl)biphenyl-2-carbonitrile

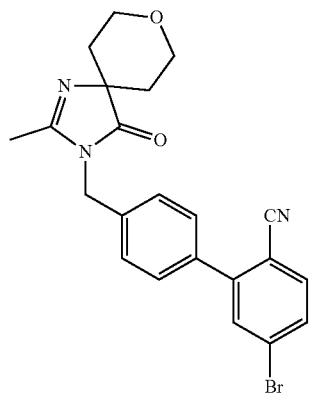

(173a)

Intermediate 172b (100 mg, 0.489 mmol) was dissolved in DMF (3 mL). NaH (44.0 mg, 1.099 mmol) was added. The mixture was stirred at rt for 15 min, I-002 (172 mg, 0.489 mmol) was added at 0° C. The reaction mixture was stirred at rt for 1 h. The reaction mixture was diluted with EtOAc, washed with saturated NH₄C₁, brine, dried over Na₂SO₄, filtered, and concentrated in vacuo. The residue was purified by ISCO (Hexanes/AcOEt, 0-100%) to give the title compound (Intermediate 173a, 120 mg, 0.274 mmol, 56.0% yield) as a white solid. LC-MS (Method A5): 2.30 min, [M+H]⁺=438.1 and 440.1; ¹H NMR (500 MHz, CDC₃) S 7.67 (d, J=1.4 Hz, 1H), 7.65-7.59 (m, 2H), 7.54 (d, J=8.0 Hz, 2H), 7.32 (d, J=8.3 Hz, 2H), 4.76 (s, 2H), 4.07-3.99 (m, 2H), 3.99-3.88 (m, 2H), 2.18 (s, 3H), 2.07 (ddd, J=13.8, 9.9, 4.4 Hz, 2H), 1.48 (br d, J=13.5 Hz, 2H).

Example 173: 2-methyl-3-((5'-(4-methylpyridin-2-yl)-2'-(2H-tetrazol-5-yl)-[1,1'-biphenyl]-4-yl)methyl)-8-oxa-1,3-diazaspiro[4.5]dec-1-en-4-one has been similarly prepared from 5-bromo-4'-((2-methyl-4-oxo-8-oxa-1,3-diazaspiro[4.5]dec-1-en-3-yl)methyl)biphenyl-2-carbonitrile (Intermediate 173a) as described above for Example 171. LC-MS (Method A5): 1.06 min, [M+H]⁺=494.23; ¹H NMR (500 MHz, DMSO-d₆) δ 8.55 (d, J=4.9 Hz, 1H), 8.22 (br d, J=8.5 Hz, 1H), 8.16 (s, 1H), 7.99 (s, 1H), 7.78 (d, J=8.2 Hz, 1H), 7.25 (br d, J=4.6 Hz, 1H), 7.22-7.16 (m, 2H), 7.12 (br d, J=7.9 Hz, 2H), 4.71 (s, 2H), 3.95-3.83 (m, 2H), 3.80-3.69 (m, 2H), 2.42 (s, 3H), 2.09 (s, 3H), 1.87-1.76 (m, 2H), 1.33 (br d, J=13.1 Hz, 2H).

Example 174-enantiomer 1:3-((6'-(2H-tetrazol-5-yl)-[1,1':3',1''-terphenyl]-4-yl)methyl)-2-methyl-7-oxa-1,3-diazaspiro[4.4]non-1-en-4-one

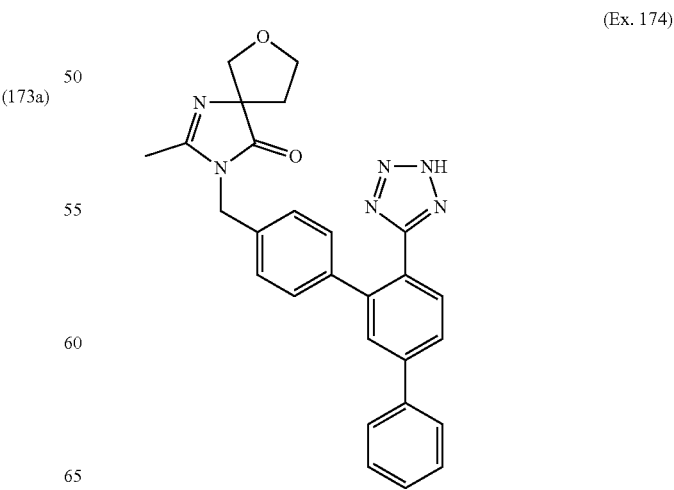

(Ex. 174)

Intermediate 174a:
N-(3-cyanotetrahydrofuran-3-yl)acetamide

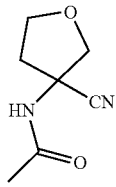

(174a)

To a solution of Intermediate 158a (500 mg, 2.7 mmol) in DCM (10 mL) was added triethylamine (1.876 mL, 13.46 mmol). The mixture was cooled with an ice bath, acetyl chloride (0.335 mL, 4.71 mmol) in DCM (2 mL) was added dropwise to the stirred solution. The reaction mixture was concentrated and the residue was directly purified by ISCO (DCM/MeOH, 0-20%) to give the title compound (Intermediate 174a, 300 mg, 1.946 mmol, 72.0% yield) as oil. $^1$H NMR (500 MHz, MeOH-$d_4$) δ 4.22 (d, J=9.6 Hz, 1H), 4.05-3.91 (m, 3H), 2.61 (ddd, J=13.3, 7.8, 6.9 Hz, 1H), 2.43 (ddd, J=13.4, 7.4, 5.9 Hz, 1H), 2.01 (s, 3H).

Intermediate 174b: 2-methyl-7-oxa-1,3-diazaspiro[4.4]non-1-en-4-one hydrochloride

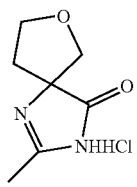

(174b)

To a solution of Intermediate 174a (300 mg, 1.946 mmol) in n-propanol (3 mL) was added 4N HCl in dioxane (4.86 mL, 19.46 mmol) dropwise. The mixture was heated up to 50° C. in oil bath for overnight. The mixture was concentrated and dried under vacuum to give the title compound (Intermediate 174b, 492 mg, 2.250 mmol, 100% yield) as a white solid. LC-MS (Method A5): 0.34 min, [M+H]$^+$=155.1; $^1$H NMR (500 MHz, MeOH-$d_4$) δ 4.20-4.11 (m, 2H), 4.07-4.02 (m, 1H), 3.91 (d, J=9.9 Hz, 1H), 2.58 (s, 2H), 2.57-2.49 (m, 1H), 2.40 (dt, J=13.7, 6.8 Hz, 1H).

Intermediate 174c: 5-bromo-4'-((2-methyl-4-oxo-7-oxa-1,3-diazaspiro[4.4]non-1-en-3-yl)methyl)biphenyl-2-carbonitrile

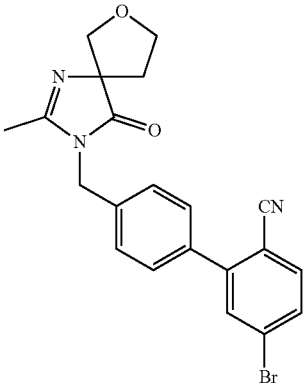

(174c)

Intermediate 174b (371 mg, 1.946 mmol) was dissolved in DMF (8 mL). NaH (175 mg, 4.38 mmol) was added. The mixture was stirred at rt for 15 min, I-002 (683 mg, 1.946 mmol) was added at 0° C. The reaction mixture was stirred at rt for 1 h. The reaction mixture was diluted with EtOAc, washed with saturated $NH_4C_1$, brine, dried over $Na_2SO_4$, filtered, and concentrated in vacuo. The residue was purified by ISCO (DCM/AcOEt, 0-100%) to give the title compound (Intermediate 174c, 560 mg, 1.320 mmol, 67.8% yield) as a white solid. LC-MS (Method A5): 2.24 min, [M+H]$^+$=424.1 and 426.1; $^1$H NMR (500 MHz, $CDC_3$) δ7.69 (d, J=1.1 Hz, 1H), 7.66-7.61 (m, 2H), 7.56 (d, J=8.3 Hz, 2H), 7.34 (d, J=8.0 Hz, 2H), 4.78 (d, J=6.3 Hz, 2H), 4.31-4.12 (m, 2H), 4.01 (d, J=8.8 Hz, 1H), 3.95-3.82 (m, 1H), 2.41 (dt, J=12.4, 8.0 Hz, 1H), 2.27-2.10 (m, 4H).

Intermediate 174d-enantiomer 1:5-bromo-4'-((2-methyl-4-oxo-7-oxa-1,3-diazaspiro[4.4]non-1-en-3-yl)methyl)biphenyl-2-carbonitrile

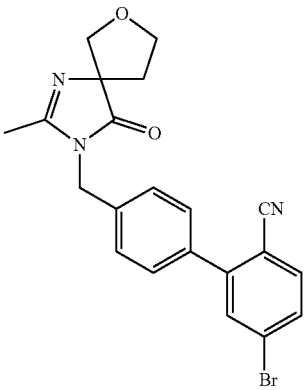

(174d)

Intermediate 174c-racemate (1.2 g, 2.83 mmol) were resolved into two peaks on Instrument PIC Solution SFC Prep-200 with the following preparative chromatographic conditions: Column: Chiralpak AD-H, 30×250 mm, 5 micron; Mobile Phase: 25% IPA/75% $CO_2$; Flow Conditions: 85 mL/min, 120 Bar, 40° C.; Detector Wavelength: 238 nm; injection details: 1 mL of ~30 mg/mL in MeOH/ACN. Purity of each fraction was determined using the analytical chromatographic condition below: Instrument: Aurora Analytical SFC; Column: Chiralpak AD-H 4.6×250 mm, 5 micron; Mobile Phase: 25% IPA/75% $CO_2$; Flow Conditions: 2.0 mL/min, 150 Bar, 40° C.; Detector Wavelength: 220 nm; Injection Details: 10 μL of 0.2 mg/mL in MeOH. Peak 1 was collected and concentrated to give Intermediate 174d-enantiomer 1 (300 mg, 0.707 mmol, 25% yield): enantiomeric excess>99.0%. Chiral analytical RT=8.14 min. LC-MS (Method A5): 2.24 min, $[M+H]^+$=424.1 and 426.1; $^1$H NMR (500 MHz, $CDCl_3$) δ 7.70 (d, J=1.1 Hz, 1H), 7.67-7.61 (m, 2H), 7.57 (d, J=8.3 Hz, 2H), 7.34 (d, J=8.0 Hz, 2H), 4.79 (d, J=6.3 Hz, 2H), 4.26-4.16 (m, 2H), 4.05-3.98 (m, 1H), 3.93 (d, J=8.5 Hz, 1H), 2.57-2.29 (m, 1H), 2.25-2.11 (m, 4H)

Example 174-enantiomer 1 was prepared from Intermediate 174d-enantiomer 1 as described above for Example 165. LC-MS (Method A3): 1.3 min, $[M+H]^+$=465.25; $^1$H NMR (500 MHz, DMSO-$d_6$) δ 7.80 (br d, J=7.9 Hz, 3H), 7.76-7.72 (m, 1H), 7.70 (s, 1H), 7.55-7.47 (m, 2H), 7.45-7.36 (m, 1H), 7.21 (d, J=7.9 Hz, 2H), 7.12 (br d, J=7.9 Hz, 2H), 4.71 (s, 2H), 4.06-3.94 (m, 2H), 3.75 (q, J=8.9 Hz, 2H), 2.17 (dt, J=12.3, 7.9 Hz, 1H), 2.08 (s, 3H), 2.02 (dt, J=11.7, 6.0 Hz, 1H).

Example 175: 2-ethyl-5, 7-dimethyl-3-((6-(3'-methyl-4-(1H-tetrazol-5-yl)biphenyl-3-yl)pyridin-3-yl)methyl)-3H-imidazo[4,5-b]pyridine

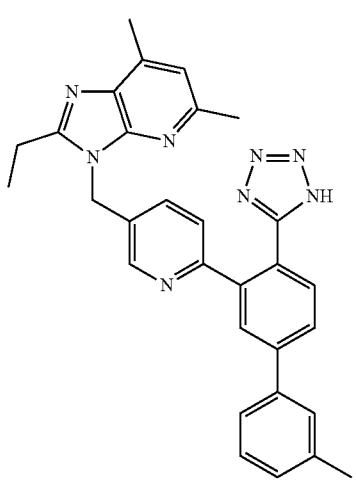
(Ex. 175)

Intermediate 175a: 4-chloro-2-(5-((2-ethyl-5,7-dimethyl-3H-imidazo[4,5-b]pyridin-3-yl)methyl)pyridin-2-yl)benzonitrile

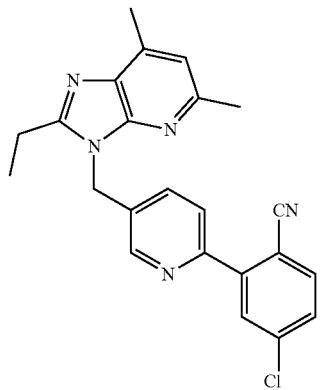
175a

A mixture of Intermediate 039a (100 mg, 0.290 mmol) and (5-chloro-2-cyanophenyl)boronic acid (68.3 mg, 0.377 mmol) in THF (3 mL) was treated with 1.5 M $Na_2CO_3$ (0.579 mL, 0.869 mmol) followed by $PdCl_2$(dppf) (11.83 mg, 0.014 mmol). The resulting mixture was degassed with $N_2$ for 2 min before the reaction vessel was sealed and irradiated in a microwave reactor at 125° C. for 70 min. The cooled reaction mixture was diluted with DCM and extracted. The combined organic layer was washed with brine, dried over $MgSO_4$, and concentrated. The crude sample in 2 ml of DCM was treated with TEA (0.202 mL, 1.448 mmol) followed by TFAA (0.061 mL, 0.434 mmol). The mixture was stirred at RT for 1 hour, then concentrated to dryness and the residue purified by ISCO (Hexanes/AcOEt, 0-100%) to afford the title compound (Intermediate 175a, 65 mg, 0.162 mmol, 55.8% yield) as an amber oil. LC-MS (Method A5): 2.18 min, $[M+H]^+$=402.1; $^1$H NMR (500 MHz, $CDCl_3$) δ 8.73 (d, J=1.7 Hz, 1H), 7.86 (d, J=1.9 Hz, 1H), 7.74 (dd, J=9.9, 8.5 Hz, 2H), 7.63 (dd, J=8.3, 2.2 Hz, 1H), 7.50 (dd, J=8.4, 2.1 Hz, 1H), 6.94 (s, 1H), 5.56 (s, 2H), 2.88 (q, J=7.7 Hz, 2H), 2.66 (s, 3H), 2.62 (s, 3H), 1.40 (t, J=7.6 Hz, 3H).

Intermediate 175b: 3-(5-((2-ethyl-5,7-dimethyl-3H-imidazo[4,5-b]pyridin-3-yl)methyl)pyridin-2-yl)-3'-methylbiphenyl-4-carbonitrile

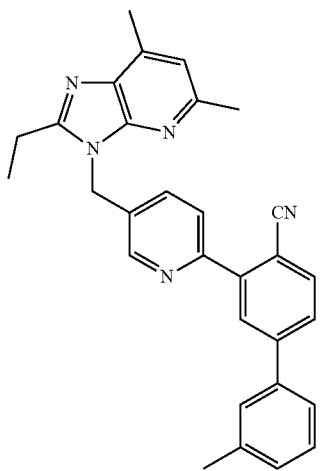

(175b)

A mixture of Intermediate 175a (32 mg, 0.080 mmol) and m-tolylboronic acid (32.5 mg, 0.239 mmol) in THF (1 mL) was treated with 1.0 M phosphoric acid, potassium salt (0.143 mL, 0.143 mmol) followed by Pd-XPhos G3 (6.74 mg, 7.96 μmol). The resulting mixture was degassed with $N_2$ for 2 min before the reaction vessel was sealed and irradiated in a microwave reactor at 140° C. for 45 min. The cooled reaction mixture was concentrated to dryness and the residue purified by ISCO (Hexanes/AcOEt, 0-100%) to afford the title compound (Intermediate 175b, 36 mg, 0.079 mmol, 99% yield) as an amber oil. LC-MS (Method A5): 2.44 min, [M+H]$^+$=458.2; $^1$H NMR (500 MHz, CDCl$_3$) δ 8.75 (d, J=1.4 Hz, 1H), 8.04 (d, J=1.7 Hz, 1H), 7.86 (d, J=8.3 Hz, 1H), 7.79 (d, J=8.3 Hz, 1H), 7.73 (dd, J=8.3, 1.7 Hz, 1H), 7.65 (dd, J=8.0, 2.2 Hz, 1H), 7.49-7.42 (m, 2H), 7.38 (t, J=7.6 Hz, 1H), 7.26 (d, J=7.4 Hz, 1H), 6.94 (s, 1H), 5.57 (s, 2H), 2.90 (q, J=7.6 Hz, 2H), 2.66 (s, 3H), 2.63 (s, 3H), 2.45 (s, 3H), 1.41 (t, J=7.6 Hz, 3H).

Example 175: 3-((6'-(2H-tetrazol-5-yl)-2''-(trifluoromethoxy)-[1,1':3',1''-terphenyl]-4-yl)methyl)-2-ethyl-5,7-dimethyl-3H-imidazo[4,5-b]pyridine To a solution of 3-(5-((2-ethyl-5,7-dimethyl-3H-imidazo[4,5-b]pyridin-3-yl)methyl)pyridin-2-yl)-3'-methyl-[1,1'-biphenyl]-4-carbonitrile (Intermediate 175b, 36 mg, 0.079 mmol) in toluene (1.5 mL) was added dibutyltin oxide (39.2 mg, 0.157 mmol) and TMS-N$_3$ (0.104 mL, 0.787 mmol). Then the reaction vessel was sealed and the mixture was heated at 100° C. overnight behind a blast shield (according to the procedure described in J. Org. Chem, 1993, 58, 4139). After cooling, the reaction mixture was concentrated, resolvated in DMF, filtered then purified via preparative HPLC (Column: XBridge C18, 19×200 mm, 5-μm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 15-55% B over 20 minutes, then a 4-minute hold at 100% B; Flow: 20 mL/min. to afford 29.6 mg (0.057 mmol, 72% yield) of the title compound Example 175. LC-MS (Method A3): 1.47 min, [M+H]$^+$=501.23; $^1$H NMR (500 MHz, DMSO-d$_6$) δ 8.36 (s, 1H), 7.95 (s, 1H), 7.91 (br d, J=8.2 Hz, 1H), 7.78 (d, J=7.9 Hz, 1H), 7.64 (s, 1H), 7.61 (br d, J=7.9 Hz, 1H), 7.56-7.54 (m, 1H), 7.53-7.48 (m, 1H), 7.40 (t, J=7.5 Hz, 1H), 7.26 (br d, J=7.3 Hz, 1H), 6.98 (s, 1H), 5.52 (s, 2H), 2.85 (q, J=7.6 Hz, 2H), 2.56 (s, 6H), 2.40 (s, 3H), 1.27 (t, J=7.5 Hz, 3H).

Example 176: 3-((6-(4-(1H-tetrazol-5-yl)-[1,1'-biphenyl]-3-yl)pyridin-3-yl)methyl)-2-ethyl-5,7-dimethyl-3H-imidazo[4,5-b]pyridine

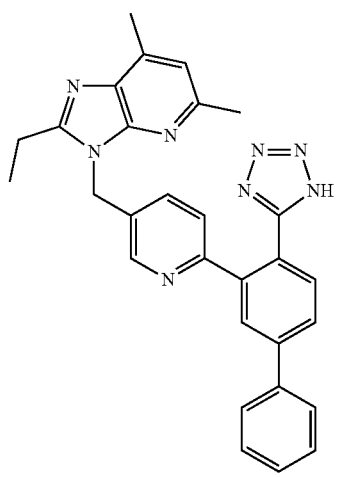

(Ex. 176)

Example 176 has been similarly prepared from Intermediate 175a as described above for Example 001. LC-MS (Method A3): 1.37 min, [M+H]$^+$=487.22; $^1$H NMR (500 MHz, DMSO-d$_6$) δ 8.36 (s, 1H), 7.94 (s, 1H), 7.90 (br d, J=8.0 Hz, 1H), 7.83-7.73 (m, 3H), 7.51 (br t, J=7.4 Hz, 3H), 7.44 (br d, J=4.7 Hz, 2H), 6.97 (s, 1H), 5.51 (s, 2H), 2.84 (q, J=7.3 Hz, 2H), 2.55 (s, 6H), 1.26 (t, J=7.4 Hz, 3H).

Example 177: 2-ethyl-5,7-dimethyl-3-((5-(3'-methyl-4-(1H-tetrazol-5-yl)biphenyl-3-yl)pyridin-2-yl)methyl)-3H-imidazo[4,5-b]pyridine

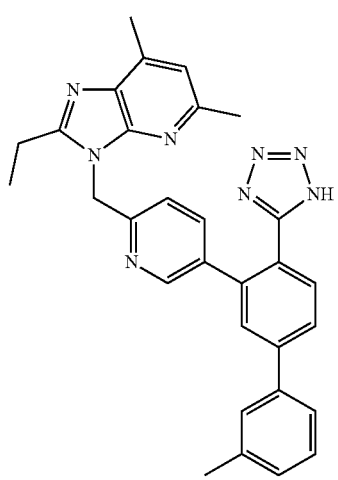

(Ex. 177)

Intermediate 177a: (5-bromopyridin-2-yl)methyl methanesulfonate

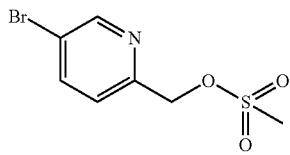
(177a)

A solution of (5-bromopyridin-2-yl)methanol (500 mg, 2.66 mmol) in THF (10 mL) was cooled to 0° C. and treated with TEA (0.482 mL, 3.46 mmol) and methanesulfonyl chloride (0.252 mL, 3.19 mmol). The mixture was slowly warmed to RT and stirred for hour. The reaction was diluted with DCM, quenched with a saturated aqueous solution of NH$_4$Cl and the mixture was extracted with DCM. The combined organic layer was washed with brine, dried over MgSO$_4$, and concentrated to (5-bromopyridin-2-yl)methyl methanesulfonate (Intermediate 177a, 700 mg, 2.63 mmol, 99% yield) which was used for next step without purification. LC-MS (Method A5): 1.72 min, [M+H]$^+$=265.9 and 267.9; $^1$H NMR (500 MHz, CDCl$_3$) δ 8.68 (d, J=2.2 Hz, 1H), 7.90 (dd, J=8.3, 2.2 Hz, 1H), 7.39 (d, J=8.3 Hz, 1H), 5.29 (s, 2H), 3.10 (s, 3H).

Intermediate 177b: 3-((5-bromopyridin-2-yl)methyl)-2-ethyl-5,7-dimethyl-3H-imidazo[4,5-b]pyridine

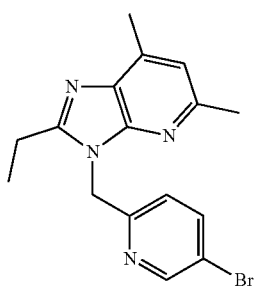
(177b)

To a solution of Intermediate 001c (200 mg, 1.141 mmol) in DMF (4.1 mL) was added sodium hydride (59.3 mg, 1.484 mmol) at RT and the reaction was stirred vigorously for 30 min. Then a solution of Intermediate 177a (349 mg, 1.313 mmol) in DMF (1.6 mL) was added and the resulting reaction mixture was allowed to stir for 2 h before being quenched with a saturated aqueous solution of NH$_4$Cl. The mixture was diluted with EtOAc and extracted. The organic phase was dried over MgSO$_4$, filtered and concentrated before being purified by ISCO (Hex/EtOAc, 0-100%) to afford the title compound (Intermediate 177b, 320 mg, 0.927 mmol, 81% yield) as a white solid. LC-MS (Method A5): 2.02 min, [M+H]$^+$=345.1 and 347.1; $^1$H NMR (500 MHz, CDCl$_3$) δ 8.62 (d, J=2.2 Hz, 1H), 7.69 (dd, J=8.3, 2.2 Hz, 1H), 7.07-6.69 (m, 2H), 5.52 (s, 2H), 2.87 (q, J=7.4 Hz, 2H), 2.64 (s, 3H), 2.58 (s, 3H), 1.34 (t, J=7.6 Hz, 3H).

Intermediate 177c: 6-((2-ethyl-5,7-dimethyl-3H-imidazo[4,5-b]pyridin-3-yl)methyl)pyridin-3-ylboronic acid

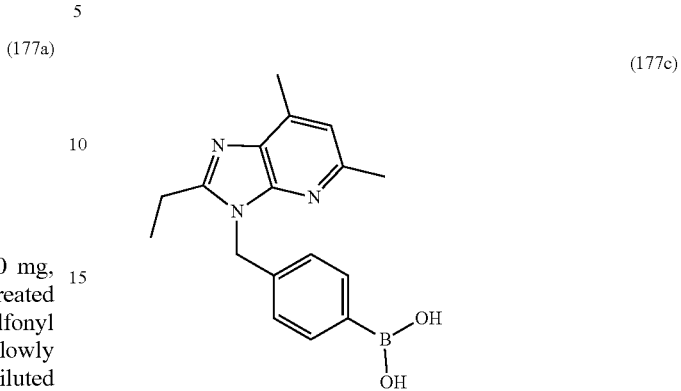
(177c)

A solution of Intermediate 177b (320 mg, 0.927 mmol), KOAc (182 mg, 1.854 mmol), 4,4,4',4',5,5,5',5'-octamethyl-2,2'-bi(1,3,2-dioxaborolane) (259 mg, 1.020 mmol) and PdCl$_2$(dppf) (37.8 mg, 0.046 mmol) in dioxane (5 mL) was degassed with N$_2$ for 2 min before the reaction vessel was sealed and heated at 100° C. for overnight. The mixture was cooled and filtered through celite and purified via preparative HPLC (Column: Phenomenex AXIA Luna 100×30 mm 5u s; Mobile Phase A: 10:90 ACN: H$_2$O with 10 mM TFA; Mobile Phase B: 90:10 ACN: H$_2$O with 10 mM TFA; Gradient: 0-100% B over 10 minutes, then a 2-minute hold at 100% B; Flow: 40 mL/min.) to afford 400 mg (0.92 mmol, 98% yield) of the title compound (Intermediate 177c) as TFA salt. LC-MS (Method A5): 1.58 min, [M+H]$^+$=311.2; $^1$H NMR (500 MHz, MeOH-d$_4$) δ 8.64 (br d, J=10.7 Hz, 1H), 8.24-8.03 (m, 1H), 7.58 (br t, J=7.0 Hz, 1H), 7.34 (s, 1H), 5.89 (br d, J=5.5 Hz, 2H), 4.92 (br s, 2H), 2.67 (s, 3H), 2.60 (s, 3H), 1.46 (t, J=7.6 Hz, 3H).

Intermediate 177d: 4-chloro-2-(6-((2-ethyl-5,7-dimethyl-3H-imidazo[4,5-b]pyridin-3-yl)methyl)pyridin-3-yl)benzonitrile

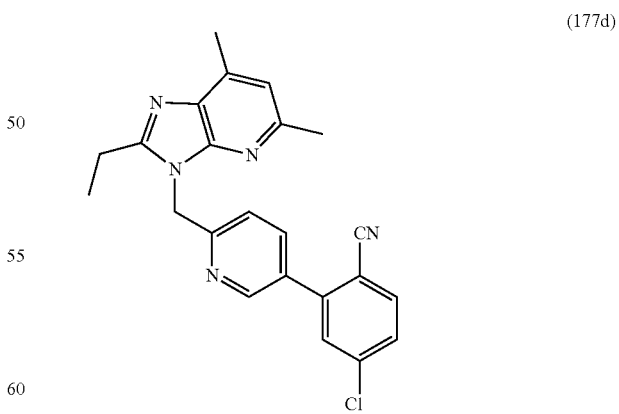
(177d)

A mixture of Intermediate 177c (177 mg, 0.418 mmol) and 4-chloro-2-iodobenzonitrile (100 mg, 0.380 mmol) in THF (5 mL) was treated with 1.5 M Na$_2$CO$_3$ (1.012 mL, 1.518 mmol) followed by PdCl$_2$(dppf) (15.50 mg, 0.019 mmol). The resulting mixture was degassed with N$_2$ for 2 min before the reaction vessel was sealed and irradiated in a microwave reactor at 100° C. for 30 min. The cooled reaction mixture was diluted with DCM and extracted. The combined organic layer was washed with brine, dried over MgSO₄, and concentrated to dryness and the residue purified by ISCO (Hexanes/AcOEt, 0-100%) to afford the title compound (Intermediate 177d, 120 mg, 0.299 mmol, 79% yield) as a yellow oil. LC-MS (Method A5): 2.17 min, [M+H]⁺=402.1; ¹H NMR (500 MHz, CDCl₃) δ 8.72 (d, J=2.2 Hz, 1H), 7.80 (dd, J=8.1, 2.3 Hz, 1H), 7.74 (d, J=8.8 Hz, 1H), 7.54-7.43 (m, 2H), 7.13 (d, J=8.3 Hz, 1H), 6.92 (s, 1H), 5.66 (s, 2H), 2.92 (q, J=7.4 Hz, 2H), 2.66 (s, 3H), 2.61 (s, 3H), 1.37 (t, J=7.6 Hz, 3H).

Intermediate 177e: 3-(6-((2-ethyl-5,7-dimethyl-3H-imidazo[4,5-b]pyridin-3-yl)methyl)pyridin-3-yl)-3'-methylbiphenyl-4-carbonitrile

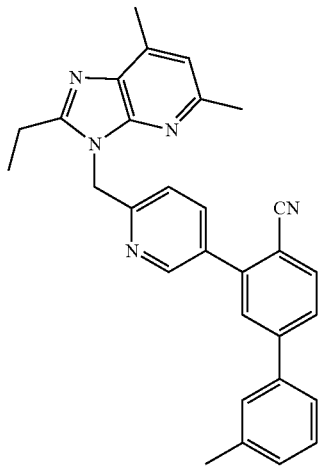

(177e)

A mixture of Intermediate 177d (33 mg, 0.082 mmol) and m-tolylboronic acid (33.5 mg, 0.246 mmol) in THF (1 mL) was treated with 1.0 M phosphoric acid, potassium salt (0.148 mL, 0.148 mmol) followed by Pd-XPhos G3 (6.95 mg, 8.21 µmol). The resulting mixture was degassed with N₂ for 2 min before the reaction vessel was sealed and irradiated in a microwave reactor at 140° C. for 45 min. The cooled reaction mixture was concentrated to dryness and the residue purified by ISCO (Hexanes/AcOEt, 0-100%) to afford the title compound (Intermediate 177e, 26 mg, 0.057 mmol, 69.2% yield) as an amber oil. LC-MS (Method A5): 2.44 min, [M+H]⁺=458.2; ¹H NMR (500 MHz, CDCl₃) δ 8.80 (d, J=1.7 Hz, 1H), 7.90-7.85 (m, 2H), 7.72 (dd, J=8.3, 1.7 Hz, 1H), 7.69 (d, J=1.4 Hz, 1H), 7.47-7.37 (m, 4H), 7.15 (d, J=8.3 Hz, 1H), 6.93 (s, 1H), 5.68 (s, 2H), 2.95 (q, J=7.4 Hz, 2H), 2.67 (s, 3H), 2.62 (s, 3H), 2.46 (s, 3H), 1.39 (t, J=7.6 Hz, 3H).

Example 177: 2-ethyl-5,7-dimethyl-3-((5-(3'-methyl-4-(1H-tetrazol-5-yl)biphenyl-3-yl)pyridin-2-yl)methyl)-3H-imidazo[4,5-b]pyridine To a solution of Intermediate 177e (26 mg, 0.057 mmol) in toluene (1.5 mL) was added dibutyltin oxide (28.3 mg, 0.114 mmol) and TMS-N₃ (0.075 mL, 0.568 mmol). Then the reaction vessel was sealed and the mixture was heated at 100° C. overnight behind a blast shield (according to the procedure described in J. Org. Chem, 1993, 58, 4139). After cooling, the reaction mixture was concentrated, re-solvated in DMF, filtered then purified via preparative HPLC (Column: XBridge C18, 19×200 mm, 5-µm particles; Mobile Phase A: 5:95 ACN: H₂O with 10 mM NH₄OAc; Mobile Phase B: 95:5 ACN: H₂O with 10 mM NH₄OAc; Gradient: 19-59% B over 19 minutes, then a 5-minute hold at 100% B; Flow: 20 mL/min) to afford 12.5 mg (0.025 mmol, 43.6% yield) of the title compound Example 177. LC-MS (Method A3): 1.54 min, [M+H]⁺=501.07; ¹H NMR (500 MHz, DMSO-d₆) δ 8.32 (d, J=1.5 Hz, 1H), 7.84-7.73 (m, 2H), 7.63 (br d, J=15.9 Hz, 2H), 7.60-7.53 (m, 2H), 7.36 (t, J=7.6 Hz, 1H), 7.21 (br d, J=7.3 Hz, 1H), 15 7.06 (d, J=7.9 Hz, 1H), 6.94 (s, 1H), 5.55 (s, 2H), 2.85 (q, J=7.3 Hz, 2H), 2.55 (s, 3H), 2.50 (s, 3H), 2.38 (s, 3H), 1.29 (t, J=7.5 Hz, 3H).

The following examples have been similarly prepared from Intermediate 177d as described above for Example 177. Two analytical LC-MS injections were used to determine the final purity. The retention time of one of them is reported for each compound and is referred as Method A3, Method A4 or Method A5.

| Ex | Structure | MW | LC-MS m/z [M + H]⁺; RT; (Method) | ¹H NMR (500 MHz, DMSO-d₆) δ ppm |
|---|---|---|---|---|
| 178 | 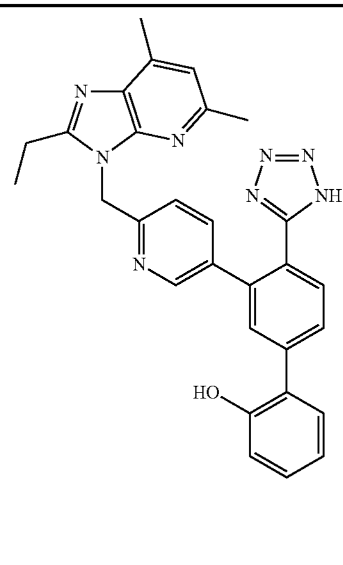 | 502.58 | 503.28; 1.27 min (Method A3) | 8.28 (s, 1H), 7.76 (s, 2H), 7.62 (s, 1H), 7.57 (br d, J = 7.9 Hz, 1H), 7.41 (br d, J = 7.3 Hz, 1H), 7.22 (br t, J = 7.6 Hz, 1H), 7.09 (d, J = 8.2 Hz, 1H), 6.99 (d, J = 7.9 Hz, 1H), 6.96-6.89 (m, 2H), 5.56 (s, 2H), 2.83 (q, J = 7.5 Hz, 2H), 2.57 (s, 3H), 2.50 (s, 3H), 1.27 (t, J = 7.5 Hz, 3H) |

-continued

| Ex | Structure | MW | LC-MS m/z [M + H]+; RT; (Method) | 1H NMR (500 MHz, DMSO-d6) δ ppm |
|---|---|---|---|---|
| 179 | 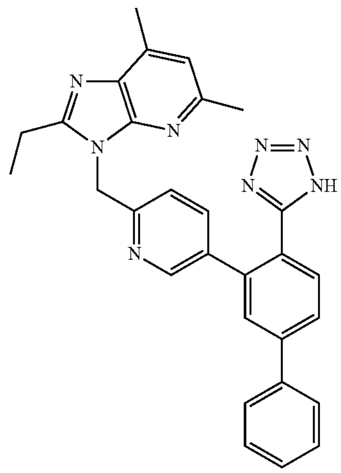 [SMILES: CCc1nc2c(C)cc(C)nc2n1Cc1ccc(-c2cc(-c3ccccc3)ccc2-c2nnn[nH]2)cn1] | 486.58 | 487.31; 1.58 min (Method A3) | 8.33 (d, J = 1.5 Hz, 1H), 7.93 (br d, J = 8.2 Hz, 1H), 7.86-7.74 (m, 4H), 7.61 (dd, J = 7.9, 2.1 Hz, 1H), 7.55-7.47 (m, 2H), 7.47-7.36 (m, 1H), 7.17 (d, J = 8.2 Hz, 1H), 6.96 (s, 1H), 5.58 (s, 2H), 2.83 (q, J = 7.6 Hz, 2H), 2.56 (s, 3H), 2.49 (s, 3H), 1.26 (t, J = 7.5 Hz, 3H) |
| 180 | 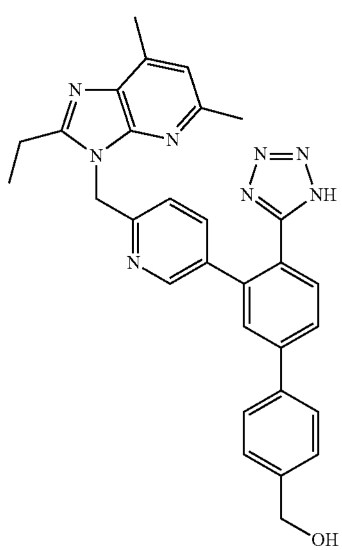 [SMILES: CCc1nc2c(C)cc(C)nc2n1Cc1ccc(-c2cc(-c3ccc(CO)cc3)ccc2-c2nnn[nH]2)cn1] | 516.61 | 517.2; 1.11 min (Method A3) | 8.34 (s, 1H), 7.95 (br d, J = 8.2 Hz, 1H), 7.89-7.77 (m, 4H), 7.64 (dd, J = 8.2, 1.8 Hz, 1H), 7.46 (br d, J = 7.9 Hz, 2H), 7.27 (s, 1H), 7.07 (s, 1H), 5.67 (s, 2H), 4.58 (s, 2H), 2.93 (q, J = 7.5 Hz, 2H), 2.57 (s, 2H), 2.56 (br s, 3H), 1.30 (t, J = 7.5 Hz, 3H) |

Example 181: 4"-((2-ethyl-5,7-dimethyl-3H-imidazo[4,5-b]pyridin-3-yl)methyl)-3,5-dimethyl-[1,1':3',1"-terphenyl]-4'-carboxylic acid

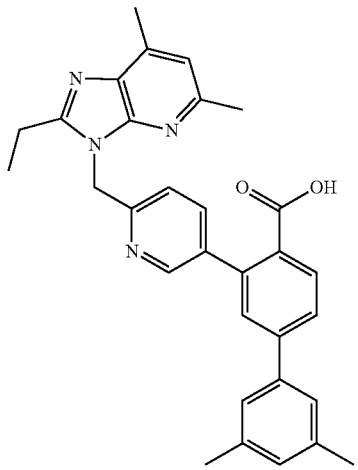

(Ex. 181)

Intermediate 181a: methyl 5-chloro-4'-((2-ethyl-5,7-dimethyl-3H-imidazo[4,5-b]pyridin-3-yl)methyl)biphenyl-2-carboxylate

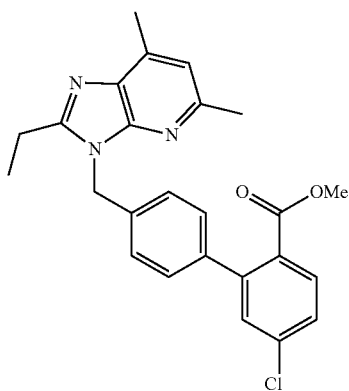

(181a)

A mixture of Intermediate 001d (100 mg, 0.256 mmol), and methyl 4-chloro-2-iodobenzoate (68.9 mg, 0.232 mmol) in THF (5 mL) was treated with 1.5 M $Na_2CO_3$ (0.465 mL, 0.697 mmol) followed by $PdCl_2(dppf)$ (9.49 mg, 0.012 mmol). The resulting mixture was degassed with $N_2$ for 2 min before the reaction vessel was sealed and irradiated in a microwave reactor at 100° C. for 30 min. The cooled reaction mixture was diluted with DCM and extracted. The combined organic layer was washed with brine, dried over $MgSO_4$, and concentrated to dryness and the residue purified by ISCO (Hexanes/AcOEt, 0-100%) to afford the title compound (Intermediate 181a, 100 mg, 0.230 mmol, 99% yield) as a yellow oil. LC-MS (Method A5): 2.30 min, $[M+H]^+$= 434.1; $^1H$ NMR (500 MHz, $CDCl_3$) δ 7.80 (d, J=8.3 Hz, 1H), 7.40 (dd, J=8.4, 2.1 Hz, 1H), 7.33 (d, J=1.9 Hz, 1H), 7.25-7.20 (m, 2H), 7.19-7.14 (m, 2H), 6.93 (s, 1H), 5.53 (s, 2H), 3.63 (s, 3H), 2.84 (q, J=7.5 Hz, 2H), 2.67 (s, 3H), 2.63 (s, 3H), 1.35 (t, J=7.6 Hz, 3H).

Example 181: 4"-((2-ethyl-5,7-dimethyl-3H-imidazo[4,5-b]pyridin-3-yl)methyl)-3,5-dimethyl-[1,1':3',1"-terphenyll-4'-carboxylic acid A mixture of Intermediate 181' (20 mg, 0.046 mmol) and (3,5-dimethylphenyl)boronic acid (20.74 mg, 0.138 mmol) in THF (1 mL) was treated with 1.0 M phosphoric acid, potassium salt (0.083 mL, 0.083 mmol) followed by Pd-XPhos G3 (1.951 mg, 2.304 μmol). The resulting mixture was degassed with $N_2$ for 2 min before the reaction vessel was sealed and irradiated in a microwave reactor at 140° C. for 45 min. The cooled reaction mixture was treated with MeOH (0.5 mL) and 2.0 M NaOH (0.138 mL, 0.277 mmol). The mixture was reheated in a microwave reactor at 100° C. for 15 min. After cooling, the reaction mixture was concentrated, re-solvated in DMF, filtered then purified via preparative HPLC (Column: XBridge C18, 19×200 mm, 5-μm particles; Mobile Phase A: 5:95 ACN: $H_2O$ with 10 mM $NH_4OAc$; Mobile Phase B: 95:5 ACN: $H_2O$ with 10 mM $NH_4OAc$; Gradient: 28-68% B over 20 minutes, then a 4-minute hold at 100% B; Flow: 20 mL/min.) to afford 8.5 mg (0.017 mmol, 37.7% yield) of the title compound Example 181. LC-MS (Method A3): 1.81 min, $[M+H]^+$= 490.34; $^1H$ NMR (500 MHz, DMSO-$d_6$) δ 7.80 (br d, J=8.0 Hz, 1H), 7.69 (br d, J=8.0 Hz, 1H), 7.53 (s, 1H), 7.36 (br d, J=8.0 Hz, 2H), 7.33 (s, 1H), 7.34-7.31 (m, 1H), 7.19 (br d, J=7.9 Hz, 2H), 7.03 (s, 1H), 6.96 (s, 1H), 5.51 (s, 2H), 2.83 (q, J=7.5 Hz, 2H), 2.54 (s, 6H), 2.33 (s, 6H), 1.29 (t, J=7.4 Hz, 3H).

The following examples have been similarly prepared from Intermediate 181a as described above for Example 181. Two analytical LC-MS injections were used to determine the final purity. The retention time of one of them is reported for each compound and is referred as Method A3, Method A4 or Method A5.

| Ex | Structure | MW | LC-MS m/z [M + H]+; RT; (Method) | 1H NMR (500 MHz, DMSO-d6) δ ppm |
|---|---|---|---|---|
| 182 | 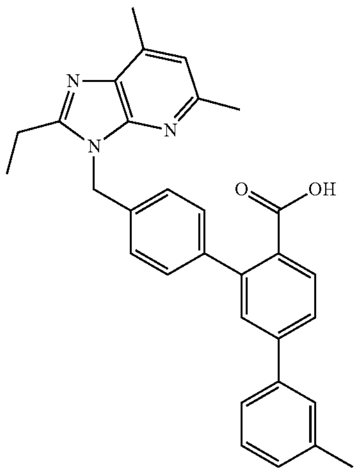 [SMILES: CCc1nc2c(C)cc(C)nc2n1Cc1ccc(-c2cc(-c3cccc(C)c3)ccc2C(=O)O)cc1] | 475.59 | 476.13; 1.67 min (Method A3) | 7.76 (br d, J = 7.9 Hz, 1H), 7.69 (br d, J = 7.6 Hz, 1H), 7.65-7.47 (m, 5H), 7.39-7.31 (m, 2H), 7.20 (br d, J = 7.0 Hz, 1H), 7.15 (br d, J = 7.6 Hz, 1H), 6.97 (s, 1H), 5.50 (s, 2H), 2.81 (q, J = 7.5 Hz, 2H), 2.55 (s, 3H), 2.51 (s, 3H), 2.35 (s, 3H), 1.28-1.23 (m, 3H). |
| 183 | 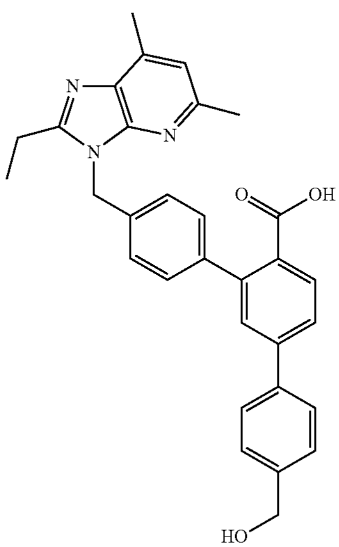 [SMILES: CCc1nc2c(C)cc(C)nc2n1Cc1ccc(-c2cc(-c3ccc(CO)cc3)ccc2C(=O)O)cc1] | 491.59 | 492.29; 1.16 min (Method A3) | 7.83 (d, J = 7.9 Hz, 1H), 7.74 (br d, J = 8.2 Hz, 1H), 7.72 (d, J = 7.9 Hz, 2H), 7.57 (s, 1H), 7.42 (br d, J = 7.9 Hz, 2H), 7.39 (br d, J = 7.9 Hz, 2H), 7.25 (br d, J = 7.6 Hz, 2H), 7.16-7.10 (m, 1H), 5.61 (s, 2H), 4.55 (s, 2H), 2.97 (q, J = 7.6 Hz, 2H), 2.57 (s, 3H), 2.56 (s, 3H), 1.29 (t, J = 7.5 Hz, 3H) |
| 184 | 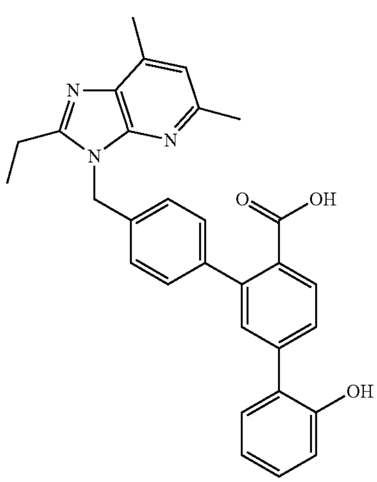 [SMILES: CCc1nc2c(C)cc(C)nc2n1Cc1ccc(-c2cc(-c3ccccc3O)ccc2C(=O)O)cc1] | 477.56 | 478.32; 1.27 min (Method A3) | 7.74 (br d, J = 7.9 Hz, 1H), 7.60 (br d, J = 7.6 Hz, 1H), 7.46 (s, 1H), 7.35-7.26 (m, 3H), 7.18 (br t, J = 7.5 Hz, 1H), 7.14 (br d, J = 7.6 Hz, 2H), 6.98-6.90 (m, 2H), 6.88 (br t, J = 7.2 Hz, 1H), 5.49 (s, 2H), 2.80 (q, J = 7.3 Hz, 2H), 2.54 (s, 6H), 1.23 (br d, J = 7.6 Hz, 3H). |

| Ex | Structure | MW | LC-MS m/z [M + H]+; RT; (Method) | 1H NMR (500 MHz, DMSO-d6) δ ppm |
|---|---|---|---|---|
| 185 | 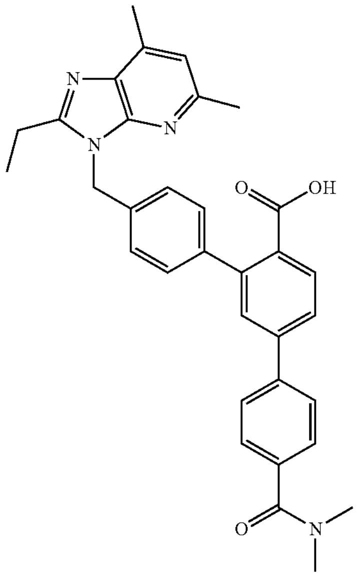 [SMILES: CCc1nc2c(C)cc(C)nc2n1Cc1ccc(-c2cc(-c3ccc(C(=O)N(C)C)cc3)ccc2C(=O)O)cc1] | 532.64 | 533.24; 1.34 min (Method A3) | 7.86-7.80 (m, 2H), 7.78 (br d, J = 7.9 Hz, 2H), 7.63 (s, 1H), 7.58-7.46 (m, 2H), 7.39 (br d, J = 7.9 Hz, 2H), 7.18 (br d, J = 8.2 Hz, 2H), 6.98 (s, 1H), 5.53 (s, 2H), 3.03-2.93 (m, 6H), 2.84 (q, J = 7.4 Hz, 2H), 2.56 (s, 3H), 2.54 (s, 3H), 1.28 (t, J = 7.5 Hz, 3H) |

Example 186: 2-ethyl-5,7-dimethyl-3-((5-(3'-methyl-4-(1H-tetrazol-5-yl)biphenyl-3-yl)pyrazin-2-yl)methyl)-3H-imidazo[4,5-b]pyridine

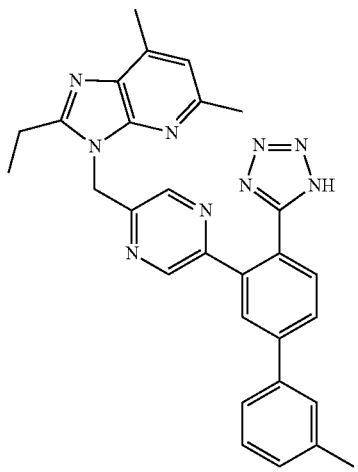

(ex. 186)

Intermediate 186a: 2-bromo-5-(bromomethyl)pyrazine

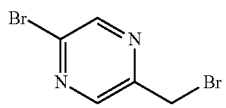

(186a)

2-bromo-5-methylpyrazine (300 mg, 1.734 mmol) was dissolved in carbon tetrachloride (8 mL), NBS (370 mg, 2.081 mmol) and benzoyl peroxide (21.00 mg, 0.087 mmol) were added, and the resulting mixture was heated and refluxed for overnight. The reaction solution was returned to RT, concentrated under reduced pressure and purified by ISCO (Hexanes/AcOEt, 0-100%) to afford the title compound (Intermediate 186a, 140 mg, 0.556 mmol, 32.1% yield) as a white solid. LC-MS (Method A5): 1.77 min, [M+H]+=250.9 and 251.9; 1H NMR (500 MHz, CDCl3) δ 8.80 (s, 2H), 4.58 (s, 2H).

Intermediate 186b: 3-((5-bromopyrazin-2-yl)methyl)-2-ethyl-5,7-dimethyl-3H-imidazo[4,5-b]pyridine

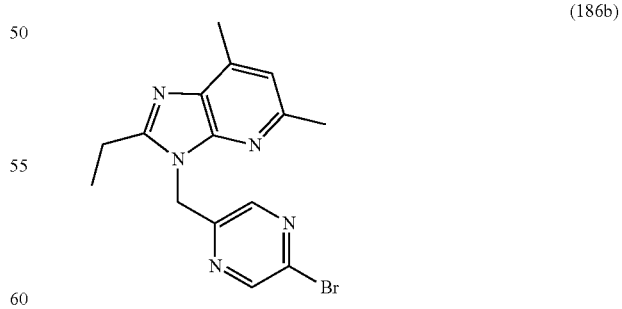

(186b)

To a solution of Intermediate 001c (108 mg, 0.618 mmol) in DMF (2.0 mL) was added sodium hydride (29.6 mg, 0.741 mmol) at RT and the reaction was stirred vigorously for 30 min. Then a solution of Intermediate 186' (140 mg, 0.648 mmol) in DMF (0.8 mL) was added and the resulting reaction mixture was allowed to stir for 2 h before being quenched with a saturated aqueous solution of NH₄Cl. The mixture was diluted with EtOAc and extracted. The organic phase was dried over MgSO₄, filtered and concentrated before being purified by ISCO (Hex/EtOAc, 0-100%) to afford the title compound (Intermediate 186b, 140 mg, 0.404 mmol, 65.5% yield) as a white solid. LC-MS (Method A5): 1.90 min, [M+H]⁺=346.0 and 348.0; ¹H NMR (500 MHz, CDCl₃) δ 8.60 (d, J=1.1 Hz, 1H), 8.36 (s, 1H), 6.89 (s, 1H), 5.53 (s, 2H), 2.96 (q, J=7.7 Hz, 3H), 2.62 (s, 3H), 2.57 (s, 3H), 1.40 (t, J=7.6 Hz, 3H).

Intermediate 186c: 4-chloro-2-(5-((2-ethyl-5,7-dimethyl-3H-imidazo[4,5-b]pyridin-3-yl)methyl)pyrazin-2-yl)benzonitrile

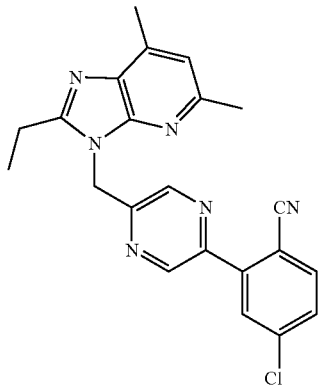

(186c)

A mixture of Intermediate 186b (100 mg, 0.289 mmol) and (5-chloro-2-cyanophenyl)boronic acid (68.1 mg, 0.375 mmol) in THF (3 mL) was treated with 1.5 M Na₂CO₃ (0.578 mL, 0.866 mmol) followed by PdCl₂(dppf) (11.79 mg, 0.014 mmol). The resulting mixture was degassed with N₂ for 2 min before the reaction vessel was sealed and irradiated in a microwave reactor at 125° C. for 1 hour. The cooled reaction mixture was diluted with DCM and extracted. The combined organic layer was washed with brine, dried over MgSO₄, and concentrated. The crude sample in 2 ml of DCM was treated with TEA (0.201 mL, 1.444 mmol) followed by TFAA (0.061 mL, 0.433 mmol).

The mixture was stirred at RT for 1 hour, then concentrated to dryness and the residue purified by ISCO (Hexanes/AcOEt, 0-100%) to afford the title compound (Intermediate 186c, 80 mg, 0.199 mmol, 68.8% yield) as an amber oil. LC-MS (Method A5): 2.16 min, [M+H]⁺=403.1; ¹H NMR (500 MHz, CDCl₃) δ 9.00 (d, J=1.4 Hz, 1H), 8.70 (d, J=0.8 Hz, 1H), 7.84 (d, J=1.9 Hz, 1H), 7.78 (d, J=8.3 Hz, 1H), 7.56 (dd, J=8.3, 1.9 Hz, 1H), 6.92 (s, 1H), 5.68 (s, 2H), 3.00 (q, J=7.4 Hz, 2H), 2.65 (s, 3H), 2.60 (s, 3H), 1.43 (t, J=7.6 Hz, 3H).

Intermediate 186d: 3-(5-((2-ethyl-5,7-dimethyl-3H-imidazo[4,5-b]pyridin-3-yl)methyl)pyrazin-2-yl)-3'-methylbiphenyl-4-carbonitrile

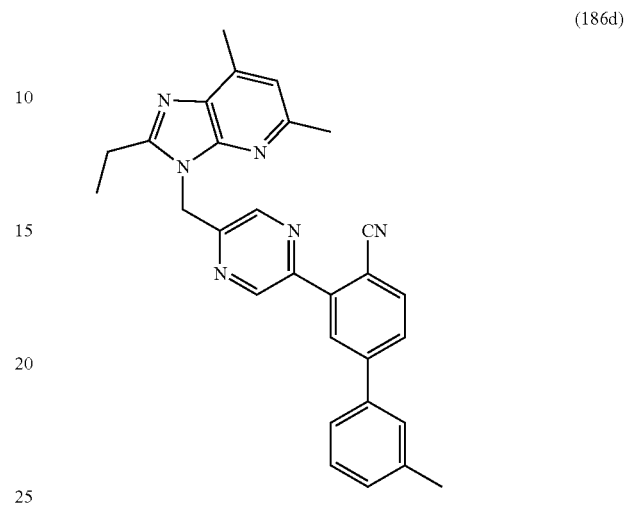

(186d)

A mixture of Intermediate 186c (40 mg, 0.099 mmol) and tolylboronic acid (40.5 mg, 0.298 mmol) in THF (1 mL) was treated with 1.0 M phosphoric acid, potassium salt (0.179 mL, 0.179 mmol) followed by Pd-XPhos G3 (8.40 mg, 9.93 μmol). The resulting mixture was degassed with N₂ for 2 min before the reaction vessel was sealed and irradiated in a microwave reactor at 140° C. for 60 min. The cooled reaction mixture was concentrated to dryness and the residue purified by ISCO (Hexanes/AcOEt, 0-100%) to afford the title compound (Intermediate 186d, 45 mg, 0.098 mmol, 99% yield) as a colorless oil. LC-MS (Method A5): 2.37 min, [M+H]⁺=459.2; ¹H NMR (500 MHz, CDCl₃) δ 9.02 (d, J=1.1 Hz, 1H), 8.71 (s, 1H), 7.99 (d, J=1.4 Hz, 1H), 7.89 (d, J=8.0 Hz, 1H), 7.77 (dd, J=8.0, 1.7 Hz, 1H), 7.46-7.41 (m, 2H), 7.40-7.33 (m, 1H), 7.30-7.23 (m, 1H), 6.91 (s, 1H), 5.68 (s, 2H), 3.01 (q, J=7.4 Hz, 2H), 2.64 (s, 3H), 2.60 (s, 3H), 2.44 (s, 3H), 1.42 (t, J=7.6 Hz, 3H)

Example 186: 2-ethyl-5,7-dimethyl-3-((5-(3'-methyl-4-(1H-tetrazol-5-yl)biphenyl-3-yl)pyrazin-2-yl)methyl)-3H-imidazo[4,5-b]pyridine To a solution of Intermediate 186d (35 mg, 0.076 mmol) in toluene (1.5 mL) was added dibutyltin oxide (38.0 mg, 0.153 mmol) and TMS-N₃ (0.101 mL, 0.763 mmol). Then the reaction vessel was sealed and the mixture was heated at 100° C. overnight behind a blast shield (according to the procedure described in J. Org. Chem, 1993, 58, 4139). After cooling, the reaction mixture was concentrated, re-solvated in DMF, filtered then purified via preparative HPLC (Column: XBridge C18, 19×200 mm, 5-μm particles; Mobile Phase A: 5:95 ACN: H₂O with 0.1% trifluoroacetic acid; Mobile Phase B: 95:5 ACN: H₂O with 0.1% trifluoroacetic acid; Gradient: 20-60% B over 19 minutes, then a 5-minute hold at 100% B; Flow: 20 mL/min) to afford 23.1 mg (0.046 mmol, 60.3% yield) of the title compound Example 186. LC-MS (Method A3): 1.49 min, [M+H]⁺=502.25; ¹H NMR (500 MHz, DMSO-d₆) δ 8.59 (s, 1H), 8.28 (br s, 1H), 7.92 (br d, J=7.9 Hz, 1H), 7.87-7.78 (m, 2H), 7.59 (br s, 1H), 7.56 (br d, J=7.6 Hz, 1H), 7.37 (br t, J=7.5 Hz, 1H), 7.21 (br d, J=7.3 Hz, 1H), 6.94 (s, 1H), 5.64 (s, 2H), 2.95-2.90 (m, 2H), 2.75 (s, 2H), 2.56 (s, 3H), 2.52 (br s, 3H), 2.39 (s, 3H), 1.31 (br t, J=7.3 Hz, 3H).

Example 187: 3-((5-(4-(1H-tetrazol-5-yl)-[1,1'-biphenyl]-3-yl)pyrazin-2-yl)methyl)-2-ethyl-5,7-dimethyl-3H-imidazo[4,5-b]pyridine

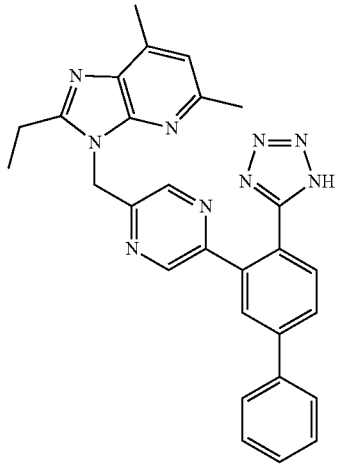

(Ex. 187)

Example 187 has been similarly prepared from Intermediate 186c as described above for Example 186. LC-MS (Method A3): 1.32 min, [M+H]$^+$=488.22; $^1$H NMR (500 MHz, DMSO-d$_6$) δ 8.78 (s, 1H), 8.65 (s, 1H), 8.06 (s, 1H), 8.02 (br d, J=8.2 Hz, 1H), 7.90 (d, J=7.9 Hz, 1H), 7.86 (br d, J=7.6 Hz, 2H), 7.56-7.50 (m, 2H), 7.48-7.43 (m, 1H), 7.12 (s, 1H), 5.80 (s, 2H), 3.12-2.96 (m, 2H), 2.56 (s, 6H), 1.40-1.32 (m, 3H).

Example 188: 2-ethyl-5,7-dimethyl-3-((5-(3'-methyl-4-(1H-tetrazol-5-yl)biphenyl-3-yl)pyrimidin-2-yl)methyl)-3H-imidazo[4,5-b]pyridine

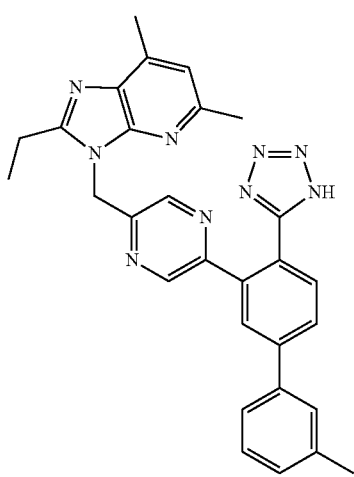

(Ex. 188)

Intermediate 188a:
5-bromo-2-(bromomethyl)pyrimidine

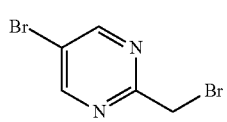

(188a)

5-bromo-2-methylpyrimidine (1.0 g, 5.78 mmol) was dissolved in carbon tetrachloride (15 mL), NBS (1.234 g, 6.94 mmol) and benzoyl peroxide (0.070 g, 0.289 mmol) were added, and the resulting mixture was heated and refluxed for overnight. The reaction solution was returned to RT, concentrated under reduced pressure and purified by ISCO (Hexanes/AcOEt, 0-100%) to afford the title compound (Intermediate 188a, 370 mg, 1.469 mmol, 25.4% yield) as a white solid. LC-MS (Method A5): 1.77 min, [M+H]$^+$=252.8; $^1$H NMR (500 MHz, CDCl$_3$) δ 8.82 (s, 2H), 4.60 (s, 2H).

Intermediate 188b: 3-((5-bromopyrimidin-2-yl)methyl)-2-ethyl-5,7-dimethyl-3H-imidazo[4,5-b]pyridine

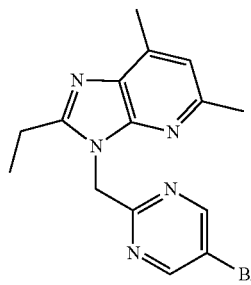

(188b)

To a solution of Intermediate 001c (370 mg, 2.111 mmol) in DMF (7.5 mL) was added sodium hydride (110 mg, 2.74 mmol) at RT and the reaction was stirred vigorously for 30 min. Then a solution of Intermediate 188a (558 mg, 2.217 mmol) in DMF (3.0 mL) was added and the resulting reaction mixture was allowed to stir for 2 h before being quenched with a saturated aqueous solution of NH$_4$Cl. The mixture was diluted with EtOAc and extracted. The organic phase was dried over MgSO$_4$, filtered and concentrated before being purified by ISCO (Hex/EtOAc, 0-100%) to afford the title compound (Intermediate 188b, 320 mg, 0.924 mmol, 43.8% yield) as a white solid. LC-MS (Method A5): 1.80 min, [M+H]$^+$=346.1 and 348.1; $^1$H NMR (500 MHz, CDCl$_3$) δ 8.72 (s, 2H), 6.89 (s, 1H), 5.66 (s, 2H), 2.83 (q, J=7.7 Hz, 2H), 2.66 (s, 3H), 2.56 (s, 3H), 1.37 (t, J=7.6 Hz, 3H).

Intermediate 188c: 2-((2-ethyl-5,7-dimethyl-3H-imidazo[4,5-b]pyridin-3-yl)methyl)pyrimidin-5-ylboronic acid

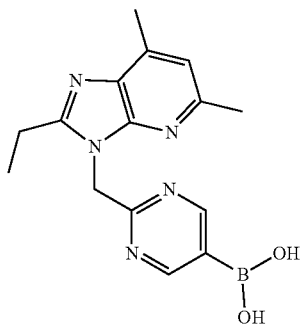

(188c)

Intermediate 188b (320 mg, 0.924 mmol), KOAc (181 mg, 1.848 mmol), 4,4,4',4',5,5,5',5'-octamethyl-2,2'-bi(1,3,2-dioxaborolane) (258 mg, 1.017 mmol) and PdCl$_2$(dppf) (37.7 mg, 0.046 mmol) in dioxane (5.0 mL) was degassed with N$_2$ for 2 min before the reaction vessel was sealed and heated at 100° C. for overnight. The mixture was cooled and filtered through CELITE and purified via preparative HPLC (Column: Phenomenex AXIA Luna 100×30 mm 5u s; Mobile Phase A: 10:90 ACN: H$_2$O with 10 mM TFA; Mobile Phase B: 90:10 ACN: H$_2$O with 10 mM TFA; Gradient: 0-100% B over 10 minutes, then a 2-minute hold at 100% B; Flow: 40 mL/min.) to afford 390 mg (0.917 mmol, 99% yield) of the title compound (Intermediate 188c) as TFA salt. LC-MS (Method A5): 1.60 min, [M+H]$^+$=312.2; $^1$H NMR (400 MHz, CDCl$_3$) δ 8.94 (s, 2H), 7.16 (s, 1H), 5.95 (s, 2H), 3.17 (q, J=7.6 Hz, 2H), 2.66 (s, 3H), 2.58 (s, 3H), 1.52-1.40 (m, 3H).

Intermediate 188d: 4-chloro-2-(2-((2-ethyl-5,7-dimethyl-3H-imidazo[4,5-b]pyridin-3-yl)methyl)pyrimidin-5-yl)benzonitrile

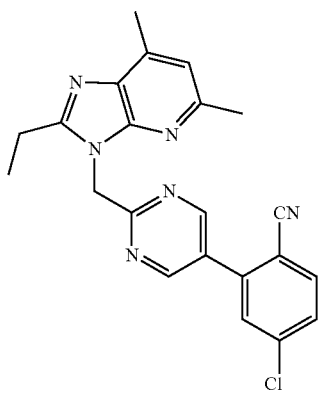

(188d)

A mixture of Intermediate 188c (200 mg, 0.470 mmol) and 4-chloro-2-iodobenzonitrile 124 mg, 0.470 mmol) in THF (8 mL) was treated with 1.5 M Na$_2$CO$_3$ (1.254 mL, 1.882 mmol)) followed by PdCl$_2$(dppf) (19.21 mg, 0.024 mmol). The resulting mixture was degassed with N$_2$ for 2 min before the reaction vessel was sealed and irradiated in a microwave reactor at 100° C. for 30 min. The cooled reaction mixture was diluted with DCM and extracted. The combined organic layer was washed with brine, dried over MgSO$_4$, and concentrated to dryness and the residue purified by ISCO (Hexanes/AcOEt, 0-100%) to afford the title compound (Intermediate 188d, 100 mg, 0.248 mmol, 52.8% yield) as an off-white solid. LC-MS (Method A5): 2.09 min, [M+H]$^+$=403.1; $^1$H NMR (500 MHz, CDCl$_3$) δ 8.86 (s, 2H), 7.78 (d, J=8.3 Hz, 1H), 7.57 (d, J=8.3 Hz, 1H), 6.90 (s, 1H), 5.80 (s, 2H), 2.88 (q, J=7.4 Hz, 2H), 2.67 (s, 3H), 2.57 (s, 3H), 1.40 (t, J=7.6 Hz, 3H).

Intermediate 188e: 3-(2-((2-ethyl-5,7-dimethyl-3H-imidazo[4,5-b]pyridin-3-yl)methyl)pyrimidin-5-yl)-3'-methylbiphenyl-4-carbonitrile

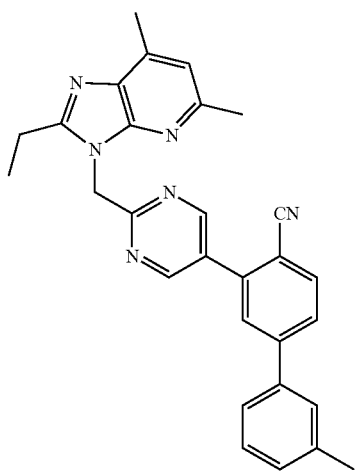

(188e)

A mixture of Intermediate 188d (25 mg, 0.062 mmol) and), m-tolylboronic acid (25.3 mg, 0.186 mmol) in THF (1 mL) was treated with 1.0 M phosphoric acid, potassium salt (0.112 mL, 0.112 mmol) followed by Pd-XPhos G3 (5.25 mg, 6.21 µmol). The resulting mixture was degassed with N$_2$ for 2 min before the reaction vessel was sealed and irradiated in a microwave reactor at 140° C. for 45 min. The cooled reaction mixture was concentrated to dryness and the residue purified by ISCO (Hexanes/AcOEt, 0-100%) to afford the title compound (Intermediate 188e, 28 mg, 0.061 mmol, 98% yield) as a colorless oil. LC-MS (Method A5): 2.41 min, [M+H]$^+$=459.2; $^1$H NMR (500 MHz, CDCl$_3$) δ 8.93 (s, 2H), 7.90 (d, J=8.0 Hz, 1H), 7.78 (dd, J=8.0, 1.7 Hz, 1H), 7.66 (d, J=1.7 Hz, 1H), 7.48-7.37 (m, 3H), 7.34-7.23 (m, 1H), 6.91 (s, 1H), 5.82 (s, 2H), 2.91 (q, J=7.7 Hz, 2H), 2.68 (s, 3H), 2.59 (s, 3H), 2.46 (s, 3H), 1.42 (t, J=7.6 Hz, 3H)

Example 188: 2-ethyl-5,7-dimethyl-3-((5-(3'-methyl-4-(1H-tetrazol-5-yl)biphenyl-3-yl)pyrimidin-2-yl)methyl)-3H-imidazo[4,5-b]pyridine To a solution of Intermediate 188e (28.4 mg, 0.062 mmol) in toluene (1.5 mL) was added dibutyltin oxide (30.9 mg, 0.124 mmol) and TMS-N$_3$ (0.082 mL, 0.620 mmol). Then the reaction vessel was sealed and the mixture was heated at 100° C. overnight behind a blast shield (according to the procedure described in J. Org. Chem, 1993, 58, 4139). After cooling, the reaction mixture was concentrated, re-solvated in DMF, filtered then purified via preparative HPLC (Column: XBridge C18, 19×200 mm, 5-µm particles; Mobile Phase A: 5:95 ACN: H$_2$O with 0.1% trifluoroacetic acid; Mobile Phase B: 95:5 ACN: H$_2$O with 0.1% trifluoroacetic acid; Gradient: 20-60% B over 23 minutes, then a 4-minute hold at 100% B; Flow: 20 mL/min) to afford 19.5 mg (0.038 mmol, 61.4% yield) of the title compound Example 188.

LC-MS (Method A3): 1.5 min, [M+H]⁺=502.21; ¹H NMR (500 MHz, DMSO-d₆) δ 8.63 (s, 2H), 7.95 (s, 2H), 7.85 (s, 1H), 7.66 (s, 1H), 7.62 (br d, J=7.7 Hz, 1H), 7.39 (t, J=7.6 Hz, 1H), 7.25 (br d, J=7.5 Hz, 1H), 6.92 (s, 1H), 5.70 (s, 2H), 3.05-2.67 (m, 2H), 2.53 (br s, 3H), 2.48 (s, 3H), 2.40 (s, 3H), 0.88 (br t, J=7.2 Hz, 3H).

The following examples have been similarly prepared from Intermediate 188d as described above for Example 188. Two analytical LC-MS injections were used to determine the final purity. The retention time of one of them is reported for each compound and is referred as Method A3, Method A4 or Method A5.

| Ex | Structure | MW | LC-MS m/z [M + H]⁺; RT; (Method) | ¹H NMR (500 MHz, DMSO-d₆) δ ppm |
|---|---|---|---|---|
| 189 | 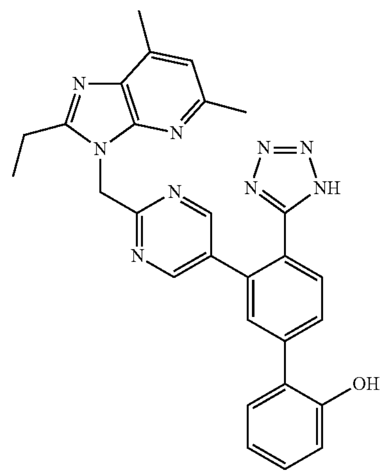 [SMILES: CCc1nc2c(C)cc(C)nc2n1Cc1ncc(-c2cc(-c3ccccc3O)ccc2-c2nnn[nH]2)cn1] | 503.57 | 504.18; 1.2 min (Method A3) | 8.61 (s, 2H), 7.88 (s, 2H), 7.71 (s, 1H), 7.43 (br d, J = 7.6 Hz, 1H), 7.29-7.19 (m, 1H), 6.99 (d, J = 7.9 Hz, 1H), 6.95-6.80 (m, 2H), 5.70 (s, 2H), 2.79 (q, J = 7.3 Hz, 2H), 2.52 (br s, 3H), 2.47 (s, 3H), 1.28 (t, J = 7.5 Hz, 3H) |
| 190 | 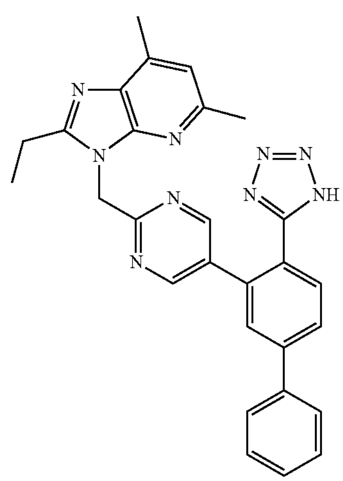 [SMILES: CCc1nc2c(C)cc(C)nc2n1Cc1ncc(-c2cc(-c3ccccc3)ccc2-c2nnn[nH]2)cn1] | 487.57 | 488.04; 1.37 min (Method A3) | 8.66 (s, 2H), 8.03-7.93 (m, 2H), 7.90 (s, 1H), 7.85 (br d, J = 7.3 Hz, 2H), 7.60-7.47 (m, 2H), 7.48-7.39 (m, 1H), 6.93 (s, 1H), 5.71 (s, 2H), 2.81 (q, J = 7.6 Hz, 2H), 2.55 (s, 3H), 2.47 (s, 3H), 1.29 (t, J = 7.3 Hz, 3H) |

Example 191: 2-ethyl-5,7-dimethyl-3-((6-(3'-methyl-4-(1H-tetrazol-5-yl)biphenyl-3-yl)pyridazin-3-yl)methyl)-3H-imidazo[4,5-b]pyridine

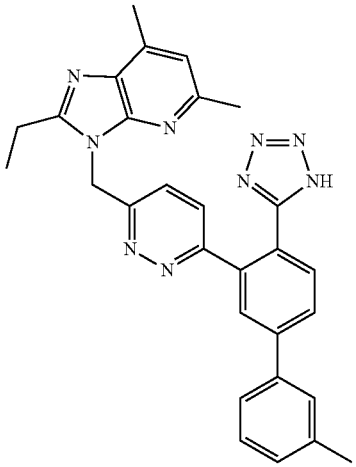
(ex. 191)

Intermediate 191a: 3-((6-bromopyridazin-3-yl)methyl)-2-ethyl-5,7-dimethyl-3H-imidazo[4,5-b]pyridine

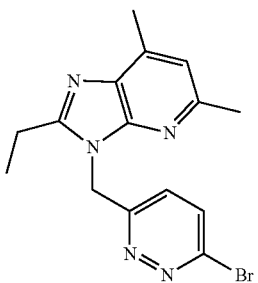
(191a)

To a solution of Intermediate 001c (200 mg, 1.141 mmol) in DMF (4.0 mL) was added sodium hydride (100 mg, 2.51 mmol) at RT and the reaction was stirred vigorously for 30 min. Then a solution of 3-bromo-6-(bromomethyl)pyridazine, hydrobromide (399 mg, 1.198 mmol) in DMF (1.6 mL) was added and the resulting reaction mixture was allowed to stir for 2 h before being quenched with a saturated aqueous solution of NH$_4$Cl.

The mixture was diluted with EtOAc and extracted. The organic phase was dried over MgSO$_4$, filtered and concentrated before being purified by ISCO (Hex/EtOAc, 0-100%) to afford the title compound (Intermediate 191a, 270 mg, 0.780 mmol, 68.3% yield) as a white solid. LC-MS (Method A5): 1.70 min, [M+H]$^+$=346.0 and 348.0; $^1$H NMR (500 MHz, CDCl$_3$) δ 7.57 (d, J=8.8 Hz, 1H), 7.34 (d, J=8.8 Hz, 1H), 6.93 (s, 1H), 5.75 (s, 2H), 2.95 (q, J=7.5 Hz, 2H), 2.64 (s, 3H), 2.61 (s, 3H), 1.37 (t, J=7.6 Hz, 3H).

Intermediate 191b: 4-chloro-2-(6-((2-ethyl-5,7-dimethyl-3H-imidazo[4,5-b]pyridin-3-yl)methyl)pyridazin-3-yl)benzonitrile

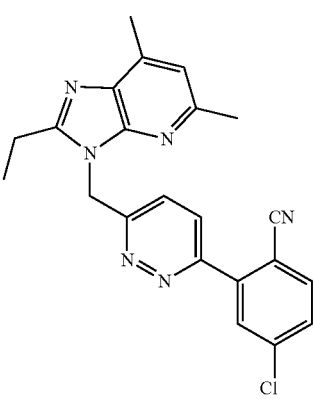
(191b)

A mixture of Intermediate 191a (100 mg, 0.289 mmol) and 4-chloro-2-(5,5-dimethyl-1,3,2-dioxaborinan-2-yl)benzonitrile (94 mg, 0.375 mmol) in THF (3 mL) was treated with 1.5 M Na$_2$CO$_3$ (0.578 mL, 0.866 mmol) followed by PdCl$_2$(dppf) (11.79 mg, 0.014 mmol). The resulting mixture was degassed with N$_2$ for 2 min before the reaction vessel was sealed and irradiated in a microwave reactor at 125° C. for 75 min. The cooled reaction mixture was diluted with DCM and extracted. The combined organic layer was washed with brine, dried over MgSO$_4$, and concentrated. The crude sample in 2 ml of DCM was treated with TEA (0.201 mL, 1.444 mmol) followed by TFAA (0.061 mL, 0.433 mmol). The mixture was stirred at RT for 1 hour, then concentrated to dryness and the residue purified by ISCO (Hexanes/AcOEt, 0-100%) to afford the title compound (Intermediate 191b, 40 mg, 0.099 mmol, 34.4% yield) as an amber oil. LC-MS (Method A5): 2.04 min, [M+H]$^+$=403.0; $^1$H NMR (500 MHz, CDCl$_3$) δ 8.06 (d, J=1.9 Hz, 1H), 7.95 (d, J=8.8 Hz, 1H), 7.79 (d, J=8.3 Hz, 1H), 7.65-7.55 (m, 2H), 6.95 (s, 1H), 5.89 (s, 2H), 3.01 (q, J=7.4 Hz, 2H), 2.65 (s, 3H), 2.63 (s, 3H), 1.40 (t, J=7.6 Hz, 3H)

Intermediate 191c: 3-(6-((2-ethyl-5,7-dimethyl-3H-imidazo[4,5-b]pyridin-3-yl)methyl)pyridazin-3-yl)-3'-methylbiphenyl-4-carbonitrile

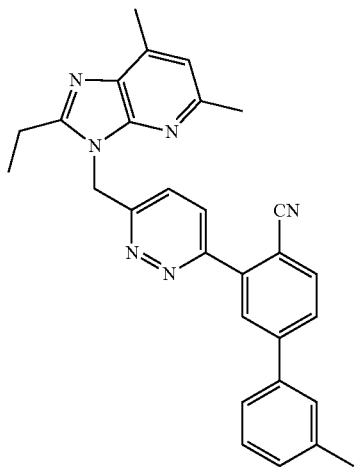

(191c)

A mixture of Intermediate 191b (40 mg, 0.099 mmol) and m-tolylboronic acid (40.5 mg, 0.298 mmol) in THF (1 mL) was treated with 1.0 M phosphoric acid, potassium salt (0.179 mL, 0.179 mmol) followed by Pd-XPhos G3 (8.40 mg, 9.93 μmol). The resulting mixture was degassed with $N_2$ for 2 min before the reaction vessel was sealed and irradiated in a microwave reactor at 140° C. for 60 min. The cooled reaction mixture was concentrated to dryness and the residue purified by ISCO (Hexanes/AcOEt, 0-100%) to afford the title compound (Intermediate 191c, 35 mg, 0.076 mmol, 77% yield) as a colorless oil. LC-MS (Method A5): 2.35 min, [M+H]$^+$=459.1; $^1$H NMR (500 MHz, CDCl$_3$) δ 8.26 (d, J=1.1 Hz, 1H), 8.01 (d, J=8.8 Hz, 1H), 7.91 (d, J=8.0 Hz, 1H), 7.83 (dd, J=8.0, 1.4 Hz, 1H), 7.63 (d, J=8.8 Hz, 1H), 7.52-7.45 (m, 2H), 7.40 (t, J=7.6 Hz, 1H), 7.33-7.20 (m, 1H), 6.95 (s, 1H), 5.90 (s, 2H), 3.04 (q, J=7.5 Hz, 2H), 2.66 (s, 3H), 2.64 (s, 3H), 2.46 (s, 3H), 1.41 (t, J=7.6 Hz, 3H).

Example 191: 2-ethyl-5,7-dimethyl-3-((6-(3'-methyl-4-(1H-tetrazol-5-yl)biphenyl-3-yl)pyridazin-3-yl)methyl)-3H-imidazo[4,5-b]pyridine To a solution of Intermediate 191c (35 mg, 0.076 mmol) in toluene (1.5 mL) was added dibutyltin oxide (38.0 mg, 0.153 mmol) and TMS-N$_3$ (0.101 mL, 0.763 mmol). Then the reaction vessel was sealed and the mixture was heated at 100° C. overnight behind a blast shield (according to the procedure described in J. Org. Chem, 1993, 58, 4139). After cooling, the reaction mixture was concentrated, re-solvated in DMF, filtered then purified via preparative HPLC (Column: XBridge C18, 19×200 mm, 5-μm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 15-55% B over 22 minutes, then a 6-minute hold at 100% B; Flow: 20 mL/min) to afford 18.2 mg (0.036 mmol, 46.7% yield) of the title compound Example 191. LC-MS (Method A3): 1.38 min, [M+H]$^+$=502.26; $^1$H NMR (500 MHz, DMSO-d$_6$) δ 8.08-7.94 (m, 2H), 7.91 (d, J=7.9 Hz, 1H), 7.75 (d, J=8.9 Hz, 1H), 7.65 (s, 1H), 7.61 (br d, J=7.6 Hz, 1H), 7.57 (d, J=8.5 Hz, 1H), 7.40 (t, J=7.6 Hz, 1H), 7.25 (br d, J=7.6 Hz, 1H), 6.96 (s, 1H), 5.78 (s, 2H), 2.98-2.78 (m, 2H), 2.56 (s, 3H), 2.51 (br s, 3H), 2.39 (s, 3H), 1.28 (t, J=7.5 Hz, 3H).

Example 192: 4'-((2-ethyl-5,7-dimethyl-3H-imidazo[4,5-b]pyridin-3-yl)methyl)-5-(pyridin-2-yl)biphenyl-2-carboxylic acid

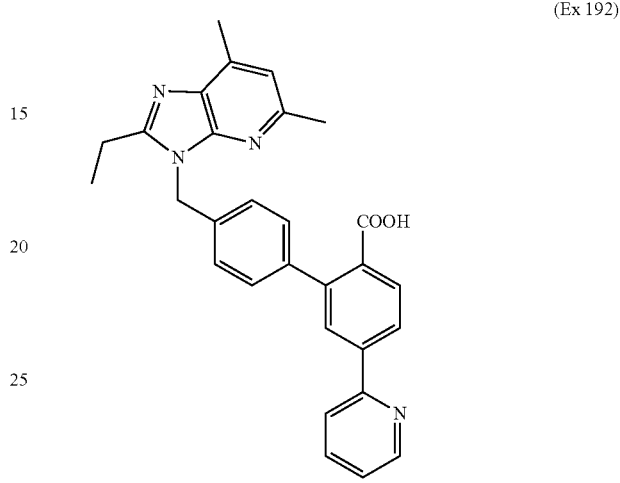

(Ex 192)

Intermediate 192a: 4'-((2-ethyl-5,7-dimethyl-3H-imidazo[4,5-b]pyridin-3-yl)methyl)-6-(methoxycarbonyl)biphenyl-3-ylboronic acid

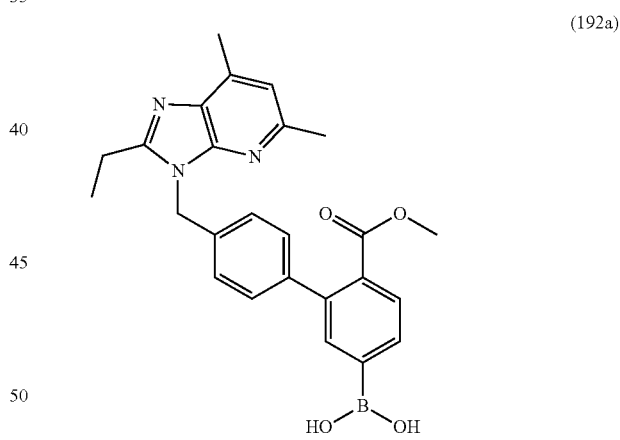

(192a)

To a pressure-rated vial containing Intermediate 181a (100 mg, 0.230 mmol), dicyclohexyl(2',4',6'-triisopropyl-[1,1'-biphenyl]-2-yl)phosphane (10.99 mg, 0.023 mmol), Pd$_2$(dba)$_3$ (21.10 mg, 0.023 mmol) and bis(pinacolato)diboron (117 mg, 0.461 mmol) was added dioxane (2 ml) followed by KOAc (113 mg, 1.152 mmol). The reaction mixture was degassed with N$_2$ for 2 min before the reaction vessel was sealed and heated at 105° C. for 60 min. The mixture was cooled and filtered through celite and purified via preparative HPLC (Column: Phenomenex AXIA Luna 100×30 mm 5u s; Mobile Phase A: 10:90 ACN: H$_2$O with 10 mM TFA; Mobile Phase B: 90:10 ACN: H$_2$O with 10 mM TFA; Gradient: 0-100% B over 10 minutes, then a 2-minute hold at 100% B; Flow: 40 mL/min.) to afford the title compound (Intermediate 192a, 88 mg, 0.199 mmol, 86% yield). LC-MS (Method A5): 2.16 min, [M+H]⁺=444.1; ¹H NMR (500 MHz, MeOH-d₄) δ 7.91-7.52 (m, 3H), 7.42-7.28 (m, 5H), 5.79 (s, 2H), 3.74-3.59 (m, 3H), 3.23 (q, J=7.6 Hz, 2H), 2.72 (s, 3H), 2.68 (s, 3H), 1.39 (t, J=7.6 Hz, 3H).

Example 192: 4'-((2-ethyl-5,7-dimethyl-3H-imidazo[4,5-b]pyridin-3-yl)methyl)-5-(pyridin-2-yl)biphenyl-2-carboxylic acid A mixture of Intermediate 192a (22 mg, 0.050 mmol) and 2-bromopyridine (23.52 mg, 0.149 mmol) in THF (1 mL) was treated with 1.0 M phosphoric acid, potassium salt (0.089 mL, 0.089 mmol) followed by Pd-XPhos G3 (4.20 mg, 4.96 μmol). The resulting mixture was degassed with N₂ for 2 min before the reaction vessel was sealed and irradiated in a microwave reactor at 130° C. for 30 min. The cooled reaction mixture was treated with MeOH (0.5 mL) and 2.0 M NaOH ((0.248 mL, 0.496 mmol). The mixture was reheated in a microwave reactor at 100° C. for 1 hour. After cooling, the reaction mixture was concentrated, re-solvated in DMF, filtered then purified via preparative HPLC (Column: XBridge C18, 19×200 mm, 5-μm particles; Mobile Phase A: 5:95 ACN: H₂O with 10 mM NH₄OAc; Mobile Phase B: 95:5 ACN: H₂O with 10 mM NH₄OAc; Gradient: 40-80% B over 19 minutes, then a 5-minute hold at 100% B; Flow: 20 mL/min) to afford 2.3 mg (0.005 mmol, 9.6% yield) of the title compound Example 192. LC-MS (Method A3): 1.14 min, [M+H]⁺=463.16; ¹H NMR (500 MHz, DMSO-d₆) δ 8.67 (br d, J=4.3 Hz, 1H), 8.07 (br dd, J=17.5, 8.1 Hz, 2H), 7.99 (s, 1H), 7.89 (br t, J=7.6 Hz, 1H), 7.73 (br d, J=7.9 Hz, 1H), 7.40 (br d, J=7.6 Hz, 3H), 7.16 (br d, J=7.9 Hz, 2H), 6.97 (s, 1H), 5.52 (s, 2H), 2.83 (q, J=7.3 Hz, 2H), 2.54 (s, 6H), 1.28 (t, J=7.3 Hz, 3H).

The following examples have been similarly prepared from Intermediate 192a as described above for Example 192. Two analytical LC-MS injections were used to determine the final purity. The retention time of one of them is reported for each compound and is referred as Method A3, Method A4 or Method A5.

| Ex | Structure | MW | LC-MS m/z [M + H]⁺; RT; (Method) | ¹H NMR (500 MHz, DMSO-d₆) δ ppm |
|---|---|---|---|---|
| 193 | 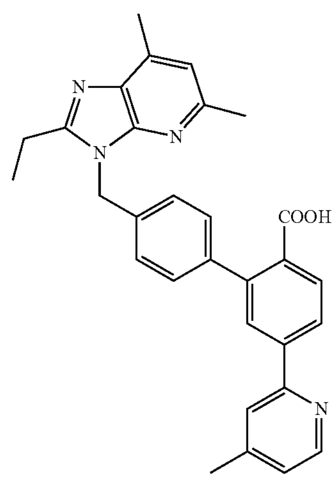 [SMILES: CCc1nc2c(C)cc(C)nc2n1Cc1ccc(-c2cc(-c3cc(C)ccn3)ccc2C(=O)O)cc1] | 476.58 | 477.21; 1.23 min (Method A1) | 8.52 (d, J = 4.9 Hz, 1H), 8.13 (br d, J = 8.5 Hz, 1H), 8.00 (s, 1H), 7.93 (s, 1H), 7.84 (d, J = 7.9 Hz, 1H), 7.36 (br d, J = 7.9 Hz, 2H), 7.25 (br d, J = 4.6 Hz, 1H), 7.21 (br d, J = 7.9 Hz, 2H), 7.04 (s, 1H), 5.56 (s, 2H), 2.92-2.83 (m, 2H), 2.55 (br s, 3H), 2.54 (s, 3H), 2.39 (s, 3H), 1.27 (t, J = 7.5 Hz, 3H) |
| 194 | 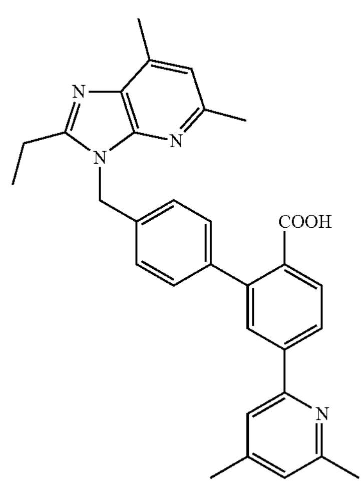 [SMILES: CCc1nc2c(C)cc(C)nc2n1Cc1ccc(-c2cc(-c3cc(C)cc(C)n3)ccc2C(=O)O)cc1] | 490.61 | 491.26; 1.41 min (Method A3) | 8.13 (br d, J = 8.2 Hz, 1H), 8.00 (s, 1H), 7.83 (d, J = 8.2 Hz, 1H), 7.73 (s, 1H), 7.36 (br d, J = 7.9 Hz, 2H), 7.19 (br d, J = 7.6 Hz, 2H), 7.10 (s, 1H), 6.98 (s, 1H), 5.53 (s, 2H), 2.84 (q, J = 7.4 Hz, 2H), 2.56 (s, 3H), 2.54 (s, 3H), 2.49 (s, 3H), 2.35 (s, 3H), 1.29 (t, J = 7.5 Hz, 3H). |

Example 195: 3-(6-((2-ethyl-5,7-dimethyl-3H-imidazo[4,5-b]pyridin-3-yl)methyl)pyridin-3-yl)-3'-methylbiphenyl-4-carboxylic acid

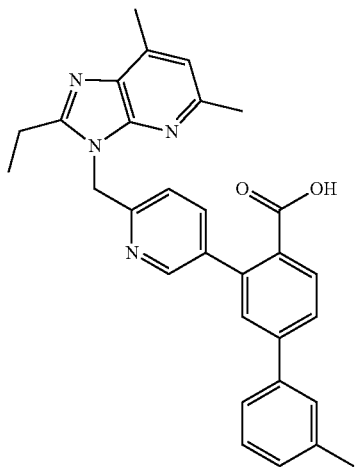

Intermediate 195a: 4-bromo-2-(6-((2-ethyl-5,7-dimethyl-3H-imidazo[4,5-b]pyridin-3-yl)methyl)pyridin-3-yl)benzoic acid

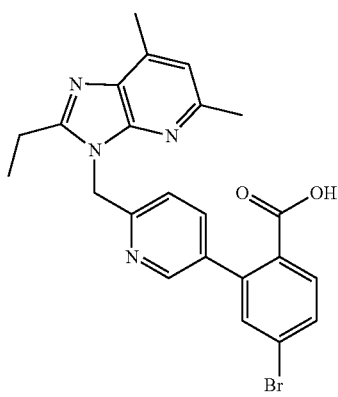

A mixture of Intermediate 177c (crude boronic ester, 60 mg, 0.107 mmol) and 4-bromo-2-iodobenzoic acid (35.0 mg, 0.107 mmol) in NMP/H$_2$O (1:1, 1 mL) was treated with K2C03 (32.6 mg, 0.236 mmol) followed by Pd$_2$(dba)$_3$ (9.80 mg, 10.71 µmol). The resulting mixture was degassed with N$_2$ for 2 min before the reaction vessel was sealed and irradiated in a microwave reactor at 120° C. for 15 min. The mixture was cooled and filtered through celite and purified via preparative HPLC (Column: Phenomenex AXIA Luna 100×30 mm 5u s; Mobile Phase A: 10:90 ACN: H$_2$O with 10 mM TFA; Mobile Phase B: 90:10 ACN: H$_2$O with 10 mM TFA; Gradient: 0-100% B over 10 minutes, then a 2-minute hold at 100% B; Flow: 40 mL/min.) to afford the title compound (Intermediate 195a, 17 mg, 0.037 mmol, 34.5% yield). LC-MS (Method A5): 2.27 min, [M+H]$^+$=465.1 and 467.1. $^1$H NMR (500 MHz, CDCl$_3$) δ 7.91 (br d, J=8.0 Hz, 1H), 7.76 (br s, 1H), 7.65 (br d, J=7.7 Hz, 1H), 7.44 (br s, 2H), 5.84 (br s, 2H), 3.26 (br s, 2H), 2.72-2.54 (m, 6H), 1.38 (br s, 3H).

Example 195: 3-(6-((2-ethyl-5,7-dimethyl-3H-imidazo[4,5-b]pyridin-3-yl)methyl)pyridin-3-yl)-3'-methylbiphenyl-4-carboxylic acid A mixture of Intermediate 195a (17 mg, 0.037 mmol) and m-tolylboronic acid (14.90 mg, 0.110 mmol) in THF (1 mL) was treated with 1.5 M Na$_2$CO$_3$ (0.073 mL, 0.110 mmol) followed by PdCl$_2$(dppf) (2.98 mg, 3.65 µmol). The resulting mixture was degassed with N$_2$ for 2 min before the reaction vessel was sealed and irradiated in a microwave reactor at 135° C. for 30 min. After cooling, the reaction mixture was concentrated, re-solvated in DMF, filtered then purified via preparative HPLC (Column: XBridge C18, 19×200 mm, 5-µm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 17-57% B over 20 minutes, then a 4-minute hold at 100% B; Flow: 20 mL/min.) to afford 7.8 mg (0.016 mmol, 44.8% yield) of the title compound Example 195. LC-MS (Method A3): 1.44 min, [M+H]$^+$=477.11; $^1$H NMR (500 MHz, DMSO-d$_6$) δ 8.50 (s, 1H), 7.87 (br d, J=8.2 Hz, 1H), 7.81 (br d, J=7.9 Hz, 1H), 7.75 (br d, J=7.6 Hz, 1H), 7.59 (s, 2H), 7.54 (br d, J=7.6 Hz, 1H), 7.36 (t, J=7.8 Hz, 1H), 7.21 (br d, J=7.3 Hz, 1H), 7.18 (d, J=8.2 Hz, 1H), 6.94 (s, 1H), 5.59 (s, 2H), 2.87 (q, J=7.3 Hz, 2H), 2.52 (br s, 3H), 2.50 (br s, 3H), 2.37 (s, 3H), 1.29 (t, J=7.5 Hz, 3H).

Example 196: 3-(6-((2-ethyl-5,7-dimethyl-3H-imidazo[4,5-b]pyridin-3-yl)methyl)pyridin-3-yl)-[1,1'-biphenyl]-4-carboxylic acid

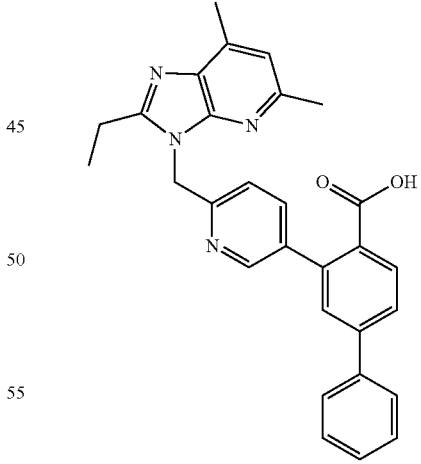

Example 196 has been similarly prepared from Intermediate 195a as described above for Example 195. LC-MS (Method A3): 1.42 min, [M+H]$^+$=463.32; $^1$H NMR (500 MHz, DMSO-d$_6$) δ 8.49 (s, 1H), 7.95 (d, J=7.9 Hz, 1H), 7.81 (br d, J=7.9 Hz, 2H), 7.77 (br d, J=7.6 Hz, 2H), 7.63 (s, 1H), 7.52-7.46 (m, 2H), 7.44-7.38 (m, 1H), 7.20 (br d, J=8.2 Hz, 1H), 6.94 (s, 1H), 5.60 (s, 2H), 2.87 (q, J=7.4 Hz, 2H), 2.52 (br s, 3H), 2.50 (br s, 3H), 1.29 (t, J=7.3 Hz, 3H).

Example 197: 2-ethyl-5,7-dimethyl-3-((2-(3'-methyl-4-(1H-tetrazol-5-yl)biphenyl-3-yl)pyrimidin-5-yl)methyl)-3H-imidazo[4,5-b]pyridine

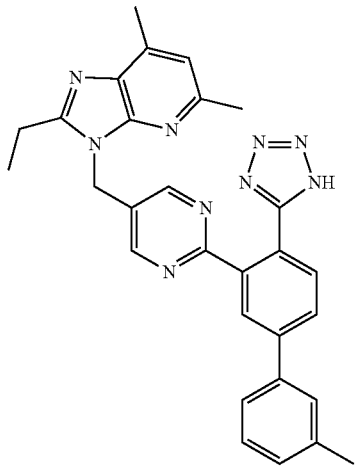

(Ex. 197)

Intermediate 197a:
2-bromo-5-(bromomethyl)pyrimidine

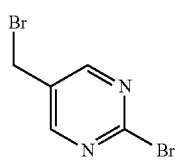

(197a)

To a suspension of (2-chloropyrimidin-5-yl)methanol (330 mg, 2.283 mmol) in DCM (6.0 mL) was added a solution of PBr₃ (0.323 ml, 3.42 mmol) in DCM (0.3 mL) dropwise.

The resulting mixture was stirred at RT for overnight. The mixture was concentrated under reduced pressure and purified by ISCO (Hexanes/AcOEt, 0-100%) to afford the title compound (Intermediate 197a, 110 mg, 0.437 mmol, 19.13% yield) as a white solid. LC-MS (Method A5): 1.72 min, [M+H]⁺=252.8; ¹H NMR (500 MHz, MeOH-d₄) δ 8.67 (s, 2H), 4.68 (s, 2H).

Intermediate 197b: 3-((2-bromopyrimidin-5-yl)methyl)-2-ethyl-5,7-dimethyl-3H-imidazo[4,5-b]pyridine

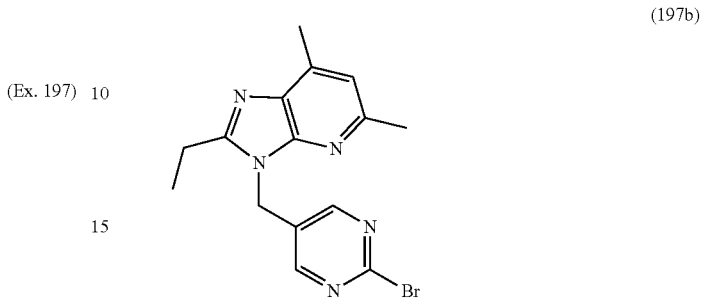

(197b)

To a solution of Intermediate 001c (69.6 mg, 0.397 mmol) in DMF (2.0 mL) was added sodium hydride (20.64 mg, 0.516 mmol)) at RT and the reaction was stirred vigorously for 30 min. Then a solution of Intermediate 197a (100 mg, 0.397 mmol) in DMF (0.8 mL) was added and the resulting reaction mixture was allowed to stir for 2 h before being quenched with a saturated aqueous solution of NH₄Cl. The mixture was diluted with EtOAc and extracted. The organic phase was dried over MgSO₄, filtered and concentrated before being purified by ISCO (Hex/EtOAc, 0-100%) to afford the title compound (Intermediate 197b, 71 mg, 0.205 mmol, 51.7% yield) as a white solid. LC-MS (Method A5): 1.80 min, [M+H]⁺=346.0 and 348.0; ¹H NMR (500 MHz, CDCl₃) δ 8.62 (s, 1H), 8.56 (s, 1H), 6.93 (s, 1H), 5.42 (d, J=12.9 Hz, 2H), 2.89 (q, J=7.4 Hz, 2H), 2.64 (s, 3H), 2.59 (d, J=1.1 Hz, 3H), 1.43 (t, J=7.6 Hz, 3H).

Intermediate 197c: 4-chloro-2-(5-((2-ethyl-5,7-dimethyl-3H-imidazo[4,5-b]pyridin-3-yl)methyl)pyrimidin-2-yl)benzonitrile

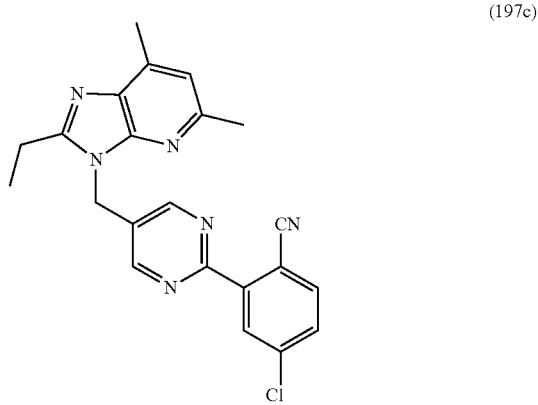 [SMILES: CCc1nc2c(C)cc(C)nc2n1Cc1cnc(-c2cc(Cl)ccc2C#N)nc1]

(197c)

A mixture of Intermediate 197b (70 mg, 0.202 mmol) and (5-chloro-2-cyanophenyl)boronic acid (47.7 mg, 0.263 mmol) in THF (3 mL) was treated with 1.5 M Na₂CO₃ (0.404 mL, 0.607 mmol) followed by PdCl2(dppf) (16.51 mg, 0.020 mmol). The resulting mixture was degassed with N₂ for 2 min before the reaction vessel was sealed and irradiated in a microwave reactor at 130° C. for 75 min. The cooled reaction mixture was diluted with DCM and extracted. The combined organic layer was washed with brine, dried over MgSO₄, and concentrated. The crude sample in 2 ml of DCM was treated with TEA (0.141 mL, 1.011 mmol) followed by TFAA (0.043 mL, 0.303 mmol).

The mixture was stirred at RT for 1 hour, then concentrated to dryness and the residue purified by ISCO (Hexanes/AcOEt, 0-100%) to afford the title compound (Intermediate 197c, 40 mg, 0.099 mmol, 49.1% yield) as an amber oil. LC-MS (Method A5): 2.27 min, [M+H]⁺=403.1.

Intermediate 197d: 3-(5-((2-ethyl-5,7-dimethyl-3H-imidazo[4,5-b]pyridin-3-yl)methyl)pyrimidin-2-yl)-3'-methylbiphenyl-4-carbonitrile

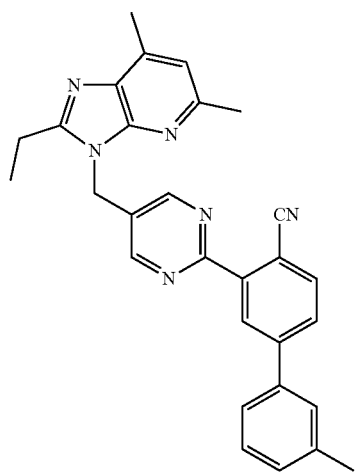

(197d)

A mixture of Intermediate 197c (20 mg, 0.050 mmol) m-tolylboronic acid (6.75 mg, 0.050 mmol) in THF (1 mL) was treated with 1.0 M phosphoric acid, potassium salt (0.089 mL, 0.089 mmol) followed by Pd-XPhos G3 (4.20 mg, 4.96 μmol). The resulting mixture was degassed with N₂ for 2 min before the reaction vessel was sealed and irradiated in a microwave reactor at 140° C. for 60 min. The cooled reaction mixture was concentrated to dryness and the residue purified by ISCO (Hexanes/AcOEt, 0-100%) to afford the title compound (Intermediate 197d, 20 mg, 0.044 mmol, 88%) as a colorless oil. LC-MS (Method A5): 2.49 min, [M+H]⁺=459.0; ¹H NMR (500 MHz, CDCl₃) δ 8.87 (s, 2H), 8.61 (d, J=1.9 Hz, 1H), 7.91 (d, J=8.0 Hz, 1H), 7.79 (dd, J=8.1, 1.8 Hz, 1H), 7.53-7.47 (m, 2H), 7.39 (t, J=7.6 Hz, 1H), 7.27 (d, J=7.7 Hz, 1H), 6.95 (s, 1H), 5.54 (s, 2H), 2.93 (q, J=7.6 Hz, 2H), 2.66 (s, 3H), 2.63 (s, 3H), 2.46 (s, 3H), 1.44 (t, J=7.6 Hz, 3H)

Example 197: 2-ethyl-5,7-dimethyl-3-((2-(3'-methyl-4-(1H-tetrazol-5-yl)biphenyl-3-yl)pyrimidin-5-yl)methyl)-3H-imidazo[4,5-b] pyridine To a solution of Intermediate 197d (20 mg, 0.044 mmol) in toluene (1.5 mL) was added dibutyltin oxide (21.71 mg, 0.087 mmol) and TMS-N₃ (0.058 mL, 0.436 mmol). Then the reaction vessel was sealed and the mixture was heated at 100° C. overnight behind a blast shield (according to the procedure described in J. Org. Chem, 1993, 58, 4139). After cooling, the reaction mixture was concentrated, re-solvated in DMF, filtered then purified via preparative HPLC (Column: XBridge C18, 19×200 mm, 5-μm particles; Mobile Phase A: 5:95 ACN: H₂O with 10 mM NH₄OAc; Mobile Phase B: 95:5 ACN: H₂O with 10 mM NH₄OAc; Gradient: 15-55% B over 20 minutes, then a 4-minute hold at 100% B; Flow: 20 mL/min) to afford 17.8 mg (0.035 mmol, 81% yield) of the title compound Example 197. LC-MS (Method A3): 1.44 min, [M+H]'=502.04; ¹H NMR (500 MHz, DMSO-d₆) δ 8.67 (s, 2H), 8.15 (s, 1H), 7.93 (br d, J=7.9 Hz, 1H), 7.84 (d, J=7.9 Hz, 1H), 7.67-7.51 (m, 2H), 7.40 (t, J=7.6 Hz, 1H), 7.25 (br d, J=7.3 Hz, 1H), 6.98 (s, 1H), 5.53 (s, 2H), 2.92 (q, J=7.4 Hz, 2H), 2.56 (s, 3H), 2.54 (s, 3H), 2.40 (s, 3H), 1.31 (t, J=7.5 Hz, 3H).

Example 198: 3-(2-((2-ethyl-5,7-dimethyl-3H-imidazo[4,5-b]pyridin-3-yl)methyl)pyrimidin-5-yl)-3'-methylbiphenyl-4-carboxylic acid

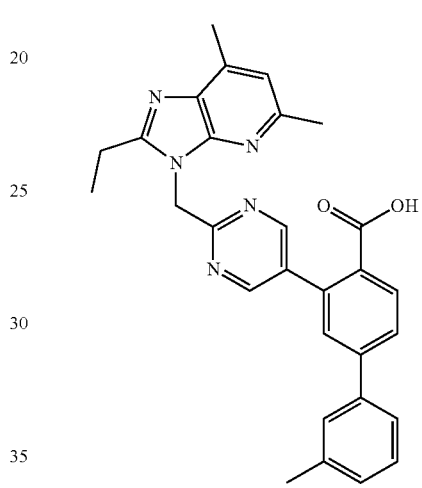

Intermediate 198a: methyl 4-chloro-2-(2-((2-ethyl-5,7-dimethyl-3H-imidazo[4,5-b]pyridin-3-yl)methyl)pyrimidin-5-yl)benzoate

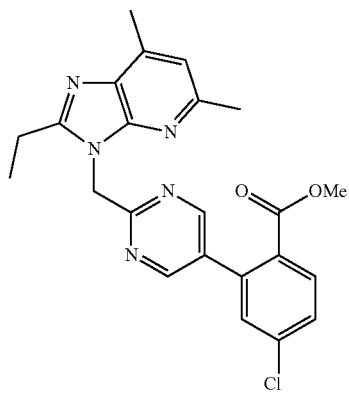 [SMILES: CCc1nc2c(C)cc(C)nc2n1Cc1ncc(-c2cc(Cl)ccc2C(=O)OC)cn1]

A mixture of (2-((2-ethyl-5,7-dimethyl-3H-imidazo[4,5-b]pyridin-3-yl)methyl)pyrimidin-5-yl)boronic acid (Intermediate 188c, 45 mg, 0.145 mmol) and methyl 4-chloro-2-iodobenzoate (40 mg, 0.135 mmol) in THF (1.5 mL) was treated with 1.5 M Na₂CO₃ (0.270 mL, 0.405 mmol) followed by PdCl₂(dppf) (5.51 mg, 6.75 μmol). The resulting mixture was degassed with N₂ for 2 min before the reaction vessel was sealed and irradiated in a microwave reactor at 100° C. for 30 min. The cooled reaction mixture was diluted with DCM and extracted. The combined organic layer was washed with brine, dried over MgSO$_4$, and concentrated to dryness and the residue purified by ISCO (Hexanes/AcOEt, 0-100%) to afford the title compound (Intermediate 198a, 36 mg, 0.083 mmol, 61.2% yield) as a yellow oil. LC-MS (Method A5): 2.20 min, [M+H]+=436.1; $^1$H NMR (500 MHz, CDCl$_3$) δ 8.59 (s, 1H), 8.67-8.44 (m, 1H), 8.03 (d, J=8.5 Hz, 1H), 7.52 (dd, J=8.5, 2.2 Hz, 1H), 6.90 (s, 1H), 5.78 (s, 2H), 3.72 (s, 3H), 2.87 (q, J=7.7 Hz, 2H), 2.67 (s, 3H), 2.59 (s, 3H), 1.39 (t, J=7.6 Hz, 3H)

Example 198: 3-(2-((2-ethyl-5,7-dimethyl-3H-imidazo[4,5-b]pyridin-3-yl)methyl)pyrimidin-5-yl)-3'-methylbiphenyl-4-carboxylic acid A mixture of methyl 4-chloro-2-(2-((2-ethyl-5,7-dimethyl-3H-imidazo[4,5-b]pyridin-3-yl)methyl)pyrimidin-5-yl)benzoate (Intermediate 198a,18 mg, 0.041 mmol) and m-tolylboronic acid (16.84 mg, 0.124 mmol) in THF (1 mL) was treated with 1.0 M phosphoric acid, potassium salt (0.074 mL, 0.074 mmol) followed by Pd-XPhos G3 (1.748 mg, 2.065 µmol). The resulting mixture was degassed with N$_2$ for 2 min before the reaction vessel was sealed and irradiated in a microwave reactor at 140° C. for 45 min. The cooled reaction mixture was treated with MeOH (0.5 mL) and 2.0 M NaOH (0.124 mL, 0.248 mmol). The mixture was reheated in a microwave reactor at 100° C. for 30 min. After cooling, the reaction mixture was concentrated, re-solvated in DMF, filtered then purified via preparative HPLC (Column: XBridge C18, 19×200 mm, 5-µm particles; Mobile Phase A: 5:95 ACN: H$_2$O with 0.1% trifluoroacetic acid; Mobile Phase B: 95:5 ACN: H$_2$O with 0.1% trifluoroacetic acid; Gradient: 30-70% B over 19 minutes, then a 5-minute hold at 100% B; Flow: 20 mL/min.) to afford 10.6 mg (0.022 mmol, 53.8% yield) of the title compound Example 198. LC-MS (Method A3): 1.42 min, [M+H]$^+$=478.35; $^1$H NMR (500 MHz, DMSO-d$_6$) δ 8.76 (s, 2H), 8.05 (d, J=8.2 Hz, 1H), 7.85 (br d, J=7.6 Hz, 1H), 7.70 (s, 1H), 7.62 (s, 1H), 7.58 (br d, J=7.4 Hz, 1H), 7.37 (t, J=7.6 Hz, 1H), 7.24 (br d, J=7.4 Hz, 1H), 6.92 (s, 1H), 5.72 (s, 2H), 2.84 (q, J=7.5 Hz, 2H), 2.55 (s, 3H), 2.48 (s, 3H), 2.39 (s, 3H), 1.31 (t, J=7.4 Hz, 3H).

Example 199: 3-(5-((2-ethyl-5,7-dimethyl-3H-imidazo[4,5-b]pyridin-3-yl)methyl)pyrazin-2-yl)-3'-methylbiphenyl-4-carboxylic acid

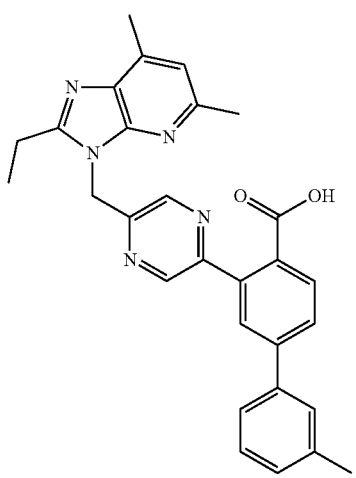 [SMILES: CCc1nc2c(C)cc(C)nc2n1Cc1cnc(-c2cc(-c3cccc(C)c3)ccc2C(=O)O)cn1]

Intermediate 199a: ethyl 4-chloro-2-(5-((2-ethyl-5,7-dimethyl-3H-imidazo[4,5-b]pyridin-3-yl)methyl)pyrazin-2-yl)benzoate

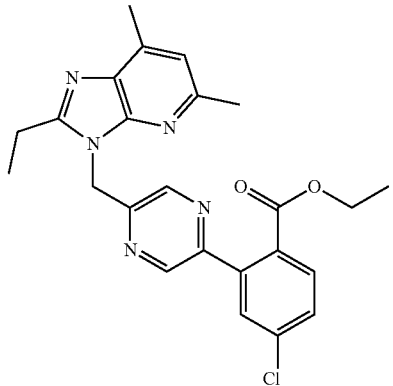 [SMILES: CCOC(=O)c1ccc(Cl)cc1-c1cnc(Cn2c(CC)nc3c(C)cc(C)nc32)cn1]

A mixture Intermediate 186b (40 mg, 0.116 mmol) and (5-chloro-2-(ethoxycarbonyl)phenyl)boronic acid (31.7 mg, 0.139 mmol) in THF (1.5 mL) was treated with 1.5 M Na$_2$CO$_3$ (0.231 mL, 0.347 mmol) followed by PdCl$_2$(dppf) (9.43 mg, 0.012 mmol). The resulting mixture was degassed with N$_2$ for 2 min before the reaction vessel was sealed and irradiated in a microwave reactor at 125° C. for 45 min. The cooled reaction mixture was diluted with DCM and extracted. The combined organic layer was washed with brine, dried over MgSO$_4$, and concentrated to dryness and the residue purified by ISCO (Hexanes/AcOEt, 0-100%) to afford the title compound (Intermediate 199a, 44 mg, 0.098 mmol, 85% yield) as an amber oil. LC-MS (Method A5): 2.23 min, [M+H]$^+$=450.1; $^1$H NMR (500 MHz, CDCl$_3$) δ 8.60 (d, J=8.5 Hz, 2H), 7.90 (d, J=8.8 Hz, 1H), 7.54-7.47 (m, 2H), 6.91 (s, 1H), 5.65 (s, 2H), 4.21-4.06 (m, 2H), 3.02 (q, J=7.4 Hz, 2H), 2.64 (s, 3H), 2.60 (s, 3H), 1.44 (t, J=7.6 Hz, 3H)

Example 199: 3-(5-((2-ethyl-5,7-dimethyl-3H-imidazo[4,5-b]pyridin-3-yl)methyl)pyrazin-2-yl)-3'-methylbiphenyl-4-carboxylic acid A mixture of ethyl 4-chloro-2-(5-((2-ethyl-5,7-dimethyl-3H-imidazo[4,5-b]pyridin-3-yl)methyl)pyrazin-2-yl)benzoate (Intermediate 199a, 44 mg, 0.098 mmol) and m-tolylboronic acid (39.9 mg, 0.293 mmol) in THF (1 mL) was treated with 1.0 M phosphoric acid, potassium salt (0.176 mL, 0.176 mmol) followed by Pd-XPhos G3 (8.28 mg, 9.78 µmol). The resulting mixture was degassed with N$_2$ for 2 min before the reaction vessel was sealed and irradiated in a microwave reactor at 140° C. for 45 min.

The cooled reaction mixture was treated with MeOH (0.5 mL) and 2.0 M NaOH (0.293 mL, 0.587 mmol). The mixture was reheated in a microwave reactor at 100° C. for 30 min.

After cooling, the reaction mixture was concentrated, re-solvated in DMF, filtered then purified via preparative HPLC (Column: XBridge C18, 19×200 mm, 5-µm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 10-50% B over 20 minutes, then a 5-minute hold at 100% B; Flow: 20 mL/min.) to afford 13.3 mg (0.027 mmol, 27.3% yield) of the title compound Example 199. LC-MS (Method A3): 1.4 min, [M+H]$^+$=478.22; $^1$H NMR (500 MHz, DMSO-d$_6$) δ 8.79 (s, 1H), 8.70 (s, 1H), 7.94-7.87

(m, 1H), 7.86-7.76 (m, 2H), 7.60 (s, 1H), 7.56 (br d, J=7.6 Hz, 1H), 7.38 (t, J=7.6 Hz, 1H), 7.24 (br d, J=7.3 Hz, 1H), 6.95 (s, 1H), 5.69 (s, 2H), 2.93 (q, J=7.6 Hz, 2H), 2.56 (s, 3H), 2.50 (s, 3H), 2.38 (s, 3H), 1.32 (t, J=7.5 Hz, 3H).

Example 200: 3-(6-((2-ethyl-5,7-dimethyl-3H-imidazo[4,5-b]pyridin-3-yl)methyl)pyridazin-3-yl)-3'-methylbiphenyl-4-carboxylic acid

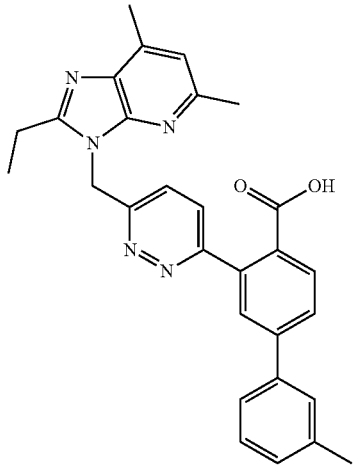
(Ex. 200)

Intermediate 200a: ethyl 4-chloro-2-(6-((2-ethyl-5,7-dimethyl-3H-imidazo[4,5-b]pyridin-3-yl)methyl)pyridazin-3-yl)benzoate

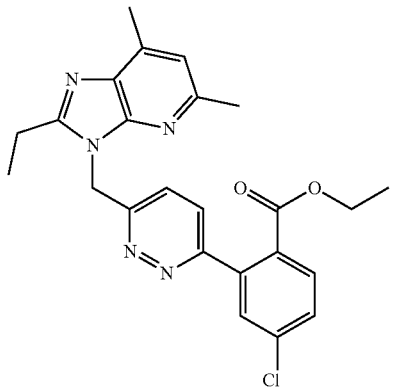
(200a)

A mixture of Intermediate 191a (50 mg, 0.144 mmol) and (5-chloro-2-(ethoxycarbonyl)phenyl)boronic acid (39.6 mg, 0.173 mmol) in THF (1.5 mL) was treated with 1.5 M $Na_2CO_3$ (0.289 mL, 0.433 mmol)) followed by $PdCl_2(dppf)$ (11.79 mg, 0.014 mmol). The resulting mixture was degassed with $N_2$ for 2 min before the reaction vessel was sealed and irradiated in a microwave reactor at 125° C. for 45 min. The cooled reaction mixture was diluted with DCM and extracted. The combined organic layer was washed with brine, dried over $MgSO_4$, and concentrated to dryness and the residue purified by ISCO (Hexanes/AcOEt, 0-100%) to afford the title compound (Intermediate 200a, 40 mg, 0.089 mmol, 61.6% yield) as an amber oil. LC-MS (Method A5): 2.19 min, [M+H]⁺=450.1; ¹H NMR (500 MHz, $CDCl_3$) δ 7.97 (d, J=8.5 Hz, 1H), 7.53 (s, 1H), 7.54 (br d, J=2.2 Hz, 1H), 7.48 (d, J=0.8 Hz, 2H), 6.93 (s, 1H), 5.85 (s, 2H), 4.14 (q, J=7.2 Hz, 2H), 3.01 (q, J=7.4 Hz, 2H), 2.65 (s, 3H), 2.62 (s, 3H), 1.39 (t, J=7.4 Hz, 3H), 1.06 (t, J=7.2 Hz, 3H)

Example 200: 3-(6-((2-ethyl-5,7-dimethyl-3H-imidazo[4,5-b]pyridin-3-yl)methyl)pyridazin-3-yl)-3'-methylbiphenyl-4-carboxylic acid A mixture of Intermediate 200a (20 mg, 0.044 mmol) and m-tolylboronic acid (18.13 mg, 0.133 mmol) in THF (1 mL) was treated with 1.0 M phosphoric acid, potassium salt (0.080 mL, 0.080 mmol) followed by Pd-XPhos G3 (3.76 mg, 4.45 µmol). The resulting mixture was degassed with $N_2$ for 2 min before the reaction vessel was sealed and irradiated in a microwave reactor at 140° C. for 45 min. The cooled reaction mixture was treated with MeOH (0.5 mL) and 2.0 M NaOH (0.133 mL, 0.267 mmol). The mixture was reheated in a microwave reactor at 100° C. for 1 hour. After cooling, the reaction mixture was concentrated, re-solvated in DMF, filtered then purified via preparative HPLC (Column: XBridge C18, 19×200 mm, 5-µm particles; Mobile Phase A: 5:95 ACN: $H_2O$ with 0.1% trifluoroacetic acid; Mobile Phase B: 95:5 ACN: $H_2O$ with 0.1% trifluoroacetic acid; Gradient: 19-59% B over 20 minutes, then a 4-minute hold at 100% B; Flow: 20 mL/min.) to afford 14.5 mg (0.032 mmol, 71.8% yield) of the title compound Example 200. LC-MS (Method A3): 1.35 min, [M+H]⁺=478.1; ¹H NMR (500 MHz, DMSO-$d_6$) δ 8.01-7.92 (m, 2H), 7.92-7.87 (m, 1H), 7.82 (s, 1H), 7.65 (d, J=8.7 Hz, 1H), 7.62 (s, 1H), 7.58 (br d, J=7.7 Hz, 1H), 7.38 (t, J=7.6 Hz, 1H), 7.25 (br d, J=7.4 Hz, 1H), 6.99 (s, 1H), 5.83 (s, 2H), 2.92 (q, J=7.4 Hz, 2H), 2.53 (s, 3H), 2.51 (s, 3H), 2.38 (s, 3H), 1.30 (t, J=7.4 Hz, 3H)

Example 201: 3-(5-((2-ethyl-5,7-dimethyl-3H-imidazo[4,5-b]pyridin-3-yl)methyl)pyridin-2-yl)biphenyl-4-carboxylic acid

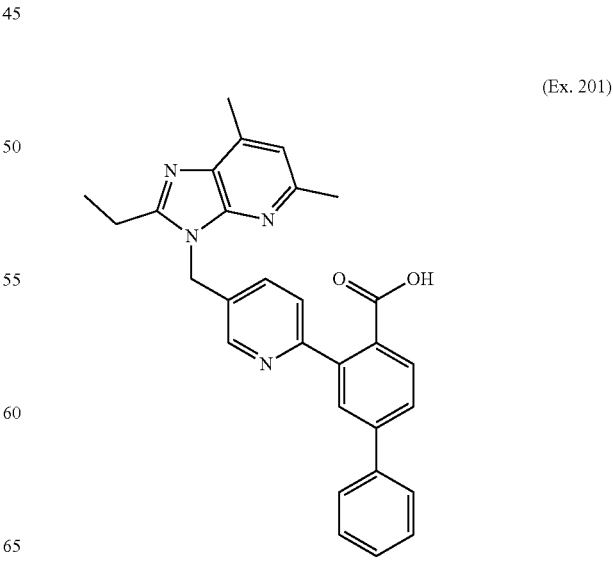
(Ex. 201)

Intermediate 201a: neopentyl 4-bromo-2-(5-((2-ethyl-5,7-dimethyl-3H-imidazo[4,5-b]pyridin-3-yl)methyl)pyridin-2-yl)benzoate

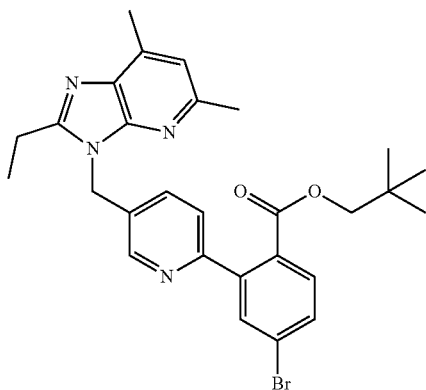

(Ex. 201a)

A mixture of Intermediate 039a (50 mg, 0.145 mmol) and (5-bromo-2-((neopentyloxy)carbonyl)phenyl)boronic acid (59.3 mg, 0.188 mmol) in THF (1.5 mL) was treated with 1.5 M Na$_2$CO$_3$ (0.290 mL, 0.434 mmol) followed by PdCl$_2$(dppf) (11.83 mg, 0.014 mmol). The resulting mixture was degassed with N$_2$ for 2 min before the reaction vessel was sealed and irradiated in a microwave reactor at 130° C. for 30 min. The cooled reaction mixture was diluted with DCM and extracted. The combined organic layer was washed with brine, dried over MgSO$_4$, and concentrated to dryness and the residue purified by ISCO (Hexanes/AcOEt, 0-100%) to afford the title compound (Intermediate 201a, 20 mg, 0.037 mmol, 25.8% yield) as an amber oil. LC-MS (Method A5): 2.51 min, [M+H]$^+$=535.2 and 537.2; $^1$H NMR (500 MHz, CDCl$_3$) δ 8.63 (d, J=1.4 Hz, 1H), 7.72 (d, J=8.3 Hz, 1H), 7.68 (d, J=1.7 Hz, 1H), 7.62 (dd, J=8.3, 1.9 Hz, 1H), 7.56 (dd, J=8.1, 2.1 Hz, 1H), 7.39 (d, J=8.3 Hz, 1H), 6.93 (s, 1H), 5.51 (s, 2H), 3.74 (s, 2H), 2.89 (q, J=7.7 Hz, 2H), 2.65 (s, 3H), 2.62 (s, 3H), 1.42 (t, J=7.6 Hz, 3H), 0.71 (s, 9H).

Example 201: 3-(5-((2-ethyl-5,7-dimethyl-3H-imidazo[4,5-b]pyridin-3-yl)methyl)pyridin-2-yl)biphenyl-4-carboxylic acid A mixture of Intermediate 201a (20 mg, 0.037 mmol) and phenylboronic acid (13.66 mg, 0.112 mmol) in THF (1.5 mL) was treated with 1.5 M Na$_2$CO$_3$ (0.075 mL, 0.112 mmol) followed by PdCl$_2$(dppf) (3.05 mg, 3.73 μmol).The resulting mixture was degassed with N$_2$ for 2 min before the reaction vessel was sealed and irradiated in a microwave reactor at 130° C. for 30 min. The cooled reaction mixture was treated with MeOH (0.5 mL) and 2.0 M NaOH (0.131 mL, 0.261 mmol). The mixture was reheated in a microwave reactor at 100° C. for 15 min. After cooling, the reaction mixture was concentrated, re-solvated in DMF, filtered then purified via preparative HPLC (Column: XBridge C18, 19×200 mm, 5-μm particles; Mobile Phase A: 5:95 ACN: H$_2$O with 0.1% trifluoroacetic acid; Mobile Phase B: 95:5 ACN: H$_2$O with 0.1% trifluoroacetic acid; Gradient: 15-55% B over 19 minutes, then a 5-minute hold at 100% B; Flow: 20 mL/min.) to afford 7.6 mg (0.016 mmol, 41.3% yield) of the title compound Example 201. LC-MS (Method A3): 1.37 min, [M+H]$^+$=463.31; $^1$H NMR (500 MHz, DMSO-d$_6$) δ 8.52 (s, 1H), 7.83-7.79 (m, 2H), 7.78 (s, 1H), 7.75 (br d, J=7.5 Hz, 2H), 7.64 (s, 2H), 7.51-7.47 (m, 2H), 7.44-7.39 (m, 1H), 6.99 (s, 1H), 5.57 (s, 2H), 2.89 (q, J=7.4 Hz, 2H), 2.55 (s, 3H), 2.53 (s, 3H), 1.29 (t, J=7.4 Hz, 3H).

Example 202: 3-(5-((2-ethyl-5,7-dimethyl-3H-imidazo[4,5-b]pyridin-3-yl)methyl)pyrimidin-2-yl)-3'-methylbiphenyl-4-carboxylic acid

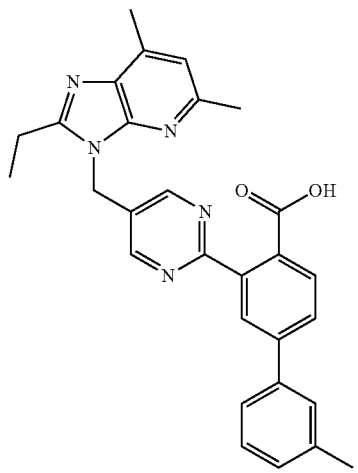

(Ex. 202)

Intermediate 202a: 5-(bromomethyl)-2-chloropyrimidine

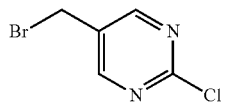

(202a)

2-chloro-5-methylpyrimidine (200 mg, 1.556 mmol) was dissolved in carbon tetrachloride (5 mL), NBS (332 mg, 1.867 mmol) and benzoyl peroxide (18.84 mg, 0.078 mmol) were added, and the resulting mixture was heated and refluxed for overnight. The reaction solution was returned to RT, concentrated under reduced pressure and purified by ISCO (Hexanes/AcOEt, 0-100%) to afford the title compound (Intermediate 202a, 116 mg, 0.559 mmol, 35.9% yield) as a white solid. LC-MS (Method A5): 1.62 min, [M+H]$^+$=206.9 and 208.9; $^1$H NMR (500 MHz, CDCl$_3$) δ 8.69 (s, 2H), 4.44 (s, 2H).

Intermediate 202b: 3-((2-chloropyrimidin-5-yl) methyl)-2-ethyl-5,7-dimethyl-3H-imidazo[4,5-b] pyridine

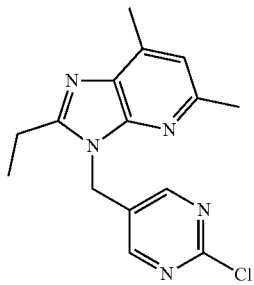

(202b)

To a solution of Intermediate 001c (90 mg, 0.514 mmol) in DMF (2.0 mL) was added sodium hydride (26.7 mg, 0.668 mmol) at RT and the reaction was stirred vigorously for 30 min. Then a solution of Intermediate 202a (112 mg, 0.539 mmol) in DMF (0.8 mL) was added and the resulting reaction mixture was allowed to stir for 2 h before being quenched with a saturated aqueous solution of NH$_4$Cl. The mixture was diluted with EtOAc and extracted. The organic phase was dried over MgSO$_4$, filtered and concentrated before being purified by ISCO (Hex/EtOAc, 0-100%) to afford the title compound (Intermediate 202b, 87 mg, 0.288 mmol, 56.1% yield) as a white solid. LC-MS (Method A5): 1.79 min, [M+H]$^+$=302.2; $^1$H NMR (500 MHz, CDCl$_3$) δ 8.60 (s, 2H), 6.92 (s, 1H), 5.42 (s, 2H), 2.88 (q, J=7.6 Hz, 2H), 2.62 (s, 3H), 2.58 (s, 3H), 1.41 (t, J=7.6 Hz, 3H).

Intermediate 202c: 2-ethyl-3-((2-iodopyrimidin-5-yl) methyl)-5,7-dimethyl-3H-imidazo[4,5-b]pyridine

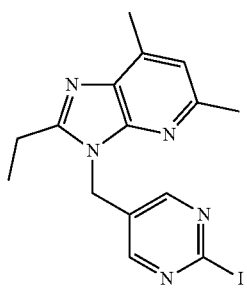

(202c)

HI (306 µl, 2.320 mmol) precooled to 0° C. was added to 3-((2-chloropyrimidin-5-yl)methyl)-2-ethyl-5,7-dimethyl-3H-imidazo[4,5-b]pyridine (70 mg, 0.232 mmol) in a small vial. The mixture was kept and vigorously stirred at 0° C. for 50 min. The light brownish green suspension was quickly neutralized at 0° C. with a saturated aqueous solution of potassium carbonate and decolorized with potassium disulfite at 0° C. The aqueous solution was extracted with diethyl ether, dried over desiccated MgSO$_4$, filtered, and evaporated under reduced pressure. The crude sample was purified by ISCO (Hexanes/AcOEt, 0-100%) to afford the title compound (Intermediate 202c, 30 mg, 0.076 mmol, 32.9% yield). LC-MS (Method A5): 1.89 min, [M+H]$^+$=394.0; $^1$H NMR (500 MHz, CDCl$_3$) δ 8.45 (s, 2H), 6.92 (s, 1H), 5.38 (s, 2H), 2.88 (q, J=7.5 Hz, 2H), 2.63 (s, 3H), 2.58 (s, 3H), 1.42 (t, J=7.6 Hz, 3H)

Intermediate 202d

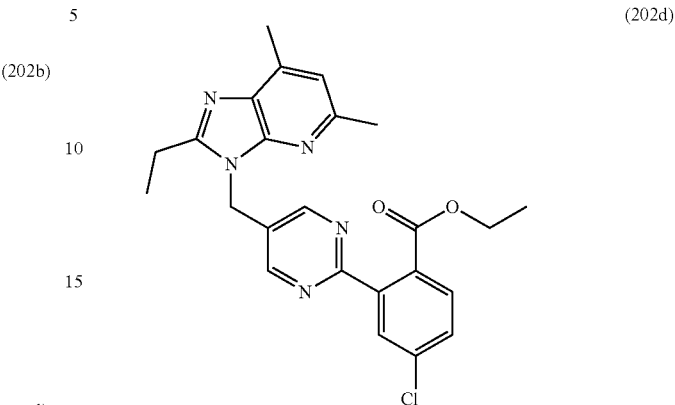

(202d)

A mixture of Intermediate 202c (30 mg, 0.076 mmol) and (5-chloro-2-(ethoxycarbonyl)phenyl)boronic acid (20.91 mg, 0.092 mmol) in THF (1.5 mL) was treated with 1.5 M Na$_2$CO$_3$ (0.153 mL, 0.229 mmol) followed by PdCl$_2$(dppf) (6.23 mg, 7.63 µmol). The resulting mixture was degassed with N$_2$ for 2 min before the reaction vessel was sealed and irradiated in a microwave reactor at 125° C. for 30 min. The cooled reaction mixture was diluted with DCM and extracted. The combined organic layer was washed with brine, dried over MgSO$_4$, and concentrated to dryness and the residue purified by ISCO (DCM/MeOH, 0-20%) to afford the title compound (Intermediate 202d, 22 mg, 0.049 mmol, 64.1% yield) as an amber oil. LC-MS (Method A5): 2.29 min, [M+H$^9$=450.1; $^1$H NMR (500 MHz, CDCl$_3$) δ 8.76 (s, 2H), 7.98 (d, J=1.9 Hz, 1H), 7.68 (d, J=8.3 Hz, 1H), 7.49 (dd, J=8.3, 1.9 Hz, 1H), 6.94 (s, 1H), 5.50 (s, 2H), 4.19 (q, J=7.2 Hz, 2H), 2.93 (q, J=7.7 Hz, 2H), 2.65 (s, 3H), 2.61 (s, 3H), 1.44 (t, J=7.4 Hz, 3H), 1.09 (t, J=7.2 Hz, 3H)

Example 202: 3-(5-((2-ethyl-5,7-dimethyl-3H-imidazo[4,5-b]pyridin-3-yl)methyl)pyrimidin-2-yl)-3'-methylbiphenyl-4-carboxylic acid A mixture of Intermediate 202d (20 mg, 0.044 mmol) and m-tolylboronic acid (18.13 mg, 0.133 mmol) in THF (1 mL) was treated with 1.0 M phosphoric acid, potassium salt (0.080 mL, 0.080 mmol) followed by Pd-XPhos G3 (3.76 mg, 4.45 µmol). The resulting mixture was degassed with N$_2$ for 2 min before the reaction vessel was sealed and irradiated in a microwave reactor at 140° C. for 45 min. The cooled reaction mixture was treated with MeOH (0.5 mL) and 2.0 M NaOH (0.133 mL, 0.267 mmol). The mixture was reheated in a microwave reactor at 100° C. for 30 min. After cooling, the reaction mixture was concentrated, re-solvated in DMF, filtered then purified via preparative HPLC (Column: XBridge C18, 19×200 mm, 5-µm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 15-55% B over 25 minutes, then a 6-minute hold at 100% B; Flow: 20 mL/min.) to afford 8.5 mg (0.018 mmol, 39.5% yield) of the title compound Example 202. LC-MS (Method A3): 1.4 min, [M+H]$^+$=478.06; $^1$H NMR (500 MHz, DMSO-d$_6$) δ 8.82 (s, 2H), 8.06 (d, 1=1.6 Hz, 1H), 7.84 (dd, J=8.0, 1.7 Hz, 1H), 7.79-7.71 (m, 1H), 7.55 (s, 1H), 7.52 (br d, J=7.7 Hz, 1H), 7.38 (t, J=7.6 Hz, 1H), 7.24 (br d, J=7.4

Hz, 1H), 7.02 (s, 1H), 5.60 (s, 2H), 2.98 (q, J=7.3 Hz, 2H), 2.56 (br s, 3H), 2.54 (s, 3H), 2.39 (s, 3H), 1.33 (t, J=7.4 Hz, 3H).

Example 203: 3-(5-((2-ethyl-5,7-dimethyl-3H-imidazo[4,5-b]pyridin-3-yl)methyl)pyridin-2-yl)-3'-methyl-[1,1'-biphenyl]-4-carboxylic acid

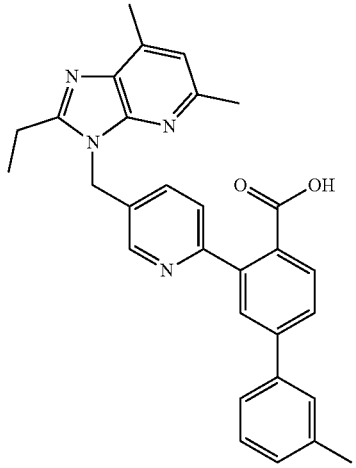

(Ex. 203)

Example 203 has been similarly prepared from Intermediate 201$^a$ as described above for Example 201. LC-MS (Method A3): 1.63 min, [M+H]$^+$=477.16; $^1$H NMR (500 MHz, DMSO-d$_6$) δ 7.89-7.64 (m, 4H), 7.60 (br s, 1H), 7.56 (br d, J=7.3 Hz, 1H), 7.38 (br t, J=7.5 Hz, 1H), 7.30-7.18 (m, 2H), 7.12-6.94 (m, 2H), 5.66 (br s, 2H), 2.96 (br d, J=4.6 Hz, 2H), 2.52 (br s, 6H), 2.38 (s, 3H), 1.30 (br s, 3H).

Example 204: 2-Ethyl-5, 7-dimethyl-3-((5'-phenoxy-2'-(1H-tetrazol-5-yl)-[1, 1'-biphenyl]-4-yl) methyl)-3H-imidazo[4,5-b]pyridine

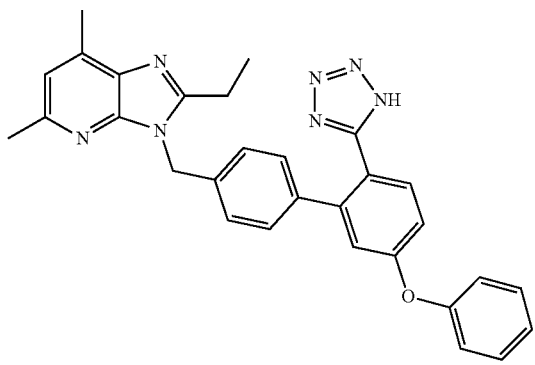

(Ex: 204)

Intermediate 204a: 2-Bromo-4-phenoxybenzonitrile

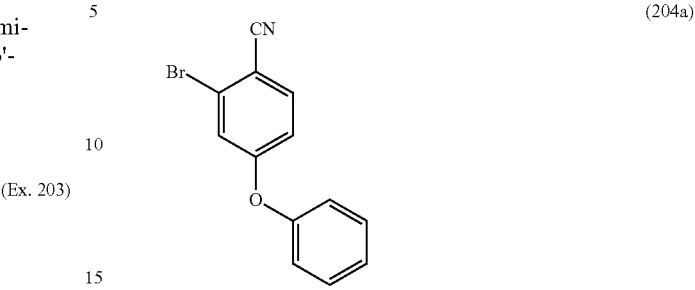

(204a)

To a solution of 2-bromo-4-fluorobenzonitrile (0.400 g, 2.000 mmol) and phenol (0.207 g, 2.200 mmol) in DMF (10 mL) was added potassium carbonate (0.332 g, 2.400 mmol) and the resulting mixture was stirred at 50° C. in a sealed vial overnight. After 16 h, LC-MS showed that the reaction was essentially complete (co-injection with starting material), with a single major peak (target mass not observed). The mixture was filtered to remove the potassium salts, the filter-cake was washed with a DMF (2 mL) and the filtrate was evaporated. The residue obtained was partitioned with EtOAc-saturated aqueous NH$_4$Cl and the organic phase was separated, dried (Na$_2$SO$_4$) and evaporated. This afforded the essentially pure product (0.466 g, 85% yield) which was used as such in the next step. LC-MS (Method J): 1.330 min, [M+H]$^+$=no ion observed; $^1$H NMR (400 MHz, DMSO-d$_6$) δ ppm 7.90 (d, J=9.0 Hz, 1H), 7.48 (t, J=8.2 Hz, 1H), 7.39 (d, J=2.3 Hz, 1H), 7.29 (t, J=7.4 Hz, 1H), 7.17 (d, J=7.4 Hz, 1H), 7.05 (dd, J=2.3, 8.6 Hz, 1H).

Intermediate 204b: 4'-((2-Ethyl-5,7-dimethyl-3H-imidazo[4,5-b]pyridin-3-yl)methyl)-5-phenoxy-[1,1'-biphenyl]-2-carbonitrile

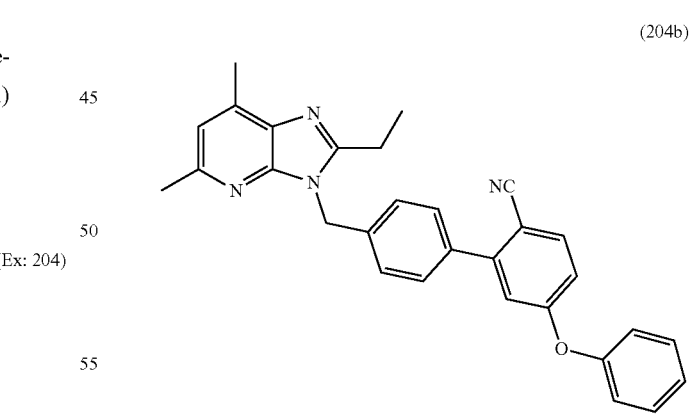

(204b)

A mixture of Intermediate 001d (0.060 g, 0.153 mmol), Intermediate 204a (0.053 g, 0.192 mmol) and 2 M Na$_2$CO$_3$ (0.192 mL, 0.383 mmol) in toluene-ethanol (9:1, 5 mL) was purged with a stream of N$_2$ for 5 min in a sealable vial. To this mixture was added Pd(Ph$_3$P)$_4$ (0.018 g, 0.015 mmol), the vial was sealed and the mixture was stirred at 95° C. (block temperature) for 3 h. The cooled mixture was diluted with EtOAc and the organic phase was separated, dried (Na$_2$SO$_4$) and evaporated to give a golden yellow gum. This material was purified by flash chromatography (ISCO/0-100% EtOAc-DCM) to give 4'-((2-ethyl-5,7-dimethyl-3H-imidazo[4,5-b]pyridin-3-yl)methyl)-5-phenoxy-[1,1'-biphenyl]-2-carbonitrile (0.041 g, 58.3% yield) as a colourless gum. This gum was lyophilized from ACN-H$_2$O to give a white solid which was used as such in the next step.

LC-MS (Method J): 1.479 min, [M+H]$^+$=459.1; $^1$H NMR (400 MHz, DMSO-d$_6$) δ ppm 7.90 (d, J=8.6 Hz, 1H), 7.50 (d, J=8.2 Hz, 2H), 7.45 (m, 2H), 7.27-7.21 (m, 3H), 7.17 (m, 2H), 7.08 (d, J=2.7 Hz, 1H), 7.02 (dd, J=2.7, 8.6 Hz, 1H), 6.94 (s, 1H), 5.51 (s, 2H), 2.78 (q, J=7.4 Hz, 2H), 2.50 (s, 3H), 2.48 (hidden, 3H), 1.23 (t, J=7.4 Hz, 3H).

Example 204: 2-Ethyl-5, 7-dimethyl-3-((5'-phenoxy-2'-(1H-tetrazol-5-yl)-[1, 1'-biphenyl]-4-yl)methyl)-3H-imidazo[4,5-b]pyridine To a mixture of 4'-((2-ethyl-5,7-dimethyl-3H-imidazo[4,5-b]pyridin-3-yl)methyl)-5-phenoxy-[1,1'-biphenyl]-2-carbonitrile (0.012 g, 0.026 mmol), TMS-N$_3$ (0.037 mL, 0.262 mmol) and dibutyltin oxide (0.013 g, 0.052 mmol) was added toluene (2 mL). The vial was briefly purged with N$_2$ and then it was sealed and the mixture was stirred at 120° C. (block temperature) for 16 h. The cooled mixture was evaporated and the residual gum was taken up in DMF (acidified with a 10 drops of AcOH) and filtered using a 0.45 μm syringe filter. The filtrate was submitted to preparative LC (Method D) and the product-containing fractions were combined and evaporated to give a white solid. This material was lyophilized from ACN-H$_2$O to give 2-ethyl-5,7-dimethyl-3-((5'-phenoxy-2'-(1H-tetrazol-5-yl)-[1,1'-biphenyl]-4-yl)methyl)-3H-imidazo[4,5-b]pyridine (0.005 g, 38.1% yield) as a white solid.

LC-MS (Method J): 1.547 min, [M+H]$^+$=502.1; $^1$H NMR (400 MHz, DMSO-d$_6$) δ ppm 7.63 (d, J=8.6 Hz, 1H), 7.43 (t, J=8.6 Hz, 2H), 7.20 (t, J=7.4 Hz, 1H), 7.14 (d, J=7.4 Hz, 2H), 7.09 (dd, J=2.3, 8.6 Hz, 1H), 7.03 (d, J=2.7 Hz, 1H), 7.01 (s, 4H), 6.92 (s, 1H), 5.41 (s, 2H), 2.72 (q, J=7.4 Hz, 2H), 2.48 (hidden, 6H), 1.19 (t, J=7.4 Hz, 3H).

Example 205: 2-Ethyl-3-((5'-(2-fluorophenoxy)-2'-(1H-tetrazol-5-yl)-[1,1'-biphenyl]-4-yl)methyl)-5,7-dimethyl-3H-imidazo[4,5-b]pyridine (Ex: 205)

Intermediate 205a: 4'-((2-Ethyl-5,7-dimethyl-3H-imidazo[4,5-b]pyridin-3-yl)methyl)-5-fluoro-[1,1'-biphenyl]-2-carbonitrile

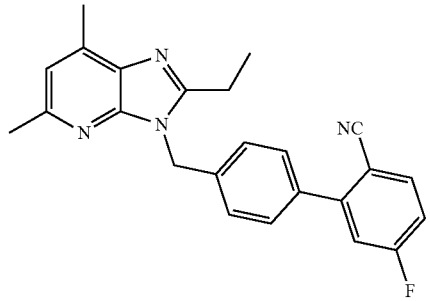

(205a)

A mixture of 2-ethyl-5,7-dimethyl-3-(4-(4,4,5,5-tetramethyl-1,3,2-dioxaborolan-2-yl)benzyl)-3H-imidazo[4,5-b]pyridine (001d, 0.262 g, 0.670 mmol), 2-bromo-4-fluorobenzonitrile (0.147 g, 0.736 mmol) and 2 M Na$_2$CO$_3$ (0.837 mL, 1.674 mmol) in toluene-ethanol (9:1, 10 mL) was purged with a stream of N$_2$ for 5 min in a sealable vial. To this mixture was added Pd(Ph$_3$P)$_4$ (0.077 g, 0.067 mmol), the vial was sealed and the mixture was stirred at 95° C. (block temperature) for 2 h. The cooled mixture was diluted with EtOAc and the organic phase was separated, dried (Na$_2$SO$_4$) and evaporated to give a pale yellow gum. This material was purified by flash chromatography (ISCO/0-100% EtOAc-DCM) to give 4'-((2-ethyl-5,7-dimethyl-3H-imidazo[4,5-b]pyridin-3-yl)methyl)-5-fluoro-[1,1'-biphenyl]-2-carbonitrile (0.174 g, 67.6% yield) as a colourless gum which solidified on standing in vacuo to give a waxy solid. This material was used as such in the next step.

LC-MS (Method J): 1.331 min, [M+H]$^+$=385.1; $^1$H NMR (400 MHz, DMSO-d$_6$) δ ppm 8.03 (dd, J=5.5, 8.6 Hz, 1H), 7.55 (d, J=8.2 Hz, 2H), 7.50 (dd, J=2.7, 9.8 Hz, 1H), 7.43 (dt, J=2.7, 8.6 Hz, 1H), 7.25 (d, J=8.2 Hz, 2H), 6.94 (s, 1H), 5.53 (s, 2H), 2.80 (q, J=7.4 Hz, 2H), 2.50 (s, 3H), 2.49 (s, 3H), 1.23 (t, J=7.4 Hz, 3H).

Intermediate 205b: 4'-((2-Ethyl-5, 7-dimethyl-3H-imidazo[4, 5-b]pyridin-3-yl)methyl)-5-(2-fluorophenoxy)-[1, 1'-biphenyl]-2-carbonitrile

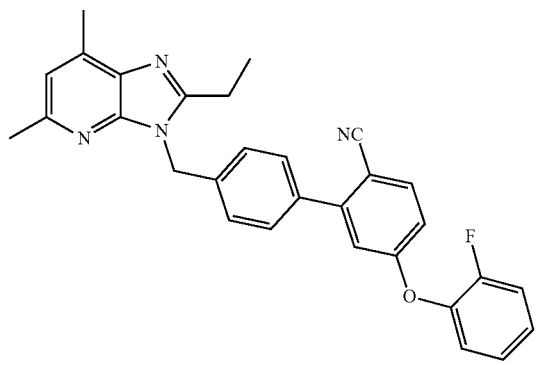

(205b)

To a solution of 4'-((2-ethyl-5,7-dimethyl-3H-imidazo[4,5-b]pyridin-3-yl)methyl)-5-fluoro-[1,1'-biphenyl]-2-carbonitrile (0.025 g, 0.065 mmol) and 2-fluorophenol (8.02 mg, 0.072 mmol) in DMF (1 mL) was added potassium carbonate (10.78 mg, 0.078 mmol) and the resulting mixture was stirred at 90° C. (block temperature) in a sealed vial for 16 h.

The cooled mixture was filtered through a small plug of cotton wool to remove the potassium salts and the residue was washed with a little DMF. The filtrate was evaporated to give a pale purple gum which was purified by flash chromatography (ISCO/0-100% EtOAc-DCM) to give a colourless gum. This material was lyophilized from ACN-H₂O to give 4'-((2-ethyl-5,7-dimethyl-3H-imidazo[4,5-b]pyridin-3-yl)methyl)-5-(2-fluorophenoxy)-[1,1'-biphenyl]-2-carbonitrile (0.026 g, 84% yield) as a white solid which was used as such in the next step. LC-MS (Method J): 1.439 min, [M+H]⁺=477.1; ¹H NMR (400 MHz, DMSO-d₆) δ ppm 7.91 (d, J=8.6 Hz, 1H), 7.50 (d, J=8.2 Hz, 2H), 7.45-7.26 (m, 4H), 7.22 (d, J=8.2 Hz, 2H), 7.11 (d, J=2.7 Hz, 1H), 7.01 (dd, J=2.3, 8.6 Hz, 1H), 6.94 (s, 1H), 5.51 (s, 2H), 2.79 (q, J=7.4 Hz, 2H), 2.50 (s, 3H), 2.48 (hidden, 3H), 1.23 (t, J=7.4 Hz, 3H).

Example 205: 2-Ethyl-3-((5'-(2-fluorophenoxy)-2'-(1H-tetrazol-5-yl)-[1,1'-biphenyl-4-yl)methyl)-5,7-dimethyl-3H-imidazo[4,5-b]pyridine To a sealable vial containing 4'-((2-ethyl-5,7-dimethyl-3H-imidazo[4,5-b]pyridin-3-yl)methyl)-5-(2-fluorophenoxy)-[1,1'-biphenyl]-2-carbonitrile (0.012 g, 0.025 mmol) and dibutyltin oxide (0.013 g, 0.050 mmol) in toluene (2 mL) was added TMS-N₃ (0.033 mL, 0.252 mmol). The vial was then sealed and the mixture were stirred at 100° C. (block temperature) for 18 h. Another portion of dibutyltin oxide (0.013 g, 0.050 mmol) and TMS-N₃ (0.033 mL, 0.252 mmol) was added and the mixture was heated at 120° C. for an additional 18 h. The cooled mixture was evaporated and the residue was taken up in DMF (1.8 mL, acidified with 10 drops of AcOH) and submitted to purification by preparative LC (Method D). The product-containing fractions were combined and evaporated to give a pale yellow-brown glass. This material was lyophilized from ACN-H₂O to give 2-ethyl-3-((5'-(2-fluorophenoxy)-2'-(1H-tetrazol-5-yl)-[1,1'-biphenyl]-4-yl)methyl)-5,7-dimethyl-3H-imidazo[4,5-b]pyridine (0.013 g, 99% yield) as a beige solid. LC-MS (Method J): 1.341 min, [M+H]⁴ ⁻² 520.1; ¹H NMR (400 MHz, DMSO-d₆) δ ppm 7.62 (d, J=8.6 Hz, 1H), 7.44-7.31 (m, 2H), 7.27 (m, 2H), 7.07-7.02 (m, 2H), 7.01 (s, 4H), 6.92 (s, 1H), 5.41 (s, 2H), 2.72 (q, J=7.4 Hz, 2H), 2.48 (hidden, 6H) 1.19 (t, J=7.4 Hz, 3H).

The following examples have been similarly prepared from 4'-((2-ethyl-5,7-dimethyl-3H-imidazo[4,5-b]pyridin-3-yl)methyl)-5-fluoro-[1,1'-biphenyl]-2-carbonitrile (Intermediate 205a) as described above for Example 205. Two analytical LC injections were used to determine the final purity. The retention time of one of them is reported for each compound and is referred as Method J.

| Ex | Structure | MW | LC-MS m/z [M + H]⁺; RT (Method) | ¹H NMR (400 MHz, DMSO-d₆) δ ppm |
|---|---|---|---|---|
| 206 | 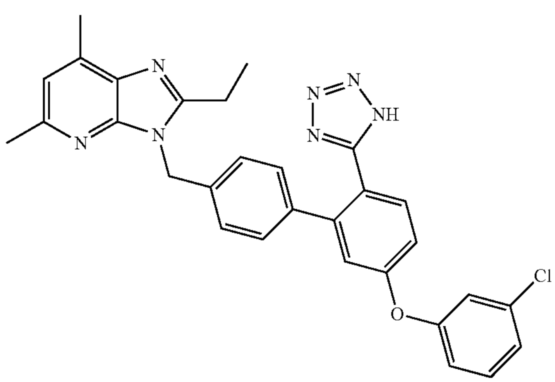 [SMILES: CCc1nc2c(C)cc(C)nc2n1Cc1ccc(-c2cc(Oc3cccc(Cl)c3)ccc2-c2nnn[nH]2)cc1] | 536.03 | 536.1; 1.426 min (Method J) | 7.64 (d, J = 8.2 Hz, 1H), 7.43 (t, J = 8.2 Hz, 1H), 7.26-7.21 (m, 2H), 7.14 (dd, J = 2.3, 8.2 Hz, 1H), 7.11-7.08 (m, 2H), 7.01 (m, 4H), 6.92 (s, 1H), 5.41 (s, 2H), 2.73 (q, J = 7.4 Hz, 2H), 2.48 (hidden, 6H), 1.19 (t, J = 7.4 Hz, 3H). |
| 207 | 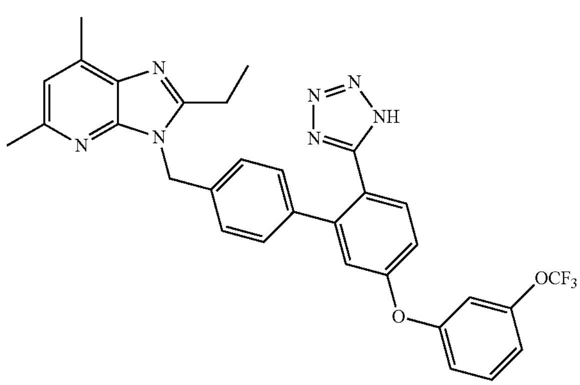 [SMILES: CCc1nc2c(C)cc(C)nc2n1Cc1ccc(-c2cc(Oc3cccc(OC(F)(F)F)c3)ccc2-c2nnn[nH]2)cc1] | 585.58 | 586.1; 1.438 min (Method J) | 7.66 (d, J = 8.2 Hz, 1H), 7.53 (t, J = 8.2 Hz, 1H), 7.19-7.12 (m, 5H), 7.01 (m, 4H), 6.92 (s, 1H), 5.41 (s, 2H), 2.72 (q, J = 7.4 Hz, 2H), 2.48 (hidden, 6H), 1.19 (t, J = 7.4 Hz, 3H). |

| Ex | Structure | MW | LC-MS m/z [M + H]+; RT (Method) | 1H NMR (400 MHz, DMSO-d6) δ ppm |
|---|---|---|---|---|
| 208 | 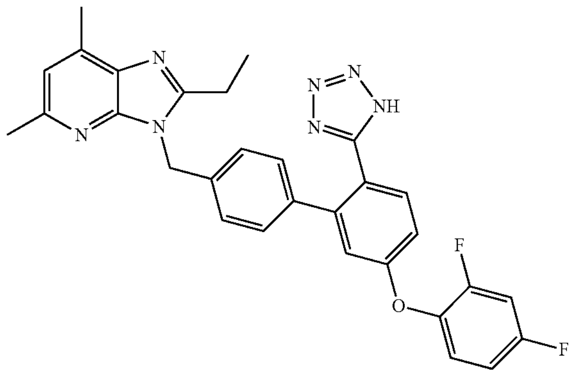 [SMILES: CCc1nc2c(C)cc(C)nc2n1Cc1ccc(-c2cc(Oc3ccc(F)cc3F)ccc2-c2nnn[nH]2)cc1] | 537.56 | 538.2; 1.387 min (Method J) | 7.58 (d, J = 8.6 Hz, 1H), 7.49 (ddd, J = 3.1, 9.0, 11.7 Hz, 1H), 7.41 (dt, J = 5.5, 9.0 Hz, 1H), 7.14 (m, 1H), 7.02 (m, 1H), 7.00 (m, 5H), 6.92 (s, 1H), 5.40 (s, 2H), 2.73 (q, J = 7.4 Hz, 2H), 2.48 (hidden, 6H), 1.20 (t, J = 7.4 Hz, 1H). |

Example 209: 3-((5'-(Cyclohexyloxy)-2'-(1H-tetrazol-5-yl)-[1,1,1'-biphenyll-4-yl)methyl)-2-ethyl-5,7-dimethyl-3H-imidazo[4,5-b]pyridine (Ex: 209)

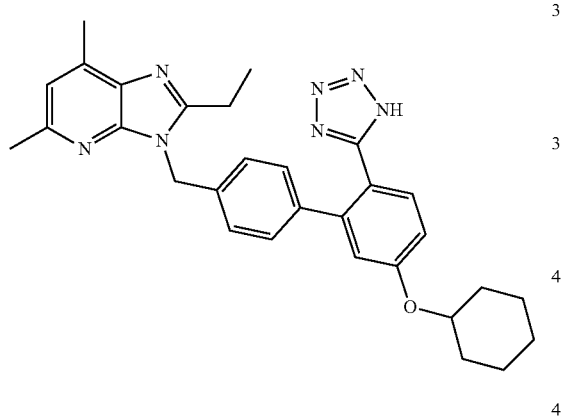

Intermediate 209a: 2-Bromo-4-(cyclohexyloxy)benzonitrile (209a)

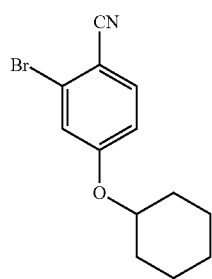

A mixture of 2-bromo-4-fluorobenzonitrile (0.400 g, 2.000 mmol), cyclohexanol (0.458 mL, 4.400 mmol) and potassium carbonate (0.664 g, 4.800 mmol) in DMF (10 mL) was reacted according to the method described for the preparation of Intermediate 204a. This afforded 2-bromo-4-(cyclohexyloxy)benzonitrile (0.042 g, 8.0% yield)) as a white solid which was used as such in the next step. LC-MS (Method J): 1.396 min, [M+H]+=no ion observed; 1H NMR (400 MHz, DMSO-d6) δ ppm 7.80 (d, J=8.6 Hz, 1H), 7.43 (d, J=2.3 Hz, 1H), 7.11 (dd, J=2.3, 8.6 Hz, 1H), 4.54 (m, 1H), 1.88 (m, 2H), 1.69 (m, 2H), 1.50 (m, 1H), 1.46-1.33 (m, 4H), 1.25 (m, 1H).

Intermediate 209b: 5-(Cyclohexyloxy)-4'-((2-ethyl-5,7-dimethyl-3H-imidazo[4,5-b]pyridin-3-yl)methyl)-[1,1'-biphenyl]-2-carbonitrile (209b)

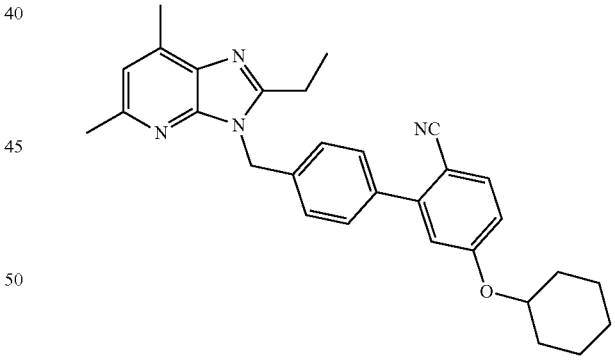

A mixture of 2-ethyl-5,7-dimethyl-3-(4-(4,4,5,5-tetramethyl-1,3,2-dioxaborolan-2-yl)benzyl)-3H-imidazo[4,5-b]pyridine (001d, 0.056 g, 0.143 mmol), 2-bromo-4-(cyclohexyloxy)-benzonitrile (0.040 g, 0.143 mmol) was reacted according to the method described for the preparation of Intermediate 204b. This afforded 5-(cyclohexyloxy)-4'-((2-ethyl-5,7-dimethyl-3H-imidazo[4,5-b]pyridin-3-yl)methyl)-[1,1'-biphenyl]-2-carbonitrile (0.044 g, 66.2% yield) as a colourless gum. This gum was lyophilized from ACN-H2O to give a white solid which was used as such in the next step. LC-MS (Method J): 1.577 min, [M+H]+=465.1; 1H NMR (400 MHz, DMSO-d6) δ ppm 7.78 (d, J=8.6 Hz, 1H), 7.51 (d, J=8.2 Hz, 2H), 7.22 (d, J=8.2 Hz, 2H), 7.08 (dd, J=2.3, 8.6 Hz, 1H), 7.03 (d, J=2.7 Hz, 1H), 6.94 (s, 1H), 5.52 (s, 2H), 4.54 (m, 1H), 2.81 (q, J=7.4 Hz, 2H), 2.50 (s, 3H), 2.48 (hidden, 3H), 1.92 (m, 2H), 1.66 (m, 2H), 1.49 (m, 2H), 1.44-1.32 (m, 4H), 1.24 (t, J=7.4 Hz, 1H).

Example 209: 3-((5'-(Cyclohexyloxy)-2'-(1H-tetrazol-5-yl)-[1,1'-biphenyl]-4-yl)methyl)-2-ethyl-5,7-dimethyl-3H-imidazo[4,5-b]pyridine The title compound was prepared from 5-(cyclohexyloxy)-4'-((2-ethyl-5,7-dimethyl-3H-imidazo[4,5-b]pyridin-3-yl)methyl)-[1,1'-biphenyl]-2-carbonitrile (0.014 g, 0.030 mmol), according to the procedure described for the preparation of Example 204, to give 3-((5'-(cyclohexyloxy)-2'-(1H-tetrazol-5-yl)-[1,1'-biphenyl]-4-yl)methyl)-2-ethyl-5,7-dimethyl-3H-imidazo[4,5-b]pyridine (0.009 g, 58.8% yield) as an off-white solid. LC-MS (Method J): 1.426 min, [M+H]$^+$=508.2; $^1$H NMR (400 MHz, DMSO-d$_6$) δ ppm 7.50 (d, J=8.6 Hz, 1H), 7.08 (dd, J=2.3, 8.6 Hz, 1H), 7.02 (m, 4H), 6.94 (d, J=2.3 Hz, 1H), 6.93 (s, 1H), 5.42 (s, 2H), 4.49 (m, 1H), 2.74 (q, J=7.4 Hz, 2H), 2.48 (hidden, 6H), 1.92 (m, 2H), 1.68 (m, 2H), 1.53-1.32 (m, 6H), 1.21 (t, J=7.4 Hz, 1H).

Example 210: (4'-((2-Ethyl-5,7-dimethyl-3H-imidazo[4,5-b]pyridin-3-yl)methyl)-6-(1H-tetrazol-5-yl)-[1,1'-biphenyl]-3-yl)(phenyl)methanone

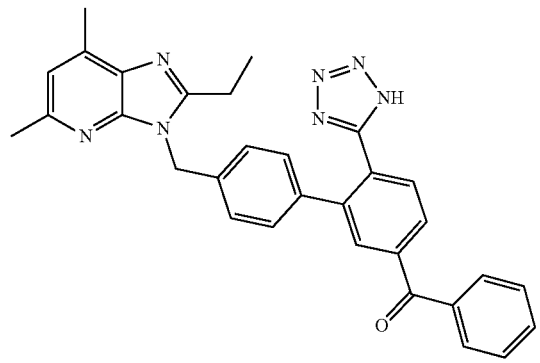

(Ex: 210)

Intermediate 210a: 4-Benzoyl-2-bromobenzonitrile

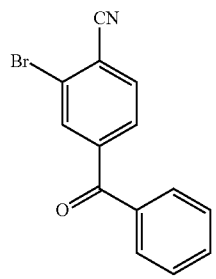

(210a)

To a vial containing 4-benzoylbenzonitrile (0.181 g, 0.873 mmol; prepared according to the procedure described by L. J. Goopen and K. Ghosh, Angew. Chem. Int. Ed. 2001, 40, 3458), NBS (0.171 g, 0.961 mmol), β-toluenesulfonic acid monohydrate (0.083 g, 0.437 mmol) and palladium (II) acetate (0.020 g, 0.087 mmol), was added DCE (10 mL). The vial was briefly purged with N$_2$ and then it was sealed and the mixture was stirred at 80° C. (block temperature) overnight. The cooled mixture was evaporated and the residue was taken up in a minimum volume of DCM and then adsorbed on a silica gel pre-column. Flash chromatography (ISCO/0-50% EtOAc-hexane) gave 4-benzoyl-2-bromobenzonitrile (0.138 g, 55.2% yield) as a white crystalline solid. LC-MS (Method J): 1.272 min, [M+H]$^+$=no ion observed; $^1$H NMR (400 MHz, DMSO-d$_6$) δ ppm 8.11 (d, J=7.8 Hz, 1H), 8.09 (d, J=1.2 Hz, 1H), 7.81 (dd, J=1.6, 7.8 Hz, 1H), 7.76 (d, J=7.4 Hz, 2H), 7.72 (t, J=7.4 Hz, 1H), 7.58 (t, J=7.6 Hz, 2H).

Intermediate 210b: 5-Benzoyl-4'-((2-ethyl-5,7-dimethyl-3H-imidazo[4,5-b]pyridin-3-yl)methyl)-[1,1,1'-biphenyl]-2-carbonitrile

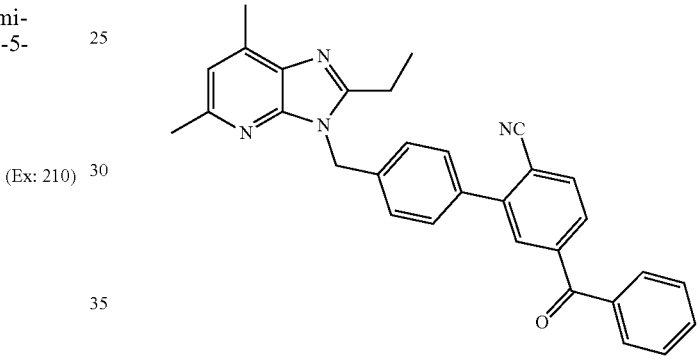

(210b)

A mixture of 2-ethyl-5,7-dimethyl-3-(4-(4,4,5,5-tetramethyl-1,3,2-dioxaborolan-2-yl)benzyl)-3H-imidazo[4,5-b]pyridine (0.079 g, 0.202 mmol) and 4-benzoyl-2-bromobenzonitrile (0.072 g, 0.253 mmol) was reacted according to the method described for the preparation of Intermediate 204b. This afforded 5-benzoyl-4'-((2-ethyl-5,7-dimethyl-3H-imidazo[4,5-b]pyridin-3-yl)methyl)-[1,1'-biphenyl]-2-carbonitrile (0.077 g, 81% yield) as a foam which was used as such in the next step. LC-MS (Method J): 1.409 min, [M+H]$^+$= 471.1; $^1$H NMR (400 MHz, CDCl$_3$) δ ppm 7.85-7.90 (m, 2H), 7.78-7.83 (m, 3H), 7.62-7.72 (m, 2H), 7.45-7.57 (m, 6H), 6.91 (s, 1H), 5.54 (s, 2H), 2.78-2.88 (m, 2H), 2.65 (s, 3H),) 2.59-2.62 (m, 3H), 1.35 (t, J=7.6 Hz, 3H).

Example 210: (4'-((2-Ethyl-5,7-dimethyl-3H-imidazo[4,5-b]pyridin-3-yl)methyl)-6-(1H-tetrazol-5-yl)-[1,1'-biphenyl]-3-yl)(phenyl)methanone The title compound was prepared from 5-benzoyl-4'-((2-ethyl-5,7-dimethyl-3H-imidazo[4,5-b]pyridin-3-yl)methyl)-[1,1'-biphenyl]-2-carbonitrile (0.031 g, 0.065 mmol), according to the procedure described for the preparation of Example 204, to give (4'-((2-ethyl-5,7-dimethyl-3H-imidazo[4,5-b]pyridin-3-yl)methyl)-6-(1H-tetrazol-5-yl)-[1,1'-biphenyl]-3-yl)(phenyl)-methanone (0.022 g, 62% yield) as a white solid. LC-MS (Method J): 1.366 min, [M+H]$^+$= 514.2; $^1$H NMR (400 MHz, CDCl$_3$) δ ppm 8.19 (d, J=7.8 Hz, 1H), 7.90 (dd, J=8.2, 1.6 Hz, 1H), 7.81-7.87 (m, 3H), 7.60-7.67 (m, 1H), 7.49-7.55 (m, 2H), 7.18 (m, J=8.2 Hz, 2H), 7.08 (m, J=8.2 Hz, 2H), 6.91 (s, 1H), 5.46 (s, 2H), 2.70 (q, J=7.4 Hz, 2H), 2.57 (s, 3H), 2.51 (s, 3H), 1.20 (t, J=7.6 Hz, 3H).

Example 211: 2-Ethyl-5,7-dimethyl-3-((3'-methyl-5'-phenoxy-2'-(1H-tetrazol-5-yl)-[1,1'-biphenyl]-4-yl)methyl)-3H-imidazo[4,5-b]pyridine

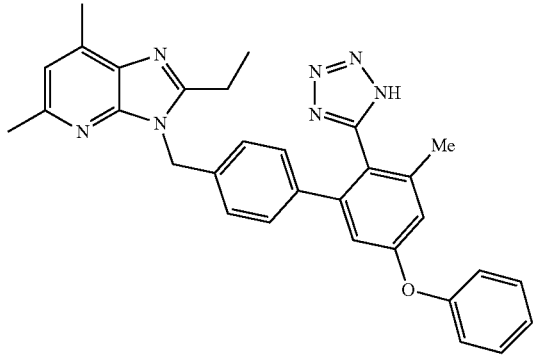

(Ex: 211)

Intermediate 211a: 4'-((2-Ethyl-5,7-dimethyl-3H-imidazo[4,5-b]pyridin-3-yl)methyl)-5-fluoro-3-methyl-[1,1'-biphenyl]-2-carbonitrile

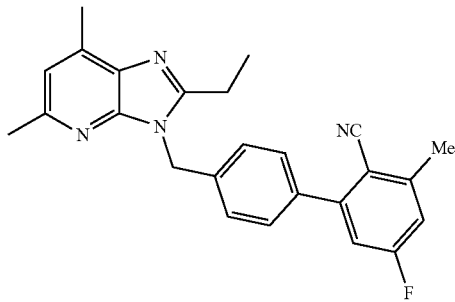

(Ex: 211a)

The title compound was prepared from 2-ethyl-5,7-dimethyl-3-(4-(4,4,5,5-tetramethyl-1,3,2-dioxaborolan-2-yl)benzyl)-3H-imidazo[4,5-b]pyridine (0.300 g, 0.767 mmol) and 2-bromo-4-fluoro-6-methylbenzonitrile (0.180 g, 0.843 mmol), according to the method described for the synthesis of Intermediate 205a, to give 4'-((2-ethyl-5,7-dimethyl-3H-imidazo[4,5-b]pyridin-3-yl)methyl)-5-fluoro-3-methyl-[1,1'-biphenyl]-2-carbonitrile (0.220 g, 72.0% yield) as a colourless gum. This material was lyophilized from ACN-H$_2$O to give a white solid which was used as such in the next step. LC-MS (Method J): 1.435 min, [M+H]$^+$=399.2; $^1$H NMR (400 MHz, DMSO-d$_6$) δ ppm 7.52 (d, J=8.2 Hz, 2H), 7.39 (dd, J=2.3, 9.4 Hz, 1H), 7.28 (dd, J=2.3, 9.4 Hz, 1H), 7.23 (d, J=8.2 Hz, 2H), 6.94 (s, 1H), 5.53 (s, 2H), 2.79 (q, J=7.4 Hz, 2H), 2.53 (s, 3H), 2.50 (s, 3H), 2.49 (s, 3H), 1.23 (t, J=7.4 Hz, 3H).

Intermediate 211b: 4'-((2-Ethyl-5,7-dimethyl-3H-imidazo[4,5-b]pyridin-3-yl)methyl)-3-methyl-5-phenoxy-[1,1'-biphenyl]-2-carbonitrile

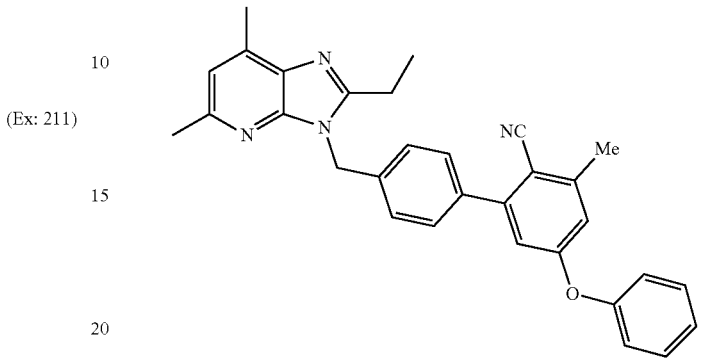

(211b)

The title compound was prepared from 4'-((2-ethyl-5,7-dimethyl-3H-imidazo[4,5-b]pyridin-3-yl)methyl)-5-fluoro-3-methyl-[1,1'-biphenyl]-2-carbonitrile (0.030 g, 0.075 mmol) and phenol (7.79 mg, 0.083 mmol), according to the method described for the synthesis of Intermediate 205b, to give 4'-((2-ethyl-5,7-dimethyl-3H-imidazo[4,5-b]pyridin-3-yl)methyl)-3-methyl-5-phenoxy-[1,1'-biphenyl]-2-carbonitrile (0.031 g, 87% yield) as a colourless gum. This material was lyophilized from ACN-H$_2$O to give a white solid which was used as such in the next step. LC-MS (Method J): 1.571 min, [M+H]$^+$=473.2; $^1$H NMR (400 MHz, DMSO-d$_6$) δ ppm 7.46 (d, J=8.2 Hz, 2H), 7.44 (m, 2H), 7.25 (d, J=7.4 Hz, 1H), 7.20 (d, J=8.2 Hz, 2H), 7.14 (dd, J=1.2, 8.6 Hz, 2H), 6.99 (d, J=2.0 Hz, 1H), 6.94 (s, 1H), 6.85 (d, J=2.3 Hz, 1H), 5.50 (s, 2H), 2.78 (q, J=7.4 Hz, 2H), 2.48 (hidden, 9H), 1.22 (t, J=7.4 Hz, 3H).

Example 211: 2-Ethyl-5,7-dimethyl-3-((3'-methyl-5'-phenoxy-2'-(1H-tetrazol-5-yl)-[1,1'-biphenyl]-4-yl)methyl)-3H-imidazo[4,5-b]pyridine The title compound was prepared from 4'-((2-ethyl-5,7-dimethyl-3H-imidazo[4,5-b]pyridin-3-yl)methyl)-3-methyl-5-phenoxy-[1,1'-biphenyl]-2-carbonitrile (0.016 g, 0.034 mmol), according to the procedure described for the preparation of Example 204, to give 2-ethyl-5,7-dimethyl-3-((3'-methyl-5'-phenoxy-2'-(1H-tetrazol-5-yl)-[1,1'-biphenyl]-4-yl)methyl)-3H-imidazo[4,5-b]pyridine (0.012 g, 68.7% yield) as a white solid. LC-MS (Method J): 1.398 min, [M+H]$^+$=516.2; $^1$H NMR (400 MHz, DMSO-d$_6$) δ ppm 7.42 (dd, J=7.8, 8.6 Hz, 2H), 7.18 (t, J=7.2 Hz, 1H), 7.12 (d, J=7.4 Hz, 2H), 7.01 (d, J=2.3 Hz, 1H), 6.93 (s, 3H), 6.91 (s, 1H), 6.84 (d, J=2.3 Hz, 1H), 5.36 (s, 2H), 2.67 (q, J=7.4 Hz, 2H), 2.48 (hidden, 3H), 2.47 (s, 3H), 2.00 (s, 3H), 1.14 (t, J=7.4 Hz, 3H).

Example 212: 3-((5'-(Benzyloxy)-2'-(1H-tetrazol-5-yl)-[1,1'-biphenyl]-4-yl)methyl)-2-ethyl-5,7-dimethyl-3H-imidazo[4,5-b]pyridine

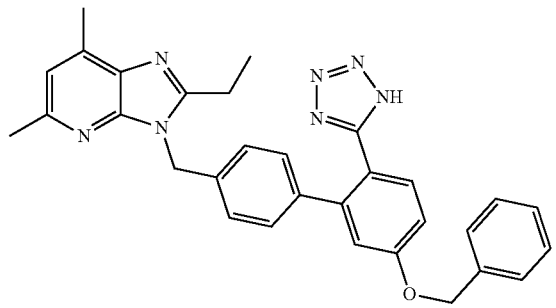

(Ex: 212)

Intermediate 212a:
4-(Benzyloxy)-2-bromobenzonitrile

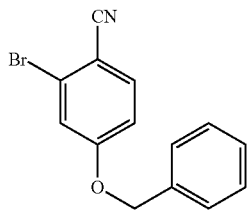

(212a)

To a solution of benzyl alcohol (0.228 mL, 2.200 mmol) in dry DMF (10 mL) was added 60% sodium hydride (0.096 g, 2.400 mmol) and the resulting mixture was stirred at RT under N$_2$ for 30 min. To the resulting clear solution was added 2-bromo-4-fluorobenzonitrile (0.400 g, 2.000 mmol) all at once and stirring was continued at RT for 3 h. The reaction mixture was then quenched with saturated aqueous NH$_4$Cl (2 mL) and then it was poured into ice-saturated aqueous NH$_4$Cl and extracted with EtOAc (×2). The combined organic phase was washed (H$_2$O, brine), dried (Na$_2$SO$_4$) and evaporated to give the crude product as an oil which solidified on standing in vacuo. This material was purified by flash chromatography (ISCO/0-50% EtOAc-hexane) to give 4-(benzyloxy)-2-bromobenzonitrile (0.394 g, 68.4% yield) as an off-white crystalline solid which was used as such in the next step. LC-MS (Method J): 1.349 min, [M+H]$^+$=no ion observed; $^1$H NMR (400 MHz, DMSO-d$_6$) δ ppm 7.85 (d, J=8.6 Hz, 1H), 7.54 (d, J=2.3 Hz, 1H), 7.45-7.32 (m, 5H), 7.19 (dd, J=2.3, 8.6 Hz, 1H), 5.22 (s, 2H).

Intermediate 212b: 5-(Benzyloxy)-4'-((2-ethyl-5,7-dimethyl-3H-imidazo[4,5-b]pyridin-3-yl)methyl)-[1,1'-biphenyl]-2-carbonitrile

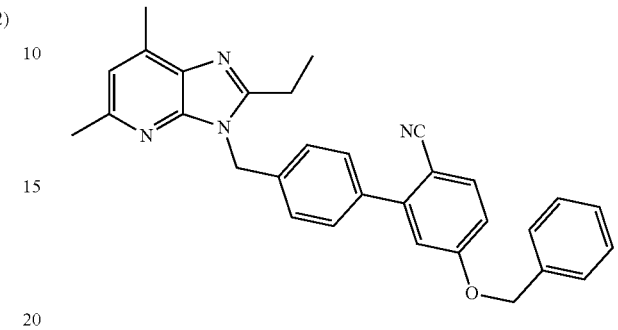

(212b)

A mixture of 2-ethyl-5,7-dimethyl-3-(4-(4,4,5,5-tetramethyl-1,3,2-dioxaborolan-2-yl)benzyl)-3H-imidazo[4,5-b]pyridine (0.056 g, 0.143 mmol) and 4-(benzyloxy)-2-bromobenzonitrile (0.049 g, 0.172 mmol) was reacted according to the method described for the preparation of Intermediate 204b. This afforded 5-(benzyloxy)-4'-((2-ethyl-5,7-dimethyl-3H-imidazo[4,5-b]pyridin-3-yl)methyl)-[1,1'-biphenyl]-2-carbonitrile (0.031 g, 45.8% yield) as a colourless gum which was used as such in the next step. LC-MS (Method J): 1.502 min, [M+H]$^+$=473.2; $^1$H NMR (400 MHz, DMSO-d$_6$) δ ppm 7.83 (d, J=9.0 Hz, 1H), 7.52 (d, J=8.2 Hz, 2H), 7.43 (d, J=7.0 Hz, 2H), 7.38 (t, J=7.2 Hz, 2H), 7.35-7.30 (m, 1H), 7.23 (d, J=8.6 Hz, 2H), 7.17 (s, 1H), 7.15 (m, 1H), 6.94 (s, 1H), 5.52 (s, 2H), 5.22 (s, 2H), 2.80 (q, J=7.4 Hz, 2H), 2.50 (s, 3H), 2.48 (hidden, 3H), 1.24 (t, J=7.4 Hz, 3H).

Example 212: 3-((5'-(Benzyloxy)-2'-(1H-tetrazol-5-yl)-[1,1'-biphenyl]-4-yl)methyl)-2-ethyl-5,7-dimethyl-3H-imidazo[4,5-bipyridine The title compound was prepared from 5-(benzyloxy)-4'-((2-ethyl-5,7-dimethyl-3H-imidazo[4,5-b]pyridin-3-yl)methyl)-[1,1'-biphenyl]-2-carbonitrile (0.013 g, 0.028 mmol), according to the procedure described for the preparation of Example 204, to give 3-((5'-(benzyloxy)-2'-(1H-tetrazol-5-yl)-[1,1'-biphenyl]-4-yl)methyl)-2-ethyl-5,7-dimethyl-3H-imidazo[4,5-b]pyridine (0.014 g, 99% yield) as a white solid. LC-MS (Method J): 1.365 min, [M+H]$^+$=516.2; $^1$H NMR (400 MHz, DMSO-d$_6$) δ ppm 7.54 (d, J=8.6 Hz, 1H), 7.45 (d, J=7.0 Hz, 2H), 7.38 (t, J=7.0 Hz, 2H), 7.32 (m, 1H), 7.16 (dd, J=2.3, 8.2 Hz, 1H), 7.09 (d, J=2.3 Hz, 1H), 7.02 (s, 4H), 6.93 (s, 1H), 5.42 (s, 2H), 5.21 (s, 2H), 2.74 (q, J=7.4 Hz, 2H), 2.48 (hidden, 6H), 1.20 (t, J=7.4 Hz, 3H).

Example 213: 4'-((2-Ethyl-5,7-dimethyl-3H-imidazo[4,5-b]pyridin-3-yl)methyl)-5-phenoxy-[1,1'-biphenyl]-2-carboxylic acid

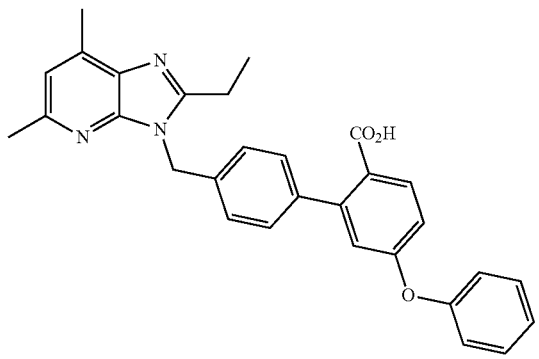

(Ex: 213)

Intermediate 213a: Methyl 2-bromo-4-phenoxybenzoate

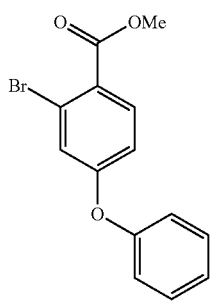

(213a)

To a solution of phenol (0.207 g, 2.200 mmol) in dry DMF (10 mL) was added 60% sodium hydride (0.096 g, 2.400 mmol) and the resulting mixture was stirred at RT under $N_2$ for 30 min. To the resulting clear solution was added methyl 2-bromo-4-fluorobenzoate (0.476 g, 2.000 mmol) all at once and stirring was continued at RT for 18 h. The reaction mixture was quenched with saturated aqueous $NH_4Cl$ (2 mL) and then it was poured into ice $H_2O$ and extracted with EtOAc (×2). The combined organic phase was dried ($Na_2SO_4$) and evaporated to give a colourless oil. This oil was purified by flash chromatography (ISCO/0-30% EtOAc-hexane) to give methyl 2-bromo-4-phenoxybenzoate (0.358 g, 58.3% yield) as a colourless oil which was used as such in the next step. LC-MS (Method J): 1.391 min, [M+H]$^+$=307.0; $^1$H NMR (400 MHz, DMSO-$d_6$) δ ppm 7.83 (d, J=8.6 Hz, 1H), 7.46 (dd, J=7.4, 8.6 Hz, 2H), 7.26 (m, 2H), 7.15 (dd, J=1.2, 9.0 Hz, 2H), 7.02 (dd, J=2.3, 8.6 Hz, 1H), 3.81 (s, 3H).

Intermediate 213b: Methyl 4'-((2-ethyl-5,7-dimethyl-3H-imidazo[4,5-b]pyridin-3-yl)methyl)-5-phenoxy-[1,1'-biphenyl]-2-carboxylate

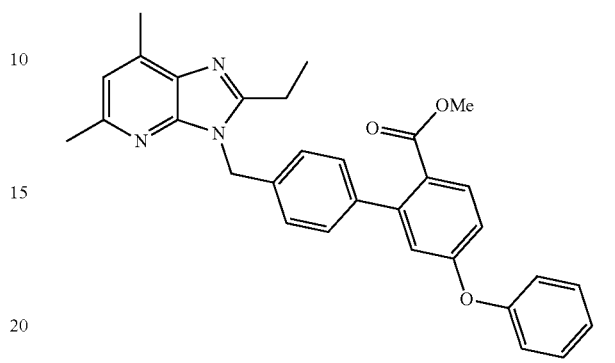

(213b)

A mixture of 2-ethyl-5,7-dimethyl-3-(4-(4,4,5,5-tetramethyl-1,3,2-dioxaborolan-2-yl)benzyl)-3H-imidazo[4,5-b]pyridine (001d, 0.060 g, 0.153 mmol), methyl 2-bromo-4-phenoxybenzoate (0.059 g, 0.192 mmol) and 2 M $Na_2CO_3$ (0.230 mL, 0.460 mmol) in toluene-methanol (9:1, 5 mL) was purged with a stream of $N_2$ for 5 min in a sealable vial. To this mixture was added Pd(Ph$_3$P)$_4$ (0.018 g, 0.015 mmol), the vial was sealed and the mixture was stirred at 95° C. (block temperature) for 16 h. The cooled mixture was diluted with EtOAc and the organic phase was separated, dried ($Na_2SO_4$) and evaporated to give a gum. This material was purified by flash chromatography (ISCO/0-100% EtOAc-DCM) to give the impure product as a colourless gum.

This gum was repurified by preparative LC (Method D) to give methyl 4'-((2-ethyl-5,7-dimethyl-3H-imidazo[4,5-b]pyridin-3-yl)methyl)-5-phenoxy-[1,1'-biphenyl]-2-carboxylate (0.020 g, 26.5% yield) as a gum. This gum was lyophilized from ACN-$H_2O$ to give a white solid which was used as such in the next step. LC-MS (Method J): 1.563 min, [M+H]$^+$=492.2; $^1$H NMR (400 MHz, DMSO-$d_6$) δ ppm 7.77 (d, J=8.6 Hz, 1H), 7.42 (dd, J=7.4, 8.2 Hz, 2H), 7.21 (d, J=8.6 Hz, 1H), 7.19 (d, J=8.2 Hz, 2H), 7.11 (t, J=8.2 Hz, 4H), 6.98 (dd, J=2.7, 8.6 Hz, 1H), 6.94 (s, 1H), 6.87 (d, J=2.3 Hz, 1H), 5.47 (s, 2H), 3.52 (s, 3H), 2.76 (q, J=7.4 Hz, 2H), 2.48 (hidden, 6H), 1.21 (t, J=7.4 Hz, 3H).

Example 213: 4'-((2-Ethyl-5,7-dimethyl-3H-imidazo[4,5-b]pyridin-3-yl)methyl)-5-phenoxy-[1,1'-biphenyl]-2-carboxylic acid To a solution of methyl 4'-((2-ethyl-5,7-dimethyl-3H-imidazo[4,5-b]pyridin-3-yl)methyl)-5-phenoxy-[1,1'-biphenyl]-2-carboxylate (0.010 g, 0.020 mmol) in THF (2 mL) was added a solution of LiOH monohydrate (1.742 mg, 0.041 mmol) in $H_2O$ (1 mL) and the resulting solution was stirred at RT for 18 h and then it was heated at 80° C. in a sealed vial for 2 days. The volatiles were then removed in vacuo, the residue was taken up in DMF (1.8 mL, acidified with 10 drops of AcOH) and the mixture was submitted to preparative LC purification (Method D). The product-containing fractions were combined and evaporated to give 4'-((2-ethyl-5,7-dimethyl-3H-imidazo[4,5-b]pyridin-3-yl)methyl)-5-phenoxy-[1,1'-biphenyl]-2-carboxylic acid (0.005 g, 51.5% yield) as a white solid. LC-MS (Method J): 1.408 min, [M+H]⁺=478.1; ¹H NMR (400 MHz, DMSO-d₆) δ ppm 12.56 (br s, 1H), 7.76 (d, J=8.6 Hz, 1H), 7.41 (dd, J=7.4, 8.6 Hz, 2H), 7.22 (d, J=8.6 Hz, 2H), 7.18 (d, J=7.4 Hz, 2H), 7.10 (t, J=8.2 Hz, 4H), 6.95 (dd, J=2.3, 8.6 Hz, 1H), 6.93 (s, 1H), 6.82 (d, J=2.3 Hz, 1H), 5.46 (s, 2H), 2.76 (q, J=7.4 Hz, 2H), 2.48 (hidden, 6H), 1.22 (t, J=7.4 Hz, 3H).

Example 214: 3-(4'-((2-Ethyl-5,7-dimethyl-3H-imidazo[4,5-b]pyridin-3-yl)methyl)-5-(2-fluorophenoxy)-[1,1'-biphenyl]-2-yl)-1,2,4-oxadiazol-5(4H)-one

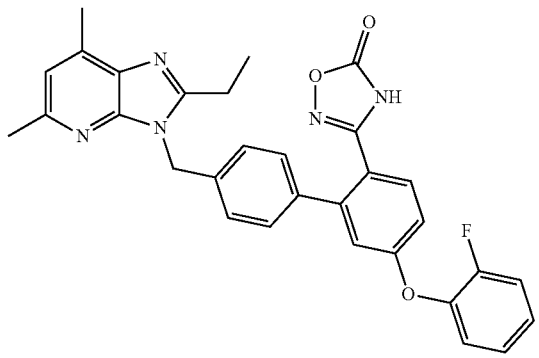

(Ex: 214)

Intermediate 214a: (Z)-4'-((2-Ethyl-5,7-dimethyl-3H-imidazo[4,5-b]pyridin-3-yl)methyl)-5-(2-fluorophenoxy)-N'-hydroxy-[1,1'-biphenyl]-2-carboximidamide

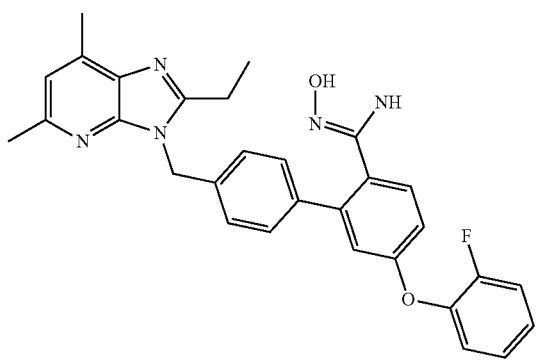

(214a)

To a sealable vial was added 4'-((2-ethyl-5,7-dimethyl-3H-imidazo[4,5-b]pyridin-3-yl)methyl)-5-(2-fluorophenoxy)-[1,1'-biphenyl]-2-carbonitrile (205b, 0.042 g, 0.088 mmol), I-butyl-3-methylimidazolium acetate (1.00 g, 5.04 mmol) and hydroxylamine hydrochloride (0.153 g, 2.203 mmol). The vial was sealed and the mixture were stirred at 50° C. (block temperature) for 16 h. The cooled mixture was diluted with DMF (1 mL) and then H₂O (0.5 mL) was added. The solution was acidified by the dropwise addition of TFA (0.5 mL) and the volume was adjusted with DMF to give 2×1.8 mL samples that were submitted to preparative LC purification (Method D). The product-containing fractions were combined and evaporated to give (Z)-4'-((2-ethyl-5,7-dimethyl-3H-imidazo[4,5-b]pyridin-3-yl)methyl)-5-(2-fluorophenoxy)-N'-hydroxy-[1,1'-biphenyl]-2-carboximidamide (0.032 g, 71.3% yield) as a gum. This material was used as such in the next step. LC-MS (Method J): 1.227 min, [M+H]⁺=510.2.

Example 214: 3-(4'-((2-Ethyl-5,7-dimethyl-3H-imidazo[4,5-b]pyridin-3-yl)methyl)-5-(2-fluorophenoxy)-[1,1'-biphenyl]-2-yl)-1,2,4-oxadiazol-5(4H)-one To a sealable vial was added (Z)-4'-((2-ethyl-5,7-dimethyl-3H-imidazo[4,5-b]pyridin-3-yl)methyl)-5-(2-fluorophenoxy)-N'-hydroxy-[1,1'-biphenyl]-2-carboximidamide (0.032 g, 0.063 mmol), N,N'-carbonyldiimidazole (0.072 g, 0.445 mmol), DBU (0.067 mL, 0.445 mmol) and dry THF (3 mL). The vial was then sealed and the mixture was stirred at 50° C. (block temperature) for 2 h. The cooled mixture was evaporated and the residue was taken up in DMF (2×1.8 mL, acidified with 20 drops of AcOH) and submitted to preparative LC purification (Method D). The product-containing fractions were combined and evaporated to give 3-(4'-((2-ethyl-5,7-dimethyl-3H-imidazo[4,5-b]pyridin-3-yl)methyl)-5-(2-fluorophenoxy)-[1,1'-biphenyl]-2-yl)-1,2,4-oxadiazol-5(4H)-one (0.023 g, 48.3% yield) as a white solid. LC-MS (Method J): 1.391 min, [M+H]⁺=536.3; ¹H NMR (400 MHz, DMSO-d₆) δ ppm 12.29 (br s, 1H), 7.62 (d, J=8.2 Hz, 1H), 7.42 (m, 1H), 7.36-7.29 (m, 2H), 7.27 (dd, J=2.0, 7.4 Hz, 1H), 7.23 (d, J=8.2 Hz, 2H), 7.13 (d, J=8.2 Hz, 2H), 7.03 (dd, J=2.7, 8.2 Hz, 1H), 7.01 (m, 1H), 6.93 (s, 1H), 5.47 (s, 2H), 2.75 (q, J=7.4 Hz, 2H), 2.48 (hidden, 6H), 1.19 (t, J=7.4 Hz, 3H).

Example 215: 3-((5'-(1H-Indazol-1-yl)-2'-(1H-tetrazol-5-yl)-[1,1'-biphenyl]-4-yl)methyl)-2-ethyl-5,7-dimethyl-3H-imidazo[4,5-b]pyridine

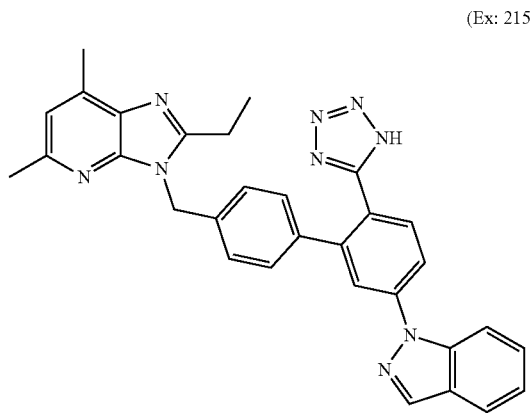

(Ex: 215)

Intermediate 215a and 215b: 2-Bromo-4-(1H-indazol-1-yl)benzonitrile and 2-Bromo-4-(2H-indazol-2-yl)benzonitrile

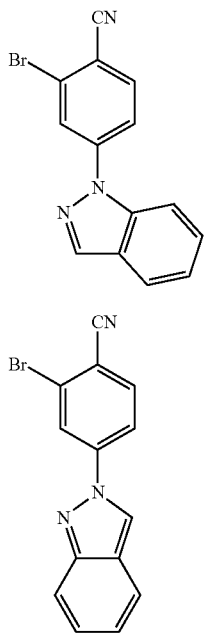

(215a)

(215b)

mixture of 2-bromo-4-fluorobenzonitrile (0.200 g, 1.000 mmol), 1H-indazole (0.130 g, 1.100 mmol) and potassium carbonate (0.276 g, 2.000 mmol) in dry DMF (5 mL) was stirred at 120° C. (block temperature) in a sealed vial for 16 h. The cooled mixture was filtered through a small plug of cotton wool to remove the potassium salts and the residue was washed with a little DMF. The filtrate was evaporated to give a turbid orange gum which was purified by flash chromatography (ISCO/50-100% DCM-hexane) to give 2-bromo-4-(1H-indazol-1-yl)benzonitrile (Intermediate 215a, 0.179 g, 60.0% yield) as a white solid. LC-MS (Method J): 1.402 min, [M+H]$^+$=297.9, 299.9; $^1$H NMR (400 MHz, DMSO-d$_6$) δ ppm 8.53 (s, 1H), 8.28 (d, J=2.0 Hz, 1H), 8.12 (d, J=8.6 Hz, 1H), 8.07 (dd, J=2.0, 8.6 Hz, 1H), 8.03 (d, J=8.6 Hz, 1H), 7.94 (d, J=7.8 Hz, 1H), 7.59 (dd, J=7.4, 8.2 Hz, 1H), 7.35 (t, J=7.4 Hz, 1H). Further elution afforded 2-bromo-4-(2H-indazol-2-yl)benzonitrile (Intermediate 215b, 0.078 g, 26.2% yield) as a white solid. LC-MS (Method J): 1.385 min, [M+H]$^+$=298.0, 300.0; $^1$H NMR (400 MHz, DMSO-d$_6$) δ ppm 9.32 (s, 1H), 8.64 (d, J=2.0 Hz, 1H), 8.33 (dd, J=2.0, 8.6 Hz, 1H), 8.16 (d, J=8.6 Hz, 1H), 7.76 (d, J=8.6 Hz, 1H), 7.70 (d, J=9.0 Hz, 1H), 7.35 (dd, J=6.7, 7.8 Hz, 1H), 7.12 (dd, J=6.7, 8.2 Hz, 2H).

Intermediate 215c: 4'-((2-Ethyl-5,7-dimethyl-3H-imidazo[4,5-b]pyridin-3-yl)methyl)-5-(1H-indazol-1-yl)-[1,1'-biphenyl]-2-carbonitrile

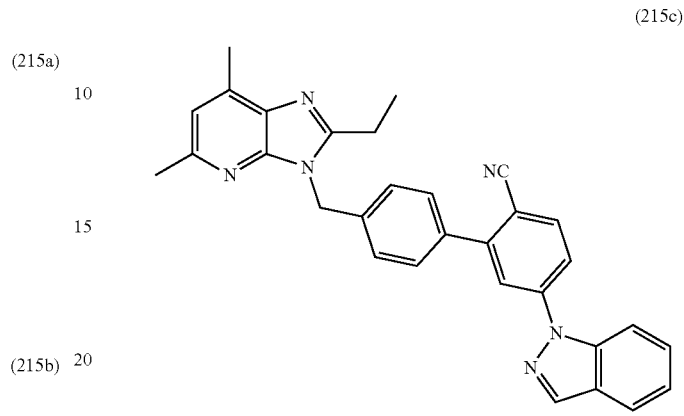

(215c)

A mixture of 2-ethyl-5,7-dimethyl-3-(4-(4,4,5,5-tetramethyl-1,3,2-dioxaborolan-2-yl)benzyl)-3H-imidazo[4,5-b]pyridine (001d, 0.100 g, 0.256 mmol), 2-bromo-4-(1H-indazol-1-yl)benzonitrile (215a, 0.084 g, 0.281 mmol) and 2 M Na$_2$CO$_3$ (0.319 mL, 0.639 mmol) in toluene-ethanol (9:1, 5 mL) was purged with a stream of N$_2$ for 5 min in a sealable vial. To this mixture was added Pd(Ph$_3$P)$_4$ (0.030 g, 0.026 mmol), the vial was sealed and the mixture was stirred at 95° C. (block temperature) for 16 h. The cooled mixture was diluted with EtOAc and the organic phase was separated, dried (Na$_2$SO$_4$) and evaporated to give a pale yellow gum. This material was purified by flash chromatography (ISCO/0-100% EtOAc-DCM) to give 4'-((2-ethyl-5,7-dimethyl-3H-imidazo[4,5-b]pyridin-3-yl)methyl)-5-(1H-indazol-1-yl)-[1,1'-biphenyl]-2-carbonitrile (0.106 g, 86% yield) as a colourless gum which solidified on standing in vacuo to give a waxy solid. This material was used as such in the next step. LC-MS (Method J): 1.396 min, [M+H]$^+$=483.2; $^1$H NMR (400 MHz, DMSO-d$_6$) δ ppm 8.49 (s, 1H), 8.12 (d, J=8.2 Hz, 1H), 8.20 (d, J=8.2 Hz, 2H), 7.95 (d, J=2.3 Hz, 11H), 7.92 (d, J=8.2 Hz, 1H), 7.66 (d, J=7.8 Hz, 2H), 7.60 (dd, J=6.7, 11.7 Hz, 2H), 7.54 (m, 2H), 7.32 (t, J=7.8 Hz, 11H), 7.28 (d, J=7.8 Hz, 2H), 6.95 (s, 1H), 5.55 (s, 2H), 2.82 (q, J=7.4 Hz, 2H), 2.51 (s, 3H), 2.50 (s, 3H), 1.25 (t, J=7.4 Hz, 3H).

Example 215: 3-((5'-(1H-Indazol-1-yl)-2'-(1H-tetrazol-5-yl)-[1,1'-biphenyl]-4-yl)methyl)-2-ethyl-5,7-dimethyl-3H-imidazo[4,5-b]pyridine To a sealable vial containing 4'-((2-ethyl-5,7-dimethyl-3H-imidazo[4,5-b]pyridin-3-yl)methyl)-5-(1H-indazol-1-yl)-[1,1'-biphenyl]-2-carbonitrile (0.025 g, 0.052 mmol) and dibutyltin oxide (0.026 g, 0.104 mmol) in toluene (2 mL) was added TMS-N$_3$ (0.138 mL, 1.036 mmol). The vial was sealed and the mixture were stirred at 120° C. (block temperature) for 16 h. The cooled mixture was evaporated and the residue was taken up in DMF (1.8 mL, acidified with 15 drops of AcOH) and submitted to preparative LC purification (Method D). The product-containing fractions were combined and evaporated to give 3-((5'-(1H-indazol-1-yl)-2'-(1H-tetrazol-5-yl)-[1,1'-biphenyl]-4-yl)methyl)-2-ethyl-5,7-dimethyl-3H-imidazo[4,5-b]pyridine (0.020 g, 73.5% yield) as a white solid. LC-MS (Method J): 1.342 min,

[M+H]⁺=526.2; ¹H NMR (400 MHz, DMSO-d₆) δ ppm 8.44 (s, 1H), 7.98 (d, J=8.6 Hz, 2H), 7.91 (d, J=7.8 Hz, 1H), 7.85 (d, J=8.2 Hz, 1H), 7.83 (br s, 1H), 7.53 (dd, J=7.4, 8.2 Hz, 1H), 7.30 (dd, J=7.0, 7.8 Hz, 1H), 7.17 (d, J=8.2 Hz, 2H), 7.06 (d, J=8.2 Hz, 2H), 6.93 (s, 1H), 5.45 (s, 2H), 2.75 (q, J=7.4 Hz, 2H), 2.48 (hidden, 6H), 1.21 (t, J=7.4 Hz, 3H).

Example 216: 3-((5'-(2H-Indazol-2-yl)-2'-(1H-tetrazol-5-yl)-[1,1'-biphenyl]-4-yl)methyl)-2-ethyl-5,7-dimethyl-3H-imidazo[4,5-b]pyridine

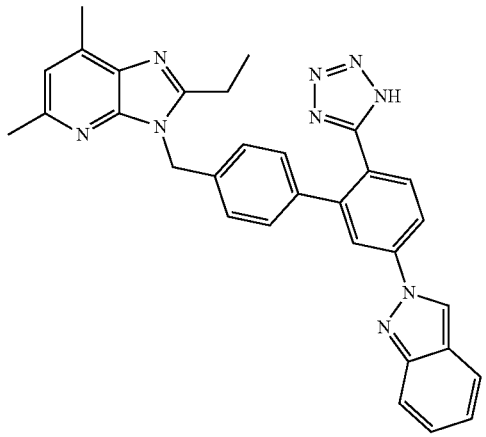
(Ex: 216)

Intermediate 216a: 4'-((2-Ethyl-5,7-dimethyl-3H-imidazo[4,5-b]pyridin-3-yl)methyl)-5-(2H-indazol-2-yl)-[1,1'-biphenyl]-2-carbonitrile

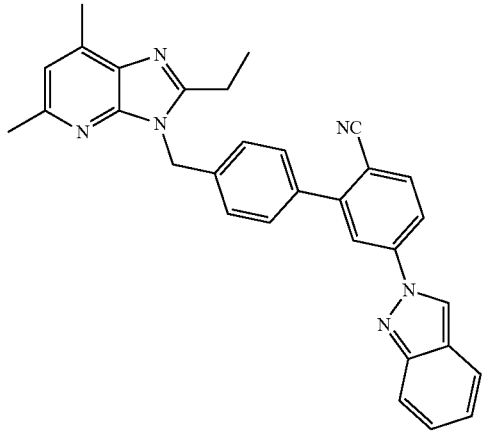
(216a)

The title compound was prepared from 2-ethyl-5,7-dimethyl-3-(4-(4,4,5,5-tetramethyl-1,3,2-dioxaborolan-2-yl)benzyl)-3H-imidazo[4,5-b]pyridine (001d, 0.080 g, 0.204 mmol) and 2-bromo-4-(2H-indazol-2-yl)benzonitrile (215b, 0.067 g, 0.225 mmol), according to the method described for the preparation of Intermediate 215c to give 4'-((2-ethyl-5,7-dimethyl-3H-imidazo[4,5-b]pyridin-3-yl)methyl)-5-(2H-indazol-2-yl)-[1,1'-biphenyl]-2-carbonitrile (0.066 g, 66.9% yield) as a colourless gum which solidified on standing in vacuo to give a waxy solid. This material was used as such in the next step. LC-MS (Method J): 1.375 min, [M+H]⁺=483.1; ¹H NMR (400 MHz, DMSO-d₆) δ ppm 9.34 (s, 1H), 8.31 (s, 1H), 8.29 (dd, J=2.0, 6.7 Hz, 1H), 8.15 (d, J=9.0 Hz, 1H), 7.75 (d, J=8.2 Hz, 1H), 7.68 (t, J=8.8 Hz, 2H), 7.63-7.51 (m, 2H), 7.33 (dd, J=6.3 Hz, 1H), 7.30 (d, J=8.2 Hz, 2H), 7.11 (dd, J=7.0, 8.6 Hz, 1H), 6.96 (s, 1H), 5.56 (s, 2H), 2.83 (q, J=7.4 Hz, 2H), 2.51 (s, 3H), 2.50 (s, 3H), 1.26 (t, J=7.4 Hz, 3H).

Example 216: 3-((5'-(2H-Indazol-2-yl)-2'-(1H-tetrazol-5-yl)-[1,1'-biphenyl]-4-yl)methyl)-2-ethyl-5,7-dimethyl-3H-imidazo[4,5-b]pyridine The title compound was prepared from 4'-((2-ethyl-5,7-dimethyl-3H-imidazo[4,5-b]pyridin-3-yl)methyl)-5-(2H-indazol-2-yl)-[1,1'-biphenyl]-2-carbonitrile (0.025 g, 0.052 mmol), according to the method described for the preparation of Example 215 to give 3-((5'-(2H-indazol-2-yl)-2'-(1H-tetrazol-5-yl)-[1,1'-biphenyl]-4-yl)methyl)-2-ethyl-5,7-dimethyl-3H-imidazo[4,5-b]pyridine (0.019 g, 69.8% yield) as a pale yellow solid. LC-MS (Method J): 1.318 min, [M+H]⁺=526.2; ¹H NMR (400 MHz, DMSO-d₆) δ ppm 9.28 (s, 1H), 8.24 (dd, J=2.0, 8.2 Hz, 1H), 8.17 (d, J=2.0 Hz, 1H), 7.85 (d, J=8.6 Hz, 1H), 7.75 (d, J=8.6 Hz, 1H), 7.69 (d, J=9.0 Hz, 1H), 7.52 (dd, J=6.7, 9.0 Hz, 1H), 7.17 (d, J=8.2 Hz, 2H), 7.11 (d, J=8.6 Hz, 1H), 7.07 (d, J=8.2 Hz, 2H), 6.94 (s, 1H), 5.46 (s, 2H), 2.77 (q, J=7.4 Hz, 2H), 2.48 (hidden, 6H), 1.23 (t, J=7.4 Hz, 3H).

Example 217: 2-Ethyl-5,7-dimethyl-3-((5'-(4-methyl-1H-pyrazol-1-yl)-2'-(11H-tetrazol-5-yl)-[1,1'-biphenyl]-4-yl)methyl)-3H-imidazo[4,5-b]pyridine

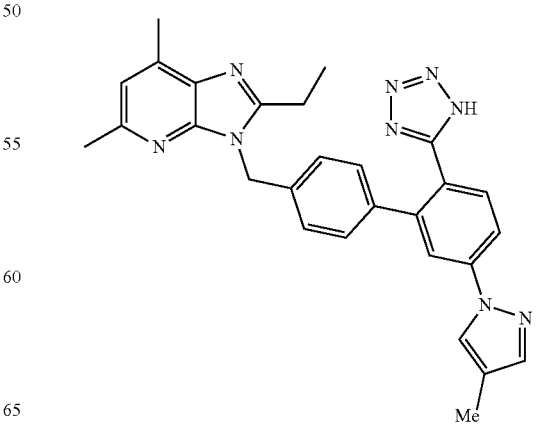
(Ex: 217)

Intermediate 217a: 4'-((2-Ethyl-5,7-dimethyl-3H-imidazo[4,5-b]pyridin-3-yl)methyl)-5-(4-methyl-1H-pyrazol-1-yl)-[1,1'-biphenyl]-2-carbonitrile

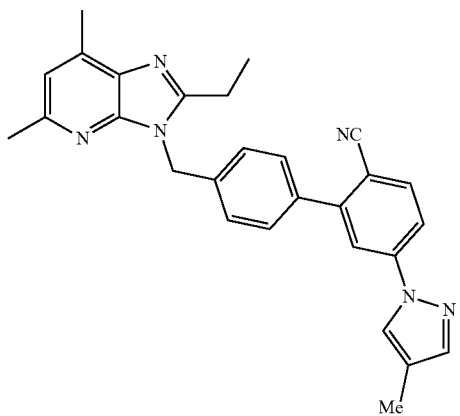

(217a)

To a solution of 4'-((2-ethyl-5,7-dimethyl-3H-imidazo[4,5-b]pyridin-3-yl)methyl)-5-fluoro-[1,1'-biphenyl]-2-carbonitrile (205a, 0.088 g, 0.229 mmol) and 4-methyl-1H-pyrazole (0.028 g, 0.343 mmol) in DMF (3 mL) was added potassium carbonate (0.095 g, 10 0.687 mmol) and the resulting mixture was stirred at 120° C. (block temperature) in a sealed vial for 18 h. The cooled mixture was filtered (0.45 μm syringe filter) to remove the potassium salts and the residue was washed with a little DMF. The combined filtrate was evaporated to give a gum which was purified by flash chromatography (ISCO/0-100% EtOAc-DCM) to give 4'-((2-ethyl-5,7-dimethyl-3H-imidazo[4,5-b]pyridin-3-yl)methyl)-5-(4-methyl-1H-pyrazol-1-yl)-[1,1'-biphenyl]-2-carbonitrile (0.102 g, 100% yield) as a colourless gum which solidified on standing in vacuo to give a white solid. This material was used as such in the next step. LC-MS (Method J): 1.340 min, [M+H]⁺=447.2; ¹H NMR (400 MHz, DMSO-d₆) δ ppm 8.50 (s, 1H), 8.01 (d, J=7.8 Hz, 1H), 7.96 (d, J=7.8 Hz, 1H), 7.95 (s, 1H), 7.65 (s, 1H), 7.59 (d, J=8.2 Hz, 2H), 7.27 (d, J=8.2 Hz, 2H), 6.95 (s, 1H), 5.55 (s, 2H), 2.81 (q, J=7.4 Hz, 2H), 2.51 (s, 3H), 2.50 (s, 3H), 2.07 (s, 3H), 1.25 (t, J=7.4 Hz, 3H).

Example 217: 2-Ethyl-5,7-dimethyl-3-((5'-(4-methyl-1H-pyrazol-1-yl)-2'-(1H-tetrazol-5-yl)-[1,1'-biphenyl]-4-yl)methyl)-3H-imidazo[4,5-b]pyridine To a sealable vial containing 4'-((2-ethyl-5,7-dimethyl-3H-imidazo[4,5-b]pyridin-3-yl)methyl)-5-(4-methyl-1H-pyrazol-1-yl)-[1,1'-biphenyl]-2-carbonitrile (0.100 g, 0.224 mmol) and dibutyltin oxide (0.084 g, 0.336 mmol) in toluene (4 mL) was added TMS-N₃ (0.297 mL, 2.239 mmol). The vial was sealed and the mixture were stirred at 120° C. (block temperature) for 16 h. The cooled mixture was evaporated and the residue was taken up in DMF (4×1.8 mL, acidified with 20 drops of AcOH) and submitted to preparative LC purification (Method D). The product-containing fractions were combined and evaporated to give a gum which was lyophilized from ACN-H₂O to give 2-ethyl-5,7-dimethyl-3-((5'-(4-methyl-1H-pyrazol-1-yl)-2'-(1H-tetrazol-5-yl)-[1,1'-biphenyl]-4-yl)methyl)-3H-imidazo[4,5-b]pyridine (0.062 g, 56.6% yield) as a white solid. LC-MS (Method J): 1.515 min, [M+H]⁺=490.2; ¹H NMR (400 MHz, DMSO-d₆) δ ppm 8.41 (s, 1H), 7.87 (d, J=8.6 Hz, 1H), 7.78 (s, 1H), 7.68 (d, J=8.2 Hz, 1H), 7.58 (s, 1H), 7.10 (d, J=8.2 Hz, 2H), 7.01 (d, J=8.2 Hz, 2H), 6.93 (s, 1H), 5.43 (s, 2H), 2.76 (q, J=7.4 Hz, 2H), 2.48 (hidden, 6H), 2.08 (s, 3H), 1.22 (t, J=7.4 Hz, 3H).

The following examples have been similarly prepared from 4'-((2-ethyl-5,7-dimethyl-3H-imidazo[4,5-b]pyridin-3-yl)methyl)-5-fluoro-[1,1'-biphenyl]-2-carbonitrile (Intermediate 205a) as described above for Example 217. Two analytical LC injections were used to determine the final purity; the retention time of one of them is reported for each compound and is referred as Method J.

| Ex | Structure | MW | LC-MS m/z [M + H]⁺; RT (Method) | ¹H NMR (400 MHz, DMSO-d₆) δ ppm |
|---|---|---|---|---|
| 218 | 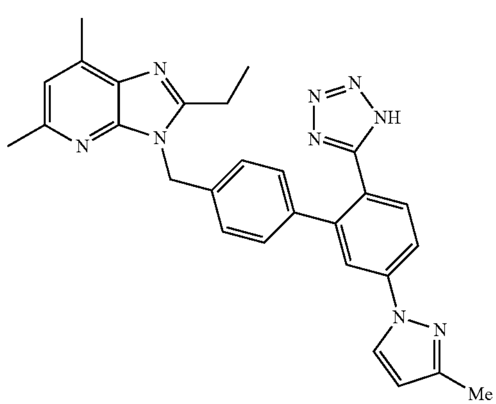 [SMILES: CCc1nc2c(C)cc(C)nc2n1Cc1ccc(-c2cc(-n3ccc(C)n3)ccc2-c2nnn[nH]2)cc1] | 489.75 | 490.1; 1.479 min (Method J) | 8.54 (d, J = 2.3 Hz, 1H), 7.94 (dd, J = 2.0, 8.2 Hz, 1H), 7.85 (d, J = 2.0 Hz, 1H), 7.72 (d, J = 8.2 Hz, 1H), 7.11 (d, J = 8.2 Hz, 2H), 7.05 (d, J = 8.6 Hz, 2H), 6.93 (s, 1H), 6.36 (d, J = 2.3 Hz, 1H), 5.45 (s, 2H), 2.75 (q, J = 7.4 Hz, 2H), 2.48 (hidden, 6H), 2.26 (s, 3H), 1.22 (t, J = 7.4 Hz, 3H). |

-continued

| Ex | Structure | MW | LC-MS m/z [M + H]+; RT (Method) | 1H NMR (400 MHz, DMSO-d6) δ ppm |
|---|---|---|---|---|
| 219 | 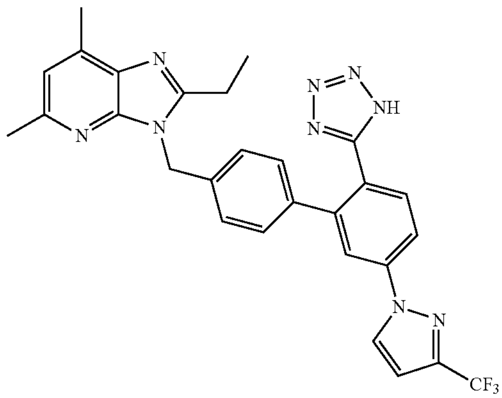 [SMILES: CCc1nc2c(C)cc(C)nc2n1Cc1ccc(-c2cc(-n3ccc(C(F)(F)F)n3)ccc2-c2nnn[nH]2)cc1] | 543.55 | 544.2; 1.520 min (Method J) | 8.89 (s, 1H), 8.02 (d, J = 8.2 Hz, 1H), 7.93 (s, 1H), 7.81 (d, J = 8.6 Hz, 1H), 7.14 (d, J = 8.2 Hz, 2H), 7.08 (d, J = 2.7 Hz, 1H), 7.05 (d, J = 8.2 Hz, 2H), 6.93 (s, 1H), 5.45 (s, 2H), 2.76 (q, J = 7.4 Hz, 2H), 2.48 (hidden, 6H), 1.23 (t, J = 7.4 Hz, 3H). |
| 220 | 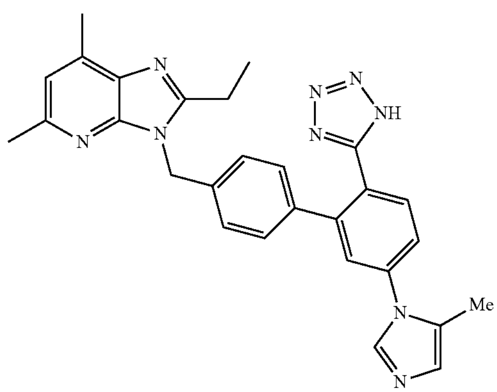 [SMILES: CCc1nc2c(C)cc(C)nc2n1Cc1ccc(-c2cc(-n3cncc3C)ccc2-c2nnn[nH]2)cc1] | 489.57 | 490.1; 1.110 min (Method J) | (MeOH-d4): 8.57 (br s, 1H), 8.15 (br s, 1H), 7.97 (s, 1H), 7.83 (br s, 1H), 7.61 (s, 2H), 7.13 (d, J = 7.0 Hz, 2H), 7.06 (d, J = 7.4 Hz, 2H), 7.01 (s, 1H), 5.53 (s, 2H), 2.84 (q, J = 7.8 Hz, 2H), 2.59 (s, 3H), 2.56 (s, 3H), 2.31 (br s, 3H), 1.25 (t, J = 7.4 Hz, 3H). |
| 221 | 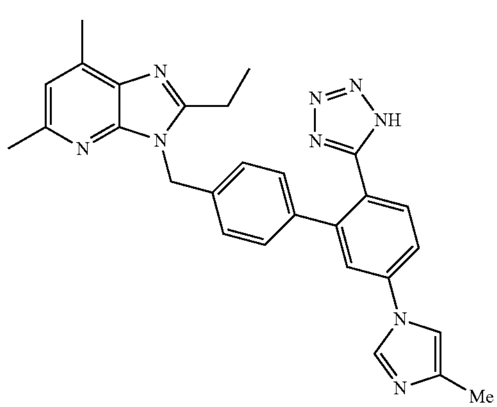 [SMILES: CCc1nc2c(C)cc(C)nc2n1Cc1ccc(-c2cc(-n3cnc(C)c3)ccc2-c2nnn[nH]2)cc1] | 489.57 | 490.1; 1.153 min (Method J) | (MeOH-d4): 8.64 (s, 1H), 8.10 (s, 1H), 7.78 (d, J = 9.0 Hz, 1H), 7.72-7.71 (m, 2H), 7.59 (s, 1H), 7.14 (d, J = 8.2 Hz, 2H), 7.07 (d, J = 8.2 Hz, 2H), 7.02 (s, 1H), 5.54 (s, 2H), 2.85 (q, J = 7.8 Hz, 2H), 2.59 (s, 3H), 2.56 (s, 3H), 2.31 (s, 3H), 1.25 (t, J = 7.4 Hz, 3H). |

| Ex | Structure | MW | LC-MS m/z [M + H]+; RT (Method) | ¹H NMR (400 MHz, DMSO-d₆) δ ppm |
|---|---|---|---|---|
| 222 | 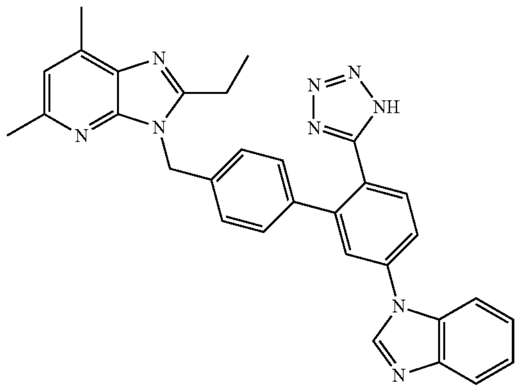 [SMILES: CCc1nc2c(C)cc(C)nc2n1Cc1ccc(-c2cc(-n3cnc4ccccc43)ccc2-c2nnn[nH]2)cc1] | 525.61 | 526.2; 1.473 min (Method J) | 8.69 (s, 1H), 7.84 (m, 2H), 7.85 (d, J = 2.0 Hz, 1H), 7.76 (dd, J = 7.0, 8.6 Hz, 1H), 7.72 (m, 1H), 7.33 (m, 1H), 7.17 (d, J = 8.2 Hz, 2H), 7.04 (d, J = 7.8 Hz, 2H), 6.92 (s, 1H), 5.44 (s, 2H), 2.75 (q, J = 7.4 Hz, 2H), 2.48 (hidden, 6H), 1.22 (t, J = 7.4 Hz, 3H). |
| 223 | 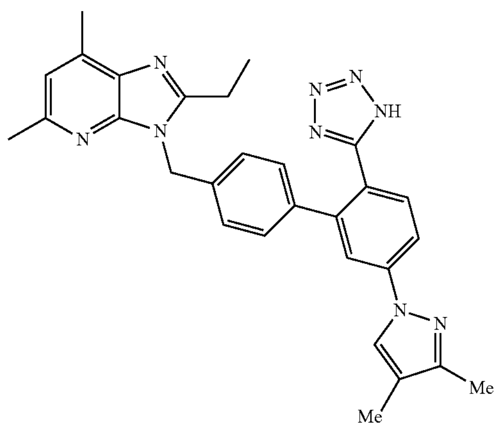 [SMILES: CCc1nc2c(C)cc(C)nc2n1Cc1ccc(-c2cc(-n3cc(C)c(C)n3)ccc2-c2nnn[nH]2)cc1] | 503.60 | 504.1; 1.329 min (Method J) | 8.35 (s, 1H), 7.88 (dd, J = 2.0, 8.2 Hz, 1H), 7.80 (d, J = 2.0 Hz, 1H), 7.69 (d, J = 8.2 Hz, 1H), 7.10 (d, J = 7.8 Hz, 2H), 7.05 (d, J = 8.2 Hz, 2H), 6.93 (s, 1H), 5.45 (s, 2H), 2.75 (q, J = 7.4 Hz, 2H), 2.48 (hidden, 6H), 2.17 (s, 3H), 2.00 (s, 3H), 1.22 (t, J = 7.4 Hz, 3H). |
| 224 | 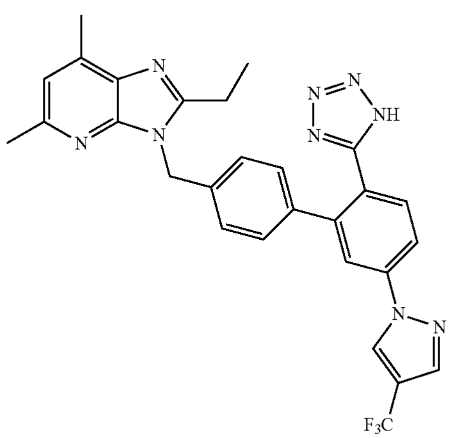 [SMILES: CCc1nc2c(C)cc(C)nc2n1Cc1ccc(-c2cc(-n3cc(C(F)(F)F)cn3)ccc2-c2nnn[nH]2)cc1] | 543.55 | 544.1; 1.317 min (Method J) | 9.37 (s, 1H), 8.26 (s, 1H), 8.05 (d, J = 8.2 Hz, 1H), 8.00 (s, 1H), 7.81 (d, J = 8.2 Hz, 1H), 7.13 (d, J = 8.2 Hz, 2H), 7.06 (d, J = 8.2 Hz, 2H), 6.93 (s, 1H), 5.45 (s, 2H), 2.76 (q, J = 7.4 Hz, 2H), 2.48 (hidden, 6H), 1.22 (t, J = 7.4 Hz, 3H). |

Example 225: 3-((5'-(4-Cyclopropyl-1H-1,2,3-triazol-1-yl)-2'-(5H-tetrazol-5-yl)-[1,1'-biphenyl]-4-yl)methyl)-2-ethyl-5,7-dimethyl-3H-imidazo[4,5-b]pyridine

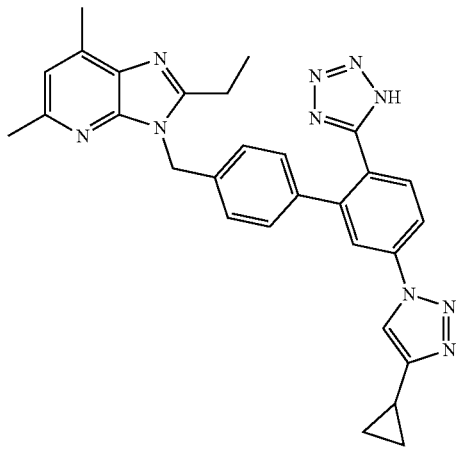

(Ex: 225)

Intermediate 225a: 5-Amino-4'-((2-ethyl-5,7-dimethyl-3H-imidazo[4,5-b]pyridin-3-yl)methyl)-[1,1'-biphenyl]-2-carbonitrile

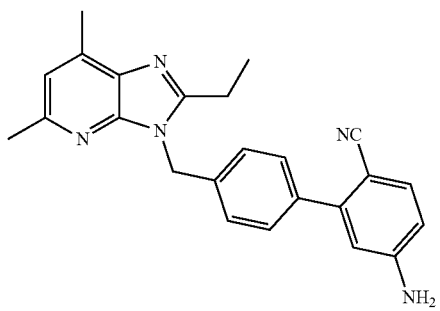

(225a)

To a mixture of 4-amino-2-bromobenzonitrile (1.00 g, 5.08 mmol), 2-ethyl-5,7-dimethyl-3-(4-(4,4,5,5-tetramethyl-1,3,2-dioxaborolan-2-yl)benzyl)-3H-imidazo[4,5-b]pyridine (001d, 1.773 g, 4.53 mmol) and K$_2$CO$_3$ (2.505 g, 18.13 mmol) was added 1,4-dioxane and H$_2$O (2:1, 30 mL). The reaction mixture was then purged with a stream of N$_2$ for 5 min in a sealable vial before Pd(Ph$_3$P)$_4$ (0.262 g, 0.227 mmol) was added. The reaction vial was sealed and the mixture heated at 100° C. for 18h. The cooled reaction mixture was then diluted with EtOAc (50 mL), washed with H$_2$O and brine, dried (Na$_2$SO$_4$) and evaporated. The crude residue was purified by flash chromatography (ISCO, 0-100% EtOAc-DCM) to afford the title compound (1.46 g, 4.53 mmol, 85%) as a white solid.
LC-MS (Method H): 1.220 min, [M+H]$^+$=382.5; $^1$H NMR (400 MHz, CDCl$_3$) δ ppm 7.37-7.55 (m, 3H), 7.19 (d, J=8.2 Hz, 2H), 6.90 (d, 1H), 6.51-6.68 (m, 2H), 5.51 (s, 2H), 4.17 (br s, 2H), 2.81 (d, J=7.4 Hz, 2H), 2.59 (s, 3H), 2.64 (s, 3H), 1.33 (t, J=7.4 Hz, 3H).

Intermediate 225b: 5-Azido-4'-((2-ethyl-5,7-dimethyl-3H-imidazo[4,5-bipyridin-3-yl)methyl)-[1,1'-biphenyll-2-carbonitrile

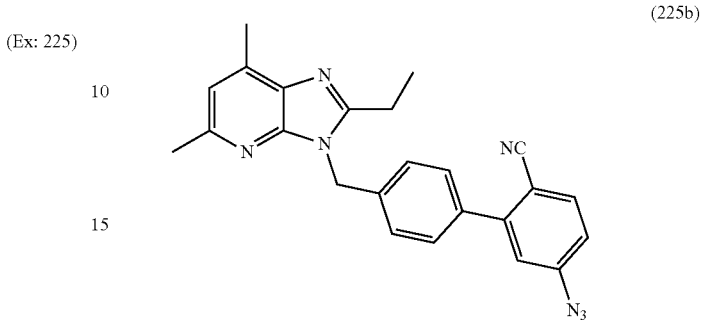

(225b)

To a solution of 5-amino-4'-((2-ethyl-5,7-dimethyl-3H-imidazo[4,5-b]pyridin-3-yl)methyl)-[1,1'-biphenyl]-2-carbonitrile (0.500 g, 1.311 mmol) in ACN (40 mL) was added TFA (0.202 mL, 2.622 mmol) and the mixture was cooled at −5° C. To this cold mixture was added tert-butyl nitrite (0.624 mL, 5.240 mmol), followed after 10 min with TMS-N$_3$ (0.522 mL, 3.930 mmol). The mixture was then stirred at RT for 4 h, after which it was evaporated to dryness. The crude residue obtained was purified by flash chromatography (ISCO, 0-100% EtOAc-DCM) to provide 5-azido-4'-((2-ethyl-5,7-dimethyl-3H-imidazo[4,5-b]pyridin-3-yl)methyl)-[1,1'-biphenyl]-2-carbonitrile (0.467 g, 1.088 mmol, 83% yield). LC-MS (Method H): 1.335 min, [M+H]$^+$= 408.5; $^1$H NMR (400 MHz, DMSO-d$_6$) δ ppm 7.88 (d, J=8.2 Hz, 1H), 7.51 (d, J=8.2 Hz, 2H), 7.29 (d, J=7.8 Hz, 2H), 7.16-7.26 (m, 2H), 7.08 (s, 1H), 5.59 (s, 2H), 2.93 (q, J=7.2 Hz, 2H), 2.49 (s, 6H), 1.21 (t, J=7.4 Hz, 3H).

Intermediate 225c: 5-(4-Cyclopropyl-1H-1,2,3-triazol-1-yl)-4'-((2-ethyl-5,7-dimethyl-3H-imidazo[4,5-b]pyridin-3-yl)methyl)-[1,1'-biphenyl]-2-carbonitrile

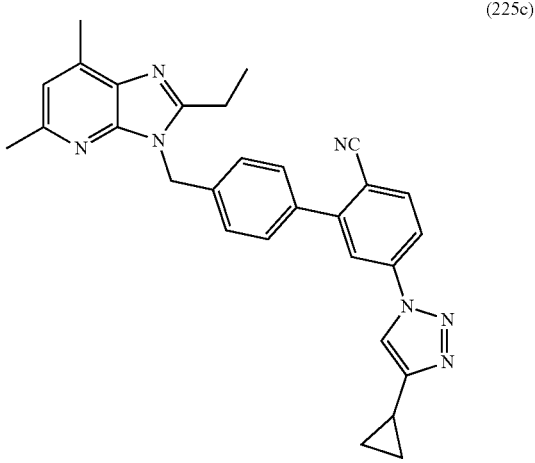 [SMILES: CCc1nc2c(C)cc(C)nc2n1Cc1ccc(-c2cc(-n3cc(C4CC4)nn3)ccc2C#N)cc1]

(225c)

To a mixture of 5-azido-4'-((2-ethyl-5,7-dimethyl-3H-imidazo[4,5-b]pyridin-3-yl)methyl)-[1,1'-biphenyl]-2-carbonitrile (0.030 g, 0.074 mmol) and ethynylcyclopropane (0.049 g, 0.736 mmol) in a mixture of t-BuOH:H$_2$O (3:1, 4 mL) were added CuSO₄·5H₂O (0.002 g, 0.008 mmol) and sodium ascorbate (0.007 g, 0.040 mmol). The reaction mixture was stirred for at RT for 16 h and then it was diluted with EtOAc (25 mL) and washed with saturated aqueous NH₄Cl and H₂O. The organic layer was separated, dried (Na₂SO₄) and evaporated to dryness. The crude product thus obtained was washed with hexane (5 mL) to remove excess alkyne and dried in vacuo to afford the title compound (0.025 g, 0.074 mmol, 64.8%) which was used as such for the next step without further purification. LC-MS (Method H): 1.313 min, [M+H]⁺=474.2.

Example 225: 3-((5'-(4-Cyclopropyl-1H-1,2,3-triazol-1-yl)-2'-(5H-tetrazol-5-yl)-[1,1'-biphenyl]-4-yl)methyl)-2-ethyl-5,7-dimethyl-3H-imidazo[4,5-b]pyridine To a mixture of 5-(4-cyclopropyl-1H-1,2,3-triazol-1-yl)-4'-((2-ethyl-5,7-dimethyl-3H-imidazo[4,5-b]pyridin-3-yl)methyl)-[1,1'-biphenyl]-2-carbonitrile (0.025 g, 0.053 mmol), TMS-N₃ (0.148 mL, 1.056 mmol) and dibutyltin oxide (0.027 g, 0.106 mmol) was added toluene (2 mL), the vial was briefly purged with N₂ and then it was sealed. The mixture was stirred at 120° C. for 16 h and then the cooled mixture was filtered through a small plug of cotton wool and the filtrate was evaporated to give a gum. This gum was purified by preparative LC (Method F) to afford 3-((5'-(4-cyclopropyl-1H-1,2,3-triazol-1-yl)-2'-(5H-tetrazol-5-yl)-[1,1'-biphenyl]-4-yl)methyl)-2-ethyl-5,7-dimethyl-3H-imidazo[4,5-b]pyridine (0.015 g, 0.053 mmol, 52.3% yield) as a white solid. LC-MS (Method H) at 1.259 min, [M+H]⁺= 517.2; ¹H NMR (400 MHz, DMSO-d₆) δ ppm 8.70 (s, 1H), 8.03 (d, J=8.2 Hz, 1H), 7.91 (s, 1H), 7.85 (d, J=8.2 Hz, 1H), 7.11-7.19 (m, J=7.8 Hz, 2H), 7.01-7.11 (m, J=8.2 Hz, 2H), 6.95 (s, 1H), 5.47 (s, 2H), 2.78 (q, J=7.4 Hz, 3H), 2.48 (hidden, 6H), 1.96-2.08 (m, 1H), 1.18-1.31 (m, 3H), 0.91-1.02 (m, 2H), 0.71-0.82 (m, 2H).

The following examples have been similarly prepared from 5-azido-4'-((2-ethyl-5,7-dimethyl-3H-imidazo[4,5-b]pyridin-3-yl)methyl)-[1,1'-biphenyl]-2-carbonitrile (Intermediate 225b) as described for the synthesis of Example 225 above. Two analytical LC-MS injections were used to determine the final purity. The retention time of one of them is reported for each compound and is referred as Method H.

| Ex | Structure | MW | LC-MS m/z [M + H]⁺; RT (Method H) | ¹H NMR (400 MHz, DMSO-d₆) δ ppm |
|---|---|---|---|---|
| 226 | 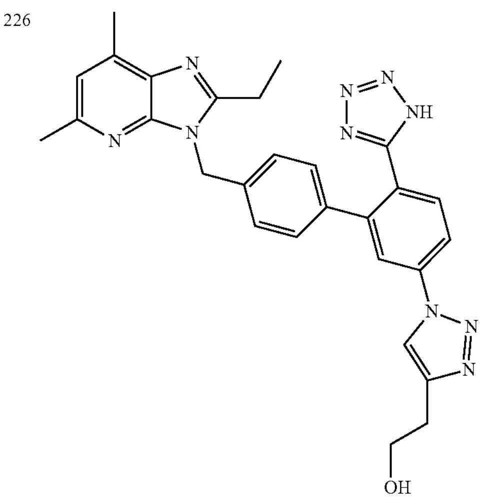 | 520.5 | 521.2; 1.18 min | 8.74 (s, 1H), 8.03 (dd, J = 1.96, 8.22 Hz, 1H), 7.92 (d, J = 2.0 Hz, 1H), 7.84 (d, J = 8.2 Hz, 1H), 7.10-7.19 (d, J = 8.2 Hz, 2H), 7.02-7.08 (d, J = 8.2 Hz, 2H), 6.95 (s, 1H), 6.53 (s, 1H), 5.46 (s, 2H), 4.76 (m, 1H), 3.64-3.73 (m, 2H), 2.86 (t, J = 6.85 Hz, 2H), 2.78 (q, J = 7.70 Hz, 2H), 2.48 (hidden, 6H), 1.25 (t, J = 7.43 Hz, 3H). |
| 227 | 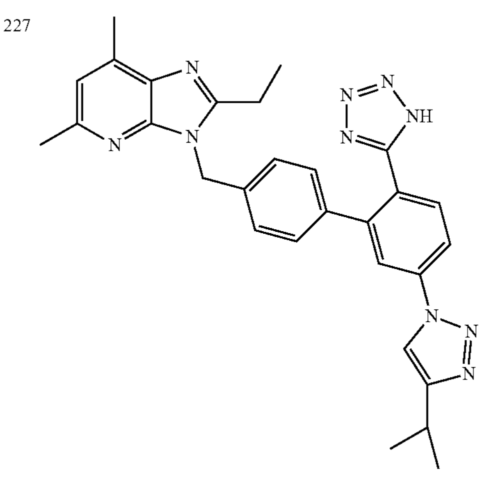 | 518.6 | 519.2; 1.283 min | 8.73 (s, 1H), 7.99 (d, J = 7.04 Hz, 1H), 7.87 (br s, 1H), 7.80 (d, J = 8.2 Hz, 1H), 7.11-7.22 (d, J = 7.8 Hz, 2H), 6.99-7.08 (d, J = 8.2 Hz, 2H), 6.94 (s, 1H), 6.53 (s, 1H), 5.45 (s, 2H), 3.06 (td, J = 6.8, 13.7 Hz, 1H), 2.78 (q, J = 7.30 Hz, 2H), 2.50 (hidden, 6H), 1.30 (d, J = 7.04 Hz, 6H), 1.25 (t, J = 7.4 Hz, 3H). |

| Ex | Structure | MW | LC-MS m/z [M + H]+; RT (Method H) | 1H NMR (400 MHz, DMSO-d6) δ ppm |
|---|---|---|---|---|
| 228 | 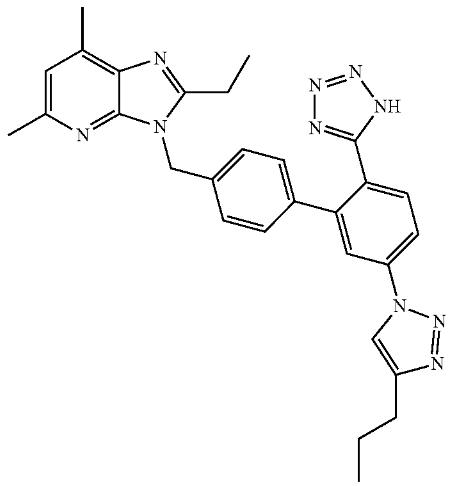 [SMILES: CCCc1cn(-c2ccc(-c3nnn[nH]3)c(-c3ccc(Cn4c(CC)nc5c(C)cc(C)nc54)cc3)c2)nn1] | 518.6 | 519.2; 1.294 min | 8.73 (s, 1H), 8.02 (d, J = 8.2 Hz, 2H), 7.91 (d, J = 1.6 Hz, 1H), 7.83 (d, J = 7.8 Hz, 1H), 7.09-7.18 (d, J = 8.2 Hz, 2H), 7.00-7.08 (d, J = 7.8 Hz, 2H), 6.93 (s, 1H), 6.50 (s, 1H), 5.44 (s, 2H), 2.76 (q, J = 7.4 Hz, 2H), 2.63-2.70 (m, 2H), 2.50 (hidden, 6H), 1.61-1.71 (m, 2H), 1.22 (t, J = 7.6 Hz, 4H), 0.94 (t, J = 7.4 Hz, 3H). |
| 229 | 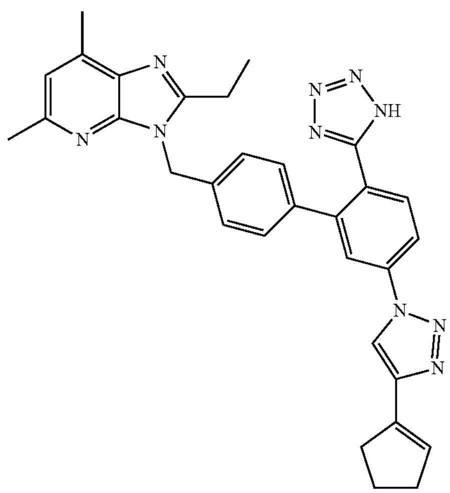 [SMILES: CCc1nc2c(C)cc(C)nc2n1Cc1ccc(-c2cc(-n3cc(C4=CCCC4)nn3)ccc2-c2nnn[nH]2)cc1] | 542.6 | 543.2; 1.356 min | 8.95 (s, 1H), 8.24 (br s, 1H), 7.92 (dd, J = 2.4, 7.8 Hz, 2H), 7.76-7.83 (m, 2H), 7.12-7.20 (d, J = 7.8 Hz, 2H), 6.99-7.04 (d, J = 8.22 Hz, 2H), 6.94 (s, 1H), 6.53 (br s, 1H), 6.32 (t, J = 2.15 Hz, 1H), 5.45 (s, 2H), 2.80 (q, J = 7.4 Hz, 3H), 2.50 (hidden, 6H), 2.65-2.72 (m, 2H), 1.93-2.02 (m, 2H), 1.24-1.31 (m, 5H). |
| 230 | 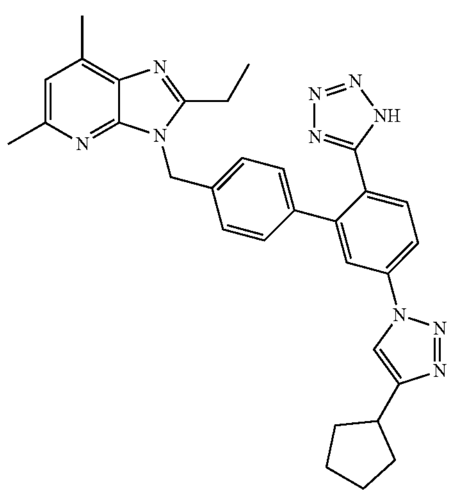 [SMILES: CCc1nc2c(C)cc(C)nc2n1Cc1ccc(-c2cc(-n3cc(C4CCCC4)nn3)ccc2-c2nnn[nH]2)cc1] | 544.2 | 545.2; 1.344 min | (MeOH-d4) 8.49 (s, 1H), 7.95-8.08 (m, 2H), 7.85 (d, J = 8.6 Hz, 1H), 7.16-7.24 (d, J = 8.2 Hz, 2H), 7.10-7.16 d, J = 8.2 Hz, 2H), 7.05 (s, 1H), 5.58 (s, 2H), 2.88 (q, J = 7.7 Hz, 2H), 2.59 (s, 3H), 2.62 (s, 3H), 2.09-2.23 (m, 2H), 1.67-1.89 (m, 6H), 1.33 (s, 1H), 1.28 (t, J = 7.4 Hz, 3H). |

| Ex | Structure | MW | LC-MS m/z [M + H]+; RT (Method H) | 1H NMR (400 MHz, DMSO-d6) δ ppm |
|---|---|---|---|---|
| 231 | 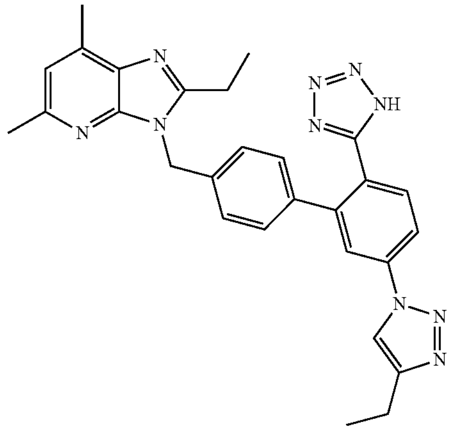 [SMILES: CCc1cn(-c2ccc(-c3nnn[nH]3)c(-c3ccc(Cn4c(CC)nc5c(C)cc(C)nc54)cc3)c2)nn1] | 504.5 | 505.5, 1.24 min | (MeOH-d4) 8.45 (s, 1H), 7.97 (s, 2H), 7.15 (d, J = 7.8 Hz, 2H), 7.09 (d, J = 7.8 Hz, 2H), 7.03 (s, 1H), 5.55 (s, 2H), 2.85 (qd, J = 7.5, 14.9 Hz, 4H), 2.59 (s, 3H), 2.62 (s, 3H), 1.36 (t, J = 7.6 Hz, 3H), 1.28 (t, J = 7.6 Hz, 3H) |
| 232 | 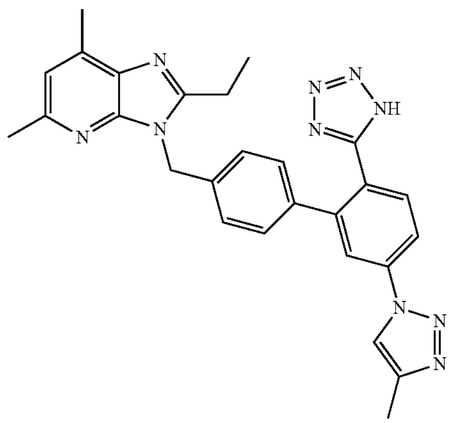 [SMILES: CCc1nc2c(C)cc(C)nc2n1Cc1ccc(-c2cc(-n3cc(C)nn3)ccc2-c2nnn[nH]2)cc1] | 490.5 | 491.2; 1.396 min | (MeOH-d4) 8.42 (s, 1H), 7.95-8.03 (m, 2H), 7.83 (d, J = 8.61 Hz, 1H), 7.15-7.21 (d, J = 8.22 Hz, 2H), 7.07-7.11 (d, J = 8.22 Hz, 2H), 7.04 (s, 1H), 5.57 (s, 2H), 2.87 (q, J = 7.43 Hz, 2H), 2.62 (s, 3H), 2.59 (s, 3H), 2.43 (s, 3H), 1.28 (t, J = 7.63 Hz, 3H). |

Example 233: 1-(4'-((2-Ethyl-5,7-dimethyl-3H-imidazo[4,5-b]pyridin-3-yl)methyl)-6-(1H-tetrazol-5-yl)-[1,1'-biphenyl]-3-yl)-1H-benzo[d][1,2,3]triazole (Ex. 233)

Intermediate 233a: 5-(1H-Benzo[d][1,2,3]triazol-1-yl)-4'-((2-ethyl-5,7-dimethyl-3H-imidazo[4,5-b]pyridin-3-yl)methyl)-[1,1'-biphenyl]-2-carbonitrile

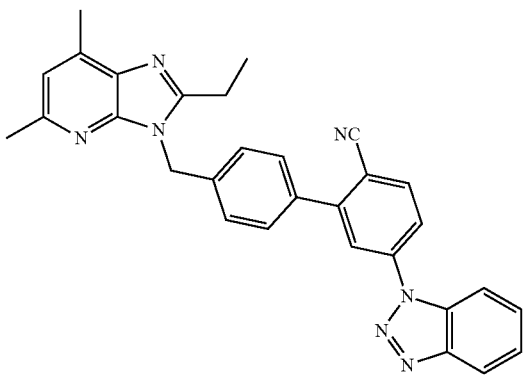

(233a)

To a mixture of 5-azido-4'-((2-ethyl-5,7-dimethyl-3H-imidazo[4,5-b]pyridin-3-yl)methyl)-[1,1'-biphenyl]-2-carbonitrile (Intermediate 225b, 0.030 g, 0.074 mmol) and trimethylsilyl)phenyl trifluoromethanesulfonate (0.088 g, 0.294 mmol) in ACN (4 mL) was added CsF (0.0122 g, 0.074 mmol) and the mixture was stirred at RT for 7 h. The mixture was then diluted with EtOAc (25 mL) and the organic layer was washed (saturated aqueous NaHCO$_3$), dried (Na$_2$SO$_4$) and evaporated to dryness. This gave crude 5-(1H-benzo[d][1,2,3]triazol-1-yl)-4'-((2-ethyl-5,7-dimethyl-3H-imidazo[4,5-b]pyridin-3-yl)methyl)-[1,1'-biphenyl]-2-carbonitrile (0.025 g, 0.052 mmol, 70.2% yield) which was used as such for the next step. LC-MS (Method H): 1.366 min, [M+H]$^+$=484.2.

Example 233: 1-(4'-((2-Ethyl-5,7-dimethyl-3H-imidazo[4,5-b]pyridin-3-yl)methyl)-6-(1H-tetrazol-5-yl)-[1,1'-biphenyl]-3-yl)-1H-benzo[d][1,2,3]triazole To a mixture of 5-(1H-benzo[d][1,2,3]triazol-1-yl)-4'-((2-ethyl-5,7-dimethyl-3H-imidazo[4,5-b]pyridin-3-yl)methyl)-[1,1'-biphenyl]-2-carbonitrile (0.025 g, 0.052 mmol), TMS-N$_3$ (0.144 mL, 1.034 mmol) and dibutyltin oxide (0.0263 g, 0.103 mmol) was added toluene (3 mL). The vial was briefly purged with N$_2$ and then it was sealed and the mixture was stirred at 120° C. for 16 h. The cooled mixture was evaporated to give a gum which was purified by preparative LC (Method F) to provide 1-(4'-((2-ethyl-5,7-dimethyl-3H-imidazo[4,5-b]pyridin-3-yl)methyl)-6-(1H-tetrazol-5-yl)-[1,1'-biphenyl]-3-yl)-1H-benzo[d][1,2,3]triazole (0.010 g, 36.7% yield) as a white solid. HRMS (ESI): Calcd. for C$_{30}$H$_{28}$N$_7$O [M+H] m/z 527.2415; found 527.2418; $^1$H NMR (400 MHz, MeOH-d$_4$) δ ppm 8.14 (d, J=8.6 Hz, 1H), 7.83-8.03 (m, 4H), 7.70 (t, J=7.43 Hz, 1H), 7.51-7.60 (m, 1H), 7.18-7.26 (d, J=7.8 Hz, 2H), 7.05-7.14 (d, J=7.8 Hz, 2H), 7.03 (s, 1H), 5.56 (s, 2H), 2.87 (q, J=7.7 Hz, 2H), 2.61 (s, 3H), 2.58 (s, 3H), 1.28 (t, J=7.43 Hz, 3H).

Example 234: 2-Ethyl-3-((5'-(1-ethyl-1H-1,2,3-triazol-4-yl)-2'-(1H-tetrazol-5-yl)-[1,1'-biphenyl]-4-yl)methyl)-5,7-dimethyl-3H-imidazo[4,5-b]pyridine (Ex. 234)

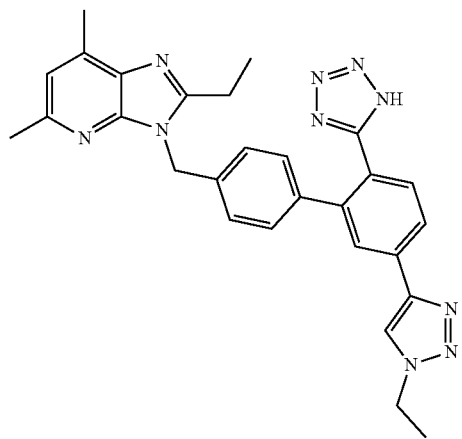

Intermediate 234a: 4-Bromo-2-iodobenzonitrile

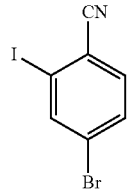

(234a)

To a mixture of 2-amino-4-bromobenzonitrile (1.00 g, 5.08 mmol) in 4 M aqueous HCl (7.5 mL) cooled at 0° C. was added a solution of sodium nitrite (0.490 g, 7.11 mmol) in H$_2$O (3 mL), followed after 10 min by the dropwise addition of a solution of potassium iodide (2.106 g, 12.69 mmol) in H$_2$O (3 mL). The reaction mixture was subsequently allowed to warm to RT and then it was extracted with EtOAc (50 mL). The organic layer was separated, washed (10% aqueous Na$_2$S$_2$O$_5$, brine), dried (Na$_2$SO$_4$) and evaporated under reduced pressure. The residue obtained was purified by flash chromatography (ISCO, 0 to 100% EtOAc-hexane) to provide 4-bromo-2-iodobenzonitrile (1.17 g, 3.81 mmol, 75% yield). LC-MS (Method H): 1.239 min, [M+H]$^+$=no ion observed. $^1$H NMR (400 MHz, CDCl$_3$) δ ppm 7.46 (d, J=8.22 Hz, 1H), 7.61 (dd, J 8.22 Hz, 1.76 Hz, 1H), 8.10 (d, J=1.96 Hz, 1H).

Intermediate 234b: 5-Bromo-4'-(bromomethyl)-[1,1'-biphenyl]-2-carbonitrile

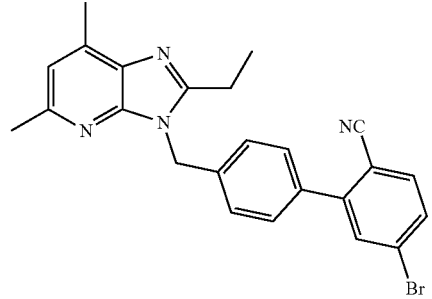

(234b)

Method A: A mixture of 4-bromo-2-iodobenzonitrile (0.300 g, 0.974 mmol), 2-ethyl-5,7-dimethyl-3-(4-(4,4,5,5-tetramethyl-1,3,2-dioxaborolan-2-yl)benzyl)-3H-imidazo[4,5-b]pyridine (001d, 0.419 g, 1.072 mmol) and K$_2$CO$_3$ (0.539 g, 3.900 mmol) in 1,4-dioxane and H$_2$O (2:1, 15 mL) was purged with a stream of N$_2$ for 10 min and then Pd(Ph$_3$P)$_4$ (0.113 g, 0.097 mmol) was added. The reaction vial was then sealed and the mixture was stirred at 95° C. for 3 h. The cooled reaction mixture was then diluted with EtOAc (50 mL) and the organic layer was washed (H$_2$O, brine), dried (Na$_2$SO$_4$) and evaporated to dryness. The crude residue obtained was purified by flash chromatography (ISCO/0 to 100% EtOAc-hexane) to give the title compound (0.270 g, 0.650 mmol, 89% yield) as a white foam. LC-MS (Method H): 1.354 min, (M+H)=445.5; $^1$H NMR (400 MHz, DMSO-d$_6$) δ ppm 7.71-7.94 (m, 3H), 7.54 (d, J=8.22 Hz, 2H), 7.24 (d, J=8.2 Hz, 2H), 6.94 (s, 1H), 5.53 (s, 2H) 2.80 (q, J=7.43 Hz, 2H), 2.50 (hidden, 6H), 1.23 (t, J=7.43 Hz, 3H).

Method B: To an ice-cold solution of 2-ethyl-5,7-dimethyl-3H-imidazo[4,5-b]pyridine (001c, 2.00 g, 11.41 mmol) in dry DMF (40 mL) was added NaH (60% in oil, 0.593 g, 14.84 mmol). The resulting brown mixture was stirred for 5 min and then the cooling bath was removed and stirring was continued at RT for 1 h. The resulting brown solution was re-cooled at 0° C. and a solution of 5-bromo-4'-(bromomethyl)-[1,1'-biphenyl]-2-carbonitrile (I-001, 4.41 g, 12.55 mmol) in dry DMF (30 mL) was added dropwise. The reaction mixture was then stirred at RT for 3 h, before being poured into ice-H₂O (100 mL) containing saturated aqueous NH₄Cl (50 mL) and vigorously stirring. This suspension was then extracted with DCM (100 mL) and the organic phase was washed (50% brine), dried (Na₂SO₄) and evaporated to give a pale amber gum. This gum was purified by flash chromatography (ISCO/0-100% EtOAc-hexane) to afford 5-bromo-4'-((2-ethyl-5,7-dimethyl-3H-imidazo[4,5-b]pyridin-3-yl)methyl)-[1,1'-biphenyl]-2-carbonitrile (3.01 g, 59% yield) as a white solid. This material was identical (LC-MS, ¹H NMR) with the material prepared by Method A above.

Intermediate 234c: 4'-((2-Ethyl-5,7-dimethyl-3H-imidazo[4,5-bipyridin-3-yl)methyl)-5-((trimethylsilyl)ethynyl)-[1,1'-biphenyl]-2-carbonitrile

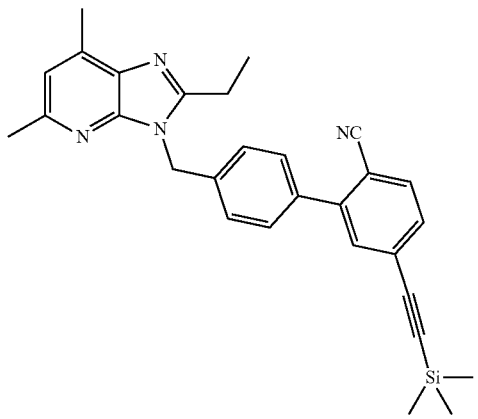

(234c)

In a 50 mL vial was added 5-bromo-4'-((2-ethyl-5,7-dimethyl-3H-imidazo[4,5-b]pyridin-3-yl)methyl)-[1,1'-biphenyl]-2-carbonitrile (1.00 g, 2.245 mmol) in THF (10 mL) and TEA (20 mL) to give a colorless solution. This mixture was degassed with a stream of N₂ for 5 min and then [Pd(PPh₃)₂Cl₂] (0.079 g, 0.112 mmol) and copper (I) iodide (0.043 g, 0.225 mmol) were added. To this mixture was added ethynyltrimethylsilane (1.598 mL, 11.230 mmol) dropwise and then it was stirred at 70° C. for 2 h. The reaction mixture was then cooled to RT and the volatiles were removed under reduced pressure. The residue was taken up in EtOAc (50 mL) and the mixture was filtered through a pad of Celite®, which was then washed with additional EtOAc (50 mL). The filtrate was evaporated to dryness and the residue was purified by flash chromatography (ISCO, 0 to 100% EtOAc-hexane) to afford 4'-((2-ethyl-5,7-dimethyl-3H-imidazo[4,5-b]pyridin-3-yl)methyl)-5-((trimethylsilyl)ethynyl)-[1,1'-biphenyl]-2-carbonitrile (0.600 g, 1.297 mmol, 57.8% yield) as a light brown oil. LC-MS (Method H): 1.553 min, (M+H)=463.2; ¹H NMR (400 MHz, DMSO-d₆) δ ppm 7.91 (d, J=8.2 Hz, 1H), 7.49-7.62 (m, 4H), 7.23 (d, J=8.2 Hz, 2H), 6.95 (s, 1H), 5.53 (s, 2H), 2.80 (q J=7.4 Hz, 2H), 2.51 (hidden, 6H), 1.23 (t, J=7.4 Hz, 3H), 0.22 (s, 9H).

Intermediate 234d: 4'-((2-Ethyl-5,7-dimethyl-3H-imidazo[4,5-b]pyridin-3-yl)methyl)-5-ethynyl-[1,1'-biphenyl]-2-carbonitrile

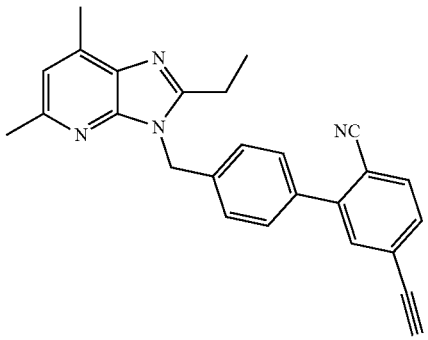

(234d)

To a solution of 4'-((2-ethyl-5,7-dimethyl-3H-imidazo[4,5-b]pyridin-3-yl)methyl)-5-((trimethylsilyl)ethynyl)-[1,1'-biphenyl]-2-carbonitrile (0.600 g, 1.297 mmol) in THF (15 mL) and MeOH (15 mL) was added K₂CO₃ (0.538 g, 3.890 mmol) and the mixture was stirred at RT for 3 h. The resulting mixture was filtered through a pad of Celite®, which was subsequently washed with EtOAc (100 mL). The filtrate was evaporated to dryness to provide 4'-((2-ethyl-5,7-dimethyl-3H-imidazo[4,5-b]pyridin-3-yl)methyl)-5-ethynyl-[1,1'-biphenyl]-2-carbonitrile (0.535 g, 1.232 mmol, 95% yield) as a brown foam which was used as such in the next step. LC-MS (Method H): 1.310 min, [M+H]⁺=391.1; ¹H NMR (400 MHz, CDC₃) δ7.71 (d, J=8.2 Hz, 1H), 7.58 (d, J=1.2 Hz, 1H), 7.50-7.54 (m, 1H), 7.45-7.50 (m, 2H), 7.25 (d, J=8.2 Hz, 2H), 6.92 (s, 1H), 5.53 (s, 2H), 3.48 (s, 1H), 2.83 (q, J=7.4 Hz, 2H), 2.66 (s, 3H), 2.61 (s, 3H), 1.34 (t, J=7.4 Hz, 3H).

Intermediate 234e: 5-(1-Ethyl-1H-1,2,3-triazol-4-yl)-4'-((2-ethyl-5,7-dimethyl-3H-imidazo[4,5-bipyridin-3-yl)methyl)-[1,1'-biphenyl]-2-carbonitrile

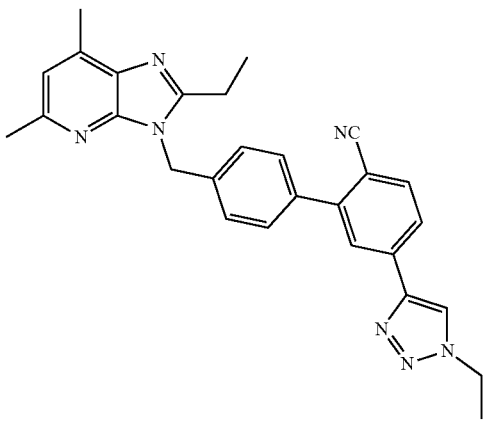

(234e)

To a mixture of 4'-((2-ethyl-5,7-dimethyl-3H-imidazo[4,5-b]pyridin-3-yl)methyl)-5-ethynyl-[1,1'-biphenyl]-2-carbonitrile (0.030 g, 0.077 mmol) and excess azidoethane [prepared by reacting a solution of bromoethane (0.250 g, 2.294 mmol) and sodium azide (0.373 g, 5.740 mmol) in 5 mL of DMSO for 4 h at RT; the mixture was filtered and the DMSO solution of the alkyne was used as such] in DMSO (4 mL) and H$_2$O (2 mL) was added sodium ascorbate (0.0034 g, 0.015 mmol) and CuSO$_4$.5H$_2$O (0.0013 g, 0.004 mmol). The reaction was stirred at RT for 16 h and then it was poured into a mixture of saturated aqueous NH$_4$Cl (10 mL) and EtOAc (25 mL). The aqueous layer was separated and re-extracted with EtOAc (30 mL) and then the combined organic extract was washed (H$_2$O and brine), dried (Na$_2$SO$_4$) and evaporated to provide 5-(1-ethyl-1H-1,2,3-triazol-4-yl)-4'-((2-ethyl-5,7-dimethyl-3H-imidazo[4,5-b]pyridin-3-yl)methyl)-[1,1'-biphenyl]-2-carbonitrile (0.025 g, 0.054 mmol, 70.5% yield) as an oil which was used as such for the next reaction. LC-MS (Method H): 1.272 min, (M+H)=462.2.

Example 234: 2-Ethyl-3-((5'-(1-ethyl-1H-1,2,3-triazol-4-yl)-2'-(1H-tetrazol-5-yl)-[1,1'-biphenyl]-4-yl)methyl)-5,7-dimethyl-3H-imidazo[4,5-b]pyridine To a mixture of 5-(1-ethyl-1H-1,2,3-triazol-4-yl)-4'-((2-ethyl-5,7-dimethyl-3H-imidazo[4,5-b]pyridin-3-yl)methyl)-[1,1'-biphenyl]-2-carbonitrile (0.025 g, 0.054 mmol), TMS-N$_3$ (0.151 mL, 1.083 mmol) and dibutyltin oxide (0.0275 g, 0.108 mmol) was added toluene (2 mL), the vial was briefly purged with N$_2$ and then it was sealed and heated at 120° C. for 16 h. The cooled mixture was evaporated to give a gum which was purified by preparative LC (Method F) to give the title compound (0.007 g, 25.6% yield) as a white solid. HRMS (ESI): Calcd. for C$_{30}$H$_{28}$N$_7$O [M+H]$^+$ m/z 505.2571; found 505.2584. $^1$H NMR (400 MHz, DMSO-d$_6$) δ ppm 8.74 (s, 1H), 7.95 (br s, 1H), 7.86 (br s, 1H), 7.72 (br s, 1H), 7.08-7.15 (m, 1H), 7.04 (br s, 2H), 6.95 (s, 1H), 6.53 (s, 1H), 5.46 (s, 2H), 4.43 (q, J=7.4 Hz, 2H), 2.78 (q, J=7.7 Hz, 3H), 2.54 (hidden, 6H), 1.55 (t, J=7.4 Hz, 4H), 1.25 (t, J=7.7 Hz, 3H).

The following examples have been similarly prepared from 4'-((2-ethyl-5,7-dimethyl-3H-imidazo[4,5-b]pyridin-3-yl)methyl)-5-ethynyl-[1,1'-biphenyl]-2-carbonitrile (Intermediate 234d) as described for the synthesis of Example 234 above. Two analytical LC-MS injections were used to determine the final purity. The retention time of one of them is reported for each compound and is referred as Method H.

| Ex | Structure | MW | LC-MS m/z [M + H]$^+$; RT (Method H) | $^1$H NMR (400 MHz, DMSO-d$_6$) δ ppm |
|---|---|---|---|---|
| 235 | 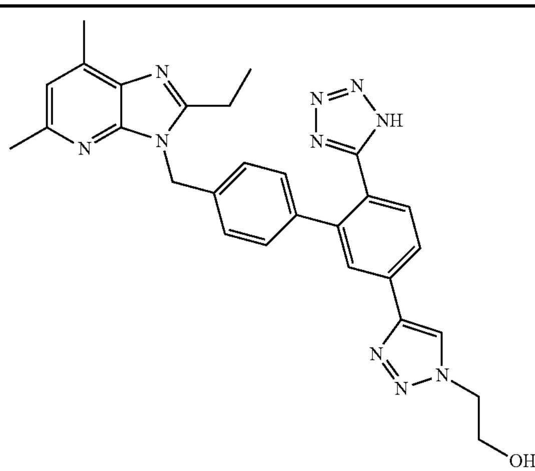 | 520.5 | 521.2; 1.161 min | 8.75 (s, 1H), 8.04 (d, J = 7.8 Hz, 1H), 7.97 (s, 1H), 7.74 (d, J = 7.8 Hz, 1H), 7.03-7.14 (m, 4H), 6.96 (s, 1H), 5.47 (s, 2H), 5.08 (t, J = 5.3 Hz, 1H), 4.46 (t, J = 5.3 Hz, 2H), 3.79-3.87 (m, 2H), 2.77 (q, J = 7.4 Hz, 2H), 2.55 (s, 6H), 1.23 (t, J = 7.4 Hz, 3H). |
| 236 | 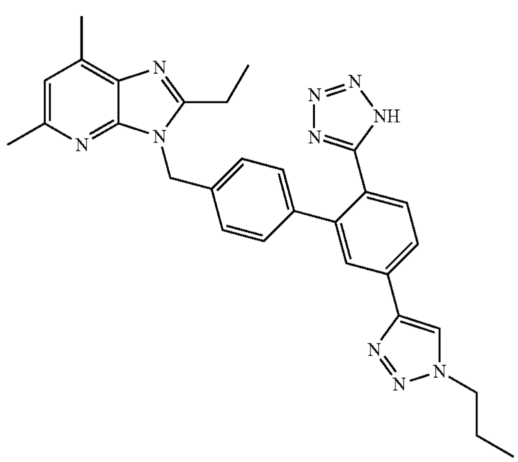 [SMILES: CCCn1cc(-c2ccc(-c3nnn[nH]3)c(-c3ccc(Cn4c(CC)nc5c(C)cc(C)nc54)cc3)c2)nn1] | 518.6 | 519.30; 1.241 min | 8.75 (s, 1H), 7.98 (d, J = 7.8 Hz, 1H), 7.90 (s, 1H), 7.72 (d, J = 7.8 Hz, 1H), 7.01-7.18 (m, 4 H), 6.95 (s, 1H), 6.53 (s, 1H), 5.46 (s, 2H), 4.37 (t, J = 6.8 Hz, 2H), 2.78 (q, J = 7.4 Hz, 2H), 2.50 (s, 6 H), 1.78-1.93 (m, 2H), 1.24 (t, J = 7.4 Hz, 6H). |

| Ex | Structure | MW | LC-MS m/z [M + H]+; RT (Method H) | 1H NMR (400 MHz, DMSO-d6) δ ppm |
|---|---|---|---|---|
| 237 | 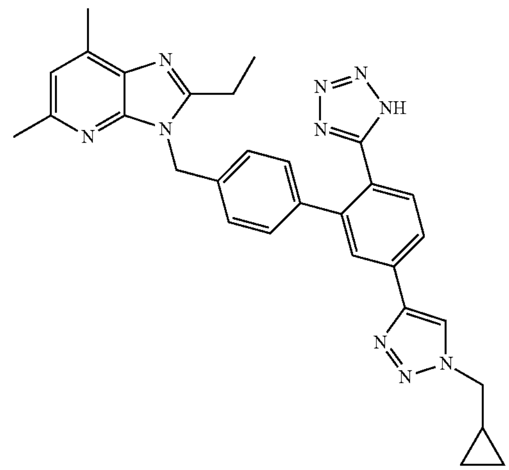 [SMILES: CCc1nc2c(C)cc(C)nc2n1Cc1ccc(-c2cc(-c3cn(CC4CC4)nn3)ccc2-c2nnn[nH]2)cc1] | 530.58 | 531.30; 1.25 min | (MeOH-d4) 8.55 (s, 1H), 7.92-8.04 (m, 2H), 7.73 (d, J = 8.6 Hz, 1H), 7.20 (d, 7 = 8.2 Hz, 2H), 7.10 (d, J = 8.2 Hz, 2H), 7.04 (s, 1H), 5.57 (s, 2H), 4.33 (d, J = 7.0 Hz, 2H), 2.87 (q, J = 7.4 Hz, 2H), 2.54 (s, 3H), 2.69 (s, 3H), 1.40 (m, 1H), 1.27 (t, J = 7.6 Hz, 3H), 0.64-0.75 (m, 2H), 0.47-0.56 (m, 2H). |
| 238 | 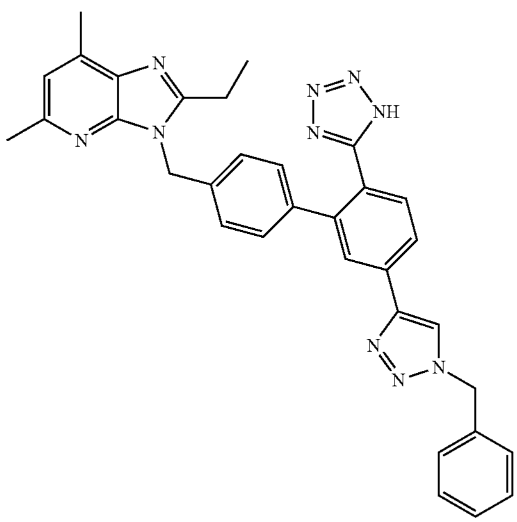 [SMILES: CCc1nc2c(C)cc(C)nc2n1Cc1ccc(-c2cc(-c3cn(Cc4ccccc4)nn3)ccc2-c2nnn[nH]2)cc1] | 566.5 | 567.2; 1.292 min | (MeOH-d4) 8.52 (s, 1 H), 7.97-8.06 (m, 2H), 7.75 (d, J = 8.2 Hz, 1H), 7.36-7.44 (m, 3 H), 7.32 (s, 1H), 7.28 (d, J = 8.2 Hz, 2H), 7.20 (d, J = 8.2 Hz, 2H), 5.74 (s, 2H), 5.68 (s, 2H), 3.12 (d, J = 7.4 Hz, 2H), 2.67 (s, 6H), 1.33 (t, J = 7.4 Hz, 3H). |
| 239 | 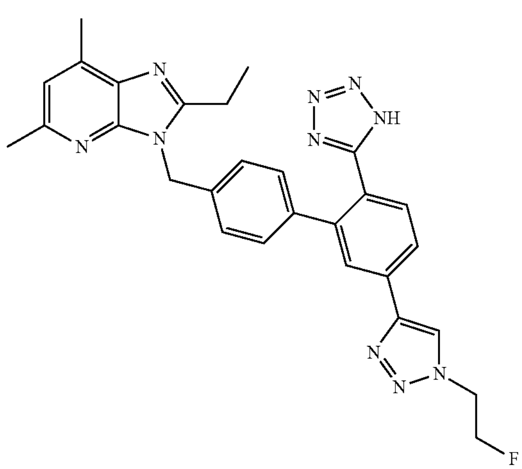 [SMILES: CCc1nc2c(C)cc(C)nc2n1Cc1ccc(-c2cc(-c3cn(CCF)nn3)ccc2-c2nnn[nH]2)cc1] | 522.5 | 523.20; 1.186 min | (MeOH-d4) 8.52 (s, 1 H), 8.29 (br. s., 1H), 7.88-8.00 (m, 2H), 7.70 (d, J = 7.8 Hz, 1H), 7.16 (d, J = 7.8 Hz, 2H), 7.06 (m, 2H), 5.56 (s, 2H), 4.91-4.99 (m, 1H) 4.72-4.86 (m, 3H), 2.87 (q, J = 7.4 Hz, 2H), 2.62 (s, 3H), 2.59 (s, 3H), 1.27 (t, J = 7.4 Hz, 3H). |

| Ex | Structure | MW | LC-MS m/z [M + H]+; RT (Method H) | 1H NMR (400 MHz, DMSO-d6) δ ppm |
|---|---|---|---|---|
| 240 | 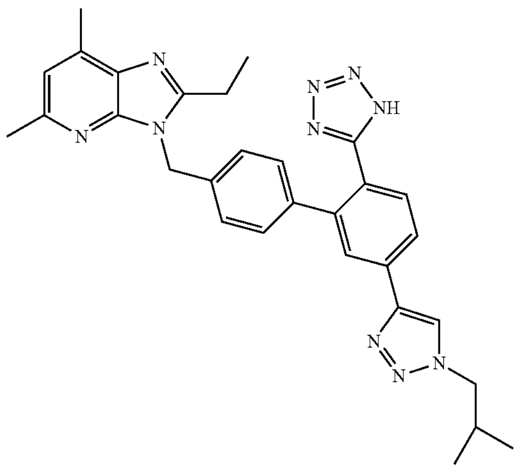 [SMILES: CCc1nc2c(C)cc(C)nc2n1Cc1ccc(-c2cc(-c3cn(CC(C)C)nn3)ccc2-c2nnn[nH]2)cc1] | 532.6 | 533.2 1.313 min | (MeOH-d4) 8.47 (s, 1H), 7.91-8.01 (m, 2H), 7.70 (d, J = 7.8 Hz, 1H), 7.11-7.20 (m, 2H), 7.00-7.11 (m, 3H), 5.56 (s, 2H), 4.29 (d, J = 7.4 Hz, 2H), 2.87 (q, J = 7.7 Hz, 3H), 2.62 (s, 3H), 2.59 (s, 3H), 2.22-2.34 (m, 2H), 1.27 (t, J = 7.4 Hz, 3H), 0.93 - 1.01 (m, 6H). |
| 241 | 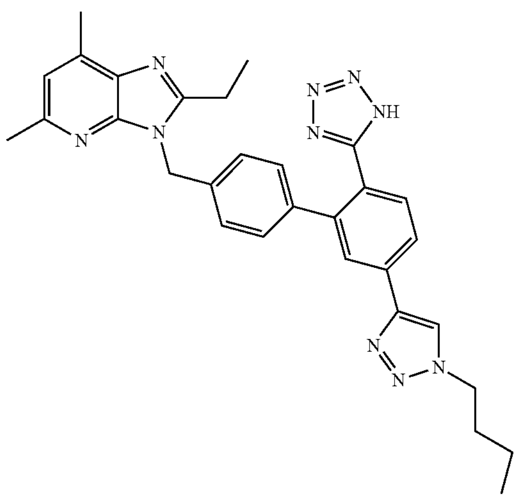 [SMILES: CCCCn1cc(-c2ccc(-c3nnn[nH]3)c(-c3ccc(Cn4c(CC)nc5c(C)cc(C)nc54)cc3)c2)nn1] | 532.2 | 533.2; 1.313 min | (MeOH-d4) 8.48 (s, 1H), 7.94-7.99 (m, 2H), 7.70 (d, J = 7.8 Hz, 1H), 7.13-7.19 (d, J = 8.2 Hz, 2H), 7.05-7.11 (m, J = 8.2 Hz, 2H), 7.04 (s, 1H), 5.56 (s, 2H), 4.48 (m, 2H), 2.87 (q, J = 7.4 Hz, 2H), 2.59 (s, 3H), 2.62 (s, 3H), 1.92-2.00 (m, 2H), 1.40 (dd, J = 7.04, 14.87 Hz, 2H), 1.27 (t, J = 7.4 Hz, 2H), 1.00 (t, J = 7.4 Hz, 3H). |
| 242 | 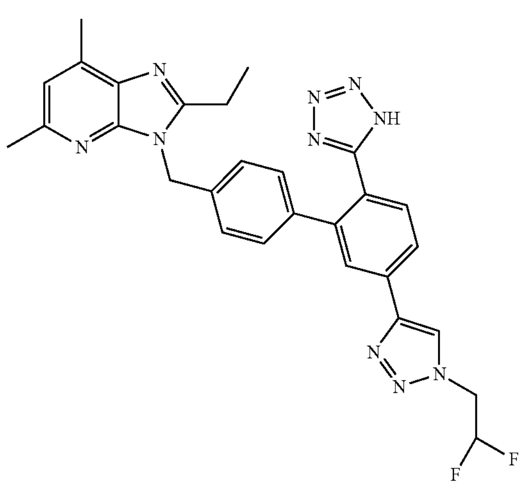 [SMILES: CCc1nc2c(C)cc(C)nc2n1Cc1ccc(-c2cc(-c3cn(CC(F)F)nn3)ccc2-c2nnn[nH]2)cc1] | 540.2 | 541.2; 1.200 min | 8.81 (s, 1H), 7.97 (s, 1H), 7.75 (d, J = 7.8 Hz, 1H), 7.13 (d, J = 8.2 Hz, 1H), 7.06 (d, J = 8.2 Hz, 1H), 6.95 (s, 1H), 6.53 (t, J = 64.0 Hz 1H), 5.47 (s, 1H), 5.02 (dt, J = 3.1, 15.8 Hz, 2H), 2.78 (q, J = 7.4 Hz, 1H), 2.50 (hidden, 6H), 1.24 (t, J = 1.4 Hz, 2H) |

Example 243: 2-Ethyl-5,7-dimethyl-3-((5'-(1-methyl-1H-1,2,3-triazol-4-yl)-2'-(1H-tetrazol-5-yl)-[1,1'-biphenyl]-4-yl)methyl)-3H-imidazo[4,5-b]pyridine (Ex. 243)

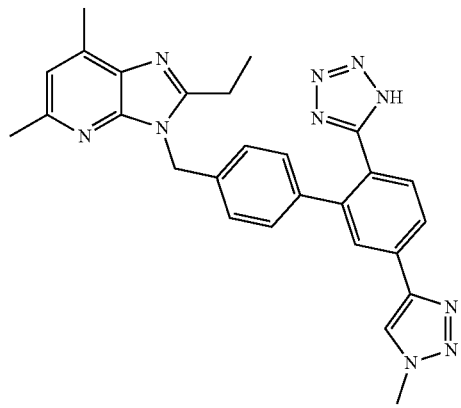

Intermediate 243a: 4'-((2-Ethyl-5,7-dimethyl-3H-imidazo[4,5-b]pyridin-3-yl)methyl)-5-(1-((trimethylsilyl)methyl)-1H-1,2,3-triazol-4-yl)-[1,1'-biphenyl]-2-carbonitrile (242a)

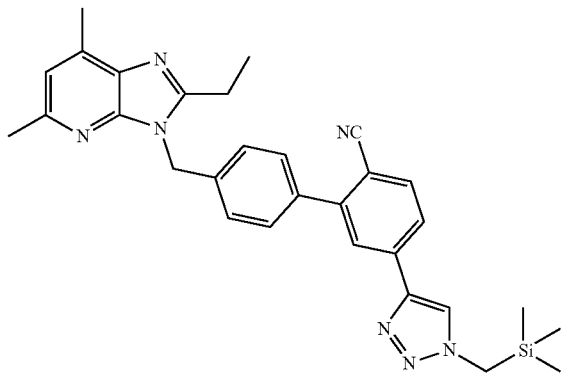

To a mixture of 4'-((2-ethyl-5,7-dimethyl-3H-imidazo[4,5-b]pyridin-3-yl)methyl)-5-ethynyl-[1,1'-biphenyl]-2-carbonitrile (Intermediate 234d, 0.030 g, 0.077 mmol) and (azidomethyl)trimethylsilane (0.0198 g, 0.154 mmol) in t-BuOH-H$_2$O (3:1) was added sodium ascorbate (0.006 g, 0.031 mmol) and CuSO$_4$·5H$_2$O (0.0014 g, 0.008 mmol). The reaction mixture was stirred at RT for 16 h and then it was poured into saturated aqueous NH$_4$Cl (10 mL). The resulting mixture was extracted with EtOAc (25 mL) and the organic phase was washed (H$_2$O, brine), dried (Na$_2$SO$_4$) and evaporated to dryness to afford 4'-((2-ethyl-5,7-dimethyl-3H-imidazo[4,5-b]pyridin-3-yl)methyl)-5-(1-((trimethylsilyl)methyl)-1H-1,2,3-triazol-4-yl)-[1,1'-biphenyl]-2-carbonitrile (0.030 g, 0.077 mmol, 75% yield). LC-MS (Method H): 1.339 min, [M+H]$^+$=520.2. This material was used as such for next reaction.

Intermediate 243b: 4'-((2-Ethyl-5,7-dimethyl-3H-imidazo[4,5-b]pyridin-3-yl)methyl)-5-(1-methyl-1H-1,2,3-triazol-4-yl)-[1,1'-biphenyl]-2-carbonitrile (243b)

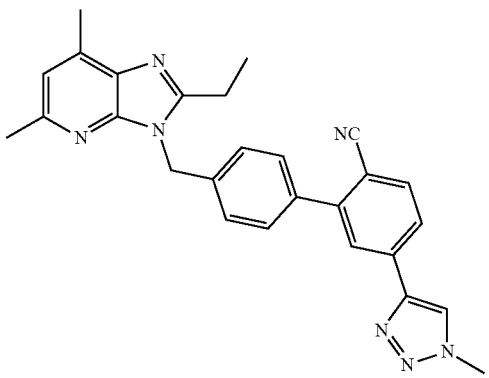

To an ice-cold solution of 4'-((2-ethyl-5,7-dimethyl-3H-imidazo[4,5-b]pyridin-3-yl)methyl)-5-(1-((trimethylsilyl)methyl)-1H-1,2,3-triazol-4-yl)-[1,1'-biphenyl]-2-carbonitrile (0.030 g, 0.058 mmol) in THF (4 mL) was added TBAF (iM in THF, 0.231 mL, 0.231 mmol). The reaction mixture was stirred at RT for 1 h before being quenched with saturated aqueous NH$_4$Cl (5 mL). This mixture was extracted with EtOAc (25 mL) and the organic extract was separated, dried (Na$_2$SO$_4$) and evaporated to dryness. The crude the residual gum obtained was purified by preparative LC (Method F) to provide 4'-((2-ethyl-5,7-dimethyl-3H-imidazo[4,5-b]pyridin-3-yl)methyl)-5-(1-methyl-1H-1,2,3-triazol-4-yl)-[1,1'-biphenyl]-2-carbonitrile (0.015 g, 0.034 mmol, 58% yield). LC-MS (Method H): 1.262 min, [M+H]$^+$= 448.2.

Example 243: 2-Ethyl-5,7-dimethyl-3-((5'-(1-methyl-1H-1,2,3-triazol-4-yl)-2'-(1H-tetrazol-5-yl)-[1,1'-biphenyl]-4-yl)methyl)-3H-imidazo[4,5-b]pyridine To a mixture of 4'-((2-ethyl-5,7-dimethyl-3H-imidazo[4,5-b]pyridin-3-yl)methyl)-5-(1-methyl-1H-1,2,3-triazol-4-yl)-[1,1'-biphenyl]-2-carbonitrile (0.015 g, 0.034 mmol), TMS-N$_3$ (0.094 mL, 0.670 mmol) and dibutyltin oxide (0.017 g, 0.067 mmol) was added toluene (2 mL), the vial was briefly purged with N$_2$ and then it was sealed and the mixture was stirred at 120° C. for 16 h. The cooled mixture was evaporated to give a gum which was purified by preparative LC (Method F) to afford the title compound (0.006 g, 36.5% yield) as a white solid. HRMS (ESI): Calcd. for C$_{27}$H$_{27}$N$_{10}$[M+H]$^+$ m/z 491.2420; found 491.2498. $^1$H NMR (400 MHz, MeOH-d$_4$) δ ppm 8.45 (s, 1H), 7.94-8.05 (m, 2H), 7.76 (d, J=7.8 Hz, 1H), 7.48 (s, 1H), 7.15-7.34 (m, 4H), 5.72 (s, 2H), 4.19 (s, 3H), 3.11 (q, J=7.4 Hz, 2H), 2.60 (s, 3H), 2.71 (s, 3H), 1.32 (t, J=7.4, 3H).

Example 244: 4"-((2-Ethyl-5,7-dimethyl-3H-imidazo[4,5-b]pyridin-3-yl)methyl)-N-(methylsulfonyl)-[1,1':3',1"-terphenyl]-4'-carboxamide

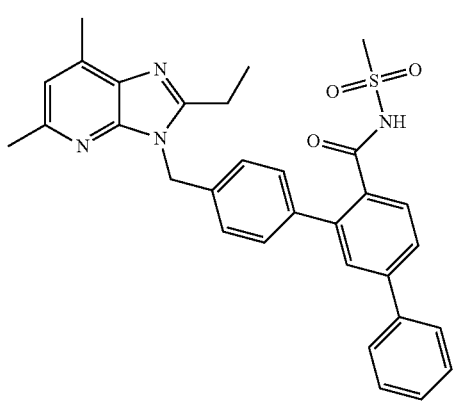

(Ex. 244)

A solution of 4"-((2-ethyl-5,7-dimethyl-3H-imidazo[4,5-b]pyridin-3-yl)methyl)-[1,1':3',1"-terphenyl]-4'-carboxylic acid (Ex. 031, 0.030 g, 0.065 mmol) in DMF (1 mL) was treated with HATU (0.023 g, 0.078 mmol), followed by methanesulfonamide (0.007 g, 0.078 mmol) and Hünig's Base (0.023 mL, 0.130 mmol). After stirring at RT for 18 h the solution was poured into H$_2$O (3 mL) and extracted with EtOAc (20 mL). The EtOAc layer was washed with H$_2$O and brine, dried (Na$_2$SO$_4$) and concentrated. The crude residual gum was purified by preparative LC (Method F) to afford the title compound (0.008 g, 0.015 mmol, 22.3% yield). LC-MS (Method H): 1.324 min, (M+H)=539.2; $^1$H NMR (400 MHz, CDCl$_3$) δ ppm 7.89 (d, J=7.8 Hz, 1H), 7.69 (dd, J=8.2, 1.6 Hz, 1H), 7.61 (d, J=7.4 Hz, 2H), 7.57 (s, 1H), 7.44-7.50 (m, 2H), 7.37-7.44 (m, 3H), 7.23-7.29 (m, 2H), 6.91 (s, 1H), 5.55 (s, 2H), 3.13 (s, 3H), 2.84 (q, J=7.4 Hz, 2H), 2.65 (s, 3H), 2.60 (s, 3H), 1.37 (t, J=7.4 Hz, 3H).

Example 245: 3-(4"-((2-Ethyl-5,7-dimethyl-3H-imidazo[4,5-b]pyridin-3-yl)methyl)-[1,1':3',1"-terphenyl]-4'-yl)-1,2,4-thiadiazol-5(4H)-one

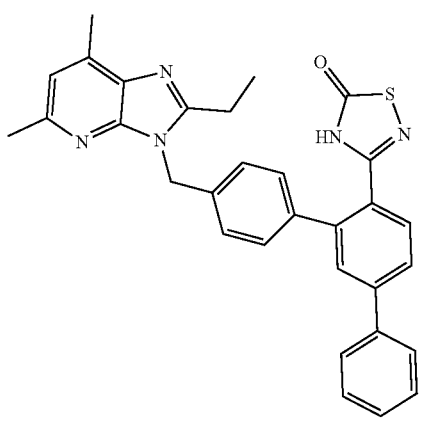

(Ex. 245)

Intermediate: 245a: (Z)-4"-((2-Ethyl-5,7-dimethyl-3H-imidazo[4,5-b]pyridin-3-yl)methyl)-N'-hydroxy-[1,1':3',1"-terphenyl]-4'-carboximidamide

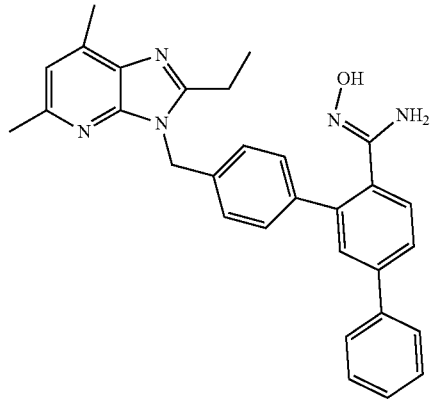

(245a)

Hydroxylamine hydrochloride (0.785 g, 11.30 mmol) was added to a vial containing 4"-((2-ethyl-5,7-dimethyl-3H-imidazo[4,5-b]pyridin-3-yl)methyl)-[1,1':3',1"-terphenyl]-4'-carbonitrile (032b, 0.200 g, 0.452 mmol) and 1-butyl-3-methylimidazolium acetate (3.00 g, 15.13 mmol). This mixture was heated at 50° C. for 18 h and then it was allowed to cool to RT. DMSO (1 mL) was added, followed by H$_2$O (0.5 mL) and formic acid (0.06 mL, 15.13 mmol) to acidify to a pH of about 4. The solution was submitted to purification by preparative LC (Method F) to provide (Z)-4"-((2-ethyl-5,7-dimethyl-3H-imidazo[4,5-b]pyridin-3-yl)methyl)-N'-hydroxy-[1,1':3',1"-terphenyl]-4'-carboximidamide (0.120 g, 0.252 mmol, 55.8% yield). LC-MS (Method H): 1.229 min, (M+H)=476.2; $^1$H NMR (400 MHz, CDCl$_3$) δ ppm 7.53-7.68 (m, 5H), 7.41-7.49 (m, 4H), 7.34-7.40 (m, 1H), 7.20 (d, J=7.8 Hz, 2H), 6.92 (s, 1H), 5.51 (s, 2H), 4.48 (br s, 2H), 4.48 (br s, 2H), 2.83 (q, J=7.4 Hz, 2H), 2.65 (s, 3H), 2.61 (s, 3H), 1.32 (t, J=7.4 Hz, 3H).

Example 245: 3-(4"-((2-Ethyl-5,7-dimethyl-3H-imidazo[4,5-b]pyridin-3-yl)methyl)-[1,1':3',1"-terphenyl]-4'-yl)-1,2,4-thiadiazol-5(4H)-one To a solution of (Z)-4"-((2-ethyl-5,7-dimethyl-3H-imidazo[4,5-b]pyridin-3-yl)methyl)-N'-hydroxy-[1,1':3',1"-terphenyl]-4'-carboximidamide (0.100 g, 0.210 mmol) in anhydrous THF (2 mL), at RT under N$_2$, was added di(1H-imidazol-1-yl)methanethione (0.056 g, 0.315 mmol) and the solution was stirred at 35° C. for 1 h. The reaction was then quenched with H$_2$O and extracted with EtOAc (25 mL). The organic extract was dried (Na$_2$SO$_4$) filtered, and evaporated to dryness. The crude residue obtained was dissolved in anhydrous THF (2 mL), then BF$_3$·OEt$_2$ (0.167 mL, 0.631 mmol) was added dropwise and the resulting mixture was stirred at RT for 16 h. The resulting mixture was diluted with H$_2$O and extracted with CH$_2$Cl$_2$ (25 mL). The organic extract was washed (1M HCQ), dried (Na$_2$SO$_4$) and evaporated under reduced pressure. The residual gum obtained was taken up in DMF (1.8 mL) and purified by preparative LC (Method F) to give the title compound (0.013 g, 0.027 mmol, 13% yield) as a white solid. LC-MS (Method H): 1.374 min, (M+H)=518.1; $^1$H NMR (400 MHz, DMSO-d$_6$) δ ppm 7.99 (d, J=7.8 Hz, 1H), 7.83-7.87 (m, 1H), 7.76-7.83

(m, 3H), 7.63 (d, J=8.2 Hz, 2H), 7.37-7.51 (m, 3H), 7.29 (d, J=8.2 Hz, 2H) 6.99 (s, 1H), 5.57 (s, 2H), 2.86 (q, J=7.4 Hz, 2H), 2.51 (s, 6H), 1.25 (t, J=7.4 Hz, 3H).

Example 246: 5-(4"-((2-Ethyl-5,7-dimethyl-3H-imidazo[4,5-b]pyridin-3-yl)methyl)-[1,1':3',1"-terphenyl]-4'-yl)-1,3,4-oxadiazole-2(3H)-thione

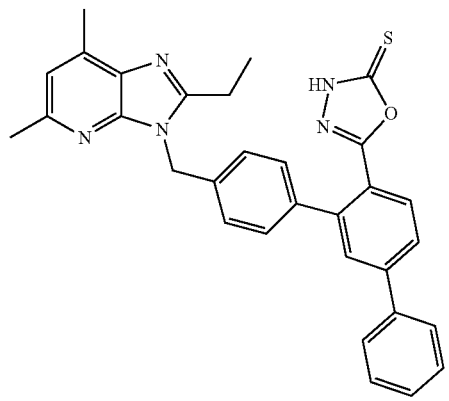

(Ex. 246)

Intermediate 246a: 4"-((2-Ethyl-5,7-dimethyl-3H-imidazo[4,5-b]pyridin-3-yl)methyl)-[1,1':3',1"-terphenyl]-4'-carbohydrazide

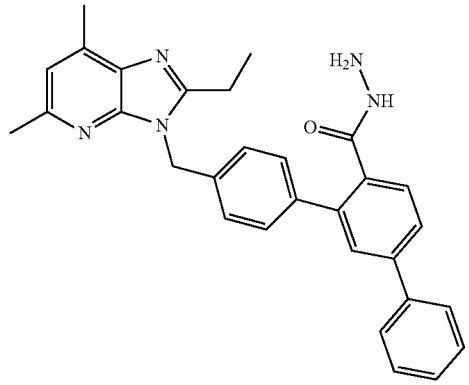

(246a)

To a mixture of 4"-((2-ethyl-5,7-dimethyl-3H-imidazo[4,5-b]pyridin-3-yl)methyl)-[1,1':3',1"-terphenyl]-4'-carboxylic acid (Ex. 031, 0.100 g, 0.217 mmol), HATU (0.099 g, 0.260 mmol), and hydrazine (1.0M in THF, 0.260 mL, 0.260 mmol) in DMF (1.30 mL) was added Hünig's base (0.076 mL, 0.433 mmol) and the mixture was stirred at RT for 18 h. The resulting mixture was poured into $H_2O$ (3 mL) and was extracted with EtOAc (25 mL). The organic extract was washed ($H_2O$, brine), dried ($Na_2SO_4$) and evaporated to dryness. The residue obtained was purified by prep LC (Method F) to give 4"-((2-ethyl-5,7-dimethyl-3H-imidazo[4,5-b]pyridin-3-yl)methyl)-[1,1':3',1"-terphenyl]-4'-carbohydrazide (0.081 g, 0.170 mmol, 79% yield). LC-MS (Method H): 1.344 min, (M+H)=476.2; $^1$H NMR (400 MHz, $CDCl_3$) δ ppm 8.03 (s, 1H), 7.70-7.77 (m, 1H), 7.65 (dd, J=8.0, 1.8 Hz, 1H), 7.59-7.63 (m, 2H), 7.55 (d, J=1.6 Hz, 1H), 7.43-7.50 (m, 2H), 7.36-7.43 (m, 3H), 7.21 (d, J=7.8 Hz, 2H), 6.93 (s, 1H), 5.53 (s, 2H), 2.97 (s, 1H), 2.90 (s, 1H), 2.78-2.89 (m, 2H), 2.65 (s, 3H), 2.62 (s, 3H), 1.34 (t, J=7.4 Hz, 3H).

Example 246: 5-(4"-((2-Ethyl-5,7-dimethyl-3H-imidazo[4,5-b]pyridin-3-yl)methyl)-[1,1':3',1"-terphenyl]-4'-yl)-1,3,4-oxadiazole-2(3H)-thione To a solution of 4"-((2-ethyl-5,7-dimethyl-3H-imidazo[4,5-b]pyridin-3-yl)methyl)-[1,1':3',1"-terphenyl]-4'-carbohydrazide (0.015 g, 0.032 mmol) in ethanol (0.2 mL) was added $CS_2$ (0.002 mL, 0.033 mmol) and KOH (0.002 g, 0.032 mmol) at 0° C. The resulting solution was heated at reflux for 12 h and then the volatiles were removed under reduced pressure and the residue was dissolved in $H_2O$ and the solution was acidified with dilute aqueous HCl. This mixture was evaporated and the residual gum was submitted to prep LC (Method F) to give the title compound (0.0073 g, 0.014 mmol, 10 44.7% yield). LC-MS (Method H): 1.495 min, (M+H)=518.1, $^1$H NMR (400 MHz, $CDCl_3$) δ ppm 7.95 (d, J=8.2 Hz, 1H), 7.72 (d, J=7.8 Hz, 1H), 7.59-7.68 (m, 3H), 7.38-7.52 (m, 3H), 7.30 (d, J=7.8 Hz, 2H), 7.17 (d, J=7.4 Hz, 2H), 6.93 (s, 1H), 5.52 (br s, 2H), 2.77 (q, J=7.4 Hz, 2H), 2.60 (s, 3H), 2.56 (s, 3H), 1.04 (t, J=7.4 Hz, 3H).

Example 247: 2-Ethyl-5,7-dimethyl-3-((5'-(pyridin-2-yloxy)-2'-(1H-tetrazol-5-yl)-[1,1'-biphenyl]-4-yl)methyl)-3H-imidazo[4,5-b]pyridine

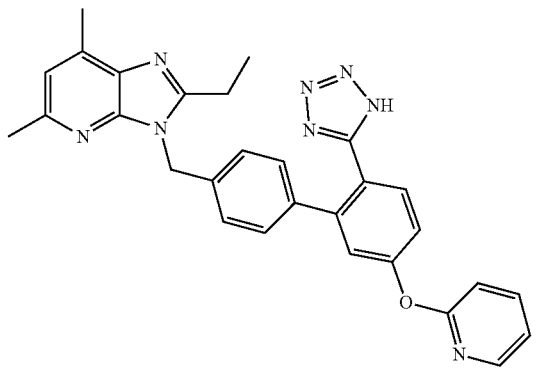

(Ex: 247)

Intermediate 247a: 4'-((2-Ethyl-5,7-dimethyl-3H-imidazo[4,5-b]pyridin-3-yl)methyl)-5-hydroxy-[1,1'-biphenyl]-2-carbonitrile

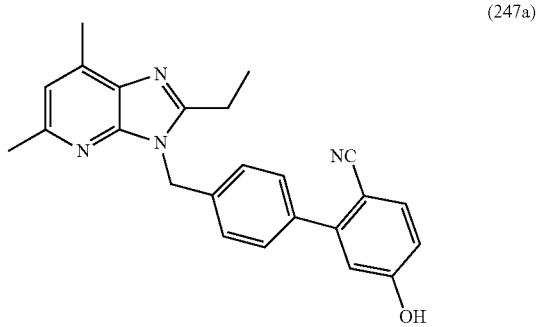 [SMILES: CCc1nc2c(C)cc(C)nc2n1Cc1ccc(-c2cc(O)ccc2C#N)cc1]

(247a)

In a 75-mL vial, a stream of Ar was passed through a mixture of Intermediate 001d (0.35 g, 0.89 mmol), 2-bromo-4-hydroxybenzonitrile (0.21 g, 1.07 mmol) and 2M $Na_2CO_3$ (1.3 mL, 2.7 mmol) in toluene (6 mL) and ethanol (0.6 mL). After 5 minutes, $Pd(PPh_3)_4$ (0.052 g, 0.045 mmol) was added, Ar was bubbled through the mixture for an additional 5 min and the sealed vial was heated at 95° C. for 16 h. The mixture was then allowed to cool to RT and saturated aqueous ammonium chloride (20 mL) and EtOAc (20 mL) were added. The aqueous layer was separated and extracted with EtOAc (2×20 mL), and the combined organic layers were washed with brine, dried (anhydrous $MgSO_4$), filtered and evaporated. The residue was triturated in DCM and the precipitate was filtered to afford the title compound (0.091 g). The mother liquor was evaporated and the residue was purified using a 24 g-RediSep column (ISCO/0-100% EtOAc-DCM) to afford another 0.069 g of the title compound which was combined with the material obtained from trituration to give 0.160 g (47% yield) of the desired product. LC-MS (Method H): 1.29 min, $[M+H]^+$=383.1. $^1$H NMR (400 MHz, DMSO-$d_6$) δ ppm 10.75 (br s, 1H), 7.71 (d, J=8.6 Hz, 1H), 7.47 (d, J=8.2 Hz, 2H), 7.22 (d, J=8.2 Hz, 2H), 6.94 (s, 1H), 6.89 (dd, J=8.6, 2.4 Hz, 1H), 6.85 (d, J=2.4 Hz, 1H), 5.52 (s, 2H), 2.80 (q, J=7.4 Hz, 2H), 2.51 (s, 6H), 1.24 (t, J=7.4 Hz, 3H).

Intermediate 247b: 4'-((2-Ethyl-5,7-dimethyl-3H-imidazo[4,5-b]pyridin-3-yl)methyl)-5-(pyridin-2-yloxy)-[1,1,1'-biphenyl]-2-carbonitrile (247b)

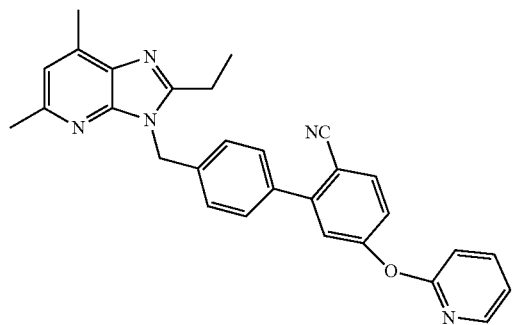

In a conical 2-mL vial, a stream of Ar was passed through a suspension of 4'-((2-ethyl-5,7-dimethyl-3H-imidazo[4,5-b]pyridin-3-yl)methyl)-5-hydroxy-[1,1'-biphenyl]-2-carbonitrile (0.044 g, 0.11 mmol), 2-chloropyridine (0.032 mL, 0.34 mmol) and cesium carbonate (0.110 g, 0.34 mmol) in toluene (0.4 mL). After 5 min, palladacycle precatalyst J009 PreCat (2.0 mg, 2.2 μmol) was added and Ar was bubbled through the mixture for an additional 5 min. The sealed vial was then heated at 100° C. for 24 h and allowed to cool to RT. Saturated aqueous ammonium chloride (5 mL) and EtOAc (10 mL) were added and the separated aqueous layer was extracted with EtOAc (2×10 mL). The combined organic layers were washed with brine, dried (anhydrous $MgSO_4$), filtered and evaporated. The residue was purified using a 24 g-RediSep column (ISCO/0-100% EtOAc-DCM) to afford 4'-((2-ethyl-5,7-dimethyl-3H-imidazo[4,5-b]pyridin-3-yl)methyl)-5-(pyridin-2-yloxy)-[1,1'-biphenyl]-2-carbonitrile (0.026 g, 50% yield). LC-MS (Method H): 1.37 min, $[M+H]^+$=460.2. $^1$H NMR (400 MHz, DMSO-$d_6$) δ ppm 8.18 (dd, J=5.1, 2.0 Hz, 1H), 7.88 (dd, J=7.4, 1.6 Hz, 1H), 7.83 (d, J=8.6 Hz, 1H), 7.50-7.56 (m, 2H), 7.26 (m, 4H), 7.11 (d, J=8.3 Hz, 1H), 7.03 (s, 1H), 5.62 (s, 2H), 2.89 (q, J=7.5 Hz, 2H), 2.61 (s, 3H), 2.58 (s, 3H), 1.28 (t, J=7.5 Hz, 3H).

Example 247: 2-Ethyl-5,7-dimethyl-3-((5'-(pyridin-2-yloxy)-2'-(1H-tetrazol-5-yl)-[1,1'-biphenyl]-4-yl)methyl)-3H-imidazo[4,5-b]pyridine In a conical 2-mL vial was added 4'-((2-ethyl-5,7-dimethyl-3H-imidazo[4,5-b]pyridin-3-yl)methyl)-5-(pyridin-2-yloxy)-[1,1'-biphenyl]-2-carbonitrile (0.020 g, 0.044 mmol), dibutyltin oxide (0.012 g, 0.048 mmol) and TMS-$N_3$ (0.046 mL, 0.35 mmol) in toluene (0.250 mL) and the sealed vial was heated at 100° C. for 12 h. The mixture was allowed to cool to RT and the volatiles were then removed under reduced pressure. The residue was dissolved in DMSO and filtered through a 0.46 μm syringe filter and purified by preparative HPLC (Method D) to afford the title compound. (0.0133 g, 61% yield). LC-MS (Method H): 1.30 min, $[M+H]^+$=503.2; $^1$H NMR (400 MHz, DMSO-$d_6$) δ ppm 8.22 (m, 1H), 7.90 (m, 1H), 7.68 (d, J=8.6 Hz, 1H), 7.28-7.34 (m, 1H), 7.25 (d, J=2.4 Hz, 1H), 7.19 (m, 1H), 7.15 (m, 1H), 7.04 (m, 4H), 6.94 (s, 1H), 5.44 (s, 2H), 2.74 (q, J=7.6 Hz, 2H), 2.51 (s, 6H), 1.20 (t, J=7.6 Hz, 3H).

The following examples have been similarly prepared from Intermediate 247a as described above for Example 247.

In Example 249, 4'-((2-ethyl-5,7-dimethyl-3H-imidazo[4,5-b]pyridin-3-yl)methyl)-5-hydroxy-[1,1'-biphenyl]-2-carbonitrile is reacted, as described above, with tert-butyl (2-chloropyridin-4-yl)carbamate instead of 2-chloropyridine. The resulting Intermediate 007b was obtained. In the subsequent step, Boc-deprotection was concomitant to tetrazole formation to afford Ex. 249.

| Ex | Structure | MW | LC-MS m/z [M + H]+; RT (Method H) | 1H NMR (400 MHz, DMSO-d6) δ ppm |
|---|---|---|---|---|
| 248 | 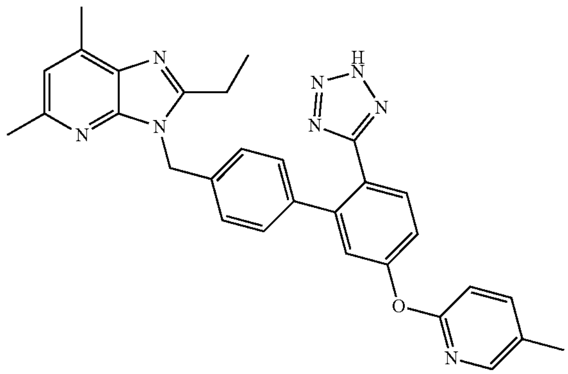 | 516.60 | 517.20; 1.30 min | 8.01 (m, 1H), 7.72 (dd, J = 8.2, 2.7 Hz, 1H), 7.66 (d, J = 8.2 Hz, 1H), 7.26 (m, 1H), 7.19 (d, J = 2.3 Hz, 1H), 7.04 (m, 5H), 6.94 (s, 1H), 5.43 (s, 2H), 2.74 (q, J = 7.6 Hz, 2 H), 2.49 (s, 6H), 2.25 (s, 3H), 1.20 (t, J = 7.6 Hz, 3H) |
| 249 | 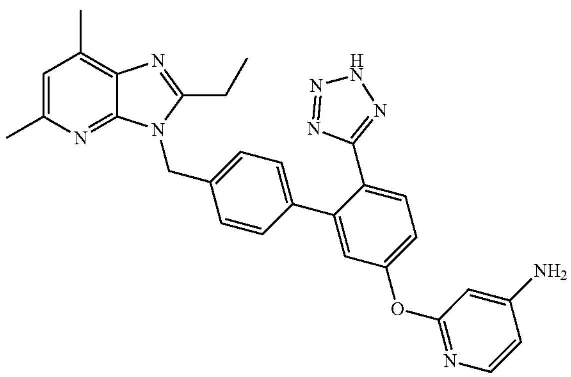 [SMILES: CCc1nc2c(C)cc(C)nc2n1Cc1ccc(-c2cc(Oc3cc(N)ccn3)ccc2-c2nn[nH]n2)cc1] | 517.58 | 518.20; 1.11 min | 7.63 (m, 2H), 7.20 (dd, J = 8.6, 2.8 Hz, 1H), 7.13 (d, J = 2.4 Hz, 1H), 7.03 (m, 4H), 6.94 (s, 1H), 6.31 (dd, J = 5.9, 2.0 Hz, 1H), 6.23 (s, 2H), 6.09 (d, J = 2.0 Hz, 1H), 5.43 (s, 2H), 2.74 (q, J = 7.6 Hz, 2 H), 2.52 (s, 6H), 1.21 (t, J = 7.6 Hz, 3H) |
| 250 | 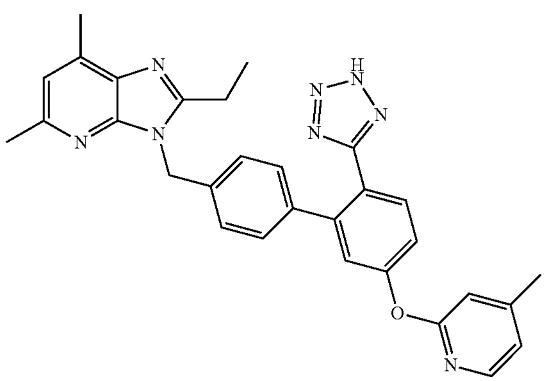 | 516.60 | 517.20; 1.29 min | 8.04 (d, J = 5.5 Hz, 1H), 7.67 (d, J = 8.6 Hz, 1H), 7.28 (m, 1H), 7.21 (d, J = 2.3 Hz, 1H), 7.04 (m, 5H), 7.01 (m, 1H), 6.94 (s, 1H), 5.44 (s, 2H), 2.74 (q, J = 7.6 Hz, 2 H), 2.50 (s, 6H), 2.35 (s, 3H), 1.20 (t, J = 7.6 Hz, 3H) |
| 251 | 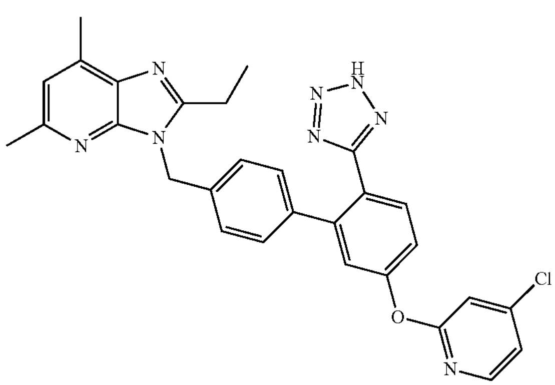 [SMILES: CCc1nc2c(C)cc(C)nc2n1Cc1ccc(-c2cc(Oc3cc(Cl)ccn3)ccc2-c2nn[nH]n2)cc1] | 537.02 | 537.10; 1.36 min | 8.16 (d, J = 5.5 Hz, 1H), 7.70 (d, J = 8.6 Hz, 1H), 7.33 (m, 4H), 7.04 (m, 4H), 6.94 (s, 1H), 5.44 (s, 2H), 2.74 (q, J = 7.4 Hz, 2 H), 2.50 (s, 6H), 1.20 (t, J = 7.4 Hz, 3H) |

-continued

| Ex | Structure | MW | LC-MS m/z [M + H]+; RT (Method H) | 1H NMR (400 MHz, DMSO-d6) δ ppm |
|---|---|---|---|---|
| 252 | 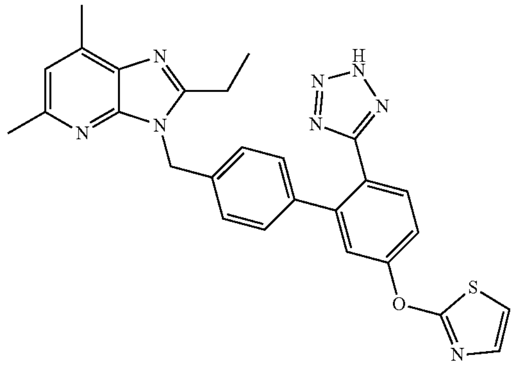 [SMILES: CCc1nc2c(C)cc(C)nc2n1Cc1ccc(-c2cc(Oc3nccs3)ccc2-c2nn[nH]n2)cc1] | 508.60 | 509.10; 1.26 min | 7.73 (d, J = 8.2 Hz, 1H), 7.52 (dd, J = 8.2, 2.3 Hz, 1H), 7.47 (d, J = 2.7 Hz, 1H), 7.30 (m, 2H), 7.04 (m, 4H), 6.93 (s, 1H), 5.43 (s, 2H), 2.74 (q, J = 7.4 Hz, 2H), 2.51 (s., 6H), 1.19 (t, J = 7.4 Hz, 3H) |
| 253 | 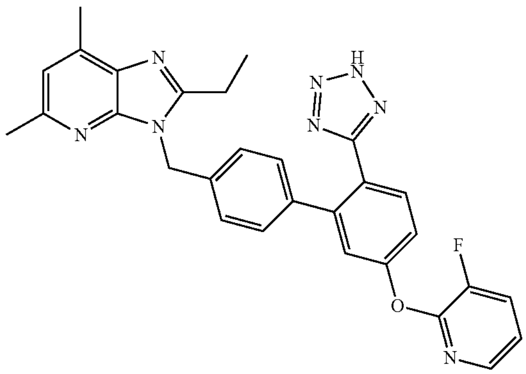 [SMILES: CCc1nc2c(C)cc(C)nc2n1Cc1ccc(-c2cc(Oc3ncccc3F)ccc2-c2nn[nH]n2)cc1] | 520.56 | 521.20; 1.27 min | 7.99 (d, J = 4.7 Hz, 1H), 7.90 (t, J = 9.0 Hz, 1H), 7.70 (d, J = 8.6 Hz, 1H), 7.37 (dd, J = 8.6, 2.4 Hz, 1H), 7.33 (d, J = 2.4 Hz, 1 H), 7.25 (m, 1H), 7.04 (m, 4H), 6.94 (s, 1H), 5.44 (s, 2H), 2.74 (q, J = 7.4 Hz, 2H), 2.51 (s., 6H), 1.19 (t, J = 7.4 Hz, 3H) |
| 254 | 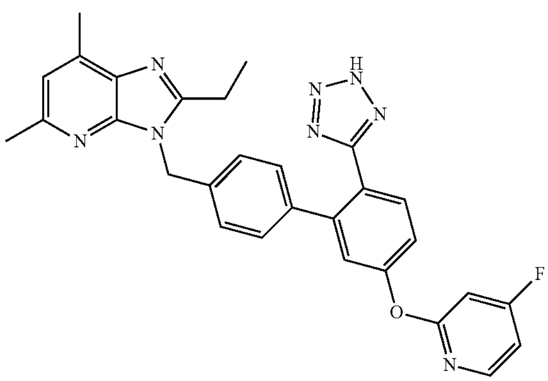 [SMILES: CCc1nc2c(C)cc(C)nc2n1Cc1ccc(-c2cc(Oc3cc(F)ccn3)ccc2-c2nn[nH]n2)cc1] | 520.56 | 521.20; 1.28 min | 8.20 (dd, J = 9.0, 5.9 Hz, 1 H), 7.68 (d, J = 8.6 Hz, 1 H), 7.33 (dd, J = 8.6, 2.4 Hz, 1 H), 7.28 (d, J = 2.4 Hz, 1 H), 7.14 (m, 2H), 7.04 (m, 4H), 6.94 (s, 1H), 5.43 (s, 2H), 2.74 (q, J = 7.4 Hz, 2H), 2.51 (s., 6H), 1.21 (t, J = 7.4 Hz, 3H) |
| 255 | 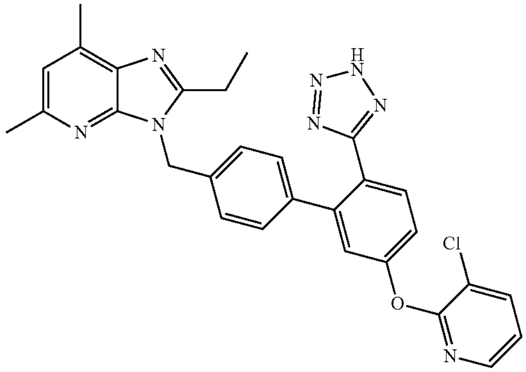 [SMILES: CCc1nc2c(C)cc(C)nc2n1Cc1ccc(-c2cc(Oc3ncccc3Cl)ccc2-c2nn[nH]n2)cc1] | 537.02 | 537.20; 1.30 min | 8.23-8.02 (m, 2 H), 7.70 (d, J = 8.6 Hz, 1 H), 7.35 (m, 1 H), 7.30 (d, J = 2.4 Hz, 1 H), 7.22 (dd, J = 7.8, 4.7 Hz, 1 H), 7.04 (m, 4H), 6.94 (s, 1H), 5.44 (s, 2H), 2.74 (q, J = 7.4 Hz, 2H), 2.50 (s., 6H), 1.20 (t, J = 7.4 Hz, 3H) |

| Ex | Structure | MW | LC-MS m/z [M + H]+; RT (Method H) | 1H NMR (400 MHz, DMSO-d6) δ ppm |
|---|---|---|---|---|
| 256 | 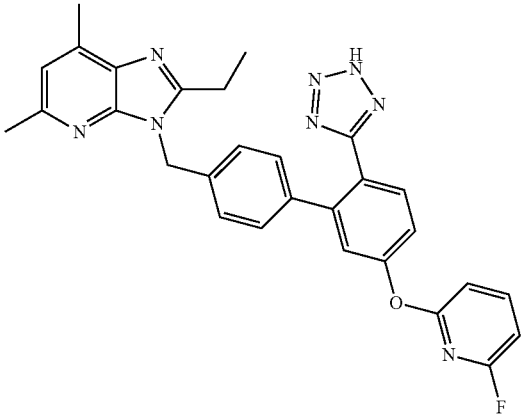 [SMILES: CCc1nc2c(C)cc(C)nc2n1Cc1ccc(-c2cc(Oc3cccc(F)n3)ccc2-c2nn[nH]n2)cc1] | 520.56 | 521.10; 1.27 min | (MeOH-d4): 7.95 (m, 1 H), 7.70 (d, J = 8.2 Hz, 1 H), 7.29 (m, 2 H), 7.09 (m, 4H), 7.03 (s, 1 H), 6.96 (m, 1H), 6.78 (m, 1H), 5.55 (s, 2H), 2.85 (q, J =7.8 Hz, 2H), 2.60 (s., 3H), 2.57 (s, 3H), 1.25 (t, J = 7.8 Hz, 3H) |

The following examples were prepared from 4'-((2-ethyl-5,7-dimethyl-3H-imidazo4,5-b]pyridin-3-yl)methyl)-5-fluoro-[1,1 1-biphenyl]-2-carbonitrile (Intermediate 205a) and the appropriate 3-hydroxypyridine or 3-hydroxypyriinidine, using a method similar to that described for the synthesis of Intermediate 205b and Example 205. Example 259 was prepared according to the method described for the synthesis of Example 214.

| Ex | Structure | MW | LC-MS m/z [M + H]+; RT (Method H) | 1H NMR (400 MHz, DMSO-d6) δ ppm |
|---|---|---|---|---|
| 257 | 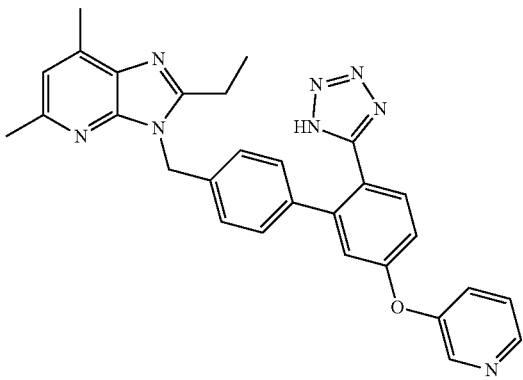 [SMILES: CCc1nc2c(C)cc(C)nc2n1Cc1ccc(-c2cc(Oc3cccnc3)ccc2-c2nnn[nH]2)cc1] | 502.57 | 503.10; 1.28 min | (MeOH-d4): 8.81 (m, 2H), 7.69 (d, J = 9.0 Hz, 1H), 7.61 (d, J =1.6 Hz, 1H), 7.50 (m, 1H), 7.19 (m, 2H) 7.08 (m, 4H), 7.05 (s, 1H), 5.56 (s, 2H), 2.86 (q, J = 7.6 Hz, 2H), 2.61 (s, 3H), 2.58 (s, 3H), 1.25 (t, J = 7.6 Hz, 3H) |
| 258 | 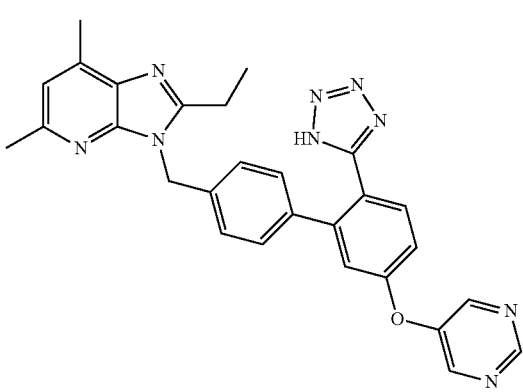 [SMILES: CCc1nc2c(C)cc(C)nc2n1Cc1ccc(-c2cc(Oc3cncnc3)ccc2-c2nnn[nH]2)cc1] | 503.56 | 504.20; 1.25 min | 9.06 (s, 1H) 8.78 (s, 2H) 7.70 (d, J = 8.22 Hz, 1H), 7.31 (dd, J = 8.6, 2.3 Hz, 1H), 7.26 (m, 1H), 7.05 (m, 4H), 6.94 (s, 1H), 5.44 (s, 2H), 2.74 (q, J = 7.6 Hz, 2 H), 2.50 (s, 6H), 1.21 (t, J = 7.6 Hz, 3H) |

| Ex | Structure | MW | LC-MS m/z [M + H]+; RT (Method H) | 1H NMR (400 MHz, DMSO-d6) δ ppm |
|---|---|---|---|---|
| 259 | 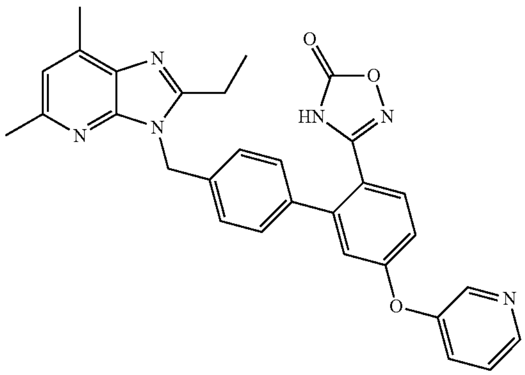 [SMILES: CCc1nc2c(C)cc(C)nc2n1Cc1ccc(-c2cc(Oc3cccnc3)ccc2-c2noc(=O)[nH]2)cc1] | 518.56 | 519.10; 1.81 min | 8.45 (d, J = 2.74 Hz, 2 H), 7.83 (d, J = 8.61 Hz, 1 H), 7.38-7.43 (m, 1H), 7.32-7.37 (m, 1 H), 7.25 (d, J = 8.22 Hz, 2 H), 7.17 (d, J = 8.22 Hz, 2 H), 7.07 (dd, J = 8.61, 2.35 Hz, 1 H), 6.96 (d, J = 2.35 Hz, 1 H), 6.90 (s, 1 H), 5.49 (s, 2 H), 2.81 (q, J = 7.70 Hz, 2 H), 2.62 (s, 3 H), 2.57 (s, 3 H), 1.34 (t, J = 7.63 Hz, 3 H) |
| 260 | 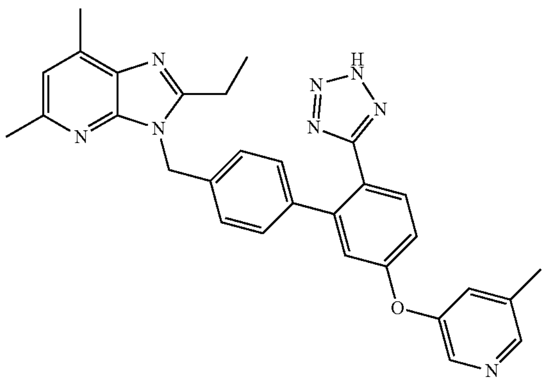 | 516.60 | 517.20; 1.28 min | 8.28 (m, 2H), 7.66 (d, J = 8.6 Hz, 1H), 7.44 (br. S, 1H), 7.15 (dd, J = 8.2, 2.4 Hz, 1H), 7.11 (m, 1H), 7.02 (m, 4H), 6.92 (s, 1H), 5.42 (s, 2H), 2.72 (q, J = 7.6 Hz, 2 H), 2.49 (s, 6H), 2.29 (s, 3H), 1.19 (t, J = 7.6 Hz, 3H) |
| 261 | 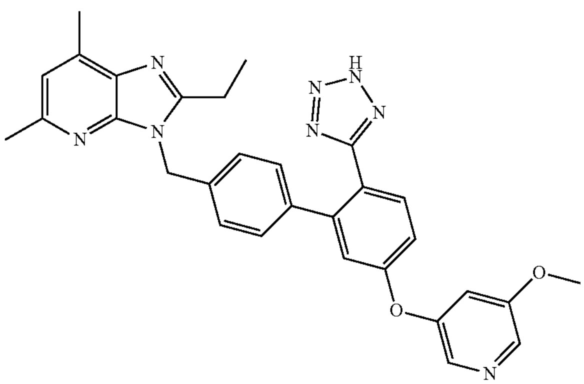 | 532.60 | 533.20; 1.30 min | 8.20 (d, J = 2.4 Hz, 1H), 8.08 (d, J = 2.3 Hz, 1H), 7.68 (d, J = 8.6 Hz, 1H), 7.29 (m, 1H), 7.23 (m, 1H), 7.15 (m, 1H), 7.04 (m, 4H), 6.95 (s, 1H), 5.44 (s, 2H), 3.83 (s, 3H), 2.74 (q, J = 7.4 Hz, 2 H), 2.51 (s, 6H), 1.21 (t, J = 7.4 Hz, 3H) |
| 262 | 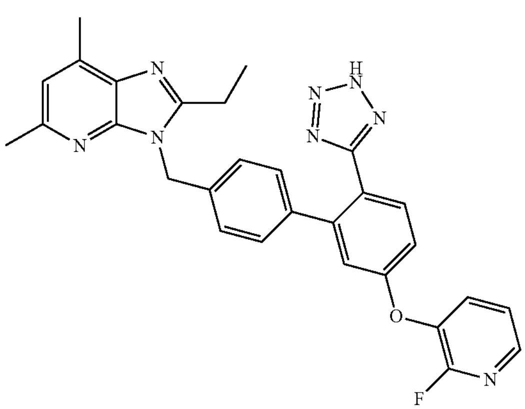 [SMILES: CCc1nc2c(C)cc(C)nc2n1Cc1ccc(-c2cc(Oc3cccnc3F)ccc2-c2nn[nH]n2)cc1] | 520.56 | 521.20; 1.36 min | (MeOH-d4) : 8.06 (m, 1 H), 7.79 (m, 1H), 7.68 (d, J = 8.6 Hz, 1 H), 7.40 (m, 1 H), 7.21 (m, 3H), 7.13 (m, 4H), 5.67 (s, 2H), 3.04 (q, J = 7.4 Hz, 2H), 2.65 (s., 3H), 2.64 (s, 3H), 1.30 (t, J = 7.4 Hz, 3H) |

Example 264: 2-ethyl-3-((3-fluoro-6'-(2H-tetrazol-5-yl)-[1,1':3',1''-terphenyl]-4-yl)methyl)-5,7-dimethyl-3H-imidazo[4,5-b]pyridine

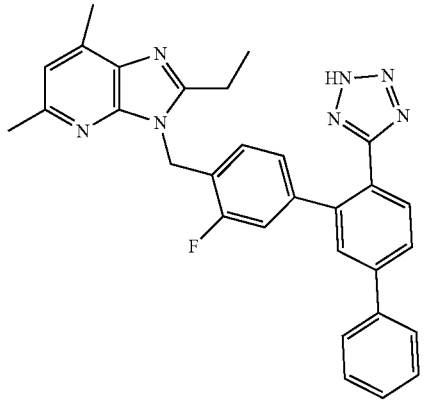 [SMILES: CCc1nc2c(C)cc(C)nc2n1Cc1ccc(-c2cc(-c3ccccc3)ccc2-c2nn[nH]n2)cc1F]

Intermediate 264a: (4-((2-ethyl-5,7-dimethyl-3H-imidazo[4,5-b]pyridin-3-yl)methyl)-3-fluorophenyl) boronic acid, TFA salt

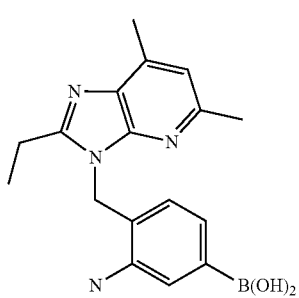 [SMILES: CCc1nc2c(C)cc(C)nc2n1Cc1ccc(B(O)O)cc1N]

Intermediate 264a was prepared in a similar manner as for Intermediate 001d, by replacing 2-(4-(bromomethyl)phenyl)-4,4,5,5-tetramethyl-1,3,2-dioxaborolane with 2-(4-(bromomethyl)-3-fluorophenyl)-4,4,5,5-tetramethyl-1,3,2-dioxaborolane.

Intermediate 264a was purified by preparative HPLC (method E). LC-MS (Method A5): 0.62 min, [M+H]$^+$= 328.0; $^1$H NMR (400 MHz, MeOH-d$_4$) δ 7.54-7.42 (m, 2H), 7.39 (s, 1H), 7.30 (t, J=7.6 Hz, 1H), 5.83 (s, 2H), 3.26 (q, J=7.7 Hz, 2H), 2.72-2.66 (m, 6H), 1.41 (t, J=7.6 Hz, 3H).

Intermediate 264b: 5-chloro-4'-((2-ethyl-5,7-dimethyl-3H-imidazo[4,5-b]pyridin-3-yl)methyl)-3'-fluoro-[1,1'-biphenyl]-2-carbonitrile

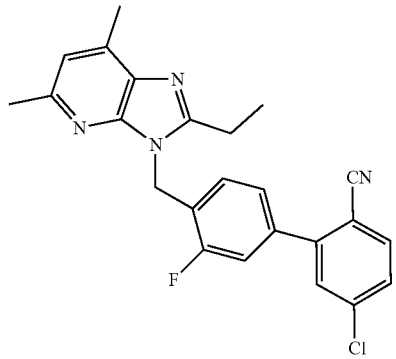 [SMILES: CCc1nc2c(C)cc(C)nc2n1Cc1ccc(-c2cc(Cl)ccc2C#N)cc1F]

Intermediate 264a was reacted with 4-chloro-2-iodobenzonitrile in a manner analogous to Intermediate 177d to give Intermediate 264b. LC-MS (Method A5): 0.85 min, [M+H]$^+$= 419.0. $^1$H NMR (400 MHz, CDCl$_3$) δ 7.69 (d, J=8.1 Hz, 1H), 7.49-7.41 (m, 2H), 7.35-7.30 (m, 1H), 7.23-7.15 (m, 1H), 7.00 (t, J=7.8 Hz, 1H), 6.92 (s, 1H), 5.58 (s, 2H), 2.87 (q, J=7.6 Hz, 2H), 2.65 (s, 3H), 2.61 (s, 3H), 1.38 (t, J=7.5 Hz, 3H).

Intermediate 264c: 4''-((2-ethyl-5,7-dimethyl-3H-imidazo[4,5-b]pyridin-3-yl)methyl)-3''-fluoro-[1,1':3',1''-terphenyl]-4'-carbonitrile Intermediate 264b was reacted with phenylboronic acid in a manner analogous to Intermediate 177e to give Intermediate 264c. LC-MS (Method A5): 0.93 min, [M+H]$^+$= 461.1; $^1$H NMR (500 MHz, CDCl$_3$) δ 7.83 (d, J=8.0 Hz, 1H), 7.70-7.66 (m, 2H), 7.61 (d, J=7.4 Hz, 2H), 7.53-7.42 (m, 3H), 7.39 (dd, J=10.6, 1.5 Hz, 1H), 7.29-7.24 (m, 1H), 7.02 (t, J=7.7 Hz, 1H), 6.93 (s, 1H), 5.60 (s, 2H), 2.89 (q, J=7.7 Hz, 2H), 2.66 (s, 3H), 2.62 (s, 3H), 1.39 (t, J=7.4 Hz, 3H).

Example 264: 2-ethyl-3-((3-fluoro-6'-(2H-tetrazol-5-yl)-[1,1':3',1''-terphenyl]-4-yl)methyl)-5,7-dimethyl-3H-imidazo[4,5-b]pyridine Intermediate 264c was reacted with dibutyltin oxide and TMS-N₃ in a manner analogous to Example 177 to give Example 264. LC-MS (Method A4): 1.70 min, [M+H]⁺= 504.22; ¹H NMR (500 MHz, DMSO-d₆) δ 7.82-7.77 (m, 2H), 7.75 (s, 2H), 7.63 (s, 1H), 7.49 (t, J=7.6 Hz, 2H), 7.43-7.38 (m, 1H), 7.10 (br d, J=11.3 Hz, 1H), 6.99-6.94 (m, 2H), 6.69 (br t, J=7.9 Hz, 1H), 5.50 (s, 2H), 3.40 (br s, 3H), 2.83 (q, J=7.3 Hz, 2H), 1.93 (s, 3H), 1.30 (t, J=7.5 Hz, 3H).

Examples 265-267 were prepared using the methods described for Example 264

| Ex | Structure | MW | LCMS m/z [M + H]⁺; RT (Method) | ¹H NMR (400 MHz, DMSO-d6) δ ppm |
|---|---|---|---|---|
| 265 | 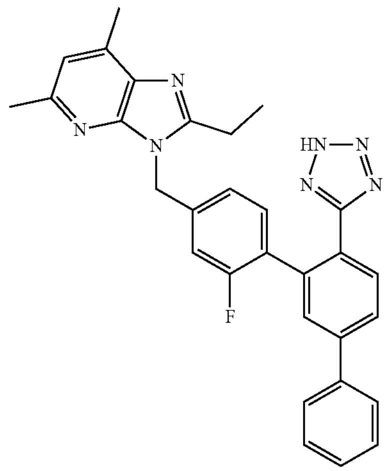 [SMILES: CCc1nc2c(C)cc(C)nc2n1Cc1ccc(-c2cc(-c3ccccc3)ccc2-c2nn[nH]n2)c(F)c1] | 503.58 | 504.23; 1.66 min (Method A4) | 7.92 (s, 2H), 7.80 (d, J = 7.7 Hz, 2H), 7.72 (s, 1H), 7.53-7.47 (m, 2H), 7.46-7.40 (m, 1H), 7.36 (t, J = 7.8 Hz, 1H), 6.98 (s, 1H), 6.94 (d, J = 9.0 Hz, 2H), 5.51 (s, 2H), 2.83 (q, J = 7.5 Hz, 2H), 2.54 (s, 3H), 2.53 (s, 3H), 1.29 (t, J = 7.5 Hz, 3H). |
| 266 | 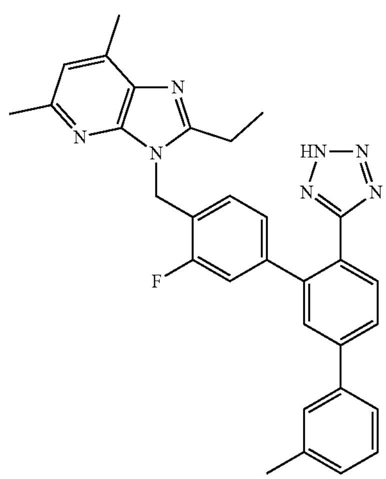 [SMILES: CCc1nc2c(C)cc(C)nc2n1Cc1ccc(-c2cc(-c3cccc(C)c3)ccc2-c2nn[nH]n2)cc1F] | 517.24 | 518.05; 1.81 min (Method A4) | 7.96 (s, 1H), 7.83 (br d, J = 7.9 Hz, 1H), 7.79-7.74 (m, 1H), 7.72 (s, 1H), 7.63 (s, 1H), 7.59 (br d, J = 7.9 Hz, 1H), 7.38 (t, J = 7.6 Hz, 1H), 7.24 (br d, J = 7.6 Hz, 1H), 7.14 (br d, J = 11.3 Hz, 1H), 6.96 (s, 1H), 6.90 (br d, J = 7.9 Hz, 1H), 6.74 (br t, J = 7.8 Hz, 1H), 5.50 (s, 2H), 2.80 (q, J = 7.3 Hz, 2H), 2.56 (s, 6H), 2.39 (s, 3H), 1.27 (t, J = 7.5 Hz, 3H). |

| Ex | Structure | MW | LCMS m/z [M + H]+; RT (Method) | 1H NMR (400 MHz, DMSO-d6) δ ppm |
|----|-----------|-----|------|------|
| 267 | 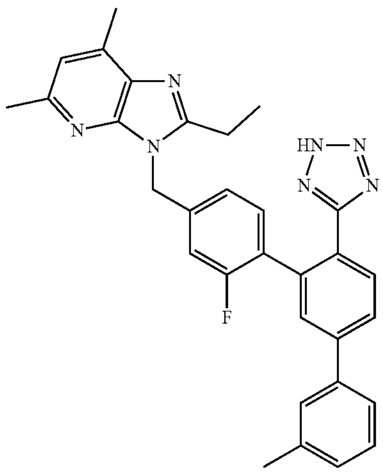 [SMILES: CCc1nc2c(C)cc(C)nc2n1Cc1ccc(-c2cc(-c3cccc(C)c3)ccc2-c2nn[nH]n2)c(F)c1] | 517.24 | 518.22; 1.78 min (Method A4) | 7.97-7.91 (m, 2H), 7.77 (br d, J = 7.9 Hz, 1H), 7.58-7.50 (m, 3H), 7.35 (t, J = 7.6 Hz, 1H), 7.25 (t, J = 7.8 Hz, 1H), 7.20 (br d, J = 7.6 Hz, 1H), 6.97 (s, 1H), 6.93-6.85 (m, 2H), 5.50 (s, 2H), 2.83 (q, J = 7.5 Hz, 2H), 2.54 (s, 3H), 2.53 (br s, 3H), 1.92 (s, 3H), 1.29 (t, J = 7.3 Hz, 3H). |

Example 268: 2-(N-((6'-(2H-Tetrazol-5-yl)-[1,1':3',1''-terphenyl]-4-yl)methyl)pentanamido)-2-methylpropanoic acid (Ex. 268)

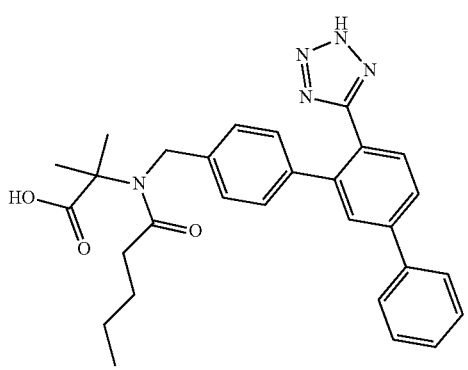

Intermediate 268a: Methyl 2-((4-bromobenzyl)amino)-2-methylpropanoate (268a)

To a mixture of methyl 2-amino-2-methylpropanoate hydrochloride (0.538 g, 3.50 mmol) in ACN (10 mL) was added 1-bromo-4-(bromomethyl)benzene (0.875 g, 3.5 mmol) and DIEA (1.22 mL, 7.00 mmol) and the mixture was heated at 80° C. for 3 h. The volatiles were then evaporated under reduced pressure and tert-butylmethyl ether (15 mL) and saturated aqueous sodium hydrogen carbonate (5 mL) were added to the residue. The aqueous phase was separated and re-extracted with tert-butylmethyl ether (10 mL), and the combined organic extract was dried over anhydrous sodium sulfate, filtered and evaporated under reduced pressure. The residue was purified by flash chromatography (12 g ISCO-type silica gel column, 0 to 10% EtOAc/hexane gradient) to afford the title compound (0.716 g, 2.50 mmol, 71% yield) as a clear, colorless oil. LC-MS (Method H): 0.96 min, [M+H]+=286.0; 1H NMR (400 MHz, DMSO-d$_6$) δ ppm 7.43-7.52 (m, 2H), 7.24-7.33 (m, 2H), 3.62 (s, 3H), 3.54 (d, J=4.7 Hz, 2H), 2.47 (br s, 1H), 1.19-1.30 (m, 6H).

Intermediate 268b: Methyl 2-(N-(4-bromobenzyl)pentanamido)-2-methylpropanoate (268b)

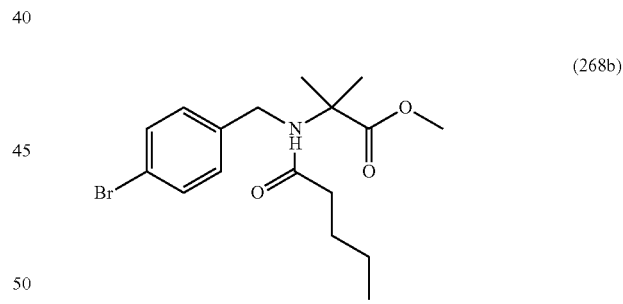

To a solution of Intermediate 268a (0.350 g, 1.22 mmol) in EtOAc (3.5 mL) was added DIEA (0.85 mL, 4.84 mmol) followed by pentanoyl chloride (0.22 mL, 1.84 mmol) and this mixture was heated at 65° C. for 18 h. The cooled mixture was diluted with tert-butylmethyl ether (25 mL), washed (5 mL of 10% aqueous citric acid, then 5 mL of saturated aqueous sodium hydrogen carbonate), dried (anhydrous sodium sulfate), filtered and evaporated under reduced pressure. The crude product was purified by flash chromatography (12 gram ISCO-type column using a 0 to 25% acetone/hexane gradient) to afford the title compound (0.716 g, 2.50 mmol, 71% yield) as an orange crystalline solid. LC-MS (Method H): 1.34 min, [M+H]+=370.0; 1H NMR (DMSO-d$_6$) δ ppm 7.54-7.62 (m, 2H), 7.33-7.42 (m, J=8.2 Hz, 2H), 4.64 (s, 2H), 3.58 (s, 3H), 2.11-2.23 (m, 2H), 1.35-1.49 (m, 2H), 1.26 (s, 6H), 1.18 (dq, J=14.8, 7.3 Hz, 2H), 0.78 (t, J=7.2 Hz, 3H).

Intermediate 268c: 3-(5,5-Dimethyl-1,3,2-dioxaborinan-2-yl)-[1,1'-biphenyl]-4-carbonitrile

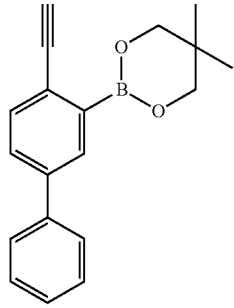
(268c)

The title compound was prepared from [1,1'-biphenyl]-4-carbonitrile according to a literature procedure (cf J. L. Kristensen, et al. *Journal of Organic Chemistry*, 2006, 71, 2518) to afford a white solid. $^1$H NMR (DMSO-d$_6$) δ ppm 8.04-8.08 (m, 1H), 7.88-7.91 (m, 2H), 7.67-7.74 (m, 2H), 7.47-7.54 (m, 2H), 7.41-7.47 (m, 1H), 3.82 (s, 4H), 0.99 (s, 6H).

Intermediate 268d: Methyl 2-(N-((6'-cyano-[1,1':3',1''-terphenyl]-4-yl)methyl)pentanamido)-2-methylpropanoate

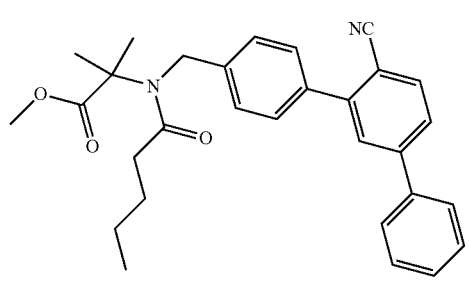
(268d)

Intermediate 268d was prepared by the reaction of Intermediate 268b (0.075 g, 0.258 mmol) with Intermediate 268c (0.114 g, 0.309 mmol), according to the method described for the synthesis of Intermediate 330b. The title compound (0.100 g, 0.213 mmol, 83% yield) was isolated as a white solid. LC-MS (Method H): 1.45 min, [M−C$_5$H$_{90}$+H]=385.1; $^1$H NMR (DMSO-d$_6$) δ ppm 8.03 (d, J=7.8 Hz, 1H), 7.80-7.93 (m, 4H), 7.68-7.77 (m, 2H), 7.57-7.63 (m, 2H), 7.43-7.55 (m, 3H), 4.78 (s, 2H), 3.61 (s, 3H), 2.25 (t, J=7.0 Hz, 2H), 1.37-1.55 (m, 2H), 1.32 (s, 6H), 1.10-1.29 (m, 2H), 0.73-0.89 (m, 3H).

Example 268: 2-(N-((6'-(2H-Tetrazol-5-yl)-[1,1':3',1''-terphenyl]-4-yl)methyl)pentanamido)-2-methylpropanoic acid To a pressure vial containing Intermediate 268d (0.045 g, 0.096 mmol) was added toluene (6 mL), dibutyltin oxide (0.024 g, 0.096 mmol) and azidotrimethylsilane (0.064 mL, 0.48 mmol). The reaction vessel was sealed and the mixture was heated at 110° C. for 18 h. The cooled mixture was then evaporated and the residue was taken up in DMSO (2.5 mL). To this mixture was added 2.5M NaOH (0.66 mL, 0.96 mmol) and the resulting mixture was heated at 60° C. for 3 days. To the cooled mixture was then added formic acid (0.072 mL, 1.92 mmol), the mixture was filtered and the filtrate was submitted to prep LC (Method F, TFA as modifier). This afforded the title compound (0.031 g, 0.062 mmol, 64% yield) as a white solid. LC-MS (Method H): 1.34 min, [M−H]=496.1; $^1$H NMR (DMSO-d$_6$) δ ppm 11.95 (br s, 2H), 7.79-7.91 (m, 4H), 7.75 (d, J=7.8 Hz, 1H), 7.48-7.57 (m, 2H), 7.41-7.48 (m, 1H), 7.36-7.41 (m, J=8.2 Hz, 2H), 7.17-7.24 (m, 2H), 4.66 (s, 2H), 2.18 (t, J=7.2 Hz, 2H), 1.43 (dt, J=14.8, 7.3 Hz, 2H), 1.27 (s, 6H), 1.19 (dq, J=15.0, 7.4 Hz, 2H), 0.79 (t, J=7.2 Hz, 3H).

The following examples were similarly prepared from the corresponding amino ester or amino ester hydrochloride salt as described for the synthesis of Example 268 above. Analytical LC-MS injections were used to determine the final purity and the retention time is reported for each compound and is referred as Method A1, Method A2 or Method H.

| | Structure | MW | LC-MS m/z [M + H]$^+$; RT (Method) | $^1$H NMR (400 MHz, DMSO-d$_6$) δ ppm |
|---|---|---|---|---|
| 269 | 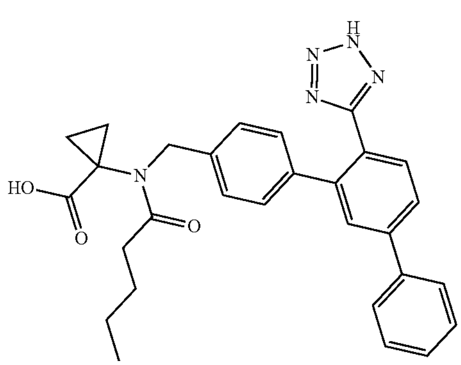 [SMILES: CCCCC(=O)N(Cc1ccc(-c2cc(-c3ccccc3)ccc2-c2nn[nH]n2)cc1)C1(C(=O)O)CC1] | 495.58 | 496.1; 1.29 min (Method H) | 7.79-7.89 (m, 3H), 7.70-7.79 (m, 2H), 7.47-7.56 (m, 2H), 7.38-7.47 (m, 1H), 7.03-7.14 (m, 4H), 4.99 (d, J = 16.0 Hz, 1H), 4.10 (d, J = 16.0 Hz, 1H), 2.52-2.60 (m, 1H), 2.22-2.37 (m, 1H), 1.66 (m, 1H), 1.37-1.59 (m, 3H), 1.14-1.37 (m, 1H), 0.98-1.12 (m, 1H), 0.87 (t, J = 7.2 Hz, 3H) |

| Structure | MW | LC-MS m/z [M + H]+; RT (Method) | 1H NMR (400 MHz, DMSO-d6) δ ppm |
|---|---|---|---|
| 270 | 509.61 | 510.2; 1.31 min (Method H) | 12.41 (br. s., 2H), 7.78-7.91 (m, 4H), 7.72-7.78 (m, 1H), 7.48-7.56 (m, 2H), 7.40-7.48 (m, 1H), 7.28-7.36 (m, 2H), 7.22-7.28 (m, 2H), 4.54 (s, 2H), 2.45 (d, J = 9.4 Hz, 1H), 2.03-2.26 (m, 3H), 1.84-2.03 (m, 1H), 1.67 (d, J = 10.2 Hz, 1H), 1.35-1.61 (m, 3H), 1.10-1.34 (m, 3H), 0.77 (t, J = 7.4 Hz, 3H). |
| 271 | 523.63 | 524.1; 1.32 min (Method H) | 12.05 (s, 2H), 7.78-7.90 (m, 4H), 7.75 (d, J = 7.8 Hz, 1H), 7.48-7.55 (m, 2H), 7.40-7.48 (m, 1H), 7.31-7.39 (m, 2H), 7.17-7.24 (m, 2H), 4.64 (s, 2H), 2.21-2.32 (m, 2H), 2.16 (t, J = 7.2 Hz, 2H), 1.61-1.75 (m, 2H), 1.48-1.61 (m, 4H), 1.43 (dt, J = 14.9, 7.4 Hz, 2H), 1.18 (dq, J = 15.0, 7.3 Hz, 2H), 0.78 (t, J = 7.2 Hz, 3H). |
| 272 | 537.66 | 538.1; 1.34 min. (Method H) | 11.93 (s, 2H), 7.78-7.90 (m, 4H), 7.74 (d, J = 8.2 Hz, 1H), 7.47-7.56 (m, 2H), 7.41-7.47 (m, 1H), 7.35-7.41 (m, 2H), 7.16-7.22 (m, 2H), 4.64 (m, 2H), 2.18 (t, J = 7.0 Hz, 2H), 2.04 (d, J = 11.7 Hz, 2H), 1.51-1.68 (m, 4H), 1.36-1.51 (m, 6H), 1.15-1.26 (m, 2H), 0.79 (t, J = 7.2 Hz, 3H). |

| Ex | Structure | MW | LC-MS m/z [M + H]+; RT (Method) | 1H NMR (400 MHz, DMSO-d6) δ ppm |
|---|---|---|---|---|
| 273 | 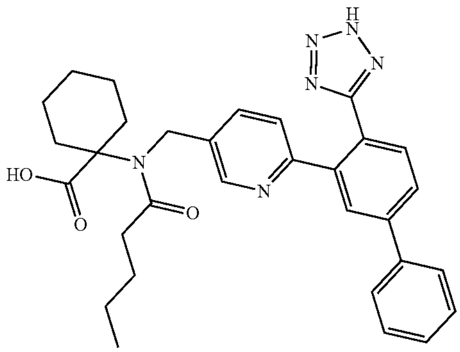 [SMILES: CCCCC(=O)N(Cc1ccc(-c2cc(-c3ccccc3)ccc2-c2nn[nH]n2)nc1)C1(C(=O)O)CCCCC1] | 538.65 | 539.2; 1.300 min (Method H) | 12.01 (s, 2H), 8.50 (s, 1H), 8.05 (d, J = 1.6 Hz, 1H), 7.90-8.00 (m, 2H), 7.73-7.90 (m, 3H), 7.67 (d, J = 8.2 Hz, 1H), 7.49-7.57 (m, 2H), 7.40-7.49 (m, 1H), 4.76 (s, 2H), 2.20 (t, J = 6.8 Hz, 2H), 2.01 (d, J = 11.3 Hz, 2H), 1.38-1.70 (m, 9H), 1.06-1.33 (m, 3H), 0.80 (t, J = 7.4 Hz, 3H). |
| 274 | 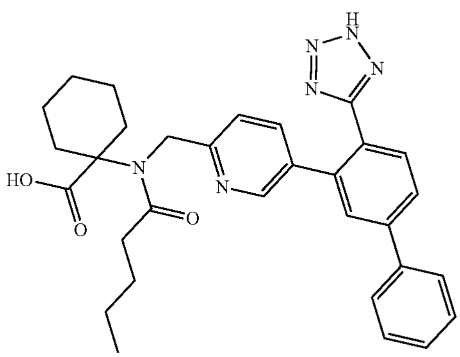 [SMILES: CCCCC(=O)N(Cc1ccc(-c2cc(-c3ccccc3)ccc2-c2nn[nH]n2)cn1)C1(C(=O)O)CCCCC1] | 538.65 | 539.2; 1.290 min (Method H) | 12.10 (s, 2H), 8.44 (d, J = 2.0 Hz, 1H), 7.92-7.99 (m, 1H), 7.81-7.92 (m, 4H), 7.72 (dd, J = 8.2, 2.3 Hz, 1H), 7.49-7.60 (m, 3H), 7.41-7.49 (m, 1H), 4.84 (s, 2H), 2.19 (t, J = 6.7 Hz, 1H), 2.06 (d, J = 9.8 Hz, 1H), 1.36-1.74 (m, 9H), 1.08-1.35 (m, 3H), 0.78 (t, J = 7.2 Hz, 3H). |

Example 275: 1-(N-((6'-(2H-Tetrazol-5-yl)-[1,1':3', 1''-terphenyl]-4-yl)methyl)pentan-amido)-4,4-dimethylcyclohexanecarboxylic acid Intermediate 275a: Methyl 4,4-dimethyl-1-(((6'-(2-trityl-2H-tetrazol-5-yl)-[1,1':3',1''-terphenyl]-4-yl)methyl)amino)cyclohexanecarboxylate

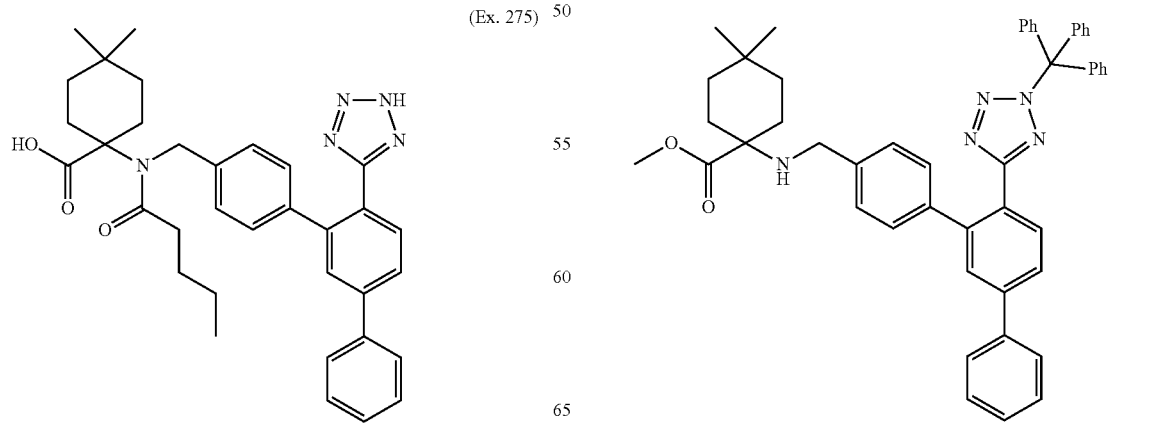

To a solution of Intermediate I-004, 0.110 g, 0.174 mmol) in ACN (2.5 mL) was added DIEA (0.121 mL, 0.694 mmol), followed by methyl 1-amino-4,4-dimethylcyclohexanecarboxylate hydrochloride (0.058 g, 0.260 mmol) and sodium iodide (0.130 g, 0.868 mmol) and the mixture was heated at 65° C. for 5 h. To the cooled mixture was added H₂O (5 mL) and EtOAc (20 mL) and the organic layer was separated, washed (H₂O brine), dried (anhydrous sodium sulfate), filtered and evaporated. This afforded the title compound as a pale yellow foam (0.130 g) which was used as such in the next step without further purification or characterization.

Example 275: 1-(N-((6'-(2H-Tetrazol-5-yl)-[1,1':3',1''-terphenyl]-4-yl)methyl)pentan-amido)-4,4-dimethylcyclohexanecarboxylic acid To a solution of Intermediate 275a (0.128 g, 0.174 mmol) in anhydrous THF (5 mL) was added sodium hydride (60% w/w in oil, 0.035 g, 0.870 mmol) in one portion and the mixture was stirred for 5 min. Pentanoyl chloride (0.103 mL, 0.870 mmol) was then added and the mixture was stirred at 50° C. for 6 h and then at RT for a further 18 h. The resulting mixture was quenched with AcOH (0.100 mL, 1.75 mmol) and then the volatiles were evaporated and the residue was taken up in trifluoroacetic acid (1 ml) to give a clear yellow solution. Triisopropylsilane was then added in 10 μL portions until the color faded to give a pale yellow solution (required approximately 40 μL). The volatiles were again removed under reduced pressure and the residue taken up in DMSO (3 mL) and was submitted to prep LC purification (Method F, TFA as modifier). This afforded the title compound (0.005 g, 0.0083 mmol, 5% yield) as a white solid. LC-MS (Method H): 1.34 min, [M+H]⁺=566.1; ¹H NMR (DMSO-d₆) δ ppm 7.80-7.89 (m, 4H), 7.77-7.80 (m, 1H), 7.48-7.55 (m, 2H), 7.43-7.48 (m, 1H), 7.38 (d, J=8.2 Hz, 2H), 7.21 (d, J=8.2 Hz, 2H), 4.68 (s, 2H), 2.21 (t, J=7.2 Hz, 2H), 1.95 (m, 2H), 1.37-1.66 (m, 6H), 1.09-1.34 (m, 4H), 0.71-0.85 (m, 9H).

The following examples were similarly prepared from the corresponding amino ester or amino ester hydrochloride salt as described for the synthesis of Example 275 above.

Analytical LC-MS injections were used to determine the final purity and the retention time is reported for each compound and is referred as Method A1, Method A2 or Method H.

| Ex | Structure | MW | LC-MS m/z [M + H]⁺; RT (Method) | ¹H NMR (400 MHz, DMSO-d₆) δ ppm |
|---|---|---|---|---|
| 276 | 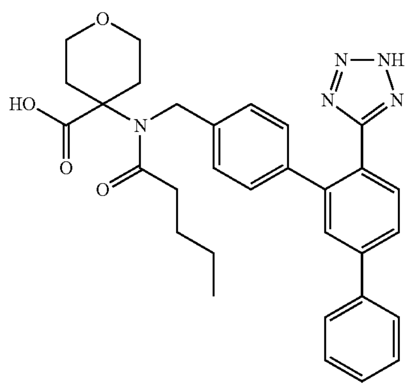 [SMILES: CCCCC(=O)N(Cc1ccc(-c2cc(-c3ccccc3)ccc2-c2nn[nH]n2)cc1)C1(C(=O)O)CCOCC1] | 539.63 | 540.1; 1.31 min (Method H) | 12.29 (br s, 2H), 7.81-7.91 (m, 4H), 7.75 (d, J = 7.8 Hz, 1H), 7.48-7.56 (m, 2H), 7.41-7.48 (m, 1H), 7.33-7.41 (m, 2H), 7.19-7.24 (m, 2H), 4.70 (s, 2H), 3.58-3.70 (m, 4H), 2.22 (t, J = 7.0 Hz, 2H), 2.04 (d, J = 12.9 Hz, 2H), 1.62-1.79 (m, 2H), 1.45 (dt, J = 14.8, 7.3 Hz, 2H), 1.21 (dq, J = 14.8, 7.3 Hz, 2H), 0.80 (t, J = 7.4 Hz, 3H). |
| 277 | 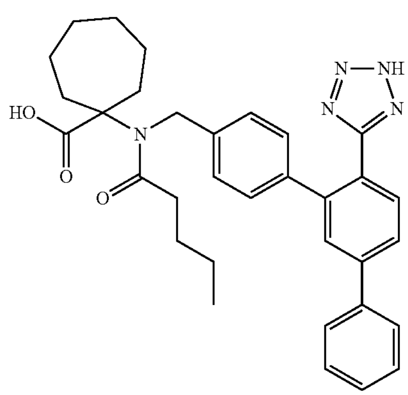 [SMILES: CCCCC(=O)N(Cc1ccc(-c2cc(-c3ccccc3)ccc2-c2nn[nH]n2)cc1)C1(C(=O)O)CCCCCC1] | 551.69 | 552.2; 1.41 min (Method H) | 11.89 (br s, 2H), 7.76-7.87 (m, 4H), 7.73 (d, J = 8.2 Hz, 1H), 7.47-7.55 (m, 2H), 7.40-7.47 (m, 1H), 7.33-7.40 (m, 2H), 7.17-7.22 (m, 2H), 4.68 (s, 2H), 2.04-2.28 (m, 4H), 1.71 (dd, J = 14.5, 7.8 Hz, 2H), 1.33-1.55 (m, 10H), 1.17 (dq, J = 15.0, 7.4 Hz, 2H), 0.78 (t, J = 7.4 Hz, 3H). |

| Ex | Structure | MW | LC-MS m/z [M + H]+; RT (Method) | 1H NMR (400 MHz, DMSO-d6) δ ppm |
|---|---|---|---|---|
| 278 | 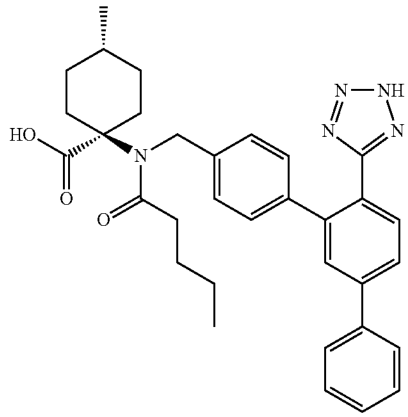 [SMILES: CCCCC(=O)N(Cc1ccc(-c2cc(-c3ccccc3)ccc2-c2nn[nH]n2)cc1)[C@]1(C(=O)O)CC[C@@H](C)CC1] | 551.69 | 552.1; 1.41 min (Method H) | 11.91 (br s, 2H), 7.80-7.86 (m, 3H), 7.77 (d, J = 2.0 Hz, 1H), 7.73 (d, J = 8.2 Hz, 1H), 7.47-7.55 (m, 2H), 7.39-7.46 (m, 1H), 7.32-7.38 (m, 2H), 7.15-7.23 (m, 2H), 4.64 (s, 2H), 2.18 (t, J = 7.0 Hz, 2H), 2.06 (d, J = 11.0 Hz, 2H), 1.38-1.52 (m, 6H), 1.31 (m, 3H), 1.12-1.25 (m, 2H), 0.72-0.86 (m, 6H). |
| 279 | 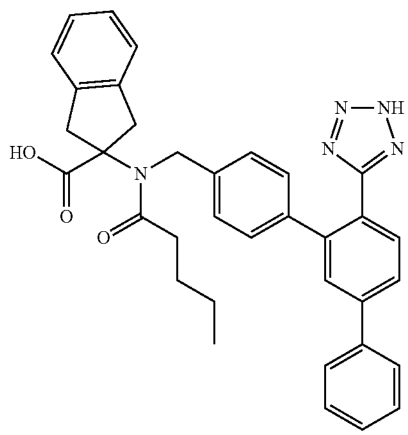 [SMILES: CCCCC(=O)N(Cc1ccc(-c2cc(-c3ccccc3)ccc2-c2nn[nH]n2)cc1)C1(C(=O)O)Cc2ccccc2C1] | 571.68 | 572.1; 1.40 min. (Method H) | 12.31 (br s, 2H), 7.77-7.85 (m, 3H), 7.68-7.77 (m, 2H), 7.46-7.55 (m, 2H), 7.38-7.46 (m, 1H), 7.27-7.36 (m, 2H), 7.16-7.23 (m, 2H), 7.07-7.16 (m, 4H), 4.60 (s, 2H), 3.62 (d, J = 16.8 Hz, 2H), 3.13 (d, J = 17.2 Hz, 2H), 2.19 (t, J = 7.0 Hz, 2H), 1.45 (dt, J = 14.8, 7.3 Hz, 2H), 1.12-1.27 (m, 2H), 0.79 (t, J = 7.2 Hz, 3H). |

Example 280: Methyl 1-(N-((6'-(5-oxo-4,5-dihydro-1,2,4-oxadiazol-3-yl)-t1,1':3',1''-terphenyll-4-yl)methyl)pentanamido)cyclohexanecarboxylate Intermediate 280a: (Z)-Methyl 1-(N-((6'-(N'-hydroxycarbamimidoyl)-[1,1':3',1''-terphenyll-4-yl)methyl)pentanamido)cyclohexanecarboxylate

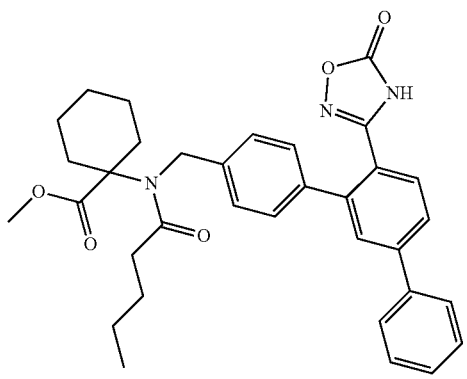
(Ex. 280)

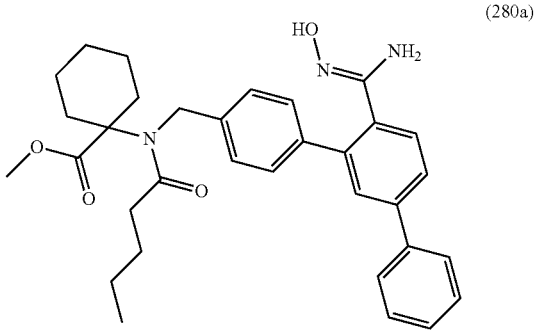 [SMILES: CCCCC(=O)N(Cc1ccc(-c2cc(-c3ccccc3)ccc2/C(N)=N/O)cc1)C1(C(=O)OC)CCCCC1]
(280a)

To a solution of methyl 1-(N-((6'-cyano-[1,1':3',1''-terphenyl]-4-yl)methyl)pentan-amido)cyclohexanecarboxylate (prepared from methyl 1-amino-4-cyclohexanecarboxylate according to the method described for the synthesis of Intermediate 268d) (0.100 g, 0.197 mmol) in ethanol (2 mL) was added hydroxylamine hydrochloride (0.137 g, 1.97 mmol) and DIEA (0.342 mL, 1.97 mmol). The vessel was sealed and the mixture was heated at 85° C. for 20 h. The cooled mixture was evaporated and to the residue was dissolved in dimethyl sulfoxide (2.5 mL) and filtered. The filtrate was submitted to purification by prep LC (Method F, TFA as modifier) to afford the title compound as a white solid (0.074 g, 0.113 mmol, 57% yield). LC-MS (Method H): 1.37 min, [M+H]$^+$=542.2; $^1$H NMR (DMSO-d$_6$) δ ppm 12.60 (br s, 1H), 11.15 (br s, 1H), 9.16 (br s, 1H), 8.98 (br s, 2H), 7.87 (dd, J=8.0, 1.8 Hz, 1H), 7.78-7.85 (m, 3H), 7.70 (d, J=8.2 Hz, 1H), 7.42-7.55 (m, 7H), 4.75 (s, 2H), 3.61 (s, 3H), 2.22 (t, J=7.0 Hz, 2H), 1.95-2.11 (m, 2H), 1.32-1.62 (m, 9H), 1.05-1.28 (m, 3H), 0.81 (t, J=7.2 Hz, 3H).

Example 280: Methyl 1-(N-((6'-(5-oxo-4,5-dihydro-1,2,4-oxadiazol-3-yl)-[1,1':3',1''-terphenyl]-4-yl)methyl)pentanamido)cyclohexanecarboxylate

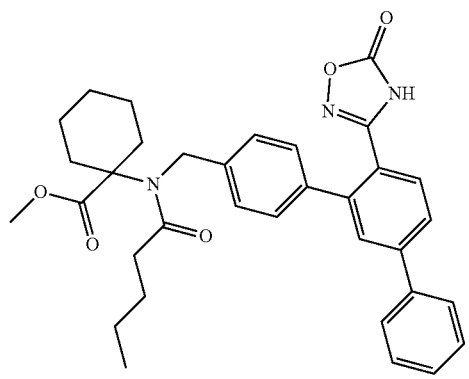

(Ex. 280)

To a solution of Intermediate 280a (0.072 g, 0.110 mmol) in THF (5 mL) was added DBU (0.084 g, 0.549 mmol) and N,N'-carbonyldiimidazole (0.089 g, 0.549 mmol) and the mixture was stirred at 50° C. for 2 h. The cooled mixture was evaporated and the residue was taken up in DMSO (2.5 mL) and trifluoroacetic acid (0.100 mL) was added.

The solution was submitted to prep LC (Method F, TFA as modifier) to afford the title compound (0.074 g, 0.113 mmol, 57% yield) as a white solid. LC-MS (Method H): 1.46 min, [M+H]$^+$=568.2; $^1$H NMR (DMSO-d$_6$) δ ppm 12.41 (br s. 1H), 7.86 (dd, J=8.0, 1.8 Hz, 1H), 7.82 (d, J=7.4 Hz, 2H), 7.79 (d, J=1.6 Hz, 1H), 7.75 (d, J=8.2 Hz, 1H), 7.39-7.56 (m, 7H), 4.73 (s, 2H), 3.59 (s, 3H), 2.22 (t, J=7.2 Hz, 2H), 2.03 (d, J=7.4 Hz, 2H), 1.33-1.63 (m, 9H), 1.03-1.29 (m, 3H), 0.80 (t, J=7.4 Hz, 3H).

Example 281: 1-(N-((6'-(5-oxo-4,5-dihydro-1,2,4-oxadiazol-3-yl)-[1,1':3',1''-terphenyll-4-yl)methyl)pentanamido)cyclohexanecarboxylic acid

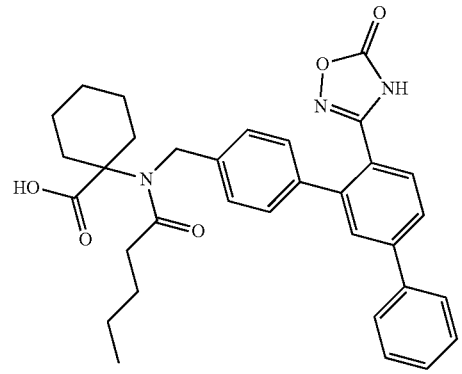

(Ex. 281)

To a solution of Example 280 (0.025 g, 0.028 mmol) in DMSO (1 mL) was added 2.5M NaOH (0.225 mL, 0.564 mmol) and the mixture was stirred at 75° C. for 18 h. To the cooled mixture was added trifluoroacetic acid (0.100 mL) and the solution was purified by prep LC (Method F, TFA as modifier) to afford the title compound (0.009 g, 0.016 mmol, 57% yield) as a white solid. LC-MS (Method H): 1.39 min, [M+H]$^+$=554.2; $^1$H NMR (DMSO-d$_6$) δ ppm 12.41 (s, 1H), 7.72-7.89 (m, 5H), 7.47-7.55 (m, 4H), 7.39-7.47 (m, 3H), 4.72 (s, 2H), 2.21 (t, J=7.0 Hz, 2H), 1.96-2.14 (m, 2H), 1.32-1.71 (m, 9H), 1.00-1.28 (m, 3H), 0.79 (t, J=7.4 Hz, 3H).

Intermediate 282a: Methyl 1-(N-(4-bromobenzyl)pentanamido)-4-oxocyclohexane-carboxylate

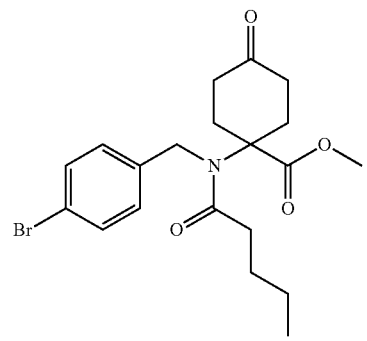

(282a)

The title compound was prepared as an orange crystalline solid from methyl 1-amino-4-oxocyclohexanecarboxylate, according to the method described for the synthesis of Intermediate 268b. LC-MS (Method H): 1.31 min, [M+H]$^+$=424.0; $^1$H NMR (CDCl$_3$) δ ppm 7.50-7.56 (m, 2H), 7.29 (m, 2H), 4.56 (s, 2H), 3.82 (s, 3H), 2.70 (ddd, J=16.0, 12.9, 6.3 Hz, 2H), 2.48-2.62 (m, 2H), 2.22-2.33 (m, 4H), 1.87 (td, J=13.1, 5.5 Hz, 2H), 1.55-1.68 (m, 2H), 1.22-1.36 (m, 2H), 0.88 (t, J=7.4 Hz, 3H).

Intermediate 282b: (1R,4R)-Methyl 1-(N-(4-bromobenzyl)pentanamido)-4-hydroxycyclohexanecarboxylate

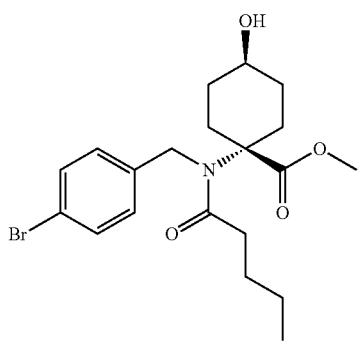
(282b)

To an ice-cold mixture of Intermediate 282a (0.300 g, 0.707 mmol) in ethanol (10 mL) was added sodium borohydride (0.080 g, 2.12 mmol) and the resulting mixture was stirred for 30 min. The reaction mixture was then quenched with H$_2$O (2 mL) and 2M HCl (2 mL) and stirring was continued for 5 min. The resulting mixture was partitioned with H$_2$O (50 mL) and tert-butylmethyl ether (50 mL) and the aqueous layer was separated and re-extracted with tert-butylmethyl ether (25 mL). The combined organic extract was dried over anhydrous sodium sulfate, filtered and evaporated. The residue was purified by flash chromatography (25 g ISCO-type column, eluting with 0 to 35% acetone/hexane) to give the title compound (0.280 g, 0.657 mmol, 93% yield) as a clear, colorless gum. LC-MS (Method H): 1.30 min, [M+H]$^+$=426.0; $^1$H NMR (CDCl$_3$) δ ppm 7.48-7.55 (m, 2H), 7.29 (d, J=8.6 Hz, 2H), 4.53 (s, 2H), 3.77 (s, 3H), 3.46-3.57 (m, 1H), 2.30 (d, J=12.1 Hz, 2H), 2.23 (t, J=7.2 Hz, 2H), 1.77-1.89 (m, 2H), 1.63-1.77 (m, 2H), 1.52-1.63 (m, 2H), 1.46 (dt, J=13.3, 3.9 Hz, 3H), 1.19-1.33 (m, 2H), 0.86 (t, J=7.4 Hz, 3H).

Intermediate 282c: (1R,4R)-Methyl 1-(N-((6'-cyano-[1,1':3',1''-terphenyl]-4-yl)methyl)pentanamido)-4-hydroxycyclohexanecarboxylate

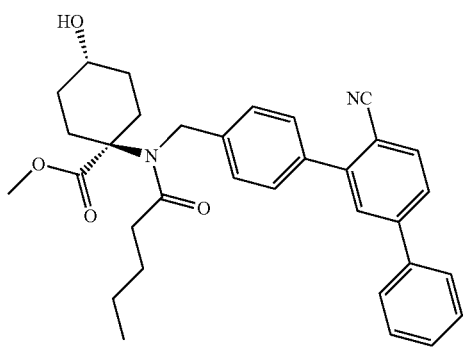
(282c)

Intermediate 282c was prepared from Intermediate 282b as an off white solid, according to the procedure described for the synthesis of Intermediate 268d. LC-MS (Method H): 1.39 min, [M+H]$^+$=525.2; $^1$H NMR (DMSO-d$_6$) δ ppm 8.03 (d, J=8.2 Hz, 1H), 7.81-7.92 (m, 3H), 7.72 (d, J=8.2 Hz, 2H), 7.42-7.67 (m, 6H), 4.76 (s, 2H), 4.53 (d, J=4.3 Hz, 1H), 3.62 (s, 3H), 3.34-3.47 (m, 1H), 2.23 (t, J=7.0 Hz, 2H), 2.04 (d, J=11.3 Hz, 2H), 1.54-1.67 (m, 3H), 1.39-1.54 (m, 3H), 1.09-1.36 (m, 4H), 0.77-0.82 (m, 2H).

Example 283: (1R,4R)-1-(N-((6'-(2H-Tetrazol-5-yl)-[1,1':3',1''-terphenyll-4-yl)methyl)-pentanamido)-4-hydroxycyclohexanecarboxylic acid

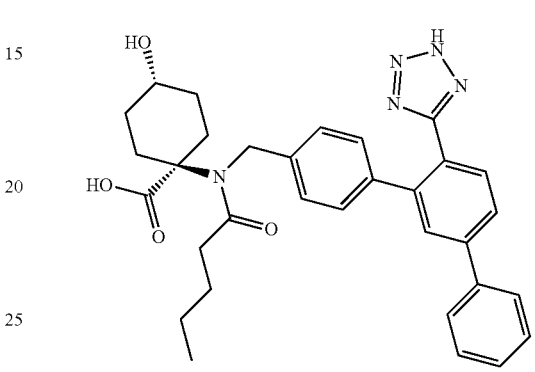
(Ex. 283)

Intermediate 283a: (1R,4R)-Methyl 1-(N-((6'-(2H-tetrazol-5-yl)-[1,1':3',1''-terphenyl]-4-yl)methyl)pentanamido)-4-hydroxycyclohexanecarboxylate

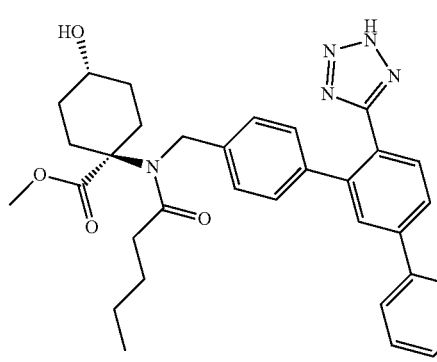
(283a)

To a vial containing Intermediate 282c (0.080 g, 0.152 mmol) in toluene (3 mL) was added azidotrimethylsilane (0.161 mL, 1.22 mmol) and dibutyltin oxide (0.038 g, 0.152 mmol). The reaction vessel was sealed and the mixture was heated at 110° C. for 18 h. The cooled mixture was evaporated and the residue was taken up in a mixture of DMSO (2.5 mL) and trifluoroacetic acid (0.100 mL). Purification by prep LC (Method F, TFA as modifier) afforded the title compound (0.050 g, 0.088 mmol, 57% yield) as a white solid. LC-MS (Method H): 1.31 min, [M−H]=566.2.

Example 283: (1R,4R)-1-(N-((6'-(2H-Tetrazol-5-yl)-[1,1':3',1''-terphenyl]-4-yl)methyl)pentan-amido)-4-hydroxycyclohexanecarboxylic acid To a solution of Intermediate 283a (0.030 g, 0.053 mmol) in THF (3 mL) was added potassium trimethylsilanolate (0.068 g, 0.528 mmol) and the mixture was stirred at RT for 18 h. Formic acid (0.100 mL) was then added, the volatiles were evaporated and the residue was dissolved in DMSO (3 mL). Purification by prep LC (Method F, TFA as modifier) afforded the title compound (0.008 g, 0.014 mmol, 27% yield) as a white solid.

LC-MS (Method H): 1.30 min, [M−H]=554.2; $^1$H NMR (15% v/v acetone-$d_6$/CDC$_3$) δ ppm 7.76 (d, J=7.8 Hz, 1H), 7.49-7.64 (m, 3H), 7.30-7.38 (m, 2H), 7.20-7.30 (m, 4H), 7.09 (d, J=7.0 Hz, 2H), 4.49 (s, 1H), 3.32-3.46 (m, 1H), 2.07-2.28 (m, 3H), 1.98 (d quint, J=4.3, 2.2 Hz, 4H), 1.66 (m, 3H), 1.28-1.52 (m, 3H), 1.06-1.20 (m, 2H), 0.70 (t, J=7.4 Hz, 3H).

Example 284: (1S,4S)-1-(N-((6'-(2H-Tetrazol-5-yl)-[1,1':3',1''-terphenyl]-4-yl)methyl)pentanamido)-4-hydroxycyclohexanecarboxylic acid

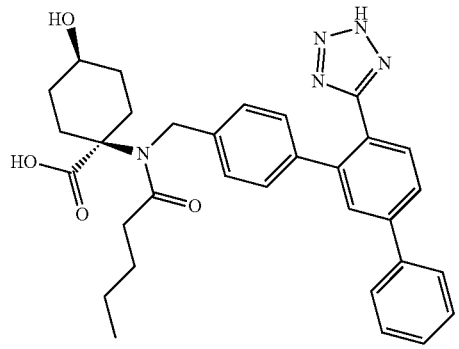

(Ex. 284)

Intermediate 284a: 1-(N-(4-Bromobenzyl)pentanamido)-4-oxocyclohexanecarboxylic acid

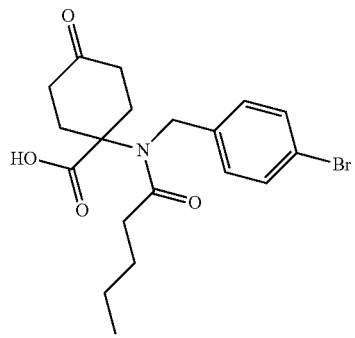

(284a)

A solution of Intermediate 282a (0.300 g, 0.707 mmol) in DCM (10 mL) was cooled at 0° C. and iodotrimethylsilane (0.300 mL, 2.12 ml) was added in one portion. The mixture was then allowed to warm to RT with stirring for 2 h. This mixture was then added to a well-stirred mixture of ACN (10 mL) and 1M HCl and stirring was continued for 30 min. The volatiles were then evaporated and the residue was taken up in DMSO (10 mL) and formic acid (0.200 mL) was added. Purification by prep LC (Method F, formic acid as modifier) afforded the title compound (0.251 g, 0.621 mmol, 87% yield) as a white solid. LC-MS (Method H): 1.29 min, [M−H]=410.1.

Intermediate 284b: 1-(N-((6'-Cyano-[1,1':3',1''-terphenyl]-4-yl)methyl)pentanamido)-4-oxocyclohexanecarboxylic acid

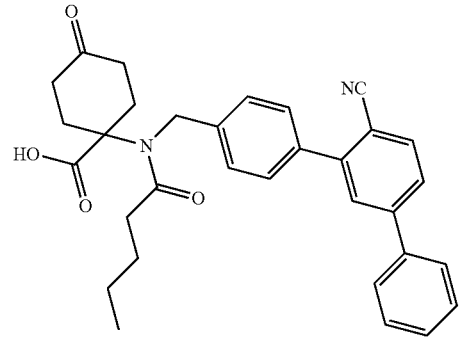

(284b)

The title compound was prepared from Intermediate 284a, according to the method described for the synthesis of Intermediate 268d, and was isolated as an off-white solid. LC-MS (Method H): 1.39 min, [M+H]$^+$=509.2; $^1$H NMR (DMSO-$d_6$) δ ppm 12.49 (br s, 1H), 8.03 (d, J=7.8 Hz, 1H), 7.80-7.92 (m, 4H), 7.72 (d, J=8.2 Hz, 2H), 7.62 (d, J=8.2 Hz, 2H), 7.41-7.56 (m, 3H), 4.82 (s, 2H), 2.43-2.57 (m, 2H), 2.15-2.36 (m, 6H), 1.96-2.15 (m, 2H), 1.48 (quint, J=7.3 Hz, 2H), 1.23 (dq, J=15.0, 7.4 Hz, 2H), 0.80 (t, J=7.4 Hz, 3H).

Intermediate 284c: 1-(N-((6'-(2H-Tetrazol-5-yl)-[1,1':3',1''-terphenyl]-4-yl)methyl)pentanamido)-4-oxo-cyclohexanecarboxylic acid

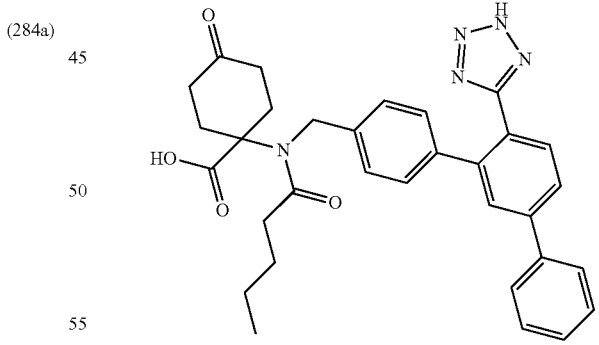

(284c)

The title compound was prepared from Intermediate 284b according to the method described for the synthesis of Intermediate 283a and was isolated as an off-white solid. LC-MS (Method H): 1.32 min, [M+H]$^+$=552.2; $^1$H NMR (CDC$_3$) δ ppm 8.03 (d, J=8.2 Hz, 1H), 7.74 (d, J=7.8 Hz, 1H), 7.53-7.64 (m, 3H), 7.36-7.47 (m, 3H), 7.28-7.34 (m, 2H), 7.00-7.10 (m, 2H), 4.65 (br s, 2H), 2.79 (m, 2H), 2.53 (m, 2H), 2.22-2.44 (m, 4H), 1.96 (dd, J=12.3, 8.0 Hz, 2H), 1.62 (dt, J=15.2, 7.5 Hz, 2H), 1.20-1.37 (m, 2H), 0.85 (t, J=7.4 Hz, 3H).

Example 284: (1S,4S)-1-(N-((6'-(2H-Tetrazol-5-yl)-[1,1':3',1''-terphenyl]-4-yl)methyl)pentanamido)-4-hydroxycyclohexanecarboxylic acid A solution of Intermediate 284c (0.030 g, 0.054 mmol) in dry THF (6 mL) was cooled at −78° C. under N₂. To this mixture was added a solution of L-Selectride (1M in THF, 0.272 mL, 0.272 mmol) and stirring was continued at the same temperature for 30 min. The reaction was quenched by the addition of AcOH (0.100 mL) and the reaction was allowed to warm to RT. The volatiles were then removed under reduced pressure and the residue was taken up in DMSO (2 mL). This solution was submitted to purification by prep LC (Method F, formic acid as modifier) to afford the title compound (0.021 g, 0.038 mmol, 69% yield) as a white solid. LC-MS (Method H): 1.29 min, [M−H]=554.1. $^1$H NMR (DMSO-d₆) δ ppm 11.97 (br s, 2H), 7.76-7.86 (m, 3H), 7.67-7.76 (m, 2H), 7.46-7.55 (m, 2H), 7.30-7.46 (m, 3H), 7.20 (dd, J=8.2, 2.7 Hz, 2H), 4.63 (d, J=7.0 Hz, 2H), 4.49 (br s, 0.5H), 3.73 (br s, 0.5H), 2.11-2.25 (m, 2H), 1.95-2.11 (m, 1H), 1.67-1.90 (m, 2H), 1.38-1.67 (m, 7H), 1.08-1.32 (m, 2H), 0.79 (t, J=7.4 Hz, 3H).

Example 285: 1-(N-((5'-Phenoxy-2'-(2H-tetrazol-5-yl)-[1,1'-biphenyl]-4-yl)methyl)pentanamido)cyclohexanecarboxylic acid

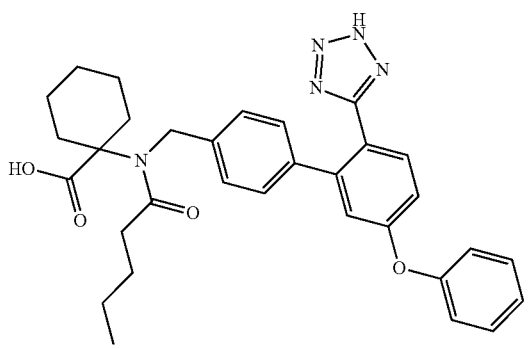

(Ex. 285)

Intermediate 285a: Methyl 1-(N-(4-bromobenzyl)pentanamido)cyclohexanecarboxylate

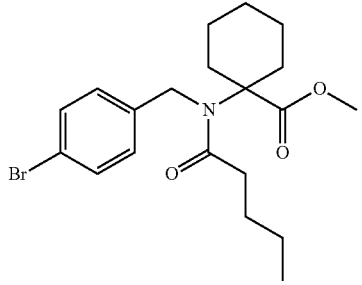

(285a)

The title compound was prepared from methyl 1-aminocyclohexanecarboxylate according to the method described for the synthesis of Intermediate 268b and was isolated as an orange crystalline solid. LC-MS (Method H): 1.43 min, [M+H]⁺=410.0; $^1$H NMR (DMSO-d₆) δ ppm 7.50-7.64 (m, 2H), 7.27-7.42 (m, 2H), 4.64 (s, 2H), 3.58 (s, 3H), 2.17 (t, J=7.0 Hz, 2H), 1.97 (d, J=10.2 Hz, 2H), 1.32-1.61 (m, 8H), 1.17 (dt, J=14.9, 7.4 Hz, 4H), 0.78 (t, J=7.2 Hz, 3H).

Intermediate 285b: Methyl 1-(N-((2'-cyano-5'-fluoro-[1,1'-biphenyl]-4-yl)methyl)pentanamido)cyclohexanecarboxylate

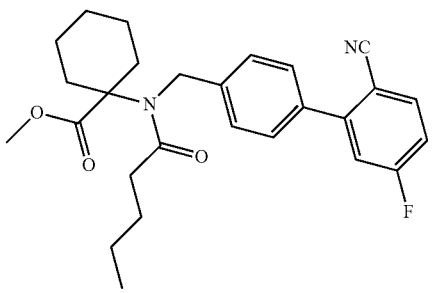

(285b)

The title compound was prepared by the reaction Intermediate 285a (0.500 g, 1.22 mmol) with 4-fluoro-2-(4,4,5,5-tetramethyl-1,3,2-dioxaborolan-2-yl)benzonitrile (0.602 g, 2.44 mmol), according to the method described for the synthesis of Intermediate 330b, to give a white solid (0.472 g, 1.05 mmol, 86% yield). HRMS (ESI): Calcd for C₂₇H₃₂FN₂O₃[M+H]⁺ m/z 451.2391; found 451.2416. $^1$H NMR (CDCl₃) δ ppm 7.79 (dd, J=8.6, 5.5 Hz, 1H), 7.52-7.62 (m, 4H), 7.23-7.27 (m, 1H), 7.17 (td, J=8.2, 2.7 Hz, 1H), 4.69 (s, 2H), 3.78 (s, 3H), 2.18-2.35 (m, 4H), 1.51-1.80 (m, 8H), 1.43 (td, J=12.8, 4.1 Hz, 2H), 1.29 (dq, J=15.2, 7.5 Hz, 2H), 0.87 (t, J=7.2 Hz, 3H).

Intermediate 285c: 1-(N-((2'-Cyano-5'-fluoro-[1,1'-biphenyl]-4-yl)methyl)pentan-amido)cyclohexanecarboxylic acid

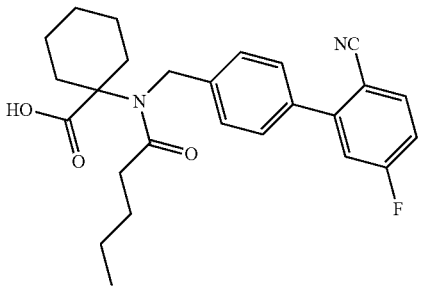

(285c)

The title compound was prepared from Intermediate 285b according to the method described for the synthesis of Intermediate 284a and was isolated as an off white solid. LC-MS (Method H): 1.37 min, [M−H]=435.1; $^1$H NMR (DMSO-d₆) δ ppm 12.01 (br s, 1H), 8.06 (dd, J=8.6, 5.5 Hz, 1H), 7.54-7.68 (m, 5H), 7.46 (td, J=8.4, 2.7 Hz, 1H), 4.75 (s, 2H), 2.21 (t, J=7.0 Hz, 2H), 2.06 (d, J=11.3 Hz, 2H), 1.35-1.61 (m, 8H), 1.02-1.27 (m, 4H), 0.79 (t, J=7.2 Hz, 3H).

Intermediate 285d: 1-(N-((2'-Cyano-5'-phenoxy-[1,1'-biphenyl]-4-yl)methyl)pentan-amido)cyclohexan-ecarboxylic acid

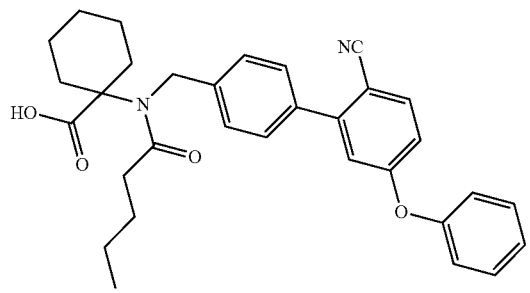

(285d)

The title compound was prepared from Intermediate 285c, according to the method described for the synthesis of Intermediate 330c and was isolated as an off-white solid. LC-MS (Method H): 1.37 min, [M–H]=509.1; $^1$H NMR (DMSO-d$_6$) δ ppm 11.98 (br s, 1H), 7.93 (d, J=8.6 Hz, 1H), 7.52-7.62 (m, 4H), 7.44-7.52 (m, 2H), 7.24-7.32 (m, 1H), 7.16-7.24 (m, 2H), 7.13 (d, J=2.7 Hz, 1H), 7.06 (dd, J=8.6, 2.3 Hz, 1H), 4.73 (s, 2H), 2.19 (t, J=7.0 Hz, 2H), 2.05 (d, J=11.7 Hz, 2H), 1.34-1.60 (m, 9H), 1.01-1.27 (m, 3H), 0.77 (t, J=7.4 Hz, 3H).

Example 285: 1-(N-((5'-Phenoxy-2'-(2H-tetrazol-5-yl)-[1,1'-biphenyl]-4-yl)methyl)pentanamido)cyclo-hexanecarboxylic acid The title compound was prepared from Intermediate 285d, according to the method described for the synthesis of Intermediate 283a and was isolated as an off-white solid. LC-MS (Method H): 1.60 min, [M–H]=552.1; $^1$H NMR (DMSO-d$_6$) δ ppm 11.91 (br s, 2H), 7.65 (d, J=8.6 Hz, 1H), 7.40-7.52 (m, 2H), 7.28-7.38 (m, 2H), 7.21-7.26 (m, 1H), 7.16-7.21 (m, 2H), 7.09-7.15 (m, 2H), 7.04-7.09 (m, 2H), 4.63 (s, 2H), 2.14 (t, J=7.0 Hz, 2H), 2.01 (d, J=11.7 Hz, 2H), 1.34-1.64 (i, 9H), 0.98-1.24 (m, 3H), 0.76 (t, J=7.4 Hz, 3H).

The following examples were similarly prepared from the appropriate phenol or hydroxypyridine, as described for the synthesis of Example 285 above. Analytical LC-MS injections were used to determine the final purity and the retention time is reported for each compound and the method used is referred to as Method A1, Method A2 or Method H.

| Ex | Structure | MW | LC-MS m/z [M + H]$^+$; RT (Method) | $^1$H NMR (400 MHz, DMSO-d$_6$) δ ppm |
|---|---|---|---|---|
| 286 | 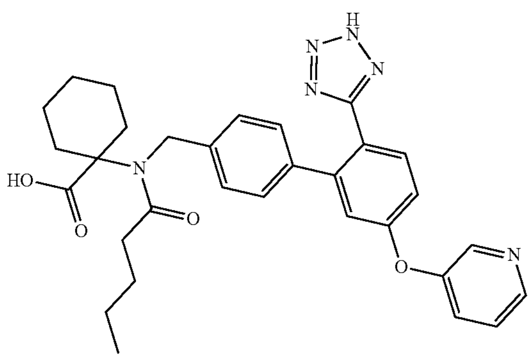 [SMILES: CCCCC(=O)N(Cc1ccc(-c2cc(Oc3cccnc3)ccc2-c2nn[nH]n2)cc1)C1(C(=O)O)CCCCC1] | 554.65 | 555.2; 1.29 min (Method H) | 11.91 (br s, 2H), 8.53 (d, J = 2.7 Hz, 1H), 8.45 (dd, J = 4.7, 1.2 Hz, 1H), 7.58-7.73 (m, 2H), 7.50 (dd, J = 8.2, 4.7 Hz, 1H), 7.28-7.40 (m, 2H), 7.14-7.25 (m, 2H), 7.02-7.14 (m, 2H), 4.63 (s, 2H), 2.14 (t, J = 7.0 Hz, 2H), 2.01 (d, J = 11.3 Hz, 2H), 1.30-1.68 (m, 6H), 1.03-1.22 (m, 3H), 0.77 (t, J = 7.2 Hz, 3H). |
| 287 | 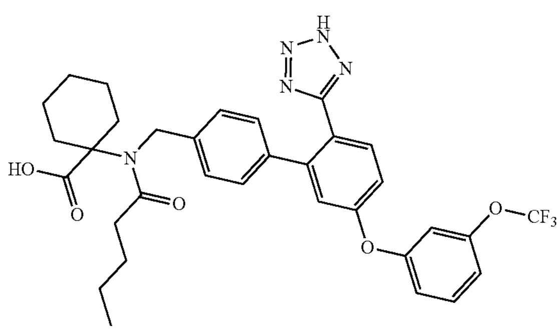 [SMILES: CCCCC(=O)N(Cc1ccc(-c2cc(Oc3cccc(OC(F)(F)F)c3)ccc2-c2nn[nH]n2)cc1)C1(C(=O)O)CCCCC1] | 637.66 | 638.1; 1.47 min (Method H) | 11.92 (br s, 2H), 7.70 (d, J = 8.2 Hz, 1H), 7.54-7.62 (m, 1H), 7.31-7.38 (m, 2H), 7.16-7.26 (m, 5H), 7.04-7.11 (m, 2H), 4.63 (s, 2H), 2.14 (t, J = 7.2 Hz, 2H), 2.02 (d, J = 12.1Hz, 2H), 1.31-1.67 (m, 9H), 1.00-1.22 (m, 3H), 0.77 (t, J = 7.2 Hz, 3H). |

Example 288: 1-(N-((5'-(1-Methyl-1H-pyrazol-4-yl)-2'-(2H-tetrazol-5-yl)-[1,1'-biphenyl]-4-yl)methyl)pentanamido)cyclohexanecarboxylic acid

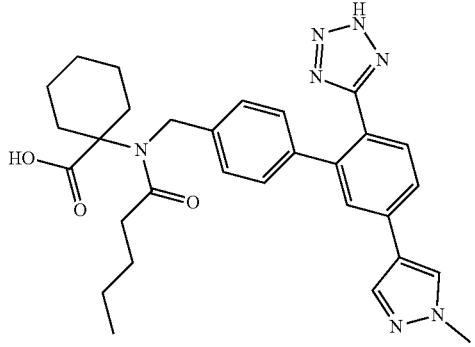

(Ex. 288)

Intermediate 288a: Methyl 1-(N-((5'-chloro-2'-cyano-[1,1'-biphenyl]-4-yl)methyl)pentanamido)cyclohexanecarboxylate

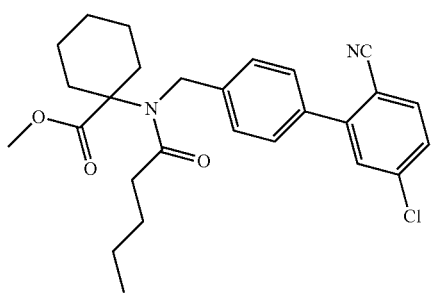

(288a)

The title compound was prepared by the reaction of Intermediate 285a 0.800 g, 1.95 mmol) with 4-chloro-2-(5,5-dimethyl-1,3,2-dioxaborinan-2-yl)benzonitrile (0.973 g, 3.90 mmol), according to the method described for the synthesis of Intermediate 330b and was isolated as a white solid (0.440 g, 0.942 mmol, 48% yield). HRMS (ESI): Calcd for $C_{27}H_{32}ClN_2O_3[M+H]^+$ m/z 467.2096; found 467.2110. $^1$H NMR (CDCl$_3$) δ ppm 7.72 (d, J=8.2 Hz, 1H), 7.58 (m, 4H), 7.55 (d, J=2.0 Hz, 1H), 7.45 (dd, J=8.4, 2.2 Hz, 1H), 4.69 (s, 2H), 3.78 (s, 3H), 2.21-2.33 (m, 4H), 1.51-1.77 (m, 8H), 1.43 (td, J=12.7, 4.3 Hz, 2H), 1.23-1.36 (m, 2H), 0.87 (t, J=7.2 Hz, 3H).

Intermediate 288b: 1-(N-((5'-Chloro-2'-cyano-[1,1'-biphenyl]-4-yl)methyl)pentan-amido)cyclohexanecarboxylic acid

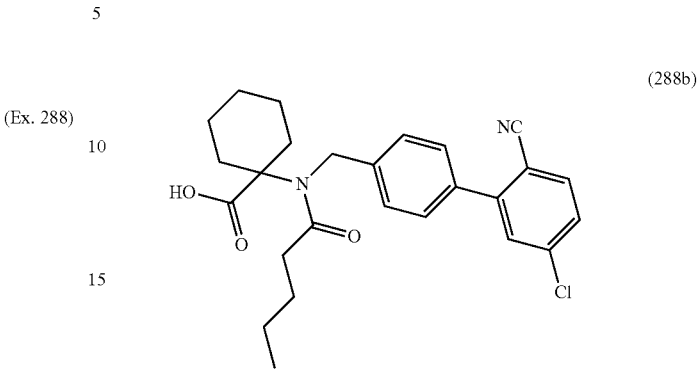

(288b)

The title compound was prepared from Intermediate 288a according to the method described for the synthesis of Intermediate 284a and was isolated as an off white solid. LC-MS (Method H): 1.37 min, [M−H]=451.0; $^1$H NMR (DMSO-d$_6$) δ ppm 11.99 (br s, 1H), 7.99 (d, J=8.2 Hz, 1H), 7.76 (d, J=2.0 Hz, 1H), 7.53-7.71 (m, 5H), 4.76 (s, 2H), 2.21 (t, J=7.0 Hz, 2H), 2.06 (d, J=11.3 Hz, 2H), 1.30-1.61 (m, 9H), 1.01-1.30 (m, 3H), 0.79 (t, J=7.2 Hz, 3H).

Intermediate 288c: 1-(N-((2'-Cyano-5'-(1-methyl-1H-pyrazol-4-yl)-[1,1'-biphenyl]-4-yl)methyl)pentanamido)cyclohexanecarboxylic acid

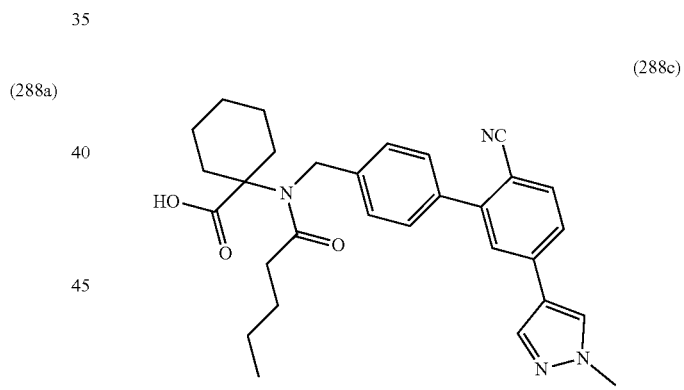

(288c)

To a solution of Intermediate 288b (0.044 g, 0.088 mmol) in 10% v/v ethanol/toluene (3 mL) was added 1-methyl-4-(4,4,5,5-tetramethyl-1,3,2-dioxaborolan-2-yl)-1H-pyrazole (0.055 g, 0.265 mmol) and 2M potassium phosphate (0.066 mL, 0.132 mmol). This stirred mixture was purged with a stream of N$_2$ for 15 min. Chloro(2-dicyclohexylphosphino-2',4',6'-triisopropyl-1,1'-biphenyl)[2-(2'-amino-1,1'-biphenyl)]palladium(II) (0.006 g, 0.0088 mmol) was then added and the mixture stirred at 100° C. for 3 h. The cooled reaction mixture was evaporated, the residue was taken up in DMSO (3.5 mL) and the mixture was filtered and the filtrate purified by prep LC (Method F, formic acid as modifier) to afford the title compound as a white solid (0.037 g, 0.074 mmol, 84% yield). LC-MS (Method H): 1.29 min, [M−H]=497.1; HRMS (ESI): Calcd for $C_{30}H_{35}N_4O_3$ [M+H]$^+$ m/z 499.2704; found 499.2707.

Example 288: 1-(N-((5'-(1-Methyl-1H-pyrazol-4-yl)-2'-(2H-tetrazol-5-yl)-[1,1'-biphenyl]-4-yl)methyl)pentanamido)cyclohexanecarboxylic acid The title compound was prepared from Intermediate 288c according to the method described for the synthesis of Intermediate 283a and was isolated as a white solid. LC-MS (Method H): 1.26 min, [M–H]=540.1; $^1$H NMR (DMSO-$d_6$) δ ppm 11.48 (s, 2H), 8.36 (s, 1H), 8.05 (s, 1H), 7.70-7.79 (m, 2H), 7.62 (d, J=8.6 Hz, 1H), 7.31-7.42 (m, 2H), 7.08-7.19 (m, 2H), 4.66 (s, 2H), 3.88 (s, 3H), 2.18 (t, J=7.0 Hz, 2H), 2.04 (d, J=12.1 Hz, 2H), 1.34-1.75 (m, 9H), 1.12-1.27 (m, 3H), 0.80 (t, J=7.2 Hz, 3H).

The following examples were similarly prepared from the appropriate boronic acids or boronate esters, as described for the synthesis of Example 288 above. Analytical LC-MS injections were used to determine the final purity, the retention time is reported for each compound and the method used is referred to as Method A1, Method A2 or Method H.

| Ex | Structure | MW | LC-MS m/z [M – H]$^-$; RT (Method) | $^1$H NMR (400 MHz, DMSO-$d_6$) δ ppm |
|---|---|---|---|---|
| 289 | 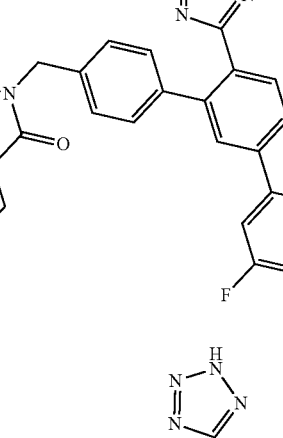 | 573.64 | 572.0; 1.41 min (Method H) | 11.92 (br s, 2H), 7.91-7.96 (m, 1H), 7.90 (d, J = 2.0 Hz, 1H), 7.75 (d, J = 7.8 Hz, 1H), 7.62-7.72 (m, 2H), 7.35-7.41 (m, 2H), 7.31 (tt, J = 9.3, 2.2 Hz, 1H), 7.17-7.24 (m, 2H), 4.66 (s, 2H), 2.18 (t, J = 7.0 Hz, 2H), 2.04 (d, J = 11.7 Hz, 2H), 1.32-1.72 (m, 9H), 1.00-1.30 (m, 3H), 0.79 (t, J = 7.4 Hz, 3H). |
| 290 | 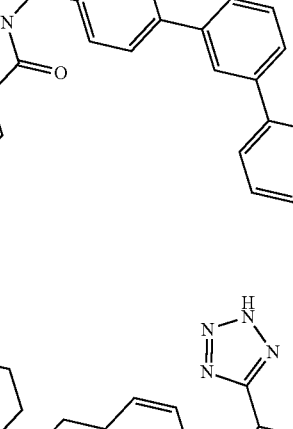 | 568.67 | 567.2; 1.33 min (Method H) | 11.92 (s, 2H), 8.24 (dd, J = 5.1, 2.0 Hz, 1H), 7.94 (dd, J = 7.2, 1.8 Hz, 1H), 7.73-7.78 (m, 1H), 7.66-7.73 (m, 2H), 7.37 (d, J = 8.2 Hz, 2H), 7.10-7.19 (m, 3H), 4.65 (s, 2H), 3.92 (s, 3H), 2.17 (t, J = 7.0 Hz, 2H), 2.03 (d, J = 12.1 Hz, 2H), 1.30-1.73 (m, 9H), 1.01-1.30 (m, 3H), 0.78 (t, J = 7.2 Hz, 3H). |
| 291 | 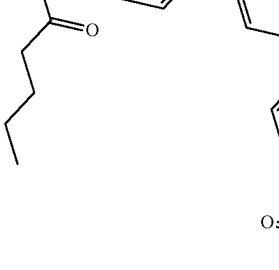 | 594.71 | 593.1; 1.28 min (Method H) | 11.92 (br s, 2H), 10.08 (s, 1H), 7.81-7.86 (m, 1H), 7.80-7.81 (m, 1H), 7.76-7.80 (m, 2H), 7.67-7.75 (m, 3H), 7.32-7.42 (m, 2H), 7.12-7.24 (m, 2H), 4.66 (s, 2H), 2.18 (t, J = 7.2 Hz, 2H), 2.07 (s, 3H), 2.03 (d, J = 12.1 Hz, 2H), 1.32-1.73 (m, 9H), 1.02-1.32 (m, 3H), 0.79 (t, J = 7.2 Hz, 3H). |

| Ex | Structure | MW | LC-MS m/z [M − H]⁻; RT (Method) | ¹H NMR (400 MHz, DMSO-d₆) δ ppm |
|---|---|---|---|---|
| 292 | 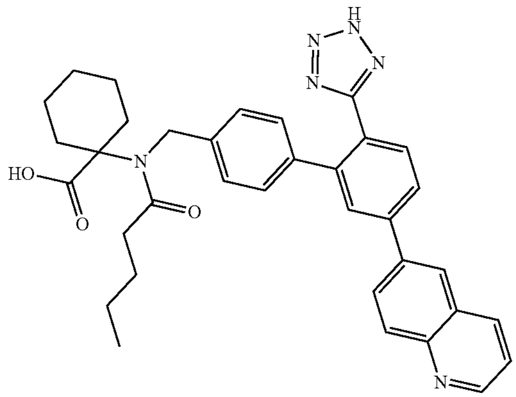 [SMILES: CCCCC(=O)N(Cc1ccc(-c2cc(-c3ccc4ncccc4c3)ccc2-c2nn[nH]n2)cc1)C1(C(=O)O)CCCCC1] | | 587.2; 1.340 min. (Method H) | 11.94 (br s, 2H), 8.94 (dd, J = 4.3, 1.6 Hz, 1H), 8.52 (d, J = 2.0 Hz, 1H), 8.47 (d, J = 7.4 Hz, 1H), 8.27 (dd, J = 9.0, 2.0 Hz, 1H), 8.14 (d, J = 8.6 Hz, 1H), 8.03 (dd, J = 7.8, 1.6 Hz, 1H), 7.99 (s, 1H), 7.81 (d, J = 7.8 Hz, 1H), 7.59 (dd, J = 8.2, 3.9 Hz, 1H), 7.35-7.45 (m, 2H), 7.18-7.29 (m, 2H), 4.67 (s, 2H), 2.19 (t, J = 7.0 Hz, 2H), 2.03 (d, J = 12.1 Hz, 2H), 1.36-1.71 (m, 9H), 1.04-1.33 (m, 3H), 0.80 (t, J = 7.4 Hz, 3H). |

Example 293: 1-(N-((5'-(Pyridin-2-yl)-2'-(2H-tetrazol-5-yl)-[1,1'-biphenyl]-4-yl)methyl)pentanamido)cyclohexanecarboxylic acid

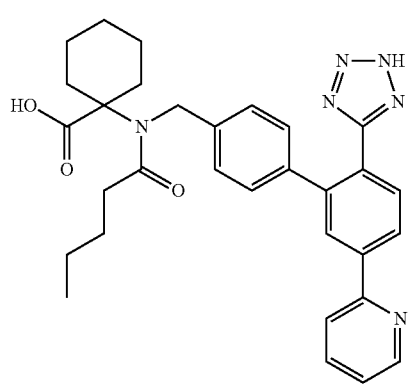

(Ex. 293)

Intermediate 293a: Methyl 1-(N-((2'-cyano-5'-(5,5-dimethyl-1,3,2-dioxaborinan-2-yl)-[1,1'-biphenyl]-4-yl)methyl)pentanamido)cyclohexanecarboxylate In a 20 mL pressure vial containing Intermediate 288a (0.700 g, 1.50 mmol) and 5,5,5',5'-tetramethyl-2,2'-bi(1,3,2-dioxaborinane (1.016 g, 4.50 mmol) was added 1,4-dioxane (15 mL), KOAc (0.446 g, 4.50 mmol) and chloro(2-dicyclohexylphosphino-2',4',6'-triisopropyl-1,1'-biphenyl)[2-(2'-amino-1,1'-biphenyl)]palladium (II) (0.236 g, 0.300 mmol). The stirred mixture was purged with a stream of N₂ for 15 min and then it was heated at 85° C. for 1.5 h. The cooled mixture was partitioned with H₂O (25 mL) and EtOAc (50 mL) and the organic phase was separated, dried over anhydrous sodium sulfate, filtered and evaporated. The residue was purified by flash chromatography using a 12 g ISCO-type column and eluting with 20 to 50% EtOAc/hexane to give the title compound (0.620 g, 1.14 mmol, 76% yield) as a yellow foam. ¹H NMR (CDCl₃) δ ppm 7.95 (s, 1H), 7.85 (dd, J=7.6, 1.0 Hz, 1H), 7.75 (d, J=7.4 Hz, 1H), 7.59-7.63 (m, 2H), 7.50-7.55 (m, 2H), 4.68 (s, 2H), 3.80 (s, 4H), 3.78 (s, 3H), 2.29 (m, 4H), 1.57-1.76 (m, 7H), 1.43 (td, J=12.9, 3.9 Hz, 2H), 1.25-1.34 (m, 3H), 1.04 (s, 6H), 0.88 (t, J=7.4 Hz, 3H).

Intermediate 293b: Methyl 1-(N-((2'-cyano-5'-(pyridin-2-yl)-[1,1'-biphenyl]-4-yl)methyl)pentanamido)cyclohexanecarboxylate

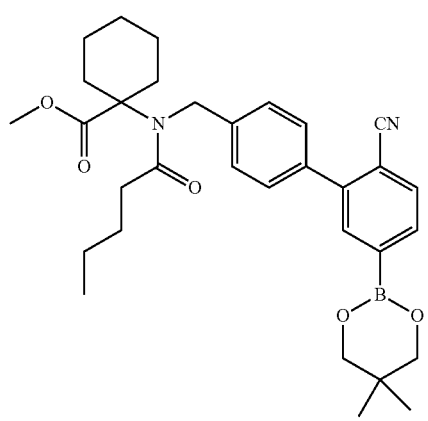

(293a)

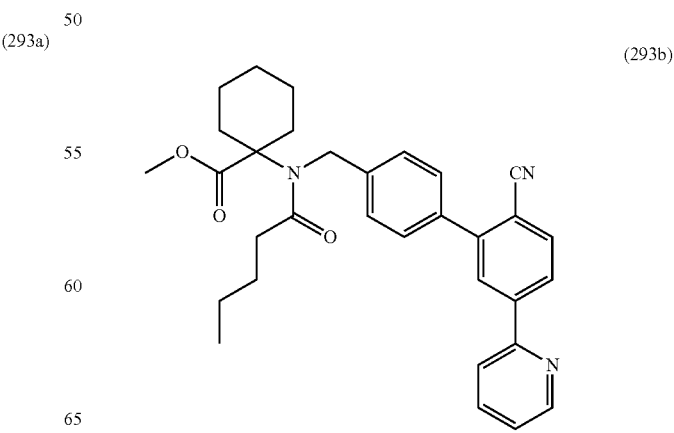

(293b)

To a mixture of Intermediate 293a (0.075 g, 0.138 mmol) in 20% v/v ethanol/toluene (3 mL) was added 2-bromopyridine (0.039 mL, 0.413 mmol) and 2M potassium phosphate (0.138 mL, 0.275 mmol). This stirred mixture was purged with a stream of $N_2$ for 15 min and then chloro(2-dicyclohexylphosphino-2',6'-diisopropoxy-1,1'-biphenyl)[2-(2'-amino-1,1'-biphenyl)]palladium(II) (0.011 g, 0.014 mmol) was added and the mixture was stirred at 100° C. for 2 h. The cooled reaction mixture was evaporated and the residue was taken up in DMSO (3.5 mL). Purification by prep LC (Method F, formic acid as modifier) afforded the title compound (26 mg, 0.051 mmol, 37% yield) as a white solid. LC-MS (Method H): 1.40 min, $[M+H]^+$=510.2; HRMS (ESI): Calcd for $C_{32}H_{36}N_3O_3$ $[M+H]^+$ m/z 510.2751; found 510.2765.

Intermediate 293c: 1-(N-((2'-Cyano-5'-(pyridin-2-yl)-[1,1'-biphenyl]-4-yl)methyl)pentanamido)cyclohexanecarboxylic acid

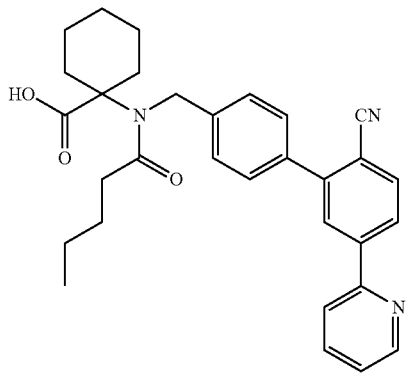

(293c)

The title compound was prepared from Intermediate 293b according to the method described for the synthesis of Intermediate 284a and was isolated as an off-white solid. LC-MS (Method H): 1.37 min, $[M+H]^+$=496.2; HRMS (ESI): Calcd for $C_{31}H_{34}N_3O_3$ $[M+H]^+$ m/z 496.2596; found 496.2606.

Example 293: 1-(N-((5'-(pyridin-2-yl)-2'-(2H-tetrazol-5-yl)-[1,1'-biphenyl]-4-yl)methyl)pentanamido)cyclohexanecarboxylic acid The title compound was prepared from Intermediate 293c according to the method described for the synthesis of Intermediate 283a and was isolated as an off-white solid. LC-MS (Method H): 1.30 min, $[M+H]^+$=539.2; $^1$H NMR (DMSO-$d_6$) δ ppm 11.93 (s, 2H), 8.73 (d, J=4.7 Hz, 1H), 8.23-8.30 (m, 2H), 8.18 (d, J=7.8 Hz, 1H), 7.95 (td, J=7.8, 1.6 Hz, 1H), 7.79 (d, J=7.8 Hz, 1H), 7.44 (dd, J=7.4, 4.7 Hz, 1H), 7.39 (d, J=8.2 Hz, 2H), 7.18 (d, J=8.2 Hz, 2H), 4.67 (s, 2H), 2.19 (t, J=7.0 Hz, 2H), 2.05 (d, J=11.7 Hz, 2H), 1.37-1.67 (m, 9H), 1.07-1.25 (m, 3H), 0.80 (t, J=7.2 Hz, 3H).

The following examples were similarly prepared from the corresponding 2-bromopyridine or 2-chloropyridine, as described for the synthesis of Example 293 above. Analytical LC-MS injections were used to determine the final purity, the retention time is reported for each compound and the method used is referred to as Method A1, Method A2 or Method H.

| Ex | Structure | MW | LC-MS m/z $[M + H]^+$; RT (Method) | $^1$H NMR (400 MHz, DMSO-$d_6$) δ ppm |
|---|---|---|---|---|
| 294 | 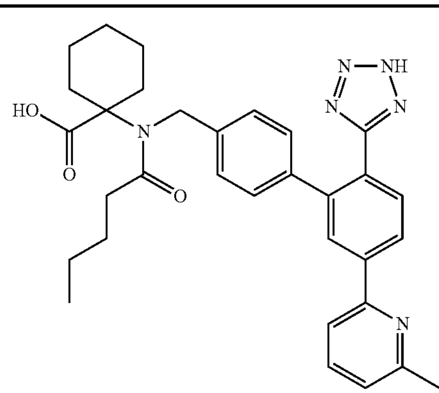 | 552.68 | 553.3; 1.33 min (Method H) | 11.94 (s, 2H), 8.16-8.25 (m, 2H), 7.94 (d, J = 7.0 Hz, 1H), 7.82 (t, J = 7.6 Hz, 1H), 7.76 (d, J = 7.8 Hz, 1H), 7.43 (br s, 2H), 7.29 (d, J = 7.8 Hz, 1H), 7.17 (d, J = 7.8 Hz, 2H), 4.67 (br s, 2H), 2.56 (s, 3H), 2.02-2.25 (m, 4H), 1.36-1.64 (m, 9H), 1.09-1.25 (m, 3H), 0.79 (t, J = 7.2 Hz, 3H). |

-continued

| Ex | Structure | MW | LC-MS m/z [M + H]+; RT (Method) | 1H NMR (400 MHz, DMSO-d6) δ ppm |
|---|---|---|---|---|
| 295 | 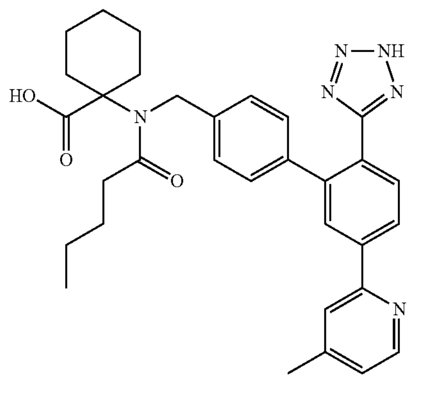 [SMILES: CCCCC(=O)N(Cc1ccc(-c2cc(-c3cc(C)ccn3)ccc2-c2nn[nH]n2)cc1)C1(C(=O)O)CCCCC1] | 552.68 | 553.3; 1.32 min (Method H) | 11.93 (s, 2H), 8.59 (d, J = 5.1 Hz, 1H), 8.27 (dd, J = 8.0, 1.8 Hz, 1H), 8.22-8.25 (m, 1H), 8.09 (s, 1H), 7.79 (d, J = 8.2 Hz, 1H), 7.37-7.42 (m, 2H), 7.32 (d, J = 4.7 Hz, 1H), 7.16-7.21 (m, 2H), 4.67 (s, 2H), 2.44 (s, 3H), 2.19 (t, J = 7.2 Hz, 2H), 2.04 (d, J = 11.3 Hz, 2H), 1.36-1.69 (m, 9H), 1.12-1.26 (m, 3H), 0.77-0.83 (m, 3H). |
| 296 | 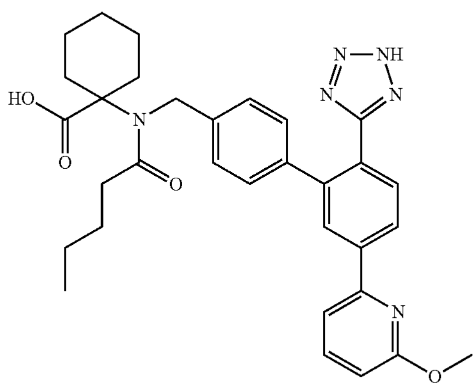 [SMILES: CCCCC(=O)N(Cc1ccc(-c2cc(-c3cccc(OC)n3)ccc2-c2nn[nH]n2)cc1)C1(C(=O)O)CCCCC1] | 568.68 | 569.2; 1.39 min (Method H) | 11.91 (s, 2H), 8.26 (dd, J = 8.0, 1.8 Hz, 1H), 8.17-8.23 (m, 1H), 7.79-7.86 (m, 1H), 7.76 (d, J = 7.4 Hz, 2H), 7.33-7.42 (m, 2H), 7.12-7.20 (m, 2H), 6.85 (d, J = 7.8 Hz, 1H), 4.65 (s, 2H), 3.95 (s, 3H), 2.16 (t, J = 7.0 Hz, 2H), 1.96-2.09 (m, 2H), 1.35-1.65 (m, 9H), 1.02-1.23 (m, 3H), 0.77 (t, J = 7.4 Hz, 3H). |

Example 297: 1-(N-((5'-(3-methylpiperidin-1-yl)-2'-(2H-tetrazol-5-yl)-[1,1'-biphenyl]-4-yl)methyl)pentanamido)cyclohexanecarboxylic acid (Ex. 297)

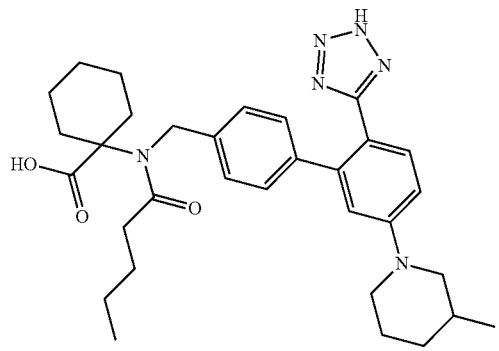

Intermediate 297a: Methyl 1-(N-((2'-cyano-5'-(3-methylpiperidin-1-yl)-[1,1'-biphenyl]-4-yl)methyl)pentanamido)cyclohexanecarboxylate (297a)

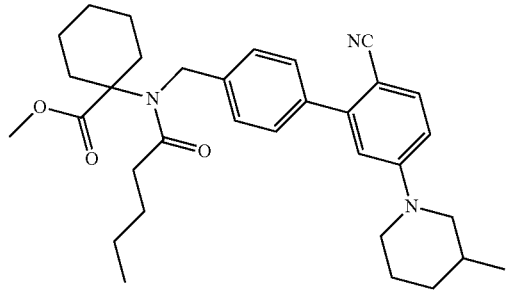

To a solution of Intermediate 288a (0.077 g, 0.165 mmol) in dry THF (3 mL) were added 3-methylpiperidine (0.055 mL, 0.495 mmol), sodium 2-methylpropan-2-olate (0.095 g, 0.989 mmol) and chloro(2-dicyclohexylphosphino-2',6'-diisopropoxy-1,1'-biphenyl)[2-(2'-amino-1,1'-biphenyl)]palladium (II) (0.013 g, 0.016 mmol) and the mixture was stirred at 65° C. for 3 h. The cooled mixture was then evaporated and the residue was taken up in DMSO (3.5 mL) and purified by prep LC (Method F, formic acid as modifier) to afford the title compound as a white solid (0.050 g, 0.094 mmol, 57% yield). LC-MS (Method H): 1.59 min, [M+H]$^+$=530.3; HRMS (ESI): Calcd for $C_{33}H_{44}N_3O_3$[M+H]$^+$ m/z 530.3377; found 530.3389.

Intermediate 297b: 1-(N-((2'-Cyano-5'-(3-methylpiperidin-1-yl)-[1,1'-biphenyl]-4-yl)methyl)pentanamido)cyclohexanecarboxylic acid (297b)

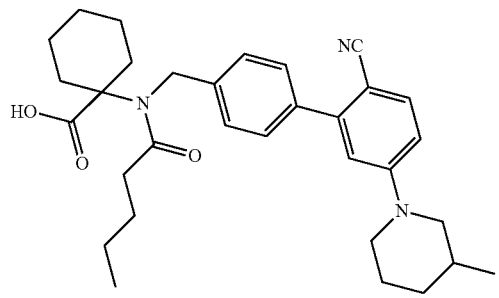

The title compound was prepared from Intermediate 297a according to the method described for the synthesis of Intermediate 284a and was isolated as an off-white solid. LC-MS (Method H): 1.52 min, [M+H]$^+$=516.3; HRMS (ESI): Calcd for $C_{32}H_{42}N_3O_3$ [M+H]$^+$ m/z 516.3221; found 516.3242.

Example 297: 1-(N-((5'-(3-Methylpiperidin-1-yl)-2'-(2H-tetrazol-5-yl)-[1,1'-biphenyl]-4-yl)methyl)pentanamido)cyclohexanecarboxylic acid The title compound was prepared from Intermediate 297b according to the method described for the synthesis of Intermediate 283a and was isolated as an off-white solid. LC-MS (Method H): 1.41 min, [M+H]$^+$=559.2; $^1$H NMR (DMSO-d$_6$) δ ppm 11.92 (br s, 2H), 7.43 (d, J=8.6 Hz, 1H), 7.34 (d, J=8.2 Hz, 2H), 7.04-7.12 (m, 3H), 6.94 (d, J=2.3 Hz, 1H), 4.64 (s, 2H), 3.75-3.90 (m, 2H), 2.75 (td, J=12.1, 2.3 Hz, 1H), 2.44 (d, J=12.1 Hz, 1H), 2.17 (t, J=7.0 Hz, 2H), 2.04 (d, J=12.1 Hz, 2H), 1.38-1.77 (m, 13H), 1.02-1.25 (m, 4H), 0.92 (d, J=6.7 Hz, 3H), 0.79 (t, J=7.4 Hz, 3H).

Example 298: 4-(N-((6'-(2H-Tetrazol-5-yl)-[1,1':3',1''-terphenyl]-4-yl)methyl)pentan-amido)-1-phenylpiperidine-4-carboxylic acid (Ex. 298)

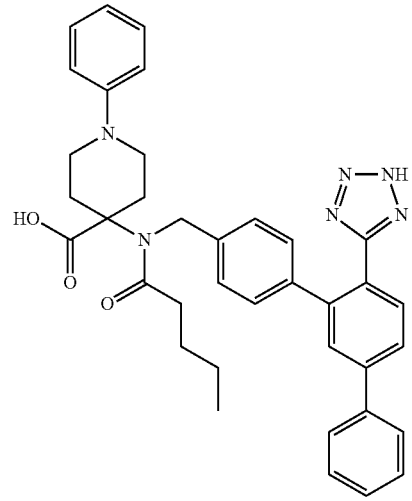

Intermediate 298a: 8-Phenyl-1,3,8-triazaspiro[4.5]decane-2,4-dione (298a)

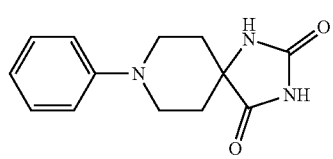

To a solution of 1-phenylpiperidin-4-one (2.53 g, 14.46 mmol) in ethanol (75 mL) and H$_2$O (25 mL) was added ammonium carbonate (12.9 g, 134.3 mmol) and potassium cyanide (2.11 g, 32.5 mmol). The reaction vessel was sealed and the mixture was then heated at 80-90° C. for 18 h. The cooled mixture was concentrated in vacuo, H$_2$O (200 mL) was added to the residue and the resulting suspension was briefly stirred at RT. This mixture was then filtered and the residue washed with H$_2$O to give the title compound as a wet solid (ca. 3 g). The aqueous filtrate and washings were combined and extracted with EtOAc (3×100 mL) and the combined organic extract was washed (H$_2$O), dried (anhydrous sodium sulfate), filtered and evaporated to provide more of the title compound as an impure solid (ca. 2 g). The combined solids thus obtained were taken up in ethanol (200 mL) and the volatiles were removed under reduced pressure to give a brown solid. This solid was triturated a mixture of 20% v/v of ethanol/tert-butylmethyl ether (50 mL) and the resulting suspension was filtered and the filter-cake was washed with tert-butylmethyl ether. The solid thus obtained was air-dried to give the title compound (3.06 g, 12.5 mmol, 86% yield) as a brown solid which was used as such without further purification. $^1$H NMR (DMSO-d$_6$) δ ppm 10.67 (br s, 1H), 8.53 (s, 1H), 7.21 (dd, J=8.6, 7.4 Hz, 2H), 6.95 (d, J=8.2 Hz, 2H), 6.76 (t, J=7.2 Hz, 1H), 3.63 (dt, J=13.0, 3.9 Hz, 2H), 2.99-3.16 (m, 2H), 1.81-1.97 (m, 2H), 1.60 (d, J=13.3 Hz, 2H).

Intermediate 298b: 4-amino-1-phenylpiperidine-4-carboxylic acid

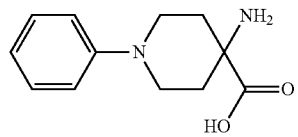

(298b)

A mixture of Intermediate 298a (3.06 g, 12.5 mmol) and 6M NaOH (100 mL, 600 mmol) were heated at 100° C. in a sealed pressure bottle for 22 h. The reaction temperature was then increased to 130° C. and stirring was continued for 24 h. The cooled mixture was neutralized (pH 6-7) by the slow addition of AcOH to give a beige precipitate. The resulting suspension was filtered and the filter-cake was washed with numerous small quantities of H$_2$O and then air-dried to give the title compound as a beige solid (2.64 g, 11.9 mmol, 96% yield). LC-MS (Method H): 0.34 min, [M+H]$^+$=221.1; HRMS (ESI): Calcd for C$_{12}$H$_{17}$N$_2$O$_2$ [M+H]$^+$ m/z 221.1285; found 221.1284.

Intermediate 298c: Methyl 4-amino-1-phenylpiperidine-4-carboxylate

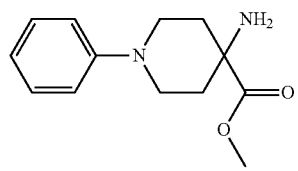

(298c)

To a suspension of Intermediate 298b (2.64 g, 11.9 mmol) in MeOH (60 mL) was slowly added thionyl chloride (2.61 mL, 36.0 mmol) and then the mixture was stirred at 65° C. for 18 h. The cooled mixture was then evaporated under reduced pressure and the residue was taken up in H$_2$O (100 mL). This mixture was neutralized by the addition of 1M NaOH to give an off-white precipitate which was filtered and the filter-cake was washed with several small portions of water. The resulting solid was air-dried to afford the title compound as an off-white solid (1.00 g, 4.27 mmol, 35% yield). LC-MS (Method H): 0.88 min, [M+H]$^+$=235.2; $^1$H NMR (CDCl$_3$) δ ppm 7.19-7.33 (m, 2H), 6.91-7.00 (m, 2H), 6.79-6.89 (m, 1H), 3.75 (s, 3H), 3.24-3.37 (m, 4H), 2.23 (ddd, J=13.5, 8.2, 5.7 Hz, 2H), 1.62-1.73 (m, 2H), 1.56 (br s, 2H).

Intermediate 298d: Methyl 4-((4-bromobenzyl)amino)-1-phenylpiperidine-4-carboxylate

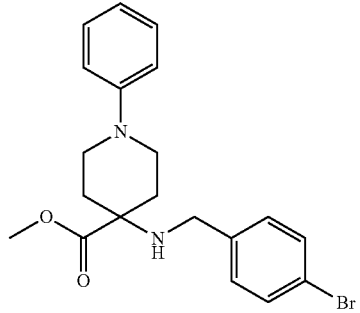

(298d)

To a mixture of Intermediate 298c (1.00 g, 4.27 mmol) in ACN (15 mL) was added 1-bromo-4-(bromomethyl)benzene (1.17 g, 4.69 mmol) and DIEA (0.97 mL, 5.55 mmol), the vessel was sealed and the mixture was heated at 80° C. for 18 h. The cooled mixture was then evaporated under reduced pressure, the residue was taken up in tert-butylmethyl ether (100 mL) and saturated aqueous NaHCO$_3$ (25 mL) was added. The organic phase was separated and the aqueous phase was re-extracted with a further portion of tert-butylmethyl ether (20 mL). The combined organic extract was dried over anhydrous sodium sulfate, filtered and evaporated. The residue obtained was purified by flash chromatography using a 25 g ISCO-type column and eluting with a 0 to 10% acetone/hexane to give the title compound as a clear light yellow oil (1.60 g, 3.97 mmol, 93% yield). LC-MS (Method H): 1.28 min, [M+H]$^+$=403.0. $^1$H NMR (CDCl$_3$) δ ppm 7.40-7.48 (m, 2H), 7.19-7.30 (m, 4H), 6.92-6.99 (m, 2H), 6.85 (t, J=7.2 Hz, 1H), 3.77 (s, 3H), 3.59 (s, 2H), 3.32-3.41 (m, 2H), 3.22-3.32 (m, 2H), 2.20 (ddd, J=13.6, 9.5, 3.9 Hz, 2H), 1.81-1.93 (m, 2H).

Intermediate 298e: Methyl 4-(N-(4-bromobenzyl)pentanamido)-1-phenylpiperidine-4-carboxylate

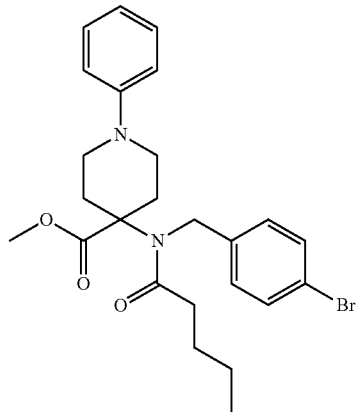

(298e)

To a mixture of Intermediate 298d (1.55 g, 3.84 mmol) in toluene (50 mL) was added DIEA (1.43 mL, 7.69 mmol) and pentanoyl chloride (0.69 mL, 5.76 mmol) and the resulting mixture was stirred at 65° C. for 18 h. Additional portions of DIEA (1.43 mL, 7.69 mmol) and pentanoyl chloride (0.69 mL, 5.76 mmol) were then added and the mixture was stirred at the same temperature for 2 h. Additional portions of DIEA (1.43 mLl, 7.69 mmol) and pentanoyl chloride (0.69 mL, 5.76 mmol) were then added and the mixture was stirred at the same temperature for another 1 h. The cooled mixture was washed sequentially with 10% w/v aqueous citric acid (50 mL) and saturated aqueous NaHCO$_3$ (50 mL), then dried over anhydrous sodium sulfate, filtered and evaporated. The residue was purified by flash chromatography using a 40 g ISCO-type column with a 0 to 20% acetone/hexane gradient to afford the title compound as an orange gum (1.59 g, 3.26 mmol, 85% yield). LC-MS (Method H): 1.46 min, [M+H]$^+$=487.1; $^1$H NMR (CDCl$_3$) δ ppm 7.48-7.55 (m, 2H), 7.28-7.34 (m, 2H), 7.19-7.26 (m, 2H), 6.79-6.90 (m, 3H), 4.59 (s, 2H), 3.79 (s, 3H), 3.50 (d, J=12.1 Hz, 2H), 3.10 (td, J=12.3, 2.0 Hz, 2H), 2.30-2.38 (m, 2H), 2.27 (t, J=7.2 Hz, 2H), 1.88 (td, J=12.7, 5.1 Hz, 2H), 1.50-1.68 (m, 2H), 1.23-1.35 (m, 2H), 0.88 (t, J=7.2 Hz, 3H).

Intermediate 298f: Methyl 4-(N-((6'-cyano-[1,1':3',1''-terphenyl]-4-yl)methyl)pentan-amido)-1-phenylpiperidine-4-carboxylate

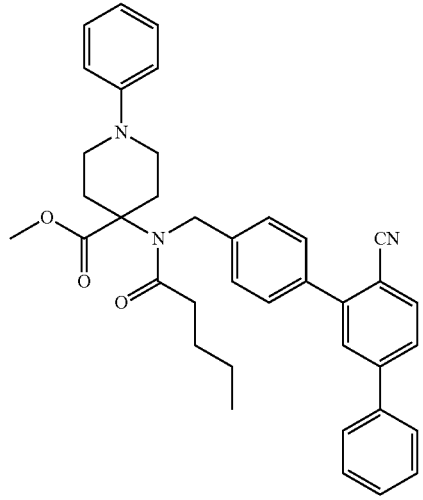

(298f)

The title compound was prepared by the reaction Intermediate 298e (0.078 g, 0.160 mmol) with Intermediate 268c (0.070 g, 0.240 mmol), according to the method described for the synthesis of Intermediate 330b, and was isolated as a white solid (0.090 g, 0.154 mmol, 96% yield).). LC-MS (Method H): 1.55 min, [M+H]$^+$=586.2; $^1$H NMR (CDCl$_3$) δ ppm 7.86 (d, J=8.2 Hz, 1H), 7.75 (d, J=2.0 Hz, 1H), 7.62-7.71 (m, 5H), 7.54-7.59 (m, 2H), 7.44-7.53 (m, 3H), 7.23 (dd, J=8.6, 7.4 Hz, 2H), 6.89 (d, J=8.2 Hz, 2H), 6.82 (t, J=7.2 Hz, 1H), 4.74 (s, 2H), 3.81 (s, 3H), 3.54 (d, J=12.5 Hz, 2H), 3.13 (t, J=11.7 Hz, 2H), 2.41 (d, J=12.9 Hz, 2H), 2.35 (t, J=7.4 Hz, 2H), 1.95 (td, J=12.6, 4.9 Hz, 2H), 1.60-1.70 (m, 2H), 1.23-1.39 (m, 2H), 0.90 (t, J=7.4 Hz, 3H).

Intermediate 298 g: 4-(N-((6'-Cyano-[1,1':3',1''-terphenyl]-4-yl)methyl)pentanamido)-1-phenylpiperidine-4-carboxylic acid

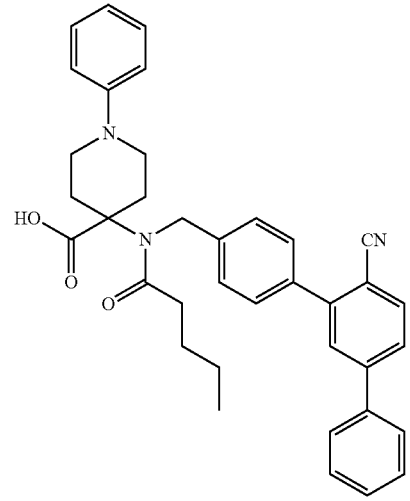

(298g)

The title compound was prepared from Intermediate 298f according to the method described for the synthesis of Intermediate 284a and was isolated as an off-white solid. LC-MS (Method H): 1.49 min, [M+H]$^+$=572.2; HRMS (ESI): Calcd for C$_{37}$H$_{38}$N$_3$O$_3$ [M+H]$^+$ m/z 572.2908; found 572.2917.

Example 298: 4-(N-((6'-(2H-Tetrazol-5-yl)-[1,1':3',1''-terphenyl]-4-yl)methyl)pentan-amido)-1-phenylpiperidine-4-carboxylic acid The title compound was prepared from Intermediate 298 g according to the method described for the synthesis of Intermediate 283a and was isolated as an off-white solid. LC-MS (Method H): 1.39 min, [M+H]$^+$=615.2; $^1$H NMR (DMSO-d$_6$) δ ppm 12.28 (s, 2H), 7.78-7.90 (m, 4H), 7.75 (d, J=7.8 Hz, 1H), 7.48-7.55 (m, 2H), 7.41-7.48 (m, 1H), 7.35-7.41 (m, 2H), 7.13-7.25 (m, 4H), 6.85-6.96 (m, 2H), 6.75 (t, J=7.0 Hz, 1H), 4.71 (s, 2H), 3.52 (d, J=12.1 Hz, 2H), 3.02 (t, J=11.3 Hz, 2H), 2.16-2.30 (m, 4H), 1.85 (dd, J=12.1, 8.6 Hz, 2H), 1.42-1.51 (m, 2H), 1.16-1.26 (m, 2H), 0.81 (t, J=7.4 Hz, 3H).

Example 299: 2-ethoxy-1-((5'-(4-methylpyridin-2-yl)-2'-(5-oxo-4,5-dihydro-1,2,4-oxadiazol-3-yl)-[1,1'-biphenyl]-4-yl)methyl)-1H-benzo[d]imidazole-7-carboxylic acid

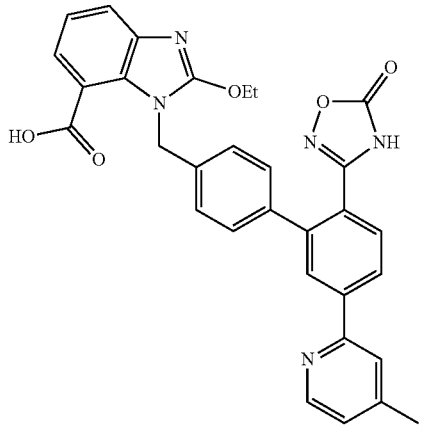

(Ex. 299)

Intermediate 299a:
2-chloro-4-(4-methylpyridin-2-yl)benzonitrile

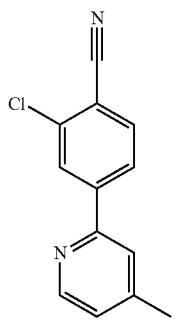

(299a)

To a solution of 2-bromo-4-methylpyridine (455 mg, 2.65 mmol) and (3-chloro-4-cyanophenyl)boronic acid (400 mg, 2.205 mmol) in 4:1 toluene/EtOH (10 mL) was added $K_3PO_4$ (2 M, aq) (2.205 mL, 4.41 mmol) followed by $PdCl_2$(dppf) (161 mg, 0.221 mmol). The resulting mixture was sparged with $N_2$ for 2 min before being sealed and heated at 120° C. for 45 min in the microwave. The reaction mixture was diluted with EtOAc, concentrated onto celite and purified by ISCO (0-100% EtOAc Hexanes) to afford the title compound (299a, 220 mg, 0.962 mmol, 43.6% yield). LC-MS: MS (ESI) m/z: 229.0 [M+H]$^+$; $^1$H NMR (500 MHz, CDCl$_3$) δ 8.61 (d, J=5.0 Hz, 1H), 8.22 (s, 1H), 8.01 (d, J=8.0 Hz, 1H), 7.78 (d, J=8.0 Hz, 1H), 7.61 (s, 1H), 7.19 (d, J=5.1 Hz, 1H), 2.48 (s, 3H).

Intermediate 299b: methyl 1-((2'-cyano-5'-(4-methylpyridin-2-yl)-[1,1'-biphenyl]-4-yl)methyl)-2-ethoxy-1H-benzo[d]imidazole-7-carboxylate

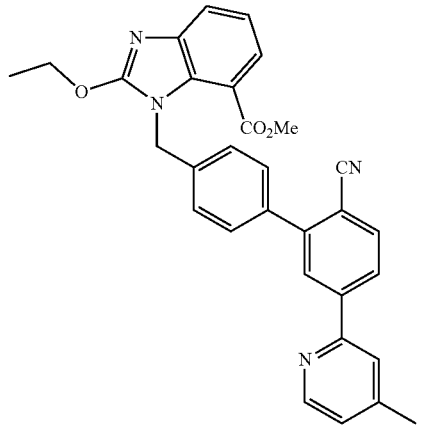

(299b)

To a pressure-rated vial containing I-005 (200 mg, 0.458 mmol), Intermediate 299a (115 mg, 0.504 mmol) and second generation xphos precatalyst (36.1 mg, 0.046 mmol) was added dioxane (2292 µl) followed by 2 M $K_3PO_4$ (2 M aq) (458 µl, 0.917 mmol). The reaction mixture was sparged with $N_2$ for 2 min before being sealed and heated at 85° C. for 18 h. The reaction mixture was then concentrated onto celite and purified by ISCO (0-100% EtOAc/Hexanes) to afford the title compound (159 mg, 0.316 mmol, 69.0% yield). LC-MS (Method A2): 0.88 min, [M+H]$^+$=503.0.

Example 299: 2-ethoxy-1-((5'-(4-methylpyridin-2-yl)-2'-(5-oxo-4,5-dihydro-1,2,4-oxadiazol-3-yl)-[1,1'-biphenyll-4-yl)methyl)-1H-benzo[d]imidazole-7-carboxylic acid Intermediate 299b (78 mg, 0.155 mmol) was dissolved in 1-butyl-3-methylimidazolium acetate (1.2 mL) along with hydroxylamine hydrochloride (270 mg, 3.88 mmol). The reaction mixture was sealed and allowed to stir at 65° C. for 24 h. The reaction mixture was diluted with $H_2O$ and extracted with EtOAc 3x. The combined organics were washed with brine, dried with sodium sulfate, filtered and concentrated. The crude residue was dissolved in 5 mL of THF and DBU (0.234 mL, 1.552 mmol) was added followed by CDI (252 mg, 1.552 mmol). The reaction mixture was allowed to stir at RT for 30 minutes. The reaction mixture was concentrated and then re-dissolved in MeOH (5 mL). 1M NaOH (3.10 mL, 3.10 mmol) was added and the reaction mixture was allowed to stir at 65° C. for 3 h. The mixture was then acidified to pH 3-4 with 10% citric acid and extracted with EtOAc 3x. The combined organic layer was washed with brine, dried with sodium sulfate, filtered and concentrated. The crude residue was purified by reverse phase HPLC (Xbridge Prep Shield RP18, 15 min gradient of 20-100% B. A=$H_2O$/MeOH 10 mM NH$_4$OAc 90:10. B=$H_2O$/MeOH 10 mM NH$_4$OAc 10:90) to afford the title compound (Example 299, 7.9 mg, 0.014 mmol, 9.30% yield). MS (ESI) m/z [M+H]$^+$=548.3. $^1$H NMR (500 MHz, DMSO-d$_6$) δ 8.53 (br d, J=4.9 Hz, 1H), 8.22 (br d, J=7.6 Hz, 1H), 8.09 (br s, 1H), 7.96 (br s, 1H), 7.75 (d, J=7.9 Hz, 1H), 7.66 (br d, J=7.0 Hz, 1H), 7.57 (br d, J=7.6 Hz, 1H), 7.31 (br d, J=7.3 Hz, 2H), 7.24 (br d, J=4.0 Hz, 1H), 7.18 (br s, 1H), 7.07 (br d, J=7.9 Hz, 2H), 5.73 (br s, 2H), 4.67-4.52 (m, J=6.7 Hz, 2H), 2.38 (s, 3H), 1.40 (br t, J=6.3 Hz, 3H). LC-MS retention time (Method A4): 1.298 min.

Example 300: 2-ethoxy-1-((5'-(5-methylpyridin-2-yl)-2'-(5-oxo-4,5-dihydro-1,2,4-oxadiazol-3-yl)-[1,1'-biphenyll-4-yl)methyl)-1H-benzo[dlimidazole-7-carboxylic acid

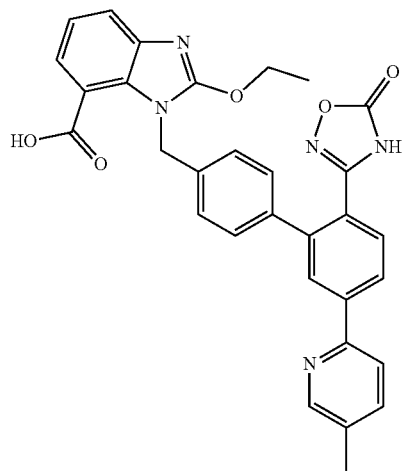

(Ex. 300)

Intermediate 300a: methyl 1-((5'-chloro-2'-cyano-[1,1'-biphenyl]-4-yl)methyl)-2-ethoxy-1H-henzoldlimidazole-7-carboxylate

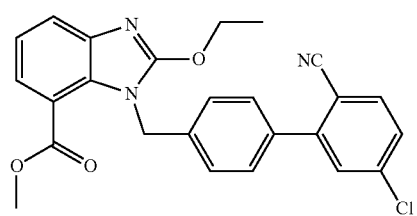

(300a)

Intermediate 300a was synthesized from I-005 and 4-chloro-2-iodobenzonitrile using the procedure described for 299b to give the title compound (Intermediate 300a, 2.55 g, 5.6 mmol, 61% yield). LC-MS (Method A2): 1.02 min, [M+H]$^+$=446.0. $^1$H NMR (500 MHz, CDC$_3$) δ7.77 (dd, J=7.8, 1.0 Hz, 1H), 7.69 (d, J=8.3 Hz, 1H), 7.60 (dd, J=7.8, 1.0 Hz, 1H), 7.49-7.39 (m, 4H), 7.21 (t, J=7.8 Hz, 1H), 7.14 (d, J=8.3 Hz, 2H), 5.73 (s, 2H), 4.70 (q, J=7.1 Hz, 2H), 3.78 (s, 3H), 1.51 (t, J=7.2 Hz, 3H).

Intermediate 300b: methyl 1-((2'-cyano-5'-(4,4,5,5-tetramethyl-1,3,2-dioxaborolan-2-yl)-[1,1'-biphenyl]-4-yl)methyl)-2-ethoxy-1H-benzo[d]imidazole-7-carboxylate

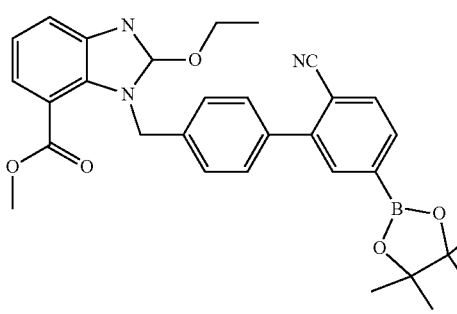

(300b)

To a flask containing Intermediate 300a (2100 mg, 4.71 mmol), bis(pinacolato)diborane (2392 mg, 9.42 mmol) and Pd$_2$(dba)$_3$ (431 mg, 0.471 mmol) was added dioxane (2.35E+04 µl) followed by KOAc (2311 mg, 23.55 mmol) and dicyclohexyl(2',4',6'-triisopropyl-[1,1'-biphenyl]-2-yl)phosphane (225 mg, 0.471 mmol) (XPhos). The reaction mixture was evacuated and backfilled with N$_2$ (3×) and heated at 100° C. for 120 minutes.

The reaction mixture was concentrated onto celite and purified by ISCO (0-60% EtOAc/DCM) to afford the title compound (Intermediate 300b, 2.2 g, 3.44 mmol, 73.0% yield). LC-MS: MS (ESI) m/z: 538.1(M+H)$^+$. $^1$H NMR (500 MHz, CDCl$_3$) δ 7.87 (s, 1H), 7.84 (dd, J=7.7, 0.8 Hz, 1H), 7.79-7.70 (m, 2H), 7.59 (dd, J=7.8, 1.0 Hz, 1H), 7.47 (d, J=8.3 Hz, 2H), 7.21 (t, J=7.8 Hz, 1H), 7.10 (d, J=8.3 Hz, 2H), 5.71 (s, 2H), 4.70 (d, l=7.2 Hz, 2H), 3.79 (s, 3H), 1.52 (t, J=7.2 Hz, 3H), 1.36 (s, 12H).

Intermediate 300c: methyl 1-((2'-cyano-5'-(5-methylpyridin-2-yl)-[1,1'-biphenyl]-4-yl)methyl)-2-ethoxy-1H-benzo[d]imidazole-7-carboxylate

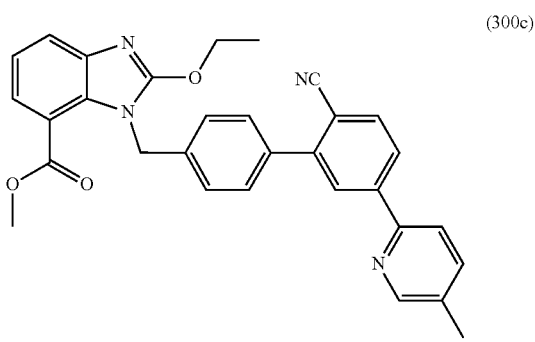 [SMILES: CCOc1nc2cccc(C(=O)OC)c2n1Cc1ccc(-c2cc(-c3ccc(C)cn3)ccc2C#N)cc1]

(300c)

Intermediate 300b (128 mg, 0.200 mmol) was dissolved in 4:1 toluene/EtOH (2 mL) along with XPhos generation two pre-catalyst (31.5 mg, 0.040 mmol), K$_3$PO$_4$ (2 M, aq) (0.300 mL, 0.600 mmol) and 2-bromo-5-methylpyridine (68.8 mg, 0.400 mmol). The reaction mixture was evacuated and backfilled with N$_2$ (3×) then allowed to stir at 65° C. for 2 h. The reaction mixture was concentrated onto celite and purified by ISCO (0-100% DCM/EtOAc) to afford the title compound (Intermediate 300c, 68 mg, 0.135 mmol, 67.7% yield). LC-MS: MS (ESI) m/z: 503.0 (M+H)+. $^1$H NMR (500 MHz, CDCl$_3$) δ 8.56 (s, 1H), 8.10 (d, J=1.4 Hz, 1H), 8.07-8.00 (m, 1H), 7.84 (d, J=8.3 Hz, 1H), 7.76 (d, J=7.8 Hz, 1H), 7.69 (d, J=8.0 Hz, 1H), 7.60 (br d, J=8.0 Hz, 2H), 7.56-7.50 (m, J=8.3 Hz, 2H), 7.21 (t, J=7.8 Hz, 1H), 7.16-7.12 (m, J=8.3 Hz, 2H), 5.73 (s, 2H), 4.71 (d, J=6.9 Hz, 2H), 3.80 (s, 3H), 2.42 (s, 3H), 1.52 (t, J=7.0 Hz, 3H).

Example 300: 2-ethoxy-1-((5'-(5-methylpyridin-2-yl)-2'-(5-oxo-4,5-dihydro-1,2,4-oxadiazol-3-yl)-[1,1'-biphenyl]-4-yl)methyl)-1H-benzo[d]imidazole-7-carboxylic acid Example 300 was synthesized from Intermediate 300c according to the same procedure described for Example 299 to give the title compound (Example 300, 2.9 mg, 5.30 μmol, 3.91% yield). MS (ESI) m/z [M+H+=548.3. $^1$H NMR (500 MHz, DMSO-d$_6$) δ 8.50 (br s, 1H), 8.09 (br d, J=8.2 Hz, 1H), 8.02-7.90 (m, 2H), 7.70 (br d, J=7.0 Hz, 1H), 7.67 (br d, J=7.9 Hz, 1H), 7.60 (br d, J=7.9 Hz, 1H), 7.49 (br d, J=7.6 Hz, 1H), 7.27 (br d, J=7.6 Hz, 2H), 7.15 (br t, J=7.6 Hz, 1H), 7.02 (br d, J=7.6 Hz, 2H), 5.70 (br s, 2H), 4.59 (q, J=7.0 Hz, 2H), 2.34 (s, 3H), 1.41 (br t, J=7.0 Hz, 3H). LC-MS retention time (Method A4): 1.291 min.

The examples in the following table were prepared from the appropriate pyridyl bromide according to the sequence described for Example 300.

| Ex | Structure | MW | LC-MS m/z [M+H]+; RT (Method A4) | $^1$H NMR (500 MHz, DMSO-d$_6$) δ ppm |
|---|---|---|---|---|
| 301 | 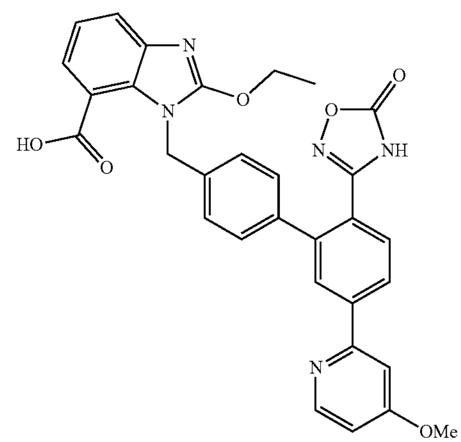 [SMILES: CCOc1nc2cccc(C(=O)O)c2n1Cc1ccc(-c2cc(-c3cc(OC)ccn3)ccc2-c2noc(=O)[nH]2)cc1] | 563.57 | 564.3; 1.213 min. | $^1$H NMR (500 MHz, DMSO-d$_6$) 8.48 (d, J = 5.5 Hz, 1H), 8.20 (br d, J = 8.2 Hz, 1H), 8.09 (s, 1H), 7.72 (d, J = 7.9 Hz, 1H), 7.68-7.59 (m, 2H), 7.54 (br d, J = 7.9 Hz, 1H), 7.30 (br d, J = 7.6 Hz, 2H), 7.18 (t, J = 7.8 Hz, 1H), 7.05 (br d, J = 7.9 Hz, 2H), 6.98 (d, J = 6.1 Hz, 1H), 5.69 (s, 2H), 4.60 (q, J = 7.0 Hz, 2H), 3.90 (s, 3H), 1.40 (t, J = 7.0 Hz, 3H). |
| 302 | 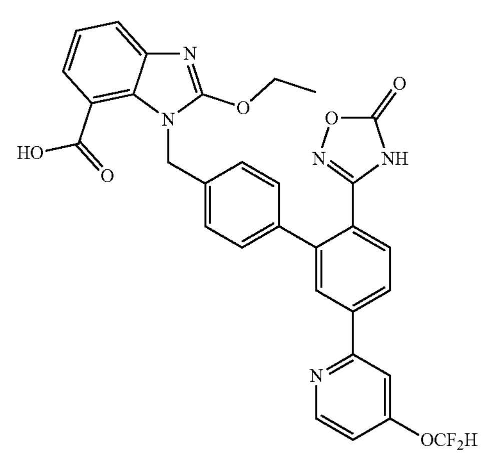 | 599.55 | 600.0; 1.615 min. | $^1$H NMR (500 MHz, DMSO-d$_6$) δ 8.67 (d, J = 5.6 Hz, 1H), 8.19 (dd, J = 8.1, 1.4 Hz, 1H), 8.13-8.03 (m, 1H), 7.92-7.80 (m, 1H), 7.77-7.68 (m, 1H), 7.63 (d, J = 7.8 Hz, 1H), 7.58-7.43 (m, 2H), 7.41-7.26 (m, J = 8.1 Hz, 2H), 7.25-7.12 (m, 2H), 7.10-7.02 (m, J = 8.1 Hz, 2H), 5.70 (s, 2H), 4.61 (q, J = 7.1 Hz, 2H), 1.42 (t, J = 7.0 Hz, 3H). |

| Ex | Structure | MW | LC-MS m/z [M +H]+; RT (Method A4) | 1H NMR (500 MHz, DMSO-d6) δ ppm |
|---|---|---|---|---|
| 303 | 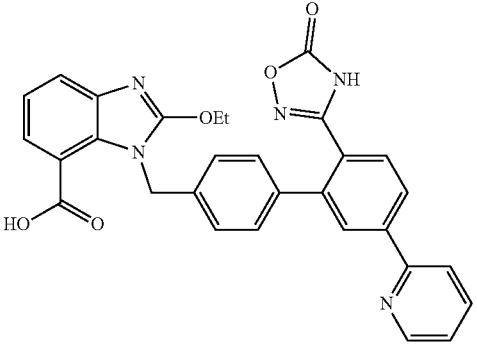 [SMILES: CCOc1nc2cccc(C(=O)O)c2n1Cc1ccc(-c2cc(-c3ccccn3)ccc2-c2noc(=O)[nH]2)cc1] | 533.54 | 534.1; 1.319 min. | |
| 304 | 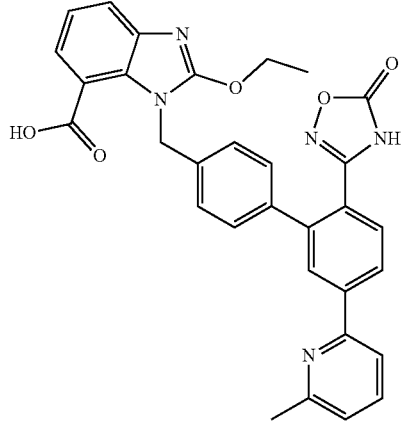 [SMILES: CCOc1nc2cccc(C(=O)O)c2n1Cc1ccc(-c2cc(-c3cccc(C)n3)ccc2-c2noc(=O)[nH]2)cc1] | 547.57 | 548.0; 1.259 min. | |
| 305 | 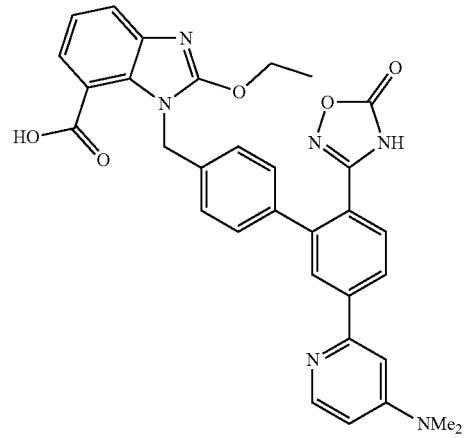 [SMILES: CCOc1nc2cccc(C(=O)O)c2n1Cc1ccc(-c2cc(-c3cc(N(C)C)ccn3)ccc2-c2noc(=O)[nH]2)cc1] | 576.61 | 577.2; 1.247 min. | 1H NMR (500 MHz, DMSO-d6) δ 8.22 (br d, J = 6.7 Hz, 1H), 8.10 (br d, J = 7.9 Hz, 1H), 8.00 (s, 1H), 7.84 (br d, J = 7.9 Hz, 1H), 7.67 (br d, J = 7.6 Hz, 1H), 7.56 (br d, J = 7.9 Hz, 1H), 7.34 (br d, J = 7.6 Hz, 2H), 7.28 (br s, 1H), 7.24-7.03 (m, 4H), 6.91 (br d, J = 6.4 Hz, 1H), 5.70 (s, 2H), 4.60 (q, J = 7.0 Hz, 2H), 3.25-3.14 (m, 6H), 1.40 (t, J = 7.0 Hz, 3H). |

| Ex | Structure | MW | LC-MS m/z [M +H]+; RT (Method A4) | 1H NMR (500 MHz, DMSO-d6) δ ppm |
|---|---|---|---|---|
| 306 | 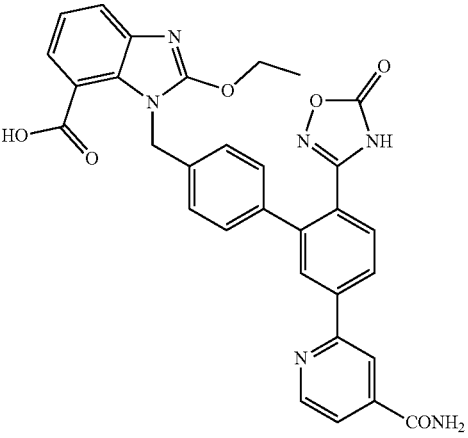 [SMILES: CCOc1nc2cccc(C(=O)O)c2n1Cc1ccc(-c2cc(-c3cc(C(N)=O)ccn3)ccc2-c2noc(=O)[nH]2)cc1] | 576.57 | 578.4; 1.192 min | 1H NMR (500 MHz, DMSO-d6) δ 8.21 (d, J = 7.0 Hz, 1H), 8.07 (br d, J = 8.2 Hz, 1H), 7.97 (s, 1H), 7.86 (d, J = 8.2 Hz, 1H), 7.67 (d, J = 7.9 Hz, 1H), 7.56 (d, J = 7.6 Hz, 1H), 7.34 (br d, J = 7.9 Hz, 3H), 7.28 (br d, J = 2.4 Hz, 1H), 7.24-7.14 (m, 1H), 7.10 (br d, J = 7.9 Hz, 2H), 7.03-6.87 (m, 2H), 5.69 (s, 2H), 4.59 (q, J = 6.9 Hz, 2H), 1.40 (t, J = 7.0 Hz, 3H). |
| 307 | 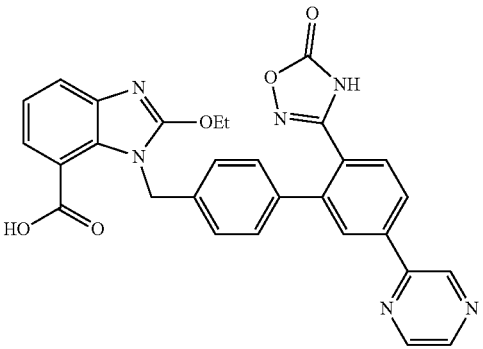 [SMILES: CCOc1nc2cccc(C(=O)O)c2n1Cc1ccc(-c2cc(-c3cnccn3)ccc2-c2noc(=O)[nH]2)cc1] | 534.53 | 535.2; 1.392 min. | 1H NMR (500 MHz, DMSO-d6) δ 9.34 (s, 1H), 8.73 (s, 1H), 8.64 (d, J = 2.1 Hz, 1H), 8.19 (br d, J = 9.2 Hz, 1H), 8.08 (s, 1H), 7.74 (d, J = 8.2 Hz, 1H), 7.64 (d, J = 7.6 Hz, 1H), 7.51 (d, J = 7.6 Hz, 1H), 7.31 (br d, J = 7.9 Hz, 2H), 7.17 (t, J = 7.8 Hz, 1H), 7.02 (br d, J = 7.9 Hz, 2H), 5.69 (s, 2H), 4.60 (q, J = 7.0 Hz, 2H), 1.42 (t, J = 7.0 Hz, 3H). |
| 308 | 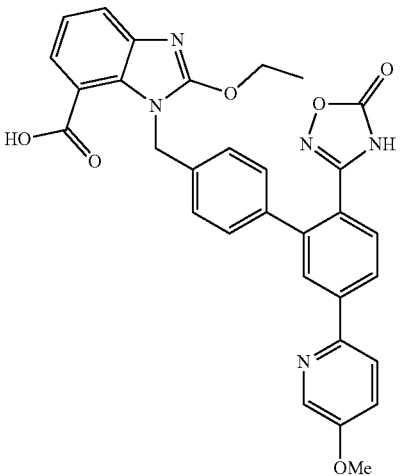 [SMILES: CCOc1nc2cccc(C(=O)O)c2n1Cc1ccc(-c2cc(-c3ccc(OC)cn3)ccc2-c2noc(=O)[nH]2)cc1] | 563.57 | 564.2; 1.458 min. | 1H NMR (500 MHz, DMSO-d6) δ 8.38 (d, J = 2.5 Hz, 1H), 8.08-7.94 (m, 3H), 7.67 (d, J = 8.1 Hz, 1H), 7.61 (d, J = 7.9 Hz, 1H), 7.51 (d, J = 7.8 Hz, 1H), 7.46 (d, J = 8.5 Hz, 1H), 7.33-7.24 (m, J = 7.9 Hz, 2H), 7.16 (t, J = 7.7 Hz, 1H), 7.08-7.01 (m, J = 7.9 Hz, 2H), 5.71 (s, 2H), 4.61 (q, J = 7.0 Hz, 2H), 2.57-2.53 (m, 3H), 1.42 (t, J = 7.0 Hz, 3H). |

487

Example 309: 2-ethoxy-1-((5'-(4-methylpyridin-2-yl)-2'-(2H-tetrazol-5-yl)-[1,1'-biphenyl]-4-yl)methyl)-1H-benzo[d]imidazole-7-carboxylic acid

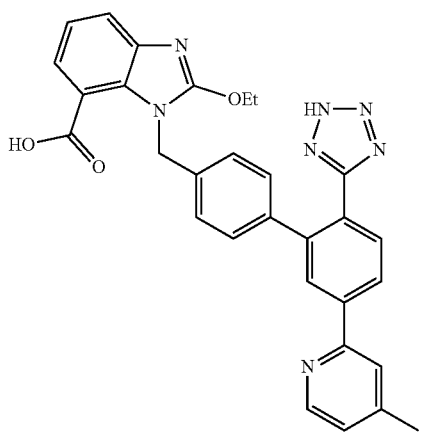

(Ex. 309)

Intermediate 299b (78 mg, 0.155 mmol) was dissolved in xylenes (1 mL). Tributylchlorostannane (0.126 mL, 0.466 mmol) was added followed by sodium azide (30.3 mg, 0.466 mmol). The reaction mixture was stirred at 140° C. in a pressure-rated vial behind a blast shield for 18 h. The reaction mixture was diluted with EtOAc and the azide was quenched with 10% CAN (246 mg, 0.449 mmol). The reaction mixture was diluted with $H_2O$ and extracted with EtOAc 3×. The combined organics were washed with brine, dried with sodium sulfate, filtered and concentrated. The crude residue was dissolved in 1:1 1M NaOH/MeOH (4 mL) and stirred at 65° C. for 1 h. The MeOH was evaporated off and the remaining aq. mixture was diluted with a small amount of $H_2O$ and extracted (3×) with 1:1 EtOAc/hexanes. The aq. mixture was then acidified to pH 3-4 with 10% citric acid and extracted with EtOAc 3×. The combined organics were washed with brine, dried with sodium sulfate, filtered and concentrated. The crude residue was dissolved in DMF, filtered and purified by reverse phase HPLC (Xbridge Prep Shield RP18, 15 min gradient of 20-100% B. A=$H_2O$/MeOH 10 mM $NH_4OAc$ 90:10. B=$H_2O$/MeOH 10 mM $NH_4OAc$ 10:90) to afford the title compound (Example 309, 4.3 mg, 8.09 μmol, 10.49% yield). MS (ESI) m/z $[M+H]^+$=532.2. $^1H$ NMR (500 MHz, DMSO-$d_6$) δ 8.53 (br d, J=4.3 Hz, 1H), 8.18 (br d, J=7.9 Hz, 1H), 8.07 (br s, 1H), 7.95 (br s, 1H), 7.74 (br d, J=7.6 Hz, 1H), 7.66 (br d, J=7.9 Hz, 1H), 7.53 (br d, J=7.6 Hz, 1H), 7.35-7.14 (m, 3H), 7.10 (br d, J=7.3 Hz, 2H), 6.93 (br d, J=7.3 Hz, 2H), 5.64 (br s, 2H), 4.60 (br d, J=6.7 Hz, 2H), 2.39 (br s, 3H), 1.47-1.37 (m, 3H). HPLC retention time (Method A4): 1.290 min.

488

Example 310: 2-ethoxy-1-((5'-(4-methoxypyridin-2-yl)-2'-(2H-tetrazol-5-yl)-[1,1'-biphenyl]-4-yl)methyl)-1H-benzo[d]imidazole-7-carboxylic acid

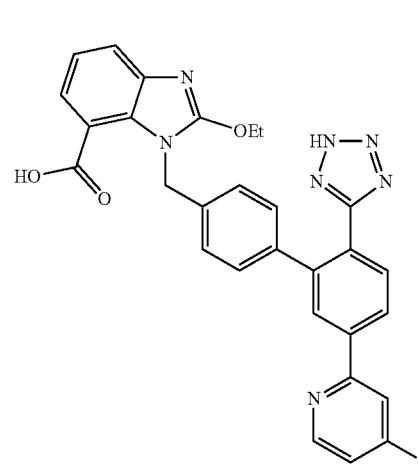

(Ex. 310)

Intermediate 310a: methyl 1-((2'-cyano-5'-(4-methoxypyridin-2-yl)-[1,1'-biphenyl]-4-yl)methyl)-2-ethoxy-1H-benzo[d]imidazole-7-carboxylate

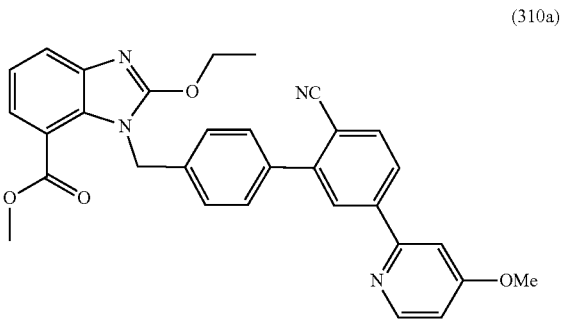 [SMILES: CCOc1nc2cccc(C(=O)OC)c2n1Cc1ccc(-c2cc(-c3cc(OC)ccn3)ccc2C#N)cc1]

(310a)

Intermediate 310a was synthesized from 2-bromo-5-methoxypyridine according to the same procedure described for Intermediate 300c to give the title compound (Intermediate 310a, 21 mg, 0.040 mmol, 45.3% yield). LC-MS (Method A2): 0.88 min, $[M+H]^+$=519.2.

Example 310: $^2$-ethoxy-1-((5'-(4-methoxypyridin-2-yl)-2'-(2H-tetrazol-5-yl)-[1,1'-biphenyll-4-yl)methyl)-1H-benzo[dlimidazole-7-carboxylic acid Example 310 was synthesized from Intermediate 310a using the procedure described for Example 309 to give the title compound (Example 310, 9.6 mg, 0.018 mmol, 31.4% yield). MS (ESI) m/z $[M+H]^+$=548.4. $^1H$ NMR (500 MHz, DMSO-$d_6$) δ 8.46 (d, J=5.7 Hz, 1H), 8.06 (br d, J=7.9 Hz, 1H), 7.98 (s, 1H), 7.71 (d, J=8.1 Hz, 1H), 7.60 (d, J=7.7 Hz, 1H), 7.56-7.45 (m, 2H), 7.20-7.05 (m, 3H), 6.97-6.87 (m, 3H), 4.60 (q, J=7.0 Hz, 2H), 3.91 (s, 3H), 1.92 (s, 3H), 1.42 (t, J=7.0 Hz, 3H. LC-MS retention time (Method A4): 1.066 min.

Example 311: 2-ethoxy-1-((6'-(5-oxo-4,5-dihydro-1,2,4-oxadiazol-3-yl)-[1,1':3',1''-terphenyl]-4-yl)methyl)-1H-benzo[d]imidazole-7-carboxylic acid

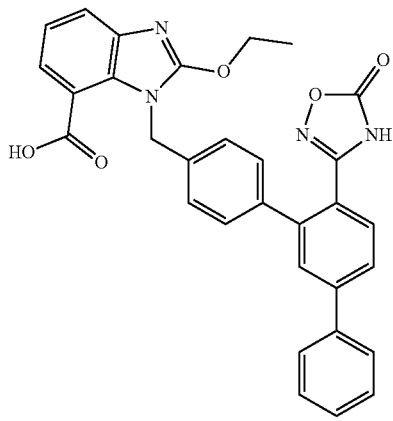
(Ex. 311)

Intermediate 311a: methyl 1-((6'-cyano-[1,1':3',1''-terphenyl]-4-yl)methyl)-2-ethoxy-1H-benzo[d]imidazole-7-carboxylate

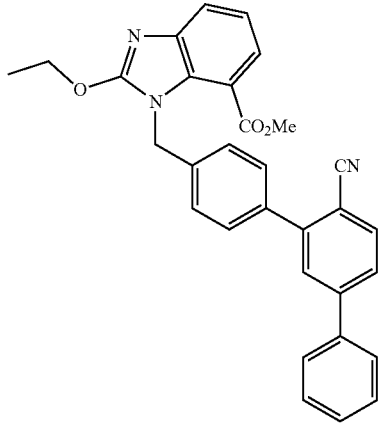
(311a)

To a pressure-rated vial I-005 (830 mg, 1.902 mmol), 3-chloro-[1,1'-biphenyl]-4-carbonitrile (488 mg, 2.283 mmol) and second generation XPHOS precatalyst (74.8 mg, 0.095 mmol) was added dioxane (9512 µl) followed by 2 M $K_3PO_4$ (2 M aq) (1902 µl, 3.80 mmol). The reaction mixture was sparged with $N_2$ for 2 min before being sealed and heated at 85° C. for 1 h. The reaction mixture was concentrated onto celite and purified by ISCO (0-100% EtOAc in hexane) to afford the title compound (Intermediate 311a, 900 mg, 1.846 mmol, 97% yield). LC-MS: MS (ESI) m/z: 488.10 (M+H)$^+$. $^1$H NMR (500 MHz, CDC$_3$) δ7.87-7.81 (m, 1H), 7.77 (d, J=8.0 Hz, 1H), 7.68-7.57 (m, 5H), 7.54-7.40 (m, 5H), 7.24-7.18 (m, 1H), 7.15 (d, J=8.3 Hz, 2H), 5.73 (s, 2H), 4.71 (d, J=6.9 Hz, 2H), 3.79 (s, 3H), 1.52 (t, J=7.0 Hz, 3H).

Example 311: 2-ethoxy-1-((6'-(5-oxo-4,5-dihydro-1,2,4-oxadiazol-3-yl)-[1,1':3',1''-terphenyl]-4-yl)methyl)-1H-benzo[d]imidazole-7-carboxylic acid Example 311 was synthesized from Intermediate 311a using the procedure described for Example 299 to give the title compound (Example 311, 255 mg, 0.479 mmol, 61%). MS (ESI) m/z [M+H]$^+$=533.4. $^1$H NMR (500 MHz, DMSO-d$_6$) δ 7.82 (d, J=7.8 Hz, 1H), 7.77 (d, J=7.3 Hz, 2H), 7.73-7.64 (m, 3H), 7.54 (d, J=7.5 Hz, 1H), 7.51-7.45 (m, 2H), 7.42 (d, J=7.2 Hz, 1H), 7.33 (d, J=7.1 Hz, 2H), 7.18 (br. s., 1H), 7.06 (d, J=7.8 Hz, 2H), 5.69 (br. s., 2H), 4.59 (d, J=6.9 Hz, 2H), 1.40 (t, J=6.9 Hz, 3H). LC-MS retention time (method A4): 1.830 min.

Example 312: 1-((6'-(2H-tetrazol-5-yl)-[1,1':3',1''-terphenyl]-4-yl)methyl)-2-ethoxy-1H-benzo[d]imidazole-7-carboxylic acid

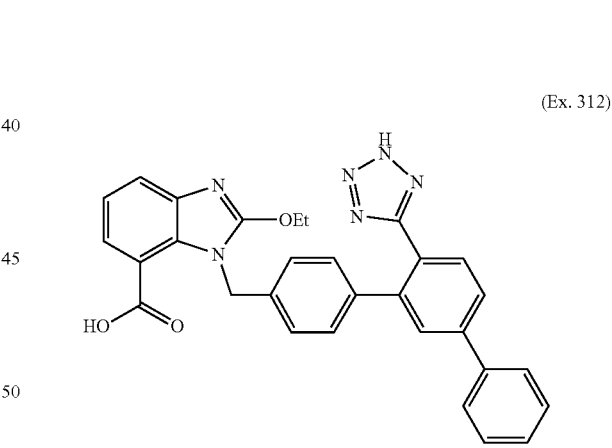
(Ex. 312)

Example 312 was synthesized from Intermediate 311a using the same procedure used to synthesize Example 309 to give the title compound (Example 312, 4 mg, 7.74 µmol, 7.61% yield). MS (ESI) m/z [M+H]$^+$=517.2. $^1$H NMR (500 MHz, DMSO-d$_6$) δ7.96 (s, 1H), 7.73 (br d, J=7.3 Hz, 2H), 7.66 (s, 2H), 7.59-7.49 (m, 2H), 7.49-7.42 (m, 3H), 7.40-7.26 (m, J=7.0 Hz, 1H), 7.17-7.06 (m, 3H), 6.91 (br d, J=7.9 Hz, 2H), 5.66 (s, 2H), 4.58 (br d, J=7.0 Hz, 2H), 1.41 (br t, J=7.0 Hz, 3H). LC-MS retention time (Method A4): 1.7969 min.

Example 313: 1-((6'-carboxy-3"-methyl-[1,1':3',1"-terphenyl]-4-yl)methyl)-2-ethoxy-1H-benzo[d]imidazole-7-carboxylic acid

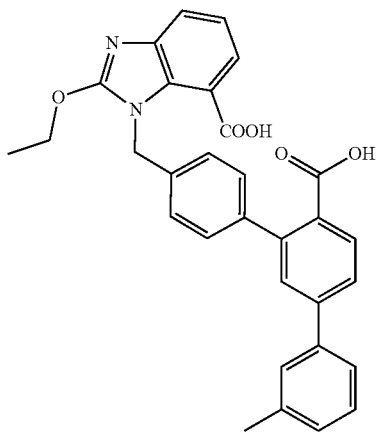

(Ex. 313)

Intermediate 313a: methyl 1-((5'-chloro-2'-(methoxycarbonyl)-[1,1'-biphenyl]-4-yl)methyl)-2-ethoxy-1H-benzo[d]imidazole-7-carboxylate

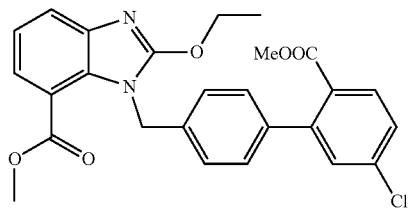

(313a)

To a via was added I-005(221 mg, 0.506 mmol), methyl 4-chloro-2-iodobenzoate (150 mg, 0.506 mmol) and PdCl$_2$(dppf)-CH$_2$Cl$_2$ (20.66 mg, 0.025 mmol). THF (3 mL) and 1.5 M Na$_2$CO$_3$ (1.012 mL, 1.518 mmol) were added. The mixture was bubbled with Ar for 3 min. The reaction mixture was sealed and irradiated in a microwave reactor at 100° C. for 30 min. The reaction mixture was diluted with EtOAc and H$_2$O and extracted with EtOAc. The combined organic layer was washed with brine, dried with MgSO$_4$ and concentrated. The crude residue was purified by ISCO (0-100% EtOAc in Hexanes) to afford the title compound (Example 313a, 160 mg, 0.334 mmol, 66.0% yield). MS (ESI) (m/z) 479 [M+H]$^+$. $^1$H NMR (500 MHz, CDCl$_3$) δ 7.79-7.72 (m, 2H), 7.56 (dd, J=8.0, 0.8 Hz, 1H), 7.38 (dd, J=8.3, 2.2 Hz, 1H), 7.32-7.25 (m, 1H), 7.23-7.18 (m, 1H), 7.17 (d, J=8.3 Hz, 2H), 7.02 (d, J=8.3 Hz, 2H), 5.68 (s, 2H), 4.15 (q, J=7.2 Hz, 2H), 3.79 (s, 3H), 3.57 (s, 3H), 1.52 (t, J=7.0 Hz, 3H).

Example 313: 1-((6'-carboxy-3"-methyl-[1,1':3',1"-terphenyl]-4-yl)methyl)-2-ethoxy-1H-benzo[d]imidazole-7-carboxylic acid A solution of Intermediate 313a (25 mg, 0.052 mmol), m-tolylboronic acid (21.29 mg, 0.157 mmol) and Pd-XPhos G3 (2.209 mg, 2.61 µmol) in THF (1 mL) and phosphoric acid, potassium salt (1.0 M aq.) (0.094 mL, 0.094 mmol) was degased with Ar for 1 min. The reaction mixture was sealed and heated at 140° C. in a microwave reactor for 30 min. 0.5 ml of MeOH was then added to the mixture followed by NaOH (0.157 mL, 0.313 mmol). The mixture was heated up in microwave for 15 min at 100° C. Additional NaOH (0.157 mL, 0.313 mmol) was added to the mixture and the mixture was stirred at 100° C. for 30 min. The mixture was filtrated and purified by via preparative LC-MS with the following conditions: Column: XBridge C18, 19×200 mm, 5-µm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 10-50% B over 22 minutes, then a 4-minute hold at 100% B; Flow: 20 mL/min to afford the title compound (Example 313, 13.3 mg, 0.025 mol, 48%). MS (ESI) m/z [M+H]$^+$=507.4. $^1$H NMR (500 MHz, DMSO-d$_6$) δ 7.74-7.61 (m, 2H), 7.54 (s, 1H), 7.52-7.45 (m, 3H), 7.40 (br d, J=7.3 Hz, 1H), 7.36-7.29 (m, 3H), 7.19 (br d, J=7.6 Hz, 1H), 7.15-7.04 (m, 3H), 5.76 (s, 2H), 4.58 (q, J=7.0 Hz, 2H), 2.36 (s, 3H), 1.42 (t, J=7.0 Hz, 3H). LC-MS retention time (Method A4): 1.986 min.

Example 314: 1-((6'-carboxy-[1,1':3',1"-terphenyl]-4-yl)methyl)-2-ethoxy-1H-benzo[d]imidazole-7-carboxylic acid

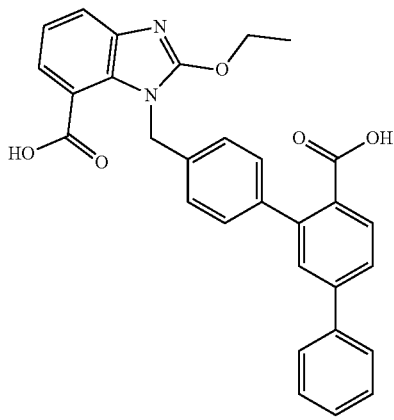

(Ex. 314)

Intermediate 314a: methyl 2-ethoxy-1-((6'-(methoxycarbonyl)-[1,1':3',1"-terphenyl]-4-yl)methyl)-1H-benzo[d]imidazole-7-carboxylate

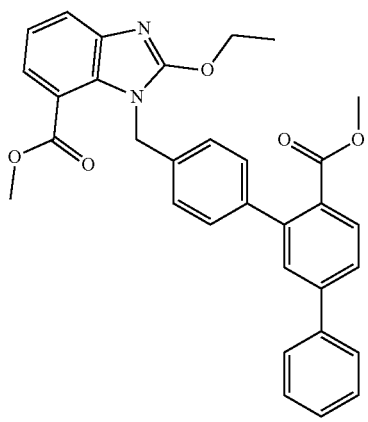

(314a)

To a solution of methyl 2-ethoxy-1H-benzo[d]imidazole-7-carboxylate (55.5 mg, 0.252 mmol) in DMF (2 mL) was added sodium hydride (60%) (16.78 mg, 0.420 mmol) at RT. The reaction mixture was stirred for 10 min at RT before methyl 4"-(bromomethyl)-[1,1':3',1"-terphenyl]-4'-carboxylate (Intermediate 400b, 80 mg, 0.210 mmol) was added in its own solution of DMF (1 mL). After 50 min of stirring at RT the reaction mixture was diluted with EtOAc and washed with 10% LiCl (aq). The organic phase was dried over MgSO₄, filtered over celite, and concentrated. The residue was dissolved DMF and purified by ISCO (0-100% EtOAc/Hexanes) to afford the title compound (Intermediate 314a, 48 mg, 0.069 mmol, 33.0% yield). LC-MS Retention time (Method A2)=1.20 min. Found m/z: 520.1 (M+H)⁺. ¹H NMR (400 MHz, CDCl₃) δ 7.89 (d, J=8.1 Hz, 1H), 7.66-7.57 (m, 4H), 7.55-7.49 (m, 2H), 7.49-7.31 (m, 4H), 7.22 (d, J=8.4 Hz, 2H), 7.01 (d, J=8.1 Hz, 2H), 5.66 (s, 2H), 4.68 (q, J=7.1 Hz, 2H), 3.78 (s, 3H), 3.57 (s, 3H), 1.54-1.48 (m, 3H).

Example 314: 1-((6'-carboxy-[1,1':3',1"-terphenyl]-4-yl)methyl)-2-ethoxy-1H-benzo[d]imidazole-7-carboxylic acid

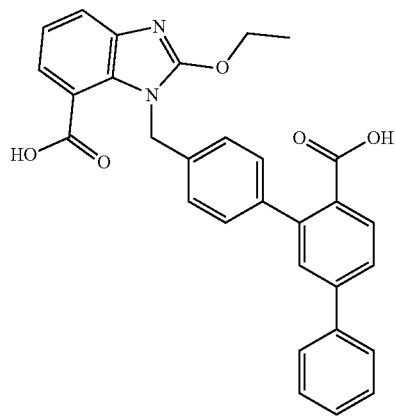

(314)

Intermediate 314a (36 mg, 0.069 mmol) was suspended in a solution of NaOH (1 M NaOH) (2.075 mL, 2.075 mmol) and THF (2 mL) and heated at 65° C. for 3h. The reaction mixture was diluted with EtOAc and washed with 1 M HCL. The aqueous phase was back extracted a second time with EtOAc and the organic phases were concentrated.

The crude residue was retaken in DMF, filtered and purified by reverse phase HPLC Column: XBridge C18, 19×200 mm, 5-μm particles; Mobile Phase A: 5:95 ACN:H₂O with 0.1% trifluoroacetic acid; Mobile Phase B: 95:5 ACN:H₂O with 0.1% trifluoroacetic acid; Gradient: 30-70% B over 20 minutes, then a 3-minute hold at 100% B; Flow: 20 mL/min) to afford the title compound (Example 314, 16 mg, 0.032 mmol, 46%). MS (ESI) m/z [M+H]⁺=493.1. ¹H NMR (500 MHz, DMSO-d₆) δ 7.79 (d, J=7.9 Hz, 1H), 7.75-7.68 (m, 3H), 7.65 (d, J=7.6 Hz, 1H), 7.56-7.51 (m, 2H), 7.49-7.43 (m, 2H), 7.42-7.36 (m, 1H), 7.32 (d, J=7.9 Hz, 2H), 7.18 (t, J=7.8 Hz, 1H), 7.05 (d, J=7.9 Hz, 2H), 5.69 (s, 2H), 4.61 (q, J=7.0 Hz, 2H), 1.42 (t, J=7.0 Hz, 3H). LC-MS retention time (Method A4): 1.846 min.

Example 315: 2-ethoxy-1-((6'-(methoxycarbonyl)-[1,1':3',1"-terphenyl]-4-yl)methyl)-1H-benzo[d]imidazole-7-carboxylate

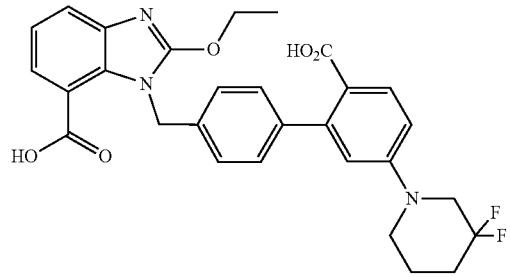

(Ex. 315)

To a via containing Intermediate 313a (18 mg, 0.038 mmol) was added 2nd generation ruphos precatalyst (5.84 mg, 7.52 μmol) followed sodium tert-butoxide (21.67 mg, 0.226 mmol). THF (1 mL) was then added followed by 3,3-difluoropiperidine, HCl (30 mg, 0.188 mmol). The reaction was degassed with N₂. The reaction vial was sealed and heated at 65° C. for 18 h. The reaction mixture was then diluted with EtOAc and filtered through celite. The filtrate was concentrated. The crude residue was dissolved in MeOH (1 mL). 1M NaOH (0.752 mL, 0.752 mmol) was added and the reaction was allowed to stir at 65° C. for 1 h. The reaction mixture was then acidified to pH 3-4 with 5% citric acid and extracted (3×) with EtOAc. The combined organics were washed with brine, dried with sodium sulfate, filtered and concentrated. The crude residue was dissolved in DMF, filtered and purified by reverse phase HPLC (Xbridge Prep Shield RP18, 15 min gradient of 20-100% B. A=H₂O/MeOH 10 mM NH₄OAc 90:10. B=H₂O/MeOH 10 mM NH₄OAc 10:90) to afford the title compound (Example 315, 2.6 mg, 4.85 μmol, 12.92% yield). MS (ESI) m/z [M+H]'= 536.0. ¹H NMR (500 MHz, DMSO-d₆) δ 7.65 (br s, 2H), 7.46 (br s, 1H), 7.42 (br s, 1H), 7.27-7.07 (m, 3H), 7.04 (br s, 2H), 6.97 (br s, 2H), 6.68 (br s, 1H), 5.75 (br s, 2H), 4.57 (br d, J=6.4 Hz, 2H), 2.05 (br d, J=16.8 Hz, 2H), 1.91 (br s, 2H), 1.73 (br s, 2H), 1.41 (br t, J=6.7 Hz, 3H), 1.00 (br d, J=6.4 Hz, 1H. LC-MS retention time (Method A4): 1.661 min.

Example 316: methyl 2-ethoxy-1-((6'-(5-oxo-4,5-dihydro-1,2,4-oxadiazol-3-yl)-[1,1':3',1"-terphenyl]-4-yl)methyl)-1H-benzo[d]imidazole-7-carboxylate

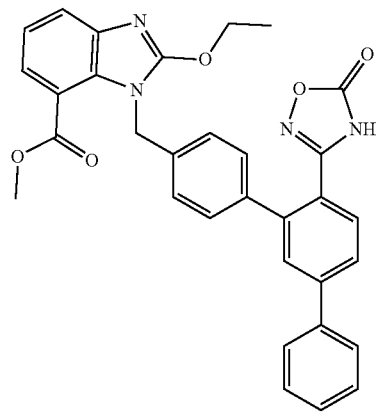

(Ex. 316)

Example 316 was synthesized from Intermediate 311a using the same procedure described for Example 299, however, the reaction sequence was stopped prior to the ester hydrolysis. The crude residue was purified by reverse phase HPLC (Xbridge Prep Shield RP18, 15 min gradient of 20-100% B. A=H$_2$O/MeOH 10 mM NH$_4$OAc 90:10. B=H$_2$O/MeOH 10 mM NH$_4$OAc 10:90) to afford the title compound (Example 316, 2.9 mg, 5.31 µmol, 19.33% yield). MS (ESI) m/z [M+H]$^+$=547.1. $^1$H NMR (500 MHz, DMSO-dh) δ 7.95-7.25 (m, 1 1 H), 7.20 (t, J=7.9 Hz, 2H), 6.93 (br. s., 2H), 5.49 (br. s., 2H), 4.59 (q, J=6.8 Hz, 2H), 3.73 (br. s., 3H), 1.39 (t, J=6.9 Hz, 3H). LC-MS retention time (Method A4): 2.198 min.

Example 317: 1-((6'-(2H-tetrazol-5-yl)-[1,1':3',1''-terphenyl]-4-yl)methyl)-2-hydroxy-1H-benzo[d]imidazole-7-carboxylic acid

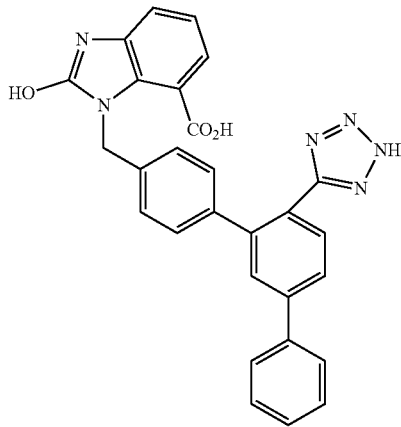

(Ex. 317)

To a small vial containing Intermediate 311a (30 mg, 0.062 mmol) was added dibutyltin oxide (15.32 mg, 0.062 mmol) and toluene (1 mL) followed by TMS-N$_3$ (0.041 mL, 0.308 mmol). The reaction mixture was sealed and heated at 100° C. behind a blast shield overnight. The reaction mixture was concentrated and the crude residue was dissolved in MeOH (2 mL). NaOH (170 mg, 4.24 mmol) was added followed by Water (2 mL). The reaction mixture was stirred at 75° C. for 45 minutes. The reaction mixture was diluted with MeOH and neutralized with AcOH. The reaction mixture was concentrated, azeotroped with toluene 2×then re-dissolved in DMF filtered and purified by reverse phase HPLC (Xbridge Prep Shield RP18, 15 min gradient of 20-100% B. A=H$_2$O/MeOH 10 mM NH$_4$OAc 90:10. B=H$_2$O/MeOH 10 mM NH$_4$OAc 10:90) to afford the title compound (Example 317, 1.6 mg, 3.24 µmol, 5.73% yield). MS (ESI) m/z [M+H]$^+$=489.1. $^1$H NMR (500 MHz, DMSO-d$_6$) δ 7.74 (d, J=7.5 Hz, 2H), 7.68 (br. s., 2H), 7.56 (s, 1H), 7.50-7.42 (m, 2H), 7.41-7.32 (m, 1H), 7.27 (d, J=6.8 Hz, 1H), 7.19-6.86 (m, 6H), 5.40 (br. s., 2H). LC-MS retention time (Method A4): 1.126 min.

Example 318: 1-((2'-carboxy-5'-(2-methoxypyridin-3-yl)-[1,1'-biphenyl]-4-yl)methyl)-2-ethoxy-1H-benzo[d]imidazole-7-carboxylic acid

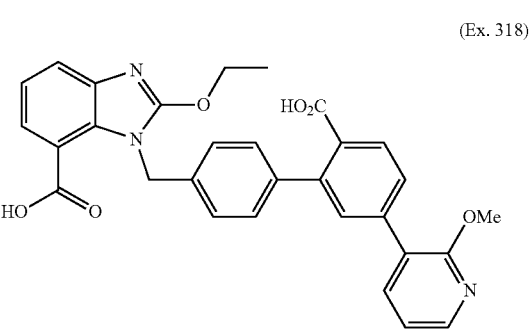 [SMILES: CCOc1nc2cccc(C(=O)O)c2n1Cc1ccc(-c2cc(-c3cccnc3OC)ccc2C(=O)O)cc1]

(Ex. 318)

To a pressure-rated vial containing Intermediate 313a (18 mg, 0.038 mmol), (2-methoxypyridin-3-yl)boronic acid (17.24 mg, 0.113 mmol) and second generation XPHOS precatalyst (8.87 mg, 0.011 mmol) was added dioxane (500 l) followed by 2 M K$_3$PO$_4$ (2 M aq) (94 µl, 0.188 mmol). The reaction mixture was sparged with N$_2$ for 2 min before being sealed and heated at 65° C. The reaction mixture was diluted with EtOAc and filtered through celite. The filtrate was concentrated and the crude residue was dissolved in MeOH (1 mL). 1M NaOH (752 µl, 0.752 mmol) was added and the reaction was allowed to stir at 65° C. for 1 hour. The reaction mixture was then acidified to pH 3-4 with 5% citric acid and extracted (3×) with EtOAC. The combined organics were washed with brine, dried with sodium sulfate, filtered and concentrated. The crude residue was dissolved in DMF, filtered and purified by reverse phase HPLC (Column: XBridge C18, 19×200 mm, 5-µm particles; Mobile Phase A: 5:95 ACN: H$_2$O with 0.1% trifluoroacetic acid; Mobile Phase B: 95:5 ACN: H$_2$O with 0.1% trifluoroacetic acid; Gradient: 20-60% B over 20 minutes, then a 4-minute hold at 100% B; Flow: 20 mL/min) to afford the title compound (Example 318, 5.5 mg, 10.51 µmol, 28.0% yield). MS (ESI) m/z [M+H]$^+$=524.2. $^1$H NMR (500 MHz, DMSO-d$_6$) δ 8.20 (br d, J=3.7 Hz, 1H), 7.83 (br d, J=6.4 Hz, 1H), 7.75 (br d, J=7.9 Hz, 1H), 7.70-7.58 (m, 2H), 7.54 (br d, J=7.0 Hz, 1H), 7.45 (br s, 1H), 7.30 (br d, J=7.0 Hz, 2H), 7.18 (br s, 1H), 7.12-7.07 (m, 1H), 7.04 (br d, J=7.3 Hz, 2H), 5.69 (br s, 2H), 4.61 (q, J=7.0 Hz, 2H), 3.87 (s, 3H), 1.42 (br t, J=6.9 Hz, 3H. LC-MS retention time (Method A4): 1.661 min.

Example 319: 1-((2'-carboxy-5'-(3,3-dimethylindolin-1-yl)-[1,1'-biphenyl]-4-yl)methyl)-2-ethoxy-1H-benzo[d]imidazole-7-carboxylic acid

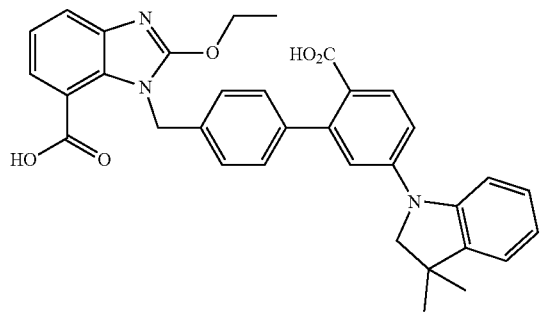

(319)

Example 319 was synthesized from 3,3-dimethylindoline and Intermediate 313a according to the same procedure described for the synthesis of Example 315 to give the title compound (Example 319, 0.6 mg, 1.068 μmol, 2.84% yield). MS (ESI) m/z [M+H]=562.1. $^1$H NMR (500 MHz, DMSO-d$_6$) δ 7.76 (br s, 1H), 7.48-7.28 (m, 3H), 7.27-7.08 (m, 7H), 7.03 (br d, J=5.4 Hz, 1H), 6.90 (br s, 1H), 6.82 (br t, J=6.8 Hz, 1H), 5.82 (br s, 2H), 4.55 (br d, J=6.7 Hz, 2H), 3.73 (br s, 2H), 3.52-3.33 (m, 2H), 3.17 (s, 1H), 1.40 (br t, J=6.6 Hz, 3H), 1.28 (br s, 6H), 1.00 (br d, J=6.3 Hz, 1H. LC-MS retention time (Method A4): 2.137 min.

Example 320: 1-((6'-carboxy-4"-(dimethylcarbamoyl)-[1,1':3',1"-terphenyll-4-yl)methyl)-2-ethoxy-1H-benzo[dlimidazole-7-carboxylic acid

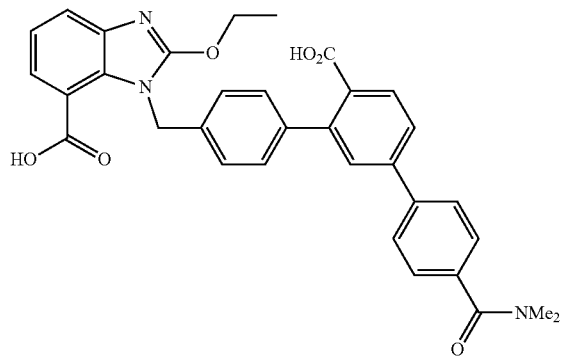

(Ex. 320)

Example 320 was synthesized from Intermediate 313a and (4-(dimethylcarbamoyl)phenyl)boronic acid using the procedure that was described for Example 299b to give the title compound (Example 320, 5.9 mg, 10.47 μmol, 27.9% yield). MS (ESI) m/z [M+H]$^+$=564.0. LC-MS retention time (Method A4): 1.533 min. Example 321: 1-((4"-(dimethylcarbamoyl)-6'-(5-oxo-4,5-dihydro-1,2,4-oxadiazol-3-yl)-[1,1':3',1"-terphenyll-4-yl)methyl)-2-ethoxy-1H-benzo[dlimidazole-7-carboxylic acid Intermediate 321a: methyl 1-((6'-cyano-4"-(dimethylcarbamoyl)-[1,1':3',1"-terphenyll-4-yl)methyl)-2-ethoxy-1H-benzo[d]imidazole-7-carboxylate

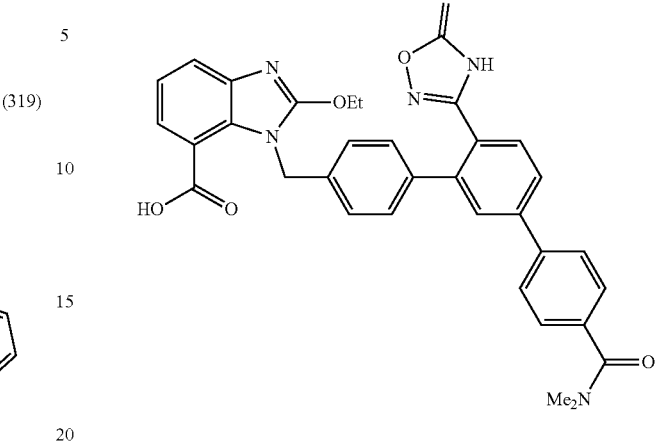

(321)

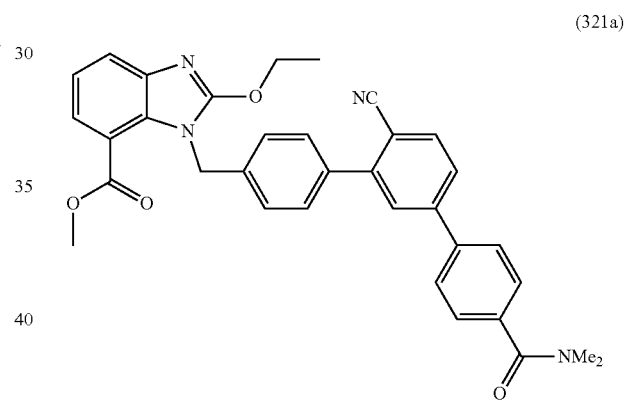

(321a)

Intermediate 321a was synthesized from Intermediate 300a and (4-(dimethylcarbamoyl)phenyl)boronic acid using the procedure that was used to synthesize Intermediate 299b to afford the title compound (Intermediate 321a, 40 mg, 0.072 mmol, 45.6% yield). MS (ESI) m/z [M+H]$^+$=559.7. LC-MS retention time (Method A2): 0.97 min.

Example 321: 1-((4"-(dimethylcarbamoyl)-6'-(5-oxo-4,5-dihydro-1,2,4-oxadiazol-3-yl)-[1,1':3',1"-terphenyll-4-yl)methyl)-2-ethoxy-1H-benzo[d]imidazole-7-carboxylic acid Example 321 was synthesized from Intermediate 321a using the procedure described for Example 299 to give the title compound (Example 321, 4.9 mg, 8.12 μmol, 11.34% yield). MS (ESI) m/z [M+H]$^+$=604.5. $^1$H NMR (500 MHz, DMSO-d$_6$) δ 7.81 (br d, J=8.2 Hz, 3H), 7.75-7.57 (m, 3H), 7.56-7.42 (m, 3H), 7.30 (br d, J=7.9 Hz, 2H), 7.17 (s, 1H), 7.05 (br d, J=8.2 Hz, 2H), 5.66 (s, 2H), 4.57 (br d, J=7.0 Hz, 2H), 2.99 (br s, 3H), 2.93 (br s, 3H), 1.38 (t, J=7.0 Hz, 3H. LC-MS retention time (Method A4): 1.479 min.

Example 322: 1-((5'-(1H-indol-3-yl)-2'-(5-oxo-4,5-dihydro-1,2,4-oxadiazol-3-yl)-[1,1'-biphenyl]-4-yl)methyl)-2-ethoxy-1H-benzo[d]imidazole-7-carboxylic acid

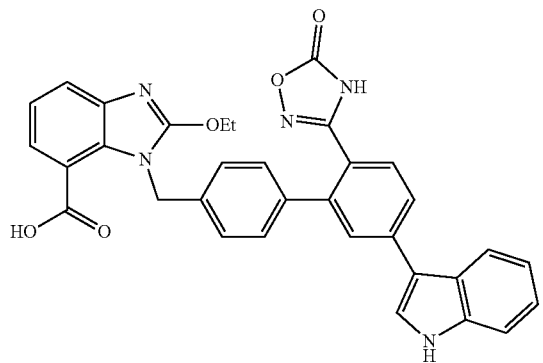

(Ex. 322)

Example 322 was synthesized from Intermediate 313a and 3-(4,4,5,5-tetramethyl-1,3,2-dioxaborolan-2-yl)-1H-indole using the sequence described for Example 321 to give the title compound (Example 322, 130 mg, 0.247 mmol, 73.2% yield). MS (ESI) m/z [M+H]$^+$=572.2. $^1$H NMR (500 MHz, DMSO-d$_6$) δ 11.57 (br s, 1H), 8.00-7.79 (m, 3H), 7.75-7.61 (m, 3H), 7.55 (br d, J=7.6 Hz, 1H), 7.47 (br d, J=8.0 Hz, 1H), 7.34 (br d, J=8.1 Hz, 2H), 7.25-7.11 (m, 3H), 7.08 (br d, J=8.0 Hz, 2H), 5.70 (s, 2H), 4.66-4.56 (m, 2H), 3.18 (s, 1H), 2.08 (s, 1H), 1.41 (t, J=7.0 Hz, 3H). LC-MS retention time (Method A4): 1.722 min.

Example 323: methyl (R)-1-((2'-cyano-5'-(3-methylpiperidin-1-yl)-[1,1'-biphenyl]-4-yl)methyl)-2-ethoxy-1H-benzo[d]imidazole-7-carboxylate

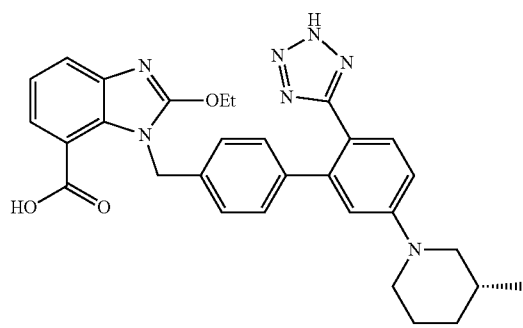

(Ex. 323)

Intermediate 323a: methyl 1-((2'-cyano-5'-fluoro-[1,1'-biphenyl]-4-yl)methyl)-2-ethoxy-1H-benzo[d]imidazole-7-carboxylate

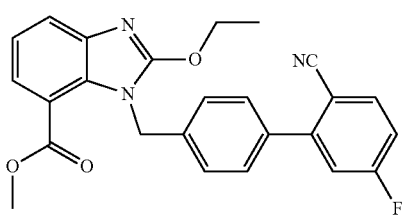

(323a)

To a solution of I-005 (600 mg, 1.375 mmol) and 2-bromo-4-fluorobenzonitrile (330 mg, 1.650 mmol) in 4:1 toluene/EtOH (12 mL) was added K$_3$PO$_4$ (2 M, aq) (2.063 mL, 4.13 mmol) followed by PdCl$_2$(dppf) (101 mg, 0.138 mmol). The resulting mixture was sparged with N$_2$ for 2 min before being sealed and heated at 120° C. for 45 min in the microwave. Additional PdCl$_2$(dppf) (101 mg, 0.138 mmol) was added to the reaction mixture which was then evacuated and backfilled with N$_2$ (3×) and stirred for an additional 45 min in the microwave at 120° C. The reaction mixture was then concentrated onto celite and purified by ISCO (80 g column 0-100% EtOAc/Hexanes) to afford the title compound (Intermediate 323a, 400 mg, 0.931 mmol, 67.7% yield). LC-MS: MS (ESI) m/z: 430.1 (M+H)$^+$. $^1$H NMR (500 MHz, CDCl$_3$) δ 7.77 (d, J=7.9 Hz, 2H), 7.59 (d, J=7.7 Hz, 1H), 7.45 (d, J=8.0 Hz, 2H), 7.23-7.09 (m, 5H), 5.73 (s, 2H), 4.73-4.67 (m, 2H), 3.78 (s, 3H), 1.51 (t, J=7.2 Hz, 3H).

Intermediate 323b: methyl (R)-1-((2'-cyano-5'-(3-methylpiperidin-1-yl)-[1,1'-biphenyl]-4-yl)methyl)-2-ethoxy-1H-benzo[d]imidazole-7-carboxylate

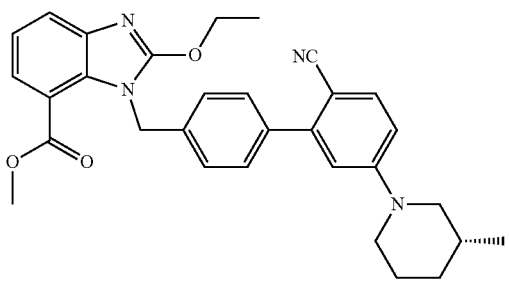

(323b)

Intermediate 323a (190 mg, 0.442 mmol) was dissolved in DMSO (1475 µl). Potassium carbonate (306 mg, 2.212 mmol) was added followed by (R)-3-methylpiperidine, HCl (132 mg, 0.973 mmol). The reaction was sealed and heated at 100° C. behind a blast shield for a total of 2 hours. The reaction mixture diluted with EtOAc and H$_2$O. The aqueous phase was extracted (3×) with EtOAc and the combined organic phases were washed with brine, dried with sodium sulfate, filtered and concentrated. The crude residue was purified by ISCO (0-100% EtOAc in hexane) to afford the title compound (Intermediate 323b, 140 mg, 0.275 mmol, 62.2% yield). LC-MS (Method A2): 1.11 min, [M+H]$^+$=509.0.

Example 323: methyl (R)-1-((2'-cyano-5'-(3-methylpiperidin-1-yl)-[1,1'-biphenyl]-4-yl)methyl)-2-ethoxy-1H-benzo[d]imidazole-7-carboxylate Example 323 was synthesized from Intermediate 323b using the same procedure as described for Example 309 to give the title compound (Example 323, 3.6 mg, 6.70 μmol, 7.74% yield). MS (ESI) m/z [M+H]$^+$=538.2. $^1$H NMR (500 MHz, DMSO-d$_6$) δ 7.63 (d, J=7.9 Hz, 1H), 7.50 (d, J=7.6 Hz, 1H), 7.41 (d, J=8.5 Hz, 1H), 7.16 (br t, J=7.6 Hz, 1H), 7.07-6.95 (m, 3H), 6.90 (br d, J=7.9 Hz, 2H), 6.85-6.66 (m, 1H), 5.62 (s, 2H), 4.59 (q, J=7.0 Hz, 2H), 3.73 (br s, 2H), 2.68 (br s, 1H), 2.48-2.36 (m, 1H), 1.80-1.53 (m, 5H), 1.41 (t, J=7.0 Hz, 3H), 0.90 (d, J=6.7 Hz, 3H). LC-MS retention time (Method A4): 1.559 min.

Example 324: (S)-2-ethoxy-1-((5'-(3-methylpiperidin-1-yl)-2'-(2H-tetrazol-5-yl)-1,1'-biphenyl-4-yl)methyl)-1H-benzo[d]imidazole-7-carboxylic acid

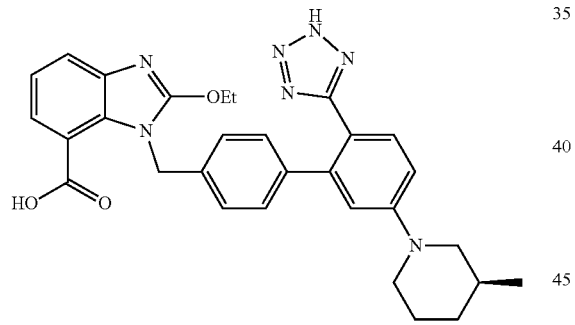

(324)

Example 324 was synthesized from I-005 and (S)-3-methylpiperidine, HCl according to the same sequence described for Example 323. MS (ESI) m/z [M+H]$^+$=538.0. $^1$H NMR (500 MHz, DMSO-d$_6$) δ 7.61 (d, J=7.8 Hz, 1H), 7.52 (br d, J=7.7 Hz, 1H), 7.42 (d, J=8.6 Hz, 1H), 7.16 (t, J=7.8 Hz, 2H), 7.07-6.98 (m, 3H), 6.93 (br d, J=8.1 Hz, 2H), 6.87-6.76 (m, 1H), 5.64 (s, 2H), 4.59 (q, J=7.0 Hz, 2H), 3.80-3.66 (m, 2H), 2.73 (br s, 1H), 2.48-2.34 (m, 1H), 1.76 (br d, J=12.7 Hz, 1H), 1.74-1.63 (m, 2H), 1.55 (br d, J=12.0 Hz, 1H), 1.40 (t, J=7.1 Hz, 3H), 1.17-1.01 (m, 1H), 0.91 (d, J=6.6 Hz, 3H). LC-MS retention time (Method A4): 1.561 min.

Example 325: (R)-2-ethoxy-1-((5'-(3-methylpiperidin-1-yl)-2'-(5-oxo-4,5-dihydro-1,2,4-oxadiazol-3-yl)-[1,1'-biphenyl-4-yl)methyl)-1H-benzo[d]imidazole-7-carboxylic acid

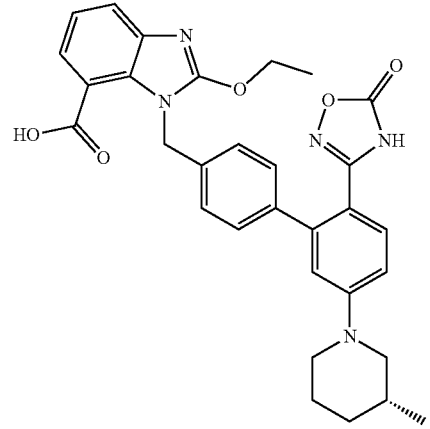

(325)

Example 325 was synthesized from Intermediate 323b according to the same procedure used to synthesize Example 299 to give the title compound (Example 325, 3.4 mg, 6.14 mol, 2.403% yield). LC-MS (Method A4):1.745 min, [M+H]$^+$=554.3;

Example 326: 2-ethoxy-1-((5'-(quinolin-3-yl)-2'-(2H-tetrazol-5-yl)-[1,1'-biphenyl]-4-yl)methyl)-1H-benzo[d]imidazole-7-carboxylic acid

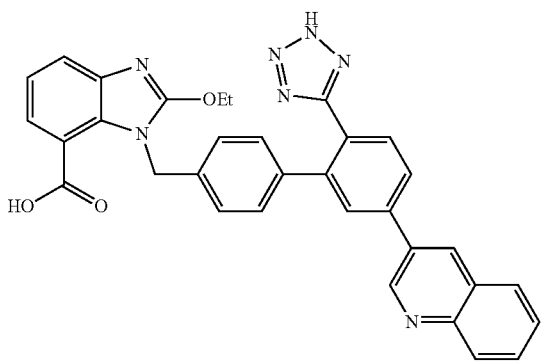

(Ex. 326)

Intermediate 326a: methyl 1-((2'-cyano-5'-(quinolin-3-yl)-[1,1'-biphenyl]-4-yl)methyl)2-ethoxy-1H-benzo)d]imidazole-7-caboxylate (326a)

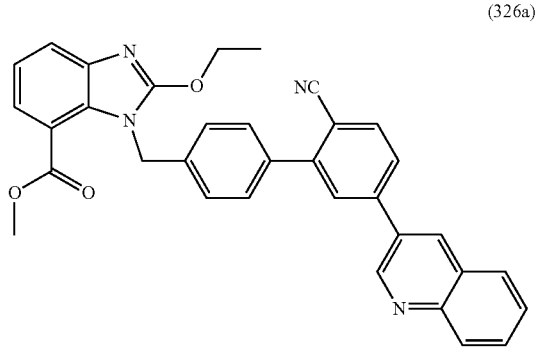 [SMILES: CCOc1nc2cccc(C(=O)OC)c2n1Cc1ccc(-c2cc(-c3cnc4ccccc4c3)ccc2C#N)cc1]

To a pressure-rated vial containing Intermediate 300a (75 mg, 0.168 m mol) and second generation XPHOS precatalyst (33.1 mg, 0.042 mmol) was added dioxane (2000 pd) followed by 2 M K$_3$PO$_4$ (2 M aq) (168 µl, 0.336 mmol). The reaction mixture was evacuated and backfilled with N$_2$ (3×) before being sealed and heated at 85° C. for 1 h.

The reaction mixture was diluted with EtOAc, filtered and concentrated onto celite and purified by ISCO (0-100% EtOAc in hexanes) to afford the title compound (Intermediate 326a, 50 mg, 0.093 mmol, 55.2% yield). LC-MS (Method A2): 0.91 min, [M+H]$^+$=539.0.

Example 326: 2-ethoxy-1-((5'-(quinolin-3-yl)-2'-(2H-tetrazol-5-yl)-[1,1'-biphenyl]-4-yl)methyl)-1H-benzo[dlimidazole-7-carboxylic acid (326)

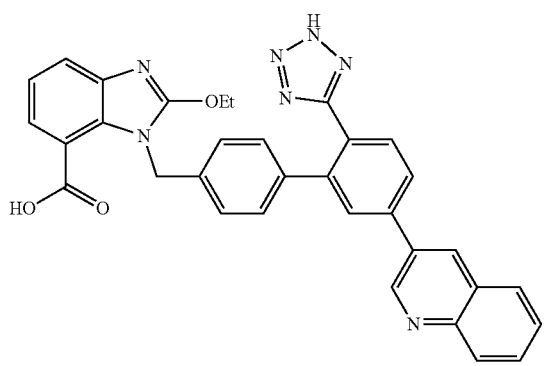

Example 326 was synthesized from Intermediate 326a according to the same procedure used to synthesize Example 309 to give the title compound (Example 326, 18 mg, 0.032 mmol, 34.2% yield). MS (ESI) m/z [M+H]$^+$=568.0. $^1$H NMR (500 MHz, DMSO-d$_6$) δ 9.38 (d, J=1.8 Hz, 1H), 8.91-8.77 (m, 1H), 8.13-8.04 (m, 3H), 7.98 (s, 1H), 7.87-7.78 (m, 2H), 7.72-7.63 (m, 2H), 7.56 (d, J=7.6 Hz, 1H), 7.25-7.11 (m, 3H), 6.99 (br d, J=7.9 Hz, 2H), 5.67 (s, 2H), 4.60 (q, J=7.0 Hz, 2H), 3.01 (s, 1H), 1.41 (t, J=7.2 Hz, 3H). LC-MS retention time (Method A4): 1.324 min.

Example 327: 1-((5'-(1-(difluoromethyl)-1H-pyrazol-4-yl)-2'-(2H-tetrazol-5-yl)-[1,1'-biphenyl]-4-yl)methyl)-2-ethoxy-1H-benzo[d]imidazole-7-carboxylic acid (327)

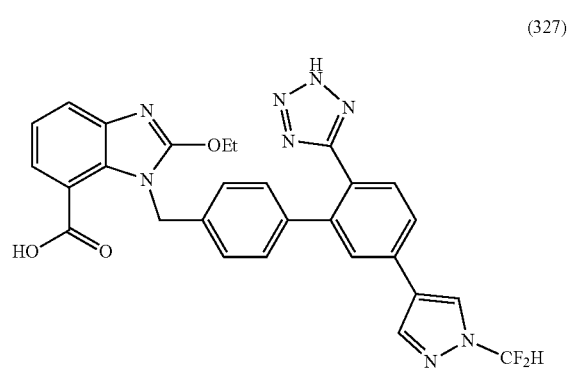 [SMILES: CCOc1nc2cccc(C(=O)O)c2n1Cc1ccc(-c2cc(-c3cnn(C(F)F)c3)ccc2-c2nn[nH]n2)cc1]

Example 32/was synthesized from Intermediate 300a and 1-(difluoromethyl)-4-(4,4,5,5-tetramethyl-1,3,2-dioxaborolan-2-yl)-1H-pyrazole according to the same sequence described for Example 326 to give the title compound (Example 327, 20 mg, 0.036 mmol, 35.1% yield). MS (ESI) m/z [M+H]$^+$=557.3. $^1$H NMR (500 MHz, DMSO-d$_6$) δ 8.78 (s, 1H), 8.33 (s, 1H), 7.96 (s, 1H), 7.79 (s, 1H), 7.71-7.65 (m, 1H), 7.63-7.57 (m, 2H), 7.52 (br d, J=7.6 Hz, 1H), 7.42 (br d, J=7.6 Hz, 1H), 7.13-7.02 (m, 3H), 6.92 (br d, J=7.6 Hz, 2H), 5.68 (s, 2H), 4.58 (q, J=6.7 Hz, 2H), 1.42 (t, J=7.0 Hz, 3H). LC-MS retention time (Method A4): 1.490 min.

Example 328: 2-ethoxy-1-((5'-(6-methoxy-5-methylpyridin-3-yl)-2'-(2H-tetrazol-5-yl)-[1,1'-biphenyl]-4-yl)methyl)-1H-benzo[d]imidazole-7-carboxylic acid (328)

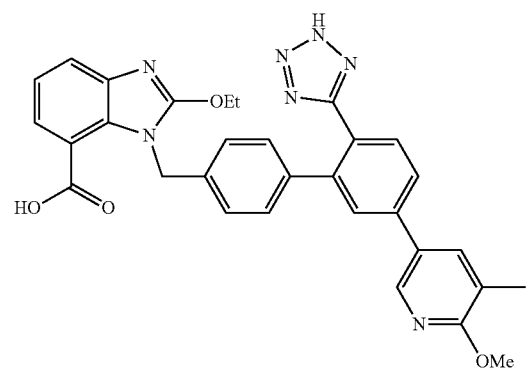

Example 328 was synthesized from Intermediate 300a and (6-methoxy-5-methylpyridin-3-yl)boronic acid according to the same sequence described for Example 326 to give the title compound (Example 328, 0.8 mg, 0.0014 mmol, 1.6% yield). MS (ESI) m/z [M+H]$^+$=562.2. $^1$H NMR (500 MHz, DMSO-d$_6$) δ 8.51-8.37 (m, 1H), 8.03 (s, 1H), 7.84 (d, J=7.9 Hz, 1H), 7.75-7.65 (m, 3H), 7.55 (d, J=7.6 Hz, 1H), 7.19 (s, 1H), 7.11 (br d, J=8.2 Hz, 2H), 6.96 (br d, J=7.9 Hz, 2H), 5.65 (s, 2H), 4.59 (d, J=7.0 Hz, 2H), 3.93 (s, 3H), 2.21 (s, 3H), 1.40 (t, J=7.0 Hz, 3H). LC-MS retention time (Method A4): 1.814 min.

Example 329: 2-ethoxy-1-((5'-(2-methoxypyridin-3-yl)-2'-(5-oxo-4,5-dihydro-1,2,4-oxadiazol-3-yl)-[1,1'-biphenyl]-4-yl)methyl)-1H-benzo[d]imidazole-7-carboxylic acid

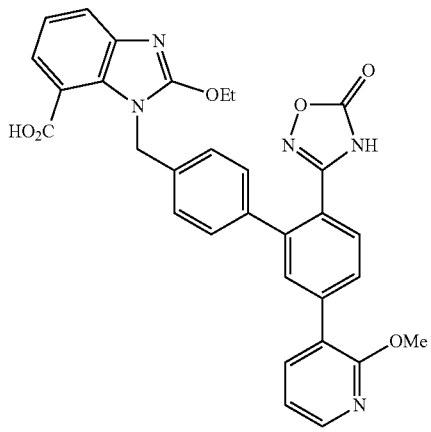

(329)

Example 329 was synthesized from Intermediate 300a and 2-methoxy-3-(4,4,5,5-tetramethyl-1,3,2-dioxaborolan-2-yl)pyridine using the sequence described for Example 321 to give the title compound (Example 329, 6.9 mg, 0.012 mmol, 17.3%). MS (ESI) m/z [M+H]⁺=564.2. ¹H NMR (500 MHz, DMSO-d₆) δ 8.19 (br d, J=4.6 Hz, 1H), 7.83 (br d, J=7.3 Hz, 1H), 7.73-7.57 (m, 3H), 7.53 (s, 2H), 7.26 (br d, J=7.6 Hz, 2H), 7.17 (br s, 1H), 7.12-7.07 (m, 1H), 7.04 (br d, J=7.9 Hz, 2H), 5.66 (br s, 2H), 4.62-4.50 (m, 2H), 3.86 (s, 2H), 2.57-2.54 (m, 2H), 1.37 (t, J=7.0 Hz, 3H). LC-MS retention time (Method A4): 1.730 min.

Example 330: 2-Ethoxy-1-((5'-phenoxy-2'-(2H-tetrazol-5-yl)-[1,1'-biphenyl]-4-yl)methyl)-1H-benzo[d]imidazole-7-carboxylic acid

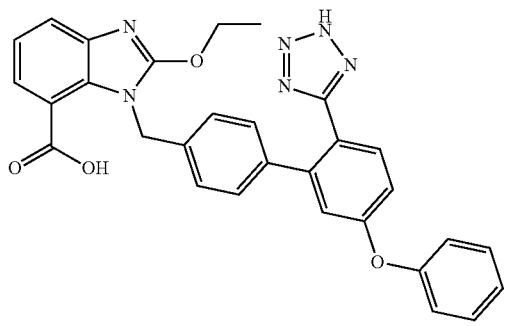

(Ex. 330)

Intermediate 330a: Methyl 1-(4-bromobenzyl)-2-ethoxy-1H-benzo[d]imidazole-7-carboxylate

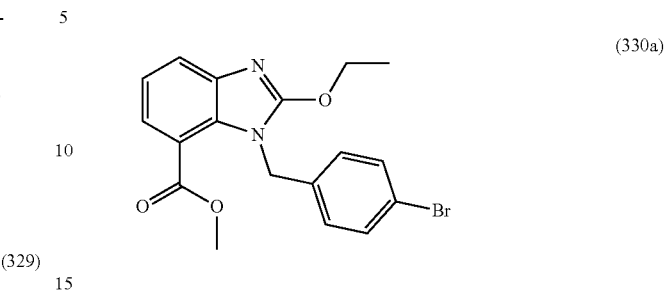

(330a)

To a 50 mL pressure vessel containing methyl 2-ethoxy-1H-benzo[d]imidazole-7-carboxylate (1.00 g, 4.54 mmol) was added 2-propanol (15 mL) and potassium carbonate (1.25 g, 9.08 mmol) and the mixture was stirred at 30° C. for 5 min. To this mixture was added 1-bromo-4-(bromomethyl)benzene (1.19 g, 4.77 mmol) and tetrabutylammonium iodide (0.084 g, 0.23 mmol) and the temperature of the reaction was raised to 45° C. After 60 min an additional 15 mL of 2-propanol was added and the reaction was stirred at the same temperature for another 90 min. The cooled reaction mixture was diluted with EtOAc (200 mL) and H₂O (50 mL), the layers were separated and the organic phase was washed (brine), dried (anhydrous sodium sulfate), filtered and evaporated. The residue was dry-packed onto silica gel (15 g) and purified on a 40 gram column (ISCO/0-60% EtOAc-hexane) to provide the title compound as a pale yellow solid (1.50 g, 3.86 mmol, 85% yield). LC-MS (Method H): 1.38 min, [M+H]⁺=389.0; ¹H NMR (400 MHz, CDCl₃) δ ppm 7.73 (dd, J=7.8, 1.2 Hz, 1H), 7.58 (dd, J=7.8, 1.2 Hz, 1H), 7.33-7.39 (m, 2H), 7.18 (t, J=8.0 Hz, 1H), 6.87 (m, J=8.6 Hz, 2H), 5.58 (s, 2H), 4.65 (q, J=7.2 Hz, 2H), 3.76 (s, 3H), 1.47 (t, J=7.0 Hz, 3H).

Intermediate 330b: Methyl 1-((2'-cyano-5'-fluoro-[1,1'-biphenyl]-4-yl)methyl)-2-ethoxy-1H-benzo[d]imidazole-7-carboxylate

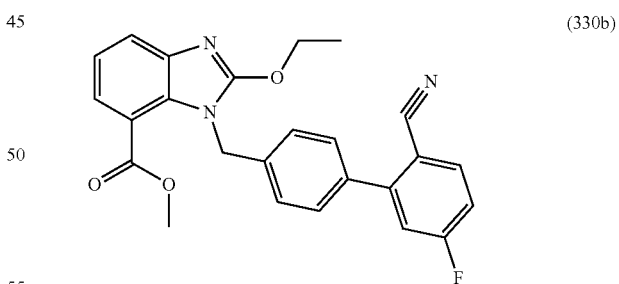

(330b)

In a 20 mL pressure vessel containing Intermediate 330a (0.750 g, 1.93 mmol) and 4-fluoro-2-(4,4,5,5-tetramethyl-1,3,2-dioxaborolan-2-yl)benzonitrile (0.952 g, 3.85 mmol) was added ethanol/toluene (10 mL, 1:9) and 2M aqueous Na₂CO₃ (2.89 mL, 5.78 mmol). The mixture was purged with a stream of Ar for 10 min and then tetrakis(triphenylphosphine)palladium(0) (0.223 g, 0.193 mmol) was added, the vial was sealed and the mixture was stirred at 110° C. for 3 h.

The cooled mixture was diluted with EtOAc (50 mL) and then it was washed (H₂O, brine), dried with anhydrous sodium sulfate, filtered and evaporated. The residue was dry-packed onto silica gel and purified by flash chromatography on a 25 gram column (ISCO/0 to 30% EtOAc/hexane) to provide the title compound as an off-white solid (0.800 g, 1.86 mmol, 97% yield). LC-MS (Method H): 1.36 min, [M+H]$^+$=430.1; $^1$H NMR (400 MHz, DMSO-d$_6$) δ ppm 8.03 (dd, J=8.6, 5.9 Hz, 1H), 7.71 (dd, J=7.8, 1.2 Hz, 11H), 7.53 (m, J=8.2 Hz, 2H), 7.40-7.51 (m, 3H), 7.20 (t, J=7.8 Hz, 1H), 7.09 (m, J=8.2 Hz, 2H), 5.58 (s, 2H), 4.62 (q, J=7.0 Hz, 2H), 3.70 (s, 3H), 1.40 (t, J=7.0 Hz, 3H).

Intermediate 330c: Methyl 1-((2'-cyano-5'-phenoxy-[1,1'-biphenyl]-4-yl)methyl)-2-ethoxy-1H-benzo[d]imidazole-7-carboxylate

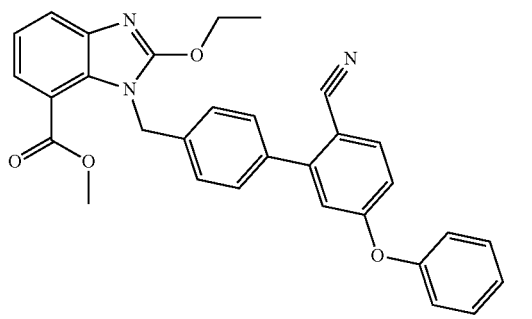

(330c)

To a solution of Intermediate 330b (0.050 g, 0.116 mmol) in DMF (2 mL) was added phenol (0.022 g, 0.233 mmol) and cesium carbonate (0.114 g, 0.349 mmol) and the mixture was stirred at 100° C. for 18 h. After cooling to RT, dimethyl sulfoxide (3.5 mL) and formic acid (0.044 mL, 1.16 mmol) were added and the mixture was filtered. The title compound was isolated by reverse phase HPLC (Method F, using formic acid as modifier) to afford a white solid (0.043 g, 0.085 mmol, 73% yield). LC-MS (Method H): 1.47 min, [M+H]$^+$=504.1; HRMS (ESI): Calcd. for $C_{31}H_{26}N_3O_4$ [M+H]$^+$ m/z 504.1918; found: 504.1909.

Example 330: 2-Ethoxy-1-((5'-phenoxy-2'-(2H-tetrazol-5-yl)-[1,1'-biphenyl]-4-yl)methyl)-1H-benzo[d]imidazole-7-carboxylic acid To a mixture of Intermediate 330c (0.033 g, 0.066 mmol) in o-xylene (3 mL) was added azidotributylstannane (0.054 mL, 0.197 mmol), the reaction vessel was sealed and the mixture was heated at 140° C. for 6 days. The volatiles were then removed under reduced pressure and ethanol (3 mL) was added, followed by 2 M aqueous LiOH (0.492 mL, 0.963 mmol). The resulting mixture was stirred at RT for 20 h and then the volatiles were evaporated and EtOAc (3 mL) was added to give a biphasic mixture which was centrifuged at approximately 1000 g. The supernatant was removed and the white residue was dissolved in H$_2$O (3 mL) and AcOH (0.075 mL, 1.31 mmol) was added. The resulting suspension was centrifuged at approximately 1000 g and then the supernatant was removed and the solid residue was taken up in DMSO (3 mL) and the solution was submitted to reverse phase HPLC purification (Method F, using formic acid as modifier) to afford the title compound as a white solid (0.025 g, 0.047 mmol, 71% yield). LC-MS (Method H): 1.44 min, [M+H]$^+$=533.1; HRMS (ESI): Calcd. for $C_{30}H_{25}N_6O_4$ [M+H]$^+$ m/z 533.1932; found: 533.1931; $^1$H NMR (400 MHz, DMSO-d$_6$) δ ppm 13.25 (br s, 2H), 7.64 (dd, J=7.6, 6.1 Hz, 2H), 7.52 (d, J=7.8 Hz, 1H), 7.38-7.48 (m, 2H), 7.06-7.26 (m, 5H), 7.03 (br s, 1H), 6.99 (m, J=7.8 Hz, 2H), 6.91 (m, J=8.2 Hz, 2H), 5.61 (s, 2H), 4.56 (q, J=7.0 Hz, 2H), 1.36 (t, J=7.0 Hz, 3H).

The following examples have been similarly prepared from Intermediate 330b and the appropriate phenols, hydroxypyridines or azoles, using a method as described for the synthesis of Example 330 above. Analytical LC-MS injections were used to determine the final purity and the retention time is reported for each compound, as determined by Method A1, Method A2 or Method H.

| Ex | Structure | MW | LC-MS m/z [M + H]$^+$; RT (Method) | $^1$H NMR (400 MHz, DMSO-d$_6$) δ ppm |
|---|---|---|---|---|
| 331 | 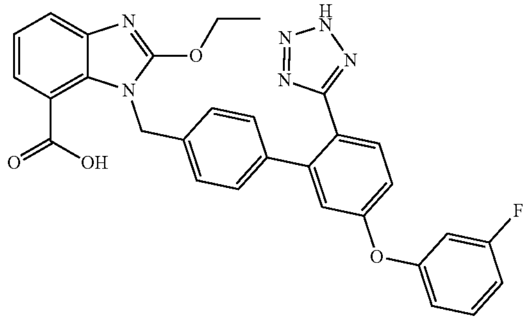 [SMILES: CCOc1nc2cccc(C(=O)O)c2n1Cc1ccc(-c2cc(Oc3cccc(F)c3)ccc2-c2nn[nH]n2)cc1] | 550.54 | 551.1; 1.53 min (Method H) | 13.13 (br s, 2H), 7.65 (dd, J = 7.8, 5.5 Hz, 2 H), 7.52 (d, J = 7.8 Hz, 1 H), 7.42-7.50 (m, 1 H), 7.13-7.20 (m, 2 H), 7.09-7.13 (m, 1H), 6.94-7.09 (m, 5 H), 6.91 (d, J = 8.2 Hz, 2 H), 5.61 (s, 2 H), 4.56 (q, J = 7.0 Hz, 2 H), 1.36 (t, J = 7.0 Hz, 3 H). |

| Ex | Structure | MW | LC-MS m/z [M + H]+; RT (Method) | 1H NMR (400 MHz, DMSO-d6) δ ppm |
|---|---|---|---|---|
| 332 | 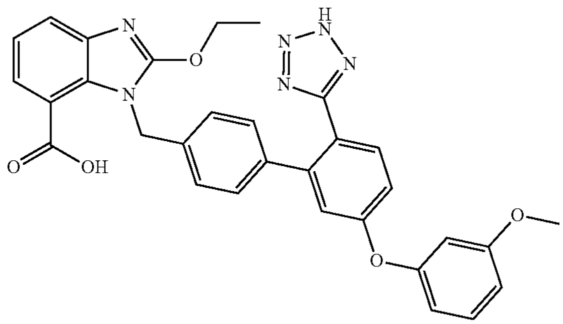 [SMILES: CCOc1nc2cccc(C(=O)O)c2n1Cc1ccc(-c2cc(Oc3cccc(OC)c3)ccc2-c2nn[nH]n2)cc1] | 562.58 | 563.1; 1.37 min (Method H) | 13.10 (br s, 2 H), 7.59-7.68 (m, 2 H), 7.52 (d, J = 6.7 Hz, 1 H), 7.33 (t, J = 8.2 Hz, 1 H), 7.16 (t, J = 7.8 Hz, 1 H), 7.11 (dd, J = 8.4, 2.5 Hz, 1 H), 7.04 (d, J = 2.3 Hz, 1 H), 6.99 (m, J = 8.2 Hz, 2 H), 6.91 (m, J = 8.2 Hz, 2 H), 6.79 (dd, J = 8.2, 2.0 Hz, 1 H), 6.72 (t, J = 2.2 Hz, 1 H), 6.69 (dd, J = 8.2, 2.0 Hz, 1 H), 5.61 (s, 2 H), 4.56 (q, J = 7.0 Hz, 2 H), 3.75 (s, 3 H), 1.36 (t, J = 7.0 Hz, 3 H). |
| 333 | 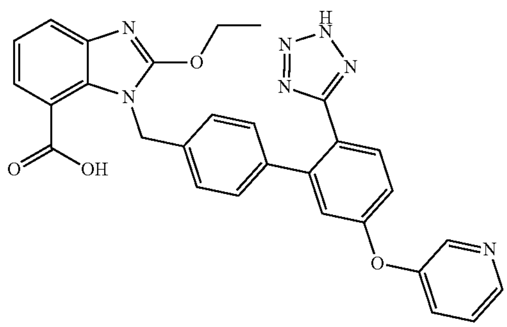 [SMILES: CCOc1nc2cccc(C(=O)O)c2n1Cc1ccc(-c2cc(Oc3cccnc3)ccc2-c2nn[nH]n2)cc1] | 533.54 | 534.1; 1.26 min (Method H) | 13.16 (br s, 2 H), 8.49 (br s, 1 H), 8.43 (d, J = 3.5 Hz, 1 H), 7.56-7.71 (m, 3 H), 7.42-7.56 (m, 2 H), 7.05-7.23 (m, 3 H), 6.85-7.05 (m, 4 H), 5.61 (br s, 2 H), 4.56 (q, J = 7.0 Hz, 2 H), 1.36 (t, J = 6.8 Hz, 3 H). |
| 334 | 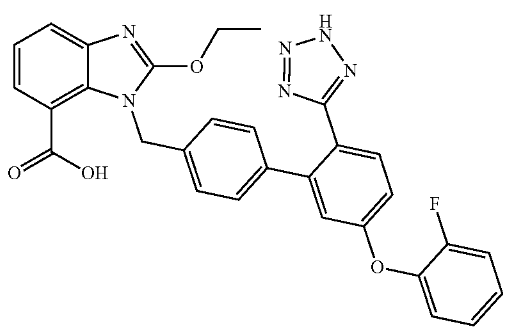 [SMILES: CCOc1nc2cccc(C(=O)O)c2n1Cc1ccc(-c2cc(Oc3ccccc3F)ccc2-c2nn[nH]n2)cc1] | 550.54 | 551.1; 1.34 min (Method H) | 13.12 (s, 2 H), 7.59-7.68 (m, 2 H), 7.52 (d, J = 7.8 Hz, 1 H), 7.38-7.47 (m, 1 H), 7.22-7.38 (m, 3 H), 7.16 (t, J = 7.8 Hz, 1 H), 7.01-7.09 (m, 2 H), 6.99 (m, J = 7.8 Hz, 2 H), 6.91 (m, J = 8.2 Hz, 2 H), 5.61 (s, 2 H), 4.56 (q, J = 7.0 Hz, 2 H), 1.36 (t, J = 7.0 Hz, 3 H). |
| 335 | 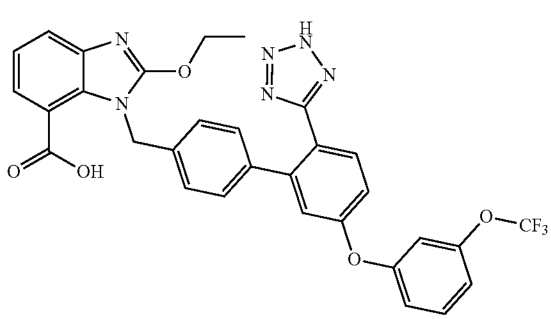 [SMILES: CCOc1nc2cccc(C(=O)O)c2n1Cc1ccc(-c2cc(Oc3cccc(OC(F)(F)F)c3)ccc2-c2nn[nH]n2)cc1] | 616.55 | 617.1, 1.42 min (Method H) | 13.12 (br s, 2 H), 7.60-7.72 (m, 2 H), 7.48-7.59 (m, 2 H), 7.09-7.24 (m, 6 H), 7.00 (m, J = 8.2 Hz, 2 H), 6.91 (m, J = 8.2 Hz, 2 H), 5.61 (s, 2 H), 4.56 (q, J = 7.0 Hz, 2 H), 1.36 (t, J = 7.0 Hz, 3 H). |

-continued

| Ex | Structure | MW | LC-MS m/z [M + H]+; RT (Method) | 1H NMR (400 MHz, DMSO-d6) δ ppm |
|---|---|---|---|---|
| 336 | 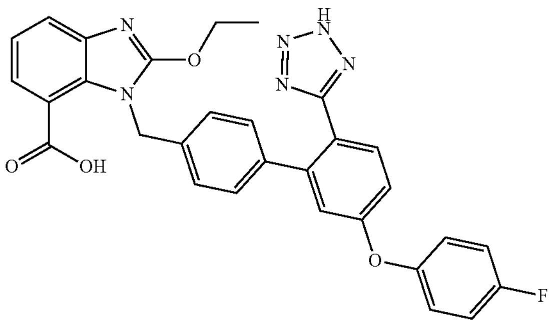 [SMILES: CCOc1nc2cccc(C(=O)O)c2n1Cc1ccc(-c2cc(Oc3ccc(F)cc3)ccc2-c2nn[nH]n2)cc1] | 550.54 | 551.1; 1.36 min (Method H) | 13.14 (br s, 2 H), 7.64 (t, J = 8.8 Hz, 2 H), 7.52 (d, J = 7.4 Hz, 1 H), 7.12-7.32 (m, 5 H), 7.08 (dd, J = 8.6, 2.7 Hz, 1 H), 6.94-7.04 (m, 3 H), 6.84-6.94 (m, 2 H), 5.61 (s, 2 H), 4.56 (q, J = 6.8 Hz, 2 H), 1.36 (t, J = 7.0 Hz, 3 H). |
| 337 | 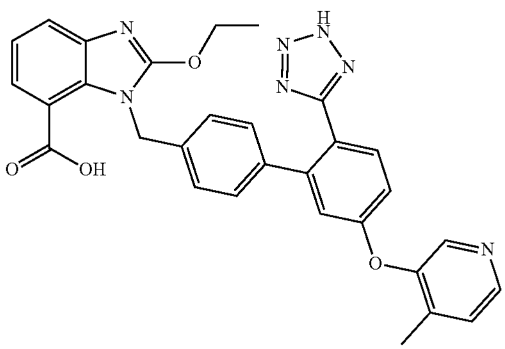 [SMILES: CCOc1nc2cccc(C(=O)O)c2n1Cc1ccc(-c2cc(Oc3cnccc3C)ccc2-c2nn[nH]n2)cc1] | 547.56 | 548.1; 1.27 min (Method H) | 13.14 (br s, 2 H), 8.28-8.41 (m, 2 H), 7.62 (d, J = 8.6 Hz, 1 H), 7.65 (d, J = 7.8 Hz, 1 H), 7.52 (d, J = 7.8 Hz, 1 H), 7.42 (d, J = 4.7 Hz, 1 H), 7.16 (t, J = 7.8 Hz, 1 H), 6.95-7.04 (m, 4 H), 6.85-6.95 (m, 2 H), 5.61 (s, 2 H), 4.56 (q, J = 7.0 Hz, 2 H), 2.21 (s, 3 H), 1.36 (t, J = 7.0 Hz, 3H). |
| 338 | 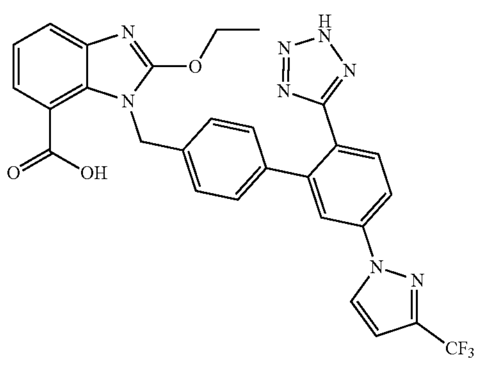 [SMILES: CCOc1nc2cccc(C(=O)O)c2n1Cc1ccc(-c2cc(-n3ccc(C(F)(F)F)n3)ccc2-c2nn[nH]n2)cc1] | 574.51 | 575.1; 1.34 min (Method H) | 13.11 (br s, 2 H) 8.93 (br s, 1 H), 8.08 (dd, J = 8.4, 2.2 Hz, 1 H), 7.94-8.01 (m, 1 H), 7.84 (d, J = 8.2 Hz, 1 H), 7.66 (d, J = 7.8 Hz, 1 H), 7.54 (d, J = 7.4 Hz, 1 H), 7.17 (t, J = 7.8 Hz, 1 H), 7.05-7.14 (m, 3 H), 6.97 (d, J = 7.8 Hz, 2 H), 5.65 (s, 2 H), 4.58 (q, J = 7.0 Hz, 2 H), 1.39 (t, J = 7.0 Hz, 3 H). |
| 339 | 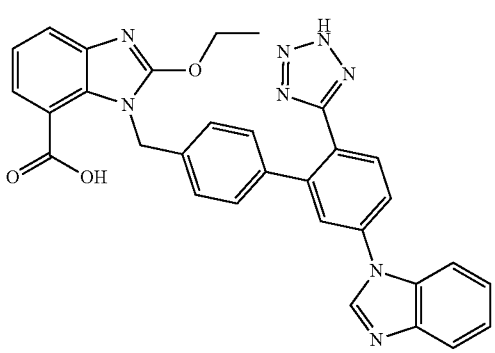 [SMILES: CCOc1nc2cccc(C(=O)O)c2n1Cc1ccc(-c2cc(-n3cnc4ccccc43)ccc2-c2nn[nH]n2)cc1] | 556.57 | 557.2; 1.29 min (Method H) | 13.15 (br s, 2 H), 8.72 (s, 1 H), 7.84-7.94 (m, 2 H), 7.71-7.83 (m, 3 H), 7.66 (d, J = 7.8 Hz, 1 H), 7.54 (d, J = 7.8 Hz, 1 H), 7.28-7.40 (m, 2 H), 7.08-7.21 (m, 3 H), 6.97 (d, J = 7.8 Hz, 2 H), 5.65 (s, 2 H), 4.58 (q, J = 7.0 Hz, 2 H), 1.38 (t, J = 7.0 Hz, 3 H). |

-continued

| Ex | Structure | MW | LC-MS m/z [M + H]+; RT (Method) | 1H NMR (400 MHz, DMSO-d6) δ ppm |
|---|---|---|---|---|
| 340 | 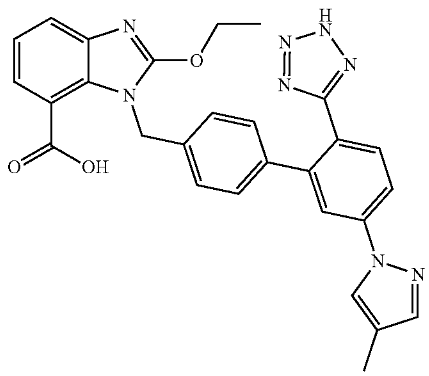 [SMILES: CCOc1nc2cccc(C(=O)O)c2n1Cc1ccc(-c2cc(-n3cc(C)cn3)ccc2-c2nn[nH]n2)cc1] | 520.54 | 521.2; 1.26 min (Method H) | 13.16 (br s, 2 H), 8.47 (s, 1 H), 7.97 (dd, J = 8.4, 2.2 Hz, 1 H), 7.86 (d, J = 2.0 Hz, 1 H), 7.74 (d, J = 8.6 Hz, 1 H), 7.66 (d, J = 7.8 Hz, 1 H), 7.62 (s, 1 H), 7.54 (d, J = 7.8 Hz, 1 H), 7.18 (t, J = 7.8 Hz, 1 H), 7.08 (m, J = 8.2 Hz, 2 H), 6.95 (m, J = 8.2 Hz, 2 H), 5.64 (s, 2 H), 4.58 (q, J = 7.0 Hz, 2 H), 2.09 (s, 3 H), 1.39 (t, J = 7.0 Hz, 3 H). |
| 341 | 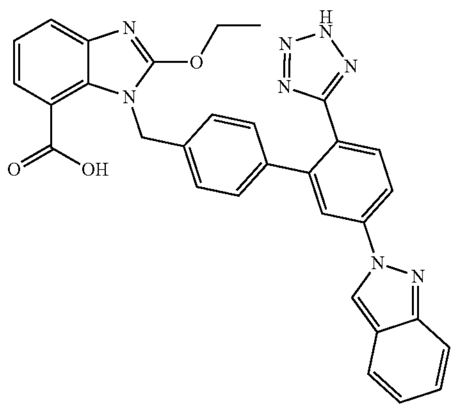 [SMILES: CCOc1nc2cccc(C(=O)O)c2n1Cc1ccc(-c2cc(-n3cc4ccccc4n3)ccc2-c2nn[nH]n2)cc1] | 556.57 | 557.1; 1.31 min (Method H) | 13.08 (br s, 2 H), 9.31 (s, 1 H), 8.28 (d, J = 8.2 Hz, 1 H), 8.12-8.24 (m, 1 H), 7.87 (d, J = 8.2 Hz, 1 H), 7.60-7.80 (m, 3 H), 7.54 (d, J = 7.0 Hz, 1 H), 7.27-7.38 (m, 1 H), 7.06-7.23 (m, 4 H), 6.97 (d, J = 8.2 Hz, 2 H), 5.66 (s, 2 H), 4.59 (q, J = 6.8 Hz, 2 H), 1.40 (t, J = 7.0 Hz, 3 H). |
| 342 | 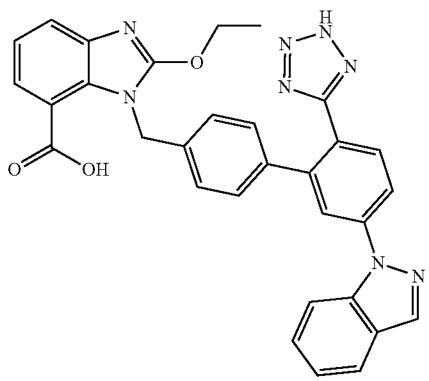 [SMILES: CCOc1nc2cccc(C(=O)O)c2n1Cc1ccc(-c2cc(-n3ncc4ccccc43)ccc2-c2nn[nH]n2)cc1] | 556.57 | 557.1; 1.32 min (Method H) | 13.17 (br s, 2 H), 8.45 (s, 1 H), 8.00 (dt, J = 8.3, 2.3 Hz, 2 H), 7.93 (d, J = 7.8 Hz, 1 H), 7.80-7.90 (m, 2 H), 7.66 (d, J = 7.8 Hz, 1 H), 7.48-7.58 (m, 2 H), 7.31 (t, J = 7.4 Hz, 1 H), 7.10-7.21 (m, 3 H), 6.97 (d, J = 7.8 Hz, 2 H), 5.64 (s, 2 H), 4.58 (q, J = 7.0 Hz, 2 H), 1.38 (t, J = 7.0 Hz, 3 H). |

Example 343: 1-((5'-(Cyclohexyloxy)-2'-(2H-tetrazol-5-yl)-[1,1'-biphenyl]-4-yl)methyl)-2-ethoxy-1H-benzo[d]imidazole-7-carboxylic acid

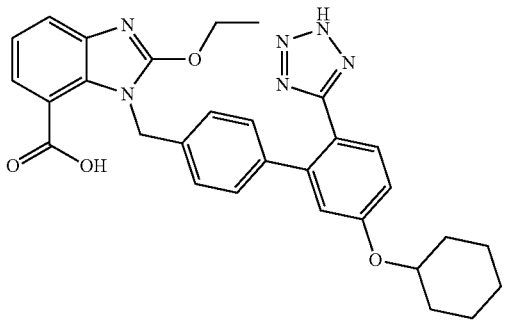

(Ex. 343)

Intermediate 343a: Methyl 2-ethoxy-1-(4-(4,4,5,5-tetramethyl-1,3,2-dioxaborolan-2-yl)benzyl)-1H-benzo[d]imidazole-7-carboxylate

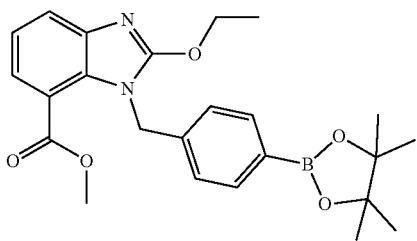

(343a)

The title compound was prepared by the reaction of methyl 2-ethoxy-1H-benzo[d]imidazole-7-carboxylate (1.00 g, 4.54 mmol) with 2-(4-(bromomethyl)phenyl)-4,4,5,5-tetramethyl-1,3,2-dioxaborolane (1.44 g, 4.77 mmol), in a similar fashion to that described for the synthesis of Intermediate 330a, and was obtained as a yellow solid (1.44 g, 3.31 mmol, 72% yield). LC-MS (Method H): 1.42 min, [M+H]$^+$=437.2; $^1$H NMR (400 MHz, CDCl$_3$) δ ppm 7.73 (dd, J=8.0, 1.0 Hz, 1H), 7.67 (m, J=8.2 Hz, 2H), 7.53 (dd, J=7.8, 1.2 Hz, 1H), 7.16 (t, J=7.8 Hz, 1H), 6.96 (m, J=8.2 Hz, 2H), 5.63 (s, 2H), 4.65 (q, J=7.0 Hz, 2H), 3.72 (s, 3H), 1.46 (t, J=7.0 Hz, 3H), 1.31 (s, 12H).

Intermediate 343b: Methyl 1-((2'-cyano-5'-(cyclohexyloxy)-[1,1'-biphenyl]-4-yl)methyl)-2-ethoxy-1H-benzo[d]imidazole-7-carboxylate

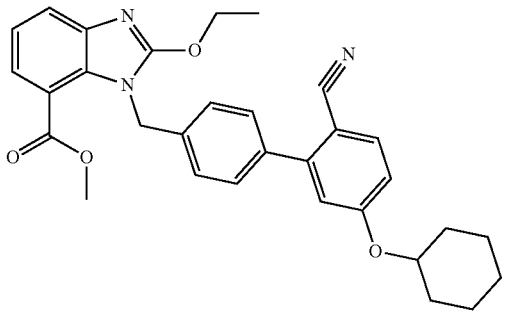

(343b)

The title compound was prepared by the reaction of methyl 2-ethoxy-1-(4-(4,4,5,5-tetramethyl-1,3,2-dioxaborolan-2-yl)benzyl)-1H-benzo[d]imidazole-7-carboxylate (Intermediate 343a, 0.100 g, 0.229 mmol) with 2-bromo-4-(cyclohexyloxy)benzonitrile (Intermediate 209a, 0.128 g, 0.458 mmol), in a similar fashion to that described for the synthesis of Intermediate 330b, and was obtained as an off-white solid (0.100 mg, 0.196 mmol, 86% yield).). LC-MS (Method H): 1.58 min, [M+H]$^+$=510.1; $^1$H NMR (400 MHz, DMSO-d$_6$) δ ppm 7.80 (d, J=8.6 Hz, 1H), 7.68-7.74 (m, 1H), 7.41-7.56 (m, 4H), 7.32-7.40 (m, 1H), 7.20 (t, J=7.8 Hz, 1H), 7.03-7.12 (m, 3H), 7.02 (d, J=2.3 Hz, 1H), 5.57 (s, 2H), 4.62 (q, J=7.0 Hz, 2H), 4.55 (dt, J=8.3, 4.3 Hz, 1H), 3.71 (s, 3H), 1.86-1.97 (m, 2H), 1.68 (dd, J=9.2, 3.3 Hz, 2H), 1.41 (t, J=7.0 Hz, 3H), 1.31-1.59 (m, 4H), 1.14-1.30 (m, 2H).

Example 343: 1-((5'-(Cyclohexyloxy)-2'-(2H-tetrazol-5-yl)-[1,1'-biphenyl]-4-yl)methyl)-2-ethoxy-1H-benzo[d]imidazole-7-carboxylic acid The title compound was prepared from Intermediate 343b (0.050 g, 0.098 mmol) according to the method described for the synthesis of Example 330 and was obtained as a white solid (0.020 g, 0.037 mmol, 37% yield).). LC-MS (Method H): 1.36 min, [M+H]$^+$=539.2; $^1$H NMR (400 MHz, DMSO-d$_6$) δ ppm 13.16 (br s, 1H), 7.66 (d, J=7.8 Hz, 1H), 7.45-7.57 (m, 2H), 7.17 (t, J=7.8 Hz, 1H), 7.10 (dd, J=8.6, 2.3 Hz, 1H), 6.98-7.04 (m, 2H), 6.88-6.98 (m, 3H), 5.62 (s, 2H), 4.57 (q, J=7.0 Hz, 2H), 4.46-4.54 (m, 1H), 1.86-2.00 (m, 2H), 1.62-1.77 (m, 2H), 1.32-1.55 (m, 4H), 1.38 (t, J=7.0 Hz, 3H), 1.21-1.31 (m, 2H).

Example 344: 2-Ethoxy-1-((5'-(4-isopropyl-1H-1,2,3-triazol-1-yl)-2'-(2H-tetrazol-5-yl)-[1,1'-biphenyl]-4-yl)methyl)-1H-benzo[d]imidazole-7-carboxylic acid

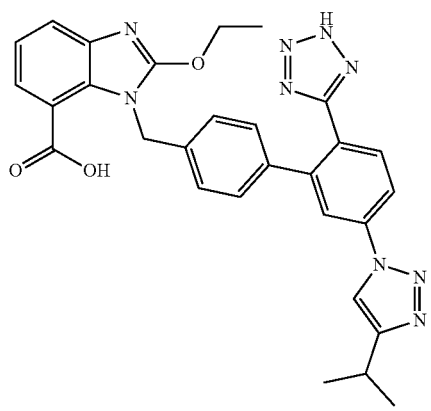

(Ex. 344)

Intermediate 344a: Methyl 1-((5'-azido-2'-cyano-[1,1'-biphenyl]-4-yl)methyl)-2-ethoxy-1H-benzo[d]imidazole-7-carboxylate

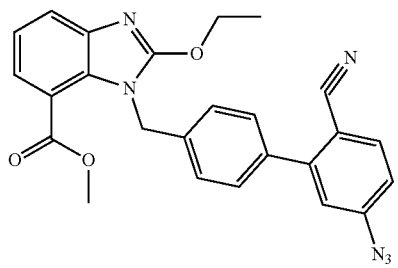

(344a)

The title compound was prepared by the reaction of methyl 1-((2'-cyano-5'-fluoro-[1,1'-biphenyl]-4-yl)methyl)-2-ethoxy-1H-benzo[d]imidazole-7-carboxylate (Intermediate 330b, 0.100 g, 0.233 mmol) with sodium azide (0.030 g, 0.466 mmol), using conditions similar to those reported for the synthesis of Intermediate 330c, to afford a white solid (0.048 g, 0.11 mmol, 45% yield).). LC-MS (Method H): 1.36 min, [M+H]$^+$=539.2; $^1$H NMR (400 MHz, DMSO-d$_6$) δ ppm 7.94 (d, J=8.2 Hz, 1H), 7.71 (dd, J=8.0, 1.0 Hz, 1H), 7.52 (m, J=8.2 Hz, 2H), 7.47 (dd, J=7.8, 0.8 Hz, 1H), 7.28 (dd, J=8.2, 2.3 Hz, 1H), 7.24 (d, J=2.3 Hz, 1H), 7.20 (t, J=7.8 Hz, 1H), 7.09 (m, J=8.2 Hz, 2H), 5.58 (s, 2H), 4.62 (q, J=7.0 Hz, 2H), 3.70 (s, 3H), 1.41 (t, J=7.0 Hz, 3H).

Intermediate 344b: Methyl 1-((2'-cyano-5'-(4-isopropyl-1H-1,2,3-triazol-1-yl)-[1,1'-biphenyl]-4-yl)methyl)-2-ethoxy-1H-benzo[d]imidazole-7-carboxylate

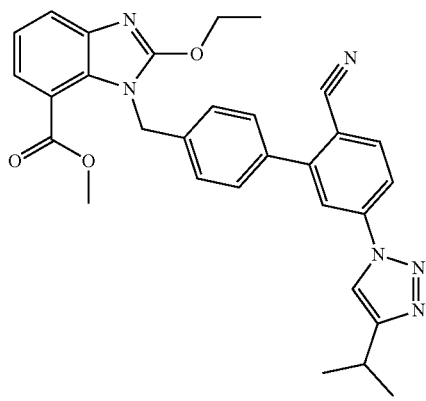

(344b)

To a mixture of Intermediate 344a (0.044 g, 0.097 mmol) in 2-methylpropan-2-ol (2 mL) and H$_2$O (2 mL) was added 3-methylbut-1-yne (0.076 mL, 0.97 mmol), copper(II) sulfate pentahydrate (0.005 g, 0.019 mmol) and sodium (R)-5-((S)-1,2-dihydroxyethyl)-4-hydroxy-2-oxo-2,5-dihydrofuran-3-olate (0.004 g, 0.019 mmol) and the mixture was stirred at RT for 18 h and then at 65° C. for 24 h. To the resulting mixture was added another portion of copper(II) sulfate pentahydrate (0.005 g, 0.019 mmol) and sodium (R)-5-((S)-1,2-dihydroxyethyl)-4-hydroxy-2-oxo-2,5-dihydrofuran-3-olate (0.004 g, 0.019 mmol) and heating was continued at 65° C. for an additional 24 h. To the cooled mixture was added H$_2$O (3 mL), brine (2 mL) and tert-butylmethyl ether (10 mL). The organic phase was separated and the aqueous phase was re-extracted with tert-butylmethyl ether (5 mL). The combined organic extract was evaporated and residue was taken up in DMSO (3 mL) and the mixture was filtered. The filtrate was submitted to reverse phase HPLC purification (Method F, using formic acid as modifier) to afford the title compound as a white solid (0.035 g, 0.067 mmol, 69% yield). LC-MS (Method H): 1.37 min, [M+H]$^+$=521.2; $^1$H NMR (400 MHz, DMSO-d$_6$) δ ppm 8.83 (s, 1H), 8.11-8.20 (m, 2H), 8.09 (d, J=1.6 Hz, 1H), 7.72 (dd, J=7.8, 1.2 Hz, 1H), 7.62 (m, J=8.2 Hz, 2H), 7.48 (dd, J=7.8, 0.8 Hz, 1H), 7.21 (t, J=7.8 Hz, 1H), 7.13 (m, J=8.2 Hz, 2H), 5.60 (s, 2H), 4.63 (q, J=7.0 Hz, 2H), 3.73 (s, 3H), 3.06 (dt, J=13.9, 6.7 Hz, 1H), 1.42 (t, J=7.0 Hz, 3H), 1.29 (d, J=7.0 Hz, 6H).

Example 344: 2-Ethoxy-1-((5'-(4-isopropyl-1H-1,2,3-triazol-1-yl)-2'-(2H-tetrazol-5-yl)-[1,1'-biphenyl]-4-yl)methyl)-1H-benzo[d]imidazole-7-carboxylic acid The reaction of Intermediate 344b (0.035 g, 0.061 mmol) according to the method described for the synthesis of Example 330 provided the title compound as a white solid (0.015 g, 0.027 mmol, 44% yield). LC-MS (Method H): 1.27 min, [M+H]$^+$=550.2; $^1$H NMR (400 MHz, DMSO-d$_6$) δ ppm 8.78 (s, 1H), 8.10 (d, J=7.8 Hz, 1H), 7.96 (br s, 1H), 7.85 (d, J=8.6 Hz, 1H), 7.66 (d, J=7.8 Hz, 1H), 7.54 (d, J=7.0 Hz, 1H), 7.17 (t, J=7.8 Hz, 1H), 7.11 (m, J=7.8 Hz, 2H), 6.96 (m, J=7.4 Hz, 2H), 5.65 (br s, 2H), 4.58 (q, J=7.0 Hz, 2H), 3.05 (tt, J=13.8, 6.7 Hz, 1H), 1.39 (t, J=7.0 Hz, 3H), 1.29 (d, J=7.0 Hz, 6H).

Example 345: 1-((6'-(2H-tetrazol-5-yl)-[1,1':3',1''-terphenyl]-4-yl)methyl)-2-butyl-1H-imidazole-5-carboxylic acid, TFA salt

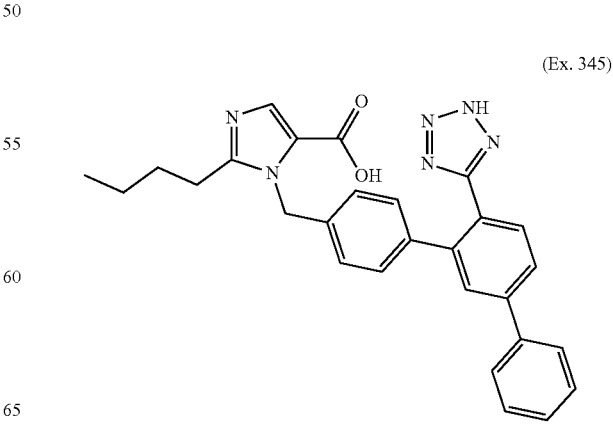

(Ex. 345)

Intermediate 345a: 2-butyl-1-(4-(4,4,5,5-tetramethyl-1,3,2-dioxaborolan-2-yl)benzyl)-1H-imidazole-5-carbaldehyde

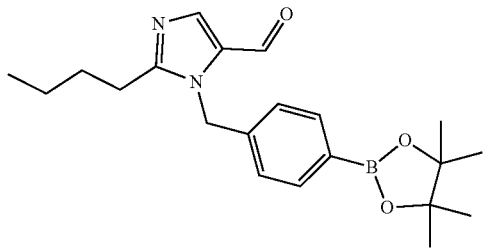
(345a)

2-Butyl-4-chloro--(4-(4,4,-tetramethyl-1,3, -dioxaborolan-2-yl)benzyl)-1H-imidazole-5-carbaldehyde (035a 2 g, 4.97 mmol) was dissolved in MeOH (100 mL). KOAc (0.585 g, 5.96 mmol) was added followed by Degussa Pd-C(0.264 g, 0.248 mmol). The reaction mixture was evacuated and backfilled with 1 atm of hydrogen and was stirred at RT for 1 hour and 45 min. The reaction mixture was then evacuated and backfilled with $N_2$ and filtered through a celite pad which was washed with MeOH. The MeOH was concentrated in vacuo. The residue was then suspended in EtOAc and extracted with $H_2O$ 2x, brine 1x, dried with sodium sulfate, filtered and concentrated to yield the title compound (345a, 3.8 g, 9.60 mmol, 97% yield). LC-MS (Method A2): 0.84 min, [M+H]$^+$=369.15; $^1$H NMR (500 MHz, CDCl$_3$) δ 9.79-9.76 (m, 1H), 9.69 (s, 1H), 7.81 (s, 1H), 7.77 (d, J=8.0 Hz, 2H), 7.02 (d, J=8.0 Hz, 2H), 5.62 (s, 2H), 5.60-5.59 (m, 1H), 2.68-2.63 (m, 2H), 1.76-1.65 (m, 2H), 1.40-1.37 (m, 2H), 1.37-1.33 (m, 12H), 0.94-0.85 (m, 3H).

Intermediate 345b: 4"-((2-butyl-5-formyl-1H-imidazol-1-yl)methyl)-[1,1':3',1"-terphenyl]-4'-carbonitrile

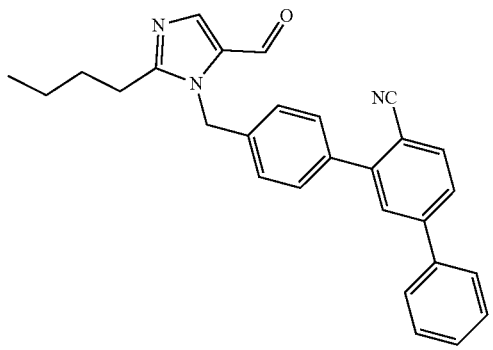
(345b)

2-butyl-1-(4-(4,4,5,5-tetramethyl-1,3,2-dioxaborolan-2-yl)benzyl)-1H-imidazole-5-carbaldehyde (345a, 1200 mg, 3.26 mmol), 3-chloro-[1,1'-biphenyl]-4-carbonitrile (766 mg, 3.58 mmol) and 2nd generation xphos precatalyst (128 mg, 0.163 mmol) were dissolved in dioxane (16 mL) followed by 2 M $K_3PO_4$ (2 M aq) (3.3 mL, 6.52 mmol). The reaction mixture was evacuated and backfilled with $N_2$ (3x) and then heated at 85° C. for h. The reaction mixture was then concentrated onto celite and purified by ISCO (0-100% EtOAc/Hexanes) to afford the title compound (345b, 0.8 g, 1.907 mmol, 52.3% yield). LC-MS: MS (ESI) m/z: 420.1 (M+H)$^+$; $^1$H NMR (500 MHz, CDCl$_3$) δ 9.72 (s, 1H), 7.85 (t, J=4.0 Hz, 2H), 7.74-7.57 (m, 6H), 7.55-7.43 (m, 3H), 7.19 (d, J=8.3 Hz, 2H), 5.68 (s, 2H), 2.80-2.70 (m, 2H), 1.77 (t, J=7.7 Hz, 2H), 1.47-1.35 (m, 2H), 0.94 (t, J=7.4 Hz, 3H).

Intermediate 345c: 2-butyl-1-((6'-cyano-[1,1':3',1"-terphenyl]-4-yl)methyl)-1H-imidazole-5-carboxylic acid

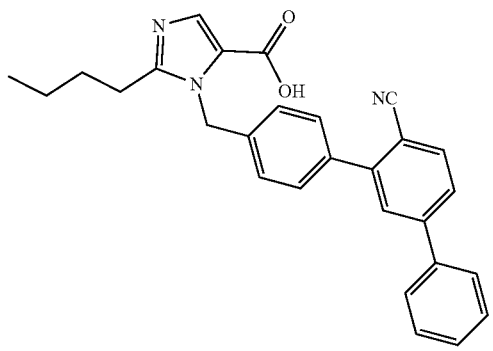
(345c)

4"-((2-butyl-5-formyl-1H-imidazol-1-yl)methyl)-[1,3', 1"-terphenyl]-4'-carbonitrile (345b, 1.5 g, 3.58 mmol) and 2M 2-methylbut-2-ene in THF (7.15 mL, 14.30 mmol) were dissolved in 1-butanol (20 mL). Water (20 mL) was added followed by sodium dihydrogen phosphate (1.287 g, 10.73 mmol) and sodium chlorite (0.970 g, 10.73 mmol). The reaction mixture was allowed to stir at RT for 15 h. The reaction mixture was then cooled to 0° C. and quenched with 10% aq. sodium sulfite (31.5 g, 25.03 mmol). The reaction mixture was allowed to stir at RT for 10 min and was then extracted with EtOAc 3x. The combined organic layer was then washed with brine, dried with sodium sulfate, filtered and concentrated to yield 2-butyl-1-((6'-cyano-[1,1':3',1"-terphenyl]-4-yl)methyl)-1H-imidazole-5-carboxylic acid (345c, 1.17 g, 2.176 mmol, 60.9% yield). LC-MS (Method A2): 0.84 min, [M+H]$^+$=436.10;

Example 345: 1-((6'-(2H-tetrazol-5-yl)-[1,1':3',1"-terphenyl]-4-yl)methyl)-2-butyl-1H-imidazole-5-carboxylic acid, TFA salt To a small vial containing 2-butyl-1-((6'-cyano-[1,1':3', 1"-terphenyl]-4-yl)methyl)-1H-imidazole-5-carboxylic acid (345c, 485 mg, 0.902 mmol) was added dibutyltin oxide (225 mg, 0.902 mmol) and toluene (20 mL) followed by TMS-$N_3$ (0.599 mL, 4.51 mmol). The reaction mixture was sealed and heated at 100° C. for 18 h. The reaction mixture was then diluted with hexanes and celite was added. The mixture was filtered and washed with hexanes. The celite was then purified using reverse phase ISCO (0-100% B. A=$H_2O$/ACN/TFA 90:10:0.1. B=ACN/$H_2O$/TFA 90:10:0.1) to afford the title compound (Example 345, 834 mg, 1.196 mmol, 66.3% yield). LC-MS (Method A4): 1.599 min, [M+H]$^+$=479.0; $^1$H NMR (500 MHz, DMSO-d$_6$) δ 7.75 (d, J=7.6 Hz, 2H), 7.69 (q, J=7.9 Hz, 2H), 7.58 (s, 2H), 7.48 (t, J=7.5 Hz, 2H), 7.42-7.35 (m, 1H), 7.16 (d, J=7.9 Hz, 2H), 6.89 (d, J=7.9 Hz, 2H), 5.59 (s, 2H), 2.58 (t, J=7.5 Hz, 2H), 1.54 (quin, J=7.5 Hz, 2H), 1.36-1.18 (m, 2H), 0.81 (t, J=7.3 Hz, 3H).

Example 346: 1-((6'-(2H-tetrazol-5-yl)-[1,1':3',1"-terphenyll-4-yl)methyl)-2-butyl-N-((1-methyl-1H-pyrazol-4-yl)methyl)-1H-imidazole-5-carboxamide (1-methyl-1H-pyrazol-4-yl)methanamine (116 mg, 1.041 mmol), 1-((6'-(2H-tetrazol-5-yl)-[1,1':3',1"-terphenyl]-4-yl)methyl)-2-butyl-1H-imidazole-5-carboxylic acid (Example 345, 200 mg, 0.347 mmol), and Hunig's Base (224 mg, 1.734 mmol) were dissolved in DMF (5 mL). HATU (264 mg, 0.694 mmol) was added and the reaction mixture was allowed to stir at RT for 18 h. The reaction mixture was then filtered and purified via preparative HPLC (XBridge C18, 19×200 mm, 5-μm particles; Mobile Phase A: 5:95 ACN:H$_2$O with 10 mM NH$_4$OAc; Mobile Phase B: 95:5 ACN:H$_2$O with 10 mM NH$_4$OAc; Gradient: 13-53% B over 20 min, then a 6-minute hold at 100% B; Flow: 20 mL/min;) to afford the title compound (Example 346, 128.1 mg, 0.217 mmol, 62.7% yield). LC-MS (Method A4): 1.542 min, [M+H]$^+$=572.4; $^1$H NMR (500 MHz, DMSO-d$_6$) δ 8.46 (br t, J=5.7 Hz, 1H), 7.82-7.69 (m, 4H), 7.68-7.62 (m, 1H), 7.56-7.46 (m, 4H), 7.45-7.37 (m, 1H), 7.28 (s, 1H), 7.22-7.12 (m, J=8.1 Hz, 2H), 7.02-6.87 (m, J=8.1 Hz, 2H), 5.63 (s, 2H), 4.22 (d, J=5.8 Hz, 2H), 2.59-2.53 (m, 5H), 1.56 (quin, J=7.5 Hz, 2H), 1.34-1.23 (m, 2H), 0.84 (t, J=7.4 Hz, 3H).

The following examples have been similarly prepared from Example 345 as described above for Example 346.

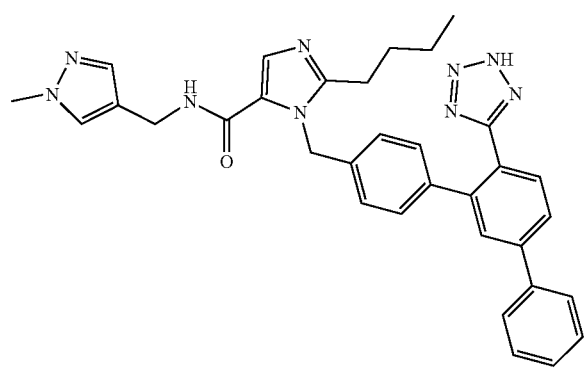

(Ex. 346)

| Ex | Structure | MW | LC-MS m/z [M + H]$^+$; RT (min) (Method A4) | $^1$H NMR (500 MHz, DMSO-d$_6$) δ ppm |
|---|---|---|---|---|
| 347 | 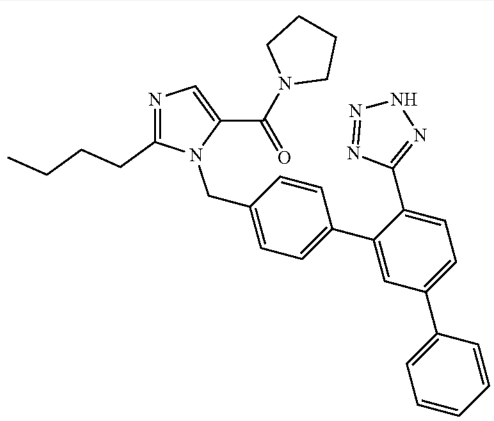 [SMILES: CCCCc1ncc(C(=O)N2CCCC2)n1Cc1ccc(-c2cc(-c3ccccc3)ccc2-c2nn[nH]n2)cc1] | 531.664 | 532.1; 1.71 | $^1$H NMR (500 MHz, DMSO-d$_6$) δ 8.60 (s, 1H), 8.33 (br d, J = 2.4 Hz, 1H), 7.93 (br d, J = 7.9 Hz, 1H), 7.84 (s, 1H), 7.81-7.73 (m, 2H), 7.27-7.11 (m, J = 7.9 Hz, 2H), 7.04-6.94 (m, J = 7.9 Hz, 2H), 5.60 (s, 2H), 3.92 (s, 3H), 2.69-2.57 (m, 2H), 1.59-1.44 (m, 2H), 1.33-1.15 (m, 2H), 0.81 (br t, J = 7.2 Hz, 3H). |
| 348 | 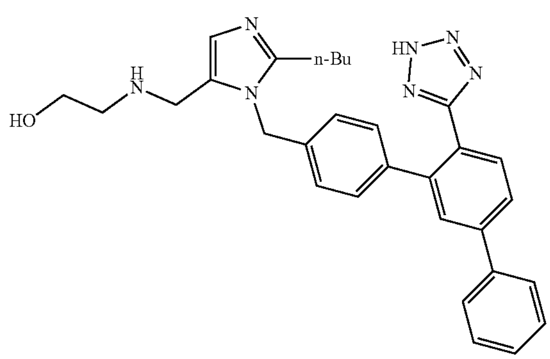 | 521.625 | 522.5; 1.424 | $^1$H NMR (500 MHz, DMSO-d$_6$) δ 8.25 (br. s., 1H), 7.82-7.72 (m, 3H), 7.67 (d, J = 8.0 Hz, 1H), 7.61 (s, 1H), 7.54 (s, 1H), 7.48 (t, J = 7.6 Hz, 2H), 7.40 (d, J = 7.4 Hz, 1H), 7.12 (d, J = 7.8 Hz, 1H), 6.91 (d, J = 8.1 Hz, 1H), 5.60 (s, 2H), 3.44 (t, J = 6.1 Hz, 2H), 3.23 (q, J = 6.0 Hz, 2H), 2.53 (br. s., 2H), 1.57-1.45 (m, 2H), 1.29-1.15 (m, 2H), 0.79 (t, J = 7.3 Hz, 3H). |

-continued

| Ex | Structure | MW | LC-MS m/z [M + H]+; RT (min) (Method A4) | 1H NMR (500 MHz, DMSO-d6) δ ppm |
|---|---|---|---|---|
| 349 | 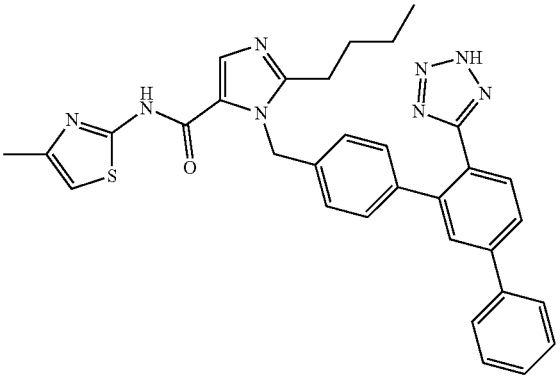 [SMILES: CCCCc1ncc(C(=O)Nc2nc(C)cs2)n1Cc1ccc(-c2cc(-c3ccccc3)ccc2-c2nn[nH]n2)cc1] | 574.71 | 575.5; 1.690 | 1H NMR (500 MHz, DMSO-d6) δ 8.08 (br s, 1H), 7.86-7.75 (m, 3H), 7.75-7.67 (m, 2H), 7.49 (br t, J = 7.5 Hz, 2H), 7.45-7.38 (m, 1H), 7.15 (br d, J = 7.7 Hz, 2H), 6.97 (br d, J = 7.9 Hz, 2H), 6.75 (s, 1H), 5.68 (br s, 2H), 2.64-2.55 (m, 2H), 2.27 (s, 3H), 1.51 (br d, J = 6.5 Hz, 2H), 1.25 (br d, J = 6.9 Hz, 2H), 0.80 (br t, J = 6.9 Hz, 3H). |
| 350 | 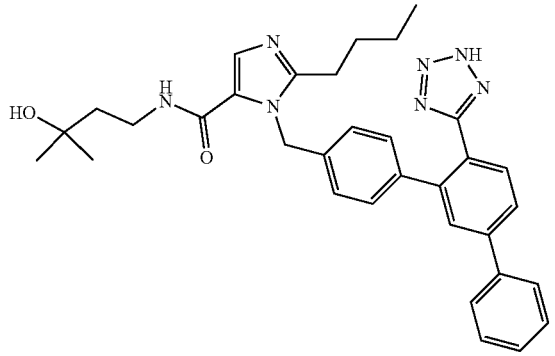 [SMILES: CCCCc1ncc(C(=O)NCCC(C)(C)O)n1Cc1ccc(-c2cc(-c3ccccc3)ccc2-c2nn[nH]n2)cc1] | 563.706 | 564.5; 1.440 | 1H NMR (500 MHz, DMSO-d6) δ 8.22 (br s, 1H), 7.87-7.76 (m, 3H), 7.72 (br d, J = 8.2 Hz, 2H), 7.55-7.46 (m, 3H), 7.46-7.39 (m, 1H), 7.13 (br d, J = 8.0 Hz, 2H), 6.95 (br d, J = 8.0 Hz, 2H), 5.62 (br s, 2H), 3.32-3.16 (m, 2H), 2.57-2.55 (m, 2H), 1.63-1.52 (m, 2H), 1.48 (br s, 2H), 1.23 (br d, J = 7.2 Hz, 2H), 1.09 (s, 6H), 0.85-0.74 (m, 3H). |
| 351 | 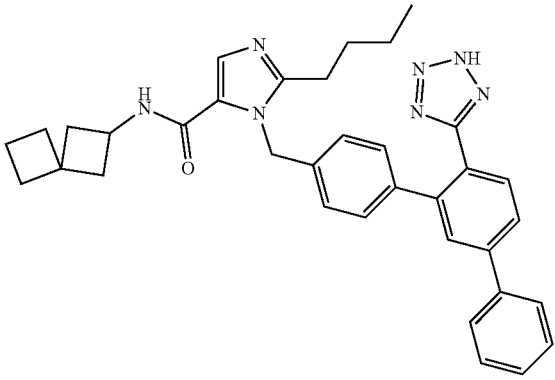 [SMILES: CCCCc1ncc(C(=O)NC2CC3(CCC3)C2)n1Cc1ccc(-c2cc(-c3ccccc3)ccc2-c2nn[nH]n2)cc1] | 571.729 | 572.5; 1.901 | 1H NMR (500 MHz, DMSO-d6) δ 8.57-8.36 (m, 1H), 7.84 (br d, J = 8.0 Hz, 1H), 7.80-7.68 (m, 4H), 7.57-7.47 (m, 3H), 7.46-7.38 (m, 1H), 7.19-7.03 (m, J = 8.0 Hz, 2H), 6.99-6.88 (m, J = 8.0 Hz, 2H), 5.58 (s, 2H), 4.23-4.05 (m, 1H), 2.59-2.54 (m, 2H), 2.31-2.18 (m, 2H), 2.00-1.83 (m, 6H), 1.75 (q, J = 7.7 Hz, 2H), 1.45 (quin, J = 7.5 Hz, 2H), 1.28-1.13 (m, 2H), 0.77 (t, J = 7.3 Hz, 3H). |
| 352 | 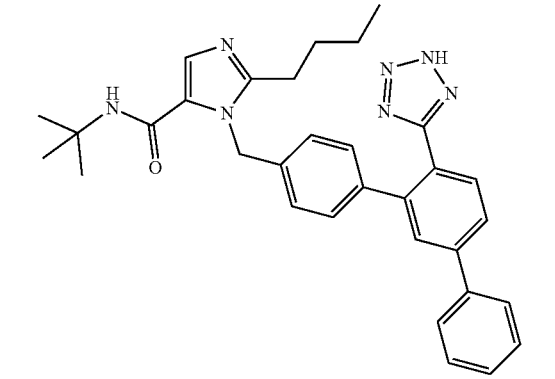 [SMILES: CCCCc1ncc(C(=O)NC(C)(C)C)n1Cc1ccc(-c2cc(-c3ccccc3)ccc2-c2nn[nH]n2)cc1] | 533.68 | 534.6; 1.675 | 1H NMR (500 MHz, DMSO-d6) δ 7.85-7.75 (m, 3H), 7.75-7.67 (m, 2H), 7.63 (br s, 1H), 7.54-7.45 (m, 3H), 7.45-7.39 (m, 1H), 7.17-7.09 (m, J = 7.8 Hz, 2H), 7.05-6.94 (m, J = 7.9 Hz, 2H), 5.55 (s, 2H), 2.58-2.52 (m, 2H), 1.46 (br d, J = 7.0 Hz, 2H), 1.29 (s, 9H), 1.22 (br d, J = 7.3 Hz, 2H), 0.78 (br t, J = 7.3 Hz, 3H). |

| Ex | Structure | MW | LC-MS m/z [M + H]+; RT (min) (Method A4) | ¹H NMR (500 MHz, DMSO-d₆) δ ppm |
|---|---|---|---|---|
| 353 | 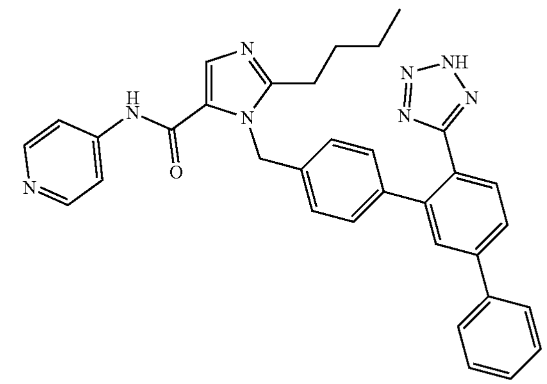 [SMILES: CCCCc1ncc(C(=O)Nc2ccncc2)n1Cc1ccc(-c2cc(-c3ccccc3)ccc2-c2nn[nH]n2)cc1] | 554.658 | 555; 1.496 | [NEED NMR] |
| 354 | 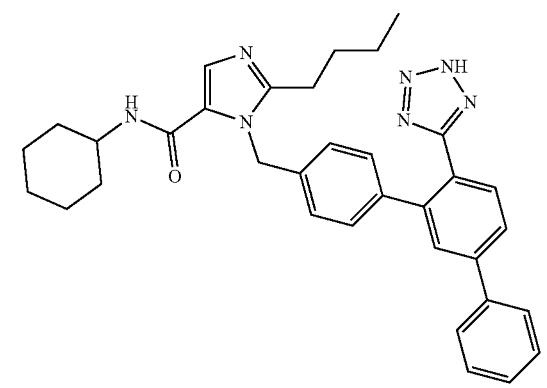 [SMILES: CCCCc1ncc(C(=O)NC2CCCCC2)n1Cc1ccc(-c2cc(-c3ccccc3)ccc2-c2nn[nH]n2)cc1] | 559.718 | 560; 1.520 | ¹H NMR (500 MHz, DMSO-d₆) δ 8.50-8.30 (m, 1H), 7.84 (br d, J = 8.0 Hz, 1H), 7.80-7.68 (m, 4H), 7.57-7.47 (m, 3H), 7.46-7.38 (m, 1H), 7.18-7.05 (m, J = 8.0 Hz, 2H), 6.99-6.88 (m, J = 8.0 Hz, 2H), 5.58 (s, 2H), 4.32-4.06 (m, J = 7.9 Hz, 1H), 2.59-2.54 (m, 2H), 2.24 (br s, 2H), 2.04-1.89 (m, 4H), 1.85 (br d, J = 7.5 Hz, 2H), 1.75 (br d, J = 7.1 Hz, 2H), 1.45 (br d, J = 7.4 Hz, 2H), 1.20 (br d, J = 7.4 Hz, 2H), 0.77 (t, J = 7.3 Hz, 3H). |
| 355 | 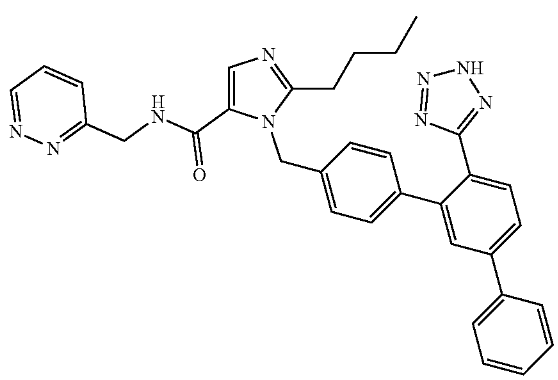 [SMILES: CCCCc1ncc(C(=O)NCc2cccnn2)n1Cc1ccc(-c2cc(-c3ccccc3)ccc2-c2nn[nH]n2)cc1] | 569.673 | 570.1; 1.571 | ¹H NMR (500 MHz, DMSO-d₆) δ 9.08 (br d, J = 4.6 Hz, 2H), 7.94-7.74 (m, 3H), 7.71 (br d, J = 8.0 Hz, 1H), 7.68-7.61 (m, 3H), 7.54-7.46 (m, 3H), 7.46-7.37 (m, 1H), 7.13 (br d, J = 7.7 Hz, 2H), 6.93 (br d, J = 8.0 Hz, 2H), 5.60 (s, 2H), 4.66 (br d, J = 5.7 Hz, 2H), 2.56 (br s, 2H), 1.57-1.44 (m, 2H), 1.31-1.19 (m, 2H), 0.80 (br t, J = 7.3 Hz, 3H). |
| 356 | 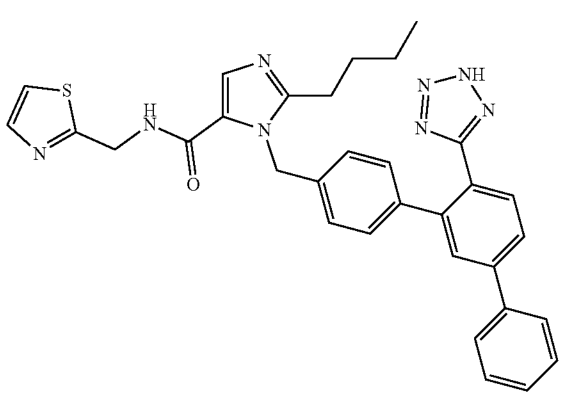 [SMILES: CCCCc1ncc(C(=O)NCc2nccs2)n1Cc1ccc(-c2cc(-c3ccccc3)ccc2-c2nn[nH]n2)cc1] | 574.71 | 575.2; 1.676 | ¹H NMR (500 MHz, DMSO-d₆) δ 9.23 (br s, 1H), 7.78 (br d, J = 8.6 Hz, 3H), 7.74-7.63 (m, 4H), 7.57 (br s, 1H), 7.53-7.40 (m, 3H), 7.21-7.06 (m, J = 7.8 Hz, 2H), 7.01-6.91 (m, J = 8.0 Hz, 2H), 5.64 (s, 2H), 4.66 (br d, J = 5.9 Hz, 2H), 2.61-2.56 (m, 2H), 1.67-1.40 (m, 2H), 1.36-1.08 (m, J = 7.2 Hz, 2H), 0.80 (br t, J = 7.2 Hz, 3H). |

-continued

| Ex | Structure | MW | LC-MS m/z [M + H]+; RT (min) (Method A4) | 1H NMR (500 MHz, DMSO-d6) δ ppm |
|---|---|---|---|---|
| 357 | 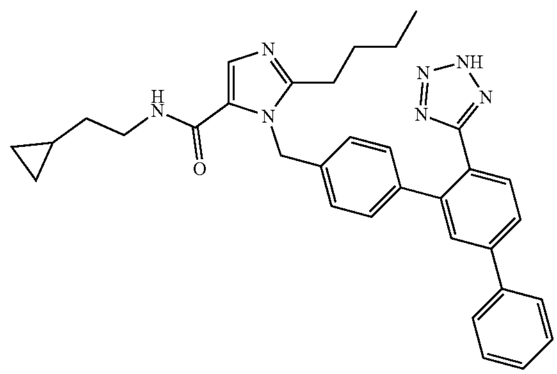 [SMILES: CCCCc1ncc(C(=O)NCCC2CC2)n1Cc1ccc(-c2cc(-c3ccccc3)ccc2-c2nn[nH]n2)cc1] | 545.29 | 546.1; 1.853 | 1H NMR (500 MHz, DMSO-d6) δ 8.30 (br s, 1H), 7.85 (br d, J = 7.9 Hz, 1H), 7.79 (br d, J = 7.4 Hz, 2H), 7.76-7.69 (m, 2H), 7.56-7.47 (m, 3H), 7.47-7.40 (m, 1H), 7.17-7.09 (m, J = 7.9 Hz, 2H), 7.01-6.91 (m, J = 7.9 Hz, 2H), 5.62 (s, 2H), 3.29-3.16 (m, 2H), 2.58-2.53 (m, 2H), 1.55-1.43 (m, 2H), 1.35 (q, J = 6.8 Hz, 2H), 1.29-1.17 (m, 2H), 0.80 (br t, J = 7.3 Hz, 3H), 0.65 (br s, 1H), 0.35 (br d, J = 7.7 Hz, 2H), 0.00 (br d, J = 3.6 Hz, 2H). |
| 358 | 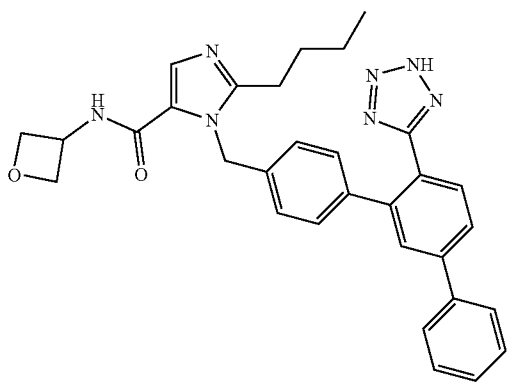 [SMILES: CCCCc1ncc(C(=O)NC2COC2)n1Cc1ccc(-c2cc(-c3ccccc3)ccc2-c2nn[nH]n2)cc1] | 533.636 | 534; 1.622 | 1H NMR (500 MHz, DMSO-d6) δ 8.94 (br s, 1H), 7.79-7.63 (m, 6H), 7.59 (s, 1H), 7.48 (t, J = 7.6 Hz, 2H), 7.44-7.35 (m, 1H), 7.22-7.05 (m, J = 7.9 Hz, 2H), 6.97-6.80 (m, J = 8.0 Hz, 2H), 5.58 (s, 2H), 5.02-4.85 (m, 1H), 4.72 (t, J = 6.9 Hz, 2H), 4.52 (t, J = 6.3 Hz, 2H), 2.57-2.53 (m, 2H), 1.60-1.44 (m, 2H), 1.32-1.18 (m, 2H), 0.81 (br t, J = 7.3 Hz, 3H). |
| 359 | 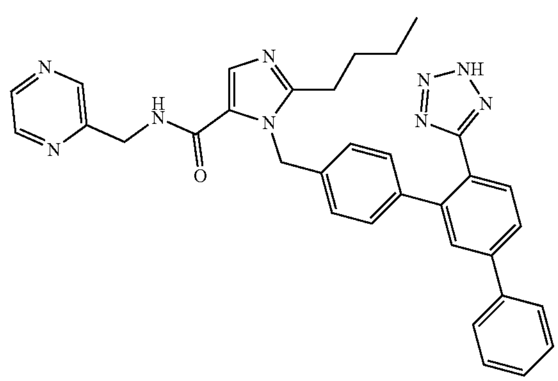 [SMILES: CCCCc1ncc(C(=O)NCc2cnccn2)n1Cc1ccc(-c2cc(-c3ccccc3)ccc2-c2nn[nH]n2)cc1] | 569.7 | 570; 1.79 | 1H NMR (500 MHz, DMSO-d6) δ 9.00 (br s, 1H), 8.56 (br s, 1H), 8.52 (s, 1H), 8.49 (br s, 1H), 7.89-7.71 (m, 5H), 7.66 (s, 1H), 7.52 (br t, J = 7.4 Hz, 2H), 7.48-7.39 (m, 1H), 7.14 (br d, J = 7.9 Hz, 2H), 6.97 (br d, J = 7.7 Hz, 2H), 5.62 (br s, 2H), 4.53 (br d, J = 5.5 Hz, 2H), 2.61-2.54 (m, 2H), 1.60-1.44 (m, 2H), 1.37-1.21 (m, 2H), 0.81 (br t, J = 7.0 Hz, 3H). |
| 360 | 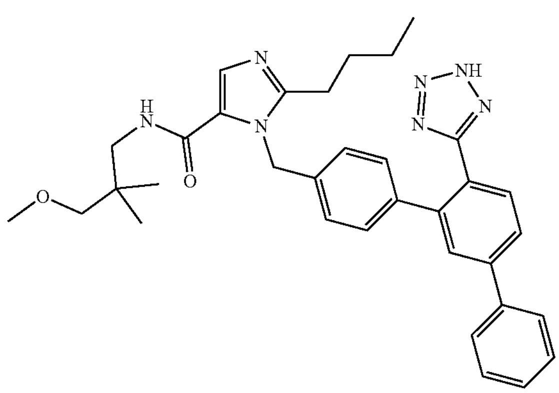 [SMILES: CCCCc1ncc(C(=O)NCC(C)(C)COC)n1Cc1ccc(-c2cc(-c3ccccc3)ccc2-c2nn[nH]n2)cc1] | 577.733 | 578.6; 1.857 | 1H NMR (500 MHz, DMSO-d6) δ 8.11 (br s, 1H), 7.83-7.73 (m, 3H), 7.73-7.63 (m, 2H), 7.56-7.46 (m, 3H), 7.46-7.38 (m, 1H), 7.11 (br d, J = 7.6 Hz, 2H), 6.94 (br d, J = 7.9 Hz, 2H), 5.59 (s, 2H), 3.24-3.14 (m, 3H), 3.06 (br d, J = 6.2 Hz, 2H), 3.00 (s, 2H), 2.57-2.53 (m, 2H), 1.54-1.42 (m, 2H), 1.32-1.14 (m, 2H), 0.82-0.74 (m, 9H). |

| Ex | Structure | MW | LC-MS m/z [M + H]+; RT (min) (Method A4) | 1H NMR (500 MHz, DMSO-d6) δ ppm |
|---|---|---|---|---|
| 361 | 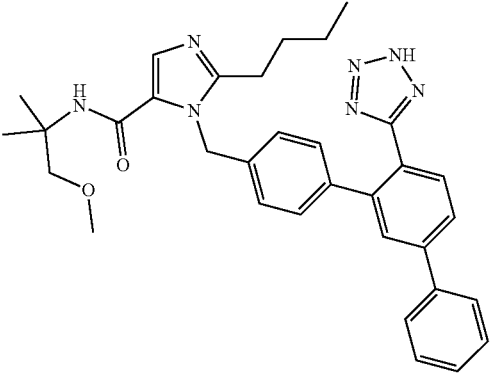 [SMILES: CCCCc1ncc(C(=O)NC(C)(C)COC)n1Cc1ccc(-c2cc(-c3ccccc3)ccc2-c2nn[nH]n2)cc1] | 563.706 | 564.2; 1.823 | 1H NMR (500 MHz, DMSO-d6) δ 7.94-7.75 (m, 3H), 7.70 (d, J = 7.8 Hz, 1H), 7.67 (s, 1H), 7.53-7.45 (m, 4H), 7.45-7.38 (m, 1H), 7.13 (br d, J = 7.7 Hz, 2H), 6.99 (br d, J = 7.9 Hz, 2H), 5.55 (s, 2H), 3.61-3.40 (m, 2H), 3.24-3.14 (m, 3H), 2.58-2.52 (m, 2H), 1.54-1.37 (m, 2H), 1.29-1.20 (m, 8H), 0.80 (br t, J = 7.2 Hz, 3H). |
| 362 | 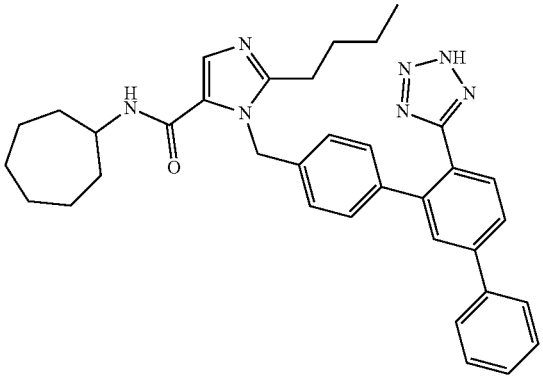 [SMILES: CCCCc1ncc(C(=O)NC2CCCCCC2)n1Cc1ccc(-c2cc(-c3ccccc3)ccc2-c2nn[nH]n2)cc1] | 573.745 | 574.0; 2.001 | 1H NMR (500 MHz, DMSO-d6) δ 8.09 (br s, 1H), 7.86 (br d, J = 8.0 Hz, 1H), 7.80 (br d, J = 7.3 Hz, 2H), 7.77-7.70 (m, 2H), 7.57-7.47 (m, 3H), 7.47-7.40 (m, 1H), 7.21-7.08 (m, J = 7.7 Hz, 2H), 7.02-6.93 (m, J = 7.7 Hz, 2H), 5.61 (br s, 2H), 2.65-2.53 (m, 2H), 1.76 (br s, 2H), 1.61 (br s, 2H), 1.57-1.44 (m, 9H), 1.43-1.33 (m, 2H), 1.24 (br d, J = 7.2 Hz, 2H), 0.80 (br t, J = 7.2 Hz, 3H). |
| 363 | 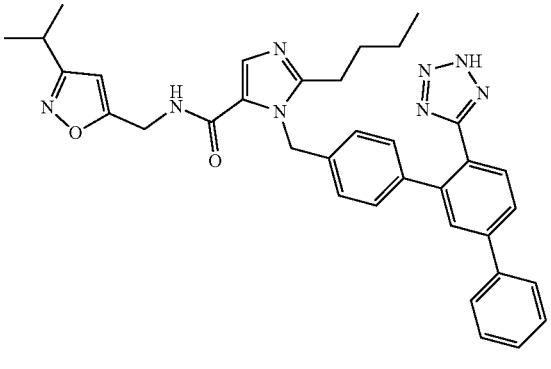 [SMILES: CCCCc1ncc(C(=O)NCc2cc(C(C)C)no2)n1Cc1ccc(-c2cc(-c3ccccc3)ccc2-c2nn[nH]n2)cc1] | 600.727 | 601.0; 1.865 | 1H NMR (500 MHz, DMSO-d6) δ 8.95 (br s, 1H), 7.86 (br d, J = 8.0 Hz, 1H), 7.80 (br d, J = 7.5 Hz, 2H), 7.77-7.71 (m, 2H), 7.65 (s, 1H), 7.51 (t, J = 7.1 Hz, 2H), 7.47-7.39 (m, 1H), 7.22-7.05 (m, J = 7.8 Hz, 2H), 7.02-6.93 (m, J = 7.8 Hz, 2H), 6.22 (br s, 1H), 5.63 (br s, 2H), 4.47 (br d, J = 5.5 Hz, 2H), 3.01-2.82 (m, 1H), 2.59-2.53 (m, 2H), 1.60-1.41 (m, 2H), 1.31-1.18 (m, 2H), 1.14 (br d, J = 6.8 Hz, 6H), 0.80 (br t, J = 7.2 Hz, 3H). |
| 364 | 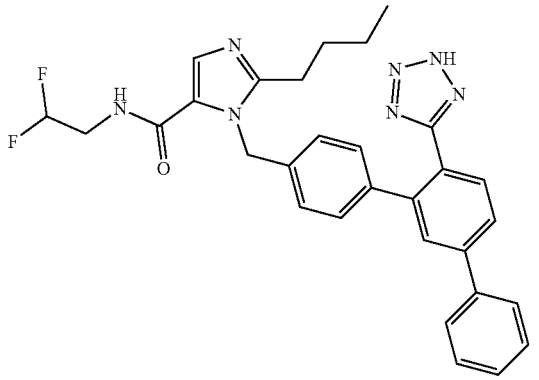 [SMILES: CCCCc1ncc(C(=O)NCC(F)F)n1Cc1ccc(-c2cc(-c3ccccc3)ccc2-c2nn[nH]n2)cc1] | 541.607 | 542.5; 1.713 | 1H NMR (500 MHz, DMSO-d6) δ 8.66 (br s, 1H), 7.94-7.75 (m, 3H), 7.73-7.62 (m, 3H), 7.49 (t, J = 7.5 Hz, 2H), 7.45-7.37 (m, 1H), 7.20-7.07 (m, J = 7.9 Hz, 2H), 6.99-6.90 (m, J = 7.9 Hz, 2H), 6.26-5.80 (m, 1H), 5.61 (s, 2H), 3.80-3.69 (m, 2H), 2.57-2.53 (m, 2H), 1.56-1.46 (m, 2H), 1.30-1.18 (m, 2H), 0.80 (br t, J = 7.2 Hz, 3H). |

-continued

| Ex | Structure | MW | LC-MS m/z [M + H]+; RT (min) (Method A4) | 1H NMR (500 MHz, DMSO-d6) δ ppm |
|---|---|---|---|---|
| 365 | 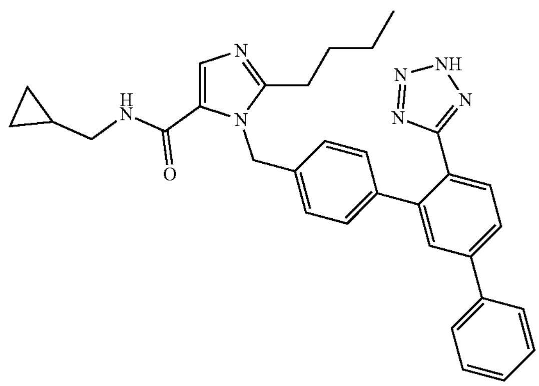 [SMILES: CCCCc1ncc(C(=O)NCC2CC2)n1Cc1ccc(-c2cc(-c3ccccc3)ccc2-c2nn[nH]n2)cc1] | 531.664 | 532.5; 1.777 | 1H NMR (500 MHz, DMSO-d6) δ 8.23 (br s, 1H), 7.78-7.59 (m, 3H), 7.59-7.50 (m, 2H), 7.41-7.30 (m, 3H), 7.30-7.22 (m, 1H), 7.04-6.91 (m, J = 7.9 Hz, 2H), 6.85-6.75 (m, J = 8.0 Hz, 2H), 5.46 (s, 2H), 2.89 (br t, J = 6.2 Hz, 2H), 2.42-2.37 (m, 2H), 1.41-1.26 (m, 2H), 1.13-1.02 (m, 2H), 0.78 (br d, J = 6.8 Hz, 1H), 0.64 (br t, J = 7.3 Hz, 3H), 0.28-0.17 (m, 2H), 0.00 (br d, J = 4.5 Hz, 2H). |
| 366 | 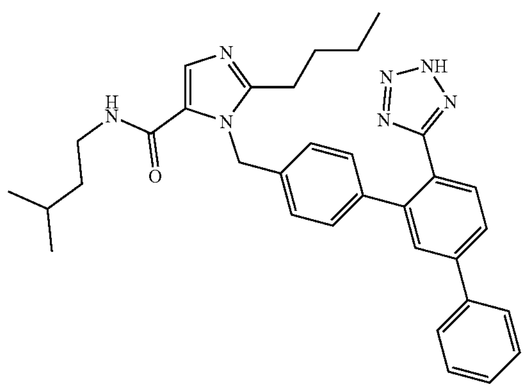 [SMILES: CCCCc1ncc(C(=O)NCCC(C)C)n1Cc1ccc(-c2cc(-c3ccccc3)ccc2-c2nn[nH]n2)cc1] | 547.707 | 548.2; 1.925 | 1H NMR (500 MHz, DMSO-d6) δ 8.24 (br s, 1H), 7.86-7.76 (m, 3H), 7.76-7.68 (m, 2H), 7.55-7.46 (m, 3H), 7.46-7.39 (m, 1H), 7.17-7.09 (m, J = 8.0 Hz, 2H), 7.00-6.92 (m, J = 7.9 Hz, 2H), 5.62 (s, 2H), 3.18 (q, J = 6.5 Hz, 2H), 2.56-2.52 (m, 2H), 1.58-1.44 (m, 3H), 1.34 (q, J = 6.9 Hz, 2H), 1.29-1.18 (m, 2H), 1.00 (d, J = 6.3 Hz, 1H), 0.90-0.77 (m, 9H). |
| 367 | 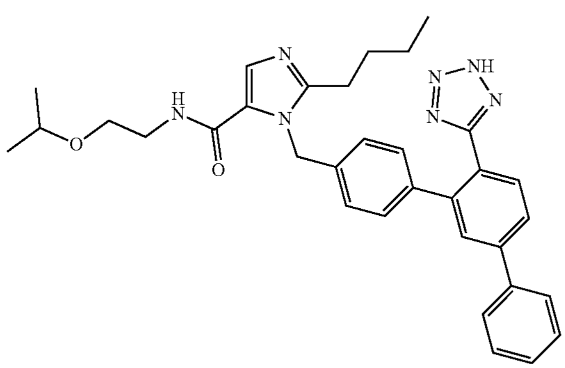 [SMILES: CCCCc1ncc(C(=O)NCCOC(C)C)n1Cc1ccc(-c2cc(-c3ccccc3)ccc2-c2nn[nH]n2)cc1] | 563.706 | 564.2; 1.925 | 1H NMR (500 MHz, DMSO-d6) δ 8.32 (br d, J = 4.8 Hz, 1H), 7.81-7.73 (m, 3H), 7.70 (br d, J = 7.9 Hz, 1H), 7.64 (s, 1H), 7.55-7.46 (m, 3H), 7.45-7.37 (m, 1H), 7.12 (br d, J = 7.7 Hz, 2H), 6.93 (br d, J = 8.0 Hz, 2H), 5.61 (br s, 2H), 3.60-3.46 (m, 1H), 3.44-3.35 (m, 2H), 3.32-3.23 (m, 2H), 2.57-2.55 (m, 2H), 1.56-1.42 (m, 2H), 1.29-1.14 (m, 2H), 1.08-0.97 (m, 6H), 0.79 (br t, J = 7.2 Hz, 3H). |
| 368 | 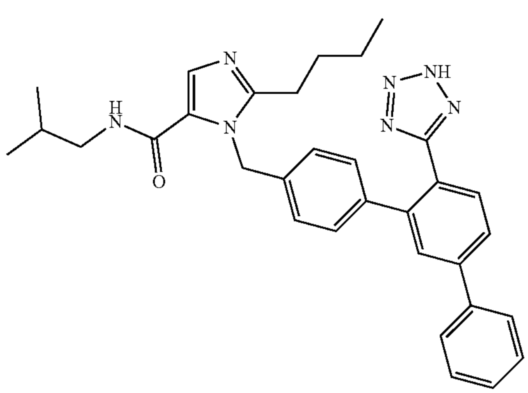 [SMILES: CCCCc1ncc(C(=O)NCC(C)C)n1Cc1ccc(-c2cc(-c3ccccc3)ccc2-c2nn[nH]n2)cc1] | 533.68 | 534.5; 1.826 | 1H NMR (500 MHz, DMSO-d6) δ 8.23 (br s, 1H), 7.78-7.59 (m, 3H), 7.59-7.50 (m, 2H), 7.41-7.30 (m, 3H), 7.30-7.22 (m, 1H), 7.04-6.91 (m, J = 7.9 Hz, 2H), 6.85-6.75 (m, J = 8.0 Hz, 2H), 5.46 (s, 2H), 3.19-3.06 (m, 1H), 2.89 (br t, J = 6.2 Hz, 2H), 2.39 (s, 2H), 1.41-1.26 (m, 2H), 1.13-1.02 (m, 2H), 0.89-0.70 (m, 2H), 0.64 (br t, J = 7.3 Hz, 3H), 0.23 (br d, J = 7.4 Hz, 2H), 0.00 (br d, J = 4.5 Hz, 2H). |

-continued

| Ex | Structure | MW | LC-MS m/z [M + H]+; RT (min) (Method A4) | 1H NMR (500 MHz, DMSO-d6) δ ppm |
|---|---|---|---|---|
| 369 | 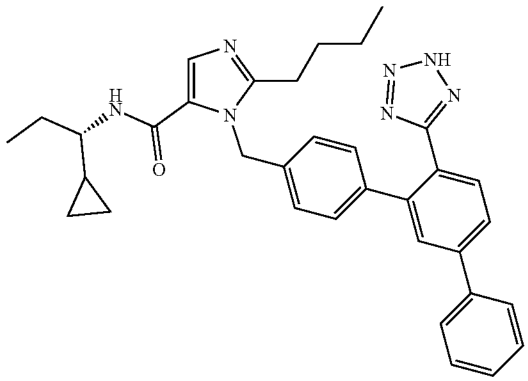 [SMILES: CCCCc1ncc(C(=O)N[C@@H](CC)C2CC2)n1Cc1ccc(-c2cc(-c3ccccc3)ccc2-c2nn[nH]n2)cc1] | 559.718 | 560.5; 1.923 | 1H NMR (500 MHz, DMSO-d6) δ 7.97 (br d, J = 7.7 Hz, 1H), 7.71 (d, J = 8.0 Hz, 1H), 7.68-7.55 (m, 4H), 7.43-7.34 (m, 3H), 7.34-7.26 (m, 1H), 7.05-6.94 (m, J = 7.9 Hz, 2H), 6.90-6.82 (m, J = 8.1 Hz, 2H), 5.46 (s, 2H), 3.16-3.01 (m, 1H), 2.51-2.45 (m, 2H), 1.51-1.31 (m, 4H), 1.19-1.02 (m, 2H), 0.78-0.63 (m, 7H), 0.36-0.23 (m, 1H), 0.15 (br dd, J = 8.0, 4.0 Hz, 1H), 0.09-0.05 (m, 2H). |
| 370 | 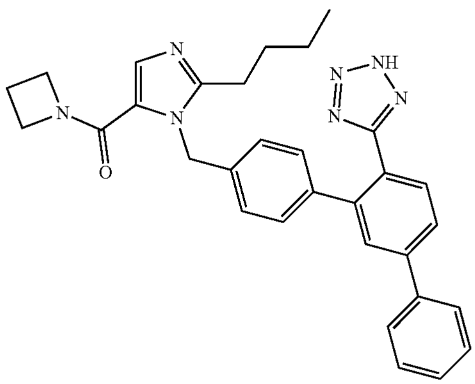 [SMILES: CCCCc1ncc(C(=O)N2CCC2)n1Cc1ccc(-c2cc(-c3ccccc3)ccc2-c2nn[nH]n2)cc1] | 517.637 | 518.5; 1.535 | 1H NMR (500 MHz, DMSO-d6) δ 7.74 (br s, 4H), 7.59 (br s, 1H), 7.48 (br t, J = 7.4 Hz, 2H), 7.44-7.26 (m, 2H), 7.12 (br s, 2H), 6.87 (br s, 2H), 5.67-5.50 (m, 2H), 4.38-4.16 (m, 2H), 4.10-3.92 (m, 2H), 2.57-2.53 (m, 2H), 2.31-2.18 (m, 2H), 1.61-1.40 (m, 2H), 1.37-1.17 (m, 2H), 0.86-0.73 (m, 3H). |
| 371 | 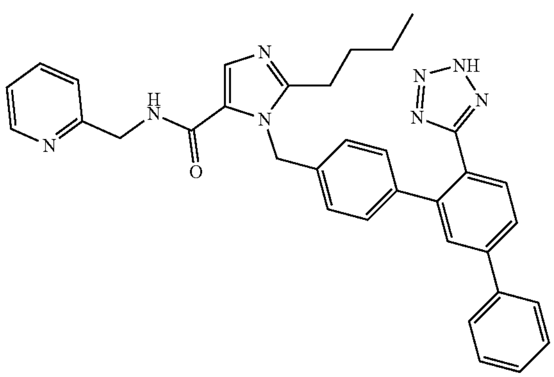 [SMILES: CCCCc1ncc(C(=O)NCc2ccccn2)n1Cc1ccc(-c2cc(-c3ccccc3)ccc2-c2nn[nH]n2)cc1] | 568.685 | 569.5; 1.377 | 1H NMR (500 MHz, DMSO-d6) δ 8.95 (br s, 1H), 8.46 (br s, 1H), 7.80-7.62 (m, 7H), 7.49 (t, J = 7.2 Hz, 2H), 7.45-7.37 (m, 1H), 7.25-7.17 (m, 2H), 7.14 (br d, J = 7.7 Hz, 2H), 6.94 (br d, J = 7.9 Hz, 2H), 5.62 (br s, 2H), 4.47 (br d, J = 5.8 Hz, 2H), 2.59-2.53 (m, 2H), 1.56-1.47 (m, 2H), 1.26 (br d, J = 7.0 Hz, 2H), 0.85-0.76 (m, 3H). |
| 372 | 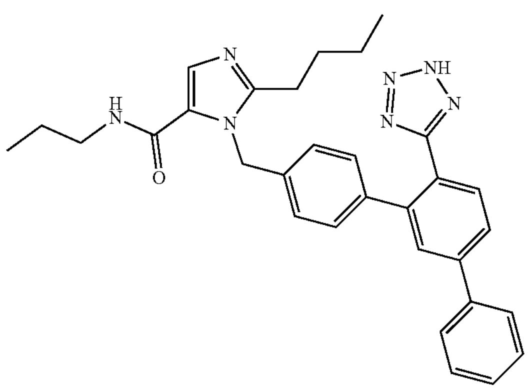 [SMILES: CCCCc1ncc(C(=O)NCCC)n1Cc1ccc(-c2cc(-c3ccccc3)ccc2-c2nn[nH]n2)cc1] | 519.653 | 520.5; 1.656 | 1H NMR (500 MHz, DMSO-d6) δ 8.28 (br s, 1H), 7.79-7.71 (m, 3H), 7.71-7.65 (m, 1H), 7.61 (s, 1H), 7.53-7.46 (m, 3H), 7.44-7.35 (m, 1H), 7.19-7.07 (m, J = 7.8 Hz, 2H), 6.95-6.88 (m, J = 7.9 Hz, 2H), 5.60 (br s, 2H), 3.19-3.05 (m, 2H), 2.57-2.52 (m, 2H), 1.56-1.40 (m, 4H), 1.31-1.17 (m, 2H), 0.87-0.75 (m, 6H). |

| Ex | Structure | MW | LC-MS m/z [M + H]+; RT (min) (Method A4) | 1H NMR (500 MHz, DMSO-d6) δ ppm |
|---|---|---|---|---|
| 373 | 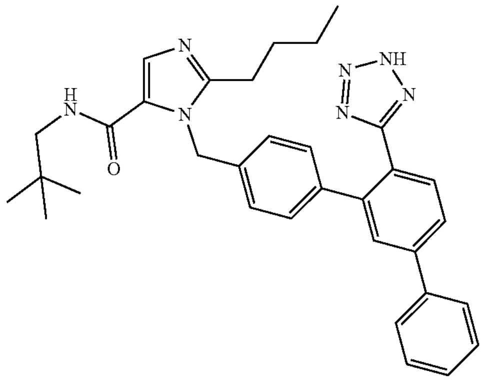 [SMILES: CCCCc1ncc(C(=O)NCC(C)(C)C)n1Cc1ccc(-c2cc(-c3ccccc3)ccc2-c2nn[nH]n2)cc1] | 547.707 | 548.6; 1.806 | 1H NMR (500 MHz, DMSO-d6) δ 8.20 (br s, 1H), 7.75 (br d, J = 7.8 Hz, 3H), 7.68 (br d, J = 8.0 Hz, 1H), 7.60 (br s, 1H), 7.58-7.53 (m, 1H), 7.49 (t, J = 7.6 Hz, 2H), 7.43-7.38 (m, 1H), 7.12 (br d, J = 7.7 Hz, 2H), 6.92 (br d, J = 7.8 Hz, 2H), 5.58 (br s, 2H), 2.99 (br d, J = 6.1 Hz, 2H), 2.58-2.53 (m, 2H), 1.55-1.45 (m, 2H), 1.29-1.20 (m, 2H), 0.85-0.76 (m, 12H). |
| 374 | 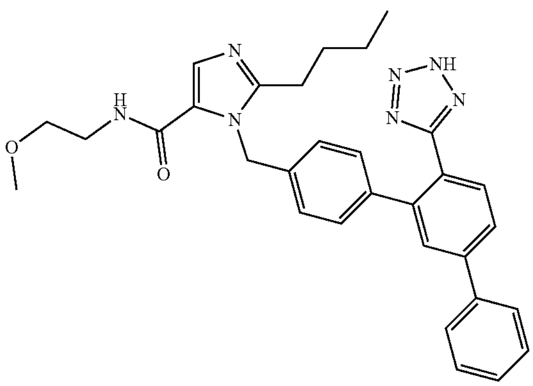 [SMILES: CCCCc1ncc(C(=O)NCCOC)n1Cc1ccc(-c2cc(-c3ccccc3)ccc2-c2nn[nH]n2)cc1] | 535.652 | 536.3; 1.703 | 1H NMR (500 MHz, DMSO-d6) δ 8.35 (br s, 1H), 7.93-7.74 (m, 3H), 7.73-7.64 (m, 2H), 7.57-7.45 (m, 3H), 7.45-7.36 (m, 1H), 7.19-7.05 (m, J = 7.9 Hz, 2H), 6.99-6.90 (m, J = 8.0 Hz, 2H), 5.61 (s, 2H), 3.43-3.24 (m, 4H), 3.21 (s, 3H), 2.57-2.52 (m, 2H), 1.56-1.43 (m, 2H), 1.30-1.14 (m, 2H), 0.78 (t, J = 7.3 Hz, 3H). |
| 375 | 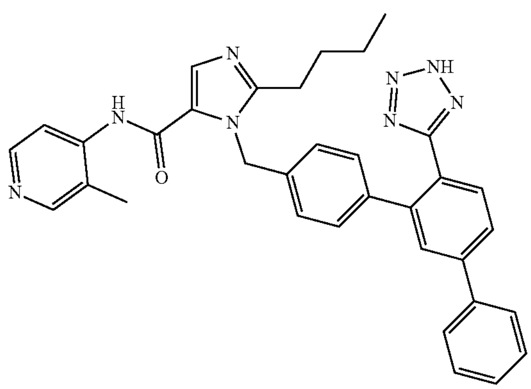 [SMILES: CCCCc1ncc(C(=O)Nc2ccncc2C)n1Cc1ccc(-c2cc(-c3ccccc3)ccc2-c2nn[nH]n2)cc1] | 568.685 | 569.5; 1.519 | 1H NMR (500 MHz, DMSO-d6) δ 8.67 (br s, 1H), 8.60 (br d, J = 5.7 Hz, 1H), 8.27 (br d, J = 6.3 Hz, 1H), 8.20 (s, 1H), 7.87 (br d, J = 7.9 Hz, 1H), 7.83-7.70 (m, 4H), 7.51 (t, J = 7.1 Hz, 2H), 7.47-7.41 (m, 1H), 7.29 (br s, 1H), 7.22-7.14 (m, J = 8.0 Hz, 2H), 7.13-7.04 (m, J = 8.0 Hz, 2H), 5.68 (s, 2H), 2.80-2.68 (m, 2H), 2.48-2.36 (m, 3H), 1.60-1.45 (m, 2H), 1.32-1.14 (m, 2H), 0.82 (br t, J = 7.3 Hz, 3H). |
| 376 | 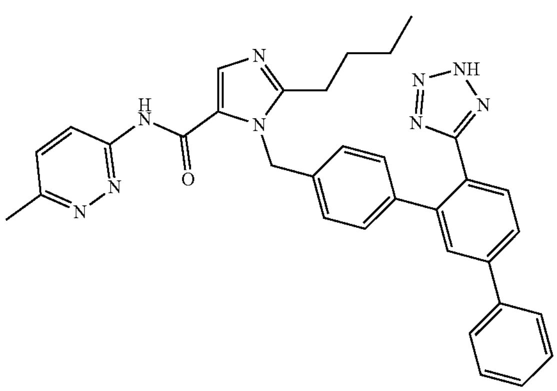 [SMILES: CCCCc1ncc(C(=O)Nc2ccc(C)nn2)n1Cc1ccc(-c2cc(-c3ccccc3)ccc2-c2nn[nH]n2)cc1] | 569.673 | 570.5; 1.644 | 1H NMR (500 MHz, DMSO-d6) δ 8.37 (s, 1H), 8.16 (d, J = 8.9 Hz, 1H), 7.87 (br d, J = 8.2 Hz, 1H), 7.83-7.71 (m, 5H), 7.60 (d, J = 9.2 Hz, 1H), 7.51 (t, J = 6.9 Hz, 2H), 7.45 (br t, J = 7.3 Hz, 1H), 7.22-7.15 (m, 2H), 7.14-7.02 (m, 2H), 5.76 (s, 2H), 2.84-2.66 (m, 2H), 2.59 (s, 3H), 1.60-1.46 (m, 2H), 1.36-1.15 (m, 2H), 0.82 (br t, J = 7.2 Hz, 3H). |

-continued

| Ex | Structure | MW | LC-MS m/z [M + H]+; RT (min) (Method A4) | 1H NMR (500 MHz, DMSO-d6) δ ppm |
|---|---|---|---|---|
| 377 | 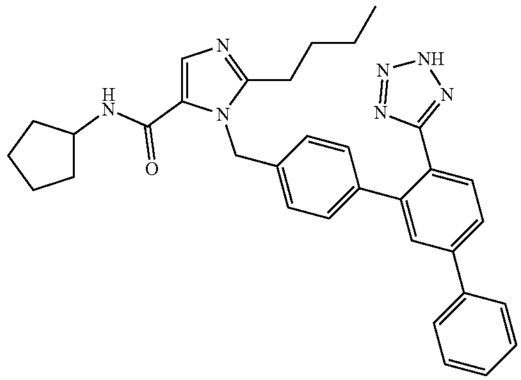 [SMILES: CCCCc1ncc(C(=O)NC2CCCC2)n1Cc1ccc(-c2cc(-c3ccccc3)ccc2-c2nn[nH]n2)cc1] | 545.691 | 546.4; 1.860 | 1H NMR (500 MHz, DMSO-d6) δ 8.14 (br d, J = 7.1 Hz, 1H), 7.87-7.76 (m, 3H), 7.76-7.68 (m, 2H), 7.58-7.46 (m, 3H), 7.46-7.39 (m, 1H), 7.18-7.10 (m, J = 7.9 Hz, 2H), 7.00-6.94 (m, J = 8.0 Hz, 2H), 5.60 (s, 2H), 4.11 (br d, J = 7.0 Hz, 1H), 2.55 (s, 2H), 1.91-1.75 (m, 2H), 1.70-1.57 (m, 2H), 1.55-1.39 (m, 6H), 1.31-1.15 (m, 2H), 0.79 (t, J = 7.3 Hz, 3H). |
| 378 | 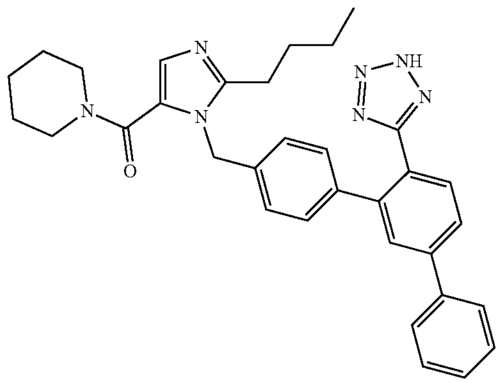 [SMILES: CCCCc1ncc(C(=O)N2CCCCC2)n1Cc1ccc(-c2cc(-c3ccccc3)ccc2-c2nn[nH]n2)cc1] | 545.691 | 546.1; 1.643 | 1H NMR (500 MHz, DMSO-d6) δ 7.80-7.63 (m, 5H), 7.57 (s, 1H), 7.49 (br t, J = 7.6 Hz, 2H), 7.45-7.36 (m, 1H), 7.15 (br d, J = 7.9 Hz, 2H), 7.04 (s, 1H), 6.93 (br d, J = 8.1 Hz, 2H), 5.29 (s, 2H), 3.57-3.36 (m, 3H), 2.66 (br t, J = 7.7 Hz, 2H), 1.63-1.53 (m, 2H), 1.49 (br s, 2H), 1.38-1.16 (m, 6H), 0.85 (t, J = 7.3 Hz, 3H). |
| 379 | 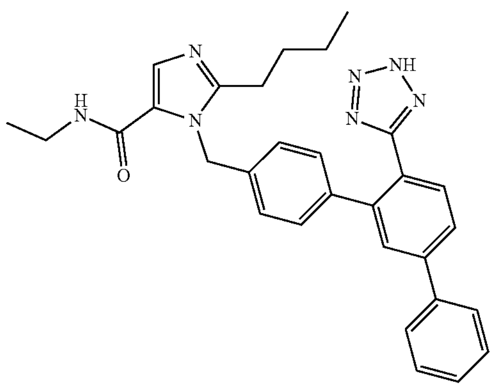 [SMILES: CCCCc1ncc(C(=O)NCC)n1Cc1ccc(-c2cc(-c3ccccc3)ccc2-c2nn[nH]n2)cc1] | 505.626 | 506.1; 1.587 | 1H NMR (500 MHz, DMSO-d6) δ 8.29 (br s, 1H), 7.83-7.74 (m, 3H), 7.70 (d, J = 8.0 Hz, 1H), 7.68 (s, 1H), 7.55-7.46 (m, 3H), 7.45-7.37 (m, 1H), 7.19-7.08 (m, J = 7.9 Hz, 2H), 6.98-6.90 (m, J = 8.0 Hz, 2H), 5.62 (s, 2H), 3.65 (br s, 2H), 3.24-3.13 (m, 2H), 1.55-1.43 (m, 2H), 1.31-1.16 (m, 2H), 1.06 (t, J = 7.2 Hz, 3H), 0.79 (t, J = 7.3 Hz, 3H). |
| 380 | 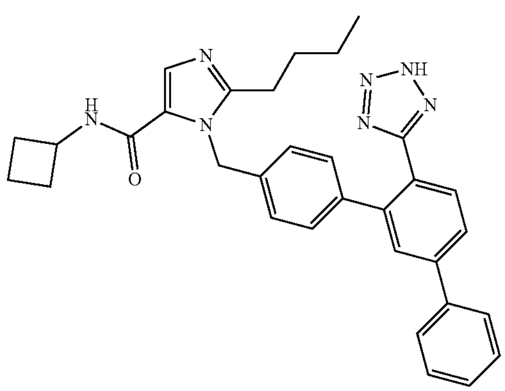 [SMILES: CCCCc1ncc(C(=O)NC2CCC2)n1Cc1ccc(-c2cc(-c3ccccc3)ccc2-c2nn[nH]n2)cc1] | 531.664 | 532.2; 1.701 | 1H NMR (500 MHz, DMSO-d6) δ 8.45 (br d, J = 7.2 Hz, 1H), 7.84-7.75 (m, 3H), 7.75-7.67 (m, 2H), 7.59 (s, 1H), 7.50 (t, J = 7.6 Hz, 2H), 7.46-7.38 (m, 1H), 7.18-7.09 (m, J = 7.8 Hz, 2H), 6.98-6.89 (m, J = 8.0 Hz, 2H), 5.60 (s, 2H), 4.31 (br d, J = 8.1 Hz, 1H), 2.57-2.53 (m, 2H), 2.22-2.10 (m, 2H), 1.99 (br t, J = 9.7 Hz, 2H), 1.69-1.55 (m, 2H), 1.55-1.43 (m, 2H), 1.30-1.15 (m, 2H), 0.79 (t, J = 7.3 Hz, 3H). |

Example 381: 1-((6'-(2H-tetrazol-5-yl)-[1,1':3',1"-terphenyl]-4-yl)methyl)-2-butyl-4-chloro-N,N-dimethyl-1H-imidazole-5-carboxamide (Ex. 381)

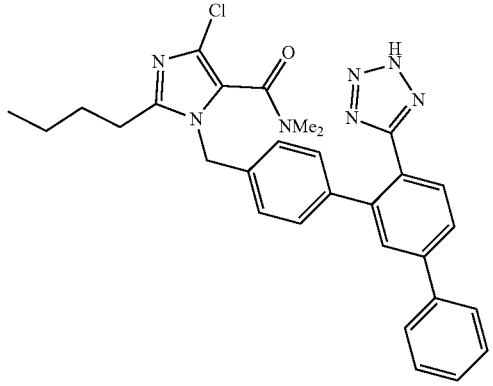

Example 381 was synthesized from Example 384 and dimethyl amine using a similar procedure as was used for the synthesis of Example 346, however, T3P was used in place of HATU as the coupling reagent. LC-MS (Method A4): 1.976 min, [M+H]$^+$=540.2; $^1$H NMR (500 MHz, DMSO-d$_6$) δ 7.87-7.69 (m, 4H), 7.64 (s, 1H), 7.54-7.46 (m, 2H), 7.45-7.37 (m, 1H), 7.18 (d, J=7.9 Hz, 2H), 6.97 (d, J=7.9 Hz, 2H), 5.15 (br. s., 2H), 2.81 (s, 3H), 2.71-2.67 (m, 2H), 2.65 (br. s., 3H), 1.67-1.54 (m, 2H), 1.40-1.26 (m, 2H), 0.87 (t, J=7.3 Hz, 3H).

Example 382: 1-((6'-(2H-tetrazol-5-yl)-[1,1':3',1"-terphenyl]-4-yl)methyl)-2-butyl-N-methyl-1H-imidazole-5-carboxamide (Ex.382)

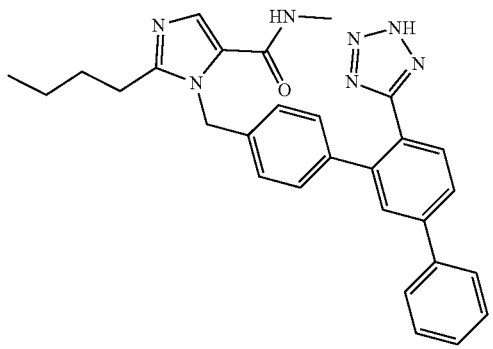

Example 382 was synthesized from 2M methanamine in MeOH and Example 345 using the same procedure described for Example 381 to give the title compound (Example 382, 2.9 mg, 5.90 μmol, 7.43% yield). MS (ESI) m/z (M+H)$^+$=492.1. $^1$H NMR (500 MHz, DMSO-d$_6$) δ 8.21 (d, J=4.6 Hz, 1H), 7.81-7.74 (m, 3H), 7.73-7.68 (m, 1H), 7.65 (s, 1H), 7.55-7.45 (m, 3H), 7.41 (d, J=7.3 Hz, 1H), 7.15 (d, J=7.9 Hz, 2H), 6.91 (d, J=7.9 Hz, 2H), 5.63 (s, 2H), 2.70 (d, J=4.6 Hz, 3H), 2.53 (br. s., 2H), 1.59-1.46 (m, 2H), 1.31-1.18 (m, 2H), 0.81 (t, J=7.3 Hz, 3H). LC-MS retention time (Method A4): 1.536 min.

Example 383: 1-((6'-(2H-tetrazol-5-yl)-[1,1':3',1"-terphenyl]-4-yl)methyl)-2-butyl-N,N-dimethyl-1H-imidazole-5-carboxamide (Ex. 383)

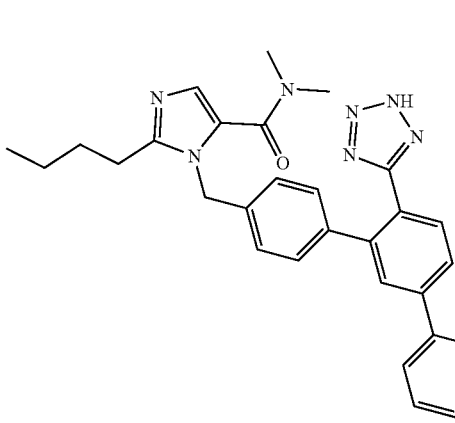

Example 383 was synthesize from 2M dimethylamine in MeOH and Example 345 using the same procedure described for Example 381 to give the title compound (Example 383, 6.2 mg, 0.012 mmol, 15.44% yield). MS (ESI) m/z (M+H)$^+$=506.1. $^1$H NMR (500 MHz, DMSO-d$_6$) δ 7.78 (d, J=7.3 Hz, 3H), 7.72 (d, J=7.9 Hz, 1H), 7.68 (s, 1H), 7.60 (s, 1H), 7.53-7.46 (m, 2H), 7.44-7.36 (m, 1H), 7.20 (d, J=7.9 Hz, 2H), 7.10 (d, J=7.9 Hz, 2H), 5.19 (s, 2H), 2.59 (t, J=7.6 Hz, 2H), 1.61-1.48 (m, 2H), 1.36-1.26 (m, 2H), 0.84 (t, J=7.3 Hz, 3H). LC-MS retention time (Method A4): 1.541 min.

Example 384: 1-((6'-(2H-tetrazol-5-yl)-[1,1':3',1"-terphenyl]-4-yl)methyl)-2-butyl-4-chloro-1H-imidazole-5-carboxylic acid (Ex. 384)

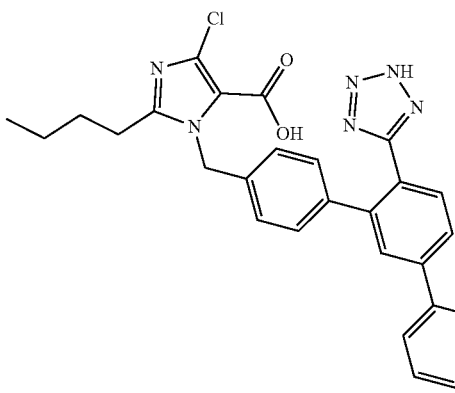

Intermediate 384a: 4'-((2-butyl-4-chloro-5-formyl-1H-imidazol-1-yl)methyl)-5-chloro-[1,1'-biphenyl]-2-carbonitrile

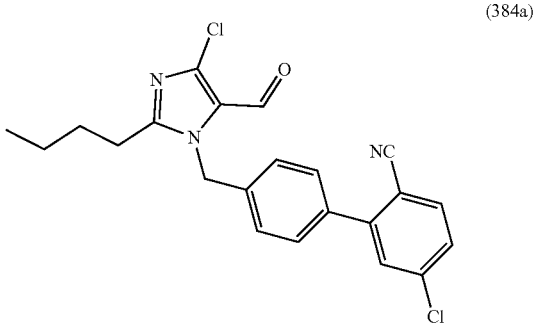 [SMILES: CCCCc1nc(Cl)c(C=O)n1Cc1ccc(-c2cc(Cl)ccc2C#N)cc1]

(384a)

To a microwave vial containing 2-butyl-4-chloro-1-(4-(4,4,5,5-tetramethyl-1,3,2-dioxaborolan-2-yl)benzyl)-1H-imidazole-5-carbaldehyde (035a, 1.4 g, 3.48 mmol), 4-chloro-2-iodobenzonitrile (1.007 g, 3.82 mmol) and 2 M $K_3PO_4$ (2 M aq) (3.48 ml, 6.95 mmol) was added 4:1 toluene/ethanol (11.59 ml) followed by PdCl2(dppf) (0.382 g, 0.521 mmol). The reaction mixture was sparged with $N_2$ for 2 min before being sealed and heated at 120° C. for 30 min in the microwave. The reaction mixture was concentrated onto celite and purified by ISCO (0-100% EtOAc/Hexanes) to afford the title compound (384a, 1.1 g, 2.67 mmol, 77% yield). LC-MS: MS (ESI) m/z: 412.00 (M+H)$^+$. $^1$H NMR (500 MHz, CDCl$_3$) δ 9.80 (s, 1H), 7.72 (d, J=8.5 Hz, 1H), 7.54 (d, J=8.3 Hz, 2H), 7.51 (d, J=1.9 Hz, 1H), 7.49-7.42 (m, 1H), 7.21 (d, J=8.3 Hz, 2H), 5.64 (s, 2H), 2.69 (d, J=8.0 Hz, 2H), 1.81-1.67 (m, 2H), 1.47-1.35 (m, 2H), 0.93 (t, J=7.3 Hz, 3H).

Intermediate 384b: 2-butyl-4-chloro-1-((5'-chloro-2'-cyano-[1,1'-biphenyl]-4-yl)methyl)-1H-imidazole-5-carboxylic acid

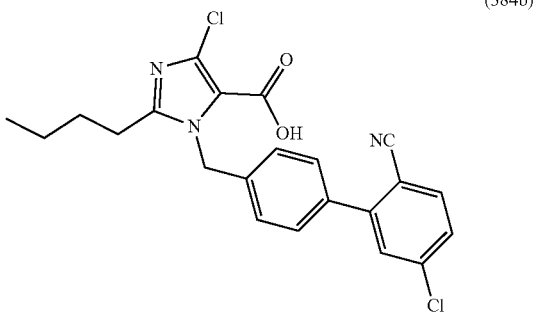

(384b)

4'-((2-butyl-4-chloro-5-formyl-1H-imidazol-1-yl)methyl)-5-chloro-[1,1'-biphenyl]-2-carbonitrile (384a, 4.37 g, 10.6 mmol) was dissolved in H$_2$O (20 mL)/1-butanol (20 mL). The reaction mixture was cooled to 0° C. 2M 2-methylbut-2-ene in THF (15.90 mL, 31.8 mmol) was added to the reaction mixture followed by sodium dihydrogen phosphate (2.54 g, 21.20 mmol) and then sodium chlorite (1.917 g, 21.20 mmol) at 0 C. The reaction mixture was allowed to warm to RT and stir at RT for 4 days. The reaction mixture was then quenched with 10% aq. sodium sulfite (53.4 g, 42.4 mmol) at 0° C. and then was allowed to stir for 30 min at RT. The reaction mixture was then diluted with EtOAc and H$_2$O. The aq. phase was washed (3×) with EtOAc. The combined organic phases were washed with brine, dried with sodium sulfate, filtered and concentrated to yield the title compound 2-butyl-4-chloro-1-((5'-chloro-2'-cyano-[1,1'-biphenyl]-4-yl)methyl)-1H-imidazole-5-carboxylic acid (384b). The product was brought forward without further purification. LC-MS (Method A2): 0.96 min, [M+H]$^+$=428.0.

Intermediate 384c: 2-butyl-4-chloro-1-((5'-chloro-2'-(2H-tetrazol-5-yl)-[1,1'-biphenyl]-4-yl)methyl)-1H-imidazole-5-carboxylic acid

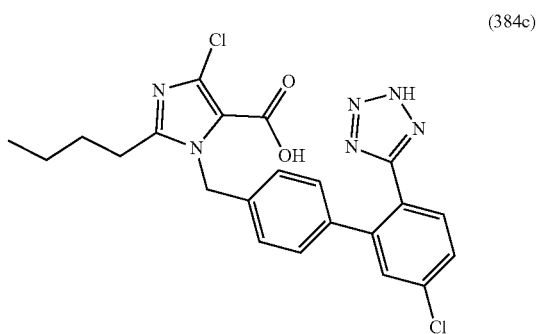 [SMILES: CCCCc1nc(Cl)c(C(=O)O)n1Cc1ccc(-c2cc(Cl)ccc2-c2nn[nH]n2)cc1]

(384c)

To a pressure-rate 40 mL vial containing 2-butyl-4-chloro-1-((5'-chloro-2'-cyano-[1,1'-biphenyl]-4-yl)methyl)-1H-imidazole-5-carboxylic acid (384b, 0.600 g, 1.401 mmol) was added dibutyltin oxide (0.349 g, 1.401 mmol) and toluene (20.01 ml) followed by TMS-N$_3$ (0.930 ml, 7.00 mmol). The reaction mixture was sealed and heated at 100° C. behind a blast shield overnight. The reaction mixture was diluted with hexanes and the solid was filtered off to yield the title compound (384c). The product was brought forward without further purification. LC-MS: MS (ESI) m/z: 471.0 (M+H)$^+$. $^1$H NMR (500 MHz, DMSO-d$_6$) δ 7.58 (d, J=8.2 Hz, 1H), 7.42 (dd, J=8.2, 2.1 Hz, 1H), 7.36-7.24 (m, 1H), 7.07 (br d, J=8.2 Hz, 2H), 6.88 (br d, J=7.9 Hz, 2H), 5.66 (br s, 2H), 2.89 (br d, J=7.3 Hz, 2H), 1.56-1.39 (m, J=7.5, 7.5 Hz, 2H), 1.32-1.19 (m, 2H), 0.80 (t, J=7.5 Hz, 3H).

Intermediate 384d: 2-butyl-4-chloro-1-((5'-chloro-2'-(2H-tetrazol-5-yl)-[1,1'-biphenyl]-4-yl)methyl)-1H-imidazole-5-carboxylic acid

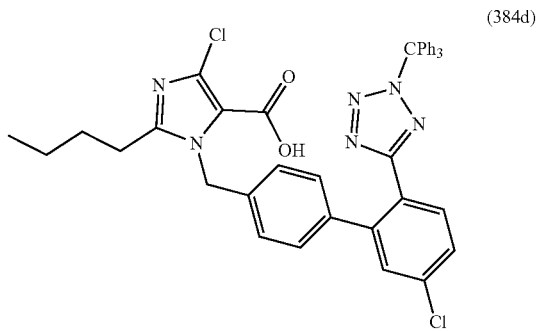

(384d)

2-butyl-4-chloro-1-((5'-chloro-2'-(2H-tetrazol-5-yl)-[1,1'-biphenyl]-4-yl)methyl)-1H-imidazole-5-carboxylic acid (384c, 2.46 g, 5.22 mmol) was dissolved in THF (52.2 ml). TEA (2.182 ml, 15.66 mmol) was added followed by trityl-$C_1$ (2.182 g, 7.83 mmol). The reaction mixture was allowed to stir at RT for 2h. 1M LiOH (15.66 ml, 15.66 mmol) was then added and the reaction mixture was allowed to stir for 20 min at RT. The reaction mixture was then concentrated onto celite and purified by ISCO (0-20% MeOH/DCM) to afford the title compound (384d, 1.88 g, 2.63 mmol, 50.5% yield). LC-MS: MS (ESI) m/z: 713.3 (M+H)$^+$. $^1$H NMR (500 MHz, CDCl$_3$) δ 7.98-7.84 (m, 1H), 7.56-7.31 (m, 10H), 7.12-7.07 (m, 3H), 6.93 (d, J=8.0 Hz, 6H), 6.80 (d, J=8.3 Hz, 2H), 5.46 (s, 2H), 2.55 (t, J=7.7 Hz, 2H), 1.78-1.67 (m, 2H), 1.36-1.23 (m, 2H), 0.96-0.81 (m, 3H).

Intermediate 384e: lithium 2-butyl-4-chloro-1-((5'-chloro-2'-(2-trityl-2H-tetrazol-5-yl)-[1,1'-biphenyl]-4-yl)methyl)-1H-imidazole-5-carboxylate

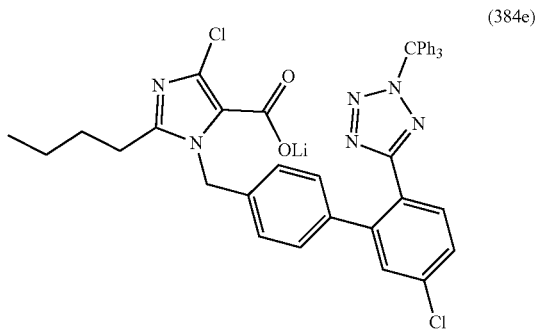

(384e)

2-butyl-4-chloro-1-((5'-chloro-2'-(2-trityl-2H-tetrazol-5-yl)-[,1'-biphenyl]-4-yl)methyl)-1H-imidazole-5-carboxylic acid (384d, 1.88 g, 2.63 mmol) was dissolved in THF (15 mL). IM LiOH (2.90 mL, 2.90 mmol) was added and the reaction mixture was allowed to stir at RT for 1 h. The reaction mixture was then concentrated and azeotroped with toluene (3×) to afford the title compound (384e). The product was brought forward without further purification. LC-MS (Method A2): 1.20 min, [M+H]$^+$=713.2.

Example 384: 1-((6'-(2H-tetrazol-5-yl)-[1,1':3',1''-terphenyl]-4-yl)methyl)-2-butyl-4-chloro-1H-imidazole-5-carboxylic acid To a pressure-rated vial containing lithium 2-butyl-4-chloro-1-((5'-chloro-2'-(2-trityl-2H-tetrazol-5-yl)-[1,1'-biphenyl]-4-yl)methyl)-1H-imidazole-5-carboxylate (384e, 71 mg, 0.099 mmol), 2nd generation xphos precatalyst (15.53 mg, 0.020 mmol) and phenylboronic acid (48 mg, 0.40 mmol) was added dioxane (1000 µl) followed by 2 M K$_3$PO$_4$ (2 M aq) (99 µl, 0.197 mmol). The reaction mixture was sparged with N$_2$ for 2 min before being sealed and heated at 65° C. for 2 h. The reaction mixture was diluted with EtOAc and filtered through celite. The filtrate was concentrated and the crude residue was dissolved in DCM (4 mL). TFA (7.60 µl, 0.099 mmol) was added followed by triethylsilane (15.76 µl, 0.099 mmol). The reaction mixture was allowed to stir at RT for 30 min. The reaction mixture was then concentrated, dissolved in DMF, filtered and purified via preparative LC-MS (Column: XBridge C18, 19×200 mm, 5-µm particles; Mobile Phase A: 5:95 ACN: H$_2$O with 0.1% trifluoroacetic acid; Mobile Phase B: 95:5 ACN: H$_2$O with 0.1% trifluoroacetic acid; Gradient: 30-70% B over 20 min, then a 5-minute hold at 100% B; Flow: 20 mL/min) to afford the title compound (Example 384, 14.5 mg, 0.028 mmol, 28.6% yield).). LC-MS (Method A4): 1.989 min, [M+H]$^+$=513.2; $^1$H NMR (500 MHz, DMSO-d$_6$) δ 7.86 (d, J=7.9 Hz, 1H), 7.81 (d, J=7.6 Hz, 2H), 7.75 (d, J=5.8 Hz, 2H), 7.55-7.48 (m, 2H), 7.44 (d, J=7.3 Hz, 1H), 7.19 (d, J=7.9 Hz, 2H), 6.99 (d, J=7.9 Hz, 2H), 5.61 (s, 2H), 2.59 (t, J=7.6 Hz, 2H), 1.53 (t, J=7.3 Hz, 2H), 1.36-1.19 (m, 2H), 0.82 (t, J=7.2 Hz, 3H).

The following examples have been similarly prepared from Intermediate 384e and the appropriate boronic acid or pinacol boronate as described above for Example 384.

| Ex | Structure | MW | LC-MS m/z [M + H]$^+$; RT (Method A4) | $^1$H NMR (500 MHz, DMSO-d$_6$) δ ppm |
|---|---|---|---|---|
| 385 | 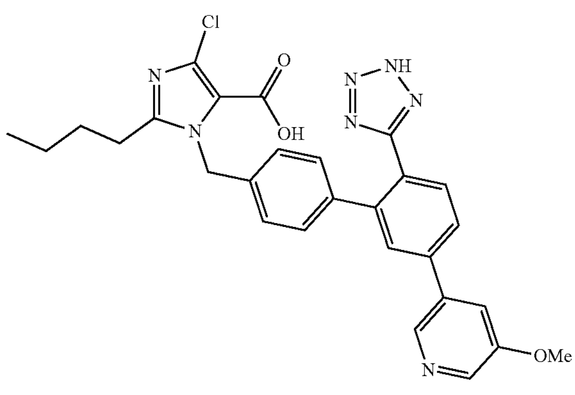 [SMILES: CCCCc1nc(Cl)c(C(=O)O)n1Cc1ccc(-c2cc(-c3cncc(OC)c3)ccc2-c2nn[nH]n2)cc1] | 543.18 | 544.1; 1.285 min | $^1$H NMR (500 MHz, DMSO-d$_6$) δ 8.60 (s, 1H), 8.33 (br d, J = 2.4 Hz, 1H), 7.93 (br d, J = 7.9 Hz, 1H), 7.84 (s, 1H), 7.81-7.73 (m, 2H), 7.27-7.11 (m, J = 7.9 Hz, 2H), 7.04-6.94 (m, J = 7.9 Hz, 2H), 5.60 (s, 2H), 3.92 (s, 3H), 2.69-2.57 (m, 2H), 1.59-1.44 (m, 2H), 1.33-1.15 (m, 2H), 0.81 (br t, J = 7.2 Hz, 3H). |

| Ex | Structure | MW | LC-MS m/z [M + H]+; RT (Method A4) | 1H NMR (500 MHz, DMSO-d6) δ ppm |
|---|---|---|---|---|
| 386 | 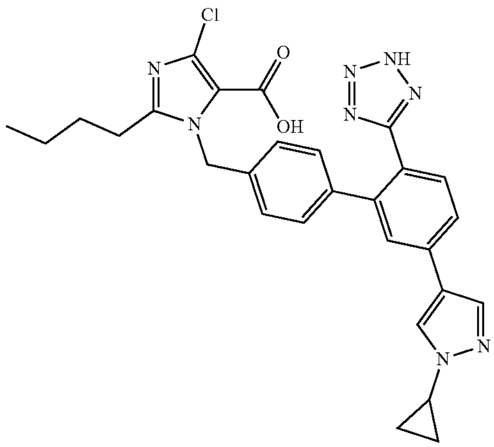 [SMILES: CCCCc1nc(Cl)c(C(=O)O)n1Cc1ccc(-c2cc(-c3cnn(C4CC4)c3)ccc2-c2nn[nH]n2)cc1] | 542.19 | 543.5; 1.562 min | 1H NMR (500 MHz, DMSO-d6) δ 8.32 (s, 1H), 7.94 (s, 1H), 7.66 (br d, J = 8.2 Hz, 1H), 7.61-7.51 (m, 2H), 7.10 (br d, J = 8.2 Hz, 2H), 6.91 (br d, J = 7.9 Hz, 2H), 5.58 (br s, 2H), 3.88-3.67 (m, 3H), 1.55-1.45 (m, 2H), 1.35-1.14 (m, 2H), 1.09-1.02 (m, 2H), 1.02-0.94 (m, 2H), 0.80 (t, J = 7.3 Hz, 3H). |
| 387 | 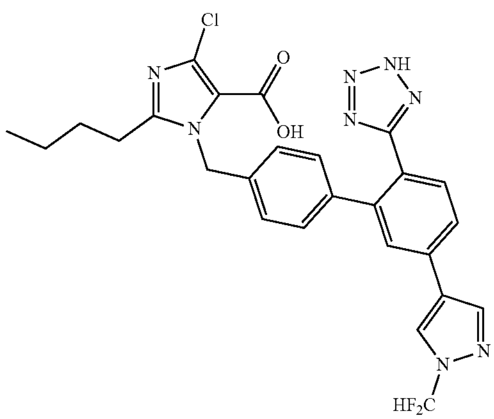 | 552.61 | 553.4; 1.592 min | 1H NMR (500 MHz, DMSO-d6) δ 8.77 (s, 1H), 8.33 (s, 1H), 7.78-7.69 (m, 2H), 7.68-7.63 (m, 1H), 7.59 (d, J = 7.9 Hz, 1H), 7.11 (br d, J = 7.9 Hz, 2H), 6.90 (br d, J = 7.9 Hz, 2H), 5.59 (br s, 2H), 2.59-2.54 (m, 2H), 1.60-1.42 (m, 2H), 1.30-1.20 (m, 2H), 0.80 (t, J = 7.3 Hz, 3H). |
| 388 | 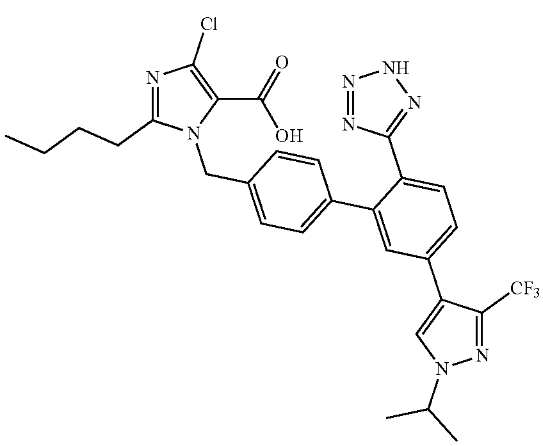 [SMILES: CCCCc1nc(Cl)c(C(=O)O)n1Cc1ccc(-c2cc(-c3cn(C(C)C)nc3C(F)(F)F)ccc2-c2nn[nH]n2)cc1] | 612.198 | 613.2; 2.089 min | 1H NMR (500 MHz, DMSO-d6) δ 8.45 (br s, 1H), 7.72 (d, J = 7.9 Hz, 1H), 7.60 (br d, J = 8.2 Hz, 1H), 7.55 (s, 1H), 7.11 (br d, J = 7.9 Hz, 2H), 6.97 (br d, J = 8.0 Hz, 2H), 5.59 (s, 2H), 4.71-4.53 (m, 1H), 2.60-2.56 (m, 2H), 1.53-1.44 (m, J = 6.6 Hz, 8H), 1.32-1.14 (m, 2H), 0.79 (br t, J = 7.3 Hz, 3H). |

| Ex | Structure | MW | LC-MS m/z [M + H]+; RT (Method A4) | 1H NMR (500 MHz, DMSO-d6) δ ppm |
|---|---|---|---|---|
| 389 | 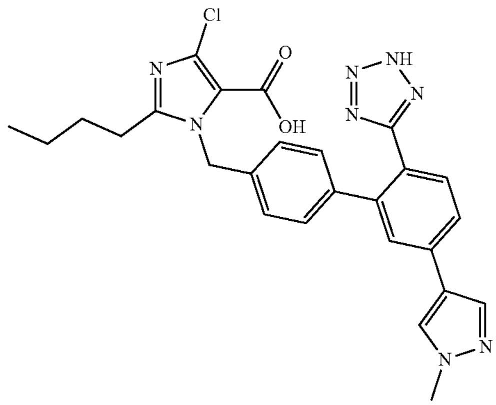 [SMILES: CCCCc1nc(Cl)c(C(=O)O)n1Cc1ccc(-c2cc(-c3cnn(C)c3)ccc2-c2nn[nH]n2)cc1] | 516.179 | 517.3; 1.430 min | 1H NMR (500 MHz, DMSO-d6) δ 8.26 (s, 1H), 7.97 (s, 1H), 7.66 (br d, J = 8.2 Hz, 1H), 7.62-7.55 (m, 2H), 7.18-7.07 (m, J = 7.9 Hz, 2H), 6.99-6.87 (m, J = 7.9 Hz, 2H), 5.60 (br s, 2H), 3.90-3.85 (m, 3H), 2.61-2.53 (m, 2H), 1.58-1.49 (m, 2H), 1.32-1.14 (m, 2H), 0.83 (br t, J = 7.2 Hz, 3H). |
| 390 | 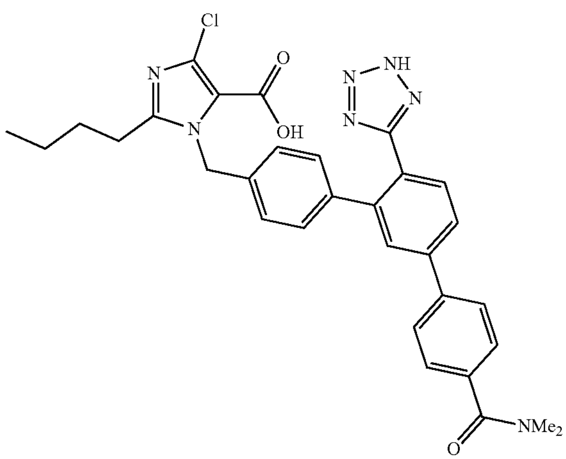 [SMILES: CCCCc1nc(Cl)c(C(=O)O)n1Cc1ccc(-c2cc(-c3ccc(C(=O)N(C)C)cc3)ccc2-c2nn[nH]n2)cc1] | 583.210 | 584.1; 1.574 min | . 1H NMR (500 MHz, DMSO-d6) δ 7.81 (d, J = 8.2 Hz, 2H), 7.75-7.70 (m, 1H), 7.70-7.66 (m, 1H), 7.59 (s, 1H), 7.49 (d, J = 8.1 Hz, 2H), 7.14 (d, J = 7.9 Hz, 2H), 6.90 (d, J = 8.0 Hz, 2H), 5.63 (br. s., 2H), 3.00 (br. s., 3H), 2.96 (br. s., 3H), 2.53-2.52 (m, 2H), 1.56-1.41 (m, 2H), 1.30-1.19 (m, 2H), 0.80 (t, J = 7.3 Hz, 3H). |
| 391 | 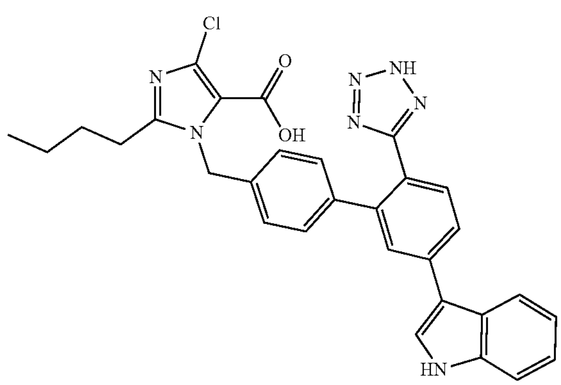 [SMILES: CCCCc1nc(Cl)c(C(=O)O)n1Cc1ccc(-c2cc(-c3c[nH]c4ccccc34)ccc2-c2nn[nH]n2)cc1] | 551.184 | 552.3; 1.7899 min | 1H NMR (500 MHz, DMSO-d6) δ 11.36 (br s, 1H), 7.91 (d, J = 7.8 Hz, 1H), 7.85-7.76 (m, 2H), 7.73-7.63 (m, 2H), 7.48 (d, J = 8.1 Hz, 1H), 7.26-7.10 (m, 4H), 6.97 (d, J = 8.1 Hz, 2H), 5.62 (s, 2H), 2.60-2.56 (m, 2H), 1.53 (br t, J = 7.4 Hz, 2H), 1.33-1.15 (m, 2H), 0.82 (t, J = 7.3 Hz, 3H). |

549

Example 392: 1-((5'-(1H-indol-4-yl)-2'-(2H-tetrazol-5-yl)-1,1'-biphenyll-4-yl)methyl)-2-butyl-4-chloro-1H-imidazole-5-carboxyimc acid (Ex. 392)

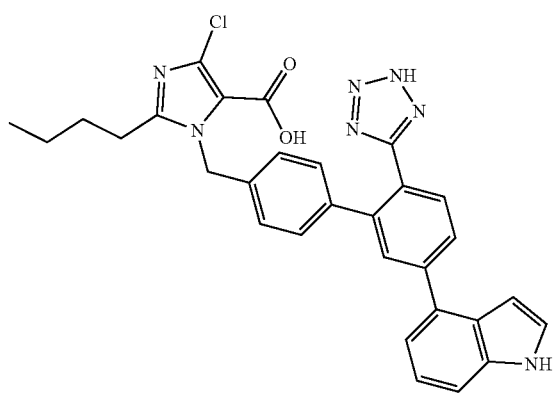

Example 392 was prepared in similar manner as Example 384, however, only 10 equiv. of TFA was used and MeOH was used as the solvent in place of DCM. LC-MS (Method A4): 1.757 min, [M+H]$^+$=552.1; $^1$H NMR (500 MHz, DMSO-d$_6$) δ 11.36 (br s, 1H), 7.88 (br d, J=7.9 Hz, 1H), 7.82-7.73 (m, 2H), 7.54-7.41 (m, 2H), 7.28-7.15 (m, 4H), 7.09-6.93 (m, 2H), 6.64 (br s, 1H), 5.61 (s, 2H), 3.18 (s, 1H), 2.59 (s, 2H), 1.54-1.44 (m, 2H), 1.34-1.14 (m, J=7.3 Hz, 2H), 0.80 (t, J=7.3 Hz, 3H).

Example 393: 1-((6'-(2H-tetrazol-5-yl)-[1,1':3',1''-terphenyl]-4-yl)methyl)-2-butyl-4-chloro-1H-imidazole-5-carboxamide (Ex. 393)

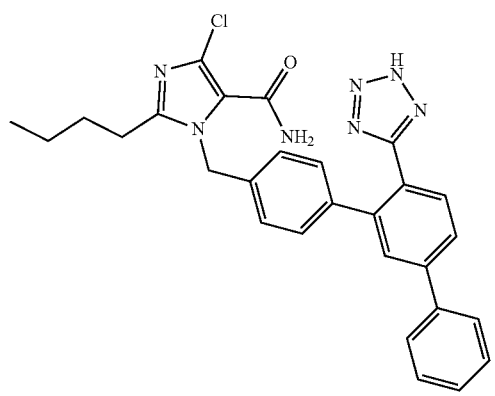

1-((6'-(2H-tetrazol-5-yl)-[1,1':3',1''-terphenyl]-4-yl) methyl)-2-butyl-4-chloro-1H-imidazole-5-carboxylic acid, TFA salt (Example 384, 16 mg, 0.026 mmol) was dissolved in THF (2 mL). CDI (62.1 mg, 0.383 mmol) was added and the reaction mixture was allowed to stir at RT for 1 h. Ammonium hydroxide (0.142 mL, 1.276 mmol) was then added and the reaction was allowed to stir at RT for 1 h. The reaction mixture was concentrated, taken up in DMF, filtered and purified via preparative LC-MS (Column: Waters XBridge C18, 2.1 mm×50 mm, 1.7 μm particles; Mobile Phase A: 5:95 ACN:H$_2$O with 10 mM NH$_4$OAc; Mobile Phase B: 95:5 ACN:H$_2$O with 10 mM NH$_4$OAc; Temperature: 50° C.; Gradient: 0% B to 100% B over 3 min, then a 0.75 min hold at 100% B; Flow: 1 mL/min;) to afford the title compound (Example 393, 10.3 mg, 0.020 mmol, 79% yield). LC-MS (Method A4): 1.956 min, [M+H]$^+$=512.0; $^1$H NMR (500 MHz, DMSO-d$_6$) δ 7.89-7.69 (m, 5H), 7.54-7.47 (m, 2H), 7.46-7.39 (m, 1H), 7.18 (d, J=7.7 Hz, 2H), 7.01 (d, J=7.7 Hz, 2H), 5.54 (s, 2H), 2.57-2.52 (m, 2H), 1.55-1.40 (m, 2H), 1.34-1.18 (m, 2H), 0.81 (t, J=7.2 Hz, 3H).

Example 394: 2-butyl-4-chloro-1-((6'-(5-oxo-4,5-dihydro-1,2,4-oxadiazol-3-yl)-[1,1':3',1''-terpheny 1-4-yl)methyl)-1H-imidazole-5-carboxamide (394)

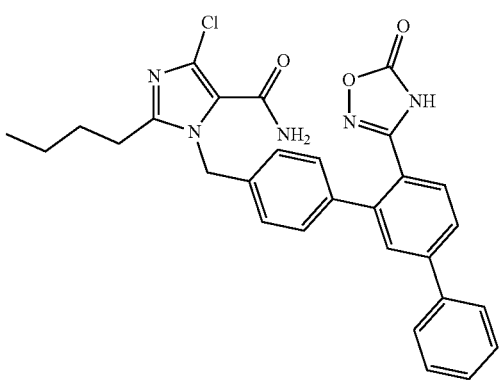

Example 394 was synthesized from Example 404 using the procedure used to synthesize Example 393 to give the title compound (Example 394, 2.3 mg, 4.36 μmol, 4.13% yield). MS (ESI) m/z (M+H)*=528.0. $^1$H NMR (500 MHz, DMSO-d$_6$) δ 7.83-7.76 (m, 3H), 7.74-7.65 (m, 3H), 7.54-7.47 (m, 2H), 7.46-7.34 (m, 4H), 7.12 (d, J=7.9 Hz, 2H), 5.58 (s, 2H), 2.61-2.56 (m, 2H), 1.50 (t, J=7.3 Hz, 2H), 1.31-1.18 (m, 2H), 0.81 (t, J=7.3 Hz, 3H). LC-MS retention time (Method A4): 2.113 min.

Example 395: ethyl 1-((6'-(2H-tetrazol-5-yl)-[1,1':3',1''-terphenyl]-4-yl)methyl)-4-ethyl-2-propyl-1H-imidazole-5-carboxylate (Ex. 395)

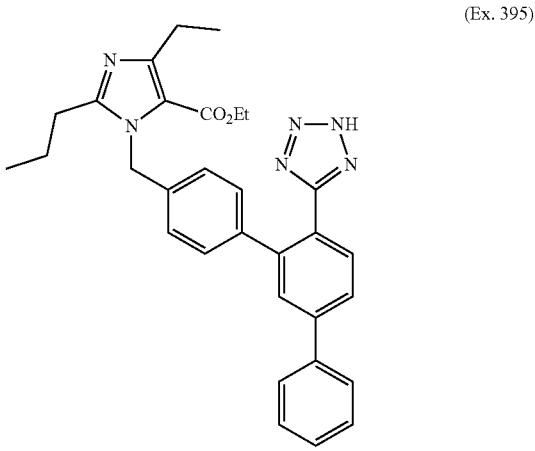 [SMILES: CCCc1nc(CC)c(C(=O)OCC)n1Cc1ccc(-c2cc(-c3ccccc3)ccc2-c2nn[nH]n2)cc1]

Intermediate 395a: methyl 4-ethyl-2-propyl-1-(4-(4,4,5,5-tetramethyl-1,3,2-dioxaborolan-2-yl)benzyl)-1H-imidazole-5-carboxylate

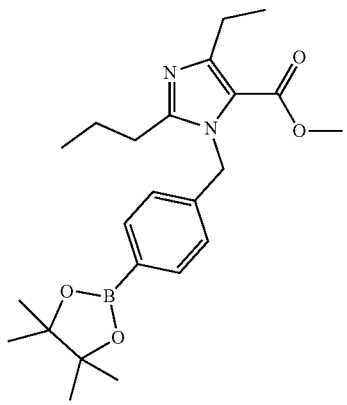

(395a)

2-(4-(bromomethyl)phenyl)-4,4,5,5-tetramethyl-1,3,2-dioxaborolane (272 mg, 0.917 mmol), methyl 4-ethyl-2-propyl-1H-imidazole-5-carboxylate (150 mg, 0.764 mmol) were dissolved in DMF (10 mL) at 0° C. 60% sodium hydride in mineral oil (33.6 mg, 0.841 mmol) was added to the reaction mixture which was allowed to stir at RT for 15 h. The reaction mixture was cooled to 0° C. and quenched with saturated ammonium chloride.

The aq. layer was extracted (3×) with EtOAc. The combined organic layer was washed with brine, dried with sodium sulfate, filtered and concentrated. The residue was purified by ISCO (0-100% EtOAc in hexane) to afford the title compound (395a, 100 mg, 0.243 mmol, 31.7% yield). LC-MS (Method A2): 0.85 min, [M+H]$^+$=413.1; $^1$H NMR (500 MHz, CDCl$_3$) δ 7.75 (d, J=8.0 Hz, 2H), 6.95 (d, J=7.7 Hz, 2H), 5.54 (s, 2H), 3.76 (s, 3H), 2.91 (q, J=7.5 Hz, 2H), 2.65-2.53 (m, 2H), 1.77-1.62 (m, 2H), 1.26 (t, J=7.4 Hz, 3H), 0.94 (t, J=7.4 Hz, 3H).

Intermediate 395b: methyl 1-((6'-cyano-[1,1':3',1''-terphenyl]-4-yl)methyl)-4-ethyl-2-propy-H-imidazole-5-carboxylate

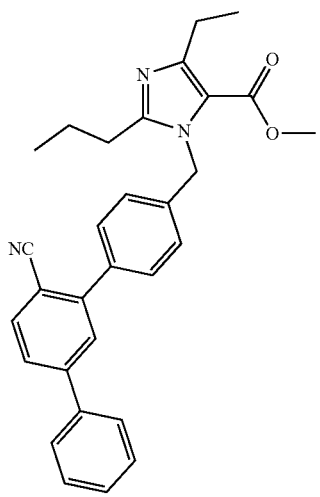

(395b)

To a solution of methyl 4-ethyl-2-propyl-1-(4-(4,4,5,5-tetramethyl-1,3,2-dioxaborolan-2-yl)benzyl)-1H-imidazole-5-carboxylate (395a, 100 mg, 0.243 mmol) and 3-bromo-[1,1'-biphenyl]-4-carbonitrile (032a, 120 mg, 0.315 mmol) in dioxane (3 mL) was added K$_3$PO$_4$ (2 M, aq) (0.364 mL, 0.728 mmol) followed by PdCl$_2$(dppf) (17.75 mg, 0.024 mmol). The resulting mixture was sparged with N$_2$ for 2 min before being sealed and heated at 120° C. for 45 min in the microwave. The reaction mixture was diluted with EtOAc and filtered through celite. The filtrate was concentrated and the residue was purified by ISCO (0-100% EtOAc in hexane) to afford the title compound (395b, 70 mg, 0.151 mmol, 62.3% yield). LC-MS (Method A2): 0.91 min, [M+H]$^+$=464.1; $^1$H NMR (500 MHz, CDCl$_3$) δ 7.88-7.81 (m, 1H), 7.72-7.71 (m, 1H), 7.69-7.66 (m, 1H), 7.66-7.63 (m, 2H), 7.60-7.56 (m, 2H), 7.53-7.47 (m, 2H), 7.48-7.44 (m, 1H), 7.18-7.09 (m, 2H), 3.82 (s, 3H), 3.04-2.86 (m, 2H), 2.77-2.60 (m, 2H), 1.82-1.70 (m, 2H), 1.34-1.20 (m, 3H), 1.05-0.95 (m, 3H).

Example 395: ethyl 1-((6'-(2H-tetrazol-5-yl)-[1,1':3',1''-terphenyl]-4-yl)methyl)-4-ethyl-2-propyl-1H-imidazole-5-carboxylate Example 395 was synthesized from 395b using the procedure described for Example 345. The crude residue was purified by reverse phase HPLC (Xbridge Prep Shield RP18, 15 min gradient of 20-100% B. A=H$_2$O/MeOH 10 mM NH$_4$OAc 90:10. B=H$_2$O/MeOH 10 mM NH$_4$OAc 10:90) to afford the title compound (Example 395, 4.5 mg, 0.0086 mmol, 29.8%). LC-MS (Method A4): 1.788 min, [M+H]$^+$=521.1; $^1$H NMR (500 MHz, DMSO-d$_6$) δ 7.86-7.74 (m, 3H), 7.71-7.63 (m, 2H), 7.54-7.45 (m, 2H), 7.41 (d, J=7.3 Hz, 1H), 7.14 (d, J=8.2 Hz, 2H), 6.88 (d, J=7.9 Hz, 2H), 5.50 (s, 2H), 4.15 (q, J=7.0 Hz, 2H), 2.77 (q, J=7.3 Hz, 2H), 2.58-2.55 (m, 2H), 1.62-1.44 (m, 2H), 1.24-1.09 (m, 6H), 0.84 (t, J=7.3 Hz, 3H).

Example 396: 1-((6'-(2H-tetrazol-5-yl)-[1,1':3',1''-terphenyl]-4-yl)methyl)-4-ethyl-2-propyl-1H-imidazole-5-carboxylic acid

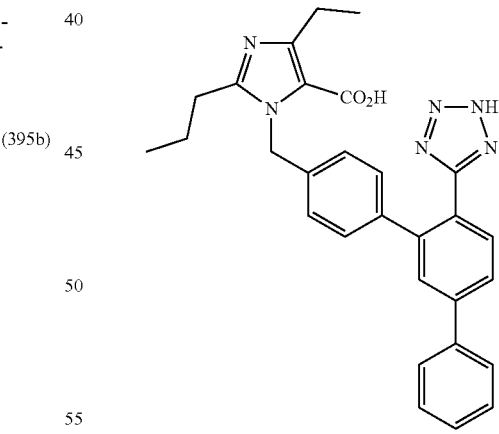

(Ex. 396)

Ethyl 1-((6'-(2H-tetrazol-5-yl)-[1,1':3',1''-terphenyl]-4-yl)methyl)-4-ethyl-2-propyl-1H-imidazole-5-carboxylate (Example 395, 130 mg, 0.250 mmol) was dissolved in 1M NaOH (1.248 mL, 1.248 mmol)/MeOH (1.2 mL). The reaction mixture was sealed and stirred at 100° C. for 2h. The reaction mixture was then acidified with 10% citric acid and extracted (3×) with EtOAc. The combined organic layer was washed with brine dried with sodium sulfate, filtered and concentrated. The residue was redissolved in MeOH, filtered and purified by reverse phase HPLC (Xbridge Prep Shield RP18, 15 min gradient of 20-100% B. A=H$_2$O/MeOH 10 mM NH$_4$OAc 90:10. B=H$_2$O/MeOH 10 mM NH$_4$OAc 10:90) to afford the title compound (Example 396, 65 mg, 0.132 mmol, 52.8% yield). LC-MS (Method A4): 1.630 min, [M+H]⁺=493.1; ¹H NMR (500 MHz, DMSO-d₆) δ 7.86-7.61 (m, 5H), 7.53-7.36 (m, 3H), 7.17 (d, J=7.6 Hz, 2H), 6.89 (d, J=7.6 Hz, 2H), 5.55 (br. s., 2H), 2.80 (q, J=7.3 Hz, 2H), 2.50-2.47 (m, 2H), 1.66-1.52 (m, 2H), 1.15 (t, J=7.3 Hz, 3H), 0.88 (t, J=7.3 Hz, 3H).

Example 397: 1-((6'-(2H-tetrazol-5-yl)-[1,1':3',1"-terphenyl]-4-yl)methyl)-4-ethyl-2-propyl-N-(2,2,2-trifluoroethyl)-1H-imidazole-5-carboxamide

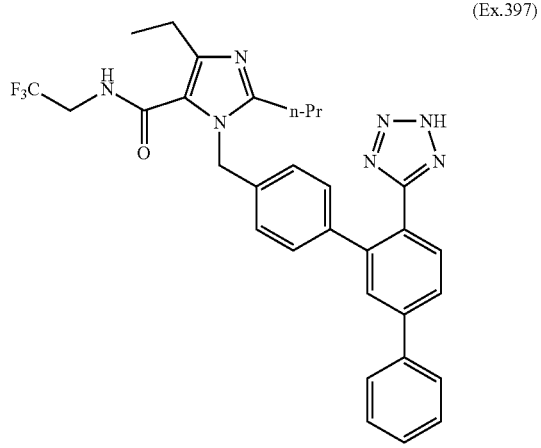
(Ex.397)

Example 397 was synthesized from Example 396 and trifluoroethyl amine using the same procedure described for the synthesis of Example 393. LC-MS (Method A4): 1.776 min, [M+H]⁺=573.9; ¹H NMR (500 MHz, DMSO-d₆) δ 8.60 (t, J=6.1 Hz, 1H), 7.82-7.59 (m, 5H), 7.55-7.45 (m, 2H), 7.45-7.35 (m, 1H), 7.11 (d, J=7.3 Hz, 2H), 6.94 (d, J=7.6 Hz, 2H), 5.31 (s, 2H), 4.11-3.86 (m, 2H), 3.72-3.64 (m, 2H), 2.64 (q, J=7.5 Hz, 2H), 1.60-1.42 (m, 2H), 1.11 (t, J=7.5 Hz, 3H), 0.84 (t, J=7.2 Hz, 3H).

Example 398: 1-((6'-(2H-tetrazol-5-yl)-[1,1':3',1"-terphenyl]-4-yl)methyl)-4-ethyl-2-propyl-1H-imidazole-5-carboxamide

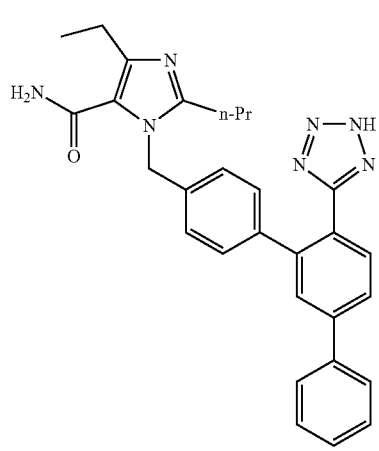
(Ex.398)

Example 398 was synthesized from Example 396 using the same procedure described for the synthesis of Example 393. LC-MS (Method A4): 1.479 min, [M+H]⁺=492.4; ¹H NMR (500 MHz, DMSO-d₆) δ 7.78 (d, J=7.3 Hz, 4H), 7.64 (s, 1H), 7.57-7.43 (m, 2H), 7.44-7.36 (m, 1H), 7.32 (br. s., 2H), 7.14 (br. s., 2H), 6.95 (d, J=6.4 Hz, 2H), 5.40 (s, 2H), 2.67 (q, J=7.5 Hz, 2H), 2.49-2.44 (m, 2H), 1.63-1.46 (m, 2H), 1.14 (t, J=7.3 Hz, 3H), 0.86 (t, J=7.3 Hz, 3H).

Example 399: 4-ethyl-1-((6'-(5-oxo-4,5-dihydro-1,2,4-oxadiazol-3-yl)-[1,1':3',1"-terphenyl]-4-yl)methyl1-2-propyl-1H-imidazole-5-carboxylic acid

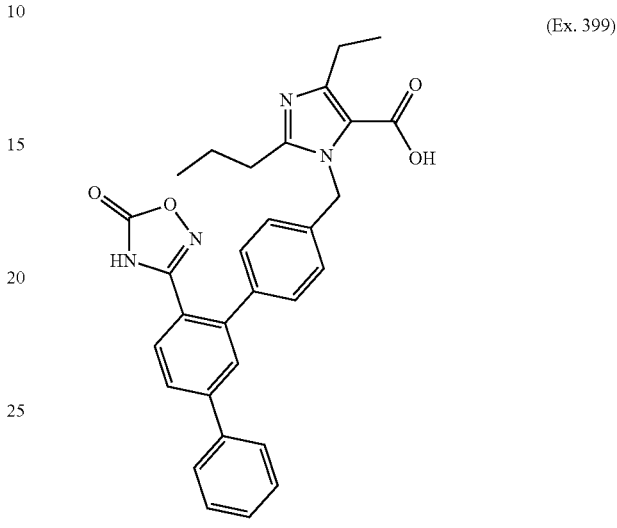
(Ex. 399)

Methyl 1-((6'-cyano-[1,1':3',1"-terphenyl]-4-yl)methyl)-4-ethyl-2-propyl-1H-imidazole-5-carboxylate (395b, 56 mg, 0.121 mmol) was dissolved in DMSO (2 mL). Hydroxylamine hydrochloride (58.8 mg, 0.846 mmol) was added followed by NaHCO₃ (71.0 mg, 0.846 mmol) in a pressure-rated vial. The reaction mixture was allowed to stir at 80° C. for 15 hours. The reaction mixture was diluted with H₂O and filtered. The precipitate was then dissolved in THF (5 mL). DBU (0.091 mL, 0.604 mmol) was added followed by CDI (98 mg, 0.604 mmol). The reaction was allowed to stir at RT for 15 min.

The reaction mixture was concentrated. The resulting residue was dissolved in MeOH (1 mL). 1M NaOH (0.906 mL, 1.812 mmol) was added and the reaction was allowed to stir at 50° C. for 15 hours. The reaction was acidified with AcOH (0.138 mL, 2.416 mmol) and diluted with EtOAc and H₂O. The aq. phase was washed with EtOAc 3×. The combined organic phase was dried with sodium sulfate, filtered and concentrated. The residue was dissolved in DMF, filtered and purified via preparative LC-MS (Column: Waters XBridge C18, 2.1 mm×50 mm, 1.7 μm particles; Mobile Phase A: 5:95 ACN:H₂O with 10 mM NH₄OAc; Mobile Phase B: 95:5 ACN:H₂O with 10 mM NH₄OAc; Temperature: 50° C.; Gradient: 0% B to 100% B over 3 min, then a 0.75 min hold at 100% B; Flow: 1 mL/min;) to afford the title compound (Example 399, 13.3 mg, 0.025 mmol, 20.35% yield). LC-MS (Method A4): 1.581 min, [M+H]⁺=509.1; ¹H NMR (500 MHz, DMSO-d₆) δ 7.92-7.70 (m, 5H), 7.57-7.35 (m, 5H), 7.19-7.07 (m, 2H), 5.74 (br. s., 2H), 2.96-2.87 (m, 2H), 2.78 (t, J=7.3 Hz, 2H), 1.64-1.49 (m, 2H), 1.21 (t, J=7.3 Hz, 3H), 0.86 (t, J=7.3 Hz, 3H).

Example 400: 1-((6'-carboxy-[1,1':3',1''-terphenyl]-4-yl)methyl)-4-ethyl-2-propyl-1H-imidazole-5-carboxylic acid

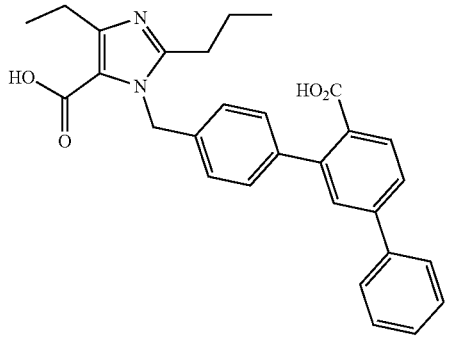

(Ex. 400)

Intermediate 400a: methyl 4''-(hydroxymethyl)-[1,1':3',1''-terphenyl]-4'-carboxylate

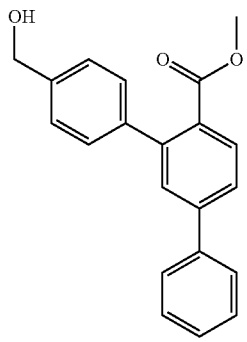

(400a) H$_2$O

To a vial containing 4-(hydroxymethyl)phenylboronic acid (251 mg, 1.650 mmol), methyl 3-chloro-[1,1'-biphenyl]-4-carboxylate (370 mg, 1.500 mmol) and 2nd generation xphos precatalyst (59.0 mg, 0.075 mmol) was added dioxane (7499 μl) followed by 2 M K$_3$PO$_4$ (2 M aq) (1500 μl, 3.00 mmol). The reaction mixture was sparged with N$_2$ for 2 min before being sealed and heated at 85° C. After 2.5 h of heating the reaction mixture was concentrated onto celite and purified by ISCO (0-100% EtOAc) to afford the title compound (400a, 470 mg, 1.476 mmol, 82% yield). LC-MS (Method A2): 1.00 min, [M+H]$^+$=319.1.1; $^1$H NMR (400 MHz, CDCl$_3$) δ 7.94 (d, J=8.1 Hz, 1H), 7.66-7.61 (m, 3H), 7.58 (d, 1=1.8 Hz, 1H), 7.51-7.34 (m, 7H), 4.77 (br. s., 2H), 3.69 (s, 3H).

Intermediate 400b: methyl 4''-(bromomethyl)-[1,1':3',1''-terphenyl]-4'-carboxylate

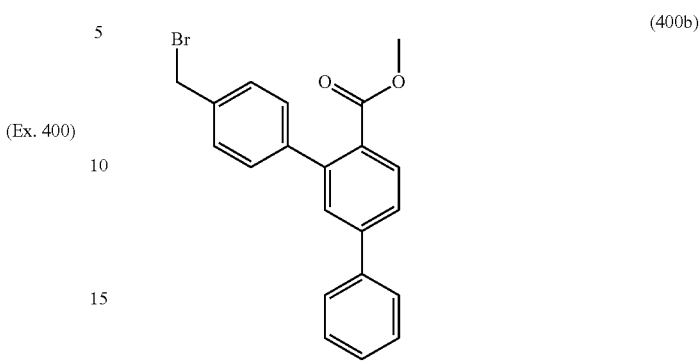

(400b)

To a flask containing methyl 4''-(hydroxymethyl)-[1,1':3',1''-terphenyl]-4'-carboxylate (400a, 470 mg, 1.476 mmol) was added DCM (14.800 mL) followed by triphenylphosphine (774 mg, 2.95 mmol). Carbon tetrabromide (979 mg, 2.95 mmol) was then added at RT and the reaction mixture was allowed to stir at RT for 1 h. The crude reaction mixture was concentrated directly onto celite and purified by ISCO (0-70% EtOAc/Hex) to afford the title compound (400b, 280 mg, 0.734 mmol, 49.7% yield).). $^1$H NMR (400 MHz, CDCl$_3$) δ 7.95 (d, J=8.1 Hz, 1H), 7.64 (ddd, J=8.1, 5.6, 1.5 Hz, 3H), 7.58 (d, J=1.8 Hz, 1H), 7.50-7.36 (m, 5H), 7.36-7.31 (m, 2H), 4.56 (s, 2H), 3.68 (s, 3H).

Intermediate 400c: ethyl 4-ethyl-1-((6'-(methoxycarbonyl)-[1,1':3',1''-terphenyl]-4-yl)methyl)-2-propyl-1H-imidazole-5-carbhxylate

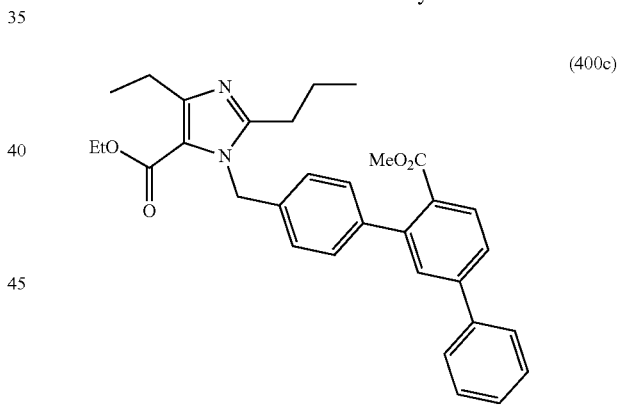

(400c)

Ethyl 4-ethyl-2-propyl-1H-imidazole-5-carboxylate, HCl (78 mg, 0.315 mmol) was dissolved in DMF (5 mL) along with methyl 4''-(bromomethyl)-[1,1':3',1''-terphenyl]-4'-carboxylate (400b, 80 mg, 0.210 mmol) at 0° C. 60% sodium hydride (30.2 mg, 1.259 mmol) was added and the reaction was allowed to stir at 0° C. for 10 min then at RT for 30 min. The reaction mixture was quenched with saturated ammonium chloride then diluted with EtOAc, washed with 10% LiCi 3×, brine, dried with sodium sulfate, filtered and concentrated. The residue was purified by ISCO (0-100% EtOAc in hexane) to afford the title compound (400c, 18 mg, 0.035 mmol, 16.80% yield).). LC-MS (Method A2): 1.00 min, [M+H]$^+$=511.15. $^1$H NMR (500 MHz, CDCl$_3$) δ 7.99-7.92 (m, 1H), 7.67-7.63 (m, 3H), 7.59-7.55 (m, 1H), 7.51-7.45 (m, 3H), 7.44-7.41 (m, 1H), 7.36-7.31 (m, 2H), 7.07-7.01 (m, 1H), 5.62-5.57 (m, 2H), 4.32-4.22 (m, 2H), 3.66 (s, 3H), 2.99-2.88 (m, 2H), 2.71-2.62 (m, 2H), 1.81-1.68 (m, 2H), 1.37-1.31 (m, 3H), 1.04-0.86 (m, 3H).

Example 400: 1-((6'-carboxy-[1,1':3',1"-terphenyl]-4-yl)methyl)-4-ethyl-2-propyl-1H-imidazole-5-carboxylic acid Ethyl 4-ethyl-1-((6'-(methoxycarbonyl)-[1,1':3',1"-terphenyl]-4-yl)methyl)-2-propyl-1H-imidazole-5-carboxylate (400c, 18 mg, 0.035 mmol) was dissolved in MeCOH (1 mL). 1M NaOH (0.529 mL, 0.529 mmol) was added and the reaction was allowed to stir at 65° C. in a sealed pressure rated vial for 18 h. The reaction mixture was concentrated, dissolved in DMF, filtered and purified via preparative LC-MS (XBridge C18, 19×200 mm, 5-μm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 13-53% B over 20 min, then a 6-minute hold at 100% B; Flow: 20 mL/min;) to afford the title compound (Example 400, 13.8 mg, 0.029 mmol, 81% yield).). LC-MS (Method A4): 1.542 min, [M+H]$^+$=469.2; $^1$H NMR (500 MHz, DMSO-d$_6$) δ 7.84-7.67 (m, 4H), 7.56 (s, 1H), 7.48 (t, J=7.5 Hz, 2H), 7.43-7.32 (m, 3H), 7.02 (d, J=7.6 Hz, 2H), 5.61 (s, 2H), 2.81 (q, J=7.3 Hz, 2H), 2.59-2.56 (m, 2H), 1.67-1.47 (m, 2H), 1.15 (t, J=7.5 Hz, 3H), 0.87 (t, J=7.2 Hz, 3H).

Example 401: ethyl 1-((6'-(2H-tetrazol-5-yl)-[1,1':3',1"-terphenyl]-4-yl)methyl)-4-(2-hydroxypropan-2-yl)-2-propyl-1H-imidazole-5-carboxylate

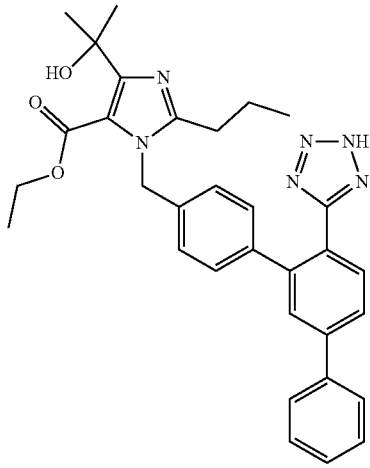

(Ex. 401)

Intermediate 401a: ethyl 4-(2-hydroxypropan-2-yl)-2-propyl-1-(4-(4,4,5,5-tetramethyl-1,3,2-dioxaborolan-2-yl)benzyl)-1H-imidazole-5-carboxylate

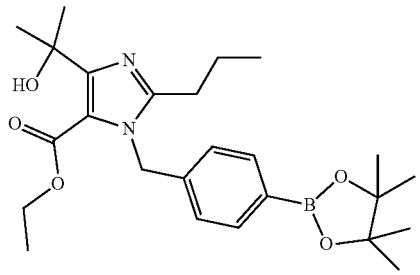

(401a)

To a solution of ethyl 4-(1-hydroxy-1-methylethyl)-2-propyl-imidazole-5-carboxylate (300 mg, 1.248 mmol) and 4-(bromomethyl)benzeneboronic acid pinacol ester (371 mg, 1.248 mmol) in Acetone (4994 μl) was added K$_2$CO$_3$ (345 mg, 2.497 mmol). The reaction mixture was sealed and heated at 60° C. overnight. The reaction mixture was then diluted with EtOAc, filtered over celite, and then concentrated onto celite for purification by ISCO (0-100% EtOAc/Hexanes) to afford the title compound (401a, 370 mg, 0.811 mmol, 64.9% yield). LC-MS (Method A2): 0.89 min, [M+H]$^+$=457.1; $^1$H NMR (400 MHz, CDCl$_3$) δ 7.74 (d, J=8.1 Hz, 2H), 6.90 (d, J=8.4 Hz, 2H), 5.45 (s, 2H), 4.18 (q, J=7.3 Hz, 2H), 2.64-2.56 (m, 2H), 1.75-1.65 (m, 2H), 1.37-1.30 (m, 12H), 1.13 (t, J=7.0 Hz, 3H), 0.93 (t, J=7.4 Hz, 3H).

Intermediate 401b: ethyl 1-((6'-cyano-[1,1':3',1"-terphenyl]-4-yl)methyl)-4-(2-hydroxypropan-2-yl)-2-propyl-1H-imidazole-5-carboxylate (401b)

To a solution of ethyl 4-(2-hydroxypropan-2-yl)-2-propyl-1-(4-(4,4,5,5-tetramethyl-1,3,2-dioxaborolan-2-yl)benzyl)-1H-imidazole-5-carboxylate (401a, 265 mg, 0.581 mmol) and 3-bromo-[1,1'-biphenyl]-4-carbonitrile (032a, 180 mg, 0.697 mmol) in dioxane (5811 μl) was added K$_3$PO$_4$ (2 M, aq) (581 μl, 1.162 mmol) followed by PdCl$_2$(dppf) (42.5 mg, 0.058 mmol). The resulting mixture was sparged with N$_2$ for 2 min before being sealed and heated at 120° C. for 45 min in the microwave. The reaction mixture was diluted with EtOAc and the organic phase was filtered over a mixture of Celite/MgSO$_4$. The resulting filtrate was concentrated onto celite and purified by ISCO (0-100% EtOAc/Hexanes) to afford the title compound (401b, 265 mg, 0.522 mmol, 90% yield). LC-MS (Method A2): 0.96 min, [M+H]$^+$=508.1. $^1$H NMR (400 MHz, CDCl$_3$) δ7.83 (d, J=8.4 Hz, 1H), 7.70-7.60 (m, 4H), 7.60-7.55 (m, 2H), 7.52-7.40 (m, 3H), 7.06 (d, J=8.4 Hz, 2H), 5.79 (br. s., 1H), 5.53 (s, 2H), 4.24 (q, J=7.3 Hz, 2H), 2.71-2.64 (m, 2H), 1.82-1.69 (m, 2H), 1.24 (s, 6H), 1.17 (t, J=7.2 Hz, 3H).

Example 401: ethyl 1-((6'-(2H-tetrazol-5-yl)-[1,1':3',1''-terphenyl]-4-yl)methyl)-4-(2-hydroxypropan-2-yl)-2-propyl-1H-imidazole-5-carboxylate Example 401 was synthesized from 401b using the procedure described for example 345. The crude residue was purified by reverse phase HPLC (Xbridge Prep Shield RP18, 15 min gradient of 20-100% B. A=$H_2O$/MeOH 10 mM $NH_4OAc$ 90:10. B=$H_2O$/MeOH 10 mM $NH_4OAc$ 10:90) to afford the title compound (Example 401, 3.9 mg, 6.66 µmol, 7.33% yield). LC-MS (Method A4): 1.774 min, $[M+H]^+$= 551.1; $^1$H NMR (500 MHz, DMSO-$d_6$) δ 7.91-7.69 (m, 5H), 7.56-7.39 (m, 3H), 7.18 (d, J=7.9 Hz, 2H), 6.94 (d, J=7.9 Hz, 2H), 5.48 (s, 2H), 4.16 (q, J=7.2 Hz, 2H), 2.68 (t, J=7.5 Hz, 2H), 1.61-1.52 (m, 2H), 1.50 (s, 6H), 1.08 (t, J=7.0 Hz, 3H), 0.88 (t, J=7.3 Hz, 3H).

Example 402: sodium 1-((6'-(2H-tetrazol-5-yl)-[1,1':3',1''-terphenyl]-4-yl)methyl)-4-(2-hydroxypropan-2-yl)-2-propyl-1H-imidazole-5-carboxylate

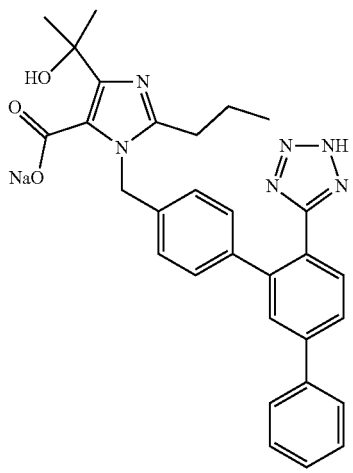
(Ex. 402)

To a solution of ethyl 1-((6'-(2H-tetrazol-5-yl)-[1,1':3',1''-terphenyl]-4-yl)methyl)-4-(2-hydroxypropan-2-yl)-2-propyl-1H-imidazole-5-carboxylate (Example 401, 4 mg, 6.97 µmol) in THF (1 mL) was added NaOH (1 M aq) (8.37 µl, 8.37 µmol). The reaction mixture was stirred at RT for 16 h. The reaction mixture was then sealed and heated at 65° C. After 1.5h of stirring more NaOH (1 M aq) (8.37 µl, 8.37 µmol) was added, and heating was continued for another 1.5 h. The reaction mixture was concentrated to afford the title compound without further purification. LC-MS (Method A2): 0.77 min, $[M+H]^+$=523.1; $^1$H NMR (400 MHz, MeOH-$d_4$) δ 7.62-7.46 (m, 5H), 7.39-7.33 (m, 2H), 7.29-7.22 (m, 1H), 7.03 (d, J=8.1 Hz, 2H), 6.82 (d, J=8.4 Hz, 2H), 5.66 (s, 2H), 2.51-2.44 (m, 2H), 1.80-1.76 (m, 2H), 1.46 (s, 6H), 0.80 (t, J=7.4 Hz, 3H).

Example 403: 4-(2-hydroxypropan-2-yl)-1-((6'-(5-oxo-4,5-dihydro-1,2,4-oxadiazol-3-yl)-[1,1':3',1''-terphenyl]-4-yl)methyl)₂-propyl-1H-imidazole-5-carboxylic acid, Na+

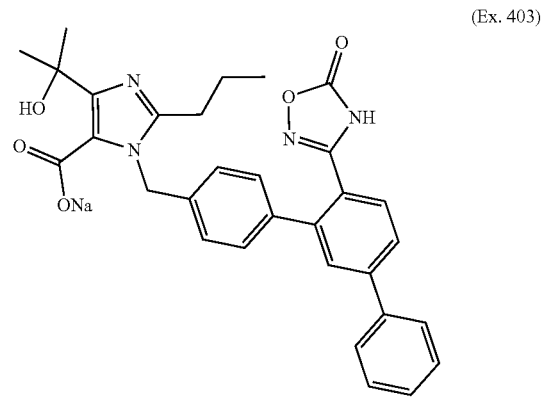
(Ex. 403)

Intermediate 403a: ethyl 4-(2-hydroxypropan-2-yl)-1-((6'-(5-oxo-4,5-dihydro-1,2,4-oxadiazol-3-yl)-[1,1':3',1''-terphenyl]-4-yl)methyl)-2-propyl-1H-imidazole-5-carboxylate (403a)

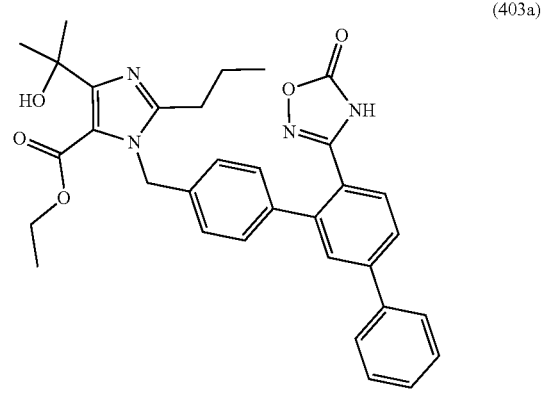 [SMILES: CCCc1nc(C(C)(C)O)c(C(=O)OCC)n1Cc1ccc(-c2cc(-c3ccccc3)ccc2-c2noc(=O)[nH]2)cc1]
(403a)

Ethyl 1-((6'-cyano-[1,1':3',1''-terphenyl]-4-yl)methyl)-4-(2-hydroxypropan-2-yl)-2-propyl-1H-imidazole-5-carboxylate (401b, 50 mg, 0.098 mmol) was dissolved in 1-butyl-3-methylimidazolium acetate (985 µl) along with hydroxylamine hydrochloride (171 mg, 2.462 mmol). The reaction mixture was allowed to stir at 50° C. for 48 h. The reaction was diluted with $H_2O$ and the amidoxime intermediate was filtered off and washed with $H_2O$. The amidoxime intermediate was dissolved in THF (2 mL). DBU (0.071 mL, 0.472 mmol) was added followed by CDI (76 mg, 0.472 mmol). The reaction mixture was allowed to stir at RT for 20 min. The reaction mixture was concentrated and the crude residue was dissolved in DMF, filtered and purified via preparative LC-MS (XBridge C18, 19×200 mm, 5-µm particles; Mobile Phase A: 5:95 ACN: $H_2O$ with 10 mM $NH_4OAc$; Mobile Phase B: 95:5 ACN: $H_2O$ with 10 mM $NH_4OAc$; Gradient: 13-53% B over 20 min, then a 6-minute hold at 100% B; Flow: 20 mL/min;) to afford the title compound (403a, 24 mg, 0.042 mmol, 44.9% yield). LC-MS (Method A2): 1.806 min, [M+H]⁺=567.4. ¹H NMR (500 MHz, DMSO-d₆) δ 7.83 (d, J=7.9 Hz, 1H), 7.79 (d, J=7.6 Hz, 2H), 7.75-7.68 (m, 2H), 7.54-7.29 (m, 5H), 7.01 (d, J=7.9 Hz, 2H), 5.51 (s, 2H), 4.16 (q, J=7.1 Hz, 2H), 2.64 (t, J=7.6 Hz, 2H), 1.67-1.55 (m, 2H), 1.09 (t, J=7.0 Hz, 3H), 0.90 (t, J=7.3 Hz, 3H).

Example 403: 4-(2-hydroxypropan-2-yl)-1-((6'-(5-oxo-4,5-dihydro-1,2,4-oxadiazol-3-yl)-[1,1':3',1''-terphenyl]-4-yl)methyl)-2-propyl-1H-imidazole-5-carboxylic acid, Na+

Ethyl 4-(2-hydroxypropan-2-yl)-1-((6'-(5-oxo-4,5-dihydro-1,2,4-oxadiazol-3-yl)-[1,1':3',1''-terphenyl]-4-yl)methyl)-2-propyl-1H-imidazole-5-carboxylate (403a, 20 mg, 0.035 mmol) was dissolved in MeOH (1 mL). 1M NaOH (0.071 mL, 0.071 mmol) was added to the reaction mixture and the reaction mixture was allowed to stir at 65° C. for 30 h. Additional 1M NaOH (0.071 mL, 0.071 mmol) was added to the reaction mixture which was allowed to stir at 65° C. for an additional 6 hours. The reaction mixture was concentrated to dryness, redissolved in MeOH and filtered. The filtrate was concentrated to afford the title compound without further purification (Example 403, 20 mg, 0.034 mmol, 96% yield).). LC-MS (Method A2): 0.83 min, [M+H]⁺=539.1. ¹H NMR (500 MHz, MeOH-d₄) δ 7.71-7.57 (m, 5H), 7.50-7.44 (m, 2H), 7.41-7.34 (m, 3H), 7.10-6.99 (m, 2H), 5.91-5.71 (m, 2H), 2.69-2.51 (m, 2H), 1.59 (s, 6H), 1.59-1.53 (m, 2H), 0.94 (t, J=7.3 Hz, 3H).

Example 404: 2-butyl-4-chloro-1-((6'-(5-oxo-4,5-dihydro-1,2,4-oxadiazol-3-yl)-[1,1':3',1''-terphenyl]-4-yl)methyl)-1H-imidazole-5-carboxylic acid (Ex. 404)

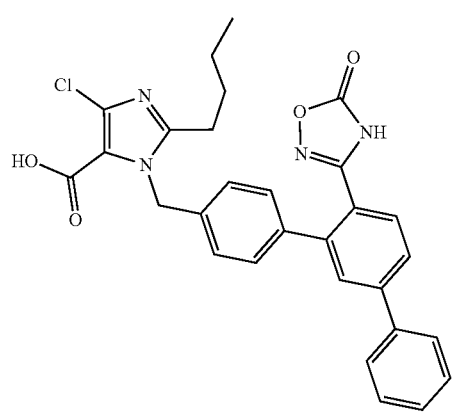

Intermediate 404a: 4''-((2-butyl-4-chloro-5-formyl-1H-imidazol-1-yl)methyl)-[1,1':3',1''-terphenyl]-4'-carbonitrile (404a)

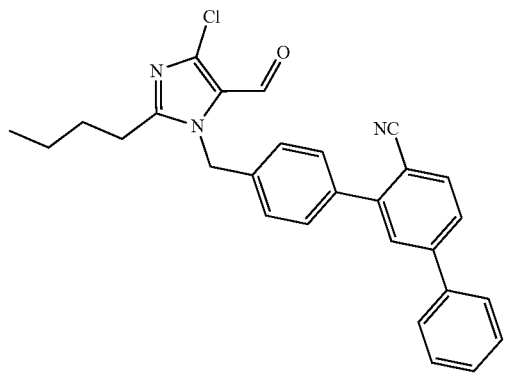

To a solution of 2-butyl-4-chloro-1-(4-(4,4,5,5-tetramethyl-1,3,2-dioxaborolan-2-yl)benzyl)-1H-imidazole-5-carbaldehyde (035a, 523 mg, 1.299 mmol) and 3-bromo-[1,1'-biphenyl]-4-carbonitrile (032a, 335 mg, 1.299 mmol) in 4:1 toluene/EtOH (10 mL) was added K₃PO₄ (2 M, aq) (1.948 mL, 3.90 mmol) followed by PdCl₂(dppf) (95 mg, 0.130 mmol). The resulting mixture was sparged with N₂ for 2 min before being sealed and heated at 120° C. for 45 min in the microwave. The reaction mixture was then filtered through celite and the filtrate was concentrated and the residue was purified by ISCO (0-100% EtOAc/Hexanes) to afford the title compound (404a, 190 mg, 0.419 mmol, 32.2% yield). LC-MS: MS (ESI) m/z: 454.0 (M+H)⁺. ¹H NMR (500 MHz, CDCl₃) δ 7.87-7.82 (m, 1H), 7.73-7.67 (m, 2H), 7.66-7.58 (m, 4H), 7.57-7.40 (m, 3H), 7.25-7.18 (m, 2H), 5.65 (s, 2H), 2.75-2.64 (m, 2H), 1.83-1.69 (m, 2H), 1.47-1.35 (m, 2H), 0.94 (s, 3H).

Intermediate 404b: 2-butyl-4-chloro-1-((6'-cyano-[1,1':3',1''-terphenyl]-4-yl)methyl)-1H-imidazole-5-carboxylic acid (404b)

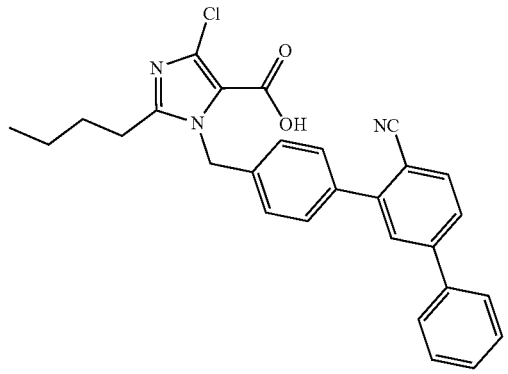

404b was synthesized using the procedure described for 345c. LC-MS: MS (ESI) m/z: 470.05 (M+H)⁺. ¹H NMR (500 MHz, DMSO-d₆) δ 8.02 (d, J=7.9 Hz, 1H), 7.89-7.79 (m, 4H), 7.72-7.63 (m, J=7.9 Hz, 2H), 7.55-7.45 (m, 3H), 7.24-7.14 (m, J=7.9 Hz, 2H), 5.70 (s, 2H), 2.65 (t, J=7.5 Hz, 2H), 1.55 (br t, J=7.5 Hz, 2H), 1.33-1.22 (m, 2H), 0.81 (t, J=7.3 Hz, 3H).

Example 404: 2-butyl-4-chloro-1-((6'-(5-oxo-4,5-dihydro-1,2,4-oxadiazol-3-yl)-[1,1':3',1''-terphenyl]-4-yl)methyl)-1H-imidazole-5-carboxylic acid Hydroxylamine hydrochloride (53.2 mg, 0.766 mmol) was dissolved in ethanol (638 μl). Potassium tert-butoxide (71.6 mg, 0.638 mmol) was added and the reaction mixture was allowed to vigorously stir for 2 h at RT. 2-butyl-4-chloro-1-((6'-cyano-[1,1':3',1''-terphenyl]-4-yl)methyl)-1H-imidazole-5-carboxylic acid (404b, 30 mg, 0.064 mmol) was then added to the reaction mixture which was sealed and allowed to stir at 80° C. for 18 h. The reaction mixture was diluted with $H_2O$ and the amidoxime intermediate was filtered off and dissolved in THF (3 mL). DBU (0.036 mL, 0.239 mmol) was added followed by CDI (90 mg, 0.557 mmol). The reaction mixture was allowed to stir at RT for 15 min. The reaction mixture was concentrated, dissolved in DMF, filtered and purified via preparative LC-MS (XBridge C18, 19×200 mm, 5-μm particles; Mobile Phase A: 5:95 ACN: $H_2O$ with 10 mM $NH_4OAc$; Mobile Phase B: 95:5 ACN: $H_2O$ with 10 mM $NH_4OAc$; Gradient: 13-53% B over 20 min, then a 6-minute hold at 100% B; Flow: 20 mL/min;) to afford the title compound (Example 404, 4.2 mg, 7.94 μmol, 9.98% yield). LC-MS (Method A4): 2.102 min, $[M+H]^+$=528.9. $^1$H NMR (500 MHz, DMSO-$d_6$) δ7.86-7.63 (m, 5H), 7.53-7.47 (m, 2H), 7.43 (d, J=7.0 Hz, 1H), 7.38 (d, J=7.6 Hz, 2H), 7.08 (d, J=7.6 Hz, 2H), 5.67 (br. s., 2H), 2.61-2.56 (m, 2H), 1.58-1.42 (m, 2H), 1.33-1.19 (m, 2H), 0.80 (t, J=7.3 Hz, 3H).

Example 405: 2-butyl-4-chloro-1-((5'-(3,3-dimethylindolin-1-yl)-2'-(5-oxo-4,5-dihydro-1,2,4-oxadiazol-3-yl)-[1,1'-biphenyl]-4-yl)methyl)-1H-imidazole-5-carboxylic acid

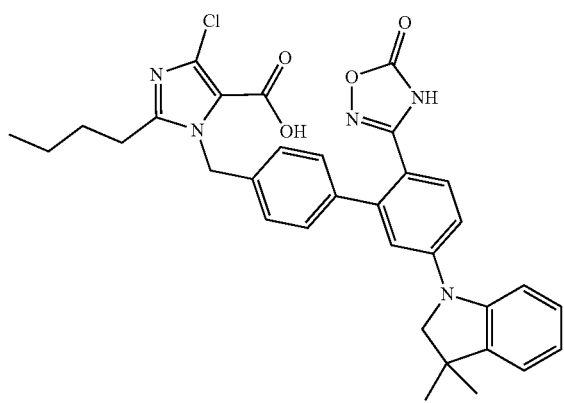

(Ex. 405)

Intermediate 405a: 2-butyl-4-chloro-1-((2'-cyano-5'-(3,3-dimethylindolin-1-yl)-[1,1'-biphenyl]-4-yl)methyl)-1H-imidazole-5-carboxylic acid, TFA salt

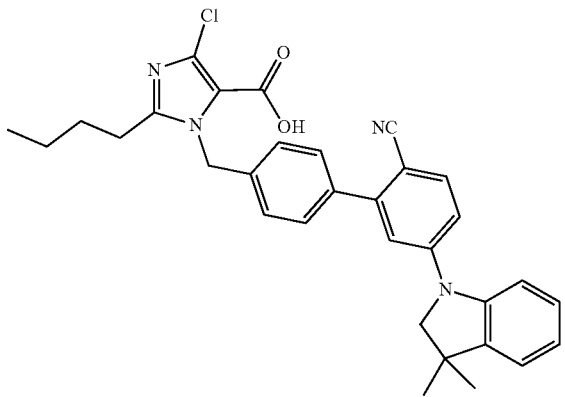

(405a)

To a vial containing 2-butyl-4-chloro-1-((5'-chloro-2'-cyano-[1,1'-biphenyl]-4-yl)methyl)-1H-imidazole-5-carboxylic acid (384b, 00 mg, 0.364 mmol) was added 2nd generation ruphos precatalyst (56.6 mg, 0.073 mmol) followed by sodium tert-butoxide (210 mg, 2.185 mmol). THF (3 mL) was added followed by 3,3-dimethylindoline (161 mg, 1.093 mmol). The reaction mixture was degassed with $N_2$ and was then was sealed and heated at 65° C. for 18 h. The reaction mixture was concentrated onto celite and purified by reverse phase ISCO (15 min gradient of 0-100% B. A=$H_2O$/ACN/TFA 90:10:0.1. B=ACN/$H_2O$/TFA 90:10: 0.1) to afford the title compound (405a, 70 mg, 0.107 mmol, 29.4% yield) as an orange solid. LC-MS (Method A2): 1.07 min, $[M+H]^+$=539.10.

Example 405: 2-butyl-4-chloro-1-((5'-(3,3-dimethylindolin-1-yl)-2'-(5-oxo-4,5-dihydro-1,2,4-oxadiazol-3-yl)-[1,1'-biphenyl]-4-yl)methyl)-1H-imidazole-5-carboxylic acid Example 405 was synthesized from 405a according to the same procedure used for the synthesis of 403a to afford the title compound (Example 405, 9.6 mg, 0.016 mmol, 24.72% yield). MS (ESI) m/z $(M+H)^+$=598.15. $^1$H NMR (500 MHz, DMSO-$d_6$) δ 7.94 (s, 1H), 7.57 (br d, J=8.5 Hz, 1H), 7.40-7.30 (m, 3H), 7.27 (d, J=8.1 Hz, 1H), 7.22 (d, J=7.6 Hz, 1H), 7.17-7.02 (m, 4H), 6.97-6.79 (m, 1H), 5.66 (br s, 2H), 3.77 (s, 1H), 3.17 (s, 1H), 2.89 (s, 2H), 2.73 (s, 2H), 2.59 (br s, 2H), 2.56-2.53 (m, 3H), 1.50 (br s, 2H), 1.30 (s, 6H), 1.25 (br d, J=7.3 Hz, 2H), 1.16 (s, 1H), 0.79 (br t, J=7.2 Hz, 3H). LC-MS retention time (Method A4): 2.318 min.

Example 406: 2-butyl-4-chloro-1-((5'-(indolin-1-yl)-2'-(5-oxo-4,5-dihydro-1,2,4-oxadiazol-3-yl)-[1,1'-biphenyl]-4-yl)methyl)-1H-imidazole-5-carboxylic acid

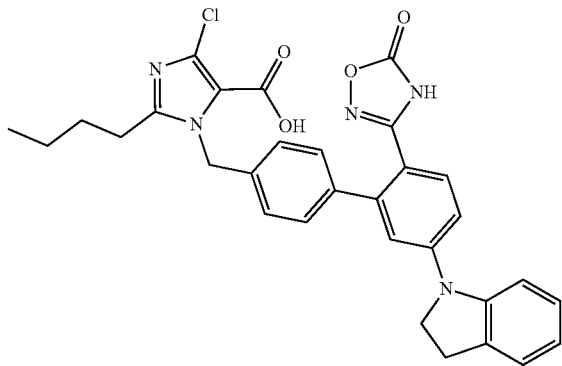
(406)

Example 406 was synthesized from indoline and 384b according to the same sequence as described for Example 405. MS (ESI) m/z (M+H)⁺=570.1. ¹H NMR (500 MHz, DMSO-d₆) δ 7.57 (d, J=8.5 Hz, 1H), 7.39-7.29 (m, 3H), 7.23 (dd, J=13.3, 7.5 Hz, 2H), 7.14-6.96 (m, 4H), 6.79 (t, J=7.3 Hz, 1H), 5.71 (br. s., 2H), 4.01 (t, J=8.4 Hz, 2H), 3.11 (t, J=8.2 Hz, 2H), 2.56-2.54 (m, 2H), 1.57-1.40 (m, 2H), 1.32-1.18 (m, 2H), 0.79 (t, J=7.3 Hz, 3H). LC-MS retention time (Method A4): 2.132 min.

Example 407: (S)-2-butyl-4-chloro-1-((5'-(3-methylpiperidin-1-yl)-2'-(5-oxo-4,5-dihydro-1,2,4-oxadiazol-3-yl)-[1,1'-biphenyl]-4-yl)methyl)-1H-imidazole-5-carboxylic acid (Ex. 407)

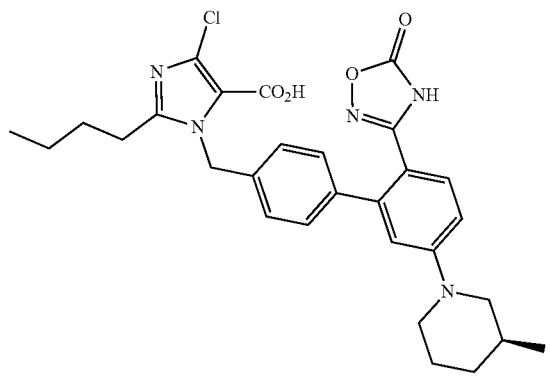
(Ex. 407)

Intermediate 407a: 4'-((2-butyl-4-chloro-5-formyl-1H-imidazol-1-yl)methyl)-5-fluoro-[1,1'-biphenyl]-2-carbonitrile

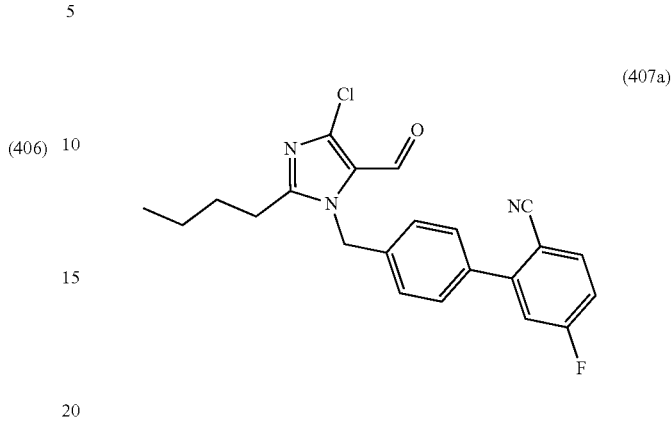
(407a)

Intermediate 407a was synthesized according to the same procedure used for Intermediate 384a to afford the title compound (407a, 1.05 g, 2.65 mmol, 71.2% yield). LC-MS: MS (ESI) m/z: 396.1 (M+H)⁺. ¹H NMR (500 MHz, CDCl₃) δ 9.80 (s, 1H), 7.80 (dd, J=8.5, 5.5 Hz, 1H), 7.55 (d, J=8.3 Hz, 2H), 7.24-7.17 (m, 4H), 5.64 (s, 2H), 2.72-2.67 (m, 2H), 1.74 (t, J=7.7 Hz, 2H), 1.46-1.33 (m, 2H), 0.93 (t, J=7.3 Hz, 3H).

Intermediate 407b: (S)-4'-((2-butyl-4-chloro-5-formyl-1H-imidazol-1-yl)methyl)-5-(3-methylpiperidin-1-yl)-[1,1'-biphenyl]-2-carbonitrile

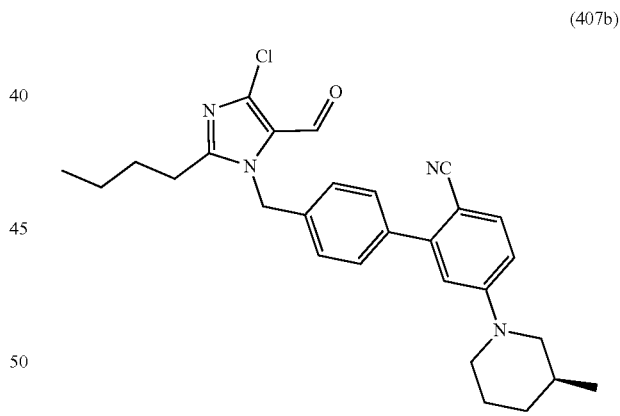
(407b)

4'-((2-butyl-4-chloro-5-formyl-]H-imidazol-1-yl)methyl)-5-fluoro-[1,1'-biphenyl]-2-carbonitrile (407a, 199 mg, 0.503 mmol) was dissolved in DMSO (1676 µl). Potassium carbonate (347 mg, 2.51 mmol) was added followed by (S)-3-methylpiperidine, HCl (150 mg, 1.106 mmol). The reaction mixture was sealed and heated at 100° C. for 2 h. The reaction mixture was diluted with EtOAc and H₂O. The aq. phase was washed with EtOAc (3×) and the combined organic phases were washed with brine, dried with sodium sulfate, filtered and concentrated. The residue was purified by ISCO (0-100% EtOAc in hexane) to afford the title compound (407b, 194 mg, 0.408 mmol, 81% yield). LC-MS (Method A2): 1.17 min, [M+H]⁺=475.1.

567

Intermediate 407c: (S)-2-butyl-4-chloro-1-((2'-cyano-5'-(3-methylpiperidin-1-yl)-[1,1'-biphenyl]-4-yl)methyl)-1H-imidazole-5-carboxylic acid

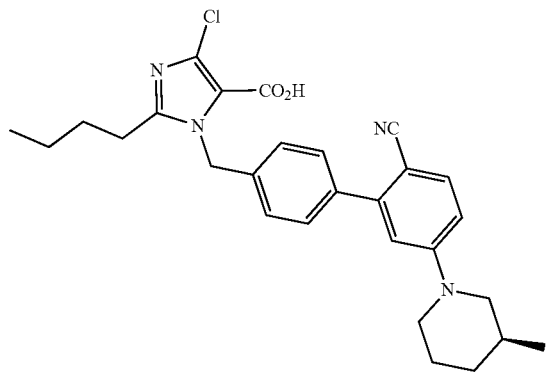

(407c)

Intermediate 407c was synthesized from 407b according to the procedure described for the synthesis of 345c to afford the title compound (407c, 0.103 g, 0.211 mmol, 100%). LC-MS (Method A2): 1.07 min, [M+H]$^+$=491.1.

Example 407: (S)-2-butyl-4-chloro-1-((5'-(3-methylpiperidin-1-yl)-2'-(5-oxo-4,5-dihydro-1,2,4-oxadiazol-3-yl)-[1,1'-biphenyl]-4-yl)methyl)-1H-imidazole-5-carboxylic acid Example 407 was synthesized from 407c according to the procedure described for Intermediate 403a to afford the title compound (Example 407, 0.9 mg, 1.636 μmol, 2.60% yield). LC-MS (Method A4): 1.943 min, [M+H]$^+$=550.1.

Example 408: 1-((5'-(1H-indol-1-yl)-2'-(5-oxo-4,5-dihydro-1,2,4-oxadiazol-3-yl)-[1,1'-biphenyll-4-yl)methyl)-2-butyl-4-chloro-1H-imidazole-5-carboxylic acid

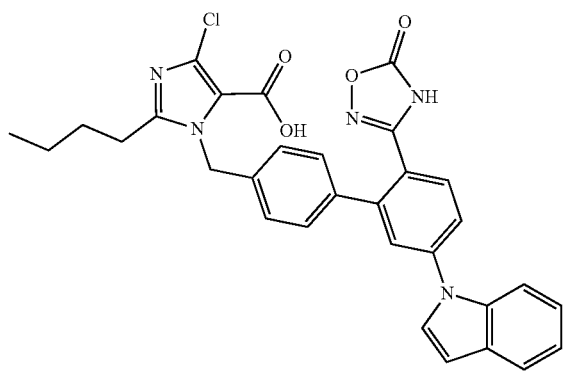

(Ex. 408)

568

Intermediate 408a: 1-((5'-bromo-2'-cyano-[1,1'-biphenyl]-4-yl)methyl)-2-butyl-4-chloro-1H-imidazole-5-carboxylic acid

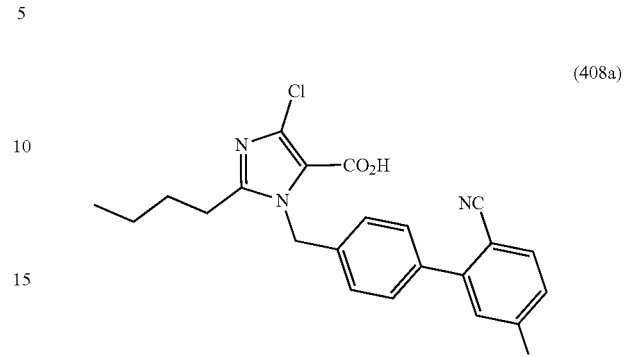

(408a)

408a was synthesized from 035a and 4-bromo-2-iodobenzonitrile according to the sequence described for the synthesis of 384b. LC-MS (Method A2): 0.961 min, [M+H]$^+$=473.95.

Intermediate 408b: 2-butyl-4-chloro-1-((2'-cyano-5'-(1H-indol-1-yl)-[1,1'-biphenyl]-4-yl)methyl)-1H-imidazole-5-carboxylic acid, TFA salt

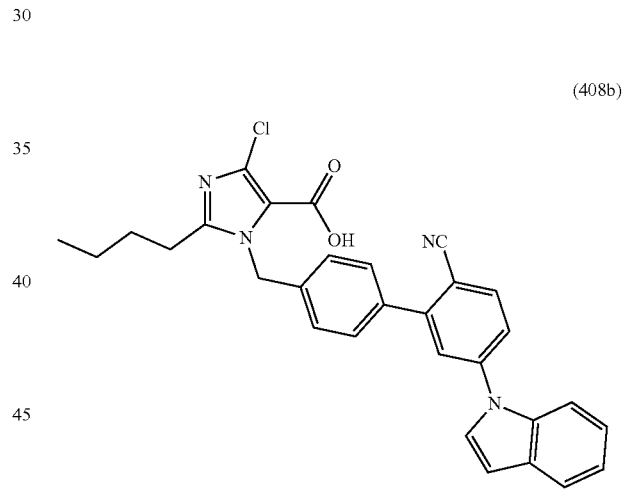

(408b)

(S)-pyrrolidine-2-carboxylic acid (50.9 mg, 0.442 mmol), 1-((5'-bromo-2'-cyano-[1,1'-biphenyl]-4-yl)methyl)-2-butyl-4-chloro-1H-imidazole-5-carboxylic acid (408, 209 mg, 0.442 mmol), 1H-indole (311 mg, 2.65 mmol), copper (I) iodide (42.1 mg, 0.221 mmol) and potassium carbonate (305 mg, 2.210 mmol) were added to a pressure-rated vial. DMSO (4421 μl) was added and the reaction was evacuated and backfilled with N$_2$ (3×) then stirred at 120° C. for 18 h. The reaction mixture was diluted with EtOAc and filtered through celite. The filtrate was then extracted with H$_2$O 2×, washed brine, dried with sodium sulfate, filtered and concentrated. The residue was redissolved in MeOH, filtered and purified by reverse phase HPLC (PhenomenexLuna AXIA 5 micron C18, 20 min gradient of 0-100% B. A=H$_2$O/ACN/TFA 90:10:0.1. B=ACN/H$_2$O/TFA 90:10:0.1) to afford the title compound (408b, 38 mg, 0.061 mmol, 13.80% yield). LC-MS (Method A2): 1.040 min, [M+H]$^+$=509.05.

Example 408: 1-((5'-(1H-indol-1-yl)-2'-(5-oxo-4,5-dihydro-1,2,4-oxadiazol-3-yl)-[1,1'-biphenyl]-4-yl)methyl)-2-butyl-4-chloro-1H-imidazole-5-carboxylic acid Example 408 was synthesized from 408b according to the procedure used for the synthesis of 403a to afford the title compound (Example 408, 0.7 mg, 1.232 μmol, 3.30% yield). MS (ESI) m/z (M+H)+=568.4. $^1$H NMR (500 MHz, DMSO-d$_6$) δ 7.84-7.66 (m, 5H), 7.58 (s, 1H), 7.51-7.35 (m, J=8.2 Hz, 2H), 7.24 (br t, J=7.6 Hz, 1H), 7.16 (t, J=7.3 Hz, 1H), 7.11-6.92 (m, J=8.2 Hz, 2H), 6.74 (d, J=3.4 Hz, 1H), 5.67 (s, 2H), 2.73-2.59 (m, J=7.6 Hz, 2H), 1.53 (quin, J=7.6 Hz, 3H), 1.38-1.21 (m, 2H), 0.81 (t, J=7.3 Hz, 3H). LC-MS retention time (Method A4): 2.115 min.

Example 409: 2-butyl-4-chloro-1-((4''-(dimethylcarbamoyl)-6'-(5-oxo-4,5-dihydro-1,2,4-oxadiazol-3-yl)-[1,1':3',1''-terphenyl]-4-yl)methyl)-1H-imidazole-5-carboxylic acid

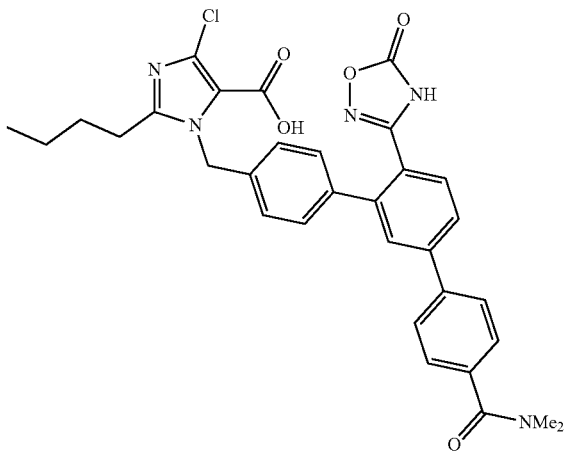
(Ex. 409)

Intermediate 409a: 2-butyl-4-chloro-1-((6'-cyano-4''-(dimethylcarbamoyl)-[1,1':3',1''-terphenyl]-4-yl)methyl)-1H-imidazole-5-carboxylic acid, TFA salt

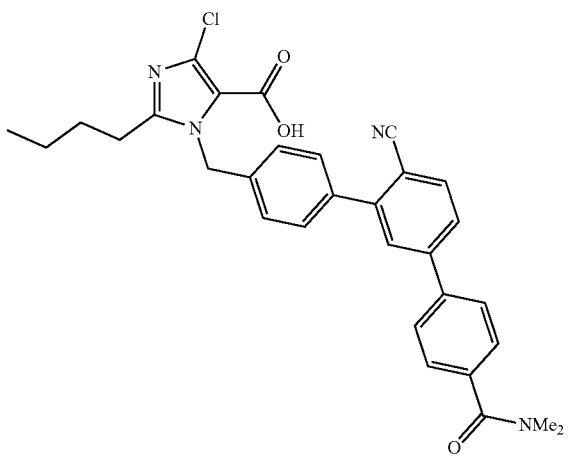
(409a)

To a pressure-rated vial containing 2-butyl-4-chloro-1-((5'-chloro-2'-cyano-[1,1'-biphenyl]-4-yl)methyl)-1H-imidazole-5-carboxylic acid (384b, 200 mg, 0.364 mmol), (4-(dimethylcarbamoyl)phenyl)boronic acid (84 mg, 0.437 mmol) and 2nd generation xphos precatalyst (28.7 mg, 0.036 mmol) was added dioxane (1821 μl) followed by 2 M K$_3$PO$_4$ (2 M aq) (364 μl, 0.728 mmol). The reaction mixture was sparged with N$_2$ for 2 min before being sealed and heated at 85° C. for 1 h. The reaction mixture was concentrated onto celite and purified by reverse phase ISCO (30 g 15 min gradient of 0-100% B. A=H$_2$O/ACN/TFA 90:10:0.1. B=ACN/H$_2$O/TFA 90:10:0.1) to afford the title compound (409a, 80 mg, 0.275 mmol, 75% yield). LC-MS: MS (ESI) m/z: 541.4 (M+H)$^+$. $^1$H NMR (500 MHz, DMSO-d$_6$) δ 8.05 (d, J=8.3 Hz, 1H), 7.95-7.89 (m, 4H), 7.69 (d, J=8.3 Hz, 2H), 7.54 (d, J=8.3 Hz, 2H), 7.30-7.22 (m, 2H), 5.70 (s, 2H), 3.01 (br s, 3H), 2.96 (br s, 3H), 2.70-2.59 (m, 2H), 1.60-1.53 (m, 2H), 1.35-1.23 (m, 2H), 0.83 (t, J=7.4 Hz, 3H).

Example 409: 2-butyl-4-chloro-1-((4''-(dimethylcarbamoyl)-6'-(5-oxo-4,5-dihydro-1,2,4-oxadiazol-3-yl)-[1,1':3',1''-terphenyll-4-yl)methyl)-1H-imidazole-5-carboxylic acid Example 409 was synthesized from 409a using the procedure described for the synthesis of 403a to afford the title compound (Example 409, 5 mg, 8.33 μmol, 6.06% yield). MS (ESI) m/z (M+H)$^+$=600.0. $^1$H NMR (500 MHz, DMSO-d$_6$) δ 7.91-7.83 (m, 3H), 7.79-7.71 (m, 2H), 7.52 (d, J=8.2 Hz, 2H), 7.39 (d, J=7.6 Hz, 2H), 7.10 (br. s., 2H), 5.66 (br. s., 2H), 3.05-2.85 (m, 8H), 1.53 (br. s., 2H), 1.27 (d, J=6.7 Hz, 2H), 1.16 (t, J=7.2 Hz, 2H). LC-MS retention time (Method A4): 1.674 min.

Example 410: 2-butyl-1-((6'-carboxy-[1,1':3',1''-terphenyl]-4-yl)methyl)-4-chloro-1H-imidazole-5-carboxylic acid

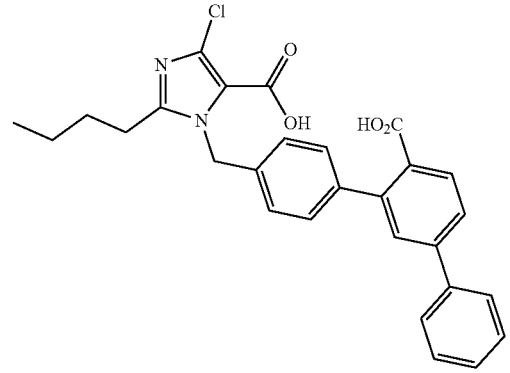
(Ex. 410)

Example 410a: 2-butyl-4-chloro-1-((6'-(methoxycarbonyl)-[1,1':3',1''-terphenyl]-4-yl)methyl)-1H-imidazole-5-carboxylic acid

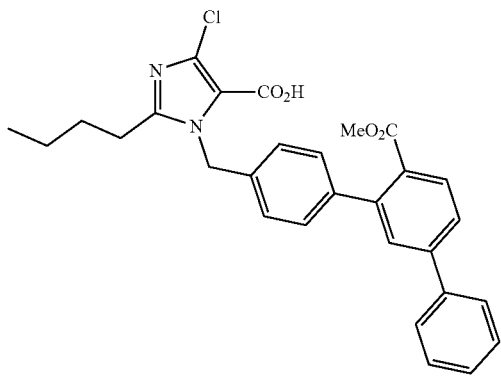

(410a)

410a was synthesized from 035a and methyl 3-chloro-[1,1'-biphenyl]-4-carboxylate according to the sequence described for the synthesis of 384b. LC-MS (Method A2): 1.00 min, [M+H]$^+$=503.05.

Example 410: 2-butyl-1-((6'-carboxy-[1,1':3',1''-terphenyl]-4-yl)methyl)-4-chloro-1H-imidazole-5-carboxylic acid 2-butyl-4-chloro-1-((6'-(methoxycarbonyl)-[1,1':3',1''-terphenyl]-4-yl)methyl)-1H-imidazole-5-carboxylic acid (410a, 25 mg, 0.050 mmol) was dissolved in 3:1 THF/MEOH (1 mL). 1M LiOH (0.149 mL, 0.149 mmol) was added and the reaction mixture was allowed to stir at 60° C. for 18 h. The reaction mixture was concentrated, dissolved in DMF, filtered and purified via preparative LC-MS (XBridge C18, 19×200 mm, 5-μm particles; Mobile Phase A: 5:95 ACN: H$_2$O with 10 mM NH$_4$OAc; Mobile Phase B: 95:5 ACN: H$_2$O with 10 mM NH$_4$OAc; Gradient: 13-53% B over 20 min, then a 6-minute hold at 100% B; Flow: 20 mL/min;) to afford the title compound (Example 410, 8.4 mg, 0.017 mmol, 34.6% yield). MS (ESI) m/z (M+H)$^+$= 489.1. $^1$H NMR (500 MHz, DMSO-d$_6$) δ 7.81 (d, J=7.9 Hz, 1H), 7.73 (d, J=7.6 Hz, 3H), 7.56 (s, 1H), 7.51-7.32 (m, 5H), 7.07 (d, J=7.9 Hz, 2H), 5.66 (s, 2H), 2.59 (t, J=7.6 Hz, 2H), 1.56-1.44 (m, J=7.6 Hz, 2H), 1.30-1.19 (m, 2H), 0.80 (t, J=7.3 Hz, 3H). LC-MS retention time (Method A4): 2.116 min.

Example 411: (5-methyl-2-oxo-1,3-dioxol-4-yl)methyl 1-((6'-(2H-tetrazol-5-yl)-[1,1':3',1''-terphenyl]-4-yl)methyl)-2-butyl-4-chloro-1H-imidazole-5-carboxylate

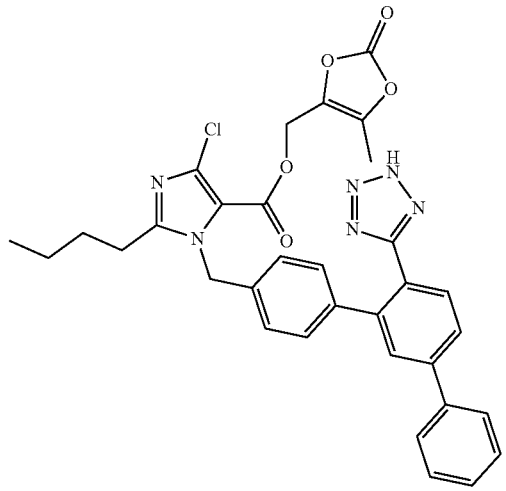

(Ex. 411)

1-((6'-(2H-tetrazol-5-yl)-[1,1':3',1''-terphenyl]-4-yl)methyl)-2-butyl-4-chloro-1H-imidazole-5-carboxylic acid, TFA salt (Example 384, 15 mg, 0.024 mmol) was dissolved in DCM (2 mL) along with 4-(hydroxymethyl)-5-methyl-1,3-dioxol-2-one (15.56 mg, 0.120 mmol). DMAP (14.61 mg, 0.120 mmol) was added followed by EDC (22.93 mg, 0.120 mmol). The reaction mixture was allowed to stir at RT for 18 h. The reaction mixture was concentrated and purified by ISCO (0-30% MeOH/DCM) to afford the title compound (Example 411, 2.9 mg, 4.41 μmol, 18.42% yield). LC-MS (Method A2): 1.09 min, [M+H]$^+$=625.1. $^1$H NMR (500 MHz, CDCl$_3$) δ 8.16 (d, J=8.0 Hz, 1H), 7.81 (dd, J=8.1, 1.8 Hz, 1H), 7.77-7.73 (m, 1H), 7.71-7.64 (m, 3H), 7.53-7.48 (m, 2H), 7.45 (d, J=7.4 Hz, 1H), 7.02 (d, J=8.3 Hz, 2H), 5.57 (s, 2H), 5.07 (s, 2H), 2.73-2.61 (m, 2H), 1.79-1.69 (m, 2H), 1.39 (q, J=7.2 Hz, 2H), 1.28 (s, 3H), 0.92 (t, J=7.3 Hz, 3H).

Example 412: (5-methyl-2-oxo-1,3-dioxol-4-yl)methyl 1-((6'-(2H-tetrazol-5-yl)-[1,1':3',1'''-terphenyl]-4-yl)methyl)-4-ethyl-2-propyl-1H-imidazole-5-carboxylate

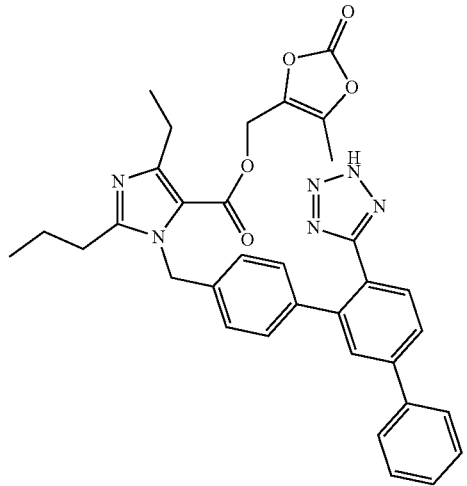

(Ex. 412)

Example 412 was synthesized from Example 396 using the procedure described for Example 411 to give the title compound (Example 412, 4.3 mg, 6.76 μmol, 13.31% yield). ¹H NMR (500 MHz, CDCl₃) δ 8.16 (d, J=8.3 Hz, 1H), 7.83-7.78 (m, 1H), 7.72-7.63 (m, 3H), 7.50 (d, J=7.7 Hz, 2H), 7.47-7.40 (m, 1H), 7.25 (d, J=8.3 Hz, 2H), 6.96 (d, J=8.0 Hz, 2H), 5.52 (s, 2H), 5.00 (s, 2H), 2.88 (d, J=7.4 Hz, 2H), 2.63-2.52 (m, 2H), 2.21 (s, 3H), 1.72 (s, 2H), 1.22 (t, J=7.6 Hz, 3H), 0.97 (t, J=7.4 Hz, 3H). LC-MS (Method A2): 0.89 min, [M+H]⁺=605.2.

Example 413: 2-(1-((6'-(2H-tetrazol-5-yl)-[1,1':3', 1"-terphenyl]-4-yl)methyl)-2-butyl-1H-imidazol-5-yl)-5-methyl-1,3,4-oxadiazole

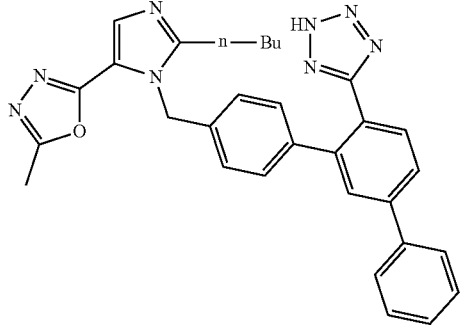
(Ex. 413)

Intermediate 413a: N'-acetyl-2-butyl-1-((6'-cyano-[1,1':3',1"-terphenyl]-4-yl)methyl)-1H-imidazole-5-carbohydrazide

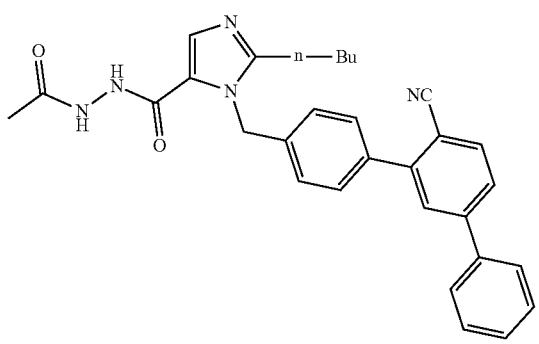
(413a)

2-butyl-1-((6'-cyano-[1,1':3',1"-terphenyl]-4-yl)methyl)-1H-imidazole-5-carboxylic acid (Example 345, 72 mg, 0.132 mmol) was dissolved in DMF (2 mL). Acetohydrazide (68.6 mg, 0.926 mmol) was added followed by HATU (151 mg, 0.397 mmol) and Hunig's Base (0.115 mL, 0.661 mmol). The reaction mixture was allowed to stir for 1 h at RT and was then diluted with EtOAc, washed with 10% LiCl 3×, brine, dried with sodium sulfate, filtered and concentrated. The residue was purified by ISCO (0-25% MeOH in methylene chloride) to afford the title compound N'-acetyl-2-butyl-1-((6'-cyano-[1,1':3',1"-terphenyl]-4-yl)methyl)-1H-imidazole-5-carbohydrazide (413a, 51 mg, 0.104 mmol, 78% yield). LC-MS: MS (ESI) m/z: 492.5 (M+H)⁺. ¹H NMR (500 MHz, CDCl₃) δ 7.80 (d, J=8.0 Hz, 1H), 7.72 (s, 1H), 7.69-7.58 (m, 4H), 7.57-7.42 (m, 5H), 7.29 (s, 1H), 7.14 (d, J=8.3 Hz, 2H), 5.62 (s, 2H), 2.67 (br t, J=7.7 Hz, 2H), 1.98 (s, 3H), 1.67 (br s, 2H), 1.39-1.21 (m, 2H), 0.87 (t, J=7.3 Hz, 3H).

Intermediate 413b: 4"-((2-butyl-5-(5-methyl-1,3,4-oxadiazol-2-yl)-1H-imidazol-1-yl)methyl)-[1,1':3', 1"-terphenyl]-4'-carbonitrile

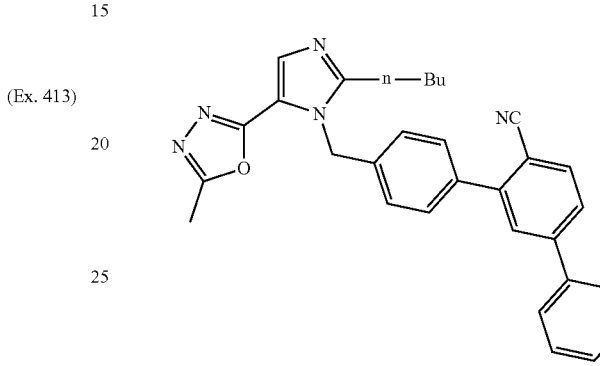
(Ex. 413b)

N'-acetyl-2-butyl-1-((6'-cyano-[1,1':3',1"-terphenyl]-4-yl)methyl)-1H-imidazole-5-carbohydrazide (413a, 51 mg, 0.104 mmol) was dissolved in POCl₃ (1 mL) and the reaction mixture was stirred at 100° C. for 30 min. The reaction mixture was carefully poured into a mixture of ice and 1.5M dipotassium phosphate. The solution was extracted with EtOAc (3×). The combined organic phase was washed with brine, dried with sodium sulfate, filtered and concentrated. The crude residue was purified by ISCO (100% EtOAc in hexanes) to afford the title compound (413b, 18 mg, 0.038 mmol, 36.6% yield). LC-MS: MS (ESI) m/z: 474.5 (M+H)⁺. ¹H NMR (500 MHz, DMSO-d₆) δ 8.02 (d, J=8.0 Hz, 1H), 7.92-7.80 (m, 4H), 7.71-7.65 (m, 3H), 7.53-7.49 (m, J=7.7 Hz, 2H), 7.48-7.43 (m, 1H), 7.20 (d, J=8.0 Hz, 2H), 5.85 (s, 2H), 2.74-2.61 (m, J=7.6, 7.6 Hz, 2H), 2.00 (s, 3H), 1.69-1.53 (m, 2H), 1.37-1.25 (m, J=7.4 Hz, 2H), 1.18 (t, J=7.2 Hz, 3H).

Example 413: 2-(1-((6'-(2H-tetrazol-5-yl)-[1,1':3', 1"-terphenyl]-4-yl)methyl)-2-butyl-1H-imidazol-5-yl)-5-methyl-1,3,4-oxadiazole Example 413 was synthesized from 413b according to the procedure used to synthesize Example 345. The crude residue was purified by reverse phase HPLC (Xbridge Prep Shield RP18, 15 min gradient of 20-100% B. A=H₂O/MeOH 10 mM NH₄OAc 90:10. B=H₂O/MeOH 10 mM NH₄OAc 10:90) to afford the title compound (Example 413, 9.1 mg, 0.018 mmol, 34.8% yield). MS (ESI) m/z (M+H)⁺=517.5. ¹H NMR (500 MHz, DMSO-d₆) δ 7.75 (br. s., 3H), 7.67 (d, J=8.0 Hz, 1H), 7.65-7.56 (m, 2H), 7.48 (t, J=7.5 Hz, 2H), 7.44-7.31 (m, 1H), 7.14 (d, J=8.0 Hz, 2H), 6.93 (d, J=8.0 Hz, 2H), 5.71 (br. s., 2H), 2.62 (t, J=7.5 Hz, 2H), 2.55 (s, 3H), 1 0.62-1.44 (m, J=5.8 Hz, 2H), 1.30-1.16 (m, 2H), 0.83-0.72 (m, 3H). LC-MS retention time (Method A4): 1.551 min.

Example 414: 2-butyl-1-((6'-(methoxycarbonyl)-[1,1':3',1''-terphenyl]-4-yl)methyl)-H-imidazole-5-carboxylic acid

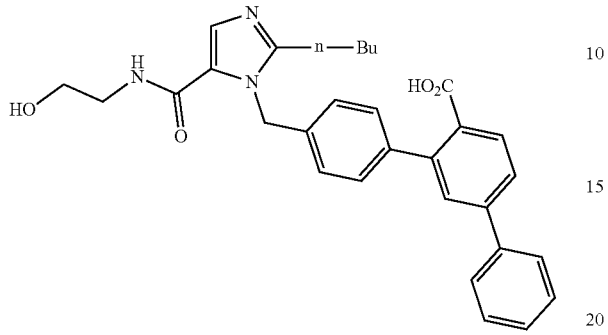
(Ex. 414)

Intermediate 414a: 2-butyl-1-((6'-(methoxycarbonyl)-[1,1':3',1''-terphenyl]-4-yl)methyl)-1H-imidazole-5-carboxylic acid

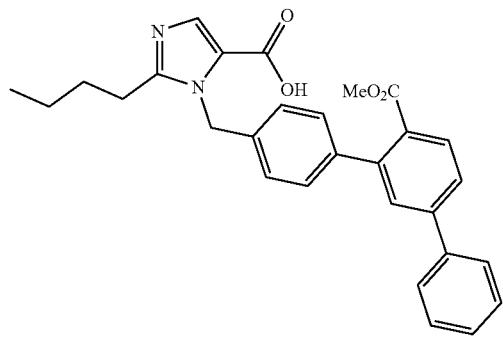
(414a)

Intermediate 414a was synthesized from 345a according to the same sequence used to synthesize 410a. LC-MS (Method A2): 0.850 min, [M+H]$^+$=469.10

Example 414: 2-butyl-1-((6'-(methoxycarbonyl)-11,1':3',1''-terphenyl]-4-yl)methyl)-H-imidazole-5-carboxylic acid 2-Butyl-1-((6'-(methoxycarbonyl)-[1,1':3',1''-terphenyl]-4-yl)methyl)-1H-imidazole-5-carboxylic acid (414a, 35 mg, 0.075 mmol) was dissolved in DMF (2 mL). 2-aminoethanol (22.81 mg, 0.373 mmol) was added followed by HATU (85 mg, 0.224 mmol) and Hunig's Base (0.065 mL, 0.373 mmol). The reaction was allowed to stir for 18 h. The reaction mixture was diluted with EtOAc, washed with 10% LiCi 3×, brine, dried with sodium sulfate, filtered and concentrated. The crude residue was dissolved in 1:1 MeOH/1N NaOH (2 mL) and stirred at 80° C. for 1 h. The reaction mixture was concentrated, dissolved in DMF, filtered and purified by reverse phase HPLC (Xbridge Prep Shield RP18, 15 min gradient of 20-100% B. A=H$_2$O/MeOH 10 mM NH$_4$OAc 90:10. B=H$_2$O/MeOH 10 mM NH$_4$OAc 10:90) to afford the title compound (Example 414, 1.7 mg, 0.0034 mmol, 4.60%). MS (ESI) m/z (M+H)$^+$=498.4. $^1$H NMR (500 MHz, DMSO-d$_6$) δ 8.25 (br. s., 1H), 7.73 (d, J=7.4 Hz, 2H), 7.66 (br. s., 2H), 7.59 (s, 1H), 7.52 (s, 1H), 7.47 (t, J=7.6 Hz, 2H), 7.44-7.35 (m, 3H), 7.03 (d, J=7.9 Hz, 2H), 5.67 (s, 2H), 3.64-3.41 (m, 2H), 3.32-3.20 (m, J=5.9 Hz, 2H), 2.61-2.56 (m, 2H), 1.63-1.46 (m, 2H), 1.37-1.19 (m, 2H), 1.00 (d, J=6.2 Hz, 1H), 0.82 (t, J=7.3 Hz, 3H). LC-MS retention time (Method A4): 1.703 min.

Example 415: 2-butyl-1-((6'-carboxy-[1,1':3',1''-terphenyll-4-yl)methyl)-1H-imidazole-5-carboxylic acid

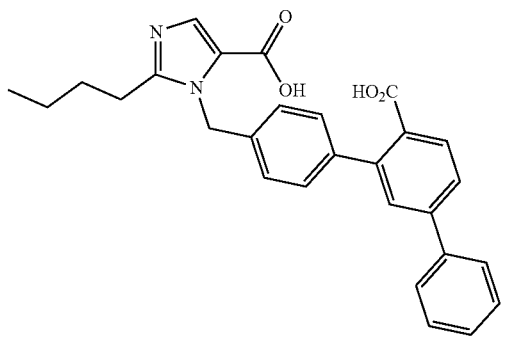
(Ex. 415)

Example 415 was synthesized from 345a according to the same sequence used to synthesize Example 410. MS (ESI) m/z (M+H)$^+$=454.9. $^1$H NMR (500 MHz, DMSO-d$_6$) δ 7.80-7.66 (m, 4H), 7.56-7.43 (m, 4H), 7.42-7.32 (m, 3H), 7.04 (d, J=7.8 Hz, 2H), 5.69 (br. s., 2H), 2.61-2.56 (m, 2H), 1.50 (quin, J=7.4 Hz, 2H), 1.29-1.13 (m, 2H), 0.78 (t, J=7.3 Hz, 3H). LC-MS retention time (Method A4): 1.731 min.

Example 416: 2-butyl-4-chloro-1-((5'-(3,3-difluoropiperidin-1-yl)-2'-(2H-tetrazol-5-yl)-[1,1'-biphenyl]-4-yl)methyl)-1H-imidazole-5-carboxylic acid

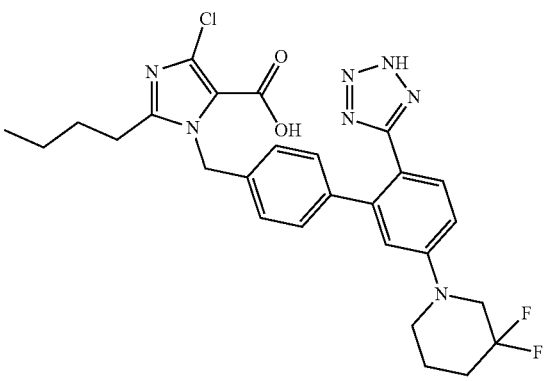
(Ex. 416)

Intermediate 416a: 2-butyl-4-chloro-1-((2'-cyano-5'-(3,3-difluoropiperidin-1-yl)-[1,1'-biphenyl]-4-yl)methyl)-1H-imidazole-5-carboxylic acid, TFA salt Example 417: 1-((5'-(1H-indol-1-yl)-2'-(2H-tetrazol-5-yl)-[1,1'-biphenyl]-4-yl)methyl)-2-butyl-4-chloro-1H-imidazole-5-carboxylic acid

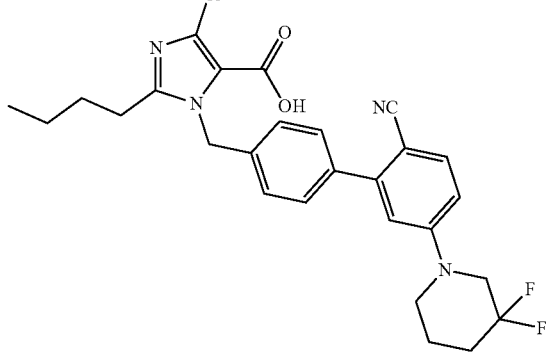

(416a)

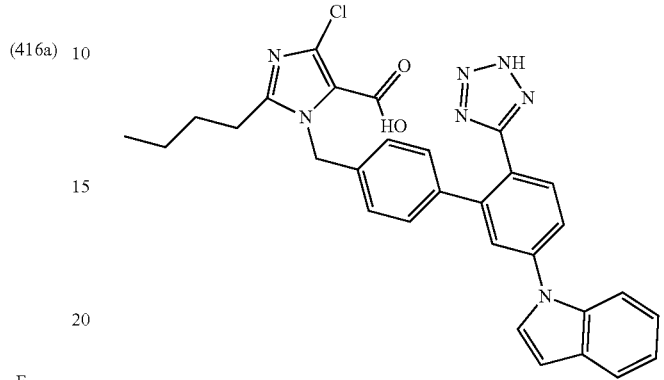

(Ex.417)

416a was synthesized from 3,3-difluoropiperidine hydrochloride according to the procedure used to synthesize 405a to give the title compound (416a, 130 mg, 0.207 mmol, 56.9% yield). LC-MS: MS (ESI) m/z: 513.10 (M+H)$^+$. $^1$H NMR (500 MHz, DMSO-d$_6$) δ 7.66 (d, J=8.8 Hz, 1H), 7.55 (d, J=8.3 Hz, 2H), 7.26 (t, J=7.3 Hz, 2H), 7.21-7.07 (m, 2H), 7.02 (d, J=2.8 Hz, 1H), 5.67 (s, 2H), 3.81 (br t, J=12.0 Hz, 2H), 3.55-3.34 (m, 2H), 2.69-2.57 (m, 2H), 2.13-2.04 (m, 2H), 1.75 (br d, J=4.4 Hz, 2H), 1.56 (br t, J=7.6 Hz, 2H), 1.35-1.20 (m, 2H), 0.83 (t, J=7.3 Hz, 3H).

Example 416: 2-butyl-4-chloro-1-((5'-(3,3-difluoropiperidin-1-yl)-2'-(2H-tetrazol-5-yl)-[1,1'-biphenyl]-4-yl)methyl)-1H-imidazole-5-carboxylic acid Example 416 was synthesized from 416a according to the procedure described for Example 345. The crude mixture was purified by reverse phase HPLC (Xbridge Prep Shield RP18, 15 min gradient of 20-100% B. A=H$_2$O/MeOH 10 mM NH$_4$OAc 90:10. B=H$_2$O/MeOH 10 mM NH$_4$OAc 10:90) to afford the title compound (Example 416, 4.2 mg, 7.55 μmol, 9.01% yield). MS (ESI) m/z (M+H)*=556.0. $^1$H NMR (500 MHz, DMSO-d$_6$) δ 7.43 (d, J=8.5 Hz, 1H), 7.07 (br d, J=7.9 Hz, 3H), 6.89 (br d, J=7.6 Hz, 3H), 5.65 (s, 2H), 3.32 (br s, 1H), 2.87 (q, J=7.0 Hz, 1H), 2.52 (br s, 2H), 2.12-1.97 (m, 2H), 1.91 (s, 1H), 1.79 (br s, 2H), 1.50 (quin, J=7.5 Hz, 2H), 1.13 (s, 4H), 0.82 (t, J=7.3 Hz, 3H. LC-MS retention time (Method A4): 1.810 min.

Example 417 was synthesized from indoline and 384b according to the sequence described for Example 416. The crude mixture was purified by reverse phase HPLC (Xbridge Prep Shield RP18, 15 min gradient of 20-100% B. A=H$_2$O/MeOH 10 mM NH$_4$OAc 90:10. B=H$_2$O/MeOH 10 mM NH$_4$OAc 10:90) to afford the title compound 2-butyl-4-chloro-1-((5'-(3,3-difluoropiperidin-1-yl)-2'-(2H-tetrazol-5-yl)-[1,1'-biphenyl]-4-yl)methyl)-1H-imidazole-5-carboxylic acid (416, 4.2 mg, 7.55 μmol, 9.01% yield). MS (ESI) m/z (M+H)$^+$=552.2. $^1$H NMR (500 MHz, DMSO-d$_6$) δ 7.80-7.71 (m, 2H), 7.71-7.58 (m, 3H), 7.44 (s, 1H), 7.25-7.11 (m, 4H), 6.90 (br d, J=7.9 Hz, 2H), 6.71 (d, J=3.1 Hz, 1H), 5.69 (br s, 2H), 2.56-2.53 (m, 2H), 1.54-1.42 (m, 2H), 1.32-1.18 (m, 2H), 0.78 (t, J=7.3 Hz, 3H). LC-MS retention time (Method A4): 2.063 min.

Example 418: (S)-2-butyl-4-chloro-1-((5'-(3-methylpiperidin-1-yl)-2'-(2H-tetrazol-5-yl)-[1,1'-biphenyl]-4-yl)methyl)-1H-imidazole-5-carboxylic acid

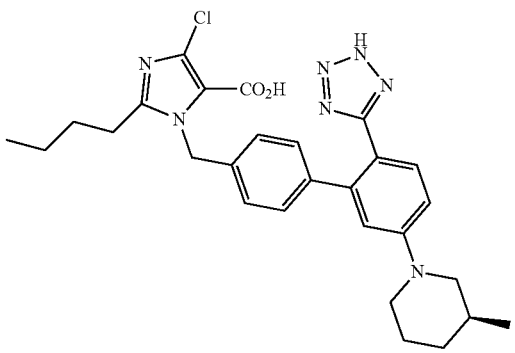

(Ex. 418)

Intermediate 418a: (S)-2-butyl-4-chloro-1-((5'-(3-methylpiperidin-1-yl)-2'-(2-trityl-2H-tetrazol-5-yl)-[1,1'-biphenyl]-4-yl)methyl)-1H-imidazole-5-carbaldehyde

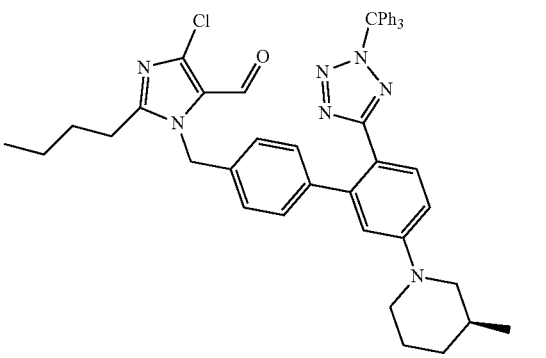

(418a)

To a small vial containing (S)-4'-((2-butyl-4-chloro-5-formyl-1H-imidazol-1-yl)methyl)-5-(3-methylpiperidin-1-yl)-[1,1'-biphenyl]-2-carbonitrile (407b, 90 mg, 0.189 mmol) was added dibutyltin oxide (47.2 mg, 0.189 mmol) and toluene (1 mL) followed by TMS-N$_3$ (0.126 mL, 0.947 mmol). The reaction mixture was sealed and heated at 100° C. for 20 hours. The reaction mixture was concentrated to dryness. The crude residue was dissolved in DCM (2 mL). TEA (0.086 mL, 0.615 mmol) was added followed by trityl-C$_1$ (129 mg, 0.461 mmol). The reaction mixture was allowed to stir at RT for 2 h. The reaction mixture was then diluted with DCM, washed with 1.5M dipotassium phosphate, brine, dried with sodium sulfate, filtered and concentrated. The product was brought forward without further purification. LC-MS (Method A2): 1.20 min, [M+H]f=760.3.

Intermediate 418b: (S)-2-butyl-4-chloro-1-((5'-(3-methylpiperidin-1-yl)-2'-(2-trityl-2H-tetrazol-5-yl)-[1,1'-biphenyl]-4-yl)methyl)-1H-imidazole-5-carboxylic acid

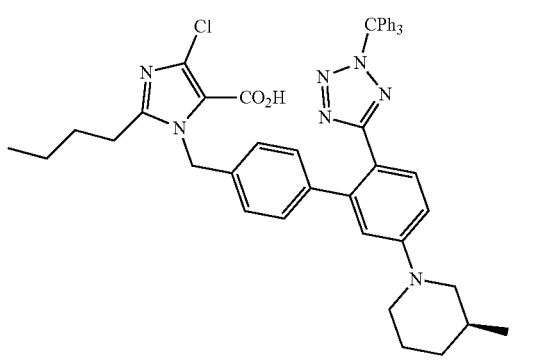

(418b)

418b was synthesized from 418a according to the same procedure described for 345c. The product was brought forward without further purification. LC-MS (Method A2): 1.16 min, [M+H]$^+$=776.08.

Example 418: (S)-2-butyl-4-chloro-1-((5'-(3-methylpiperidin-1-yl)-2'-(2H-tetrazol-5-yl)-[1,1'-biphenyl]-4-yl)methyl)-1H-imidazole-5-carboxylic acid Example 418 was prepared from 418b according to the same procedure described for Example 384. The crude mixture was purified by reverse phase HPLC (Xbridge Prep Shield RP18, 15 min gradient of 20-100% B. A=H$_2$O/MeOH 10 mM NH$_4$OAc 90:10. B=H$_2$O/MeOH 10 mM NH$_4$OAc 10:90) to afford the title compound (Example 418, 7.3 mg, 0.014 mmol, 14.60% yield). MS (ESI) m/z (M+H)$^{+0}$=534.1. $^1$H NMR (500 MHz, DMSO-d$_6$) δ 7.44 (d, J=8.6 Hz, 1H), 7.15-7.04 (m, J=8.0 Hz, 2H), 7.00 (dd, J=8.6, 2.3 Hz, 1H), 6.96-6.90 (m, J=7.9 Hz, 2H), 6.83 (d, J=2.2 Hz, 1H), 5.64 (s, 2H), 2.79-2.65 (m, 2H), 2.57-2.53 (m, 2H), 2.47-2.35 (m, 1H), 1.71 (br dd, J=9.9, 3.3 Hz, 3H), 1.63-1.46 (m, 3H), 1.36-1.22 (m, 3H), 1.09 (br dd, J=11.5, 3.2 Hz, 1H), 0.93 (d, J=6.6 Hz, 3H), 0.83 (t, J=7.3 Hz, 3H. LC-MS retention time (Method A4): 1.780 min.

Example 419: (R)-2-butyl-4-chloro-1-((5'-(3-methylpiperidin-1-yl)-2'-(2H-tetrazol-5-yl)-[1,1'-biphenyl]-4-yl)methyl)-1H-imidazole-5-carboxylic acid

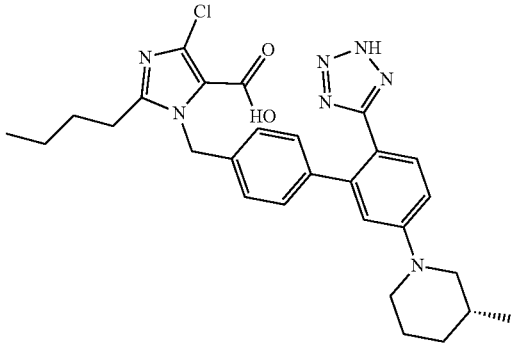

(Ex. 419)

Example 419 was synthesized from (R)-3-methylpiperidine hydrochloride using the same sequence described for Example 418. The crude mixture was purified by reverse phase HPLC: Column: XBridge C18, 19×200 mm, 5-µm particles; Mobile Phase A: 5:95 ACN: H$_2$O with 0.1% trifluoroacetic acid; Mobile Phase B: 95:5 ACN: H$_2$O with 0.1% trifluoroacetic acid; Gradient: 26-66% B over 20 min, then a 4-minute hold at 100% B; Flow: 20 mL/min to afford the title compound (R)-2-butyl-4-chloro-1-((5'-(3-methylpiperidin-1-yl)-2'-(2H-tetrazol-5-yl)-[1,1'-biphenyl]-4-yl)methyl)-1H-imidazole-5-carboxylic acid (Example 419, 1.7 mg, 3.18 µmol, 8.23% yield). LC-MS (Method A2): 1.811 min, [M+H]$^+$=534.4. $^1$H NMR (500 MHz, DMSO-d$_6$) δ 7.45 (d, J=8.5 Hz, 1H), 7.14-7.02 (m, J=7.9 Hz, 3H), 6.95 (br d, J=7.9 Hz, 2H), 6.87 (s, 1H), 5.60 (s, 2H), 3.79 (br t, J=13.7 Hz, 1H), 3.40-3.23 (m, 1H), 3.21-3.12 (m, 1H), 2.79-2.64 (m, 1H), 2.49-2.31 (m, 2H), 1.77 (br d, J=10.4 Hz, 1H), 1.73-1.61 (m, 2H), 1.60-1.40 (m, 4H), 1.31-1.16 (m, 2H), 1.01 (d, J=6.4 Hz, 3H), 0.88-0.74 (m, 3H).

Example 420: (S)-2-butyl-4-chloro-1-((5'-(3-methylpiperidin-1-yl)-2'-(2H-tetrazol-5-yl)-[1,1'-biphenyl]-4-yl)me

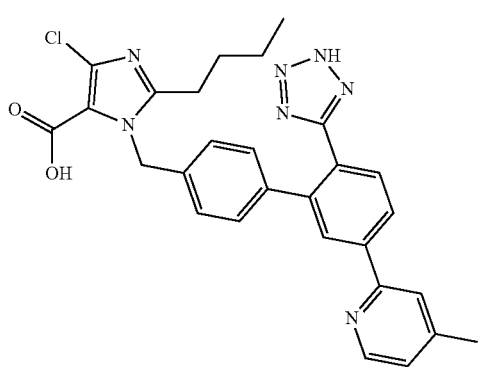
(Ex. 420)

Example 421: 2-butyl-4-chloro-1-((5'-(4-methoxypyridin-2-yl)-2'-(2H-tetrazol-5-yl)-[1,1'-biphenyl]-4-yl)methyl)-1H-imidazole-5-carboxylic acid

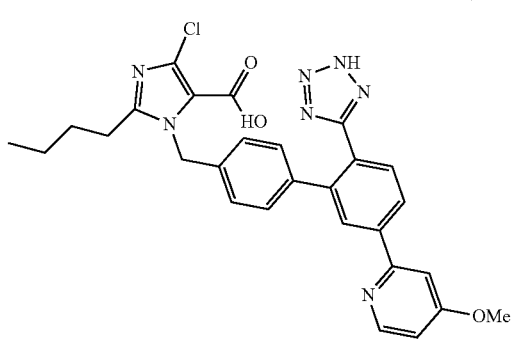
(Ex. 421)

To a pressure-rated vial containing 2-butyl-4-chloro-1-((5'-chloro-2'-(2-trityl-2H-tetrazol-5-yl)-[1,1'-biphenyl]-4-yl)methyl)-1H-imidazole-5-carboxylic acid (384d, 65 mg, 0.091 mmol), 2nd generation xphos precatalyst (14.33 mg, 0.018 mmol) and bis(pinacolato)diborane (34.7 mg, 0.137 mmol) was added dioxane (2 mL) followed by KOAc (44.7 mg, 0.455 mmol). The reaction mixture was evacuated and backfilled with $N_2$ (3×) then heated at 85° C. for 18 h. To the reaction mixture was then added additional 2nd generation xphos precatalyst (14.33 mg, 0.018 mmol) as well as 2-bromo-4-methylpyridine (94 mg, 0.546 mmol) and 2-bromo-4-methylpyridine (94 mg, 0.546 mmol). The reaction mixture was evacuated and backfilled with $N_2$ (3×) then allowed to stir at 85° C. for 18 h. The reaction mixture was diluted with EtOAc, filtered through celite. The filtrate was concentrated then redissolved in DCM (2 mL). Triethylsilane (0.145 mL, 0.911 mmol) was added followed by TFA (0.351 mL, 4.55 mmol). The reaction mixture was allowed to stir at RT for 30 min. The mixture was then concentrated, dissolved in DMF, filtered and purified by reverse phase HPLC (Xbridge Prep Shield RP18, 15 min gradient of 20-100% B. A=$H_2O$/MeOH 10 mM $NH_4OAc$ 90:10. B=$H_2O$/MeOH 10 mM $NH_4OAc$ 10:90) to afford the title compound (2.2 mg, 4.17 μmol, 4.57% yield). MS (ESI) m/z (M−H)$^{−}$=525.9. $^1$H NMR (500 MHz, DMSO-$d_6$) δ 8.56 (d, J=4.9 Hz, 1H), 8.24 (br d, J=7.9 Hz, 1H), 8.01 (s, 1H), 7.78 (d, J=8.2 Hz, 1H), 7.33-7.27 (m, 2H), 7.21-7.14 (m, 3H), 6.99 (br d, J=7.9 Hz, 2H), 5.60 (s, 2H), 2.61-2.56 (m, 2H), 2.42 (s, 3H), 1.50 (br t, J=7.3 Hz, 2H), 1.30-1.19 (m, 2H), 0.81 (t, J=7.3 Hz, 3H. LC-MS retention time (Method A4): 1.409 min.

Example 421 was prepared according to the same procedure as described for Example 420 to give the title compound (Example 421, 0.5 mg, 0.00092 mmol, 1.5%). MS (ESI) m/z (M+H)$^{+}$=544.1. $^1$H NMR (500 MHz, DMSO-$d_6$) δ 8.48 (d, J=5.5 Hz, 1H), 8.13 (br d, J=7.9 Hz, 1H), 8.06 (s, 1H), 7.72 (d, J=7.9 Hz, 1H), 7.59 (d, J=1.8 Hz, 1H), 7.18 (br d, J=8.2 Hz, 2H), 7.07-6.87 (m, 3H), 5.63 (br s, 2H), 3.93 (s, 3H), 1.61-1.44 (m, 2H), 1.34-1.20 (m, 2H), 0.84 (t, J=7.3 Hz, 3H). LC-MS retention time (Method A4): 1.235 min.

Example 422: 2-butyl-4-chloro-1-((5'-(4,4,5,5-tetramethyl-1,3,2-dioxaborolan-2-yl)-2'-(2-trityl-2H-tetrazol-5-yl)-[1,1'-biphenyl]-4-yl)methyl)-1H-imidazole-5-carboxylic acid

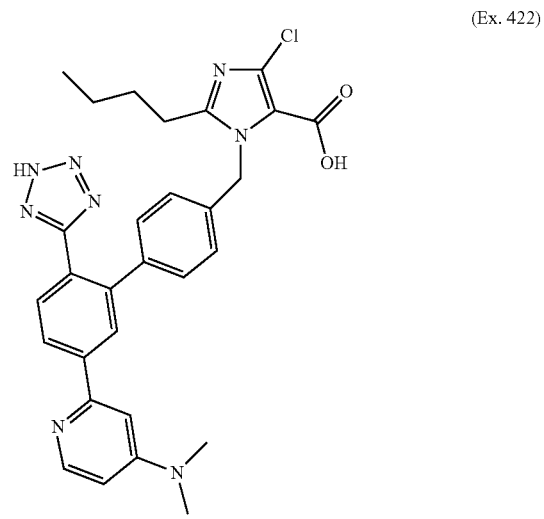 [SMILES: CCCCc1nc(Cl)c(C(=O)O)n1Cc1ccc(-c2cc(-c3cc(N(C)C)ccn3)ccc2-c2nn[nH]n2)cc1]
(Ex. 422)

Intermediate 422a: 2-butyl-4-chloro-1-((5'-(4,4,5,5-tetramethyl-1,3,2-dioxaborolan-2-yl)-2'-(2-trityl-2H-tetrazol-5-yl)-[1,1'-biphenyl]-4-yl)methyl)-1H-imidazole-5-carboxylic acid

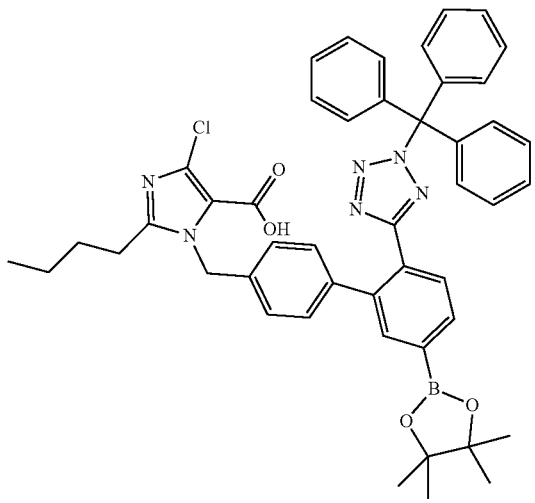
(422a)

To a pressure-rated vial containing 2-butyl-4-chloro-1-((5'-chloro-2'-(2-trityl-2H-tetrazol-5-yl)-[1,1'-biphenyl]-4-yl)methyl)-1H-imidazole-5-carboxylic acid (384d, 0.615 g, 0.862 mmol), bis(pinacolato)diborane (0.438 g, 1.724 mmol) Pd$_2$(dba)$_3$ (79 mg, 0.086 mmol) was added dioxane (7 ml) followed by KOAc (0.423 g, 4.31 mmol). The reaction mixture was evacuated and backfilled with N$_2$ (3×) and heated at 105° C. for 40 min. The reaction mixture was then diluted with EtOAc and filtered through celite. The filtrate was then concentrated and the crude residue was suspended in hexanes. The filtered off solid was purified by ISCO (0-20% MeOH/DCM) to afford the title compound (0.7 g, 0.869 mmol, 50.4% yield). LC-MS (Method A2): 1.24 min, [M+H]$^+$=805.4.

Example 422: 2-butyl-4-chloro-1-((5'-(4-(dimethylamino)pyridin-2-yl)-2'-(2H-tetrazol-5-yl)-[1,1'-biphenyl]-4-yl)methyl)-1H-imidazole-5-carboxylic acid To a vial containing 2-bromo-N,N-dimethylpyridin-4-amine (6.49 mg, 0.032 mmol) was added chloro(2-dicyclohexylphosphino-2',4',6'-triisopropyl-1,1'-biphenyl)[2-(2'-amino-1,1'-biphenyl)]palladium(ii) (XPhos Pd G2) (5.08 mg, 6.46 µmol) followed by 2-butyl-4-chloro-1-((5'-(4,4,5,5-tetramethyl-1,3,2-dioxaborolan-2-yl)-2'-(2-trityl-2H-tetrazol-5-yl)-[1,1'-biphenyl]-4-yl)methyl)-1H-imidazole-5-carboxylic acid (422a, 0.064M in dioxane, 0.497 mL, 0.032 mmol) and tripotassium phosphate (0.042 mL, 0.084 mmol).

The vial was evacuated and backfilled with Ar (2×), sealed with septa caps and stirred at 105° C. for 2 h. The reaction mixture was filtered and dissolved in DCM (0.5 mL). Triethylsilane (0.022 mL, 0.136 mmol) and TFA (0.095 mL, 1.227 mmol) were added. The resulting reaction mixture was then stirred at RT for 1 h then concentrated, dissolved in DMF, filtered and purified by reverse phase HPLC (Xbridge Prep Shield RP18, 15 min gradient of 20-100% B. A=H$_2$O/MeOH 10 mM NH$_4$OAc 90:10. B=H$_2$O/MeOH 10 mM NH$_4$OAc 10:90) to afford the title compound (Example 422, 0.7 mg, 0.0012 mmol, 3.9%). LC-MS (Method A4): 1.279 min, [M+H]$^+$=557.2; $^1$H NMR (500 MHz, DMSO-d$_6$) δ 8.21 (d, J=5.8 Hz, 1H), 8.02 (br d, J=7.9 Hz, 1H), 7.94 (s, 1H), 7.65 (br d, J=8.2 Hz, 1H), 7.12 (br d, J=7.0 Hz, 3H), 6.91 (br d, J=7.6 Hz, 2H), 6.60 (br d, J=5.8 Hz, 1H), 5.76 (br s, 2H), 2.49-2.39 (m, 2H), 1.91 (s, 6H), 1.51 (br t, J=7.0 Hz, 2H), 1.30-1.13 (m, 2H), 0.90-0.74 (m, 3H).

Example 423: 2-butyl-4-chloro-1-((5'-(6-(difluoromethyl)pyridin-2-yl)-2'-(2H-tetrazol-5-yl)-[1,1'-biphenyl]-4-yl)methyl)-1H-imidazole-5-carboxylic acid

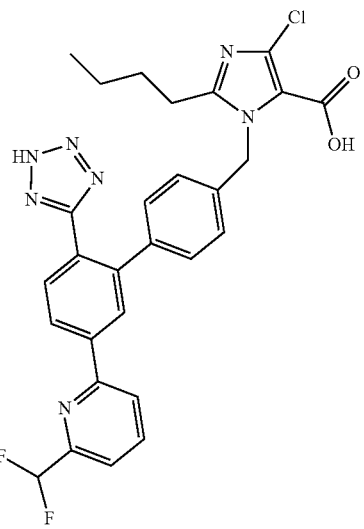
(Ex. 423)

Example 423 was synthesized from 2-bromo-6-(difluoromethyl)pyridine using the same procedure described for Example 422 to give the title compound (2.3 mg, 0.0041 mmol, 12.8%). LC-MS (Method A4): 1.379 min, [M+H]$^+$=564.1; $^1$H NMR (500 MHz, DMSO-d$_6$) δ 8.29 (br d, J=7.9 Hz, 1H), 8.21 (br d, J=7.9 Hz, 1H), 8.17-8.08 (m, 2H), 7.81 (br d, J=8.2 Hz, 1H), 7.70 (br d, J=7.6 Hz, 1H), 7.18 (br d, J=7.9 Hz, 2H), 7.16-6.91 (m, J=55.1, 55.1 Hz, 1H), 6.97 (br d, J=7.6 Hz, 2H), 5.62 (br s, 2H), 1.59-1.48 (m, 2H), 1.33-1.14 (m, 4H), 0.84 (br t, J=7.3 Hz, 3H).

Example 424: 2-butyl-4-chloro-1-((5'-cyclohexyl-2'-(2H-tetrazol-5-yl)-[1,1'-biphenyl]-4-yl)methyl)-1H-imidazole-5-carboxylic acid

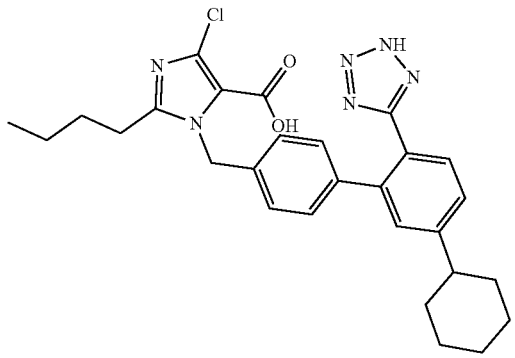

(Ex. 424)

Intermediate 424a: lithium 2-butyl-4-chloro-1-((5'-chloro-2'-cyano-[1,1'-biphenyl]-4-yl)methyl)-1H-imidazole-5-carboxylate

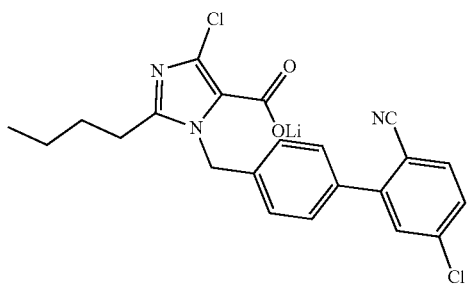

(424a)

2-butyl-4-chloro-1-((5'-chloro-2'-cyano-[1,1'-biphenyl]-4-yl)methyl)-1H-imidazole-5-carboxylic acid (384b, 2 g, 4.67 mmol) was dissolved in Tetrahydrofuran (20 mL). 1M LiOH (5.14 mL, 5.14 mmol) was added and the reaction was allowed to stir at RT for 30 min. The reaction was concentrated to dryness and azeotroped with toluene (3×) to yield the title compound. The product was brought forward without further purification. LC-MS (Method A2): 0.96 min, [M+H]$^+$=428.0;

Intermediate 424b: 2-butyl-4-chloro-1-((6'-cyano-2'',3'',4'',5''-tetrahydro-[1,1':3',1''-terphenyl]-4-yl)methyl)-1H-imidazole-5-carboxylic acid

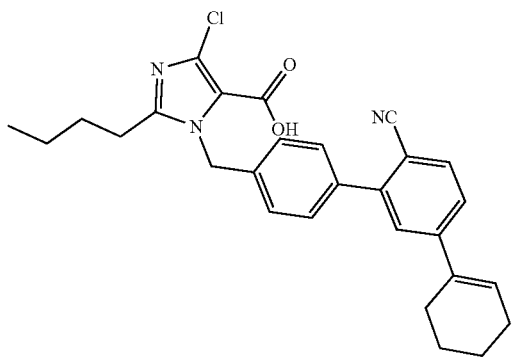

(424b)

Lithium 2-butyl-4-chloro-1-((5'-chloro-2'-cyano-[1,1'-biphenyl]-4-yl)methyl)-1H-imidazole-5-carboxylate (424a, 200 mg, 0.461 mmol), cyclohex-1-en-1-ylboronic acid (69.6 mg, 0.553 mmol), 2nd generation xphos precatalyst (36.2 mg, 0.046 mmol) and 2M K$_3$PO$_4$ (0.461 mL, 0.921 mmol) were dissolved in dioxane (2 mL). The reaction mixture was evacuated and backfilled with N$_2$ (3×) then heated at 85° C. for 1 hour. The reaction mixture was diluted with EtOAc and concentrated onto celite and purified by ISCO (0-20% MeOH/DCM) to afford the title compound 2-butyl-4-chloro-1-((6'-cyano-2'',3'',4'',5''-tetrahydro-[1,1':3',1''-terphenyl]-4-yl)methyl)-1H-imidazole-5-carboxylic acid (424b, 200 mg, 0.139 mmol, 30.2% yield). LC-MS (Method A2): 1.11 min, [M+H]$^+$=474.0;

Intermediate 424c: 2-butyl-4-chloro-1-((2'-cyano-5'-cyclohexyl-[1,1'-biphenyl]-4-yl)methyl)-1H-imidazole-5-carboxylic acid

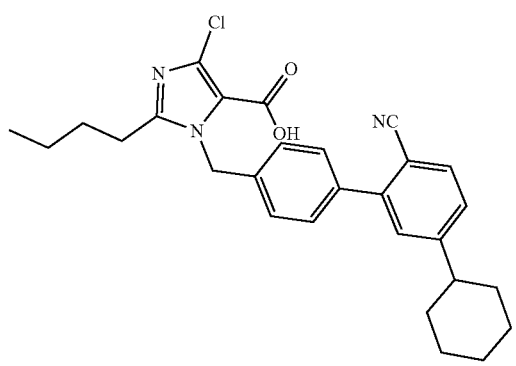

(424c)

2-butyl-4-chloro-1-((6'-cyano-2'',3'',4'',5''-tetrahydro-[1,1':3',1''-terphenyl]-4-yl)methyl)-1H-imidazole-5-carboxylic acid (424b, 200 mg, 0.127 mmol) was dissolved in MeOH (15 mL). Pd-C(26.9 mg, 0.025 mmol) was added and the reaction mixture was evacuated and backfilled with 1 atm of H$_2$. The reaction mixture was allowed to stir at RT for 60 min. The reaction mixture was then evacuated and backfilled with N$_2$ (3×) then filtered through celite. The filtrate was concentrated and purified by Prep HPLC (0-100% A/B 10 minute gradient Solvent A: 10% ACN-90% H$_2$O-0.1% TFA, Solvent B: 90% ACN-10% H$_2$O-0.1% TFA Vial: 51 Column: 2: Phenomenex Luna Axia 5u 30×100 (10 min grad)) to afford the title compound (424c, 38 mg, 0.080 mmol, 63.1% yield). LC-MS (Method A2): 1.12 min, [M+H]$^+$= 476.0;

Example 424: 2-butyl-4-chloro-1-((5'-cyclohexyl-2'-(2H-tetrazol-5-yl)-[1,1'-biphenyl]-4-yl)methyl)-1H-imidazole-5-carboxylic acid Example 424 was synthesized from 424c using the procedure described for Example 345. The crude residue was purified by reverse phase HPLC (Column: XBridge C18, 19×200 mm, 5-μm particles; Mobile Phase A: 5:95 ACN: H$_2$, with 0.1% trifluoroacetic acid; Mobile Phase B: 95:5 ACN: H$_{27}$ with 0.13% trifluoroacetic acid; Gradient: 42-82% B over 20 mi, then a 6-minute hold at 100% B; Flow: 20 mL/min) to afford the title compound 2-butyl-4-chloro-1-((5'-cyclohexyl-2'-(2H-tetrazol-5-yl)-[1,1'-biphenyl]-4-yl)methyl)-1H-imidazole-5-carboxylic acid (Example 424, 4.0 mg, 7.71 μmol, 23.93% yield). MS (ESI) m/z (M+H)$^+$=519.1. $^1$H NMR (500 MHz, DMSO-d$_6$) δ 7.56 (hr d, J=7.9 Hz, 1H), 7.43 (br d, J=7.6 Hz, 1H), 7.34 (br s, H), 7.08 (br d, J=7.3 Hz, 2H), 6.96 (br d, J=7.9 Hz, 2H), 5.60 (s, 2H), 1.89-1.82 (n, 1=13.1 Hz, 3H), 1.80 (hr s, ,H), 1.71 (hr s, H), 1.55-1.34 (m, 7H), 1.33-1.16 (s, 4H), 0.82 (t, J=7.3 Hz, 4H). LC-MS retention time (Method A4): 2.192 mAr.

The compounds in the following table are prepared using the methods for Example 396 and Example 398, respectively: IDC-65 1,TRE

| Ex | Structure | MW | LC-MS m/z [M + H]$^+$; RT (Method) | $^1$H NMR (500 MHz, DMSO-d$_6$) δ ppm |
|---|---|---|---|---|
| 425 | 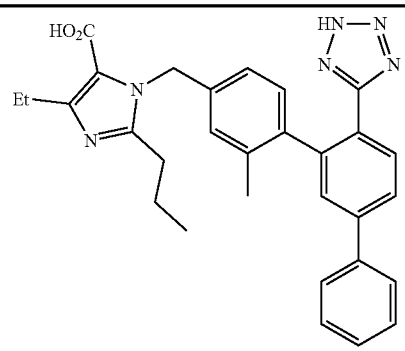 | 506.61 | 507.23; 1.55 min (Method A4) | 7.94-7.83 (m, 2H), 7.80 (br d, J = 7.3 Hz, 2H), 7.62 (s, 1H), 7.54-7.40 (m, 3H), 7.17-7.02 (m, 2H), 7.00 (s, 1H), 6.81 (br d, J = 7.6 Hz, 1H), 5.67 (br s, 2H), 2.91 (q, J = 7.3 Hz, 2H), 1.96 (s, 3H), 1.58-1.49 (m, 2H), 1.21 (t, J = 7.5 Hz, 3H), 0.86 (t, J = 7.3 Hz, 3H). |
| 426 | 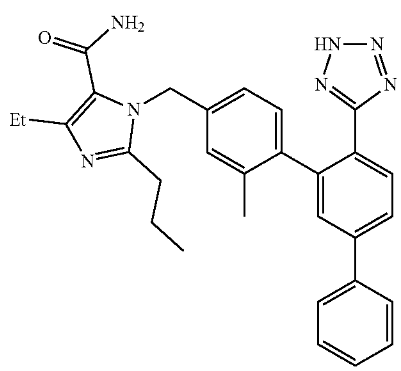 [SMILES: CCCc1nc(CC)c(C(N)=O)n1Cc1ccc(-c2cc(-c3ccccc3)ccc2-c2nn[nH]n2)c(C)c1] | 505.63 | 506.2; 1.51 min (Method A4) | 7.88 (d, J = 7.9 Hz, 1H), 7.79-7.70 (m, 3H), 7.47 (t, J = 7.5 Hz, 2H), 7.43 (s, 1H), 7.41-7.31 (m, 3H), 7.00 (d, J = 7.6 Hz, 1H), 6.90 (s, 1H), 6.77 (br d, J = 7.9 Hz, 1H), 5.39 (s, 2H), 2.68 (q, J = 7.3 Hz, 2H), 1.89 (s, 3H), 1.62-1.54 (m, 2H), 1.15 (t, J = 7.5 Hz, 3H), 0.88 (t, J = 7.3 Hz, 3H). |

Example 427: 2-Butyl-4-chloro-1-((5'-(pyridin-2-yloxy)-2'-(2H-tetrazol-5-yl)-[1,1'-biphenyl]-4-yl)methyl)-1H-imidazole-5-carboxylic acid Intermediate 427a: 4'-((2-Butyl-4-chloro-5-formyl-1H-imidazol-1-yl)methyl)-5-hydroxy-[1,1'-biphenyl]-2-carbonitrile

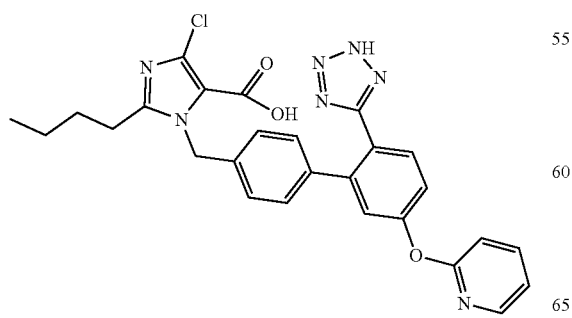

(Ex.427)

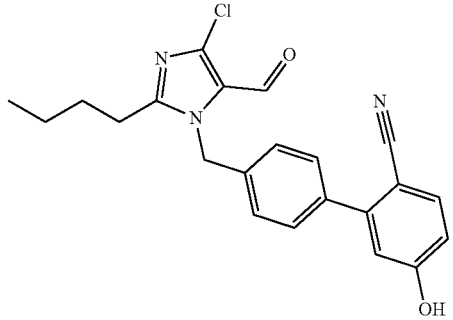

(427a)

The title compound was obtained from 2-butyl-4-chloro-1-(4-(4,4,5,5-tetramethyl-1,3,2-dioxaborolan-2-yl)benzyl)-1H-imidazole-5-carbaldehyde (Intermediate 35a) and 2-bromo-4-hydroxybenzonitrile, according to the procedure described for the synthesis of Intermediate 247a. LC-MS (Method H): 1.26 min, [M+H]$^+$=394.0. HRMS (ESI): Calcd. for $C_{22}H_{21}ClN_3O_2$[M+H]$^+$ m/z 394.1317; found 394.1294.

Intermediate 427b: 4'-((2-Butyl-4-chloro-5-formyl-1H-imidazol-1-yl)methyl)-5-(pyridin-2-yloxy)-[1,1'-biphenyl]-2-carbonitrile (427b)

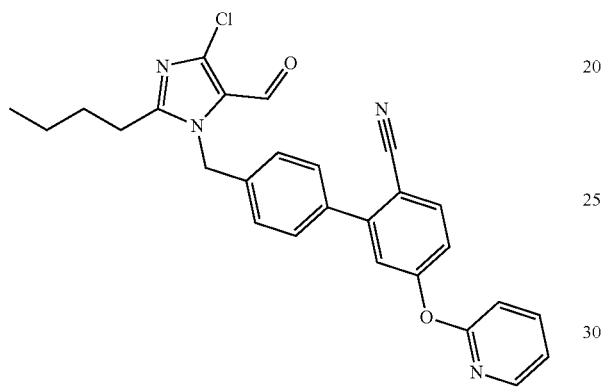

The title compound was prepared from 4'-((2-butyl-4-chloro-5-formyl-1H-imidazol-1-yl)methyl)-5-hydroxy-[1,1'-biphenyl]-2-carbonitrile (Intermediate 427a) and 2-chloropyridine, according to the method described for the synthesis of Example 247. LC-MS (Method H): 1.36 min, [M+H]$^+$=471.1. HRMS (ESI): Calcd. for $C_{27}H_{24}ClN_4O_2$[M+H]$^+$ m/z 471.1582; found 471.1577.

Intermediate 427c: 2-Butyl-4-chloro-1-((2'-cyano-5'-(pyridin-2-yloxy)-[1,1'-biphenyl]-4-yl)methyl)-1H-imidazole-5-carboxylic acid (427c)

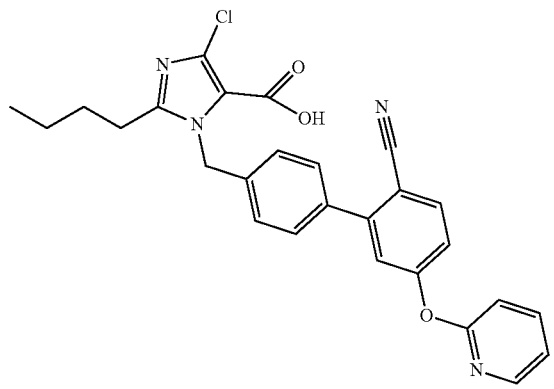

4'-((2-Butyl-4-chloro-5-formyl-1H-imidazol-1-yl)methyl)-5-(pyridin-2-yloxy)-[1,1'-biphenyl]-2-carbonitrile was converted to the title compound using an oxidation procedure similar to that described for the synthesis of 345b. LC-MS (Method H): 1.44 min, [M+H]$^+$=487.1. HRMS (ESI): Calcd. for $C_{27}H_{24}ClN_4O_3$[M+H]$^+$ m/z 487.1531; found 487.1537. $^1$H NMR (400 MHz, DMSO-d$_6$) δ ppm 8.22 (m, 1H), 7.98 (d, J=8.2 Hz, 1H), 7.93 (m, 1H), 7.58 (d, J=8.2 Hz, 2H) 7.34 (m, 2H), 7.21 (m, 1H), 7.15 (m, 3H), 5.67 (s, 2H), 2.62 (t, J=7.2 Hz, 2H), 1.51 (m, 2H), 1.19 (m, 2H), 0.79 (t, J=7.2 Hz, 3H).

Example 427: 2-Butyl-4-chloro-1-((5'-(pyridin-2-yloxy)-2'-(2H-tetrazol-5-yl)-[1,1'-biphenyl]-4-yl)methyl)-1H-imidazole-5-carboxylic acid The title compound was prepared from 2-butyl-4-chloro-1-((2'-cyano-5'-(pyridin-2-yloxy)-[1,1'-biphenyl]-4-yl)methyl)-1H-imidazole-5-carboxylic acid (Intermediate 427c), according to the procedure described for the synthesis of Example 345. LC-MS (Method H): 1.29 min, [M+H]$^+$=530.1. HRMS (ESI): Calcd. for $C_{27}H_{24}ClN_7O_3$[M+H]$^+$ m/z 530.1702; found 530.1688. $^1$H NMR (400 MHz, MeOH-d$_4$) δ ppm 8.19 (m, 1H), 7.89 (m, 1H), 7.72 (d, J=8.6 Hz, 1H), 7.28 (m, 2H), 7.19 (m, 1H), 7.11 (m, 3H), 7.00 (d, J=7.8 Hz, 2H), 5.65 (s, 2H), 2.64 (t, J=7.8 Hz, 2H), 1.56 (m, 2H), 1.30 (m, 2H), 0.87 (t, J=7.5 Hz, 3H).

The following examples have been similarly prepared from 4'-((2-butyl-4-chloro-5-formyl-1H-imidazol-1-yl)methyl)-5-hydroxy-[1,1'-biphenyl]-2-carbonitrile (Intermediate 427a) and 2-chloro-4-methylpyridine or from 4'-((2-butyl-4-chloro-5-formyl-1H-imidazol-1-yl)methyl)-5-fluoro-[1,1'-biphenyl]-2-carbonitrile [obtained from 2-butyl-4-chloro-1-(4-(4,4,5,5-tetramethyl-1,3,2-dioxaborolan-2-yl)benzyl)-1H-imidazole-5-carbaldehyde (Intermediate 35a) and 2-bromo-4-fluorobenzonitrile, according to the procedure described for the synthesis of Intermediate 247a] and 3-hydroxypyridine, using the procedures described above.

| Ex | Structure | MW | LC-MS m/z [M + H]+; RT (Method H) | $^1$H NMR (400 MHz, DMSO-d$_6$) δ ppm |
|---|---|---|---|---|
| 428 | 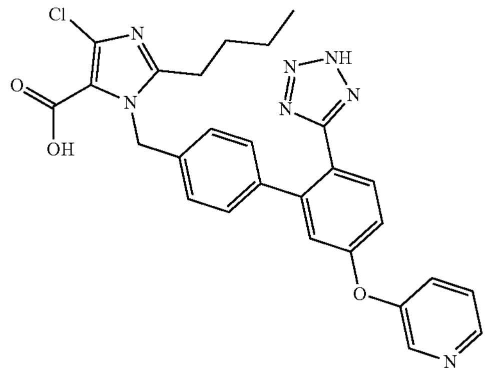 [SMILES: CCCCc1nc(Cl)c(C(=O)O)n1Cc1ccc(-c2cc(Oc3cccnc3)ccc2-c2nn[nH]n2)cc1] | 529.98 | 530.10; 1.24 min | (MeOH-d$_4$): 8.41 (br. s, 1H), 8.37 (m, 1H), 7.70 (d, J = 8.6 Hz, 1H), 7.65 (m, 1H), 7.50 (m, 1H), 7.22 (m, 2H), 7.11 (d, J = 7.8 Hz, 2H), 7.03 (d, J = 7.8 Hz, 2H), 5.65 (s, 2H), 2.61 (t, J = 7.8 Hz, 2H), 1.56 (m, 2H), 1.30 (m, 2H), 0.87 (t, J = 7.5 Hz, 3H) |

Example 430: (S)-2-(N-((6-(4-(2H-Tetrazol-5-yl)-[1,1'-biphenyl]-3-yl)pyridin-3-yl)methyl)pentanamido)-3-methylbutanoic acid

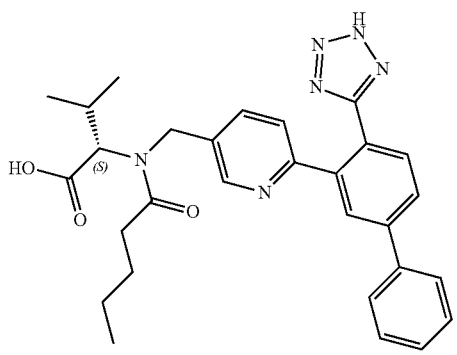

(Ex. 430)

Intermediate 430a: (S)-Methyl 2-(((6-bromopyridin-3-yl)methyl)amino)-3-methylbutanoate

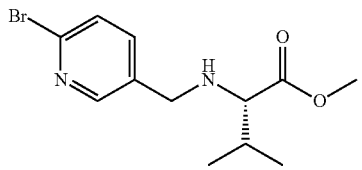

(430a)

To a mixture of 6-bromopicolinaldehyde (5.02 g, 27.0 mmol), (S)-methyl 2-amino-3-methylbutanoate hydrochloride (4.52 g, 27.0 mmol) and sodium acetate (4.43 g, 54.0 mmol) in MeOH (500 mL) was added 4A molecular sieves (25 g) and the mixture was stirred at RT for 30 min. To this mixture was then added sodium cyanoborohydride (3.39 g, 54.0 mmol) and the mixture stirred at RT for 18 h. The pH of the mixture was then adjusted, first to ca.2 by the addition of 4M HCl (25 mL) and then to pH ca. 10 with 2M Na$_2$CO$_3$ (25 mL). The resulting suspension was filtered and the filter-cake was washed with small amounts of MeOH. The combined filtrate was concentrated under reduced pressure and the concentrate was extracted with tert-butylmethyl ether (200 mL). The organic extract was washed with washed with brine, dried over anhydrous sodium sulfate, filtered and evaporated. The residue obtained was purified by flash chromatography using an 80 gram ISCO-type column and a 0 to 30% EtOAc/hexane gradient to afford the title compound as a clear colorless oil (7.50 g, 24.9 mmol, 92% yield). LC-MS (Method H): 1.07 min, [M+H]+=301.1; $^1$H NMR (DMSO-d$_6$) δ ppm 8.27-8.31 (m, 1H), 7.69 (dd, J=8.2, 2.7 Hz, 1H), 7.58 (d, J=7.8 Hz, 1H), 3.76 (d, J=14.1 Hz, 1H), 3.61 (s, 3H), 3.51 (d, J=14.1 Hz, 1H), 2.87 (br s, 1H), 2.59 (br s, 1H), 1.83 (dq, J=13.6, 6.7 Hz, 1H), 0.89 (d, J=7.0 Hz, 3H), 0.84 (d, J=7.0 Hz, 3H).

Intermediate 430b: (S)-Methyl 2-(N-((6-bromopyridin-3-yl)methyl)pentanamido)-3-methylbutanoate

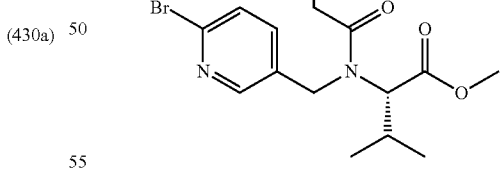

(430b)

To a mixture of (S)-methyl 2-(((6-bromopyridin-3-yl)methyl)amino)-3-methylbutanoate (5.30 g, 17.6 mmol) and potassium carbonate (7.30 g, 52.8 mmol) in ACN (50 mL) was added pentanoyl chloride (5.22 mL, 44.0 mmol) dropwise over about 5 min and the mixture was then stirred at RT for 2 h. The resulting mixture was then diluted with H$_2$O (50 mL) and the mixture was concentrated to half-volume under reduced pressure. The aqueous concentrate was extracted with tert-butylmethyl ether (150 mL) and the organic phase was separated, washed (10% aqueous citric acid×3, saturated aqueous Na$_2$CO$_3$, and brine), dried over anhydrous sodium sulfate, filtered and evaporated. The residue obtained was purified by flash chromatography on a 40 g Icso-type column using a 10 to 30% EtOAc/hexane gradient to provide the title compound as a white solid (4.69 g, 12.3 mmol, 69% yield). LC-MS (Method H): 1.27 min, [M+H]$^+$=385.1; $^1$H NMR (DMSO-d$_6$) δ ppm 8.27 (d, J=2.3 Hz, 0.5H), 8.14 (d, J=2.3 Hz, 0.5H), 7.62-7.68 (m, 0.5H), 7.52-7.61 (m, 1H), 7.46 (dd, J=8.2, 2.3 Hz, 0.5H), 4.67-4.76 (m, 1H), 4.56-4.67 (m, 0.5H), 4.44 (d, J=9.8 Hz, 0.5H), 4.17-4.28 (m, 1H), 3.40 (s, 1.5H), 3.39 (s, 1.5H), 2.40-2.58 (m, 1H), 2.24-2.38 (m, 1.5H), 2.12-2.23 (m, 0.5H), 1.38-1.62 (m, 2H), 1.13-1.38 (m, 2H), 0.70-0.99 (m, 9H).

Intermediate 430c: (S)-Methyl 2-(N-((6-(4-cyano-[1,1'-biphenyll-3-yl)pyridin-3-yl)methyl)pentanamido)-3-methylbutanoate

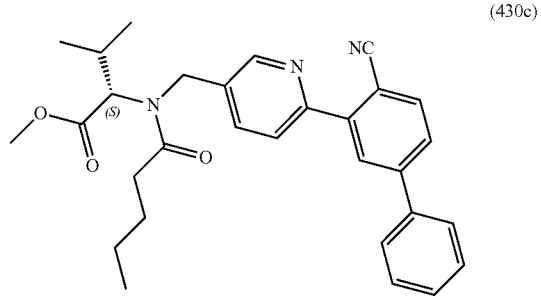

(430c)

The title compound was prepared by the reaction of (S)-methyl 2-(N-((6-bromopyridin-3-yl)methyl)pentanamido)-3-methylbutanoate (0.075 g, 0.195 mmol) with 3-(5,5-dimethyl-1,3,2-dioxaborinan-2-yl)-[1,1'-biphenyl]-4-carbonitrile (Intermediate 268c, 0.068 g, 0.234 mmol), according to the method described for the synthesis of Intermediate 330b, to give a white solid (0.083 g, 0.172 mmol, 88% yield). LC-MS (Method H): 1.36 min, [M+H]$^+$=484.2; $^1$H NMR (DMSO-d$_6$) δ ppm 8.62 (s, 0.5H), 8.49 (s, 0.5H), 8.08-8.15 (m, 1H), 7.98-8.08 (m, 1.5H), 7.89-7.98 (m, 1.5H), 7.77-7.89 (m, 2.5H), 7.64-7.71 (m, 0.5H), 7.42-7.58 (m, 3H), 4.89 (dd, J=16.8, 13.3 Hz, 1H), 4.73 (d, J=16.8 Hz, 0.5H), 4.56 (d, J=10.2 Hz, 1H), 4.24-4.35 (m, 0.5H), 3.41 (s, 1.5H), 3.37 (s, 1.5H), 2.52-2.63 (m, 1H), 2.17-2.47 (m, 2H), 1.41-1.66 (m, 2H), 1.15-1.41 (m, 2H), 0.76-1.00 (m, 9H).

Example 430: (S)-2-(N-((6-(4-(2H-Tetrazol-5-yl)-[1,1'-biphenyll-3-yl)pyridin-3-yl)methyl)pentanamido)-3-methylbutanoic acid The title compound was prepared from (S)-methyl 2-(N-((6-(4-cyano-[1,1'-biphenyl]-3-yl)pyridin-3-yl)methyl)pentanamido)-3-methylbutanoate according to the method described for the synthesis of Example 283 and was isolated as an off-white solid. LC-MS (Method H): 1.29 min, [M+H]$^+$=513.2; $^1$H NMR (DMSO-d$_6$) δ ppm 12.62 (s, 2H), 8.33 (s, 0.5H), 8.21 (s, 0.5H), 7.94-8.00 (m, 1H), 7.86-7.94 (m, 1H), 7.82 (d, J=7.4 Hz, 2.5H), 7.75 (t, J=8.0 Hz, 1H), 7.69 (d, J=8.2 Hz, 0.5H), 7.48-7.59 (m, 2.5H), 7.37-7.48 (m, 1.5H), 4.68 (s, 1H), 4.48-4.59 (m, 0.5H), 4.31-4.48 (m, 1H), 4.09 (m, 0.5H), 2.36-2.46 (m, 1H), 1.99-2.33 (m, 2H), 1.34-1.61 (m, 2H), 1.11-1.34 (m, 2H), 0.63-1.01 (m, 9H).

The following examples were similarly prepared according to the method described for the synthesis of Example 430 above. Analytical LC-MS injections were used to determine the final purity and the retention time is reported for each compound and the method used is referred to as Method A1, Method A2 or Method H.

| Ex | Structure | MW | LC-MS m/z [M + H]$^+$; RT (Method) | $^1$H NMR (400 MHz, DMSO-d$_6$) δ ppm |
|---|---|---|---|---|
| 431 | 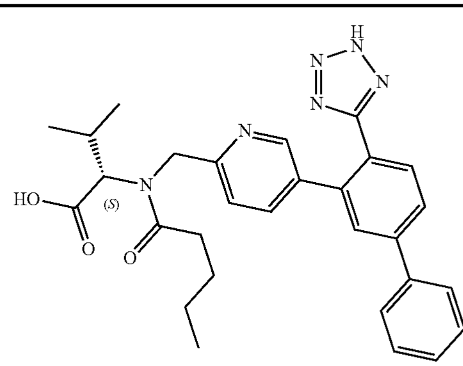 | 512.25 | 513.2; 1.27 min (Method H) | 13.05 (s, 2H), 8.36 (m, 1H), 7.95 (td, J = 8.2, 1.6 Hz, 2H), 7.77-7.91 (m, 4H), 7.60-7.77 (m, 1H), 7.51-7.52 (m, 2H),7.39-7.47 (m, 1H), 4.53-4.96 (m, 2H), 4.15 (dd, J = 9.6, 5.3 Hz, 1H), 2.57 (m, 1H), 2.07-2.37 (m, 2H), 1.13-1.62 (m, 4H), 0.69-0.98 (m, 9H). |

| Ex | Structure | MW | LC-MS m/z [M + H]+; RT (Method) | 1H NMR (400 MHz, DMSO-d6) δ ppm |
|---|---|---|---|---|
| 432 | 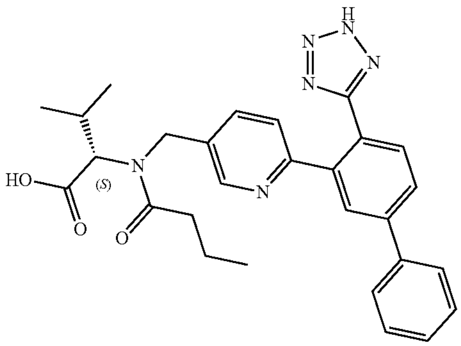 | 498.24 | 499.1; 1.27 min (Method H) | 13.06 (br s, 1H), 12.61 (br s, 1H), 8.35 (s, 0.5H), 8.26 (s, 0.5H), 7.97-8.04 (m, 1H), 7.94 (dt, J = 8.0, 2.2 Hz, 1H), 7.85 (d, J = 7.8 Hz, 2H), 7.70-7.82 (m, 1.5H), 7.62 (t, J = 6.3 Hz, 1H), 7.49-7.58 (m, 2.5H), 7.40-7.49 (m, 1H), 4.71 (s, 1H), 4.58 (d, J = 15.7 Hz, 0.5H), 4.46 (d, J = 16.0 Hz, 0.5H), 4.39 (d, J = 9.8 Hz, 0.5H), 4.12 (d, J = 10.6 Hz, 0.5H), 2.41-2.52 (m, 1H), 2.02-2.31 (m, 2H), 1.36-1.64 (m, 2H), 0.70-1.01 (m, 9H). |
| 433 | 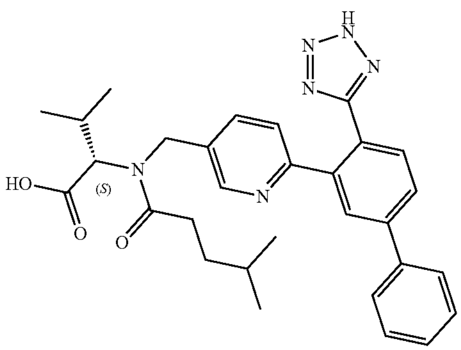 | 526.27 | 527.2; 1.32 min (Method H) | 13.06 (br s, 1H), 12.64 (br s, 1H), 8.37 (s, 0.5H), 8.25 (s, 0.5H), 7.99 (br s, 1H), 7.94 (d, J = 7.8 Hz, 1H), 7.84 (d, J = 7.4 Hz, 2H), 7.70-7.81 (m, 1.5H), 7.58-7.65 (m, 1H), 7.49-7.58 (m, 2.5H), 7.40-7.49 (m, 1H), 4.71 (s, 1H), 4.57 (d, J = 15.7 Hz, 0.5H), 4.46 (d, J = 16.0 Hz, 0.5H), 4.39 (d, J = 9.8 Hz, 0.5H), 4.12 (d, J = 10.2 Hz, 0.5H), 2.39-2.48 (m, 1H), 2.04-2.31 (m, 2H), 1.29-1.58 (m, 3H), 1.22-1.29 (m, 1.5H), 1.13 (d, J = 6.3 Hz, 1.5H), 0.68-1.02 (m, 9H). |

Example 434: (S)-3-Methyl-2-(N-((6-(4-(5-oxo-4,5-dihydro-1,2,4-oxadiazol-3-yl)-[1,1'-biphenyl]-3-yl)pyridin-3-yl)methyl)pentanamido)butanoic acid 2,2,2-trifluoroacetate (Ex. 434)

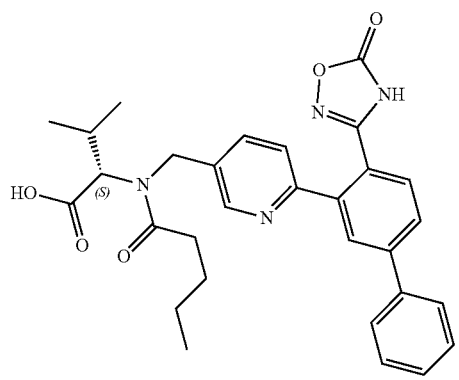

Intermediate 434a: (S)-tert-Butyl 2-(N-((6-(4-cyano-[1,1'-biphenyl]-3-yl)pyridin-3-yl)methyl)pentanamido)-3-methylbutanoate (434a)

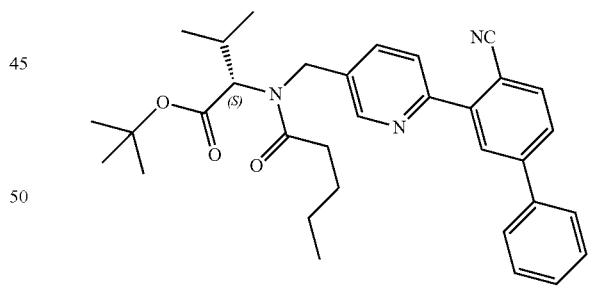

The title compound was prepared from 6-bromonicotinaldehyde and (S)-tert-butyl 2-amino-3-methylbutanoate hydrochloride, according to the method described for the synthesis of Intermediate 430c and was isolated as an off-white solid. LC-MS (Method H): 1.49 min, [M+H]+= 526.2; 1H NMR (DMSO-d6) δ ppm 8.86 (m, 0.5H), 8.53 (m, 0.5H), 8.02-8.12 (2.5H), 7.82-7.96 (m, 4H), 7.69-7.72 (m, 0.5H), 7.45-7.56 (m, 3H), 4.76-4.86 (m, 1.5H), 4.33-4.43 (m, 1H), 4.09-4.11 (m, 0.5H), 2.44-2.85 (m, 1H), 2.17-2.40 (m, 2H), 1.31-1.86 (m, 4H), 1.22-1.26 (m, 9H), 0.77-0.98 (m, 9H).

Intermediate 434b: (S,Z)-tert-Butyl 2-(N-((6-(4-(N'-hydroxycarbamimidoyl)-[1,1'-biphenyl]-3-yl)pyridin-3-yl)methyl)pentanamido)-3-methylbutanoate 2,2,2-trifluoroacetate

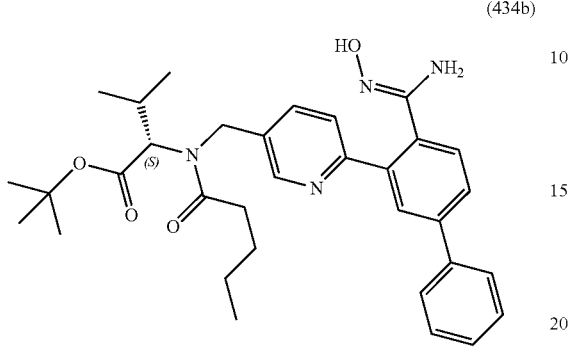

(434b)

To a solution of (S)-tert-butyl 2-(N-((6-(4-cyano-[1,1'-biphenyl]-3-yl)pyridin-3-yl)methyl)pentanamido)-3-methylbutanoate (0.050 g, 0.095 mmol) in ethanol (2 mL) was added hydroxylamine hydrochloride (0.066 g, 0.952 mmol) and DIEA (0.166 mL, 0.951 mmol). The reaction vessel was sealed and the mixture heated at 85° C. for 3 h. The cooled mixture was then evaporated under reduced pressure and the residue was taken up in DMSO (2.5 mL) and formic acid (0.125 mL) was added. The mixture was purified by prep LC (Method F, TFA as modifier) to afford the title compound (as TFA salt) as a white solid (52 mg, 0.077 mmol, 81% yield). LC-MS (Method H): 1.41 min, [M+H]'=559.3; HRMS (ESI): Calcd for $C_{33}H_{43}N_4O_4$ [M+H]$^+$ m/z 559.3279; found 559.3281.

Example 434: (S)-3-Methyl-2-(N-((6-(4-(5-oxo-4,5-dihydro-1,2,4-oxadiazol-3-yl)-[1,1'-biphenyl]-3-yl)pyridin-3-yl)methyl)pentanamido)butanoic acid 2,2,2-trifluoroacetate To a solution of(S,Z)-tert-butyl 2-(N-((6-(4-(N'-hydroxycarbamimidoyl)-[1,1'-biphenyl]-3-yl)pyridin-3-yl)methyl)pentanamido)-3-methylbutanoate.TFA (0.050 g, 0.074 mmol) in THF (2 mL) was added DBU (0.057 g, 0.372 mmol) and N,N'-carbonyldiimidazole (0.060 g, 0.372 mmol) and the mixture was stirred in a sealed vial at 50° C. for 2 h. The cooled mixture was then evaporated, trifluoroacetic acid (1 mL) was added to the residue and the mixture was stirred for 1 h before again being evaporated to dryness. The residue was taken up in DMSO (2 mL) and the mixture was purified by prep LC (Method F, TFA as modifier) to afford the title compound (as TFA salt) as a white solid (0.028 g, 0.053 mmol, 70% yield). LC-MS (Method H): 1.31 min, [M+H]$^+$=529.2; $^1$H NMR (DMSO-d) δ ppm 13.08 (s, 1H), 12.43 (br s, 1H), 8.53 (s, 0.5H) 8.40-8.45 (m, 0.5H), 8.00-8.05 (m, 1H), 7.93 (dt, J=7.8, 2.2 Hz, 1H), 7.68-7.90 (m, 5H), 7.49-7.58 (m, 2H), 7.42-7.49 (m, 1H), 4.76 (s, 1H), 4.62 (d, J=16.0 Hz, 0.5H), 4.51 (d, J=16.0 Hz, 0.5H), 4.39 (d, J=9.8 Hz, 0.5H), 4.14 (d, J=10.6 Hz, 0.5H), 2.43-2.58 (m, 11H), 2.07-2.36 (m, 2H), 1.50-1.63 (m, 1H), 1.39-1.49 (m, 1H), 1.26-1.38 (m, 1H), 1.15-1.24 (m, 1H), 0.71-0.98 (m, 9H).

Example 435: (S)-3-Methyl-2-(N-((5'-phenoxy-2'-(2H-tetrazol-5-yl)-[1,1'-biphenyl]-4-yl)methyl)pentanamido)butanoic acid

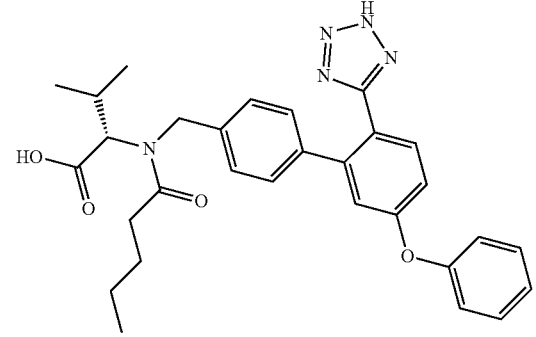

(435)

Intermediate 435a: (S)-Methyl 2-(N-(4-bromobenzyl)pentanamido)-3-methylbutanoate

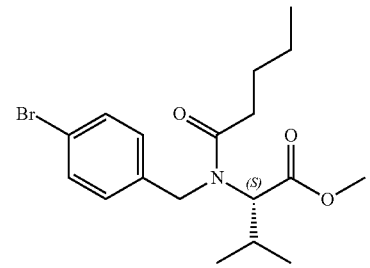

(435a)

The title compound was prepared from (S)-methyl 2-amino-3-methylbutanoate hydrochloride, according to the method described for the synthesis of Intermediate 268b, and was isolated as a pale brown oil. LC-MS (Method H): 1.36 min, [M+H]$^+$=384.1; $^1$H NMR (DMSO-d$_6$) δ ppm 7.41-7.55 (m, 2H), 7.01-7.18 (m, 2H), 4.47-4.74 (m, 2H), 4.11-4.26 (m, 1H), 3.35-3.42 (m, 3H), 2.41-2.60 (m, 1H), 2.05-2.36 (m, 2H), 1.13-1.59 (m, 5H), 0.68-0.97 (m, 9H).

Intermediate 435b: (S)-Methyl 2-(N-((2'-cyano-5'-fluoro-[1,1'-biphenyl]-4-yl)methyl)pentanamido)-3-methylbutanoate

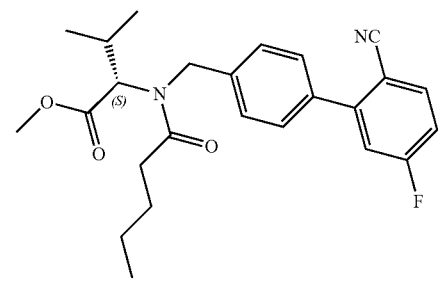

(435b)

The title compound was prepared by the reaction of (S)-methyl 2-(N-(4-bromobenzyl)pentan-amido)-3-methylbutanoate (0.700 g, 1.82 mmol) with 4-fluoro-2-(4,4,5,5-tetramethyl-1,3,2-dioxaborolan-2-yl)benzonitrile (0.900 g, 3.64 mmol), according to the method described for the synthesis of Intermediate 330b, to give a white solid (0.665 g, 1.57 mmol, 86% yield). LC-MS (Method H): 1.38 min, [M+H]$^+$=425.2; $^1$H NMR (CDCl$_3$) δ ppm 7.77 (ddd, J=11.0, 8.6, 5.5 Hz, 1H), 7.54 (d, J=8.2 Hz, 1H), 7.46 (d, J=8.2 Hz, 1H), 7.28-7.36 (m, 2H), 7.08-7.25 (m, 2H), 4.94-5.13 (m, 1H), 4.07-4.29 (m, 1H), 3.39-3.47 (s, 3H), 2.55-2.68 (m, 1H), 2.22-2.52 (m, 2H), 1.23-1.83 (m, 5H), 0.79-1.05 (m, 9H).

Intermediate 435c: (S)-Methyl 2-(N-((2'-cyano-5'-phenoxy-[1,1'-biphenyl]-4-yl)methyl)pentanamido)-3-methylbutanoate

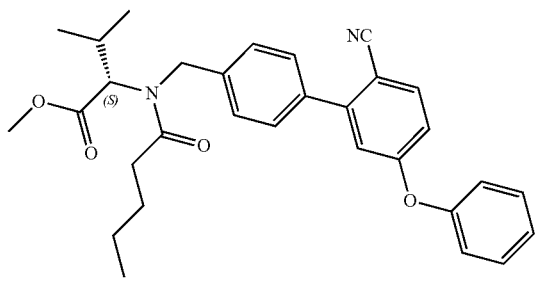

(435c)

The title compound was prepared from (S)-methyl 2-(N-((2'-cyano-5'-fluoro-[1,1'-biphenyl]-4-yl)methyl)pentanamido)-3-methylbutanoate and phenol, according to the method described for the synthesis of Intermediate 330c. The crude product was purified by prep LC (Method F, TFA as modifier) to afford the pure product as a white solid. LC-MS (Method H): 1.48 min, [M+H]$^+$=499.2; HRMS (ESI): Calcd for C$_{31}$H$_{35}$N$_2$O$_4$ [M+H]$^+$ m/z 499.2591; found 499.2609.

Example 435: (S)-3-Methyl-2-(N-((5'-phenoxy-2'-(2H-tetrazol-5-yl)-[1,1'-biphenyl]-4-yl)methyl)pentanamido)butanoic acid The title compound was prepared from (S)-methyl 2-(N-((2'-cyano-5'-phenoxy-[1,1'-biphenyl]-4-yl)methyl)pentanamido)-3-methylbutanoate, according to the method described for the synthesis of Example 268. The crude material was purified by prep LC (Method F, TFA as modifier) to afford the pure product as a white solid. LC-MS (Method H): 1.37 min, [M+H]$^+$=528.2; $^1$H NMR (DMSO-d$_6$) δ ppm 7.64 (dd, J=8.4, 5.7 Hz, 1H), 7.37-7.53 (m, 2H), 7.06-7.29 (m, 6H), 6.86-7.03 (d, J=2.3 Hz, 3H), 6.94 (br s, 1H), 3.90-4.85 (m, 3H), 2.41-2.48 (m, 1H), 1.90-2.30 (m, 2H), 1.46-1.71 (m, 1H), 1.41 (br s, 3H), 1.07-1.60 (m, 5H), 0.65-1.05 (m, 9H).

The following examples were similarly prepared using the appropriate phenol or hydroxypyridine, according to the method described for the synthesis of Example 435 above. Analytical LC-MS injections were used to determine the final purity, the retention time is reported for each compound and the method used is referred to as Method A1, Method A2 or Method H.

| Ex | Structure | MW | LC-MS m/z [M + H]$^+$; RT (Method) | $^1$H NMR (400 MHz, DMSO-d$_6$) δ ppm |
|---|---|---|---|---|
| 436 | 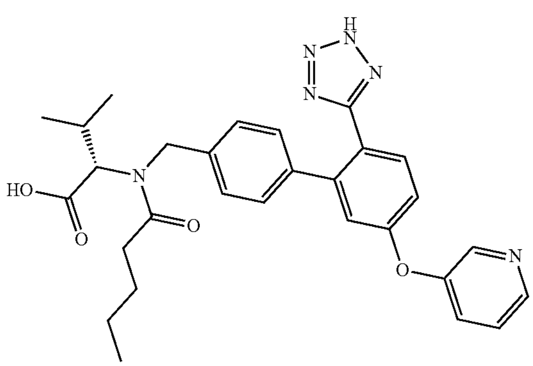 [SMILES: CCCCC(=O)N(Cc1ccc(-c2cc(Oc3cccnc3)ccc2-c2nn[nH]n2)cc1)[C@H](C(=O)O)C(C)C] | 528.6 | 529.2; 1.29 min (Method H) | 12.93 (s, 1H), 12.58 (br. s., 1H), 8.53 (br. s., 1H), 8.46 (d, J = 4.3 Hz, 1H), 7.60-7.74 (m, 2H), 7.50 (dd, J = 8.6, 4.7 Hz, 1H), 7.16-7.25 (m, 2H), 7.03-7.16 (m, 3H), 6.97 (d, J = 7.8 Hz, 1H), 4.53-4.69 (m, 1H), 4.44 (br. s., 1.5H), 4.07 (d, J = 9.4 Hz, 0.5H), 2.39-2.48 (m, 1H), 1.89-2.27 (m, 2H), 1.07-1.57 (m, 5H), 0.66-0.96 (m, 9H) |

-continued

| Ex | Structure | MW | LC-MS m/z [M + H]+; RT (Method) | 1H NMR (400 MHz, DMSO-d6) δ ppm |
|---|---|---|---|---|
| 437 | 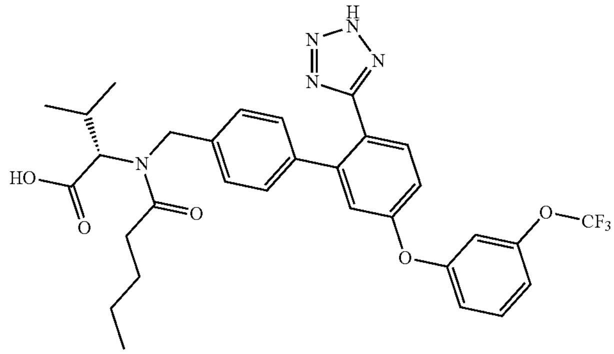 [SMILES: CCCCC(=O)N(Cc1ccc(-c2cc(Oc3cccc(OC(F)(F)F)c3)ccc2-c2nn[nH]n2)cc1)[C@H](C(=O)O)C(C)C] | 611.1 | 612.2; 1.45 min (Method H) | 12.59 (s, 2H), 7.63-7.74 (m, 1H), 7.57 (t, J = 8.4 Hz, 1H), 7.16-7.28 (m, 5H), 7.14 (br. s., 1H), 7.01-7.12 (m, 2H), 6.97 (d, J = 7.8 Hz, 1H), 4.61 (br. s., 1H), 4.45 (d, J = 9.8 Hz, 1.5H), 4.07 (d, J = 9.0 Hz, 0.5H), 2.37-2.48 (m, 1H), 1.85-2.28 (m, 2H), 1.07-1.62 (m, 5H), 0.63-0.98 (m, 9H) |

Example 438: (S)-2-(N-((3",5"-Difluoro-6'-(2H-tetrazol-5-yl)-[1,1':3',1"-terphenyl]-4-yl)methyl)pentanamido)-3-methylbutanoic acid

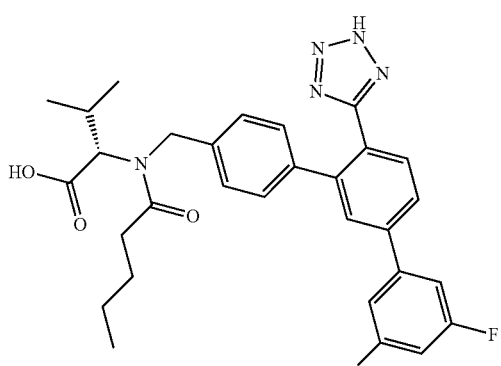

(Ex. 438)

Intermediate 438a: (S)-Methyl 2-(N-((5'-chloro-2'-cyano-[1,1'-biphenyl]-4-yl)methyl)pentanamido)-3-methylbutanoate

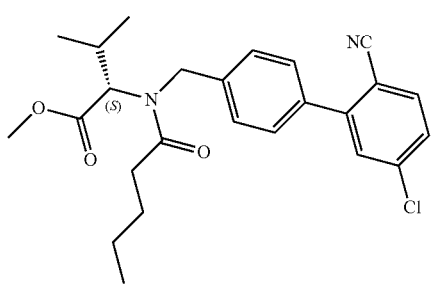

(438a)

The title compound was prepared by the reaction of (S)-methyl 2-(N-(4-bromobenzyl)pentan-amido)-3-methylbutanoate (0.700 g, 1.82 mmol) with 4-chloro-2-(5,5-dimethyl-1,3,2-dioxaborinan-2-yl)benzonitrile (909 mg, 3.64 mmol), according to the method described for the synthesis of Intermediate 330b, to give a white solid (0.384 g, 0.871 mmol, 48% yield). LC-MS (Method H): 1.44 min, [M+H]+=441.2; 1H NMR (CDCl3) δ ppm 7.65-7.74 (m, 1H), 7.36-7.57 (m, 4H), 7.28-7.36 (m, 2H), 4.94-5.13 (m, 11H), 4.29 (d, J=15.7 Hz, 0.5H), 4.07 (d, J=11.0 Hz, 0.5H), 3.47 (s, 2H), 3.39 (s, 1H), 2.54-2.70 (m, 1H), 2.22-2.52 (m, 2H), 1.59-1.82 (m, 2H), 1.21-1.51 (m, 3H), 0.80-1.04 (m, 9H).

Intermediate 438b: (S)-Methyl 2-(N-((6'-cyano-3",5"-difluoro-[1,1':3',1"-terphenyl]-4-yl)methyl)pentanamido)-3-methylbutanoate

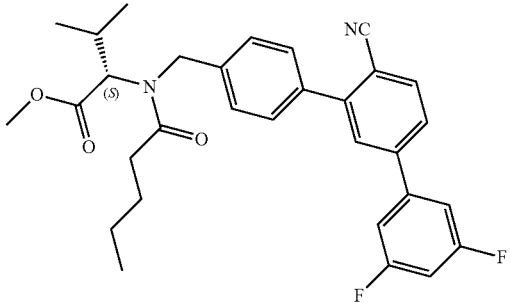

(438b)

The title compound was prepared by the reaction of (S)-methyl 2-(N-((5'-chloro-2'-cyano-[1,1'-biphenyl]-4-yl)methyl)pentanamido)-3-methylbutanoate with (3,5-difluorophenyl)boronic acid, according to the method described for the synthesis of Intermediate 288c, and was isolated as a white solid. LC-MS (Method H): 1.48 min, [M+H]+= 519.2; HRMS (ESI): Calcd for $C_{31}H_{33}F_2N_2O_3[M+H]^+$ m/z 519.2454; found 519.2483.

Example 438: (S)-2-(N-((3",5"-Difluoro-6'-(2H-tetrazol-5-yl)-[1,1':3',1"-terphenyl]-4-yl)methyl)pentanamido)-3-methylbutanoic acid The title compound was prepared from (S)-methyl 2-(N-((6'-cyano-3",5"-difluoro-[1,1':3',1"-terphenyl]-4-yl)

methyl)pentanamido)-3-methylbutanoate, according to the method described for the synthesis of Example 268. The crude material obtained was purified by prep LC (Method F, TFA as modifier) to afford the pure product as a white solid. LC-MS (Method H): 1.39 min, [M+H]⁺=548.2; ¹H NMR (DMSO-d₆) δ ppm 7.90 (d, J=7.0 Hz, 1H), 7.70-7.86 (m, 2H), 7.62 (d, J=7.0 Hz, 2H), 7.08-7.35 (m, 5H), 4.04-4.63 (m, 2H), 2.40-2.48 (m, 1H), 2.07-2.21 (m, 2H), 1.12-1.63 (m, 5H), 0.69-1.00 (m, 9H).

The following examples have been similarly prepared from the corresponding boronic acids or boronate esters according to the methods described for the synthesis of Example 438 above. Analytical LC-MS injections were used to determine the final purity, the retention time is reported for each compound and the method used is referred to as Method A1, Method A2 or Method H.

| Ex | Structure | MW | LC-MS m/z [M + H]⁺; RT (Method) | ¹H NMR (400 MHz, DMSO-d₆) δ ppm |
|---|---|---|---|---|
| 439 | 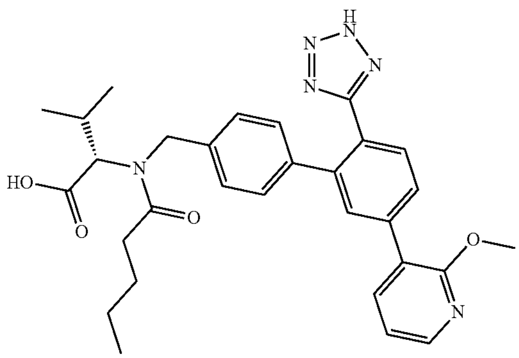 [SMILES: CCCCC(=O)N(Cc1ccc(-c2cc(-c3cccnc3OC)ccc2-c2nn[nH]n2)cc1)[C@H](C(=O)O)C(C)C] | 542.6 | 543.3; 1.32 min (Method H) | 8.23 (dd, J = 4.9, 1.4 Hz, 1H), 7.92 (br s, 1H), 7.55-7.77 (m, 3H), 7.04-7.21 (m, 5H), 4.63 (br s, 1H), 4.47 (d, J = 9.0 Hz, 1H), 3.91 (s, 3H), 2.46 (m, 1H), 1.91-2.25 (m, 2H), 1.10-1.58 (m, 5H), 0.72-0.97 (m, 9H). |
| 440 | 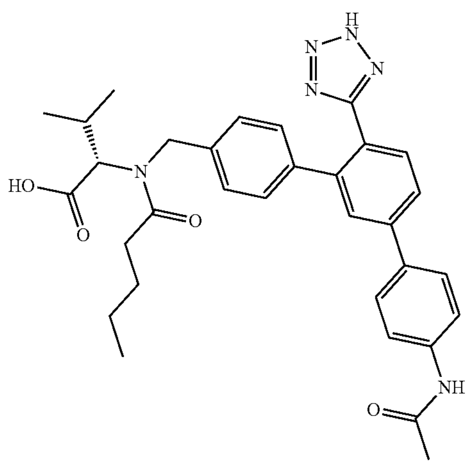 [SMILES: CCCCC(=O)N(Cc1ccc(-c2cc(-c3ccc(NC(C)=O)cc3)ccc2-c2nn[nH]n2)cc1)[C@H](C(=O)O)C(C)C] | 568.7 | 569.3; 1.28 min (Method H) | 12.59 (s, 2H), 10.09 (s, 1H), 7.62-7.89 (m, 7H), 6.96-7.22 (m, 4H), 4.40-4.70 (m, 1H), 4.00-4.20 (m, 1H), 2.45-2.50 (m, 1H), 2.00-2.25 (m, 2H), 2.07 (s, 3H), 1.13-1.60 (m, 5H), 0.68-0.98 (m, 9H). |
| 441 | 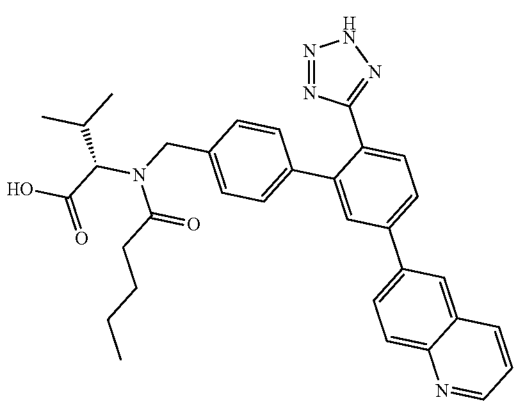 [SMILES: CCCCC(=O)N(Cc1ccc(-c2cc(-c3ccc4ncccc4c3)ccc2-c2nn[nH]n2)cc1)[C@H](C(=O)O)C(C)C] | 562.7 | 563.2; 1.33 min (Method H) | 8.93 (dd, J = 4.3, 1.6 Hz, 1H), 8.46 (d, J = 9.0 Hz, 2H), 8.24 (d, J = 7.4 Hz, 1H), 8.13 (d, J = 8.6 Hz, 1H), 8.00 (d, J = 7.8 Hz, 1H), 7.92 (br s, 1H), 7.80 (dd, J = 7.8, 5.5 Hz, 1H), 7.59 (dd, J = 8.2, 4.3 Hz, 1H), 7.11-7.29 (m, 4H), 4.40-4.75 (m, 1H), 3.90-4.25 (m, 1H), 2.45-2.50 (m, 1H), 2.00-2.30 (m, 2H), 1.10-1.60 (m, 5H), 0.70-1.00 (m, 9H). |

| Ex | Structure | MW | LC-MS m/z [M + H]+; RT (Method) | ¹H NMR (400 MHz, DMSO-d₆) δ ppm |
|---|---|---|---|---|
| 442 | 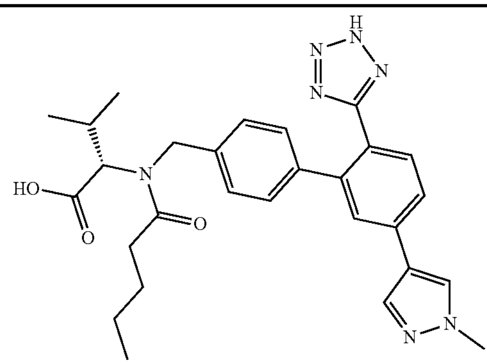 | 515.6 | 516.2; 1.26 min. (Method H) | 13.01 (br s, 1H), 12.61 (br s, 1H), 8.35 (s, 1H), 8.03 (s, 1H), 7.66-7.79 (m, 2H), 7.55-7.66 (m, 1H), 7.22 (d, J = 8.2 Hz, 1H), 7.07-7.17 (m, 2H), 6.98-7.07 (m, 1H), 4.55-4.66 (m, 1H), 4.36-4.55 (m, 1H), 3.88 (s, 3H), 2.45-2.50 (m, 1H), 1.98-2.28 (m, 2H), 1.13-1.55 (m, 5H), 0.65-0.99 (m, 9H). |

Example 443: (S)-3-Methyl-2-(N-((5'-(pyridin-2-yl)-2'-(2H-tetrazol-5-yl)-[1,1'-biphenyl]-4-yl)methyl)pentanamido)butanoic

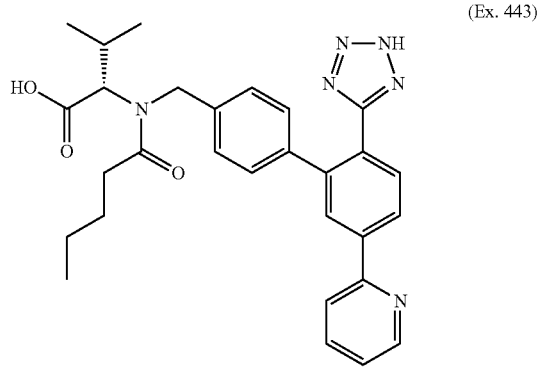 [SMILES: CCCCC(=O)N(Cc1ccc(-c2cc(-c3ccccn3)ccc2-c2nn[nH]n2)cc1)[C@H](C(=O)O)C(C)C]

(Ex. 443)

Intermediate 443a: (S)-Methyl 2-(N-((2'-cyano-5'-(5,5-dimethyl-1,3,2-dioxaborinan-2-yl)-[1,1'-biphenyl]-4-yl)methyl)pentanamido)-3-methylbutanoate

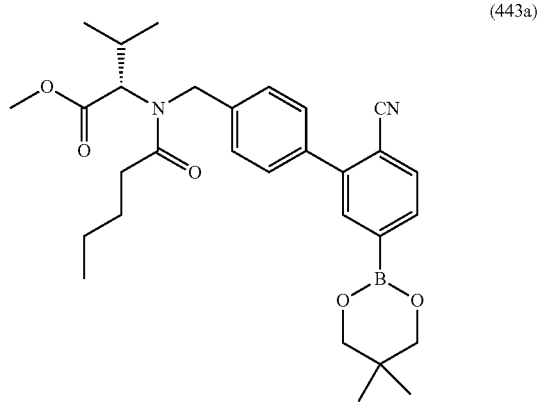 [SMILES: CCCCC(=O)N(Cc1ccc(-c2cc(B3OCC(C)(C)CO3)ccc2C#N)cc1)[C@H](C(=O)OC)C(C)C]

(443a)

The title compound was prepared by the reaction of (S)-methyl 2-(N-((5'-chloro-2'-cyano-[1,1'-biphenyl]-4-yl)methyl)pentanamido)-3-methylbutanoate (Intermediate 438a) with 5,5,5',5'-tetramethyl-2,2'-bi(1,3,2-dioxaborinane), according to the method described for the synthesis of Intermediate 293a. The unpurified product was used as such in the next step. LC-MS (Method H): 1.33 min, [M+H]⁺=no ion observed; ¹H NMR (CDCl₃) δ ppm 7.87-7.93 (m, 1H), 7.78-7.87 (m, 1H), 7.67-7.76 (m, 1H), 7.55 (d, J=8.2 Hz, 1H), 7.47 (d, J=8.2 Hz, 1H), 7.24-7.33 (m, 2H), 4.91-5.12 (m, 1H), 4.26 (d, J=15.3 Hz, 0.5H), 4.05 (d, J=15.3 Hz, 0.5H) 3.76-3.82 (m, 3H), 3.57-3.63 (s, 4H), 2.61 (dd, J=14.7, 8.0 Hz, 1H), 2.23-2.51 (m, 2H), 1.62-1.82 (m, 2H), 1.38-1.52 (m, 1H), 1.21-1.37 (m, 2H), 0.83-1.02 (m, 15H)

Intermediate 443b: (S)-Methyl 2-(N-((2'-cyano-5'-(pyridin-2-yl)-[1,1'-biphenyl]-4-yl)methyl)pentanamido)-3-methylbutanoate

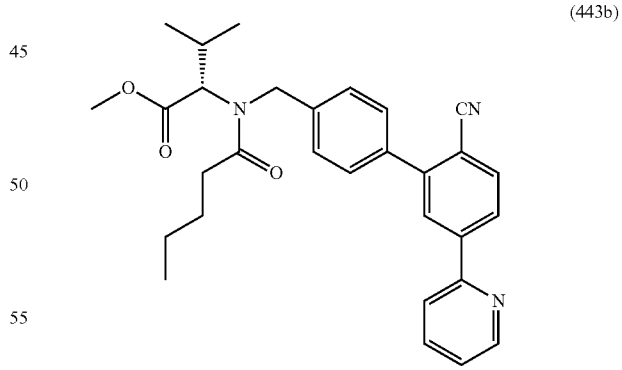

(443b)

The title compound was prepared by the reaction of (S)-methyl 2-(N-((2'-cyano-5'-(5,5-dimethyl-1,3,2-dioxaborinan-2-yl)-[1,1'-biphenyl]-4-yl)methyl)pentanamido)-3-methylbutanoate (Intermediate 443a) with 2-bromopyridine, according to the method described for the synthesis of Intermediate 293b. The crude material obtained was purified with prep LC (Method F, formic acid as modifier) to afford the pure product as a white solid. LC-MS (Method H): 1.38 min,

[M+H]⁺=484.3; HRMS (ESI): Calcd for C₃₀H₃₄N₃O₃ [M+H]⁺ m/z 484.2595; found 484.2635.

Example 443: (S)-3-Methyl-2-(N-((5'-(pyridin-2-yl)-2'-(2H-tetrazol-5-yl)-[1,1'-biphenyl]-4-yl)methyl)pentanamido)butanoic The title compound was prepared by the reaction of (S)-methyl 2-(N-((2'-cyano-5'-(pyridin-2-yl)-[1,1'-biphenyl]-4-yl)methyl)pentanamido)-3-methylbutanoate (Intermediate 443b) according to the method described for the synthesis of Example 268. The crude material obtained was purified by prep LC (Method F, TFA as modifier) to afford the product (TFA salt) as a white solid. LC-MS (Method H): 1.30 min, [M+H]⁺=513.2; ¹H NMR (DMSO-d₆) δ ppm 12.96 (s, 1H), 12.59 (s, 1H), 8.71 (d, J=3.9 Hz, 1H), 8.18-8.28 (m, 2H), 8.15 (d, J=7.8 Hz, 1H), 7.91-7.97 (m, 1H), 7.73-7.80 (m, 1H), 7.41-7.46 (m, 1H), 7.22 (d, J=8.2 Hz, 1H), 7.08-7.17 (m, 2H), 7.02-7.08 (m, 1H), 4.63 (s, 1H), 4.44-4.49 (m, 1H), 2.46 (m, 1H), 2.05-2.28 (m, 2H), 1.10-1.54 (m, 5H), 0.65-0.95 (m, 9H).

The following examples have been similarly prepared from the corresponding 2-bromo-or 2-chloropyridines according to the methods described for the synthesis of Example 443 above. Analytical LC-MS injections were used to determine the final purity, the retention time is reported for each compound and the method used is referred to as Method A1, Method A2 or Method H.

| Ex | Structure | MW | LC-MS m/z [M + H]⁺; RT (Method) | ¹H NMR (400 MHz, DMSO-d₆) δ ppm |
|---|---|---|---|---|
| 444 | 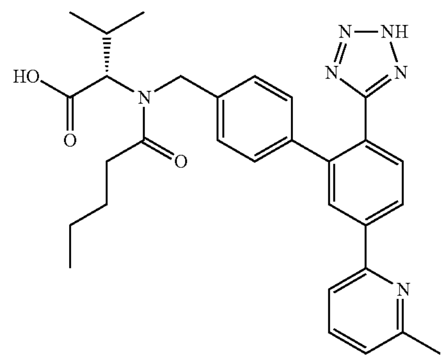 [SMILES: CCCCC(=O)N(Cc1ccc(-c2cc(-c3cccc(C)n3)ccc2-c2nn[nH]n2)cc1)[C@H](C(=O)O)C(C)C] | 526.6 | 527.2; 1.32 min (Method H) | 12.99 (s, 1H), 12.61 (s, 1H), 8.21-8.26 (m, 1H), 8.19 (d, J = 5.5 Hz, 1H), 7.95 (d, J = 7.8 Hz, 1H), 7.84 (t, J = 7.6 Hz, 1H), 7.73-7.80 (m, 1H), 7.31 (d, J = 7.4 Hz, 1H), 7.23 (d, J = 7.8 Hz, 1H), 7.10-7.18 (m, 2H), 7.04-7.08 (m, 1H), 4.64 (s, 1H), 4.45-4.51 (m, 1H), 2.56 (s, 3H), 2.39-2.48 (m, 1H), 1.97-2.29 (m, 2H), 1.12-1.64 (m, 5H), 0.66-0.99 (m, 9H). |
| 445 | 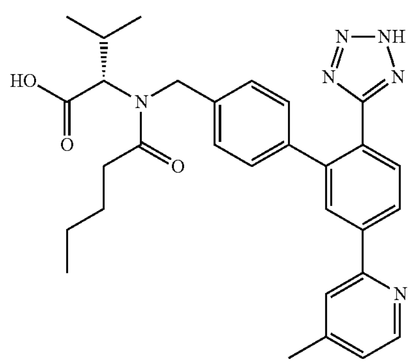 [SMILES: CCCCC(=O)N(Cc1ccc(-c2cc(-c3cc(C)ccn3)ccc2-c2nn[nH]n2)cc1)[C@H](C(=O)O)C(C)C] | 526.6 | 527.2; 1.31 min (Method H) | 12.97 (s, 1H), 12.58 (s, 1H), 8.57 (d, J = 5.1 Hz, 1H), 8.21-8.26 (m, 1H), 8.16-8.21 (m, 1H), 8.05 (s, 1H), 7.74-7.80 (m, 1H), 7.31 (d, J = 4.7 Hz, 1H), 7.22 (d, J = 8.2 Hz, 1H), 7.09-7.17 (m, 2H), 7.03-7.08 (m, 1H), 4.63 (s, 1H), 4.43-4.49 (m, 1H), 2.39-2.46 (m, 3H), 1.98-2.28 (m, 2H), 1.10-1.58 (m, 5H), 0.63-0.97 (m, 9H). |
| 446 | 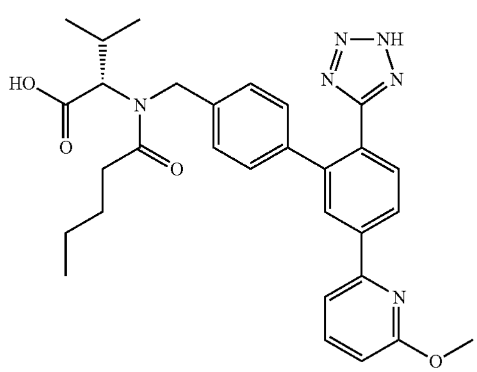 [SMILES: CCCCC(=O)N(Cc1ccc(-c2cc(-c3cccc(OC)n3)ccc2-c2nn[nH]n2)cc1)[C@H](C(=O)O)C(C)C] | 542.6 | 543.2; 1.38 min (Method H) | 8.22 (dd, J = 7.8, 1.6 Hz, 1H), 8.15 (s, 1H), 7.78-7.85 (m, 1H), 7.67-7.77 (m, 2H), 7.25 (d, J = 7.4 Hz, 1H), 7.09-7.16 (m, 2H), 7.03 (d, J = 7.4 Hz, 1H), 6.84 (d, J = 8.2 Hz, 1H), 4.71 (br s, 1H), 4.54 (br s, 1H), 3.94 (s, 3H), 2.40-2.50 (m, 1H), 1.94-2.30 (m, 2H), 1.10-1.60 (m, 5H), 0.60-1.00 (m, 9H). |

The following examples have been similarly prepared from (S)-methyl 2-(N-((5'-chloro-2'-cyano-[1,1'-biphenyl]-4-yl)methyl)pentanamido)-3-methylbutanoate (Intermediate 438a) together with the appropriate amine, according to the method described for the synthesis of Example 297. Analytical LC-MS injections were used to determine the final purity, the retention time is reported for each compound and the method used is referred as Method A1, Method A2 or Method H.

| Ex | Structure | MW | LC-MS m/z [M + H]+; RT (Method) | 1H NMR (400 MHz, DMSO-d6) δ ppm |
|---|---|---|---|---|
| 447 | 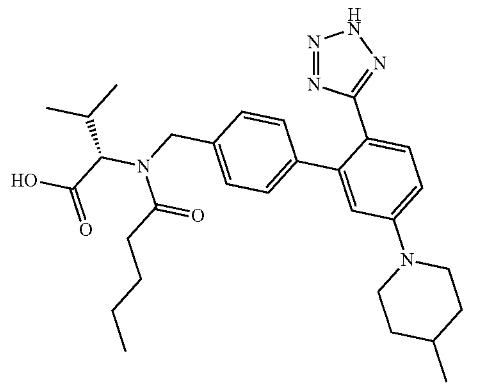 [SMILES: CCCCC(=O)N(Cc1ccc(-c2cc(N3CCC(C)CC3)ccc2-c2nn[nH]n2)cc1)[C@H](C(=O)O)C(C)C] | 532.7 | 533.3; 1.40 min (Method H) | 12.58 (s, 2H), 7.37-7.46 (m, 1H), 7.16 (d, J = 8.2 Hz, 1H), 7.06 (d, J = 8.2 Hz, 3H), 6.96 (d, J = 8.2 Hz, 1H), 6.88 (d, J = 2.7 Hz, 1H), 4.53-4.67 (m, 1H), 4.38-4.50 (m, 1H), 3.86 (d, J = 12.5 Hz, 2H), 2.78 (t, J = 12.3 Hz, 2H), 2.36-2.46 (m, 1H), 1.96-2.26 (m, 2H), 1.68 (d, J = 11.7 Hz, 2H), 1.10-1.62 (m, 8H), 0.63-0.98 (m, 12H). |
| 448 | 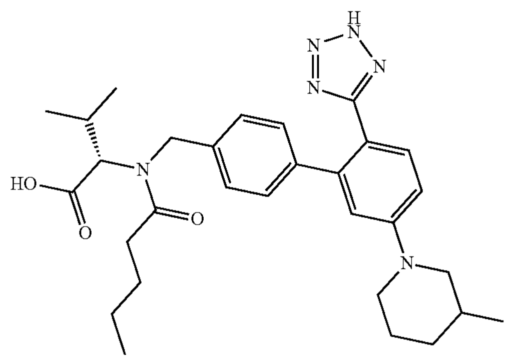 [SMILES: CCCCC(=O)N(Cc1ccc(-c2cc(N3CCCC(C)C3)ccc2-c2nn[nH]n2)cc1)[C@H](C(=O)O)C(C)C] | 532.7 | 533.2; 1.41 min (Method H) | 12.60 (br s, 2H), 7.38-7.45 (m, 1H), 7.17 (d, J = 7.8 Hz, 1H), 7.01-7.09 (m, 3H), 6.96 (d, J = 7.8 Hz, 1H), 6.88 (d, J = 2.3 Hz, 1H), 4.53-4.68 (m, 1H), 4.36-4.50 (m, 1H), 3.71-3.87 (m, 2H), 2.74 (t, J = 12.1 Hz, 1H), 2.37-2.46 (m, 2H), 1.97-2.26 (m, 2H), 1.24-1.80 (m, 8H), 1.01-1.20 (m, 2H), 0.60-0.98 (m, 12H). |
| 449 | 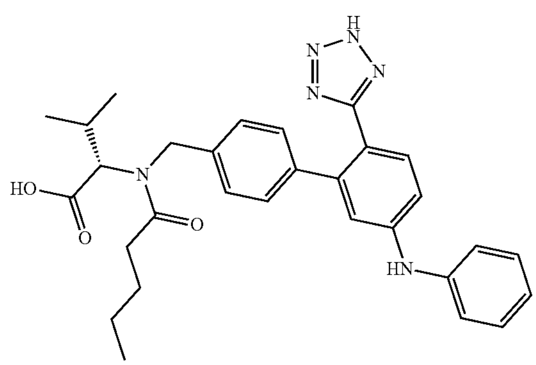 [SMILES: CCCCC(=O)N(Cc1ccc(-c2cc(Nc3ccccc3)ccc2-c2nn[nH]n2)cc1)[C@H](C(=O)O)C(C)C] | 526.6 | 527.2; 1.33 min (Method H) | 12.57 (s, 2H), 8.59-8.68 (m, 1H), 7.40-7.50 (m, 1H), 7.25-7.35 (m, 2H), 7.10-7.23 (m, 4H), 7.01-7.10 (m, 3H), 6.88-6.99 (m, 2H), 4.60 (s, 1H), 4.35-4.52 (m, 1H), 2.37-2.46 (m, 1H), 1.96-2.25 (m, 2H), 1.03-1.60 (m, 5H), 0.61-0.96 (m, 9H). |

| Ex | Structure | MW | LC-MS m/z [M + H]+; RT (Method) | 1H NMR (400 MHz, DMSO-d6) δ ppm |
|---|---|---|---|---|
| 450 | 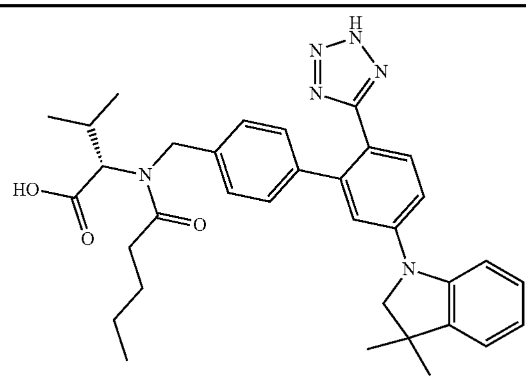 | 580.2 | 581.3; 1.48 min. (Method H) | 7.58 (t, J = 7.6 Hz, 1H), 7.39 (d, J = 8.2 Hz, 1H), 6.96-7.32 (m, 8H), 6.83 (t, J = 7.4 Hz, 1H), 4.55-4.68 (m, 1H), 4.46 (d, J = 9.8 Hz, 1H), 2.38-2.46 (m, 1H), 1.93-2.19 (m, 2H), 1.03-1.56 (m, 11H), 0.65-0.98 (m, 9H). |

Example 451: 3-((6-(4-(2H-Tetrazol-5-yl)-[1,1'-biphenyl]-3-yl)pyridin-3-yl)methyl)-2-butyl-1,3-diazaspiro[4.4]non-1-en-4-one

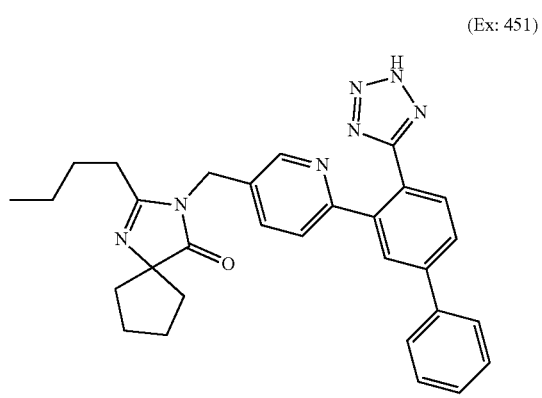 [SMILES: CCCCC1=NC2(CCCC2)C(=O)N1Cc1ccc(-c2cc(-c3ccccc3)ccc2-c2nn[nH]n2)nc1]

(Ex: 451)

Intermediate 451a: 3-((6-Bromopyridin-3-yl)methyl)-2-butyl-1,3-diazaspiro[4.4]non-1-en-4-one

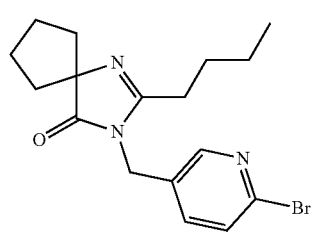

(451a)

To a solution of 2-butyl-1,3-diazaspiro[4.4]non-1-en-4-one.HCl (0.218 g, 0.918 mmol) in DMF (3 mL) at 30-35° C. was added freshly pulverized NaOH (0.084 g, 2.112 mmol). The resulting mixture was stirred at the same temperature under $N_2$ for 30 min. Then a solution of 2-bromo-5-(bromomethyl)pyridine (0.240 g, 0.918 mmol) in DMF (2 mL) was added dropwise and the reaction mixture was stirred at the same temperature for 16 h. The mixture was then cooled at 0° C. and $H_2O$ (12 mL) was added dropwise. The cooling bath was then removed and the resulting mixture was stirred at RT for 30 min, after which the resulting slurry was filtered and the filter-cake washed with $H_2O$. The wet filter-cake was partitioned with DCM-saturated aqueous $Na_2CO_3$ and the organic phase was separated, dried ($Na_2SO_4$) and evaporated to give a nearly colourless gum. This material was triturated with hexane to give a crystalline solid, which was filtered and washed with a little more hexane. After drying in vacuo, this gave the pure product (191 mg, 57%) as an off-white solid. The filtrate was evaporated and the residue was again triturated with a minimum volume of hexane. The supernatant was decanted and the residue was dried in vacuo to give another 45 mg (13%) of the pure product as a white crystalline solid. These solids were combined to give pure 3-((6-bromopyridin-3-yl)methyl)-2-butyl-1,3-diazaspiro[4.4]non-1-en-4-one (0.236 g, 70.6% yield), which was used as such in the next step. LC-MS (Method H): 1.265 min, [M+H]+=364.0. 1H NMR (400 MHz, DMSO-d6) δ ppm 8.25 (d, J=2.7 Hz, 1H), 7.63 (d, J=8.2 Hz, 1H), 7.50 (dd, J=2.7, 8.2 Hz, 1H), 4.68 (s, 2H), 2.34 (t, J=7.4 Hz, 2H), 1.81 (m, 6H), 1.63 (m, 2H), 1.46 (quint, J=7.4 Hz, 2H), 1.26 (m, 2H), 0.80 (t, J=7.4 Hz, 3H).

Intermediate 451b: 3-(5-((2-Butyl-4-oxo-1,3-diazaspiro[4.4]non-1-en-3-yl)methyl)pyridin-2-yl)-[1,1'-biphenyl]-4-carbonitrile

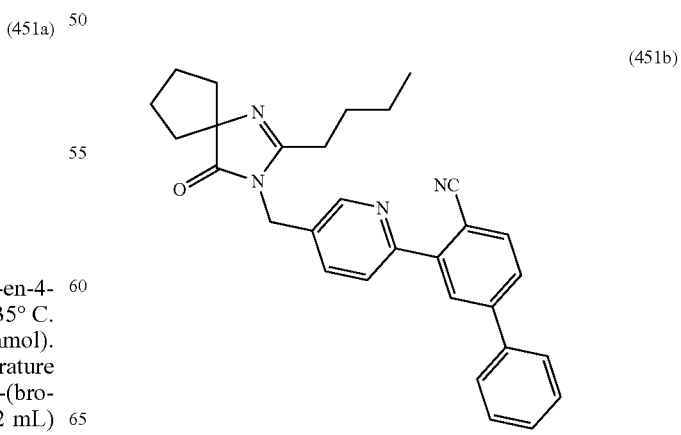

(451b)

The title compound was prepared by the reaction of 3-((6-bromopyridin-3-yl)methyl)-2-butyl-1,3-diazaspiro[4.4]non-1-en-4-one (Intermediate 451a, 0.044 g, 0.121 mmol) with 3-(5,5-dimethyl-1,3,2-dioxaborinan-2-yl)-[1,1'-biphenyl]-4-carbonitrile (Intermediate 268c, 0.042 g, 0.145 mmol), according to the method described for the synthesis of Intermediate 330b, to give a white solid (0.062 g, 111%). This material was contaminated with residual Ph₃PO, but was sufficiently pure to be used as such in the next step. LC-MS (Method H): 1.34 min, [M+H]⁺=463.2; ¹H NMR (DMSO-d₆) δ ppm 8.63 (d, J=2.0 Hz, 1H), 8.13 (d, J=2.0 Hz, 1H), 8.05 (d, J=8.2 Hz, 1H), 8.02 (d, J=7.8 Hz, 1H), 7.91-7.98 (m, 1H), 7.81-7.89 (m, 2H), 7.75 (dd, J=8.2, 2.3 Hz, 1H), 7.50-7.56 (m, 2H), 7.44-7.50 (m, 1H), 4.31 (t, J=5.5 Hz, 2H), 2.42 (t, J=7.4 Hz, 2H), 1.77-1.96 (m, 6H), 1.61-1.77 (m, 2H), 1.52 (dt, J=15.1, 7.3 Hz, 2H), 1.19-1.36 (m, 2H), 0.82 (t, J=7.4 Hz, 3H).

Example 451: 3-((6-(4-(1H-Tetrazol-5-yl)-[1,1'-biphenyl]-3-yl)pyridin-3-yl)methyl)-2-butyl-1,3-diazaspiro[4.4]non-1-en-4-one The title compound was prepared by the reaction of 3-(5-((2-butyl-4-oxo-1,3-diazaspiro[4.4]non-1-en-3-yl)methyl)pyridin-2-yl)-[1,1'-biphenyl]-4-carbonitrile (Intermediate 451b, 0.055 g, 0.119 mmol), according to the method described for the synthesis of Intermediate 283a, to give a white solid (0.047 g, 78%). LC-MS (Method H): 1.28 min, [M+H]⁺=506.1; ¹H NMR (DMSO-d₆) δ ppm 8.38 (d, J=2.0 Hz, 1H), 8.00 (d, J=2.0 Hz, 1H), 7.95 (dd, J=8.2, 2.0 Hz, 1H), 7.77-7.87 (m, 3H), 7.72 (dd, J=8.2, 2.3 Hz, 1H), 7.63 (d, J=8.2 Hz, 1H), 7.49-7.56 (m, 2H), 7.39-7.49 (m, 1H), 4.89 (s, 2H), 2.66 (t, J=7.2 Hz, 2H), 1.77-2.04 (m, 8H), 1.43-1.62 (m, 2H), 1.23-1.40 (m, 2H), 0.79-0.92 (m, 3H).

Example 452: 3-((5-Bromopyridin-2-yl)methyl)-2-butyl-1,3-diazaspiro[4.4]non-1-en-4-one

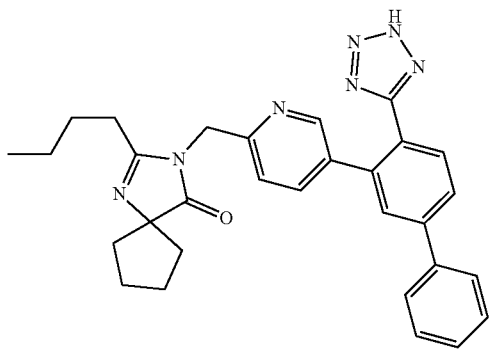

(Ex: 452)

Intermediate 452a: 3-((5-Bromopyridin-2-yl)methyl)-2-butyl-1,3-diazaspiro[4.4]non-1-en-4-one

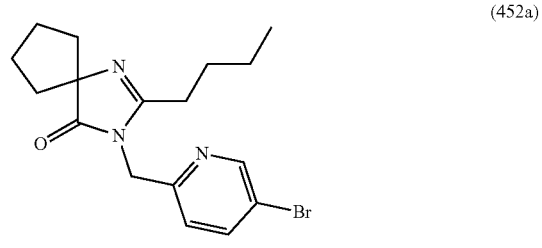 [SMILES: CCCCC1=NC2(CCCC2)C(=O)N1Cc1ccc(Br)cn1]

(452a)

The title compound was prepared by the reaction of 2-butyl-1,3-diazaspiro[4.4]non-1-en-4-one.HCl (0.250 g, 1.083 mmol) with 5-bromo-2-(chloromethyl)pyridine.HCl (0.263 g, 1.083 mmol), according to the method described for the synthesis of Intermediate 451a, to give a white solid (0.300 g, 76%). LC-MS (Method H): 1.23 min, [M+H]⁺=364.0; ¹H NMR (DMSO-d₆) δ ppm 8.63 (dd, J=2.3, 0.8 Hz, 1H), 8.04 (dd, J=8.2, 2.3 Hz, 1H), 7.24 (d, J=8.2 Hz, 1H), 4.75 (s, 2H), 2.25-2.41 (m, 2H), 1.71-1.94 (m, 6H), 1.56-1.71 (m, 2H), 1.43-1.56 (m, 2H), 1.27 (dq, J=15.0, 7.4 Hz, 2H), 0.81 (t, J=7.2 Hz, 3H).

Intermediate 452b: 3-(6-((2-Butyl-4-oxo-1,3-diazaspiro[4.4]non-1-en-3-yl)methyl)pyridin-3-yl)-1,1'-biphenyl]-4-carbonitrile

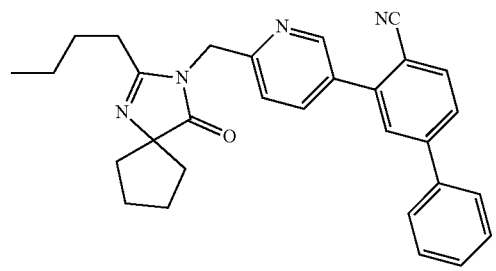

(452b)

The title compound was prepared by the reaction of 3-((5-bromopyridin-2-yl)methyl)-2-butyl-1,3-diazaspiro[4.4]non-1-en-4-one (Intermediate 452a, 0.100 g, 0.275 mmol) with 3-(5,5-dimethyl-1,3,2-dioxaborinan-2-yl)-[1,1'-biphenyl]-4-carbonitrile (Intermediate 268c, 0.096 g, 0.329 mmol), according to the method described for the synthesis of Intermediate 330b, to give a white solid (0.121 g, 95%) which was used as such in the next step. LC-MS (Method H): 1.39 min, [M+H]⁺=463.1; ¹H NMR (DMSO-d₆) δ ppm 8.83 (d, J=2.0 Hz, 1H), 8.15 (dd, J=8.2, 2.3 Hz, 1H), 8.07 (d, J=7.8 Hz, 1H), 7.97 (d, J=1.6 Hz, 1H), 7.94 (dd, J=8.2, 2.0 Hz, 1H), 7.80-7.90 (m, 2H), 7.39-7.57 (m, 4H), 4.88 (s, 2H), 2.42 (t, J=7.6 Hz, 2H), 1.76-1.96 (m, 6H), 1.61-1.76 (m, 2H), 1.54 (quint, J=7.5 Hz, 2H), 1.19-1.37 (m, 2H), 0.83 (t, J=7.4 Hz, 3H).

Example 452: 3-((5-(4-(2H-Tetrazol-5-yl)-[1,1'-biphenyl]-3-yl)pyridin-2-yl)methyl)-2-butyl-1,3-diazaspiro[4.4]non-1-en-4-one The title compound was prepared by the reaction of 3-(6-((2-butyl-4-oxo-1,3-diazaspiro[4.4]non-1-en-3-yl)

methyl)pyridin-3-yl)-[1,1'-biphenyl]-4-carbonitrile (Intermediate 452b, 0.055, 0.119 mmol), according to the method described for the synthesis of Intermediate 283a, to give a white solid (0.055 g, 91%). LC-MS (Method H): 1.33 min, [M+H]$^+$=506.2; $^1$H NMR (DMSO-d$_6$) δ ppm 8.39 (d, J=2.0 Hz, 1H), 7.93-7.98 (m, 1H), 7.81-7.90 (m, 4H), 7.68 (dd, J=8.0, 2.2 Hz, 1H), 7.48-7.57 (m, 2H), 7.41-7.48 (m, 1H), 7.38 (d, J=8.2 Hz, 1H), 5.03 (s, 2H), 2.70 (t, J=6.8 Hz, 2H), 1.75-2.05 (m, 8H), 1.58 (dt, J=15.2, 7.5 Hz, 2H), 1.32 (dq, J=14.9, 7.4 Hz, 2H), 0.85 (t, J=7.4 Hz, 3H).

Example 453: 3-(3-(6-((2-Butyl-4-oxo-1,3-diazaspiro[4.4]non-1-en-3-yl)methyl)pyridin-3-yl)-[1,1'-biphenyl]-4-yl)-1,2,4-oxadiazol-5(4H)-one

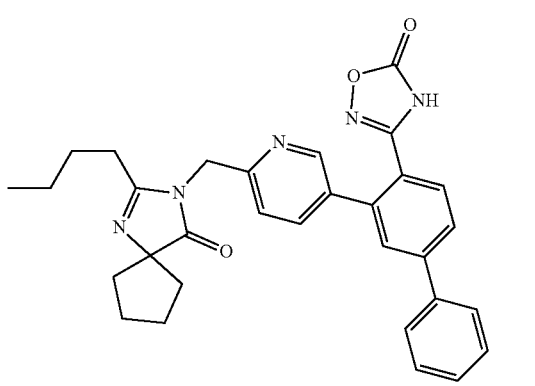

(Ex: 453)

Intermediate 453a: (Z)-3-(6-((2-Butyl-4-oxo-1,3-diazaspiro[4.4]non-1-en-3-yl)methyl)pyridin-3-yl)-N'-hydroxy-[1,1'-biphenyl]-4-carboximidamide

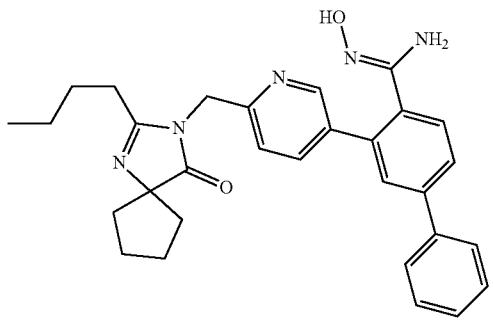

(453a)

The title compound was prepared by the reaction of 3-(6-((2-butyl-4-oxo-1,3-diazaspiro[4.4]non-1-en-3-yl)methyl)pyridin-3-yl)-[1,1'-biphenyl]-4-carbonitrile (Intermediate 452b, 0.060 g, 0.130 mmol) with hydroxylamine hydrochloride, according to the method described for the synthesis of Intermediate 280a, to give a white solid (0.011 g, 17.1%) which was used as such in the next step. LC-MS (Method H): 1.32 min, [M+H]$^+$=496.2; HRMS (ESI): Calcd for C$_{30}$H$_{34}$N$_5$O$_2$ [M+H]$^+$ m/z 496.2702; found 496.2720.

Example 453: 3-(3-(6-((2-Butyl-4-oxo-1,3-diazaspiro[4.4]non-1-en-3-yl)methyl)pyridin-3-yl)-[1,1'-biphenyl]-4-yl)-1,2,4-oxadiazol-5(4H)-one The title compound was prepared by the reaction of (Z)-3-(6-((2-butyl-4-oxo-1,3-diazaspiro[4.4]non-1-en-3-yl)methyl)pyridin-3-yl)-N'-hydroxy-[1,1'-biphenyl]-4-carboximidamide (Intermediate 453a, 0.011 g, 0.022 mmol), according to the method described for the synthesis of Example 280, to give a white solid (0.006 g, 51.8%). LC-MS (Method H): 1.36 min, [M+H]$^+$=522.2; $^1$H NMR (DMSO-d$_6$) δ ppm 12.63 (br s, 1H), 8.57 (d, J=2.0 Hz, 1H), 7.91-7.97 (m, 1H), 7.86-7.91 (m, 1H), 7.80-7.86 (m, 4H), 7.42-7.57 (m, 4H), 5.05 (s, 2H), 2.61-2.78 (m, 2H), 1.76-2.03 (m, 8H), 1.58 (dt, J=15.3, 7.6 Hz, 2H), 1.32 (dq, J=15.0, 7.4 Hz, 2H), 0.85 (t, J=7.4 Hz, 3H).

Example 454: 2-Butyl-3-((5'-phenoxy-2'-(1H-tetrazol-5-yl)-[1,1'-biphenyl]-4-yl)methyl)-1,3-diazaspiro[4.4]non-1-en-4-one

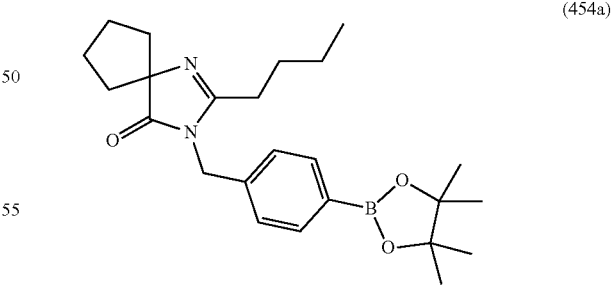

(Ex: 454)

Intermediate 454a: 2-Butyl-3-(4-(4,4,5,5-tetramethyl-1,3,2-dioxaborolan-2-yl)benzyl)-1,3-diazaspiro[4.4]non-1-en-4-one (454a)

To a suspension of sodium hydride (60% in oil, 0.150 g, 3.75 mmol) in DMF (7.5 mL) was added 2-butyl-1,3-diazaspiro[4.4]non-1-en-4-one.HCl (0.357 g, 1.500 mmol) all at once and the mixture was stirred at RT under N$_2$ for 30 min. To this mixture was added a solution of 2-(4-(bromomethyl)phenyl)-4,4,5,5-tetramethyl-1,3,2-dioxaborolane (0.535 g, 1.800 mmol) in DMF (2.5 mL) dropwise and stirring was continued at the RT for 1 h. The volatiles were then removed under reduced pressure to give a milky white gum that was taken up in a minimum volume of DCM and applied to a silica gel pre-column. Flash chromatography (ISCO/0-100% EtOAc-hexane) afforded 2-butyl-3-(4-(4,4,5,5-tetramethyl-1,3,2-dioxaborolan-2-yl)benzyl)-1,3-diazaspiro[4.4]non-1-en-4-one (0.477 g, 77% yield) as a clear, colourless gum. $^1$H NMR (400 MHz, DMSO-d$_6$) δ ppm 7.63 (d, J=7.8 Hz, 2H), 7.15 (d, J=8.2 Hz, 2H), 4.68 (s, 2H), 2.26 (t, J=7.4 Hz, 2H), 1.82 (m, 6H), 1.64 (m, 2H), 1.43 (quint, J=7.4 Hz, 2H), 1.26 (s, 12H), 1.22 (m, 2H), 0.76 (t, J=7.4 Hz, 3H).

Intermediate 454b: 4'-((2-Butyl-4-oxo-1,3-diazaspiro[4.4]non-1-en-3-yl)methyl)-5-phenoxy-[1,1'-biphenyl]-2-carbonitrile

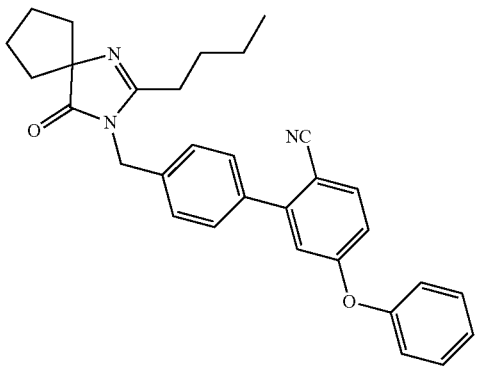

(454b)

A mixture of 2-butyl-3-(4-(4,4,5,5-tetramethyl-1,3,2-dioxaborolan-2-yl)benzyl)-1,3-diazaspiro[4.4]non-1-en-4-one (0.060 g, 0.146 mmol), 2-bromo-4-phenoxybenzonitrile (Intermediate 204a, 0.050 g, 0.183 mmol) and 2 M Na$_2$CO$_3$ (0.183 mL, 0.383 mmol) in toluene-ethanol (9:1, 5 mL) was purged with a stream of N$_2$ for 5 min in a sealable vial. To this mixture was added Pd(Ph$_3$P)$_4$ (0.017 g, 0.015 mmol), the vial was sealed and the mixture was stirred at 95° C. (block temperature) for 16 h. The cooled mixture was diluted with EtOAc and the organic phase was separated, dried (Na$_2$SO$_4$) and evaporated to give a clear gum. This material was purified by flash chromatography (ISCO/0-100% EtOAc-DCM) to give 4'-((2-ethyl-5,7-dimethyl-3H-imidazo[4,5-b]pyridin-3-yl)methyl)-5-phenoxy-[1,1'-biphenyl]-2-carbonitrile (0.039 g, 55.8% yield) as a colourless gum. This gum was lyophilized from ACN-H$_2$O to give a white solid which was used as such in the next step. LC-MS (Method H): 1.482 min, [M+H]$^+$=478.1; $^1$H NMR (400 MHz, DMSO-d$_6$) δ ppm 7.92 (d, J=8.6 Hz, 2H), 7.54 (d, J=8.2 Hz, 2H), 7.46 (t, J=8.0 Hz, 2H), 7.28-7.24 (m, 3H), 7.18 (d, J=8.2 Hz, 2H), 7.09 (d, J=2.3 Hz, 1H), 7.05 (dd, J=2.7, 8.6 Hz, 1H), 4.74 (s, 2H), 2.32 (t, J=7.4 Hz, 2H), 1.83 (m, 6H), 1.66 (m, 2H), 1.45 (quint, J=7.4 Hz, 2H), 1.23 (m, 2H), 0.75 (t, J=7.4 Hz, 3H).

Example 454: 2-Butyl-3-((5'-phenoxy-2'-(1H-tetrazol-5-yl)-[1,1'-biphenyl]-4-yl)methyl)-1,3-diazaspiro[4.4]non-1-en-4-one To a mixture of 4'-((2-butyl-4-oxo-1,3-diazaspiro[4.4]non-1-en-3-yl)methyl)-5-phenoxy-[1,1'-biphenyl]-2-carbonitrile (0.015 g, 0.031 mmol), TMS-N$_3$ (0.044 mL, 0.314 mmol) and dibutyltin oxide (0.016 g, 0.063 mmol) in a 4 mL vial was added toluene (2 mL). The vial was briefly purged with N$_2$ and then it was sealed and the mixture was stirred at 120° C. (block temperature) for 16 h. The cooled mixture was evaporated and the residual gum was taken up in DMF (acidified with a 10 drops of AcOH) and filtered using a 0.45 μm syringe filter. The filtrate was submitted to prep LC purification (Method D) and the product-containing fractions were combined and evaporated to give a gum. This material was lyophilized from ACN-H$_2$O to give 2-butyl-3-((5'-phenoxy-2'-(1H-tetrazol-5-yl)-[1,1'-biphenyl]-4-yl)methyl)-1,3-diazaspiro[4.4]non-1-en-4-one (0.009 g, 55.0% yield) as a white solid. LC-MS (Method H): 1.388 min, [M+H]$^+$=521.1; HRMS (ESI): Calcd. for C$_{31}$H$_{33}$N$_6$O$_2$ [M+H]$^+$ m/z 521.2665; found 521.2672. $^1$H NMR (400 MHz, DMSO-d$_6$) δ ppm 7.65 (d, J=8.6 Hz, 1H), 7.44 (t, J=8.0 Hz, 2H), 7.21 (t, J=7.4 Hz, 1H), 7.16 (d, J=7.8 Hz, 2H), 7.12 (dd, J=2.3, 8.2 Hz, 1H), 7.05 (s, 5H), 4.64 (s, 2H), 2.25 (t, J=7.4 Hz, 2H), 1.81 (m, 6H), 1.63 (m, 2H), 1.43 (quint, J=7.4 Hz, 2H), 1.22 (m, 2H), 0.75 (t, J=7.4 Hz, 3H).

Example 455: 2-Butyl-3-((5'-((4-methylpyridin-2-yl)oxy)-2'-(2H-tetrazol-5-yl)-[1,1'-biphenyl]-4-yl)methyl)-1,3-diazaspiro[4.4]non-1-en-4-one

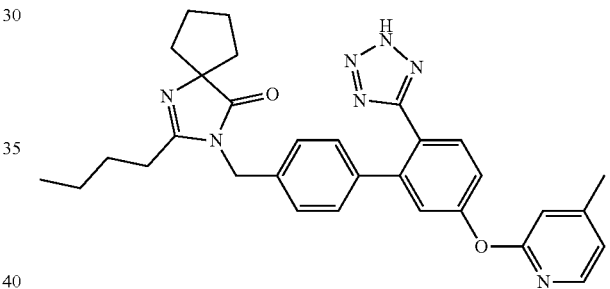

(Ex. 455)

Intermediate 455a: 4'-((2-Butyl-4-oxo-1,3-diazaspiro[4.4]non-1-en-3-yl)methyl)-5-hydroxy-[1,1'-biphenyl]-2-carbonitrile

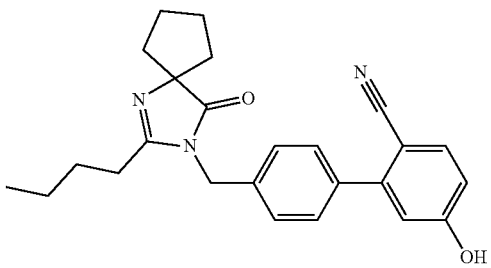

(455a)

In a 15-mL vial, a stream of Ar was passed through a mixture of 2-butyl-3-(4-(4,4,5,5-tetramethyl-1,3,2-dioxaborolan-2-yl)benzyl)-1,3-diazaspiro[4.4]non-1-en-4-one (Intermediate 454a, 0.259 g, 0.63 mmol), 2-bromo-4-hydroxybenzonitrile (0.15 g, 0.76 mmol) and 2M Na$_2$CO$_3$ (0.95 mL, 1.9 mmol) in a mixture of toluene (3 mL) and ethanol (0.3 mL) for 5 min. To this mixture was added Pd(PPh$_3$)$_4$ (0.036 g, 0.032 mmol) and Ar was again bubbled through the mixture for an additional 5 min. The vial was then sealed and the mixture was heated at 95° C. for 12 h. The mixture was allowed to cool to RT and saturated aqueous ammonium chloride (20 mL) and EtOAc (20 mL) were added. The organic phase was separated and the aqueous layer was re-extracted with EtOAc (2×20 mL). The combined organic extract was washed with brine, dried (anhydrous MgSO$_4$), filtered and evaporated. The residue obtained was purified using a 12 g RediSep column on an ISCO instrument eluting with 0-100% EtOAc-DCM to afford the title compound (0.070 g, 27.7% yield). LC-MS (Method H): 1.25 min, [M+H]$^+$=402.2.

Intermediate 455b: 4'-((2-Butyl-4-oxo-1,3-diazaspiro[4.4]non-1-en-3-yl)methyl)-5-((4-methylpyridin-2-yl)oxy)-[1,1'-biphenyl]-2-carbonitrile

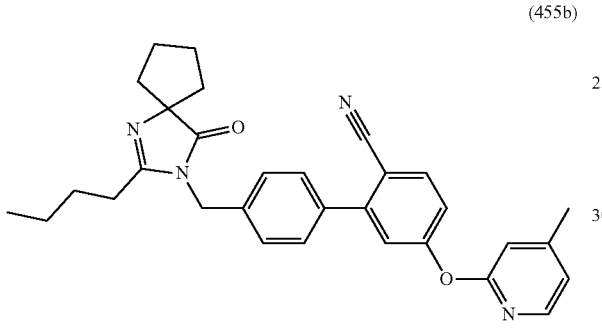

(455b)

In a conical 2-mL vial, a stream of Ar was passed through a suspension of 4'-((2-butyl-4-oxo-1,3-diazaspiro[4.4]non-1-en-3-yl)methyl)-5-hydroxy-[1,1'-biphenyl]-2-carbonitrile (0.038 g, 0.095 mmol), 2-chloro-4-methylpyridine (0.025 mL, 0.28 mmol) and cesium carbonate (0.093 g, 0.28 mmol) in toluene (0.24 mL). After 5 min, palladacycle precatalyst J009 PreCat (0.0015 g, 1.6 µmol) was added and Ar was bubbled through the mixture for an additional 5 min. The vial was then sealed and heated at 100° C. for 24 h.

The mixture was then allowed to cool to RT, saturated aqueous ammonium chloride (5 mL) and EtOAc (10 mL) were added and the separated aqueous layer was extracted with EtOAc (2×10 mL). The combined organic extract was washed with brine, dried (anhydrous MgSO$_4$), filtered and evaporated. The residue obtained was purified using a 24 g RediSep column on an ISCO instrument eluting with 0-100% EtOAc-DCM to afford 4'-((2-butyl-4-oxo-1,3-diazaspiro[4.4]non-1-en-3-yl)methyl)-5-((4-methylpyridin-2-yl)oxy)-[1,1'-biphenyl]-2-carbonitrile (0.026 g, 55.8% yield). LC-MS (Method H): 1.33 min, [M+H]$^+$=493.2. HRMS (ESI): Calcd for C$_{31}$H$_{33}$N$_4$O$_2$ [M+H]$^+$ m/z 493.2598; found: 493.2580.

Example 455: 2-Butyl-3-((5'-((4-methylpyridin-2-yl)oxy)-2'-(2H-tetrazol-5-yl)-[1,1'-biphenyl]-4-yl)methyl)-1,3-diazaspiro[4.4]non-1-en-4-one In a conical 2-mL vial was added 4'-((2-butyl-4-oxo-1,3-diazaspiro[4.4]non-1-en-3-yl)methyl)-5-((4-methylpyridin-2-yl)oxy)-[1,1'-biphenyl]-2-carbonitrile (0.026 g, 0.053 mmol), dibutyltin oxide (0.014 g, 0.058 mmol) and TMS-N$_3$ (0.056 mL, 0.42 mmol) in toluene (0.3 mL) and the sealed vial was heated at 100° C. for 12 h. The mixture was then allowed to cool to RT and the volatiles were removed under reduced pressure. The residue was dissolved in DMSO and the mixture was filtered (0.46 µm syringe filter) and the filtrate purified by preparative HPLC (Method D) to afford 2-butyl-3-((5'-((4-methylpyridin-2-yl)oxy)-2'-(2H-tetrazol-5-yl)-[1,1'-biphenyl]-4-yl)methyl)-1,3-diazaspiro[4.4]non-1-en-4-one (0.014 g, 50.2%) as a solid. LC-MS (Method H): 1.28 min, [M+H]$^+$=536.2. $^1$H NMR (400 MHz, DMSO-d$_6$) δ ppm 8.05 (d, J=5.1 Hz, 1H), 7.69 (d, J=8.6 Hz, 1H), 7.30 (dd, J=8.6, 2.4 Hz, 1H), 7.24 (d, J=2.4 Hz, 1H), 7.08 (m, 4H), 7.01 (m, 2H), 4.66 (s, 2H), 2.36 (s, 3H), 2.27 (t, J=7.4 Hz, 2H), 1.84 (m, 6H), 1.64 (m, 2H), 1.45 (q, J=7.4 Hz, 2H), 1.24 (m, 2H), 0.78 (t, J=7.2 Hz, 3H).

Example 456: 5-(4"-((3,5-Dimethyl-1H-1,2,4-triazol-1-yl)methyl)-[1,1':3',1"-terphenyl]-4'-yl)-2H-tetrazole

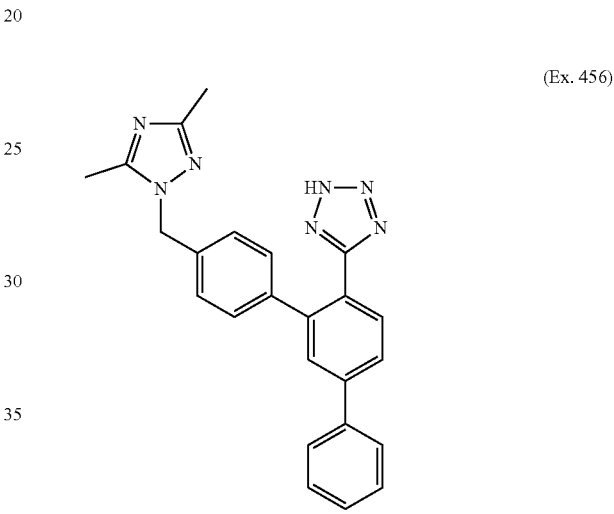

(Ex. 456)

Intermediate 456a: 1-(4-Bromobenzyl)-3,5-dimethyl-1H-1,2,4-triazole

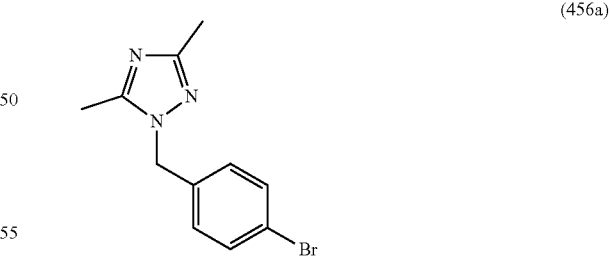

(456a)

In a 50 mL round-bottomed flask under N$_2$ at 0° C., sodium hydride (60% in mineral oil, 0.184 g, 4.60 mmol) was added to a solution of 3,5-dimethyl-1H-1,2,4-triazole (0.311 g, 3.20 mmol) in DMF (12 mL) and the mixture was stirred for 20 min. 4-Bromobenzyl bromide (0.960 g, 3.84 mmol) was then added to the mixture and stirring was continued at RT for 2.5 h. The reaction mixture was then poured into H$_2$O and the product was extracted with EtOAc (×3). The combined organic extract was washed with H$_2$O (×3) and brine, dried over anhydrous sodium sulfate and concentrated to dryness. The residue was purified on ISCO using a 40 g column (0-20% MeOH-DCM) to afford the title compound (0.382 g, 1.44 mmol, 45% yield) as an off-white solid. LC (Method B): 1.538 min. MS (APCI): calcd for $Cu_{11}H_{13}BrN_3$ [M+H]$^+$ m/z 266.0, found 266.1. $^1$H NMR (400 MHz, CDCl$_3$) δ ppm 7.43-7.52 (m, 2H), 7.00-7.08 (m, J=8.22 Hz, 2H), 5.16 (s, 2H), 2.37 (s, 3H), 2.35 (s, 3H).

Intermediate 456b: 4"-((3,5-Dimethyl-1H-1,2,4-triazol-1-yl)methyl)-[1,1':3',1"-terphenyl]-4'-carbonitrile

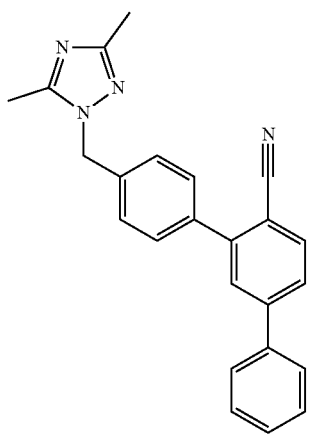

(456b)

In a 5 mL sealable vial, a solution of 1-(4-bromobenzyl)-3,5-dimethyl-1H-1,2,4-triazole (0.059 g, 0.22 mmol) and 3-(5,5-dimethyl-1,3,2-dioxaborinan-2-yl)-[1,1'-biphenyl]-4-carbonitrile (Intermediate 268c, 0.078 g, 0.27 mmol) in a mixture of ethanol (0.2 mL) and toluene (1.8 mL) was purged with a stream of N$_2$ for 10 min. Tetrakis(triphenylphosphine) palladium (0) (0.026 g, 0.022 mmol) and 2M aqueous Na$_2$CO$_3$ (0.33 mL, 0.66 mmol) were added, the vial was sealed and the mixture was stirred at 100° C. for 1.75 h. After being stored at RT for 16 h, the mixture was diluted in EtOAc and filtered over Celite®. The filtrate was then concentrated to dryness and the residue was purified on ISCO using a 12 g column (0-5% MeOH-DCM) to afford the title compound (0.096 g, 0.18 mmol, 70% purity, 83% yield), contaminated with triphenylphosphine oxide, as a white solid. LC (Method B): 1.985 min. MS (APCI): calcd for $C_{24}H_{21}N_4$[M+H]$^+$ m/z 365.2, found 365.2. $^1$H NMR (400 MHz, CDCl$_3$) δ ppm 7.84 (d, J=7.83 Hz, 1H), 7.65-7.71 (m, 3H), 7.59-7.65 (m, 3H), 7.45-7.51 (m, 3H), 7.31 (d, J=8.22 Hz, 2H), 5.30 (s, 2H), 2.43 (s, 3H), 2.38 (s, 3H).

Example 456: 5-(4"-((3,5-Dimethyl-1H-1,2,4-triazol-1-yl)methyl)-[1,1':3',1"-terphenyll-4'-yl)-2H-tetrazole In a vial under N$_2$, a mixture of 4"-((3,5-dimethyl-1H-1,2,4-triazol-1-yl)methyl)-[1,1':3',1"-terphenyl]-4'-carbonitrile (0.040 g, 0.077 mmol), dibutyltin oxide (0.034 g, 0.14 mmol) and TMS-N$_3$ (0.180 mL, 1.36 mmol) in toluene (3 mL) was stirred at 120° C. for 16.5 h. The cooled reaction mixture was poured into MeOH and the resulting mixture was concentrated to dryness. The crude residue was dissolved in DMF and purified twice by reverse-phase preparative LC (Method D) and the product was lyophilized from ACN-H$_2$O to afford the title compound (0.019 mg, 0.046 mmol, 60% yield) as a white solid. LC (Method B): 1.838 min. MS (APCI): calcd for $C_{24}H_{22}N_7$[M+H]$^+$ m/z 408.2, found 408.1. $^1$H NMR (400 MHz, CDCl$_3$) δ ppm 8.10 (d, J=8.22 Hz, 1H), 7.80 (dd, J=1.76, 8.02 Hz, 1H), 7.63-7.72 (m, 3H), 7.47-7.54 (m, 2H), 7.39-7.47 (m, 1H), 7.16-7.23 (m, 2H), 6.96-7.05 (m, 2H), 5.19 (s, 2H), 2.27 (s, 3H), 2.08 (s, 3H).

Example 457: 5-(4'-((3,5-Dimethyl-1H-1,2,4-triazol-1-yl)methyl)-5-(4-methyl-1H-pyrazol-1-yl)-[1,1'-biphenyl]-2-yl)-2H-tetrazole

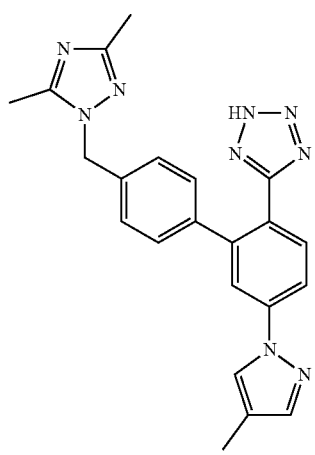

(Ex. 457)

Intermediate 457a: 4'-((3,5-Dimethyl-1H-1,2,4-triazol-1-yl)methyl)-5-fluoro-[1,1'-biphenyl]-2-carbonitrile

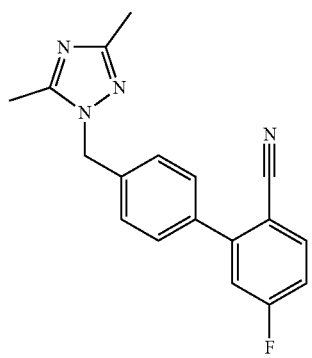

(457a)

In a 5 mL sealable vial, a solution of 1-(4-bromobenzyl)-3,5-dimethyl-1H-1,2,4-triazole (0.165 g, 0.620 mmol) and 4-fluoro-2-(4,4,5,5-tetramethyl-1,3,2-dioxaborolan-2-yl)benzonitrile (0.229 g, 0.927 mmol) in a mixture of ethanol (0.6 mL) and toluene (5.4 mL) was purged with a stream of N$_2$ for 20 min. Tetrakis(triphenylphosphine) palladium (0) (0.072 g, 0.062 mmol) and 2M aqueous Na$_2$CO$_3$ (0.93 mL, 1.860 mmol) were added, the vial was sealed and the mixture was stirred at 100° C. for 3.5 h. The cooled mixture was diluted with EtOAc and the resulting mixture was filtered over Celite®. The filtrate was then concentrated to dryness and the residue was purified twice on ISCO using a 40 g column (0-5% MeOH-DCM). The material obtained was dissolved in DMF and repurified by reverse-phase preparative LC (Method D) and the product obtained was lyophilized from ACN-H$_2$O to afford the title compound (0.094 g, 0.31 mmol, 50% yield) as a white solid. LC (Method B): 1.617 min. MS (APCI): calcd for C$_{18}$H$_{16}$FN$_4$ [M+H]$^+$ m/z 307.1, found 307.1. $^1$H NMR (400 MHz, CDCl$_3$) δ ppm 7.78 (dd, J=5.67, 8.41 Hz, 1H), 7.52-7.57 (m, 2H), 7.28-7.32 (m, 2H), 7.13-7.22 (m, 2H), 5.29 (s, 2H), 2.42 (s, 3H), 2.38 (s, 3H).

Intermediate 457b: 4'-((3,5-Dimethyl-1H-1,2,4-triazol-1-yl)methyl)-5-(4-methyl-1H-pyrazol-1-yl)-[1,1'-biphenyl]-2-carbonitrile

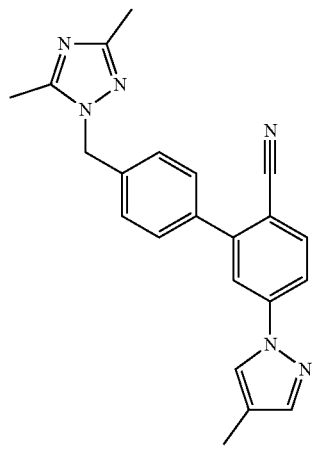

(457b)

In a vial under N$_2$, a mixture of 4'-((3,5-dimethyl-1H-1,2,4-triazol-1-yl)methyl)-5-fluoro-[1,1'-biphenyl]-2-carbonitrile (0.038 g, 0.12 mmol), 4-methyl-1H-pyrazole (0.020 mL, 0.24 mmol) and potassium carbonate (0.040 g, 0.29 mmol) in DMF (2 mL) was heated at 100° C. for 18 h. Additional 4-methyl-1H-pyrazole (0.020 mL, 0.24 mmol) was added and the mixture was heated at 100° C. for another 3 days. The cooled mixture was acidified with formic acid (0.050 mL) and the solution was purified by reverse-phase preparative LC (Method D). The product obtained was lyophilized from ACN-H$_2$O to afford the title compound (0.038 g, 0.10 mmol, 84% yield) as a white solid. LC (Method B): 1.828 min. MS (APCI): calcd for C$_{22}$H$_{21}$N$_6$ [M+H]$^+$ m/z 369.2, found 369.2. $^1$H NMR (400 MHz, CDCl$_3$) δ ppm 7.77-7.84 (m, 3H), 7.73 (dd, J=2.20, 8.40 Hz, 1H), 7.58-7.63 (m, 3H), 7.28-7.33 (m, 2H), 5.30 (s, 2H), 2.43 (s, 3H), 2.38 (s, 3H), 2.18 (s, 3H).

Example 457: 5-(4'-((3,5-Dimethyl-1H-1,2,4-triazol-1-yl)methyl)-5-(4-methyl-1H-pyrazol-1-yl)-[1,1'-biphenyl]-2-yl)-2H-tetrazole In a vial under N$_2$, a mixture of 4'-((3,5-dimethyl-1H-1,2,4-triazol-1-yl)methyl)-5-(4-methyl-1H-pyrazol-1-yl)-[1,1'-biphenyl]-2-carbonitrile (0.036 g, 0.098 mmol), dibutyltin oxide (0.031 g, 0.13 mmol) and TMS-N$_3$ (0.13 mL, 0.98 mmol) in toluene (3 mL) was stirred at 120° C. for 17 h. The cooled reaction mixture was poured into MeOH and the resulting mixture was concentrated to dryness. The crude material was dissolved in DMF and purified twice by reverse-phase preparative LC (Method D) and the product obtained was lyophilized from ACN-H$_2$O to afford the title compound (0.027 g, 0.066 mmol, 67% yield) as a white solid. LC (Method B): 1.632 min. MS (APCI): calcd for C$_{22}$H$_{22}$N$_9$[M+H]$^+$ m/z 412.2, found 412.2. $^1$H NMR (400 MHz, DMSO-d$_6$) δ ppm 8.49 (s, 1H), 7.99 (dd, J=8.4, 2.2 Hz, 1H), 7.92 (d, J=2.0 Hz, 1H), 7.77 (d, J=8.2 Hz, 1H), 7.64 (s, 1H), 7.16 (s, 4H), 5.27 (s, 2H), 2.35 (s, 3H), 2.17 (s, 3H), 2.11 (s, 3H).

Example 458: 2-(4'-((3,5-Dimethyl-1H-1,2,4-triazol-1-yl)methyl)-6-(2H-tetrazol-5-yl)-[1,1'-biphenyl]-3-yl)-4-methylpyridine

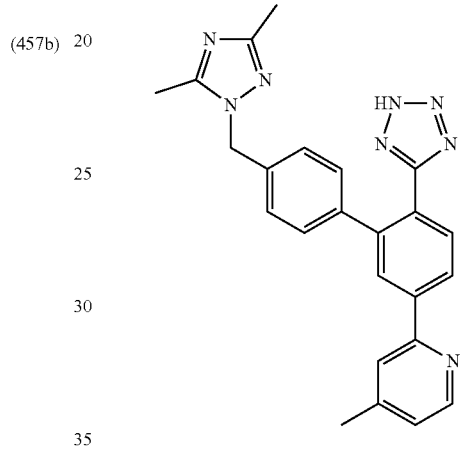

(Ex. 458)

Intermediate 458a: 5-Bromo-4'-((3,5-dimethyl-1H-1,2,4-triazol-1-yl)methyl)-[1,1'-biphenyl]-2-carbonitrile

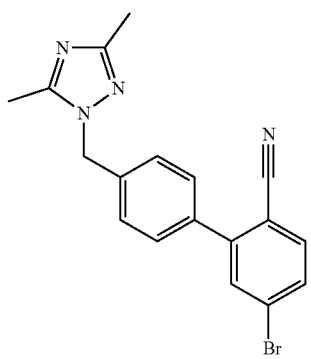

(458a)

In a 25 mL round-bottomed flask under N$_2$ at 0° C., sodium hydride (60% in mineral oil, 0.059 g, 1.48 mmol) was added to a solution of 3,5-dimethyl-1H-1,2,4-triazole (0.112 g, 1.15 mmol) in DMF (5 mL) and the mixture was stirred for 30 min. To this mixture was then added 5-bromo-4'-(bromomethyl)-[1,1'-biphenyl]-2-carbonitrile (I-002, 0.407 g, 1.16 mmol) and the mixture was stirred at RT for 3.5 h. The resulting mixture was then poured into H$_2$O and the product was extracted with EtOAc (×3). The combined organic extract was washed with H₂O (×3) and brine, dried over anhydrous sodium sulfate and concentrated to dryness. The residue was purified on ISCO using a 40 g column (0-5% MeOH-DCM) to afford the title compound (0.248 mg, 0.675 mmol, 59% yield) as a colorless gum. LC (Method B): 1.795 min. MS (APCI): calcd for $C_{18}H_{16}BrN_4$ [M+H]⁺ m/z 367.1, found 367.0. ¹H NMR (400 MHz, CDCl₃) δ ppm 7.66 (dd, J=0.78, 1.57 Hz, 1H), 7.61-7.63 (m, 2H), 7.51-7.56 (m, 2H), 7.28-7.31 (m, 2H), 5.29 (s, 2H), 2.42 (s, 3H), 2.38 (s, 3H).

Intermediate 458b: 5-(5,5-Dimethyl-1,3,2-dioxaborinan-2-yl)-4'-((3,5-dimethyl-1H-1,2,4-triazol-1-yl)methyl)-[1,1'-biphenyl]-2-carbonitrile (458b)

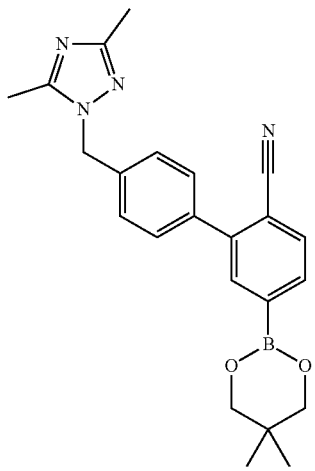

In a 5 mL sealable vial, a mixture of 5-bromo-4'-((3,5-dimethyl-1H-1,2,4-triazol-1-yl)methyl)-[1,1'-biphenyl]-2-carbonitrile (0.079 g, 0.22 mmol) and 5,5,5',5'-tetramethyl-2,2'-bi(1,3,2-dioxaborinane) (0.122 g, 0.540 mmol) in 1,4-dioxane (3 mL) was purged with a stream of N₂ for 10 min. To this mixture was added XPhos Pd G2 (0.030 g, 0.038 mmol), followed by KOAc (0.066 g, 0.67 mmol) and the mixture was heated at 85° C. for 2.75 h. The cooled reaction mixture was poured into H₂O, the product was extracted with EtOAc (×3) and the combined organic extract was washed with brine, dried over anhydrous sodium sulfate and concentrated to dryness. The residue was purified on ISCO using a 25 g column (0-5% MeOH-DCM) to afford the title compound (0.106 g, 0.169 mmol, 64% purity, 79% yield) as a white solid. LC (Method B): 1.534 min. MS (APCI): calcd for $C_{18}H_{18}BN_4O_2[M-C_5H_{10}O_2+2OH]^+$ m/z 333.2, found 333.1. ¹H NMR (400 MHz, CDC₃) δ ppm 7.90 (s, 1H), 7.85 (dd, J=7.6, 1.0 Hz, 1H), 7.73 (d, J=7.8 Hz, 1H), 7.54-7.59 (m, 2H), 7.27 (d, J=8.2 Hz, 2H), 5.28 (s, 2H), 3.79 (s, 4H), 2.41 (s, 3H), 2.38 (s, 3H), 1.04 (s, 6H).

Intermediate 458c: 4'-((3,5-Dimethyl-1H-1,2,4-triazol-1-yl)methyl)-5-(4-methylpyridin-2-yl)-[1,1'-biphenyl]-2-carbonitrile (458c)

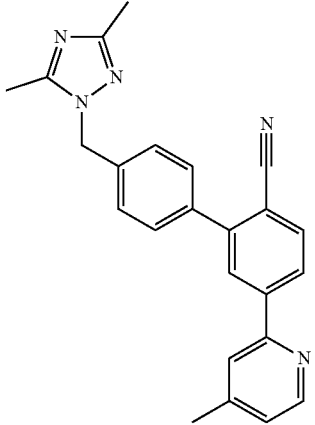

In a 5 mL sealable vial, a mixture of 5-(5,5-dimethyl-1,3,2-dioxaborinan-2-yl)-4'-((3,5-dimethyl-1H-1,2,4-triazol-1-yl)methyl)-[1,1'-biphenyl]-2-carbonitrile (0.068 g, 0.17 mmol) and 2-bromo-4-methylpyridine (0.060 mL, 0.54 mmol) in DME (2 mL) was purged with a stream of N₂ for 10 min. To this mixture was added tetrakis(triphenylphosphine) palladium (0) (0.024 g, 0.021 mmol) and 2M aqueous Na₂CO₃ (0.35 mL, 0.70 mmol) and the mixture was heated at 85° C. for 17 h. The cooled reaction mixture was concentrated to dryness and the residue was purified on ISCO using a 25 g column (0-10% MeOH-DCM) to afford the title compound (0.064 g, 0.17 mmol, 100% yield) as an off-white solid. LC (Method B): 1.579 min. MS (APCI): calcd for $C_{24}H_{22}N_5$ [M+H]⁺ m/z 380.2, found 380.2. ¹H NMR (400 MHz, DMSO-d₆) δ ppm 8.57 (d, J=5.1 Hz, 1H), 8.25-8.32 (m, 2H), 8.03-8.09 (m, 2H), 7.64-7.69 (m, 2H), 7.35-7.41 (m, 2H), 7.29 (d, J=5.1 Hz, 1H), 5.37 (s, 2H), 3.15 (s, 3H), 3.13 (s, 3H), 2.19 (s, 3H).

Example 458: 2-(4'-((3,5-Dimethyl-1H-1,2,4-triazol-1-yl)methyl)-6-(2H-tetrazol-5-yl)-[1,1'-biphenyl]-3-yl)-4-methylpyridine In a vial under N₂, a mixture of 4'-((3,5-dimethyl-1H-1,2,4-triazol-1-yl)methyl)-5-(4-methylpyridin-2-yl)-[1,1'-biphenyl]-2-carbonitrile (0.064 g, 0.17 mmol), dibutyltin oxide (0.052 g, 0.21 mmol) and TMS-N₃ (0.23 mL, 1.73 mmol) in toluene (3.5 mL) was stirred at 120° C. for 17 h. The cooled reaction mixture was poured into MeOH and the resulting mixture was concentrated to dryness. The crude material was purified twice by reverse-phase preparative LC (Method D) and the product obtained was lyophilized from ACN-H₂O to afford the title compound (0.035 g, 0.082 mmol, 49% yield) as a white solid. LC (Method B): 1.281 min. MS (APCI): calcd for $C_{24}H_{23}N_8$[M+H]⁺ m/z 423.2, found 423.1. ¹H NMR (400 MHz, DMSO-d₆) δ ppm 8.55 (d, J=4.7 Hz, 1H), 8.27 (dd, J=7.8, 1.6 Hz, 1H), 8.19 (d, J=1.6 Hz, 1H), 8.02 (s, 1H), 7.79 (d, J=8.2 Hz, 1H), 7.25 (d, J=5.1 Hz, 1H), 7.11-7.21 (m, 4H), 5.27 (s, 2H), 2.41 (s, 3H), 2.35 (s, 3H), 2.17 (s, 3H).

Example 459: 5-(5-(4-Methyl-1H-pyrazol-1-yl)-4'-((3-methyl-4H-1,2,4-triazol-4-yl)methyl)-[1,1'-biphenyl]-2-yl)-2H-tetrazole

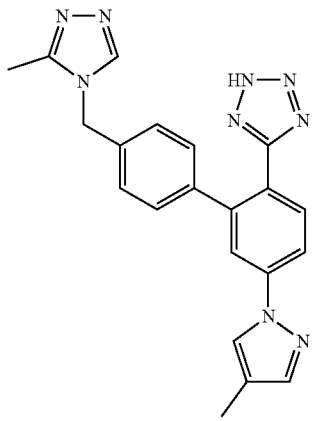
(Ex. 459)

Intermediate 459a:
4-(4-Bromobenzyl)-3-methyl-4H-1,2,4-triazole

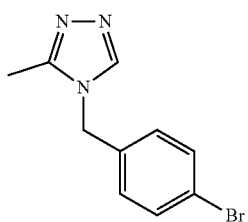
(459a)

In a 100 mL round-bottomed flask equipped with a condenser, a mixture of triethyl orthoformate (0.5 mL, 3.01 mmol), acetohydrazide (0.219 g, 2.96 mmol) and DBU (0.33 mL, 2.19 mmol) in xylene (10 mL) was heated at reflux under N₂ for 1.5 h. The reaction mixture was allowed to cool to RT and then (4-bromophenyl)methanamine hydrochloride (0.445 g, 2.00 mmol) was added. The reaction mixture was then again heated at reflux for 19 h. The cooled reaction mixture was diluted with EtOAc, washed with H₂O and brine, dried over anhydrous sodium sulfate and concentrated to dryness. The residue was purified on ISCO using a 40 g column (0-5% MeOH-DCM) to afford the title compound (0.20 g, 0.79 mmol, 40% yield) as an off-white solid. LC (Method B): 1.342 min. MS (APCI): calcd for $C_{10}H_{11}BrN_3$ [M+H]⁺ m/z 252.0, found 252.1. ¹H NMR (400 MHz, CDCl₃) δ ppm 8.09 (s, 1H), 7.50-7.55 (m, 2H), 6.95-7.01 (m, J=8.61 Hz, 2H), 5.05 (s, 2H), 2.39 (s, 3H).

Intermediate 459b: 5-Fluoro-4'-((3-methyl-4H-1,2,4-triazol-4-yl)methyl)-[1,1'-biphenyl]-2-carbonitrile

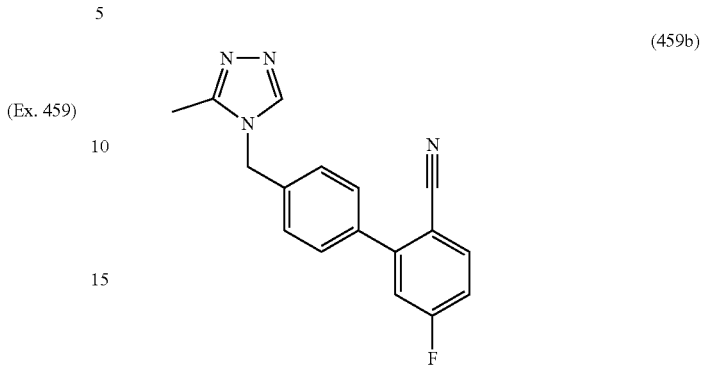
(459b)

In a 5 mL sealable vial, a solution of 4-(4-bromobenzyl)-3-methyl-4H-1,2,4-triazole (0.148 g, 0.59 mmol) and 4-fluoro-2-(4,4,5,5-tetramethyl-1,3,2-dioxaborolan-2-yl)benzonitrile (0.215 g, 0.87 mmol) in a mixture of ethanol (0.6 mL) and toluene (5.4 mL) was purged with a stream of N₂ for 20 min. To this mixture was added tetrakis(triphenylphosphine) palladium (0) (0.066 g, 0.057 mmol) and 2M aqueous Na₂CO₃ (0.88 mL, 1.760 mmol) and the mixture was stirred at 100° C. for 3.5 h. The cooled mixture was diluted in EtOAc and then filtered over Celite®. The filtrate was concentrated to dryness and the residue was purified on ISCO using a 40 g column (0-10% MeOH-DCM) to afford the title compound (0.138 g, 0.47 mmol, 80% yield) as a yellowish solid. LC (Method B): 1.476 min. MS (APCI): calcd for $C_{17}H_{14}FN_4$ [M+H]⁺ m/z 293.1, found 293.1. ¹H NMR (400 MHz, CDCl₃) δ ppm 8.16 (s, 1H), 7.80 (dd, J=5.48, 8.22 Hz, 1H), 7.59 (d, J=8.22 Hz, 2H), 7.16-7.26 (m, 4H), 5.18 (s, 2H), 2.44 (s, 3H).

Intermediate 459c: 5-(4-Methyl-1H-pyrazol-1-yl)-4'-((3-methyl-4H-1,2,4-triazol-4-yl)methyl)-[1,1'-biphenyl]-2-carbonitrile

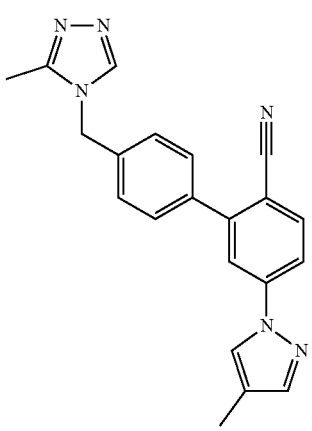
(459c)

In a vial under N₂, a mixture of 5-fluoro-4'-((3-methyl-4H-1,2,4-triazol-4-yl)methyl)-[1,1'-biphenyl]-2-carbonitrile (0.043 g, 0.15 mmol), 4-methyl-1H-pyrazole (0.020 mL, 0.24 mmol) and potassium carbonate (0.047 g, 0.34 mmol) in DMF (2 mL) was heated at 100° C. for 18 h. Additional 4-methyl-1H-pyrazole (0.020 mL, 0.24 mmol) was added and heating was continued at the same temperature for 3 days. The cooled reaction mixture was acidified with formic acid (0.050 mL) and this mixture was purified by reverse-phase preparative LC (Method D). The product obtained was lyophilized from ACN-H$_2$O to afford the title compound (0.043 g, 0.12 mmol, 82% yield) as a white solid. LC (Method B): 1.698 min. MS (APCI): calcd for C$_{21}$H$_{19}$N$_6$ [M+H]$^+$ m/z 355.2, found 355.1. $^1$H NMR (400 MHz, CDCl$_3$) δ ppm 8.16 (s, 1H), 7.79-7.87 (m, 3H), 7.74 (dd, J=1.90, 8.60 Hz, 1H), 7.61-7.66 (m, 2H), 7.60 (s, 1H), 7.22-7.26 (m, 2H), 5.19 (s, 2H), 2.44 (s, 3H), 2.18 (s, 3H).

Example 459: 5-(5-(4-Methyl-1H-pyrazol-1-yl)-4'-((3-methyl-4H-1,2,4-triazol-4-yl)methyl)-[1,1'-biphenyl]-2-yl)-2H-tetrazole In a vial under N$_2$, a mixture of 5-(4-methyl-1H-pyrazol-1-yl)-4'-((3-methyl-4H-1,2,4-triazol-4-yl)methyl)-[1,1'-biphenyl]-2-carbonitrile (0.043 g, 0.12 mmol), dibutyltin oxide (0.038 g, 0.15 mmol) and TMS-N$_3$ (0.160 mL, 1.21 mmol) in toluene (3.5 mL) was stirred at 120° C. for 17 h. The cooled reaction mixture was poured into MeOH and this mixture was concentrated to dryness. The crude material was purified twice by reverse-phase preparative LC (Method D) and the product obtained was lyophilized from ACN-H$_2$O to afford the title compound (0.022 g, 0.056 mmol, 47% yield) as a white solid. LC (Method B): 1.513 min. MS (APCI): calcd for C$_{21}$H$_{20}$N$_9$[M+H]$^+$ m/z 398.2, found 398.1. $^1$H NMR (400 MHz, DMSO-d$_6$) δ ppm 8.53 (br s, 1H), 8.49 (s, 1H), 7.99 (d, J=7.4 Hz, 1H), 7.92 (d, J=2.0 Hz, 1H), 7.78 (d, J=8.2 Hz, 1H), 7.64 (s, 1H), 7.18 (s, 4H), 5.23 (s, 2H), 2.27 (s, 3H), 2.11 (s, 3H).

Example 460: 3-((6'-(2H-tetrazol-5-yl)-[1,1':3',1''-terphenyl]-4-yl)methyl)-2,6-dimethylpyrimidin-4(3H)-one

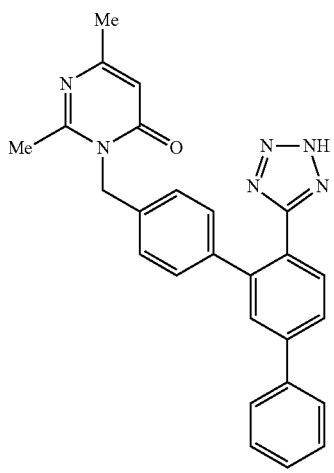

(Ex. 460)

Intermediate 460a: 5-bromo-4'-((2,4-dimethyl-6-oxopyrimidin-1(6H)-yl)methyl)-[1,1'-biphenyl]-2-carbonitrile

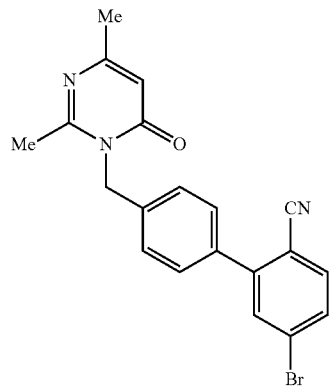

(460a)

2,6-Dimethylpyrimidin-4(3H)-one (0.250 g, 2.014 mmol) was dissolved in DMF (3.66 ml). NaH (0.366 g, 9.15 mmol) was added and allowed to stir for 15 min. Intermediate I-002 (0.643 g, 1.831 mmol) was added. The reaction was stirred for 30 min and was diluted with EtOAc and washed with saturated NH$_4$Cl then brine, dried (Na$_2$SO$_4$), filtered, and concentrated in vacuo. The material was purified by column chromatography (ISCO, 40 g silica gel column, 25 minute gradient of 0 to 100% EtOAc in hexanes) to yield Intermediate 460a (0.180 g, 0.456 mmol, 25% yield) as a white solid. LC-MS (Method A2) RT=0.85 min, MS (ESI) m/z: 384.5 (M+H)$^+$. $^1$H NMR (400 MHz, CDC$_3$) δ 7.62-7.61 (m, 3H), 7.40 (s, 2H), 7.03 (s, 2H), 6.46 (s, 1H), 5.48 (s, 2H), 2.61 (s, 3H), 2.42 (s, 3H). Compound contains residual starting material.

Intermediate 460b: 4'-((2,4-dimethyl-6-oxopyrimidin-1(6H)-yl)methyl)-5-(4,4,5,5-tetramethyl-1,3,2-dioxaborolan-2-yl)-[1,1'-biphenyl]-2-carbonitrile

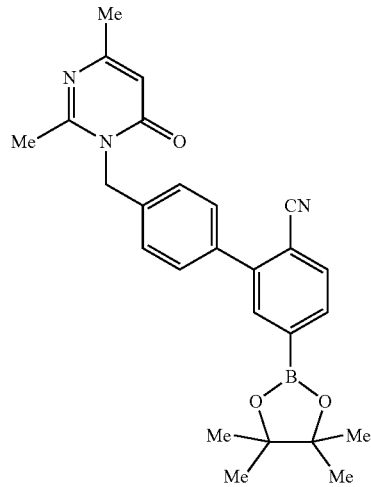

(460b)

Intermediate 460a (0.400 g, 1.015 mmol), bis(pinacolato)diborane (0.515 g, 2.029 mmol), X-Phos (0.048 g, 0.101 mmol), Pd$_2$(dba)$_3$ (0.093 g, 0.101 mmol), and KOAc (0.498 g, 5.07 mmol) were dissolved in dioxane (10.15 ml). The reaction was heated at 105° C. for one hour. The reaction was cooled to ambient temperature, diluted with EtOAc, filtered through Celite, and concentrated in vacuo. The crude material was purified by column chromatography (ISCO, 24 g silica gel column, 19 minute gradient of 0 to 100% EtOAc in DCM) to yield Intermediate 460b (0.235 g, 0.535 mmol, 53%) LC-MS (Method A2) RT=0.65 min, MS (ESI) m/z: 360.0 (M+H)⁺. See mass of the boronic acid in LC-MS. $^1$H NMR (400 MHz, CDCl$_3$) δ 7.85 (dd, J=7.6, 1.0 Hz, 1H), 7.75 (d, J=7.7 Hz, 1H), 7.61-7.57 (m, 1H), 7.55-7.50 (m, 2H), 7.43-7.38 (m, 2H), 6.46 (s, 1H), 5.48-5.45 (m, 2H), 2.61 (s, 3H), 2.42 (s, 3H), 1.35 (s, 12H).

Intermediate 460c: 4"-((2,4-dimethyl-6-oxopyrimidin-1(6H)-yl)methyl)-[1,1':3',1"-terphenyl]-4'-carbonitrile

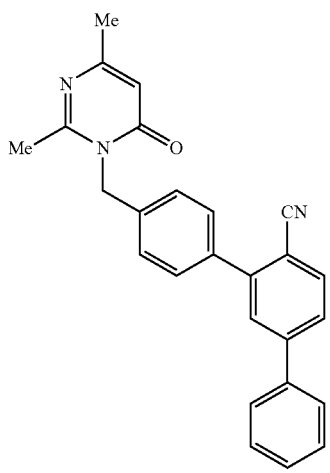

(460c)

Intermediate 460b (35 mg, 0.079 mmol), bromobenzene (37.4 mg, 0.238 mmol), and 2nd Generation XPhos Precatalyst (6.24 mg, 7.93 μmol) were dissolved in toluene (0.1269 ml), EtOH (317 μl), and tripotassium phosphate (79 μl, 0.159 mmol). The reaction was heated at 100° C. for 3 hours. The reaction was diluted with EtOAc, filtered through Celite and concentrated in vacuo. The crude material will be used as-is without further purification for the subsequent reaction. Intermediate 460c (0.030 g, 0.077 mmol, 97%). LC-MS (Method A2) RT=0.93 min, MS (ESI) m/z: 392.2 (M+H)⁺.

Example 460: 3-((6'-(2H-tetrazol-5-yl)-[1,1':3',1"-terphenyl]-4-yl)methyl)-2,6-dimethylpyrimidin-4(3H)-one To a vial containing Intermediate 460c (0.030 g, 0.077 mmol) was added dibutyltin oxide (50.9 mg, 0.204 mmol) and toluene (3 mL) followed by azidotrimethylsilane (0.068 mL, 0.511 mmol). The reaction mixture was sealed and heated at 100° C. behind a blast shield overnight. MeOH was added to the reaction followed by EtOAc. CAN (10% Aqueous) (560 mg, 1.022 mmol) was added until gas evolution ceased. The layers were separated and the organic layer was washed with brine, dried with sodium sulfate, and concentrated. The residue was dissolved in DMF, and the crude material was purified via preparative LC-MS with the following conditions: Column: XBridge C18, 19×200 mm, 5-μm particles; Mobile Phase A: 5:95 ACN: H$_2$O with 0.1% trifluoroacetic acid; Mobile Phase B: 95:5 ACN: H$_2$O with 0.1% trifluoroacetic acid; Flow: 20 mL/min to yield Example 460 (1.6 mg, 0.0036 mmol, 3.6% yield). LC-MS (Method A2) RT=0.82 min, MS (ESI) m/z: 435.2. $^1$H NMR (500 MHz, DMSO-d$_6$) δ 7.87 (br d, J=8.0 Hz, 1H), 7.82 (br d, J=7.7 Hz, 2H), 7.80-7.76 (m, 2H), 7.52 (br t, J=7.5 Hz, 2H), 7.47-7.43 (m, 1H), 7.41 (br d, J=7.8 Hz, 2H), 7.23 (br d, J=7.8 Hz, 2H), 6.64 (s, 1H), 5.40 (s, 2H), 2.49 (s, 3H), 2.34 (s, 3H). One exchangeable proton not observed.

Example 461: 2,6-dimethyl-3-((5'-(4-methylpyridin-2-yl)-2'-(2H-tetrazol-5-yl)-1,1'-biphenyl]-4-yl)methyl)pyrimidin-4(3H)-one

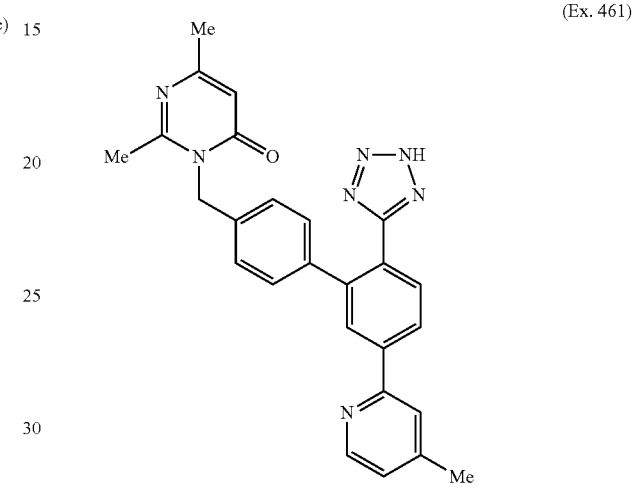

(Ex. 461)

Intermediate 461a: 4'-((2,4-dimethyl-6-oxopyrimidin-1(6H)-yl)methyl)-5-(4-methylpyridin-2-yl)-[1,1'-biphenyl]-2-carbonitrile

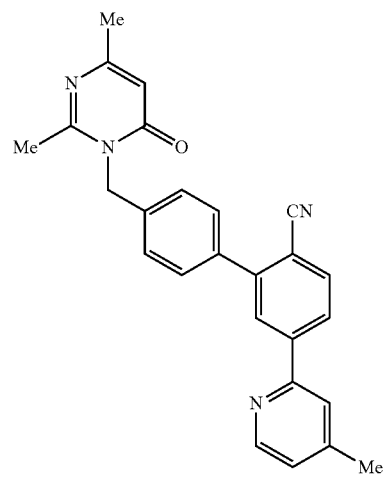

(461a)

Synthesized in an analogous manner to Intermediate 460c using Intermediate 460b (0.035 g, 0.079 mmol) and 2-bromo-4-methylpyridine (0.041 g, 0.238 mmol) to yield Intermediate 461a (0.030 g, 0.074 mmol, 93%). LC-MS (Method A2) RT=0.72 min, MS (ESI) m/z: 407.1. Used without further purification in the next step.

Example 461: 2,6-dimethyl-3-((5'-(4-methylpyridin-2-yl)-2'-(2H-tetrazol-5-yl)-[1,1'-biphenyl]-4-yl)methyl)pyrimidin-4(3H)-one Synthesized in an analogous manner to Example 460 using Intermediate 461a (0.030 g, 0.074 mmol). The crude material was purified via preparative LC-MS with the following conditions: Column: XBridge C18, 19×200 mm, 5-μm particles; Mobile Phase A: 5:95 ACN: H$_2$O with 0.1% trifluoroacetic acid; Mobile Phase B: 95:5 ACN: H$_2$O with 0.1% trifluoroacetic acid; Flow: 20 mL/min to yield to yield Example 461. LC-MS (Method A2) RT=0.60 min, MS (ESI) m/z: 450.3.

Example 462: 3-((5'-(4-methoxypyridin-2-yl)-2'-(2H-tetrazol-5-yl)-[1,1'-biphenyl]-4-yl)methyl)-2,6-dimethylpyrimidin-4(3H)-one

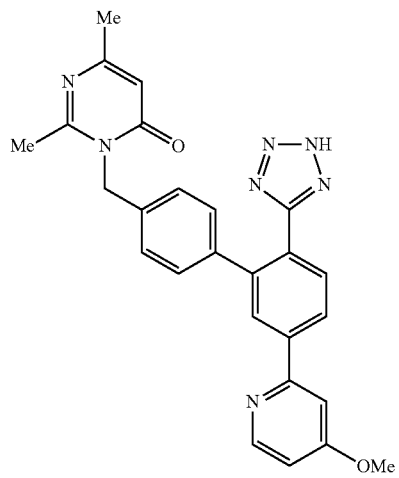

(Ex. 462)

Intermediate 462a: 4'-((2,4-dimethyl-6-oxopyrimidin-1(6H)-yl)methyl)-5-(4-methoxypyridin-2-yl)-[1,1'-biphenyl]-2-carbonitrile

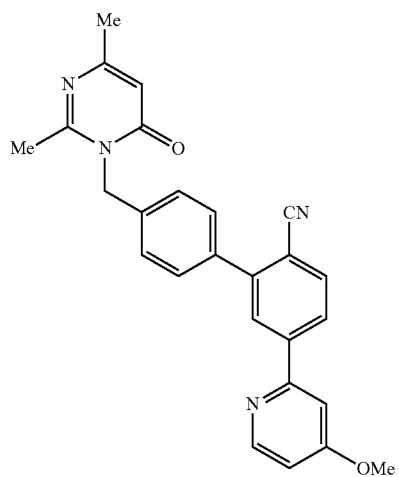

(462a)

Synthesized in an analogous manner to Intermediate 460c using Intermediate 460b (0.035 g, 0.079 mmol) and 2-bromo-4-methoxypyridine (0.044 g, 0.238 mmol) to yield Intermediate 462a (0.030 g, 0.071 mmol, 90%). Used without further purification in the next step. LC-MS (Method A2) RT=0.65 min, MS (ESI) m/z: 423.1.

Example 462: 3-((5'-(4-methoxypyridin-2-yl)-2'-(2H-tetrazol-5-yl)-[1,1'-biphenyl]-4-yl)methyl)-2,6-dimethylpyrimidin-4(3H)-one Synthesized in an analogous manner to Example 460 using Intermediate 462a (0.030 g, 0.071 mmol). The crude material was purified via preparative LC-MS with the following conditions: Column: XBridge C18, 19×200 mm, 5-m particles; Mobile Phase A: 5:95 ACN: H$_2$O with 0.1% trifluoroacetic acid; Mobile Phase B: 95:5 ACN: H$_2$O with 0.1% trifluoroacetic acid; Flow: 20 mL/min to yield to yield Example 462 (0.0008 g, 0.0014 mmol, 1.5%). LC-MS (Method A2) RT=0.57 min, MS (ESI) m/z: 466.2. $^1$H NMR (500 MHz, DMSO-d$_6$) δ 8.48 (d, J=5.6 Hz, 1H), 8.07 (br d, J=7.9 Hz, 1H), 8.03 (s, 1H), 7.74 (d, J=8.0 Hz, 1H), 7.54 (s, 1H), 7.32 (br d, J=8.0 Hz, 2H), 7.27-7.21 (m, 2H), 6.96-6.92 (m, 1H), 6.65 (s, 1H), 5.39 (s, 2H), 3.96-3.91 (m, 3H), 2.55 (s, 3H), 2.34 (s, 3H). One exchangeable proton not observed.

IV. Biology

Methods

Membrane Radioligand Binding Assay

In one aspect of the invention, AT1R biased agonist compounds were assessed for their ability to directly interact with the AT1R or AT2R by using isolated cell membranes to study the ability of these compounds to compete with radiolabeled AII for binding to the receptor.

Membrane Preparation for Binding Assays

HEK293 cells stably expressing either the hAT1R or hAT2R were grown to confluency in culture media (DMEM, 10% FBS, 1% Penicillin/streptomycin, 250pg/mL G418). Cells were washed with PBS, detached with 37° C. 5 mM EDTA in PBS, transferred to ice cold centrifugation tubes and pelleted for 5 min at 300 g, 4° C. Cell pellets were re-suspended in cold homogenization buffer (50 mM HEPES, pH 7.4 (KOH), 2 mM EDTA, protease inhibitor cocktail) and membranes were prepared by differential centrifugation (500 g for 5 min and then 45000 g for 20 min, at 4° C.) following cell lysis on ice with a Janke & 120 Kunkel Ultra-Turrax T25 homogenizer at maximum speed, 3×7 seconds. The final pellet was re-suspended in homogenization buffer, homogenized 3×with a 25 g needle, frozen on dry ice and stored at −80° C.

Radioligand Binding Using the Scintillation Proximity Assays (SPA) Technology

Equilibrium competition assays were performed in incubation buffer (50 mM HEPES pH 7.4 (KOH), 0.0001% (w/v) BSA, 10 mM MgCl$_2$) containing ten singlicate concentrations of competing ligands in DMSO (kept at ≤1% per incubation well), 5 nM [$^3$H]angiotensin II (36.7 Ci/mmol, 1mCi/mL), 15 μg of membrane preparation and 0.5 mg SPA Wheat-Germ Agglutinin (WGA) beads, in a final volume of 100 μL. Total (T) and non-specific (NS) binding were determined in the absence and presence of 3 μM unlabelled angiotensin II, respectively. Assays were conducted for 60 min at room temperature with mixing. Bound radioactivity was counted in a PerkinElmer MicroBeta plate counter for 1 min per well, following a 30 min adjustment in the dark. Under those conditions total binding was ≤10% of total radioligand and the specific binding window (total minus non-specific binding) was ≥8 fold. Non-recombinant HEK293 cell membranes showed no specific binding window. Counts per minute (cpm) obtained from the counter were converted into percentage of [$^3$H]angiotensin II specific binding according to the formula ((sample−NS)/(T−NS))*100. Sigmoidal concentration-response curves were generated by expressing the percentage of residual specific binding as a function of competitor concentration using a 4-parameter logistic equation (IDBS ActivityBase software) to determine the IC$_{50}$ i.e. the concentration of competing ligand necessary to reduce specific radioligand binding by 50%. Finally, the competing ligand binding affinities (K$_i$) were calculated from IC$_{50}$/(1+([radioligand]/K$_d$), where K$_d$ is the angiotensin II affinity constant, determined previously by saturation analysis (n=4).

Signaling Assays

In one aspect of the invention, signaling bias of compounds was assessed by comparing the relative activity of compounds to activate both the β-arrestin and Gq signaling pathways. In order to confirm signaling bias, compounds were studied in two different assay formats.

DiscoveRx β-arrestin2 Recruitment and IP1 Assays

β-arrestin2 recruitment to activated receptors can be assessed using an enzyme complementation method (Zhao, Jones et al. 2008). In this case, the enzyme complementation assay utilized the DiscoveRx (Fremont, CA) Pathunter CHO-K1 AGTR1 β-arrestin cell line and accompanying detection reagents. Cells (5000/well) were plated into 1536 well plates (Cellocoat plates, Greiner Bio One, Monroe, NC) 14-16 hours before each experiment in 20 μl DMEM/F12 medium (Thermo-Fisher Scientific, Carlsbad, CA) containing heat-inactivated 1% fetal bovine serum. Subsequently, the compounds of interest were added at varying concentrations to the wells in a volume of 200 nl and the cells incubated for 90 min at 37° C. The detection reagent (10 μl) was added to each well and the plates incubated at room temperature for 1 hour before measurement of chemiluminescence using an EnVision Multilabel Reader (Perkin-Elmer, Waltham, MA). The data are processed using Toolset for Runmaster QCMulti. Concentration-response curves are fitted and EC$_{50s}$ (agonist mode) and IC$_{50s}$ (antagonist mode) estimated using a 4-parameter logistic equation. Compound activities are reported as a relative percentage to the maximal effect of AII in the assays.

Gq activation can be assessed by measuring the accumulation of inositol phosphates (e.g. IP3, IP1) that are liberated following activation of phospholipase C by Gq (Thomsen, Frazer et al. 2005). In the current invention we have utilized the DiscoveRx Pathunter CHO-K1 AGTR1 β-arrestin cell line to also measure IP1 accumulation in response to compounds. IP1 accumulation was measured in both agonist and antagonist modes. In agonist mode, cells are plated as above 14-16 hours before the experiment. The medium is then removed and compounds at varying concentrations added in a final volume of 20 μl. The cells are incubated at 37° C. for 90 min. IP1 accumulation detected using a commercial HTRF assay according to manufacturer's instructions (Cisbio, Bedford, MA). Specifically, 4 μl of D2-conjugate solution (diluted 1:20 in Cisbio HTRF assay buffer) is added to each well, followed by the addition of 4 μl of anti-IP1 cryptate diluted 1:20 in HTRF assay buffer and the plates incubated for 20 min at room temperature. 14 μl from each well is measured using an Envision multi-label reader and data processed using Toolset for Runmaster QCMulti. Concentration-response curves are fitted and EC$_{50s}$ (agonist mode) and IC$_{50s}$ (antagonist mode) estimated using a 4-parameter logistic equation. Compound activities are reported as a relative percentage to the maximal effect of AII in the assays.

The ability of compounds to antagonize the AII IP1 response in this assay is measured by pre-incubating cells for 30 min in 10 pd of HTRF assay buffer at 37° C. followed by the addition of 10 μl of 1 nM AII to each well and the plates incubated at 37° C. for 90 min. Detection and measurement of fluorescence is performed as above. Compound activity is reported as percent inhibition of the effect of AII alone.

BRET β-arrestin2 and Gq Activation Assays

In another aspect of the invention, association of the ATIR with signaling proteins is assessed using bioluminescence resonance energy transfer assays (Stephane Angers, Ali Salahpour et al. 2002). This technology measures the association between bioluminescent and fluorescent protein tags.

Materials

Several of the plasmid constructs used in BRET experiments were previously described. Briefly, the coding sequence of β-arrestin2 was fused to *Renilla* luciferase II to generate β-arrestin2-Rluc (Quoyer, Janz et al. 2013). The membrane targeting motif from K-Ras, CAAX motif (GKKKKKKSKTKCVIM), was fused to *Renilla* GFP to create rGFP-CAAX plasmid (Namkung Y et al., Nat Commun (2016) 7, 12178). The *Renilla* luciferase II was inserted in the Gaq protein to generate Gaq-Rluc (Breton, Sauvageau et al. 2010). The Gγ1 protein was tagged with GFP10 to obtain GFP-Gyl, using the same strategy described previously for GFP-Gy2 (Gales, Rebois et al. 2005). The Gaq binding domain of the p63RhoGEF protein (amino acids 295-502) was fused to *Renilla* luciferase II to create P63-Rluc. Finally, the hAT1R plasmid construct encoding the receptor was generated by optimizing the coding sequence of human angiotensin II receptor (GeneOptimizer from ThermoFisher), and adding an artificial cleavable signal peptide from bovine prolactin (MDSKGSSQKGSRLLLLL-VVSNLLLCQGVVS) in N-terminus of the receptor to increase cell surface expression.

Protocols

β-arrestin2 Biosensor Assay

The BRET β-arrestin2 assay was studied in two separate formats which differed in the expression level of AT1R. For higher receptor expression, cells were transfected with 5 ng/well of plasmid DNA and for lower receptor expression cells were transfected with 0.04 ng/well of plasmid DNA. In either case, HEK293 cells were cultured in DMEM supplemented with Penicillin-Streptomycin and 10% fetal bovine serum. Two days before the BRET experiment, HEK293 cells were transfected with hAT1R (5 ng/well or 0.04 ng/well) as well as β-arrestin2-Rluc (1.25 ng/well) and rGFP-CAAX (12.5 ng/well) using linear polyethylenimine 25 kDa (PEI) at a PEI:DNA ratio of 3:1. Transfected cells were directly seeded in 384-well plates, at a density of 10 000 cells per well, and maintained in culture for the next 48 h.

BRET experiments were carried out subsequently using the following procedures: cells were washed once with Tyrode's buffer (137 mM NaCl, 1 mM CaCl$_2$, 0.9 mM KCl, mM MgCl$_2$, 3.6 mM NaH$_2$PO$_4$, 5.5 mM glucose, 12 mM NaHCO$_3$, and 25 mM HEPES, pH 7.4) and 20 μl of Tyrode's buffer was added to each well. Cells were equilibrated in their new buffer at room temperature for at least 30 minutes. Following the equilibration period, the coelenterazine substrate was first added to the cells, 10 μl per well of a 3×solution of prolume purple coelenterazine (final concentration of 2 μM), immediately followed by compound addition using the HP D300 digital dispenser from Tecan (10 singlicate concentrations). Cells were incubated for 15 min at room temperature and BRET readings were then collected using a Spark10M multimode reader from Tecan with BRET2 filters 360-440/505-575, to record agonist response. The BRET signal was determined by calculating the ratio of the light emitted by GFP (505-575 nm) over the light emitted by the Rluc (360-440 nm). BRET signal values were converted into percentage of activation using the non-stimulated control as 0% and AngII maximal response as 100%. Sigmoidal concentration-response curves were generated with those normalized values using a 4-parameter logistic equation (IDBS ActivityBase software), to determine $EC_{50}$ of the different compounds.

Gq Biosensor Assay HEK293 cells were cultured in DMEM supplemented with Penicillin-Streptomycin and 10% fetal bovine serum. Two days before the BRET experiment, HEK293 cells were transfected with hAT1R expression plasmid (200 ng/well) as well as Gαq-Rluc (100 ng/well), Gβ1 (375 ng/well) and GFP-Gγ1 (625 ng/well), using linear polyethylenimine 25 kDa (PEI) at a PEI:DNA ratio of 3:1. Transfected cells were directly seeded in 96-well plates, at a density of 35 000 cells per well, and maintained in culture for the next 48 h.

BRET experiments were carried out subsequently using the following procedures: cells were washed once with Tyrode's buffer (137 mM NaCl, 1 mM $CaCl_2$, 0.9 mM KCl, mM $MgCl_2$, 3.6 mM $NaH_2PO_4$, 5.5 mM glucose, 12 mM $NaHCO_3$, and 25 mM HEPES, pH 7.4) and 90 µl of Tyrode's buffer was added to each well. Cells were equilibrated in their new buffer at room temperature for at least 30 minutes. Following the equilibration period, the coelenterazine substrate was first added to the cells, 10 µl per well of a 10×solution (prolume purple coelenterazine at a final concentration of 2 µM), immediately followed by compound addition using the HP D300 digital dispenser from Tecan (10 singlicate concentrations). Cells were incubated for 5 min at room temperature and BRET readings were then collected using a Synergy Neo Multi-Mode reader from BioTek with BRET2 filters 410/515, to record agonist response. Cells were then further incubated at room temperature for an additional 20 min (for a total of 25 min pre-incubation period with the compounds), before addition of a fixed dose of AngII corresponding to the $EC_{50}$. A second reading was collected 5 min after this second addition, using the Synergy Neo Multi-Mode reader from BioTek with BRET2 filters 410/515, to record antagonist response. The BRET signal was determined by calculating the ratio of the light emitted by GFP (515 nm) over the light emitted by the Rluc (410 nm). To analyze agonist response, BRET signal values were converted into percentage of activation using the non-stimulated control as 0% and AngII maximal response as 100%. Sigmoidal concentration-response curves were generated with those normalized values using a 4-parameter logistic equation (IDBS ActivityBase software), to determine $EC_{50}$ of the different compounds. In the case of antagonist response analysis, BRET signal values were converted into percentage of inhibition using the fixed dose of AngII (corresponding to the $EC_{50}$) as 0% and non-stimulated control as 100%. Sigmoidal concentration-response curves were generated with those normalized values using a 4-parameter logistic equation (IDBS ActivityBase software), to determine $IC_{50}$ of the different compounds.

P63 Rho-GEF Biosensor Assay

Assessment of Gq signaling activation was also determined using an alternative BRET format targeting the recruitment of P63 Rho-GEF following activation of Gq. This was performed in both agonist and antagonist modes.

HEK293 cells were cultured in DMEM supplemented with Penicillin-Streptomycin and 10% fetal bovine serum. Two days before the BRET experiment, HEK293 cells were transfected with hAT1R (0.04 ng/well) as well as P63-Rluc (1.25 ng/well) and rGFP-CAAX (12.5 ng/well) using linear polyethylenimine 25 kDa (PEI) at a PEI:DNA ratio of 3:1. Transfected cells were directly seeded in 384-well plates, at a density of 10 000 cells per well, and maintained in culture for the next 48 h.

BRET experiments were carried out subsequently using the following procedures: cells were washed once with Tyrode's buffer (137 mM NaCl, 1 mM $CaCl_2$, 0.9 mM KCl, mM $MgCl_2$, 3.6 mM $NaH_2PO_4$, 5.5 mM glucose, 12 mM $NaHCO_3$, and 25 mM HEPES, pH 7.4) and 20 µl of Tyrode's buffer was added to each well. Cells were equilibrated in their new buffer at room temperature for at least 30 minutes. Following the equilibration period, the coelenterazine substrate was first added to the cells, 10 µl per well of a 3×solution of prolume purple coelenterazine (final concentration of 2 µM), immediately followed by compound addition using the HP D300 digital dispenser from Tecan (10 singlicate concentrations). Cells were incubated for 15 min at room temperature and BRET readings were then collected using a Spark1OM multimode reader from Tecan with BRET2 filters 360-440/505-575, to record agonist response. Cells were then further incubated at room temperature for an additional 10 min (for a total of 25 min pre-incubation period with the compounds), before addition of a fixed dose of AngII corresponding to the $EC_{50}$. A second reading was collected 15 min after this second addition, using a Spark10M multimode reader from Tecan with BRET2 filters 360-440/505-575, to record antagonist response. The BRET signal was determined by calculating the ratio of the light emitted by GFP (505-575 nm) over the light emitted by the Rluc (360-440 nm). BRET signal values were converted into percentage of activation using the non-stimulated control as 0% and AngII maximal response as 100%. Sigmoidal concentration-response curves were generated with those normalized values using a 4-parameter logistic equation (IDBS ActivityBase software), to determine $EC_{50}$ of the different compounds. In the case of antagonist response analysis, BRET signal values were converted into percentage of inhibition using the fixed dose of AngII (corresponding to the $EC_{50}$) as 0% and non-stimulated control as 100%. Sigmoidal concentration-response curves were generated with those normalized values using a 4-parameter logistic equation (IDBS ActivityBase software), to determine $IC_{50}$ of the different compounds.

Rat Isolated Aortic Ring Assay

Male rats approximately 225-250 g were euthanized according to IACUC guidelines. The thoracic aorta was quickly removed and placed in cold bicarbonate-buffered physiological salt solution (PSS) containing: 118.4 mM NaCl, 4.6 mM KCl, 1.2 mM $KH_2PO_4$, 1.2 mM $MgSO_4$, 1.9 mM $CaCl_2$), 25.0 mM $NaHCO_3$, and 10.1 mM glucose. Adherent connective tissue was carefully removed and rings cut into approximately 3 mm width. The endothelium was removed from the ring by sliding it onto a dissecting probe and gently rolling on filter paper saturated with PSS. Each ring was individually mounted for isometric force recording using stainless steel pin supports on a DMT720MO Tissue Bath System (ADInstruments; one pin support connected to the force transducer and the other pin support connected to a micrometer) for control of tissue length and a Power Lab Chart Pro 8/35 for transducer. The rings were mounted on pin supports in individual 8 ml chambers containing PSS maintained at 37° C. and aerated with 95% $O_2$-5% $CO_2$. Mechanical responses were recorded using a PowerLab system.

The aortic rings were gradually stretched over a 2 hr equilibration period to a preload of 2 g which was maintained throughout the experiment. During this equilibration period, the rings were stimulated with 20 mM KCl to determine contractility. The absence of the endothelium was then determined by contracting the rings with phenylephrine (PE; 30 nM) until a steady state level of contraction was attained. Subsequently, 1 μM acetylcholine (Ach) was added to each ring to induce relaxation. If relaxation was observed, it was gently rubbed again to remove any remaining endothelium. The rings were then extensively washed until the tension returned to the preload of 2 g prior to the start of the experimental protocol.

The rings were pretreated (20 min) with test articles to determine the effects on baseline contraction. A concentration-response curve for AII was performed in the absence and presence of varying concentrations of test compounds by exposing the ring to increasing concentrations of the hormone and determining the contractile response. Between concentrations, the force was allowed to increase to a steady state level before the addition of the next concentration (approximately 5 min). If no change in force was detected after a 5 min exposure to a given concentration, the next higher concentration was administered. After the highest concentration, 60 mM KCl was added to assess the tissue's maximal contractile response.

All force determinations were made assuming the level of force on baseline is zero and the maximal force attained in the presence of AII alone (control ring) is 100%. Force is reported relative to these levels. The $EC_{50}$ values (the concentration of AII or compound that induces 50% of the maximal response in that tissue) were determined using a four-parameter logistic equation using EXCELFit software. The relative contraction of AII max/KCl is also determined to gauge whether a given compound affects the max contraction by AII. Schild plot analysis was performed for any compounds which induced a significant shift to the right of the AII concentration-response curve.

Rat Isolated Working Heart Preparation

Sprague-Dawley rats (250-300 g) were anesthetized with ketamine/xylazine (25 mg/kg/15 mg/kg IM, respectively) and heparin (200 U/kg, IV). After induction of anesthesia, the trachea was exposed, intubated and the animal mechanically ventilated with room air. A mid-sternal thoracotomy was made and the ribs retracted to expose the heart. The pericardium was removed and the aorta cleared of any connective tissue. A silk suture was placed around the aorta before its bifurcation. The inferior vena cava was clamped just above the diaphragm and a cannula quickly inserted into the aorta and secured with suture. While being ventilated, hearts were perfused in situ with the cannula via retrograde perfusion of the aorta. The cannula was connected to a reservoir containing oxygenated Krebs-Henseleit bicarbonate buffer with the following composition: 118 mM NaCl, 4.0 mM KCl, 0.4 mM $NaH_2PO_4$, 1.1 mM $MgCl_2$, 1.8 mM $CaCl_2$, 22 mM $NaHCO_3$, 5.0 mM glucose, 0.038 mM creatine and 2.0 mM pyruvic acid at pH 7.4. Once the heart was perfused, it was carefully excised from the chest and transferred to the isolated heart apparatus and perfused in Langendorff mode with the buffer solution at a constant pressure (70 mmHg) and temperature (38±0.2° C.). The ambient temperature around the preparation was maintained by a heated vessel. During this time, a small incision was made in the left atrium into which another cannula was inserted and tied off. This non-working preparation was run for 10 minutes and then converted to a working system by switching the supply of perfusate from the aorta to the left atrial cannula at a hydrostatic pressure of 12 mmHg (preload). The working heart ejected perfusate through the aortic valve into the aortic cannula. The hydrostatic pressure in the aortic cannula was maintained at 70 mmHg (after-load) throughout the working phase. A Millar catheter (840-4079) was inserted into the left ventricle for recording of left ventricular pressure (LVP), contractility (+dp/dt max) and lusitropy (−dP/dt min).

After a 20 min equilibration period, hearts underwent 10 min of global isothermic ischemia, and 60 min of post-ischemic reperfusion. The hearts were randomly assigned to one of two groups: (1) control (without compound); (2) compound perfused in the 60 min post-ischemic period. Left atrial and aortic flow were measured using in-line ultrasonic flow probes; stroke volume was estimated using aortic flow and heart rate. All measured data was stored and analyzed by PLUGSYS Modular and Ponemah physiology platform systems.

Acute Rat Cardiac Function Testing

Surgical Preparation

Male Sprague Dawley rats (200-300 g) were anesthetized with ketamine-xylazine cocktail. The trachea was intubated and ventilated with oxygenated room air. The left side of the chest was clipped of hair and disinfected according to standard aseptic procedure. The rat was placed on a warm surgical table and a small incision made at the level of the 4th and 5th intercostal space. A loose purse string pocket surrounding the incision was formed by using vicryl suture with taper needle threaded through the skin and muscle layers. A lateral thoracotomy was performed, the region containing the left descending coronary artery was identified, and a 6-0 silk suture with taper needle was quickly threaded under the LAD and tied permanently with a double knot. Myocardial infarction was verified by blanching of the tissue following vessel ligation. Following the closure of the skin and muscle layer using the purse-string suture with evacuation of the pneumothorax, the rat was given an analgesic agent, kept in the recovery hood for 24 hours, and transferred back to the housing unit. Animals were maintained for 4 weeks following surgery. Reduced cardiac function of each animal was confirmed by ultrasound imaging prior to being placed into a study.

On the day of the study, rats were anesthetized with 4% isoflurane and surgical anesthesia was maintained with 1.5%-2% isoflurane. The left femoral artery was exposed, isolated and catheterized with a Millar SPR-671 (1.4F) pressure catheter which was advanced into the abdominal aorta for measurement of aortic blood pressure. The right jugular vein and the right common carotid artery were exposed via a midline incision in the ventral neck. The right jugular vein was cannulated with a length of PE50 for administration of test substances. The right carotid artery was catheterized with a 2F Millar pressure-volume transducer (model SPR-838) which was advanced into the left ventricle for measurement of cardiac left ventricular pressure and conductance.

Hemodynamic Analyses

Following completion of the surgical preparation, animals were allowed to equilibrate prior to administration of vehicle or test article for approximately 10-15 min. Animals without stable ventricular conductance during this equilibration period were not used. Vehicle or compounds were administered via intravenous infusion for 15 min. During this period, the following parameters were measured and collected using LabChart 7 software (AD Instruments, Colorado Springs, CO): heart rate, aortic blood pressure and ventricular pressure. Stroke volume, cardiac output, pressure-volume loops, +dP/dt and τ were automatically calculated from the collected data by the software. Following the infusion, saline calibration (for calculation of parallel conductance, Vp) was performed according to manufacturer's instructions (AD Instruments). From one rat, at the end of the experiment 3 ml of blood was withdrawn from the abdominal vena cava onto 0.1 ml heparin (1000 u/ml) and used to construct a standard curve of volume vs. conductance. The equation for the line constructed through these points was used to calculate volume from the conductance data collected during the experiment. This equation was used to calculate volume data from the conductance data collected from the subsequent rats run that day.

Statistical analysis to determine differences was performed on the data averaged over the entire 15 min infusion period by Students t-test comparing vehicle and compound treatment data.

REFERENCES

Abraham, D. M., R. T. Davis, C. M. Warren, L. Mao, B. M. Wolska, R. J. Solaro and H. A.

Rockman (2016). "β-Arrestin mediates the Frank-Starling mechanism of cardiac contractility." Proceedings of the National Academy of Sciences 113(50): 14426-14431.

Aplin, M., G. L. Christensen, M. Schneider, A. Heydorn, S. Gammeltoft, A. L. Kjolbye, S. P.

Sheikh and J. L. Hansen (2007). "The Angiotensin Type 1 Receptor Activates Extracellular Signal-Regulated Kinases 1 and 2 by G Protein-Dependent and Independent Pathways in Cardiac Myocytes and Langendorff-Perfused Hearts." Basic & Clinical Pharmacology & Toxicology 100(5): 289-295.

Bhatia, R. S., J. V. Tu, D. S. Lee, P. C. Austin, J. Fang, A. Haouzi, Y. Gong and P. P. Liu (2006). "Outcome of Heart Failure with Preserved Ejection Fraction in a Population-Based Study." New England Journal of Medicine 355(3): 260-269.

Boerrigter, G., D. G. Soergel, J. D. Violin, M. W. Lark and J. C. Burnett (2012). "TRV120027, a Novel β-Arrestin Biased Ligand at the Angiotensin II Type I Receptor, Unloads the Heart and Maintains Renal Function When Added to Furosemide in Experimental Heart Failure." Circulation: Heart Failure 5(5): 627-634.

Breton, B., E. Sauvageau, J. Zhou, H. Bonin, C. Le Gouill and M. Bouvier (2010). "Multiplexing of Multicolor Bioluminescence Resonance Energy Transfer." Biophysical Journal 99(12): 4037-4046.

Brown, N. J. and D. E. Vaughan (1998). "Angiotensin-Converting Enzyme Inhibitors." Circulation 97(14): 1411-1420.

Dandona, P., S. Dhindsa, H. Ghanim and A. Chaudhuri (2006). "Angiotensin II and inflammation: the effect of angiotensin-converting enzyme inhibition and angiotensin 11 receptor blockade." J Hum Hypertens 21(1): 20-27.

De Witt, B. J., E. A. Garrison, H. C. Champion and P. J. Kadowitz (2000). "L-163,491 is a partial angiotensin AT1 receptor agonist in the hindquarters vascular bed of the cat." European Journal of Pharmacology 404(1): 213-219.

Desai, A. S. and L. W. Stevenson (2012). "Rehospitalization for Heart Failure: Predict or Prevent?" Circulation 126(4): 501-506.

Farsang, C. (2011). "Indications for and utilization of angiotensin receptor II blockers in patients at high cardiovascular risk." Vascular Health and Risk Management 7: 605-622.

Felker, G. M., J. Butler, S. P. Collins, G. Cotter, B. A. Davison, J. A. Ezekowitz, G. Filippatos, P.

D. Levy, M. Metra, P. Ponikowski, D. G. Soergel, J. R. Teerlink, J. D. Violin, A. A. Voors and P.

S. Pang (2015). "Heart Failure Therapeutics on the Basis of a Biased Ligand of the Angiotensin-2 Type 1 Receptor." Rationale and Design of the BLAST-AHF Study (Biased Ligand of the Angiotensin Receptor Study in Acute Heart Failure) 3(3): 193-201.

Felker, G. M., J. Butler, S. P. Collins, G. Cotter, B. A. Davison, J. A. Ezekowitz, G. Filippatos, P.

D. Levy, M. Metra, P. Ponikowski, D. G. Soergel, J. R. Teerlink, J. D. Violin, A. A. Voors and P.

S. Pang (2015). "Heart Failure Therapeutics on the Basis of a Biased Ligand of the Angiotensin-2 Type I Receptor-Rationale and Design of the BLAST-AHF Study (Biased Ligand of the Angiotensin Receptor Study in Acute Heart Failure)." JACC: Heart Failure 3(3): 193-201.

Fonarow, G. C., W. G. Stough, W. T. Abraham, N. M. Albert, M. Gheorghiade, B. H. Greenberg, C. M. O'Connor, J. L. Sun, C. W. Yancy and J. B. Young (2007). "Characteristics, Treatments, and Outcomes of Patients With Preserved Systolic Function Hospitalized for Heart FailureA Report From the OPTIMIZE-HF Registry." Journal of the American College of Cardiology 50(8): 768-777.

Gales, C., R. V. Rebois, M. Hogue, P. Trieu, A. Breit, T. E. Hebert and M. Bouvier (2005). "Real-time monitoring of receptor and G-protein interactions in living cells." Nature Methods 2(3): 177-184.

Gheorghiade, M., M. Vaduganathan, G. C. Fonarow and R. O. Bonow (2013). "Rehospitalization for Heart FailureProblems and Perspectives." Journal of the American College of Cardiology 61(4): 391-403.

Go, A. S., D. Mozaffarian, V. L. Roger, E. J. Benjamin, J. D. Berry, W. B. Borden, D. M.

Bravata, S. Dai, E. S. Ford, C. S. Fox, S. Franco, H. J. Fullerton, C. Gillespie, S. M. Hailpern, J.

A. Heit, V. J. Howard, M. D. Huffman, B. M. Kissela, S. J. Kittner, D. T. Lackland, J. H.

Lichtman, L. D. Lisabeth, D. Magid, G. M. Marcus, A. Marelli, D. B. Matchar, D. K. McGuire, E.

R. Mohler, C. S. Moy, M. E. Mussolino, G. Nichol, N. P. Paynter, P. J. Schreiner, P. D. Sorlie, J.

Stein, T. N. Turan, S. S. Virani, N. D. Wong, D. Woo and M. B. Turner (2013). "Heart Disease and Stroke Statistics-2013 Update: A Report From the American Heart Association." Circulation 127(1): e6-e245.

Gring, C. N. and G. S. Francis (2004). "A hard look at angiotensin receptor blockers in heart failure." Journal of the American College of Cardiology 44(9): 1841-1846.

James, P. A., S. Oparil, B. L. Carter and et al. (2014). "2014 evidence-based guideline for the management of high blood pressure in adults: Report from the panel members appointed to the eighth joint national committee jne 8)." JAMA 311(5): 507-520.

Kendall, R. T., E. G. Strungs, S. M. Rachidi, M.-H. Lee, H. M. El-Shewy, D. K. Luttrell, M. G. Janech and L. M. Luttrell (2011). "The β-Arrestin Pathway-selective Type IA Angiotensin Receptor (ATIA) Agonist [Sarl,Ile4,Ile8] Angiotensin II Regulates a Robust G Protein-independent Signaling Network." Journal of Biological Chemistry 286(22): 19880-19891.

Kim, K.-S., D. Abraham, B. Williams, J. D. Violin, L. Mao and H. A. Rockman (2012). "Q0-Arrestin-biased ATIR stimulation promotes cell survival during acute cardiac injury." American Journal of Physiology Heart and Circulatory Physiology 303(8): H1001-H1010.

Kitzman, D. W., W. C. Little, P. H. Brubaker and et al. (2002). "PAthophysiological characterization of isolated diastolic heart failure in comparison to systolic heart failure." JAMA 288(17): 2144-2150.

Luft, F. C. (2002). "Proinflammatory effects of angiotensin 11 and endothelin: targets for progression of cardiovascular and renal diseases." Current Opinion in Nephrology and Hypertension 11(1): 59-66.

Main, J. (2005). "Atherosclerotic renal artery stenosis, ACE inhibitors, and avoiding cardiovascular death." Heart 91(4): 548-552.

Mason, R. P., R. F. Jacob, R. Kubant, A. Jacoby, F. Louka, J. J. Corbalan and T. Malinski (2012). "Effects of angiotensin receptor blockers on endothelial nitric oxide release: the role of eNOS variants." British Journal of Clinical Pharmacology 74(1): 141-146.

McMurray, J. J. V., M. Packer, A. S. Desai, J. Gong, M. P. Lefkowitz, A. R. Rizkala, J. L.

Rouleau, V. C. Shi, S. D. Solomon, K. Swedberg and M. R. Zile (2014). "Angiotensin-Neprilysin Inhibition versus Enalapril in Heart Failure." New England Journal of Medicine 371(11): 993-1004.

Mederos y Schnitzler, M., U. Storch and T. Gudermann (2011). "AT1 receptors as mechanosensors." Current Opinion in Pharmacology 11(2): 112-116.

Miura, S.-i., Y. Kiya, H. Hanzawa, N. Nakao, M. Fujino, S. Imaizumi, Y. Matsuo, H.

Yanagisawa, H. Koike, I. Komuro, S. S. Karnik and K. Saku (2012). "Small molecules with similar structures exhibit agonist, neutral antagonist or inverse agonist activity toward angiotensin II type 1 receptor." PLOS ONE 7(6): e37974.

Mozaffarian, D., E. J. Benjamin, A. S. Go, D. K. Arnett, M. J. Blaha, M. Cushman, S. de Ferranti, J.-P. Despr6s, H. J. Fullerton, V. J. Howard, M. D. Huffman, S. E. Judd, B. M. Kissela, D. T.

Lackland, J. H. Lichtman, L. D. Lisabeth, S. Liu, R. H. Mackey, D. B. Matchar, D. K. McGuire, E. R. Mohler, C. S. Moy, P. Muntner, M. E. Mussolino, K. Nasir, R. W. Neumar, G. Nichol, L.

Palaniappan, D. K. Pandey, M. J. Reeves, C. J. Rodriguez, P. D. Sorlie, J. Stein, A. Towfighi, T.

N. Turan, S. S. Virani, J. Z. Willey, D. Woo, R. W. Yeh and M. B. Turner (2015). "Heart Disease and Stroke Statistics-2015 Update: A Report From the American Heart Association." Circulation 131(4): e29-e322.

Ong, H. T., L. M. Ong and J. J. Ho (2013). "Angiotensin-Converting Enzyme Inhibitors (ACEIs) and Angiotensin-Receptor Blockers (ARBs) in Patients at High Risk of Cardiovascular Events: A Meta-Analysis of 10 Randomised Placebo-Controlled Trials." ISRN Cardiology 2013:478597.

Owan, T. E. and M. M. Redfield (2005). "Epidemiology of Diastolic Heart Failure." Progress in Cardiovascular Diseases 47(5): 320-332.

Pang, P. S., J. Butler, S. P. Collins, G. Cotter, B. A. Davison, J. A. Ezekowitz, G. Filippatos, P. D.

Levy, M. Metra, P. Ponikowski, J. R. Teerlink, A. A. Voors, D. Bharucha, K. Goin, D. G. Soergel and G. M. Felker (2017). Biased ligand of the angiotensin II type 1 receptor in patients with acute heart failure: a randomized, double-blind, placebo-controlled, phase IIB, dose ranging trial (BLAST-AHF)." European Heart Journal 00(Epub): 1-10.

Perlman, S., C. M. Costa-Neto, A. A. Miyakawa, H. T. Schambye, S. A. Hjorth, A. C. M. Paiva, R. A. Rivero, W. J. Greenlee and T. W. Schwartz (1997). "Dual agonistic and antagonistic property of nonpeptide angiotensin AT1 ligands: susceptibility to receptor mutations." Molecular Pharmacology 51(2): 301-311.

Perlman, S., H. T. Schambye, R. A. Rivero, W. J. Greenlee, S. A. Hjorth and T. W. Schwartz (1995). "Non-peptide Angiotensin Agonist: Functional and molecular interaction with the ATL receptor." Journal of Biological Chemistry 270(4): 1493-1496.

Quoyer, J., J. M. Janz, J. Luo, Y. Ren, S. Armando, V. Lukashova, J. L. Benovic, K. E. Carlson, S. W. Hunt and M. Bouvier (2013). "Pepducin targeting the C—X-C chemokine receptor type 4 acts as a biased agonist favoring activation of the inhibitory G protein." Proceedings of the National Academy of Sciences 110(52): E5088-E5097.

Rajagopal, K., E. J. Whalen, J. D. Violin, J. A. Stiber, P. B. Rosenberg, R. T. Premont, T. M.

Coffman, H. A. Rockman and R. J. Lefkowitz (2006). "β-Arrestin2-mediated inotropic effects of the angiotensin II type IA receptor in isolated cardiac myocytes." Proceedings of the National Academy of Sciences 103(44): 16284-16289.

Ravenni, R., J. F. Jabre, E. Casiglia and A. Mazza (2011). "Primary stroke prevention and hypertension treatment: which is the first-line strategy?" Neurology International 3(2): e12.

Satomura, H., H. Wada, K. Sakakura, N. Kubo, N. Ikeda, Y. Sugawara, J. Ako and S.-i.

Momomura "Congestive heart failure in the elderly: Comparison between reduced ejection fraction and preserved ejection fraction." Journal of Cardiology 59(2): 215-219.

Soergel, D., R. A. Subach, I. E. James, C. L. Cowan, M. Gowen and M. Lark (2013). "TRVO27, a beta-arrestin biased ligand at the angiotensin 2 type 1 receptor, produces rapid, reversible changes in hemodynamics in patients with stable systolic heart failure." Journal of the American College of Cardiology 61(10_S).

Soergel, D. G., R. A. Subach, C. L. Cowan, J. D. Violin and M. W. Lark (2013). "First Clinical Experience with TRV027: Pharmacokinetics and Pharmacodynamics in Healthy Volunteers." The Journal of Clinical Pharmacology 53(9): 892-899.

Staessen, J. A., Y. Li, L. Thijs and J.-G. Wang (2005). "Blood Pressure Reduction and Cardiovascular Prevention: An Update Including the 2003-2004 Secondary Prevention Trials." Hypertens Res 28(5): 385-407.

Stephane Angers, Ali Salahpour and M. Bouvier (2002). "Dimerization: An Emerging Concept for G Protein-Coupled Receptor Ontogeny and Function." Annual Review of Pharmacology and Toxicology 42(1): 409-435.

Tang, W., R. T. Strachan, R. J. Lefkowitz and H. A. Rockman (2014). "Allosteric Modulation of β-Arrestin-biased Angiotensin II Type 1 Receptor Signaling by Membrane Stretch." Journal of Biological Chemistry 289(41): 28271-28283.

Thomsen, W., J. Frazer and D. Unett (2005). "Functional assays for screening GPCR targets." Current Opinion in Biotechnology 16: 655-665.

Violin, J. D., S. M. DeWire, D. Yamashita, D. H. Rominger, L. Nguyen, K. Schiller, E. J.

Whalen, M. Gowen and M. W. Lark (2010). "Selectively Engaging β-Arrestins at the Angiotensin II Type 1 Receptor Reduces Blood Pressure and Increases Cardiac Performance." Journal of Pharmacology and Experimental Therapeutics 335(3): 572-579.

Wei, H., S. Ahn, S. K. Shenoy, S. S. Karnik, L. Hunyady, L. M. Luttrell and R. J. Lefkowitz (2003). "Independent β-arrestin 2 and G protein-mediated pathways for angiotensin II activation of extracellular signal-regulated kinases 1 and 2." Proceedings of the National Academy of Sciences 100(19): 10782-10787.

Yancy, C. W., M. Jessup, B. Bozkurt, J. Butler, D. E. Casey, M. H. Drazner, G. C. Fonarow, S. A. Geraci, T. Horwich, J. L. Januzzi, M. R. Johnson, E. K. Kasper, W. C. Levy, F. A. Masoudi, P. E. McBride, J. J. V. McMurray, J. E. Mitchell, P. N. Peterson, B. Riegel, F. Sam, L. W. Stevenson, W. H. W. Tang, E. J. Tsai and B. L. Wilkoff (2013). "2013 ACCF/AHA Guideline for the Management of Heart Failure: Executive SummaryA Report of the American College of Cardiology Foundation/American Heart Association Task Force on Practice Guidelines." Journal of the American College of Cardiology 62(16): 1495-1539.

Zhao, X., A. Jones, K. R. Olson, K. Peng, T. Wehrman, A. Park, R. Mallari, D. Neblasca, S. W. Young and S.-H. Xiao (2008). "A Homogeneous Enzyme Fragment Complementation-Based β-Arrestin Translocation Assay for High-Throughput Screening of G-Protein-Coupled Receptors." Journal of Biomolecular Screening 13(8): 737-747.

Compounds were tested in the assays described above with the following results:

| Example Numbe | DiscoveRx β-arrestin2 $EC_{50}$ (nM) | DiscoveRx β-arrestin2 Ymax (%) |
|---|---|---|
| 1 | 15.5 | 44.1 |
| 2 | 19.8 | 21.8 |
| 3 | 21.2 | 22.9 |
| 4 | 7.5 | 48.9 |
| 5 | 14.5 | 30.9 |
| 6 | 14.1 | 27.0 |
| 7 | 14.4 | 21.6 |
| 8 | 6.0 | 42.2 |
| 9 | 3.7 | 66.7 |
| 10 | 1.4 | 60.3 |
| 11 | 9.9 | 36.3 |
| 12 | 6.3 | 21.4 |
| 13 | 12.9 | 24.8 |
| 14 | 10.3 | 20.8 |
| 15 | 22.6 | 14.9 |
| 16 | 59.8 | 17.1 |
| 17 | 15.7 | 11.9 |
| 18 | 139.9 | 54.2 |
| 19 | 7.5 | 57.9 |
| 20 | 4.9 | 38.7 |
| 21 | 22.1 | 21.1 |
| 22 | 10.3 | 14.8 |
| 23 | 54.1 | 26.8 |
| 24 | 13.4 | 24.1 |
| 25 | 15.9 | 23.1 |
| 26 | 10.8 | 25.0 |
| 27 | 205.8 | 10.6 |
| 28 | 321.7 | 11.9 |
| 29 | 8.6 | 29.8 |
| 30 | 4.9 | 48.0 |
| 31 | 33.9 | 55.1 |
| 32 | 34.3 | 86.1 |
| 33 | 9.7 | 29.9 |
| 34 | 40.3 | 35.6 |
| 35 | 64.0 | 28.2 |
| 39 | 33.1 | 23.3 |
| 40 | 9.3 | 36.4 |
| 45 | 24.6 | 60.3 |

-continued

| Example Numbe | DiscoveRx β-arrestin2 $EC_{50}$ (nM) | DiscoveRx β-arrestin2 Ymax (%) |
|---|---|---|
| 46 | 32.0 | 45.1 |
| 47 | 10.1 | 24.5 |
| 48 | 106.3 | 20.6 |
| 49 | 10.9 | 47.6 |
| 50 | 10.9 | 21.8 |
| 51 | 21.2 | 21.1 |
| 52 | 5.5 | 5.0 |
| 53 | 2.6 | 39.4 |
| 54 | 5.9 | 39.5 |
| 55 | 9.3 | 44.9 |
| 56 | 58.3 | 20.8 |
| 57 | 16.6 | 26.3 |
| 58 | 86.2 | 12.7 |
| 59 | 12.5 | 29.5 |
| 60 | 53.7 | 33.5 |
| 61 | 31.5 | 43.7 |
| 62 | 15.1 | 50.0 |
| 63 | 10.2 | 26.1 |
| 64 | 6.9 | 67.8 |
| 65 | 27.3 | 31.0 |
| 66 | 5.8 | 25.8 |
| 67 | 19.3 | 30.9 |
| 69 | 376.0 | 8.5 |
| 70 | 13.1 | 58.7 |
| 71 | 17.4 | 46.8 |
| 72 | 22.6 | 63.6 |
| 73 | 107.9 | 26.4 |
| 74 | 390.6 | 3.9 |
| 75 | 543.2 | 7.1 |
| 76 | 840.2 | 13.2 |
| 77 | 60.2 | 21.1 |
| 78 | 19.9 | 50.0 |
| 79 | 285.9 | 31.7 |
| 80 | 73.4 | 33.5 |
| 81 | 38.3 | 17.6 |
| 82 | 95.7 | 16.8 |
| 83 | 23.9 | 40.5 |
| 84 | 91.6 | 35.3 |
| 85 | 18.2 | 16.9 |
| 86 | 158.8 | 38.0 |
| 87 | 42.5 | 16.7 |
| 88 | 8.1 | 22.1 |
| 89 | 49.4 | 22.5 |
| 90 | 55.4 | 23.2 |
| 91 | 60.6 | 22.6 |
| 93 | 7.9 | 32.6 |
| 94 | 13.1 | 35.9 |
| 95 | 137.3 | 21.0 |
| 96 | 12.6 | 33.0 |
| 97 | 15.1 | 34.3 |
| 98 | 18.8 | 72.9 |
| 99 | 32.4 | 6.3 |
| 100 | 28.8 | 12.7 |
| 101 | 30.0 | 21.4 |
| 102 | 44.4 | 41.0 |
| 103 | 111.7 | 8.8 |
| 104 | 116.1 | 9.1 |
| 105 | 16.0 | 31.0 |
| 106 | 17.6 | 6.3 |
| 107 | 26.7 | 24.6 |
| 108 | 42.3 | 38.8 |
| 109 | 19.6 | 17.4 |
| 110 | 35.9 | 26.9 |
| 111 | 6.4 | 63.3 |
| 112 | 124.4 | 33.4 |
| 113 | 14.9 | 66.3 |
| 114 | 49.9 | 46.5 |
| 115 | 13.3 | 30.8 |
| 116 | 14.1 | 42.1 |
| 117 | 74.0 | 30.6 |
| 118 | 66.0 | 50.0 |
| 119 | 47.5 | 51.4 |
| 120 | 12.5 | 44.5 |
| 121 | 302.4 | 47.4 |
| 122 | 16.1 | 33.8 |
| 123 | 9.7 | 4.9 |
| 124 | 64.9 | 28.1 |
| 125 | 45.3 | 16.6 |
| 126 | 5.3 | 17.3 |

| | | | | | | |
|---|---|---|---|---|---|---|
| 128 | 25.7 | 14.5 | | 209 | 45.9 | 49.6 |
| 129 | 33.5 | 12.9 | | 210 | 8.6 | 48.4 |
| 130 | 21.9 | 31.2 | | 211 | 96.8 | 21.2 |
| 131 | 13.7 | 19.1 | | 212 | 10.1 | 11.2 |
| 132 | 87.2 | 14.1 | | 213 | 215.3 | 27.3 |
| 133 | 5.7 | 18.0 | | 214 | 76.1 | 74.1 |
| 134 | 73.5 | 40.3 | | 215 | 5.1 | 46.1 |
| 135 | 13.7 | 38.6 | | 216 | 9.6 | 33.4 |
| 136 | 4.9 | 43.2 | | 217 | 4.6 | 70.3 |
| 137 | >100000 | | | 218 | 45.9 | 21.5 |
| 138 | 13.4 | 27.9 | | 219 | 35.2 | 21.6 |
| 139 | 10.5 | 50.1 | | 222 | 56.9 | 42.7 |
| 140 | 9.7 | 22.1 | | 225 | 29.0 | 35.4 |
| 141 | 13.5 | 31.5 | | 226 | 242.3 | 17.5 |
| 142 | 27.5 | 22.7 | | 227 | 32.0 | 51.6 |
| 143 | 8.4 | 47.4 | | 228 | 30.4 | 32.1 |
| 144 | 12.3 | 33.3 | | 229 | 39.0 | 24.0 |
| 145 | 27.3 | 36.3 | | 230 | 63.1 | 16.7 |
| 146 | 31.6 | 34.0 | | 231 | 28.7 | 36.8 |
| 147 | 107.1 | 23.0 | | 232 | 16.9 | 41.5 |
| 148 | 103.2 | 34.8 | | 233 | 10.5 | 59.2 |
| 149 | 38.9 | 55.2 | | 234 | 9.2 | 59.9 |
| 150 | 13.7 | 45.6 | | 235 | 56.6 | 56.0 |
| 151 | 76.4 | 44.3 | | 236 | 12.5 | 60.8 |
| 152 | 11.6 | 28.6 | | 237 | 55.3 | 62.3 |
| 153 | 28.7 | 19.6 | | 238 | 198.1 | 22.4 |
| 154 | 14.1 | 48.7 | | 239 | 5.4 | 59.1 |
| 155 | 40.8 | 32.0 | | 240 | 48.6 | 42.0 |
| 156 | 85.1 | 19.9 | | 241 | 41.5 | 44.3 |
| 157 | 30.3 | 44.7 | | 243 | 22.4 | 37.7 |
| 158 | 191.1 | 41.6 | | 244 | 96.5 | 34.7 |
| 159 | 51.4 | 44.0 | | 245 | 114.7 | 75.5 |
| 160 | 87.8 | 50.2 | | 246 | 234.2 | 38.3 |
| 161 | 88.5 | 40.7 | | 247 | 6.9 | 30.8 |
| 162 | 147.3 | 31.9 | | 248 | 26.5 | 18.2 |
| 163 | 69.2 | 34.6 | | 249 | 23.8 | 34.2 |
| 164 | 76.0 | 58.7 | | 250 | 23.0 | 43.9 |
| 165 | 56.8 | 45.7 | | 251 | 33.6 | 20.2 |
| 166 | 23.1 | 47.5 | | 252 | 34.3 | 15.8 |
| 167 | 36.0 | 78.8 | | 253 | 31.2 | 37.2 |
| 168 | 352.4 | 34.5 | | 254 | 35.8 | 26.9 |
| 169 | 110.7 | 50.1 | | 255 | 122.8 | 26.3 |
| 170 | 170.2 | 63.4 | | 257 | 9.0 | 34.9 |
| 171 | 33.5 | 38.6 | | 258 | 23.1 | 35.2 |
| 172 | 196.5 | 27.1 | | 259 | 12.9 | 80.6 |
| 175 | 6.0 | 37.0 | | 260 | 51.7 | 36.4 |
| 176 | 31.8 | 32.0 | | 261 | 136.6 | 17.3 |
| 177 | 11.8 | 52.2 | | 262 | 19.9 | 50.8 |
| 178 | 7.1 | 75.6 | | 264 | 19.2 | 52.9 |
| 179 | 40.7 | 58.3 | | 265 | 30.1 | 53.4 |
| 180 | 51.9 | 40.4 | | 266 | 64.3 | 75.8 |
| 181 | 48.0 | 88.8 | | 267 | 9.8 | 62.5 |
| 182 | 84.9 | 74.2 | | 268 | 628.3 | 39.8 |
| 183 | 66.2 | 36.2 | | 269 | 6542.6 | 14.2 |
| 184 | 31.0 | 51.2 | | 270 | 6551.9 | 28.6 |
| 185 | 138.8 | 48.9 | | 271 | 383.7 | 45.5 |
| 186 | 11.8 | 55.6 | | 272 | 16.5 | 43.5 |
| 187 | 44.4 | 34.0 | | 273 | 21.4 | 39.3 |
| 188 | 41.7 | 53.3 | | 274 | 251.4 | 37.5 |
| 189 | 9.2 | 53.0 | | 275 | 26.6 | 50.9 |
| 190 | 137.7 | 57.0 | | 276 | 50.0 | 50.9 |
| 191 | 20.7 | 53.0 | | 277 | 36.1 | 46.0 |
| 192 | 94.3 | 45.1 | | 278 | 45.1 | 51.9 |
| 193 | 52.2 | 60.7 | | 279 | 189.8 | 33.7 |
| 194 | 63.2 | 36.6 | | 280 | 904.4 | 35.2 |
| 195 | 694.3 | 77.6 | | 281 | 41.6 | 47.4 |
| 196 | 3015.8 | 50.4 | | 283 | 44.5 | 57.5 |
| 197 | 282.3 | 20.2 | | 284 | 21.1 | 62.7 |
| 198 | 122.1 | 33.0 | | 285 | 66.4 | 24.8 |
| 199 | 273.0 | 34.2 | | 286 | 113.1 | 35.8 |
| 200 | 708.9 | 25.1 | | 287 | 175.2 | 30.5 |
| 201 | 348.2 | 7.0 | | 288 | 185.8 | 29.6 |
| 202 | 1114.0 | 19.4 | | 289 | 48.2 | 51.1 |
| 203 | 161.8 | 32.3 | | 290 | 88.5 | 30.7 |
| 204 | 26.4 | 42.4 | | 291 | 134.4 | 10.0 |
| 205 | 31.8 | 42.2 | | 292 | 177.0 | 32.1 |
| 206 | 11.1 | 21.2 | | 293 | 186.9 | 40.4 |
| 207 | 11.5 | 23.1 | | 294 | 87.3 | 28.9 |
| 208 | 20.8 | 44.8 | | 295 | 47.5 | 60.3 |

| | 649 -continued | |
|---|---|---|
| 296 | 127.9 | 41.8 |
| 297 | 142.2 | 30.5 |
| 298 | 277.5 | 31.3 |
| 299 | 7.7 | 83.0 |
| 302 | 10.2 | 61.1 |
| 303 | 42.3 | 58.9 |
| 305 | 25.5 | 69.3 |
| 308 | 29.1 | 51.8 |
| 309 | 4.1 | 80.4 |
| 310 | 14.9 | 51.4 |
| 311 | 3.9 | 77.6 |
| 312 | 22.5 | 79.9 |
| 313 | 28.1 | 46.1 |
| 314 | 3.5 | 66.8 |
| 315 | 242.3 | 21.5 |
| 316 | 53.0 | 51.6 |
| 317 | 87.2 | 51.5 |
| 318 | 47.5 | 54.6 |
| 319 | 71.1 | 49.0 |
| 320 | 40.7 | 55.7 |
| 321 | 56.8 | 83.4 |
| 322 | 39.2 | 33.7 |
| 323 | 22.2 | 43.2 |
| 324 | 17.4 | 55.2 |
| 326 | 9.5 | 45.9 |
| 327 | 9.4 | 64.2 |
| 328 | 801.8 | 51.8 |
| 329 | 7.1 | 77.6 |
| 330 | 13.2 | 57.8 |
| 331 | 13.2 | 44.5 |
| 332 | 24.1 | 30.6 |
| 333 | 10.0 | 67.8 |
| 334 | 10.8 | 73.5 |
| 335 | 36.1 | 22.7 |
| 336 | 16.4 | 61.4 |
| 337 | 40.6 | 85.6 |
| 338 | 17.8 | 68.9 |
| 339 | 10.6 | 58.0 |
| 345 | 18.1 | 44.8 |
| 346 | 13.0 | 44.5 |
| 347 | 57.2 | 26.8 |
| 348 | 7.3 | 50.9 |
| 349 | 69.2 | 24.8 |
| 350 | 8.3 | 47.0 |
| 351 | 18.0 | 45.4 |
| 352 | 234.3 | 35.7 |
| 353 | 55.0 | 22.4 |
| 354 | 59.9 | 48.3 |
| 355 | 8.6 | 42.4 |
| 356 | 27.3 | 41.5 |
| 357 | 19.6 | 41.8 |
| 358 | 10.1 | 40.2 |
| 359 | 17.4 | 43.5 |
| 360 | 29.2 | 37.2 |
| 361 | 97.8 | 29.3 |
| 362 | 123.3 | 49.8 |
| 363 | 10.7 | 46.2 |
| 364 | 23.2 | 30.3 |
| 365 | 46.2 | 39.7 |
| 366 | 11.1 | 37.0 |
| 367 | 5.7 | 35.9 |
| 368 | 59.8 | 39.1 |
| 369 | 174.4 | 30.9 |
| 370 | 16.3 | 26.8 |
| 371 | 5.7 | 40.8 |
| 372 | 58.8 | 41.7 |
| 373 | 14.2 | 29.5 |
| 374 | 10.5 | 44.3 |
| 375 | 89.7 | 35.8 |
| 376 | 18.5 | 22.1 |
| 377 | 49.5 | 39.0 |
| 378 | 106.9 | 15.7 |
| 379 | 21.2 | 30.2 |
| 380 | 59.2 | 43.1 |
| 381 | 343.8 | 37.4 |
| 382 | 13.2 | 27.6 |
| 383 | 70.4 | 22.8 |
| 384 | 8.0 | 49.3 |
| 385 | 31.4 | 35.4 |

| | 650 -continued | |
|---|---|---|
| 386 | 8.4 | 27.3 |
| 387 | 16.6 | 32.8 |
| 388 | 44.7 | 71.7 |
| 389 | 91.8 | 26.7 |
| 390 | 11.8 | 53.5 |
| 391 | 45.8 | 23.3 |
| 392 | 45.2 | 29.2 |
| 393 | 9.1 | 41.2 |
| 394 | 365.3 | 59.1 |
| 395 | 16.1 | 54.1 |
| 396 | 5.0 | 57.8 |
| 397 | 78.2 | 46.5 |
| 398 | 12.7 | 53.6 |
| 399 | 13.4 | 45.8 |
| 400 | 149.8 | 40.4 |
| 401 | 544.3 | 43.7 |
| 402 | 9.9 | 57.0 |
| 403 | 14.2 | 61.4 |
| 404 | 9.6 | 38.6 |
| 405 | 57.5 | 32.8 |
| 406 | 9.0 | 33.9 |
| 407 | 173.4 | 24.6 |
| 408 | 23.3 | 32.5 |
| 409 | 59.3 | 50.6 |
| 410 | 26.9 | 41.9 |
| 411 | 30.9 | 56.4 |
| 412 | 11.7 | 64.1 |
| 413 | 21.8 | 16.3 |
| 414 | 166.3 | 21.5 |
| 415 | 110.8 | 29.3 |
| 416 | 18.0 | 29.5 |
| 417 | 5.9 | 39.6 |
| 418 | 67.8 | 31.2 |
| 419 | 120.7 | 33.9 |
| 420 | 6.5 | 73.6 |
| 421 | 9.4 | 38.5 |
| 422 | 68.7 | 26.7 |
| 423 | 22.9 | 22.8 |
| 424 | 99.3 | 28.6 |
| 425 | 27.3 | 54.2 |
| 426 | 34.2 | 52.5 |
| 427 | 89.9 | 19.6 |
| 430 | 33.2 | 55.2 |
| 431 | 194.3 | 26.0 |
| 432 | 40.1 | 42.9 |
| 433 | 59.1 | 49.6 |
| 434 | 72.0 | 40.9 |
| 435 | 1407.3 | 19.1 |
| 436 | 993.5 | 31.2 |
| 437 | 3916.7 | 26.4 |
| 438 | 20.4 | 41.7 |
| 439 | 108.5 | 26.4 |
| 440 | 241.2 | 13.6 |
| 441 | 100.6 | 39.3 |
| 442 | 104.7 | 10.9 |
| 443 | 124.4 | 36.5 |
| 444 | 125.2 | 36.3 |
| 445 | 37.7 | 61.2 |
| 446 | 179.3 | 29.8 |
| 447 | 294.7 | 35.0 |
| 448 | 160.5 | 20.8 |
| 449 | 263.0 | 17.8 |
| 450 | 479.4 | 23.1 |
| 451 | 23.3 | 11.4 |
| 452 | 8.1 | 36.1 |
| 453 | 31.4 | 59.5 |
| 454 | 22.7 | 11.2 |
| 455 | 46.8 | 14.4 |

| Example Number | BRET β-Arrestin2 High AT1R Expression $EC_{50}$ (nM) | BRET β-Arrestin2 High AT1R Expression Ymax (%) |
|---|---|---|
| 1 | 7.2 | 86.9 |
| 2 | 11.3 | 74.2 |
| 3 | 14.9 | 79.6 |
| 4 | 3.8 | 95.4 |
| 5 | 16.0 | 76.2 |
| 6 | 51.0 | 73.5 |

651
-continued

| | | |
|---|---|---|
| 7 | 37.4 | 60.0 |
| 8 | 4.1 | 93.0 |
| 9 | 5.6 | 87.8 |
| 10 | 1.4 | 86.9 |
| 11 | 22.0 | 79.2 |
| 12 | 9.0 | 83.6 |
| 13 | 11.5 | 53.8 |
| 16 | 24.7 | 69.9 |
| 19 | 2.4 | 89.8 |
| 20 | 4.3 | 85.5 |
| 21 | 51.4 | 64.0 |
| 22 | 33.7 | 57.1 |
| 23 | 170.5 | 66.3 |
| 24 | 13.5 | 73.1 |
| 25 | 19.8 | 74.5 |
| 27 | 89.5 | 20.1 |
| 29 | 11.3 | 82.7 |
| 30 | 5.6 | 87.5 |
| 31 | 58.2 | 85.5 |
| 32 | 5.1 | 91.6 |
| 33 | 16.5 | 83.0 |
| 34 | 50.6 | 68.4 |
| 35 | 147.7 | 76.7 |
| 39 | 18.8 | 37.9 |
| 40 | 14.0 | 84.6 |
| 45 | 34.7 | 92.2 |
| 46 | 13.1 | 84.8 |
| 47 | 14.7 | 56.6 |
| 48 | 40.6 | 43.8 |
| 49 | 11.2 | 78.3 |
| 50 | 16.8 | 64.9 |
| 51 | 99.0 | 43.8 |
| 52 | 30.7 | 23.4 |
| 53 | 5.4 | 90.6 |
| 54 | 5.7 | 89.7 |
| 56 | 48.9 | 63.0 |
| 57 | 15.2 | 66.3 |
| 58 | 190.3 | 46.2 |
| 59 | 14.0 | 52.1 |
| 60 | 19.6 | 85.8 |
| 61 | 16.1 | 81.4 |
| 63 | 7.5 | 76.6 |
| 64 | 1.9 | 92.5 |
| 69 | 1504.5 | 10.3 |
| 70 | 7.1 | 94.7 |
| 71 | 23.3 | 86.6 |
| 72 | 33.2 | 85.8 |
| 74 | >100000 | 3.2 |
| 75 | 1124.5 | 53.9 |
| 77 | 90.6 | 77.1 |
| 78 | 15.0 | 94.3 |
| 82 | 142.5 | 49.6 |
| 83 | 52.1 | 87.3 |
| 84 | 36.4 | 88.9 |
| 85 | 10.5 | 88.3 |
| 87 | 451.2 | 29.1 |
| 90 | 27.7 | 77.7 |
| 93 | 7.5 | 82.8 |
| 94 | 20.8 | 76.8 |
| 96 | 12.9 | 77.6 |
| 97 | 31.1 | 79.7 |
| 98 | 20.3 | 86.6 |
| 99 | 144.4 | 9.6 |
| 100 | 155.1 | 19.4 |
| 102 | 99.6 | 71.6 |
| 104 | 345.8 | 23.4 |
| 105 | 28.9 | 58.0 |
| 106 | 138.2 | 12.4 |
| 107 | 225.9 | 54.3 |
| 109 | 73.1 | 59.9 |
| 112 | 30.6 | 78.5 |
| 114 | 11.9 | 89.2 |
| 117 | 94.2 | 35.0 |
| 121 | 431.1 | 98.0 |
| 122 | 17.5 | 94.3 |
| 123 | 65.3 | 20.6 |
| 124 | 137.8 | 32.6 |
| 125 | 300.0 | 15.1 |
| 126 | 47.1 | 65.1 |

652
-continued

| | | |
|---|---|---|
| 127 | 23.6 | 82.7 |
| 128 | 132.9 | 11.0 |
| 129 | 240.0 | 40.7 |
| 130 | 26.1 | 80.0 |
| 131 | 49.0 | 42.5 |
| 132 | 496.2 | 22.0 |
| 133 | 38.4 | 69.0 |
| 134 | 157.7 | 77.0 |
| 135 | 28.7 | 94.8 |
| 136 | 9.9 | 94.2 |
| 137 | 35.3 | 12.2 |
| 138 | 56.9 | 73.2 |
| 139 | 11.2 | 95.0 |
| 141 | 10.0 | 88.6 |
| 142 | 59.2 | 82.9 |
| 143 | 8.2 | 94.6 |
| 144 | 26.8 | 104.0 |
| 145 | 64.4 | 81.5 |
| 146 | 38.2 | 85.6 |
| 147 | 126.5 | 66.6 |
| 148 | 90.4 | 72.8 |
| 149 | 24.1 | 85.7 |
| 175 | 5.2 | 93.0 |
| 176 | 25.5 | 79.1 |
| 177 | 4.0 | 91.8 |
| 178 | 4.8 | 89.3 |
| 179 | 20.7 | 90.6 |
| 180 | 50.8 | 85.3 |
| 181 | 4.8 | 94.1 |
| 182 | 7.0 | 90.4 |
| 183 | 62.9 | 90.0 |
| 184 | 14.7 | 85.9 |
| 185 | 149.1 | 86.7 |
| 190 | 83.6 | 88.8 |
| 195 | 100.6 | 87.0 |
| 196 | 617.8 | 83.3 |
| 198 | 428.3 | 95.8 |
| 199 | 223.1 | 88.5 |
| 200 | 1777.7 | 54.3 |
| 202 | 1620.6 | 52.0 |
| 203 | 123.8 | 79.1 |
| 204 | 3.6 | 85.9 |
| 205 | 4.8 | 92.1 |
| 206 | 15.8 | 57.9 |
| 207 | 22.0 | 74.8 |
| 208 | 6.0 | 103.1 |
| 209 | 7.2 | 90.6 |
| 210 | 9.0 | 88.2 |
| 211 | 67.0 | 80.2 |
| 212 | 10.6 | 29.2 |
| 213 | 92.9 | 89.9 |
| 214 | 4.2 | 86.5 |
| 225 | 10.9 | 82.1 |
| 226 | 348.4 | 35.0 |
| 227 | 7.4 | 87.8 |
| 228 | 31.9 | 93.1 |
| 229 | 25.7 | 82.1 |
| 230 | 61.2 | 53.5 |
| 234 | 3.4 | 93.3 |
| 235 | 29.6 | 89.5 |
| 236 | 3.6 | 93.3 |
| 237 | 16.3 | 84.4 |
| 238 | 280.7 | 62.6 |
| 245 | 4.9 | 88.8 |
| 247 | 13.8 | 74.4 |
| 248 | 14.0 | 79.5 |
| 249 | 8.0 | 80.3 |
| 250 | 3.8 | 79.8 |
| 251 | 10.6 | 57.2 |
| 252 | 29.4 | 41.4 |
| 253 | 17.9 | 85.3 |
| 254 | 20.0 | 75.6 |
| 255 | 24.3 | 80.2 |
| 257 | 10.0 | 87.3 |
| 258 | 41.5 | 75.7 |
| 259 | 6.9 | 83.2 |
| 260 | 7.8 | 87.9 |
| 261 | 40.0 | 62.3 |
| 268 | 1034.6 | 73.8 |

| | | |
|---|---:|---:|
| 269 | 30667.7 | 58.7 |
| 270 | 12881.4 | 74.3 |
| 271 | 560.9 | 80.3 |
| 272 | 15.2 | 84.0 |
| 273 | 23.2 | 88.1 |
| 274 | 279.1 | 82.5 |
| 275 | 21.5 | 71.5 |
| 276 | 77.9 | 73.6 |
| 277 | 28.9 | 79.4 |
| 278 | 13.0 | 87.2 |
| 279 | 209.6 | 82.6 |
| 280 | 699.5 | 75.7 |
| 281 | 10.5 | 93.1 |
| 283 | 22.8 | 88.5 |
| 284 | 33.0 | 92.9 |
| 285 | 57.3 | 33.4 |
| 286 | 47.1 | 45.3 |
| 287 | 54.1 | 45.9 |
| 288 | 474.3 | 69.2 |
| 289 | 13.0 | 85.2 |
| 290 | 67.3 | 31.2 |
| 291 | 1645.6 | 9.6 |
| 292 | 72.2 | 36.5 |
| 293 | 135.8 | 70.2 |
| 294 | 150.0 | 24.7 |
| 295 | 14.0 | 92.5 |
| 296 | 68.8 | 79.9 |
| 297 | 327.4 | 74.5 |
| 298 | 269.7 | 68.8 |
| 311 | 1.5 | 92.0 |
| 312 | 2.6 | 91.8 |
| 313 | 7.7 | 92.9 |
| 314 | 5.8 | 90.3 |
| 315 | 1838.6 | 29.1 |
| 316 | 46.2 | 97.5 |
| 317 | 319.3 | 39.8 |
| 318 | 131.6 | 93.9 |
| 320 | 172.6 | 86.8 |
| 321 | 108.2 | 86.7 |
| 322 | 8.4 | 80.9 |
| 329 | 2.8 | 91.4 |
| 345 | 17.9 | 92.0 |
| 346 | 7.1 | 92.1 |
| 347 | 172.5 | 48.8 |
| 348 | 34.3 | 85.4 |
| 349 | 117.3 | 67.6 |
| 350 | 15.6 | 94.3 |
| 351 | 38.9 | 89.6 |
| 352 | 290.0 | 62.2 |
| 353 | 65.5 | 49.1 |
| 354 | 19.3 | 99.5 |
| 355 | 23.3 | 92.5 |
| 356 | 17.7 | 84.7 |
| 357 | 23.4 | 72.5 |
| 358 | 21.4 | 88.8 |
| 359 | 15.3 | 90.8 |
| 360 | 35.1 | 75.0 |
| 361 | 127.7 | 61.3 |
| 362 | 26.4 | 97.0 |
| 363 | 23.8 | 100.4 |
| 364 | 50.5 | 79.4 |
| 365 | 35.9 | 82.7 |
| 366 | 27.4 | 78.7 |
| 367 | 17.6 | 63.3 |
| 368 | 32.5 | 82.6 |
| 369 | 73.3 | 73.8 |
| 370 | 45.3 | 85.5 |
| 371 | 11.0 | 94.4 |
| 372 | 44.8 | 78.9 |
| 373 | 38.5 | 71.4 |
| 374 | 13.4 | 94.4 |
| 375 | 89.4 | 55.7 |
| 376 | 45.5 | 44.2 |
| 377 | 25.4 | 80.9 |
| 378 | 238.3 | 26.3 |
| 379 | 56.3 | 72.7 |
| 380 | 35.0 | 76.0 |
| 381 | 828.2 | 73.9 |
| 382 | 47.1 | 67.5 |

| | | |
|---|---:|---:|
| 383 | 308.7 | 66.3 |
| 384 | 6.9 | 83.8 |
| 385 | 57.1 | 87.0 |
| 386 | 45.2 | 66.7 |
| 387 | 18.2 | 81.9 |
| 388 | 4.6 | 96.2 |
| 389 | 188.5 | 35.3 |
| 390 | 24.4 | 95.3 |
| 391 | 11.7 | 78.3 |
| 392 | 17.2 | 79.1 |
| 393 | 12.0 | 86.1 |
| 394 | 37.3 | 94.9 |
| 395 | 20.4 | 92.4 |
| 396 | 6.4 | 88.8 |
| 397 | 80.9 | 87.9 |
| 398 | 13.4 | 91.0 |
| 399 | 7.2 | 92.1 |
| 400 | 171.9 | 88.3 |
| 401 | 255.8 | 74.5 |
| 402 | 17.9 | 77.8 |
| 403 | 9.2 | 88.6 |
| 404 | 14.3 | 89.7 |
| 405 | 42.0 | 95.8 |
| 406 | 10.6 | 97.5 |
| 409 | 73.2 | 88.7 |
| 410 | 82.1 | 69.7 |
| 413 | 55.6 | 47.5 |
| 414 | 504.6 | 36.4 |
| 415 | 206.2 | 26.8 |
| 416 | 114.8 | 69.0 |
| 423 | 26.0 | 73.3 |
| 424 | 67.8 | 76.7 |
| 430 | 70.4 | 78.9 |
| 431 | 1593.1 | 92.7 |
| 432 | 163.0 | 88.4 |
| 433 | 115.4 | 92.4 |
| 434 | 316.1 | 96.6 |
| 435 | 305.4 | 12.3 |
| 436 | 13566.5 | 58.0 |
| 437 | 167.6 | 16.4 |
| 438 | 34.8 | 74.6 |
| 439 | 116.6 | 35.8 |
| 440 | 28291.3 | 50.1 |
| 441 | 57.0 | 64.3 |
| 442 | 302.8 | 17.2 |
| 443 | 153.4 | 83.9 |
| 444 | 146.8 | 46.5 |
| 445 | 9.8 | 91.3 |
| 446 | 143.7 | 84.3 |
| 447 | 335.8 | 63.1 |
| 448 | 598.6 | 58.5 |
| 449 | 345.3 | 30.1 |
| 450 | 307.5 | 77.6 |
| 451 | 13667.2 | 44.8 |
| 452 | 33.8 | 84.6 |
| 453 | 13.0 | 95.9 |
| 454 | 56.2 | 18.4 |

| Example Number | BRET β-Arrestin2 Low AT1R Expression EC$_{50}$ (nM) | BRET β-Arrestin2 Low AT1R Expression Ymax (%) |
|---|---:|---:|
| 1 | 29.5 | 61.8 |
| 2 | 11.0 | 15.2 |
| 3 | 24.2 | 30.6 |
| 4 | 8.2 | 69.3 |
| 5 | 12.1 | 22.9 |
| 8 | 5.4 | 80.5 |
| 9 | 9.4 | 80.3 |
| 10 | 2.4 | 86.8 |
| 11 | 35.3 | 16.9 |
| 14 | >10000 | |
| 19 | 12.1 | 73.7 |
| 20 | 12.2 | 59.5 |
| 24 | 13.9 | 21.6 |
| 25 | 32.9 | 10.1 |
| 29 | 18.9 | 42.2 |
| 30 | 14.5 | 72.9 |
| 31 | 84.7 | 42.4 |

655 -continued

| | | |
|---|---|---|
| 32 | 12.5 | 80.9 |
| 33 | 26.7 | 27.5 |
| 53 | 14.0 | 61.8 |
| 56 | 54.0 | 14.2 |
| 57 | 19.9 | 8.9 |
| 59 | >10000 | |
| 60 | 93.3 | 39.4 |
| 61 | 108.3 | 38.2 |
| 62 | 3.7 | 74.7 |
| 63 | 26.5 | 59.3 |
| 64 | 3.1 | 98.7 |
| 65 | 23.6 | 54.5 |
| 66 | 16.6 | 39.4 |
| 67 | 14.5 | 40.7 |
| 68 | 15.3 | 91.1 |
| 72 | 58.2 | 44.4 |
| 78 | 37.5 | 85.0 |
| 79 | 464.4 | 21.1 |
| 80 | 30.4 | 29.8 |
| 81 | 38.3 | 16.3 |
| 83 | 152.1 | 43.1 |
| 91 | >10000 | |
| 92 | 309.2 | 66.5 |
| 110 | 95.5 | 22.1 |
| 111 | 14.7 | 80.7 |
| 112 | 174.3 | 39.3 |
| 113 | 9.8 | 88.6 |
| 114 | 36.6 | 57.2 |
| 115 | 16.8 | 53.3 |
| 116 | 17.2 | 81.9 |
| 117 | >100000 | |
| 118 | 172.6 | 78.7 |
| 119 | 53.9 | 63.9 |
| 120 | 34.3 | 50.1 |
| 122 | 30.8 | 31.6 |
| 127 | 17.3 | 29.5 |
| 129 | >10000 | |
| 133 | >10000 | |
| 138 | >10000 | |
| 139 | 41.4 | 83.5 |
| 141 | 40.4 | 58.9 |
| 146 | 52.6 | 35.0 |
| 147 | 109.2 | 26.1 |
| 148 | 140.7 | 17.7 |
| 149 | 82.7 | 42.1 |
| 150 | 76.9 | 65.7 |
| 151 | 419.2 | 42.5 |
| 152 | 21.8 | 47.9 |
| 153 | 54.1 | 34.1 |
| 154 | 63.9 | 82.9 |
| 155 | 42.7 | 31.4 |
| 156 | 250.1 | 22.1 |
| 157 | 61.1 | 86.5 |
| 159 | 40.3 | 64.9 |
| 160 | 98.5 | 74.5 |
| 161 | 46.3 | 54.4 |
| 162 | 372.7 | 41.9 |
| 163 | 91.8 | 45.7 |
| 164 | 159.6 | 85.0 |
| 165 | 281.3 | 69.1 |
| 166 | 64.5 | 81.0 |
| 167 | 58.3 | 97.4 |
| 168 | 997.9 | 26.5 |
| 169 | 270.9 | 59.9 |
| 170 | 590.4 | 65.3 |
| 171 | 68.4 | 67.5 |
| 172 | >10000 | |
| 173 | 80.4 | 81.8 |
| 174 | 634.1 | 25.0 |
| 175 | 10.7 | 73.1 |
| 176 | 30.6 | 17.8 |
| 177 | 11.5 | 84.1 |
| 178 | 19.4 | 80.7 |
| 179 | 61.4 | 55.4 |
| 180 | 178.3 | 66.3 |
| 181 | 15.7 | 89.4 |
| 182 | 26.3 | 73.5 |
| 183 | 137.9 | 54.6 |
| 186 | 22.8 | 80.0 |

656 -continued

| | | |
|---|---|---|
| 187 | 180.9 | 45.4 |
| 188 | 24.6 | 82.4 |
| 189 | 49.2 | 77.2 |
| 190 | 154.1 | 72.1 |
| 191 | 76.0 | 75.5 |
| 192 | 127.2 | 22.6 |
| 193 | 132.9 | 92.2 |
| 194 | 294.8 | 53.2 |
| 195 | 281.9 | 73.0 |
| 196 | 1700.3 | 45.2 |
| 197 | >10000 | |
| 204 | 9.8 | 37.1 |
| 205 | 21.3 | 72.2 |
| 208 | 26.4 | 67.5 |
| 209 | 50.0 | 80.0 |
| 210 | 28.4 | 49.5 |
| 214 | 15.9 | 100.6 |
| 215 | 4.1 | 77.5 |
| 216 | 6.6 | 67.3 |
| 217 | 3.0 | 102.6 |
| 218 | >10000 | |
| 219 | 33.2 | 33.6 |
| 220 | 36.0 | 63.8 |
| 221 | 158.7 | 32.4 |
| 222 | 98.5 | 33.8 |
| 223 | 9.2 | 54.5 |
| 224 | 7.6 | 60.6 |
| 225 | 187.0 | 51.8 |
| 227 | 31.4 | 86.1 |
| 228 | 209.9 | 66.6 |
| 230 | 140.2 | 10.1 |
| 231 | 98.8 | 85.7 |
| 232 | 101.4 | 34.1 |
| 233 | 9.7 | 107.9 |
| 234 | 12.2 | 96.5 |
| 235 | 128.6 | 67.0 |
| 236 | 17.3 | 107.0 |
| 237 | 111.8 | 71.7 |
| 239 | 9.0 | 112.7 |
| 240 | 344.8 | 62.0 |
| 241 | 50.2 | 60.8 |
| 242 | 28.2 | 92.5 |
| 243 | 71.5 | 58.2 |
| 244 | 111.0 | 55.8 |
| 245 | 24.1 | 83.8 |
| 246 | 916.2 | 52.2 |
| 247 | 22.7 | 17.7 |
| 250 | 11.0 | 49.2 |
| 251 | 8.2 | 19.0 |
| 253 | 46.0 | 42.3 |
| 254 | 59.1 | 37.6 |
| 255 | 87.8 | 36.3 |
| 256 | 34.5 | 77.4 |
| 257 | 29.1 | 44.2 |
| 258 | 81.9 | 27.3 |
| 259 | 38.8 | 71.7 |
| 260 | 49.9 | 53.5 |
| 262 | 14.3 | 71.5 |
| 264 | 12.9 | 87.4 |
| 265 | 18.9 | 98.5 |
| 266 | 5.7 | 105.1 |
| 267 | 8.2 | 102.1 |
| 295 | 39.0 | 46.3 |
| 299 | 4.7 | 104.3 |
| 300 | 12.8 | 70.3 |
| 301 | 14.8 | 87.0 |
| 302 | 14.9 | 84.2 |
| 303 | 38.2 | 81.7 |
| 304 | 38.3 | 81.2 |
| 305 | 90.3 | 91.5 |
| 306 | 133.5 | 99.3 |
| 307 | 962.0 | 27.1 |
| 309 | 6.5 | 109.1 |
| 310 | 10.9 | 109.0 |
| 311 | 4.2 | 80.0 |
| 312 | 5.8 | 71.0 |
| 313 | 21.5 | 62.6 |
| 314 | 36.6 | 78.7 |
| 322 | 9.7 | 31.7 |

| | | |
|---|---|---|
| 323 | 24.4 | 41.2 |
| 324 | 63.2 | 71.8 |
| 325 | 201.3 | 59.5 |
| 326 | 24.7 | 42.4 |
| 327 | 33.0 | 39.7 |
| 330 | 16.7 | 44.6 |
| 331 | 8.4 | 45.3 |
| 332 | 12.1 | 18.9 |
| 333 | 11.3 | 33.9 |
| 334 | 5.9 | 73.1 |
| 335 | 6.0 | 21.1 |
| 336 | 12.4 | 37.6 |
| 337 | 631.1 | 96.2 |
| 338 | 16.3 | 81.2 |
| 339 | 12.8 | 40.4 |
| 340 | 5.8 | 64.3 |
| 341 | 12.2 | 54.7 |
| 342 | 3.6 | 78.7 |
| 343 | 26.2 | 47.0 |
| 344 | 767.3 | 52.1 |
| 346 | 11.1 | 49.8 |
| 384 | 10.8 | 29.2 |
| 388 | 26.7 | 98.4 |
| 390 | 97.0 | 53.7 |
| 391 | 11.0 | 29.6 |
| 396 | 14.1 | 52.9 |
| 404 | 69.4 | 54.7 |
| 410 | 98.2 | 23.0 |
| 418 | 154.2 | 27.1 |
| 419 | 85.2 | 21.5 |
| 424 | 35.3 | 19.7 |
| 425 | 47.4 | 35.0 |
| 426 | 49.6 | 40.7 |
| 427 | >10000 | 6.5 |
| 428 | 121.9 | 12.1 |
| 445 | 36.0 | 92.0 |
| 455 | 181.7 | 13.2 |
| 456 | 1965.2 | 26.7 |
| 457 | 993.4 | 35.1 |
| 458 | 385.3 | 52.4 |
| 459 | 1241.1 | 18.9 |

| Example Number | IP-1 EC$_{50}$ (nM) | IP-1 Ymax (%) |
|---|---|---|
| 1 | 20.7 | 18.7 |
| 2 | 71.8 | 13.1 |
| 3 | 45603.6 | 29.9 |
| 4 | 19.0 | 9.8 |
| 5 | 23.8 | 15.1 |
| 6 | 14.6 | 4.9 |
| 7 | 83.9 | 9.2 |
| 8 | 6.0 | 6.9 |
| 9 | 8.7 | 7.1 |
| 10 | 5.0 | 14.4 |
| 11 | 17.8 | 3.8 |
| 12 | >1000 | |
| 13 | >1000 | |
| 14 | 14.5 | 8.1 |
| 15 | 21.7 | 2.4 |
| 16 | 55.3 | 3.6 |
| 17 | 8.7 | 3.3 |
| 18 | 499.1 | 15.4 |
| 19 | 27.4 | 12.2 |
| 20 | 12.8 | 9.9 |
| 21 | 77.3 | 6.9 |
| 22 | 34.4 | 2.4 |
| 23 | 211.0 | 7.3 |
| 24 | 20.7 | 14.5 |
| 25 | 40.8 | 6.7 |
| 26 | 24.2 | 7.5 |
| 27 | >100000 | |
| 28 | 3779.3 | 2.3 |
| 29 | 38.7 | 12.1 |
| 30 | 15.9 | 12.3 |
| 31 | 233.8 | 12.3 |
| 32 | 38.4 | 10.8 |
| 33 | 80.8 | 3.3 |
| 34 | 177.8 | 3.8 |
| 35 | >50000 | |
| 39 | 126.1 | 4.8 |
| 40 | 11.9 | 8.5 |
| 45 | 14.4 | 14.5 |
| 46 | 354.8 | 15.4 |
| 47 | 6.2 | 3.8 |
| 48 | 356.7 | 10.0 |
| 49 | 21.0 | 4.2 |
| 50 | 132.1 | 6.7 |
| 51 | 92.1 | 3.7 |
| 52 | >1000 | |
| 53 | 7.9 | 5.8 |
| 54 | 10.5 | 7.0 |
| 55 | 26.8 | 6.8 |
| 56 | >100000 | |
| 57 | >100000 | |
| 58 | 426.5 | 3.1 |
| 59 | 21.9 | 10.4 |
| 60 | 83.1 | 5.3 |
| 61 | 150.3 | 9.8 |
| 62 | 29.0 | 22.7 |
| 63 | 51.3 | 21.4 |
| 64 | 23.2 | 30.8 |
| 65 | 62.7 | 12.2 |
| 66 | 8.5 | 6.9 |
| 67 | 26.5 | 10.2 |
| 69 | >100000 | |
| 70 | >50000 | |
| 71 | 48592.6 | 11.8 |
| 72 | 92.0 | 8.5 |
| 73 | 5940.0 | 11.6 |
| 74 | >100000 | |
| 75 | >100000 | |
| 76 | >100000 | |
| 77 | 203.6 | 7.1 |
| 78 | 79.5 | 37.8 |
| 79 | 498.6 | 9.4 |
| 80 | 425.2 | 14.6 |
| 81 | >100000 | |
| 82 | >100000 | |
| 83 | 26.9 | 9.0 |
| 84 | 126.1 | 6.6 |
| 85 | >100000 | |
| 86 | >100000 | |
| 87 | 42.0 | 7.2 |
| 88 | >100000 | |
| 89 | >100000 | |
| 90 | 39.8 | 6.0 |
| 91 | >100000 | |
| 92 | 1395.2 | 51.1 |
| 93 | 21.2 | 5.4 |
| 94 | 32.7 | 9.0 |
| 95 | 248.9 | 6.3 |
| 96 | 28.7 | 5.3 |
| 97 | 47.3 | 7.3 |
| 98 | 26.7 | 6.6 |
| 99 | >100000 | |
| 100 | 49.9 | 6.1 |
| 101 | >100000 | |
| 102 | 723.5 | 3.8 |
| 103 | >100000 | |
| 104 | >100000 | |
| 105 | >100000 | |
| 106 | >100000 | |
| 107 | >100000 | |
| 108 | 219.5 | 12.8 |
| 109 | >100000 | |
| 110 | 108.3 | 9.0 |
| 111 | 12.6 | 15.7 |
| 112 | 284.4 | 7.7 |
| 113 | 83.5 | 17.8 |
| 114 | 121.9 | 8.3 |
| 115 | 39.3 | 13.6 |
| 116 | 39.7 | 15.1 |
| 117 | >100000 | |
| 118 | 154.8 | 17.1 |
| 119 | 108.3 | 18.4 |
| 120 | 75.3 | 20.7 |
| 121 | 367.7 | 7.2 |

659 -continued

| | | |
|---|---|---|
| 122 | 35.4 | 5.5 |
| 123 | >100000 | |
| 124 | >100000 | |
| 125 | >100000 | |
| 126 | >100000 | |
| 128 | >100000 | |
| 129 | 119.1 | 2.0 |
| 130 | 108.3 | 5.9 |
| 131 | >100000 | |
| 133 | >100000 | |
| 134 | 101.6 | 4.0 |
| 135 | >100000 | |
| 136 | 14.4 | 18.1 |
| 137 | >100000 | |
| 138 | 54.1 | 6.3 |
| 139 | 19.2 | 16.8 |
| 140 | 26.1 | 4.5 |
| 141 | >100000 | |
| 142 | 140.1 | 4.8 |
| 143 | 18.3 | 5.2 |
| 144 | >100000 | |
| 145 | 57.1 | 3.1 |
| 146 | 76.2 | 8.3 |
| 147 | 177.5 | 3.6 |
| 148 | 310.7 | 6.1 |
| 149 | 142.7 | 7.5 |
| 150 | 20.7 | 17.2 |
| 151 | 606.5 | 14.0 |
| 152 | 30.7 | 7.0 |
| 153 | 228.9 | 6.0 |
| 154 | 40.6 | 14.4 |
| 155 | >100000 | |
| 156 | 189.0 | 7.2 |
| 157 | 60.1 | 11.4 |
| 158 | 214.4 | 8.6 |
| 159 | 78.1 | 11.3 |
| 160 | 132.1 | 15.8 |
| 161 | 203.3 | 14.2 |
| 162 | 234.6 | 8.9 |
| 163 | 180.7 | 7.8 |
| 164 | 231.4 | 17.3 |
| 165 | 191.9 | 17.7 |
| 166 | 103.3 | 14.8 |
| 167 | 165.2 | 32.4 |
| 168 | 825.5 | 13.8 |
| 169 | 484.0 | 14.5 |
| 170 | 468.7 | 13.2 |
| 171 | 8124.9 | 68.1 |
| 172 | 782.4 | 9.4 |
| 175 | 12.8 | 24.1 |
| 176 | 48.9 | 9.8 |
| 177 | 112.5 | 22.9 |
| 178 | 21.5 | 20.8 |
| 179 | 81.7 | 12.2 |
| 180 | 226.5 | 27.5 |
| 181 | 78.4 | 6.1 |
| 182 | 131.7 | 6.6 |
| 183 | 200.3 | 14.1 |
| 184 | 109.6 | 12.0 |
| 185 | 203.6 | 13.8 |
| 186 | 85.9 | 22.2 |
| 187 | 103.7 | 16.1 |
| 188 | 172.8 | 24.2 |
| 189 | 18.4 | 12.7 |
| 190 | 485.2 | 17.5 |
| 191 | 118.2 | 29.9 |
| 192 | 223.3 | 11.1 |
| 193 | 132.4 | 25.0 |
| 194 | 213.7 | 14.5 |
| 195 | 357.9 | 5.3 |
| 196 | 868.9 | 12.1 |
| 197 | 492.6 | 5.7 |
| 198 | 645.9 | 14.6 |
| 199 | 713.4 | 9.3 |
| 200 | 2718.8 | 11.4 |
| 201 | 453.9 | 5.6 |
| 202 | 2935.9 | 5.7 |
| 203 | 5366.6 | 34.9 |
| 204 | 66.8 | 14.4 |

660 -continued

| | | |
|---|---|---|
| 205 | 70.2 | 16.7 |
| 206 | 35.4 | 4.8 |
| 207 | 39.1 | 2.5 |
| 208 | 105.8 | 19.9 |
| 209 | 110.3 | 25.5 |
| 210 | 82.7 | 14.8 |
| 211 | 234.9 | 8.7 |
| 212 | 20.1 | 3.8 |
| 213 | 861.6 | 6.9 |
| 214 | 89.6 | 50.0 |
| 215 | 17.6 | 17.3 |
| 216 | 29.1 | 10.6 |
| 217 | 22.5 | 21.8 |
| 218 | 33.3 | 4.6 |
| 219 | 117.5 | 6.9 |
| 222 | 187.3 | 4.9 |
| 225 | 25.2 | 7.0 |
| 226 | 499.4 | 6.7 |
| 227 | 268.5 | 9.8 |
| 228 | 146.7 | 13.0 |
| 229 | 195.5 | 6.7 |
| 230 | 340.4 | 12.7 |
| 231 | 30.1 | 8.4 |
| 232 | 60.0 | 7.5 |
| 233 | 31.3 | 10.2 |
| 234 | 19.3 | 18.8 |
| 235 | 213.1 | 14.9 |
| 236 | 48.2 | 19.2 |
| 237 | 79.7 | 13.7 |
| 238 | 1255.5 | 9.6 |
| 239 | 30.7 | 34.2 |
| 240 | 122.4 | 14.1 |
| 241 | 150.3 | 12.8 |
| 243 | 52.0 | 14.7 |
| 244 | 200.7 | 11.0 |
| 245 | 89.4 | 12.7 |
| 246 | 281.4 | 4.8 |
| 247 | >100000 | |
| 248 | 81.7 | 6.8 |
| 249 | 70.5 | 17.6 |
| 250 | 50.5 | 28.9 |
| 251 | 182.5 | 10.9 |
| 252 | 144.2 | 8.8 |
| 253 | 133.2 | 18.7 |
| 254 | 176.5 | 30.0 |
| 255 | 471.1 | 7.8 |
| 257 | 28.3 | 10.7 |
| 258 | 42.8 | 15.1 |
| 259 | 21.1 | 9.9 |
| 260 | 174.7 | 18.5 |
| 261 | 781.8 | 11.5 |
| 262 | 37.9 | 8.6 |
| 264 | 42.8 | 15.1 |
| 265 | 29.2 | 15.6 |
| 266 | 26.1 | 17.7 |
| 267 | 36.6 | 10.9 |
| 268 | 1093.8 | 7.0 |
| 269 | >100000 | |
| 270 | 4681.8 | 6.7 |
| 271 | 589.7 | 2.9 |
| 272 | >100000 | |
| 273 | 154.6 | 3.3 |
| 274 | 1491.5 | 3.5 |
| 275 | >100000 | |
| 276 | 400.8 | 3.5 |
| 277 | >100000 | |
| 278 | 1208.5 | 2.1 |
| 279 | >100000 | |
| 280 | 2865.4 | 3.8 |
| 281 | 231.7 | 3.2 |
| 283 | 155.0 | 4.2 |
| 284 | 151.2 | 7.5 |
| 285 | 1535.4 | 7.9 |
| 286 | 301.5 | 5.3 |
| 287 | >100000 | |
| 288 | >100000 | |
| 289 | 546.5 | 4.3 |
| 290 | 502.5 | 4.7 |
| 291 | >100000 | |

661
-continued

| | | |
|---|---|---|
| 292 | >100000 | |
| 293 | 1240.6 | 8.5 |
| 294 | 427.2 | 5.4 |
| 295 | 216.9 | 7.2 |
| 296 | 619.2 | 11.0 |
| 297 | 620.5 | 6.6 |
| 298 | 957.7 | 5.8 |
| 299 | 21.3 | 20.3 |
| 302 | 47.3 | 16.9 |
| 303 | 108.7 | 20.1 |
| 305 | 82.9 | 10.1 |
| 308 | 27.3 | 22.3 |
| 309 | 7.9 | 17.2 |
| 310 | 35.3 | 21.3 |
| 311 | 18.1 | 10.6 |
| 312 | 20.7 | 8.9 |
| 313 | 82.1 | 6.1 |
| 314 | 128.9 | 5.6 |
| 315 | >100000 | |
| 316 | >100000 | |
| 317 | 17118.1 | 9.9 |
| 318 | 552.2 | 8.4 |
| 319 | 786.6 | 7.9 |
| 320 | >100000 | |
| 321 | 47.9 | 9.9 |
| 322 | 93.3 | 5.9 |
| 323 | >100000 | |
| 324 | 42.3 | 7.9 |
| 326 | 16.2 | 5.3 |
| 327 | 22.1 | 12.6 |
| 328 | 2622.6 | 7.9 |
| 329 | 31.5 | 9.4 |
| 330 | 40.1 | 8.1 |
| 331 | 26.4 | 8.5 |
| 332 | 105.7 | 4.9 |
| 333 | 17.8 | 6.2 |
| 334 | 41.3 | 10.7 |
| 335 | 721.3 | 3.9 |
| 336 | 47.2 | 8.7 |
| 337 | 55.8 | 7.1 |
| 338 | 30.8 | 6.2 |
| 339 | 52.1 | 5.7 |
| 345 | 12.5 | 7.4 |
| 346 | 67.1 | 6.4 |
| 347 | 242.2 | 5.7 |
| 348 | 89.2 | 5.2 |
| 349 | 173.7 | 3.5 |
| 350 | 25.3 | 4.5 |
| 351 | 81.1 | 4.6 |
| 352 | 1178.2 | 6.8 |
| 353 | 565.6 | 5.9 |
| 354 | 45.5 | 3.4 |
| 355 | >1000 | |
| 356 | 36.7 | 3.3 |
| 357 | 46.3 | 3.3 |
| 358 | 44.7 | 4.3 |
| 359 | 39.4 | 6.4 |
| 360 | >100000 | |
| 361 | 295.5 | 5.1 |
| 362 | 34.2 | 3.1 |
| 363 | 59.6 | 6.5 |
| 364 | 118.8 | 5.3 |
| 365 | 40.8 | 4.2 |
| 366 | 42.9 | 3.5 |
| 367 | 59.1 | 3.9 |
| 368 | 96.1 | 2.1 |
| 369 | 172.9 | 4.4 |
| 370 | 71.9 | 9.3 |
| 371 | >1000 | |
| 372 | 73.8 | 5.5 |
| 373 | 734.5 | 5.4 |
| 374 | 16.2 | 7.7 |
| 375 | 272.9 | 8.7 |
| 376 | 123.0 | 5.0 |
| 377 | 145.9 | 4.2 |
| 378 | 688.5 | 7.5 |
| 379 | 106.3 | 5.4 |
| 380 | 103.8 | 6.3 |
| 381 | 2109.2 | 5.3 |

662
-continued

| | | |
|---|---|---|
| 382 | >100000 | |
| 383 | 7742.2 | 11.0 |
| 384 | 39.1 | 4.2 |
| 385 | 1109.5 | 10.3 |
| 386 | 59063.4 | 21.2 |
| 387 | 3416.2 | 13.6 |
| 388 | 810.2 | 23.4 |
| 389 | 2022.2 | 6.3 |
| 390 | 23.7 | 10.1 |
| 391 | 181.0 | 4.5 |
| 392 | 3322.3 | 6.7 |
| 393 | 48.8 | 5.7 |
| 394 | 76.4 | 3.1 |
| 395 | 12.7 | 6.0 |
| 396 | 273.6 | 3.1 |
| 397 | 124.0 | 5.3 |
| 398 | 35.1 | 13.0 |
| 399 | 1166.8 | 10.1 |
| 400 | 891.6 | 4.5 |
| 401 | 2238.4 | 5.0 |
| 402 | 64.9 | 2.3 |
| 403 | 70.9 | 4.1 |
| 404 | 70.4 | 3.7 |
| 405 | 491.7 | 3.3 |
| 407 | 16587.0 | 43.4 |
| 408 | >100000 | |
| 409 | 135.5 | 8.0 |
| 410 | >100000 | |
| 411 | 17.0 | 4.8 |
| 412 | 62.7 | 6.0 |
| 413 | 350.8 | 5.4 |
| 414 | 460.1 | 5.2 |
| 415 | 486.7 | 3.6 |
| 416 | >100000 | |
| 417 | >100000 | |
| 418 | 478.5 | 5.3 |
| 419 | 227.8 | 4.4 |
| 420 | 79.7 | 8.2 |
| 421 | 92.5 | 5.5 |
| 422 | 209.5 | 7.1 |
| 423 | 25.4 | 3.5 |
| 424 | 2788.6 | 7.0 |
| 425 | 104.7 | 8.3 |
| 426 | 86.0 | 5.6 |
| 427 | 574.9 | 5.4 |
| 430 | 275.2 | 2.1 |
| 431 | 910.5 | 3.2 |
| 432 | 285.5 | 3.9 |
| 433 | 581.1 | 5.2 |
| 434 | 1278.6 | 8.2 |
| 435 | >100000 | |
| 436 | >100000 | |
| 437 | >100000 | |
| 438 | 718.0 | 4.9 |
| 439 | 386.2 | 3.9 |
| 440 | 582.3 | 2.7 |
| 441 | >100000 | |
| 442 | >100000 | |
| 443 | 77.1 | 8.6 |
| 444 | 258.3 | 6.2 |
| 445 | 140.4 | 13.2 |
| 446 | >100000 | |
| 447 | 1384.5 | 9.0 |
| 448 | 856.2 | 4.4 |
| 449 | >100000 | |
| 450 | 5264.0 | 11.1 |
| 451 | 4107.7 | 6.2 |
| 452 | 44.8 | 4.4 |
| 453 | 24.0 | 4.2 |
| 454 | >100000 | |
| 455 | 93.8 | 4.0 |

| Example Number | BRET P63 EC$_{50}$ (nM) | BRET P63 Ymax (%) |
|---|---|---|
| 2 | 22.0 | 2.7 |
| 4 | 4.8 | 13.0 |
| 8 | 7.7 | 14.0 |
| 9 | 19.5 | 14.2 |

| | | | | | | |
|---|---|---|---|---|---|---|
| 10 | 2.8 | 26.1 | | 186 | 33.0 | 14.7 |
| 14 | >10000 | | | 187 | 167.7 | 8.4 |
| 20 | 10.8 | 12.0 | | 188 | 33.1 | 17.2 |
| 25 | >100000 | | | 189 | 32.1 | 17.5 |
| 30 | 19.1 | 23.5 | | 190 | 432.4 | 16.4 |
| 32 | 21.1 | 25.2 | | 191 | 100.9 | 24.2 |
| 33 | >10000 | | | 192 | >100000 | |
| 53 | >100000 | | | 193 | 160.4 | 29.3 |
| 56 | 42.6 | 4.0 | | 194 | 278.2 | 16.2 |
| 57 | 14.3 | 5.0 | | 195 | 264.0 | 13.6 |
| 59 | >10000 | | | 196 | 1098.0 | 7.6 |
| 60 | >10000 | | | 197 | >100000 | |
| 61 | 22.3 | 6.4 | | 198 | 7623.5 | 13.4 |
| 62 | 4.2 | 35.7 | | 199 | 570.7 | 9.6 |
| 63 | 23.2 | 12.4 | | 200 | 2041.1 | 4.3 |
| 64 | 2.6 | 41.3 | | 202 | >100000 | |
| 65 | 17.2 | 13.1 | | 203 | 154.0 | 5.4 |
| 66 | >10000 | | | 204 | 10.7 | 9.4 |
| 67 | 7.3 | 14.3 | | 205 | 18.4 | 20.2 |
| 68 | 15.0 | 41.7 | | 208 | 13.3 | 17.4 |
| 72 | 43.0 | 11.8 | | 209 | 37.6 | 32.6 |
| 78 | 72.3 | 36.1 | | 214 | 35.6 | 43.3 |
| 79 | >10000 | | | 215 | 4.0 | 22.7 |
| 80 | >100000 | | | 216 | 1.8 | 10.1 |
| 81 | >100000 | | | 217 | 2.7 | 32.1 |
| 83 | 54.8 | 8.2 | | 218 | >10000 | |
| 91 | >100000 | | | 220 | 36.8 | 18.2 |
| 92 | 278.0 | 17.8 | | 221 | 28.0 | 5.4 |
| 110 | >100000 | | | 222 | >100000 | |
| 111 | 22.3 | 24.1 | | 223 | 5.9 | 9.8 |
| 112 | 46.8 | 8.2 | | 224 | 11.3 | 20.8 |
| 113 | 17.2 | 28.6 | | 225 | 29.5 | 7.1 |
| 114 | 66.5 | 11.8 | | 226 | >100000 | |
| 115 | 11.9 | 22.1 | | 227 | 30.4 | 19.9 |
| 116 | 14.7 | 27.7 | | 228 | 125.0 | 11.4 |
| 117 | >100000 | | | 229 | >100000 | |
| 118 | 101.9 | 21.8 | | 230 | >100000 | |
| 119 | 40.5 | 21.8 | | 231 | 36.2 | 13.8 |
| 120 | 18.4 | 17.8 | | 232 | >100000 | |
| 122 | >10000 | | | 233 | 13.2 | 17.9 |
| 127 | >10000 | | | 234 | 28.2 | 37.1 |
| 133 | >10000 | | | 235 | 160.9 | 17.7 |
| 139 | 34.4 | 20.6 | | 236 | 34.6 | 36.2 |
| 141 | 13.3 | 14.9 | | 237 | 60.5 | 21.1 |
| 146 | >100000 | | | 238 | >100000 | |
| 147 | >100000 | | | 239 | 16.7 | 44.3 |
| 150 | 105.1 | 14.6 | | 240 | 60.1 | 9.5 |
| 151 | 174.2 | 11.0 | | 241 | 40.5 | 17.5 |
| 152 | >100000 | | | 242 | 41.6 | 45.6 |
| 153 | >100000 | | | 243 | 42.1 | 15.2 |
| 154 | 57.7 | 25.3 | | 244 | 69.6 | 15.3 |
| 155 | >100000 | | | 245 | 27.2 | 23.3 |
| 156 | >100000 | | | 246 | 82.6 | 10.1 |
| 157 | 37.6 | 16.5 | | 247 | >10000 | |
| 159 | 79.3 | 11.5 | | 249 | 9.5 | 6.6 |
| 160 | 79.7 | 18.6 | | 250 | 9.3 | 14.1 |
| 161 | 49.6 | 10.9 | | 251 | 11.1 | 6.7 |
| 162 | >10000 | | | 252 | >100000 | |
| 163 | >10000 | | | 253 | 38.3 | 12.6 |
| 164 | 105.9 | 15.6 | | 254 | 39.9 | 7.1 |
| 165 | 261.6 | 14.1 | | 255 | 22.5 | 6.0 |
| 166 | 65.0 | 22.7 | | 256 | 43.0 | 30.5 |
| 167 | 91.5 | 32.0 | | 257 | 23.7 | 10.8 |
| 168 | >10000 | | | 258 | 139.6 | 17.5 |
| 169 | 127.1 | 13.3 | | 260 | >100000 | |
| 170 | 632.7 | 13.5 | | 261 | >100000 | |
| 171 | 30.9 | 20.1 | | 262 | 11.2 | 14.4 |
| 172 | >10000 | | | 264 | 7.4 | 15.7 |
| 173 | 79.1 | 19.3 | | 265 | 7.0 | 17.9 |
| 174 | 770.1 | 10.3 | | 266 | 5.7 | 19.1 |
| 175 | 21.1 | 12.4 | | 267 | 7.5 | 17.7 |
| 176 | >100000 | | | 293 | >100000 | |
| 177 | 36.2 | 23.8 | | 294 | >100000 | |
| 178 | 25.6 | 19.6 | | 295 | 119.7 | 12.9 |
| 179 | 52.3 | 11.6 | | 296 | 306.6 | 6.9 |
| 180 | 209.8 | 14.9 | | 297 | >100000 | |
| 181 | 47.5 | 16.1 | | 298 | >100000 | |
| 183 | 179.4 | 13.2 | | 299 | 4.9 | 31.7 |
| 185 | 446.7 | 11.7 | | 300 | 9.0 | 25.1 |

| | | |
|---|---:|---:|
| 301 | 13.6 | 31.2 |
| 302 | 10.2 | 25.2 |
| 303 | 49.7 | 30.4 |
| 304 | 29.7 | 17.3 |
| 305 | 67.0 | 24.3 |
| 306 | 104.3 | 24.8 |
| 307 | >10000 | |
| 309 | 3.8 | 28.6 |
| 310 | 7.2 | 29.1 |
| 311 | 3.6 | 13.2 |
| 312 | 17.2 | 9.4 |
| 313 | 46.7 | 6.3 |
| 314 | 67.8 | 12.8 |
| 322 | 53.7 | 5.1 |
| 323 | >10000 | |
| 324 | >10000 | |
| 325 | >10000 | |
| 326 | >100000 | |
| 327 | 26.9 | 10.8 |
| 330 | >10000 | |
| 331 | >10000 | |
| 332 | >10000 | |
| 333 | >10000 | |
| 334 | 15.7 | 13.9 |
| 335 | >10000 | |
| 336 | >10000 | |
| 337 | >10000 | |
| 338 | >10000 | |
| 339 | >10000 | |
| 340 | 2.9 | 17.3 |
| 341 | 4.4 | 18.8 |
| 342 | 3.3 | 16.5 |
| 343 | 26.7 | 15.3 |
| 344 | 16.8 | 10.4 |
| 346 | 19.3 | 6.0 |
| 384 | >10000 | |
| 388 | 39.8 | 30.4 |
| 390 | 127.1 | 11.9 |
| 391 | >100000 | |
| 392 | >100000 | |
| 396 | >100000 | |
| 404 | >10000 | |
| 410 | >10000 | |
| 418 | >10000 | |
| 419 | >10000 | |
| 424 | >100000 | |
| 425 | >10000 | |
| 426 | >10000 | |
| 427 | >10000 | |
| 428 | >10000 | |
| 443 | 364.6 | 4.5 |
| 444 | >100000 | |
| 445 | 102.6 | 24.0 |
| 446 | 668.0 | 4.5 |
| 447 | >100000 | |
| 448 | >100000 | |
| 449 | >100000 | |
| 450 | >100000 | |
| 455 | >100000 | |
| 456 | 1867.0 | 9.4 |
| 457 | 1139.9 | 31.5 |
| 458 | 253.0 | 31.7 |
| 459 | >10000 | |

As used herein, the term "patient" encompasses all mammalian species.

As used herein, the term "subject" refers to any human or non-human organism that could potentially benefit from treatment with an AII biased agonist, or β-Arrestin agonist of the angiotensin II receptor. Exemplary subjects include human beings of any age with risk factors for development of heart failure and the sequelae thereof, angina, ischemia, cardiac ischemia, myocardial infarction, reperfusion injury, angioplastic restenosis, hypertension, vascular complications of diabetes, obesity or endotoxemia, stroke, as well as atherosclerosis, coronary artery disease, acute coronary syndrome, and/or dyslipidemias.

As used herein, "treating" or "treatment" cover a treatment of a disease-state in a mammal, particularly in a human, and include: (a) inhibiting a disease-state, i.e., arresting it development; and/or (b) relieving a disease-state, i.e., causing regression of a disease state.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a or a stereoisomer, a tautomer, a pharmaceutically acceptable salt, or a solvate thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

As used herein, "risk reduction" covers therapies that lower the incidence of development of a clinical disease state. As such, primary and secondary prevention therapies are examples of risk reduction. "Therapeutically effective amount" is intended to include an amount of a compound of the present invention that is effective when administered alone or in combination to modulate AII biased agonism, or β-Arrestin agonism of the angiotensin II receptor to prevent or treat the disorders listed herein. When applied to a combination, the term refers to combined amounts of the active ingredients that result in the preventive or therapeutic effect, whether administered in combination, serially, or simultaneously.

In addition to their affects due to their activity as biased agonists or β-Arrestin agonists of the Angiotensin II Receptor, due to their Angiotensin 11 receptor activity, the compounds of the invention may be used in the treatment, prevention and/or prophylaxis of multiple diseases or disorders associated with the AT1R, such as heart failure such as acute decompensated heart failure (ADHF), chronic heart failure, fibrosis atrial fibrillation, coronary artery disease, peripheral vascular disease, atherosclerosis, renal disease, diabetes, obesity, metabolic syndrome, hypertension, pulmonary hypertension, cerebrovascular disorders and the sequelae thereof, cardiovascular disorders, angina, ischemia, stroke, myocardial infarction, acute coronary syndrome, reperfusion injury, angioplastic restenosis, vascular complications of diabetes and obesity.

In addition to their affects due to their activity as biased agonists or β-Arrestin agonists of the Angiotensin II Receptor, due to their Angiotensin II receptor activity, the compounds of the invention may be used in the treatment, prevention and/or prophylaxis of multiple diseases or disorders associated with the ATIR, such as of heart failure, coronary artery disease, peripheral vascular disease, atherosclerosis, fibrosis, diabetes, obesity, metabolic syndrome, insulin resistance, hypertension, pulmonary hypertension, atrial fibrillation, angina, ischemia, stroke, myocardial infarction, acute coronary syndrome, reperfusion injury, angioplastic restenosis, vascular complications of diabetes, obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Additionally, the compounds may be useful for the treatment and/or prophylaxis of heart failure, coronary artery disease, cardiomyopathy, atrial fibrillation, and related conditions including but not limited to acute coronary syndrome, myocardial ischemia, hypertension, atherosclerosis, pulmonary hypertension, peripheral arterial disease, ischemia/reperfusion injury, angina, renal disease, V. Pharmaceutical Compositions, Formulations and Combinations The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted.

Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., Remington: *The Science and Practice of Pharmacy* (2 Volumes), 22nd Edition, Pharmaceutical Press (2012), The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. I gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., agents used in treatment of heart failure or other pharmaceutically active material.

The compounds of the present invention may be employed in combination with one or more other suitable therapeutic agents useful in the treatment of the aforementioned disorders including: agents for treating heart failure, anti-hypertensive agents, anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, and agents for treating peripheral arterial disease.

The compounds of the present invention may be employed in combination with additional therapeutic agent(s) selected from one or more, preferably one to three, of the following therapeutic agents in treating heart failure and coronary artery disease: ACE inhibitors (such as enalapril), neprilysin inhibitors (such as sacubitril), β-blockers, diuretics (such as furosemide), mineralocorticoid receptor antagonists, renin inhibitors, calcium channel blockers, nitrates, *digitalis* compounds, inotropic agents and β-receptor agonists, anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol), low density lipoprotein receptor inducers, clofibrate, fenofibrate, benzofibrate, cipofibrate, gemfibrizol, vitamin $B_6$, vitamin $B_{12}$, anti-oxidant vitamins, anti-diabetes agents, platelet aggregation inhibitors, fibrinogen receptor antagonists, aspirin and fibric acid derivatives.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; dipeptidyl peptidase IV (DPP4) inhibitor (such as sitagliptin, saxagliptin),GLP-1 agonists or analogs (such as exenatide), a-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating heart failure and atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, β₃-adrenergic receptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated.

By enteric coating one of the active ingredients, it is possible not only to minimize the contact between the combined active ingredients but also to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the ATIR and All, orbiased agonists or β-Arrestin agonists of the angiotensin II receptor. Such compounds may be provided in a commercial kit, for example, for use in pharmaceutical research involving ATIR and All, or biased agonists or β-Arrestin agonists of the angiotensin II receptor, or anti-heart failure activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving AT1 R and All, or biased agonists or β-Arrestin agonism of the angiotensin II receptor.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment and/or prophylaxis of multiple diseases or disorders associated with AT1R and AII, or biased agonism or β-Arrestin agonism of the angiotensin II receptor, (as defined previously). In another embodiment, the package insert states that the pharmaceutical composition can be used in combination (as defined previously) with a second therapeutic agent for the treatment and/or prophylaxis of multiple diseases or disorders associated with AT1R and AII, or biased agonism or β-Arrestin agonism of the angiotensin II receptor. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

What is claimed is:
1. A compound of formula (I), or salt thereof:

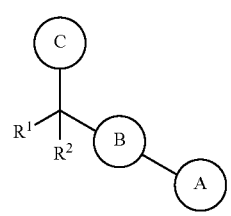

(I)

wherein
ring A is

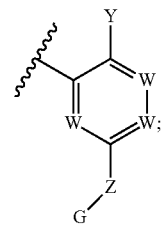

W is N, or $CR^{16}$

W', at each occurrence, is independently selected from N, O, S and $CR^{16}$ where at least one W' is not $CR^{16}$, and at most only one W' is selected as O or S;

$R^1$ and $R^2$ are independently selected from H, $C_1$-$C_6$ alkyl, $C_1$-$C_6$ haloalkyl, $C_1$-$C_6$ hydroxyalkyl, $C_1$-$C_6$ alkoxyalkyl, and $C_3$-$C_6$ cycloalkyl;

alternatively, $R^1$ and $R^2$, together with the atom to which they are attached, join together to form a $C_3$-$C_6$ cycloalkyl, or a 4 to 6 membered heterocycle having 1-2 heteroatoms, the cycloalkyl or heterocycle is substituted with 0-4 F and 0-1 OH;

$R^{16}$, at each occurrence, is independently selected from H, F, Cl, Br, I, CN, OH, $N(R^a)_2$, $C_1$-$C_3$-alkyl, $C_1$-$C_3$-haloalkyl, $C_1$-$C_3$-alkoxy, $C_1$-$C_4$-hydroxyalkyl, $C_1$-$C_3$-haloalkoxy, $C_3$-$C_6$-cycloalkyl, and $C_3$-$C_6$-halocycloalkyl $R^a$ is, at each occurrence, independently selected from H, $C_1$-$C_4$-alkyl, $C_1$-$C_4$-haloalkyl, $C_1$-$C_4$-hydroxyalkyl, and $C_3$-$C_6$-cycloalkyl;

or two $R^a$, along with the nitrogen atom to which they are attached, join to form a 5 to 6 membered heterocycle containing 0-2 additional heteroatoms selected from N, O and S;

Y is 5-tetrazolyl, $SO_3H$, $PO_2H_2$, $PO_3H_2$, COOR,

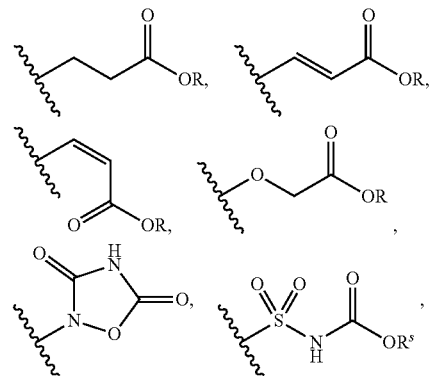

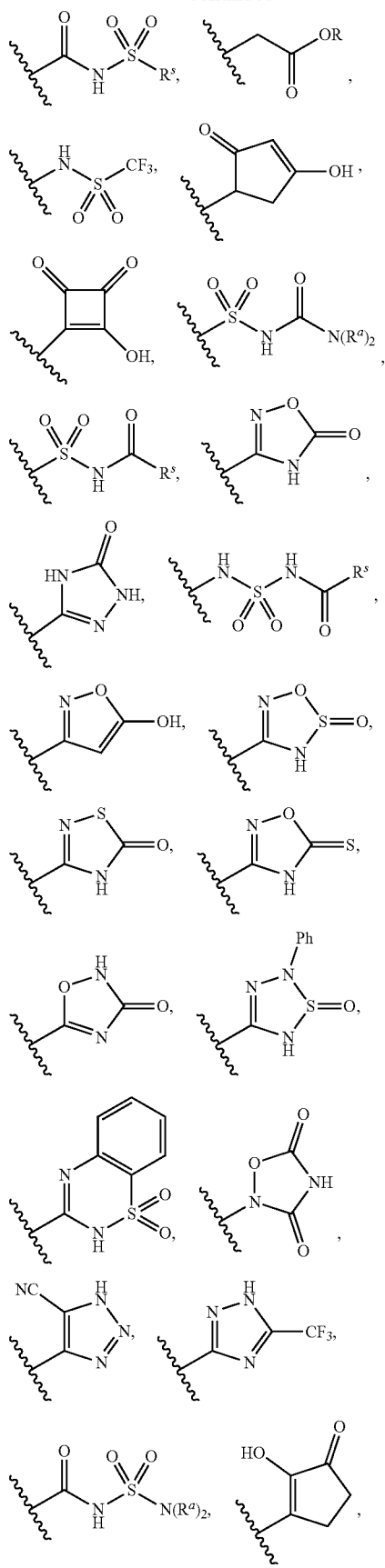

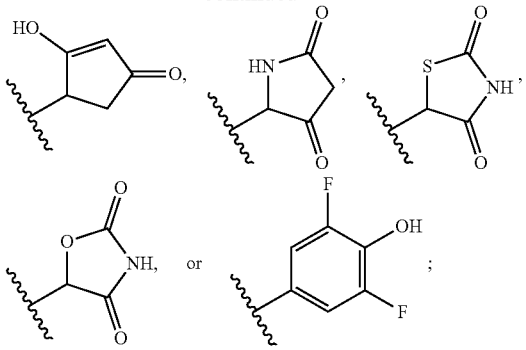

R, at each occurrence, is independently selected from H, $C_1$-$C_6$ alkyl, $C_1$-$C_6$-haloalkyl, $C_1$-$C_6$-hydroxyalkyl, $C_3$-$C_7$ cycloalkyl, $C_6$aryl-$C_1$-$C_6$ alkyl heterocycle-$C_1$-$C_6$ alkyl, wherein said heterocycle is a 4-10 membered group having 1-3 heteroatoms selected from N, O, or S, said aryl and heterocycle are each substituted with 0-3 groups chosen from $C_1$-$C_3$ alkyl, halo, OH, or $C_1$-$C_3$ fluoroalkyl;

$R^8$ at each occurrence, is independently selected from H, $C_1$-$C_6$ alkyl, $C_1$-$C_6$-haloalkyl, $C_1$-$C_6$-hydroxyalkyl, $C_3$-$C_7$ cycloalkyl, $C_3$-$C_7$ cycloalkyl-$C_1$-$C_3$ alkyl, $C_{6-10}$ aryl, $C_{6-10}$-aryl-$C_1$-$C_6$-alkyl, heteroaryl, heteroaryl-$C_1$-$C_6$-alkyl, heterocyclyl, heterocycle-$C_1$-$C_6$-alkyl, wherein the heteroaryl and heterocycle are each a 4-10 membered group having 1-3 heteroatoms selected from N, O, or S;

Z, at each occurrence, is independently selected from a bond, O, S, N($R^z$), C($R^z$)$_2$, C=O, C(=O)N($R^z$), N($R^z$)C(=O), C($R^z$)$_2$C($R^z$)$_2$, OC($R^z$)$_2$, SC($R^z$)$_2$, N($R^z$)C($R^z$)$_2$, C($R^z$)$_2$O, C($R^z$)$_2$S, C($R^z$)$_2$N($R^z$);

$R^z$ is at each occurrence independently selected from H, $C_1$-$C_4$-alkyl, $C_1$-$C_4$-hydroxyalkyl, $C_1$-$C_4$-haloalkyl, $C_3$-$C_6$-cycloalkyl or, alternatively, two $R^z$ groups either on the same atom or on adjacent atoms can join to form a $C_3$-$C_6$-cycloalkyl or a 4 to 7 membered heterocycle containing 1-2 heteroatoms selected from N, O and S;

G is selected from a 4 to 11 membered heterocycle having 1-4 atoms selected from N, O, and S, a $C_3$-C8-cycloalkyl, $C_6$-$C_{10}$-aryl or a 5 to 10 membered heteroaryl having 1-4 atoms selected from N, O, and S; wherein the heterocycle, cycloalkyl, aryl and heteroaryl are substituted with 0-3 substituents independently selected from the group consisting of =O, F, Cl, Br, I, $C_1$-$C_6$-alkyl, $C_1$-$C_6$-alkoxy, $C_1$-$C_6$-haloalkyl, $C_1$-$C_6$-hydroxyalkyl, OH, $OR^x$, $SR^x$, $N(R^x)_2$, $CO(R^x)$, $CON(R^x)_2$, $CO_2R^x$, $N(R^x)CO_2(R^x)$, $N(R^x)CO(R^x)$, $N(R^x)CON(R^x)_2$, $S(O)_2(R^x)$, $S(O)_2N(R^x)_2$, or $N(R^x)S(O)_2(R^x)$;

$R^x$ is H, $C_{1-6}$ alkyl, $C_{1-4}$ haloalkyl, $C_{1-4}$ hydroxyalkyl, phenyl, $CH_2$-phenyl; ring B is

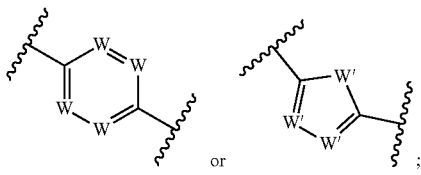

Group C is

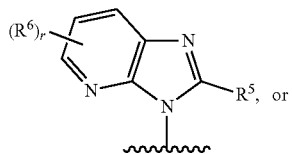
IE

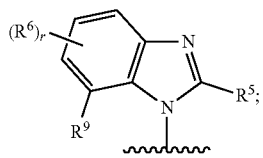
IF

R[5] is $C_{1-6}$ alkyl, $C_{1-6}$ haloalkyl $C_{1-6}$ alkoxyalkyl, $C_{3-6}$-cycloalkyl$C_{0-4}$-alkyl which may be substituted with 1-3 halogens or a $C_{1-3}$-alkoxy group;

R[6] is H, F, Cl, Br, $CF_3$, CN, $N(R^z)_2$, $CON(R^z)_2$, $C_{1-4}$ alkyl, $C_{1-4}$ haloalkyl $C_{1-4}$ alkoxyalkyl, $C_{1-4}$ hydroxyalkyl, $C_{3-6}$-cycloalkyl, $C_{3-6}$-halocycloalkyl, $C_{3-6}$-alkoxycycloalkyl, or $C_{3-6}$-hydroxycycloalkyl;

R[9] is COOR, $CON(R^z)_2$; and r is 0 to 3;

provided that the compounds of Formula (I) are not

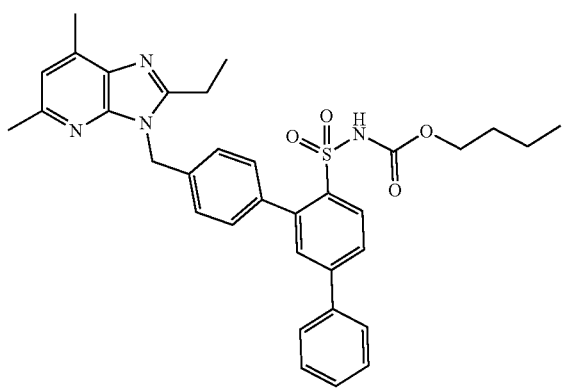

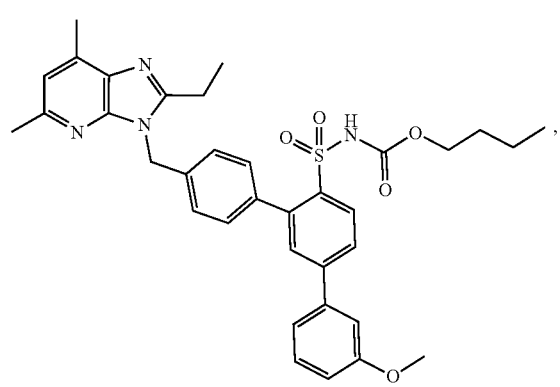

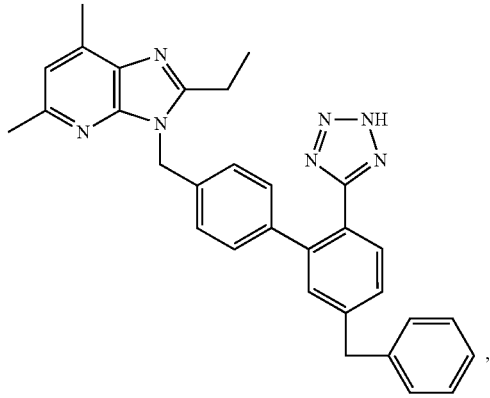

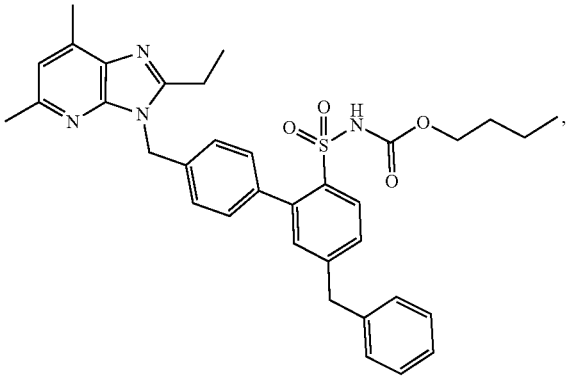

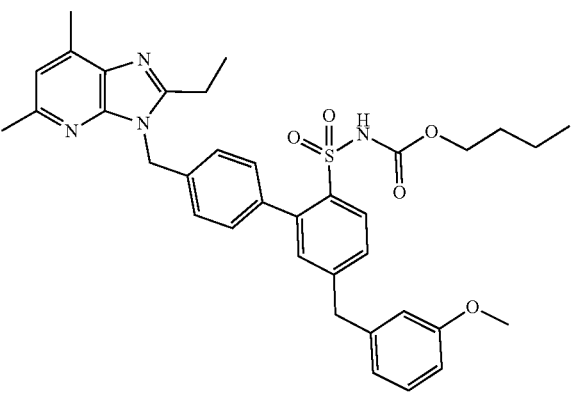

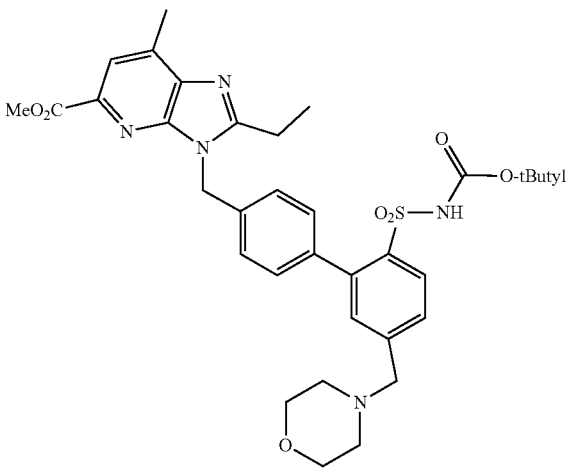

677
-continued
678
-continued
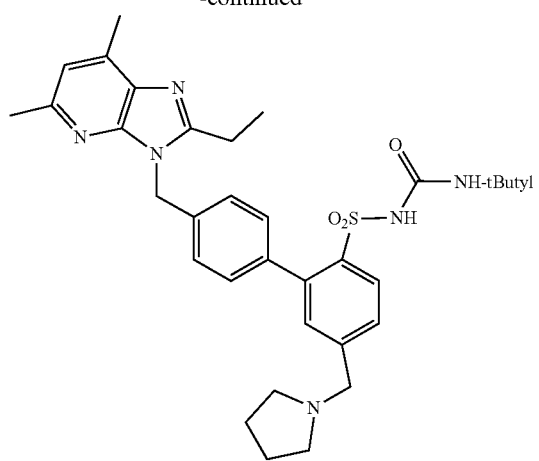
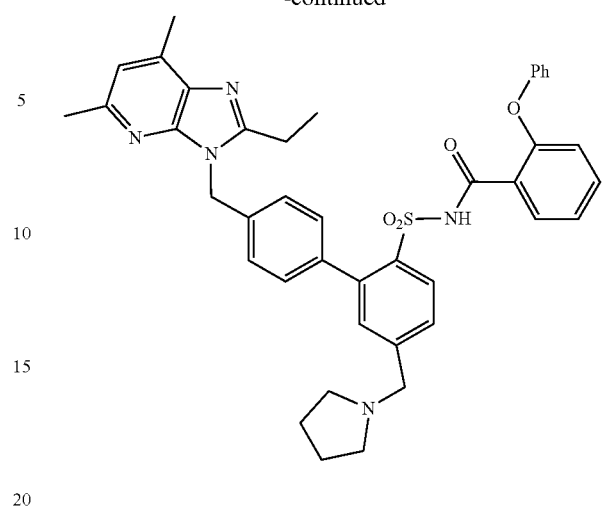
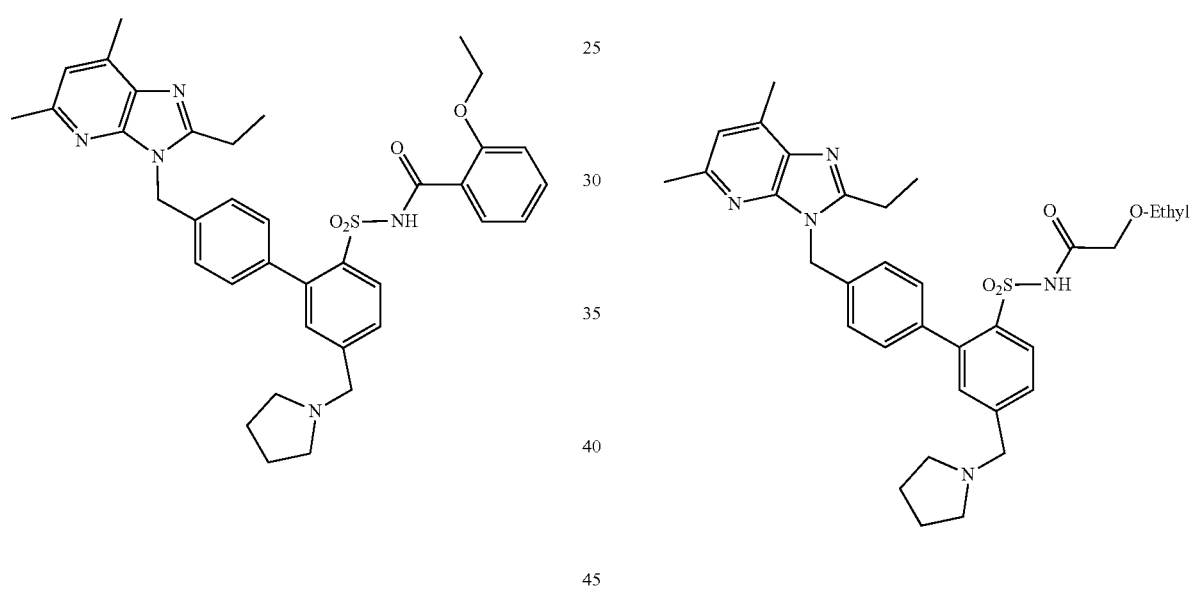
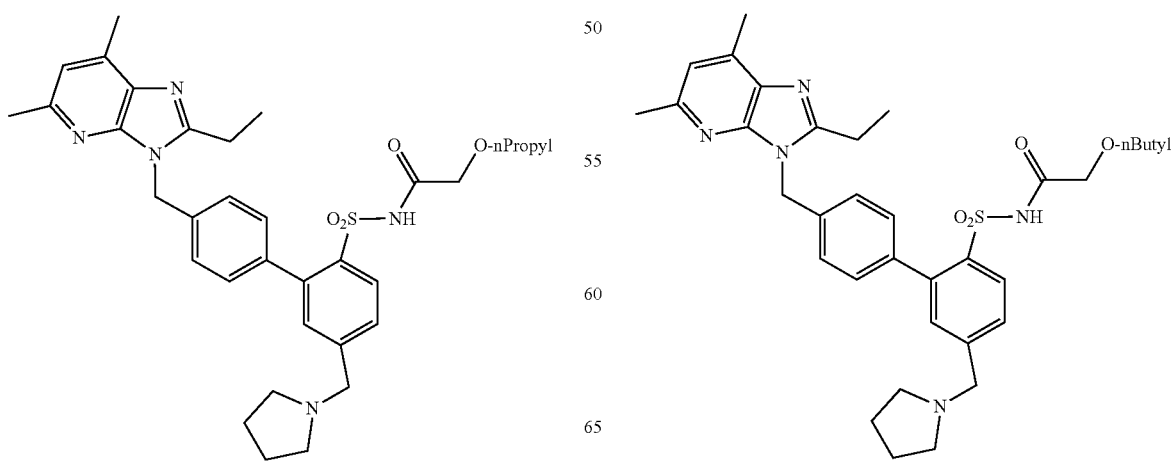

679                                                                 680
-continued                                                      -continued
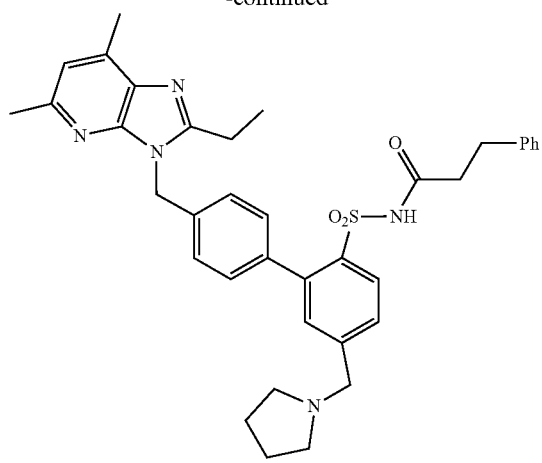
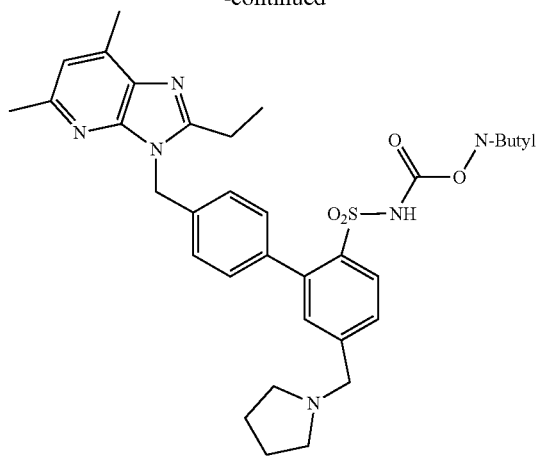
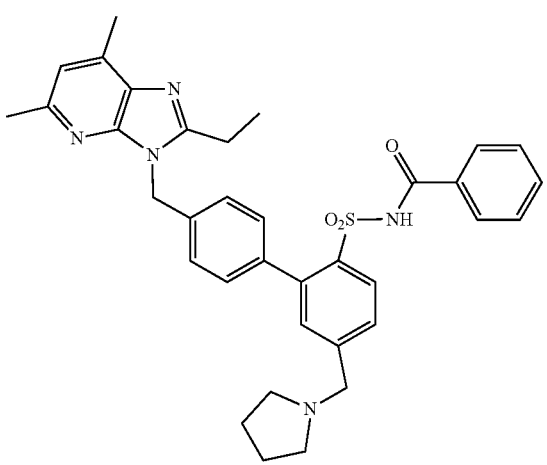
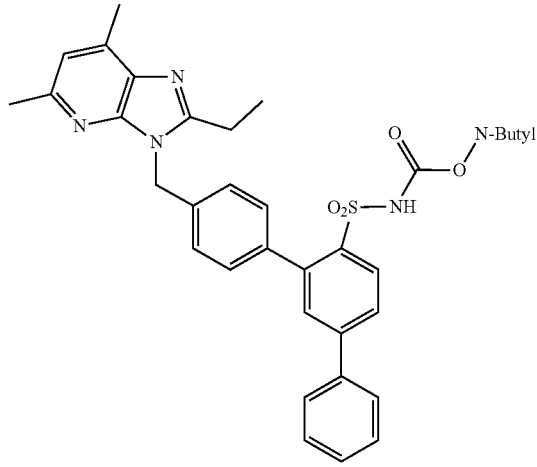
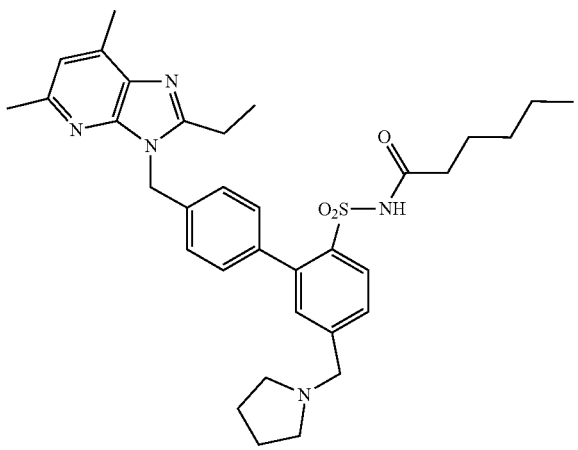
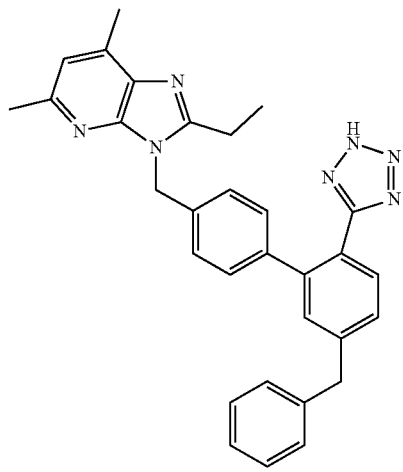

| 681 -continued | 682 -continued |
|---|---|
| 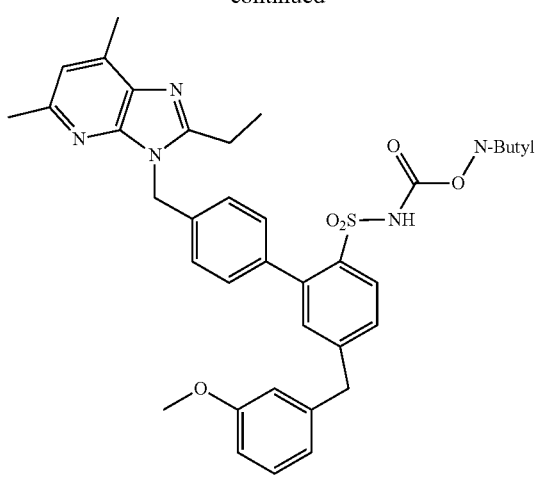 | 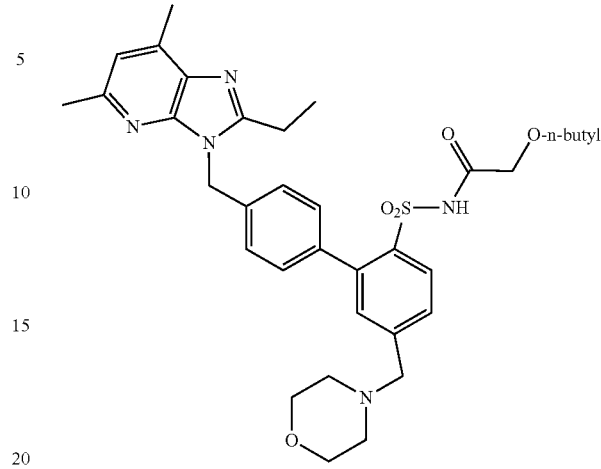 |
| 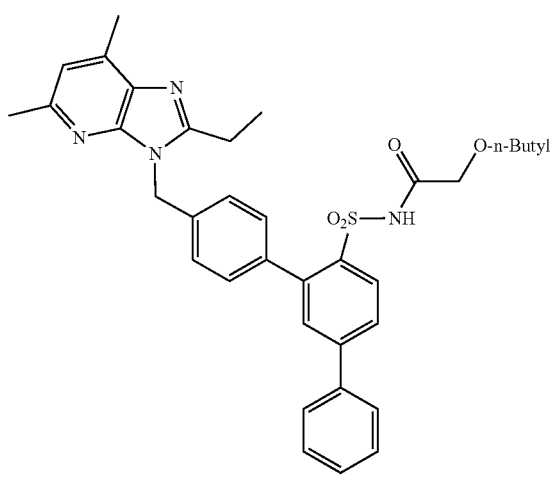 | 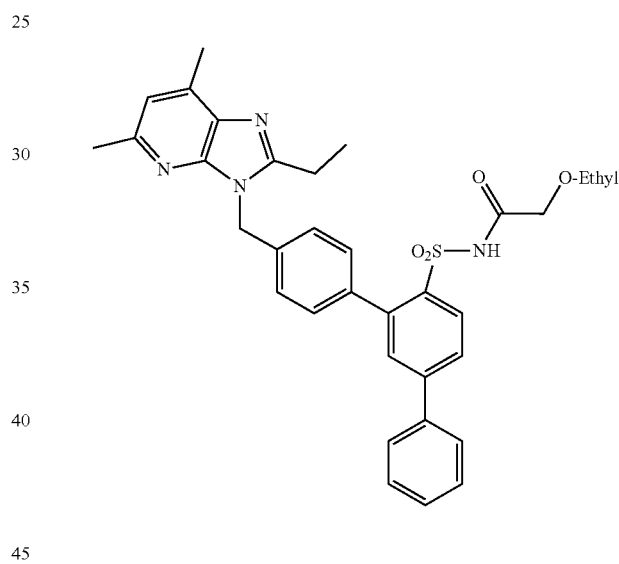 |
|  | 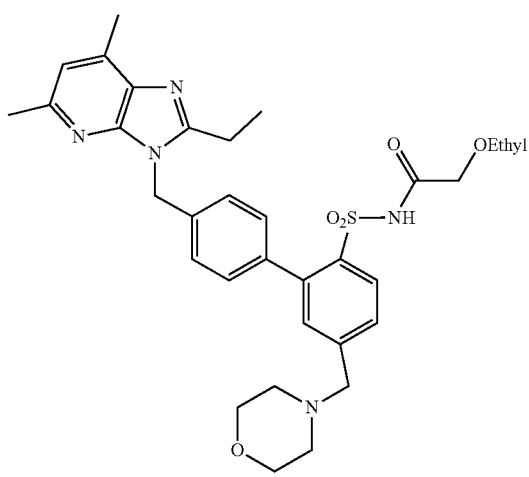 |

683
-continued
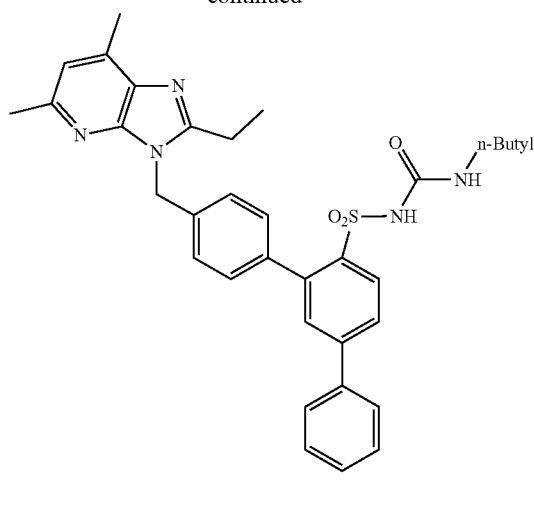
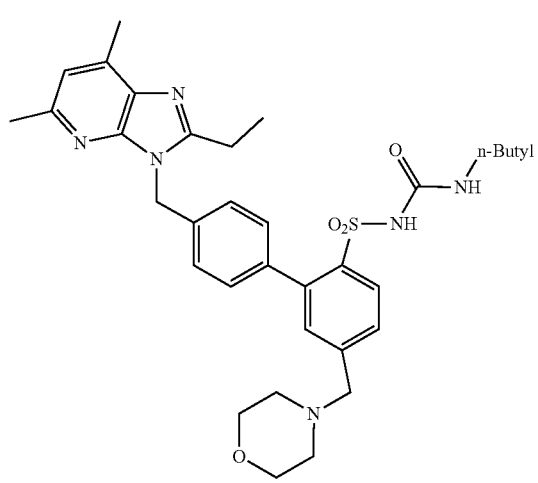
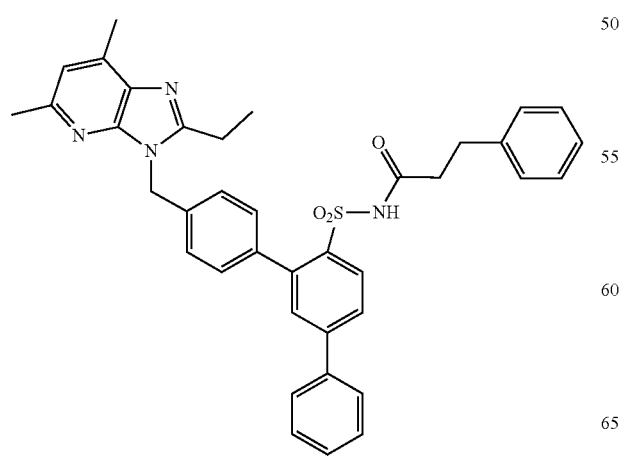
684
-continued
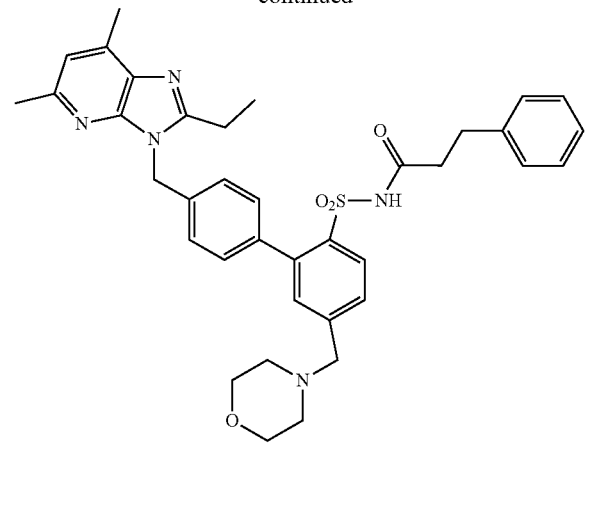
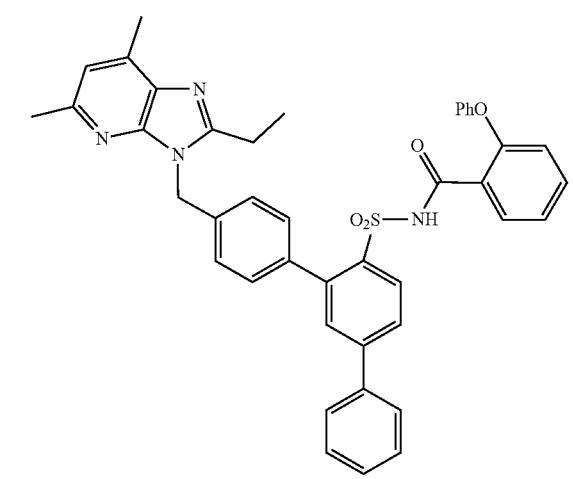
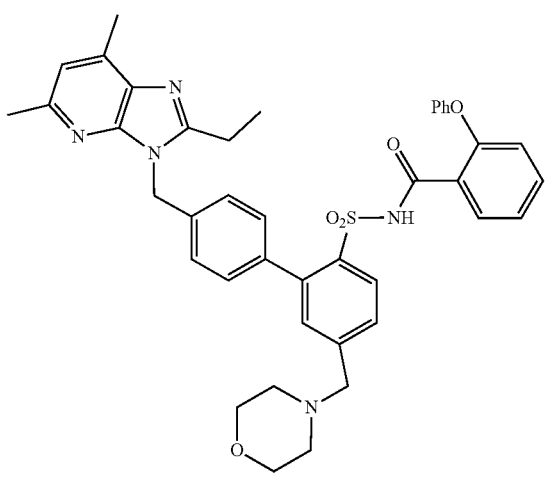

685
-continued
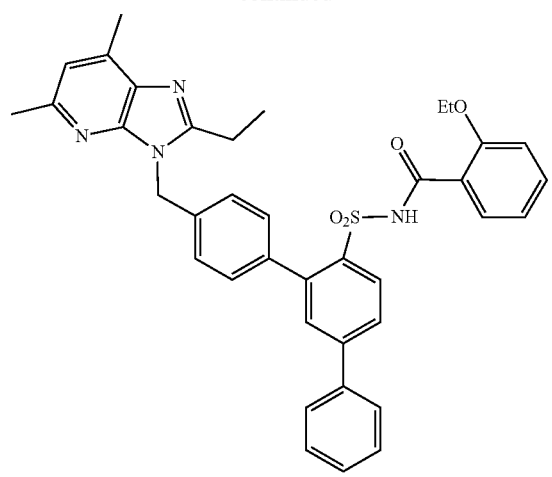
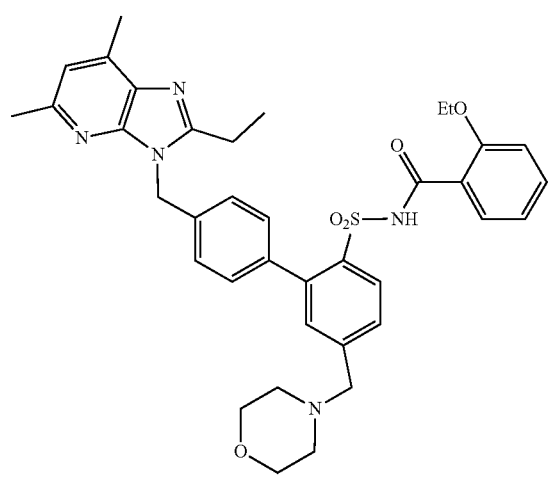
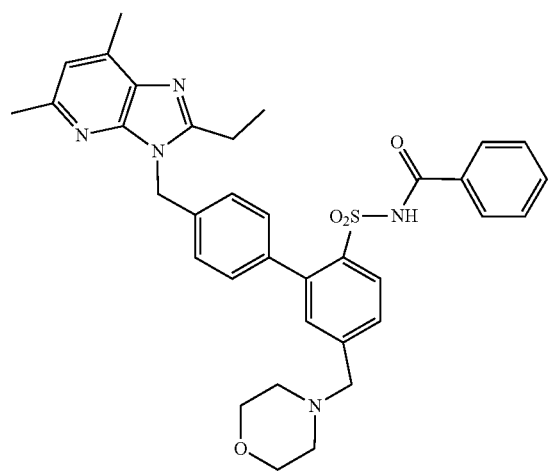
686
-continued
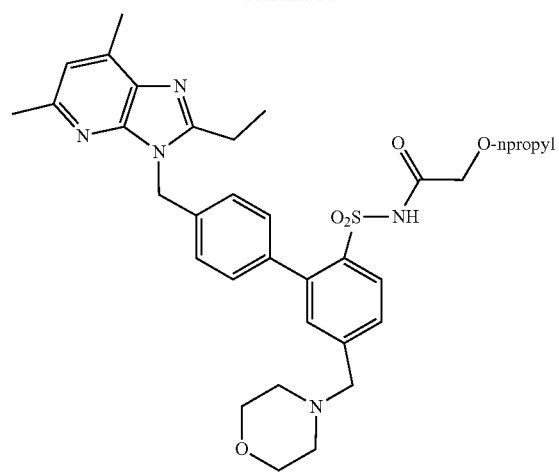
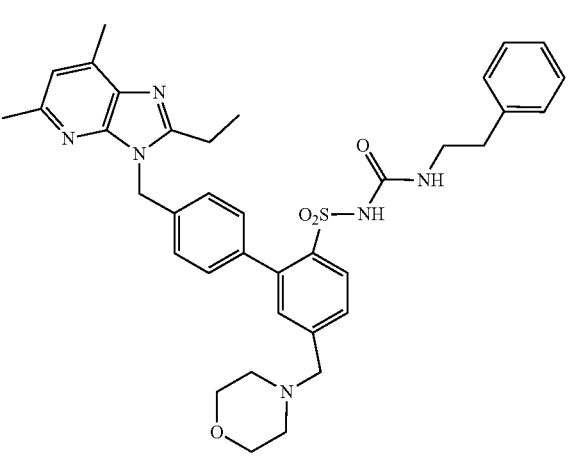

687
-continued

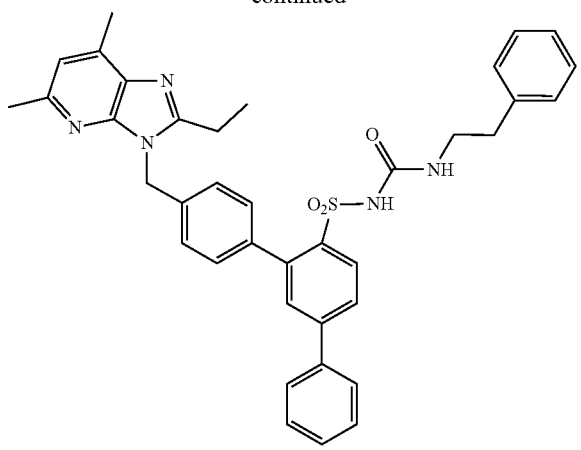

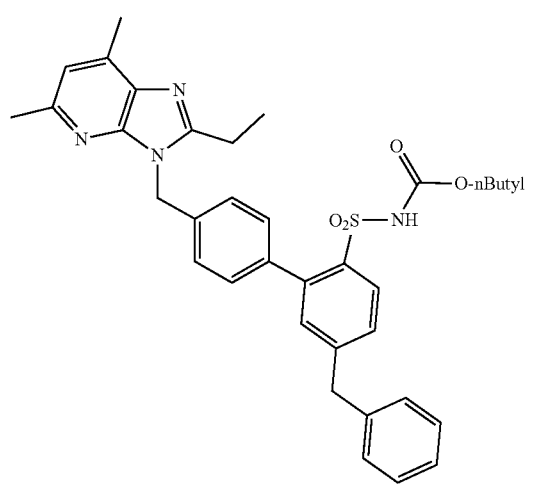

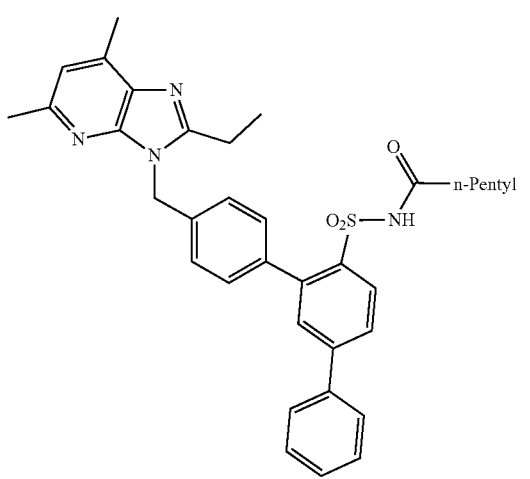

688
-continued

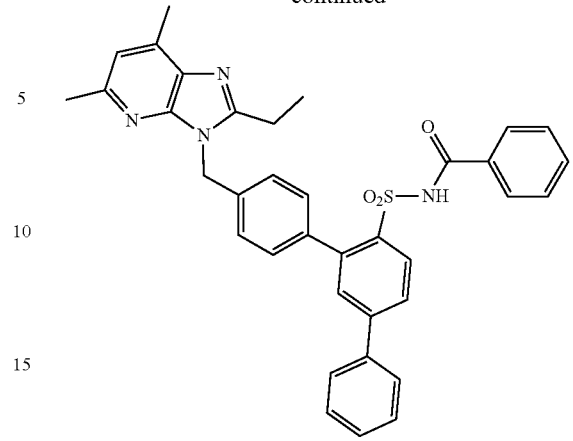

or

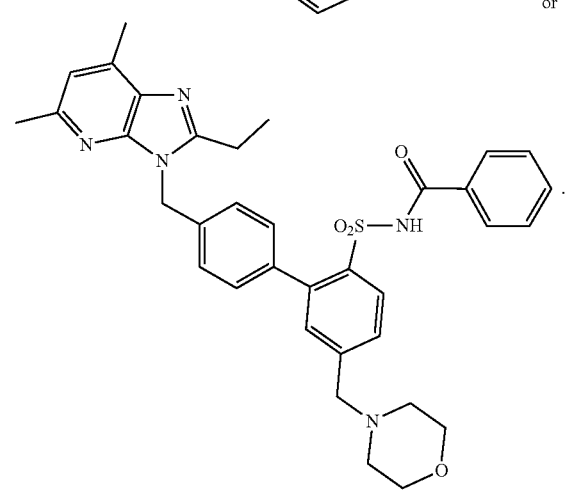

2. A compound of claim 1, or salt thereof, wherein $R^5$ is $C_{1-6}$ alkyl or $C_{3-6}$ cycloalkyl;

$R^9$ is $CO_2H$, $CO_2$-$C_{1-6}$-alkyl; and $R^6$ is hydrogen, or $C_{1-4}$ alkyl.

3. A compound of claim 1, or salt thereof, wherein

G is selected from a 5 to 10 membered heterocycle having 1-3 atoms selected from N, O, and S, phenyl or a $C_6$-$C_{10}$-heteroaryl having 1-3 atoms selected from N, O, and S; wherein the heterocycle, phenyl and heteroaryl are substituted with 0-3 substituents independently selected from the group consisting of =O, Cl, Br, I, F, $C_1$-$C_6$-alkyl, $C_1$-$C_6$-alkoxy, $C_1$-$C_6$-haloalkyl, $C_1$-$C_6$-alkylthio, $C_1$-$C_6$-hydroxyalkyl, OH, $OR^x$, $N(R^x)_2$, $CO(R^x)$, $CON(R^x)_2$, $CO_2R^x$, $N(R^x)CO_2(R^x)$, $N(R^x)CO(R^x)$, $N(R^x)CON(R^x)_2$, $S(O)_2(R^x)$, $S(O)_2N(R^x)_2$, or $N(R^x)S(O)_2R^x$;

$R^x$ is H, $C_{1-6}$ alkyl, $CF_3$, phenyl, $CH_2$-phenyl.

4. A compound of claim 1, or salt thereof, wherein Ring B is

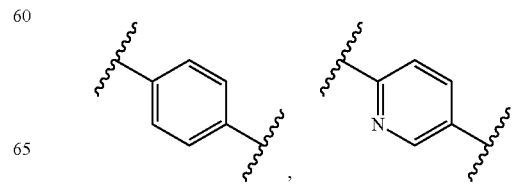

,

-continued

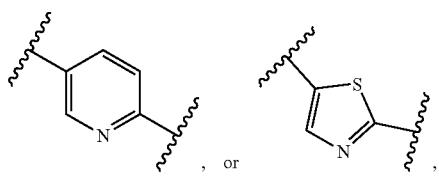

, or any of which are optionally substituted with 0-2 F.

5. A compound of claim 1, or salt thereof, wherein Ring B is

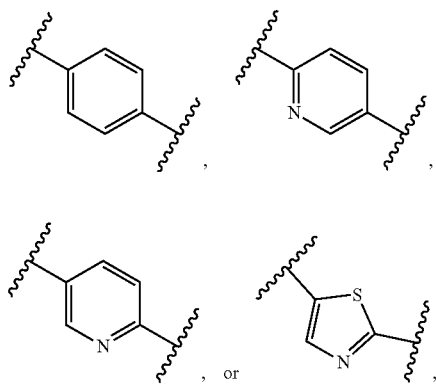 [SMILES: *c1ccc(*)cc1 ; *c1ccc(*)nc1 ; *c1ccc(*)nc1 ; *c1cnc(*)s1]

, or any of which are optionally substituted with 0-2 F, Y is COOH, COOMe, COOEt,

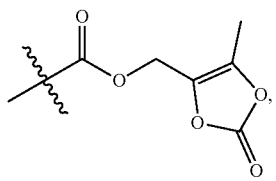 [SMILES: *C(=O)OCc1oc(=O)oc1C]

5-tetrazolyl, SO$_3$H,

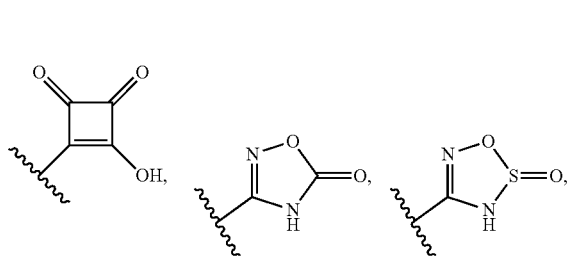

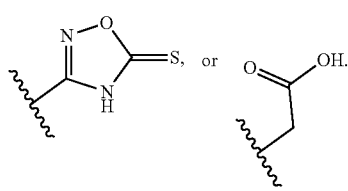

6. A compound of claim 1, or salt thereof, wherein wherein Y is COOH, 5-tetrazolyl, SO$_3$H,

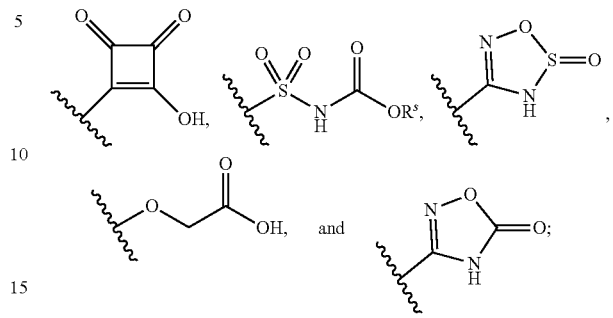

R=C$_{1-6}$ alkyl, C$_{6-10}$-aryl-C$_1$-C$_6$-alkyl, or (CH$_2$phenyl).

7. A compound of claim 1, or salt thereof, wherein Ring A is

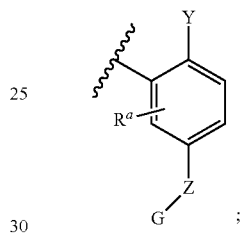

and
R$^a$ is H or F.

8. A compound of claim 1, or salt thereof, wherein
G is selected from a phenyl, thiophenyl, quinolinyl, isoquinolinyl, indolyl, pyrazolyl, pyrrolyl, pyridinyl, isoindolinyl, pyrrolidinyl; any of which are substituted with 0-3 substituents independently selected from the group consisting of =O, Cl, Br, I, F, C$_1$-C$_6$-alkyl, C$_1$-C$_6$-haloalkyl, C$_1$-C$_6$-hydroxyalkyl, OH, OR$^x$, N(R$^x$)$_2$, CO(R$^x$), CON(R$^x$)$_2$, CO$_2$R$^x$, N(R$^x$)CO$_2$(R$^x$), N(R$^x$)CO(R$^x$), N(R$^x$)CON(R$^x$)$_2$, S(O)$_2$(R$^x$), S(O)$_2$N(R$^x$)$_2$, or N(R$^x$)S(O)$_2$R$^x$;
R$^x$ is H, C$_{1-3}$ alkyl, CF$_3$, phenyl, CH$_2$-phenyl.

9. A compound of claim 1, or salt thereof, wherein Y is carboxyl, 5-tetrazolyl,

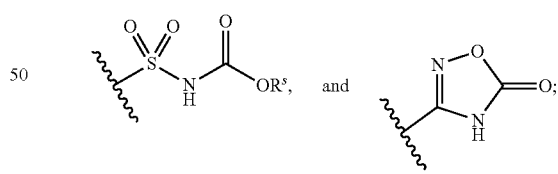

R is C$_{1-6}$ alkyl.

10. A compound of claim 1, or salt thereof, wherein Ring B is

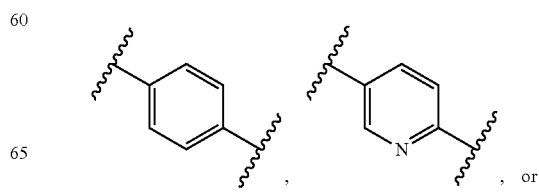

, or

-continued

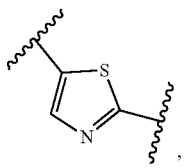, any of which are substituted with 0-2 F.

11. A compound of claim 1, or salt thereof wherein Ring B is

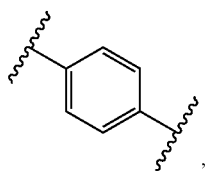, 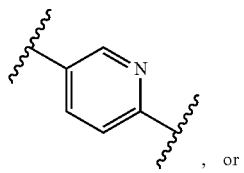, or

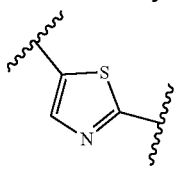

Ring A is

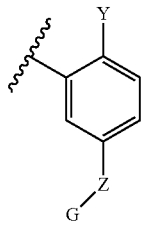

Z is a bond or $NR^a$

G is isoindolinyl-1,3-dione, pyrrolidine-2,5-dione, phenyl, thiazolyl, pyridinyl, pyrrolyl, pyrazolyl, quinolinyl, isoquinolinyl, any of which may be substituted with 0-3 substituents selected from =O, $C_{1-4}$ alkyl, $-O-R^x$, $C_{1-4}$ haloalkyl, $-N(R^x)_2$, and F;

$R^5$ is $C_{3-4}$ alkyl;

$R^6$ is $C_{3-4}$ alkyl;

$R^a$ is hydrogen, $C_{1-4}$alkyl, and $C_{1-2}$ haloalkyl; and

Y is tetrazolyl, COOH, 1,2,4-oxadiazol-5(4H)-one, or $-SO_2NHCOO$-nbutyl.

12. A compound of formula (X), or salt thereof:

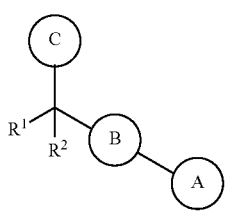 (X)

or a stereoisomer, an enantiomer, a diastereoisomer, a tautomer, a pharmaceutically acceptable salt, or a solvate thereof, wherein:

ring A is

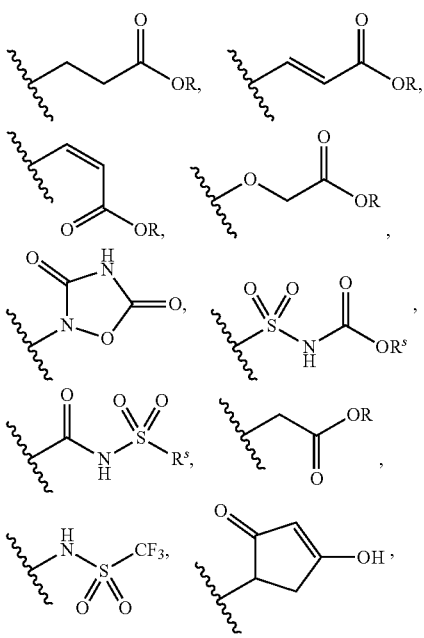

W is N, or $CR^{16}$;

W', at each occurrence, is independently selected from N, O, S and $CR^{16}$, wherein at least one W' is not $CR^{16}$, and at most only one W' is selected as O or S;

$R^1$ and $R^2$ are independently selected from H, $C_1$-$C_6$ alkyl, $C_1$-$C_6$ haloalkyl, $C_1$-$C_6$ hydroxyalkyl, $C_1$-$C_6$ alkoxyalkyl, and $C_3$-$C_6$ cycloalkyl;

alternatively, $R^1$ and $R^2$, together with the atom to which they are attached, join together to form a $C_3$-$C_6$ cycloalkyl, or a 4 to 6 membered heterocycle having 1-2 heteroatoms, the cycloalkyl or heterocycle is substituted with 0-4 F and 0-1 OH;

$R^{16}$, at each occurrence, is independently selected from H, F, Cl, Br, I, CN, OH, $N(R^a)_2$, $C_1$-$C_3$-alkyl, $C_1$-$C_3$-haloalkyl, $C_1$-$C_3$-alkoxy, $C_1$-$C_4$-hydroxyalkyl, $C_1$-$C_3$-haloalkoxy, $C_3$-$C_6$-cycloalkyl, and $C_3$-$C_6$-halocycloalkyl $R^a$ is, at each occurrence, independently selected from H, $C_1$-$C_4$-alkyl, $C_1$-$C_4$-haloalkyl, $C_1$-$C_4$-hydroxyalkyl, and $C_3$-$C_6$-cycloalkyl;

or two $R^a$, along with the nitrogen atom to which they are attached, join to form a 5 to 6 membered heterocycle containing 0-2 additional heteroatoms selected from N, O and S; Y is 5-tetrazolyl, $SO_3H$, $PO_2H$, $PO_3H_2$, COOR, -continued

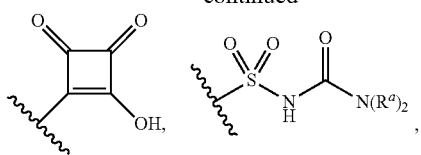
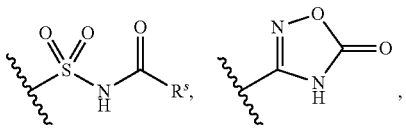
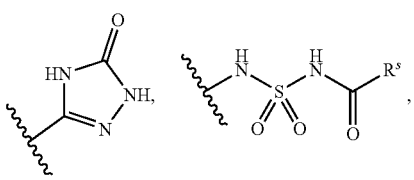
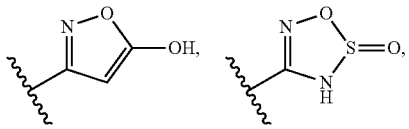
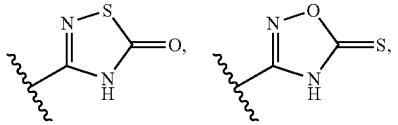
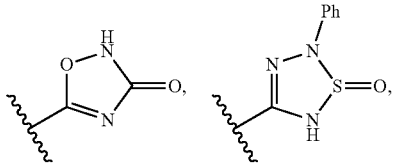
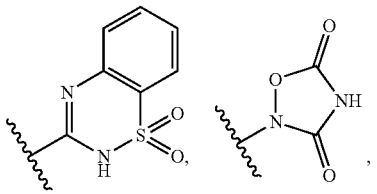
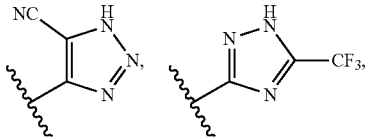
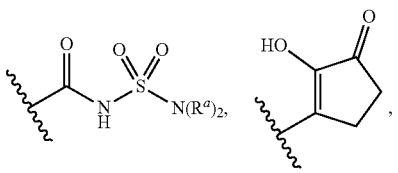
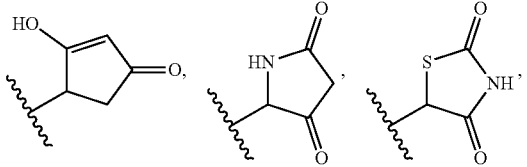

-continued

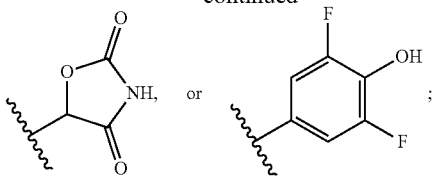

R, at each occurrence, is independently selected from H, $C_1$-$C_6$ alkyl, $C_1$-$C_6$-haloalkyl, $C_1$-$C_6$-hydroxyalkyl, $C_3$-$C_7$ cycloalkyl, $C_{6-10}$-aryl-$C_1$-$C_6$ alkyl, heterocycle-$C_1$-$C_6$ alkyl, wherein said heterocycle is a 4-10 membered group having 1-3 heteroatoms selected from N, O, or S, said aryl and heterocycle are each substituted with 0-3 groups chosen from $C_1$-$C_3$ alkyl, halo, OH, or $C_1$-$C_3$ fluoroalkyl;

$R^s$ at each occurrence, is independently selected from H, $C_1$-$C_6$ alkyl, $C_1$-$C_6$-haloalkyl, $C_1$-$C_6$-hydroxyalkyl, $C_3$-$C_7$ cycloalkyl, $C_3$-$C_7$ cycloalkyl $C_1$-$C_3$ alkyl, $C_{6-10}$ aryl, $C_{6-10}$-aryl-$C_1$-$C_6$-alkyl, heteroaryl, heteroaryl-$C_1$-$C_6$-alkyl, heterocyclyl, heterocycle-$C_1$-$C_6$-alkyl wherein the heteroaryl is a 5-10 membered group and the heterocycle is a 4-10 membered each having 1-3 heteroatoms selected from N, O, or S;

Z, at each occurrence, is independently selected from a bond, O, S, N($R^z$), C($R^z$)$_2$, C=O, C(=O)N($R^z$), N($R^z$)C(=O), C($R^z$)$_2$C($R^z$)$_2$, OC($R^z$)$_2$, SC($R^z$)$_2$, N($R^z$)C($R^z$)$_2$, C($R^z$)$_2$O, C($R^z$)$_2$S, C($R^z$)$_2$N($R^z$);

$R^z$ is at each occurrence independently selected from H, $C_1$-$C_4$-alkyl, $C_1$-$C_6$-hydroxyalkyl, $C_1$-$C_6$-alkoxyalkyl, $C_1$-$C_4$-haloalkyl, $C_3$-$C_{10}$-cycloalkyl, 5-10-membered heterocycle-$C_1$-$C_6$-alkyl, 5-10-membered heterocycle, $C_3$-$C_{10}$-cycloalkyl-$C_{1-6}$-alkyl, 4 to 7 membered heterocyclyl having 1-2 heteroatoms selected from N, O, or S, or, alternatively, two $R^z$ groups either on the same atom or on adjacent atoms can join to form a $C_3$-$C_6$-cycloalkyl or a 4 to 7 membered heterocycle containing 1-2 heteroatoms selected from N, O and S;

G is selected from a 4 to 11 membered heterocycle having 1-4 atoms selected from N, O, and S, a $C_3$-C8-cycloalkyl, $C_6$-$C_{10}$-aryl or a 5 to 10 membered heteroaryl having 1-4 atoms selected from N, O, and S; wherein the heterocycle, cycloalkyl, aryl and heteroaryl are substituted with 0-3 substituents independently selected from the group consisting of =O, F, Cl, Br, I, $C_1$-$C_6$-alkyl, $C_1$-$C_6$-alkoxy, $C_1$-$C_6$-haloalkyl, $C_1$-$C_6$-hydroxyalkyl, $C_3$-$C_8$ cycloalkyl, $C_3$-$C_8$ cycloalkenyl, CH$_2$-phenyl, OH, OR$^x$, SR$^x$, N(R$^x$)$_2$, CO(R$^x$), CON(R$^x$)$_2$, CO$_2$R$^x$, N(R$^x$)CO$_2$(R$^x$), N(R$^x$)CO(R$^x$), N(R$^x$)CON(R$^x$)$_2$, S(O)$_2$(R$^x$), S(O)$_2$N(R$^x$)$_2$, or N(R$^x$)S(O)$_2$(R$^x$);

$R^x$ is H, $C_{1-6}$ alkyl, $C_{1-4}$ haloalkyl, $C_{1-4}$ hydroxyalkyl, phenyl, CH$_2$-phenyl;

ring B is

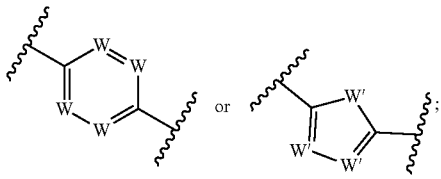

Group C is

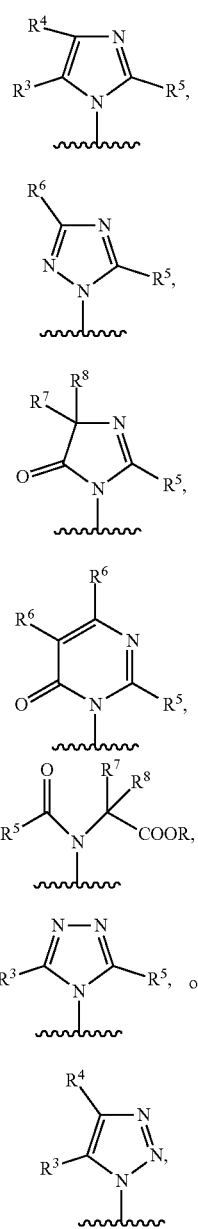

$R^3$ is $C_{1-4}$ hydroxyalkyl, $C_{1-4}$ haloalkyl, $C_{1-6}$-hydroxycycloalkyl, $C_1$-$C_6$-halocycloalkyl, COOR, CON($R^z$)$_2$, 5-6 membered heteroaryl or

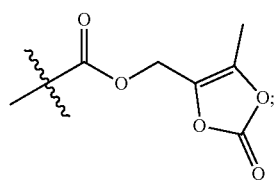 [SMILES: *C(=O)OCc1oc(=O)oc1C]

$R^4$ is H, F, Cl, Br, CF$_3$, CN, N($R^z$)$_2$, CON($R^z$)$_2$, C$_1$0.4 alkyl, $C_{1-4}$ haloalkyl $C_{1-4}$ alkoxyalkyl, $C_{1-4}$ hydroxyalkyl, $C_{3-6}$-cycloalkyl, $C_{3-6}$-halocycloalkyl, $C_{3-6}$-alkoxycycloalkyl, $C_3$-$C_6$-cycloalkyl-$C_1$-$C_6$-alkyl, or $C_{3-6}$-hydroxycycloalkyl;

$R^5$ is $C_{1-6}$ alkyl, $C_{1-6}$ haloalkyl; $C_{1-6}$ alkoxyalkyl, $C_{3-6}$-cycloalkyl-$C_{0-4}$-alkyl which may be substituted with 1-3 halogens or a $C_{1-3}$-alkoxy group;

$R^6$ is H, F, Cl, Br, CF$_3$, CN, N($R^z$)$_2$, CON($R^z$)$_2$, $C_1$-$C_4$-alkyl, $C_1$-$C_4$-haloalkyl, $C_1$0.4-alkoxyalkyl, $C_{1-4}$ hydroxyalkyl, $C_{3-6}$-cycloalkyl, $C_{3-6}$-halocycloalkyl, $C_{1-6}$-alkoxy-$C_3$-$C_6$-cycloalkyl, or $C_3$, 6-hydroxycycloalkyl; and $R^7$ and $R^8$, are independently selected from H, $C_1$-$C_4$-alkyl, $C_1$-$C_4$-hydroxyalkyl, $C_1$-$C_4$-haloalkyl, $C_3$-$C_6$-cycloalkyl or, alternatively, $R^7$ and $R^8$, along with the atom to which they are attached, can join to form a $C_3$-$C_9$ cycloalkyl, a $C_3$-$C_9$-halocycloalkyl, a $C_3$-$C_9$-hydroxycycloalkyl or a 4 to 7 membered heterocycle having 1-2 heteroatoms selected from N, O, or S each of said cycloalkyl and heterocycle being optionally substituted with 1-4 F, OH, $C_{1-4}$ alkyl, $C_{1-4}$ haloalkyl $C_{1-4}$ alkoxyalkyl, or $C_{1-4}$ hydroxyalkyl, and may be fused with a 6-membered aryl or 5-6 membered heteroaryl ring, provided the compounds of Formula (X) are not

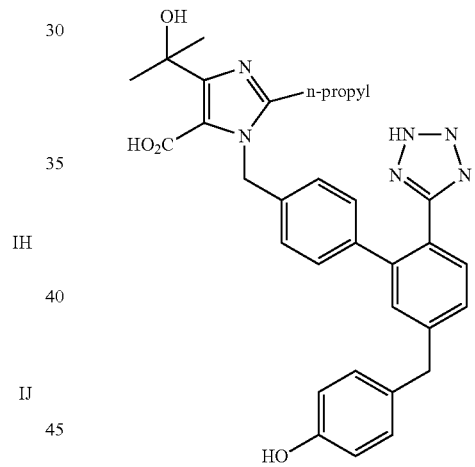

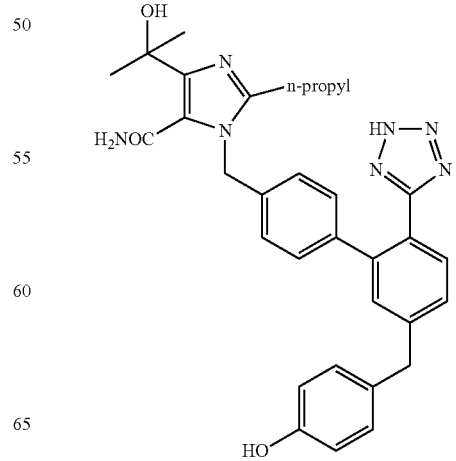

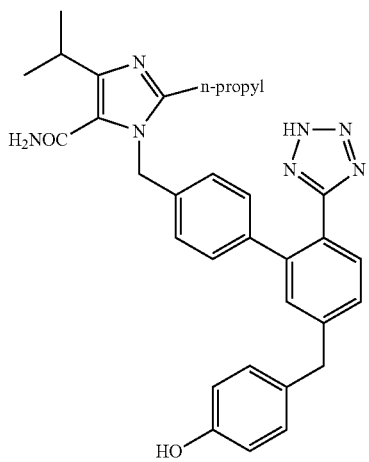

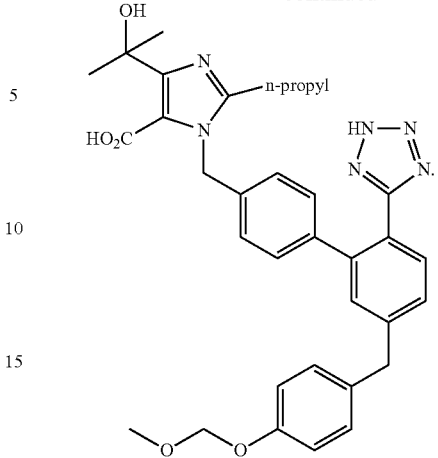

13. A compound of claim 1, or salt thereof, wherein the compound is

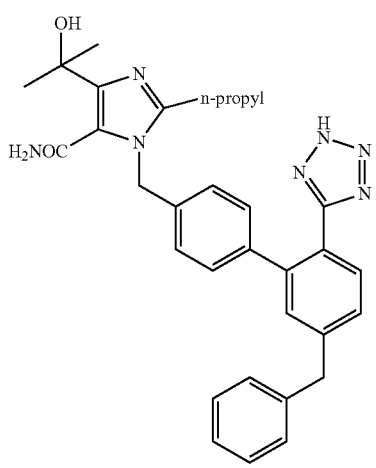

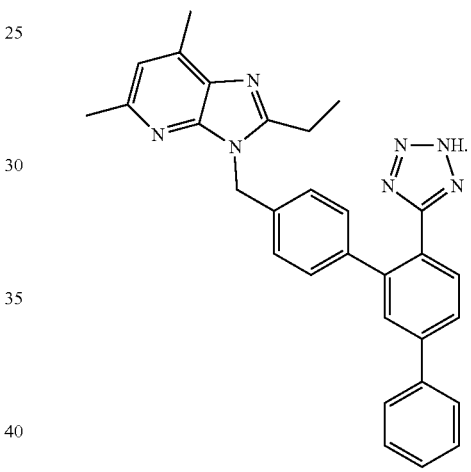

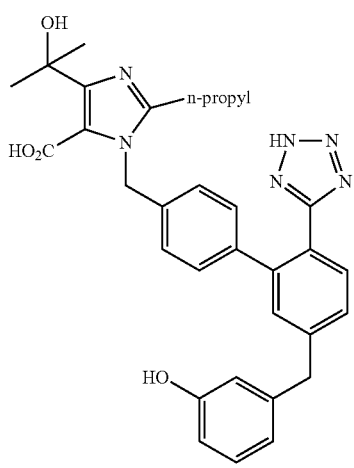

14. A method for the treatment or prophylaxis of diseases or disorders which can be modulated by biased agonism or β-Arrestin agonism of the angiotensin II receptor, comprising administering to a patient in need of such treatment or prophylaxis a therapeutically effective amount of at least one of the compounds of claim 1, wherein the disease or disorder is heart failure with preserved ejection fraction, heart failure with reduced ejection fraction, and/or renal disease.

15. A method for the treatment or prophylaxis of diseases or disorders which can be modulated by biased agonism or β-Arrestin agonism of the angiotensin II receptor, wherein the compund of claim 11 is administered in combination with at least one other type of therapeutic agent.

16. A method for the treatment or prophylaxis of diseases or disorders, comprising administering to a patient in need of such treatment or prophylaxis a therapeutically effective amount of at least one of the compounds of claim 1, wherein the disease or disorder is heart failure with preserved ejection fraction, heart failure with reduced ejection fraction, and/or renal disease.

17. A method for the treatment or prophylaxis of diseases or of claim 15, wherein the compound is administered in combination with at least one other type of therapeutic agent.

* * * * *

UNITED STATES PATENT AND TRADEMARK OFFICE
CERTIFICATE OF CORRECTION

PATENT NO. : 12,037,324 B2  
APPLICATION NO. : 17/861809  
DATED : July 16, 2024  
INVENTOR(S) : Eldon Scott Priestley et al.

Page 1 of 3

It is certified that error appears in the above-identified patent and that said Letters Patent is hereby corrected as shown below:

In the Claims

Under Column 672, Line 27: Change "$CR^{16}$"" to "$CR^{16}$;"  
Under Column 672, Lines 42-43: Change "halocycloalkyl" to "halocycloalkyl;"  
Under Column 674, Line 19: Change "$C_6$aryl-$C_1$-$C_6$ alkyl" to "$C_{6-10}$-aryl-$C_1$-$C_6$ alkyl,"  
Under Column 674, Line 25: Change "$R^8$"" to "$R^s$""  
Under Column 675, Line 24: Change "haloalkyl" to "haloalkyl,"  
Under Column 675, Lines 53-67; Column 676, Lines 2-30: Change

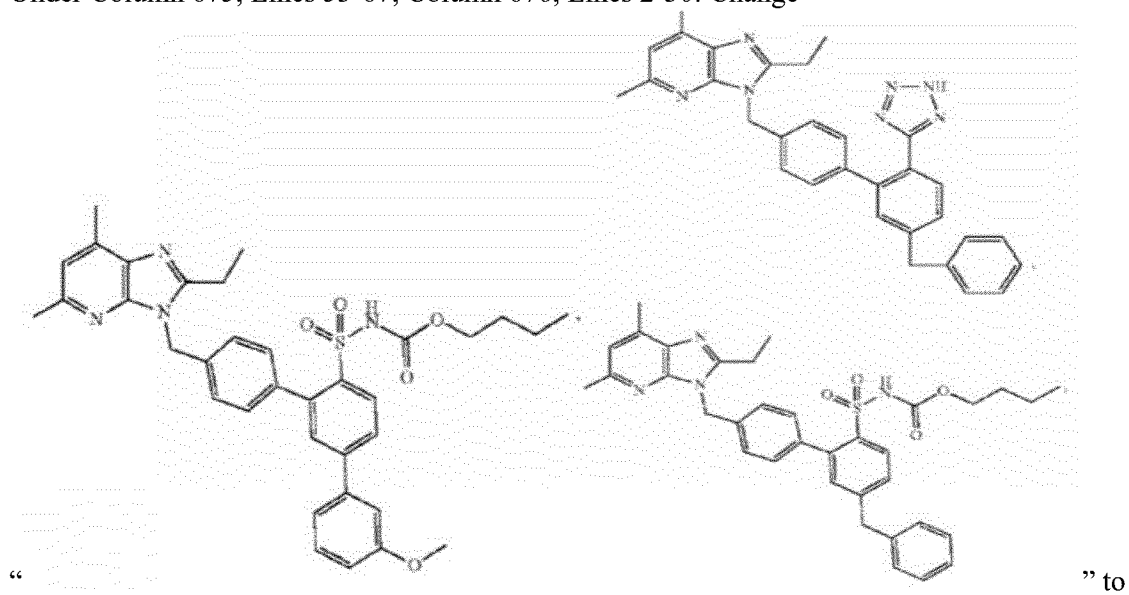

" to

Signed and Sealed this  
Fifteenth Day of April, 2025

Coke Morgan Stewart  
*Acting Director of the United States Patent and Trademark Office*

CERTIFICATE OF CORRECTION (continued)
U.S. Pat. No. 12,037,324 B2

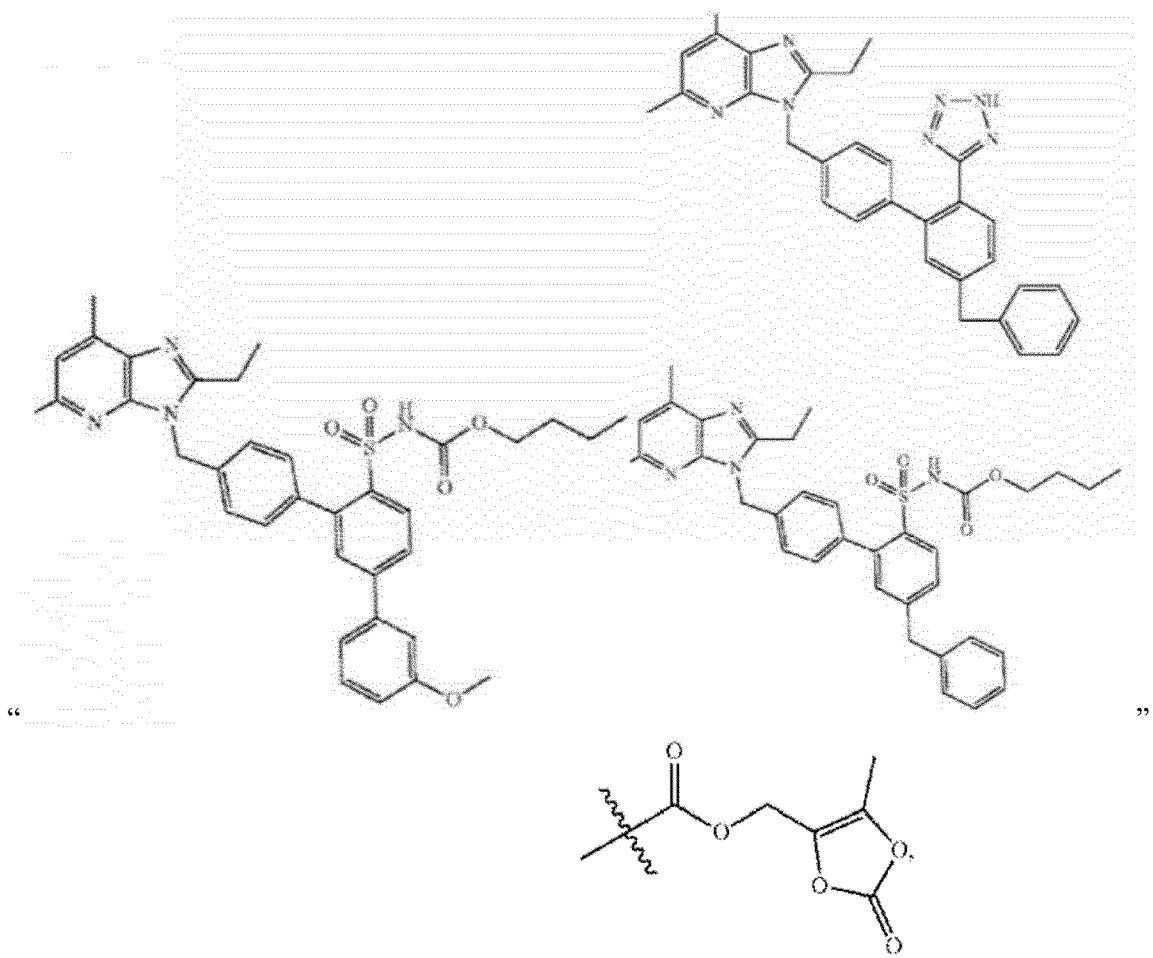

Under Column 689, Lines 37-47: Change " 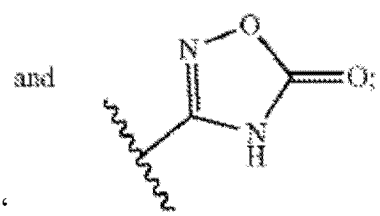 " to "5-tetrazolyl, SO₃H,"

Under Column 690, Lines 10-16: Change " 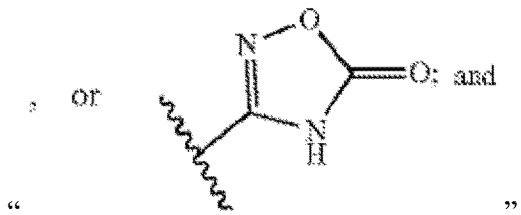 " to

" "

Under Column 690, Line 17: Change "R" to "Rˢ"
Under Column 690, Line 17: Change "(CH₂phenyl)." to "CH₂-phenyl."

Under Column 690, Lines 48-53: Change " 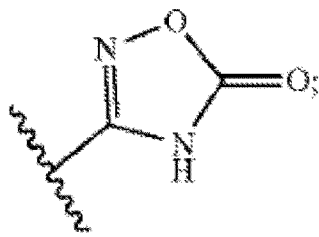 " to " 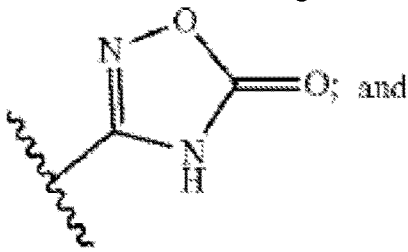 "

Under Column 690, Line 56: Change "R" to "$R^s$"
Under Column 691, Line 41: Change "$NR^a$" to "$NR^a;$"
Under Column 692, Lines 30-31: Change "halocycloalkyl" to "halocycloalkyl;"
Under Column 694, Line 21: Change "cycloalkyl" to "cycloalkyl,"
Under Column 694, Line 23: Change "alkyl" to "alkyl,"
Under Column 694, Line 25: Change "each" to "ring each"
Under Column 694, Line 35: Change "$C_{1-6}$-alkyl," to "$C_1$-$C_6$-alkyl,"
Under Column 694, Line 37: Change "$R^Z$groups" to "$R^Z$ groups"

Under Column 695, Lines 44-50: Change " 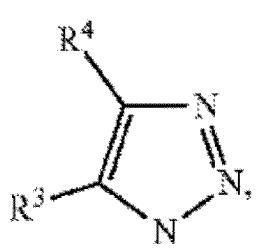 " to " 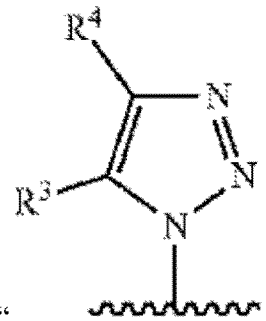 "
Under Column 695, Line 66: Change "$C_10.4$" to "$C_{1-4}$"
Under Column 695, Line 67: Change "haloalkyl" to "haloalkyl,"
Under Column 696, Line 4: Change "haloalkyl;" to "haloalkyl,"
Under Column 696, Line 9: Change "$C_10.4$" to "$C_{1-4}$"
Under Column 696, Line 11: Change "$C_3$, 6-" to "$C_{3-6}$"
Under Column 696, Line 22: Change "haloalkyl" to "haloalkyl,"
Under Column 698, Line 54: Change "compund" to "compound,"
Under Column 698, Lines 63-64: Change "A method for the treatment or prophylaxis of diseases or" to "A method for the treatment or prophylaxis of diseases or disorders"